(12) United States Patent
Liu et al.

(10) Patent No.: US 12,065,442 B2
(45) Date of Patent: *Aug. 20, 2024

(54) TROPOMYOSIN RECEPTOR KINASE (TRK) DEGRADATION COMPOUNDS AND METHODS OF USE

(71) Applicant: Cullgen (Shanghai), Inc., Shanghai (CN)

(72) Inventors: Jing Liu, Oradell, NJ (US); Liqun Chen, Shanghai (CN)

(73) Assignee: CULLGEN (SHANGHAI), INC., Shanghai (CN)

( * ) Notice: Subject to any disclaimer, the term of this patent is extended or adjusted under 35 U.S.C. 154(b) by 545 days.

This patent is subject to a terminal disclaimer.

(21) Appl. No.: 17/269,670

(22) PCT Filed: Aug. 21, 2019

(86) PCT No.: PCT/CN2019/101850
§ 371 (c)(1),
(2) Date: Feb. 19, 2021

(87) PCT Pub. No.: WO2020/038415
PCT Pub. Date: Feb. 27, 2020

(65) Prior Publication Data
US 2021/0363146 A1  Nov. 25, 2021

(30) Foreign Application Priority Data

Aug. 22, 2018 (WO) ............... PCT/CN2018/101715
May 14, 2019 (WO) ............... PCT/CN2019/086894

(51) Int. Cl.
C07D 487/04 (2006.01)
C07D 405/14 (2006.01)
C07D 417/14 (2006.01)
C07D 471/04 (2006.01)

(52) U.S. Cl.
CPC ......... *C07D 487/04* (2013.01); *C07D 405/14* (2013.01); *C07D 417/14* (2013.01); *C07D 471/04* (2013.01)

(58) Field of Classification Search
CPC ... C07D 487/04; C07D 405/14; C07D 417/14
See application file for complete search history.

(56) References Cited

U.S. PATENT DOCUMENTS

| | | | |
|---|---|---|---|
| 6,306,663 B1 | 10/2001 | Kenten et al. | |
| 6,559,280 B2 | 5/2003 | Kenten et al. | |
| 7,074,620 B2 | 7/2006 | Kenten et al. | |
| 7,273,920 B2 | 9/2007 | Kenten et al. | |
| 8,299,057 B2 | 10/2012 | Lombardi Borgia et al. | |
| 8,507,488 B2 | 8/2013 | Albaugh et al. | |
| 8,673,893 B2 | 3/2014 | Lombardi Borgia et al. | |
| 9,029,356 B2 | 5/2015 | Lombardi Borgia et al. | |
| 9,085,558 B2 | 7/2015 | Lombardi Borgia et al. | |
| 9,102,662 B2 | 8/2015 | Lombardi Borgia et al. | |
| 9,255,087 B2 | 2/2016 | Lombardi Borgia et al. | |
| 9,500,653 B2 | 11/2016 | Crews et al. | |
| 9,616,059 B2 | 4/2017 | Lombardi Borgia et al. | |
| 9,632,089 B2 | 4/2017 | Crews et al. | |
| 9,758,522 B2 | 9/2017 | Gray et al. | |
| 9,765,019 B2 | 9/2017 | Hedstrom et al. | |
| 9,821,068 B2 | 11/2017 | Bradner et al. | |
| 9,938,264 B2 | 4/2018 | Crews et al. | |
| 9,938,302 B2 | 4/2018 | Chan et al. | |
| 10,040,804 B2 | 8/2018 | Chan et al. | |
| 10,081,622 B2 | 9/2018 | Lombardi Borgia et al. | |
| 10,144,745 B2 | 12/2018 | Chan et al. | |
| 10,145,848 B2 | 12/2018 | Crews et al. | |
| 10,730,862 B2 | 8/2020 | Crews et al. | |
| 10,730,870 B2 | 8/2020 | Crew et al. | |
| 10,849,980 B2 | 12/2020 | Bradner et al. | |
| 2011/0263595 A1 | 10/2011 | Zhang et al. | |
| 2012/0065233 A1 | 3/2012 | Gregor et al. | |
| 2012/0108568 A1 | 5/2012 | Allen et al. | |
| 2014/0356322 A1 | 12/2014 | Crews et al. | |
| 2015/0119435 A1 | 4/2015 | Crews et al. | |
| 2015/0291562 A1 | 10/2015 | Crew et al. | |
| 2016/0058872 A1 | 3/2016 | Crew et al. | |
| 2016/0272639 A1 | 9/2016 | Crew et al. | |
| 2017/0037004 A1 | 2/2017 | Crew et al. | |
| 2017/0065719 A1 | 3/2017 | Qian et al. | |
| 2018/0050021 A1 | 2/2018 | Ciulli et al. | |
| 2018/0118733 A1 | 5/2018 | Harling et al. | |
| 2018/0186785 A1 | 7/2018 | Crews et al. | |

(Continued)

FOREIGN PATENT DOCUMENTS

CN 104736569 A 6/2015
CN 105085620 A 11/2015

(Continued)

OTHER PUBLICATIONS

U.S. Appl. No. 17/239,356 Office Action dated May 31, 2023.
Aguilar et al.: Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido)bicyclo[2.2.2]octane-1-carboxylic Acid (AA-115/APG-115): A Potent and Orally Active Murine Double Minute 2 (MDM2) Inhibitor in Clinical Development. J Med Chem 60, 2819-2839 (2017).
Amatu et al. NTRK gene fusions as novel targets of cancer therapy across multiple tumour types. ESMO Open 1(2):e000023 (2016).
Bailey et al.: Tropomyosin receptor kinase inhibitors: an updated patent review for 2010-2016—Part I. Expert Opin Ther Pat 27, 733-751 (2017).
Bailey et al. Tropomyosin receptor kinase inhibitors: an updated patent review for 2010-2016—Part II. Expert Opinion on Therapeutic Patents 27(7):831-849 (2017).

(Continued)

*Primary Examiner* — Ana Z Muresan
(74) *Attorney, Agent, or Firm* — WILSON SONSINI GOODRICH & ROSATI

(57) ABSTRACT

Bivalent compounds, compositions comprising one or more of the bivalent compounds, and methods of use the bivalent compounds for the treatment of certain disease in a subject in need thereof are provided. Methods for identifying such bivalent compounds are provided, either.

6 Claims, 16 Drawing Sheets

(56) References Cited

U.S. PATENT DOCUMENTS

| | | | |
|---|---|---|---|
| 2018/0215731 A1 | 8/2018 | Crew et al. | |
| 2018/0228907 A1 | 8/2018 | Crew et al. | |
| 2018/0298027 A1 | 10/2018 | Chan et al. | |
| 2019/0127359 A1 | 5/2019 | Crews et al. | |
| 2019/0151457 A1 | 5/2019 | Bradner et al. | |
| 2019/0241546 A1 | 8/2019 | Lombardi Borgia et al. | |
| 2020/0155689 A1 | 5/2020 | Crew et al. | |
| 2020/0155690 A1 | 5/2020 | Crew et al. | |
| 2020/0306273 A1* | 10/2020 | Yang | C07F 9/6561 |
| 2020/0392131 A1 | 12/2020 | Crew et al. | |
| 2021/0315999 A1* | 10/2021 | Liu | C12N 9/1205 |
| 2023/0257380 A1* | 8/2023 | Liu | C07D 487/04 514/210.16 |

FOREIGN PATENT DOCUMENTS

| | | |
|---|---|---|
| CN | 106456582 A | 2/2017 |
| CN | 106458993 A | 2/2017 |
| CN | 106543185 A | 3/2017 |
| CN | 108601764 A | 9/2018 |
| EP | 2802608 A2 | 11/2014 |
| EP | 2846784 A1 | 3/2015 |
| EP | 3131588 A4 | 1/2018 |
| EP | 3270917 A1 | 1/2018 |
| EP | 3608317 A1 | 2/2020 |
| WO | WO-2009013126 A1 | 1/2009 |
| WO | WO-2013106643 A2 | 7/2013 |
| WO | WO-2013170147 A1 | 11/2013 |
| WO | WO-2015112445 A1 | 7/2015 |
| WO | WO-2015160845 A2 | 10/2015 |
| WO | WO-2016096709 A1 | 6/2016 |
| WO | WO-2016146985 A1 | 9/2016 |
| WO | WO-2016149668 A1 | 9/2016 |
| WO | WO-2016169989 A1 | 10/2016 |
| WO | WO-2016201328 A1 | 12/2016 |
| WO | WO-2017011371 A1 | 1/2017 |
| WO | WO-2017176957 A1 | 10/2017 |
| WO | WO-2017176958 A1 | 10/2017 |
| WO | WO-2017180417 A1 | 10/2017 |
| WO | WO-2017197046 A1 | 11/2017 |
| WO | WO-2017197051 A1 | 11/2017 |
| WO | WO-2017197055 A1 | 11/2017 |
| WO | WO-2017204445 A2 | 11/2017 |
| WO | WO-2017212329 A1 | 12/2017 |
| WO | WO-2017223452 A1 | 12/2017 |
| WO | WO-2018052949 A1 | 3/2018 |
| WO | WO-2018071606 A1 | 4/2018 |
| WO | WO-2018089736 A1 | 5/2018 |
| WO | WO-2018102067 A2 | 6/2018 |
| WO | WO-2018118598 A1 | 6/2018 |
| WO | WO-2018119357 A1 | 6/2018 |
| WO | WO-2018119441 A1 | 6/2018 |
| WO | WO-2018119448 A1 | 6/2018 |
| WO | WO-2018140809 A1 | 8/2018 |
| WO | WO-2018144649 A1 | 8/2018 |
| WO | WO-2018189554 A1 | 10/2018 |
| WO | WO-2018223909 A1 | 12/2018 |
| WO | WO-2018226542 A1 | 12/2018 |
| WO | WO-2019114770 A1 | 6/2019 |
| WO | WO-2020023549 A1 | 1/2020 |
| WO | WO-2020038415 A1 | 2/2020 |
| WO | WO-2021170109 A1 | 9/2021 |
| WO | WO-2023055952 A1 | 4/2023 |

OTHER PUBLICATIONS

Blake et al.: The development of LOXO-195, a second generation TRK kinase inhibitor that overcomes acquired resistance to 1st generation inhibitors observed in patients with TRK-fusion cancers. Eur J Cancer 69, S144-S145 (2016).
Bondeson, et al., Catalytic in vivo protein knockdown by small-molecule PROTACs. Nat Chem Biol, Aug. 2015; 11(8):611-617.
Brasca et al.: Identification of N, 1,4,4-tetramethyl-8-{[4-(4-methylpiperazin-1-yl)phenyl]amino}-4,5-dihydro-1H-py razolo[4,3-h]quinazoline-3-carboxamide (PHA-848125), a potent, orally available cyclin dependent kinase inhibitor. J Med Chem 52, 5152-5163 (2009).
Buckley et al.: HaloPROTACS: Use of Small Molecule PROTACs to Induce Degradation of Halo Tag Fusion Proteins. ACS Chem Biol 10, 1831-1837 (2015).
Buckley et al.: Small-molecule control of intracellular protein levels through modulation of the ubiquitin proteasome system. Angew Chem Int Ed Engl 53, 2312-2330 (2014).
Buckley et al. Small-molecule inhibitors of the interaction between the E3 ligase VHL and HIF1α. Angew Chem Int Ed Engl 51:11463-11467 (2012).
Buckley et al.: Targeting the von Hippel-Lindau E3 ubiquitin ligase using small molecules to disrupt the VHL/HIF-1alpha interaction. J Am Chem Soc 134, 4465-4468 (2012).
Chamberlain et al.: Structure of the human Cereblon-DDB1-lenalidomide complex reveals basis for responsiveness to thalidomide analogs. Nat Struct Mol Biol 21, 803-809 (2014).
Chen et al., Discovery of first-in-class potent and selective tropomyosin receptor kinase degraders. J. Med. Chem. 63(23):14562-14575 (2020).
Choi et al.: (R)-2-Phenylpyrrolidine Substituted Imidazopyridazines: A New Class of Potent and Selective Pan-TRK Inhibitors. ACS Med Chem Lett 6, 562-567 (2015).
Chong et al.: Identification of Existing Drugs That Effectively Target NTRK1 and ROS1 Rearrangements in Lung Cancer. Clin Cancer Res 23, 204-213 (2017).
Cranston et al.: Tropomyosin Receptor Antagonism in Cylindromatosis (TRAC), an early phase trial of a topical tropomyosin kinase inhibitor as a treatment for inherited CYLD defective skin tumours: study protocol for a randomised controlled trial. Trials 18, 111 (2017).
Cui et al.: TPX-0005, a novel ALK/ROS1/TRK inhibitor, effectively inhibited a broad spectrum of mutations including solvent front Alk G1202R, ROS1 G2032R and Trka G595R mutants. Eur J Cancer 69, S32 (2016).
Davies et al.: Monoacidic Inhibitors of the Kelch-like ECH-Associated Protein 1: Nuclear Factor Erythroid 2-Related Factor 2 (KEAP1:NRF2) Protein-Protein Interaction with High Cell Potency Identified by Fragment-Based Discovery. J Med Chem 59, 3991-4006 (2016).
Denk et al.: Nerve Growth Factor and Pain Mechanisms. Annual review of neuroscience 40, 307-325 (2017).
Drilon et al.: Efficacy of Larotrectinib in TRK Fusion-Positive Cancers in Adults and Children. N Engl J Med 378, 731-739 (2018).
Drilon et al.: Safety and Antitumor Activity of the Multitargeted Pan-TRK, ROS1, and ALK Inhibitor Entrectinib: Combined Results from Two Phase I Trials (ALKA-372-001 and STARTRK-1). Cancer discovery 7, 400-409 (2017).
Fischer et al.: Structure of the DDB1-CRBN E3 ubiquitin ligase in complex with thalidomide. Nature 512, 49-53 (2014).
Fujiwara et al.: Safety and pharmacokinetics of DS-6051b in Japanese patients with non-small cell lung cancer harboring ROS1 fusions: a phase I study. Oncotarget 9, 23729-23737 (2018).
Fuse et al.: Mechanisms of Resistance to NTRK Inhibitors and Therapeutic Strategies in NTRK1-Rearranged Cancers. Mol Cancer Ther 16, 2130-2143 (2017).
Galdeano et al.: Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem 57, 8657-8663 (2014).
Ito et al.: Identification of a primary target of thalidomide teratogenicity. Science 327, 1345-1350 (2010).
Khotskaya et al.: Targeting TRK family proteins in cancer. Pharmacol Ther 173, 58-66 (2017).
Lai et al. Modular PROTAC Design for the Degradation of Oncogenic BCR-ABL. Angew chem Int Ed Engl. 55:807-810 (2016).
Li et al.: Trk inhibitor attenuates the BDNF/TrκB-induced protection of neuroblastoma cells from etoposide in vitro and in vivo. Cancer Biol Ther 16, 477-483 (2015).

(56) References Cited

OTHER PUBLICATIONS

Lu et al., Hijacking the E3 ubiquitin ligase cereblon to efficiently target BRD4. Chem Biol. 22(6):755-763 (2015).
Maniaci et al.: Homo-PROTACs: bivalent small-molecule dimerizers of the VHL E3 ubiquitin ligase to induce self-degradation. Nat Commun 8, 830 (2017).
Menichincheri et al.: Discovery of Entrectinib: A New 3-Aminoindazole as a Potent Anaplastic Lymphoma Kinase (ALK), c-ros Oncogene 1 Kinase (ROS1), and Pan-Tropomyosin Receptor Kinases (Pan-TRKs) inhibitor. J Med Chem 59, 3392-3408 (2016).
Miller et al.: Nerve growth factor blockade for the management of osteoarthritis pain: what can we learn from clinical trials and preclinical models? Current opinion in rheumatology 29, 110-118 (2017).
Ohoka et al.: In Vivo Knockdown of Pathogenic Proteins via Specific and Nongenetic Inhibitor of Apoptosis Protein (IAP)-dependent Protein Erasers (SNIPERs). J Biol Chem 292, 4556-4570 (2017).
Okuhira et al.: Specific degradation of CRABP-II via cIAP1-mediated ubiquitylation induced by hybrid molecules that crosslink cIAP1 and the target protein. FEBS Lett 585, 1147-1152 (2011).
Patwardhan et al.: Significant blockade of multiple receptor tyrosine kinases by MGCD516 (Sitravatinib), a novel small molecule inhibitor, shows potent anti-tumor activity in preclinical models of sarcoma. Oncotarget 7, 4093-4109 (2016).
PCT/CN2019/101850 International Search Report and Written Opinion dated Nov. 20, 2019.
Raina and Crews et al., Targeted protein knockdown using small molecule degraders. Curr Opin Chem Biol. 39:46-53 (2017).
Ricciuti et al.: Targeting NTRK fusion in non-small cell lung cancer: rationale and clinical evidence. Med Oncol 34, 105 (2017).
Sakamoto et al., Protacs: chimeric molecules that target proteins to the Skp1-Cullin-F box complex for ubiquitination and degradation. Proc Natl Acad Sci U S A 98(15):8554-8559 (2001).
Schnitzer et al.: A systematic review of the efficacy and general safety of antibodies to NGF in the treatment of OA of the hip or knee. Osteoarthritis and cartilage 23 Suppl 1, S8-17 (2015).
Shibata et al.: Development of protein degradation inducers of oncogenic BCR-ABL protein by conjugation of ABL kinase inhibitors and IAP ligands. Cancer Sci 108, 1657-1666 (2017).
Skerratt et al.: The Discovery of a Potent, Selective, and Peripherally Restricted Pan-Trk Inhibitor (PF-06273340) for the Treatment of Pain. J Med Chem 59, 10084-10099 (2016).
Smith et al.: Altiratinib Inhibits Tumor Growth, Invasion, Angiogenesis, and Microenvironment-Mediated Drug Resistance via Balanced Inhibition of Met, TIE2, and VEGFR2. Mol Cancer Ther 14, 2023-2034 (2015).
Subbiah et al.: First-in-human trial of multikinase VEGF inhibitor regorafenib and anti-EGFR antibody cetuximab in advanced cancer patients. JCI Insight 2 (2017).
Sun et al.: Discovery of AMG 232, a potent, selective, and orally bioavailable MDM2-p53 inhibitor in clinical development. J Med Chem 57, 1454-1472 (2014).
Tatematsu et al.: Investigation of neurotrophic tyrosine kinase receptor 1 fusions and neurotrophic tyrosine kinase receptor family expression in non-small-cell lung cancer and sensitivity to AZD7451 in vitro. Mol Clin Oncol 2, 725-730 (2014).
Varfolomeev et al.: IAP antagonists induce autoubiquitination of c-IAPs, NF-kappaB activation, and TNFalpha-dependent apoptosis. Cell 131, 669-681 (2007).
Vassilev et al.: In vivo activation of the p53 pathway by small-molecule antagonists of MDM2. Science 303, 844-848 (2004).
Vu et al.: Discovery of RG7112: A Small-Molecule MDM2 Inhibitor in Clinical Development. ACS Med Chem Lett 4, 466-469 (2013).
Wakeling. Use of pure antioestrogens to elucidate the mode of action of oestrogens. Biochem Pharmacol 49, 1545-1549 (1995).
Weisberg et al.: Smac mimetics: implications for enhancement of targeted therapies in leukemia. Leukemia 24, 2100-2109 (2010).
Winter et al.: Phthalimide conjugation as a strategy for in vivo target protein degradation. Science 348, 1376-1381 (2015).
Xie et al.: Pharmacological targeting of the pseudokinase Her3. Nat Chem Biol 10, 1006-1012 (2014).
Zengerle et al.: Selective Small Molecule Induced Degradation of the BET Bromodomain Protein BRD4. ACS Chem Biol 10, 1770-1777 (2015).
Robinson et al. The protein tyrosine kinase family of the human genome. Oncogene 19(49):5548-57 (2000).
PCT/CN2021/078240 International Search Report dated Jul. 7, 2021.

\* cited by examiner

A

B

A

B

A

B

TROPOMYOSIN RECEPTOR KINASE (TRK) DEGRADATION COMPOUNDS AND METHODS OF USE

This application is a § 371 U.S. National Stage Entry of International Application No. PCT/CN2019/101850, filed Aug. 21, 2019, and claims the benefit of International Application No. PCT/CN2019/086894, filed May 14, 2019, and International Application No. PCT/CN2018/101715, filed Aug. 22, 2018, each of which is hereby incorporated by reference in its entirety.

BACKGROUND OF THE INVENTION

This disclosure relates to bivalent compounds (e.g., bifunctional small molecule compounds), compositions comprising one or more of the bivalent compounds, and to methods of use of the bivalent compounds for the treatment of certain diseases in a subject in need thereof. The disclosure also relates to methods for identifying such bivalent compounds.

SUMMARY OF THE INVENTION

According to one aspect of the present disclosure, a bivalent compound disclosed herein comprises a tropomyosin receptor kinase (TRK) ligand conjugated to a degradation tag, or a pharmaceutically acceptable salt or analog thereof.

In one embodiment, the TRK ligand is capable of binding to a TRK protein comprising TRK, a TRK mutant, TRK deletion, or a TRK fusion protein.

In another embodiment, the TRK ligand is a TRK kinase inhibitor or a portion of TRK kinase inhibitor.

In another embodiment, the TRK ligand is selected from the group consisting of altiratinib (DCC2701, DCC-270, DP-5164), sitravatinib (MGCD516), cabozantinib (XL-184, BMS-907351), dovitinib (TKI-258, CHIR-258), entrectinib (RXDX-101), milciclib (PHA-848125AC), belizatinib (TSR-011), GZ389988, pegcantratinib, AZD7451, larotrectinib (LOXO-101; ARRY-470), TPX-0005, LOXO-195, regorafenib, DS-6051b, F17752, PLX7486, AZD-6918, ASP7962, ONO-4474, PF-06273340, GNF-8625, and analogs thereof.

In another embodiment, the degradation tag binds to an ubiquitin ligase, or is a hydrophobic group or a tag that leads to misfolding of the TRK protein.

In another embodiment, the ubiquitin ligase is an E3 ligase.

In another embodiment, the E3 ligase is selected from the group consisting of a cereblon E3 ligase, a VHL E3 ligase, a MDM2 ligase, a TRIM24 ligase, a TRIM21 ligase, a KEAP1 ligase, and an IAP ligase.

In another embodiment, the degradation tag is selected from the group consisting of pomalidomide, thalidomide, lenalidomide, VHL-1, adamantane, 1-((4,4,5,5,5-pentafluoropentyl)sulfinyl)nonane, nutlin-3a, RG7112, RG7338, AMG232, AA-115, bestatin, MV-1, LCL161, and analogs thereof.

In another embodiment, the TRK ligand is conjugated to the degradation tag via a linker moiety.

In another embodiment, the TRK ligand comprises a moiety of Formula 1

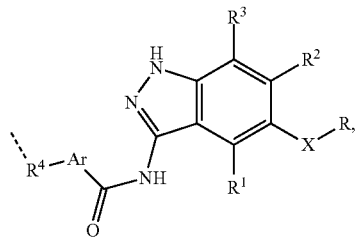

FORMULA 1 wherein
X is selected from CR'R", CO, O, S, SO, $SO_2$, and NR', wherein
  R' and R" are independently selected from hydrogen, halogen, OH, optionally substituted $C_1$-$C_8$ alkyl, optionally substituted $C_{1-8}$ alkoxy, optionally substituted $C_1$-$C_8$alkoxy$C_1$-$C_8$alkyl, optionally substituted $C_1$-$C_8$ alkylamino, optionally substituted $C_1$-$C_8$alkylamino$C_1$-$C_8$alkyl, optionally substituted $C_3$-$C_{10}$ cycloalkyl, optionally substituted $C_3$-$C_{10}$ cycloalkoxy, and optionally substituted 3-10 membered heterocyclyl; or
  R' and R" together with the atom to which they are connected form an optionally substituted 3-8 membered cycloalkyl or heterocyclyl ring;
R is selected from optionally substituted $C_1$-$C_8$ alkyl, optionally substituted $C_3$-$C_{10}$ cycloalkyl, optionally substituted 3-10 membered heterocyclyl, optionally substituted aryl, and optionally substituted heteroaryl;
$R^1$, $R^2$, and $R^3$ are independently selected from hydrogen, halogen, CN, $NO_2$, $OR^5$, $SR^6$, $NR^7R^8$, $COR^5$, $CO_2R^5$, $C(O)NR^7R^8$, $SOR^5$, $SO_2R^5$, $SO_2NR^7R^8$, $NR^7C(O)R^8$, $NR^5C(O)NR^7R^8$, $NR^7SOR^8$, $NR^7SO_2R^8$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted $C_3$-$C_{10}$ cycloalkoxy, optionally substituted 3-10 membered heterocyclyl, optionally substituted $C_2$-$C_8$ alkenyl, and optionally substituted $C_2$-$C_8$ alkynyl, wherein
$R^5$, $R^6$, $R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-10 membered heterocyclyl, optionally substituted $C_2$-$C_8$ alkenyl, optionally substituted $C_2$-$C_8$ alkynyl, optionally substituted aryl, or optionally substituted heteroaryl, or
  $R^7$ and $R^8$ together with the atom to which they are connected form an optionally substituted 4-8 membered heterocyclyl ring;
$R^4$ is connected to the linker moiety of the bivalent compound, and is selected from a bond, $OR^9$, $SR^9$, $NR^{10}R^{11}$, $COR^9$, $CO_2R^9$, $CONR^{10}R^{11}$, $SOR^9$, $SO_2R^9$, $SO_2NR^{10}R^{11}$, $NR^{10}COR^{11}$, $NR^9CONR^{10}R^{11}$, $NR^{10}SOR^{11}$, $NR^{10}SO_2R^{11}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, aryl, and optionally substituted heteroaryl, wherein $R^9$, $R^{10}$, and $R^{11}$ are independently selected from null, a bond, hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, or $R^{10}$ and $R^{11}$ together with the atom to which they are connected form a 4-8 membered cycloalkyl or heterocyclyl ring; and Ar is selected from aryl and heteroaryl group, each of which is optionally substituted with one or more substituents independently selected from hydrogen, halogen, CN, $NO_2$, $OR^{12}$, $SR^{12}$, $NR^{13}R^{14}$, $COR^{12}$, $CO_2R^{12}$, $CONR^{13}R^{14}$, $SOR^{12}$, $SO_2R^{12}$, $SO_2NR^{13}R^{14}$, $NR^{13}COR^{14}$, $NR^{15}C(O)NR^{13}R^{14}$, $NR^{13}SOR^{14}$, $NR^{13}SO_2R^{14}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^{12}$, $R^{13}$, $R^{14}$, and $R^{15}$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, or $R^{13}$ and $R^{14}$ together with the atom to which they are connected form a 4-8 membered cycloalkyl or heterocyclyl ring.

In one embodiment, X is selected from CR'R", O, and NR'; wherein

R' and R" are independently selected from hydrogen, F, OH, optionally substituted C1-C3 alkyl, and optionally substituted C1-C3 alkoxy; or R' and R" together with the atom to which they are connected form an optionally substituted 3-6 membered cycloalkyl or heterocyclyl ring.

In another embodiment, X is selected from $CH_2$, cyclopropylene, CHF, $CF_2$, O, NH, $NCH_3$, $NCH_2CH_3$, and N-isopropyl.

In another embodiment, R is selected from optionally substituted $C_3$-$C_8$ cycloalkyl, optionally substituted 3-8 membered heterocyclyl, optionally substituted aryl, and optionally substituted heteroaryl.

In another embodiment, R is selected from optionally substituted phenyl and optionally substituted heteroaryl.

In another embodiment, X is $CH_2$; and R is 3,5-difluorophenyl.

In another embodiment, $R^2$, and $R^3$ are independently selected from hydrogen, F, Cl, and OH.

In another embodiment, $R^4$—Ar is selected from a moiety of formulae A1, A2, A3, and A4:

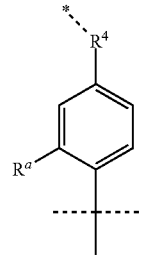

FORMULA A1

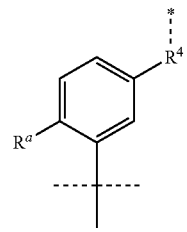

FORMULA A2

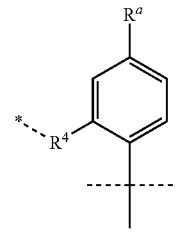

FORMULA A3

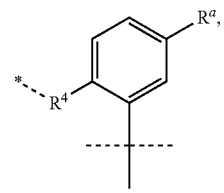

FORMULA A4 wherein
* indicates the connection to the linker moiety of the bivalent compound; and $R^a$ is selected from hydrogen, halogen, CN, $NO_2$, $OR^{12}$, $SR^{12}$, $NR^{13}R^{14}$, $COR^{12}$, $CO_2R^{12}$, $CONR^{13}R^{14}$, $SOR^{12}$, $SO_2R^{12}$, $SO_2NR^{13}R^{14}$, $NR^{13}COR^{14}$, $NR^{15}C(O)NR^{13}R^{14}$, $NR^{13}SOR^{14}$, $NR^{13}SO_2R^{14}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^{12}$, $R^{13}$, $R^{14}$, and $R^{15}$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, aryl, and optionally substituted heteroaryl, or $R^{13}$ and $R^{14}$ together with the atom to which they are connected form a 4-8 membered cycloalkyl or heterocyclyl ring.

In another embodiment, $R^4$—Ar is selected from a moiety of formulae A1, A3, A3, and A4:

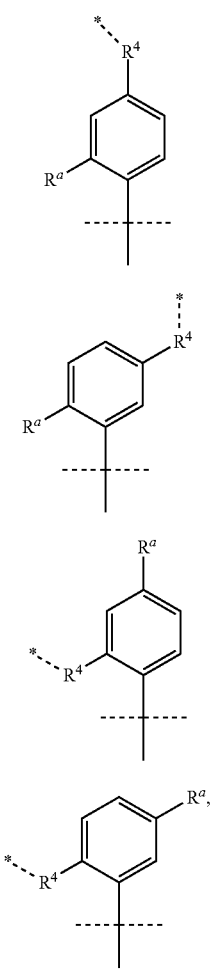

FORMULA A1

FORMULA A2

FORMULA A3

FORMULA A4 wherein
* indicates the connection to the linker moiety of the bivalent compound; and
$R^a$ is selected from hydrogen, halogen, $NR^{13}R^{14}$, and $NR^{13}COR^{14}$, wherein
$R^{13}$ and $R^{14}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted arylalkyl, optionally substituted heteroarylalkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, phenyl, and optionally substituted $C_5$-$C_6$ heteroaryl, or
$R^{13}$ and $R^{14}$ together with the atom to which they are connected form a 4-8 membered cycloalkyl or heterocyclyl ring.

In another embodiment, $R^a$ is (tetrahydro-2H-pyran-4-yl) amino.

In another embodiment, the TRK ligand comprises a moiety of Formula 2:

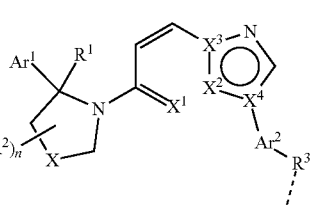

FORMULA 2 wherein
$X^1$, $X^2$, $X^3$, and $X^4$ are independently selected from C, CR', and N (preferably, $X^1$ is selected from CR' and N, $X^2$, $X^3$, and $X^4$ are independently selected from C and N), wherein
R' is selected from hydrogen, halogen, CN, $NO_2$, optionally substituted $C_1$-$C_6$ alkyl, optionally substituted $C_3$-$C_6$ cycloalkyl, and optionally substituted 3-6 membered heterocyclyl; X is selected from null, a bond, $C(R^2)_2$, $C(R^2)_2C(R^2)_2$, CO, $C(R^2)_2CO$, $CONR^2$, $C(R^2)_2O$, $C(R^2)_2NR^2$ and $CH_2NR^2$;
$R^1$ and $R^2$, at each occurrence, are independently selected from hydrogen, halogen, OH, $NH_2$, CN, $NO_2$, optionally substituted $C_1$-$C_4$ alkyl, optionally substituted $C_1$-$C_4$ alkoxy, optionally substituted $C_1$-$C_4$ alkylamino, optionally substituted $C_1$-$C_4$ alkoxyalkyl, optionally substituted $C_1$-$C_4$ haloalkyl, optionally substituted $C_1$-$C_4$ hydroxyalkyl, optionally substituted $C_1$-$C_4$alkylamino$C_1$-$C_4$alkyl, optionally substituted $C_3$-$C_6$ cycloalkyl, optionally substituted $C_3$-$C_6$ cycloalkoxy, and optionally substituted 3-6 membered heterocyclyl;
n is 1 to 4;
$R^3$ is connected to the linker moiety of the bivalent compound either directly or through $R^4$;
$R^3$ and $R^4$ are independently selected from null, a bond, $OR^5$, $SR^5$, $NR^6R^7$, $COR^5$, $CO_2R^5$, $CONR^6R^7$, $SOR^5$, $SO_2R^5$, $SO_2NR^6R^7$, $NR^6COR^7$, $NR^5C(O)NR^6R^7$, $NR^6SOR^7$, $NR^6SO_2R^7$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein
$R^5$, $R^6$ and $R^7$ are independently selected from null, a bond, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or
$R^6$ and $R^7$ together with the atom to which they are connected form a 3-8 membered cycloalkyl or 4-8 membered heterocyclyl ring; and
$Ar^1$ and $Ar^2$ are independently selected from aryl and heteroaryl, each of which is optionally substituted with one or more substituents independently selected from halogen, CN, $NO_2$, $OR^{10}$, $NR^{11}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $C(O)NR^{11}R^{12}$, $NR^{11}SOR^{12}$, $NR^{11}SO_2R^{12}$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, optionally substituted $C_2$-$C_8$ alkynyl, optionally substituted aryl, and optionally substituted heteroaryl, wherein $R^{10}$, $R^{11}$, and $R^{12}$ are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_7$ cycloalkyl, optionally substituted 3-7 membered heterocyclyl, optionally substituted aryl, and optionally substituted heteroaryl, or $R^{11}$ and $R^{12}$ together with the atom to which they are connected form a 4-8 membered cycloalkyl or heterocyclyl ring.

In one embodiment, $X^1$ is selected from CR' and N, wherein R' is selected from hydrogen, F, Cl, $CH_3$, $CF_3$, and cyclopropyl.

In another embodiment, $X^2$, $X^3$, and $X^4$ are independently selected from C and N.

In another embodiment, X is selected from a bond, $CH_2$, $CH_2CH_2$, CO, $CH_2CO$, CONH, $CONCH_3$, $CH_2O$, $CH_2NH$, and $CH_2NCH_3$.

In another embodiment, R' and $R^2$, at each occurrence, are independently selected from hydrogen, F, Cl, OH, optionally substituted $C_1$-$C_4$ alkyl, optionally substituted $C_1$-$C_4$ alkoxy, optionally substituted $C_1$-$C_4$ alkylamino, optionally substituted $C_1$-$C_4$ haloalkyl, optionally substituted $C_3$-$C_6$ cycloalkyl, optionally substituted $C_3$-$C_6$ cycloalkoxy, and optionally substituted 3-6 membered heterocyclyl.

In another embodiment, X is $CH_2$; and $Ar^1$ is 3-fluorophenyl.

In another embodiment, $R^3$ is connected to the linker moiety of the bivalent compound directly, and $R^3$ is selected from null, a bond, $OR^5$, $SR^5$, $NR^6R^7$, $COR^5$, $CO_2R^5$, $CONR^6R^7$, $SOR^5$, $SO_2R^5$, $SO_2NR^6R^7$, $NR^6COR^7$, $NR^5C(O)NR^6R^7$, $NR^6SOR^7$, $NR^6SO_2R^7$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^5$, $R^6$ and $R^7$ are independently selected from null, a bond, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or $R^6$ and $R^7$ together with the atom to which they are connected form a 4-8 membered cycloalkyl or heterocyclyl ring.

In another embodiment, $R^3$ is connected to the linker moiety of the bivalent compound through $R^4$, and $R^3$ and $R^4$ are independently selected from null, a bond, $OR^5$, $SR^5$, $NR^6R^7$, $COR^5$, $CO_2R^5$, $CONR^6R^7$, $SOR^5$, $SO_2R^5$, $SO_2NR^6R^7$, $NR^6COR^7$, $NR^5C(O)NR^6R^7$, $NR^6SOR^7$, $NR^6SO_2R^7$, optionally substituted $C_r$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^5$, $R^6$ and $R^7$ are independently selected from null, a bond, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or $R^6$ and $R^7$ together with the atom to which they are connected form a 4-8 membered cycloalkyl or heterocyclyl ring.

In another embodiment, $Ar^1$ is selected from $C_6$-$C_{10}$ aryl and $C_5$-$C_{10}$ heteroaryl, each of which is optionally substituted with one or more substituents independently selected from F, Cl, CN, $NO_2$, $OR^{10}$, $NR^{11}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $NR^{10}C(O)NR^{11}R^{12}$, $NR^{11}SOR^{12}$, $NR^{11}SO_2R^{12}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl, wherein $R^{10}$, $R^{11}$, and $R^{12}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl, or $R^{11}$ and $R^{12}$ together with the atom to which they are connected form a 4-8 membered cycloalkyl or heterocyclyl ring.

In another embodiment, $Ar^2$ is selected from $C_6$-$C_{10}$ aryl and $C_5$-$C_{10}$ heteroaryl, each of which is optionally substituted with one or more substituents independently selected from F, Cl, CN, $NO_2$, $OR^{10}$, $NR^{10}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $NR^{10}C(O)NR^{11}R^{12}$, $NR^{11}SOR^{12}$, $NR^{11}SO_2R^{12}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl, wherein $R^{10}$, $R^{11}$, and $R^{12}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl, or $R^{11}$ and $R^{12}$ together with the atom to which they are connected form a 4-8 membered cycloalkyl or heterocyclyl ring.

In another embodiment, $R^3$—$Ar^2$ is selected from a moiety of formulae B1 and B2:

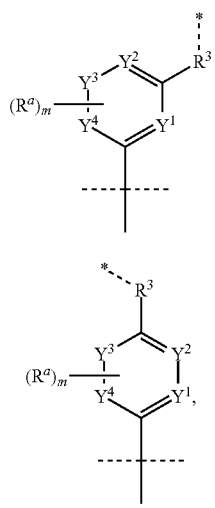

FORMULA B1

FORMULA B2 wherein
* indicates the connection to the linker moiety of the bivalent compound;
$Y^1$, $Y^2$, $Y^3$, and $Y^4$ are independently selected from CH and N, with the proviso that up to 3 of $Y^1$, $Y^2$, $Y^3$, and $Y^4$ are N;
each $R^a$ is independently selected from hydrogen, halogen, CN, $NO_2$, $OR^{12}$, $SR^{12}$, $NR^{13}R^{14}$, $COR^{12}$, $CO_2R^{12}$, $CONR^{13}R^{14}$, $SOR^{12}$, $SO_2R^{12}$, $SO_2NR^{13}R^{14}$, $NR^{13}COR^{14}$, $NR^{15}C(O)NR^{13}R^{14}$, $NR^{13}SOR^{14}$, $NR^{13}SO_2R^{14}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein
$R^{12}$, $R^{13}$, $R^{14}$, and $R^{15}$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, or
$R^{13}$ and $R^{14}$ together with the atom to which they are connected form a 4-8 membered cycloalkyl or heterocyclyl ring;
m is 0 to 4; and
$R^3$ is the same as defined in Formula 2.

In another embodiment, $R^3$—$Ar^2$ is selected from a moiety of formula B3:

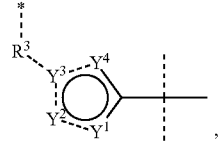

FORMULA B3 wherein
* indicates the connection to the linker moiety of the bivalent compound;
$Y^1$, $Y^2$, $Y^3$, and $Y^4$ are independently selected from $CR^a$, N, O, and S, with the proviso that up to 3 of $Y^1$, $Y^2$, $Y^3$, and $Y^4$ are N;
each $R^a$ is independently selected from hydrogen, halogen, CN, $NO_2$, $OR^{12}$, $SR^{12}$, $NR^{13}R^{14}$, $COR^{12}$, $CO_2R^{12}$, $CONR^{13}R^{14}$, $SOR^{12}$, $SO_2R^{12}$, $SO_2NR^{13}R^{14}$, $NR^{13}COR^{14}$, $NR^{15}C(O)NR^{13}R^{14}$, $NR^{13}SOR^{14}$, $NR^{13}SO_2R^{14}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein
$R^{12}$, $R^{13}$, $R^{14}$, and $R^{15}$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, or
$R^{13}$ and $R^{14}$ together with the atom to which they are connected form a 4-8 membered cycloalkyl or heterocyclyl ring;
m is 0 to 4; and
$R^3$ is the same as defined in Formula 2.

In another embodiment, $X^1$ is N; $X^2$ is N; $X^3$ is C; $X^4$ is C; X is $CH_2$; $Ar^1$ is 3-fluorophenyl; and $Ar^2$ is 2-pyridyl.

In another embodiment, the TRK ligand comprises a moiety of FORMULA 3:

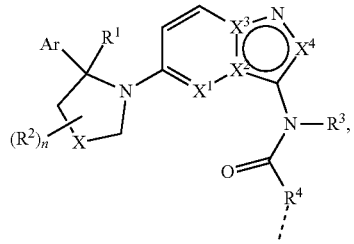

FORMULA 3 wherein
- $X^1$, $X^2$, $X^3$, and $X^4$ are independently selected from C, CR', and N (preferably, $X^1$ and $X^4$ are independently selected from CR' and N; $X^2$ and $X^3$ are independently selected from C and N), wherein
  - R' is selected from hydrogen, halogen, CN, $NO_2$, and optionally substituted $C_1$-$C_6$ alkyl, $C_3$-$C_6$ cycloalkyl, or 3-6 membered heterocyclyl;
- X is selected from null, a bond, $C(R^2)_2$, $C(R^2)_2C(R^2)_2$, CO, $C(R^2)_2CO$, $NR^2CO$, $OC(R^2)_2$, and $NR^2C(R^2)_2$; R' and each $R^2$ are independently selected from hydrogen, halogen, OH, $NH_2$, CN, $NO_2$, optionally substituted $C_1$-$C_4$ alkyl, optionally substituted $C_1$-$C_4$ alkoxy, optionally substituted $C_1$-$C_4$ alkylamino, optionally substituted $C_1$-$C_4$ alkoxyalkyl, optionally substituted $C_1$-$C_4$ haloalkyl, optionally substituted $C_1$-$C_4$ hydroxyalkyl, optionally substituted $C_1$-$C_4$alkylamino$C_1$-$C_4$alkyl, optionally substituted $C_3$-$C_6$ cycloalkyl, optionally substituted $C_3$-$C_6$ cycloalkoxy, and optionally substituted 3-6 membered heterocyclyl;
- n is 1 to 4;
- $R^3$ is selected from hydrogen, optionally substituted $C_1$-$C_6$ alkyl, optionally substituted $C_3$-$C_6$ cycloalkyl, optionally substituted 3-6 membered heterocyclyl, optionally substituted $C_1$-$C_6$ alkoxyalkyl, optionally substituted $C_1$-$C_6$ haloalkyl, optionally substituted $C_1$-$C_6$ hydroxyalkyl, and optionally substituted $C_1$-$C_6$alkylamino$C_1$-$C_6$alkyl;
- $R^4$ is connected to the linker moiety of the bivalent compound either directly or through $R^5$, wherein $R^4$ and $R^5$ are independently selected from null, $OR^6$, $SR^6$, $NR^7R^8$, $COR^6$, $CO_2R^6$, $CONR^7R^8$, $SOR^6$, $SO_2R^6$, $SO_2NR^7R^8$, $NR^7COR^8$, $NR^9C(O)NR^7R^8$, $NR^7SOR^8$, $NR^7SO_2R^8$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein
  - $R^6$, $R^7$, $R^8$, and $R^9$ are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or
  - $R^7$ and $R^8$ together with the atom to which they are connected form a 4-8 membered cycloalkyl or heterocyclyl ring;
- Ar is selected from aryl and heteroaryl, each of which is optionally substituted with one or more substituents independently selected from halogen, CN, $NO_2$, $OR^{10}$, $SR^{10}$, $NR^{11}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $NR^{10}C(O)NR^{11}R^{12}$, $NR^{11}SOR^{12}$, $NR^{11}SO_2R^{12}$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, optionally substituted $C_2$-$C_8$ alkynyl, optionally substituted aryl, and optionally substituted heteroaryl, wherein
  - $R^{10}$, $R^{11}$, and $R^{12}$ are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_7$ cycloalkyl, optionally substituted 3-7 membered heterocyclyl, optionally substituted aryl, and optionally substituted heteroaryl, or
  - $R^{11}$ and $R^{12}$ together with the atom to which they are connected form a 4-8 membered cycloalkyl or heterocyclyl rings.

In one embodiment, $X^1$ and $X^4$ is selected from CR' and N, and R' is selected from hydrogen, F, Cl, $CH_3$, $CF_3$, and cyclopropyl.

In another embodiment, $X^2$ and $X^3$ are independently selected from C and N.

In another embodiment, X is selected from a bond, $CH_2$, $CH_2CH_2$, CO, $CH_2CO$, CONH, $CONCH_3$, $CH_2O$, $CH_2NH$, and $CH_2NCH_3$.

In another embodiment, $R^1$ and each $R^2$ are independently selected from hydrogen, F, Cl, OH, optionally substituted $C_1$-$C_4$ alkyl, optionally substituted $C_1$-$C_4$ alkoxy, optionally substituted $C_1$-$C_4$ alkylamino, optionally substituted $C_1$-$C_4$ haloalkyl, optionally substituted $C_3$-$C_6$ cycloalkyl, optionally substituted $C_3$-$C_6$ cycloalkoxy, and optionally substituted 3-6 membered heterocyclyl.

In another embodiment, $R^3$ is selected from hydrogen, $CH_3$, $CH_2CH_3$, propyl, isopropyl, cyclopropyl, $CH_2F$, $CHF_2$, and $CF_3$.

In another embodiment,
- $R^4$ is connected to the linker moiety of the bivalent compound directly, and
- $R^4$ is selected from null, $OR^6$, $SR^6$, $NR^7R^8$, $COR^6$, $CO_2R^6$, $CONR^7R^8$, $SOR^6$, $SO_2R^6$, $SO_2NR^7R^8$, $NR^7COR^8$, $NR^9C(O)NR^7R^8$, $NR^7SOR^8$, $NR^7SO_2R^8$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein
  - $R^6$, $R^7$, $R^8$, and $R^9$ are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, heteroarylalkyl, optionally substituted aryl, and optionally substituted heteroaryl, or
  - $R^7$ and $R^8$ together with the atom to which they are connected form a 4-8 membered cycloalkyl or heterocyclyl ring.

In another embodiment,
- $R^4$ is connected to the linker moiety of the bivalent compound through $R^5$, and
- $R^4$ and $R^5$ are independently selected from null, $OR^6$, $SR^6$, $NR^7R^8$, $COR^6$, $CO_2R^6$, $CONR^7R^8$, $SOR^6$, $SO_2R^6$, $SO_2NR^7R^8$, $NR^7COR^8$, $NR^9C(O)NR^7R^8$, $NR^7SOR^8$, $NR^7SO_2R^8$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted C$_1$-C$_8$ hydroxyalkyl, optionally substituted C$_1$-C$_8$alkylaminoC$_1$-C$_8$alkyl, optionally substituted C$_3$-C$_8$ cycloalkyl, optionally substituted 3-8 membered heterocyclyl, optionally substituted C$_2$-C$_8$ alkenyl, optionally substituted C$_2$-C$_8$ alkynyl, optionally substituted aryl, and optionally substituted heteroaryl, wherein R$^6$, R$^7$, R$^8$, and R$^9$ are independently selected from null, hydrogen, optionally substituted C$_1$-C$_8$ alkyl, optionally substituted C$_2$-C$_8$ alkenyl, optionally substituted C$_2$-C$_8$ alkynyl, optionally substituted C$_3$-C$_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or R$^7$ and R$^8$ together with the atom to which they are connected form a 4-8 membered cycloalkyl or heterocyclyl ring.

In another embodiment,

Ar is selected from aryl and heteroaryl, each of which is optionally substituted with one or more substituents independently selected from F, Cl, CN, NO$_2$, OR$^{10}$, NR$^{11}$R$^{12}$, COR$^{10}$, CO$_2$R$^{10}$, CONR$^{11}$R$^{12}$, SOR$^{10}$, SO$_2$R$^{10}$, SO$_2$NR$^{11}$R$^{12}$, NR$^{11}$COR$^{12}$, NR$^{10}$C(O)NR$^{11}$R$^{12}$, NR$^{11}$SOR$^{12}$, NR$^{11}$SO$_2$R$^{12}$, optionally substituted C$_1$-C$_6$ alkyl, optionally substituted C$_1$-C$_6$ alkoxyalkyl, optionally substituted C$_1$-C$_6$ haloalkyl, optionally substituted C$_1$-C$_6$ hydroxyalkyl, optionally substituted C$_1$-C$_6$alkylaminoC$_1$-C$_6$alkyl, optionally substituted C$_3$-C$_7$ cycloalkyl, optionally substituted 3-7 membered heterocyclyl, optionally substituted C$_2$-C$_6$ alkenyl, optionally substituted C$_2$-C$_6$ alkynyl, optionally substituted aryl, and optionally substituted C$_4$-C$_5$ heteroaryl, wherein R$^{10}$, R$^{11}$, and R$^{12}$ are independently selected from null, hydrogen, optionally substituted C$_1$-C$_6$ alkyl, optionally substituted C$_2$-C$_6$ alkenyl, optionally substituted C$_2$-C$_6$ alkynyl, optionally substituted C$_3$-C$_7$ cycloalkyl, optionally substituted 3-7 membered heterocyclyl, optionally substituted aryl, and optionally substituted heteroaryl, or R$^{11}$ and R$^{12}$ together with the atom to which they are connected form a 4-8 membered cycloalkyl or heterocyclyl ring.

In another embodiment, the TRK ligand is derived from any of the following:

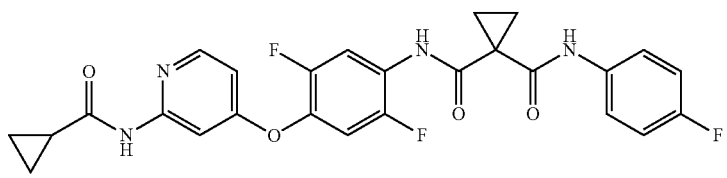

Altiratinib (DCC-2701, DCC-270, DP-5164)

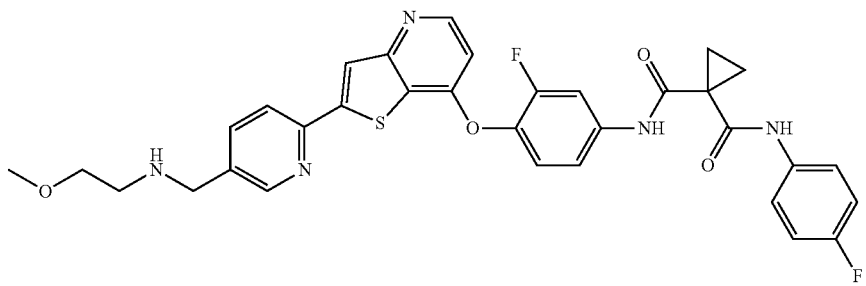

Sitravatinib (MGCD516)

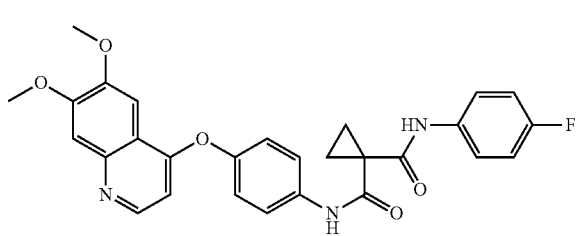

Cabozantinib (XL-184, BMS-907351)

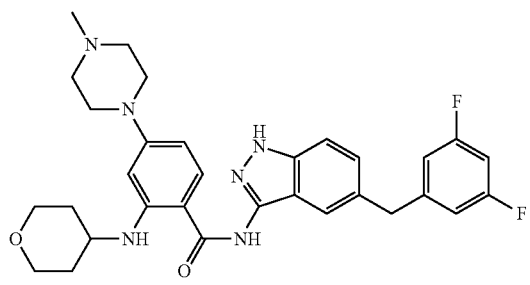

Entrectinib (RXDX-101)

-continued
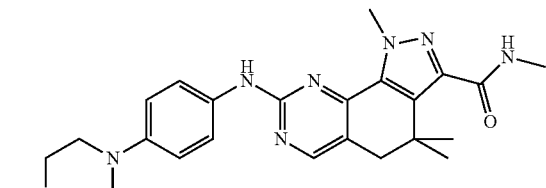
Milciclib (PHA-848125AC)
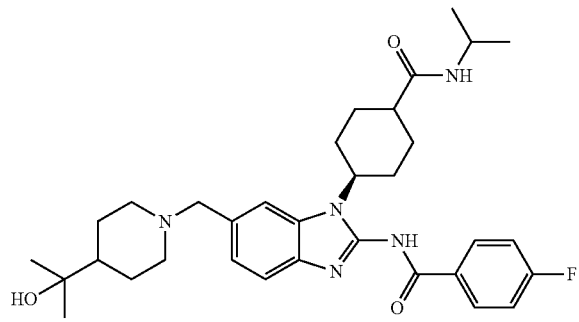
Belizatinib (TSR-011)
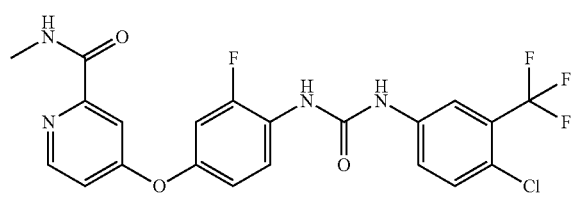
Regoratenlb
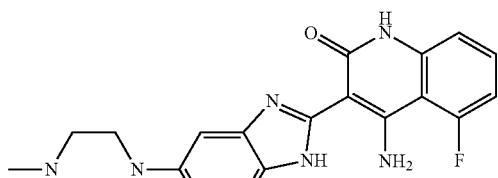
Dovitinib (TKI-258, CHIR-258)
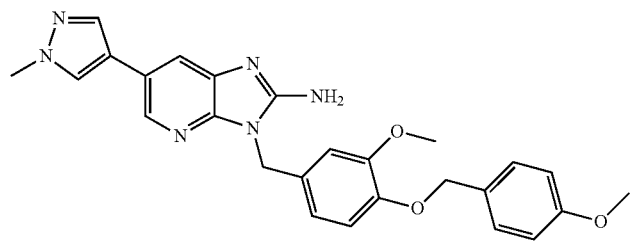
GZ389988
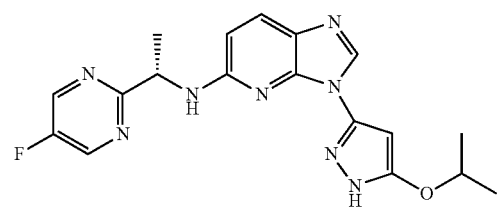
AZD7451
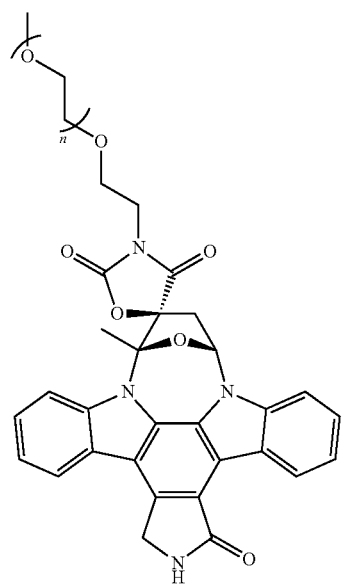
Pegcantratinib
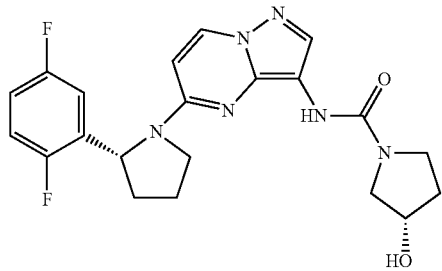
Larotrectinib (LOXO-101; ARRY-470)

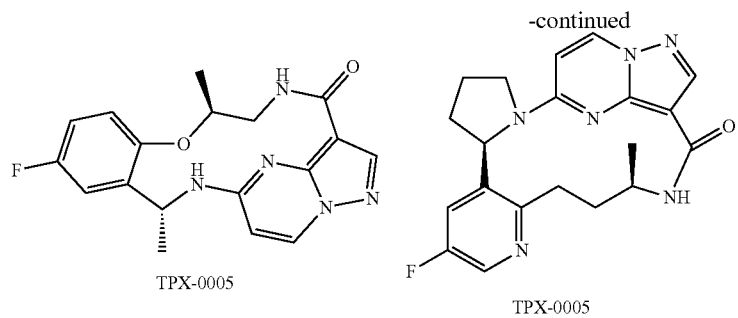
TPX-0005
TPX-0005
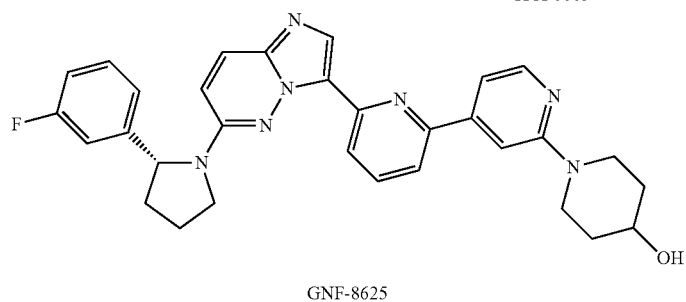
GNF-8625
In another embodiment, the TRK ligand is derived from the following TRK kinase inhibitors: DS-6051b, $F_{1775}2$, $PLX^{748}6$, AZD-6918, ASP7962, VM902A, $PF_{062}73340$, and $ONO_{447}4$.
In another embodiment, the TRK ligand is selected from the group consisting of:
FORMULA 4A
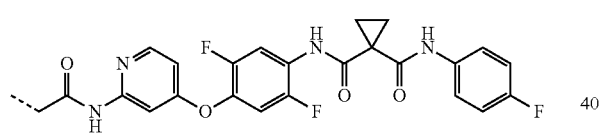
FORMULA 4B
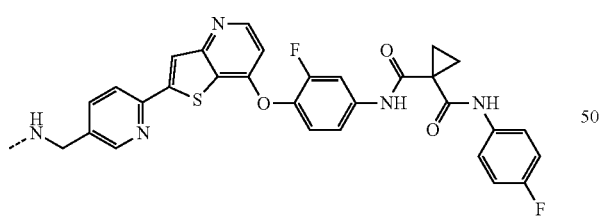
FORMULA 4C
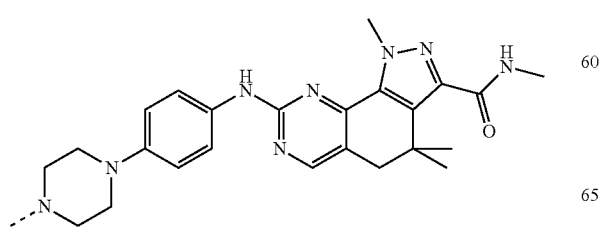
FORMULA 4D
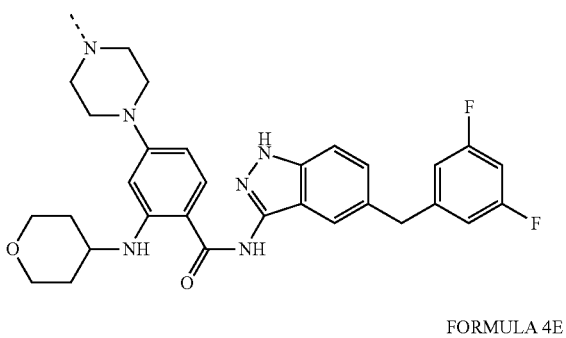
FORMULA 4E
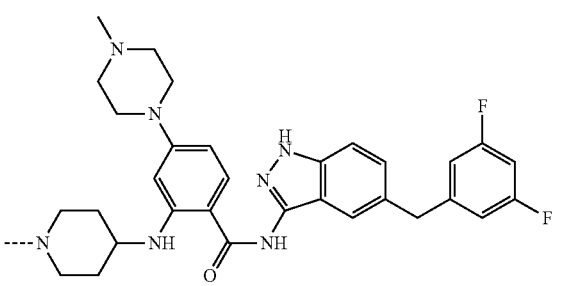
FORMULA 4F
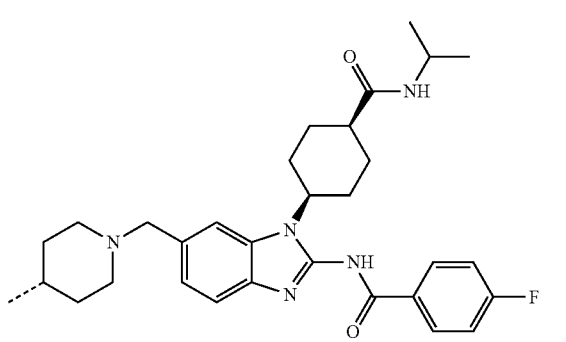

-continued

FORMULA 4G

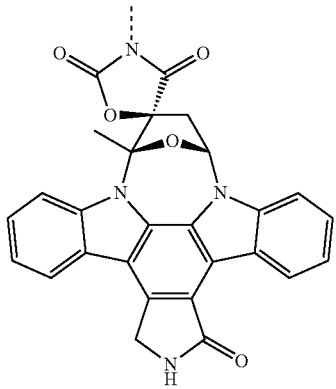

FORMULA 4H

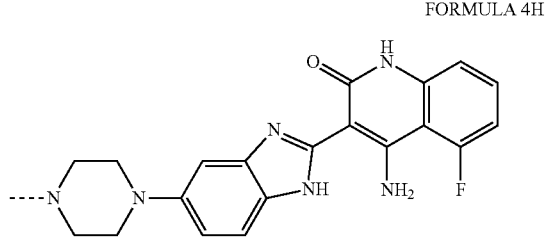

FORMULA 4I

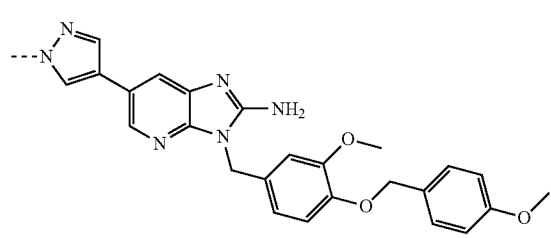

FORMULA 4J

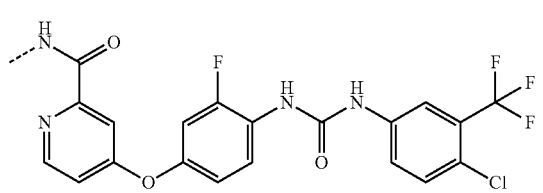

FORMULA 4K

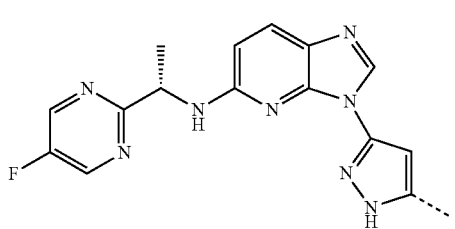

FORMULA 4L

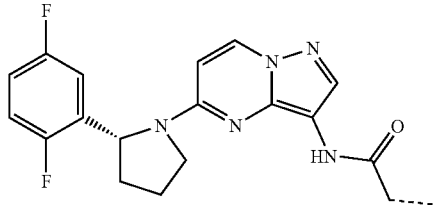

-continued

FORMULA 4M

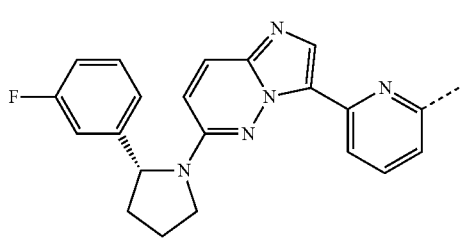

In some embodiments, the degradation tag is a moiety selected from the group consisting of FORMULAE 5A, 5B, 5C, and 5D:

FORMULA 5A

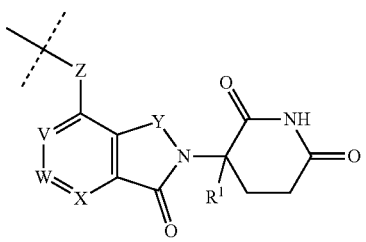

FORMULA 5B

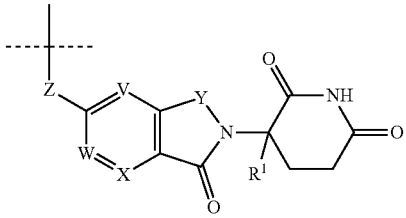

FORMULA 5C

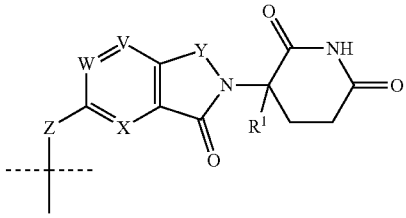

FORMULA 5D

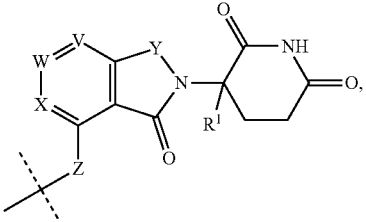

wherein
V, W, and X are independently selected from $CR^2$ and N;
Y is selected from CO, $CR^3R^4$, and N=N;
Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, $CH=CH$, $C\equiv C$, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

In some embodiments, the degradation tag is a moiety selected from the group consisting of FORMULAE 5A, 5B, 5C, and 5D:

FORMULA 5A

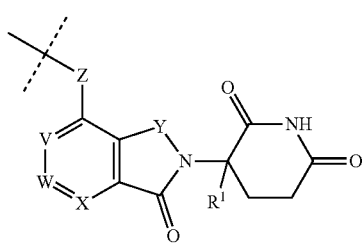

FORMULA 5B

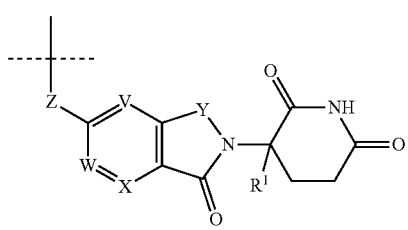

FORMULA 5C

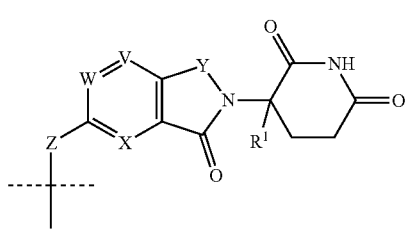

FORMULA 5D

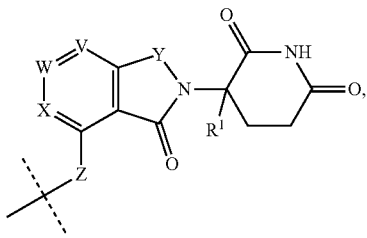

wherein

V, W, and X are independently selected from $CR^2$ and N;

Y is selected from CO and $CH_2$;

Z is selected from $CH_2$, NH and O;

$R^1$ is selected from hydrogen, $C_1$-$C_5$ alkyl and halogen; and $R^2$ is selected from hydrogen, halogen, and $C_1$-$C_5$ alkyl.

In some embodiments, the degradation tag is a moiety selected from the group consisting of FORMULAE 5E, 5F, 5G, 5H, and 5I:

FORMULA 5E

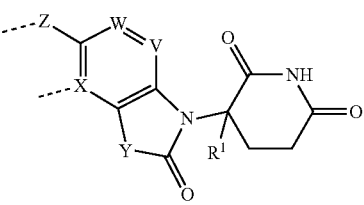

FORMULA 5F

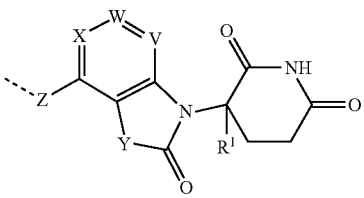

FORMULA 5G

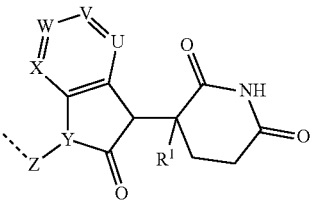

FORMULA 5H

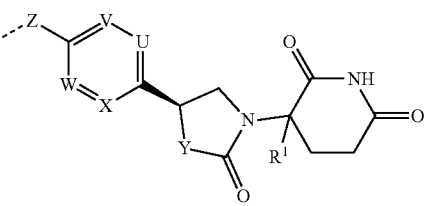

-continued

FORMULA 5I

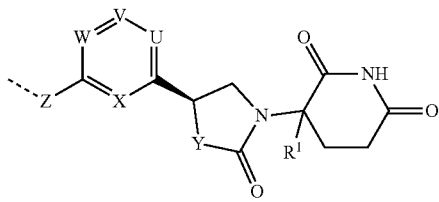

wherein
- U, V, W, and X are independently selected from $CR^2$ and N;
- Y is selected from $CR^3R^4$, Me and O; preferably, Y is selected from $CH_2$, NH, $NCH_3$ and O;
- Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH=CH, C≡C, NH and O;
- $R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;
- $R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and
- $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

In one embodiment, the degradation tag is a moiety of FORMULA 6A:

wherein
- $R^1$ and $R^2$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; and
- $R^3$ is hydrogen, optionally substituted $C(O)C_1$-$C_8$ alkyl, optionally substituted $C(O)C_1$-$C_8$alkoxy$C_1$-$C_8$alkyl, optionally substituted $C(O)C_1$-$C_8$ haloalkyl, optionally substituted $C(O)C_1$-$C_8$ hydroxyalkyl, optionally substituted $C(O)C_1$-$C_8$aminoalkyl, optionally substituted $C(O)C_1$-$C_8$alkylamino$C_1$-$C_8$alkyl, optionally substituted $C(O)C_3$-$C_7$cycloalkyl, optionally substituted C(O)(3-7 membered heterocyclyl), optionally substituted $C(O)C_2$-$C_8$ alkenyl, optionally substituted $C(O)C_2$-$C_8$ alkynyl, optionally substituted $C(O)OC_1$-$C_8$alkoxy$C_1$-$C_8$alkyl, optionally substituted $C(O)OC_1$-$C_8$ haloalkyl, optionally substituted $C(O)OC_1$-$C_8$ hydroxyalkyl, optionally substituted $C(O)OC_1$-$C_8$aminoalkyl, optionally substituted $C(O)OC_1$-$C_8$alkylamino$C_1$-$C_8$alkyl, optionally substituted $C(O)OC_3$-$C_7$ cycloalkyl, optionally substituted C(O)O(3-7 membered heterocyclyl), optionally substituted $C(O)OC_1$-$C_8$ alkenyl, optionally substituted $C(O)OC_1$-$C_8$ alkynyl, optionally substituted $C(O)NC_1$-$C_8$alkoxy$C_1$-$C_8$alkyl, optionally substituted $C(O)NC_1$-$C_8$ haloalkyl, optionally substituted $C(O)NC_1$-$C_8$ hydroxyalkyl, optionally substituted $C(O)NC_1$-$C_8$ aminoalkyl, optionally substituted $C(O)NC_1$-$C_8$alkylamino$C_1$-$C_8$alkyl, optionally substituted $C(O)NC_3$-$C_7$ cycloalkyl, optionally substituted C(O)N(3-7 membered heterocyclyl), optionally substituted $C(O)NC_2$-$C_8$ alkenyl, optionally substituted $C(O)NC_2$-$C_8$ alkynyl, optionally substituted $P(O)(OH)_2$, optionally substituted $P(O)(OC_1$-$C_8$alkyl$)_2$, and optionally substituted $P(O)(OC_1$-$C_8$ aryl$)_2$.

In one embodiment, the degradation tag is a moiety selected from the group consisting of FORMULAE 6B, 6C, 6D, 6E and 6F:

FORMULA 6B

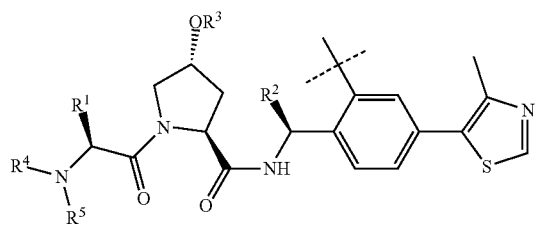

FORMULA 6A

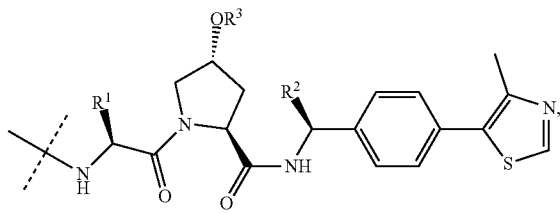

FORMULA 6C

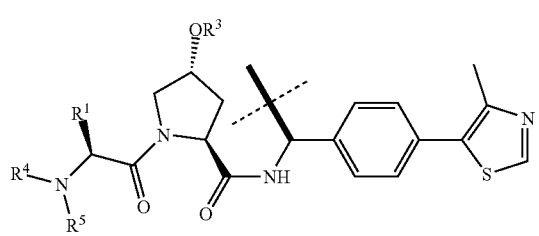

FORMULA 6D

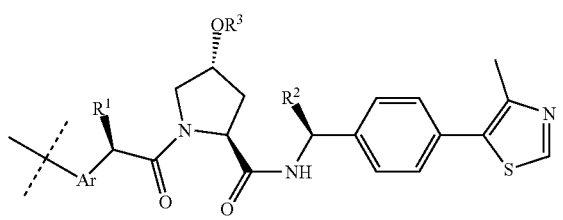

FORMULA 6E

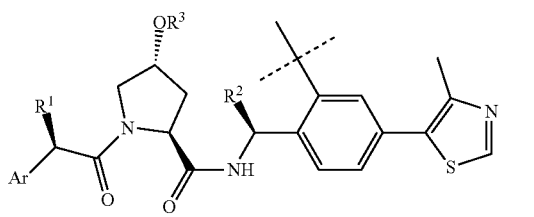

FORMULA 6F

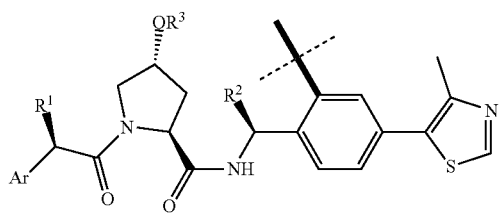

wherein
- $R^1$ and $R^2$ are independently selected from hydrogen, halogen, OH, $NH_2$, CN, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; (preferably, $R^1$ is selected from iso-propyl or tert-butyl; and $R^2$ is selected from hydrogen or methyl);
- $R^3$ is hydrogen, optionally substituted C(O)$C_1$-$C_8$ alkyl, optionally substituted C(O)$C_1$-$C_8$alkoxy$C_1$-$C_8$alkyl, optionally substituted C(O)$C_1$-$C_8$ haloalkyl, optionally substituted C(O)$C_1$-$C_8$ hydroxyalkyl, optionally substituted C(O)$C_1$-$C_8$ aminoalkyl, optionally substituted C(O)$C_1$-$C_8$alkylamino$C_1$-$C_8$alkyl, optionally substituted C(O)$C_3$-$C_7$ cycloalkyl, optionally substituted C(O)(3-7 membered heterocyclyl), optionally substituted C(O)$C_2$-$C_8$ alkenyl, optionally substituted C(O)$C_2$-$C_8$ alkynyl, optionally substituted C(O)O$C_1$-$C_8$alkoxy$C_1$-$C_8$alkyl, optionally substituted C(O)O$C_1$-$C_8$ haloalkyl, optionally substituted C(O)O$C_1$-$C_8$ hydroxyalkyl, optionally substituted C(O)O$C_1$-$C_8$aminoalkyl, optionally substituted C(O)O$C_1$-$C_8$alkylamino$C_1$-$C_8$alkyl, optionally substituted C(O)O$C_3$-$C_7$ cycloalkyl, optionally substituted C(O)O(3-7 membered heterocyclyl), optionally substituted C(O)O$C_1$-$C_8$ alkenyl, optionally substituted C(O)O$C_2$-$C_8$ alkynyl, optionally substituted C(O)N$C_1$-$C_8$alkoxy$C_1$-$C_8$alkyl, optionally substituted C(O)N$C_1$-$C_8$ haloalkyl, optionally substituted C(O)N$C_1$-$C_8$ hydroxyalkyl, optionally substituted C(O)N$C_1$-$C_8$ aminoalkyl, optionally substituted C(O)N$C_1$-$C_8$alkylamino$C_1$-$C_8$alkyl, optionally substituted C(O)N$C_3$-$C_7$ cycloalkyl, optionally substituted C(O)N(3-7 membered heterocyclyl), optionally substituted C(O)N$C_2$-$C_8$ alkenyl, optionally substituted C(O)N$C_2$-$C_8$ alkynyl, optionally substituted P(O)(OH)$_2$, optionally substituted P(O)(O$C_1$-$C_8$ alkyl)$_2$, and optionally substituted P(O)(O$C_1$-$C_8$ aryl)$_2$; and
- $R^4$ and $R^5$ are independently selected from hydrogen, COR$^6$, CO$_2$R$^6$, CONR$^6$R$^7$, SOR$^6$, SO$_2$R$^6$, SO$_2$NR$^6$R$^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl, wherein
- $R^6$ and $R^7$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl, or
- $R^4$ and $R^5$; $R^6$ and $R^7$ together with the atom to which they are connected form a 4-8 membered cycloalkyl or heterocyclyl ring;
- Ar is selected from aryl and heteroaryl, each of which is optionally substituted with one or more substituents independently selected from F, Cl, CN, NO$_2$, OR$^8$, NR$^8$R$^9$, COR$^8$, CO$_2$R$^8$, CONR$^8$R$^9$, SOR$^8$, SO$_2$R$^8$, SO$_2$NR$^9$R$^{10}$, NR$^9$COR$^{10}$, NR$^8$C(O)NR$^9$R$^{10}$, NR$^9$SOR$^{10}$, NR$^9$SO$_2$R$^{10}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl, wherein
- $R^8$, $R^9$, and $R^{10}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl, or
- $R^8$ and $R^9$; $R^9$ and $R^{10}$ together with the atom to which they are connected form a 4-8 membered cycloalkyl or heterocyclyl ring.

In another embodiment, the degradation tag is a moiety of FORMULA 7A:

FORMULA 7A

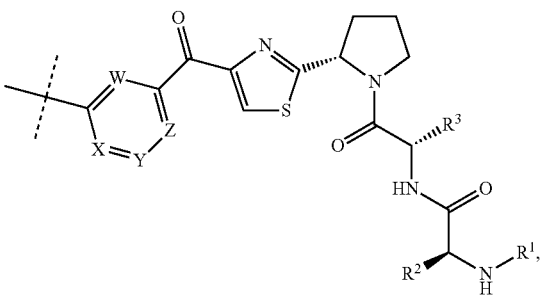

wherein
V, W, X, and Z are independently selected from $CR^4$ and N.

$R^1$, $R^2$, $R^3$, and $R^4$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl.

In another embodiment, the degradation tag is a moiety of FORMULA 7B:

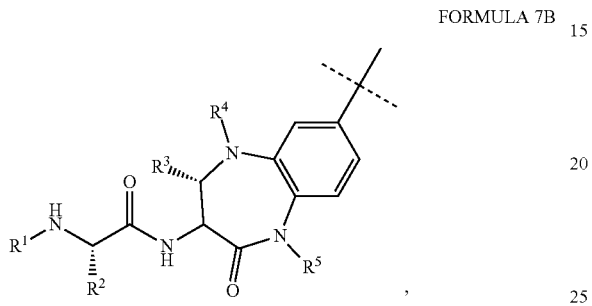

FORMULA 7B wherein
  $R^1$, $R^2$, and $R^3$ are independently selected from hydrogen, halogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl;
  $R^4$ and $R^5$ are independently selected from hydrogen, $COR^6$, $CO_2R^6$, $CONR^6R^7$, $SOR^6$, $SO_2R^6$, $SO_2NR^6R^7$, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted aryl-$C_1$-$C_8$alkyl, optionally substituted 3-8 membered cycloalkyl, optionally substituted 3-8 membered heterocyclyl, optionally substituted aryl, and optionally substituted heteroaryl, wherein
  $R^6$ and $R^7$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted 3-8 membered cycloalkyl, optionally substituted 3-8 membered heterocyclyl, optionally substituted aryl, and optionally substituted heteroaryl, or
  $R^6$ and $R^7$ together with the atom to which they are connected form a 4-8 membered cycloalkyl or heterocyclyl ring.

In another embodiment, the degradation tag is derived from any of the following:

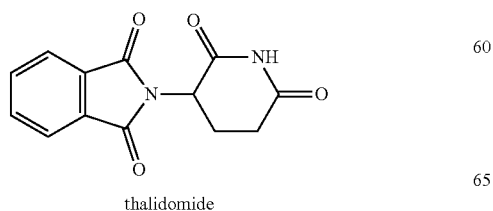

thalidomide

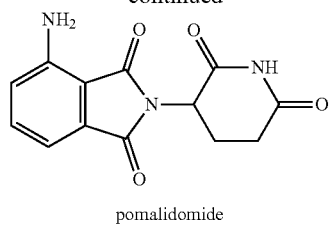

pomalidomide

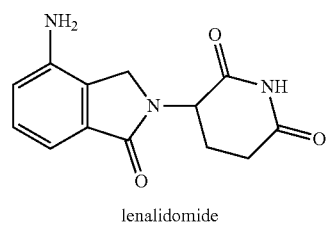

lenalidomide

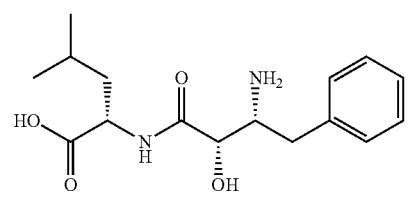

bestatin

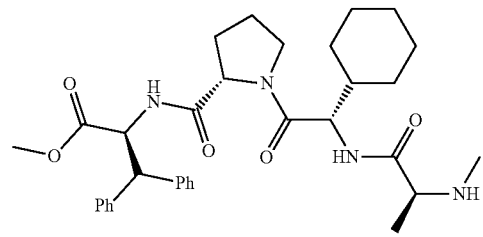

MV1

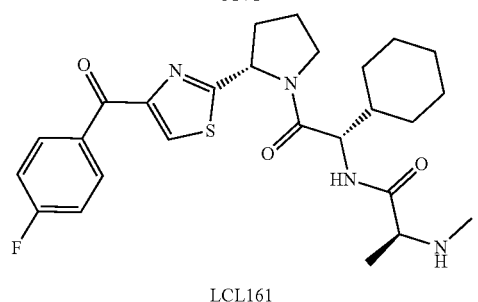

LCL161

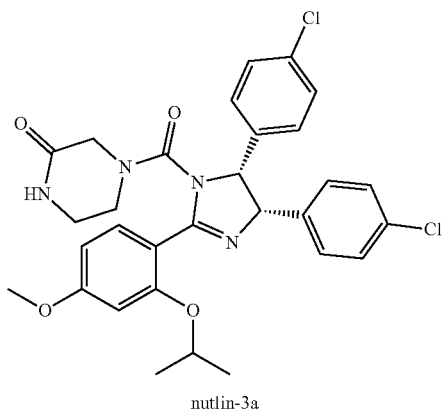

nutlin-3a

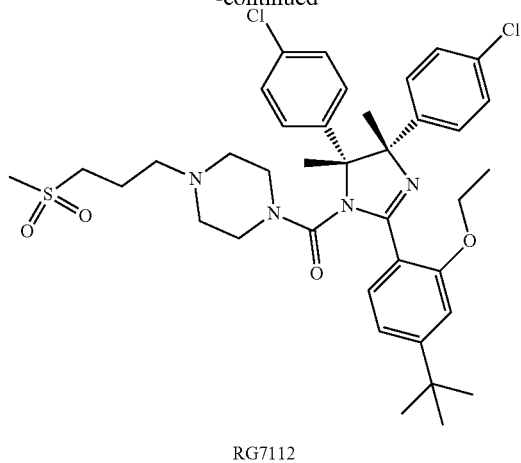
RG7112
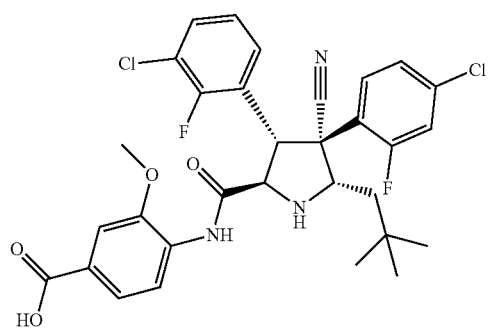
RG7338
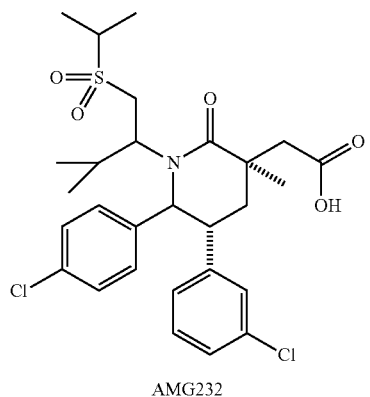
AMG232
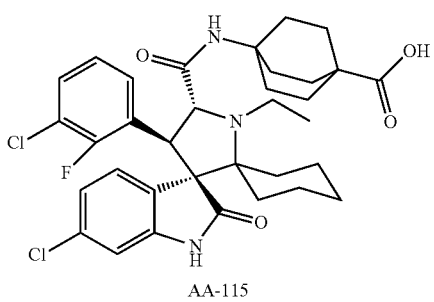
AA-115
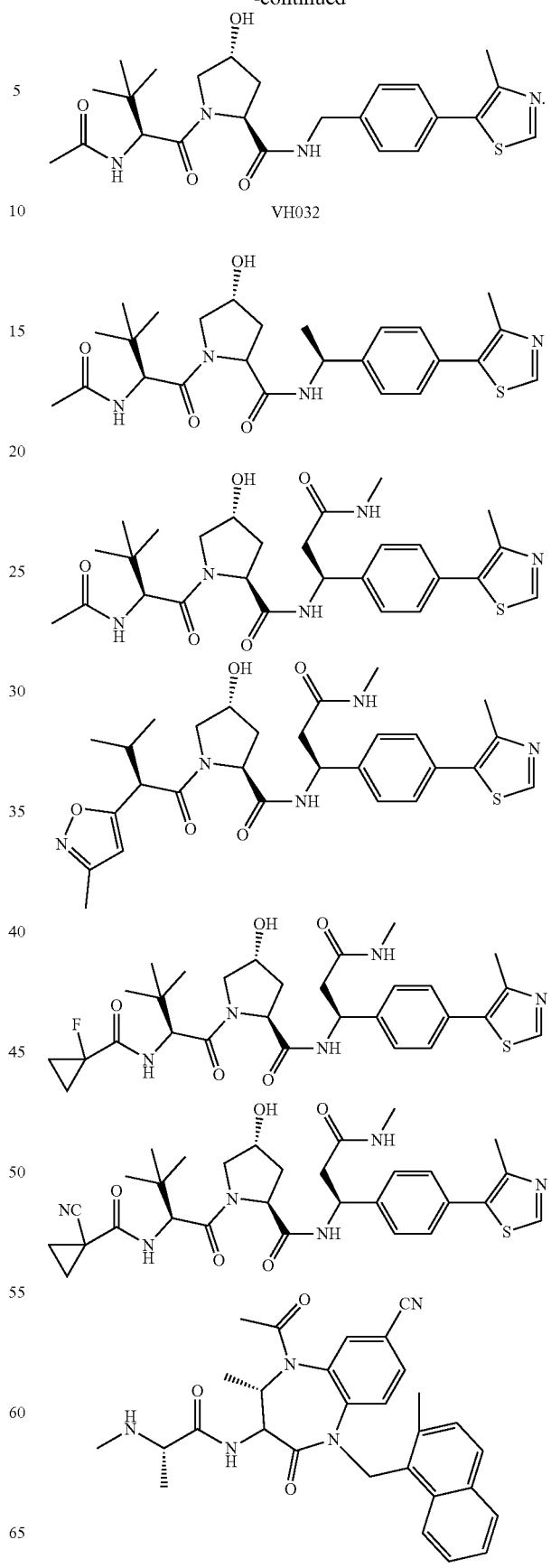
VH032

-continued
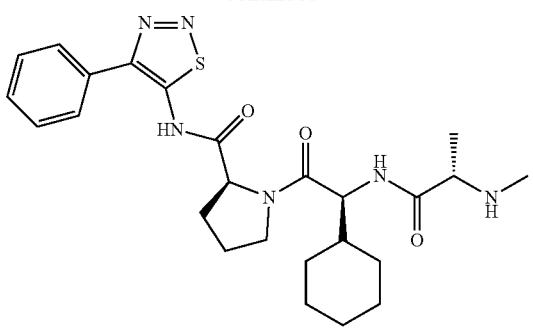
GDC-0152
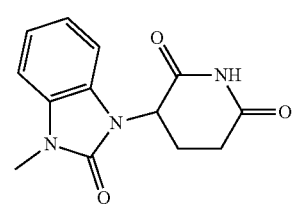
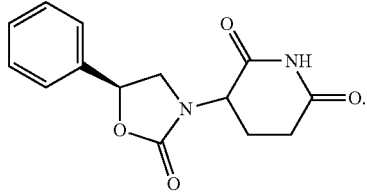
In another embodiment, the degradation tag is selected from the group consisting of:
FORMULA 8A
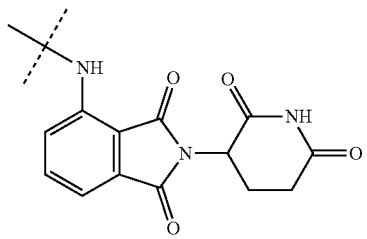
FORMULA 8B
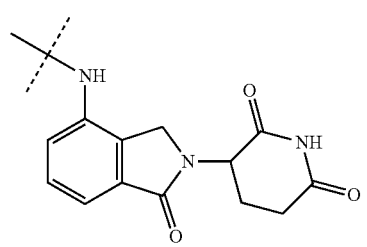
FORMULA 8C
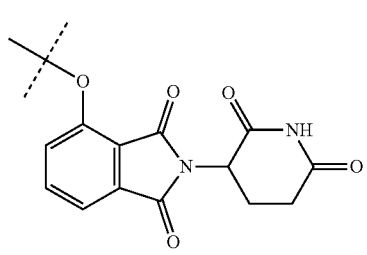
FORMULA 8D
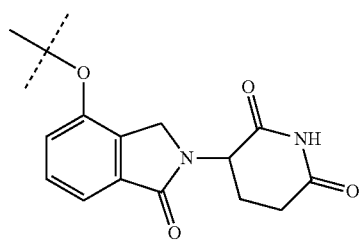
FORMULA 8E
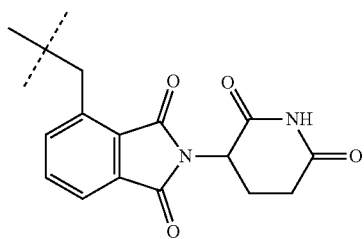
FORMULA 8F
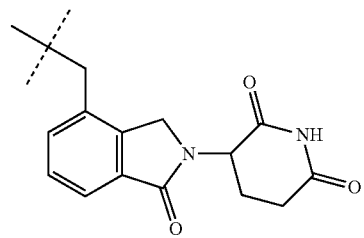
FORMULA 8G
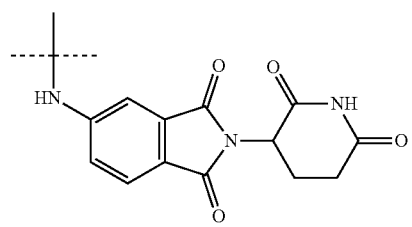
FORMULA 8H
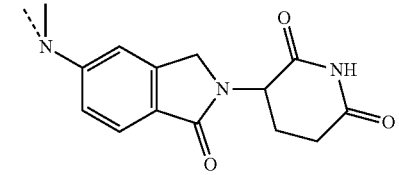
FORMULA 8I
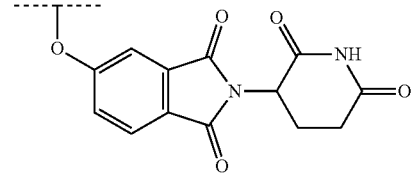
FORMULA 8J
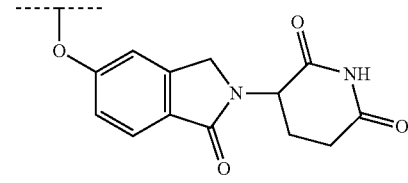

FORMULA 8K
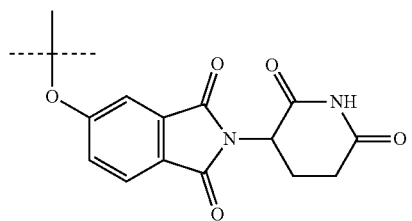
FORMULA 8R
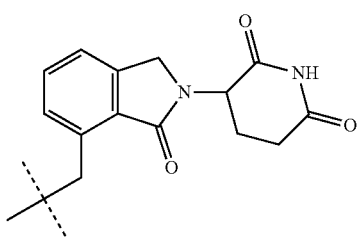
FORMULA 8L
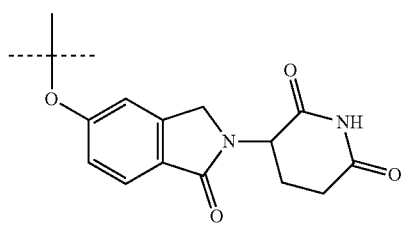
FORMULA 8S
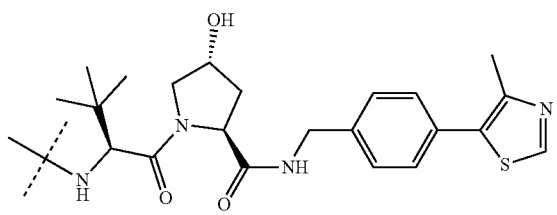
FORMULA 8M
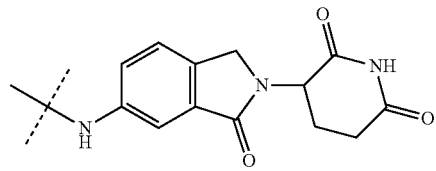
FORMULA 8T
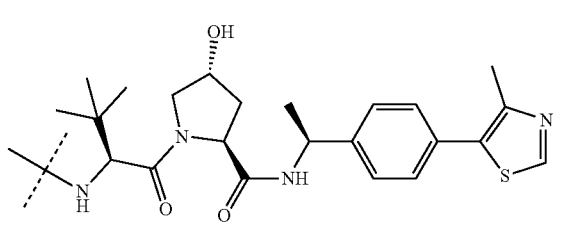
FORMULA 8N
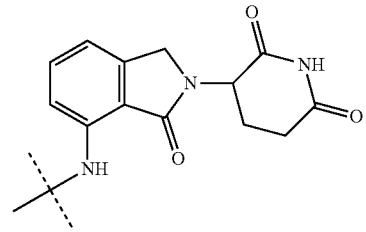
FORMULA 8U
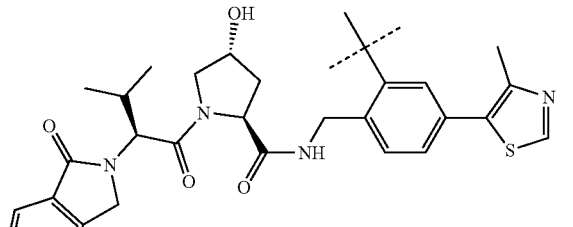
FORMULA 8O
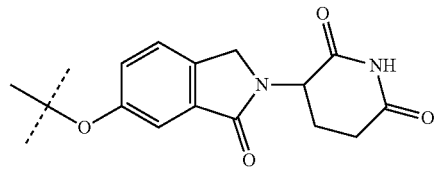
FORMULA 8V
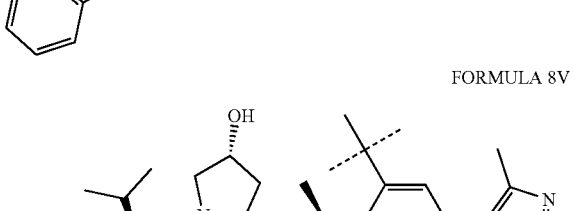
FORMULA 8P
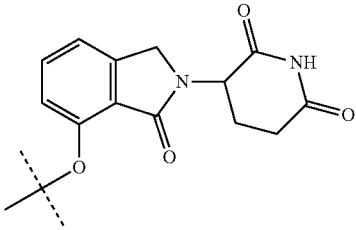
FORMULA 8W
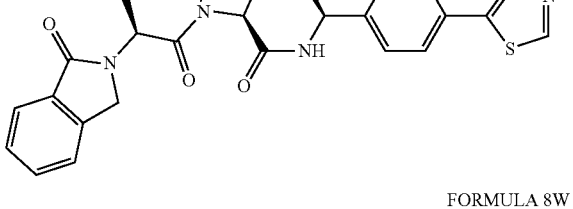
FORMULA 8Q
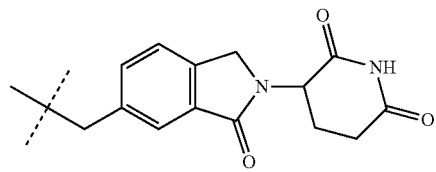
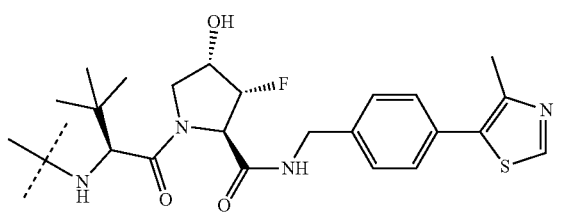

FORMULA 8X
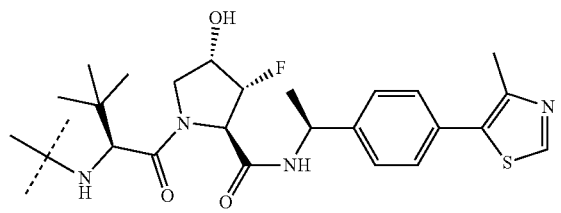
FORMULA 8Y
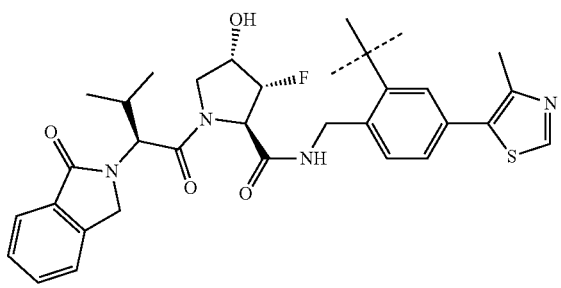
FORMULA 8Z
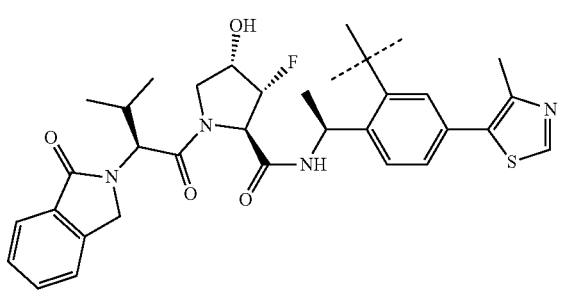
FORMULA 8AA
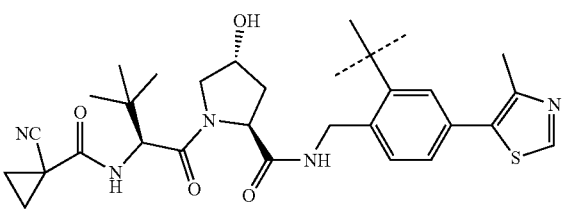
FORMULA 8AB
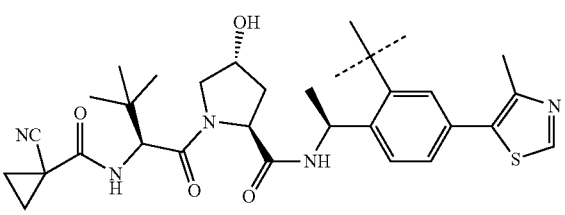
FORMULA 8AC
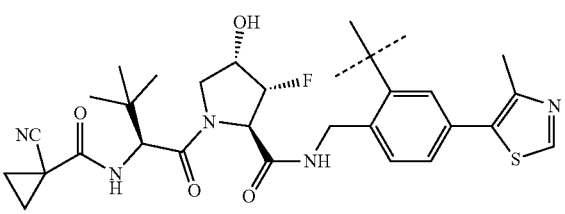
FORMUAL 8AD
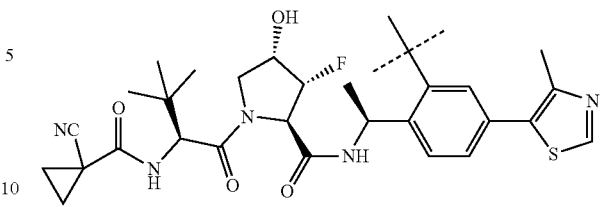
FORMULA 8AE
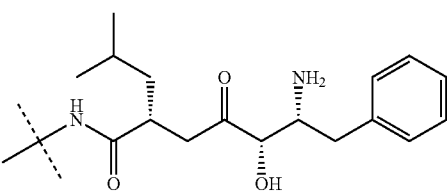
FORMULA 8AF
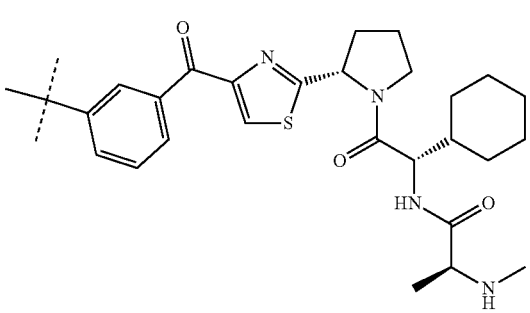
FORMULA 8AG
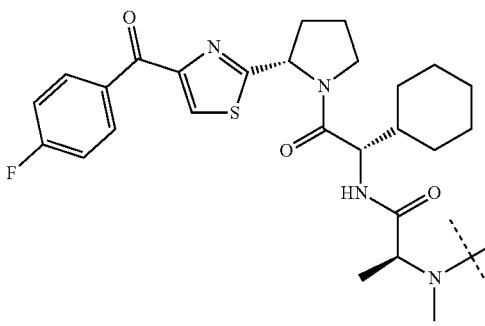
FORMULA 8AH
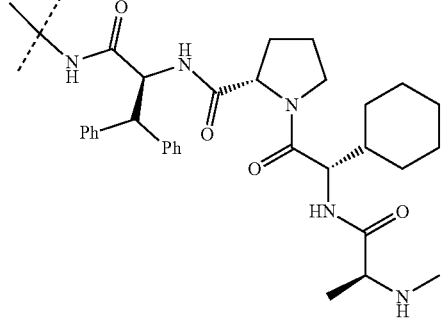

FORMULA 8AI
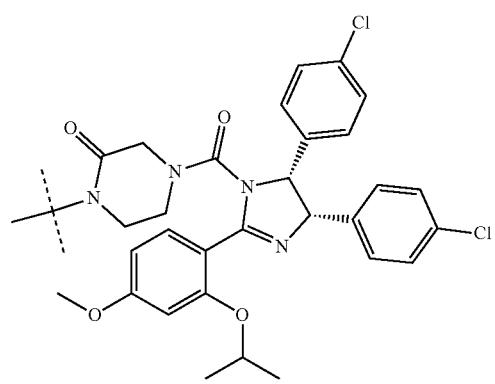
FORMULA 8AJ
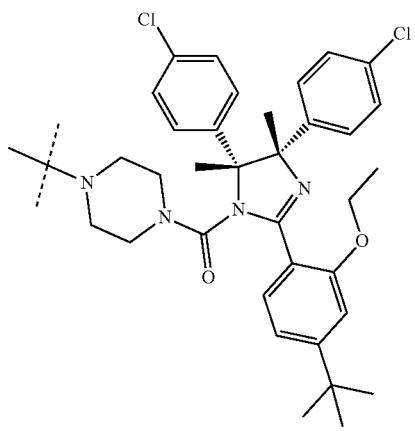
FORMULA 8AK
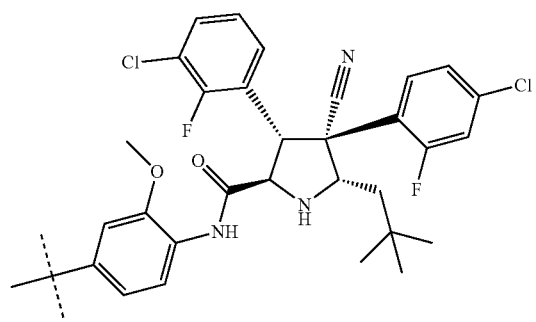
FORMULA 8AL
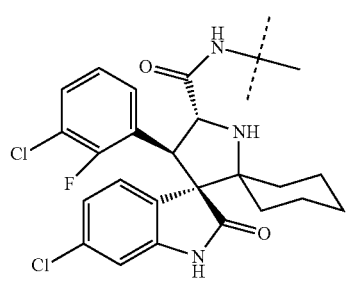
FORMULA 8AM
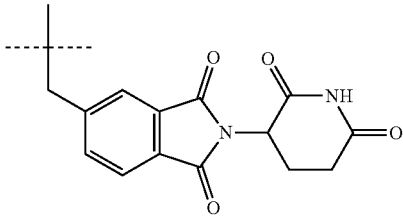
FORMULA 8AN
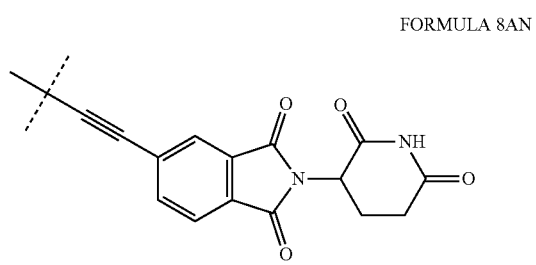
FORMULA 8AO
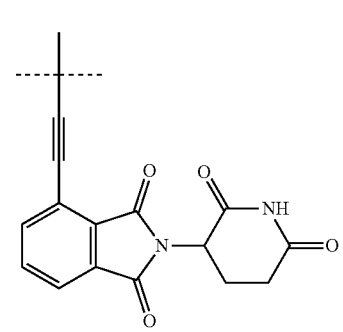
FORMULA 8AP
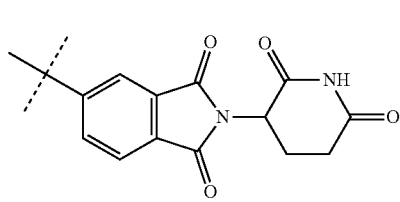
FORMULA 8AQ
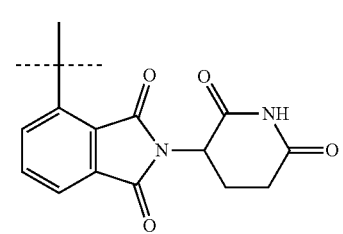
FORMULA 8AR
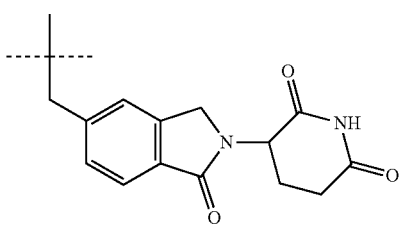

FORMULA 8AS
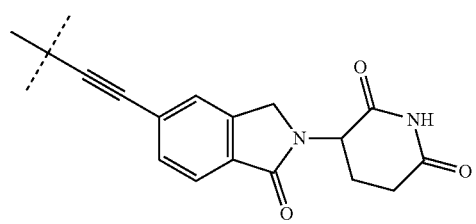
FORMULA 8AT
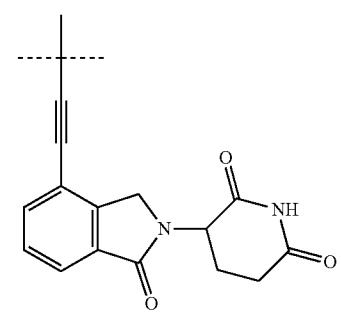
FORMULA 8AU
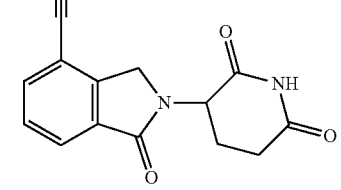
FORMULA 8AV
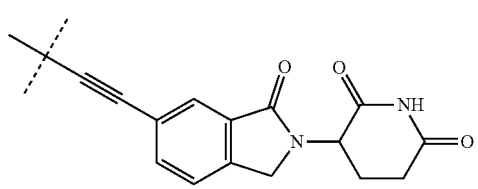
FORMULA 8AW
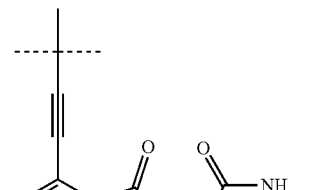
FORMULA 8AX
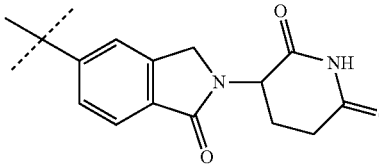
FORMULA 8AY
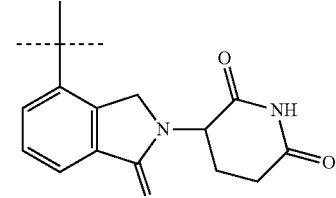
FORMULA 8AZ
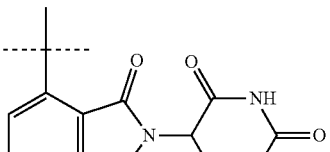
FORMULA 8BA
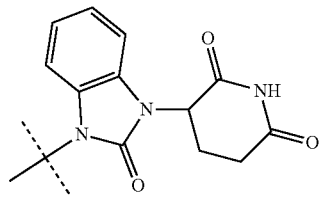
FORMULA 8BB
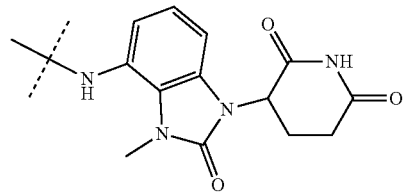
FORMULA 8BC
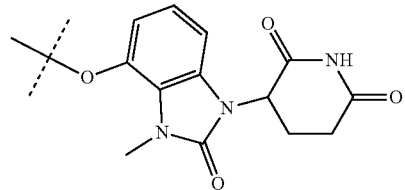
FORMULA 8BD
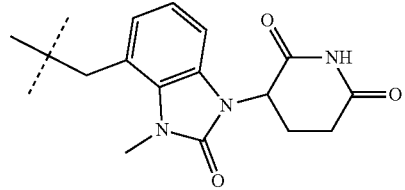
FORMULA 8BE
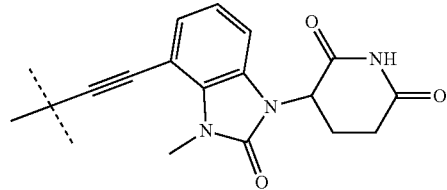
FORMULA 8BF
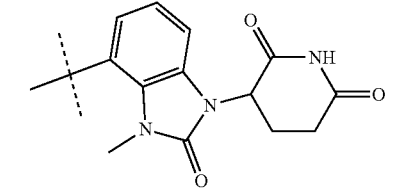

FORMULA 8BG
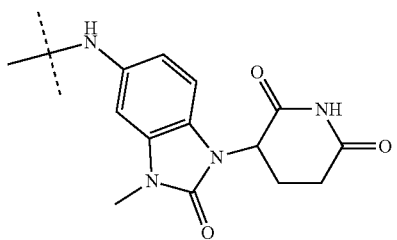
FORMULA 8BM
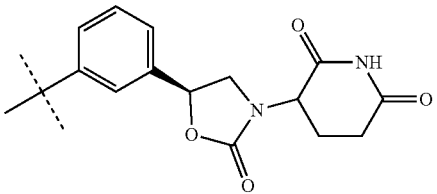
FORMULA 8BH
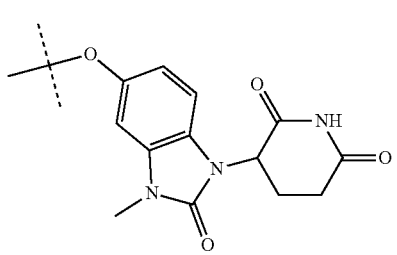
FORMULA 8BN
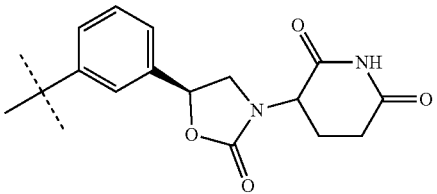
FORMULA 8BI
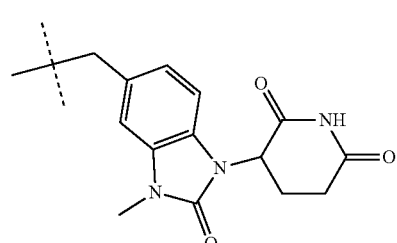
FORMULA 8BO
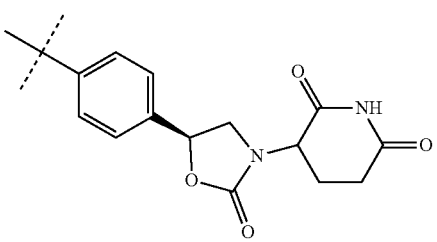
FORMULA 8BJ
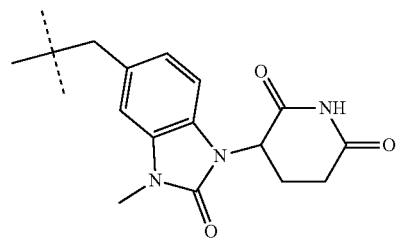
FORMULA 8BP
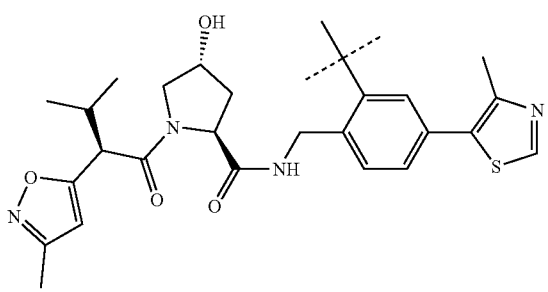
FORMULA 8BK
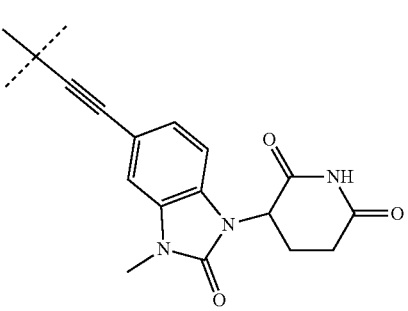
FORMULA 8BQ
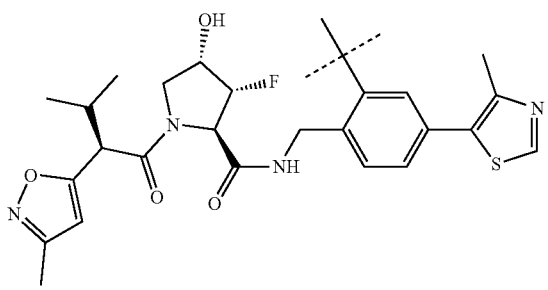
FORMULA 8BL
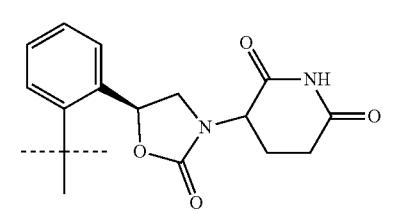

FORMULA 8BR
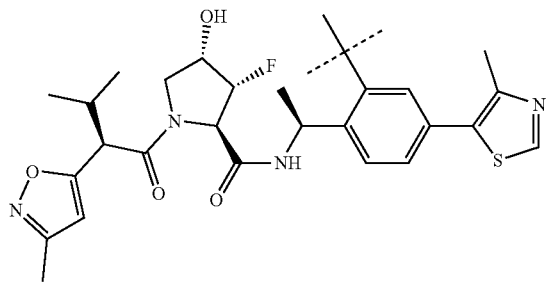

FORMULA 8BS

FORMULA 8BT

FORMULA 8BU

FORMULA 8BV

FORMULA 8BW
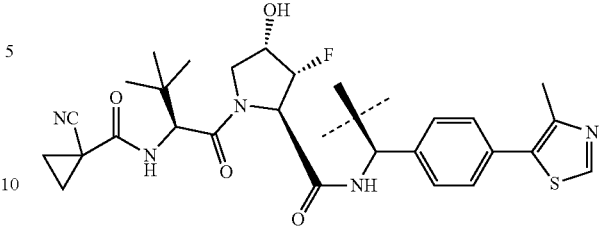

FORMULA 8BX

FORMULA 8BY
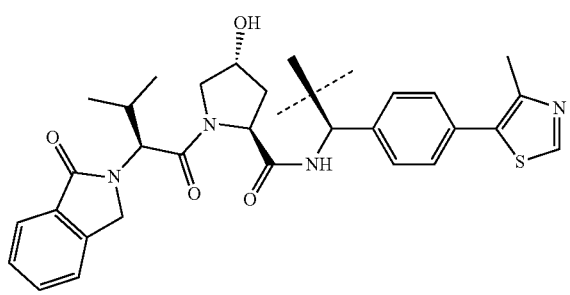

In some embodiments, the linker moiety is of FORMULA 9:

FORMULA 9

wherein
A, W and B, at each occurrence, are independently selected from null, or bivalent moiety selected from R'—R", R'COR", R'CO₂R", R'C(O)N(R¹)R", R'C(S)N(R¹)R", R'OR", R'OC(O)R", R'OC(O)OR", R'OCON(R¹)R", R'SR", R'SOR", R'SO₂R", R'SO₂N(R¹)R", R'N(R¹)R", R'NR¹COR", R'NR¹C(O)OR", R'NR¹CON(R²)R", R'NR¹C(S)R", R'NR¹S(O)R", R'NR¹S(O)₂R", and R'NR¹S(O)₂N(R²)R", wherein
R' and R" are independently selected from null, optionally substituted R''—(C₁-C₈ alkyl), or a moiety comprising of optionally substituted C₁-C₈ alkyl, optionally substituted C₂-C₈ alkenyl, optionally substituted C₂-C₈ alkynyl, optionally substituted C₁-C₈ hydroxyalkyl, optionally substituted C₁-C₈alkoxyC₁-C₈alkyl, optionally substituted C₁-C₈alkylaminoC₁-C₈alkyl, optionally substituted C₁-C₈ haloalkyl, optionally substituted C₁-C₈ alkylene, optionally substituted C₂-C₈ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^1$ and $R^2$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^1$ and $R^2$, R' and $R^1$, R' and $R^2$, R" and $R^1$, R" and $R^2$ together with the atom to which they are connected form a 3-20 membered cycloalkyl or 4-20 membered heterocyclyl ring; and m is 0 to 15.

In one embodiment, the linker moiety is of FORMULA 9:

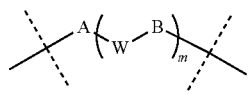

FORMULA 9 wherein

A, W, and B, at each occurrence, are independently selected from null, CO, $CO_2$, $C(O)NR^1$, $C(S)NR^1$, O, S, SO, $SO_2$, $SO_2NR^1$, $NR^1$, $NR^1CO$, $NR^1CONR^2$, $NR^1C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl, wherein $R^1$ and $R^2$ are independently selected from hydrogen, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl; and m is 0 to 15.

In one embodiment, the linker moiety is of FORMULA 9A:

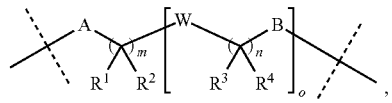

FORMULA 9A wherein $R^1$, $R^2$, $R^3$ and $R^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-8 membered heterocyclyl, optionally substituted aryl, and optionally substituted heteroaryl, or $R^1$ and $R^2$, $R^3$ and $R^4$ together with the atom to which are connected form a 3-20 membered cycloalkyl or 4-20 membered heterocyclyl ring;

A, W and B, at each occurrence, are independently selected from null, or bivalent moiety selected from R'—R", R'COR", $R'CO_2R"$, $R'C(O)N(R^5)R"$, $R'C(S)N(R^5)R"$, R'OR", R'OC(O)R", R'OC(O)OR", $R'OCONR^5R"$, R'SR", R'SOR", $R'SO_2R"$, $R'SO_2N(R^5)R"$, $R'N(R^5)R"$, $R'NR^5COR"$, $R'NR^5C(O)OR"$, $R'NR^5CON(R^6)R"$, $R'NR^5C(S)R"$, $R'NR^5S(O)R"$, $R'NR^5S(O)_2R"$, and $R'NR^5S(O)_2N(R^6)R"$, wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^5$ and $R^6$, R' and $R^5$, R' and $R^6$, R" and $R^5$, R" and $R^6$ together with the atom to which they are connected form a 3-20 membered cycloalkyl or 4-20 membered heterocyclyl ring;

m is 0 to 15;
n, at each occurrence, is 0 to 15; and
o is 0 to 15.

In one embodiment, the linker moiety is of FORMULA 9A,

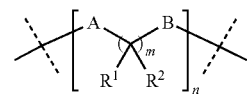

FORMULA 9A wherein
$R^1$, $R^2$, $R^3$, and $R^4$, at each occurrence, are independently selected from hydrogen, halogen, CN, OH, $NH_2$, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl;

A, W, and B, at each occurrence, are independently selected from null, CO, $CO_2$, C(O)$NR^5$, C(S)$NR^5$, O, S, SO, $SO_2$, $SO_2NR^5$, $NR^5$, $NR^5$CO, $NR^5CONR^6$, $NR^5$C(S), optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl, wherein $R^5$ and $R^6$ are independently selected from hydrogen, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl;

m is 0 to 15;
each n is 0 to 15; and
o is 0 to 15.

In another embodiment, the linker moiety is of FORMULA 9B:

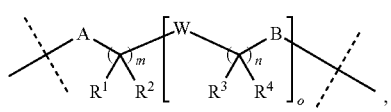

FORMULA 9B wherein
$R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'—R", R'COR", R'CO$_2$R", R'C(O)NR$^3$R", R'C(S)NR$^3$R", R'OR", R'OC(O)R", R'OC(O)OR", R'OCON(R$^3$)R", R'SR", R'SOR", R'SO$_2$R", R'SO$_2$N(R$^3$)R", R'N(R$^3$)R", R'NR$^3$COR", R'NR$^3$C(O)OR", R'NR$^3$CON(R$^4$)R", R'NR$^3$C(S)R", R'NR$^3$S(O)R", R'NR$^3$S(O)$_2$R", and R'NR$^3$S(O)$_2$N(R$^4$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^3$ and $R^4$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R" and $R^3$, R" and $R^4$ together with the atom to which they are connected form a 3-20 membered cycloalkyl or 4-20 membered heterocyclyl ring;

each m is 0 to 15; and n is 0 to 15.

In another embodiment, the linker moiety is of FORMULA 9B,

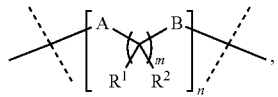

FORMULA 9B wherein, each $R^1$, and each $R^2$ are independently selected from hydrogen, halogen, CN, OH, NH$_2$, and optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, or $C_1$-$C_6$alkylamino$C_1$-$C_6$alkyl;

each A and each B are independently selected from null, CO, CO$_2$, C(O)NR$^3$, C(S)NR$^3$, O, S, SO, SO$_2$, SO$_2$NR$^3$, NR$^3$, NR$^3$CO, NR$^3$CONR$^4$, NR$^3$C(S), and optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, or $C_3$-$C_{13}$ spiro heterocyclyl, wherein $R^3$ and $R^4$ are independently selected from hydrogen, and optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, or $C_1$-$C_6$alkylamino$C_1$-$C_6$alkyl;

each m is 0 to 15; and n is 0 to 15.

In another embodiment, in FORMULA 9B, m is 1 to 15.

In another embodiment, in FORMULA 9B, n is 1.

In another embodiment, in FORMULA 9B, $R^1$ and $R^2$ are independently selected from hydrogen, and optionally substituted $C_1$-$C_8$ alkyl.

In another embodiment, the linker moiety is of FORMULA 9C:

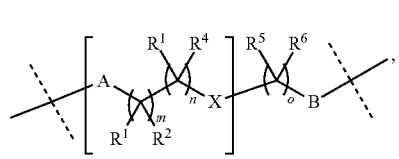

FORMULA 9C wherein

X is selected from O, NH, and NR$^7$;

$R^1$, $R^2$, $R^3$, $R^4$, $R^5$, and $R^6$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", R'CO$_2$R", R'C(O)N(R$^8$)R", R'C(S)N(R$^8$)R", R'OC(O)R", R'OC(O)OR", R'OCON(R$^8$)R", R'SR", R'SOR", R'SO$_2$R", R'SO$_2$N(R$^8$)R", R'N(R$^8$)R", R'NR$^8$COR", R'NR$^8$C(O)OR", R'NR$^8$CON(R$^9$)R", R'NR$^8$C(S)R", R'NR$^8$S(O)R", R'NR$^8$S(O)$_2$R", and R'NR$^8$S(O)$_2$N(R$^9$)R", wherein R' and R" are independently selected from null, optionally substituted R$^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^7$, $R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

$R'$ and $R''$, $R^8$ and $R^9$, $R'$ and $R^8$, $R'$ and $R^9$, $R''$ and $R^8$, $R''$ and $R^9$ together with the atom to which they are connected form a 3-20 membered cycloalkyl or 4-20 membered heterocyclyl ring;

m, at each occurrence, is 0 to 15;

n, at each occurrence, is 0 to 15;

o is 0 to 15; and p is 0 to 15.

In another embodiment, the linker moiety is of FORMULA 9C,

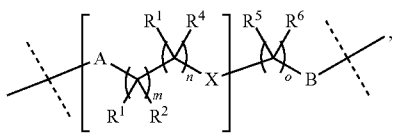

FORMULA 9C

Wherein,

X is selected from O, NH, and $NR^7$;

$R^1$, $R^2$, $R^3$, $R^4$, $R^5$, and $R^6$, at each occurrence, are independently selected from hydrogen, halogen, CN, OH, $NH_2$, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl;

A and B, at each occurrence, are independently selected from null, CO, $CO_2$, C(O)NR, C(S)NR, O, S, SO, $SO_2$, $SO_2NR^7$, $NR^7$, $NR^7CO$, $NR^7CONR^8$, $NR^7C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ Spiro cycloalkyl, and optionally substituted $C_3$-$C_{13}$ Spiro heterocyclyl, wherein $R^7$ and $R^8$ are independently selected from hydrogen, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl;

each m is 0 to 15;

each n is 0 to 15;

o is 0 to 15; and p is 0 to 15.

In one embodiment, in FORMULA 9C, m and n is 1, and p is 1 to 15;

In one embodiment, in FORMULA 9C, X is selected from O and NH;

In one embodiment, in FORMULA 9C, $R^1$, $R^2$, $R^3$, $R^4$, $R^5$, and $R^6$, are independently selected from hydrogen, optionally substituted $C_1$-$C_6$ alkyl.

In another embodiment, the linker moiety comprises a ring selected from the group consisting of a 3 to 13 membered ring, a 3 to 13 membered fused ring, a 3 to 13 membered bridged ring, and a 3 to 13 membered spiro ring.

In another embodiment, the linker moiety comprises a ring selected from the group consisting of Formula C1, C2, C3, C4 and C5:

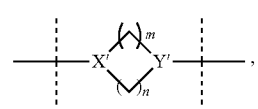

Formula C1

$X' = $ N or CH
$Y' = $ N or CH
m = 0-5
n = 0-5

Formula C2

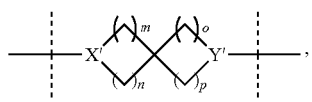

X' = N or CH
Y' = N or CH
m = 0-5
n = 0-5
o = 0-5
p = 0-5

Formula C3

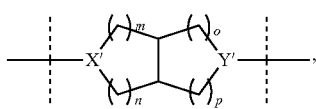

X' = N or CH
Y' = N or CH
m = 0-5
n = 0-5
o = 0-5
p = 0-5

Formula C4

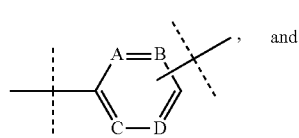

A = CH, C($C_{1-3}$ alkyl), or N
B = CH, C($C_{1-3}$ alkyl), or N
C = CH, C($C_{1-3}$ alkyl), or N
D = CH, C($C_{1-3}$ alkyl), or N Formula C5

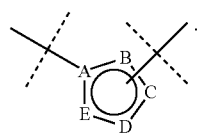

A = C, CH, C($C_{1-3}$ alkyl), N, NH, N($C_{1-3}$ alkyl), O, S
B = C, CH, C($C_{1-3}$ alkyl), N, NH, N($C_{1-3}$ alkyl), O, S
C = C, CH, C($C_{1-3}$ alkyl), N, NH, N($C_{1-3}$ alkyl), O, S
D = C, CH, C($C_{1-3}$ alkyl), N, NH, N($C_{1-3}$ alkyl), O, S
E = C, CH, C(C1-3 alkyl), N, NH, N(C1-3 alkyl), O, S In one embodiment, A, B and W, at each occurrence, are independently selected from null, CO, NH, NH—CO, CO—NH, $CH_2$—NH—CO, $CH_2$—CO—NH, NH—CO—$CH_2$, CO—NH—$CH_2$, $CH_2$—NH—$CH_2$—CO—NH, $CH_2$—NH—$CH_2$—NH—CO, NH—CO—$CH_2$—NH—$CH_2$, CO—NH—$CH_2$—NH—$CH_2$, $CH_2$—NH—$CH_2$, $R_r$—CO, $R_r$—NH, $R_r$—NH—CO, $R_r$—CO—NH, $R_r$—$CH_2$—NH—CO, $R_r$—$CH_2$—CO—NH, $R_r$—NH—CO—$CH_2$, $R_r$—CO—NH—$CH_2$, $R_r$—$CH_2$—NH—$CH_2$—CO—NH, $R_r$—$CH_2$—NH—$CH_2$—NH—CO, $R_r$—NH—CO—$CH_2$—NH—$CH_2$, $R_r$, CO—NH—$CH_2$—NH—$CH_2$, $R_r$—$CH_2$—NH—$CH_2$.

In one embodiment, R$^r$ is of Formula C1, C2, C3, C4 or C5.

In one embodiment, R$^r$ is selected from

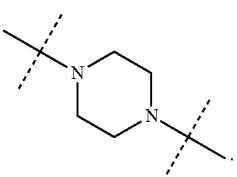

In another embodiment, the length of the linker is 0 to 40 linear atoms.

In another embodiment, the length of the linker is 0 to 20 linear atoms.

In another embodiment, the length of the linker is 0 to 8 linear atoms.

In another embodiment, the linker is selected from —(CO)—$(CH_2)_{1-8}$—, —$(CH_2)_{1-9}$—, —$(CH_2)_{1-2}$—(CO)—NH—$(CH_2)_{2-9}$—, —$(CH_2)_{1-2}$—(CO)—NH—$(CH_2)_{1-3}$—$(OCH_2CH_2)_{1-7}$—, —$(CH_2)_{0-1}$—(CO)—$(CH_2)_{1-3}$—$(OCH_2CH_2)_{1-7}$—, —(CO)—$(CH_2)_{0-3}$-(alkenylene)-$(CH_2)_{0-3}$—, —(CO)—$(CH_2)_{0-3}$-(alkynylene)-$(CH_2)_{0-3}$—, —(CO)—$(CH_2)_{0-3}$-(3-8 membered carbocyclyl)-$(CH_2)_{0-3}$—, —(CO)—$(CH_2)_{0-3}$-(3-8 membered heterocarbocyclyl)-$(CH_2)_{0-3}$—, —$(CH_2)_{0-3}$-(alkenylene)-$(CH_2)_{0-3}$—, —$(CH_2)_{0-3}$-(alkynylene)-$(CH_2)_{0-3}$—, —$(CH_2)_{0-3}$-(3-8 membered carbocyclyl)-$(CH_2)_{0-3}$—, and —$(CH_2)_{0-3}$-(3-8 membered heterocarbocyclyl)-$(CH_2)_{0-3}$—;
$R^r$—(CO)—$(CH_2)_{1-8}$—, $R^r$—$(CH_2)_{1-9}$—, $R^r$—$(CH_2)_{1-2}$—(CO)—NH—$(CH_2)_{2-9}$—, $R^r$—$(CH_2)_{1-2}$—(CO)—NH—$(CH_2)_{1-3}$—$(OCH_2CH_2)_{1-7}$—, $R^r$—$(CH_2)_{0-1}$—(CO)—$(CH_2)_{1-3}$—$(OCH_2CH_2)_{1-7}$—, $R^r$—(CO)—$(CH_2)_{0-3}$-(alkenylene)-$(CH_2)_{0-3}$—, $R^r$—(CO)—$(CH_2)_{0-3}$-(alkynylene)-$(CH_2)_{0-3}$—, $R^r$—(CO)—$(CH_2)_{0-3}$-(3-8 membered carbocyclyl)-$(CH_2)_{0-3}$—, $R^r$—(CO)—$(CH_2)_{0-3}$-(3-8 membered heterocarbocyclyl)-$(CH_2)_{0-3}$—, $R^r$—$(CH_2)_{0-3}$-(alkenylene)-$(CH_2)_{0-3}$—, $R^r$—$(CH_2)_{0-3}$-(alkynylene)-$(CH_2)_{0-3}$—, $R^r$—$(CH_2)_{0-3}$-(3-8 membered carbocyclyl)-$(CH_2)_{0-3}$—, and $R^r$—$(CH_2)_{0-3}$-(3-8 membered heterocarbocyclyl)-$(CH_2)_{0-3}$—.

In some embodiments, the bivalent compound is selected from the group consisting of CPD-001 to CPD-206, or a pharmaceutically acceptable salt or analog thereof.

In some embodiments, the bivalent compound is selected from the group consisting of CPD-009, CPD-010, CPD-013, CPD-014, CPD-015, CPD-021, CPD-022, CPD-023, CPD-024, CPD-025, CPD-026, CPD-027, CPD-028, CPD-029, CPD-030, CPD-031, CPD-032, CPD-033, CPD-044, CPD-047, CPD-049, CPD-050, CPD-051, CPD-052, CPD-053, CPD-054, CPD-055, CPD-056, CPD-057, CPD-059, CPD-060, CPD-062, CPD-064, CPD-065, and a pharmaceutically acceptable salt or analog thereof.

In some embodiments, the bivalent compound is selected from the group consisting of TR-104, TR-105, TR-106, TR-107, TR-108, TR-109, TR-113, TR-115, TR-116, TR-117, TR-118, TR-119, TR-120, TR-121, TR-122, TR-123, TR-124, TR-125, TR-127, TR-128, TR-129, TR-130, TR-131, TR-132, TR-134, TR-135, TR-137, TR-140, TR-141, TR-142, TR-143, TR-144, TR-145, TR-146, TR-147, TR-149, TR-151, TR-152, TR-153, TR-155, TR-156, TR-157, TR-158, TR-160, TR-161, TR-162, TR-163, TR-164, TR-165, TR-166, TR-167, TR-168, TR-169, TR-171, TR-172, TR-173, TR-176, TR-177, TR-181, TR-184, TR-186, TR-189, TR-190, TR-191, TR-194, TR-196, TR-198, and a pharmaceutically acceptable salt or analog thereof.

In some embodiments, the bivalent compound is selected from the group consisting of TR-106, TR-108, TR-109, TR-113, TR-115, TR-116, TR-117, TR-119, TR-121, TR-122, TR-123, TR-124, TR-125, TR-127, TR-128, TR-129, TR-130, TR-131, TR-132, TR-135, TR-137, TR-140, TR-141, TR-142, TR-143, TR-144, TR-145, TR-146, TR-149, TR-151, TR-152, TR-155, TR-156, TR-160, TR-161, TR-162, TR-165, TR-166, TR-167, TR-168, TR-169, TR-171, TR-172, TR-173, TR-176, TR-177, TR-181, TR-186, TR-189, TR-190, TR-191, TR-194, TR-196, TR-198, and a pharmaceutically acceptable salt or analog thereof.

In some embodiments, the bivalent compound is selected from the group consisting of TR-123), TR-172, TR-173, TR-181, TR-185, TR-186, TR-191, TR-196, TR-198, and a pharmaceutically acceptable salt or analog thereof.

In some embodiments, the bivalent compound is 2-(2,6-Dioxopiperidin-3-yl)-4-((7-(4-(6-(6-((R)-2-(3-fluorophenyl)pyrrolidin-1-yl)imidazo[1,2-b]pyridazin-3-yl)pyridin-2-yl)piperazin-1-yl)-7-oxoheptyl)amino)isoindoline-1,3-dione (CPD-009).

In some embodiments, the bivalent compound is 2-(2,6-Dioxopiperidin-3-yl)-4-((2-(2-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethoxy)ethyl)amino)isoindoline-1,3-dione (CPD-010).

In some embodiments, the bivalent compound is 2-(2,6-Dioxopiperidin-3-yl)-4-((4-(4-(6-(6-((R)-2-(3-fluorophenyl)pyrrolidin-1-yl)imidazo[1,2-b]pyridazin-3-yl)pyridin-2-yl)piperazin-1-yl)-4-oxobutyl)amino)isoindoline-1,3-dione (CPD-013).

In some embodiments, the bivalent compound is 2-(2,6-Dioxopiperidin-3-yl)-4-((5-(4-(6-(6-((R)-2-(3-fluorophenyl)pyrrolidin-1-yl)imidazo[1,2-b]pyridazin-3-yl)pyridin-2-yl)piperazin-1-yl)-5-oxopentyl)amino)isoindoline-1,3-dione (CPD-014).

In some embodiments, the bivalent compound is 2-(2,6-Dioxopiperidin-3-yl)-4-((5-(4-(6-(6-((R)-2-(3-fluorophenyl)pyrrolidin-1-yl)imidazo[1,2-b]pyridazin-3-yl)pyridin-2-yl)piperazin-1-yl)-5-oxopentyl)amino)isoindoline-1,3-dione (CPD-015).

In some embodiments, the bivalent compound is 2-(2,6-Dioxopiperidin-3-yl)-4-((15-(4-(6-(6-((R)-2-(3-fluorophenyl)pyrrolidin-1-yl)imidazo[1,2-b]pyridazin-3-yl)pyridin-2-yl)piperazin-1-yl)-15-oxo-3,6,9,12-tetraoxapentadecyl)amino)isoindoline-1,3-dione (CPD-021).

In some embodiments, the bivalent compound is (2S,4R)-1-((S)-2-(11-(4-(6-(6-((R)-2-(3-Fluorophenyl)pyrrolidin-1-yl)imidazo[1,2-b]pyridazin-3-yl)pyridin-2-yl)piperazin-1-yl)-11-oxoundecanamido)-3,3-dimethylbutanoyl)-4-hydroxy-N-(4-(4-methylthiazol-5-yl)benzyl)pyrrolidine-2-carboxamide (CPD-022).

In some embodiments, the bivalent compound is 2-(2,6-Dioxopiperidin-3-yl)-4-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)isoindoline-1,3-dione (CPD-023).

In some embodiments, the bivalent compound is 2-(2,6-Dioxopiperidin-3-yl)-4-((8-(4-(6-(6-((R)-2-(3-fluorophenyl)pyrrolidin-1-yl)imidazo[1,2-b]pyridazin-3-yl)pyridin-2-yl)piperazin-1-yl)-8-oxooctyl)amino)isoindoline-1,3-dione (CPD-024).

In some embodiments, the bivalent compound is 2-(2,6-Dioxopiperidin-3-yl)-4-((18-(4-(6-(6-((R)-2-(3-fluorophenyl)pyrrolidin-1-yl)imidazo[1,2-b]pyridazin-3-yl)pyridin-2-yl)piperazin-1-yl)-18-oxo-3,6,9,12,15-pentaoxaoctadecyl)amino)isoindoline-1,3-dione (CPD-025).

In some embodiments, the bivalent compound is 2-(2,6-Dioxopiperidin-3-yl)-4-((3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropyl)amino)isoindoline-1,3-dione (CPD-026).

In some embodiments, the bivalent compound is 2-(2,6-Dioxopiperidin-3-yl)-4-((2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethyl)amino)isoindoline-1,3-dione (CPD-027).

In some embodiments, the bivalent compound is 2-(2,6-Dioxopiperidin-3-yl)-4-((2-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethyl)amino)isoindoline-1,3-dione (CPD-028).

In some embodiments, the bivalent compound is (2S,4R)-1-((S)-2-(8-(4-(6-(6-((R)-2-(3-Fluorophenyl)pyrrolidin-1-yl)imidazo[1,2-b]pyridazin-3-yl)pyridin-2-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide (CPD-029).

In some embodiments, the bivalent compound is N-(5-(3,5-Difluorobenzyl)-1H-indazol-3-yl)-4-(4-(3-(2-((2-(2,6-dioxopiperidin-3-yl)-1,3-dioxoisoindolin-4-yl)amino)ethoxy)propanoyl)piperazin-1-yl)-2-((tetrahydro-2H-pyran-4-yl)amino)benzamide (CPD-030).

In some embodiments, the bivalent compound is N-(5-(3,5-Difluorobenzyl)-1H-indazol-3-yl)-4-(4-(1-((2-(2,6-dioxopiperidin-3-yl)-1,3-dioxoisoindolin-4-yl)amino)-3,6,9,12-tetraoxapentadecan-15-oyl)piperazin-1-yl)-2-((tetrahydro-2H-pyran-4-yl)amino)benzamide (CPD-031).

In some embodiments, the bivalent compound is N-(5-(3,5-Difluorobenzyl)-1H-indazol-3-yl)-4-(4-(3-(2-(2-((2-(2,6-dioxopiperidin-3-yl)-1,3-dioxoisoindolin-4-yl)amino)ethoxy)ethoxy)propanoyl)piperazin-1-yl)-2-((tetrahydro-2H-pyran-4-yl)amino)benzamide (CPD-032).

In some embodiments, the bivalent compound is (2S,4R)-1-((S)-2-(8-(4-(4-((5-(3,5-difluorobenzyl)-1H-indazol-3-yl)carbamoyl)-3-((tetrahydro-2H-pyran-4-yl)amino)phenyl)piperazin-1-yl)-8-oxooctanamido)-3,3-dimethylbutanoyl)-4-hydroxy-N-(4-(4-methylthiazol-5-yl)benzyl)pyrrolidine-2-carboxamide (CPD-033).

In some embodiments, the bivalent compound is (2S,4R)-1-((S)-2-(6-(4-(4-((5-(3,5-difluorobenzyl)-1H-indazol-3-yl)carbamoyl)-3-((tetrahydro-2H-pyran-4-yl)amino)phenyl)piperazin-1-yl)-6-oxohexanamido)-3,3-dimethylbutanoyl)-4-hydroxy-N-(4-(4-methylthiazol-5-yl)benzyl)pyrrolidine-2-carboxamide (CPD-044).

In some embodiments, the bivalent compound is (2S,4R)-1-((S)-2-(7-(4-(4-((5-(3,5-difluorobenzyl)-1H-indazol-3-yl)carbamoyl)-3-((tetrahydro-2H-pyran-4-yl)amino)phenyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide (CPD-047).

In some embodiments, the bivalent compound is N-(5-(3,5-difluorobenzyl)-1H-indazol-3-yl)-4-(4-(7-((2-(2,6-dioxopiperidin-3-yl)-1,3-dioxoisoindolin-4-yl)amino)heptanoyl)piperazin-1-yl)-2-((tetrahydro-2H-pyran-4-yl)amino)benzamide (CPD-049).

In some embodiments, the bivalent compound is N-(5-(3,5-difluorobenzyl)-1H-indazol-3-yl)-4-(4-(5-((2-(2,6-dioxopiperidin-3-yl)-1,3-dioxoisoindolin-4-yl)amino)pentanoyl)piperazin-1-yl)-2-((tetrahydro-2H-pyran-4-yl)amino)benzamide (CPD-050).

In some embodiments, the bivalent compound is N-(5-(3,5-difluorobenzyl)-1H-indazol-3-yl)-4-(4-(3-((2-(2,6-dioxopiperidin-3-yl)-1,3-dioxoisoindolin-4-yl)amino)propanoyl)piperazin-1-yl)-2-((tetrahydro-2H-pyran-4-yl)amino)benzamide (CPD-051).

In some embodiments, the bivalent compound is N-(5-(3,5-difluorobenzyl)-1H-indazol-3-yl)-4-(4-(8-((2-(2,6-dioxopiperidin-3-yl)-1,3-dioxoisoindolin-4-yl)amino)octanoyl)piperazin-1-yl)-2-((tetrahydro-2H-pyran-4-yl)amino)benzamide (CPD-052).

In some embodiments, the bivalent compound is N-(5-(3,5-Difluorobenzyl)-1H-indazol-3-yl)-4-(4-(4-((2-(2,6-dioxopiperidin-3-yl)-1,3-dioxoisoindolin-4-yl)amino)butanoyl)piperazin-1-yl)-2-((tetrahydro-2H-pyran-4-yl)amino)benzamide (CPD-053).

In some embodiments, the bivalent compound is N-(5-(3,5-difluorobenzyl)-1H-indazol-3-yl)-4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-2-((tetrahydro-2H-pyran-4-yl)amino)benzamide (CPD-054).

In some embodiments, the bivalent compound is N-(5-(3,5-difluorobenzyl)-1H-indazol-3-yl)-4-(4-((2-(2,6-dioxopiperidin-3-yl)-1,3-dioxoisoindolin-4-yl)glycyl)piperazin-1-yl)-2-((tetrahydro-2H-pyran-4-yl)amino)benzamide (CPD-055).

In some embodiments, the bivalent compound is N-(5-(3,5-difluorobenzyl)-1H-indazol-3-yl)-4-(4-(6-((2-(2,6-dioxopiperidin-3-yl)-1,3-dioxoisoindolin-4-yl)amino)hexanoyl)piperazin-1-yl)-2-((tetrahydro-2H-pyran-4-yl)amino)benzamide (CPD-056).

In some embodiments, the bivalent compound is N-(5-(3,5-Difluorobenzyl)-1H-indazol-3-yl)-4-(4-(3-(2-(2-(2-((2-(2,6-dioxopiperidin-3-yl)-1,3-dioxoisoindolin-4-yl)amino)ethoxy)ethoxy)ethoxy)propanoyl)piperazin-1-yl)-2-((tetrahydro-2H-pyran-4-yl)amino)benzamide (CPD-057).

In some embodiments, the bivalent compound is N-(2-(2-(2-(2-((2-(2,6-dioxopiperidin-3-yl)-1,3-dioxoisoindolin-4-yl)amino)ethoxy)ethoxy)-ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (CPD-059).

In some embodiments, the bivalent compound is N-(2-((2-(2,6-dioxopiperidin-3-yl)-1,3-dioxoisoindolin-4-yl)amino)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (CPD-060).

In some embodiments, the bivalent compound is N-(5-(3,5-difluorobenzyl)-1H-indazol-3-yl)-4-(4-(2-((2-((2-(2,6-dioxopiperidin-3-yl)-1,3-dioxoisoindolin-4-yl)amino)ethyl)amino)-2-oxoethyl)piperazin-1-yl)-2-((tetrahydro-2H-pyran-4-yl)amino)benzamide (CPD-062).

In some embodiments, the bivalent compound is N-(5-(3,5-difluorobenzyl)-1H-indazol-3-yl)-4-(4-(14-((2-(2,6-dioxopiperidin-3-yl)-1,3-dioxoisoindolin-4-yl)amino)-2-oxo-6,9,12-trioxa-3-azatetradecyl)piperazin-1-yl)-2-((tetrahydro-2H-pyran-4-yl)amino)benzamide (CPD-064).

In some embodiments, the bivalent compound is N-(5-(3,5-difluorobenzyl)-1H-indazol-3-yl)-4-(4-(20-((2-(2,6-dioxopiperidin-3-yl)-1,3-dioxoisoindolin-4-yl)amino)-2-oxo-6,9,12,15,18-pentaoxa-3-azaicosyl)piperazin-1-yl)-2-((tetrahydro-2H-pyran-4-yl)amino)benzamide (CPD-065).

In some embodiments, the bivalent compound is 2-(2,6-dioxopiperidin-3-yl)-5-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)isoindoline-1,3-dione (TR-123).

In some embodiments, the bivalent compound is 2-(2,6-dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)propyl)isoindoline-1,3-dione (TR-172).

In some embodiments, the bivalent compound is 2-(2,6-dioxopiperidin-3-yl)-5-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)isoindoline-1,3-dione (TR-173).

In some embodiments, the bivalent compound is 2-(2,6-dioxopiperidin-3-yl)-5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)isoindoline-1,3-dione (TR-181).

In some embodiments, the bivalent compound is 3-(6-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-1-oxoisoindolin-2-yl)piperidine-2,6-dione (TR-185).

In some embodiments, the bivalent compound is 3-(5-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-1-oxoisoindolin-2-yl)piperidine-2,6-dione (TR-186).

In some embodiments, the bivalent compound is 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-1-oxoisoindolin-2-yl)piperidine-2,6-dione (TR-191).

In some embodiments, the bivalent compound is 3-(6-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-1-oxoisoindolin-2-yl)piperidine-2,6-dione (TR-196).

In some embodiments, the bivalent compound is 2-(2,6-dioxopiperidin-3-yl)-5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)azetidin-1-yl)isoindoline-1,3-dione (TR-198).

According to one aspect of the present disclosure, a composition disclosed herein comprises the bivalent compound or a pharmaceutically acceptable salt or analog thereof.

According to one aspect of the present disclosure, a method of treating a tropomyosin receptor kinase (TRK)-mediated disease disclosed herein comprises administering to a subject with a TRK-mediated disease the bivalent compound or a pharmaceutically acceptable salt or analog thereof.

In one embodiment, the TRK-mediated disease results from TRK expression, mutation, or fusion.

In one embodiment, wherein the subject with the TRK-mediated disease has an elevated TRK function relative to a healthy subject without the TRK-mediated disease.

In one embodiment, the bivalent compound is selected from the group consisting of CPD-001 to CPD-206, or analogs thereof.

In one embodiment, the bivalent compound is administered to the subject orally, parenterally, intradermally, subcutaneously, topically, or rectally. In one embodiment, the method further comprises administering to the subject an additional therapeutic regimen for treating cancer.

In one embodiment, the additional therapeutic regimen is selected from the group consisting of surgery, chemotherapy, radiation therapy, hormone therapy, and immunotherapy.

In one embodiment, the TRK-mediated disease is selected from the group consisting of non-small cell lung cancer, colorectal cancer, gastric cancer, liver cancer, invasive breast cancer, lung adenocarcinoma, uterine cancer, adrenal cancer, pancreatic cancer, ovarian cancer, esophageal cancer, urinary bladder cancer, endometrial cancer, prostate cancer low-grade glioma, glioblastoma, Spitzoid cancer, soft tissue sarcoma, papillary thyroid carcinoma, head and neck squamous cell carcinoma, congenital fibrosarcoma, congenital mesoblastic nephroma, secretory breast carcinoma, mammary analogue secretory carcinoma, acute myeloid leukemia, ductal carcinoma, pulmonary neuroendocrine tumors, pheochromocytoma, and Wilms' tumor.

In one embodiments, the TRK-mediated disease or condition comprises cancer, inflammatory diseases, acute and chronic pain, pruritus, bone-related diseases, neurodegenerative diseases, infectious diseases, and other diseases, including but not limited to neuroblastoma, prostate cancer, pancreatic cancer, melanoma, head and neck cancer, gastric carcinoma, lung carcinoma, liver cancer, uterine cancer, adrenal cancer, biliary tree cancer, intestinal cancer, colorectal cancer, ovarian cancer, lung carcinoma, small cell lung cancer, non-small cell lung cancer, gastric carcinoma, breast cancer, esophageal cancer, urinary bladder cancer, endometrial cancer, brain cancer, low-grade glioma, glioblastoma, medulloblastoma, secratory breast cancer, secretory breast carcinoma, salivary gland cancer, papillary thyroid carcinoma, ductal carcinoma, adult myeloid leukemia, acute myeloid leukemia, large cell neuroendocrine tumors, pulmonary neuroendocrine tumors, sarcomas, pheochromocytoma, fibrosarcoma, congenital fibrosarcoma, congenital mesoblastic nephroma, secretory breast carcinoma, malignant fibrous histiocytoma, embryonal rhabdomysocarcoma, leiomysosarcoma, neuro-fibrosarcoma, neoplasms of the central nervous systems, osteosarcoma, synovial sarcoma, liposarcoma, alveolar soft part sarcoma, Spitzoid cancer, Wilms' tumor, lymphomas (e.g. including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma), inflammatory lung diseases (e.g. asthma), inflammatory bowel diseases, (e.g. ulcerative colitis, Crohn's disease), inflammatory skin diseases (e.g. atopic dermatitis, eczema and psoriasis), interstitial cystitis, rhinitis, acute pain, chronic pain, cancer pain, surgical pain, inflammatory pain, neuropathic pain, nociceptive pain, pain of osteoarthritis, chronic low back pain, low back pain of osteoporosis, pain of bone fracture, pain of rheumatoid arthritis, postherpetic pain, pain of diabetic neuropathy, fibromyalgia, pain of pancreatitis, pain of interstitial cystitis, pain of endometriosis, pain of irritable bowel syndrome, migraine, pain of pulpitis, interstitial cystitis pain, painful bladder syndrome, central pain syndromes, postsurgical pain syndromes, bone and joint pain, repetitive motion pain, dental pain, myofascial pain, perioperative pain, dysmennorhea, myofascial pain, angina pain, headache, primary hyperalgesia, secondary hyperalgesia, primary allodynia, secondary allodynia, other pain caused by central sensitization, systemic cutaneous pruritus, localized cutaneous pruritus, senile cutaneous pruritus, gestational pruritus, pruritus ani, vulvar pruritus, metastatic bone disease, treatment-induce bone loss, osteoporosis, rheumatoid arthritis, bone metastases, ankylosing spondylitis, Paget's disease, periodontal disease, osteolytic disease, multiple sclerosis, Parkinson's disease, Alzheimer's disease, Chagas disease, cachexia, anorexia, demyelination and dysmyelination. In certain embodiments, the disease or condition is a relapsed disease.

In one embodiment, the TRK-mediated disease is a relapsed cancer.

In one embodiment, the TRK-mediated disease is refractory to one or more previous treatments.

According to one aspect of the present disclosure, a method for identifying a bivalent compound which mediates degradation or reduction of TRK is disclosed. The method comprises:

providing a heterobifunctional test compound comprising an TRK ligand conjugated to a degradation tag through a linker;

contacting the heterobifunctional test compound with a cell comprising a ubiquitin ligase and TRK;

determining whether TRK level is decreased in the cell; and identifying the heterobifunctional test compound as a bivalent compound which mediates degradation or reduction of TRK.

In one embodiment, the cell is a cancer cell.

In one embodiment, the cancer cell is a TRK-mediated cancer cell.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
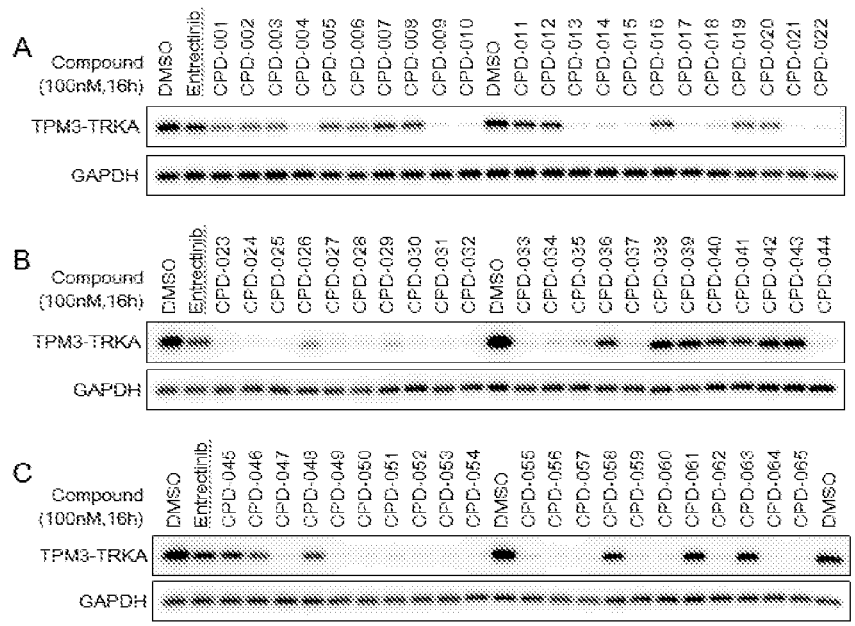
FIG. 1A shows an immunoblot of TPM3-TRKA fusion protein expressed by KM12 cells after treatment with Entrectinib or bivalent compounds CPD-001-CPD-022.
FIG. 1B shows an immunoblot of TPM3-TRKA fusion protein expressed by KM12 cells after treatment with Entrectinib or bivalent compounds CPD-023-CPD-044.
FIG. 1C shows an immunoblot of TPM3-TRKA fusion protein expressed by KM12 cells after treatment with Entrectinib or bivalent compounds CPD-045-CPD-065.

It is recognized in the present disclosure that tropomyosin receptor kinase (TRK) receptor family comprises three members, TRKA, TRKB and TRKC that are encoded by the NTRK1, NTRK2 and NTRK3 genes, respectively (Khotskaya et al., 2017). TRKs are receptor tyrosine kinases primarily implicated in development and functions of the neuronal tissues. The main ligands of TRKs include nerve growth factor (NGF) for TRKA, brain-derived growth factor (BDGF) for TRKB, and neurotrophins for TRKC (Vaishnavi et al., 2015). The binding of ligands to the extracellular domains of TRKs induces dimerization and activation of the receptors, which activates downstream signal transduction pathways, such as PI3K/AKT, RAF/MEK/ERK, and PLCγ pathways. These pathways have well established roles to support cellular proliferation, survival, and promote oncogenesis (Hanahan and Weinberg, 2011).

It is further recognized herein that, like many other oncogenic receptor tyrosine kinases, TRKs are aberrantly activated in a variety of human malignancies. Interestingly, the primary molecular mechanism activating TRKs in cancer is not point mutations but in-frame fusions of NTRK genes (Vaishnavi et al., 2015). Typically, the 3' regions of the NTRK genes are joined with the 5' regions of a partner gene due to chromosomal rearrangement. The resulted chimeric proteins always retain the kinase domain of TRK proteins, indicating that the catalytic functions are crucial to the transforming activities. Loss of the 5' regions of the NTRK genes that encode the self-inhibitory domains renders these fusion kinases constitutively active. Additionally, expression of the chimeric proteins is driven by the promoters of the fusion partners, which often result in overexpression. The most common TRK fusions include LMNA-TRKA, TPM3-TRKA, and ETV6-TRKC (Amatu et al., 2016). Hence, genetic events lead to overexpressed and constitutively active TRK-fusion kinases. These fusions are oncogenic, as shown by their ability to transform mouse embryonic fibroblasts and normal epithelium (Russell et al., 2000; Vaishnavi et al., 2015).

TRK fusion was first reported in a human colon carcinoma, which was named as oncD at that time (Martin-Zanca et al., 1986). Recent advances in high-throughput RNA sequencing greatly promote the efficiency of identifying chromosomal rearrangement events in patient samples. Consequently, TRK fusions have been found across a wide range of human malignancies, including but are not limited to non-small cell lung cancer, colorectal cancer, gastric cancer, low-grade glioma glioblastoma, Spitzoid cancer, soft tissue sarcoma, papillary thyroid carcinoma, head and neck squamous cell carcinoma, congenital fibrosarcoma, congenital mesoblastic nephroma, secretory breast carcinoma, mammary analogue secretory carcinoma, acute myeloid leukemia, and ductal carcinoma (Amatu et al., 2016; Khotskaya et al., 2017). The frequency of TRK fusions is relatively low. For example, approximately 0.5% to 2.7% colon cancers are affected by TRK fusions (Creancier et al., 2015; Lee et al., 2015). However, for certain cancer types, such as secretory breast carcinoma, TRK fusions can be found in the vast majority of cases (Tognon et al., 2002).

TRK mutations and deletions have been observed in additional human diseases, such as pulmonary neuroendocrine tumors, anhidrosis syndrome, obesity, congenital heart defects, and acute myeloid leukemia (Khotskaya et al., 2017). In addition, TRK amplification are associated with several human diseases, such as liver cancer, invasive breast cancer, lung adenocarcinoma, uterine cancer, adrenal cancer, pancreatic cancer, ovarian cancer, esophageal cancer, urinary bladder cancer, endometrial cancer, pheochromocytoma, Wilms' tumor, and prostate cancer (Khotskaya et al., 2017).

The never growth factor (NGF) and its main receptor, tropomyosin receptor kinase A (TRKA), have long been recognized for their roles in central and peripheral pain (Denk et al., 2017). Nociceptive neurons express TRKA and mediate pain sensation by transmitting pain signals to the central nervous system. Multiple NGF-neutralizing antibodies, such as tanezumab, are undergoing clinical assessment in patients with osteoarthritis, lower back pain, cancer pain, neuropathic pain, and other pain conditions (Miller et al., 2017). The efficacy of NGF antibodies in pain relief has been clearly documented in clinics. However, administration of NGF neutralizing antibodies has been shown to result in rapidly progressed joint destruction in some patients that leads to total joint replacement (Schnitzer and Marks, 2015). These adverse events may be related to sustained exposure to NGF antibodies. Targeting TRK represents another promising therapeutic strategy blocking the NGF/TRK signaling pathway for pain management. However, currently available pan-TRK kinase inhibitors may induce significant on-target adverse effects through modulating TRK family members in the central nervous system. Peripherally restricted TRK bifunctional degraders are expected to selective block the NGF/TRK pathway in peripheral nerves while spare these targets in the central nervous system.

TRK is associated with cancer, inflammatory diseases, acute and chronic pain, pruritus, bone-related diseases, neurodegenerative diseases, infectious diseases, and other diseases, including but no limited to neuroblastoma, prostate cancer, pancreatic cancer, melanoma, head and neck cancer, gastric carcinoma, lung carcinoma, liver cancer, uterine cancer, adrenal cancer, biliary tree cancer, intestinal cancer, colorectal cancer, ovarian cancer, lung carcinoma, small cell lung cancer, non-small cell lung cancer, gastric carcinoma, breast cancer, esophageal cancer, urinary bladder cancer, endometrial cancer, brain cancer, low-grade glioma, glioblastoma, medulloblastoma, secretory breast carcinoma, salivary gland cancer, papillary thyroid carcinoma, ductal carcinoma, acute myeloid leukemia, large cell neuroendocrine tumors, pulmonary neuroendocrine tumors, sarcomas, pheochromocytoma, fibrosarcoma, congenital fibrosarcoma, congenital mesoblastic nephroma, secretory breast carcinoma, malignant fibrous histiocytoma, embryonal rhabdomysocarcoma, leiomysosarcoma, neuro-fibrosarcoma, neoplasms of the central nervous systems, osteosarcoma, synovial sarcoma, liposarcoma, alveolar soft part sarcoma, Spitzoid cancer, Wilms' tumor, lymphomas (e.g. including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma), inflammatory lung diseases (e.g. asthma), inflammatory bowel diseases, (e.g. ulcerative colitis, Crohn's disease), inflammatory skin diseases (e.g. atopic dermatitis, eczema and psoriasis), interstitial cystitis, rhinitis, acute pain, chronic pain, cancer pain, surgical pain, inflammatory pain, neuropathic pain, nociceptive pain, pain of osteoarthritis, chronic low back pain, low back pain of osteoporosis, pain of bone fracture, pain of rheumatoid arthritis, postherpetic pain, pain of diabetic neuropathy, fibromyalgia, pain of pancreatitis, pain of interstitial cystitis, pain of endometriosis, pain of irritable bowel syndrome, migraine, pain of pulpitis, interstitial cystitis pain, painful bladder syndrome, central pain syndromes, postsurgical pain syndromes, bone and joint pain, repetitive motion pain, dental pain, myofascial pain, perioperative pain, dysmennorhea, myofascial pain, angina pain, headache, primary hyperalgesia, secondary hyperalgesia, primary allodynia, secondary allodynia, other pain caused by central sensitization, systemic cutaneous pruritus, localized cutaneous pruritus, senile cutaneous pruritus, gestational pruritus, pruritus ani, vulvar pruritus, metastatic bone disease, treatment-induce bone loss, osteoporosis, rheumatoid arthritis, bone metastases, ankylosing spondylitis, Paget's disease, periodontal disease, osteolytic disease, multiple sclerosis, Parkinson's disease, Alzheimer's disease, Chagas disease, cachexia, anorexia, demyelination and dysmyelination.

TRK kinase inhibitors are currently undergoing clinical or pre-clinical development, including but are not limited to altiratinib (DCC2701, DCC-270, DP-5164) (Smith et al., 2015), sitravatinib (MGCD516) (Patwardhan et al., 2016), cabozantinib (XL-184, BMS-907351) (Fuse et al., 2017), dovitinib (TKI-258, CHIR-258) (Chong et al., 2017), entrectinib (RXDX-101) (Menichincheri et al., 2016), milciclib (PHA-848125AC) (Brasca et al., 2009), belizatinib (TSR-011) (Ricciuti et al., 2017), GZ389988 (Bailey et al., 2017a, b), pegcantratinib (Cranston et al., 2017), AZD7451 (Tatematsu et al., 2014), larotrectinib (LOXO-101; ARRY-470) (Drilon et al., 2018), TPX-0005 (Cui et al., 2016), LOXO-195 (Blake et al., 2016), regorafenib (Subbiah et al., 2017), DS-6051b (Fujiwara et al., 2018), F17752 (Amatu et al., 2016), PLX7486 (Amatu et al., 2016), AZD-6918 (Li et al., 2015), ASP7962 (Bailey et al., 2017a, b), VM902A (Bailey et al., 2017a, b), ONO-4474 (Bailey et al., 2017a, b), PF-06273340 (Skerratt et al., 2016) and GNF-8625 (Choi et al., 2015). The most advanced ones are entrectinib and larotrectinib (Khotskaya et al., 2017). These agents are tested in basket trials that recruit patients according to detection of TRK-fusions instead of histology. The phase 2 results of larotrectinib demonstrated that most patients (75%) responded to the therapy and that 55% patient remained progression-free at 1 year (Drilon et al., 2018). Phase 1 results of entrectinib also recorded marked and durable response in patients with TRK-fusion tumors (Drilon et al., 2017b). The remarkable efficacy of TRK inhibitors was independent of tumor types. These substantial results collectively highlight a role of TRK fusions as the sole oncogenic drivers in a subset of human malignancies, irrespective of tissue of origin.

Non-specific side effects and the development of resistance to TRK kinase inhibitors remain a challenge in development of effective treatments. Thus, new small-molecule targeting TRK's functions through inhibition and/or degradation will be very useful.

Without wishing to be bound by any theory, the present disclosure is believed to be based, at least in part, on the discovery that novel heterobivalent small molecules which degrade TRK, TRK fusion proteins, and/or TRK mutant proteins are useful in the treatment of TRK-mediated diseases, particularly non-small cell lung cancer, colorectal cancer, gastric cancer, liver cancer, invasive breast cancer, lung adenocarcinoma, uterine cancer, adrenal cancer, pancreatic cancer, ovarian cancer, esophageal cancer, urinary bladder cancer, endometrial cancer, prostate cancer, low-grade glioma, glioblastoma, Spitzoid cancers, soft tissue sarcoma, papillary thyroid carcinoma, head and neck squamous cell carcinoma, congenital fibrosarcoma, congenital mesoblastic nephroma, secretory breast carcinoma, mammary analogue secretory carcinoma, acute myeloid leukemia, ductal carcinoma, pulmonary neuroendocrine tumors, pheochromocytoma, and Wilms' tumor (Amatu et al., 2016; Khotskaya et al., 2017). The disclosed novel bifunctional TRK degraders are useful in the treatment of TRK-mediated cancer, inflammatory diseases, acute and chronic pain, pruritus, bone-related diseases, neurodegenerative diseases, infectious diseases, and other diseases, including but not limited to neuroblastoma, prostate cancer, pancreatic cancer, melanoma, head and neck cancer, gastric carcinoma, lung carcinoma, liver cancer, uterine cancer, adrenal cancer, biliary tree cancer, intestinal cancer, colorectal cancer, ovarian cancer, lung carcinoma, small cell lung cancer, non-small cell lung cancer, gastric carcinoma, breast cancer, esophageal cancer, urinary bladder cancer, endometrial cancer, brain cancer, low-grade glioma, glioblastoma, medulloblastoma, secratory breast cancer, secretory breast carcinoma, salivary gland cancer, papillary thyroid carcinoma, ductal carcinoma, adult myeloid leukemia, acute myeloid leukemia, large cell neuroendocrine tumors, pulmonary neuroendocrine tumors, sarcomas, pheochromocytoma, fibrosarcoma, congenital fibrosarcoma, congenital mesoblastic nephroma, secretory breast carcinoma, malignant fibrous histiocytoma, embryonal rhabdomysocarcoma, leiomysosarcoma, neuro-fibrosarcoma, neoplasms of the central nervous systems, osteosarcoma, synovial sarcoma, liposarcoma, alveolar soft part sarcoma, Spitzoid cancer, Wilms' tumor, lymphomas (e.g. including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma), inflammatory lung diseases (e.g. asthma), inflammatory bowel diseases, (e.g. ulcerative colitis, Crohn's disease), inflammatory skin diseases (e.g. atopic dermatitis, eczema and psoriasis), interstitial cystitis, rhinitis, acute pain, chronic pain, cancer pain, surgical pain, inflammatory pain, neuropathic pain, nociceptive pain, pain of osteoarthritis, chronic low back pain, low back pain of osteoporosis, pain of bone fracture, pain of rheumatoid arthritis, postherpetic pain, pain of diabetic neuropathy, fibromyalgia, pain of pancreatitis, pain of interstitial cystitis, pain of endometriosis, pain of irritable bowel syndrome, migraine, pain of pulpitis, interstitial cystitis pain, painful bladder syndrome, central pain syndromes, postsurgical pain syndromes, bone and joint pain, repetitive motion pain, dental pain, myofascial pain, perioperative pain, dysmennorhea, myofascial pain, angina pain, headache, primary hyperalgesia, secondary hyperalgesia, primary allodynia, secondary allodynia, other pain caused by central sensitization, systemic cutaneous pruritus, localized cutaneous pruritus, senile cutaneous pruritus, gestational pruritus, pruritus ani, vulvar pruritus, metastatic bone disease, treatment-induce bone loss, osteoporosis, rheumatoid arthritis, bone metastases, ankylosing spondylitis, Paget's disease, periodontal disease, osteolytic disease, multiple sclerosis, Parkinson's disease, Alzheimer's disease, Chagas disease, cachexia, anorexia, demyelination and dysmyelination.

Selective degradation of a target protein induced by a small molecule may be achieved by recruiting an E3 ubiquitin ligase and mimicking protein misfolding with a hydrophobic tag (Buckley and Crews, 2014). Additionally, the small molecule has one moiety that binds to an E3 ubiquitin ligase and another moiety that binds the protein target of interest (Buckley and Crews, 2014). The induced proximity leads to ubiquitination of the target followed by its degradation via proteasome-mediated proteolysis. Several types of high affinity small-molecule E3 ligase ligands have been identified or developed. They include (1) immunomodulatory drugs (IMiDs) such as thalidomide and pomalidomide, which bind cereblon (CRBN or CRL4CRBN), a component of a cullin-RING ubiquitin ligase (CRL) complex (Bondeson et al., 2015; Chamberlain et al., 2014; Fischer et al., 2014; Ito et al., 2010; Winter et al., 2015); (2) VHL-1, a hydroxyproline-containing ligand, which binds van Hippel-Lindau protein (VHL or CRL2VHL), a component of another CRL complex (Bondeson et al., 2015; Buckley et al., 2012a; Buckley et al., 2012b; Galdeano et al., 2014; Zengerle et al., 2015); (3) compound 7, which selectively binds KEAP1, a component of a CRL3 complex (Davies et al., 2016); (4) AMG232, which selectively binds MDM2, a heterodimeric RING E3 ligase (Sun et al., 2014); and (5) LCL161, which selectively binds IAP, a homodimeric RING E3 ligase (Ohoka et al., 2017; Okuhira et al., 2011; Shibata et al., 2017). The E3 ligase recruiting bifunctional degrader technology has been applied to degradation of several protein targets (Bondeson et al., 2015; Buckley et al., 2015; Lai et al., 2016; Lu et al., 2015; Winter et al., 2015; Zengerle et al., 2015). In addition, a hydrophobic tagging approach, which utilizes a bulky and hydrophobic adamantyl group, has been developed to mimic protein misfolding, leading to the degradation of the target protein by proteasome (Buckley and Crews, 2014). This approach has been applied to selective degradation of the pseudokinase HER3 (Xie et al., 2014). The inventors have not yet seen any efforts applying any of these approaches to degradation of TRK, TRK mutant, TRK deletion, or TRK fusion proteins.

Currently available small molecules targeting TRK focus on inhibition of the kinase activity of TRK. A number of selective small-molecule TRK kinase inhibitors, such as altiratinib (DCC2701, DCC-270, DP-5164) (Smith et al., 2015), sitravatinib (MGCD516) (Patwardhan et al., 2016), cabozantinib (XL-184, BMS-907351) (Fuse et al., 2017), dovitinib (TKI-258, CHIR-258) (Chong et al., 2017), entrectinib (RXDX-101) (Menichincheri et al., 2016), milciclib (PHA-848125AC) (Brasca et al., 2009), belizatinib (TSR-011) (Ricciuti et al., 2017), GZ389988 (Bailey et al., 2017a, b), pegcantratinib (Cranston et al., 2017), AZD7451 (Tatematsu et al., 2014), larotrectinib (LOXO-101; ARRY-470) (Drilon et al., 2018), TPX-0005 (Cui et al., 2016), LOXO-195 (Blake et al., 2016), regorafenib (Subbiah et al., 2017), DS-6051b (Fujiwara et al., 2018), F17752 (Amatu et al., 2016), PLX7486 (Amatu et al., 2016), AZD-6918 (Li et al., 2015), ASP7962 (Bailey et al., 2017a, b), VM902A (Bailey et al., 2017a, b), ONO-4474 (Bailey et al., 2017a, b), PF-06273340 (Skerratt et al., 2016) and GNF-8625 (Choi et al., 2015) have been reported.

In the present disclosure, a novel approach is taken: to develop compounds that directly and selectively modulate not only the kinase activity of TRK, but also its protein level. Strategies for inducing protein degradation include recruiting E3 ubiquitin ligases, mimicking protein misfolding with hydrophobic tags, and inhibiting chaperones. Such an approach, based on the use of bivalent small molecule compounds, permits more flexible regulation of protein levels in vitro and in vivo compared with techniques such as gene knockout or short hairpin RNA-mediated (shRNA) knockdown. Unlike gene knockout or shRNA knockdown, a small molecule approach further provides an opportunity to study dose and time dependency in a disease model through modulating the administration routes, concentrations and frequencies of administration of the corresponding small molecule.

Bivalent Compounds

For the purpose of the present disclosure, the terms "bifunctional compound", "bifunctional degrader", "bifunctional TRK degrader", "bivalent compound" and "heterobifunctional compound" are used interchangeably.

In some aspects, the present disclosure provides bivalent compounds including a TRK ligand conjugated to a degradation tag, or a pharmaceutically acceptable salt or analog thereof. The TRK ligand may be conjugated to the degradation tag directly or via a linker moiety. In certain embodiments, the TRK ligand may be conjugated to the degradation tag directly. In certain embodiments, the TRK ligand may be conjugated to the degradation tag via a linker moiety.

As used herein, the terms "tropomyosin receptor kinase ligand" and "TRK ligand", or "TRK targeting moiety" are to be construed to encompass any molecules ranging from small molecules to large proteins that associate with or bind to TRK protein. In certain embodiments, the TRK ligand is capable of binding to a TRK protein comprising TRK, a TRK mutant, a TRK deletion, or a TRK fusion protein. The TRK ligand can be, for example but not limited to, a small molecule compound (i.e., a molecule of molecular weight less than about 1.5 kilodaltons (kDa)), a peptide or polypeptide, nucleic acid or oligonucleotide, carbohydrate such as oligosaccharides, or an antibody or fragment thereof.

TRK Ligand

The TRK ligand or targeting moiety can be a TRK kinase inhibitor or a portion of TRK kinase inhibitor. In certain embodiments, the TRK kinase inhibitor comprises one or more of (e.g., altiratinib (DCC2701, DCC-270, DP-5164) (Smith et al., 2015), sitravatinib (MGCD516) (Patwardhan et al., 2016), cabozantinib (XL-184, BMS-907351) (Fuse et al., 2017), dovitinib (TKI-258, CHIR-258) (Chong et al., 2017), entrectinib (RXDX-101) (Menichincheri et al., 2016), milciclib (PHA-848125AC) (Brasca et al., 2009), belizatinib (TSR-011) (Ricciuti et al., 2017), GZ389988 (Bailey et al., 2017a, b), pegcantratinib (Cranston et al., 2017), AZD7451 (Tatematsu et al., 2014), larotrectinib (LOXO-101; ARRY-470) (Drilon et al., 2018), TPX-0005 (Cui et al., 2016), LOXO-195 (Blake et al., 2016), regorafenib (Subbiah et al., 2017), DS-6051b (Fujiwara et al., 2018), F17752 (Amatu et al., 2016), PLX7486 (Amatu et al., 2016), AZD-6918 (Li et al., 2015), ASP7962 (Bailey et al., 2017a, b), VM902A (Bailey et al., 2017a, b), ONO-4474 (Bailey et al., 2017a, b), PF-06273340 (Skerratt et al., 2016) and GNF-8625 (Choi et al., 2015), and analogs thereof), which is capable of inhibiting the kinase activity of TRK. As used herein, a "TRK kinase inhibitor" refers to an agent that restrains, retards, or otherwise causes inhibition of a physiological, chemical or enzymatic action or function and causes a decrease in binding of at least 5%. An inhibitor can also or alternately refer to a drug, compound, or agent that prevents or reduces the expression, transcription, or translation of a gene or protein. An inhibitor can reduce or prevent the function of a protein, e.g., by binding to or activating/inactivating another protein or receptor.

In certain embodiments, the TRK ligand is derived from a TRK kinase inhibitor comprising:

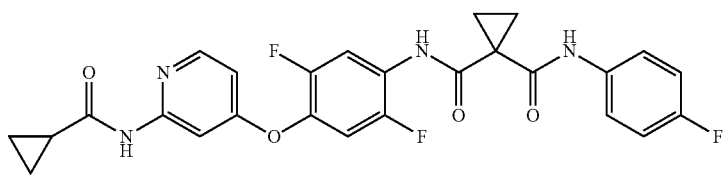

Altiratinib (DCC-2701, DCC-270, DP-5164)

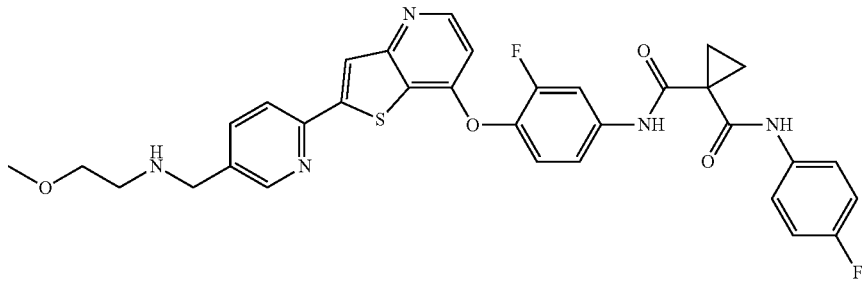

Sitravatinib (MGCD516)

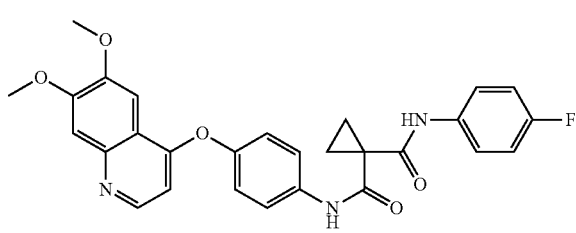

Cabozantinib (XL-184, BMS-907351)

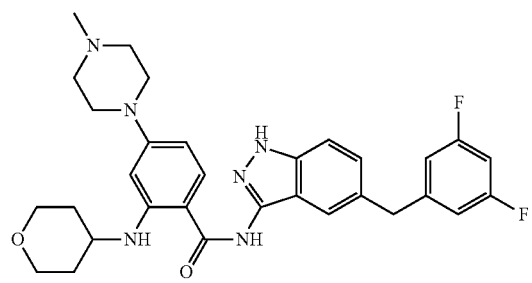

Entrectinib (RXDX-101)

-continued
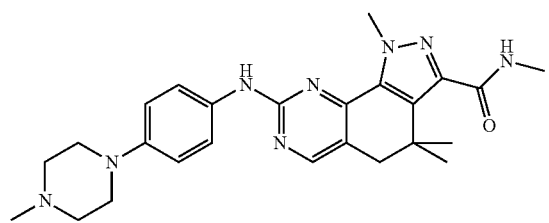
Milciclib (PHA-848125AC)
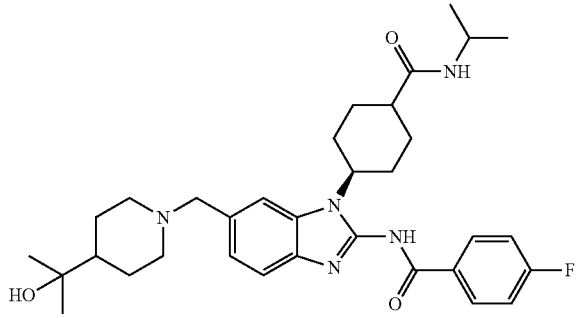
Belizatinib (TSR-011)
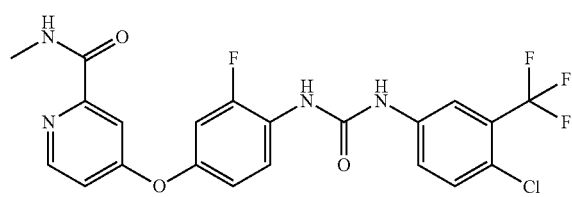
Regoratenlb
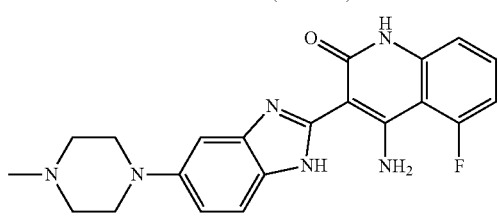
Dovitinib (TKI-258, CHIR-258)
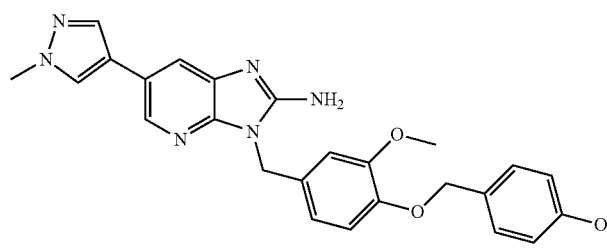
GZ389988
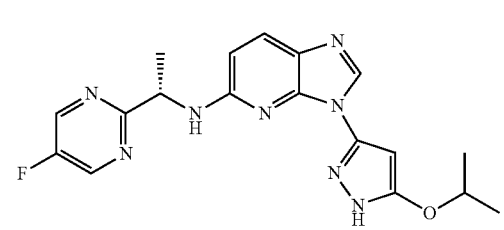
AZD7451
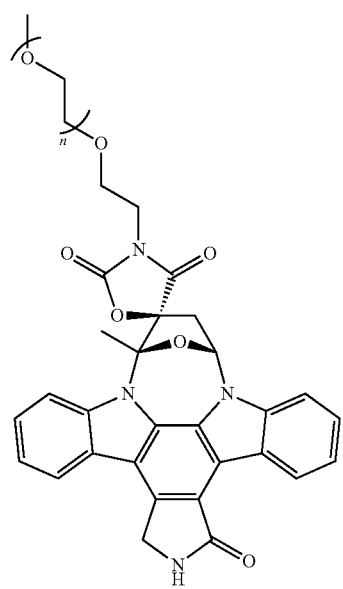
Pegcantratinib
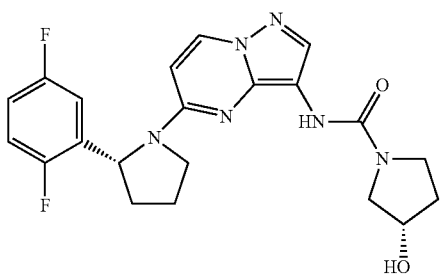
Larotrectinib (LOXO-101; ARRY-470)

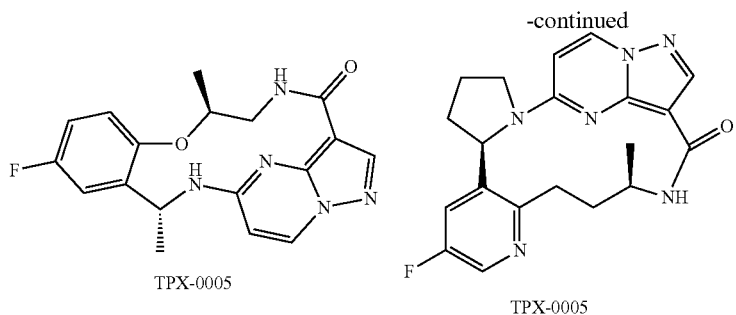

TPX-0005      TPX-0005

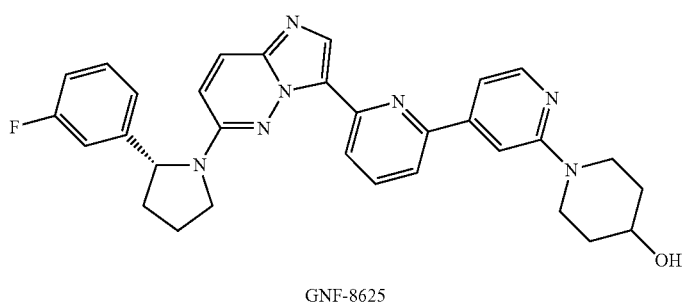

GNF-8625

In certain embodiments, the TRK ligand include, but are not limited to DS-6051b (Fujiwara et al., 2018), F17752 (Amatu et al., 2016), PLX7486 (Amatu et al., 2016), AZD-6918 (Li et al., 2015), ASP7962 (Bailey et al., 2017a, b), VMV902A (Bailey et al., 2017a, b), PF-06273340 (Skerratt et al., 2016) and ONO-4474 (Bailey et al., 2017a, b). In certain embodiments, the TRK ligand is derived from any one or more of DS-6051b (Fujiwara et al., 2018), F17752 (Amatu et al., 2016), PLX7486 (Amatu et al., 2016), AZD-6918 (Li et al., 2015), ASP7962 (Bailey et al., 2017a, b), VM902A (Bailey et al., 2017a, b), PF-06273340 (Skerratt et al., 2016) and ONO-4474 (Bailey et al., 2017a, b).

In another embodiment, the TRK ligand comprises a moiety of Formula 1;

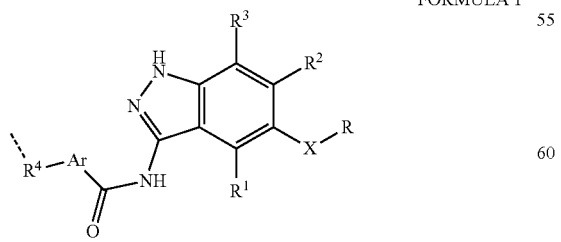

FORMULA 1

Wherein,
$R^1$, $R^2$, $R^3$, $R^4$, Ar, and X are defined as before.

In another embodiment, the TRK ligand comprises a moiety of Formula 1

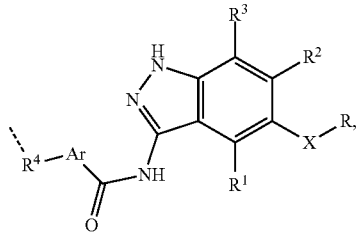

FORMULA 1 wherein
X is selected from CR'R", CO, O, S, SO, SO$_2$, and NR',
wherein
R' and R" are independently selected from hydrogen, halogen, OH, optionally substituted $C_1$-$C_8$ alkyl, optionally substituted $C_{1-8}$ alkoxy, optionally substituted $C_1$-$C_8$alkoxy$C_1$-$C_8$alkyl, optionally substituted $C_1$-$C_8$ alkylamino, optionally substituted $C_1$-$C_8$alkylamino$C_1$-$C_8$alkyl, optionally substituted $C_3$-$C_{10}$ cycloalkyl, optionally substituted $C_3$-$C_{10}$ cycloalkoxy, and optionally substituted 3-10 membered heterocyclyl; or
R' and R" together with the atom to which they are connected form an optionally substituted 3-8 membered cycloalkyl or heterocyclyl ring;
R is selected from optionally substituted $C_1$-$C_8$ alkyl, optionally substituted $C_3$-$C_{10}$ cycloalkyl, optionally substituted 3-10 membered heterocyclyl, optionally substituted aryl, and optionally substituted heteroaryl;

$R^1$, $R^2$, and $R^3$ are independently selected from hydrogen, halogen, CN, $NO_2$, $OR^5$, $SR^6$, $NR^7R^8$, $COR^5$, $CO_2R^5$, $C(O)NR^7R^8$, $SOR^5$, $SO_2R^5$, $SO_2NR^7R^8$, $NR^7C(O)R^8$, $NR^5C(O)NR^7R^8$, $NR^7SOR^8$, $NR^7SO_2R^8$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted $C_3$-$C_{10}$ cycloalkoxy, optionally substituted 3-10 membered heterocyclyl, optionally substituted $C_2$-$C_8$ alkenyl, and optionally substituted $C_2$-$C_8$ alkynyl, wherein $R^5$, $R^6$, $R^7$, and $R^8$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_{10}$ cycloalkyl, optionally substituted 3-10 membered heterocyclyl, optionally substituted $C_2$-$C_8$ alkenyl, optionally substituted $C_2$-$C_8$ alkynyl, optionally substituted aryl, or optionally substituted heteroaryl, or $R^7$ and $R^8$ together with the atom to which they are connected form an optionally substituted 4-8 membered heterocyclyl ring;

$R^4$ is connected to the linker moiety of the bivalent compound, and is selected from a bond, $OR^9$, $SR^9$, $NR^{10}R^{11}$, $COR^9$, $CO_2R^9$, $CONR^{10}R^{11}$, $SOR^9$, $SO_2R^9$, $SO_2NR^{10}R^{11}$, $NR^{10}COR^{11}$, $NR^9CONR^{10}R^{11}$, $NR^{10}SOR^{11}$, $NR^{10}SO_2R^{11}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, aryl, and optionally substituted heteroaryl, wherein $R^9$, $R^{10}$, and $R^{11}$ are independently selected from null, a bond, hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, or $R^{10}$ and $R^{11}$ together with the atom to which they are connected form a 4-8 membered cycloalkyl or heterocyclyl ring; and Ar is selected from aryl and heteroaryl group, each of which is optionally substituted with one or more substituents independently selected from hydrogen, halogen, CN, $NO_2$, $OR^{12}$, $SR^{12}$, $NR^{13}R^{14}$, $COR^{12}$, $CO_2R^{12}$, $CONR^{13}R^{14}$, $SOR^{12}$, $SO_2R^{12}$, $SO_2NR^{13}R^{14}$, $NR^{13}COR^{14}$, $NR^{15}C(O)NR^{13}R^{14}$, $NR^{13}SOR^{14}$, $NR^3SO_2R^{14}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^{12}$, $R^{13}$, $R^{14}$, and $R^{15}$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, or $R^{13}$ and $R^{14}$ together with the atom to which they are connected form a 4-8 membered cycloalkyl or heterocyclyl ring.

In one embodiment,

X is selected from CR'R", O, and NR', wherein

R' and R" are independently selected from hydrogen, F, OH, optionally substituted $C_1$-$C_3$ alkyl, and optionally substituted $C_1$-$C_3$ alkoxy, or R' and R" together with the atom to which they are connected form an optionally substituted 3-6 membered cycloalkyl or heterocyclyl ring.

In another embodiment, X is selected from $CH_2$, cyclopropylene, CHF, $CF_2$, O, NH, $NCH_3$, $NCH_2CH_3$, and N-isopropyl.

In another embodiment, R is selected from optionally substituted $C_3$-$C_8$ cycloalkyl, optionally substituted 3-8 membered heterocyclyl, optionally substituted aryl, and optionally substituted heteroaryl.

In another embodiment, R is selected from optionally substituted phenyl and optionally substituted heteroaryl.

In another embodiment, X is $CH_2$; and R is 3,5-difluorophenyl.

In another embodiment, $R^1$, $R^2$, and $R^3$ are independently selected from hydrogen, F, Cl, and OH.

In another embodiment, $R^4$—Ar is selected from a moiety of formulae A1, A2, A3, and A4:

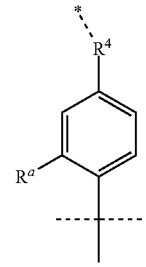

FORMULA A1

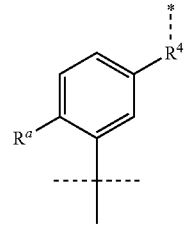

FORMULA A2

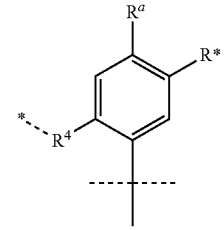

FORMULA A3

FORMULA A4

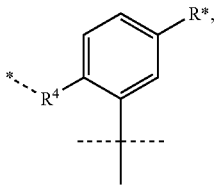

wherein
* indicates the connection to the linker moiety of the bivalent compound; and $R^a$ is selected from hydrogen, halogen, CN, $NO_2$, $OR^{12}$, $SR^{12}$, $NR^{13}R^{14}$, $COR^{12}$, $CO_2R^{12}$, $CONR^{13}R^{14}$, $SOR^{12}$, $SO_2R^{12}$, $SO_2NR^{13}R^{14}$, $NR^{13}COR^{14}$, $NR^{15}C(O)NR^{13}R^{14}$, $NR^{13}SOR^{14}$, $NR^{13}SO_2R^{14}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^{12}$, $R^{13}$, $R^{14}$, and $R^{15}$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, aryl, and optionally substituted heteroaryl, or $R^{13}$ and $R^{14}$ together with the atom to which they are connected form a 4-8 membered cycloalkyl or heterocyclyl ring.

In another embodiment, $R^4$—Ar is selected from a moiety of formulae A1, A3, A3 and A4:

FORMULA A1

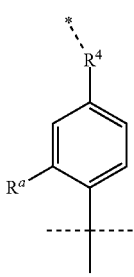

FORMULA A2

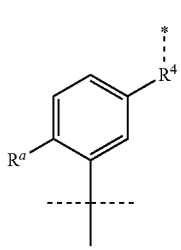

FORMULA A3

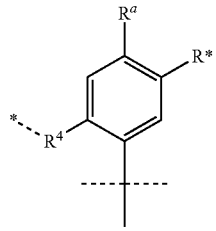

FORMULA A4

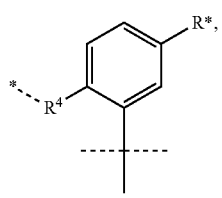

wherein
* indicates the connection to the linker moiety of the bivalent compound; and $R^a$ is selected from hydrogen, halogen, $NR^{13}R^{14}$, and $N^{13}COR^{14}$, wherein $R^{13}$ and $R^{14}$ are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$alkylamino$C_1$-$C_8$alkyl, optionally substituted arylalkyl, optionally substituted heteroarylalkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, phenyl, and optionally substituted $C_5$-$C_6$ heteroaryl, or $R^{13}$ and $R^{14}$ together with the atom to which they are connected form a 4-8 membered cycloalkyl or heterocyclyl ring.

In another embodiment, $R^a$ is (tetrahydro-2H-pyran-4-yl)amino.

In another embodiment, the TRK ligand comprises a moiety of Formula 2;

FORMULA 2

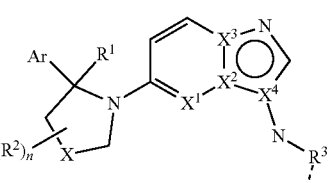

Wherein,
$R^1$, $R^2$, $R^3$, $R^4$, $Ar^1$, $Ar^2$, X, $X^1$, $X^2$, $X^3$, $X^4$ and n are defined as before.

In another embodiment, the TRK ligand comprises a moiety of Formula 2:

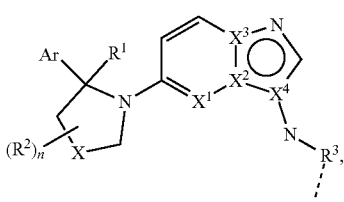

FORMULA 2 wherein
$X^1$, $X^2$, $X^3$, and $X^4$ are independently selected from C, CR', and N (preferably, $X^1$ is selected from CR' and N, $X^2$, $X^3$, and $X^4$ are independently selected from C and N), wherein
R' is selected from hydrogen, halogen, CN, $NO_2$, optionally substituted $C_1$-$C_6$ alkyl, optionally substituted $C_3$-$C_6$ cycloalkyl, and optionally substituted 3-6 membered heterocyclyl;
X is selected from null, a bond, $C(R^2)_2$, $C(R^2)_2C(R^2)_2$, CO, $C(R^2)_2CO$, $CONR^2$, $C(R^2)_2O$, $C(R^2)_2NR^2$, and $CH_2NR^2$;
$R^1$ and $R^2$, at each occurrence, are independently selected from hydrogen, halogen, OH, $NH_2$, CN, $NO_2$, optionally substituted $C_1$-$C_4$ alkyl, optionally substituted $C_1$-$C_4$ alkoxy, optionally substituted $C_1$-$C_4$ alkylamino, optionally substituted $C_1$-$C_4$ alkoxyalkyl, optionally substituted $C_1$-$C_4$ haloalkyl, optionally substituted $C_1$-$C_4$ hydroxyalkyl, optionally substituted $C_1$-$C_4$alkylamino$C_1$-$C_4$alkyl, optionally substituted $C_3$-$C_6$ cycloalkyl, optionally substituted $C_3$-$C_6$ cycloalkoxy, and optionally substituted 3-6 membered heterocyclyl;
n is 1 to 4;
$R^3$ is connected to the linker moiety of the bivalent compound either directly or through $R^4$;
$R^3$ and $R^4$ are independently selected from null, a bond, $OR^5$, $SR^5$, $NR^6R^7$, $COR^5$, $CO_2R^5$, $CONR^6R^7$, $SOR^5$, $SO_2R^5$, $SO_2NR^6R^7$, $NR^6COR^7$, $NR^5C(O)NR^6R^7$, $NR^6SOR^7$, $NR^6SO_2R^7$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein
$R^5$, $R^6$ and $R^7$ are independently selected from null, a bond, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or
$R^6$ and $R^7$ together with the atom to which they are connected form a 3-8 membered cycloalkyl or 4-8 membered heterocyclyl ring; and
$Ar^1$ and $Ar^2$ are independently selected from aryl and heteroaryl, each of which is optionally substituted with one or more substituents independently selected from halogen, CN, $NO_2$, $OR^{10}$, $NR^{11}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $NR^{10}C(O)NR^{11}R^{12}$, $NR^{11}SOR^{12}$, $NR^{11}SO_2R^{12}$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, optionally substituted $C_2$-$C_8$ alkynyl, optionally substituted aryl, and optionally substituted heteroaryl, wherein
$R^{10}$, $R^{11}$, and $R^{12}$ are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_7$ cycloalkyl, optionally substituted 3-7 membered heterocyclyl, optionally substituted aryl, and optionally substituted heteroaryl, or
$R^{11}$ and $R^{12}$ together with the atom to which they are connected form a 4-8 membered cycloalkyl or heterocyclyl ring.

In one embodiment, $X^1$ is selected from CR' and N, wherein R' is selected from hydrogen, F, Cl, $CH_3$, $CF_3$, and cyclopropyl.

In another embodiment, $X^2$, $X^3$, and $X^4$ are independently selected from C and N.

In another embodiment, X is selected from a bond, $CH_2$, $CH_2CH_2$, CO, $CH_2CO$, CONH, $CONCH_3$, $CH_2O$, $CH_2NH$, and $CH_2NCH_3$.

In another embodiment, $R^1$ and $R^2$, at each occurrence, are independently selected from hydrogen, F, Cl, OH, optionally substituted $C_1$-$C_4$ alkyl, optionally substituted $C_1$-$C_4$ alkoxy, optionally substituted $C_1$-$C_4$ alkylamino, optionally substituted $C_1$-$C_4$ haloalkyl, optionally substituted $C_3$-$C_6$ cycloalkyl, optionally substituted $C_3$-$C_6$ cycloalkoxy, and optionally substituted 3-6 membered heterocyclyl.

In another embodiment, X is $CH_2$; and $Ar^1$ is 3-fluorophenyl.

In another embodiment, $R^3$ is connected to the linker moiety of the bivalent compound directly, and $R^3$ is selected from null, a bond, $OR^5$, $SR^5$, $NR^6R^7$, $COR^5$, $CO_2R^5$, $CONR^6R^7$, $SOR^5$, $SO_2R^5$, $SO_2NR^6R^7$, $NR^6COR^7$, $NR^5C(O)NR^6R^7$, $NR^6SOR^7$, $NR^6SO_2R^7$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein
$R^5$, $R^6$ and $R^7$ are independently selected from null, a bond, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or
$R^6$ and $R^7$ together with the atom to which they are connected form a 4-8 membered cycloalkyl or heterocyclyl ring.

In another embodiment, $R^3$ is connected to the linker moiety of the bivalent compound through $R^4$, and $R^3$ and $R^4$ are independently selected from null, a bond, $OR^5$, $SR^5$, $NR^6R^7$, $COR^5$, $CO_2R^5$, $CONR^6R^7$, $SOR^5$, $SO_2R^5$, $SO_2NR^6R^7$, $NR^6COR^7$, $NR^5C(O)NR^6R^7$, $NR^6SOR^7$, $NR^6SO_2R^7$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^5$, $R^6$ and $R^7$ are independently selected from null, a bond, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or $R^6$ and $R^7$ together with the atom to which they are connected form a 4-8 membered cycloalkyl or heterocyclyl ring.

In another embodiment, $Ar^1$ is selected from $C_6$-$C_{10}$ aryl and $C_5$-$C_{10}$ heteroaryl, each of which is optionally substituted with one or more substituents independently selected from F, Cl, CN, $NO_2$, $OR^{10}$, $NR^{11}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $NR^{10}C(O)NR^{11}R^{12}$, $NR^{11}SOR^{12}$, $NR^{11}SO_2R^{12}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl, wherein $R^{10}$, $R^{11}$, and $R^{12}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl, or $R^{11}$ and $R^{12}$ together with the atom to which they are connected form a 4-8 membered cycloalkyl or heterocyclyl ring.

In another embodiment, $Ar^2$ is selected from $C_6$-$C_{10}$ aryl and $C_5$-$C_{10}$ heteroaryl, each of which is optionally substituted with one or more substituents independently selected from F, Cl, CN, $NO_2$, $OR^{10}$, $NR^{11}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $NR^{10}C(O)NR^{11}R^{12}$, $NR^{11}SOR^{12}$, $NR^{11}SO_2R^{12}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl, wherein $R^{10}$, $R^{11}$, and $R^{12}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl, or $R^{11}$ and $R^{12}$ together with the atom to which they are connected form a 4-8 membered cycloalkyl or heterocyclyl ring.

In another embodiment, $R^3$—$Ar^2$ is selected from a moiety of formulae B1 and B2:

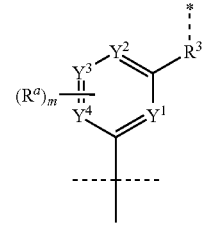

FORMULA B1

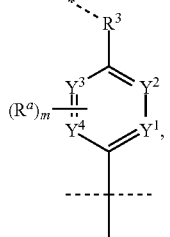

FORMULA B2 wherein

* indicates the connection to the linker moiety of the bivalent compound;

$Y^1$, $Y^2$, $Y^3$, and $Y^4$ are independently selected from CH and N, with the proviso that up to 3 of $Y^1$, $Y^2$, $Y^3$, and $Y^4$ are N;

each $R^a$ is independently selected from hydrogen, halogen, CN, $NO_2$, $OR^{12}$, $SR^{12}$, $NR^{13}R^{14}$, $COR^{12}$, $CO_2R^{12}$, $CONR^{13}R^{14}$, $SOR^{12}$, $SO_2R^{12}$, $SO_2NR^{13}R^{14}$, $NR^{13}COR^{14}$, $NR^{15}C(O)NR^{13}R^{14}$, $NR^{13}SOR^{14}$, $NR^{13}SO_2R^{14}$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^{12}$, $R^{13}$, $R^{14}$, and $R^{15}$ are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, or R[13] and R[14] together with the atom to which they are connected form a 4-8 membered cycloalkyl or heterocyclyl ring;

m is 0 to 4; and

R[3] is the same as defined in Formula 2.

In another embodiment, R[3]—Ar[2] is selected from a moiety of formula B3:

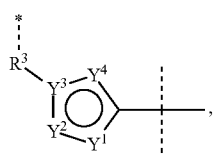

FORMULA B3 wherein
* indicates the connection to the linker moiety of the bivalent compound;

$Y^1$, $Y^2$, $Y^3$, and $Y^4$ are independently selected from $CR^a$, N, O, and S, with the proviso that up to 3 of $Y^1$, $Y^2$, $Y^3$, and $Y^4$ are N;

each $R^a$ is independently selected from hydrogen, halogen, CN, NO$_2$, OR[12], SR[12], NR[13]R[14], COR[12], CO$_2$R[12], CONR[13]R[14], SOR[12], SO$_2$R[12], SO$_2$NR[13]R[14], NR[13]COR[14], NR[15]C(O)NR[13]R[14], NR[13]SOR[14], NR[13]SO$_2$R[14], optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein R[12], R[13], R[14], and R[15] are independently selected from hydrogen, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$alkylamino$C_1$-$C_8$alkyl, optionally substituted $C_3$-$C_8$ cycloalkyl, optionally substituted $C_3$-$C_8$ cycloalkoxy, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, or R[13] and R[14] together with the atom to which they are connected form a 4-8 membered cycloalkyl or heterocyclyl ring;

m is 0 to 4; and

R[3] is the same as defined in Formula 2.

In another embodiment, $X^1$ is N; $X^2$ is N; $X^3$ is C; $X^4$ is C; X is CH$_2$; Ar[1] is 3-fluorophenyl; and Ar[2] is 2-pyridyl.

In another embodiment, the TRK ligand comprises a moiety of Formula 3;

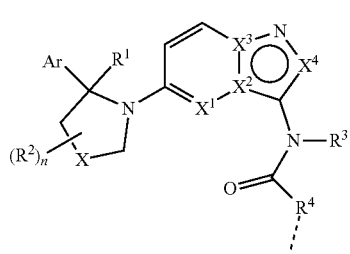

FORMULA 3

Wherein,
R[1], R[2], R[3], R[4], Ar, X, $X^1$, $X^2$, $X^3$, $X^4$ and n are defined as before.

In another embodiment, the TRK ligand comprises a moiety of FORMULA 3:

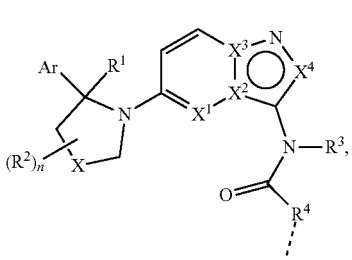

FORMULA 3 wherein
$X^1$, $X^2$, $X^3$, and $X^4$ are independently selected from C, CR', and N (preferably, $X^1$ and $X^4$ are independently selected from CR' and N; $X^2$ and $X^3$ are independently selected from C and N), wherein R' is selected from hydrogen, halogen, CN, NO$_2$, and optionally substituted $C_1$-$C_6$ alkyl, $C_3$-$C_6$ cycloalkyl, or 3-6 membered heterocyclyl;

X is selected from null, a bond, C(R$^2$)$_2$, C(R$^2$)$_2$C(R$^2$)$_2$, CO, C(R$^2$)$_2$CO, NR$^2$CO, OC(R$^2$)$_2$, and NR$^2$C(R$^2$)$_2$; R[1] and each R[2] are independently selected from hydrogen, halogen, OH, NH$_2$, CN, NO$_2$, optionally substituted $C_1$-$C_4$ alkyl, optionally substituted $C_1$-$C_4$ alkoxy, optionally substituted $C_1$-$C_4$ alkylamino, optionally substituted $C_1$-$C_4$ alkoxyalkyl, optionally substituted $C_1$-$C_4$ haloalkyl, optionally substituted $C_1$-$C_4$ hydroxyalkyl, optionally substituted $C_1$-$C_4$alkylamino$C_1$-$C_4$alkyl, optionally substituted $C_3$-$C_6$ cycloalkyl, optionally substituted $C_3$-$C_6$ cycloalkoxy, and optionally substituted 3-6 membered heterocyclyl;

n is 1 to 4;

R[3] is selected from hydrogen, optionally substituted $C_1$-$C_6$ alkyl, optionally substituted $C_3$-$C_6$ cycloalkyl, optionally substituted 3-6 membered heterocyclyl, optionally substituted $C_1$-$C_6$ alkoxyalkyl, optionally substituted $C_1$-$C_6$ haloalkyl, optionally substituted $C_1$-$C_6$ hydroxyalkyl, and optionally substituted $C_1$-$C_6$alkylamino$C_1$-$C_6$alkyl;

R[4] is connected to the linker moiety of the bivalent compound either directly or through R[5], wherein R[4] and R[5] are independently selected from null, OR[6], SR[6], NR[7]R[8], COR[6], CO$_2$R[6], CONR[7]R[8], SOR[6], SO$_2$R[6], SO$_2$NR[7]R[8], NR[7]COR[8], NR[9]C(O)NR[7]R[8], NR[7]SOR[8], NR[7]SO$_2$R[8], optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein R[6], R[7], R[8], and R[9] are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or $R^7$ and $R^8$ together with the atom to which they are connected form a 4-8 membered cycloalkyl or heterocyclyl ring;

Ar is selected from aryl and heteroaryl, each of which is optionally substituted with one or more substituents independently selected from halogen, CN, $NO_2$, $OR^{10}$, $SR^{10}$, $NR^{11}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $NR^{10}C(O)NR^{11}R^{12}$, $NR^{11}SOR^{12}$, $NR^{11}SO_2R^{12}$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, optionally substituted $C_2$-$C_8$ alkynyl, optionally substituted aryl, and optionally substituted heteroaryl, wherein $R^{10}$, $R^{11}$, and $R^{12}$ are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_7$ cycloalkyl, optionally substituted 3-7 membered heterocyclyl, optionally substituted aryl, and optionally substituted heteroaryl, or $R^{11}$ and $R^{12}$ together with the atom to which they are connected form a 4-8 membered cycloalkyl or heterocyclyl rings.

In one embodiment, $X^1$ and $X^4$ is selected from CR' and N, and R' is selected from hydrogen, F, Cl, $CH_3$, $CF_3$, and cyclopropyl.

In another embodiment, $X^2$ and $X^3$ are independently selected from C and N.

In another embodiment, X is selected from a bond, $CH_2$, $CH_2CH_2$, CO, $CH_2CO$, CONH, $CONCH_3$, $CH_2O$, $CH_2NH$, and $CH_2NCH_3$.

In another embodiment, $R^1$ and each $R^2$ are independently selected from hydrogen, F, Cl, OH, optionally substituted $C_1$-$C_4$ alkyl, optionally substituted $C_1$-$C_4$ alkoxy, optionally substituted $C_1$-$C_4$ alkylamino, optionally substituted $C_1$-$C_4$ haloalkyl, optionally substituted $C_3$-$C_6$ cycloalkyl, optionally substituted $C_3$-$C_6$ cycloalkoxy, and optionally substituted 3-6 membered heterocyclyl.

In another embodiment, $R^3$ is selected from hydrogen, $CH_3$, $CH_2CH_3$, propyl, isopropyl, cyclopropyl, $CH_2F$, $CHF_2$, and $CF_3$.

In another embodiment, $R^4$ is connected to the linker moiety of the bivalent compound directly, and $R^4$ is selected from null, $OR^6$, $SR^6$, $NR^7R^8$, $COR^6$, $CO_2R^6$, $CONR^7R^8$, $SOR^6$, $SO_2R^6$, $SO_2NR^7R^8$, $NR^7COR^8$, $NR^9C(O)NR^7R^8$, $NR^7SOR^8$, $NR^7SO_2R^8$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^6$, $R^7$, $R^8$, and $R^9$ are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, heteroarylalkyl, optionally substituted aryl, and optionally substituted heteroaryl, or $R^7$ and $R^8$ together with the atom to which they are connected form a 4-8 membered cycloalkyl or heterocyclyl ring.

In another embodiment, $R^4$ is connected to the linker moiety of the bivalent compound through $R^5$, and $R^4$ and $R^5$ are independently selected from null, $OR^6$, $SR^6$, $NR^7R^8$, $COR^6$, $CO_2R^6$, $CONR^7R^8$, $SOR^6$, $SO_2R^6$, $SO_2NR^7R^8$, $NR^7COR^8$, $NR^9C(O)NR^7R^8$, $NR^7SOR^8$, $NR^7SO_2R^8$, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted $C_3$-$C_8$ cycloalkyl, optionally substituted 3-8 membered heterocyclyl, optionally substituted $C_2$-$C_8$ alkenyl, optionally substituted $C_2$-$C_8$ alkynyl, optionally substituted aryl, and optionally substituted heteroaryl, wherein $R^6$, $R^7$, $R^8$, and $R^9$ are independently selected from null, hydrogen, optionally substituted $C_1$-$C_8$ alkyl, optionally substituted $C_2$-$C_8$ alkenyl, optionally substituted $C_2$-$C_8$ alkynyl, optionally substituted $C_3$-$C_6$ cycloalkyl, optionally substituted 3-8 membered heterocyclyl, optionally substituted heterocycloalkyl, optionally substituted arylalkyl, optionally substituted heteroarylalkyl, optionally substituted aryl, and optionally substituted heteroaryl, or $R^7$ and $R^8$ together with the atom to which they are connected form a 4-8 membered cycloalkyl or heterocyclyl ring.

In another embodiment,

Ar is selected from aryl and heteroaryl, each of which is optionally substituted with one or more substituents independently selected from F, Cl, CN, $NO_2$, $OR^{10}$, $NR^{11}R^{12}$, $COR^{10}$, $CO_2R^{10}$, $CONR^{11}R^{12}$, $SOR^{10}$, $SO_2R^{10}$, $SO_2NR^{11}R^{12}$, $NR^{11}COR^{12}$, $NR^{10}C(O)NR^{11}R^{12}$, $NR^{11}SOR^{12}$, $NR^{11}SO_2R^{12}$, optionally substituted $C_1$-$C_6$ alkyl, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$alkylamino$C_1$-$C_6$alkyl, optionally substituted $C_3$-$C_7$ cycloalkyl, optionally substituted 3-7 membered heterocyclyl, optionally substituted $C_2$-$C_6$ alkenyl, optionally substituted $C_2$-$C_6$ alkynyl, optionally substituted aryl, and optionally substituted $C_4$-$C_5$ heteroaryl, wherein $R^{10}$, $R^{11}$, and $R^{12}$ are independently selected from null, hydrogen, optionally substituted $C_1$-$C_6$ alkyl, optionally substituted $C_2$-$C_6$ alkenyl, optionally substituted $C_2$-$C_6$ alkynyl, optionally substituted $C_3$-$C_7$ cycloalkyl, optionally substituted 3-7 membered heterocyclyl, optionally substituted aryl, and optionally substituted heteroaryl, or $R^{11}$ and $R^{12}$ together with the atom to which they are connected form a 4-8 membered cycloalkyl or heterocyclyl ring.

In another embodiment, the TRK ligand is selected from the group consisting of:

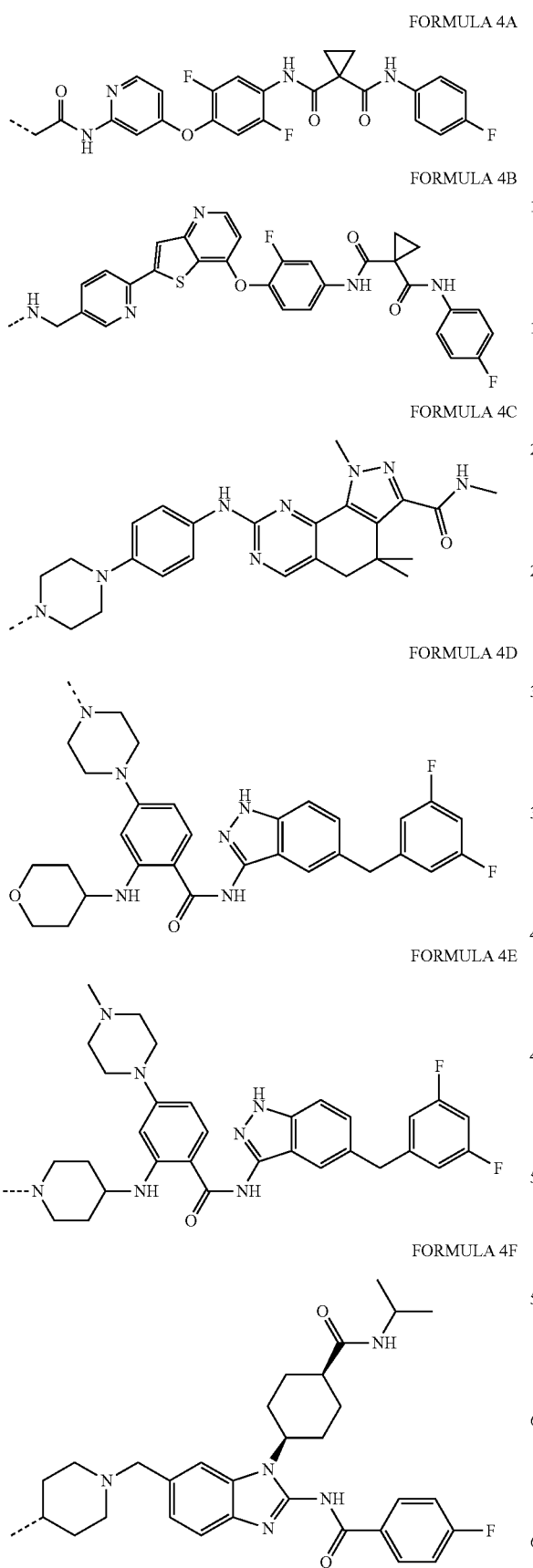

-continued

FORMULA 4M

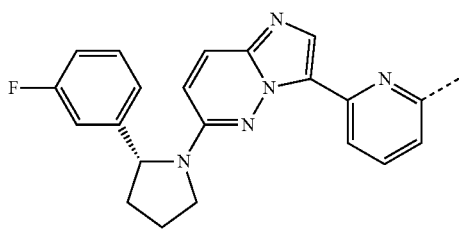

Degradation Tag

As used herein, the term "degradation tag" refers to a compound, which associates with or binds to an ubiquitin ligase for recruitment of the corresponding ubiquitination machinery to TRK or is a hydrophobic group or a tag that leads to misfolding of the TRK protein and subsequent degradation at the proteasome or loss of function.

In some embodiments, the degradation tag is a moiety selected from the group consisting of FORMULAE 5A, 5B, 5C, and 5D:

FORMULA 5A

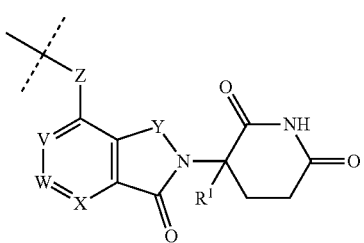

FORMULA 5B

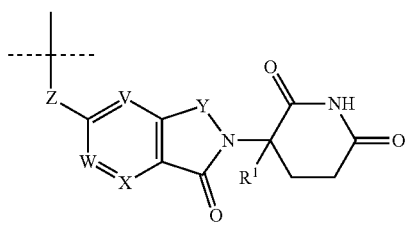

FORMULA 5C

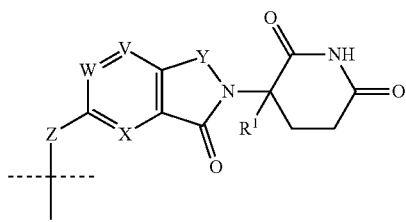

FORMULA 5D

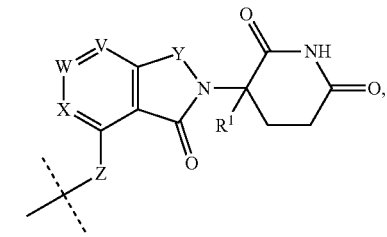

wherein
V, W, and X are independently selected from $CR^2$ and N;
Y is selected from CO, $CR^3R^4$, and N=N;
Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH=CH, C≡C, NH and O;

$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;

$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and $R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

In some embodiments, the degradation tag is a moiety selected from the group consisting of FORMULAE 5A, 5B, 5C, and 5D:

FORMULA 5A

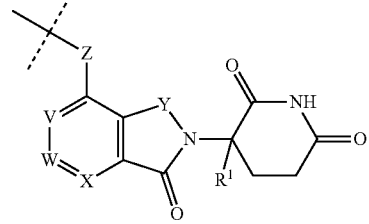

FORMULA 5B

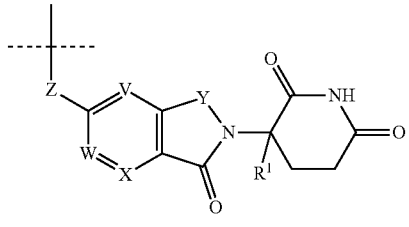

FORMULA 5C

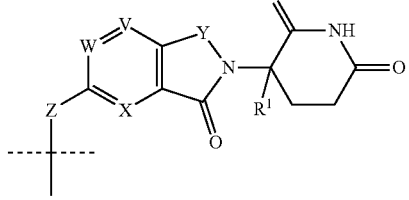

-continued

FORMULA 5D

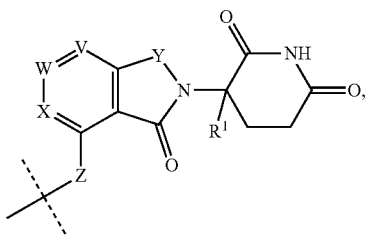

wherein,
V, W, and X are independently selected from $CR^2$ and N;
Y is selected from CO and $CH_2$;
Z is selected from $CH_2$, NH and O;
$R^1$ is selected from hydrogen, $C_1$-$C_5$ alkyl and halogen; and
$R^2$ is selected from hydrogen, halogen, and $C_1$-$C_5$ alkyl.

In one embodiment, the degradation tag is a moiety selected from the group consisting of FORMULA 5B and FORMULA 5C.

In some embodiments, the degradation tag is a moiety selected from the group consisting of FORMULAE 5E, 5F, 5G, 5H, and 5I:

FORMULA 5E

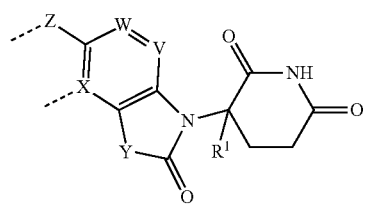

FORMULA 5F

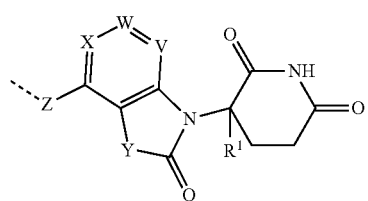

FORMULA 5G

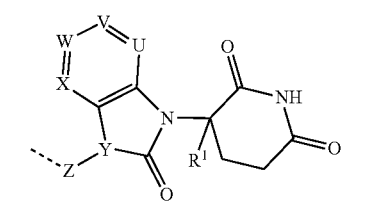

FORMULA 5H

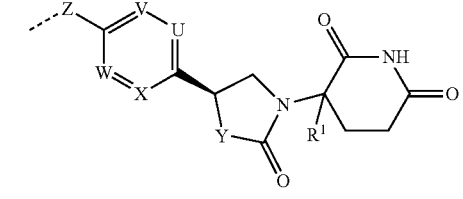

FORMULA 5I

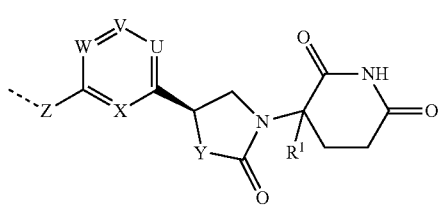

wherein
U, V, W, and X are independently selected from $CR^2$ and N;
Y is selected from $CR^3R^4$, $NR^3$ and O; preferably, Y is selected from $CH_2$, NH, $NCH_3$ and O;
Z is selected from null, CO, $CR^5R^6$, $NR^5$, O, optionally substituted $C_1$-$C_{10}$ alkylene, optionally substituted $C_1$-$C_{10}$ alkenylene, optionally substituted $C_1$-$C_{10}$ alkynylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl; preferably, Z is selected from null, $CH_2$, CH=CH, C≡C, NH and O;
$R^1$, and $R^2$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl;
$R^3$, and $R^4$ are independently selected from hydrogen, halogen, cyano, nitro, optionally substituted $C_1$-$C_6$ alkyl, optionally substituted 3 to 6 membered carbocyclyl, and optionally substituted 4 to 6 membered heterocyclyl; or $R^3$ and $R^4$ together with the atom to which they are connected form a 3-6 membered carbocyclyl, or 4-6 membered heterocyclyl; and
$R^5$ and $R^6$ are independently selected from null, hydrogen, halogen, oxo, hydroxyl, amino, cyano, nitro, optionally substituted $C_1$-$C_6$ alkyl, optionally substituted 3 to 6 membered carbocyclyl, and optionally substituted 4 to 6 membered heterocyclyl; or $R^5$ and $R^6$ together with the atom to which they are connected form a 3-6 membered carbocyclyl, or 4-6 membered heterocyclyl.

In one embodiment, the degradation tag is a moiety of FORMULA 6A:

FORMULA 6A

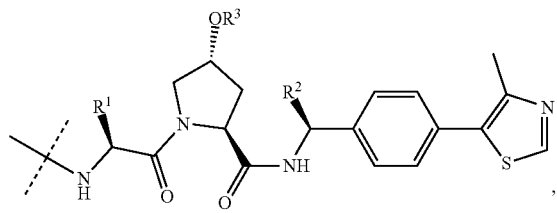

wherein

R¹ and R² are independently selected from hydrogen, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; and R³ is hydrogen, optionally substituted $C(O)C_1$-$C_8$ alkyl, optionally substituted $C(O)C_1$-$C_8$alkoxy$C_1$-$C_8$alkyl, optionally substituted $C(O)C_1$-$C_8$ haloalkyl, optionally substituted $C(O)C_1$-$C_8$ hydroxyalkyl, optionally substituted $C(O)C_1$-$C_8$ aminoalkyl, optionally substituted $C(O)C_1$-$C_8$alkylamino$C_1$-$C_8$alkyl, optionally substituted $C(O)C_3$-$C_7$ cycloalkyl, optionally substituted C(O)(3-7 membered heterocyclyl), optionally substituted $C(O)C_2$-$C_8$ alkenyl, optionally substituted $C(O)C_2$-$C_8$ alkynyl, optionally substituted $C(O)OC_1$-$C_8$alkoxy$C_1$-$C_8$alkyl, optionally substituted $C(O)OC_1$-$C_8$ haloalkyl, optionally substituted $C(O)OC_1$-$C_8$ hydroxyalkyl, optionally substituted $C(O)OC_1$-$C_8$aminoalkyl, optionally substituted $C(O)OC_1$-$C_8$alkylamino$C_1$-$C_8$alkyl, optionally substituted $C(O)OC_3$-$C_7$cycloalkyl, optionally substituted C(O)O(3-7 membered heterocyclyl), optionally substituted $C(O)OC_2$-$C_8$ alkenyl, optionally substituted $C(O)OC_2$-$C_8$ alkynyl, optionally substituted $C(O)NC_1$-$C_8$alkoxy$C_1$-$C_8$alkyl, optionally substituted $C(O)NC_1$-$C_8$ haloalkyl, optionally substituted $C(O)NC_1$-$C_8$ hydroxyalkyl, optionally substituted $C(O)NC_1$-$C_8$ aminoalkyl, optionally substituted $C(O)NC_1$-$C_8$alkylamino$C_1$-$C_8$alkyl, optionally substituted $C(O)NC_3$-$C_7$ cycloalkyl, optionally substituted C(O)N(3-7 membered heterocyclyl), optionally substituted $C(O)NC_2$-$C_8$ alkenyl, optionally substituted $C(O)NC_2$-$C_8$ alkynyl, optionally substituted $P(O)(OH)_2$, optionally substituted $P(O)(OC_1$-$C_8$alkyl$)_2$, and optionally substituted $P(O)(OC_1$-$C_8$ aryl$)_2$.

In one embodiment, the degradation tag is a moiety selected from the group consisting of FORMULAE 6B, 6C, 6D, 6E and 6F:

FORMULA 6B

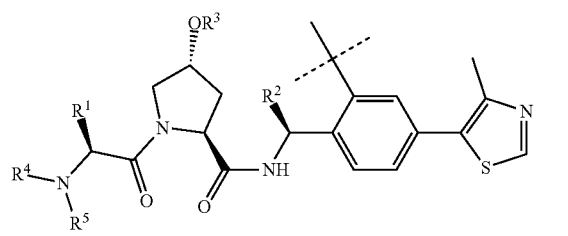

FORMULA 6C

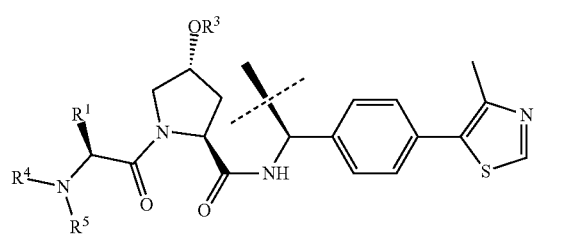

FORMULA 6D

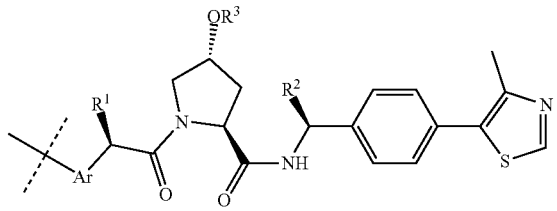

FORMULA 6E

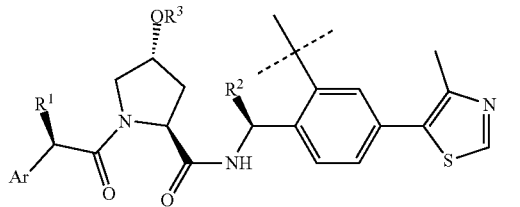

FORMULA 6F

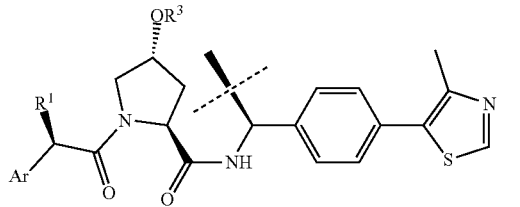

wherein

R¹ and R² are independently selected from hydrogen, halogen, OH, $NH_2$, CN, optionally substituted $C_1$-$C_8$ alkyl, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_1$-$C_8$ aminoalkyl, optionally substituted $C_1$-$C_8$alkylamino$C_1$-$C_8$alkyl, optionally substituted $C_3$-$C_7$ cycloalkyl, optionally substituted 3-7 membered heterocyclyl, optionally substituted $C_2$-$C_8$ alkenyl, and optionally substituted $C_2$-$C_8$ alkynyl; (preferably, R¹ is selected from iso-propyl or tert-butyl; and R² is selected from hydrogen or methyl);

R³ is hydrogen, optionally substituted $C(O)C_1$-$C_8$ alkyl, optionally substituted $C(O)C_1$-$C_8$alkoxy$C_1$-$C_8$alkyl, optionally substituted $C(O)C_1$-$C_8$ haloalkyl, optionally substituted $C(O)C_1$-$C_8$ hydroxyalkyl, optionally substituted $C(O)C_1$-$C_8$ aminoalkyl, optionally substituted $C(O)C_1$-$C_8$alkylamino$C_1$-$C_8$alkyl, optionally substituted $C(O)C_3$-$C_7$ cycloalkyl, optionally substituted C(O)(3-7 membered heterocyclyl), optionally substituted $C(O)C_2$-$C_8$ alkenyl, optionally substituted C(O) $C_2$-$C_8$ alkynyl, optionally substituted $C(O)OC_1$-$C_8$alkoxy$C_1$-$C_8$alkyl, optionally substituted $C(O)OC_1$-$C_8$ haloalkyl, optionally substituted $C(O)OC_1$-$C_8$ hydroxyalkyl, optionally substituted $C(O)OC_1$-$C_8$ aminoalkyl, optionally substituted $C(O)OC_1$-$C_8$alkylamino$C_1$-$C_8$alkyl, optionally substituted $C(O)OC_3$-$C_7$ cycloalkyl, optionally substituted C(O)O(3-7 membered heterocyclyl), optionally substituted $C(O)OC_2$-$C_8$ alkenyl, optionally substituted $C(O)OC_2$-$C_8$ alkynyl, optionally substituted $C(O)NC_1$-$C_8$alkoxy$C_1$-$C_8$alkyl, optionally substituted $C(O)NC_1$-$C_8$ haloalkyl, optionally substituted $C(O)NC_1$-$C_8$ hydroxyalkyl, optionally substituted $C(O)NC_1$-$C_8$ aminoalkyl, optionally substituted $C(O)NC_1$-$C_8$alkylamino$C_1$-$C_8$alkyl, optionally substituted C(O)NC$_3$-C$_7$ cycloalkyl, optionally substituted C(O)N(3-7 membered heterocyclyl), optionally substituted C(O)NC$_2$-C$_8$ alkenyl, optionally substituted C(O)NC$_2$-C$_8$ alkynyl, optionally substituted P(O)(OH)$_2$, optionally substituted P(O)(OC$_1$-C$_8$ alkyl)$_2$, and optionally substituted P(O)(OC$_1$-C$_8$ aryl)$_2$; and R$^4$ and R$^5$ are independently selected from hydrogen, COR$^6$, CO$_2$R$^6$, CONR$^6$R$^7$, SOR$^6$, SO$_2$R$^6$, SO$_2$NR$^6$R$^7$, optionally substituted C$_1$-C$_8$ alkyl, optionally substituted C$_1$-C$_8$alkoxyC$_1$-C$_8$alkyl, optionally substituted C$_1$-C$_8$alkylaminoC$_1$-C$_8$alkyl, optionally substituted 3-8 membered cycloalkyl, optionally substituted 3-8 membered heterocyclyl, optionally substituted aryl, and optionally substituted heteroaryl, wherein R$^6$ and R$^7$ are independently selected from hydrogen, optionally substituted C$_1$-C$_8$ alkyl, optionally substituted C$_1$-C$_8$ alkoxy, optionally substituted C$_1$-C$_8$alkoxyC$_1$-C$_8$alkyl, optionally substituted C$_1$-C$_8$alkylaminoC$_1$-C$_8$alkyl, optionally substituted 3-8 membered cycloalkyl, optionally substituted 3-8 membered heterocyclyl, optionally substituted aryl, and optionally substituted heteroaryl, or R$^4$ and R$^5$; R$^6$ and R$^7$ together with the atom to which they are connected form a 4-8 membered cycloalkyl or heterocyclyl ring;

Ar is selected from aryl and heteroaryl, each of which is optionally substituted with one or more substituents independently selected from F, Cl, CN, NO$_2$, OR$^8$, NR$^8$R$^9$, COR$^8$, CO$_2$R$^8$, CONR$^8$R$^9$, SOR$^8$, SO$_2$R$^8$, SO$_2$NR$^9$R$^{10}$, NR$^9$COR$^{10}$, NR$^8$C(O)NR$^9$R$^{10}$, NR$^9$SOR$^{10}$, NR$^9$SO$_2$R$^{10}$, optionally substituted C$_1$-C$_6$ alkyl, optionally substituted C$_1$-C$_6$ alkoxyalkyl, optionally substituted C$_1$-C$_6$ haloalkyl, optionally substituted C$_1$-C$_6$ hydroxyalkyl, optionally substituted C$_1$-C$_6$alkylaminoC$_1$-C$_6$alkyl, optionally substituted C$_3$-C$_7$ cycloalkyl, optionally substituted 3-7 membered heterocyclyl, optionally substituted C$_2$-C$_6$ alkenyl, optionally substituted C$_2$-C$_6$ alkynyl, optionally substituted aryl, and optionally substituted C$_4$-C$_5$ heteroaryl, wherein R$^8$, R$^9$, and R$^{10}$ are independently selected from null, hydrogen, optionally substituted C$_1$-C$_6$ alkyl, optionally substituted C$_2$-C$_6$ alkenyl, optionally substituted C$_2$-C$_6$ alkynyl, optionally substituted C$_3$-C$_7$ cycloalkyl, optionally substituted 3-7 membered heterocyclyl, optionally substituted aryl, and optionally substituted heteroaryl, or R$^8$ and R$^9$; R$^9$ and R$^{10}$ together with the atom to which they are connected form a 4-8 membered cycloalkyl or heterocyclyl ring.

In another embodiment, the degradation tag is a moiety of FORMULA 7A:

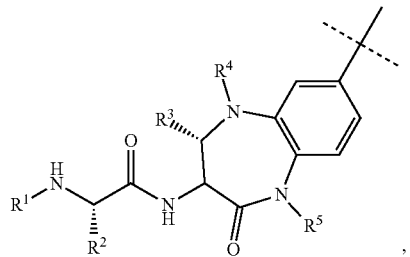

FORMULA 7A wherein V, W, X, and Z are independently selected from CR$^4$ and N.

R$^1$, R$^2$, R$^3$, and R$^4$ are independently selected from hydrogen, optionally substituted C$_1$-C$_8$ alkyl, optionally substituted C$_1$-C$_8$alkoxyC$_1$-C$_8$alkyl, optionally substituted C$_1$-C$_8$ haloalkyl, optionally substituted C$_1$-C$_8$ hydroxyalkyl, optionally substituted C$_3$-C$_7$ cycloalkyl, optionally substituted 3-7 membered heterocyclyl, optionally substituted C$_2$-C$_8$ alkenyl, and optionally substituted C$_2$-C$_8$ alkynyl.

In another embodiment, the degradation tag is a moiety of FORMULA 7B:

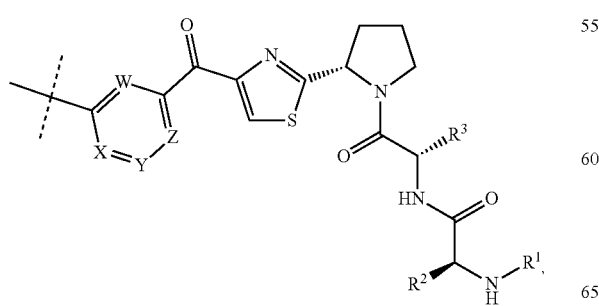

FORMULA 7B wherein

R$^1$, R$^2$, and R$^3$ are independently selected from hydrogen, halogene, optionally substituted C$_1$-C$_8$ alkyl, optionally substituted C$_1$-C$_8$alkoxyC$_1$-C$_8$alkyl, optionally substituted C$_1$-C$_8$ haloalkyl, optionally substituted C$_1$-C$_8$ hydroxyalkyl, optionally substituted C$_3$-C$_7$ cycloalkyl, optionally substituted 3-7 membered heterocyclyl, optionally substituted C$_2$-C$_8$ alkenyl, and optionally substituted C$_2$-C$_8$ alkynyl;

R$^4$ and R$^5$ are independently selected from hydrogen, COR$^6$, CO$_2$R$^6$, CONR$^6$R$^7$, SOR$^6$, SO$_2$R$^6$, SO$_2$NR$^6$R$^7$, optionally substituted C$_1$-C$_8$ alkyl, optionally substituted C$_1$-C$_8$alkoxyC$_1$-C$_8$alkyl, optionally substituted C$_1$-C$_8$alkylaminoC$_1$-C$_8$alkyl, optionally substituted aryl-C$_1$-C$_8$alkyl, optionally substituted 3-8 membered cycloalkyl, optionally substituted 3-8 membered heterocyclyl, optionally substituted aryl, and optionally substituted heteroaryl, wherein R$^6$ and R$^7$ are independently selected from hydrogen, optionally substituted C$_1$-C$_8$ alkyl, optionally substituted C$_1$-C$_8$alkoxyC$_1$-C$_8$alkyl, optionally substituted C$_1$-C$_8$alkylaminoC$_1$-C$_8$alkyl, optionally substituted 3-8 membered cycloalkyl, optionally substituted 3-8 membered heterocyclyl, optionally substituted aryl, and optionally substituted heteroaryl, or R$^6$ and R$^7$ together with the atom to which they are connected form a 4-8 membered cycloalkyl or heterocyclyl ring.

In another embodiment, the degradation tag is derived from any of the following:

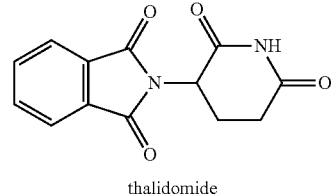

thalidomide

-continued
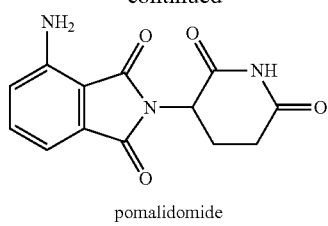
pomalidomide
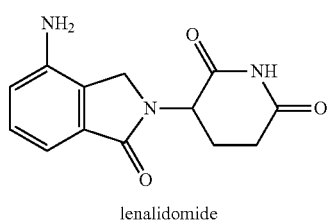
lenalidomide
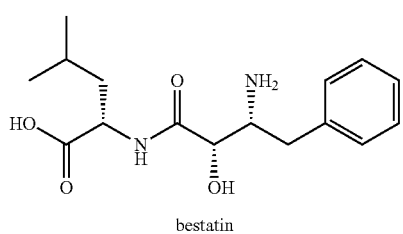
bestatin
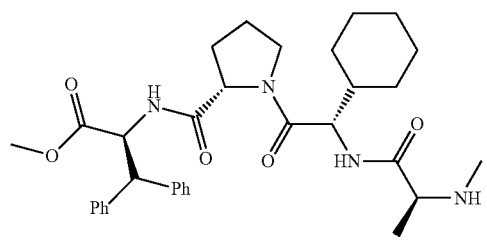
MV1
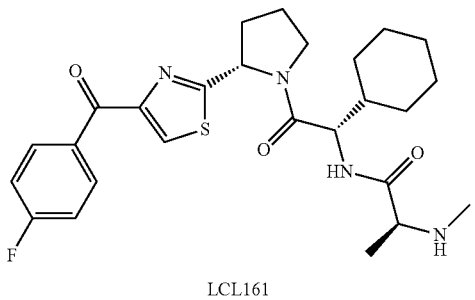
LCL161
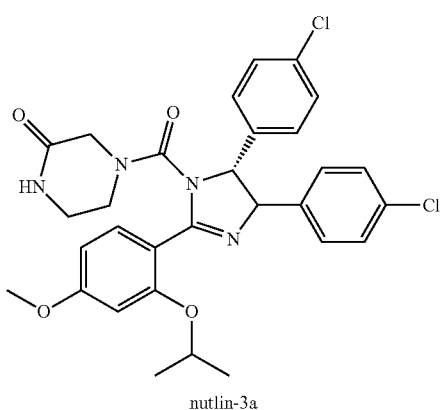
nutlin-3a
-continued
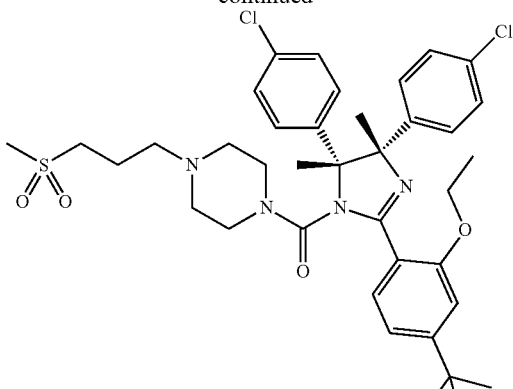
RG7112
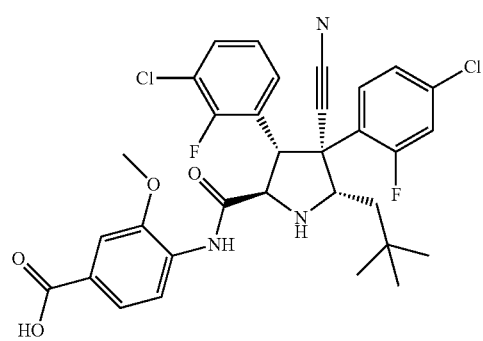
RG7338
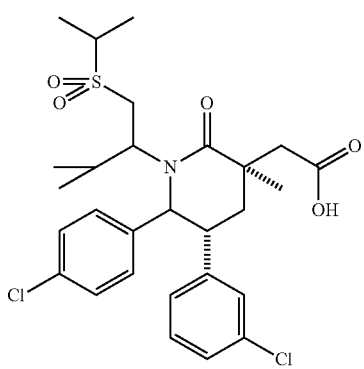
AMG232
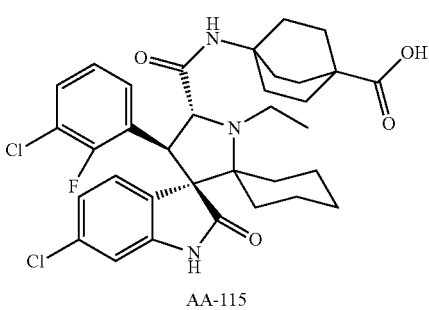
AA-115

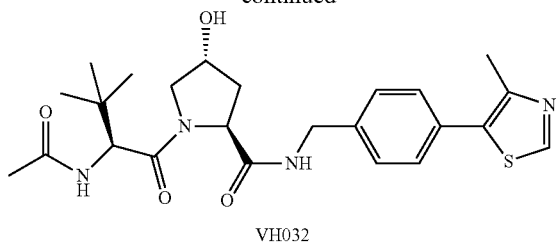

VH032

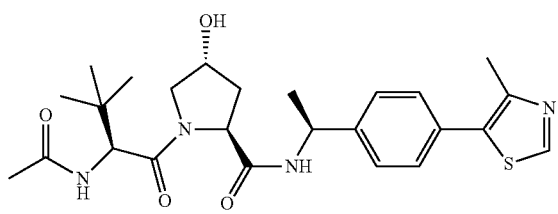

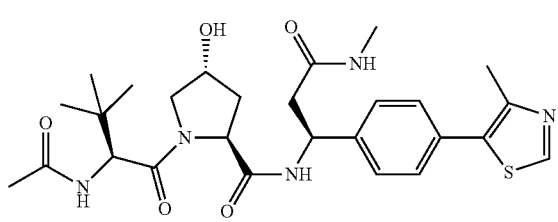

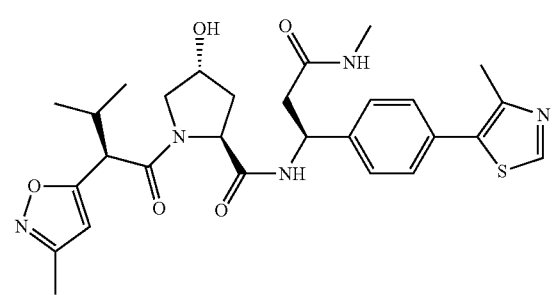

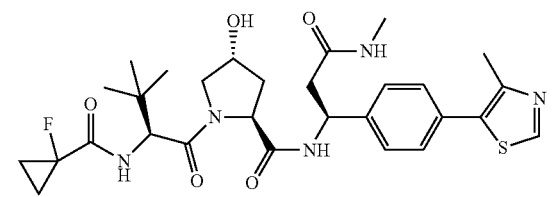

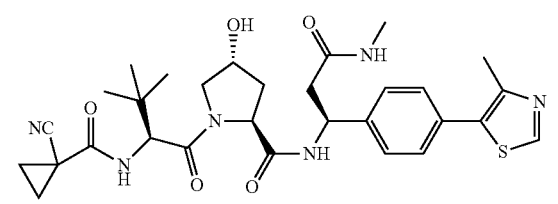

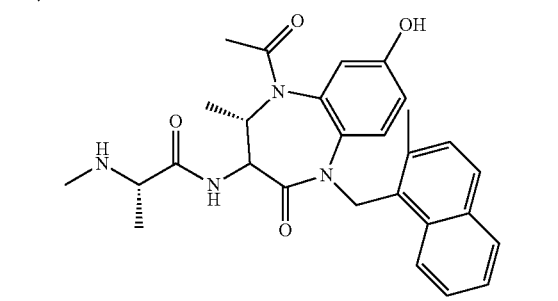

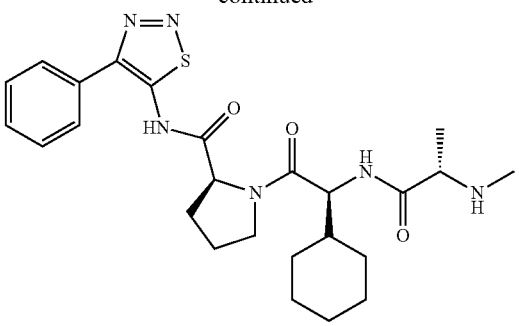

GDC-0152

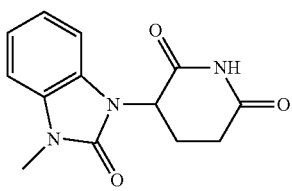

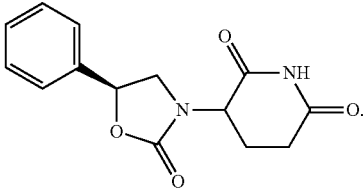

In certain embodiments, the degradation tag is an E3 ligase. In certain embodiments, the degradation tag comprises one or more of cereblon E3 ligase, a VHL E3 ligase, a MDM2 ligase, a TRIM24 ligase, a TRIM21 ligase, a KEAP1 ligase, and an IAP ligase. In certain embodiments, the degradation tags of the present disclosure include, e.g., pomalidomide (Fischer et al., 2014), thalidomide (Fischer et al., 2014), lenalidomide (Fischer et al., 2014), VH032 (Galdeano et al., 2014; Maniaci et al., 2017), adamantane (Xie et al., 2014), 1-((4,4,5,5,5-pentafluoropentyl)sulfinyl) nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), and/or analogs thereof. In certain embodiments, the degradation tag is derived from a compound comprising pomalidomide (Fischer et al., 2014), thalidomide (Fischer et al., 2014), lenalidomide (Fischer et al., 2014), VH032 (Galdeano et al., 2014; Maniaci et al., 2017), adamantane (Xie et al., 2014), 1-((4,4,5,5,5-pentafluoropentyl)sulfinyl)nonane (E. Wakeling, 1995), nutlin-3a (Vassilev et al., 2004), RG7112 (Vu et al., 2013), RG7338, AMG 232 (Sun et al., 2014), AA-115 (Aguilar et al., 2017), bestatin (Hiroyuki Suda et al., 1976), MV1 (Varfolomeev et al., 2007), LCL161 (Weisberg et al., 2010), and/or analogs thereof.

In another embodiment, the degradation tag is selected from the group consisting of:
FORMULA 8A
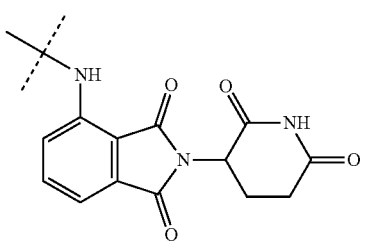
FORMULA 8B
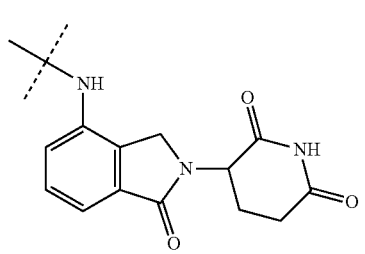
FORMULA 8C
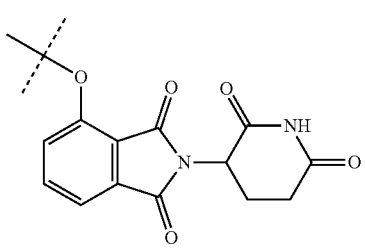
FORMULA 8D
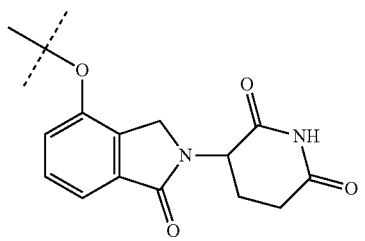
FORMULA 8E
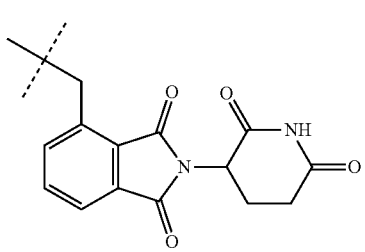
FORMULA 8F
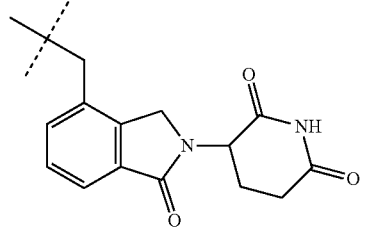
FORMULA 8G
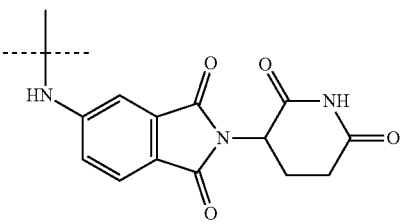
FORMULA 8H
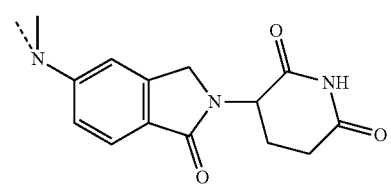
FORMULA 8I
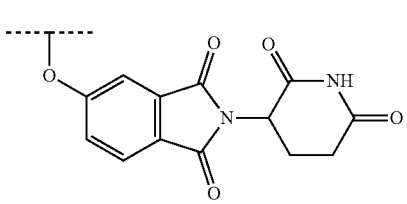
FORMULA 8J
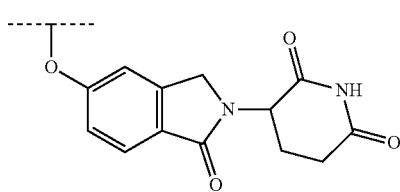
FORMULA 8K
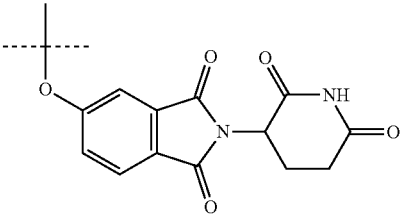
FORMULA 8L
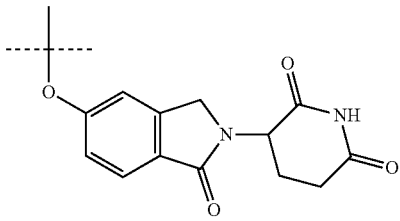
FORMULA 8M
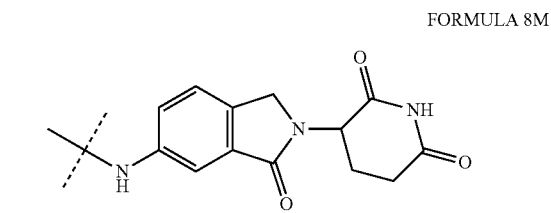

FORMULA 8N
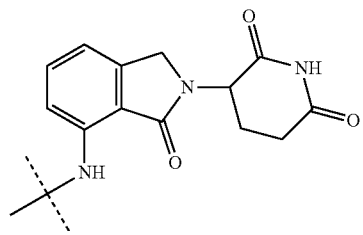
FORMULA 8O
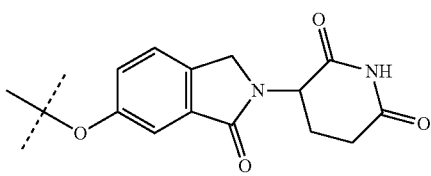
FORMULA 8P
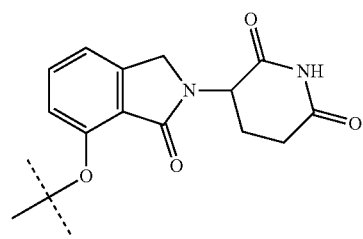
FORMULA 8Q
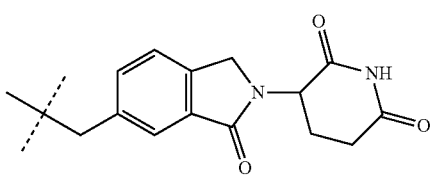
FORMULA 8R
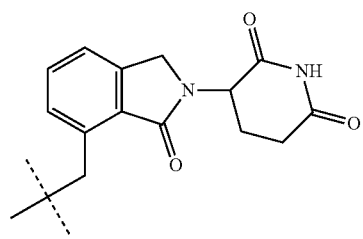
FORMULA 8S
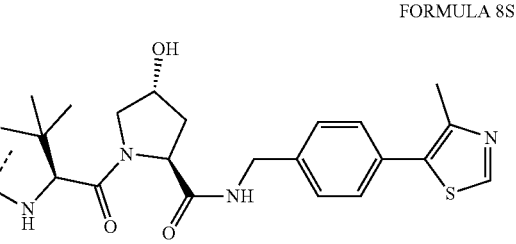
FORMULA 8T
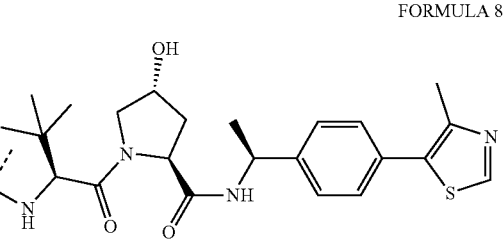
FORMULA 8U
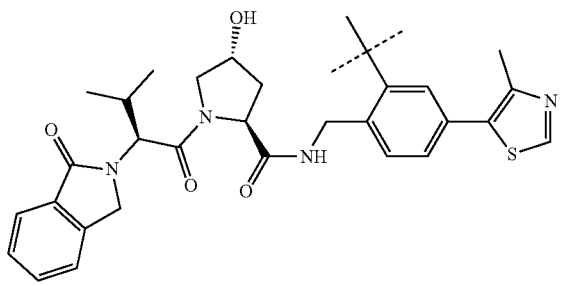
FORMULA 8V
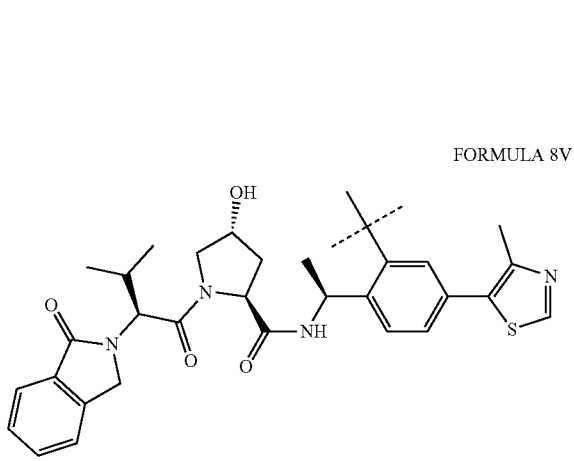
FORMULA 8W
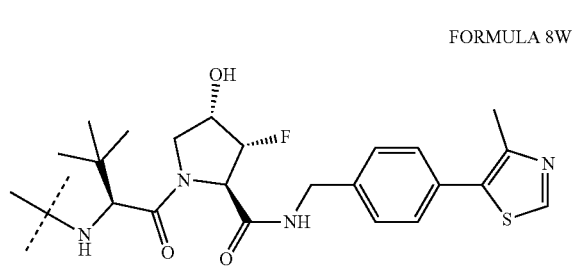
FORMULA 8X
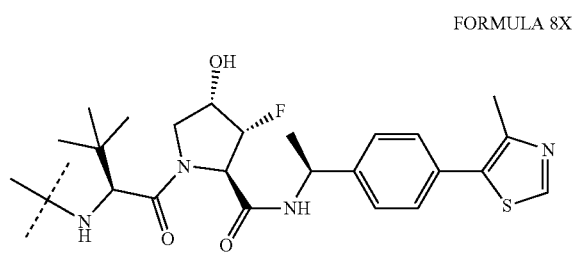
FORMULA 8Y
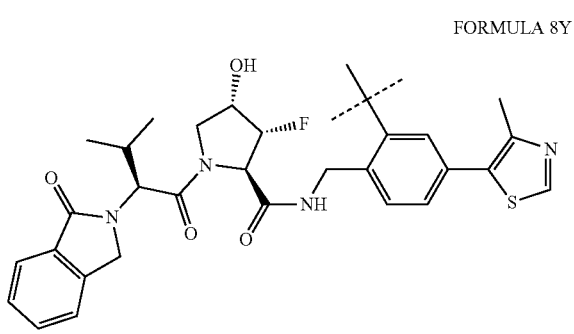

FORMULA 8Z
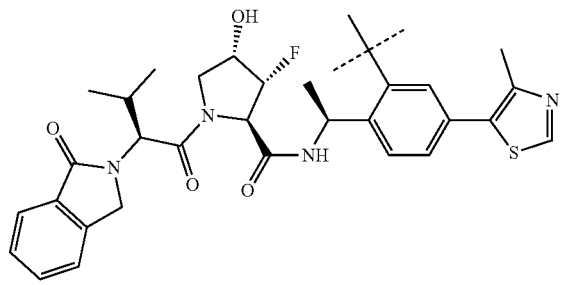
FORMULA 8AA
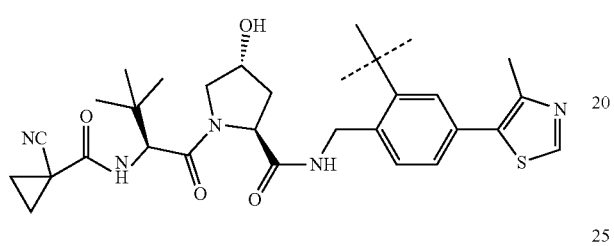
FORMULA 8AB
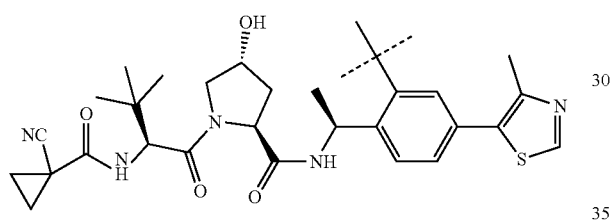
FORMULA 8AC
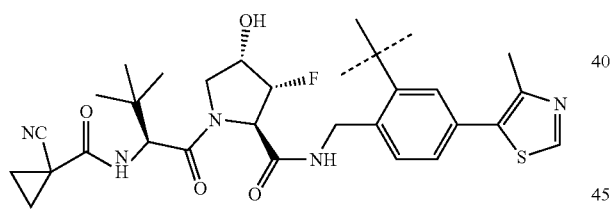
FORMUAL 8AD
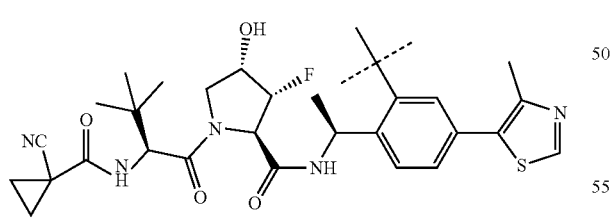
FORMULA 8AE
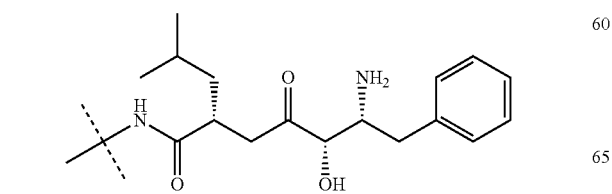
FORMULA 8AF
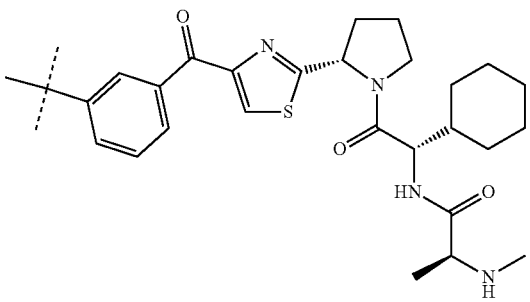
FORMULA 8AG
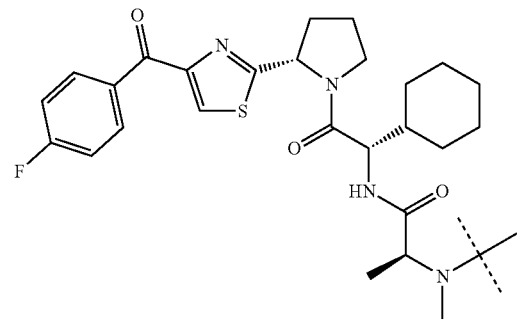
FORMULA 8AH
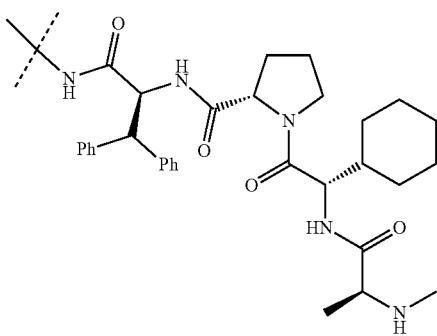
FORMULA 8AI
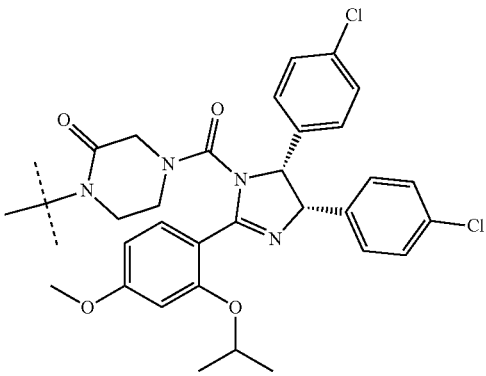

FORMULA 8AJ
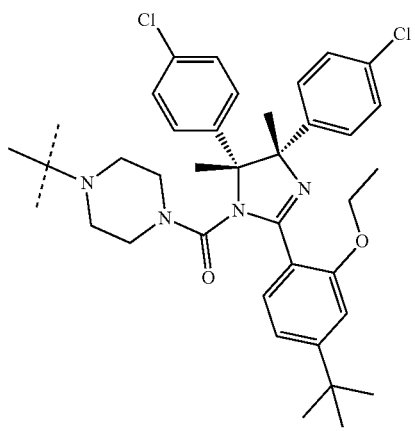
FORMULA 8AO
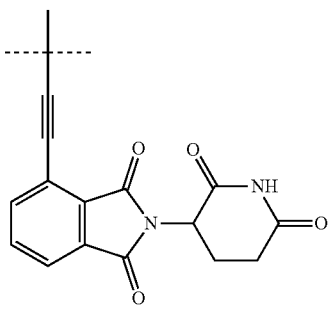
FORMULA 8AK
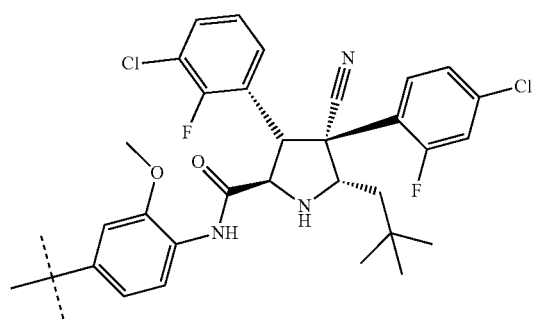
FORMULA 8AP
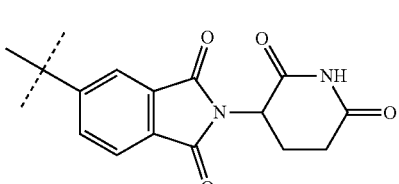
FORMULA 8AQ
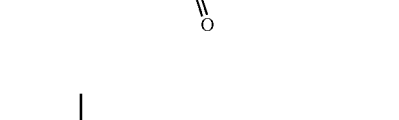
FORMULA 8AL
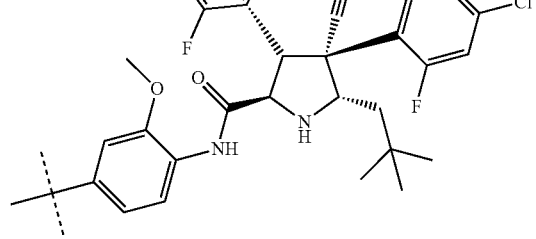
FORMULA 8AR
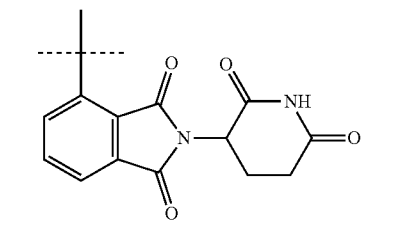
FORMULA 8AM
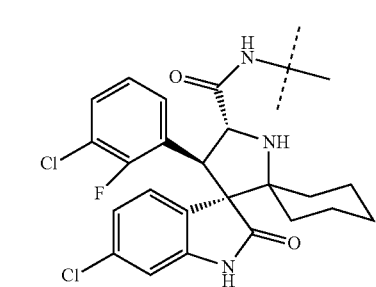
FORMULA 8AS
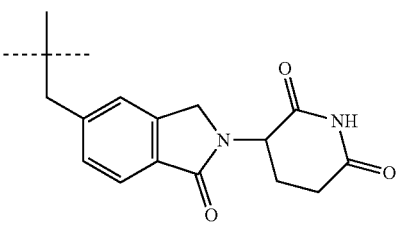
FORMULA 8AN
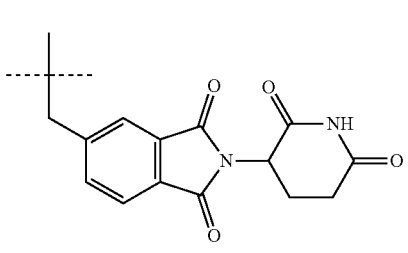
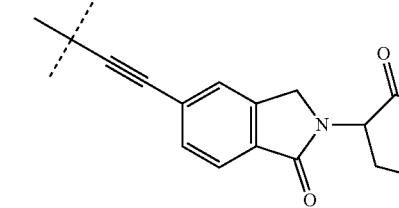
FORMULA 8AT
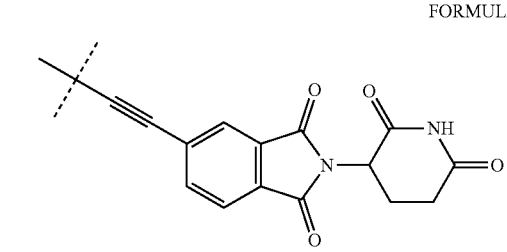
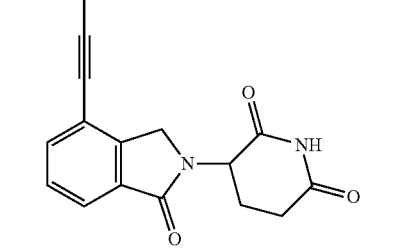

FORMULA 8AU
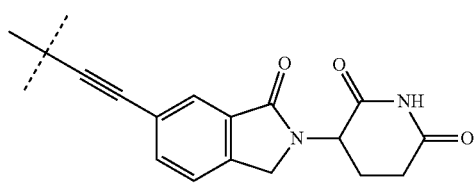
FORMULA 8AV
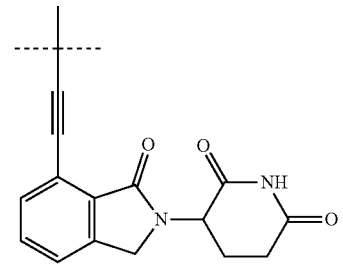
FORMULA 8AW
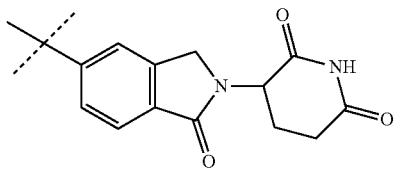
FORMULA 8AX
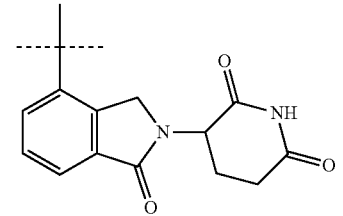
FORMULA 8AY
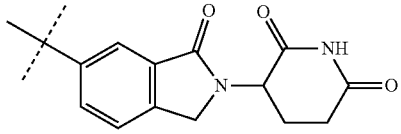
FORMULA 8AZ
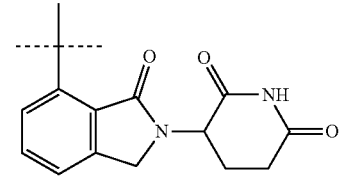
FORMULA 8BA
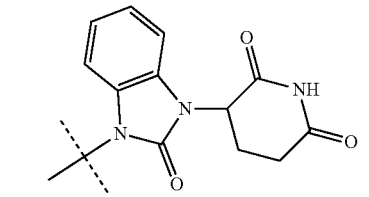
FORMULA 8BB
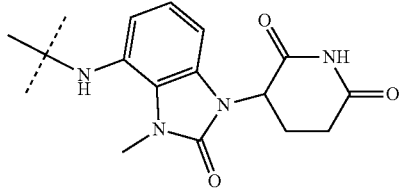
FORMULA 8BC
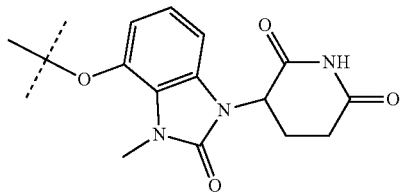
FORMULA 8BD
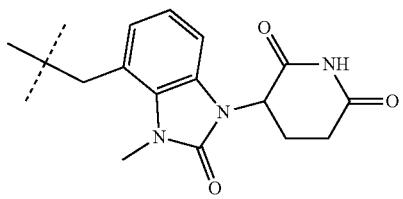
FORMULA 8BE
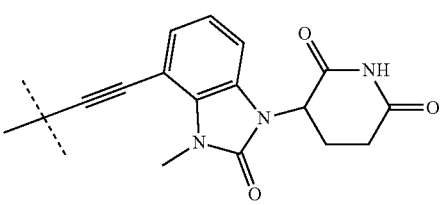
FORMULA 8BF
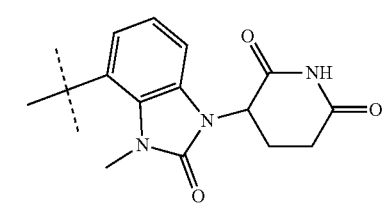
FORMULA 8BG
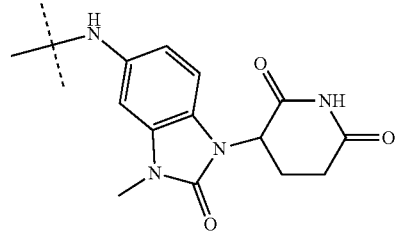
FORMULA 8BH
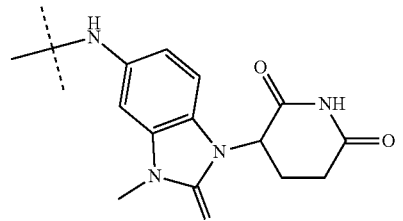
FORMULA 8BI
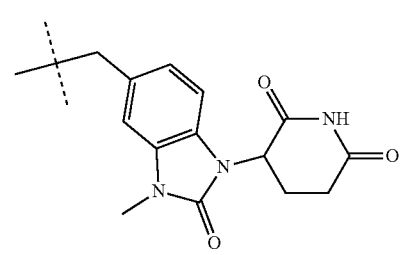

FORMULA 8BJ
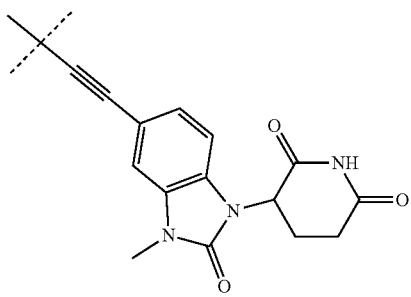
FORMULA 8BP
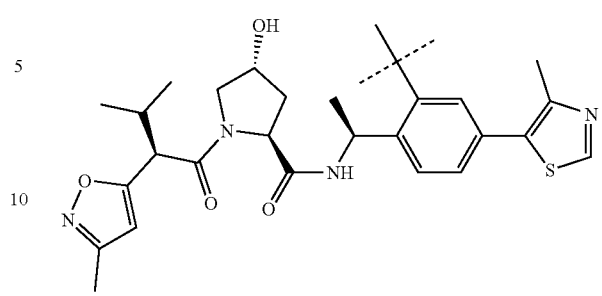
FORMULA 8BK
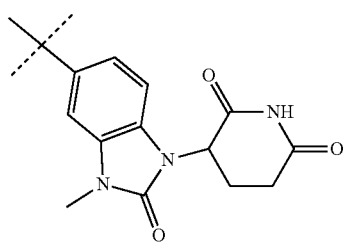
FORMULA 8BQ
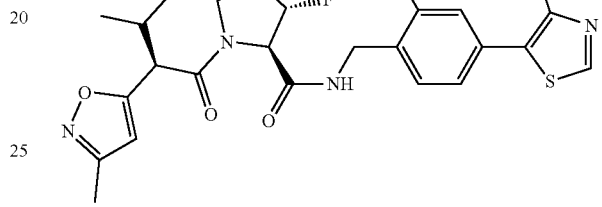
FORMULA 8BL
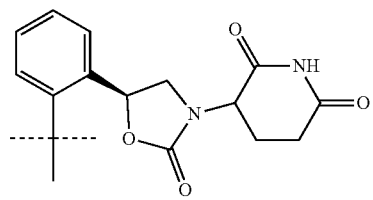
FORMULA 8BR
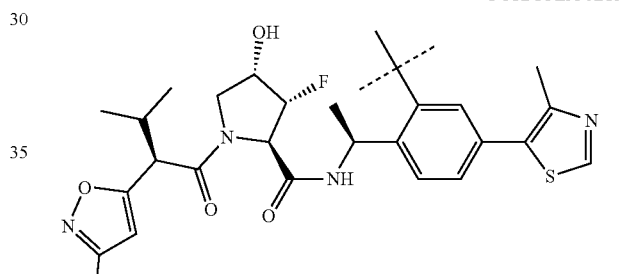
FORMULA 8BM
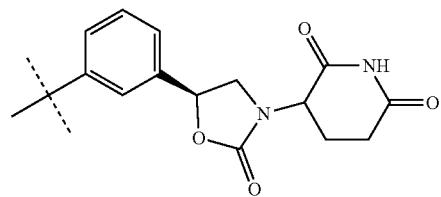
FORMULA 8BS
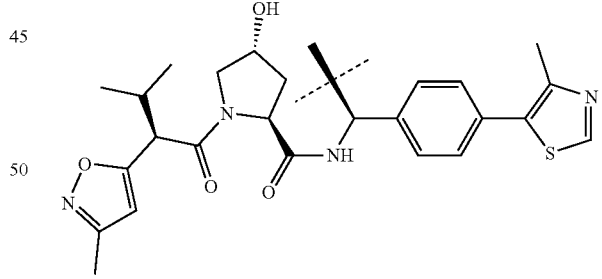
FORMULA 8BN
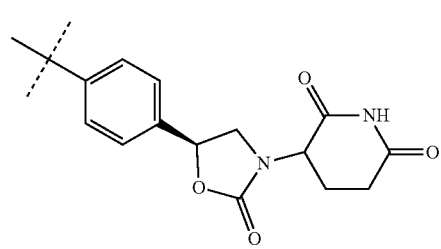
FORMULA 8BT
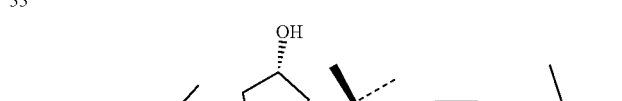
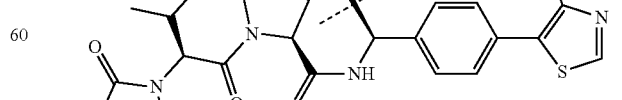
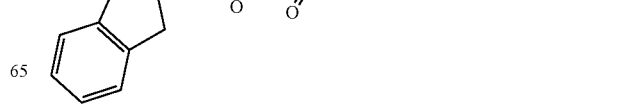
FORMULA 8BO
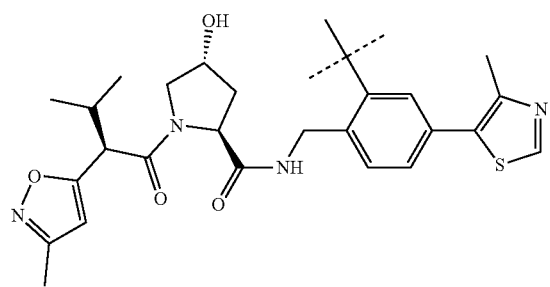

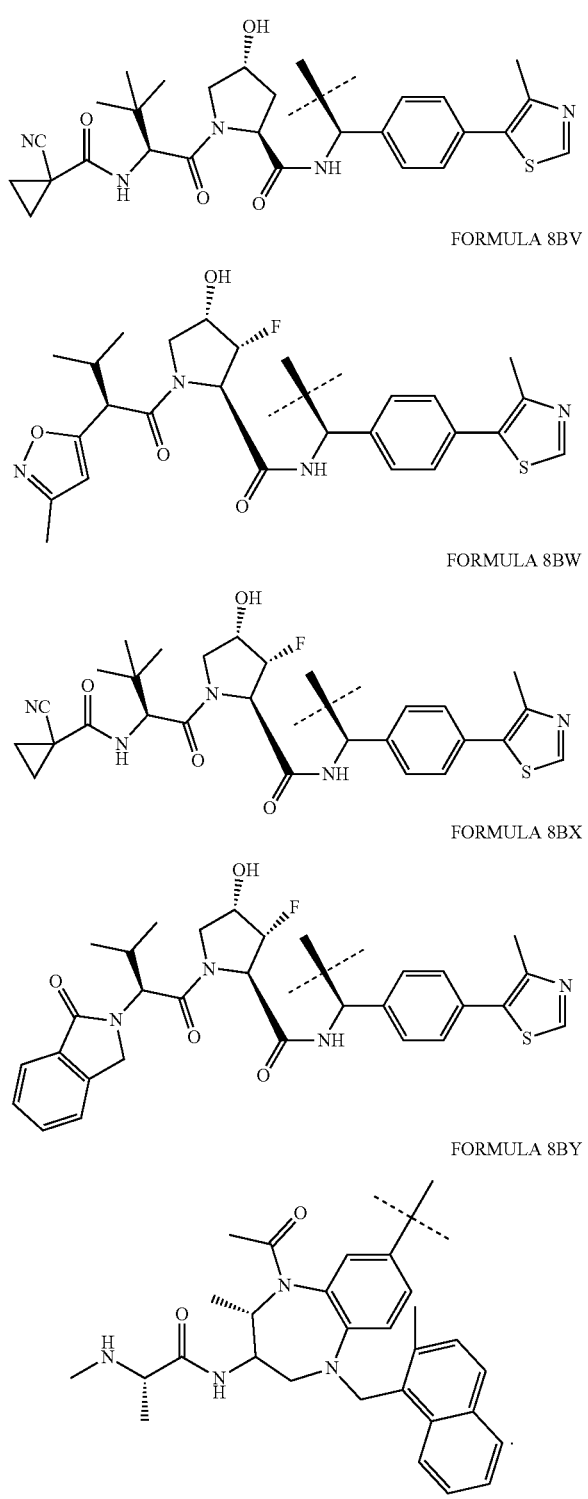

FORMULA 8BU

FORMULA 8BV

FORMULA 8BW

FORMULA 8BX

FORMULA 8BY

Linker Moiety

As used herein, a "linker" or "linker moiety" is a bond, molecule, or group of molecules that binds two separate entities to one another. Linkers provide for optimal spacing of the two entities. The term "linker" in some aspects refers to any agent or molecule that bridges the TRK ligand to the degradation tag. One of ordinary skill in the art recognizes that sites on the TRK ligand or the degradation tag, which are not necessary for the function of the degraders of the present disclosure, are ideal sites for attaching a linker, provided that the linker, once attached to the conjugate of the present disclosures, does not interfere with the function of the TRK ligand, i.e., its ability to bind TRK, or the function of the degradation tag, i.e., its ability to recruit a ubiquitin ligase.

The length of the linker of the bivalent compound can be adjusted to minimize the molecular weight of the bivalent compounds, avoid the clash of the TRK ligand or targeting moiety with the ubiquitin ligase and/or induce TRK misfolding by the hydrophobic tag. In certain embodiments, the linker comprises acyclic or cyclic saturated or unsaturated carbon, ethylene glycol, amide, amino, ether, urea, carbamate, aromatic, heteroaromatic, heterocyclic or carbonyl groups. In certain embodiments, the length of the linker is 0, 1, 2, 3, 4, 5, 6, 7, 8, 9, 10, 11, 12, 13, 14, 15, 16, 17, 18, 19, 20 or more atoms.

In some embodiments, the linker moiety is of FORMULA 9:

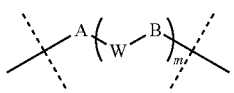

FORMULA 9 wherein
A, W and B, at each occurrence, are independently selected from null, or bivalent moiety selected from R'—R", R'COR", R'CO$_2$R", R'C(O)N(R$^1$)R", R'C(S)N(R$^1$)R", R'OR", R'OC(O)R", R'OC(O)OR", R'OCON(R$^1$)R", R'SR", R'SOR", R'SO$_2$R", R'SO$_2$N(R$^1$)R", R'N(R$^1$)R", R'NR$^1$COR", R'NR$^1$C(O)OR", R'NR$^1$CON(R$^2$)R", R'NR$^1$C(S)R", R'NR$^1$S(O)R", R'NR$^1$S(O)$_2$R", and R'NR$^1$S(O)$_2$N(R$^2$)R", wherein R' and R" are independently selected from null, optionally substituted R$^r$—(C$_1$-C$_8$ alkyl), or a moiety comprising of optionally substituted C$_1$-C$_8$ alkyl, optionally substituted C$_2$-C$_8$ alkenyl, optionally substituted C$_2$-C$_8$ alkynyl, optionally substituted C$_1$-C$_8$ hydroxyalkyl, optionally substituted C$_1$-C$_8$alkoxyC$_1$-C$_8$alkyl, optionally substituted C$_1$-C$_8$alkylaminoC$_1$-C$_8$alkyl, optionally substituted C$_1$-C$_8$ haloalkyl, optionally substituted C$_1$-C$_8$ alkylene, optionally substituted C$_2$-C$_8$ alkenylene, optionally substituted C$_2$-C$_8$ alkynylene, optionally substituted C$_1$-C$_8$ hydroxyalkylene, optionally substituted C$_1$-C$_8$alkoxyC$_1$-C$_8$alkylene, optionally substituted C$_1$-C$_8$alkylaminoC$_1$-C$_8$alkylene, optionally substituted C$_1$-C$_8$ haloalkylene, optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted C$_3$-C$_{13}$ spiro cycloalkyl, optionally substituted C$_3$-C$_{13}$ spiro heterocyclyl, optionally substituted aryl, and optionally substituted heteroaryl;

R$^r$ is selected from optionally substituted 3-10 membered carbocyclyl, optionally substituted 4-10 membered heterocyclyl, optionally substituted C$_3$-C$_{13}$ fused cycloalkyl, optionally substituted C$_3$-C$_{13}$ fused heterocyclyl, optionally substituted C$_3$-C$_{13}$ bridged cycloalkyl, optionally substituted C$_3$-C$_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^1$ and $R^2$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^1$ and $R^2$, R' and $R^1$, R' and $R^2$, R" and $R^1$, R" and $R^2$ together with the atom to which they are connected form a 3-20 membered cycloalkyl or 4-20 membered heterocyclyl ring; and m is 0 to 15.

In some embodiments, the linker moiety is of FORMULA 9:

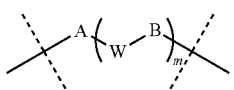

FORMULA 9 wherein

A, W, and B, at each occurrence, are independently selected from null, CO, $CO_2$, C(O)$NR^1$, C(S)$NR^1$, O, S, SO, $SO_2$, $SO_2NR^1$, $NR^1$, $NR^1CO$, $NR^1CONR^2$, $NR^1C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl, wherein $R^1$ and $R^2$ are independently selected from hydrogen, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl; and m is 0 to 15.

In one embodiment, the linker moiety is of FORMULA 9A:

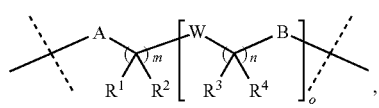

FORMULA 9A

Wherein $R^1$, $R^2$, $R^3$ and $R^4$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$ alkylamino, and optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 3-10 membered carbocyclylamino, optionally substituted 4-8 membered heterocyclyl, optionally substituted aryl, and optionally substituted heteroaryl, or $R^1$ and $R^2$, $R^3$ and $R^4$ together with the atom to which they are connected form a 3-20 membered cycloalkyl or 4-20 membered heterocyclyl ring;

A, W and B, at each occurrence, are independently selected from null, or bivalent moiety selected from R'—R", R'COR", R'$CO_2$R", R'C(O)N($R^5$)R", R'C(S)N($R^5$)R", R'OR", R'OC(O)R", R'OC(O)OR", R'OCON$R^5$R", R'SR", R'SOR", R'$SO_2$R", R'$SO_2$N($R^5$)R", R'N($R^5$)R", R'$NR^5$COR", R'$NR^5$C(O)OR", R'$NR^5$CON($R^6$)R", R'$NR^5$C(S)R", R'$NR^5$S(O)R", R'$NR^5$S(O)$_2$R", and R'$NR^5$S(O)$_2$N($R^6$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^5$ and $R^6$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R'', $R^5$ and $R^6$, R' and $R^5$, R' and $R^6$, R'' and $R^5$, R'' and $R^6$ together with the atom to which they are connected form a 3-20 membered cycloalkyl or 4-20 membered heterocyclyl ring;

m is 0 to 15;

n, at each occurrence, is 0 to 15; and o is 0 to 15.

In one embodiment, the linker moiety is of FORMULA 9A:

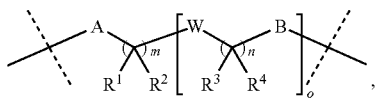

FORMULA 9A wherein $R^1$, $R^2$, $R^3$, and $R^4$, at each occurrence, are independently selected from hydrogen, halogen, CN, OH, $NH_2$, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl;

A, W, and B, at each occurrence, are independently selected from null, CO, $CO_2$, $C(O)NR^5$, $C(S)NR^5$, O, S, SO, $SO_2$, $SO_2NR^5$, $NR^5$, $NR^5CO$, $NR^5CONR^6$, $NR^5C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl, wherein $R^5$ and $R^6$ are independently selected from hydrogen, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl;

m is 0 to 15;

each n is 0 to 15; and o is 0 to 15.

In another embodiment, the linker moiety is of FORMULA 9B:

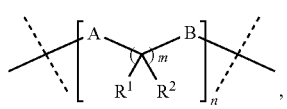

FORMULA 9B wherein $R^1$ and $R^2$, at each occurrence, are independently selected from hydrogen, halogen, hydroxyl, amino, cyano, nitro, and optionally substituted $C_1$-$C_8$ alkyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, $C_1$-$C_8$alkylamino$C_1$-$C_8$alkyl, optionally substituted 3-10 membered carbocyclyl, optionally substituted 3-8 membered cycloalkoxy, optionally substituted 3-10 membered carbocyclylamino, optionally substituted 4-10 membered heterocyclyl, optionally substituted aryl, and optionally substituted heteroaryl, or $R^1$ and $R^2$ together with the atom to which they are connected form a 3-20 membered cycloalkyl or 4-20 membered heterocyclyl ring;

A and B, at each occurrence, are independently selected from null, or bivalent moiety selected from R'—R'', R'COR'', $R'CO_2R''$, $R'C(O)NR^3R''$, $R'C(S)NR^3R''$, R'OR'', R'OC(O)R'', R'OC(O)OR'', $R'OCON(R^3)R''$, R'SR'', R'SOR'', $R'SO_2R''$, $R'SO_2N(R^3)R''$, $R'N(R^3)R''$, $R'NR^3COR''$, $R'NR^3C(O)OR''$, $R'NR^3CON(R^4)R'$, $R'NR^3C(S)R''$, $R'NR^3S(O)R''$, $R'NR^3S(O)_2R''$, and $R'NR^3S(O)_2N(R^4)R''$, wherein R' and R'' are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^3$ and $R^4$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^3$ and $R^4$, R' and $R^3$, R' and $R^4$, R" and $R^3$, R" and $R^4$ together with the atom to which they are connected form a 3-20 membered cycloalkyl or 4-20 membered heterocyclyl ring;

each m is 0 to 15; and n is 0 to 15.

In another embodiment, the linker moiety is of FORMULA 9B:

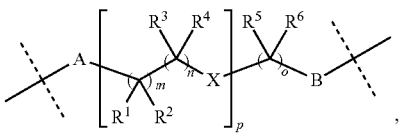

FORMULA 9B wherein each $R^1$, and each $R^2$ are independently selected from hydrogen, halogen, CN, OH, $NH_2$, and optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, or $C_1$-$C_6$alkylamino$C_1$-$C_6$alkyl;

each A and each B are independently selected from null, CO, $CO_2$, C(O)$NR^3$, C(S)$NR^3$, O, S, SO, $SO_2$, $SO_2NR^3$, $NR^3$, $NR^3CO$, $NR^3CONR^4$, $NR^3C(S)$, and optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, or $C_3$-$C_{13}$ spiro heterocyclyl, wherein $R^3$ and $R^4$ are independently selected from hydrogen, and optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, or $C_1$-$C_6$alkylamino$C_1$-$C_6$alkyl;

each m is 0 to 15; and n is 0 to 15.

In another embodiment, in FORMULA 9B, m is 1 to 15.

In another embodiment, in FORMULA 9B, n is 1.

In another embodiment, in FORMULA 9B, $R^1$ and $R^2$ are independently selected from hydrogen, and optionally substituted $C_1$-$C_8$ alkyl.

In another embodiment, the linker moiety is of FORMULA 9C:

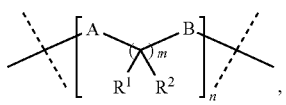

FORMULA 9C wherein

X is selected from O, NH, and $NR^7$;

$R^1$, $R^2$, $R^3$, $R^4$, $R^5$, and $R^6$, at each occurrence, are independently selected from hydrogen, halogen, hydroxyl, amino, cyano, nitro, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxy, optionally substituted $C_1$-$C_8$ alkoxy $C_1$-$C_8$ alkyl, optionally substituted $C_1$-$C_8$ haloalkyl, optionally substituted $C_1$-$C_8$ hydroxyalkyl, optionally substituted $C_1$-$C_8$ alkylamino, optionally substituted $C_1$-$C_8$ alkylamino$C_1$-$C_8$ alkyl, optionally substituted 3-10 membered carbocyclyl, optionally substituted 3-8 membered cycloalkoxy, optionally substituted 4-10 membered heterocyclyl, optionally substituted aryl, and optionally substituted heteroaryl;

A and B are independently selected from null, or bivalent moiety selected from R'—R", R'COR", R'$CO_2$R", R'C(O)N($R^8$)R", R'C(S)N($R^8$)R", R'OR", R'OC(O)R", R'OC(O)OR", R'OCON($R^8$)R", R'SR", R'SOR", R'$SO_2$R", R'$SO_2$N($R^8$)R", R'N($R^8$)R", R'$NR^8$COR", R'$NR^8$C(O)OR", R'$NR^8$CON($R^9$)R", R'$NR^8$C(S)R", R'$NR^8$S(O)R", R'$NR^8$S(O)$_2$R", and R'$NR^8$S(O)$_2$N($R^9$)R", wherein R' and R" are independently selected from null, optionally substituted $R^r$—($C_1$-$C_8$ alkyl), or a moiety comprising of optionally substituted $C_1$-$C_8$ alkyl, optionally substituted $C_2$-$C_8$ alkenyl, optionally substituted $C_2$-$C_8$ alkynyl, optionally substituted $C_1$-$C_8$ hydroxyalkyl, optionally substituted $C_1$-$C_8$alkoxy$C_1$-$C_8$alkyl, optionally substituted $C_1$-$C_8$alkylamino$C_1$-$C_8$alkyl, optionally substituted $C_1$-$C_8$ haloalkyl, optionally substituted $C_1$-$C_8$ alkylene, optionally substituted $C_2$-$C_8$ alkenylene, optionally substituted $C_2$-$C_8$ alkynylene, optionally substituted $C_1$-$C_8$ hydroxyalkylene, optionally substituted $C_1$-$C_8$alkoxy$C_1$-$C_8$alkylene, optionally substituted $C_1$-$C_8$alkylamino$C_1$-$C_8$alkylene, optionally substituted $C_1$-$C_8$ haloalkylene, optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^r$ is selected from optionally substituted 3-10 membered carbocyclyl, optionally substituted 4-10 membered heterocyclyl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, optionally substituted $C_3$-$C_{13}$ spiro heterocyclyl, optionally substituted aryl, and optionally substituted heteroaryl;

$R^7$, $R^8$ and $R^9$ are independently selected from hydrogen, optionally substituted $C_1$-$C_8$ alkyl, optionally substituted $C_2$-$C_8$ alkenyl, optionally substituted $C_2$-$C_8$ alkynyl, optionally substituted $C_1$-$C_8$ alkoxyalkyl, optionally substituted $C_1$-$C_8$ haloalkyl, optionally substituted $C_1$-$C_8$ hydroxyalkyl, optionally substituted $C_1$-$C_8$alkylamino$C_1$-$C_8$alkyl, optionally substituted 3-10 membered carbocyclyl, optionally substituted 4-10 membered heterocyclyl, optionally substituted aryl, and optionally substituted heteroaryl;

R' and R", $R^8$ and $R^9$, R' and $R^8$, R' and $R^9$, R" and $R^8$, R" and $R^9$ together with the atom to which they are connected form a 3-20 membered cycloalkyl or 4-20 membered heterocyclyl ring;

m, at each occurrence, is 0 to 15;
n, at each occurrence, is 0 to 15;
o is 0 to 15; and
p is 0 to 15.

In another embodiment, the linker moiety is of FORMULA 9C:

FORMULA 9C

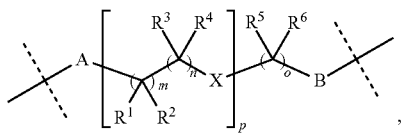

wherein
X is selected from O, NH, and $NR^7$;
$R^1$, $R^2$, $R^3$, $R^4$, $R^5$, and $R^6$, at each occurrence, are independently selected from hydrogen, halogen, CN, OH, $NH_2$, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl;

A and B, at each occurrence, are independently selected from null, CO, $CO_2$, $C(O)NR^7$, $C(S)NR^7$, O, S, SO, $SO_2$, $SO_2NR^7$, $NR^7$, $NR^7CO$, $NR^7CONR^8$, $NR^7C(S)$, optionally substituted $C_1$-$C_8$ alkyl, optionally substituted $C_1$-$C_8$ alkoxy, optionally substituted $C_1$-$C_8$alkoxy$C_1$-$C_8$alkyl, optionally substituted $C_1$-$C_8$ haloalkyl, optionally substituted $C_1$-$C_8$ hydroxyalkyl, optionally substituted $C_2$-$C_8$ alkenyl, optionally substituted $C_2$-$C_8$ alkynyl, optionally substituted $C_3$-$C_8$ cycloalkyl, optionally substituted $C_3$-$C_8$ cycloalkoxy, optionally substituted 3-8 membered heterocyclyl, optionally substituted aryl, optionally substituted heteroaryl, optionally substituted $C_3$-$C_{13}$ fused cycloalkyl, optionally substituted $C_3$-$C_{13}$ fused heterocyclyl, optionally substituted $C_3$-$C_{13}$ bridged cycloalkyl, optionally substituted $C_3$-$C_{13}$ bridged heterocyclyl, optionally substituted $C_3$-$C_{13}$ spiro cycloalkyl, and optionally substituted $C_3$-$C_{13}$ spiro heterocyclyl, wherein $R^7$ and $R^8$ are independently selected from hydrogen, optionally substituted $C_1$-$C_6$ alkyl, optionally substituted $C_3$-$C_6$ cycloalkyl, optionally substituted $C_3$-$C_6$ cycloalkoxy, optionally substituted 3-6 membered heterocyclyl, optionally substituted $C_1$-$C_6$ alkoxy, optionally substituted $C_1$-$C_6$ alkoxyalkyl, optionally substituted $C_1$-$C_6$ haloalkyl, optionally substituted $C_1$-$C_6$ hydroxyalkyl, optionally substituted $C_1$-$C_6$ alkylamino, and optionally substituted $C_1$-$C_6$alkylamino$C_1$-$C_6$alkyl;

each m is 0 to 15;
each n is 0 to 15;
o is 0 to 15; and
p is 0 to 15.

In one embodiment, in FORMULA 9C, m and n is 1, and p is 1 to 15;

In one embodiment, in FORMULA 9C, X is selected from O and NH; In one embodiment, in FORMULA 9C, $R^1$, $R^2$, $R^3$, $R^4$, $R^5$, and $R^6$, are independently selected from hydrogen, optionally substituted $C_1$-$C_6$ alkyl.

In another embodiment, the linker moiety comprises a ring selected from the group consisting of a 3 to 13 membered ring, a 3 to 13 membered fused ring, a 3 to 13 membered bridged ring, and a 3 to 13 membered Spiro ring.

In another embodiment, the linker moiety comprises a ring selected from the group consisting of Formula C1, C2, C3, C4 and C5:

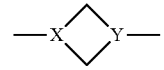

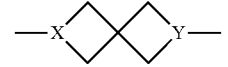

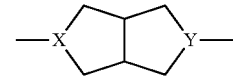

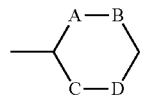

In one embodiment, A, B and W, at each occurrence, are independently selected from null, CO, NH, NH—CO, CO—NH, CH$_2$—NH—CO, CH$_2$—CO—NH, NH—CO—CH$_2$, CO—NH—CH$_2$, CH$_2$—NH—CH$_2$—CO—NH, CH$_2$—NH—CH$_2$—NH—CO, NH—CO—CH$_2$—NH—CH$_2$CO—NH—CH$_2$—NH—CH$_2$, and CH$_2$—NH—CH$_2$, R$_r$—CO, R$_r$—NH, R$_r$—NH—CO, R$_r$—CO—NH, R$_r$—CH$_2$—NH—CO, R$_r$—CH$_2$—CO—NH, R$_r$—NH—CO—CH$_2$, R$_r$—CO—NH—CH$_2$, R$_r$—CH$_2$—NH—CH$_2$—CO—NH, R$_r$—CH$_2$—NH—CH$_2$—NH—CO, R$_r$—NH—CO—CH$_2$—NH—CH$_2$, R$_r$ CO—NH—CH$_2$—NH—CH$_2$, R$_r$—CH$_2$—NH—CH$_2$.

In one embodiment, R$^r$ is of Formula C1, C2, C3, C4 or C5.

In one embodiment, R$^r$ is selected from

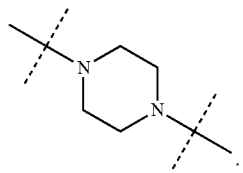

In another embodiment, the length of the linker is 0 to 40 linear atoms.

In another embodiment, the length of the linker is 0 to 20 linear atoms.

In another embodiment, the length of the linker is 0 to 8 linear atoms.

In another embodiment, the linker is selected from —(CO)—(CH$_2$)$_{1-8}$—, —(CH$_2$)$_{1-9}$—, —(CH$_2$)$_{1-2}$—(CO)—NH—(CH$_2$)$_{2-9}$—, —(CH$_2$)$_{1-2}$—(CO)—NH—(CH$_2$)$_{1-3}$(OCH$_2$CH$_2$)$_{1-7}$—, —(CH$_2$)$_{0-1}$—(CO)—(CH$_2$)$_{1-3}$(OCH$_2$CH$_2$)$_{1-7}$—, —(CO)—(CH$_2$)$_{0-3}$-(alkenylene)-(CH$_2$)$_{0-3}$—, —(CO)—(CH$_2$)$_{0-3}$-(alkynylene)-(CH$_2$)$_{0-3}$—, —(CO)—(CH$_2$)$_{0-3}$-(3-8 membered carbocyclyl)-(CH$_2$)$_{0-3}$—, —(CO)—(CH$_2$)$_{0-3}$-(3-8 membered heterocarbocyclyl)-(CH$_2$)$_{0-3}$—, —(CH$_2$)$_{0-3}$-(alkenylene)-(CH$_2$)$_{0-3}$—, —(CH$_2$)$_{0-3}$-(alkynylene)-(CH$_2$)$_{0-3}$—, —(CH$_2$)$_{0-3}$-(3-8 membered carbocyclyl)-(CH$_2$)$_{0-3}$—, and —(CH$_2$)$_{0-3}$-(3-8 membered heterocarbocyclyl)-(CH$_2$)$_{0-3}$—;

R$^r$—(CO)—(CH$_2$)$_{1-8}$—, R$^r$—(CH$_2$)$_{1-9}$—, R$^r$—(CH$_2$)$_{1-2}$—(CO)—NH—(CH$_2$)$_{2-9}$—, R$^r$—(CH$_2$)$_{1-2}$—(CO)—NH—(CH$_2$)$_{1-3}$—(OCH$_2$CH$_2$)$_{1-7}$—, R$^r$—(CH$_2$)$_{0-1}$—(CO)—(CH$_2$)$_{1-3}$—(OCH$_2$CH$_2$)$_{1-7}$—, R$^r$—(CO)—(CH$_2$)$_{0-3}$-(alkenylene)-(CH$_2$)$_{0-3}$—, R$^r$—(CO)—(CH$_2$)$_{0-3}$-(alkynylene)-(CH$_2$)$_{0-3}$—, R$^r$—(CO)—(CH$_2$)$_{0-3}$-(3-8 membered carbocyclyl)-(CH$_2$)$_{0-3}$—, R$^r$—(CO)—(CH$_2$)$_{0-3}$-(3-8 membered heterocarbocyclyl)-(CH$_2$)$_{0-3}$—, R$^r$—(CH$_2$)$_{0-3}$-(alkenylene)-(CH$_2$)$_{0-3}$—, R$^r$—(CH$_2$)$_{0-3}$-(alkynylene)-(CH$_2$)$_{0-3}$—, R$^r$—(CH$_2$)$_{0-3}$-(3-8 membered carbocyclyl)-(CH$_2$)$_{0-3}$—, and R$^r$—(CH$_2$)$_{0-3}$-(3-8 membered heterocarbocyclyl)-(CH$_2$)$_{0-3}$—.

Without wishing to be bound by any particular theory, it is contemplated herein that, in some embodiments, attaching pomalidomide or VHL-1 to either portion of the molecule can recruit the cereblon E3 ligase or VHL E3 ligase to TRK.

The bivalent compounds disclosed herein can selectively affect TRK-mediated disease cells compared to WT (wild type) cells (i.e., an bivalent compound able to kill or inhibit the growth of an TRK-mediated disease cell while also having a relatively low ability to lyse or inhibit the growth of a WT cell), e.g., possess a GI$_{50}$ for one or more TRK-mediated disease cells more than 1.5-fold lower, more than 2-fold lower, more than 2.5-fold lower, more than 3-fold lower, more than 4-fold lower, more than 5-fold lower, more than 6-fold lower, more than 7-fold lower, more than 8-fold lower, more than 9-fold lower, more than 10-fold lower, more than 15-fold lower, or more than 20-fold lower than its GI$_{50}$ for one or more WT cells, e.g., WT cells of the same species and tissue type as the TRK-mediated disease cells.

In some aspects, provided herein is a method for identifying a bivalent compound which mediates degradation or reduction of TRK, the method comprising: providing a heterobifunctional test compound comprising an TRK ligand conjugated to a degradation tag through a linker; contacting the heterobifunctional test compound with a cell comprising a ubiquitin ligase and TRK; determining whether TRK level is decreased in the cell; and identifying the heterobifunctional test compound as a bivalent compound which mediates degradation or reduction of TRK. In certain embodiments, the cell is a cancer cell. In certain embodiments, the cancer cell is a TRK-mediated cancer cell.

Cross-Reactivity with Protein Kinases

In some aspects, the TRK ligand can be bound to TRK, TRK fusion proteins, and/or TRK mutant proteins. In some aspects, the TRK ligand can be bound to ROS1, ROS1 fusion proteins, and/or ROS1 mutant proteins. In some aspects, the TRK ligand can be bound to ALK, ALK fusion proteins, and/or ALK mutant proteins. In some aspects, the TRK ligand can be bound to TRK, ROS1, or ALK. In some aspects, the TRK ligand can be bound to TRK or ROS1. In some aspects, the TRK ligand can be bound to TRK or ALK. In some aspects, the TRK ligand can be bound to ROS1 or ALK.

Synthesis and Testing of Bivalent Compounds

The binding affinity of novel synthesized bivalent compounds can be assessed using standard biophysical assays known in the art (e.g., isothermal titration calorimetry (ITC), surface plasmon resonance (SPR)). Cellular assays can then be used to assess the bivalent compound's ability to induce TRK degradation and inhibit cancer cell proliferation. Besides evaluating a bivalent compound's induced changes in the protein levels of TRK, TRK mutants, or TRK fusion proteins, enzymatic activity can also be assessed. Assays suitable for use in any or all of these steps are known in the art, and include, e.g., western blotting, quantitative mass spectrometry (MS) analysis, flow cytometry, enzymatic activity assay, ITC, SPR, cell growth inhibition, xenograft, orthotopic, and patient-derived xenograft models. Suitable cell lines for use in any or all of these steps are known in the art and include, cancer cell lines: 1); KM12, 2); CUTO3.29, 3); MO91, 4); HEL. Suitable mouse models for use in any or all of these steps are known in the art and include subcutaneous xenograft models, orthotopic models, patient-derived xenograft models, and patient-derived orthotopic models.

By way of non-limiting example, detailed synthesis protocols are described in the Examples for specific exemplary bivalent compounds.

Pharmaceutically acceptable isotopic variations of the compounds disclosed herein are contemplated and can be synthesized using conventional methods known in the art or methods corresponding to those described in the Examples (substituting appropriate reagents with appropriate isotopic variations of those reagents). Specifically, an isotopic variation is a compound in which at least one atom is replaced by an atom having the same atomic number, but an atomic mass different from the atomic mass usually found in nature. Useful isotopes are known in the art and include, for example, isotopes of hydrogen, carbon, nitrogen, oxygen, phosphorus, sulfur, fluorine, and chlorine. Exemplary isotopes thus include, e.g., $^2H$, $^3H$, $^{13}C$, $^{14}C$, $^{15}N$, $^{17}O$, $^{18}O$, $^{32}P$, $^{35}S$, $^{18}F$, and $^{36}Cl$.

Isotopic variations (e.g., isotopic variations containing $^2H$) can provide therapeutic advantages resulting from greater metabolic stability, e.g., increased in vivo half-life or reduced dosage requirements. In addition, certain isotopic variations (particularly those containing a radioactive isotope) can be used in drug or substrate tissue distribution studies. The radioactive isotopes tritium ($^3H$) and carbon-14 ($^{14}C$) are particularly useful for this purpose in view of their ease of incorporation and ready means of detection.

Pharmaceutically acceptable solvates of the compounds disclosed herein are contemplated. A solvate can be generated, e.g., by substituting a solvent used to crystallize a compound disclosed herein with an isotopic variation (e.g., $D_2O$ in place of $H_2O$, $d_6$-acetone in place of acetone, or $d_6$-DMSO in place of DMSO).

Pharmaceutically acceptable fluorinated variations of the compounds disclosed herein are contemplated and can be synthesized using conventional methods known in the art or methods corresponding to those described in the Examples (substituting appropriate reagents with appropriate fluorinated variations of those reagents). Specifically, a fluorinated variation is a compound in which at least one hydrogen atom is replaced by a fluoro atom. Fluorinated variations can provide therapeutic advantages resulting from greater metabolic stability, e.g., increased in vivo half-life or reduced dosage requirements.

Pharmaceutically acceptable prodrugs of the compounds disclosed herein are contemplated and can be synthesized using conventional methods known in the art or methods corresponding to those described in the Examples (e.g., converting hydroxyl groups or carboxylic acid groups to ester groups). As used herein, a "prodrug" refers to a compound that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

Characterization of Exemplary Bivalent Compounds

Specific exemplary bivalent compounds were characterized in KM12 cells. KM12 cells that express TPM3-TRKA fusion protein were treated with 100 nM entrectinib (Entrec) or the bivalent compounds disclosed herein (CPD-001-CPD-065) for 16 hours. Cells were collected, lysed and subject to immunoblotting using an antibody specific to TRK proteins. GAPDH was included as the loading control. DMSO was used as the negative control. Following a 16-hour treatment of various bivalent compounds at 100 nM, TPM3-TRKA levels in KM12 cells were significantly decreased (FIGS. 1A-1C).

Figure 2:
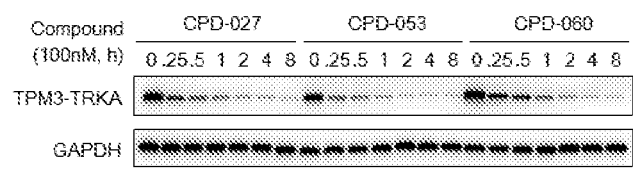
FIG. 2 shows an immunoblot of TPM3-TRKA fusion protein expressed by KM12 cells after treatment with Entrectinib or bivalent compounds CPD-027, CPD-053, and CPD-060 at various time points.
Figure 5:
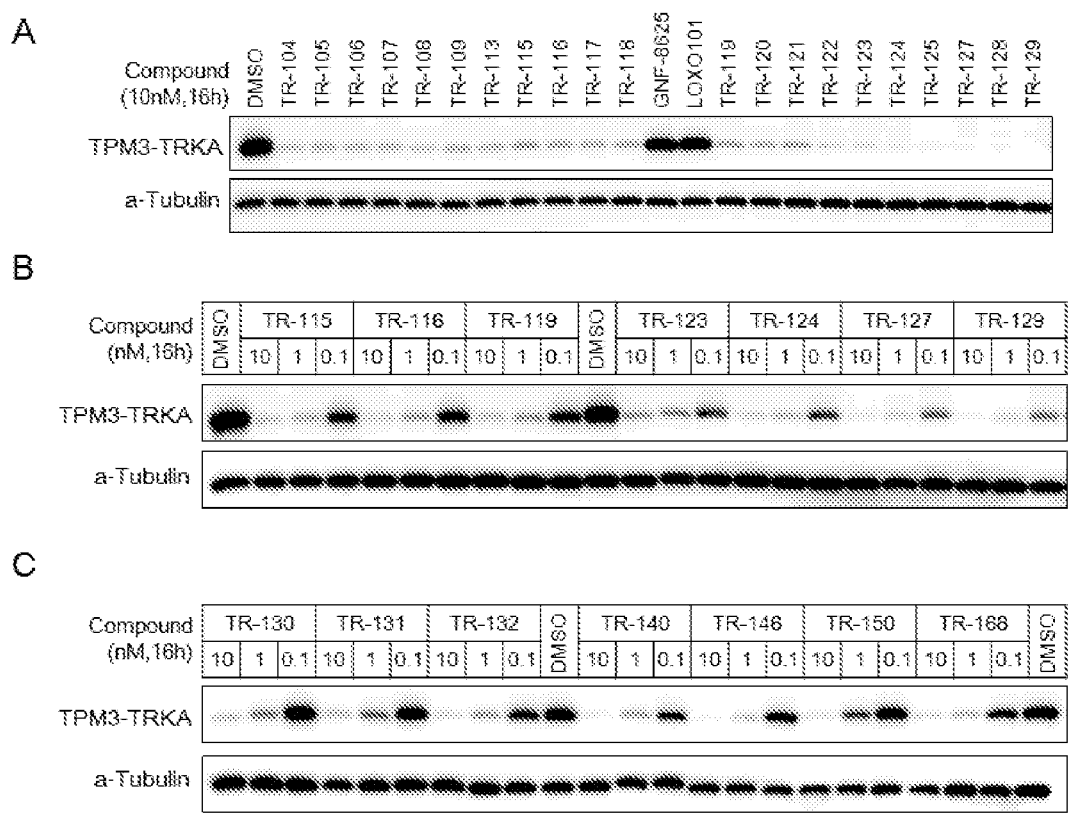
FIG. 5A shows an immunoblot of TPM3-TRKA fusion protein expressed by KM12 cells after treatment with GNF-8625, LOXO101 or bivalent compounds TR-104-TR-129.
FIG. 5B shows an immunoblot of TPM3-TRKA fusion protein expressed by KM12 cells after treatment with a dose range of TR-115, TR-116, TR-119, TR-123, TR-124, TR-127 or TR-129.
FIG. 5C shows an immunoblot of TPM3-TRKA fusion protein expressed by KM12 cells after treatment with a dose range of TR-130, TR-131, TR-132, TR-140, TR-146, TR-150 or TR-168.
Figure 6:
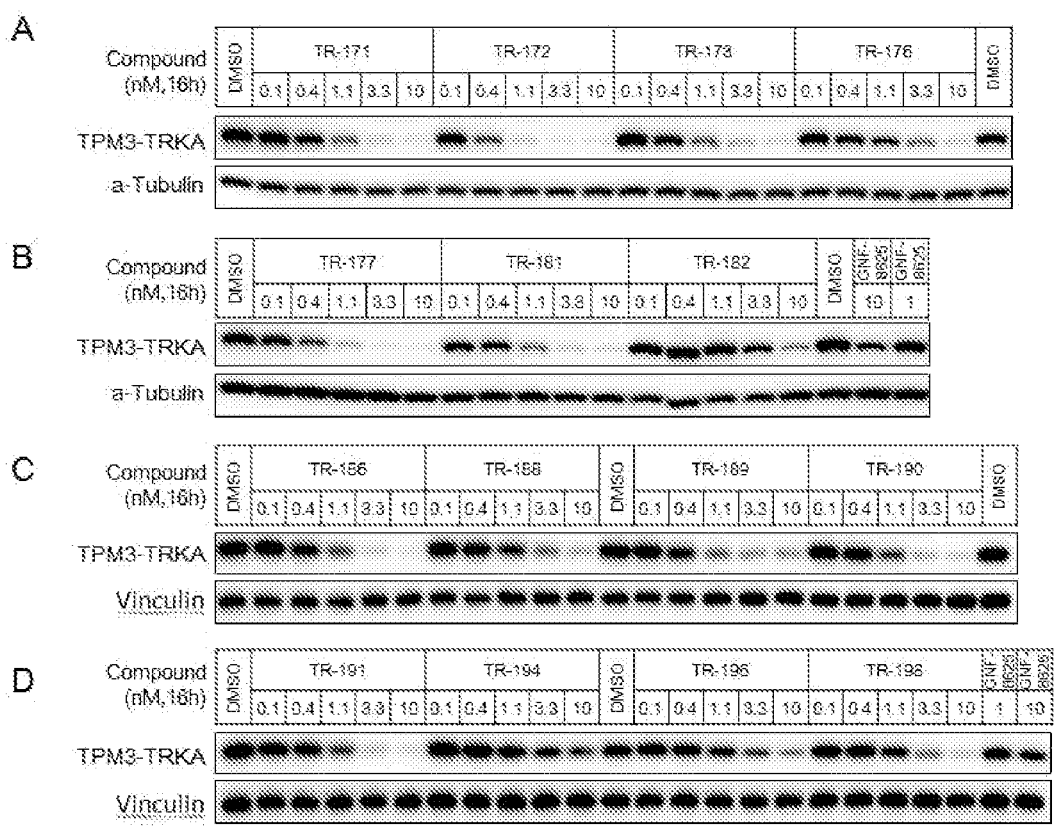
FIG. 6A shows an immunoblot of TPM3-TRKA fusion protein expressed by KM12 cells after treatment with a dose range of TR-171, TR-172, TR-173 or TR-176.
FIG. 6B shows an immunoblot of TPM3-TRKA fusion protein expressed by KM12 cells after treatment with a dose range of TR-177, TR-181, TR-182 or GNF-8625.
FIG. 6C shows an immunoblot of TPM3-TRKA fusion protein expressed by KM12 cells after treatment with a dose range of TR-186, TR-188, TR-189 or TR-190.
FIG. 6D shows an immunoblot of TPM3-TRKA fusion protein expressed by KM12 cells after treatment with a dose range of TR-191, TR-194, TR-196, TR198 or GNF-8625.
Figure 7:
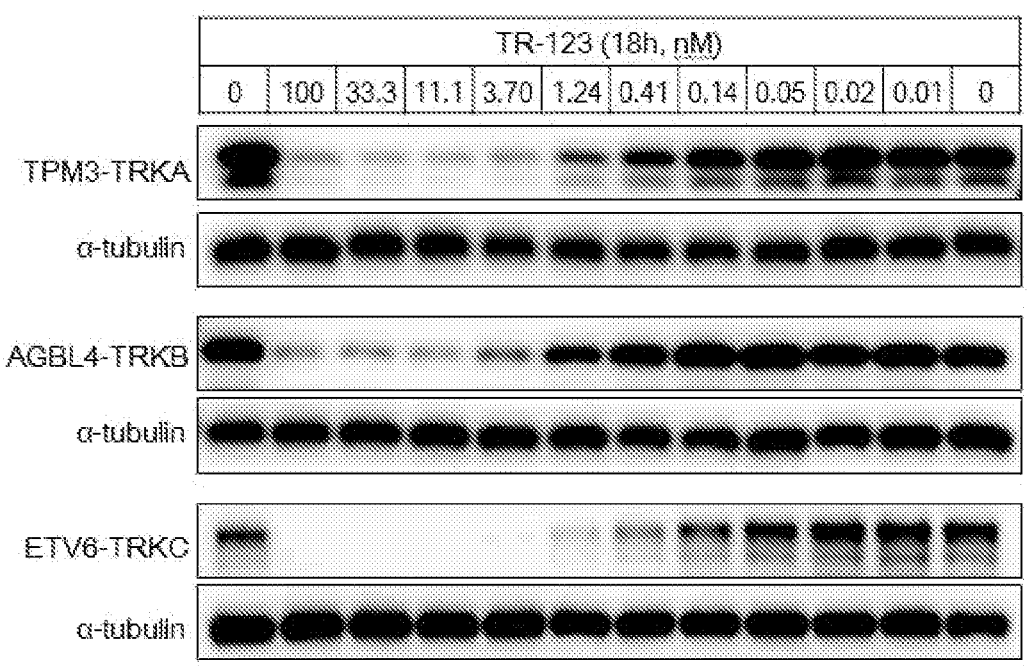
FIG. 7 shows immunoblots of overexpressed TPM3-TRKA, AGBL4-TRKB and ETV6-TRKC fusion protein in KM12 cells after treatment with a dose range of TR-123.
Figure 8:
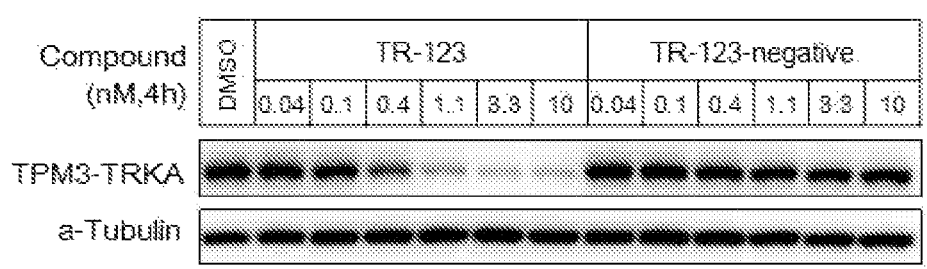
FIG. 8A shows an immunoblot of TPM3-TRKA fusion protein expressed by KM12 cells after treatment with a dose range of compound TR-123 or TR-123-neg.
FIG. 8B shows an immunoblot of wild type TRKA protein expressed by HEL cells after treatment with a dose range of compound TR-123 or TR-123-neg.
Figure 8:
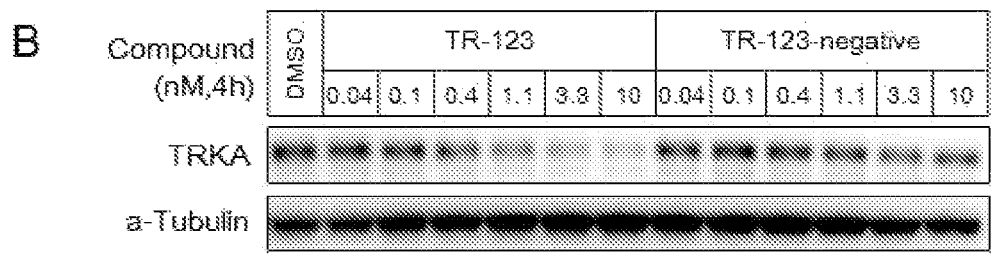
Figure 9:
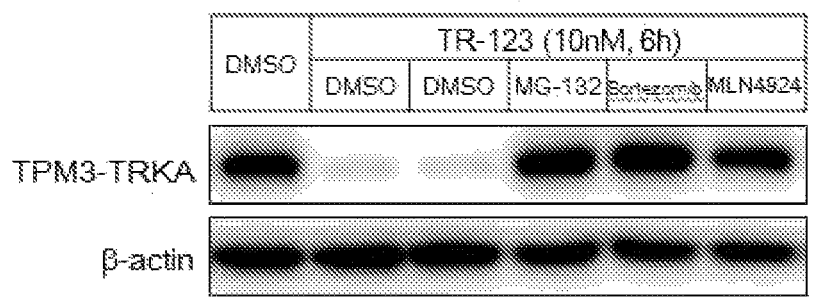
FIG. 9A shows an immunoblot of TPM3-TRKA fusion protein expressed by KM12 cells after treatment with a single dose of TR-123 or combinations with MG-132, Bortezomib or MLN4924.
FIG. 9B shows an immunoblot of wild type TRKA protein expressed by HEL cells after treatment with a single dose of TR-123 or combinations with MG-132, Bortezomib, MLN4924 or Pomalidomide.
Figure 9:
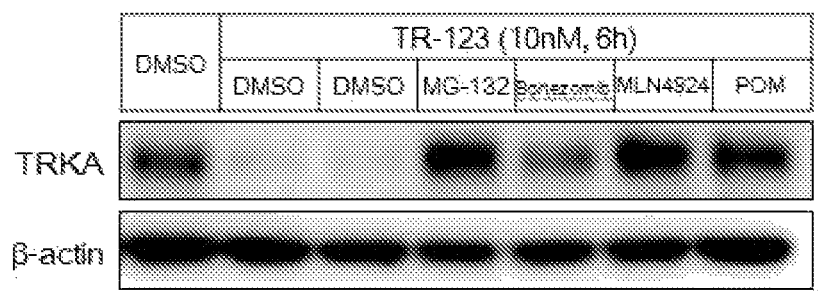
Figure 13:
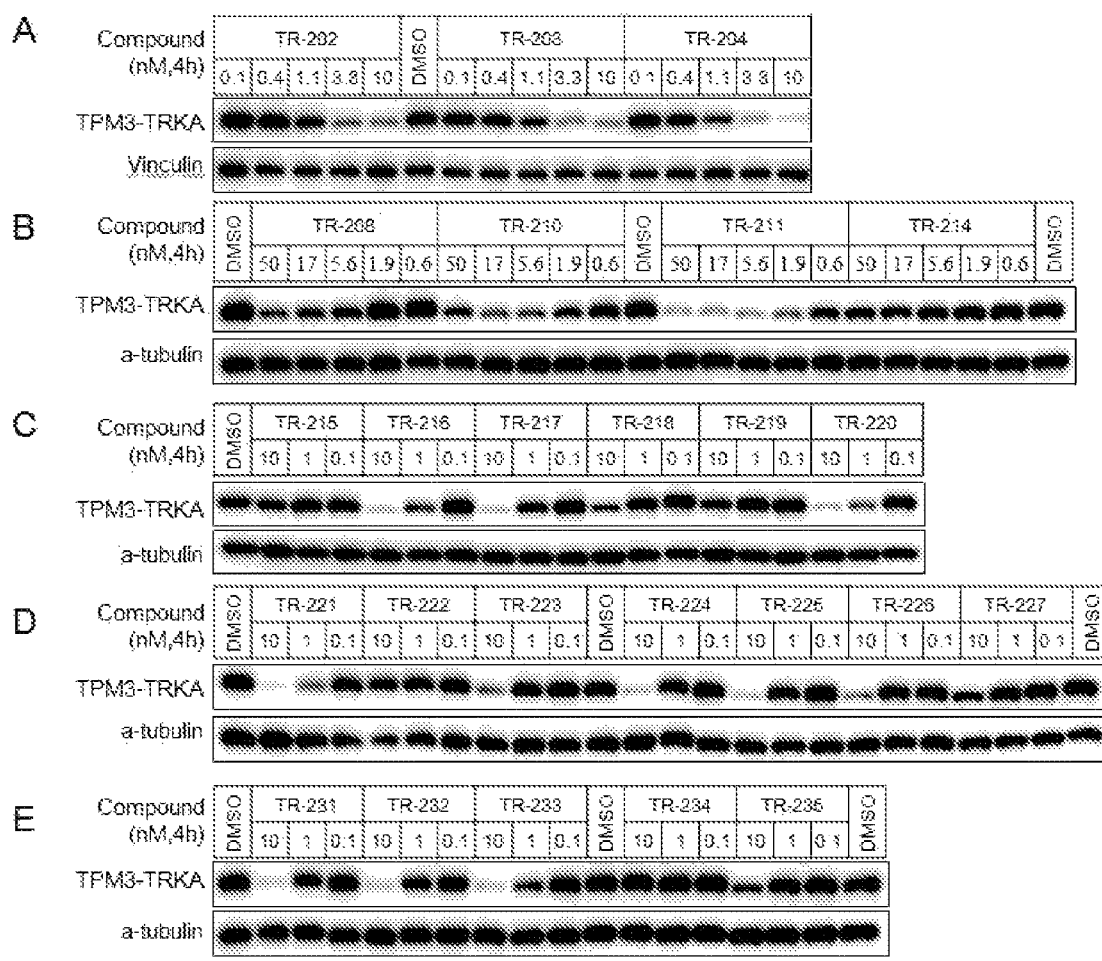
FIG. 13A shows an immunoblot of TPM3-TRKA fusion protein expressed by KM12 cells after treatment with a dose range of TR-202, TR-203 or TR-204.
FIG. 13B shows an immunoblot of TPM3-TRKA fusion protein expressed by KM12 cells after treatment with a dose range of TR-208, TR-210, TR-211 or TR-214.
FIG. 13C shows an immunoblot of TPM3-TRKA fusion protein expressed by KM12 cells after treatment with a dose range of TR-215, TR216, TR-217, TR218, TR-219 or TR-220.
FIG. 13D shows an immunoblot of TPM3-TRKA fusion protein expressed by KM12 cells after treatment with a dose range of TR-221, TR-222, TR-223, TR-224, TR-225, TR-226 or TR-227.
FIG. 13E shows an immunoblot of TPM3-TRKA fusion protein expressed by KM12 cells after treatment with a dose range of TR-231, TR-232, TR-233, TR-234 or TR-235.

Bi-functional compounds, exemplified by CPD-027, CPD-053, and CPD-060, were found to be particularly effective in reducing TPM3-TRKA protein levels in KM12 cells (FIGS. 1A-1C). Treated with 100 nM CPD-027, CPD-053, or CPD-060 for various time points, significant degradation of TPM3-TRKA in KM12 cells was readily detected 15 minutes after adding the bivalent compounds (FIG. 2). Additionally, a panel of selected compounds demonstrated the ability to induce significant degradation of TPM3-TRKA at concentration below 10 nM (FIGS. 5, 6 and 13). In addition to TPM3-TRKA, other TRK fusion proteins, such as AGBL4-TRKB and ETV6-TRKC, were also subject to bispecific compound-induced degradation (FIG. 7). The interaction with cereblon is critical to the ability of bispecific compounds to induce degradation of TRK proteins, as a chemical modification that disrupted cereblon binding abolished TRKA degradation induced by TR-123 (FIG. 8). The degradation was also dependent on the ubiquitin-proteasome system, because it could be neutralized by co-administration of proteasome inhibitors, MG-132 and bortezomib, a cullin E3 ligase inhibitor, MLN4924, or high concentration of pomalidomide that compete for cereblon binding (FIG. 9). These findings collectively demonstrate that bispecific compounds induce degradation of TRK family proteins via a mechanism specifically mediated by cereblon, cullin E3 ligases, and the proteasome.

Figure 3:
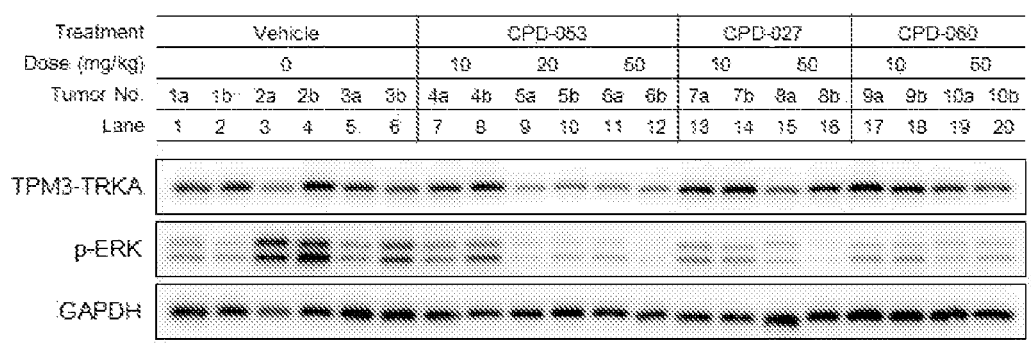
FIG. 3 shows immunoblots of TPM3-TRKA fusion protein expressed by KM12 cells in subcutaneous xenograft tumors after treatment with a dose range of CPD-027, CPD-053, and CPD-060.
Figure 10:
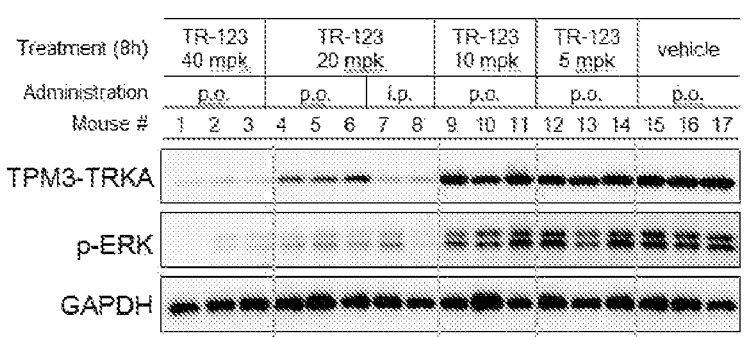
FIG. 10A shows an immunoblot of TPM3-TRKA fusion protein in subcutaneous KM12 xenograft tumors after treatment with a dose range of TR-123.
FIG. 10B shows an immunoblot of TPM3-TRKA fusion protein expressed in subcutaneous KM12 xenograft tumors after treatment with TR-171, TR-172, TR-173, TR-177 or TR-181.
Figure 10:
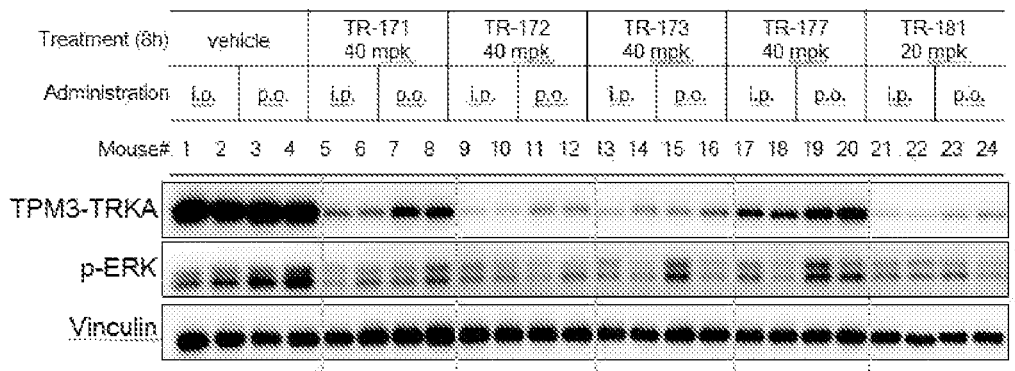

In addition to cultured cells, athymic nude mice bearing KM12 subcutaneous xenograft tumors at the right flank were intraperitoneally treated with 10, 20, or 50 mg/kg CPD-053, CPD-027, or CPD-060. Four hours after drug administration, animals were sacrificed for immunoblotting of TPM3-TPKA in homogenized xenograft tumor masses. The label "a" or "b" represents two different samples of the same xenograft tumor. Bivalent compounds, CPD-027, CPD-053, and CPD-060, exhibited the ability of significantly reducing TPM3-TRKA protein levels in KM12 subcutaneous xenograft tumors within 4 hours after a single dose of drug administration (FIG. 3). Additional compounds, as exemplified by TR-123, TR-171, TR-172, TR-173, TR-177, and TR-181, also exhibited the activities to induce TPM3-TRKA degradation in KM12 subcutaneous tumors through intraperitoneal or oral administration (FIG. 10).

Figure 11:
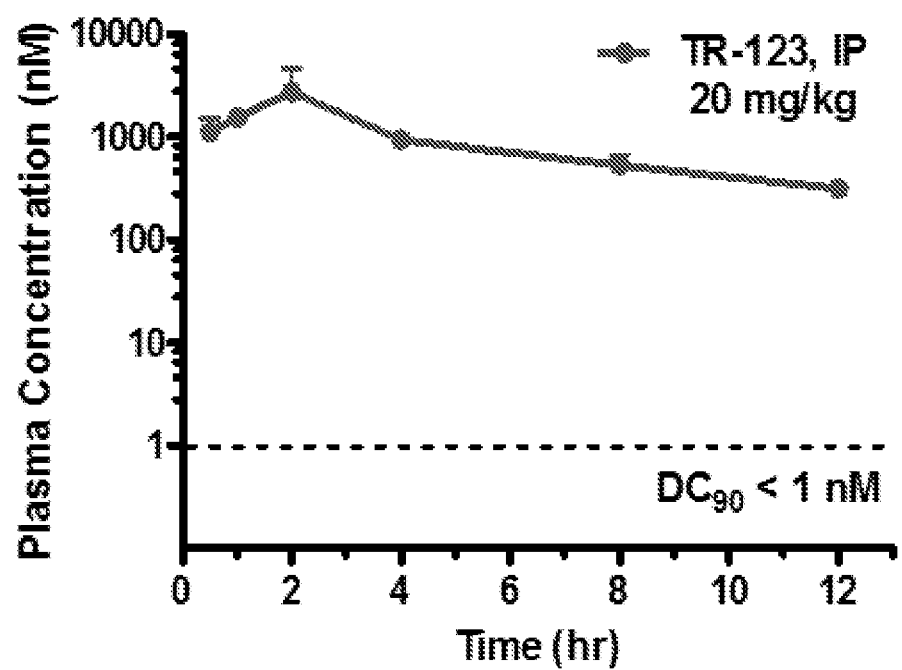
FIG. 11 shows a graph of plasma concentration of TR-123 vs. time points post dosing.
Figure 14:
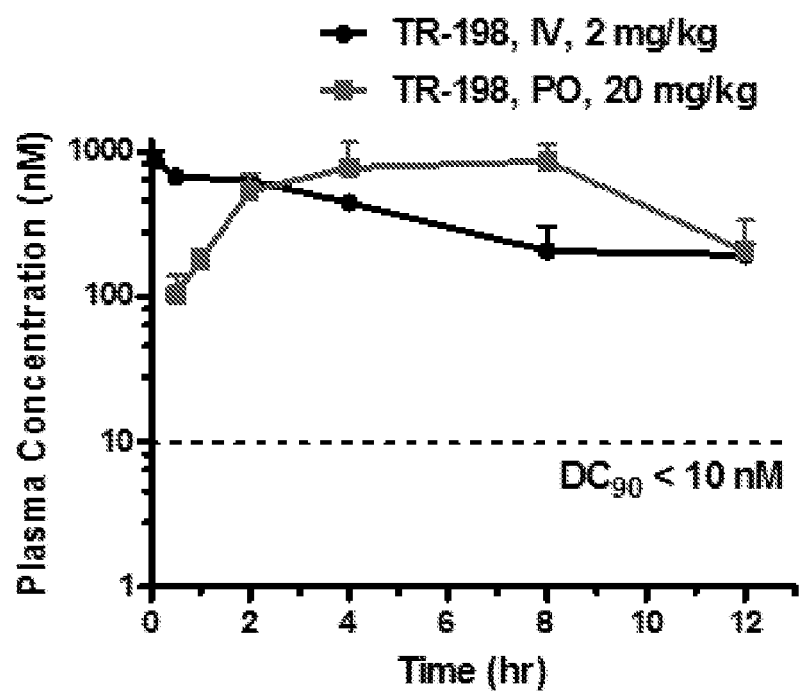
FIG. 14 shows a graph of plasma concentration of TR-198 over time after dosing via intravenous injection or oral gavage.

To investigate the pharmacokinetics of bi-functional compounds, exemplified by TR-123, a single 20 mg/kg intraperitoneal injection was evaluated. Plasma concentration of TR-123 reported at each time point represents the mean value derived from 3 experimental animals Our data showed significant plasma exposure of TR-123 over 12 hours (FIG. 11). Additionally, doses of 2 mg/kg TR-198 via intravenous injection and 20 mg/kg TR-198 via oral gavage were evaluated in mice. Data showed that the oral bioavailability of TR-198 in mice was approximately 16% (FIG. 14).

Figure 12:
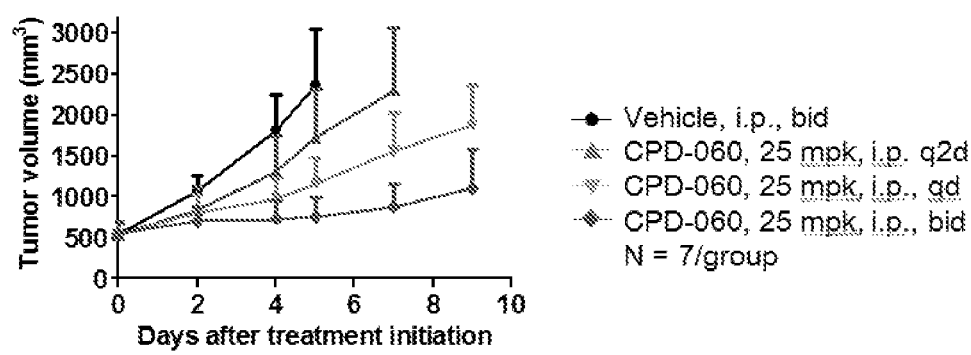
FIG. 12A shows a graph of subcutaneous KM12 xenograft tumor volume vs. days after treatment with a dose range of CPD-060.
FIG. 12B shows a graph of body weight vs. days after treatment with a dose range of CPD-060.
Figure 12:
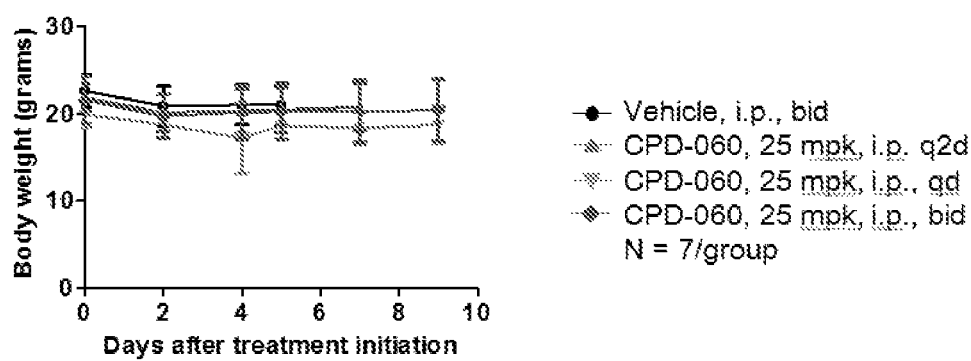
Figure 15:
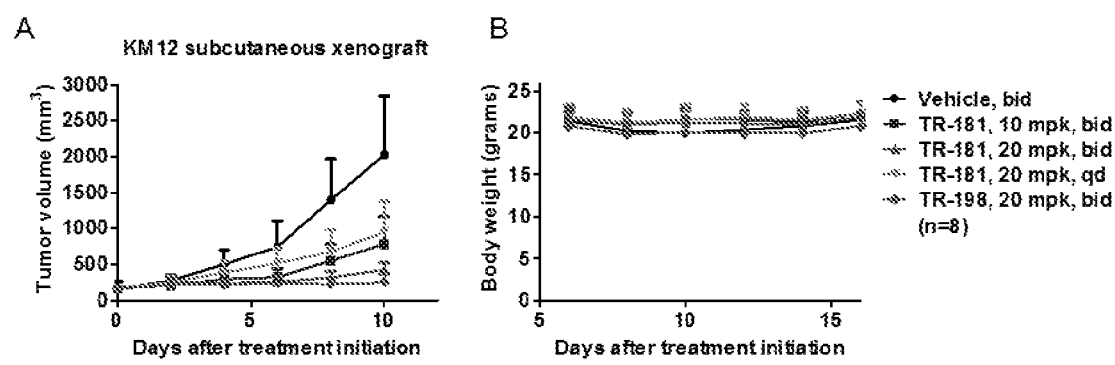
FIG. 15A shows a graph of subcutaneous KM12 xenograft tumor volume as a function of days after treatment with a dose range of TR-181 or a single dose of TR-198.
FIG. 15B shows a graph of body weight as a functional of days after treatment with a dose range of TR-181 or a single dose of TR-198.

The kinase activity of TRK is known to play important roles in tumors expressing TRK-fusion proteins, as TRK kinase inhibitors compromise cell proliferation, survival, and induce marked clinical responses (Amatu et al., 2016; Drilon et al., 2018; Drilon et al., 2017; Khotskaya et al., 2017). KM12 cells seeded in 96-well plates were treated with 500 nM entrectinib or bivalent compounds, i.e. CPD-010, CPD-053, and CPD-057 following a 12-point 2-fold serial dilution. Three days after treatment, cell viability was determined using the CellTiter-Glo kit following manufacturer's instructions. Cell viability was normalized to the mean values of 3 replicates of untreated cells. Dose-dependent response was analyzed following the least-squares non-linear regression method using the GraphPad Prism 5.0 software. Each data point in the figure represents the mean values of three technical replicates±standard deviation. Bivalent compounds also dose-dependently suppressed viability of TPM3-TRKA-expressing KM12 cells, as exemplified by CPD-010, CPD-053, and CPD-057 (FIG. 4A). More specifically, all bivalent compounds that had $IC_{50}$ values smaller than 1000 nM in KM12 cells induced degradation of TPM3-TRKA (FIG. 1 and Table 2-4). In contrast, when KM12 or H358 cells were treated with 1000 nM CPD-053 following an 8-point 3-fold serial dilution, bivalent compounds, as exemplified by CPD-053, did not affect cell viability in KRAS-mutant H358 cells (FIG. 4B). Finally, administration of bivalent compounds, as exemplified by CPD-060, TR-181, and TR-198, significantly repressed the growth of KM12 subcutaneous xenograft tumors without inducing substantial weight losses (FIGS. 12 and 15). Take together, these results indicate that bivalent compounds impair KM12 cell proliferation, survival and tumorigenic potential through specifically inducing degradation of TPM3-TRKA.

Figure 16:
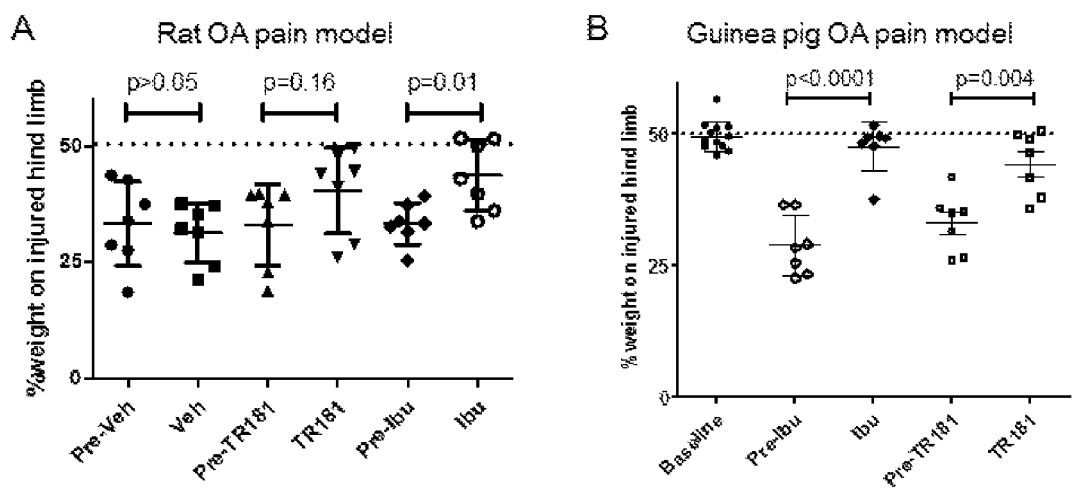
FIG. 16A shows a graph of the percentage of weight born on the injured limb following treatment with a single dose of vehicle (Veh), TR-181 or ibuprofen (Ibu) in rats.
FIG. 16B shows a graph of the percentage of weight born on the injured limb following treatment with a single dose of TR-181 or ibuprofen (Ibu) in guinea pigs.

NGF and its primary receptor TRKA have been well recognized for their roles in pain sensory (Denk et al., 2017). Targeting TRKA represents a promising therapeutic strategy for chronic pain management. Bivalent compounds, exemplified by TR-123, have demonstrated the ability to induce significant degradation of full-length TRKA, same as TPM3-TRKA fusion (FIGS. 8, and 9). The analgesic activities of bivalent compounds were assessed using a widely used chronic pain model associated with osteoarthritis. Osteoarthritis was induced in the right knee of adult male rats or guinea pigs following monoiodoacetate injection. One week later, animals were treated with TR-181 with ibuprofen as the positive control. The pain sensory was assessed as weight distribution between the injured limb and the contralateral limb using an incapacitance meter. Data showed significant analgesic activity of TR-181 in the osteoarthritis models of rats and guinea pigs (FIG. 16).

Definition of Terms

As used herein, the terms "comprising" and "including" are used in their open, non-limiting sense.

"Alkyl" refers to a straight or branched hydrocarbon chain radical consisting solely of carbon and hydrogen atoms, containing no unsaturation. An alkyl may comprise one, two, three, four, five, six, seven, eight, nine, ten, eleven, twelve, thirteen, fourteen, fifteen, or sixteen carbon atoms. In certain embodiments, an alkyl comprises one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), pentyl, 3-methylhexyl, 2-methylhexyl, and the like.

"Alkenyl" refers to a straight or branched hydrocarbon chain radical group consisting solely of carbon and hydrogen atoms, containing at least one double bond. An alkenyl may comprise two, three, four, five, six, seven, eight, nine, ten, eleven, twelve, thirteen, fourteen, fifteen, or sixteen carbon atoms. In certain embodiments, an alkenyl comprises two to twelve carbon atoms (e.g., $C_2$-$C_{12}$ alkenyl). In certain embodiments, an alkenyl comprises two to eight carbon atoms (e.g., $C_2$-$C_8$ alkenyl). In certain embodiments, an alkenyl comprises two to six carbon atoms (e.g., $C_2$-$C_6$ alkenyl). In other embodiments, an alkenyl comprises two to four carbon atoms (e.g., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

The term "allyl," as used herein, means a $CH_2CH=CH_2$ group.

As used herein, the term "alkynyl" refers to a straight or branched hydrocarbon chain radical group consisting solely of carbon and hydrogen atoms, containing at least one triple bond. An alkynyl may comprise two, three, four, five, six, seven, eight, nine, ten, eleven, twelve, thirteen, fourteen, fifteen, or sixteen carbon atoms. In certain embodiments, an alkynyl comprises two to twelve carbon atoms (e.g., $C_2$-$C_{12}$ alkynyl). In certain embodiments, an alkynyl comprises two to eight carbon atoms (e.g., $C_2$-$C_8$ alkynyl). In other embodiments, an alkynyl has two to six carbon atoms (e.g., $C_2$-$C_6$ alkynyl). In other embodiments, an alkynyl has two to four carbon atoms (e.g., $C_2$-$C_4$ alkynyl). The alkynyl is attached to the rest of the molecule by a single bond. Examples of such groups include, but are not limited to, ethynyl, propynyl, 1-butynyl, 2-butynyl, 1-pentynyl, 2-pentynyl, 1-hexynyl, 2-hexynyl, 3-hexynyl, and the like.

The term "alkoxy", as used herein, means an alkyl group as defined herein which is attached to the rest of the molecule via an oxygen atom. Examples of such groups include, but are not limited to, methoxy, ethoxy, n-propyloxy, iso-propyloxy, n-butoxy, iso-butoxy, tert-butoxy, pentyloxy, hexyloxy, and the like.

The term "aryl", as used herein, "refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms. An aryl may comprise from six to eighteen carbon atoms, where at least one of the rings in the ring system is fully unsaturated, i.e., it contains a cyclic, delocalized (4n+2) π-electron system in accordance with the Hückel theory. In certain embodiments, an aryl comprises six to fourteen carbon atoms ($C_6$-$C_{14}$ aryl). In certain embodiments, an aryl comprises six to ten carbon atoms ($C_6$-$C_{10}$ aryl). Examples of such groups include, but are not limited to, phenyl, fluorenyl and naphthyl. The terms "Ph" and "phenyl," as used herein, mean a —$C_6H_5$ group.

The term "heteroaryl", refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. In certain embodiments, a heteroaryl refers to a radical derived from a 3- to 10-membered aromatic ring radical (3-10 membered heteroaryl). In certain embodiments, a heteroaryl refers to a radical derived from 5- to 7-membered aromatic ring radical (5-7 membered heteroaryl). Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of such groups include, but are not limited to, pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. In certain embodiments, an heteroaryl is attached to the rest of the molecule via a ring carbon atom. In certain embodiments, an heteroaryl is attached to the rest of the molecule via a nitrogen atom (N-attached) or a carbon atom (C-attached). For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached).

The term "heterocyclyl", as used herein, means a non-aromatic, monocyclic, bicyclic, tricyclic, or tetracyclic radical having a total of from 4, 5, 6, 7, 8, 9, 10, 11, 12, or 13 atoms in its ring system, and containing from 3 to 12 carbon atoms and from 1 to 4 heteroatoms each independently selected from O, S and N, and with the proviso that the ring of said group does not contain two adjacent 0 atoms or two adjacent S atoms. A heterocyclyl group may include fused, bridged or spirocyclic ring systems. In certain embodiments, a hetercyclyl group comprises 3 to 10 ring atoms (3-10 membered heterocyclyl). In certain embodiments, a heterocyclyl group comprises 3 to 8 ring atoms (3-8 membered heterocyclyl). In certain embodiments, a heterocyclyl group comprises 4 to 8 ring atoms (4-8 membered heterocyclyl). In certain embodiments, a hetercyclyl group comprises 3 to 6 ring atoms (3-6 membered heterocyclyl). A heterocyclyl group may contain an oxo substituent at any available atom that will result in a stable compound. For example, such a group may contain an oxo atom at an available carbon or nitrogen atom. Such a group may contain more than one oxo substituent if chemically feasible. In addition, it is to be understood that when such a heterocyclyl group contains a sulfur atom, said sulfur atom may be oxidized with one or two oxygen atoms to afford either a sulfoxide or sulfone. An example of a 4 membered heterocyclyl group is azetidinyl (derived from azetidine). An example of a 5 membered cycloheteroalkyl group is pyrrolidinyl. An example of a 6 membered cycloheteroalkyl group is piperidinyl. An example of a 9 membered cycloheteroalkyl group is indolinyl. An example of a 10 membered cycloheteroalkyl group is 4H-quinolizinyl. Further examples of such heterocyclyl groups include, but are not limited to, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclopioiheptanyl, 3H-indolyl, quinolizinyl, 3-oxopiperazinyl, 4-methylpiperazinyl, 4-ethylpiperazinyl, and 1-oxo-2,8,diazaspiro[4.5]dec-8-yl. A heteroaryl group may be attached to the rest of molecular via a carbon atom (C-attached) or a nitrogen atom (N-attached). For instance, a group derived from piperazine may be piperazin-1-yl (N-attached) or piperazin-2-yl (C-attached).

The term "cycloalkyl" means a saturated, monocyclic, bicyclic, tricyclic, or tetracyclic radical having a total of from 4, 5, 6, 7, 8, 9, 10, 11, 12, or 13 carbon atoms in its ring system. A cycloalkyl may be fused, bridged or spirocyclic. In certain embodiments, a cycloalkyl comprises 3 to 8 carbon ring atoms ($C_3$-$C_8$ cycloalkyl). In certain embodiments, a cycloalkyl comprises 3 to 6 carbon ring atoms ($C_3$-$C_6$ cycloalkyl). Examples of such groups include, but are not limited to, cyclopropyl, cyclobutyl, cyclopentyl, cyclopentenyl, cyclohexyl, cycloheptyl, adamantyl, and the like.

The term "cycloalkylene" is a bidentate radical obtained by removing a hydrogen atom from a cycloalkyl ring as defined above. Examples of such groups include, but are not limited to, cyclopropylene, cyclobutylene, cyclopentylene, cyclopentenylene, cyclohexylene, cycloheptylene, and the like.

The term "spirocyclic" as used herein has its conventional meaning, that is, any ring system containing two or more rings wherein two of the rings have one ring carbon in common. Each ring of the spirocyclic ring system, as herein defined, independently comprises 3 to 20 ring atoms. Preferably, they have 3 to 10 ring atoms. Non-limiting examples of a spirocyclic system include spiro[3.3]heptane, spiro[3.4]octane, and spiro[4.5]decane.

The term cyano" refers to a —C≡N group.

An "aldehyde" group refers to a C(O)H group.

An "alkoxy" group refers to both an O-alkyl, as defined herein.

An "alkoxycarbonyl" refers to a —C(O)-alkoxy, as defined herein.

An "alkylaminoalkyl" group refers to an -alkyl-NR-alkyl group, as defined herein.

An "alkylsulfonyl" group refers to a —$SO_2$alkyl, as defined herein.

An "amino" group refers to an optionally substituted —$NH_2$.

An "aminoalkyl" group refers to an alky-amino group, as defined herein.

An "aminocarbonyl" refers to a —C(O)-amino, as defined herein.

An "arylalkyl" group refers to -alkylaryl, where alkyl and aryl are defined herein.

An "aryloxy" group refers to both an O-aryl and an O-heteroaryl group, as defined herein.

An "aryloxycarbonyl" refers to —C(O)-aryloxy, as defined herein.

An "arylsulfonyl" group refers to a —$SO_2$aryl, as defined herein.

A "carbonyl" group refers to a —C(O)— group, as defined herein.

A "carboxylic acid" group refers to a C(O)OH group.

A "cycloalkoxy" refers to a O-cycloalkyl group, as defined herein.

A "halo" or "halogen" group refers to fluorine, chlorine, bromine or iodine.

A "haloalkyl" group refers to an alkyl group substituted with one or more halogen atoms.

A "hydroxy" group refers to an —OH group.

A "nitro" group refers to a —$NO_2$ group.

An "oxo" group refers to the =O substituent.

A "trihalomethyl" group refers to a methyl substituted with three halogen atoms.

The term "substituted," means that the specified group or moiety bears one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo, —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$—SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$ ($C_1$-$C_4$ haloalkyl).

The term "null" means the absence of an atom or moiety, and there is a bond between adjacent atoms in the structure.

The term "optionally substituted" means that the specified group may be either unsubstituted or substituted by one or more substituents as defined herein. It is to be understood that in the compounds of the present invention when a group is said to be "unsubstituted," or is "substituted" with fewer groups than would fill the valencies of all the atoms in the compound, the remaining valencies on such a group are filled by hydrogen. For example, if a $C_6$ aryl group, also called "phenyl" herein, is substituted with one additional substituent, one of ordinary skill in the art would understand that such a group has 4 open positions left on carbon atoms of the $C_6$ aryl ring (6 initial positions, minus one at which the remainder of the compound of the present invention is attached to and an additional substituent, remaining 4 positions open). In such cases, the remaining 4 carbon atoms are each bound to one hydrogen atom to fill their valencies. Similarly, if a $C_6$ aryl group in the present compounds is said to be "disubstituted," one of ordinary skill in the art would understand it to mean that the $C_6$ aryl has 3 carbon atoms remaining that are unsubstituted. Those three unsubstituted carbon atoms are each bound to one hydrogen atom to fill their valencies.

As used herein, the same symbol in different FORMULA means different definition, for example, the definition of R1 in FORMULA 1 is as defined with respect to FORMULA 1 and the definition of R1 in FORMULA 6 is as defined with respect to FORMULA 6.

As used herein, when m (or nor o or p) is defined by a range, for example, "m is 0 to 15" or "m=0-3" mean that m is an integer from 0 to 15 (i.e. m is 0, 1, 2, 3, 4, 5, 6, 7, 8, 9, 10, 11, 12, 13, 14, or 15) or m is an integer from 0 to 3 (i.e. m is 0, 1, 2, or 3) or is any integer in the defined range.

"Pharmaceutically acceptable salt" includes both acid and base addition salts. A pharmaceutically acceptable salt of any one of the bivalent compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

Pharmaceutical Compositions

In some aspects, the compositions and methods described herein include the manufacture and use of pharmaceutical compositions and medicaments that include one or more bivalent compounds as disclosed herein. Also included are the pharmaceutical compositions themselves.

In some aspects, the compositions disclosed herein can include other compounds, drugs, or agents used for the treatment of cancer. For example, in some instances, pharmaceutical compositions disclosed herein can be combined with one or more (e.g., one, two, three, four, five, or less than ten) compounds. Such additional compounds can include, e.g., conventional chemotherapeutic agents or any other cancer treatment known in the art. When co-administered, bivalent compounds disclosed herein can operate in conjunction with conventional chemotherapeutic agents or any other cancer treatment known in the art to produce mechanistically additive or synergistic therapeutic effects.

In some aspects, the pH of the compositions disclosed herein can be adjusted with pharmaceutically acceptable acids, bases, or buffers to enhance the stability of the bivalent compound or its delivery form.

Pharmaceutical compositions typically include a pharmaceutically acceptable excipient, adjuvant, or vehicle. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. A pharmaceutically acceptable excipient, adjuvant, or vehicle is a substance that can be administered to a patient, together with a compound of the invention, and which does not compromise the pharmacological activity thereof and is nontoxic when administered in doses sufficient to deliver a therapeutic amount of the compound. Exemplary conventional nontoxic pharmaceutically acceptable excipients, adjuvants, and vehicles include, but not limited to, saline, solvents, dispersion media, coatings, antibacterial and antifungal agents, isotonic and absorption delaying agents, and the like, compatible with pharmaceutical administration.

In particular, pharmaceutically acceptable excipients, adjuvants, and vehicles that can be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

Depending on the dosage form selected to deliver the bivalent compounds disclosed herein, different pharmaceutically acceptable excipients, adjuvants, and vehicles may be used. In the case of tablets for oral use, pharmaceutically acceptable excipients, adjuvants, and vehicles may be used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening, flavoring, or coloring agents can be added.

As used herein, the bivalent compounds disclosed herein are defined to include pharmaceutically acceptable derivatives or prodrugs thereof. A "pharmaceutically acceptable derivative" means any pharmaceutically acceptable salt, solvate, or prodrug, e.g., carbamate, ester, phosphate ester, salt of an ester, or other derivative of a compound or agent disclosed herein, which upon administration to a recipient is capable of providing (directly or indirectly) a compound described herein, or an active metabolite or residue thereof. Particularly favored derivatives and prodrugs are those that increase the bioavailability of the compounds disclosed herein when such compounds are administered to a subject (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group that enhances aqueous solubility or active transport through the gut membrane is appended to the structure of formulae described herein. Such derivatives are recognizable to those skilled in the art without undue experimentation. Nevertheless, reference is made to the teaching of Burger's Medicinal Chemistry and Drug Discovery, $5^{th}$ Edition, Vol. 1: Principles and Practice, which is incorporated herein by reference to the extent of teaching such derivatives.

The bivalent compounds disclosed herein include pure enantiomers, mixtures of enantiomers, pure diastereoisomers, mixtures of diastereoisomers, diastereoisomeric racemates, mixtures of diastereoisomeric racemates and the meso-form and pharmaceutically acceptable salts, solvent complexes, morphological forms, or deuterated derivatives thereof.

In some aspects, the pharmaceutical compositions disclosed herein can include an effective amount of one or more bivalent compounds. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment or prevention of cell growth, cell proliferation, or cancer). In some aspects, pharmaceutical compositions can further include one or more additional compounds, drugs, or agents used for the treatment of cancer (e.g., conventional chemotherapeutic agents) in amounts effective for causing an intended effect or physiological outcome (e.g., treatment or prevention of cell growth, cell proliferation, or cancer).

In some aspects, the pharmaceutical compositions disclosed herein can be formulated for sale in the United States, import into the United States, or export from the United States.

Administration of Pharmaceutical Compositions

The pharmaceutical compositions disclosed herein can be formulated or adapted for administration to a subject via any route, e.g., any route approved by the Food and Drug Administration (FDA). Exemplary methods are described in the FDA Data Standards Manual (DSM) (available at http://www.fda.gov/Drugs/DevelopmentApprovalProcess/Forms-SubmissionRequirements/ElectronicSubmissions/DataStandardsManualmonographs). In particular, the pharmaceutical compositions can be formulated for and administered via oral, parenteral, or transdermal delivery. The term "parenteral" as used herein includes subcutaneous, intracutaneous, intravenous, intramuscular, intraperitoneal, intra-articular, intra-arterial, intrasynovial, intrasternal, intrathecal, intralesional, and intracranial injection or infusion techniques.

For example, the pharmaceutical compositions disclosed herein can be administered, e.g., topically, rectally, nasally (e.g., by inhalation spray or nebulizer), buccally, vaginally, subdermally (e.g., by injection or via an implanted reservoir), or ophthalmically.

For example, pharmaceutical compositions of this invention can be orally administered in any orally acceptable dosage form including, but not limited to, capsules, tablets, emulsions and aqueous suspensions, dispersions and solutions.

For example, the pharmaceutical compositions of this invention can be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, and polyethylene glycols.

For example, the pharmaceutical compositions of this invention can be administered by nasal aerosol or inhalation Such compositions are prepared according to techniques well-known in the art of pharmaceutical formulation and can be prepared as solutions in saline, employing benzyl alcohol or other suitable preservatives, absorption promoters to enhance bioavailability, fluorocarbons, or other solubilizing or dispersing agents known in the art.

For example, the pharmaceutical compositions of this invention can be administered by injection (e.g., as a solution or powder). Such compositions can be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, e.g., as a solution in 1,3-butanediol. Among the acceptable vehicles and solvents that may be employed are mannitol, water, Ringer's solution, and isotonic sodium chloride solution. In addition, sterile, fixed oils are conventionally employed as a solvent or suspending medium. For this purpose, any bland fixed oil can be employed, including synthetic mono- or diglycerides. Fatty acids, such as oleic acid and its glyceride derivatives are useful in the preparation of injectables, as are natural pharmaceutically-acceptable oils, e.g., olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens, Spans, or other similar emulsifying agents or bioavailability enhancers which are commonly used in the manufacture of pharmaceutically acceptable solid, liquid, or other dosage forms can also be used for the purposes of formulation.

In some aspects, an effective dose of a pharmaceutical composition of this invention can include, but is not limited to, e.g., about 0.00001, 0.0001, 0.001, 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.25, 1.5, 1.75, 2, 2.5, 3, 4, 5, 6, 7, 8, 9, 10, 15, 20, 30, 40, 50, 60, 70, 80, 90, 100, 200, 300, 400, 500, 600, 700, 800, 900, 1000, 2500, 5000, or 10000 mg/kg/day, or according to the requirements of the particular pharmaceutical composition.

When the pharmaceutical compositions disclosed herein include a combination of the bivalent compounds described herein and one or more additional compounds (e.g., one or more additional compounds, drugs, or agents used for the treatment of cancer or any other condition or disease, including conditions or diseases known to be associated with or caused by cancer), both the bivalent compounds and the additional compounds may be present at dosage levels of between about 1 to 100%, and more preferably between about 5 to 95% of the dosage normally administered in a monotherapy regimen. The additional agents can be administered separately, as part of a multiple dose regimen, from the compounds of this invention. Alternatively, those agents can be part of a single dosage form, mixed together with the compounds of this invention in a single composition.

In some aspects, the pharmaceutical compositions disclosed herein can be included in a container, pack, or dispenser together with instructions for administration.

Methods of Treatment

The methods disclosed herein contemplate administration of an effective amount of a compound or composition to achieve the desired or stated effect. Typically, the compounds or compositions of the invention will be administered from about 1 to about 6 times per day or, alternately or in addition, as a continuous infusion. Such administration can be used as a chronic or acute therapy. The amount of active ingredient that can be combined with the carrier materials to produce a single dosage form will vary depending upon the host treated and the particular mode of administration. A typical preparation will contain from about 5% to about 95% active compound (w/w). Alternatively, such preparations can contain from about 20% to about 80% active compound.

In some aspects, provided herein are a bivalent compound described herein for preventing or treating a disease or condition.

In some aspects, provided herein are a bivalent compound described herein for treating or preventing one or more diseases or conditions disclosed herein in a subject in need thereof. In certain embodiments, the disease or condition is a TRK-mediated disease or condition. In certain embodiments, the disease or condition is resulted from TRK expression, mutation, or fusion. In certain embodiments, the disease or condition comprises non-small cell lung cancer, colorectal cancer, gastric cancer, liver cancer, invasive breast cancer, lung adenocarcinoma, uterine cancer, adrenal cancer, pancreatic cancer, ovarian cancer, esophageal cancer, urinary bladder cancer, endometrial cancer, prostate cancer low-grade glioma, glioblastoma, Spitzoid cancer, soft tissue sarcoma, papillary thyroid carcinoma, head and neck squamous cell carcinoma, congenital fibrosarcoma, congenital mesoblastic nephroma, secretory breast carcinoma, mammary analogue secretory carcinoma, acute myeloid leukemia, ductal carcinoma, pulmonary neuroendocrine tumors, pheochromocytoma, and Wilms' tumor. In certain embodiments, the disease or condition comprises cancer, inflammatory diseases, acute and chronic pain, pruritus, bone-related diseases, neurodegenerative diseases, infectious diseases, and other diseases, including but not limited to neuroblastoma, prostate cancer, pancreatic cancer, melanoma, head and neck cancer, gastric carcinoma, lung carcinoma, liver cancer, uterine cancer, adrenal cancer, biliary tree cancer, intestinal cancer, colorectal cancer, ovarian cancer, lung carcinoma, small cell lung cancer, non-small cell lung cancer, gastric carcinoma, breast cancer, esophageal cancer, urinary bladder cancer, endometrial cancer, brain cancer, low-grade glioma, glioblastoma, medulloblastoma, secratory breast cancer, secretory breast carcinoma, salivary gland cancer, papillary thyroid carcinoma, ductal carcinoma, adult myeloid leukemia, acute myeloid leukemia, large cell neuroendocrine tumors, pulmonary neuroendocrine tumors, sarcomas, pheochromocytoma, fibrosarcoma, congenital fibrosarcoma, congenital mesoblastic nephroma, secretory breast carcinoma, malignant fibrous histiocytoma, embryonal rhabdomysocarcoma, leiomysosarcoma, neuro-fibrosarcoma, neoplasms of the central nervous systems, osteosarcoma, synovial sarcoma, liposarcoma, alveolar soft part sarcoma Spitzoid cancer, Wilms' tumor, lymphomas (e.g. including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma), inflammatory lung diseases (e.g. asthma), inflammatory bowel diseases, (e.g. ulcerative colitis, Crohn's disease), inflammatory skin diseases (e.g. atopic dermatitis, eczema and psoriasis), interstitial cystitis, rhinitis, acute pain, chronic pain, cancer pain, surgical pain, inflammatory pain, neuropathic pain, nociceptive pain, pain of osteoarthritis, chronic low back pain, low back pain of osteoporosis, pain of bone fracture, pain of rheumatoid arthritis, postherpetic pain, pain of diabetic neuropathy, fibromyalgia, pain of pancreatitis, pain of interstitial cystitis, pain of endometriosis, pain of irritable bowel syndrome, migraine, pain of pulpitis, interstitial cystitis pain, painful bladder syndrome, central pain syndromes, postsurgical pain syndromes, bone and joint pain, repetitive motion pain, dental pain, myofascial pain, perioperative pain, dysmennorhea, myofascial pain, angina pain, headache, primary hyperalgesia, secondary hyperalgesia, primary allodynia, secondary allodynia, other pain caused by central sensitization, systemic cutaneous pruritus, localized cutaneous pruritus, senile cutaneous pruritus, gestational pruritus, pruritus ani, vulvar pruritus, metastatic bone disease, treatment-induce bone loss, osteoporosis, rheumatoid arthritis, bone metastases, ankylosing spondylitis, Paget's disease, periodontal disease, osteolytic disease, multiple sclerosis, Parkinson's disease, Alzheimer's disease, Chagas disease, cachexia, anorexia, demyelination and dysmyelination. In certain embodiments, the disease or condition is a relapsed disease. In certain embodiments, the disease or condition is a relapsed cancer. In certain embodiments, the disease or condition is refractory to one or more previous treatments.

In some aspects, provided herein are use of a bivalent compound in manufacture of a medicament for preventing or treating one or more diseases or conditions disclosed herein.

In some aspects, the methods disclosed include the administration of a therapeutically effective amount of one or more of the compounds or compositions described herein to a subject (e.g., a mammalian subject, e.g., a human subject) who is in need of, or who has been determined to be in need of, such treatment. In some aspects, the methods disclosed include selecting a subject and administering to the subject an effective amount of one or more of the compounds or compositions described herein, and optionally repeating administration as required for the prevention or treatment of cancer.

In some aspects, subject selection can include obtaining a sample from a subject (e.g., a candidate subject) and testing the sample for an indication that the subject is suitable for selection. In some aspects, the subject can be confirmed or identified, e.g. by a health care professional, as having had, having an elevated risk to have, or having a condition or disease. In some aspects, suitable subjects include, for example, subjects who have or had a condition or disease but that resolved the disease or an aspect thereof, present reduced symptoms of disease (e.g., relative to other subjects (e.g., the majority of subjects) with the same condition or disease), or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some aspects, exhibition of a positive immune response towards a condition or disease can be made from patient records, family history, or detecting an indication of a positive immune response. In some aspects, multiple parties can be included in subject selection. For example, a first party can obtain a sample from a candidate subject and a second party can test the sample. In some aspects, subjects can be selected or referred by a medical practitioner (e.g., a general practitioner). In some aspects, subject selection can include obtaining a sample from a selected subject and storing the sample or using the in the methods disclosed herein. Samples can include, e.g., cells or populations of cells.

In some aspects, methods of treatment can include a single administration, multiple administrations, and repeating administration of one or more compounds disclosed herein as required for the prevention or treatment of the disease or condition disclosed herein (e.g., an TRK-mediated disease). In some aspects, methods of treatment can include assessing a level of disease in the subject prior to treatment, during treatment, or after treatment. In some aspects, treatment can continue until a decrease in the level of disease in the subject is detected.

The term "subject," as used herein, refers to any animal. In some instances, the subject is a mammal. In some instances, the term "subject," as used herein, refers to a human (e.g., a man, a woman, or a child).

The terms "administer," "administering," or "administration," as used herein, refer to implanting, ingesting, injecting, inhaling, or otherwise absorbing a compound or composition, regardless of form. For example, the methods disclosed herein include administration of an effective amount of a compound or composition to achieve the desired or stated effect.

The terms "treat", "treating," or "treatment," as used herein, refer to partially or completely alleviating, inhibiting, ameliorating, or relieving the disease or condition from which the subject is suffering. This means any manner in which one or more of the symptoms of a disease or disorder (e.g., cancer) are ameliorated or otherwise beneficially altered. As used herein, amelioration of the symptoms of a particular disorder (e.g., cancer) refers to any lessening, whether permanent or temporary, lasting or transient that can be attributed to or associated with treatment by the bivalent compounds, compositions and methods of the present invention. In some embodiments, treatment can promote or result in, for example, a decrease in the number of tumor cells (e.g., in a subject) relative to the number of tumor cells prior to treatment; a decrease in the viability (e.g., the average/mean viability) of tumor cells (e.g., in a subject) relative to the viability of tumor cells prior to treatment; a decrease in the rate of growth of tumor cells; a decrease in the rate of local or distant tumor metastasis; or reductions in one or more symptoms associated with one or more tumors in a subject relative to the subject's symptoms prior to treatment.

The terms "prevent," "preventing," and "prevention," as used herein, shall refer to a decrease in the occurrence of a disease or decrease in the risk of acquiring a disease or its associated symptoms in a subject. The prevention may be complete, e.g., the total absence of disease or pathological cells in a subject. The prevention may also be partial, such that the occurrence of the disease or pathological cells in a subject is less than, occurs later than, or develops more slowly than that which would have occurred without the present invention. In certain embodiments, the subject has an elevated risk of developing one or more TRK-mediated diseases. Exemplary TRK-mediated diseases that can be treated with bivalent compounds include, for example, non-small cell lung cancer, colorectal cancer, gastric cancer, liver cancer, invasive breast cancer, lung adenocarcinoma, uterine cancer, adrenal cancer, pancreatic cancer, ovarian cancer, esophageal cancer, urinary bladder cancer, endometrial cancer, prostate cancer low-grade glioma, glioblastoma, spitzoid cancer, soft tissue sarcoma, papillary thyroid carcinoma, head and neck squamous cell carcinoma, congenital fibrosarcoma, congenital mesoblastic nephroma, secretory breast carcinoma, mammary analogue secretory carcinoma, acute myeloid leukemia, ductal carcinoma, pulmonary neuroendocrine tumors, pheochromocytoma, and Wilms' tumor. Exemplary TRK-mediated diseases that can be treated with bivalent compounds include, for example, cancer, inflammatory diseases, acute and chronic pain, pruritus, bone-related diseases, neurodegenerative diseases, infectious diseases, and other diseases, including but not limited to neuroblastoma, prostate cancer, pancreatic cancer, melanoma, head and neck cancer, gastric carcinoma, lung carcinoma, liver cancer, uterine cancer, adrenal cancer, biliary tree cancer, intestinal cancer, colorectal cancer, ovarian cancer, lung carcinoma, small cell lung cancer, non-small cell lung cancer, gastric carcinoma, breast cancer, esophageal cancer, urinary bladder cancer, endometrial cancer, brain cancer, low-grade glioma, glioblastoma, medulloblastoma, secratory breast cancer, secretory breast carcinoma, salivary gland cancer, papillary thyroid carcinoma, ductal carcinoma, adult myeloid leukemia, acute myeloid leukemia, large cell neuroendocrine tumors, pulmonary neuroendocrine tumors, sarcomas, pheochromocytoma, fibrosarcoma, congenital fibrosarcoma, congenital mesoblastic nephroma, secretory breast carcinoma, malignant fibrous histiocytoma, embryonal rhabdomysocarcoma, leiomysosarcoma, neuro-fibrosarcoma, neoplasms of the central nervous systems, osteosarcoma, synovial sarcoma, liposarcoma, alveolar soft part sarcoma Spitzoid cancer, Wilms' tumor, lymphomas (e.g. including Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma), inflammatory lung diseases (e.g. asthma), inflammatory bowel diseases, (e.g. ulcerative colitis, Crohn's disease), inflammatory skin diseases (e.g. atopic dermatitis, eczema and psoriasis), interstitial cystitis, rhinitis, acute pain, chronic pain, cancer pain, surgical pain, inflammatory pain, neuropathic pain, nociceptive pain, pain of osteoarthritis, chronic low back pain, low back pain of osteoporosis, pain of bone fracture, pain of rheumatoid arthritis, postherpetic pain, pain of diabetic neuropathy, fibromyalgia, pain of pancreatitis, pain of interstitial cystitis, pain of endometriosis, pain of irritable bowel syndrome, migraine, pain of pulpitis, interstitial cystitis pain, painful bladder syndrome, central pain syndromes, postsurgical pain syndromes, bone and joint pain, repetitive motion pain, dental pain, myofascial pain, perioperative pain, dysmennorhea, myofascial pain, angina pain, headache, primary hyperalgesia, secondary hyperalgesia, primary allodynia, secondary allodynia, other pain caused by central sensitization, systemic cutaneous pruritus, localized cutaneous pruritus, senile cutaneous pruritus, gestational pruritus, pruritus ani, vulvar pruritus, metastatic bone disease, treatment-induce bone loss, osteoporosis, rheumatoid arthritis, bone metastases, ankylosing spondylitis, Paget's disease, periodontal disease, osteolytic disease, multiple sclerosis, Parkinson's disease, Alzheimer's disease, Chagas disease, cachexia, anorexia, demyelination and dysmyelination.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. Moreover, treatment of a subject with a therapeutically effective amount of the compounds or compositions described herein can include a single treatment or a series of treatments. For example, effective amounts can be administered at least once. The compositions can be administered from one or more times per day to one or more times per week; including once every other day. The skilled artisan will appreciate that certain factors can influence the dosage and timing required to effectively treat a subject, including but not limited to the severity of the disease or disorder, previous treatments, the general health or age of the subject, and other diseases present.

Following administration, the subject can be evaluated to detect, assess, or determine their level of disease. In some instances, treatment can continue until a change (e.g., reduction) in the level of disease in the subject is detected. Upon improvement of a patient's condition (e.g., a change (e.g., decrease) in the level of disease in the subject), a maintenance dose of a compound, or composition disclosed herein can be administered, if necessary. Subsequently, the dosage or frequency of administration, or both, can be reduced, e.g., as a function of the symptoms, to a level at which the improved condition is retained. Patients may, however, require intermittent treatment on a long-term basis upon any recurrence of disease symptoms.

The present disclosure is also described and demonstrated by way of the following examples. However, the use of these and other examples anywhere in the specification is illustrative only and in no way limits the scope and meaning of the invention or of any exemplified term. Likewise, the invention is not limited to any particular preferred embodiment or aspect described herein. Indeed, many modifications and variations may be apparent to those skilled in the art upon reading this specification, and such variations can be made without departing from the invention in spirit or in scope. The invention is therefore to be limited only by the terms of the appended claims along with the full scope of equivalents to which those claims are entitled.

EXAMPLES

Example 1: 4-((2-Aminoethyl)amino)-2-(2,6-dioxopiperidin-3-yl)isoindoline-1,3-dione (Linker 1)

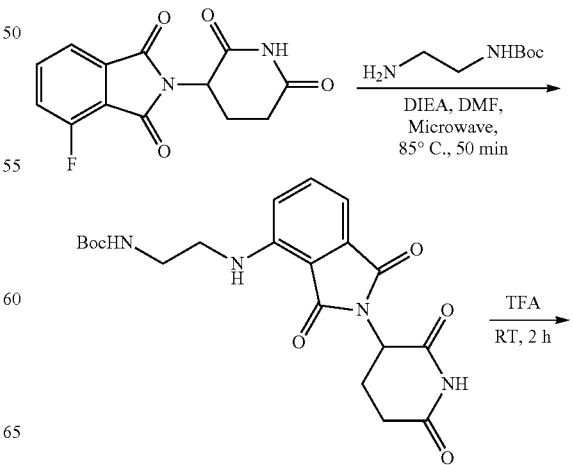

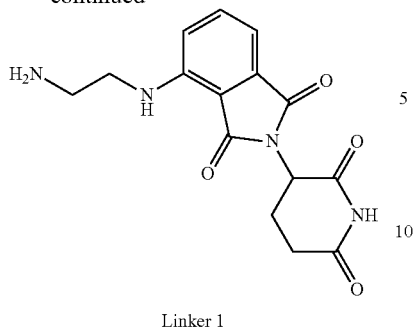

Linker 1

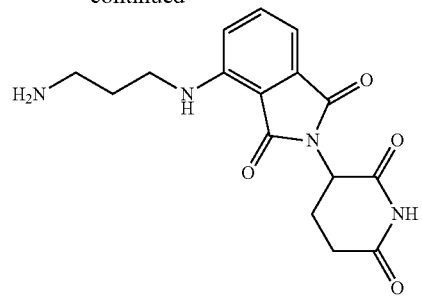

Linker 2

A solution of 2-(2,6-dioxopiperidin-3-yl)-4-fluoroisoindoline-1,3-dione (1.66 g, 6.0 mmol), tert-butyl (2-aminoethyl)carbamate (1.25 g, 6.6 mmol) and N,N-diisopropylethylamine (2.32 g, 18 mmmol) in DMF (12 mL) was heated to 85° C. in a microwave reactor for 50 min. Three batches were combined and diluted with EtOAc (200 mL). The reaction was washed with water and brine. The separated organic layer was dried over anhydrous sodium sulfate and concentrated under reduced pressure. The resulting residue was purified by silica gel chromatography (eluted with hexanes/EtOAc=1:1) to give tert-butyl (2-((2-(2,6-dioxopiperidin-3-yl)-1,3-dioxoisoindolin-4-yl)amino)ethyl)carbamate (1.3 g, yield: 16%) as a yellow solid. MS (ESI) m/z=317.1 [M−100+H]$^+$. A solution of tert-butyl (2-((2-(2,6-dioxopiperidin-3-yl)-1,3-dioxoisoindolin-4-yl)amino)ethyl)carbamate (2.0 g, 4.5 mmol) in DCM (10 mL) and TFA (5 mL) was stirred at room temperature for 2 h. The reaction was concentrated and triturated with EtOAc.

The solid precipitate was filtered. And the solid was washed with MTBE, and dried to give 4-((2-aminoethyl)amino)-2-(2,6-dioxopiperidin-3-yl)isoindoline-1,3-dione as a yellow solid (Linker 1) (1.3 g, yield: 98%). $^1$H NMR (400 MHz, DMSO-d$_6$) δ 11.14 (s, 1H), 7.85 (s, 3H), 7.45 (t, J=7.2 Hz, 1H), 7.19 (d, J=7.2 Hz, 1H), 7.10 (d, J=7.2 Hz, 1H), 6.84 (t, J=6.4 Hz, 1H), 5.07 (dd, J=5.2, 12.8 Hz, 1H), 3.58 (q, J=6.4 Hz, 2H), 3.00 (s, 2H), 2.94-2.85 (m, 1H), 2.62-2.50 (m, 2H), 2.05-2.00 (m, 1H). MS (ESI) m/z=317.1 [M+H]$^+$.

Example 2: 4-((3-Aminopropyl)amino)-2-(2,6-dioxopiperidin-3-yl)isoindoline-1,3-dione (Linker 2)

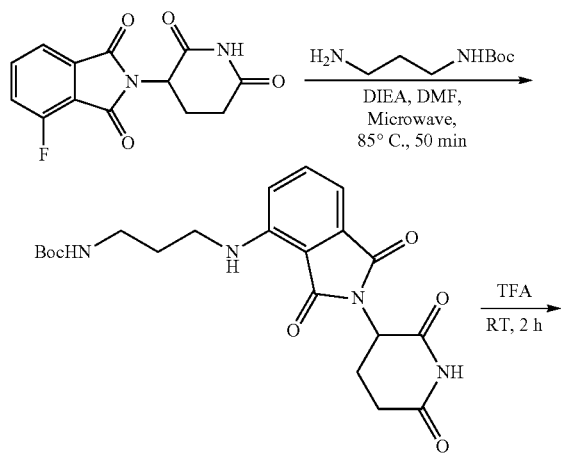

Linker 2 was synthesized following the same procedures as Linker 1 as described in Example 1. (1.2 g, yield: 11% over 2 steps). $^1$H NMR (400 MHz, DMSO-d6) 11.11 (s, 1H), 7.74 (s, 3H), 7.62-7.58 (m, 1H), 7.15 (d, J=8.4 Hz, 1H), 7.05 (d, J=7.2 Hz, 1H), 6.78-6.75 (m, 1H), 5.08-5.04 (m, 1H), 3.43-3.36 (m, 2H), 2.90-2.86 (m, 3H), 2.62-2.51 (m, 2H), 2.08-2.01 (m, 1H), 1.86-1.80 (m, 2H). MS (ESI) m/z=331.1 [M+H]$^+$.

Example 3: 4-((4-Aminobutyl)amino)-2-(2,6-dioxopiperidin-3-yl)isoindoline-1,3-dione (Linker 3)

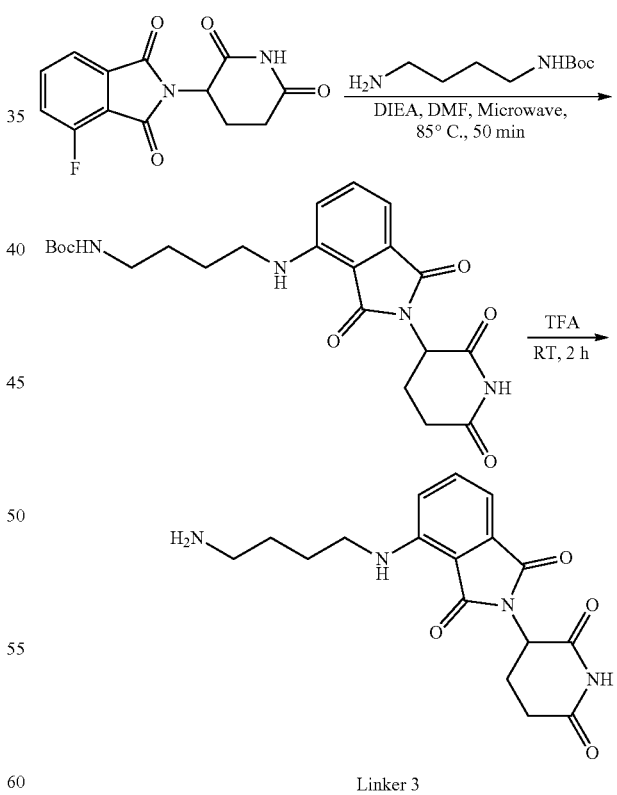

Linker 3

Linker 3 was synthesized following the same procedures as Linker 1 as described in Example 1. (1.4 g, yield: 15% over 2 steps). $^1$H NMR (400 MHz, DMSO-d6) 11.11 (s, 1H), 7.84 (s, 3H), 7.62-7.57 (m, 1H), 7.13 (d, J=8.4 Hz, 1H), 7.04 (d, J=6.8 Hz, 1H), 6.62 (s, 1H), 5.08-5.04 (m, 1H), 3.34 (s, 2H), 2.90-2.83 (m, 3H), 2.62-2.51 (m, 2H), 2.06-2.01 (m, 1H), 1.65-1.60 (m, 4H). MS (ESI) m/z=345.1 [M+H]+.

Example 4: 4-((5-Aminopentyl)amino)-2-(2,6-dioxopiperidin-3-yl)isoindoline-1,3-dione (Linker 4)

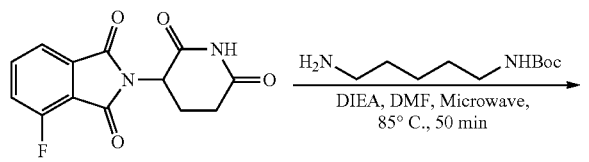

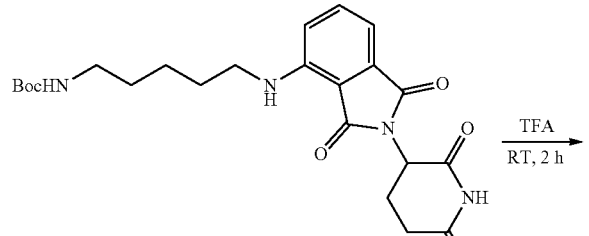

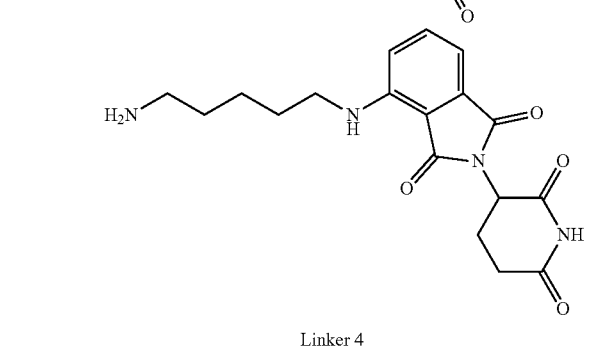

Linker 4

Linker 4 was synthesized following the same procedures as Linker 1 as described in Example 1. (2.3 g, yield: 26% over 2 steps). $^1$H NMR (400 MHz, DMSO-d$_6$) δ 11.14 (s, 1H), 7.72 (s, 3H), 7.61-7.57 (m, 1H), 7.10 (d, J=8.4 Hz, 1H), 7.03 (d, J=7.2 Hz, 1H), 6.56-6.53 (m, 1H), 5.07-5.03 (m, 1H), 3.32-3.28 (m, 2H), 2.90-2.78 (m, 3H), 2.62-2.51 (m, 2H), 2.05-1.90 (m, 1H), 1.62-1.54 (m, 4H), 1.41-1.37 (m, 2H). MS (ESI) m/z=359.1 [M+H]$^+$.

Example 5: 4-((6-Aminohexyl)amino)-2-(2,6-dioxopiperidin-3-yl)isoindoline-1,3-dione (Linker 5)

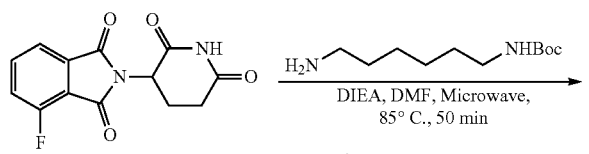

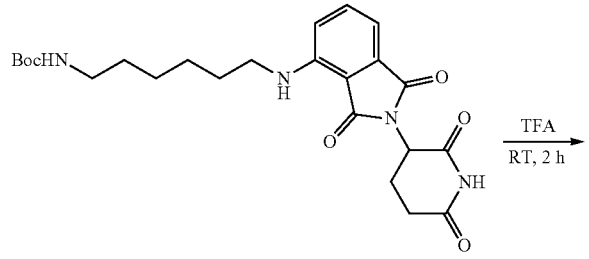

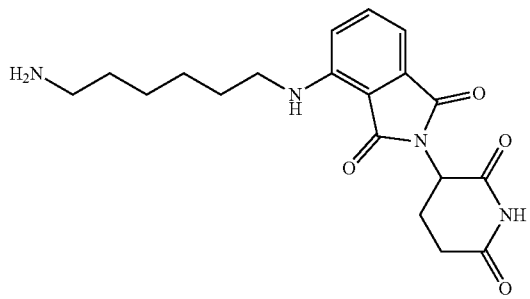

Linker 5

Linker 5 was synthesized following the same procedures as Linker 1 as described in Example 1. (1.8 g, yield: 20% over 2 steps). $^1$H NMR (400 MHz, DMSO-d6) δ 11.10 (s, 1H), 7.76 (s, 3H), 7.58 (t, J=7.2 Hz, 1H), 7.10 (d, J=8.4 Hz, 1H), 7.03 (d, J=7.2 Hz, 1H), 6.54 (t, J=6.0 Hz, 1H), 5.07-5.03 (m, 1H), 3.37-3.27 (m, 2H), 2.88-2.78 (m, 3H), 2.61-2.50 (m, 2H), 2.04-2.01 (m, 1H), 1.57-1.52 (m, 4H), 1.40-1.30 (m, 4H). MS (ESI) m/z=373.1 [M+H]$^+$.

Example 6: 4-((7-Aminoheptyl)amino)-2-(2,6-dioxopiperidin-3-yl)isoindoline-1,3-dione (Linker 6)

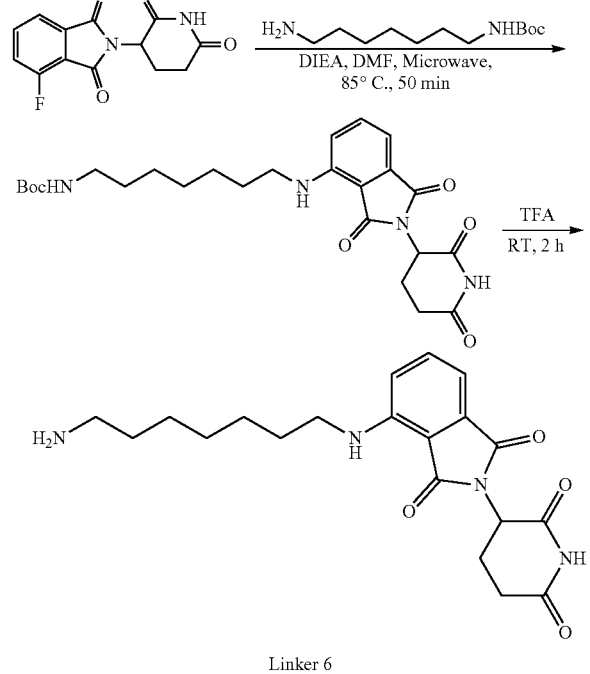

Linker 6

Linker 6 was synthesized following the same procedures as Linker 1 as described in Example 1. (2.0 g, yield: 25% over 2 steps). $^1$H NMR (400 MHz, DMSO-d6) δ 11.05 (br, 1H), 7.94-7.56 (m, 4H), 7.10-7.02 (m, 2H), 6.52 (t, J=6.0 Hz, 1H), 5.07-5.02 (m, 1H), 3.32-3.27 (m, 2H), 2.88-2.77 (m, 1H), 2.75-2.61 (m, 2H), 2.60-2.50 (m, 2H), 2.04-2.02 (m, 1H), 1.59-1.50 (m, 4H), 1.35-1.30 (m, 6H). MS (ESI) m/z=387.2 [M+H]$^+$.

Example 7: 4-((8-Aminooctyl)amino)-2-(2,6-dioxopiperidin-3-yl)isoindoline-1,3-dione (Linker 7)

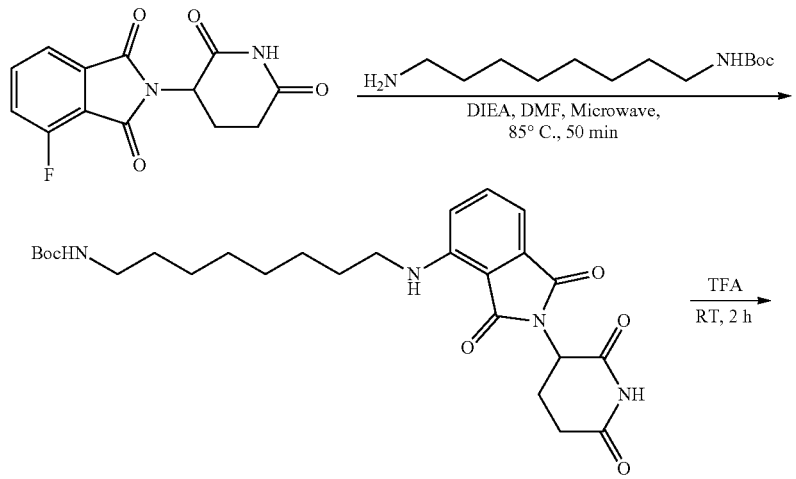

Linker 7

Linker 7 was synthesized following the same procedures as Linker 1 as described in Example 1. (1.1 g, yield: 18% over 2 steps). $^1$H NMR (400 MHz, DMSO-$d_6$) δ 11.10 (s, 1H), 7.69-7.56 (m, 4H), 7.09 (d, J=8.4 Hz, 1H), 7.03 (d, J=6.8 Hz, 1H), 6.52 (t, J=6.0 Hz, 1H), 5.07-5.03 (m, 1H), 3.34-3.26 (m, 2H), 2.89-2.85 (m, 1H), 2.76 (s, 2H), 2.61-2.56 (m, 2H), 2.04-2.00 (m, 1H), 1.59-1.49 (m, 4H), 1.35-1.27 (m, 8H). MS (ESI) m/z=401.2 [M+H]$^+$.

Example 8: 4-((2-(2-Aminoethoxy)ethyl)amino)-2-(2,6-dioxopiperidin-3-yl)isoindoline-1,3-dione (Linker 8)

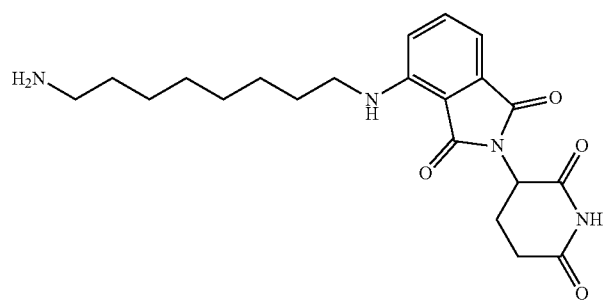

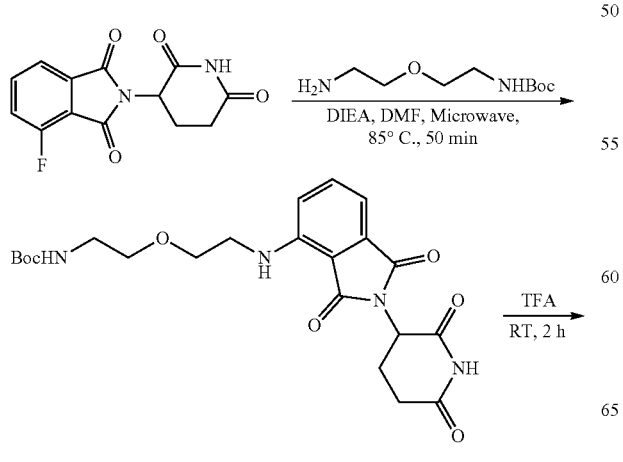

-continued

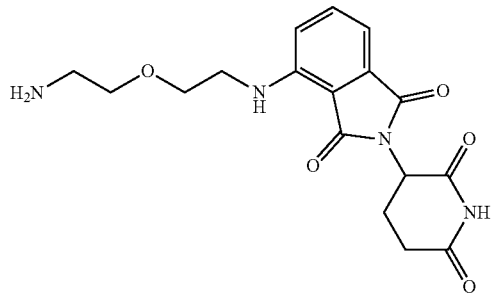

Linker 8

Linker 8 was synthesized following the same procedures as Linker 1 as described in Example 1. (2.0 g, yield: 23% over 2 steps). $^1$H NMR (400 MHz, DMSO-$d_6$) δ 10.10 (s, 1H), 7.88 (s, 3H), 7.60 (t, J=8.0 Hz, 1H), 7.17 (d, J=8.4 Hz, 1H), 7.06 (d, J=6.8 Hz, 1H), 6.40 (d, J=5.6 Hz, 1H), 5.05 (dd, J=5.2, 12.8 Hz, 1H), 3.67-3.62 (m, 4H), 3.54-3.50 (m, 2H), 3.00 (s, 2H), 2.90-2.85 (m, 1H), 2.62-2.50 (m, 2H), 2.03 (t, J=7.6 Hz, 1H). MS (ESI) m/z=361.1 [M+H]$^+$.

Example 9: 4-((2-(2-(2-Aminoethoxy)ethoxy)ethyl)amino)-2-(2,6-dioxopiperidin-3-yl)isoindoline-1,3-dione (Linker 9)

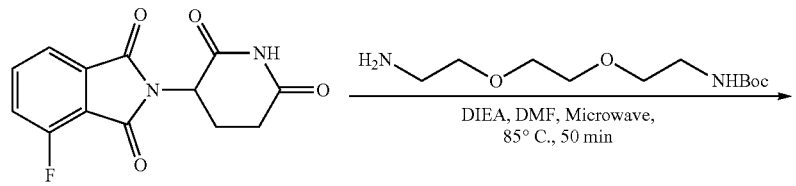

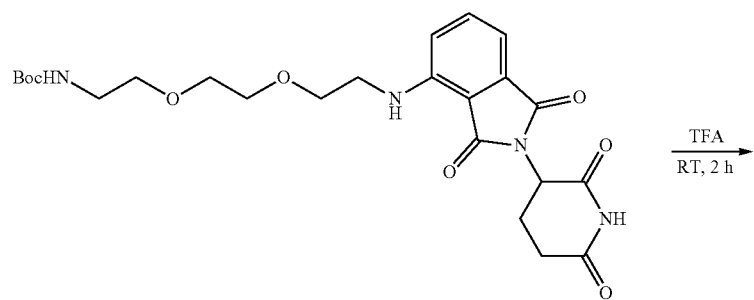

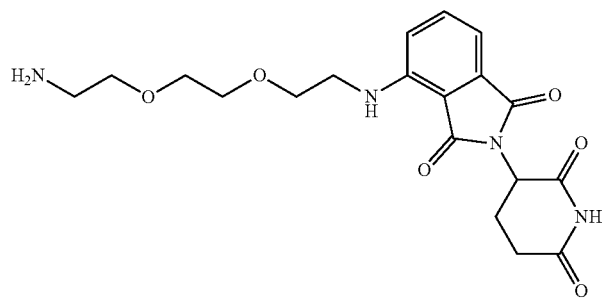

Linker 9

Linker 9 was synthesized following the same procedures as Linker 1 as described in Example 1. (1.1 g, yield: 17% over 2 steps). $^1$H NMR (400 MHz, DMSO-d6) δ 11.11 (s, 1H), 7.84 (s, 3H), 7.62-7.58 (m, 1H), 7.15 (d, J=8.8 Hz, 1H), 7.05 (d, J=6.8 Hz, 1H), 6.62-6.59 (m, 1H), 5.08-5.04 (m, 1H), 3.65-3.59 (m, 8H), 3.50-3.46 (m, 2H), 2.97-2.86 (m, 3H), 2.62-2.51 (m, 2H), 2.05-1.99 (m, 1H). MS (ESI) m/z=405.2 [M+H]$^+$.

Example 10: 4-((2-(2-(2-(2-Aminoethoxy)ethoxy)ethoxy)ethyl)amino)-2-(2,6-dioxopiperidin-3-yl)isoindoline-1,3-dione (Linker 10)

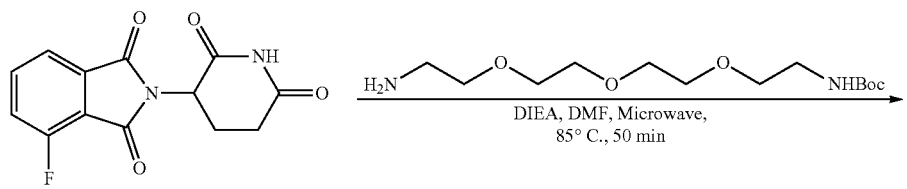

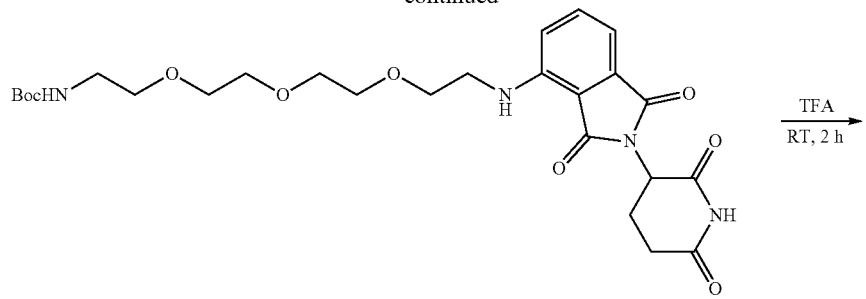
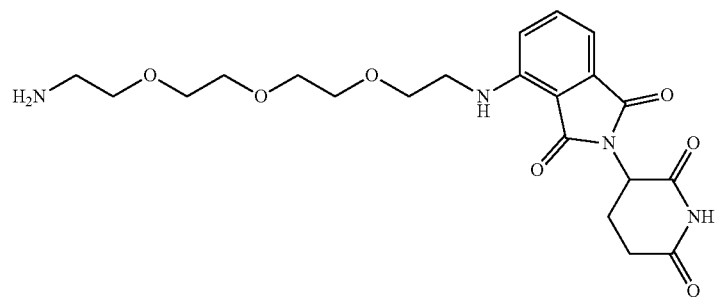
Linker 10
Linker 10 was synthesized following the same procedures as Linker 1 as described in Example 1. (1.3 g, yield: 17% over 2 steps). $^1$H NMR (400 MHz, DMSO-d6) δ 11.11 (s, 1H), 7.83 (s, 3H), 7.61-7.57 (m, 1H), 7.15 (d, J=8.8 Hz, 1H), 7.05 (d, J=6.8 Hz, 1H), 6.62-6.59 (m, 1H), 5.08-5.04 (m, 1H), 3.64-3.45 (m, 14H), 2.97-2.86 (m, 3H), 2.62-2.51 (m, 2H), 2.08-2.01 (m, 1H). MS (ESI) m/z=449.2 [M+H]$^+$.
Example 11: 4-((14-Amino-3,6,9,12-tetraoxatetradecyl)amino)-2-(2,6-dioxopiperidin-3-yl)isoindoline-1,3-dione (Linker 11)
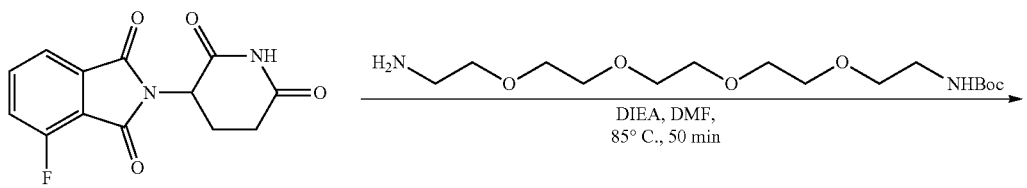
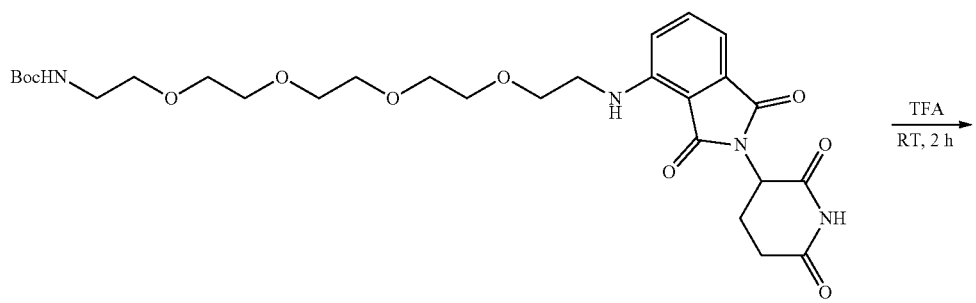

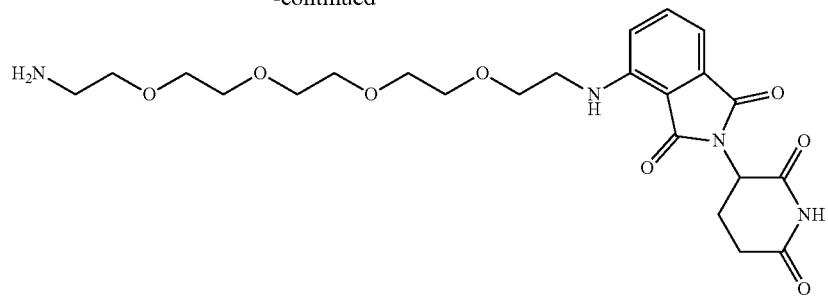
Linker 11
Linker 11 was synthesized following the same procedures as Linker 1 as described in Example 1. (1.2 g, yield: 16% over 2 steps). $^1$H NMR (400 MHz, DMSO-d6) δ 11.11 (s, 1H), 7.84 (s, 3H), 7.61-7.57 (m, 1H), 7.15 (d, J=8.8 Hz, 1H), 7.05 (d, J=6.8 Hz, 1H), 6.61 (s, 1H), 5.08-5.04 (m, 1H), 3.64-3.47 (m, 18H), 2.99-2.86 (m, 3H), 2.62-2.51 (m, 2H), 2.08-2.01 (m, 1H). MS (ESI) m/z=493.2 [M+H]$^+$.
Example 12: 4-((17-Amino-3,6,9,12,15-pentaoxa-heptadecyl)amino)-2-(2,6-dioxopiperidin-3-yl)isoindoline-1,3-dione (Linker 12)
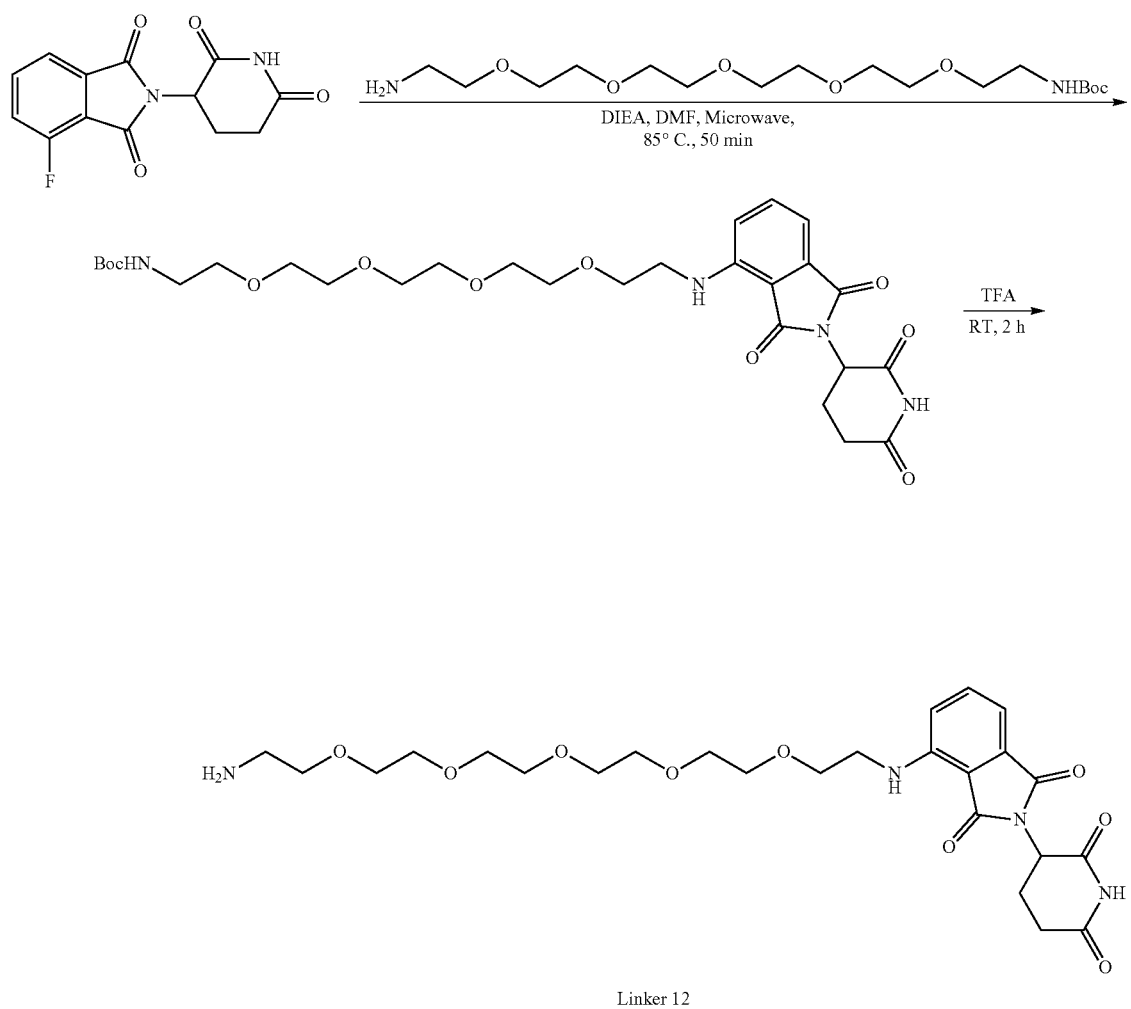
Linker 12

Linker 12 was synthesized following the same procedures as Linker 1 as described in Example 1. (1.2 g, yield: 15% over 2 steps). $^1$H NMR (400 MHz, DMSO-d6) δ 11.11 (s, 1H), 7.82 (s, 1H), 7.61-7.57 (m, 1H), 7.15 (d, J=8.4 Hz, 1H), 7.05 (d, J=7.2 Hz, 1H), 6.61-6.59 (m, 1H), 5.08-5.03 (m, 1H), 3.64-3.47 (m, 22H), 3.00-2.86 (m, 3H), 2.62-2.51 (m, 2H), 2.05-2.02 (m, 1H). MS (ESI) m/z=537.2 [M+H]$^+$.

Example 13: (2-(2,6-Dioxopiperidin-3-yl)-1,3-dioxoisoindolin-4-yl)glycine (Linker 13)

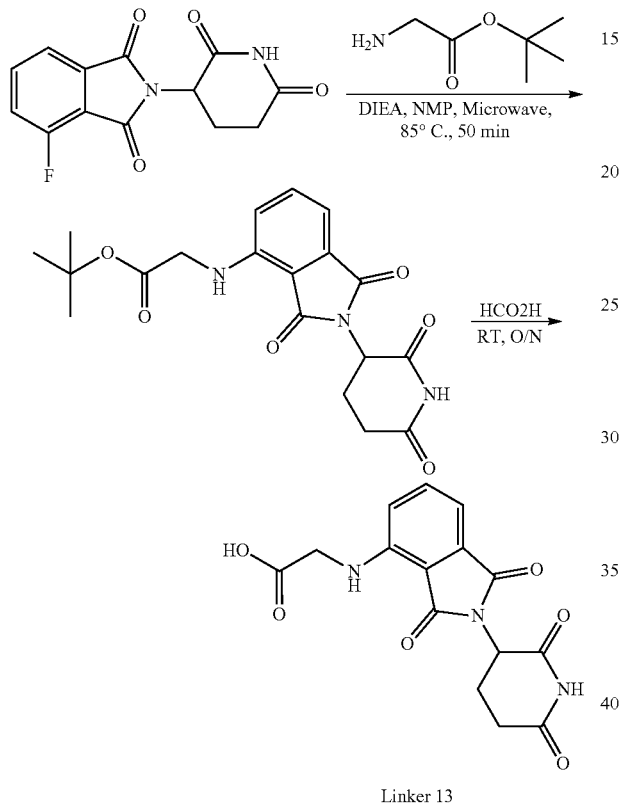

Linker 13

Linker 13 was synthesized following the same procedures as Linker 1 as described in Example 1. (840 mg, yield: 16% over 2 steps). $^1$H NMR (400 MHz, DMSO-d6) δ 11.07 (s, 1H), 7.52 (t, J=7.6 Hz, 1H), 6.99-6.88 (m, 3H), 5.04 (dd, J=5.2, 12.8 Hz, 1H), 3.73 (s, 2H), 2.93-2.83 (m, 1H), 2.61-2.50 (m, 2H), 2.02 (t, J=5.6 Hz, 1H). MS (ESI) m/z=330.1 [M−H]$^−$.

Example 14: 3-((2-(2,6-Dioxopiperidin-3-yl)-1,3-dioxoisoindolin-4-yl)amino)propanoic acid (Linker 14)

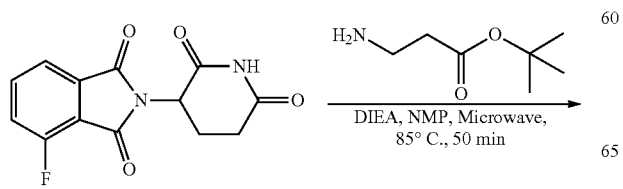

-continued

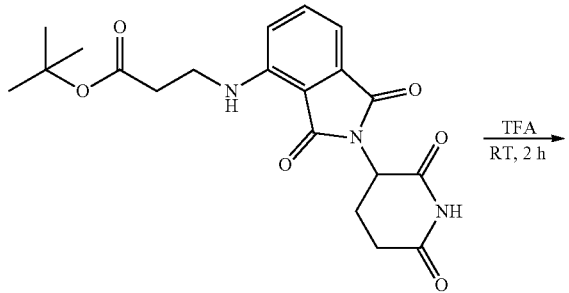

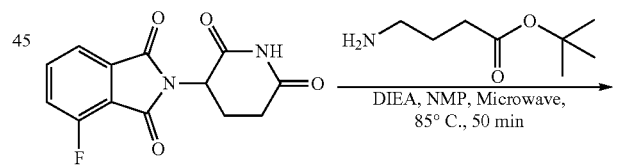

Linker 14

Linker 14 was synthesized following the same procedures as Linker 1 as described in Example 1. (1.42 g, yield: 24% over 2 steps). $^1$H NMR (400 MHz, DMSO-d$_6$) δ 11.61 (br, 1H), 11.08 (s, 1H), 7.58 (dd, J=7.2, 8.8 Hz, 1H), 7.15 (d, J=8.8 Hz, 1H), 7.04 (d, J=7.2 Hz, 1H), 6.64 (s, 1H), 5.05 (dd, J=5.2, 12.8 Hz, 1H), 3.53 (t, J=6.4 Hz, 2H), 2.92-2.83 (m, 1H), 2.61-2.50 (m, 4H), 2.05-2.00 (m, 1H). MS (ESI) m/z=346.1 [M+H]$^+$.

Example 15: 4-((2-(2,6-Dioxopiperidin-3-yl)-1,3-dioxoisoindolin-4-yl)amino)butanoic acid (Linker 15)

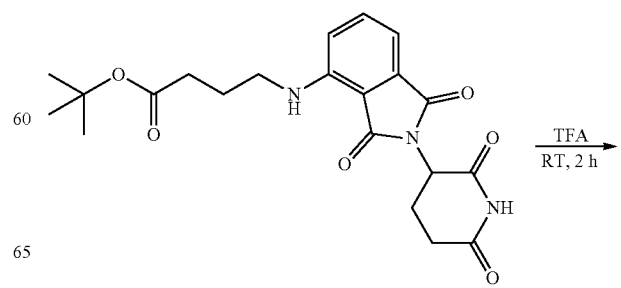

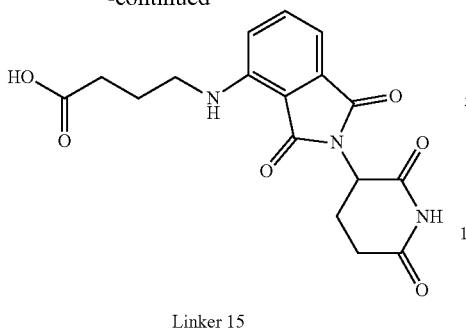

Linker 15

Linker 15 was synthesized following the same procedures as Linker 1 as described in Example 1. (1.27 g, yield: 13% over 2 steps). $^1$H NMR (400 MHz, DMSO-d6) δ 12.12 (br, 1H), 11.08 (s, 1H), 7.58 (dd, J=7.2, 8.8 Hz, 1H), 7.13 (d, J=8.8 Hz, 1H), 7.03 (d, J=7.2 Hz, 1H), 6.64 (t, J=6.0 Hz, 1H), 5.05 (dd, J=5.6, 12.8 Hz, 1-1), 3.33 (q, J=6.8 Hz, 2H), 2.93-2.83 (m, 1-1), 2.61-2.50 (m, 2H), 2.31 (t, J=6.8 Hz, 2H), 2.07-2.00 (m, 1H), 1.83-1.75 (m, 2H). MS (ESI) m/z=360.1 [M+H]$^+$.

Example 16: 5-((2-(2,6-Dioxopiperidin-3-yl)-1,3-dioxoisoindolin-4-yl)amino)pentanoic acid (Linker 16)

Linker 16 was synthesized following the same procedures as Linker 1 as described in Example 1. (1.4 g, yield: 15% over 2 steps). $^1$H NMR (400 MHz, DMSO-d$_6$) δ12.02 (br, 1H), 11.08 (s, 1H), 7.58 (dd, J=8.8, 7.2 Hz, 1H), 7.10 (d, J=8.4 Hz, 1H), 7.02 (d, J=7.2 Hz, 1H), 6.64 (t, J=5.6 Hz, 1H), 5.07-5.03 (m, 1H), 3.32-3.02 (m, 2H), 2.93-2.84 (m, 1H), 2.61-2.54 (m, 2H), 2.28-2.25 (m, 2H), 2.05-2.01 (m, 1H), 1.60-1.51 (m, 4H). MS (ESI) m/z=374.1 [M+H]$^+$.

Example 17: 6-((2-(2,6-Dioxopiperidin-3-yl)-1,3-dioxoisoindolin-4-yl)amino)hexanoic acid (Linker 17)

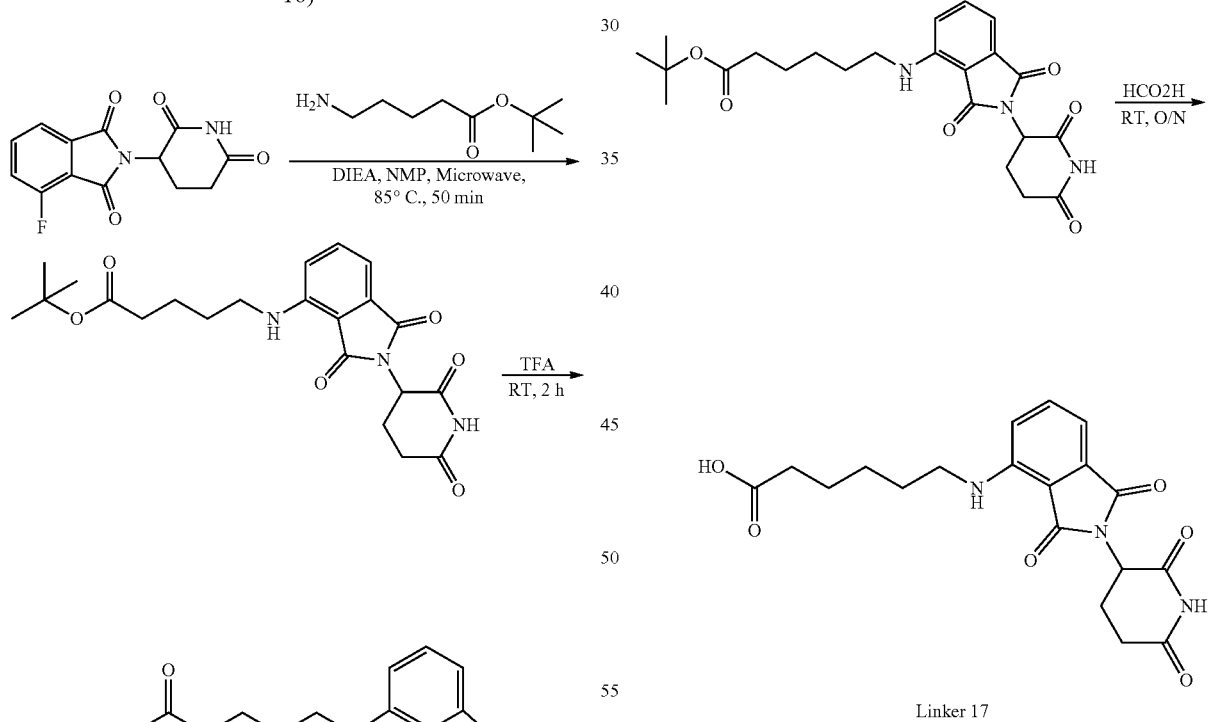

Linker 17

Linker 17 was synthesized following the same procedures as Linker 1 as described in Example 1. (1.43 g, yield: 18% over 2 steps). $^1$H NMR (400 MHz, DMSO-d$_6$) δ 11.97 (s, 1H), 11.08 (s, 1H), 7.57 (dd, J=7.2, 8.8 Hz, 1H), 7.08 (d, J=8.8 Hz, 1H), 7.02 (d, J=7.2 Hz, 1H), 6.52 (t, J=6.0 Hz, 1H), 5.05 (dd, J=5.6, 12.8 Hz, 1H), 3.30 (q, J=6.8 Hz, 2H), 2.93-2.83 (m, 1H), 2.61-2.50 (m, 2H), 2.32 (t, J=7.2 Hz, 2H), 2.07-2.00 (m, 1H), 1.61-1.50 (m, 4H), 1.39-1.33 (m, 2H). MS (ESI) m/z=388.1 [M+H]$^+$.

Example 18: 7-((2-(2,6-Dioxopiperidin-3-yl)-1,3-dioxoisoindolin-4-yl)amino)heptanoic acid (Linker 18)

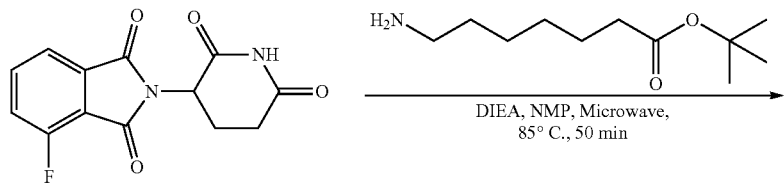

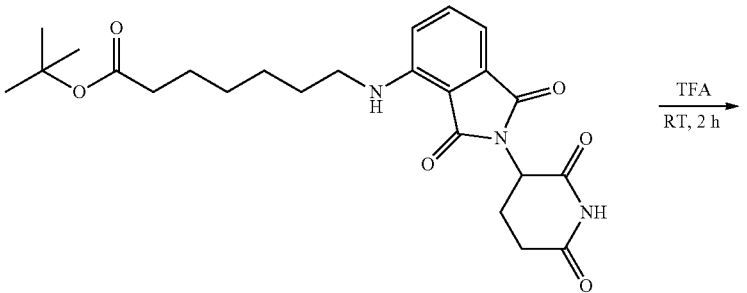

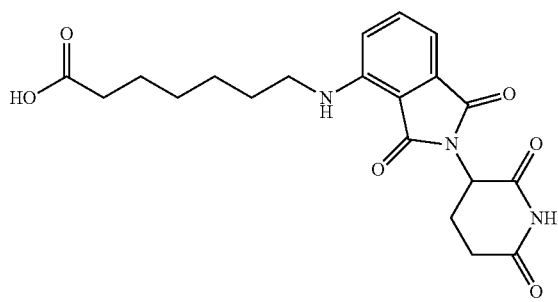

Linker 18

Linker 18 was synthesized following the same procedures as Linker 1 as described in Example 1. (2.3 g, yield: 24% over 2 steps). $^1$H NMR (400 MHz, DMSO-d6) δ 11.92 (br, 1H), 11.08 (s, 1H), 7.57 (t, J=8.0 Hz, 1H), 7.13 (d, J=8.8 Hz, 1H), 7.03 (d, J=6.8 Hz, 1H), 6.52 (t, J=5.6 Hz, 1H), 5.05 (dd, J=5.6, 12.8 Hz, 1H), 3.30 (q, J=6.4 Hz, 2H), 2.93-2.83 (m, 1H), 2.61-2.50 (m, 2H), 2.31 (t, J=7.2 Hz, 2H), 2.07-2.00 (m, 1H), 1.58-1.48 (m, 4H), 1.34-1.31 (m, 4H). MS (ESI) m/z=402.1 [M+H]$^+$.

Example 19: 8-((2-(2,6-Dioxopiperidin-3-yl)-1,3-dioxoisoindolin-4-yl)amino)octanoic acid (Linker 19)

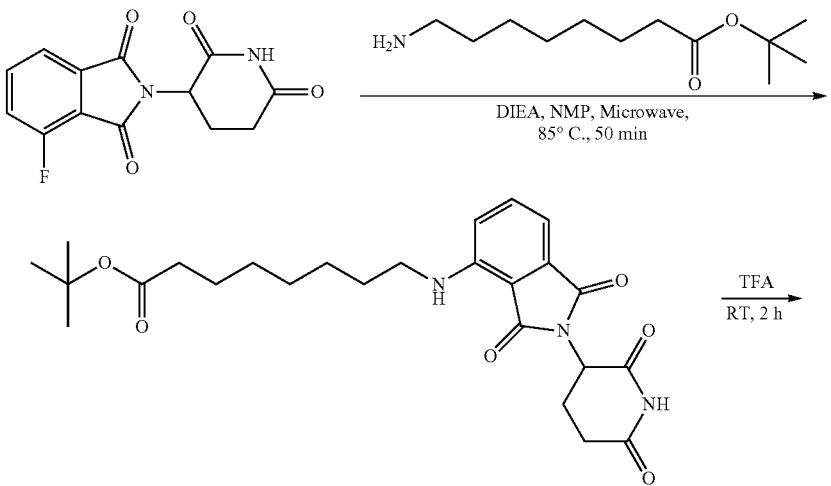

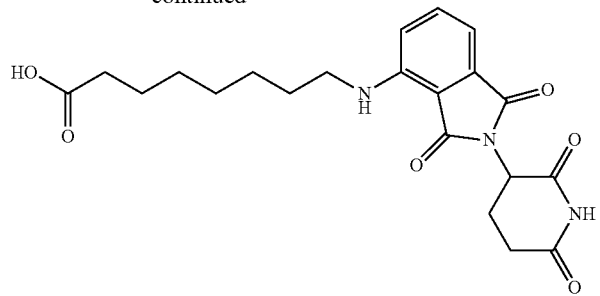

Linker 19

Linker 19 was synthesized following the same procedures as Linker 1 as described in Example 1. (1.14 g, yield: 35% over 2 steps). $^1$H NMR (400 MHz, DMSO-d6) δ 11.94 (s, 1H), 11.08 (s, 1H), 7.57 (t, J=8.0 Hz, 1H), 7.08 (d, J=8.4 Hz, 1H), 7.02 (d, J=6.8 Hz, 1H), 6.52 (t, J=5.6 Hz, 1H), 5.05 (dd, J=5.6, 12.8 Hz, 1H), 3.31-3.26 (m, 2H), 2.93-2.83 (m, 1H), 2.61-2.50 (m, 2H), 2.19 (t, J=7.2 Hz, 2H), 2.05-2.00 (m, 1H), 1.58-1.47 (m, 4H), 1.35-1.25 (s, 6H). MS (ESI) m/z=416.1 [M+H]$^+$.

Example 20: 3-(2-((2-(2,6-Dioxopiperidin-3-yl)-1,3-dioxoisoindolin-4-yl)amino)ethoxy) propanoic acid (Linker 20)

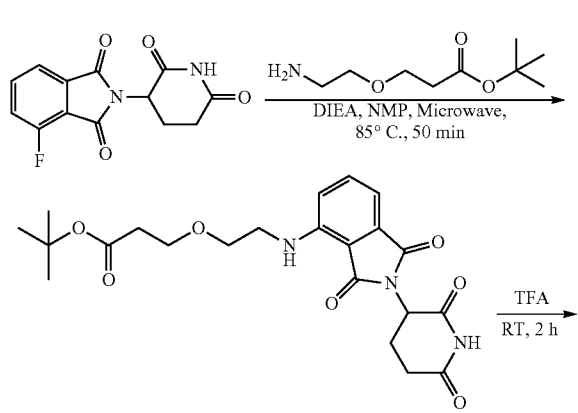

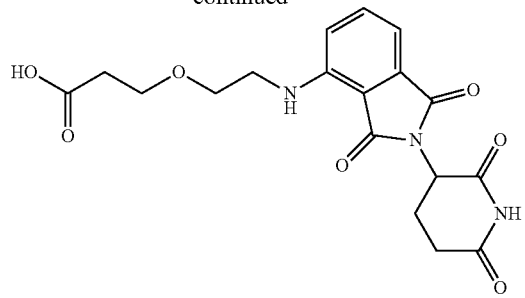

Linker 20

Linker 20 was synthesized following the same procedures as Linker 1 as described in Example 1. (3.5 g, yield: 18% over 2 steps). $^1$H NMR (400 MHz, DMSO-d6) δ 12.18 (s, 1H), 11.08 (s, 1H), 7.58 (dd, J=7.2 Hz, 8.8 Hz, 1H), 7.13 (d, J=8.4 Hz, 1H), 7.04 (d, J=7.2 Hz, 1H), 6.58 (t, J=5.6 Hz 1H), 5.05 (dd, J=6.4 Hz, 12.8 Hz, 1H), 3.67-3.58 (m, 4H), 3.47-3.43 (m, 2H), 2.93-2.84 (m, 1H), 2.61-2.45 (m, 4H), 2.07-2.01 (m, 1H). MS (ESI) m/z=390.1 [M+H]$^+$.

Example 21: 3-(2-(2-((2-(2,6-Dioxopiperidin-3-yl)-1,3-dioxoisoindolin-4-yl)amino)ethoxy)ethoxy)propanoic acid (Linker 21)

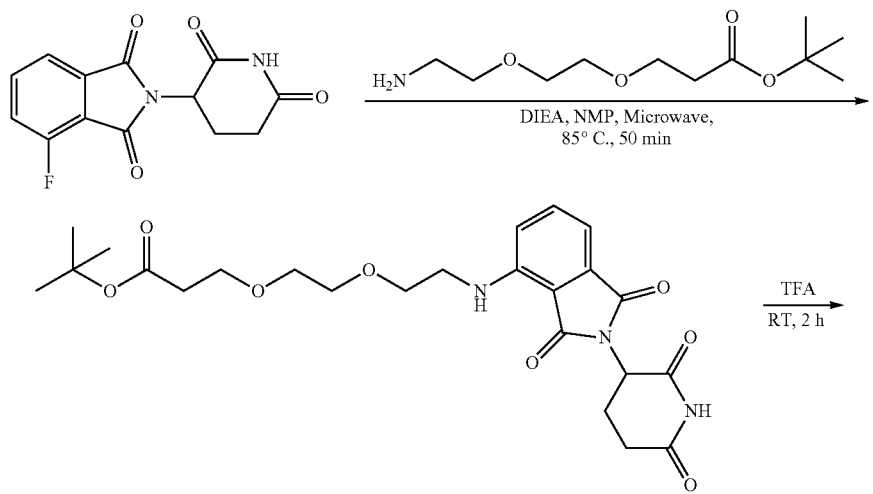

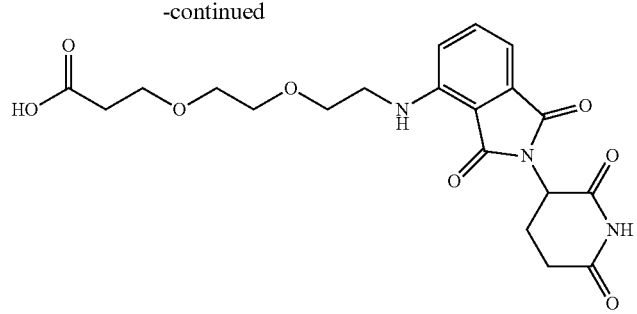
Linker 21
Linker 21 was synthesized following the same procedures as Linker 1 as described in Example 1. (2.0 g, yield: 24% over 2 steps). $^1$H NMR (400 MHz, DMSO-d6) δ 12.13 (s, 1H), 11.08 (s, 1H), 7.58 (dd, J=7.2 Hz, 8.4 Hz, 1H), 7.14 (d, J=8.4 Hz, 1H), 7.04 (d, J=6.8 Hz, 1H), 6.60 (t, J=6.0 Hz 1H), 5.05 (dd, J=5.2 Hz, 12.4 Hz, 1H), 3.63-3.44 (m, 10H), 2.88-2.85 (m, 1H), 2.61-2.49 (m, 2H), 2.44-2.41 (m, 2H), 2.04-2.01 (m, 1H). MS (ESI) m/z=434.1 [M+H]$^+$.
Example 22: 3-(2-(2-(2-((2-(2,6-Dioxopiperidin-3-yl)-1,3-dioxoisoindolin-4-yl)amino)ethoxy)ethoxy)ethoxy)propanoic acid (Linker 22)
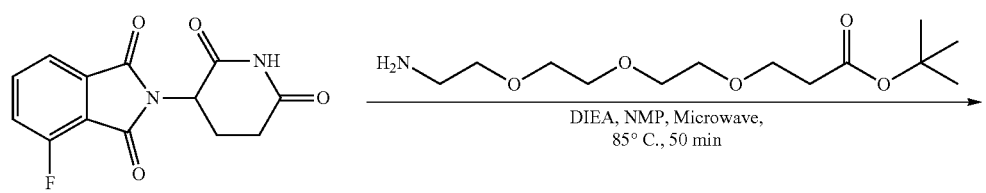
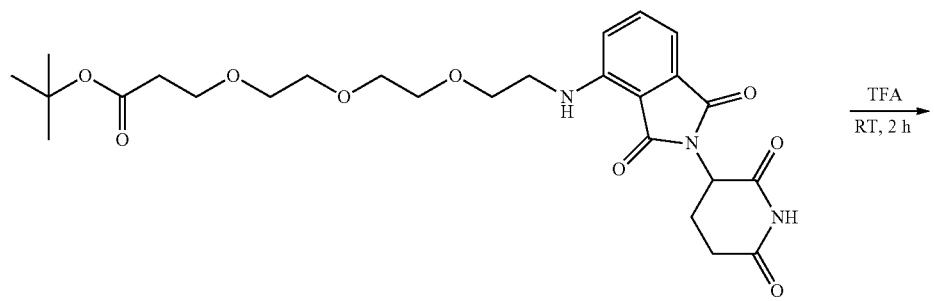
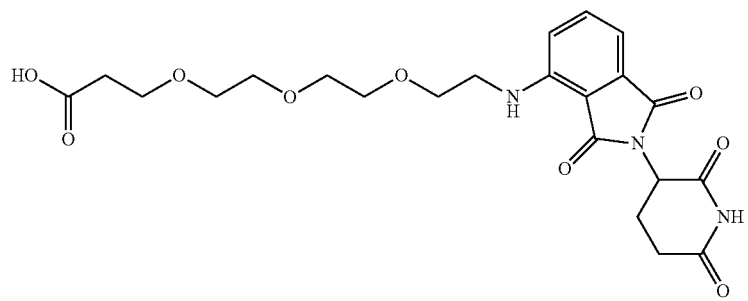
Linker 22

Linker 22 was synthesized following the same procedures as Linker 1 as described in Example 1. (3.2 g, yield: 42% over 2 steps). $^1$H NMR (400 MHz, DMSO-d6) δ 12.14 (s, 1H), 11.08 (s, 1H), 7.58 (dd, J=7.2 Hz, 8.4 Hz, 1H), 7.14 (d, J=8.8 Hz, 1H), 7.04 (d, J=6.8 Hz, 1H), 6.60 (t, J=6.0 Hz, 1H), 5.05 (dd, J=5.2 Hz, 12.8 Hz, 1H), 3.63-3.45 (m, 14H), 2.88-2.85 (m, 1H), 2.61-2.49 (m, 2H), 2.44-2.40 (m, 2H), 2.04-2.01 (m, 1H). MS (ESI) m/z=478.2 [M+H]$^+$.

Example 23: 1-((2-(2,6-Dioxopiperidin-3-yl)-1,3-dioxoisoindolin-4-yl)amino)-3,6,9,12-tetraoxapentadecan-15-oic acid (Linker 23)

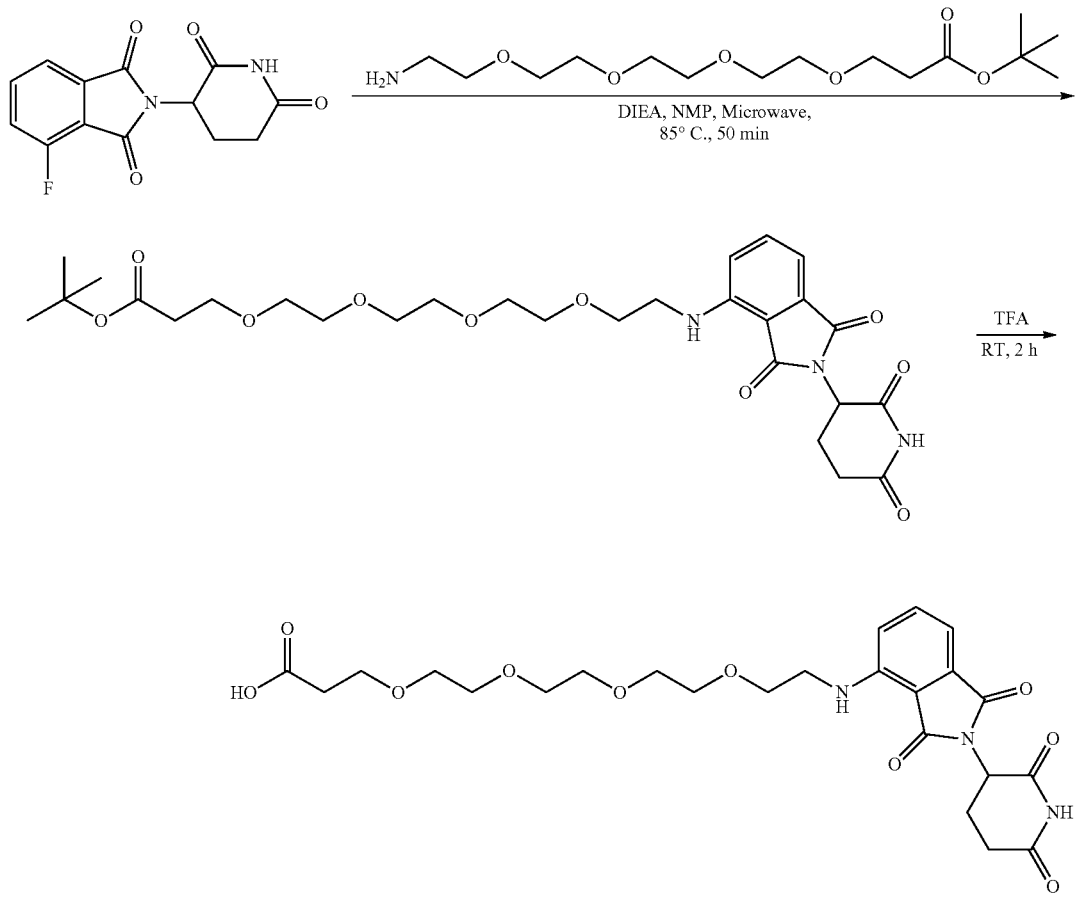

Linker 23

Linker 23 was synthesized following the same procedures as Linker 1 as described in Example 1. (2.3 g, yield: 31% over 2 steps). $^1$H NMR (400 MHz, DMSO-d6) δ 12.14 (s, 1H), 11.08 (s, 1H), 7.58 (dd, J=7.2 Hz, 8.8 Hz, 1H), 7.14 (d, J=8.4 Hz, 1H), 7.04 (d, J=7.2 Hz, 1H), 6.60 (t, J=6.0 Hz, 1H), 5.05 (dd, J=5.2 Hz, 12.8 Hz, 1H), 3.63-3.48 (m, 18H), 2.898-2.85 (m, 1H), 2.61-2.49 (m, 2H), 2.44-2.41 (m, 2H), 2.04-2.01 (m, 1H). MS (ESI) m/z=522.2 [M+H]$^+$.

Example 24: 1-((2-(2,6-Dioxopiperidin-3-yl)-1,3-dioxoisoindolin-4-yl)amino)-3,6,9,12,15-pentaoxaoctadecan-18-oic acid (Linker 24)

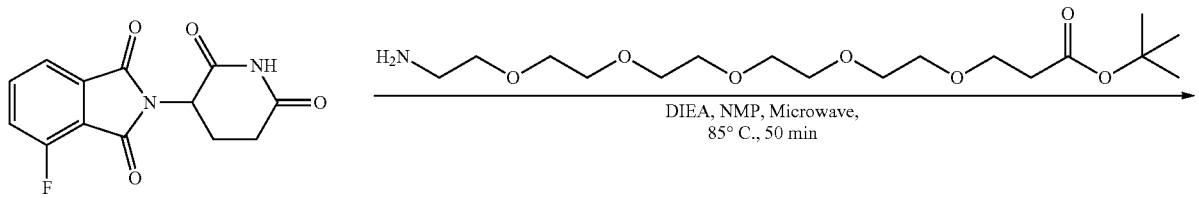

-continued
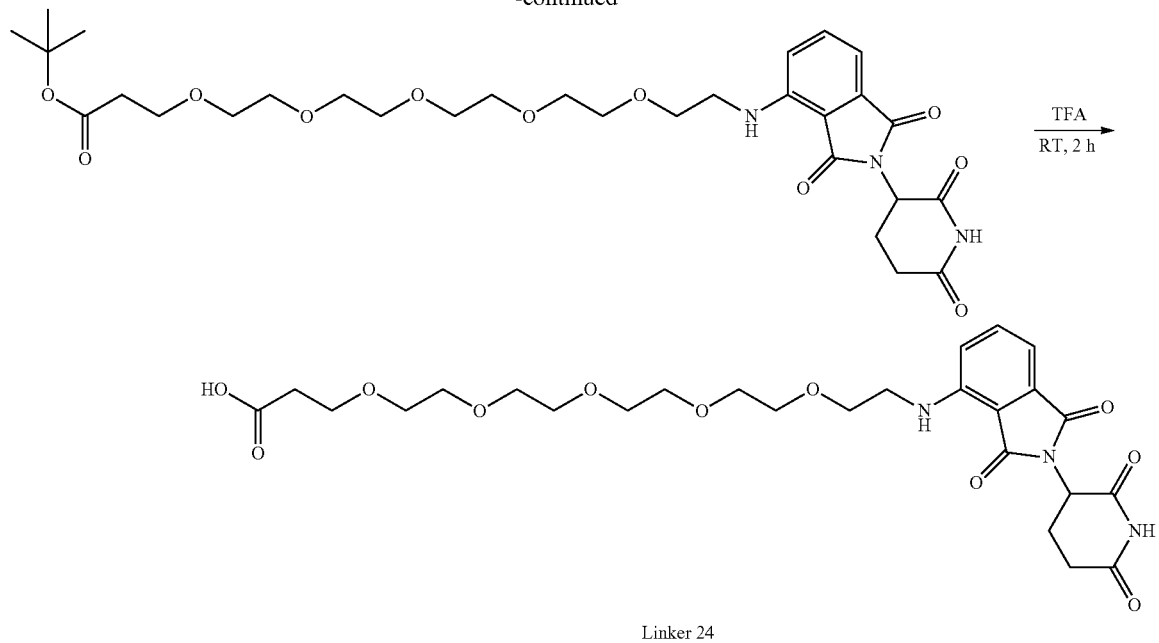
Linker 24
Linker 24 was synthesized following the same procedures as Linker 1 as described as Example 1. (2.4 g, yield: 36% over 2 steps). $^1$H NMR (400 MHz, DMSO-d6) δ 11.09 (s, 1H), 7.58 (dd, J=7.2, 8.4 Hz, 1H), 7.13 (d, J=8.4 Hz, 1H), 7.04 (d, J=7.2 Hz, 1H), 6.60 (t, J=5.6 Hz, 1H), 5.05 (dd, J=5.6, 12.8 Hz, 1H), 3.64-3.46 (m, 22H), 2.93-2.83 (m, 1H), 2.61-2.50 (m, 2H), 2.44-2.40 (m, 2H), 2.02 (t, J=6.4 Hz, 1H). MS (ESI) m/z=566.2 [M+H]$^+$.
Example 25: (2S,4R)-1-((S)-2-(2-Aminoacetamido)-3,3-dimethylbutanoyl)-4-hydroxy-N-(4-(4-methyl-thiazol-5-yl)benzyl)pyrrolidine-2-carboxamide (Linker 25)
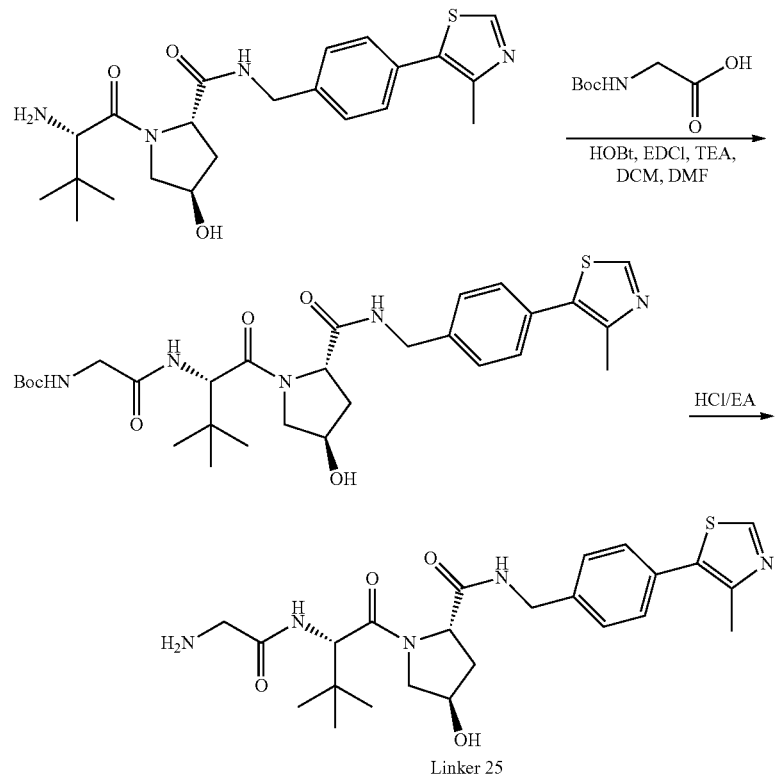
Linker 25

Step 1: To a solution of (2S,4R)-1-((S)-2-amino-3,3-dimethylbutanoyl)-4-hydroxy-N-(4-(4-methylthiazol-5-yl)benzyl)pyrrolidine-2-carboxamide (2.00 g, 4.67 mmol), 2-((tert-butoxycarbonyl)amino) acetic acid (900 mg, 5.14 mmol) and triethylamine (TEA) (3.2 mL, 23.35 mmol) in DCM/DMF (225 mL/11 mL) were added EDCI (1.07 g, 5.60 mmol), HOBt (756 mg, 5.60 mmol) at 0° C. The mixture was stirred at room temperature for 16 hours. The mixture was poured into water and extracted with DCM. The combined organic layers were concentrated and the residue was purified by chromatography on a silica gel column (DCM/MeOH=20/1, v/v) to give the desired product tert-butyl (2-(((S)-1-((2S,4R)-4-hydroxy-2-((4-(4-methylthiazol-5-yl)benzyl)carbamoyl)pyrrolidin-1-yl)-3,3-dimethyl-1-oxobutan-2-yl)amino)-2-oxoethyl)carbamate (1.5 g, yield: 55%). MS (ESI) m/z=588.2 [M+H]$^+$.

Step 2: To a solution of tert-butyl (2-(((S)-1-((2S,4R)-4-hydroxy-2-((4-(4-methylthiazol-5-yl) benzyl)carbamoyl)pyrrolidin-1-yl)-3,3-dimethyl-1-oxobutan-2-yl)amino)-2-oxoethyl)carbamate (1.50 g, 2.56 mmol) in ethylacetate (EtOAc) (30 mL) was added HCl/EtOAc (100 mL). The mixture was stirred at room temperature for 3 hours and filtered to give the desired product which was dissolved in water (100 mL) and lyophilized to give (2S,4R)-1-((S)-2-(2-aminoacetamido)-3,3-dimethylbutanoyl)-4-hydroxy-N-(4-(4-methylthiazol-5-yl)benzyl)pyrrolidine-2-carboxamide hydrochloride (Linker 25) (1.07 g, yield: 80%). $^1$H NMR (400 MHz, DMSO-d$_6$) δ 9.29 (s, 1H), 8.72 (s, 1H), 8.56 (d, J=9.2 Hz, 1H), 8.26 (s, 3H), 7.38-7.47 (m, 4H), 4.61 (d, J=9.2 Hz, 1H), 4.36-4.47 (m, 3H), 4.20-4.25 (m, 1H), 3.60-3.70 (m, 4H), 2.46 (s, 3H), 2.10-2.05 (m, 1H), 1.97-1.89 (m, 1H), 0.95 (s, 9H). MS (ESI) m/z=488.3 [M+H]$^+$.

Example 26: (2S,4R)-1-((S)-2-(3-Aminopropanamido)-3,3-dimethylbutanoyl)-4-hydroxy-N-(4-(4-methylthiazol-5-yl)benzyl)pyrrolidine-2-carboxamide (Linker 26)

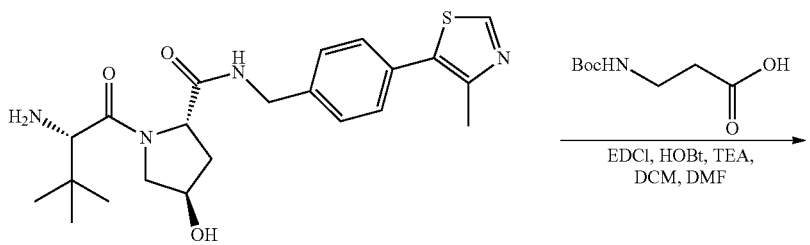

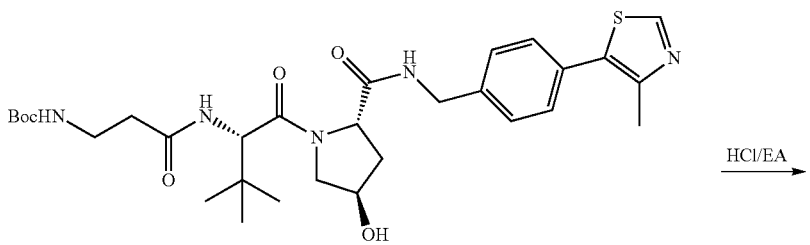

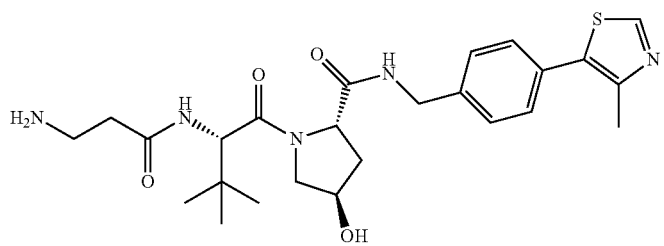

Linker 26

Linker 26 was synthesized following the same procedures as Linker 25 as described in Example 25. (1.38 g, yield: 37% over 2 steps). $^1$H NMR (400 MHz, DMSO-$d_6$) δ 9.36 (s, 1H), 8.68 (s, 1H), 8.26 (d, J=9.2 Hz, 1H), 8.16 (s, 3H), 7.49-7.39 (m, 4H), 4.53 (d, J=9.2 Hz, 1H), 4.47-4.35 (m, 3H), 4.24-4.19 (m, 1H), 3.69-3.60 (m, 2H), 2.94-2.93 (m, 2H), 2.64 (t, J=7.2 Hz, 2H), 2.48 (s, 3H), 2.06-2.01 (m, 1H), 1.92-1.85 (m, 1H), 0.95 (s, 9H). MS (ESI) m/z=502.3 [M+H]$^+$.
Example 27: (2S,4R)-1-((S)-2-(4-Aminobutanamido)-3,3-dimethylbutanoyl)-4-hydroxy-N-(4-(4-methylthiazol-5-yl)benzyl)pyrrolidine-2-carboxamide (Linker 27)
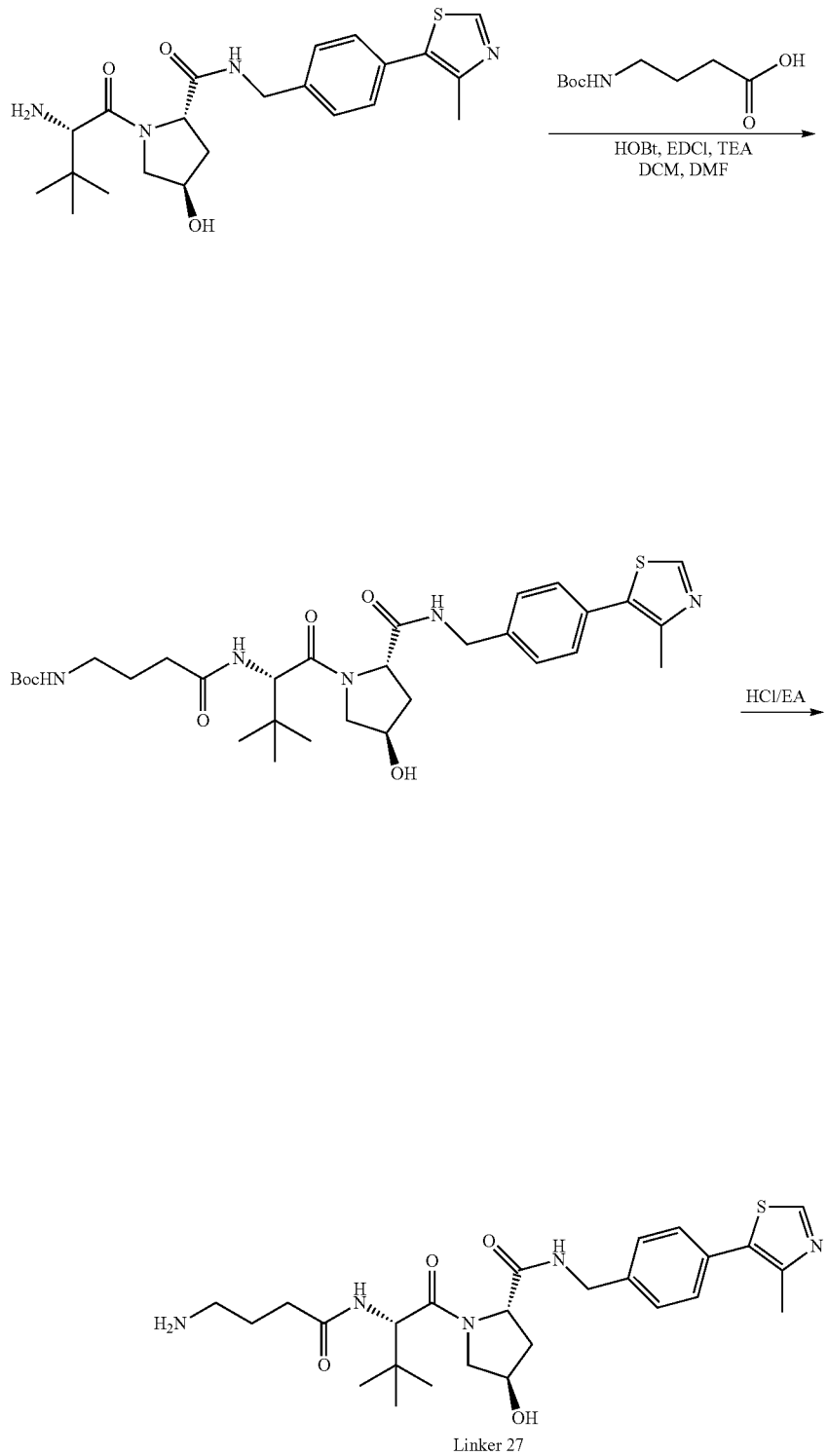
Linker 27

Linker 27 was synthesized following the same procedures as Linker 25 as described in Example 25. (1.38 g, yield: 46% over 2 steps). ¹H NMR (400 MHz, DMSO-d₆) δ 9.66 (s, 1H), 8.74 (t, J=6.0, 1H), 8.25 (s, 3H), 8.03 (d, J=9.2 Hz, 1H), 7.49-7.41 (m, 4H), 4.53 (d, J=9.2 Hz, 1H), 4.51-4.35 (m, 3H), 4.29-4.24 (m, 1H), 3.71-3.65 (m, 2H), 2.79-2.77 (m, 2H), 2.52 (s, 3H), 2.45-2.27 (m, 2H), 2.12-2.07 (m, 1H), 1.94-1.80 (m, 3H), 0.94 (s, 9H). MS (ESI) m/z=516.0 [M+H]⁺.

Example 28: (2S,4R)-1-((S)-2-(5-Aminopentanamido)-3,3-dimethylbutanoyl)-4-hydroxy-N-(4-(4-methylthiazol-5-yl)benzyl)pyrrolidine-2-carboxamide (Linker 28)

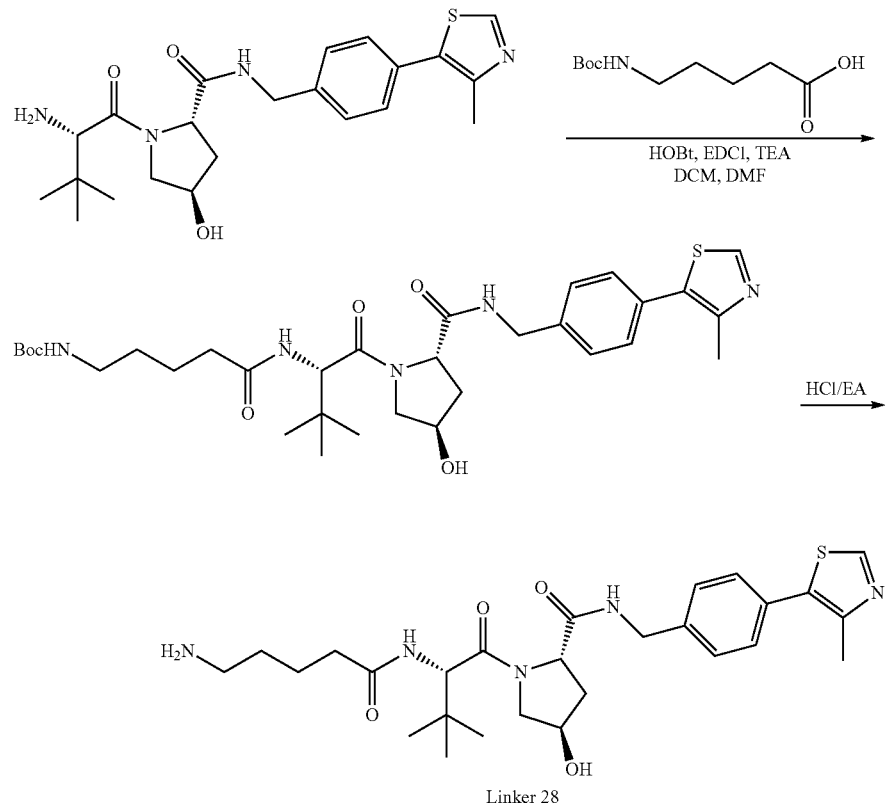

Linker 28

Linker 28 was synthesized following the same procedures as Linker 25 as described in Example 25. (1.50 g, yield: 57% over 2 steps). ¹H NMR (400 MHz, DMSO-d₆) δ 9.52 (s, 1H), 8.73 (t, J=11.6 Hz, 1H), 8.20 (s, 3H), 7.95 (d, J=9.6 Hz, 1H), 7.43-7.50 (m, 4H), 4.55 (d, J=9.2 Hz, 1H), 4.38-4.50 (m, 3H), 4.23-4.29 (m, 1H), 3.64-3.71 (m, 2H), 2.74-2.78 (m, 2H), 2.51 (s, 3H), 2.30-2.35 (m, 1H), 2.18-2.23 (m, 1H), 2.07-2.12 (m, 1H), 1.88-1.95 (m, 1H), 1.58 (d, J=4.4 Hz, 4H), 0.96 (s, 9H). MS (ESI) m/z=530.1 [M+H]⁺.

Example 29: (2S,4R)-1-((S)-2-(6-Aminohexanamido)-3,3-dimethylbutanoyl)-4-hydroxy-N-(4-(4-methylthiazol-5-yl)benzyl)pyrrolidine-2-carboxamide (Linker 29)

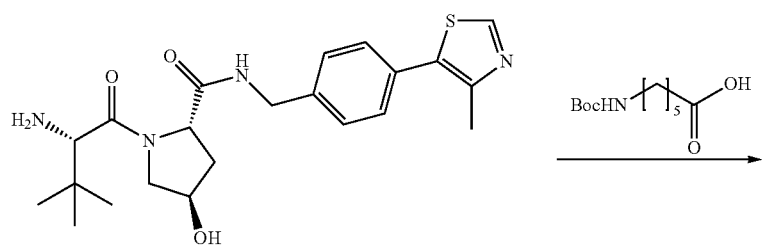

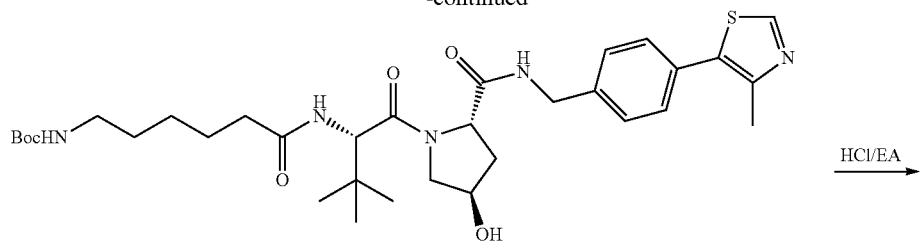
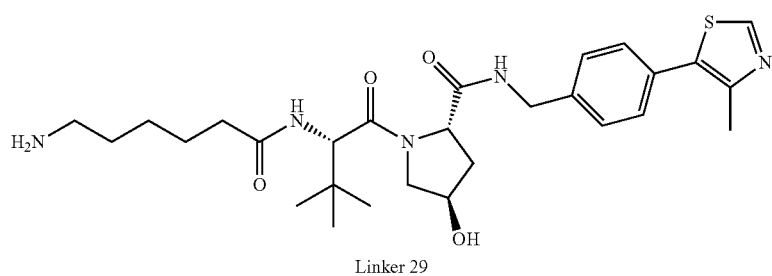
Linker 29
Linker 29 was synthesized following the same procedures as Linker 25 as described in Example 25. (2.70 g, yield: 87% over 2 steps). $^1$H NMR (400 MHz, DMSO-d6): δ 9.36 (s, 1H), 8.69 (t, J=6.4 Hz, 1H), 8.12 (brs, 3H), 7.92 (d, J=9.6 Hz, 1H), 7.44 (dd, J=13.6, 8.4 Hz, 4H), 4.54 (d, J=9.6 Hz, 1H), 4.48-4.39 (m, 2H), 4.36 (brs, 1H), 4.28-4.19 (m, 1H), 3.72-3.60 (m, 2H), 2.79-2.67 (m, 2H), 2.49 (s, 3H), 2.31-2.21 (m, 1H), 2.20-2.12 (m, 1H), 2.10-2.01 (m, 1H), 1.94-1.85 (m, 1H), 1.62-1.54 (m, 2H), 1.53-1.44 (m, 2H), 1.34-1.22 (m, 2H), 0.94 (s, 9H). MS (ESI) m/z=544.3 [M+H]$^+$.
Example 30: (2S,4R)-1-((S)-2-(7-Aminoheptanamido)-3,3-dimethylbutanoyl)-4-hydroxy-N-(4-(4-methylthiazol-5-yl)benzyl)pyrrolidine-2-carboxamide (Linker 30)
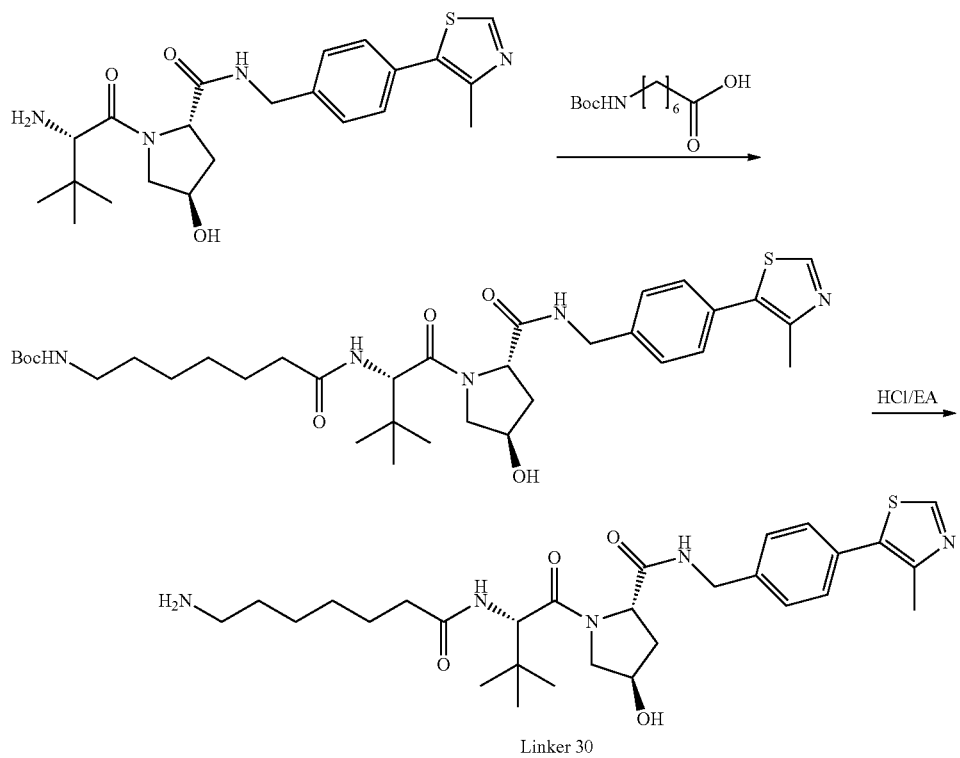
Linker 30

Linker 30 was synthesized following the same procedures as Linker 25 as described in Example 25. (2.13 g, yield: 76% over 2 steps). $^1$H NMR (400 MHz, DMSO-d6): δ 9.45 (s, 1H), 8.70 (t, J=6.0 Hz, 1H), 8.14 (brs, 3H), 7.86 (d, J=9.2 Hz, 1H), 7.44 (dd, J=12.8, 8.4 Hz, 4H), 4.54 (d, J=9.2 Hz, 1H), 4.49-4.40 (m, 2H), 4.36 (brs, 1H), 4.29-4.20 (m, 1H), 3.71-3.61 (m, 2H), 2.78-2.67 (m, 2H), 2.50 (s, 3H), 2.31-2.22 (m, 1H), 2.21-2.13 (m, 1H), 2.11-2.03 (m, 1H), 1.95-1.85 (m, 1H), 1.60-1.44 (m, 4H), 1.35-1.18 (m, 4H), 0.94 (s, 9H). MS (ESI) m/z=558.3 [M+H]$^+$.

Example 31: (2S,4R)-1-((S)-2-(8-Aminooctanamido)-3,3-dimethylbutanoyl)-4-hydroxy-N-(4-(4-methylthiazol-5-yl)benzyl)pyrrolidine-2-carboxamide (Linker 31)

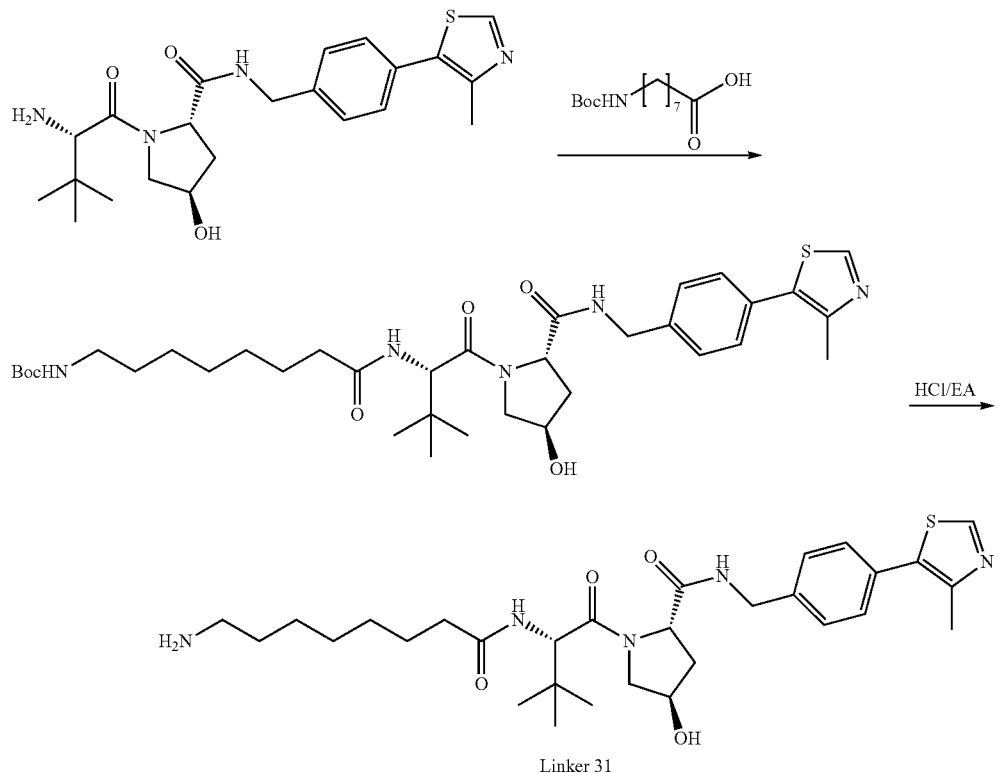

Linker 31

Linker 31 was synthesized following the same procedures as Linker 25 as described in Example 25. (1.81 g, yield: 65% over 2 steps). $^1$H NMR (400 MHz, DMSO-d6): δ 9.35 (s, 1H), 8.69 (t, J=6.0 Hz, 1H), 8.11 (brs, 3H), 7.88 (d, J=9.2 Hz, 1H), 7.44 (dd, J=14.0, 8.4 Hz, 4H), 4.54 (d, J=9.6 Hz, 1H), 4.48-4.39 (m, 2H), 4.36 (brs, 1H), 4.27-4.20 (m, 1H), 3.71-3.60 (m, 2H), 2.78-2.68 (m, 2H), 2.49 (s, 3H), 2.31-2.22 (m, 1H), 2.18-2.11 (m, 1H), 2.09-2.01 (m, 1H), 1.94-1.85 (m, 1H), 1.58-1.44 (m, 4H), 1.32-1.19 (m, 6H), 0.94 (s, 9H). MS (ESI) m/z=572.3 [M+H]$^+$.

Example 32: (2S,4R)-1-((S)-2-(9-Aminononanamido)-3,3-dimethylbutanoyl)-4-hydroxy-N-(4-(4-methylthiazol-5-yl)benzyl)pyrrolidine-2-carboxamide (Linker 32)

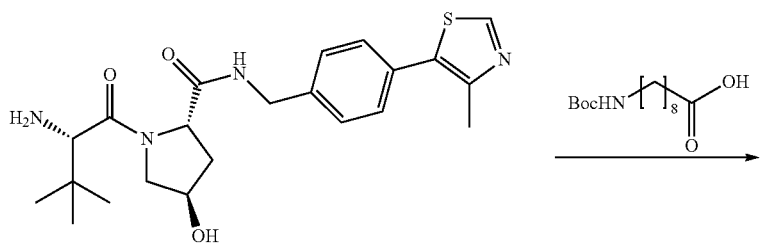

-continued

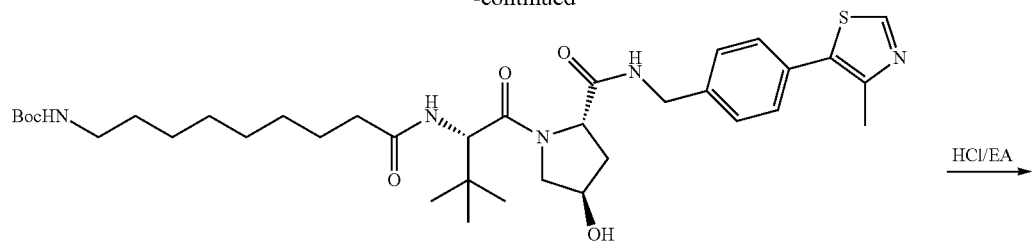

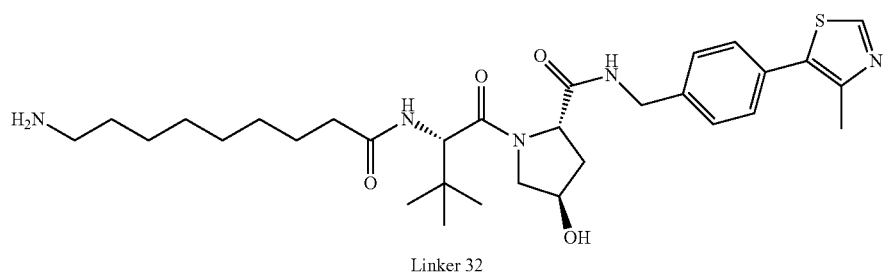

Linker 32

Linker 32 was synthesized following the same procedures as Linker 25 as described in Example 25. (2.32 g, yield: 80% over 2 steps). $^1$H NMR (400 MHz, DMSO-d6): δ 9.30 (s, 1H), 8.67 (t, J=6.4 Hz, 1H), 8.10 (brs, 3H), 7.88 (d, J=9.2 Hz, 1H), 7.43 (dd, J=14.0, 8.8 Hz, 4H), 4.55 (d, J=9.2 Hz, 1H), 4.48-4.39 (m, 2H), 4.35 (brs, 1H), 4.28-4.19 (m, 1H), 3.71-3.60 (m, 2H), 2.77-2.67 (m, 2H), 2.48 (s, 3H), 2.31-2.22 (m, 1H), 2.17-2.10 (m, 1H), 2.09-2.01 (m, 1H), 1.94-1.85 (m, 1H), 1.60-1.40 (m, 4H), 1.33-1.19 (m, 8H), 0.94 (s, 9H). MS (ESI) m/z=586.3 [M+H]$^+$.

Example 33: (2S,4R)-1-((S)-2-(10-Aminodecanamido)-3,3-dimethylbutanoyl)-4-hydroxy-N-(4-(4-methylthiazol-5-yl)benzyl)pyrrolidine-2-carboxamide (Linker 33)

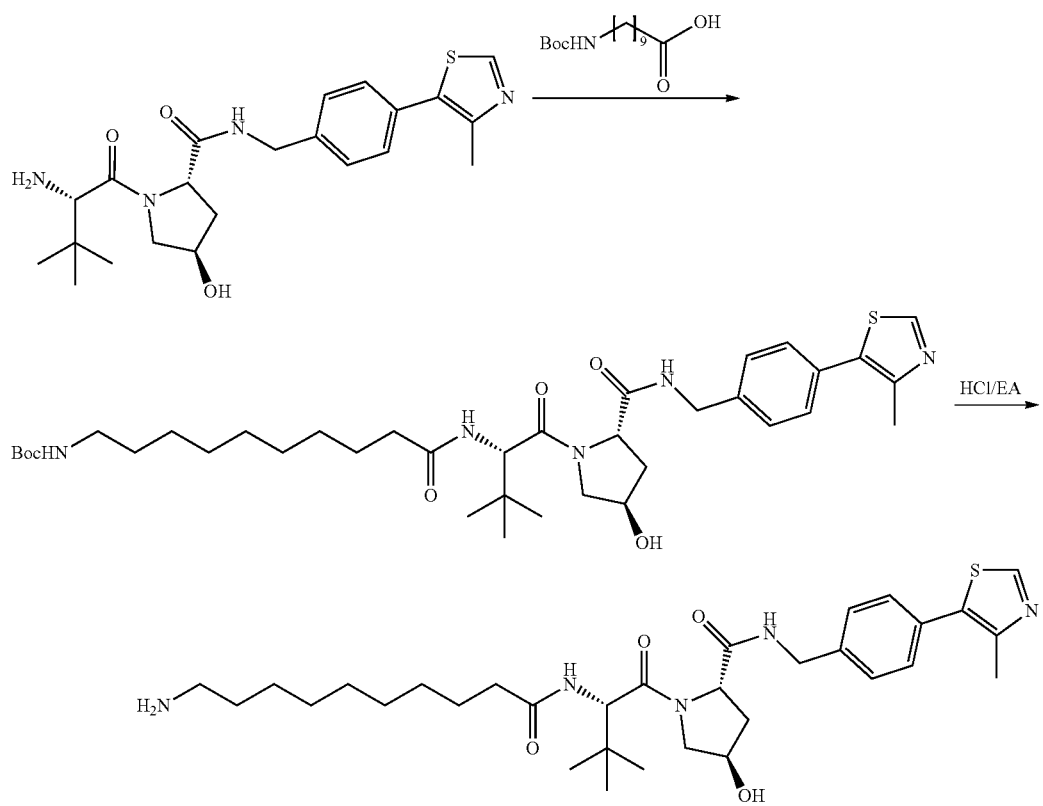

Linker 33

Linker 33 was synthesized following the same procedures as Linker 25 as described as Example 25. (2.29 g, yield: 77% over 2 steps). ¹H NMR (400 MHz, DMSO-d6): δ 9.41 (s, 1H), 8.67 (t, J=6.0 Hz, 1H), 8.14 (brs, 3H), 7.85 (d, J=8.8 Hz, 1H), 7.44 (dd, J=13.6, 8.8 Hz, 4H), 4.54 (d, J=8.8 Hz, 1H), 4.48-4.39 (m, 2H), 4.36 (brs, 1H), 4.29-4.20 (m, 1H), 3.71-3.60 (m, 2H), 2.78-2.67 (m, 2H), 2.49 (s, 3H), 2.32-2.22 (m, 1H), 2.17-2.11 (m, 1H), 2.10-2.01 (m, 1H), 1.95-1.86 (m, 1H), 1.62-1.40 (m, 4H), 1.34-1.16 (m, 10H), 0.94 (s, 9H). MS (ESI) m/z=600.4 [M+H]⁺.
Example 34: (2S,4R)-1-((S)-2-(11-Aminoundecanamido)-3,3-dimethylbutanoyl)-4-hydroxy-N-(4-(4-methylthiazol-5-yl)benzyl)pyrrolidine-2-carboxamide (Linker 34)
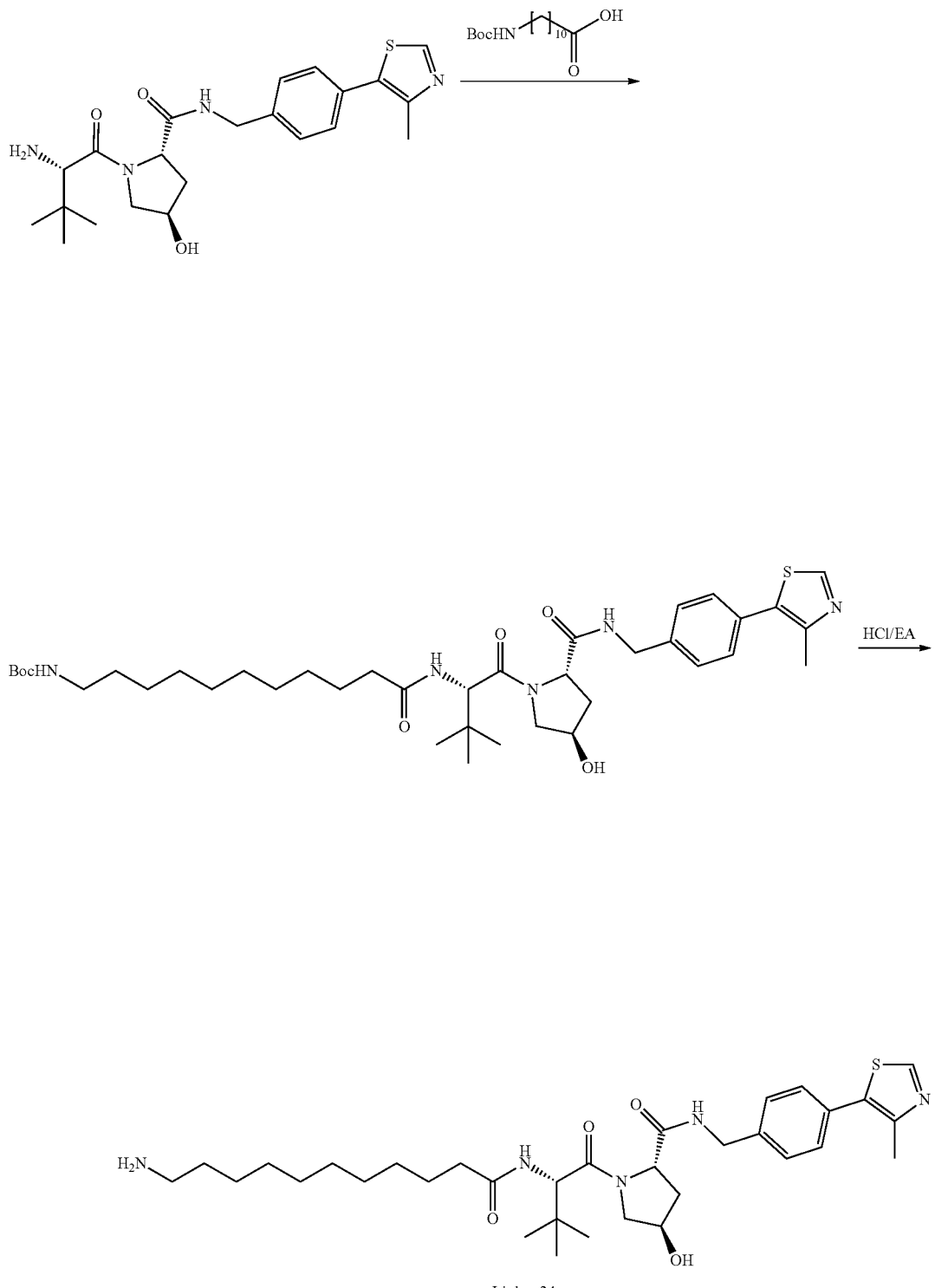
Linker 34

Linker 34 was synthesized following the same procedures as Linker 25 as described as Example 25. (1.10 g, yield: 37% over 2 steps). $^1$H NMR (400 MHz, DMSO-d6): δ 8.99 (s, 1H), 8.61 (t, J=6.4 Hz, 1H), 7.87 (d, J=8.8 Hz, 1H), 7.41 (dd, J=17.6, 8.0 Hz, 4H), 4.55 (d, J=9.6 Hz, 1H), 4.49-4.40 (m, 2H), 4.36 (brs, 1H), 4.26-4.17 (m, 1H), 3.70-3.64 (m, 2H), 2.59-2.52 (m, 2H), 2.45 (s, 3H), 2.31-2.22 (m, 1H), 2.16-2.08 (m, 1H), 2.06-1.99 (m, 1H), 1.96-1.86 (m, 1H), 1.56-1.42 (m, 2H), 1.39-1.30 (m, 2H), 1.28-1.19 (m, 12H), 0.94 (s, 9H). MS (ESI) m/z=614.4 [M+H]$^+$.
Example 35: (2S,4R)-1-((S)-2-(2-(2-Aminoethoxy)acetamido)-3,3-dimethylbutanoyl)-4-hydroxy-N-(4-(4-methylthiazol-5-yl)benzyl)pyrrolidine-2-carboxamide (Linker 35)
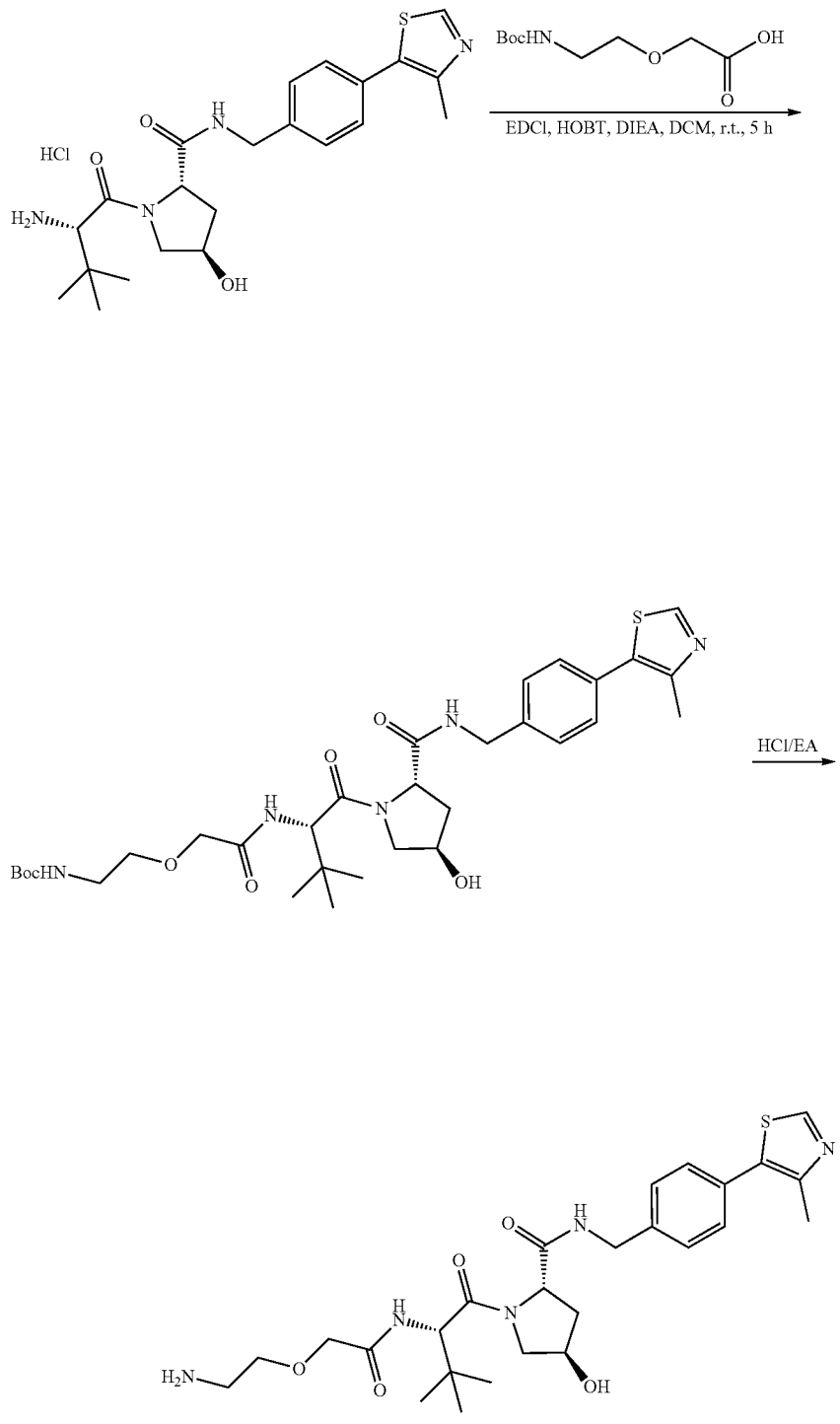
Linker 35

Linker 35 was synthesized following the same procedures as Linker 25 as described in Example 25. (1.35 g, yield: 55% over 2 steps). $^1$H NMR (400 MHz, DMSO-$d_6$) δ 9.23 (s, 1H), 8.70 (t, J=6.0 Hz, 1H), 8.35-8.14 (m, 3H), 7.78 (d, J=9.6 Hz, 1H), 7.47-7.38 (m, 4H), 4.61 (d, J=9.6 Hz, 1H), 4.49-4.34 (m, 3H), 4.30-4.21 (m, 1H), 4.09-3.99 (m, 2H), 3.75-3.58 (m, 4H), 3.06-2.94 (m, 2H), 2.48 (s, 3H), 2.13-2.03 (m, 1H), 1.95-1.85 (m, 1H), 0.95 (s, 9H). MS (ESI) m/z=532.0 [M+H]$^+$.
Example 36: (2S,4R)-1-((S)-2-(3-(2-Aminoethoxy)propanamido)-3,3-dimethylbutanoyl)-4-hydroxy-N-(4-(4-methylthiazol-5-yl)benzyl)pyrrolidine-2-carboxamide (Linker 36)
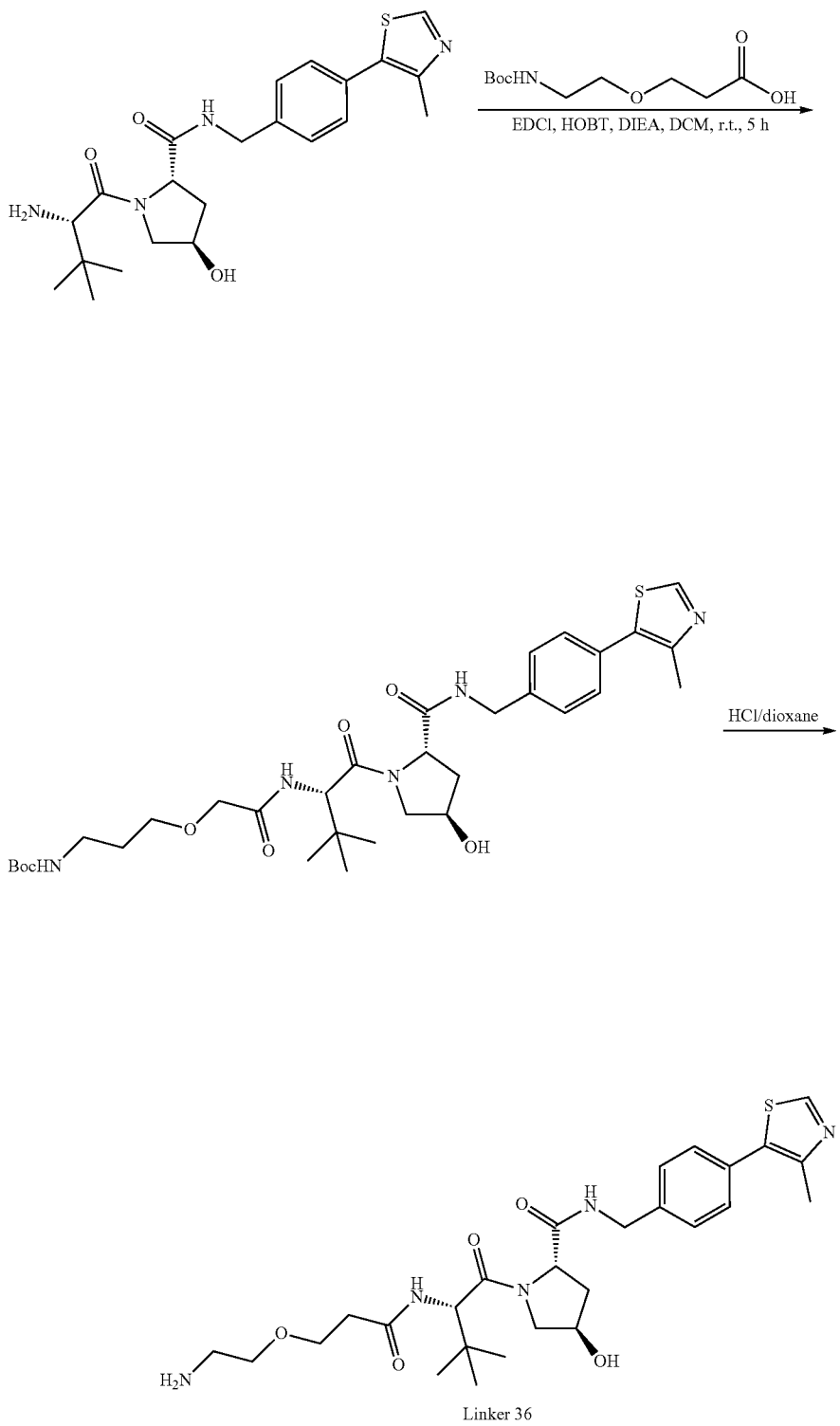
Linker 36

Linker 36 was synthesized following the same procedures as Linker 25 as described in Example 25. (1.32 g, yield: 49% over 2 steps). $^1$H NMR (400 MHz, DMSO-d$_6$) δ 8.99 (s, 1H), 8.57 (t, J=6.0 Hz, 1H), 8.03 (d, J=8 Hz, 1H), 7.85 (s, 3H), 7.43-7.37 (m, 4H), 4.57 (d, J=9.2 Hz, 1H), 4.46-4.31 (m, 3H), 4.26-4.20 (m, 1H), 3.69-3.55 (m, 6H), 3.99-2.95 (m, 2H), 2.60-2.56 (m, 1H), 2.46-2.42 (m, 4H), 2.05-2.03 (m, 1H), 1.93-1.92 (m, 1H), 0.95 (s, 9H). MS (ESI) m/z=546.0 [M+H]$^+$.

Example 37: (2S,4R)-1-((S)-2-(2-(2-(2-Aminoethoxy)ethoxy)acetamido)-3,3-dimethylbutanoyl)-4-hydroxy-N-(4-(4-methylthiazol-5-yl)benzyl)pyrrolidine-2-carboxamide (Linker 37)

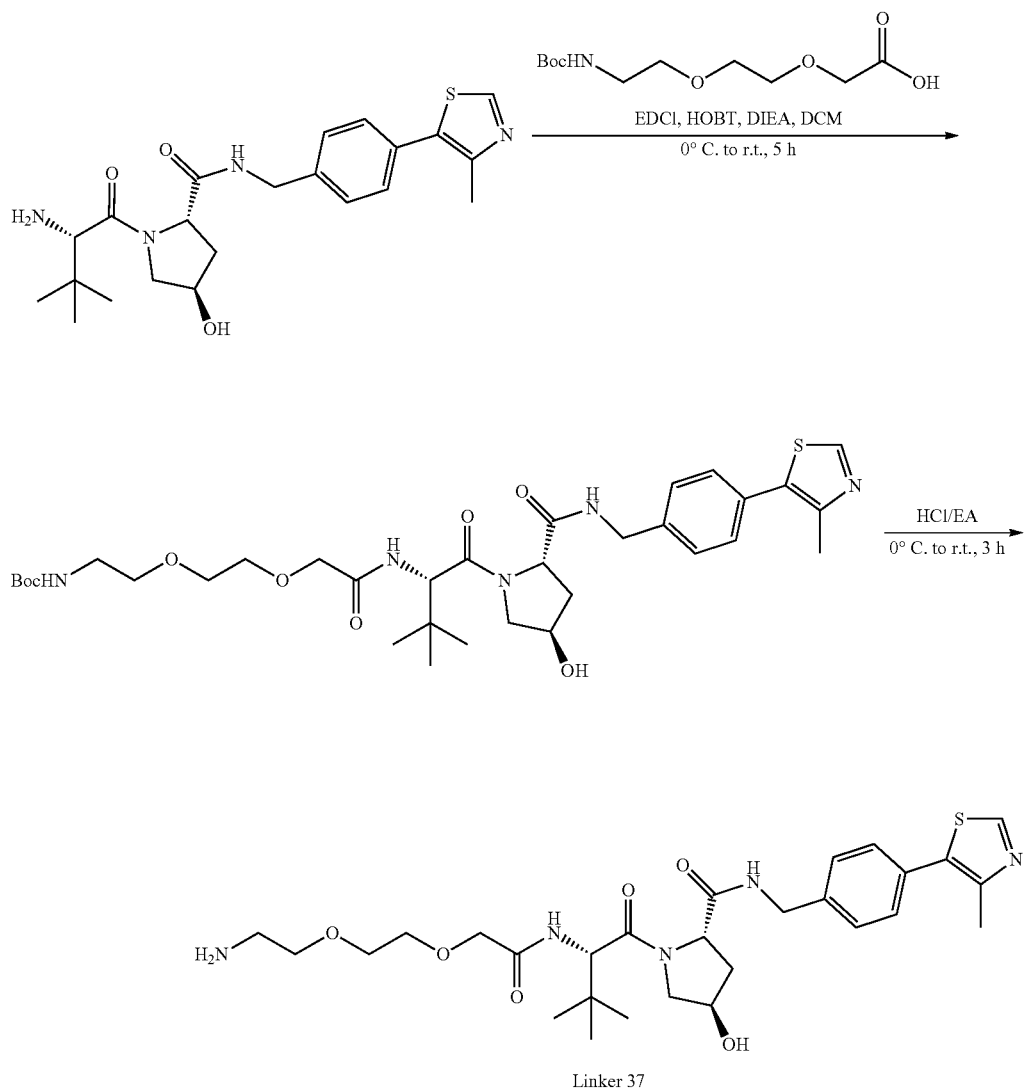

Linker 37

Linker 37 was synthesized following the same procedures as Linker 25 as described as Example 25. (1.2 g, yield: 49% over 2 steps). $^1$H NMR (400 MHz, DMSO-d6) δ 9.38 (s, 1H), 8.78 (t, J=6.0 Hz, 1H), 8.18 (s, 3H), 7.59-7.37 (m, 5H), 4.58 (d, J=9.6 Hz, 1H), 4.49 (t, J=8.2 Hz, 1H), 4.42-4.26 (m, 3H), 4.09-3.95 (m, 2H), 3.72-3.55 (m, 8H), 2.99-2.92 (m, 2H), 2.49 (s, 3H), 2.15-2.04 (m, 1H), 1.95-1.85 (m, 1H), 0.95 (s, 9H). MS (ESI) m/z=576.1 [M+H]$^+$.

Example 38: (2S,4R)-1-((S)-2-(3-(2-(2-Aminoethoxy)ethoxy)propanamido)-3,3-dimethylbutanoyl)-4-hydroxy-N-(4-(4-methylthiazol-5-yl)benzyl)pyrrolidine-2-carboxamide (Linker 38)
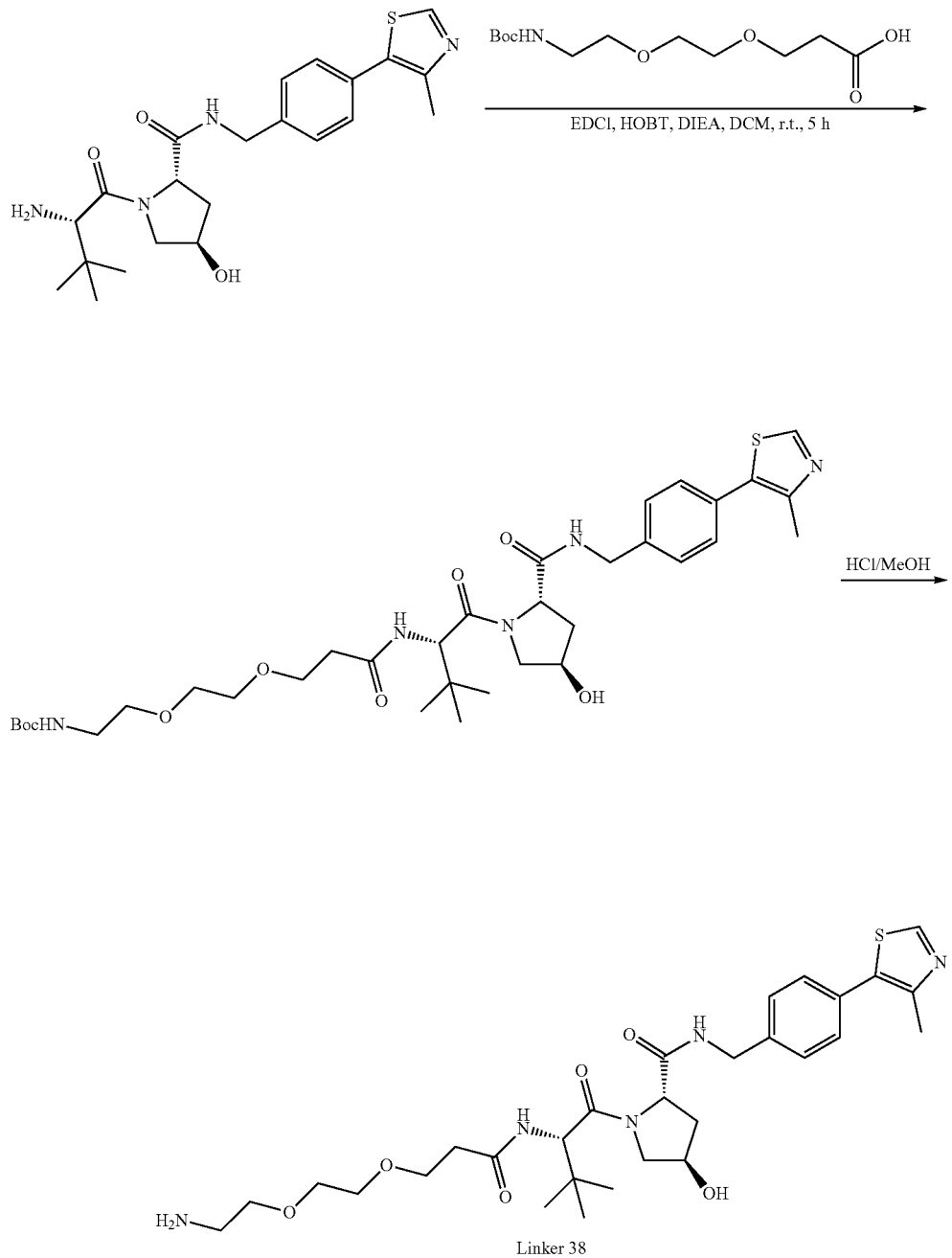
Linker 38 was synthesized following the same procedures as Linker 25 as described as Example 25. (1.34 g, yield: 49% over 2 steps). $^1$H NMR (400 MHz, DMSO-d$_6$) δ 9.02 (s, 1H), 8.58 (t, J=6.0 Hz, 1H), 7.94 (d, J=8 Hz, 1H), 7.82 (s, 3H), 7.42-7.30 (m, 4H), 4.58 (d, J=9.2 Hz, 1H), 4.60-4.37 (m, 3H), 4.25-4.31 (m, 1H), 3.70-3.50 (m, 10H), 3.00-2.96 (m, 2H), 2.57-2.55 (m, 1H), 2.45 (s, 3H), 2.41-2.38 (m, 1H), 2.06-2.04 (m, 1H), 1.95-1.93 (m, 1H), 0.95 (s, 9H). MS (ESI) m/z=590.1 [M+H]$^+$.

Example 39: (2S,4R)-1-((S)-14-Amino-2-(tert-butyl)-4-oxo-6,9,12-trioxa-3-azatetradecanoyl)-4-hydroxy-N-(4-(4-methylthiazol-5-yl)benzyl)pyrrolidine-2-carboxamide (Linker 39)
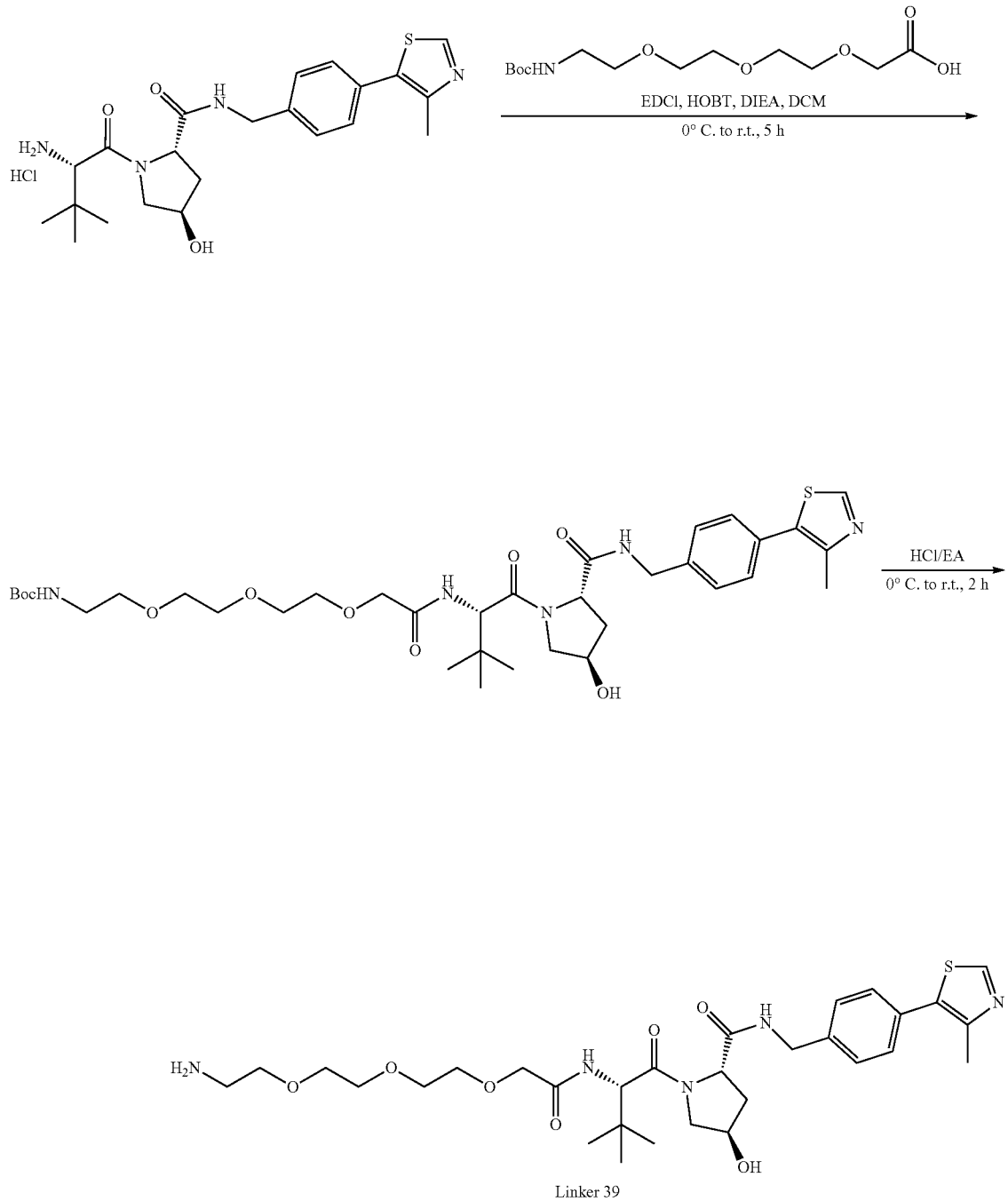
Linker 39
Linker 39 was synthesized following the same procedures as Linker 25 as described as Example 25. (1.53 g, yield: 56% over 2 steps). $^1$H NMR (400 MHz, DMSO-d6) δ 9.01 (s, 1H), 8.59 (t, J=6.0 Hz, 1H), 7.81 (s, 3H), 7.48-7.41 (m, 5H), 4.58 (d, J=9.6 Hz, 1H), 4.47-4.26 (m, 4H), 3.99 (s, 2H), 3.70-3.58 (m, 12H), 3.0-2.96 (m, 2H), 2.46 (s, 3H), 2.11-2.06 (m, 1H), 1.95-1.88 (m, 1H), 0.96 (s, 9H). MS (ESI) m/z=621.1 [M+H]$^+$.

Example 40: (2S,4R)-1-((S)-1-Amino-14-(tert-butyl)-12-oxo-3,6,9-trioxa-13-azapentadecan-15-oyl)-4-hydroxy-N-(4-(4-methylthiazol-5-yl)benzyl)pyrrolidine-2-carboxamide (Linker 40)

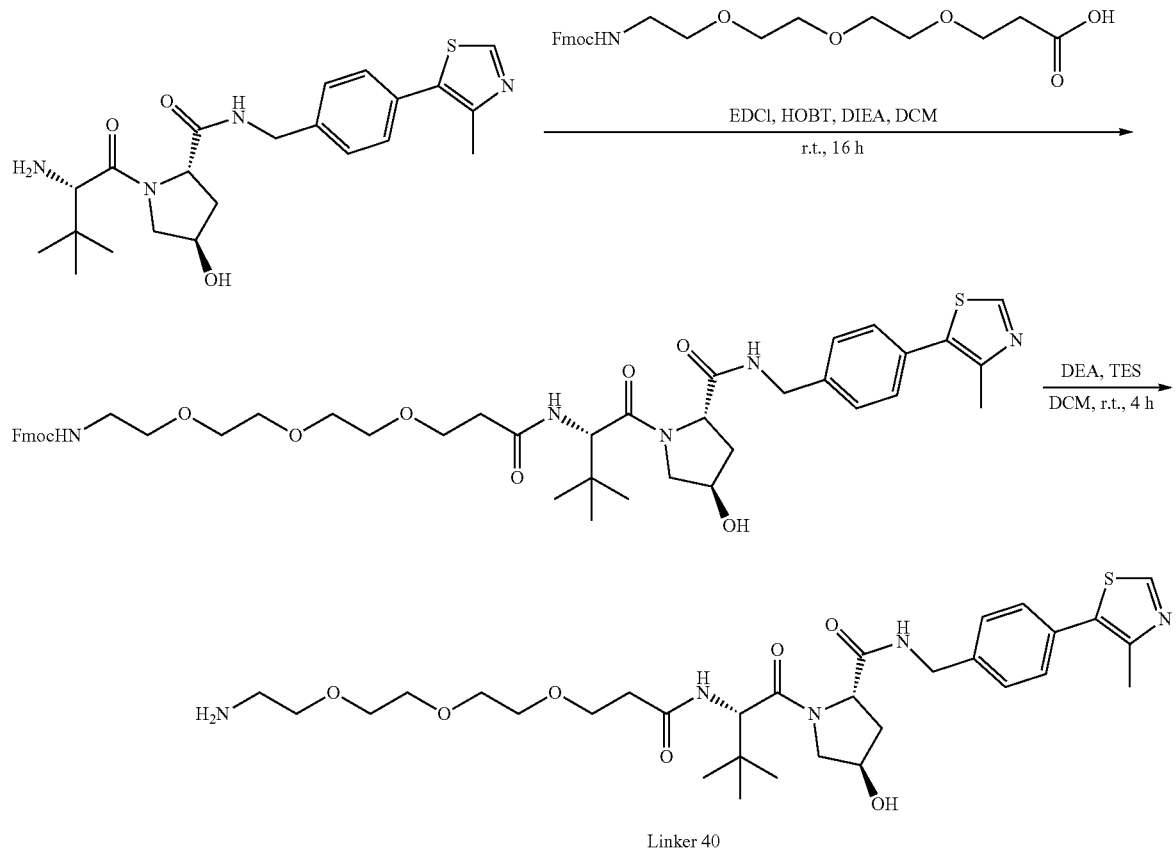

Linker 40 was synthesized following the same procedures as Linker 25 as described as Example 25. (1.52 g, yield: 51% over 2 steps). $^1$H NMR (400 MHz, DMSO-d6) δ 9.01 (s, 1H), 8.57 (t, J=6.0 Hz, 1H), 7.91 (d, J=9.2 Hz, 1H), 7.81 (s, 3H), 7.44-7.38 (m, 4H), 4.58-4.55 (m, 1H), 4.45-4.36 (m, 3H), 4.25-4.21 (m, 1H), 3.70-3.48 (m, 14H), 3.00-2.97 (m, 2H), 2.59-2.52 (m, 1H), 2.46 (s, 3H), 2.39-2.34 (m, 1H), 2.08-2.03 (m, 1H), 1.95-1.88 (m, 1H), 0.94 (s, 9H). MS (ESI) m/z=633.8 [M+H]$^+$.

Example 41: (2S,4R)-1-((S)-1-Amino-17-(tert-butyl)-15-oxo-3,6,9,12-tetraoxa-16-azaoctadecan-18-oyl)-4-hydroxy-N-(4-(4-methylthiazol-5-yl)benzyl)pyrrolidine-2-carboxamide (Linker 41)

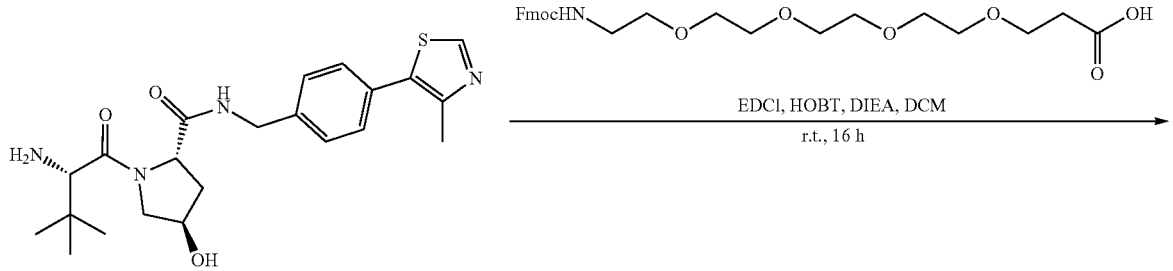

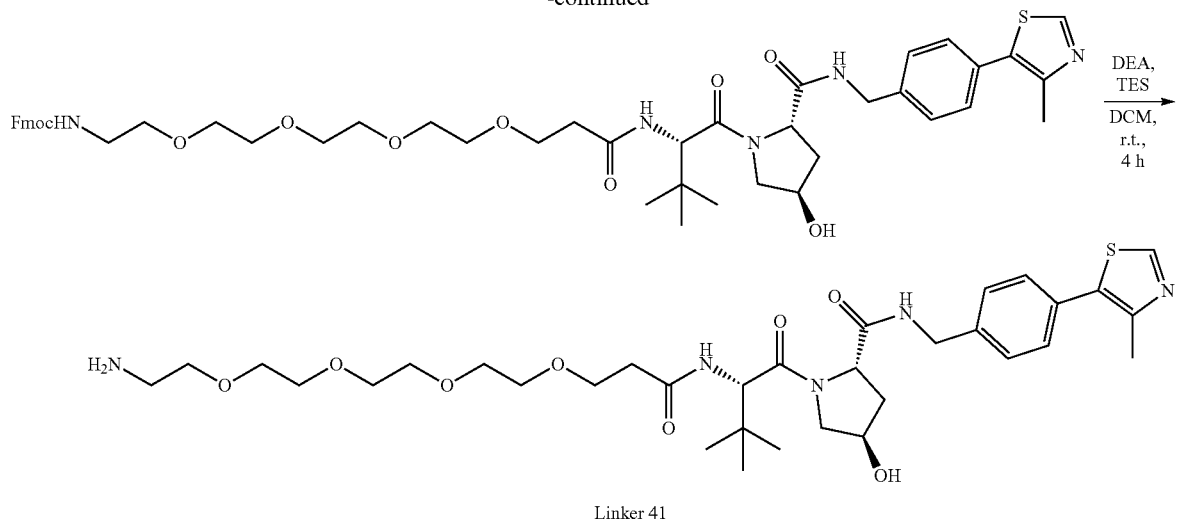
Linker 41
Linker 41 was synthesized following the same procedures as Linker 25 as described as Example 25. (1.12 g, yield: 37% over 2 steps). $^1$H NMR (400 MHz, DMSO-d6) δ 8.98 (s, 1H), 8.58 (t, J=5.6 Hz, 1H), 7.92 (d, J=9.2 Hz, 1H), 7.44-7.38 (m, 4H), 4.56 (d, J=9.2 Hz, 1H), 4.47-4.41 (m, 2H), 4.38-4.34 (m, 1H), 4.26-4.19 (m, 1H), 3.70-3.55 (m, 5H), 3.53-3.45 (m, 14H), 3.35 (t, J=5.6 Hz, 2H), 2.64 (t, J=5.6 Hz, 2H), 2.58-2.50 (m, 1H), 2.45 (s, 3H), 2.40-2.35 (m, 1H), 2.08-2.00 (m, 1H), 1.94-1.91 (m, 1H), 0.94 (s, 9H). MS (ESI) m/z=678.1 [M+H]$^+$.
Example 42: (2S,4R)-1-((S)-1-Amino-20-(tert-butyl)-18-oxo-3,6,9,12,15-pentaoxa-19-azahenicosan-21-oyl)-4-hydroxy-N-(4-(4-methylthiazol-5-yl)benzyl)pyrrolidine-2-carboxamide (Linker 42)
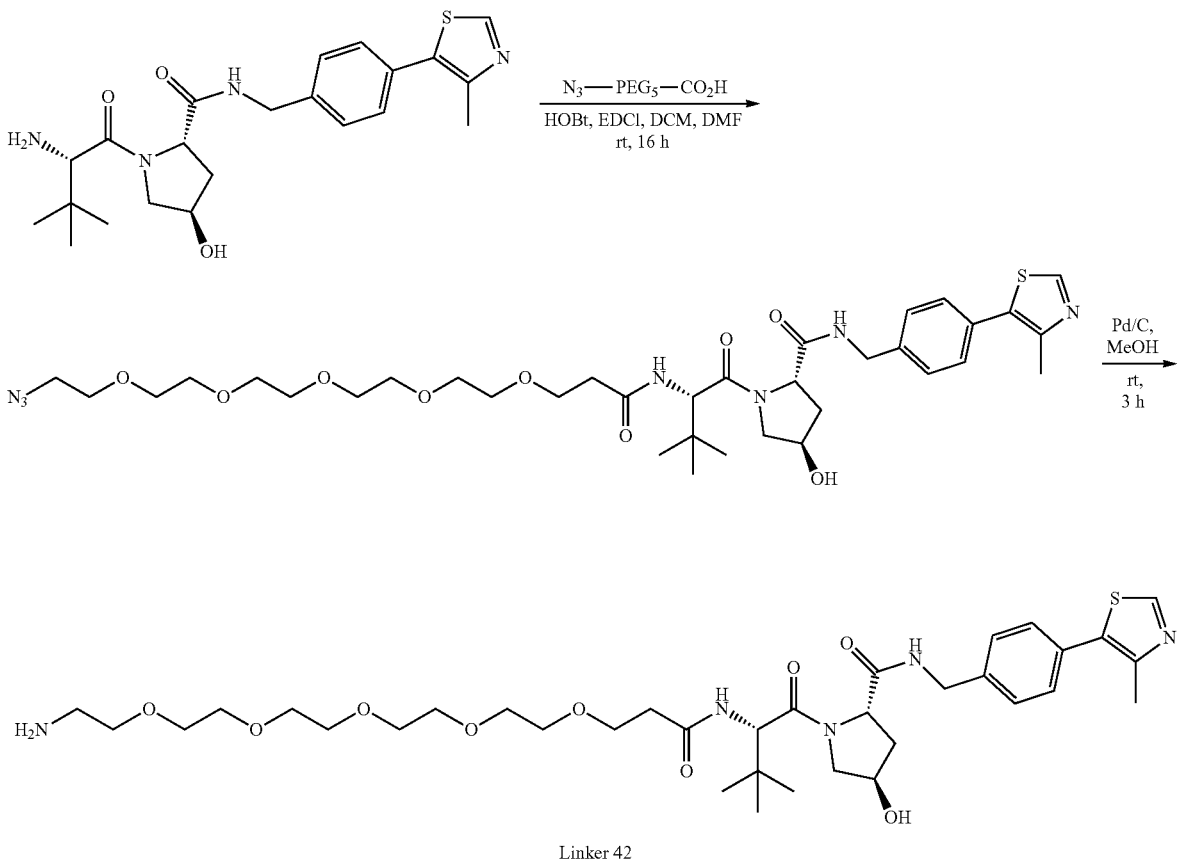
Linker 42

Linker 42 was synthesized following the same procedures as Linker 25 as described as Example 25. (1.1 g, 1.52 mmol, yield: 32% over 2 steps). $^1$H NMR (400 MHz, DMSO-$d_6$) δ 9.38 (s, 1H), 8.67 (t, J=16 Hz, 1H), 8.14 (br, 3H), 7.91 (d, J=9.2 Hz, 1H), 7.39-7.48 (m, 4H), 4.53 (d, J=9.2 Hz, 1H), 4.39-4.46 (m, 2H), 4.36-4.34 (m, 1H), 4.20-4.25 (m, 1H), 3.45-3.68 (m, 22H), 2.91-2.95 (m, 2H), 2.52-2.58 (m, 1H), 2.47 (s, 3H), 2.32-2.39 (m, 1H), 2.03-2.08 (m, 1H), 1.85-1.92 (m, 1H), 0.92 (s, 9H). MS (ESI) m/z=722.4 [M+H]$^+$.

Example 43: 4-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-4-oxobutanoic acid (Linker 43)

Example 44: 5-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-5-oxopentanoic acid (Linker 44)

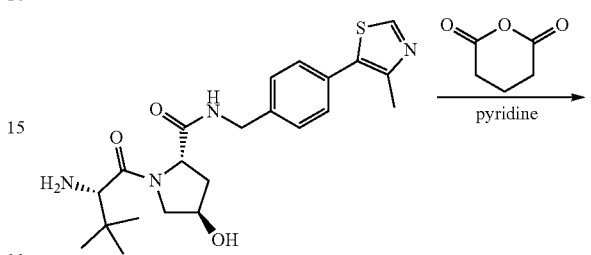

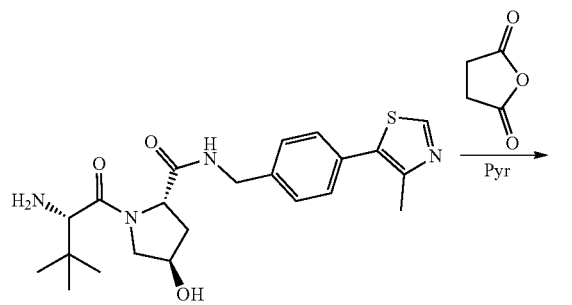

Linker 43

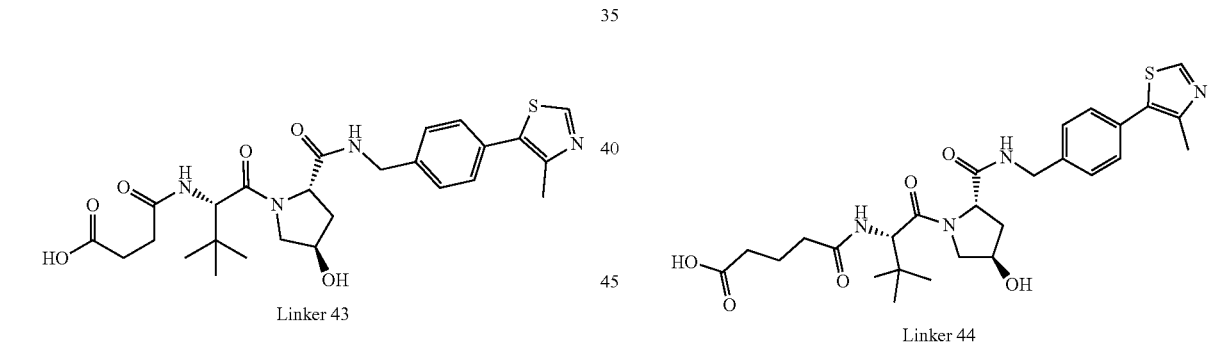

Linker 44

A mixture of (2S,4R)-1-((S)-2-amino-3,3-dimethylbutanoyl)-4-hydroxy-N-(4-(4-methylthiazol-5-yl)benzyl)pyrrolidine-2-carboxamide (1.0 g, 2.3 mmol) and succinic anhydride (465 mg, 4.65 mmol) in pyridine (5 mL) was stirred at room temperature for overnight. The mixture was concentrated. The residue was purified by flash chromatography (reversed-phase, MeCN/H$_2$O) to give the title compound Linker 43 (1.05 g, yield: 86%). $^1$H NMR (400 MHz, DMSO-$d_6$): δ 12.02 (s, 1H), 8.99 (s, 1H), 8.58 (t, J=6.0 Hz, 1H), 7.96 (d, J=9.2 Hz, 1H), 7.43-7.37 (m, 4H), 5.13 (d, J=3.6 Hz, 1H), 4.53 (d, J=9.2 Hz, 1H), 4.46-4.40 (m, 2H), 4.34 (s, 1H), 4.21 (dd, J=16.0, 5.2 Hz, 1H), 3.69-3.60 (m, 2H), 2.45 (s, 3H), 2.44-2.33 (m, 4H), 2.06-2.01 (m, 1H), 1.93-1.87 (m, 1H), 0.93 (s, 9H). $^{13}$C NMR (100 MHz, DMSO-d6): δ 173.83, 171.92, 170.86, 169.56, 151.41, 147.70, 139.48, 131.15, 129.63, 128.62, 127.41, 68.87, 58.70, 56.44, 56.34, 41.65, 37.91, 35.35, 29.74, 29.25, 26.35, 15.92. MS (ESI) m/z=531.2 [M+H]$^+$.

Linker 44 was synthesized following the same procedures as Linker 43 as described as Example 43. (1.5 g, yield: 79%). $^1$H NMR (400 MHz, DMSO-$d_6$): δ8.99 (s, 1H), 8.59 (t, J=6.0 Hz, 1H), 7.91 (d, J=9.2 Hz, 1H), 7.44-7.37 (m, 4H), 5.16 (brs, 1H), 4.54 (d, J=9.2 Hz, 1H), 4.47-4.42 (m, 2H), 4.36 (s, 1H), 4.21 (dd, J=16.0, 5.2 Hz, 1H), 3.7-3.64 (m, 2H), 2.45 (s, 3H), 2.31-2.14 (m, 4H), 2.07-2.02 (m, 1H), 1.94-1.81 (m, 1H), 1.74-1.68 (m, 2H), 0.94 (s, 9H). $^{13}$C NMR (100 MHz, DMSO-$d_6$): δ 174.18, 171.94, 171.63, 169.66, 151.41, 147.70, 139.46, 131.15, 129.61, 128.62, 127.41, 68.86, 58.69, 56.38, 41.65, 37.91, 35.16, 34.03, 33.10, 26.35, 20.89, 15.92. MS (ESI) m/z=543.2 [M-H]$^-$.

Example 45: 6-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-6-oxohexanoic acid (Linker 45)

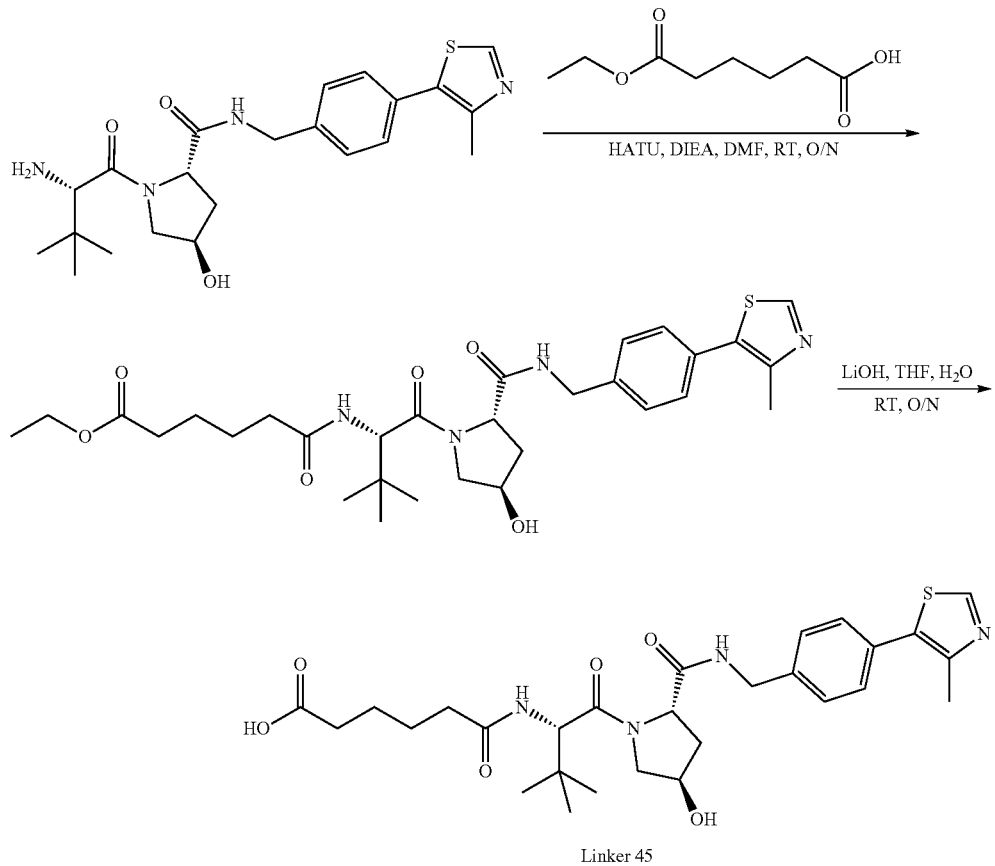

Linker 45

(40)

Linker 45 was synthesized following the same procedures as Linker 25 as described as Example 25. (1.2 g, yield: 55% over 2 steps). $^1$H NMR (400 MHz, CDCl$_3$) δ 8.68 (s, 1H), 7.75 (s, 1H), 7.32-7.27 (m, 5H), 4.64-4.57 (m, 3H), 4.56-4.50 (m, 1H), 4.28-4.25 (m, 1H), 4.02-3.99 (m, 1H), 3.71-3.68 (m, 1H), 2.47 (s, 3H), 2.24-2.18 (m, 6H), 1.59-1.48 (m, 4H), 0.96 (s, 9H). MS (ESI) m/z=559.3 [M+H]$^+$.

Example 46: 7-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-7-oxoheptanoic acid (Linker 46)

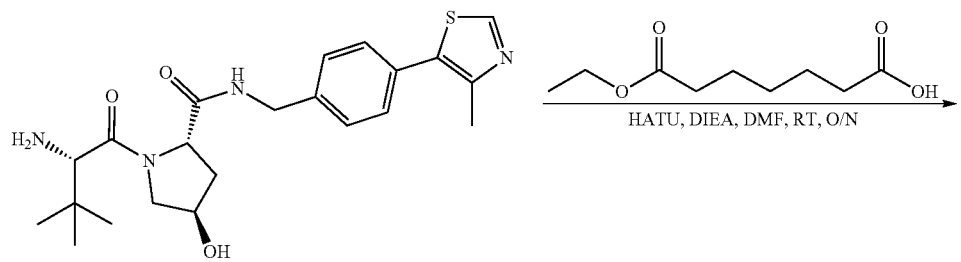

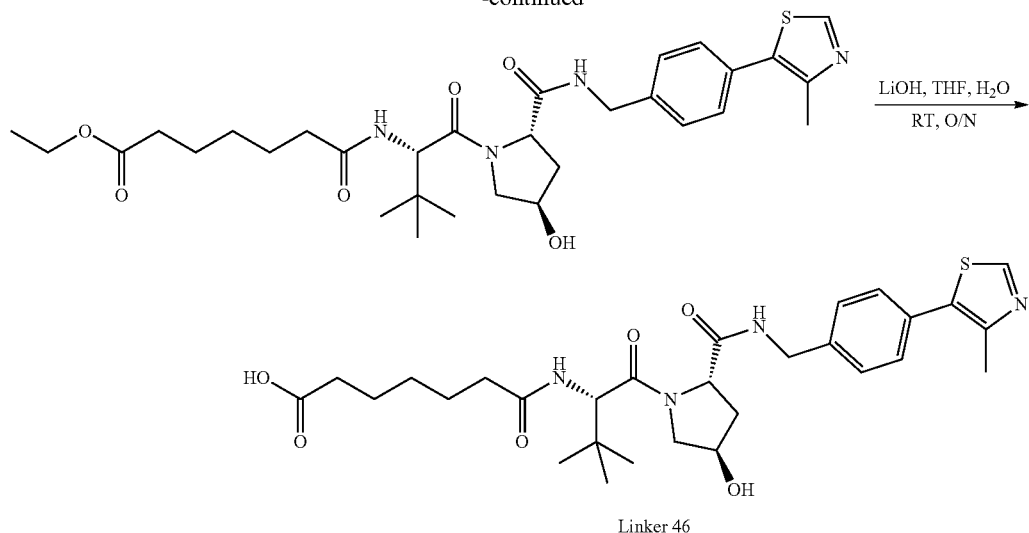
Linker 46
Linker 46 was synthesized following the same procedures as Linker 45 as described as Example 45. (1.1 g, yield: 33% over 2 steps). $^1$H NMR (400 MHz, CDCl$_3$) δ 8.67 (s, 1H), 7.56-7.55 (m, 1H), 7.34-7.30 (m, 5H), 4.68-4.59 (m, 3H), 4.59-4.51 (m, 1H), 4.25 (dd, J=4.8 Hz, 15.2 Hz, 1H), 4.06-4.03 (m, 1H), 3.70-3.68 (m, 1H), 2.46 (s, 3H), 2.31-2.11 (m, 6H), 1.55-1.51 (m, 4H), 1.29-1.24 (m, 2H), 0.94 (s, 9H). MS (ESI) m/z=573.1 [M+H]$^+$.
Example 47: 8-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-8-oxooctanoic acid Linker 47)
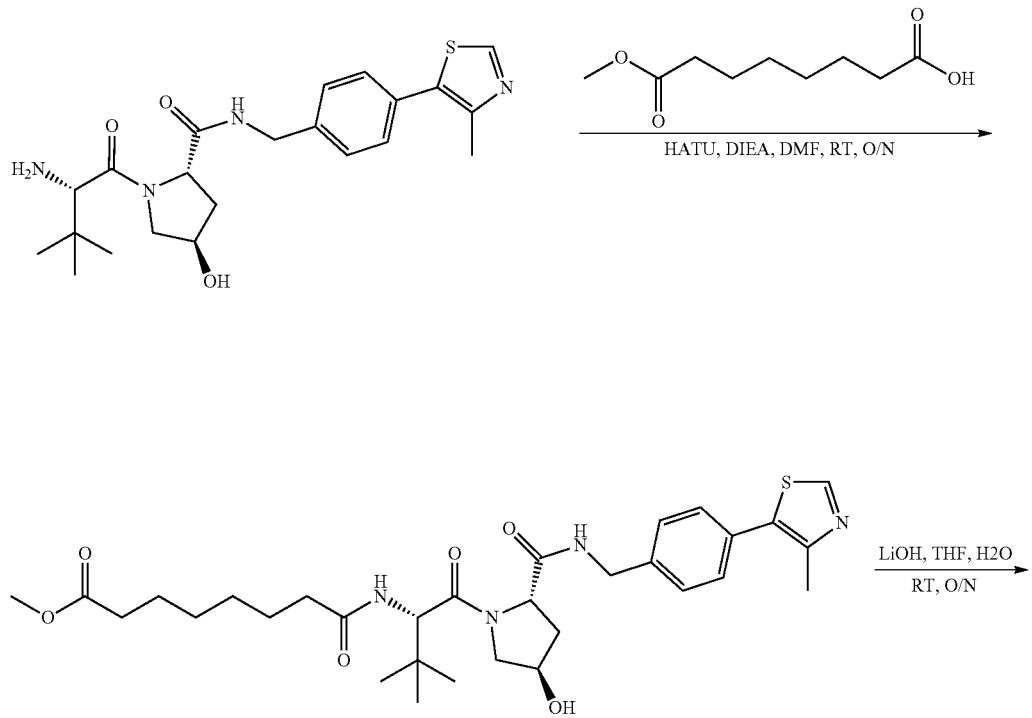

-continued
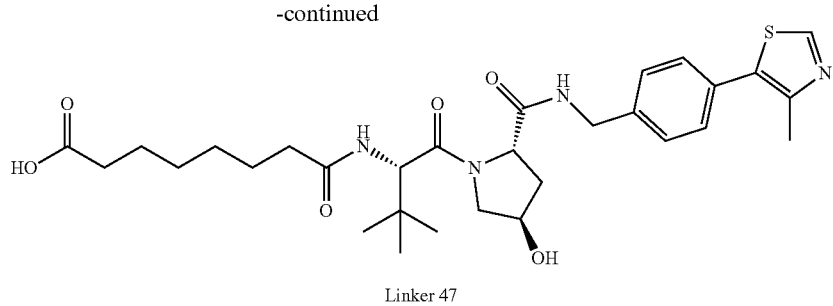
Linker 47
Linker 47 was synthesized following the same procedures as Linker 45 as described as Example 45. (1.08 g, yield: 52% over 2 steps). ¹H NMR (400 MHz, DMSO-d6) δ 8.99 (s, 1H), 8.55 (t, J=2.4 Hz, 1H), 7.83 (d, J=9.2 Hz, 1H), 7.44-7.38 (m, 4H), 4.55 (d, J=9.6 Hz, 1H), 4.52-4.41 (m, 2H), 4.36 (s, 1H), 4.25-4.21 (m, 1H), 3.67-3.66 (m, 2H), 2.45 (s, 3H), 2.30-1.91 (m, 6H), 1.49-1.47 (m, 4H), 1.26-1.24 (m, 4H), 0.92 (s, 9H). MS (ESI) m/z=587.3 [M+H]⁺.
Example 48: 9-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-9-oxononanoic acid (Linker 48)
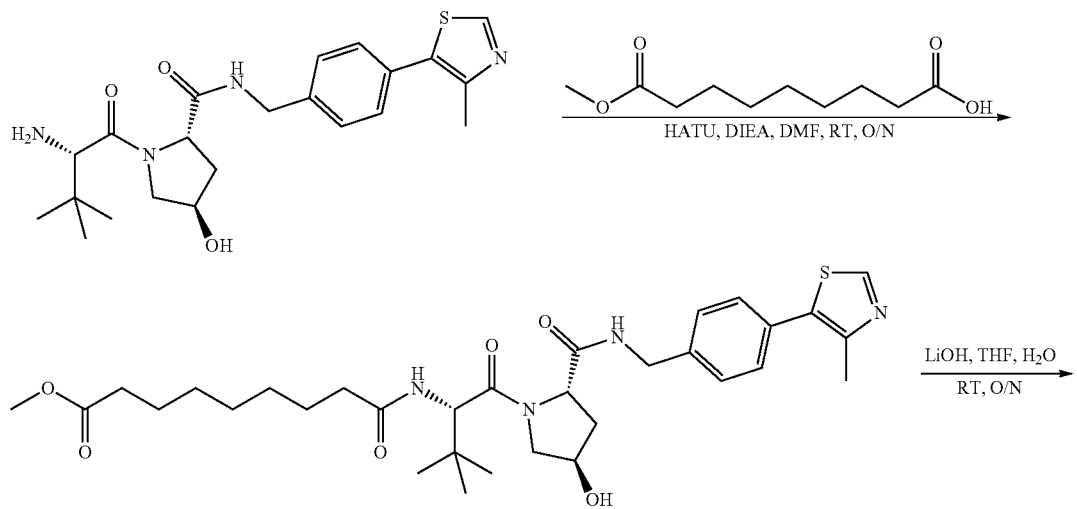
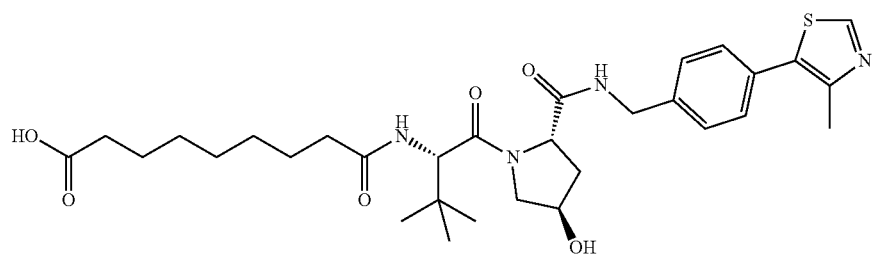
Linker 48

Linker 48 was synthesized following the same procedures as Linker 45 as described in Example 45. (1.16 g, yield: 44% over 2 steps). ¹H NMR (400 MHz, CDCl₃) δ 8.70 (s, 1H), 7.55 (s, 1H), 7.33-7.27 (m, 4H), 7.08 (d, J=8.0 Hz, 1H), 4.68-4.52 (m, 4H), 4.31-4.27 (m, 1H), 4.08-4.05 (m, 1H), 3.69-3.67 (m, 1H), 2.48 (s, 3H), 2.33-2.11 (m, 6H), 1.60-1.47 (m, 4H), 1.29-1.20 (m, 6H), 0.96 (s, 9H). MS (ESI) m/z=601.1 [M+H]⁺.

Example 49: 10-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-10-oxodecanoic acid (Linker 49)

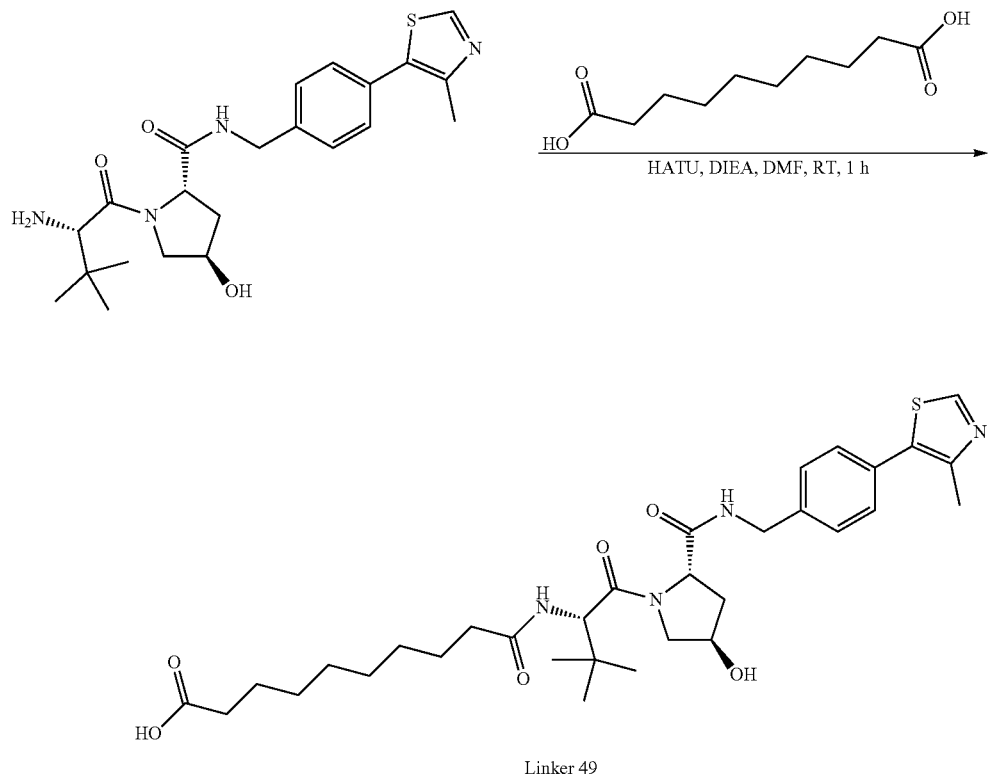

Linker 49

Linker 49 was synthesized following the same procedure as Linker 45 as described as Example 45. (1.1 g, yield: 35%). ¹H NMR (400 MHz, DMSO-d₆): δ8.99 (s, 1H), 8.58 (t, J=6.0 Hz, 1H), 7.85 (d, J=9.2 Hz, 1H), 7.43-7.37 (m, 4H), 4.54 (d, J=9.2 Hz, 1H), 4.47-4.41 (m, 2H), 4.35 (s, 1H), 4.21 (dd, J=16.0, 5.6 Hz, 1H), 3.69-3.63 (m, 2H), 2.45 (s, 3H), 2.29-2.09 (m, 4H), 2.03-2.01 (m, 1H), 1.94-1.88 (m, 1H), 1.47 (m, 4H), 1.24 (b, 8H), 0.94 (s, 9H). ¹³C NMR (100 MHz, DMSO-d₆): δ 172.07, 171.92, 169.69, 151.41, 147.70, 139.48, 131.14, 129.62, 128.61, 127.40, 68.84, 58.67, 56.32, 56.26, 41.64, 37.93, 35.18, 34.85, 28.62, 26.36, 25.39, 15.93. MS (ESI) m/z=615.3 [M+H]⁺.

Example 50: 11-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-11-oxoundecanoic acid (Linker 50)

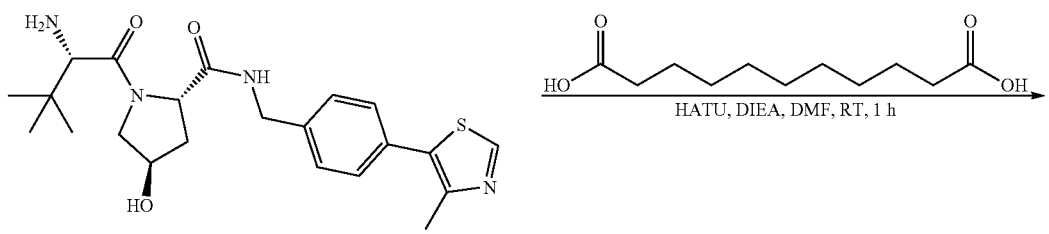

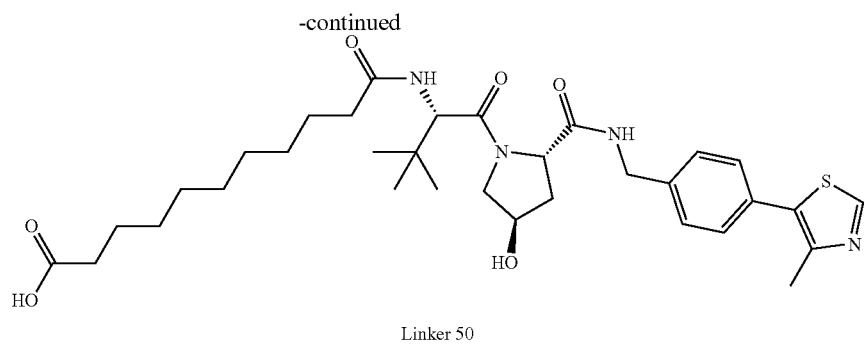
Linker 50
Linker 50 was synthesized following the same procedure as Linker 45 as described as Example 45. (1.1 g, yield: 50%). $^1$H NMR (400 MHz, DMSO-$d_6$): δ8.99 (s, 1H), 8.58 (t, J=6.0 Hz, 1H), 7.85 (t, J=9.2 Hz, 1H), 7.37-7.43 (m, 4H), 4.56-4.19 (m, 5H), 3.70-3.60 (m, 2H), 2.45 (s, 3H), 2.27-1.90 (m, 6H), 1.49-1.45 (m, 4H), 1.23 (m, 10H), 0.93 (s, 9H). $^{13}$C NMR (100 MHz, DMSO-$d_6$): δ174.59, 172.07, 171.92, 169.69, 151.42, 147.70, 139.49, 131.14, 129.62, 128.61, 127.41, 68.84, 58.67, 56.32, 56.25, 41.64, 37.93, 35.19, 34.85, 33.80, 28.82, 28.70, 28.68, 28.62, 28.55, 26.37, 25.42, 24.55, 15.93. MS (ESI) m/z=629.4 [M+H]$^+$.
Example 51: 3-(3-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-3-oxopropoxy)propanoic acid (Linker 51)
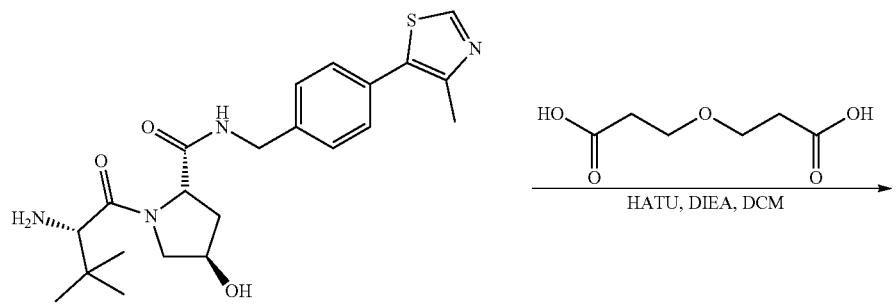
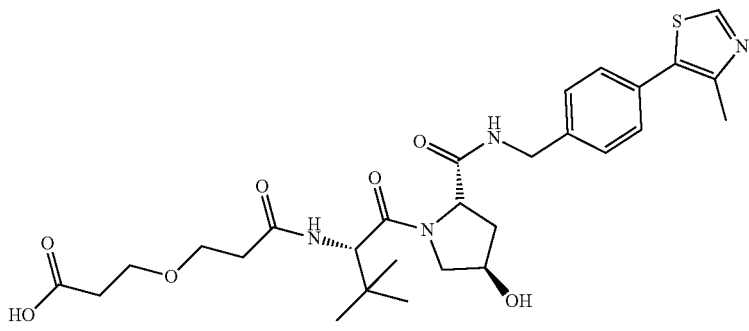
Linker 51

Linker 51 was synthesized following the same procedure as Linker 45 as described in Example 45. (1.1 g, yield: 42%). $^1$H NMR (400 MHz, DMSO-d6) δ 8.98 (s, 1H), 8.55 (t, J=6.0 Hz, 1H), 7.91 (d, J=9.2 Hz, 1H), 7.43-7.37 (m, 4H), 4.55-4.53 (m, 1H), 4.45-4.40 (m, 2H), 4.35 (s, 1H), 4.24-4.19 (m, 1H), 3.68-3.52 (m, 6H), 2.54-2.56 (m, 1H), 2.45-2.37 (m, 5H), 2.34-2.30 (m, 1H), 2.05-2.00 (m, 1H), 1.93-1.86 (m, 1H), 0.93 (s, 9H). MS (ESI) m/z=575 [M+H]$^+$.

Example 52: 2-(2-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-2-oxoethoxy)acetic acid (Linker 52)

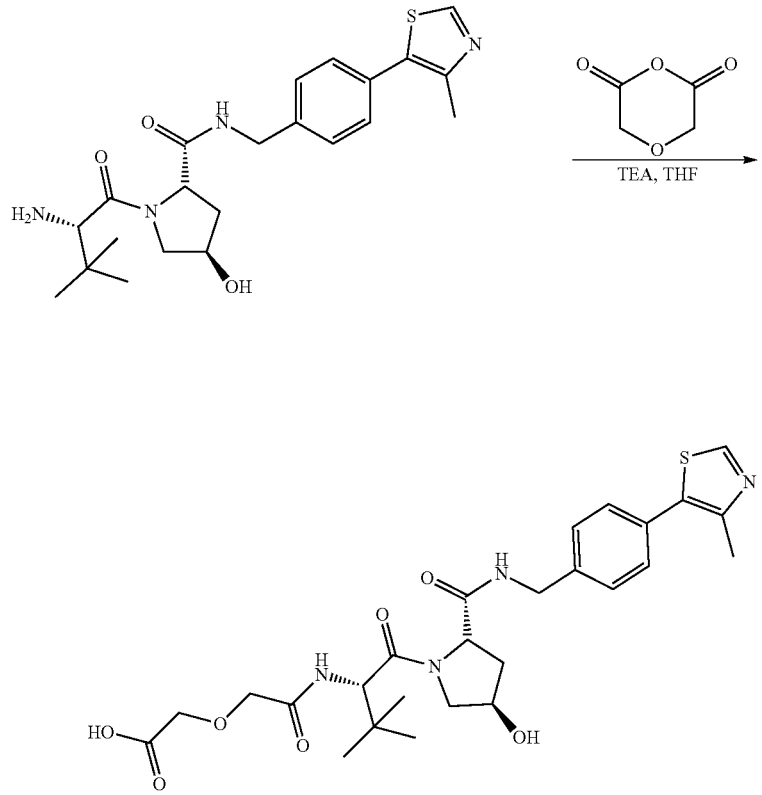

Linker 52

Linker 52 was synthesized following the same procedure as Linker 43 as described as Example 43. (1.2 g, yield: 63%). $^1$H NMR (400 MHz, DMSO-d6) δ 12.81 (br s, 1H), 8.98 (s, 1H), 8.58 (t, J=6.0 Hz, 1H), 7.60 (d, J=9.6 Hz, 1H), 7.45-7.35 (m, 4H), 5.14 (br, 1H), 4.58-4.55 (m, 1H), 4.46-4.36 (m, 3H), 4.28-4.26 (m, 1H), 4.14 (s, 2H), 4.04 (s, 2H), 3.69-3.60 (m, 2H), 2.44 (s, 3H), 2.08-2.03 (m, 1H), 1.93-1.87 (m, 1H), 0.95 (s, 9H). MS (ESI) m/z=547 [M+H]$^+$.

Example 53: 3-(2-(3-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-3-oxopropoxy)ethoxy)propanoic acid (Linker 53)

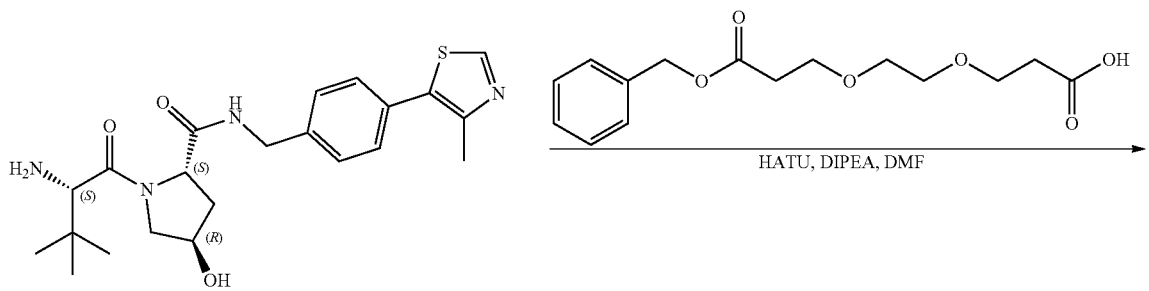

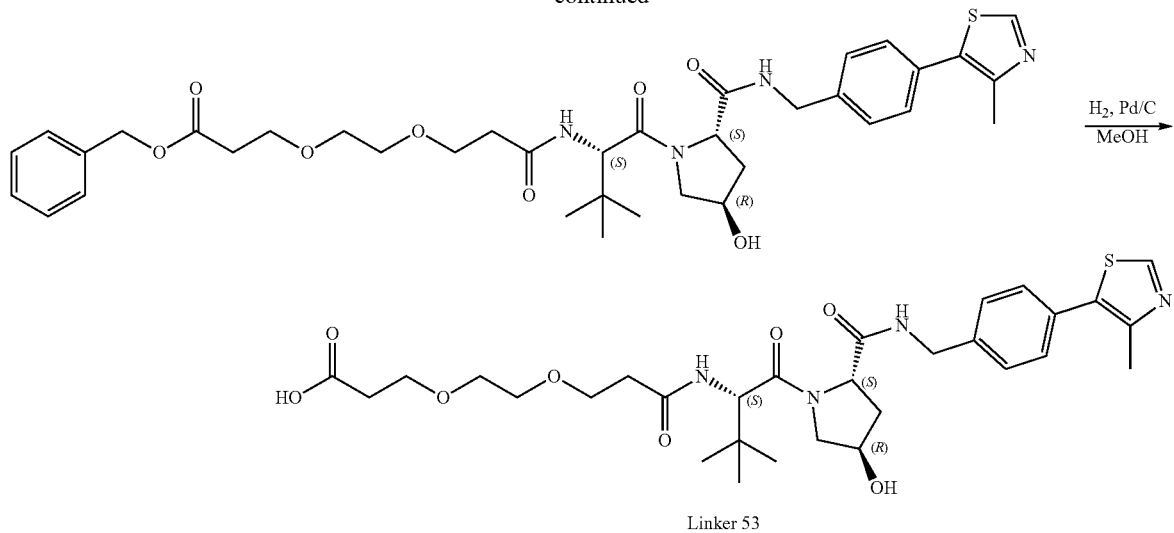
Linker 53 was synthesized following the same procedures as Linker 45 as described as Example 45. (1.4 g, yield 23% over 2 steps). $^1$H NMR (400 MHz, DMSO-$d_6$): δ 8.98 (s, 1H), 8.56 (t, J=6.0 Hz, 1H), 7.91 (d, J 9.2 Hz, 1H), 7.43-7.37 (m, 4H), 4.55 (d, J 9.6 Hz, 1H), 4.46-4.41 (m, 2H), 4.35 (s, 1H), 4.29-4.20 (m, 1H), 3.70-3.57 (m, 7H), 3.50-3.45 (m, 5H), 2.57-2.55 (m, 1H), 2.45 (s, 3H), 2.43-2.41 (m, 1H), 2.37-2.32 (m, 1H), 2.09-2.01 (m, 1H), 1.94-1.87 (m, 1H), 0.94 (s, 9H). MS (ESI) m/z=619.3 [M+H]$^+$.
Example 54: 2-(2-(2-(((S)-1-((2S,4R)-4-Hydroxy-2-((4-(4-methylthiazol-5-yl)benzyl)carbamoyl)pyrrolidin-1-yl)-3,3-dimethyl-1-oxobutan-2-yl)amino)-2-oxoethoxy)ethoxy)acetic acid (Linker 54)

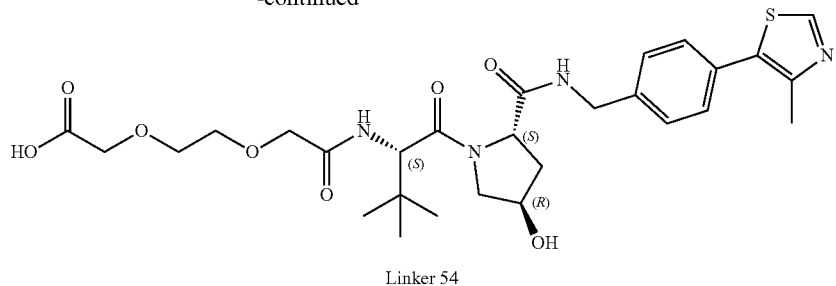

Linker 54

Linker 54 was synthesized following the same procedures as Linker 53 as described as Example 53. (1.13 g, yield 20% over 2 steps). $^1$H NMR (400 MHz, DMSO-$d_6$): δ 8.98 (s, 1H), 8.60 (t, J=6.0 Hz, 1H), 7.49 (d, J=9.2 Hz, 1H), 7.40 (s, 4H), 4.57 (d, J=9.2 Hz, 1H), 4.47-4.36 (m, 3H), 4.28-4.23 (m, 1H), 4.05-3.93 (m, 4H), 3.69-3.61 (m, 6H), 2.45 (s, 3H), 2.08-2.03 (m, 1H), 1.94-1.87 (m, 1H), 0.94 (s, 9H). MS (ESI) m/z=591.2 [M+H]$^+$.

Example 55: (S)-15-((2S,4R)-4-Hydroxy-2-((4-(4-methylthiazol-5-yl)benzyl) carbamoyl)pyrrolidine-1-carbonyl)-16,16-dimethyl-13-oxo-4,7,10-trioxa-14-azaheptadecanoic acid (Linker 55)

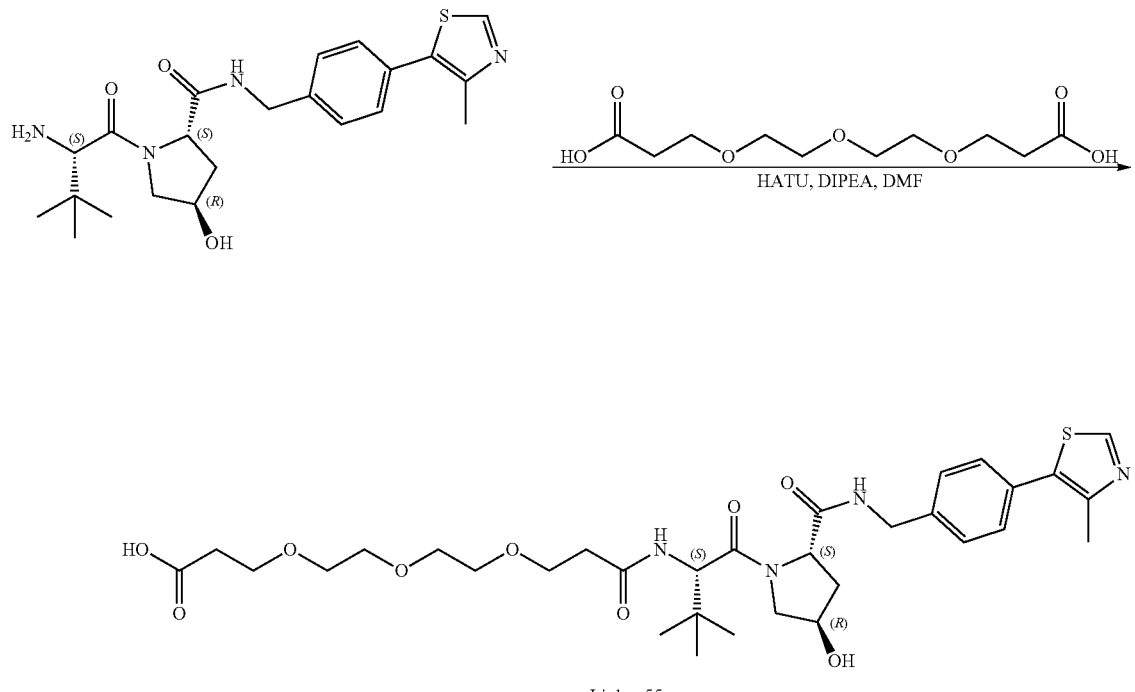

Linker 55

Linker 55 was synthesized following the same procedure as Linker 45 as described in Example 45. (1.7 g, yield 37%). $^1$H NMR (400 MHz, DMSO-$d_6$): δ 8.99 (s, 1H), 8.56 (t, J=6.0 Hz, 1H), 7.91 (d, J=9.6 Hz, 1H), 7.44-7.38 (m, 4H), 4.56 (d, J=9.2 Hz, 1H), 4.47-4.42 (m, 2H), 4.36 (s, 1H), 4.25-4.20 (m, 1H), 3.70-3.55 (m, 6H), 3.50-3.46 (m, 8H), 2.58-2.51 (m, 3H), 2.45-2.42 (m, 5H), 2.40-2.33 (m, 1H), 2.07-2.02 (m, 1H), 1.94-1.88 (m, 1H), 0.94 (s, 9H). LCMS (ESI) m/z=661.0 [M−H]$^-$.

Example 56: (S)-13-((2S,4R)-4-Hydroxy-2-((4-(4-methylthiazol-5-yl)benzyl)carbamoyl)pyrrolidine-1-carbonyl)-14,14-dimethyl-11-oxo-3,6,9-trioxa-12-azapentadecanoic acid (Linker 56)

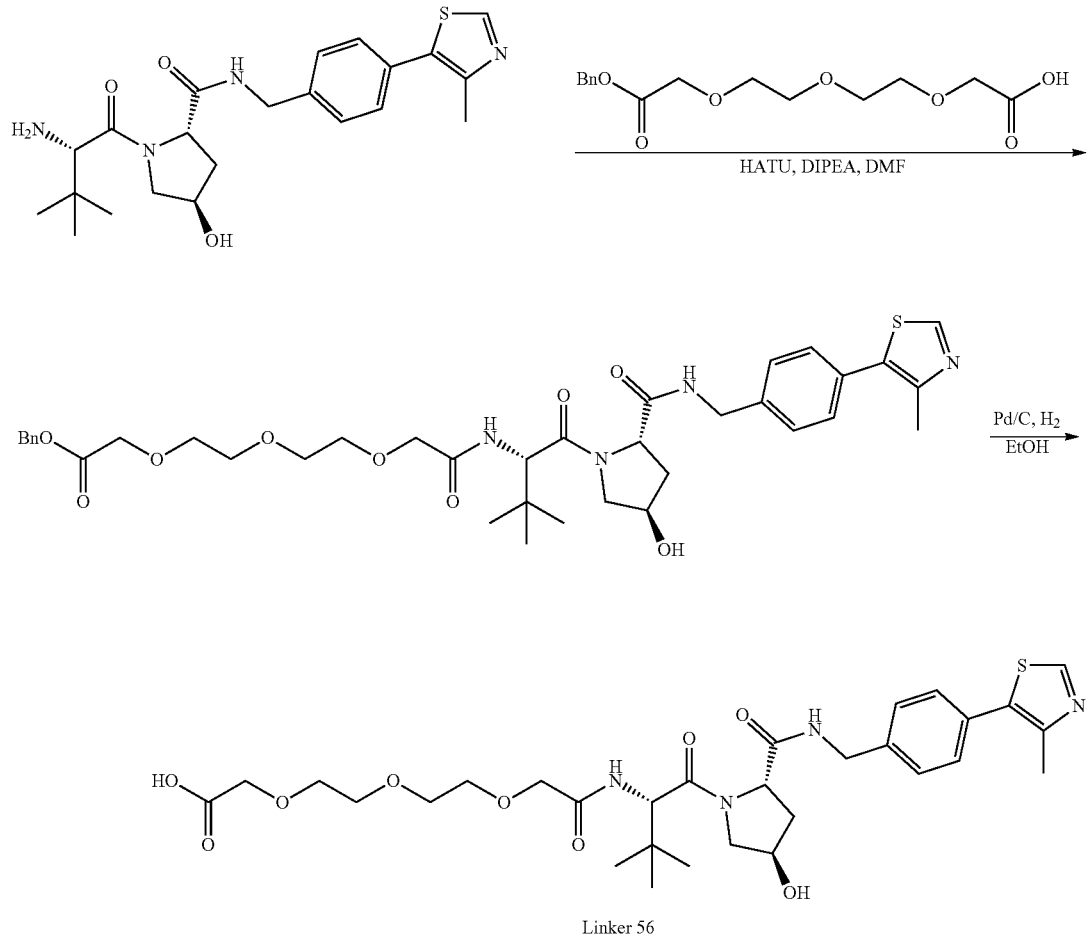

Linker 56 was synthesized following the same procedures as Linker 45 as described as Example 45. (1.21 g, yield 31% over 2 steps). $^1$H NMR (400 MHz, CDCl$_3$): δ 8.68 (s, 1H), 7.80-7.71 (m, 11H), 7.41-7.33 (m, 5H), 4.71-7.65 (m, 1H), 4.61-4.50 (m, 3H), 4.37-4.33 (m, 1H), 4.07-3.94 (m, 5H), 3.77-3.58 (m, 10H), 2.51 (s, 3H), 2.38-2.30 (m, 1H), 2.24-2.19 (m, 1H), 0.98 (s, 9H). LCMS (ESI) m/z=635.0 [M+H]$^+$.

Example 57: (S)-18-((2S,4R)-4-Hydroxy-2-((4-(4-methylthiazol-5-yl)benzyl)carbamoyl)pyrrolidine-1-carbonyl)-19,19-dimethyl-16-oxo-4,7,10,13-tetraoxa-17-azaicosanoic acid (Linker 57)

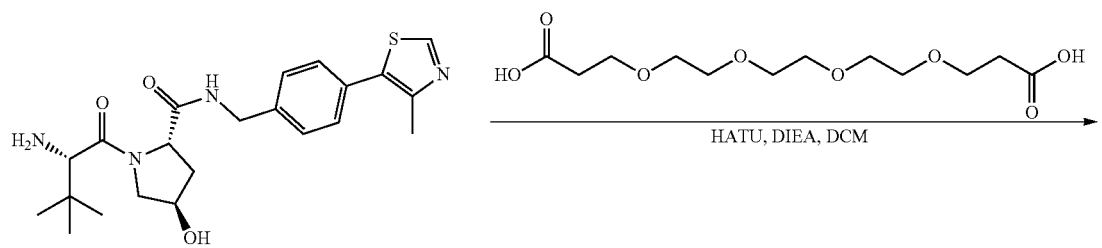

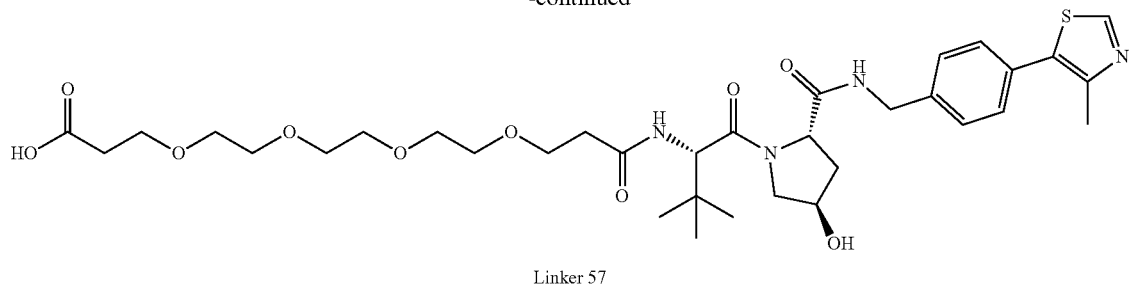

Linker 57

Linker 57 was synthesized following the same procedure as Linker 45 as described as Example 45. (1.6 g, yield 43%). ¹H NMR (400 MHz, CDCl₃): δ 8.69 (s, 1H), 7.55-7.52 (m, 1H), 7.47-7.45 (m, 1H), 7.36 (s, 4H), 4.70-4.66 (m, 1H), 4.62-4.57 (m, 2H), 4.50 (s, 1H), 4.34-4.29 (m, 1H), 4.12-4.09 (m, 1H), 3.75-3.48 (m, 18H), 2.56-2.47 (m, 7H), 2.40-2.33 (m, 1H), 2.23-2.18 (m, 1H), 0.96 (s, 9H). MS (ESI) m/z=707.1 [M+H]⁺.

Example 58: (S)-21-((2S,4R)-4-Hydroxy-2-((4-(4-methylthiazol-5-yl)benzyl)carbamoyl)pyrrolidine-1-carbonyl)-22,22-dimethyl-19-oxo-4,7,10,13,16-pentaoxa-20-azatricosanoic acid (Linker 58)

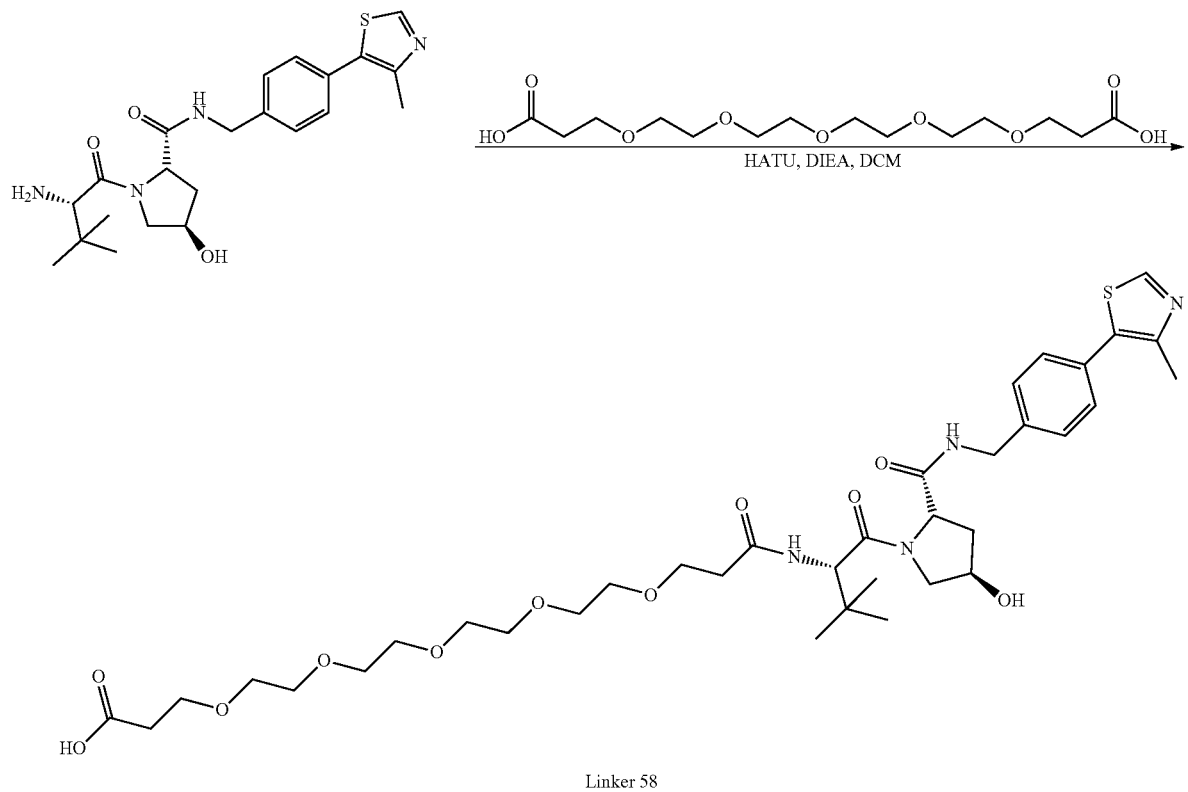

Linker 58

Linker 58 was synthesized following the same procedure as Linker 45 as described as Example 45. (1.2 g, yield: 23%). ¹H NMR (400 MHz, DMSO-d₆) δ 8.98 (s, 1H), 8.57 (t, J=6.0 Hz, 1H), 7.91 (d, J=9.6 Hz, 1H), 7.43-7.31 (m, 4H), 4.56-4.53 (m, 1H), 4.45-4.35 (m, 3H), 4.24-4.19 (m, 1H), 3.69-3.55 (m, 6H), 3.49-3.47 (m, 16H), 2.57-2.53 (m, 1H), 2.45 (s, 3H), 2.39-2.32 (m, 3H), 2.06-2.01 (m, 1H), 1.93-1.86 (m, 1H), 0.95 (s, 9H). MS (ESI) m/z=751 [M+H]⁺.

Example 59: (S)-19-((2S,4R)-4-Hydroxy-2-((4-(4-methylthiazol-5-yl)benzyl)carbamoyl)pyrrolidine-1-carbonyl)-20,20-dimethyl-17-oxo-3,6,9,12,15-pentaoxa-18-azahenicosanoic acid (Linker 59)
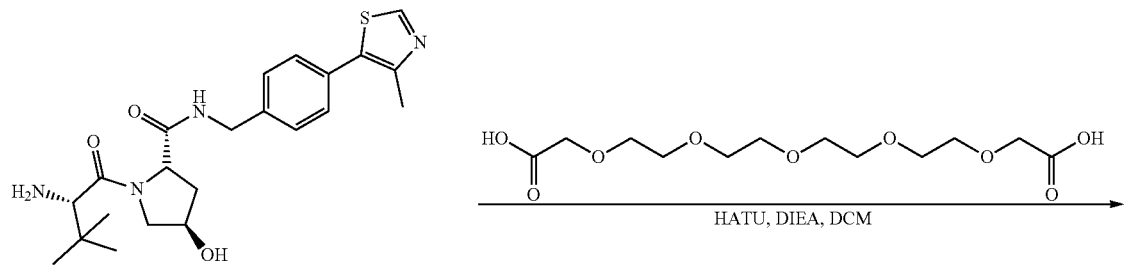
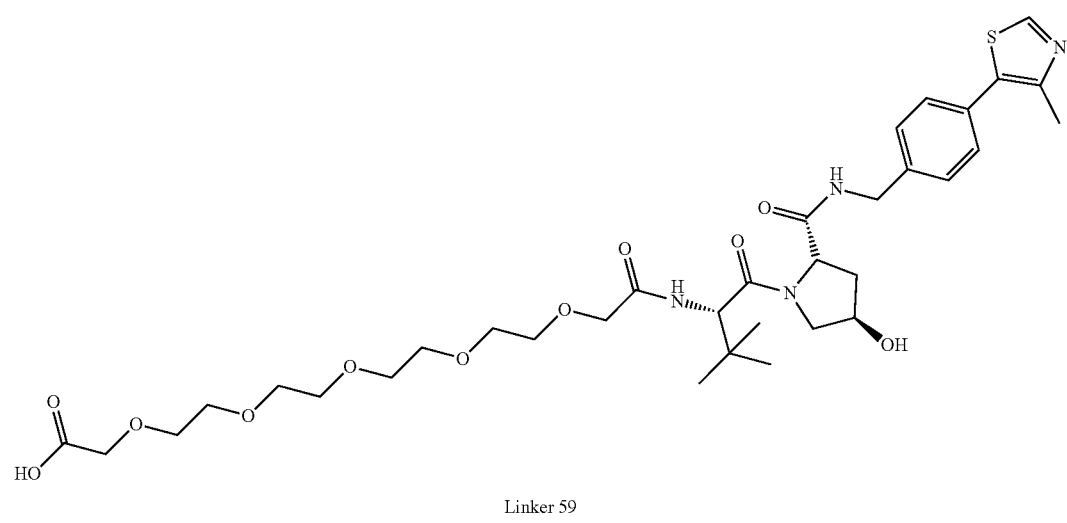
Linker 59
Linker 59 was synthesized following the same procedure as Linker 45 as described as Example 45. (1.3 g, yield: 39%). $^1$H NMR (400 MHz, DMSO-d$_6$) δ 8.98 (s, 1H), 8.69 (t, J=6.0 Hz, 1H), 7.45 (d, J=9.6 Hz, 1H), 7.43-7.37 (m, 4H), 4.57-4.55 (m, 1H), 4.47-4.34 (m, 3H), 4.27-4.22 (m, 1H), 3.97 (s, 2H), 3.68-3.65 (m, 2H), 3.61-3.48 (m, 18H), 2.45 (s, 3H), 2.09-2.04 (m, 1H), 1.92-1.86 (m, 1H), 0.94 (s, 9H). MS (ESI) m/z=723 [M+H]$^+$.
Example 60. Synthesis of TRKi-1
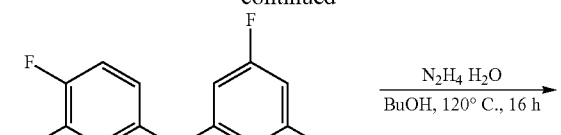
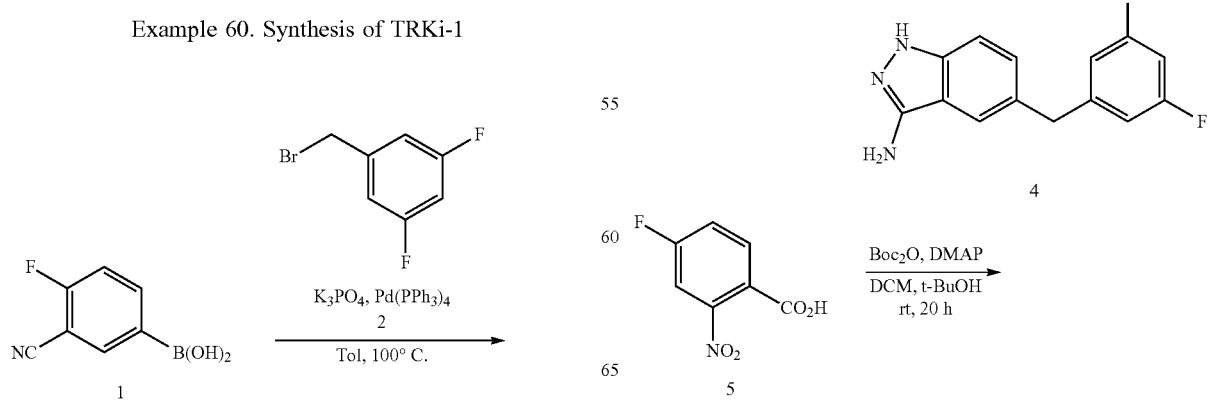

-continued
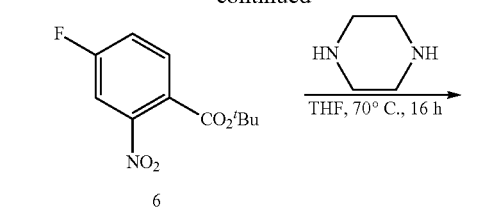
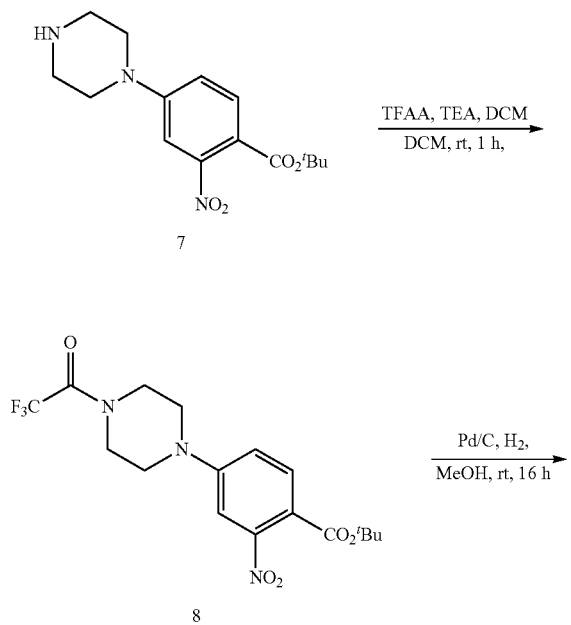
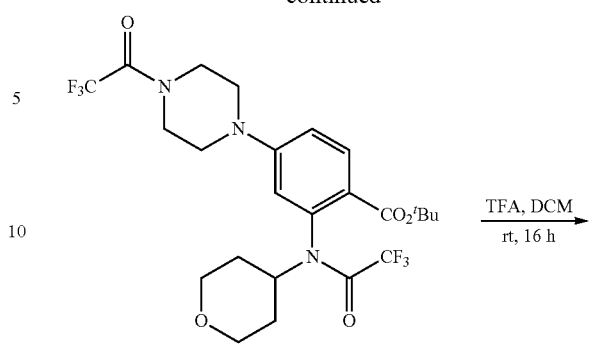
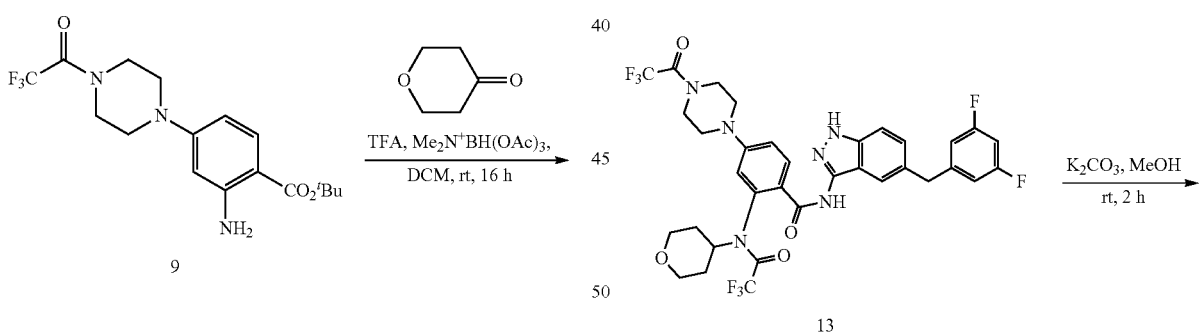
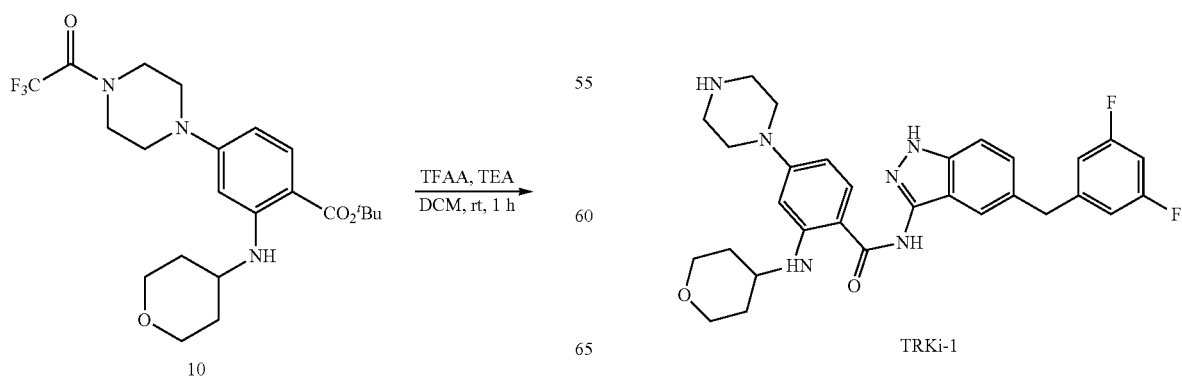

Step 1

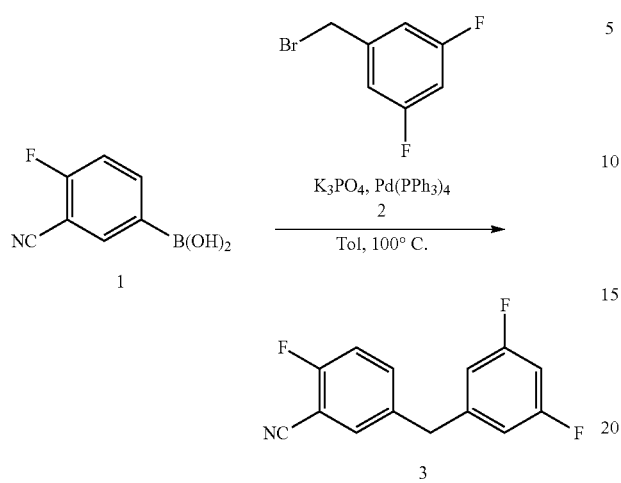

To a solution of 3-cyano-4-fluorophenylboronic acid (1) (3.3 g, 20 mmol) in toluene (30 mL) were added potassium phosphate (8.5 g, 40 mmol) and tetrakis(triphenylphosphine)palladium (462 mg, 0.4 mmol), followed by 3,5-difluorobenzyl bromide (2) (4.2 g, 10 mmol). The reaction mixture was heated at 100° C. for 2 hours. After the reaction was completed, the resulting black mixture was diluted with ether (200 mL), washed with saturated aqueous ammonium chloride (2×50 mL) and brine (3×50 mL). The organic layer was dried over sodium sulphate, evaporated and purified by silica gel flash chromatography (n-hexane/ethyl acetate 95:5) to yield 5-(3,5-difluorobenzyl)-2-fluorobenzonitrile (3) (2.9 g, yield 59%) as a white solid. $^1$H NMR (400 MHz, DMSO-$d_6$) 7.90 (dd, J=6.0 Hz, 2.0 Hz, 1H), 7.73-7.69 (m, 1H), 7.46 (t, J=8.8 Hz, 1H), 7.09-7.04 (m, 3H), 4.01 (s, 2H). MS (ESI) m/z=248.2[M+H]$^+$.

Step 2

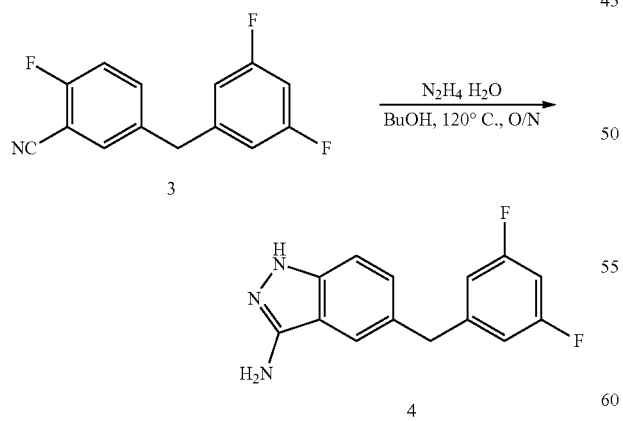

A mixture of 5-(3,5-difluoro-benzyl)-2-fluoro-benzonitrile (3) (2.9 g, 11.74 mmol) and hydrazine hydrate (1.76 mL, 35.22 mmol) in n-butanol (200 mL) was heated at 120° C. overnight. The reaction mixture was diluted with water and ethyl acetate. The organic phase was washed twice with brine, dried and concentrated. The resulting residue was purified by silica gel chromatography (DCM/MeOH=95:5) to afford 5-(3,5-difluorobenzyl)-1H-indazol-3-amine (4) (2.7 g, yield 89%) as a white solid. $^1$H NMR (400 MHz, DMSO-$d_6$) δ 11.32 (s, 1H), 7.52 (s, 1H), 7.18-7.11 (m, 2H), 7.04 (t, J=9.6 Hz, 1H), 6.95-6.93 (m, 2H), 5.26 (s, 2H), 4.00 (s, 2H). MS (ESI) m/z=260.0 [M+H]$^+$.

Step 3

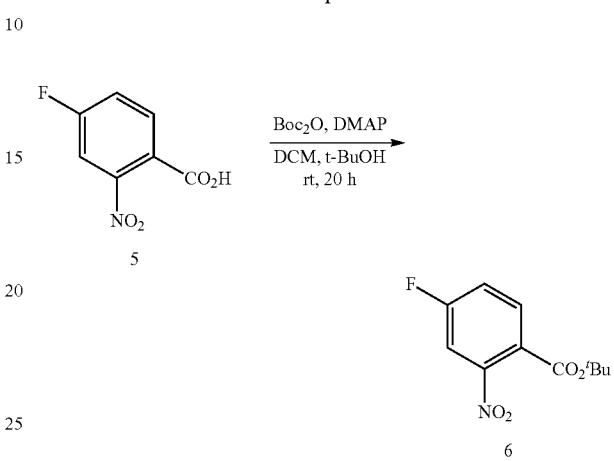

A solution of 4-fluoro-2-nitro-benzoic acid (5) (10 g, 54 mmol), di-tert-butyl-dicarbonate (23.6 g, 108 mmol) and 4-dimethylaminopyridine (1.98 g, 16.2 mmol) in tert-butanol (100 mL) and dichloromethane (100 mL) was stirred at room temperature overnight. The reaction mixture was then diluted with ethyl acetate (500 mL), washed with 1N hydrochloric acid (500 mL), water (500 mL) and brine (500 mL). The organic phase was dried over sodium sulfate, concentrated and purified by silica gel chromatography column (DCM/MeOH=20/1) to afford tert-butyl 4-fluoro-2-nitrobenzoate (6) as a yellow solid (10.7 g, yield 82%). $^1$H NMR (400 MHz, DMSO-$d_6$): δ 8.04 (dd, J=8.4 Hz, 2.8 Hz, 1H), 7.94 (dd, J=8.8 Hz, 1.6 Hz, 1H), 7.71 (ddd, J=8.4 Hz, 2.4 Hz, 1H), 1.50 (s, 9H). MS (ESI) m/z=242.2 [M+H]$^+$.

Step 4

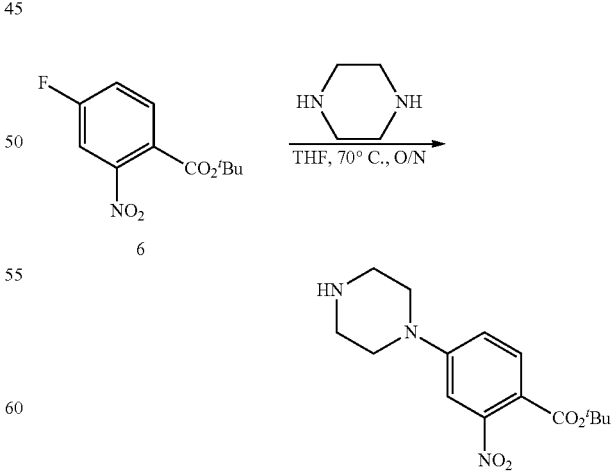

To a solution of piperazine (13.7 g, 159.75 mmol) in tetrahydrofuran (150 mL) was added tert-butyl 4-fluoro-2- nitrobenzoate (6) (7.7 g, 31.95 mmol). The mixture was stirred at 70° C. for 16 h, before being poured into water and extracted with ethyl acetate (100 mL×3). The combined organic layers were washed with water, brine, dried over sodium sulfate and concentrated to give crude tert-butyl 2-nitro-4-(piperazin-1-yl)benzoate (7) (9.7 g, yield 99%) as yellow oil, which was used in the next step without further purification. MS (ESI) m/z=308.1 [M+H]+.

Step 5

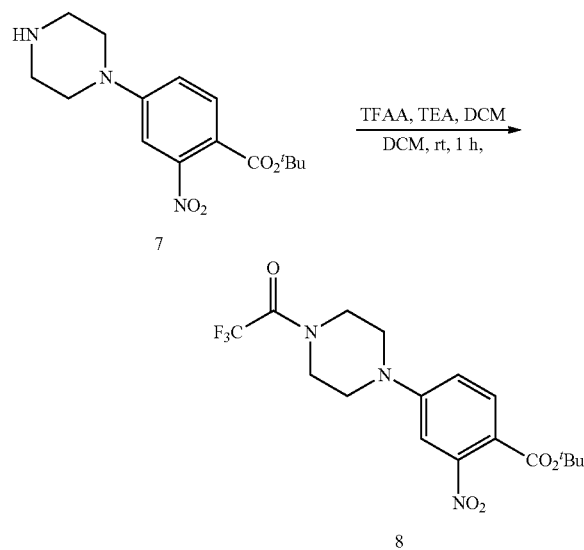

To a solution of 2-nitro-4-piperazin-1-yl-benzoic acid tert-butyl ester (7) (13.5 g, 44.12 mmol) in dichloromethane (200 mL) were added triethylamine (13.4 g, 132.35 mmol) and trifluoroacetic anhydride (18.5 g, 88.24 mmol) at 0° C. The mixture was stirred at room temperature for 1 h. The solvent was evaporated to give a residue, which was purified by flash chromatography silica gel column (petroleum ether/ethyl acetate=1/1) to give tert-butyl 2-nitro-4-(4-(2,2,2-trifluoroacetyl)piperazin-1-yl)benzoate (8) (16.5 g, yield: 93%) as a yellow solid. $^1$H NMR (400 MHz, DMSO-d$_6$): δ 7.72 (d, J=9.2 Hz, 1H), 7.32 (d, J=2.8 Hz, 1H), 7.16 (dd, J=2.8, 9.2 Hz, 1H), 3.72-3.70 (m, 4H), 3.56-3.52 (m, 4H), 1.45 (s, 9H). MS (ESI) m/z=404.3 [M+H]+.

Step 6

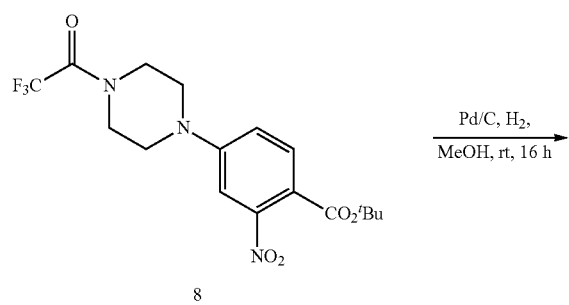

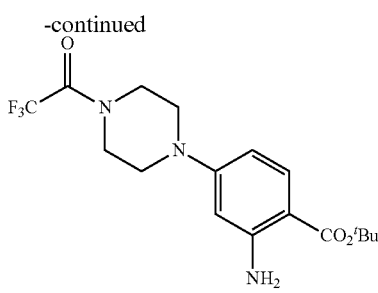

tert-butyl 2-nitro-4-(4-(2,2,2-trifluoroacetyl)piperazin-1-yl)benzoate (8) (8.0 g, 19.85 mmol) was dissolved in methanol (150 ml), before Pd/C (1.0 g) was added. The resulting mixture was stirred under hydrogen at atmosphere pressure for 16 h. The solution was filtered over a pad of celite and washed with methanol several times. The filtrate was concentrated under vacuum to afford tert-butyl 2-amino-4-(4-(2,2,2-trifluoroacetyl)piperazin-1-yl)benzoate (9) (6.3 g, yield 85%) as a yellow solid. $^1$H NMR (400 MHz, DMSO-d$_6$): δ 7.51 (d, J=9.2 Hz, 1H), 6.47 (br, 2H), 6.20 (dd, J=2.8, 9.2 Hz, 1H), 6.13 (d, J=2.8 Hz, 1H), 3.71-3.69 (m, 4H), 3.31-3.29 (m, 4H), 1.50 (s, 9H). MS (ESI) m/z=374.0 [M+H]+.

Step 7

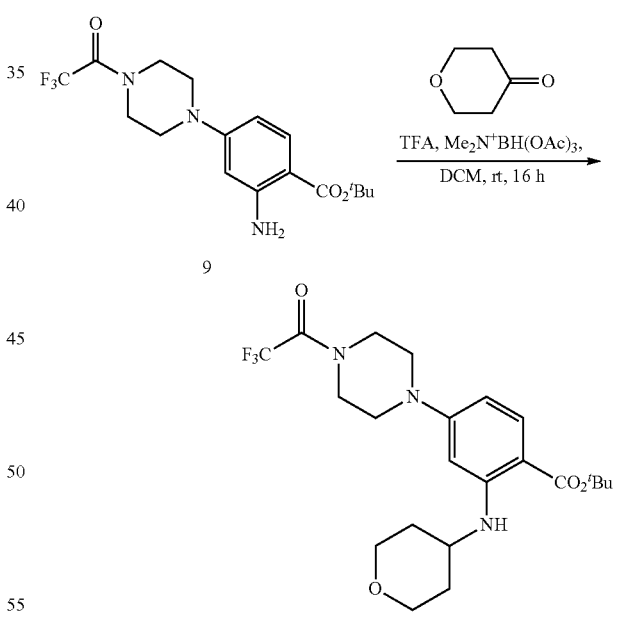

To a solution of tert-butyl 2-amino-4-(4-(2,2,2-trifluoroacetyl)piperazin-1-yl)benzoate (6.3 g, 16.89 mmol) in dichloromethane (9) (150 mL) were added tetrahydropyran-4-one (2.1 g, 21.11 mmol), trifluoroacetic acid (3.5 mL) and tetramethylammonium triacetoxyborohydride (6.7 g, 25.34 mmol). The mixture was stirred at room temperature for 16 h, before being washed sequentially with 0.5 N hydrochloric acid, 0.5 N sodium hydroxide, and a saturated solution of sodium bicarbonate. The organic layer was dried over sodium sulfate and concentrated to afford tert-butyl 2-((tetrahydro-2H-pyran-4-yl)amino)-4-(4-(2,2,2-trifluoroacetyl)piperazin-1-yl)benzoate (10) (3.5 g, yield 50%) as a pale yellow solid. $^1$HNMR (400 MHz, DMSO-$d_6$): δ 7.72 (d, J=7.6 Hz, 1H), 7.60 (d, J=9.2 Hz, 1H), 6.20 (dd, J=2.4, 9.2 Hz, 1H), 6.09 (d, J=2.0 Hz, 1H), 3.86-3.82 (m, 2H), 3.70-3.69 (m, 5H), 3.52-3.46 (m, 2H), 3.39-3.38 (m, 4H), 1.97-1.94 (m, 2H), 1.50 (s, 9H), 1.43-1.34 (m, 2H). MS (ESI) m/z=458.1 [M+H]$^+$.

Step 8

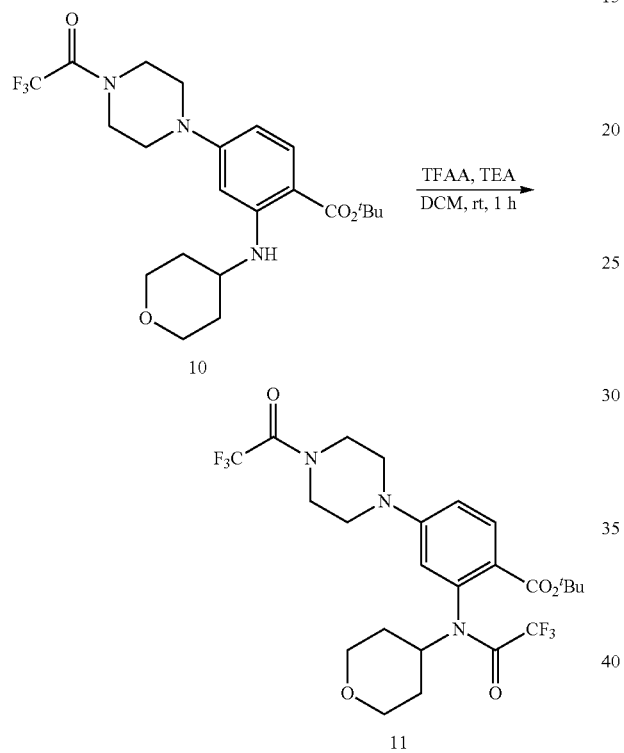

Step 9

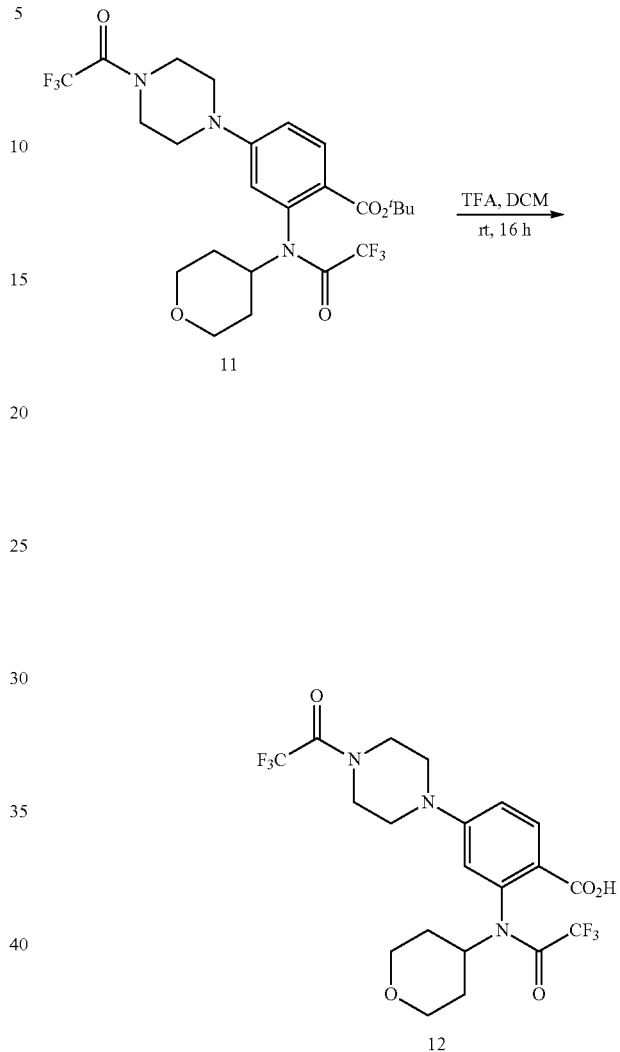

tert-butyl 2-((tetrahydro-2H-pyran-4-yl)amino)-4-(4-(2,2,2-trifluoroacetyl)piperazin-1-yl)benzoate (10) (3.8 g, 8.32 mmol) was dissolved in dichloromethane (100 ml) and cooled to 0° C. To the resulting solution was added triethylamine (1.3 g, 12.47 mmol) followed by a slow addition of trifluoroacetic anhydride (2.3 g, 10.81 mmol). After being stirred for 1 h, the reaction was quenched with water and diluted with DCM. The organic layer was washed with a saturated solution of aqueous sodium bicarbonate and brine. The organic layer was dried over sodium sulfate, concentrated and purified by silica gel chromatography column (petroleum ether/ethyl acetate=2/1) to give tert-butyl 2-(2,2,2-trifluoro-N-(tetrahydro-2H-pyran-4-yl)acetamido)-4-(4-(2,2,2-trifluoroacetyl)piperazin-1-yl)benzoate (11) (4.2 g, yield 91%) as a yellow solid. $^1$HNMR (400 MHz, DMSO-$d_6$): δ 7.85 (d, J=8.8 Hz, 1H), 7.08 (dd, J=2.4, 8.8 Hz, 1H), 6.85 (d, J=2.4 Hz, 1H), 4.52-4.44 (m, 1H), 3.89-3.77 (m, 2H), 3.75-3.72 (m, 4H), 3.55-3.49 (m, 4H), 3.45-3.32 (m, 2H), 1.99-1.97 (m, 1H), 1.65-1.53 (m, 1H), 1.48-1.45 (m, 1H), 1.45 (s, 9H), 1.08-0.96 (m, 1H). MS (ESI) m/z 554.1 [M+H]$^+$.

To a solution of tert-butyl 2-(2,2,2-trifluoro-N-(tetrahydro-2H-pyran-4-yl)acetamido)-4-(4-(2,2,2-trifluoroacetyl)piperazin-1-yl)benzoate (11) (4.2 g, 7.59 mmol) in DCM (50 ml) was added TFA (50 mL) at 0° C. After the reaction was stirred at room temperature for 16 h, the solvent was removed under vacuum. The residue was washed with diethyl ether to give 2-(2,2,2-trifluoro-N-(tetrahydro-2H-pyran-4-yl)acetamido)-4-(4-(2,2,2-trifluoroacetyl)piperazin-1-yl)benzoic acid (12) (3.5 g, yield 93%) as a white solid. $^1$H NMR (400 MHz, DMSO-$d_6$) δ 12.70 (s, 1H), 7.90 (d, J=8.8 Hz, 1H), 7.06 (dd, J=2.8, 9.2 Hz, 1H), 6.86 (d, J=2.0 Hz, 1H), 4.51-4.43 (m, 1H), 3.88-3.79 (m, 2H), 3.75-3.72 (m, 4H), 3.55-3.41 (m, 6H), 1.97-1.94 (m, 1H), 1.64-1.49 (m, 2H), 1.12-1.02 (m, 1H). MS (ESI) m/z 498.0 [M+H]$^+$.

Step 10

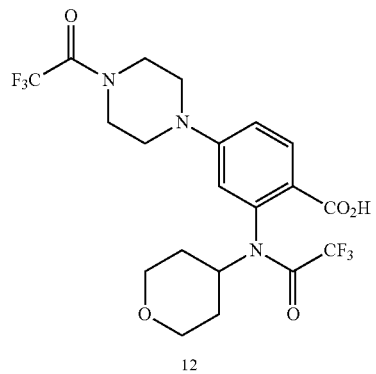

1. (COCl)₂, DCM, 0° C., 1.5 h
2. Et₃N, 4, DCM, rt, 16 h

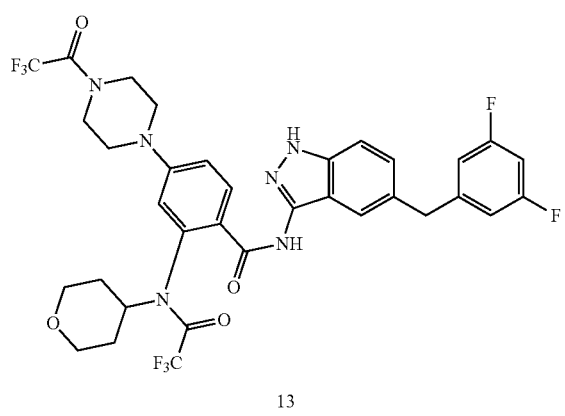

13

To a suspension of 2-(2,2,2-trifluoro-N-(tetrahydro-2H-pyran-4-yl)acetamido)-4-(4-(2,2,2-trifluoroacetyl)piperazin-1-yl)benzoic acid (12) (3.5 g, 7.04 mmol) in dry dichloromethane (150 mL) were added catalytic amount of N,N-dimethylformamide, oxalyl chloride (2.7 g, 21.13 mmol) at 0° C. The mixture was stirred for about 1.5 h before being concentrated. The residue was azeotroped with dry dichloromethane twice. The acyl chloride was dissolved in dry dichloromethane (50 mL). The resulting suspension was added slowly to a solution of 5-(3,5-difluoro-benzyl)-1H-indazol-3-ylamine (1.86 g, 7.04 mol) and triethylamine (2.2 g, 21.13 mmol) in dry tetrahydrofuran (100 mL) at −20° C. The mixture was stirred at room temperature for 16 h before being concentrated. The resulting residue was purified by silica gel chromatography column (petroleum ether/ethyl acetate=1/1) to give N-(5-(3,5-difluorobenzyl)-1H-indazol-3-yl)-2-(2,2,2-trifluoro-N-(tetrahydro-2H-pyran-4-yl)acetamido)-4-(4-(2,2,2-trifluoroacetyl) piperazin-1-yl)benzamide (13) (4.0 g, yield 77%) as a yellow solid. ¹H NMR (400 MHz, DMSO-d₆) δ 12.70 (s, 1H), 10.58 (s, 1H), 7.86 (d, J=8.4 Hz, 1H), 7.43-7.41 (m, 2H), 7.27 (d, J=9.2 Hz, 1H), 7.18-7.11 (m, 1H), 7.04-6.99 (m, 1H), 6.95-6.93 (m, 3H), 4.47-4.41 (m, 1H), 4.01 (s, 2H), 3.80-3.72 (m, 4H), 3.22-3.17 (m, 4H), 3.51-3.47 (m, 4H), 1.93-1.90 (m, 1H), 1.67-1.64 (m, 1H), 1.60-1.50 (m, 1H), 1.37-1.26 (m, 1H). MS (ESI) m/z 739.0 [M+H]⁺.

Step 11

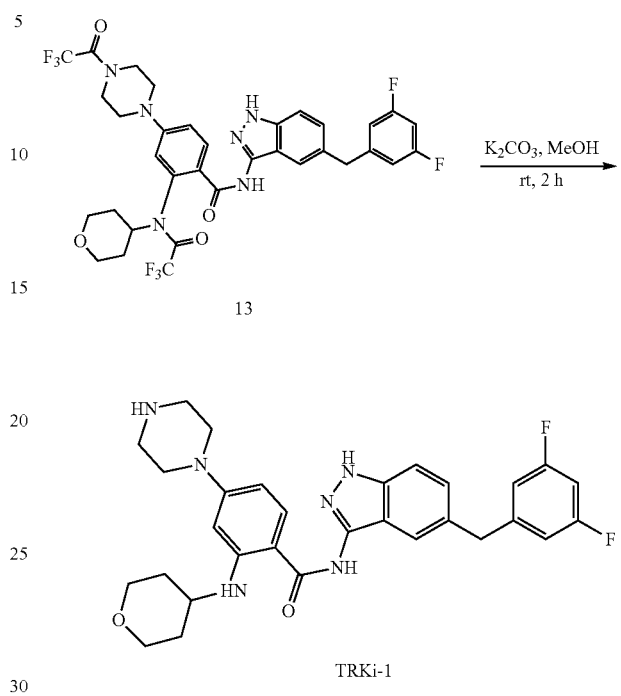

K₂CO₃, MeOH
rt, 2 h

TRKi-1

To a solution of N-(5-(3,5-difluorobenzyl)-1H-indazol-3-yl)-2-(2,2,2-trifluoro-N-(tetrahydro-2H-pyran-4-yl)acetamido)-4-(4-(2,2,2-trifluoroacetyl)piperazin-1-yl)benzamide (13) (4.0 g, 5.42 mmol) in methanol (100 mL) was added potassium carbonate (3.7 g, 27.1 mmol). The mixture was stirred at room temperature for 2 h before being filtered. The filtrate was evaporated and the residue was purified by silica gel chromatography (DCM/MeOH=10:1) to give N-(5-(3,5-difluorobenzyl)-1H-indazol-3-yl)-4-(piperazin-1-yl)-2-((tetrahydro-2H-pyran-4-yl)amino) benzamide (TRKi-1) (1.9 g, yield: 64%) as a blue solid. ¹H NMR (400 MHz, DMSO-d₆) δ 12.68 (s, 1H), 10.12 (s, 1H), 8.31 (d, J=6.8 Hz, 1H), 7.81 (d, J=8.4 Hz, 1H), 7.50 (s, 1H), 7.41 (d, J=8.4 Hz, 1H), 7.26 (d, J=8.4 Hz, 1H), 7.03-6.98 (m, 3H), 6.23 (d, J=8.4 Hz, 1H), 6.13 (s, 1H), 4.04 (s, 2H), 3.83-3.80 (m, 2H), 3.68-3.62 (m, 1H), 3.52-3.47 (m, 2H), 3.22-3.17 (m, 4H), 2.87-2.80 (m, 4H), 1.95-1.92 (m, 2H), 1.36-1.34 (m, 2H). MS (ESI) m/z 547.2 [M+H]⁺.

Example 61. Synthesis of TRKI-2

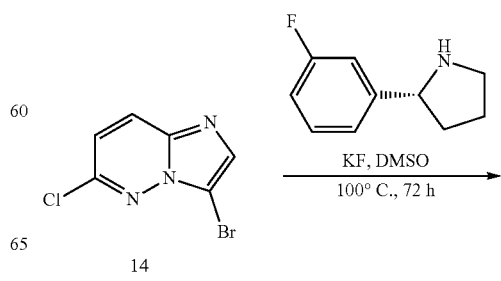

KF, DMSO
100° C., 72 h

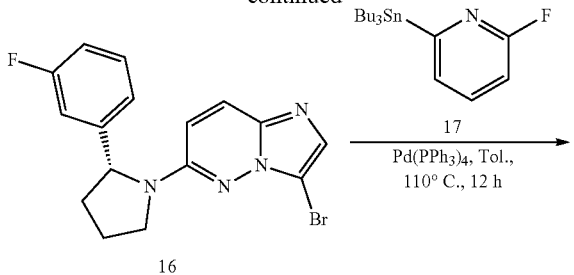

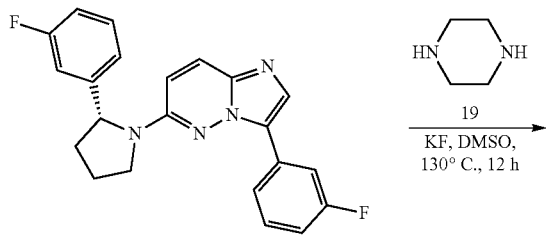

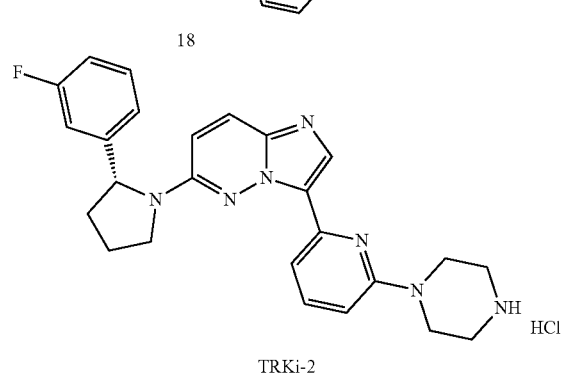

TRKi-2

Step 1

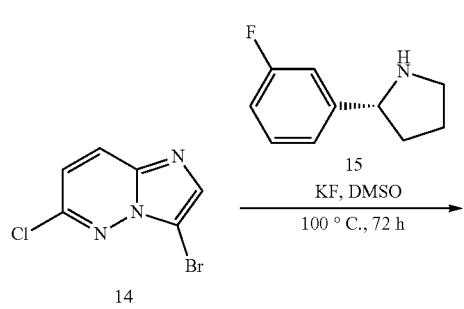

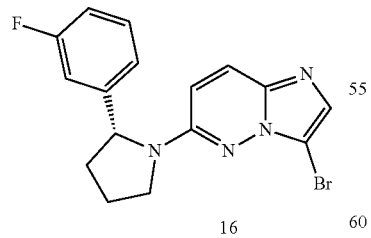

To a solution of 3-bromo-6-chloroimidazo[1,2-b]pyridazine (14) (4.6 g, 20.0 mmol) in dimethylsuphoxide (40 mL) were added potassium fluoride (20 g, 362 mmol) and (R)-2-(3-fluorophenyl)pyrrolidine (15) (3 g, 18.2 mmol). The resulting mixture was stirred at 100° C. for 12 h. The mixture was diluted with ethyl acetate, washed with water. The organic layer was concentrated and the residue was purified by column chromatography (ethyl acetate) to give (R)-3-bromo-6-(2-(3-fluorophenyl)pyrrolidin-1-yl)imidazo[1,2-b]pyridazine (16) (1.8 g, yield 28%) as a yellow solid. MS (ESI) m/z 360.9 [M+H]$^+$.

Step 2

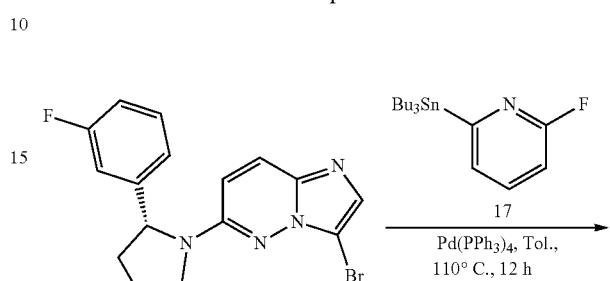

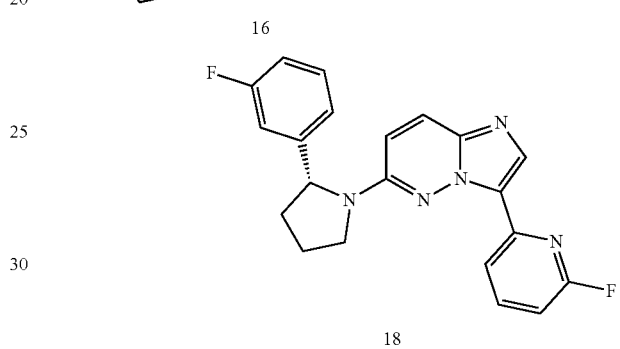

To a solution of (R)-3-bromo-6-(2-(3-fluorophenyl)pyrrolidin-1-yl)imidazo[1,2-b]pyridazine (16) (2.17 g, 6.03 mmol) in toluene (50 mL) were added 2-fluoro-6-(tributylstannyl)pyridine (17) (3.5 g, 9.04 mmol) and tetrakis(triphenylphosphine)palladium (566 mg, 0.49 mmol). The resulting mixture was stirred at 110° C. for 12 h under nitrogen atmosphere before being poured into ethyl acetate and sat. potassium fluoride. After stirring at room temperature for 2 h, the mixture was extracted with ethyl acetate. The combined organic layers were concentrated and purified by column chromatography (hexanes:ethyl acetate=1:1 to 100% ethyl acetate) to give (R)-6-(2-(3-fluorophenyl)pyrrolidin-1-yl)-3-(6-fluoropyridin-2-yl)imidazo[1,2-b]pyridazine (18) (2.2 g, yield 97%) as yellow oil. MS (ESI) m/z 378.0 [M+H]$^+$.

Step 3

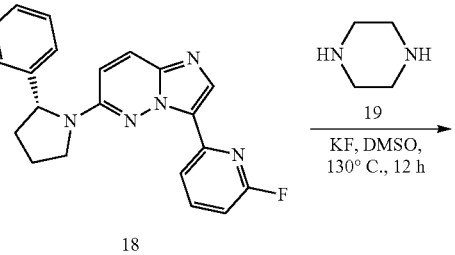

-continued

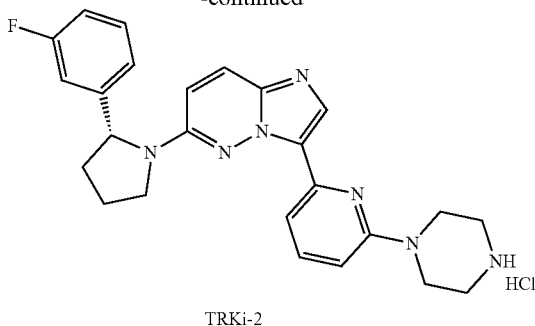

TRKi-2

To a solution of (R)-6-(2-(3-fluorophenyl)pyrrolidin-1-yl)-3-(6-fluoropyridin-2-yl)imidazo[1,2-b]pyridazine (18, 1.4 g, 3.7 mmol) in dimethylsuphoxide (40 mL) was added piperazine (6.4 g, 74 mmol), followed by potassium fluoride (8.6 g, 148 mmol). The resulting mixture was stirred at 130° C. for 12 h before being poured into water and extracted with ethyl acetate. The combined organic layers were washed with water, concentrated and purified by column chromatography (dichloromethane:methanol=10:1 to 5:1) to give desired product as a yellow oil, which was dissolved in hydrochloric acid/ethyl acetate (4 M), and stirred for 1 h, concentrated to give (R)-6-(2-(3-fluorophenyl)pyrrolidin-1-yl)-3-(6-(piperazin-1-yl)pyridin-2-yl)imidazo[1,2-b]pyridazine hydrochloride (TRKi-2) (1.168 g, yield 66%) as a yellow solid. $^1$H NMR (400 MHz, DMSO-$d_6$): δ 9.62 (s, 2H), 8.63 (s, 1H), 8.21 (s, 1H), 7.62-7.19 (m, 6H), 7.06-7.01 (m, 2H), 5.26-5.25 (m, 1H), 4.07-4.02 (m, 1H), 3.86-3.85 (m, 4H), 3.74-3.72 (m, 1H), 3.16-3.15 (m, 4H), 2.08-2.07 (m, 2H), 1.92-1.91 (m, 2H). MS (ESI) m/z=444.2 [M+H]$^+$.

Example 62. Synthesis of TRKi-3

To a solution of (R)-6-(2-(3-fluorophenyl)pyrrolidin-1-yl)-3-(6-(piperazin-1-yl)pyridine-2-yl)imidazo[1,2-b]pyridazine (TRKi-2) (1 g, 2.25 mmol) in DMF (40 ml) were added K$_2$CO$_3$ (621 mg, 4.50 mmol) and tert-butyl 2-bromoacetate (510 mg, 2.60 mmol). The resulting mixture was stirred at room temperature for 3 hours. After the amine was totally consumed, the reaction was poured into water (300 mL) and extracted with ethyl acetate (3×50 mL). The combined organic layers were washed with saturated brine (100 mL) and dried over anhydrous sodium sulfate. After filtration, the filtrate was concentrated under reduced pressure. The resulting residue was purified by silica gel column chromatography to give tert-butyl (R)-2-(4-(6-(6-(2-(3-fluoro phenyl)pyrrolidin-1-yl) imidazo[1,2-b]pyridazin-3-yl)pyridin-2-yl)piperazin-1-yl)acetate (1.05 g, yield: 84%) as a light yellow solid. MS (ESI) m/z: 558.7 [M+H]$^+$.

To a solution of tert-butyl (R)-2-(4-(6-(6-(2-(3-fluorophenyl)pyrrolidin-1-yl)imidazo[1,2-b]pyridazin-3-yl)pyridin-2-yl)piperazin-1-yl)acetate (1 g, 1.79 mmol) in dichloromethane (20 ml) was added trifluoroacetic acid (20 mL). The resulting mixture was stirred at room temperature for 3 hours. After the starting material was totally consumed, the reaction was evaporated under reduced pressure. The resulting residue was purified by reverse-phase chromatography to give (R)-2-(4-(6-(6-(2-(3-fluorophenyl)pyrrolidin-1-yl) imidazo[1,2-b]pyridazin-3-yl)pyridin-2-yl)piperazin-1-yl) acetic acid (TRKi-3) (860 mg, yield: 79% over two steps) as a light yellow solid. MS (ESI) m/z: 502.6 [M+H]$^+$.

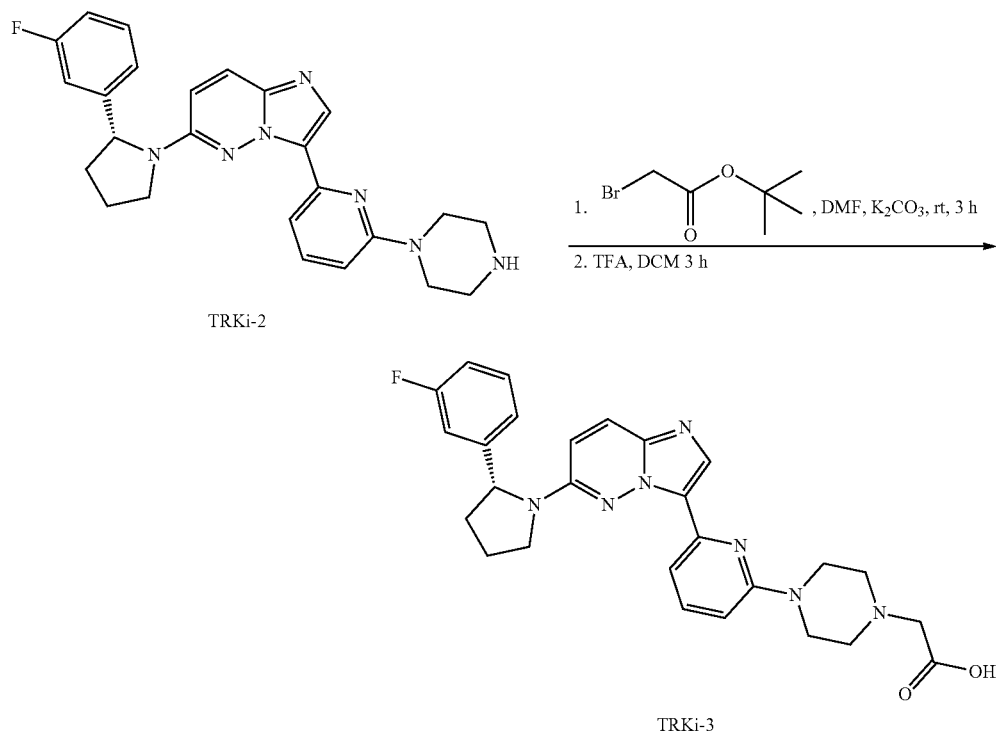

Example 63. Synthesis of TRKi-4

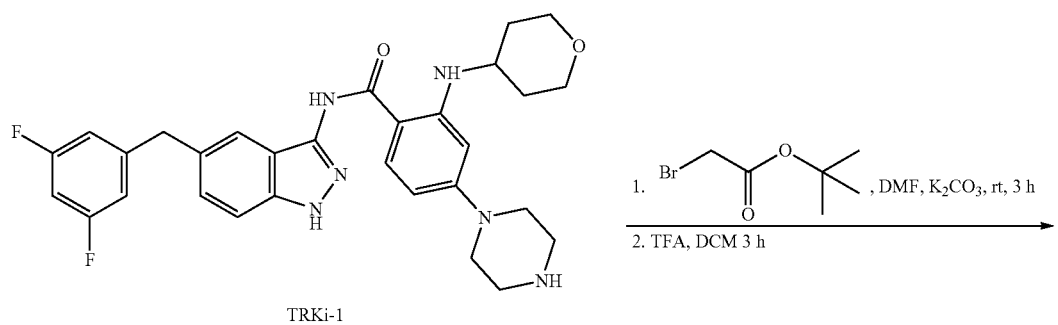

To a solution of N-(5-(3,5-difluorobenzyl)-1H-indazol-3-yl)-4-(piperazin-1-yl)-2-((tetrahydro-2H-pyran-4-yl)amino)benzamide (TRKi-1) (1.0 g, 1.83 mmol) in DMF (40 ml) were added $K_2CO_3$ (505 mg, 3.66 mmol) and tert-butyl 2-bromoacetate (357 mg, 1.83 mmol). The resulting mixture was stirred at room temperature for 3 hours. After the amine was totally consumed, the reaction was poured into water (300 mL) and extracted with ethyl acetate (3×50 mL). The combined organic layers were washed with saturated brine (100 mL) and dried over anhydrous sodium sulfate. After filtration, the filtrate was concentrated under reduced pressure. The resulting residue was purified by silica gel column chromatography to give tert-butyl 2-(4-(4-((5-(3,5-difluorobenzyl)-1H-indazol-3-yl) carbamoyl)-3-((tetrahydro-2H-pyran-4-yl)amino)phenyl)piperazin-1-yl)acetate (1.03 g, yield: 85%) as a light yellow solid. MS (ESI) m/z: 661.3 $[M+H]^+$.

To a solution of tert-butyl 2-(4-(4-((5-(3,5-difluorobenzyl)-1H-indazol-3-yl)carbamoyl)-3-((tetrahydro-2H-pyran-4-yl)amino)phenyl)piperazin-1-yl)acetate (1 g, 1.51 mmol) in dichloromethane (20 ml) was added trifluoroacetic acid (20 mL). The resulting mixture was stirred at room temperature for 3 hours. After the starting material was totally consumed, the reaction was evaporated under reduced pressure. The resulting residue was purified by reverse-phase chromatography to give 2-(4-(4-((5-(3,5-difluorobenzyl)-1H-indazol-3-yl) carbamoyl)-3-((tetrahydro-2H-pyran-4-yl)amino)phenyl)piperazin-1-yl)acetic acid (TRKi-4) (790 mg, yield 73%) as a light yellow solid. MS (ESI) m/z: 605.3 $[M+H]^+$.

Example 64: N-(5-(3,5-Difluorobenzyl)-1H-indazol-3-yl)-4-(4-(4-((2-(2,6-dioxopiperidin-3-yl)-1,3-dioxoisoindolin-4-yl)amino)butanoyl)piperazin-1-yl)-2-((tetrahydro-2H-pyran-4-yl)amino)benzamide (CPD-053)

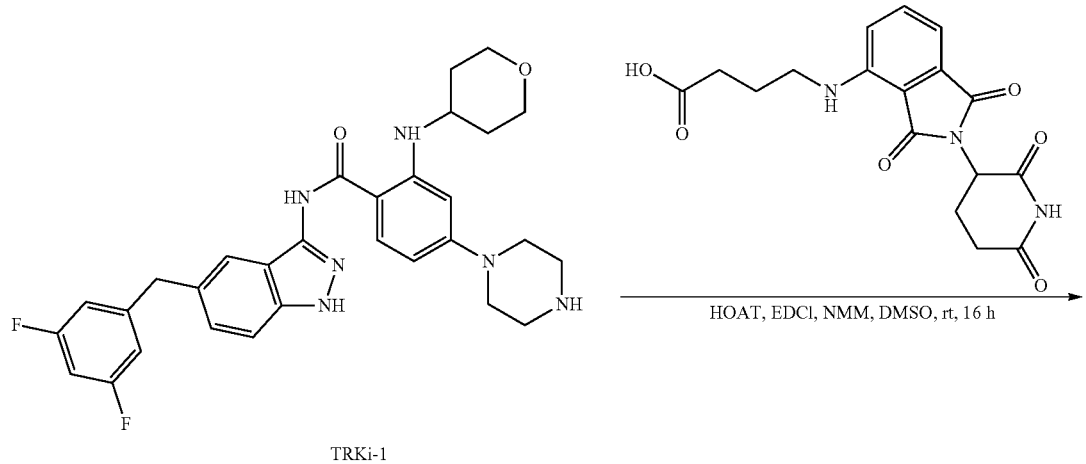

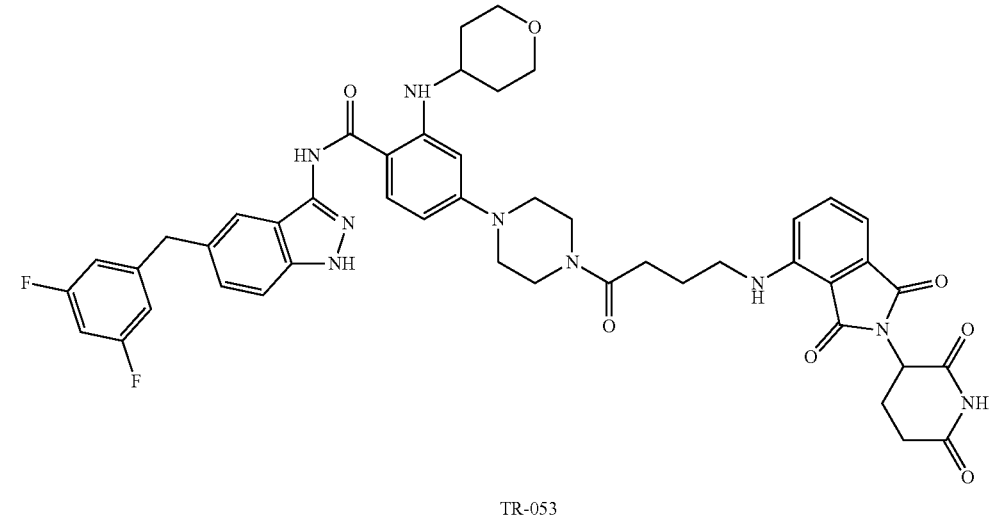

To a solution of 4-((2-(2,6-dioxopiperidin-3-yl)-1,3-dioxoisoindolin-4-yl)amino)butanoic acid (657 mg, 1.83 mmol) in DMSO (30 mL) were added NMM (926 mg, 9.15 mmol), HOAT (373 mg, 2.74 mmol), EDCI (526 mg, 2.74 mmol) and N-(5-(3,5-difluorobenzyl)-1H-indazol-3-yl)-4-(piperazin-1-yl)-2-((tetrahydro-2H-pyran-4-yl)amino)benzamide (TRKi-1) (1 g, 1.83 mmol) sequentially. The resulting solution was stirred at room temperature for 16 hours, before the reaction was poured into water (200 mL) and extracted with ethyl acetate (3×50 mL). The combined organic layers were washed with saturated brine (100 mL) and dried over anhydrous sodium sulfate. After filtration, the filtrate was concentrated under reduced pressure. The resulting residue was purified by reverse-phase chromatography to give N-(5-(3,5-difluoro benzyl)-1H-indazol-3-yl)-4-(4-(4-((2-(2,6-dioxopiperidin-3-yl)-1,3-dioxoisoindolin-4-yl)amino)butanoyl)piperazin-1-yl)-2-((tetrahydro-2H-pyran-4-yl)amino)benzamide (CPD-053) (1.2 g, yield 74%) as a light yellow solid. $^1$H NMR (400 MHz, DMSO-$d_6$) δ 11.09 (s, 1H), 10.28 (s, 1H), 7.89 (d, J=9.0 Hz, 1H), 7.59 (dd, J=8.4, 7.2 Hz, 1H), 7.52 (s, 1H), 7.42 (d, J=8.6 Hz, 1H), 7.26 (d, J=9.9 Hz, 1H), 7.19 (d, J=8.6 Hz, 1H), 7.08-6.94 (m, 4H), 6.47-6.28 (m, 2H), 5.06 (dd, J=12.9, 5.3 Hz, 1H), 4.04 (s, 2H), 3.84 (s, 2H), 3.63 (s, 5H), 3.57 (s, 1H), 3.46 (t, J=10.5 Hz, 3H), 3.40-3.24 (m, 6H), 3.17 (s, 1H), 2.87 (d, J=12.0 Hz, 1H), 2.57 (dd, J=19.7, 10.5 Hz, 1H), 2.47 (d, J=6.8 Hz, 2H), 2.08-1.76 (m, 5H), 1.48-1.34 (m, 2H), 1.23 (s, 1H). MS (ESI) m/z: 888.6 [M+H]$^+$.

Example 65: (2S,4R)-1-((S)-2-(6-(4-(6-(6-((R)-2-(3-Fluorophenyl)pyrrolidin-1-yl)imidazo[1,2-b]pyridazin-3-yl)pyridin-2-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide (CPD-001)

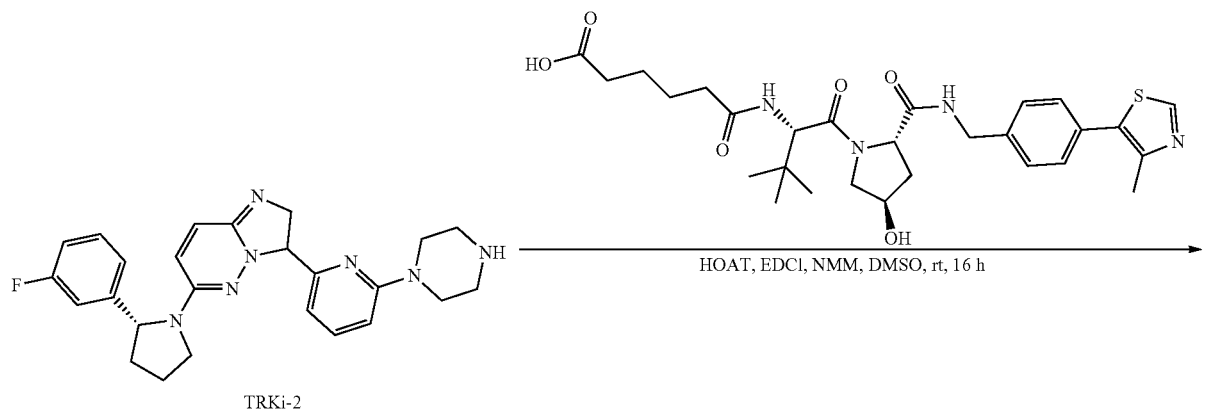

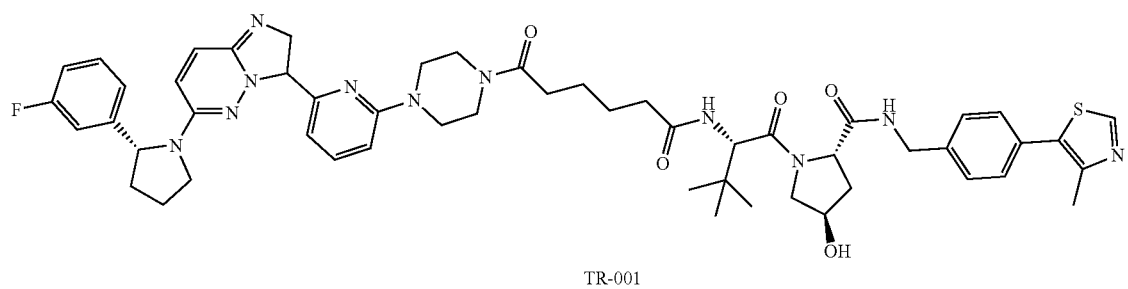

CPD-001 was synthesized following the standard procedure for preparing CPD-053 (12 mg, yield 76%). MS (ESI) m/z: 984.7 [M+H]⁺.

Example 66: (2S,4R)-1-((S)-2-(2-(2-(2-(4-(6-(6-((R)-2-(3-Fluorophenyl)pyrrolidin-1-yl)imidazo[1,2-b]pyridazin-3-yl)pyridin-2-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide (CPD-002)

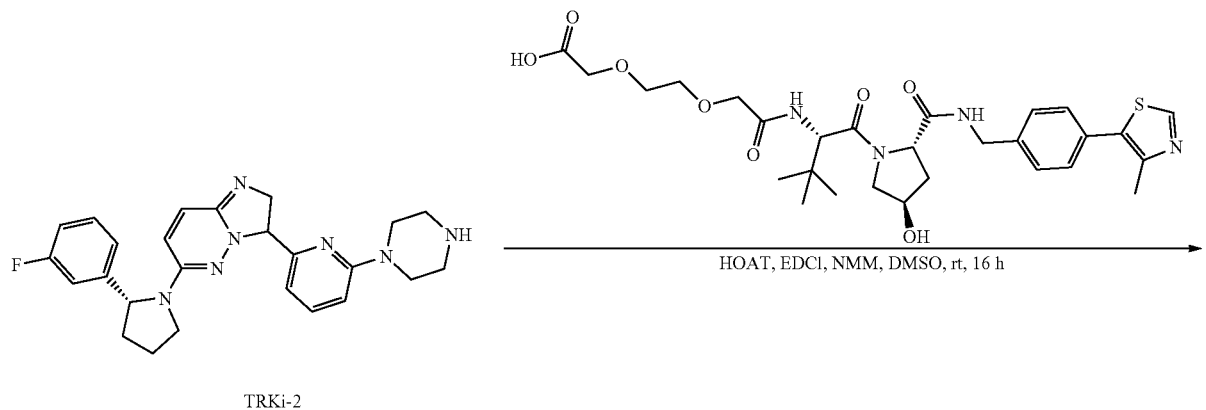

-continued

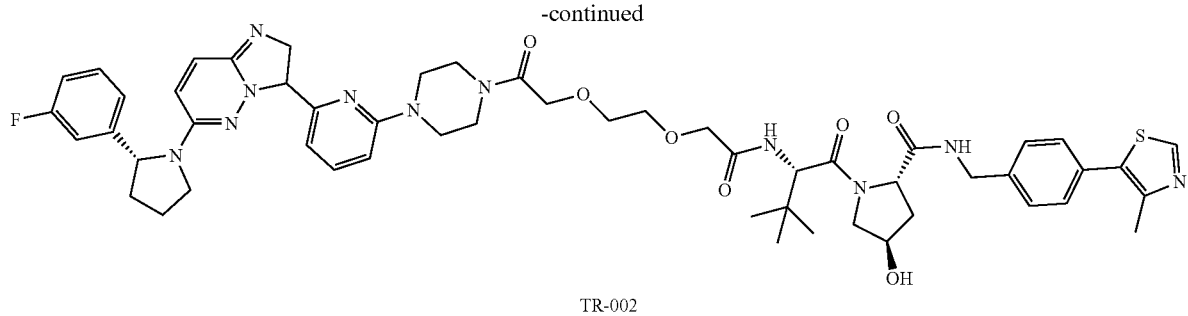
TR-002

CPD-002 was synthesized following the standard procedure for preparing CPD-053 (11 mg, yield 69%). MS (ESI) m/z: 1016.6 [M+H]$^+$.

Example 67: (2S,4R)-1-((S)-2-(tert-butyl)-20-(4-(6-(6-((R)-2-(3-Fluorophenyl)pyrrolidin-1-yl)imidazo[1,2-b]pyridazin-3-yl)pyridin-2-yl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide (CPD-003)

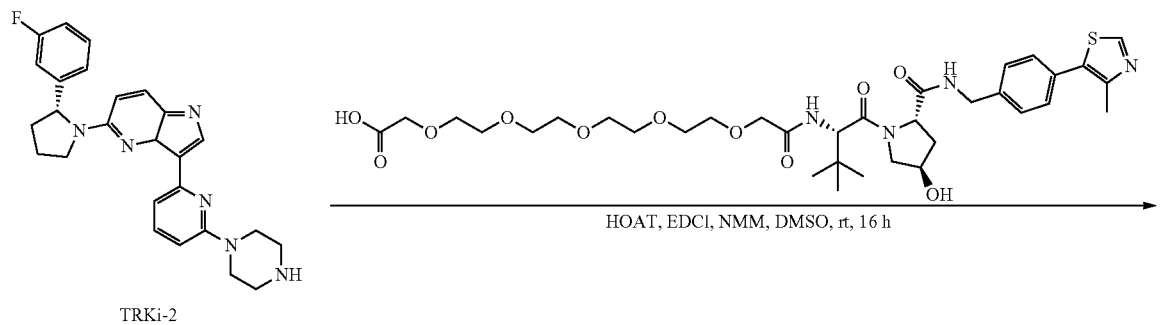
TRKi-2

HOAT, EDCl, NMM, DMSO, rt, 16 h

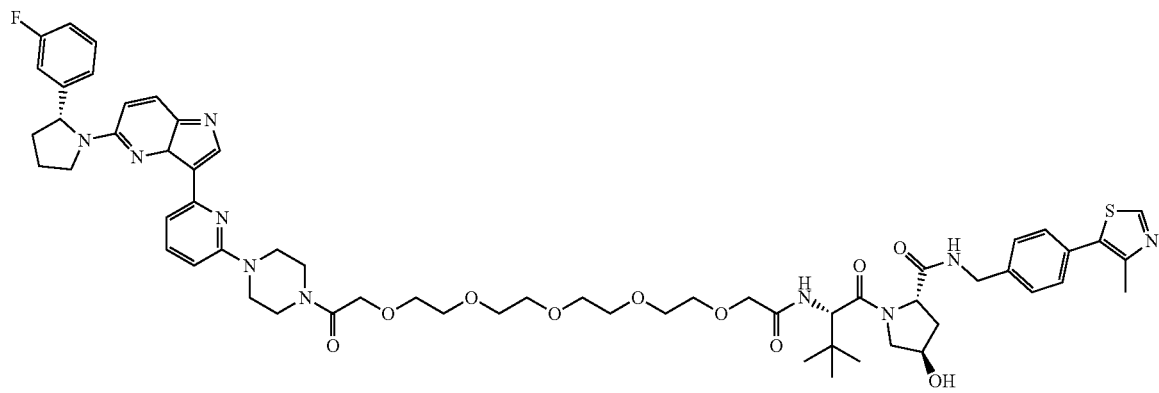
TR-003

CPD-003 was synthesized following the standard procedure for preparing CPD-053 (14 mg, yield 72%). MS (ESI) m/z: 1148.8 [M+H]$^+$.

Example 68: (2S,4R)-1-((S)-2-(7-(4-(6-(6-((R)-2-(3-Fluorophenyl)pyrrolidin-1-yl)imidazo[1,2-b]pyridazin-3-yl)pyridin-2-yl)piperazin-1-yl)-7-oxo-heptanamido)-3,3-dimethylbutanoyl)-4-hydroxy-N-(4-(4-methylthiazol-5-yl)benzyl)pyrrolidine-2-carboxamide (CPD-004)

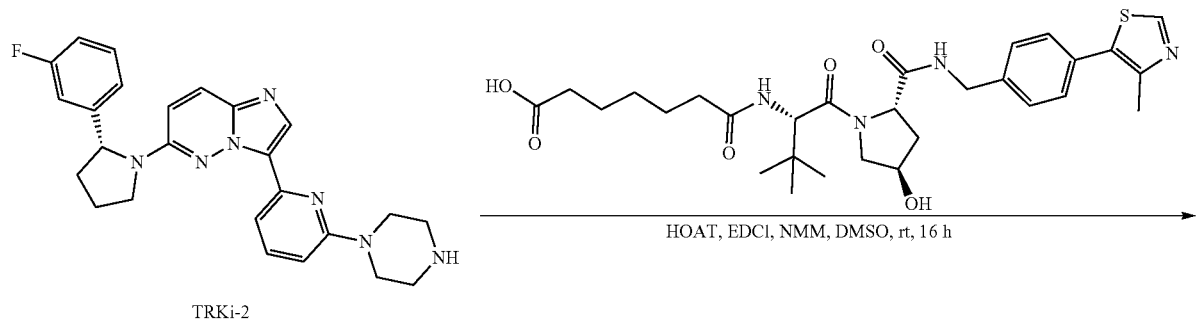

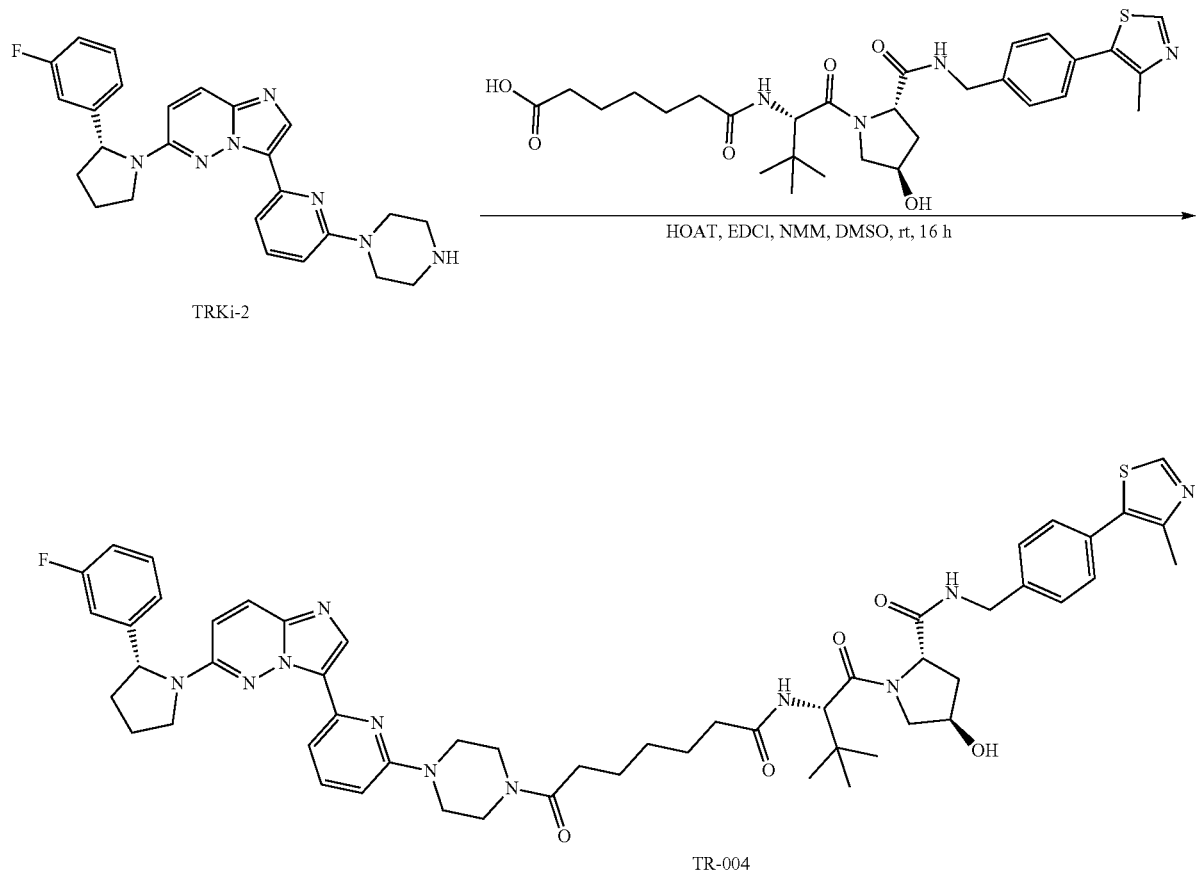

CPD-004 was synthesized following the standard procedure for preparing CPD-053 (11 mg, yield 70%). MS (ESI) m/z: 997.8 [M+H]⁺.

Example 69: (2S,4R)-1-((S)-2-(tert-butyl)-22-(4-(6-(6-((R)-2-(3-Fluorophenyl)pyrrolidin-1-yl)imidazo[1,2-b]pyridazin-3-yl)pyridin-2-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide (CPD-005)

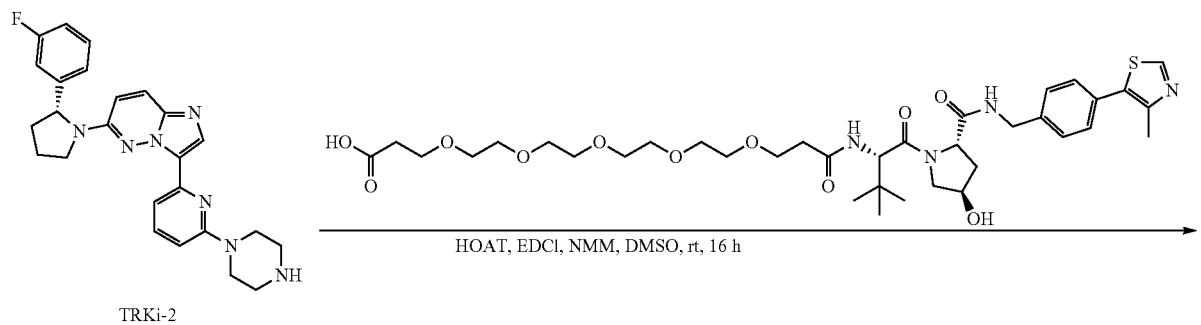

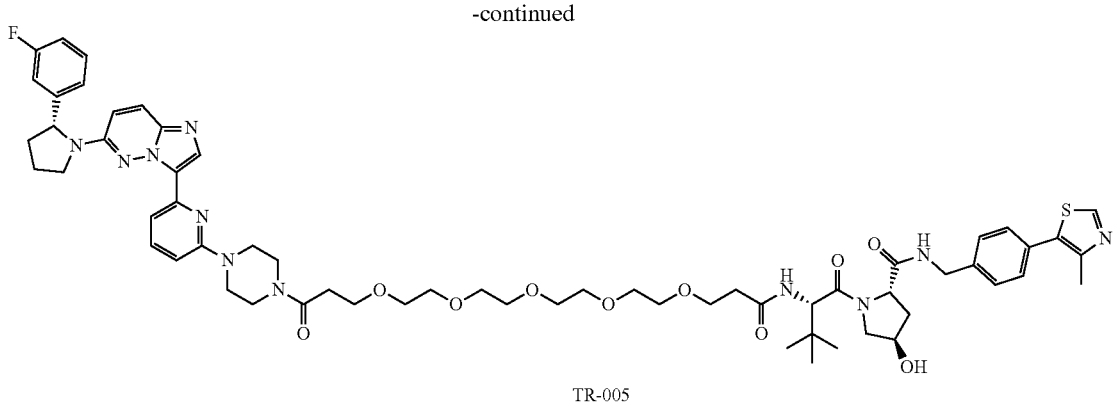
TR-005

CPD-005 was synthesized following the standard procedure for preparing CPD-053 (13 mg, yield 76%). MS (ESI) m/z: 1176.6 [M+H]+.

Example 70: (2S,4R)-1-((S)-2-(4-(4-(6-(6-((R)-2-(3-Fluorophenyl)pyrrolidin-1-yl)imidazo[1,2-b]pyridazin-3-yl)pyridin-2-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide (CPD-006)

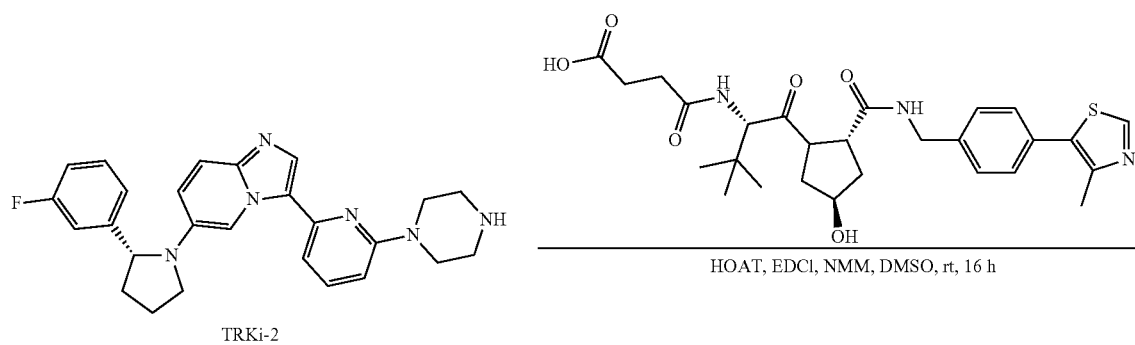

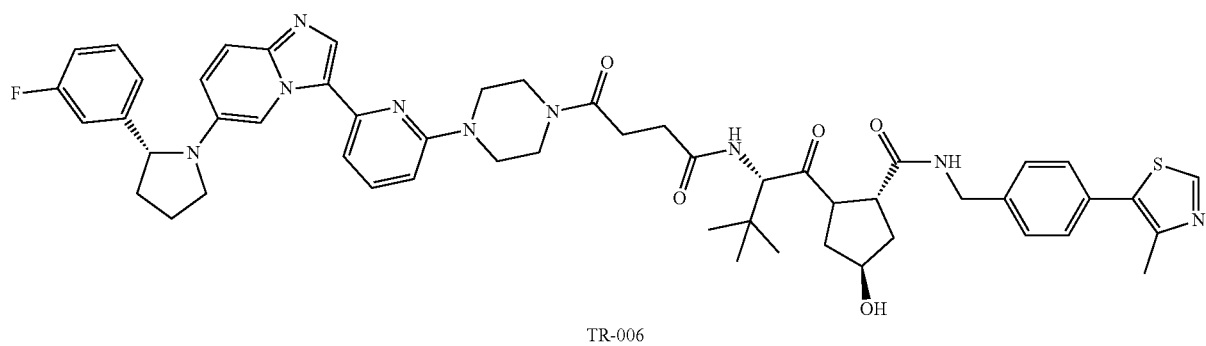
TR-006

CPD-006 was synthesized following the standard procedure for preparing CPD-053 (9 mg, yield 63%). MS (ESI) m/z: 956.4 [M+H]+.

Example 71: (2S,4R)-1-((S)-2-(3-(3-(4-(6-(6-((R)-2-(3-Fluorophenyl)pyrrolidin-1-yl)imidazo[1,2-b]pyridazin-3-yl)pyridin-2-yl)piperazin-1-yl)-3-oxo-propoxy)propanamido)-3,3-dimethylbutanoyl)-4-hydroxy-N-(4-(4-methylthiazol-5-yl)benzyl)pyrrolidine-2-carboxamide (CPD-007)

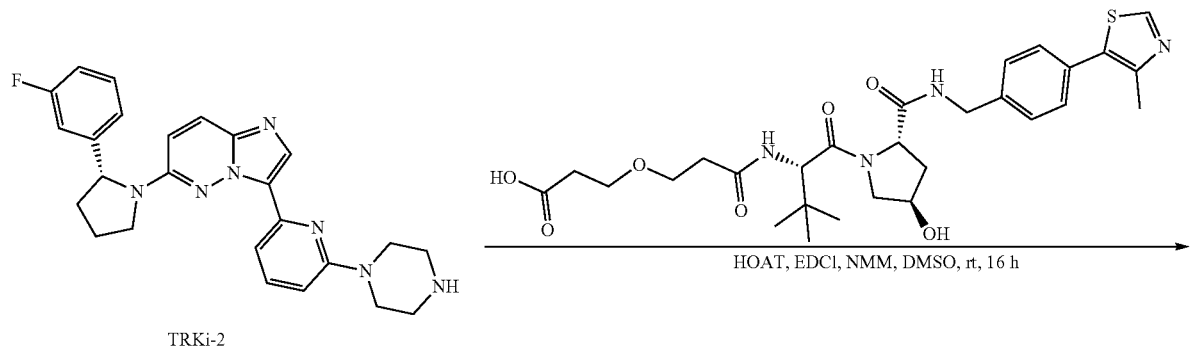

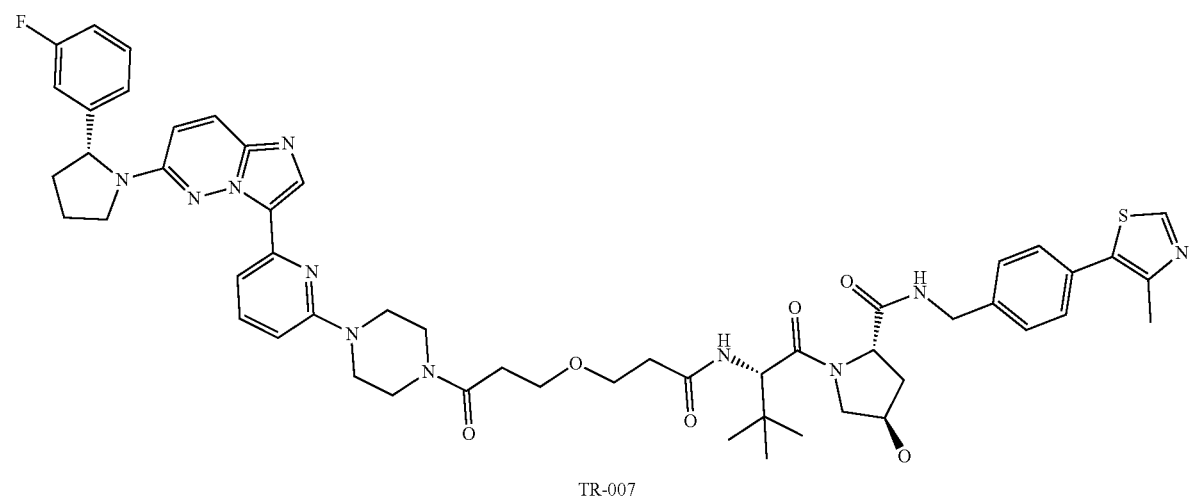

CPD-007 was synthesized following the standard procedure for preparing CPD-053 (12 mg, yield 73%). MS (ESI) m/z: 1000.5 [M+H]$^+$.

Example 72: (2S,4R)-1-((S)-2-(2-(2-(4-(6-(6-((R)-2-(3-Fluorophenyl)pyrrolidin-1-yl)imidazo[1,2-b]pyridazin-3-yl)pyridin-2-yl)piperazin-1-yl)-2-oxo-ethoxy)acetamido)-3,3-dimethylbutanoyl)-4-hydroxy-N-(4-(4-methylthiazol-5-yl)benzyl)pyrrolidine-2-carboxamide (CPD-008)

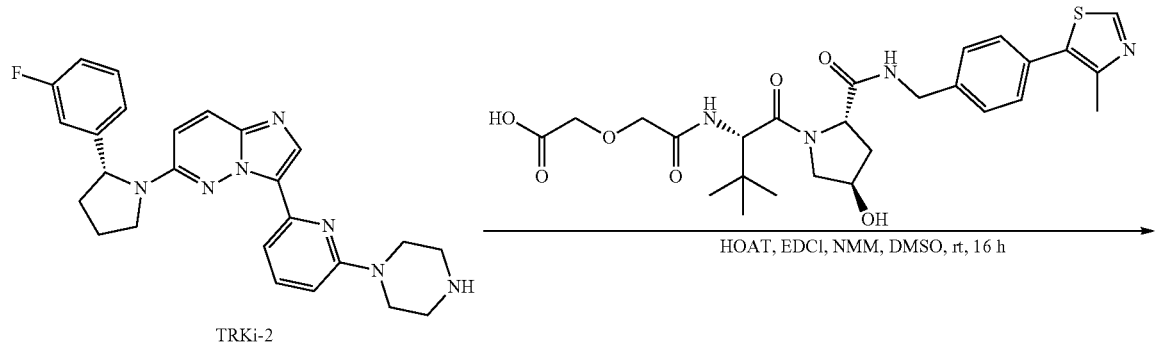

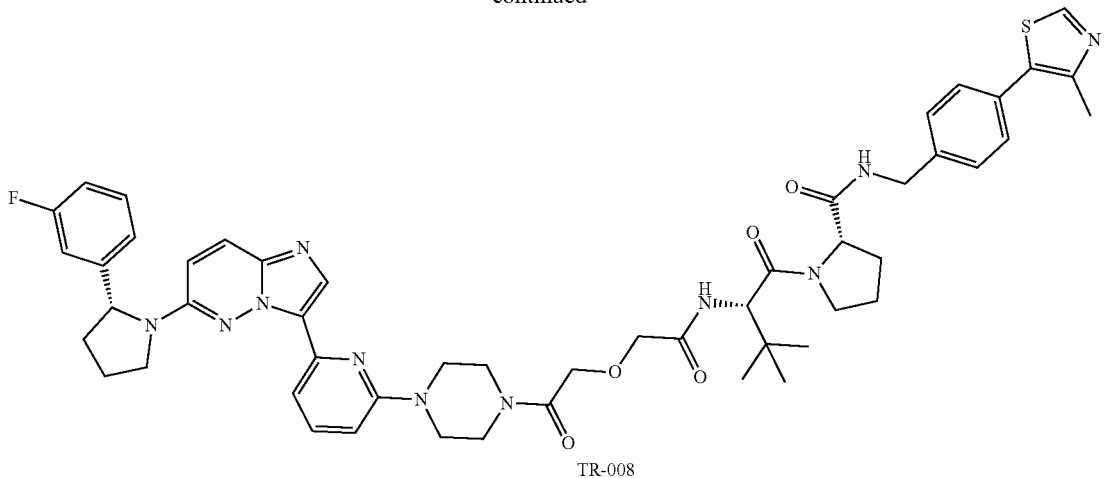

TR-008

CPD-008 was synthesized following the standard procedure for preparing CPD-053 (11 mg, yield 75%). MS (ESI) m/z: 972.4 [M+H]+.

Example 73: 2-(2,6-Dioxopiperidin-3-yl)-4-((7-(4-(6-(6-((R)-2-(3-fluorophenyl)pyrrolidin-1-yl)imidazo[1,2-b]pyridazin-3-yl)pyridin-2-yl)piperazin-1-yl)-7-oxoheptyl)amino)isoindoline-1,3-dione (CPD-009)

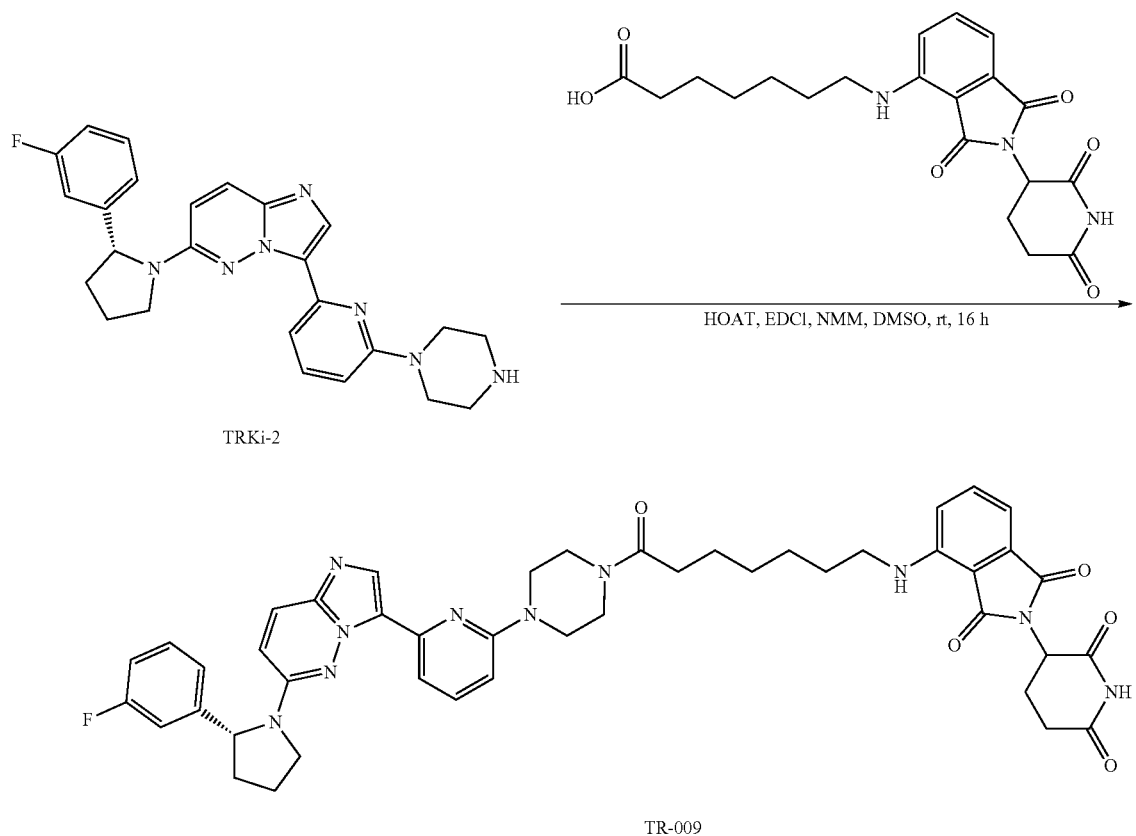

TRKi-2

HOAT, EDCl, NMM, DMSO, rt, 16 h

TR-009

CPD-009 was synthesized following the standard procedure for preparing CPD-053 (13 mg, yield 79%). MS (ESI) m/z: 827.4 [M+H]+.

Example 74: 2-(2,6-Dioxopiperidin-3-yl)-4-((2-(2-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethoxy)ethyl)amino)isoindoline-1,3-dione (CPD-010)

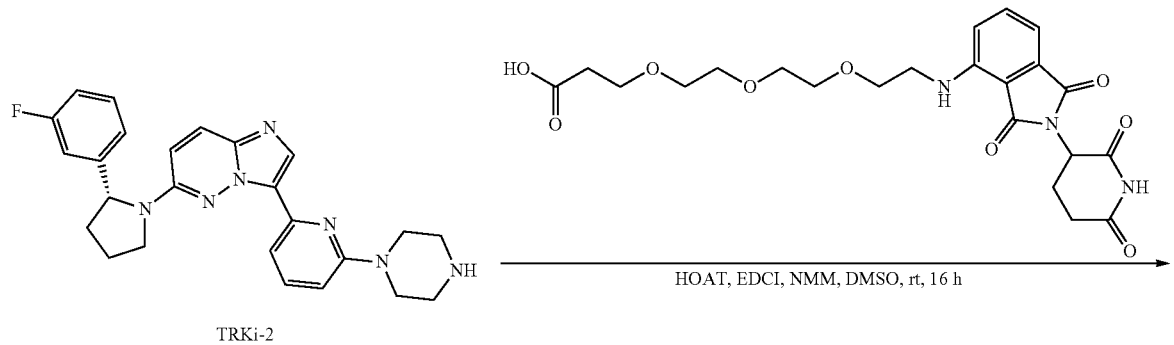
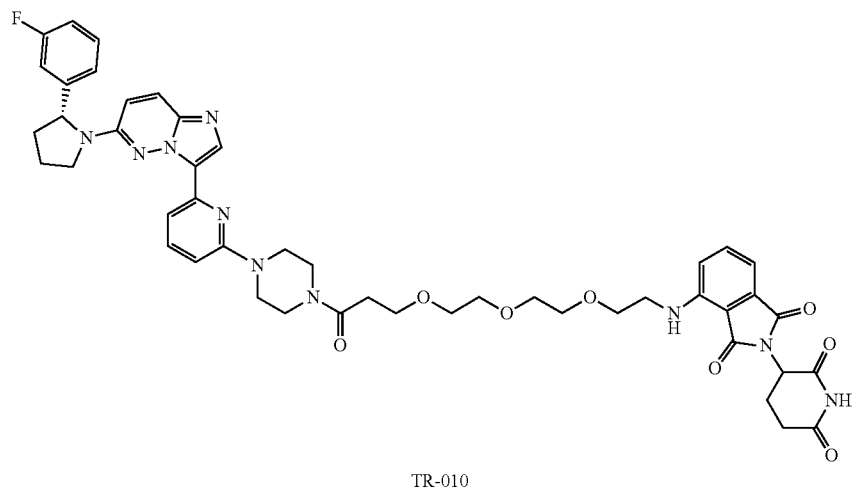

CPD-010 was synthesized following the standard procedure for preparing CPD-053 (11 mg, yield 73%). MS (ESI) m/z: 903.4 [M+H]$^+$.

Example 75: (2S,4R)-1-((S)-2-(tert-butyl)-14-(4-(6-(6-((R)-2-(3-Fluorophenyl)pyrrolidin-1-yl)imidazo[1,2-b]pyridazin-3-yl)pyridin-2-yl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide (CPD-011)

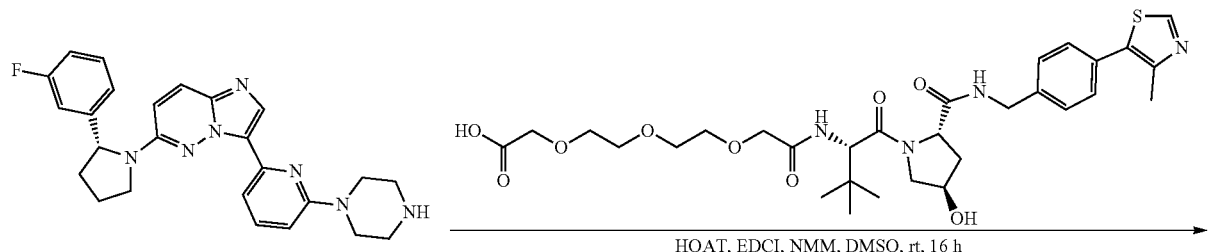

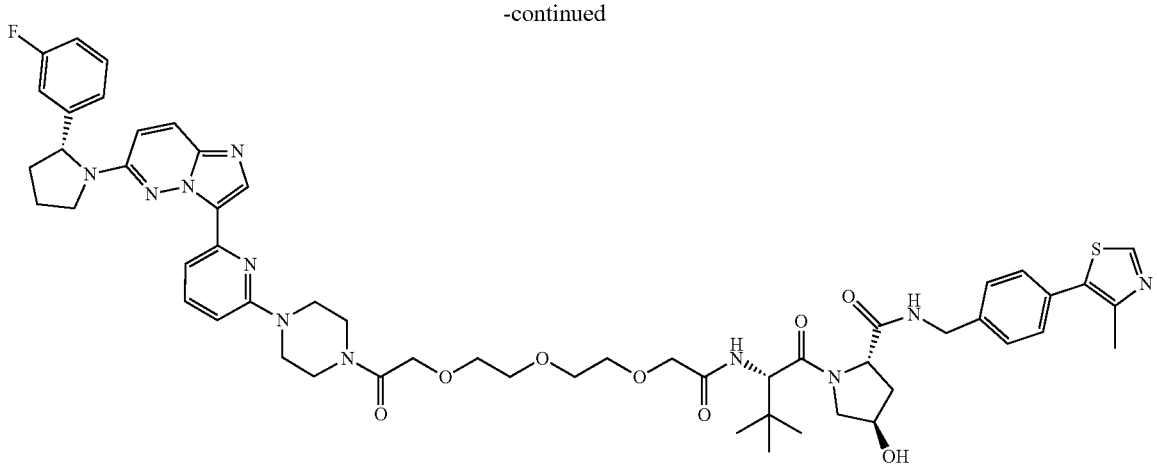
TR-011
CPD-011 was synthesized following the standard procedure for preparing CPD-053 (15 mg, yield 81%). MS (ESI) m/z: 1060.5 [M+H]$^+$.
Example 76: (2S,4R)-1-((S)-2-(5-(4-(6-(6-((R)-2-(3-Fluorophenyl)pyrrolidin-1-yl)imidazo[1,2-b]pyridazin-3-yl)pyridin-2-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide (CPD-012)
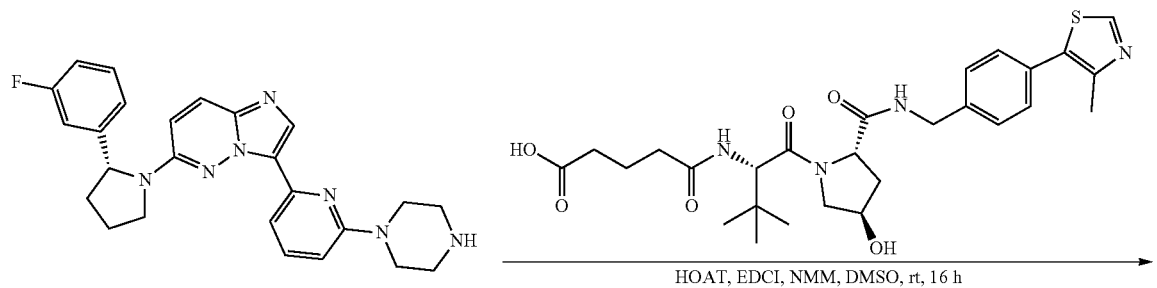
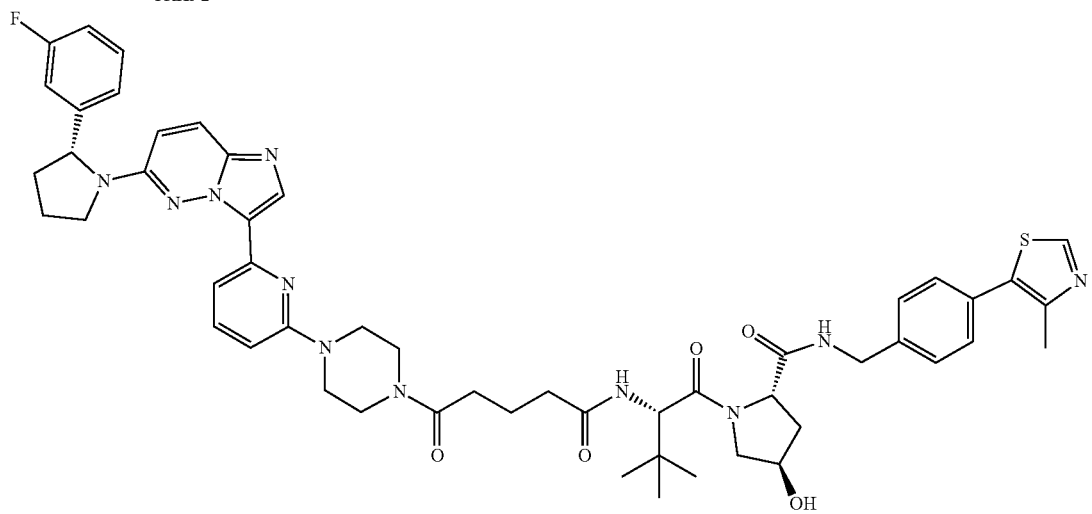
TR-012

CPD-012 was synthesized following the standard procedure for preparing CPD-053 (11 mg, yield 72%). MS (ESI) m/z: 970.4 [M+H]+.

Example 77: 2-(2,6-Dioxopiperidin-3-yl)-4-((4-(4-(6-(6-((R)-2-(3-fluorophenyl)pyrrolidin-1-yl)imidazo[1,2-b]pyridazin-3-yl)pyridin-2-yl)piperazin-1-yl)-4-oxobutyl)amino)isoindoline-1,3-dione (CPD-013)

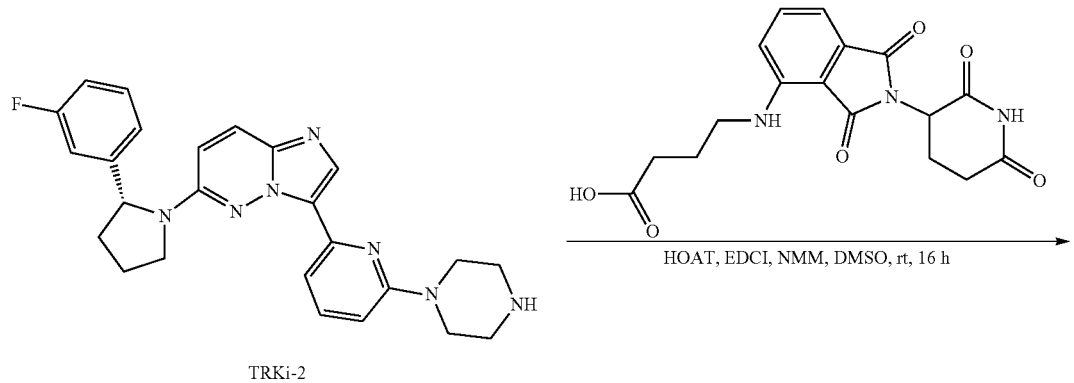

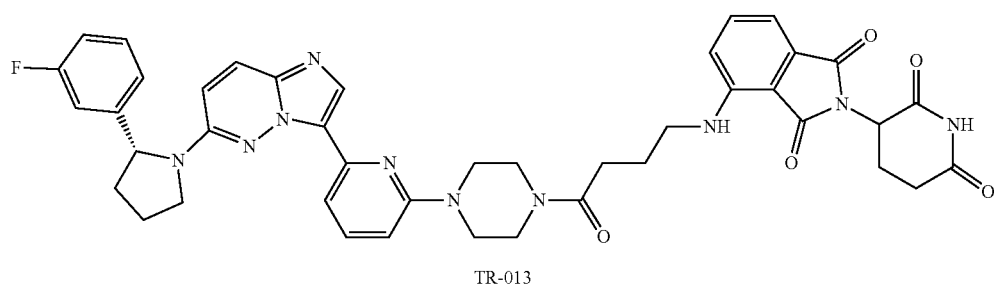

CPD-013 was synthesized following the standard procedure for preparing CPD-053 (8 mg, yield 69%). MS (ESI) m/z: 785.3 [M+H]+.

Example 78: 2-(2,6-Dioxopiperidin-3-yl)-4-((5-(4-(6-(6-((R)-2-(3-fluorophenyl)pyrrolidin-1-yl)imidazo[1,2-b]pyridazin-3-yl)pyridin-2-yl)piperazin-1-yl)-5-oxopentyl)amino)isoindoline-1,3-dione (CPD-014)

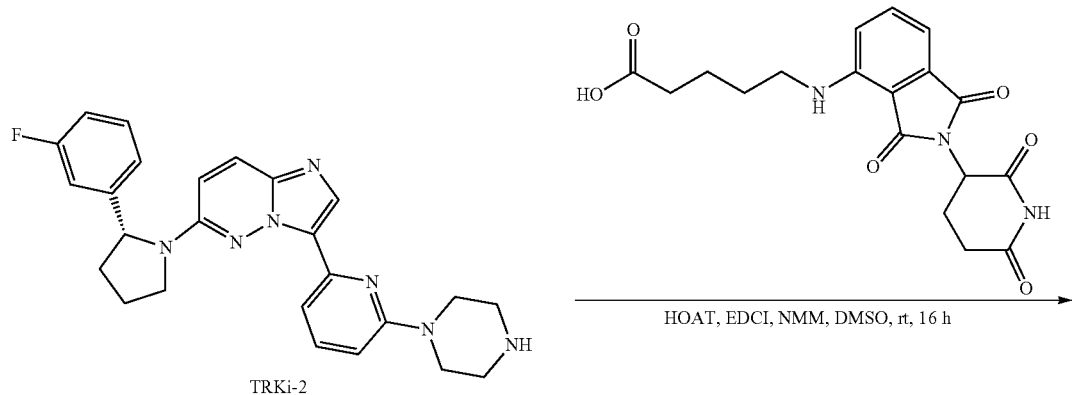

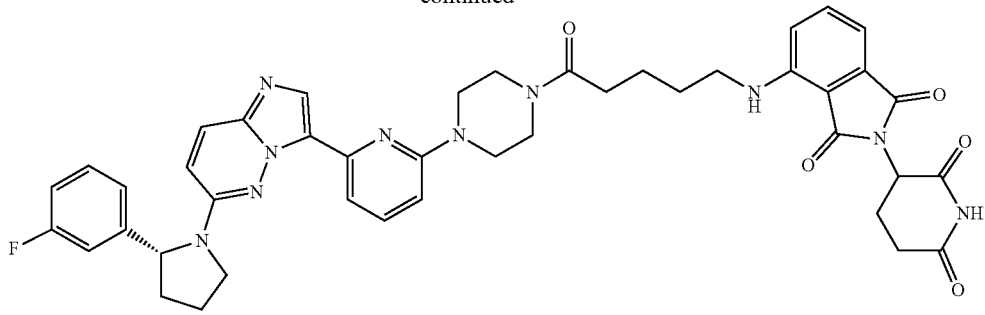
TR-014
CPD-014 was synthesized following the standard procedure for preparing CPD-053 (11 mg, yield 73%). MS (ESI) m/z: 799.3 [M+H]$^+$.
Example 79: 2-(2,6-Dioxopiperidin-3-yl)-4-((6-(4-(6-(6-((R)-2-(3-fluorophenyl)pyrrolidin-1-yl)imidazo[1,2-b]pyridazin-3-yl)pyridin-2-yl)piperazin-1-yl)-6-oxohexyl)amino)isoindoline-1,3-dione (CPD-015)
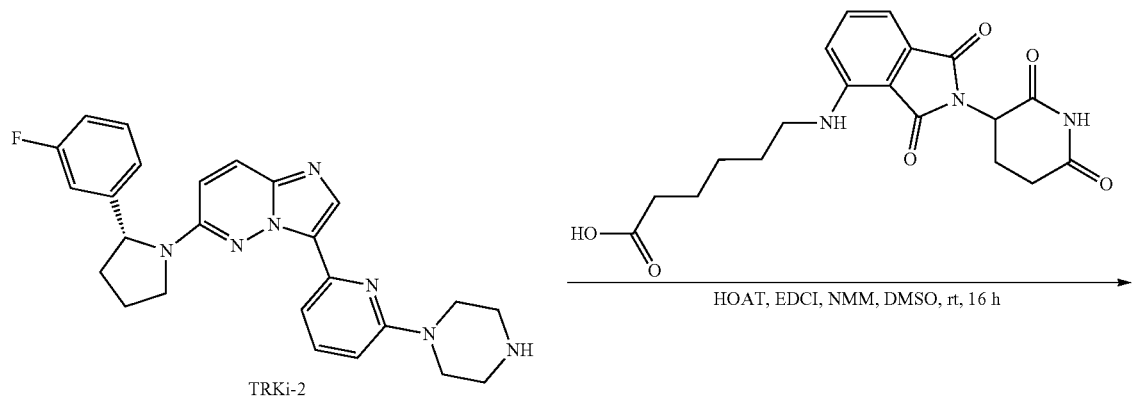
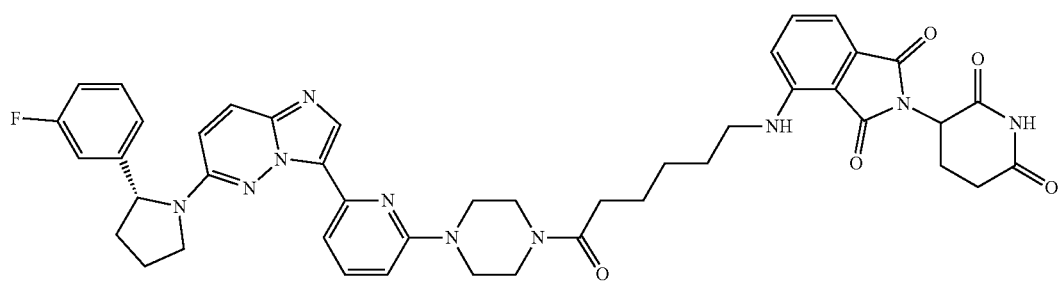
TR-015
CPD-015 was synthesized following the standard procedure for preparing CPD-053 (11 mg, yield 74%). MS (ESI) m/z: 813.4 [M+H]$^+$.

Example 80: (2S,4R)-1-((S)-2-(tert-butyl)-16-(4-(6-(6-((R)-2-(3-Fluorophenyl)pyrrolidin-1-yl)imidazo[1,2-b]pyridazin-3-yl)pyridin-2-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide (CPD-016)

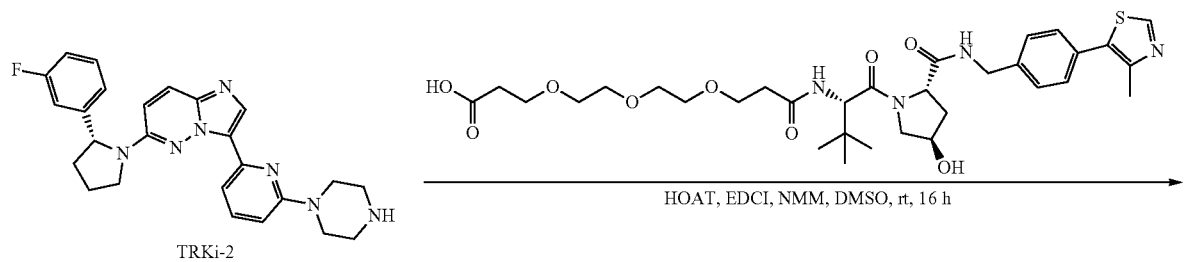

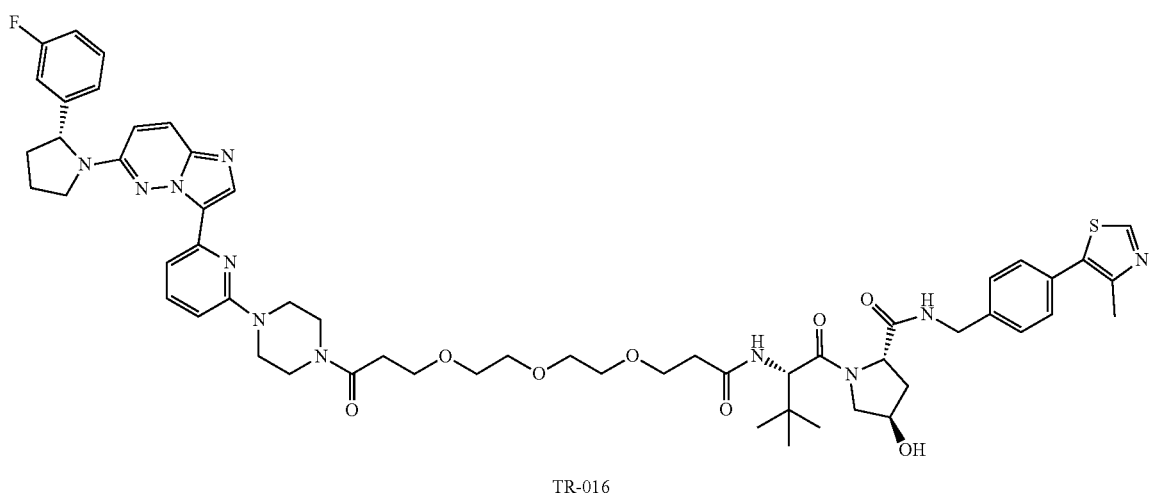

TR-016

CPD-016 was synthesized following the standard procedure for preparing CPD-053 (13 mg, yield 73%). MS (ESI) m/z: 1088.5 [M+H]⁺.

Example 81: (2S,4R)-1-((S)-2-(10-(4-(6-(6-((R)-2-(3-Fluorophenyl)pyrrolidin-1-yl)imidazo[1,2-b]pyridazin-3-yl)pyridin-2-yl)piperazin-1-yl)-10-oxo-decanamido)-3,3-dimethylbutanoyl)-4-hydroxy-N-(4-(4-methylthiazol-5-yl)benzyl)pyrrolidine-2-carboxamide (CPD-017)

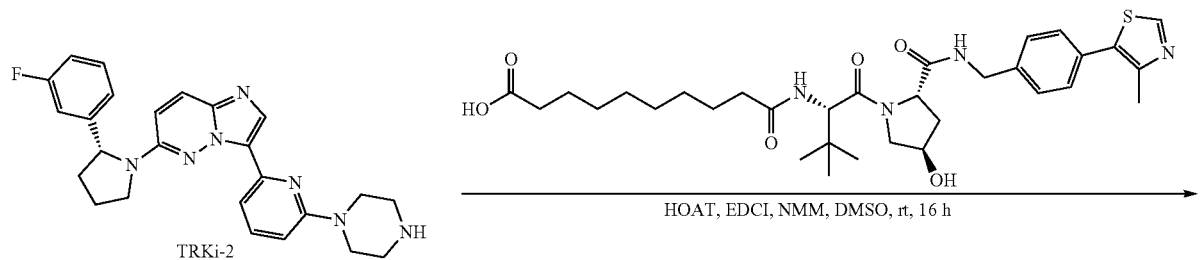

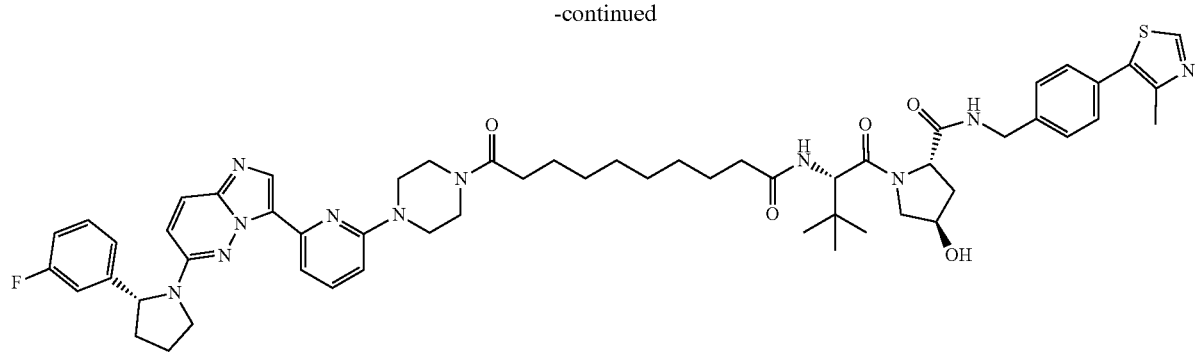

TR-017

CPD-017 was synthesized following the standard procedure for preparing CPD-053 (11 mg, yield 70%). $^1$H NMR (400 MHz, DMSO-d$_6$) δ 11.09 (s, 1H), 8.21 (s, 1H), 7.97 (d, J=9.9 Hz, 1H), 7.54 (dd, J=20.1, 12.4 Hz, 2H), 7.39 (dd, J=14.1, 7.9 Hz, 1H), 7.26-7.08 (m, 2H), 7.02 (dt, J=15.3, 7.8 Hz, 2H), 6.76 (d, J=8.6 Hz, 1H), 6.58 (s, 1H), 5.19 (d, J=5.9 Hz, 1H), 5.03 (dd, J=12.8, 5.2 Hz, 1H), 4.01 (d, J=5.0 Hz, 1H), 3.76-3.66 (m, 2H), 3.65-3.50 (m, 8H), 3.45 (s, 3H), 2.94-2.79 (m, 1H), 2.77 (d, J=4.9 Hz, 1H), 2.64 (t, J=6.4 Hz, 1H), 2.56 (d, J=7.2 Hz, 1H), 2.53 (s, 1H), 2.47-2.43 (m, 1H), 2.33 (s, 1H), 2.02 (dd, J=15.7, 8.4 Hz, 3H), 1.90 (s, 1H), 1.27 (d, J=25.3 Hz, 3H), 0.84 (d, J=6.8 Hz, 1H). MS (ESI) m/z: 1040.5 [M+H]$^+$.

Example 82: (2S,4R)-1-((S)-2-(9-(4-(6-(6-((R)-2-(3-Fluorophenyl)pyrrolidin-1-yl)imidazo[1,2-b]pyridazin-3-yl)pyridin-2-yl)piperazin-1-yl)-9-oxononanamido)-3,3-dimethylbutanoyl)-4-hydroxy-N-(4-(4-methylthiazol-5-yl)benzyl)pyrrolidine-2-carboxamide (CPD-018)

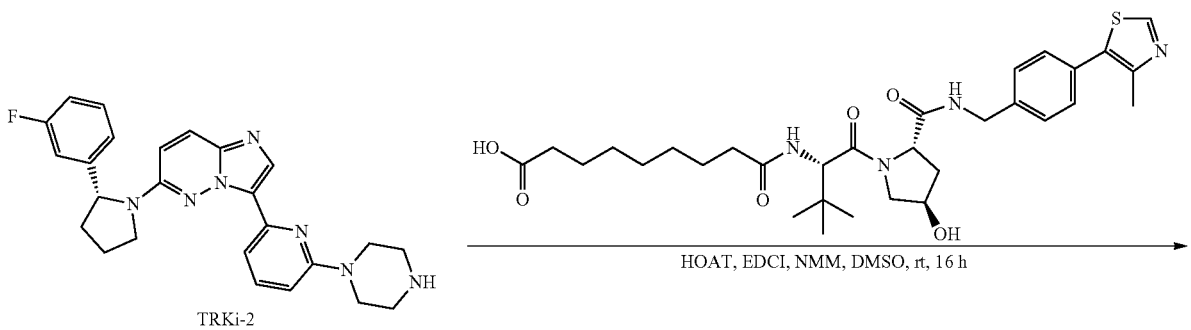

TRKi-2

HOAT, EDCI, NMM, DMSO, rt, 16 h

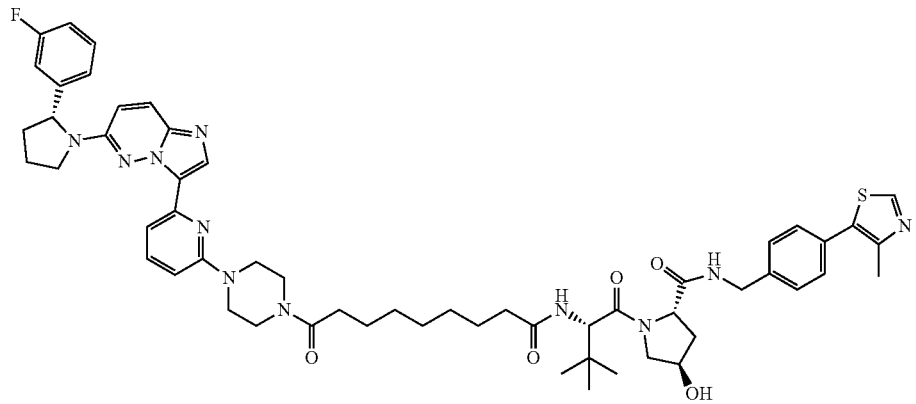

TR-018

CPD-018 was synthesized following the standard procedure for preparing CPD-053 (9 mg, yield 72%). MS (ESI) m/z: 1026.5 [M+H]$^+$.

Example 83: (2S,4R)-1-((S)-2-(tert-butyl)-19-(4-(6-(6-((R)-2-(3-Fluorophenyl)pyrrolidin-1-yl)imidazo[1,2-b]pyridazin-3-yl)pyridin-2-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide (CPD-019)

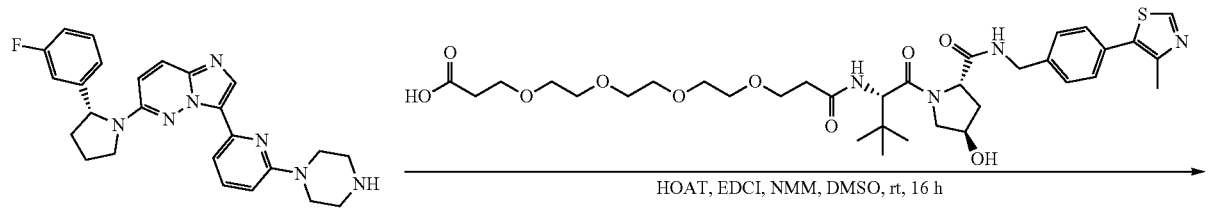

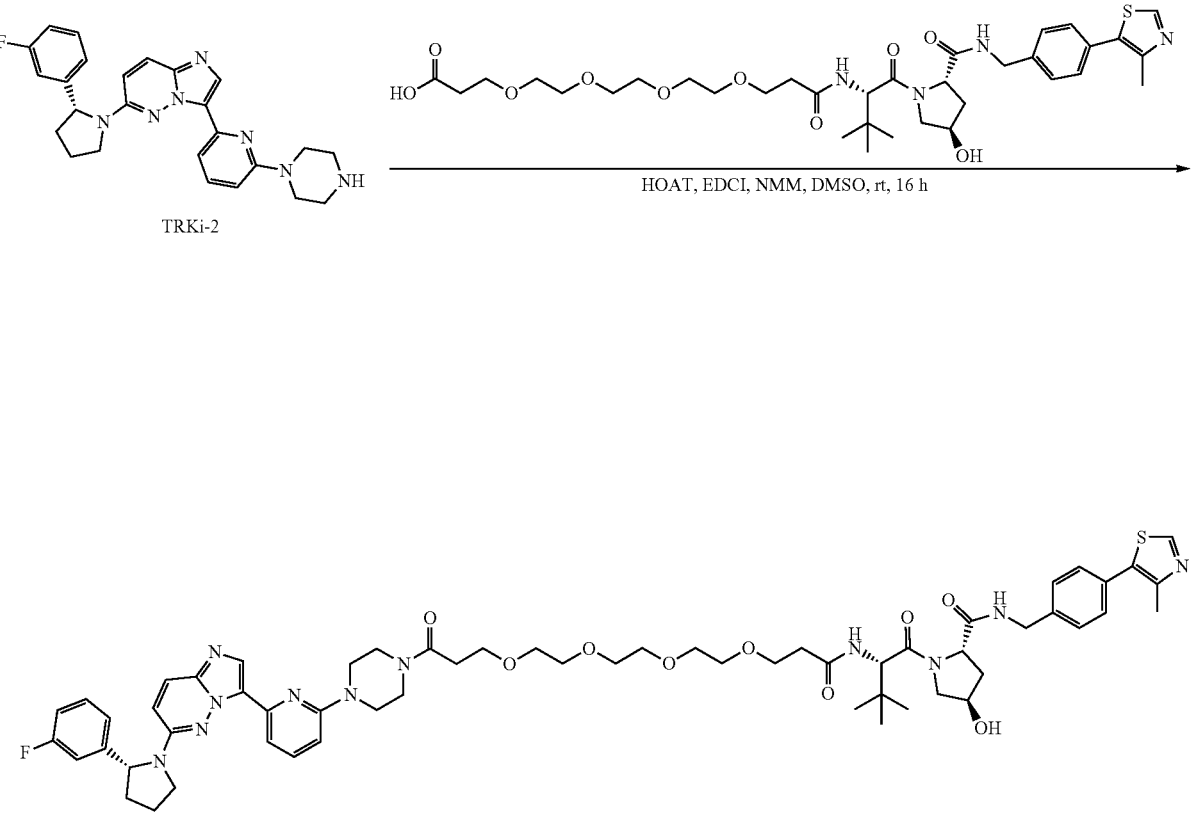

CPD-019 was synthesized following the standard procedure for preparing CPD-053 (12 mg, yield 78%). MS (ESI) m/z: 1132.5 [M+H]+.

Example 84: (2S,4R)-1-((S)-2-(3-(2-(3-(4-(6-(6-((R)-2-(3-Fluorophenyl)pyrrolidin-1-yl)imidazo[1,2-b]pyridazin-3-yl)pyridin-2-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide (CPD-020)

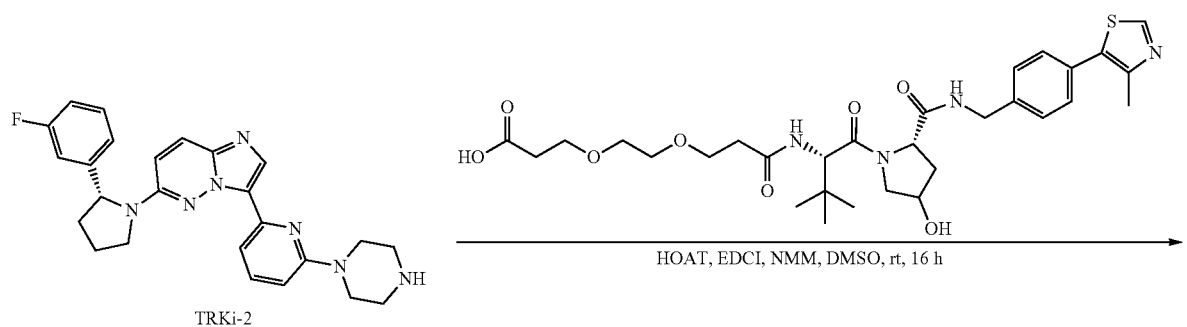

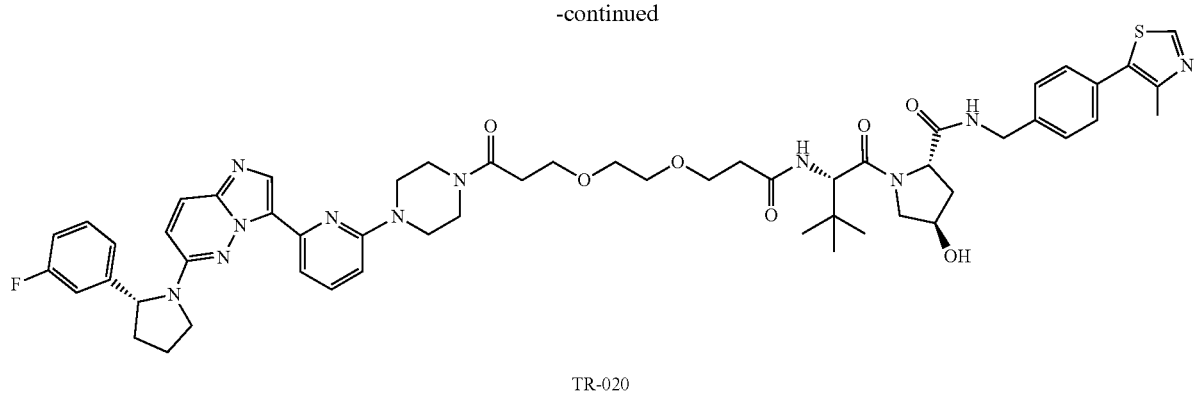
TR-020
CPD-020 was synthesized following the standard procedure for preparing CPD-053 (10 mg, yield 71%). MS (ESI) m/z: 1044.5 [M+H]+.
Example 85: 2-(2,6-Dioxopiperidin-3-yl)-4-((15-(4-(6-(6-((R)-2-(3-fluorophenyl)pyrrolidin-1-yl)imidazo[1,2-b]pyridazin-3-yl)pyridin-2-yl)piperazin-1-yl)-15-oxo-3,6,9,12-tetraoxapentadecyl)amino)isoindoline-1,3-dione (CPD-021)
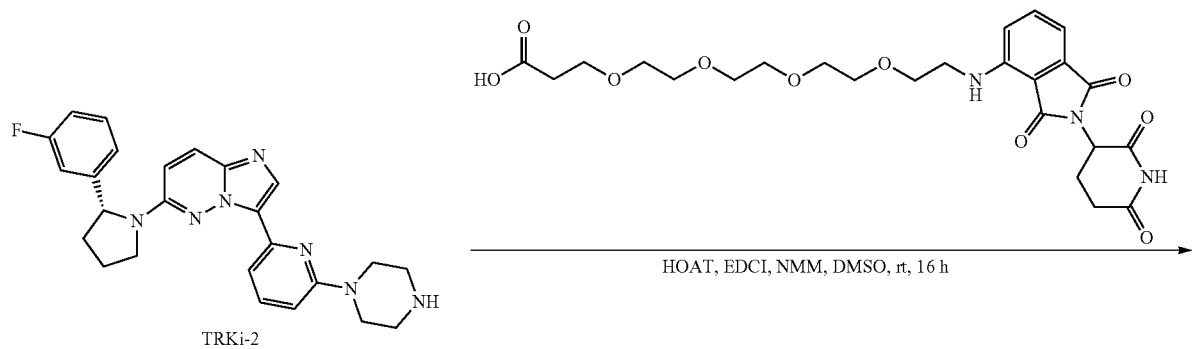
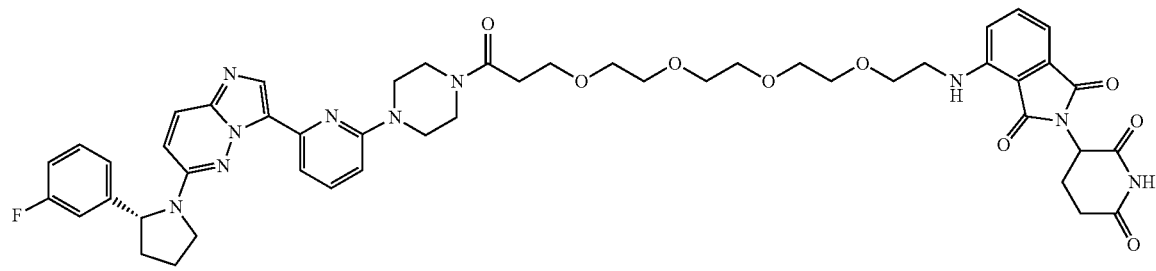
TR-021
CPD-021 was synthesized following the standard procedure for preparing CPD-053 (12 mg, yield 76%). MS (ESI) m/z: 947.4 [M+H]+.

Example 86: (2S,4R)-1-((S)-2-(11-(4-(6-(6-((R)-2-(3-Fluorophenyl)pyrrolidin-1-yl)imidazo[1,2-b]pyridazin-3-yl)pyridin-2-yl)piperazin-1-yl)-11-oxoundecanamido)-3,3-dimethylbutanoyl)-4-hydroxy-N-(4-(4-methylthiazol-5-yl)benzyl)pyrrolidine-2-carboxamide (CPD-022)

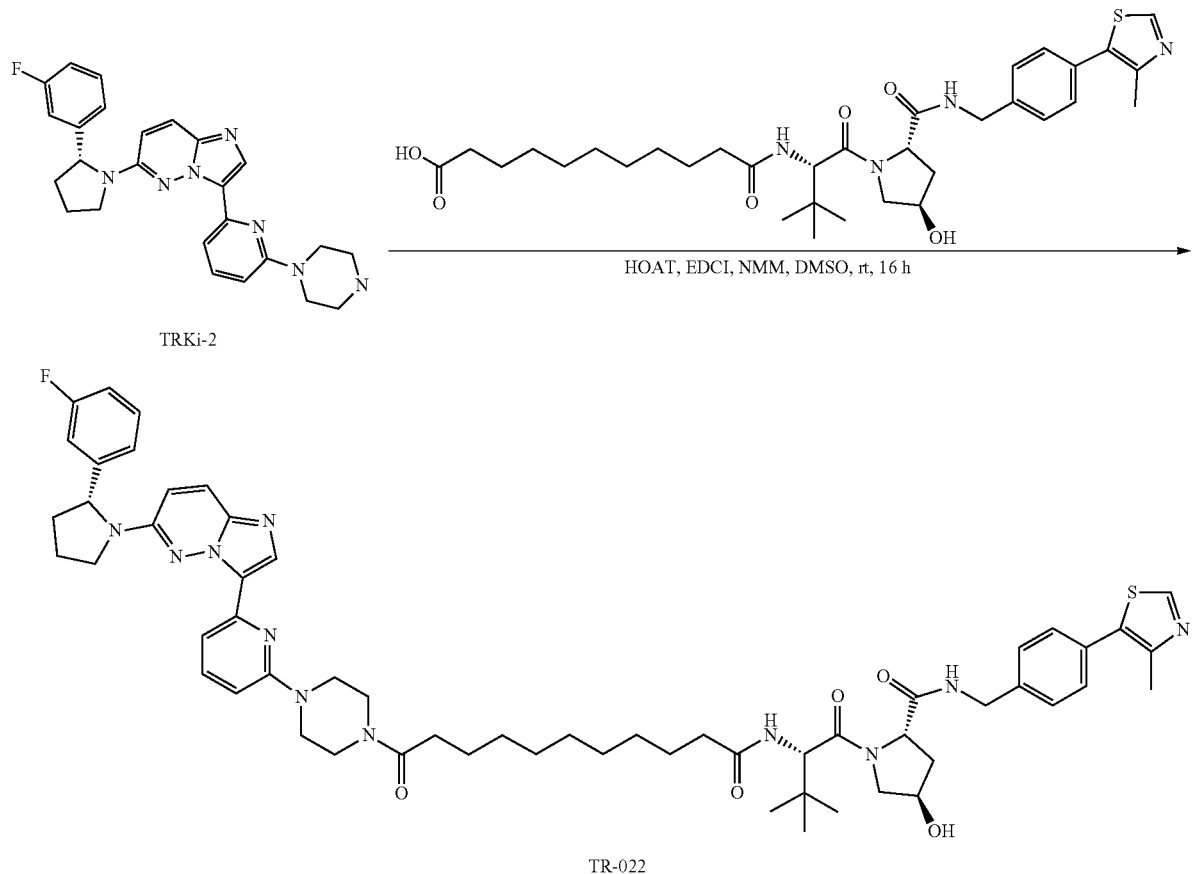

CPD-022 was synthesized following the standard procedure for preparing CPD-053 (13 mg, yield 78%). MS (ESI) m/z: 1054.5 [M+H]+.

Example 87: 2-(2,6-Dioxopiperidin-3-yl)-4-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)isoindoline-1,3-dione (CPD-023)

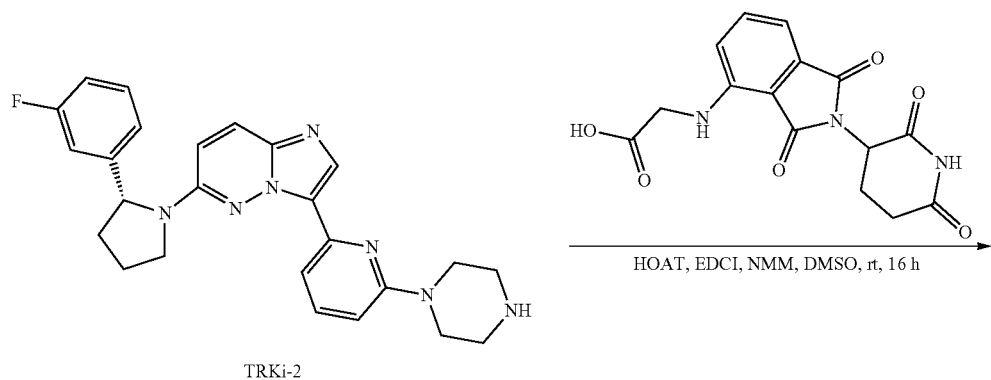

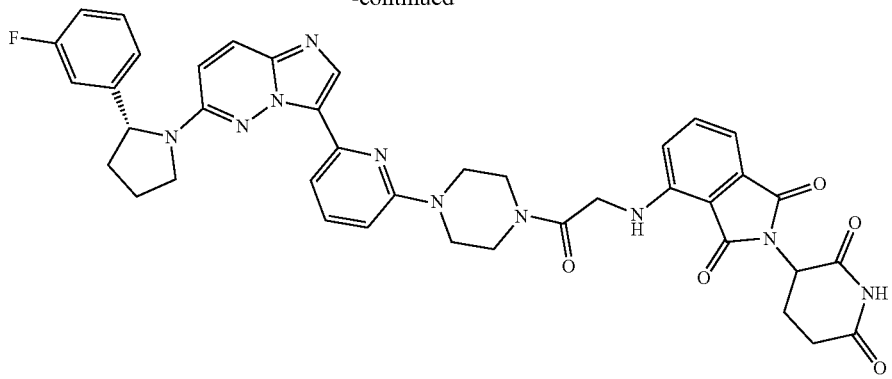
TR-023
CPD-023 was synthesized following the standard procedure for preparing CPD-053 (11 mg, yield 72%). MS (ESI) m/z: 757.3 [M+H]$^+$.
Example 88: 2-(2,6-Dioxopiperidin-3-yl)-4-((8-(4-(6-(6-((R)-2-(3-fluorophenyl)pyrrolidin-1-yl)imidazo[1,2-b]pyridazin-3-yl)pyridin-2-yl)piperazin-1-yl)-8-oxooctyl)amino)isoindoline-1,3-dione (CPD-024)
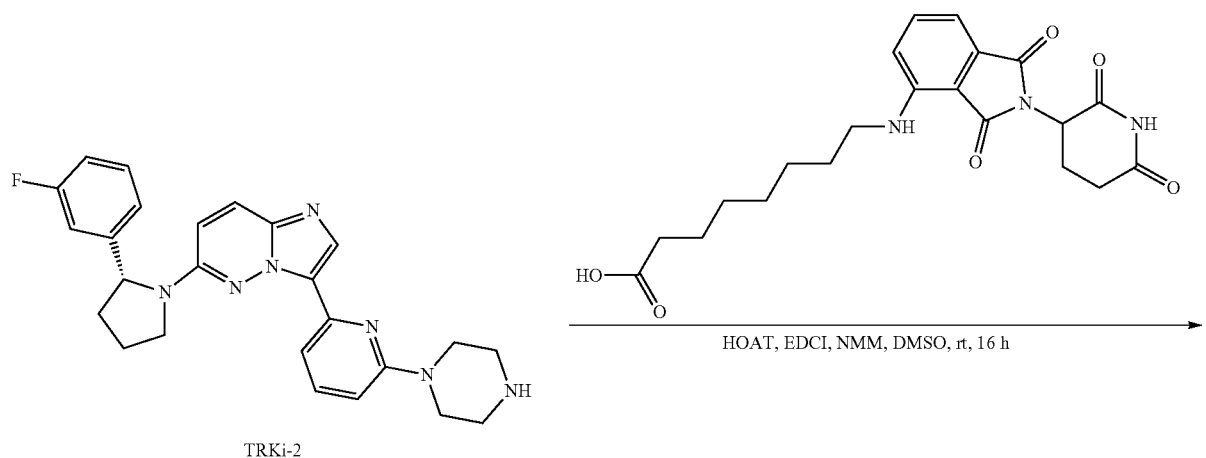
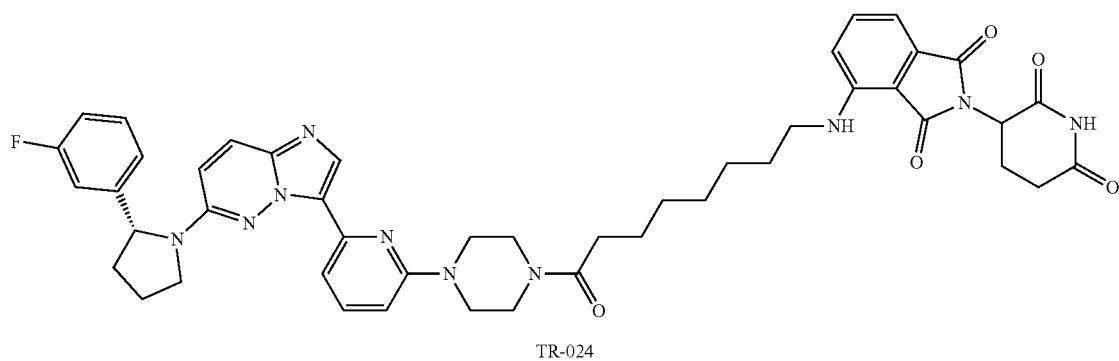
TR-024

CPD-024 was synthesized following the standard procedure for preparing CPD-053 (13 mg, yield 75%). MS (ESI) m/z: 841.4 [M+H]+.
Example 89: 2-(2,6-Dioxopiperidin-3-yl)-4-((18-(4-(6-(6-((R)-2-(3-fluorophenyl)pyrrolidin-1-yl)imidazo[1,2-b]pyridazin-3-yl)pyridin-2-yl)piperazin-1-yl)-18-oxo-3,6,9,12,15-pentaoxaoctadecyl)amino)isoindoline-1,3-dione (CPD-025)
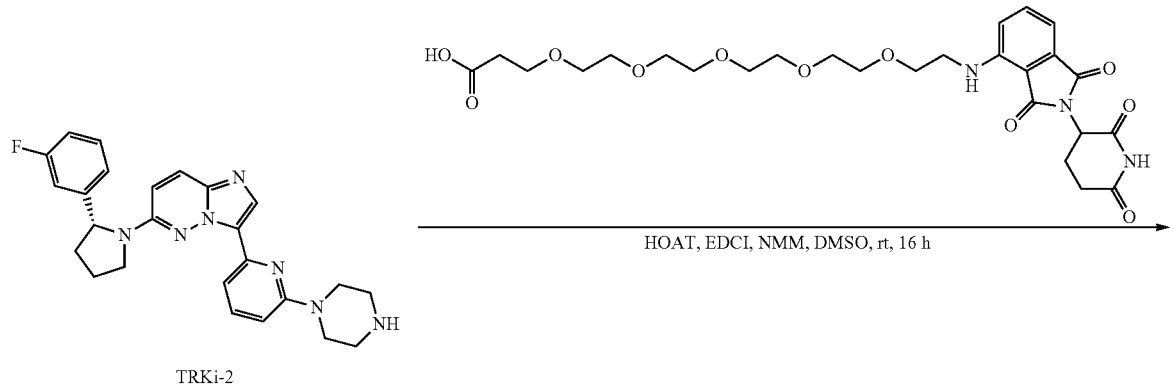
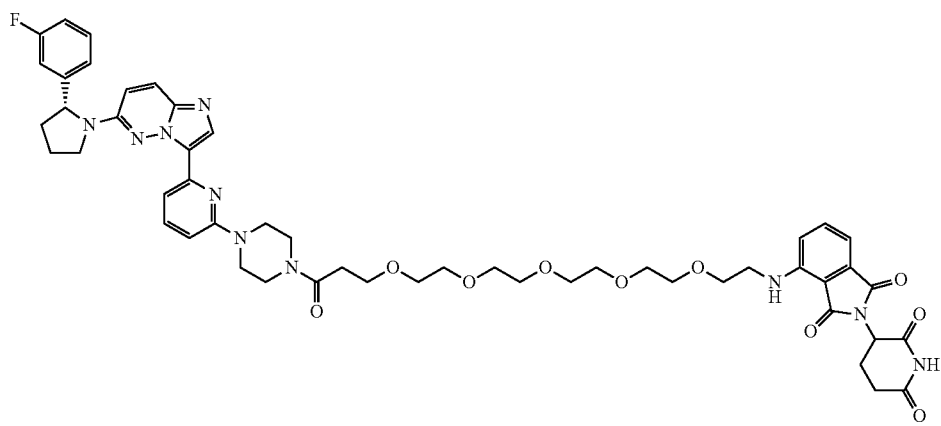 [SMILES: O=C1CCC(N2C(=O)c3cccc(NCCOCCOCCOCCOCCOCCC(=O)N4CCN(c5cccc(-c6cnc7ccc(N8CCC[C@@H]8c8cccc(F)c8)nn67)n5)CC4)c3C2=O)C(=O)N1]
TR-025
CPD-025 was synthesized following the standard procedure for preparing CPD-053 (14 mg, yield 76%). MS (ESI) m/z: 991.4 [M+H]+.

Example 90: 2-(2,6-Dioxopiperidin-3-yl)-4-((3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropyl)amino)isoindoline-1,3-dione (CPD-026)
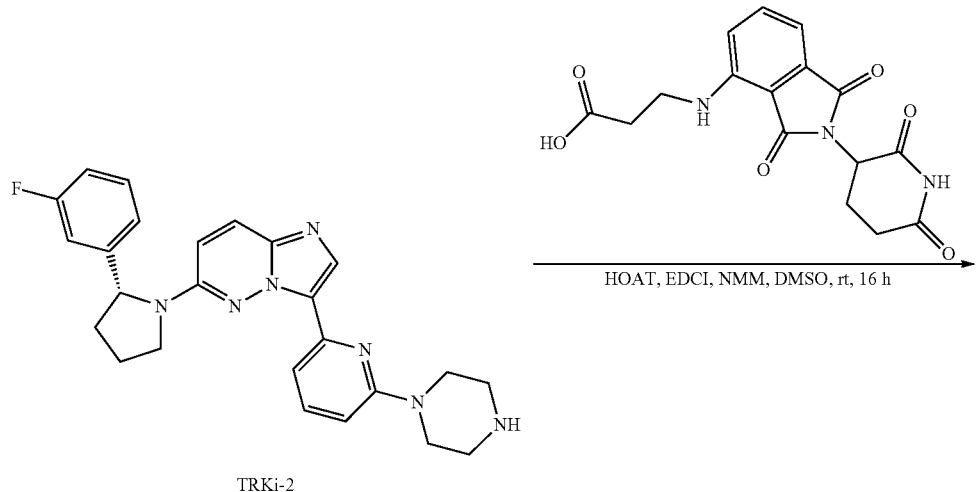
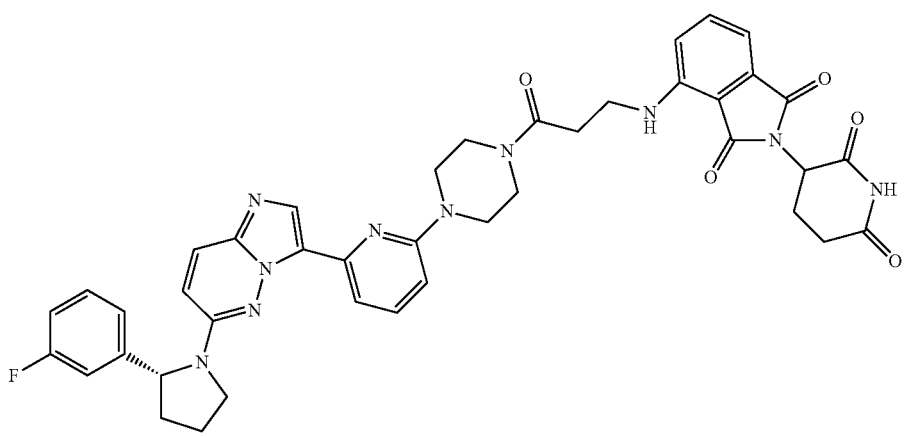 [SMILES: O=C1CCC(N2C(=O)c3cccc(NCCC(=O)N4CCN(c5cccc(-c6cnc7ccc(N8CCC[C@@H]8c8cccc(F)c8)nn67)n5)CC4)c3C2=O)C(=O)N1]
CPD-026 was synthesized following the standard procedure for preparing CPD-053 (12 mg, yield 71%). MS (ESI) m/z: 771.3 [M+H]+.

Example 91: 2-(2,6-Dioxopiperidin-3-yl)-4-((2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethyl)amino)isoindoline-1,3-dione (CPD-027)
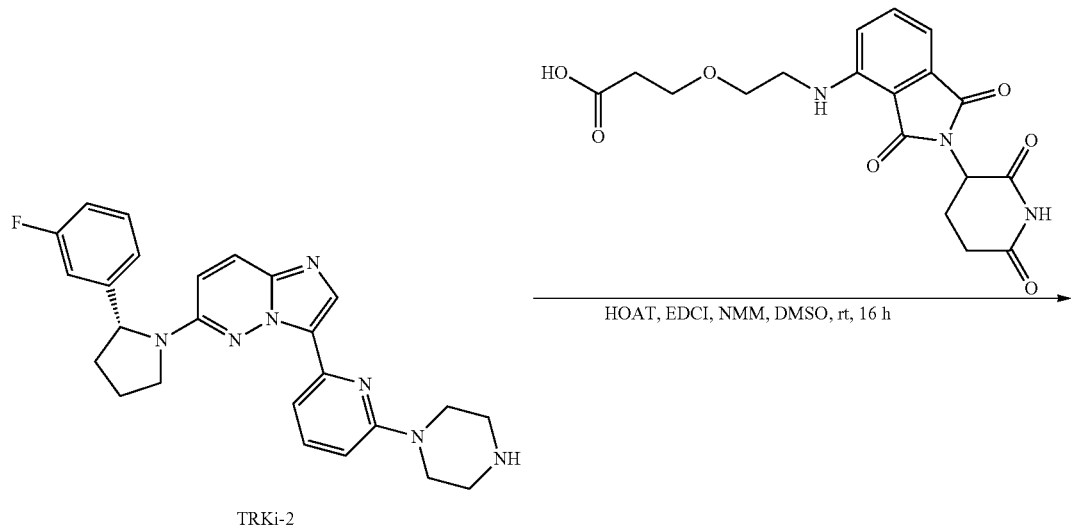
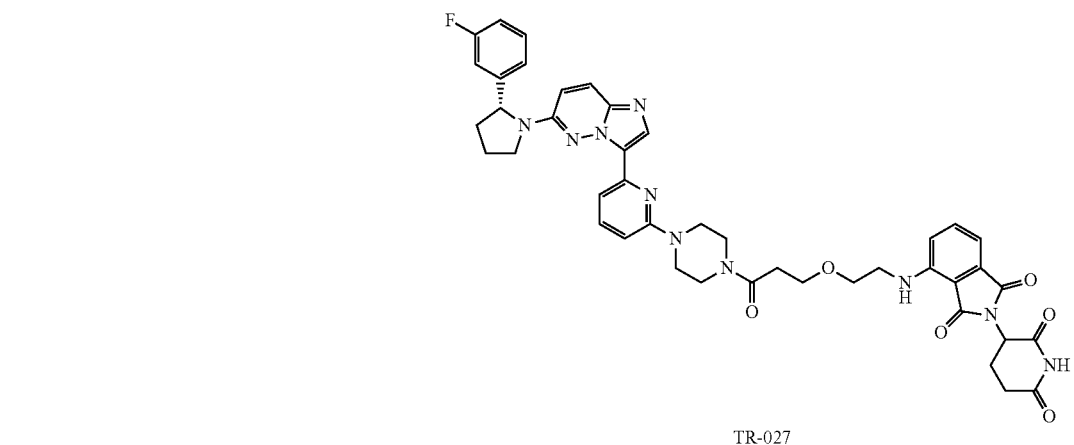
CPD-027 was synthesized following the standard procedure for preparing CPD-053 (14 mg, yield 77%). MS (ESI) m/z: 815.3 [M+H]$^+$.

Example 92: 2-(2,6-Dioxopiperidin-3-yl)-4-((2-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethyl)amino)isoindoline-1,3-dione (CPD-028)

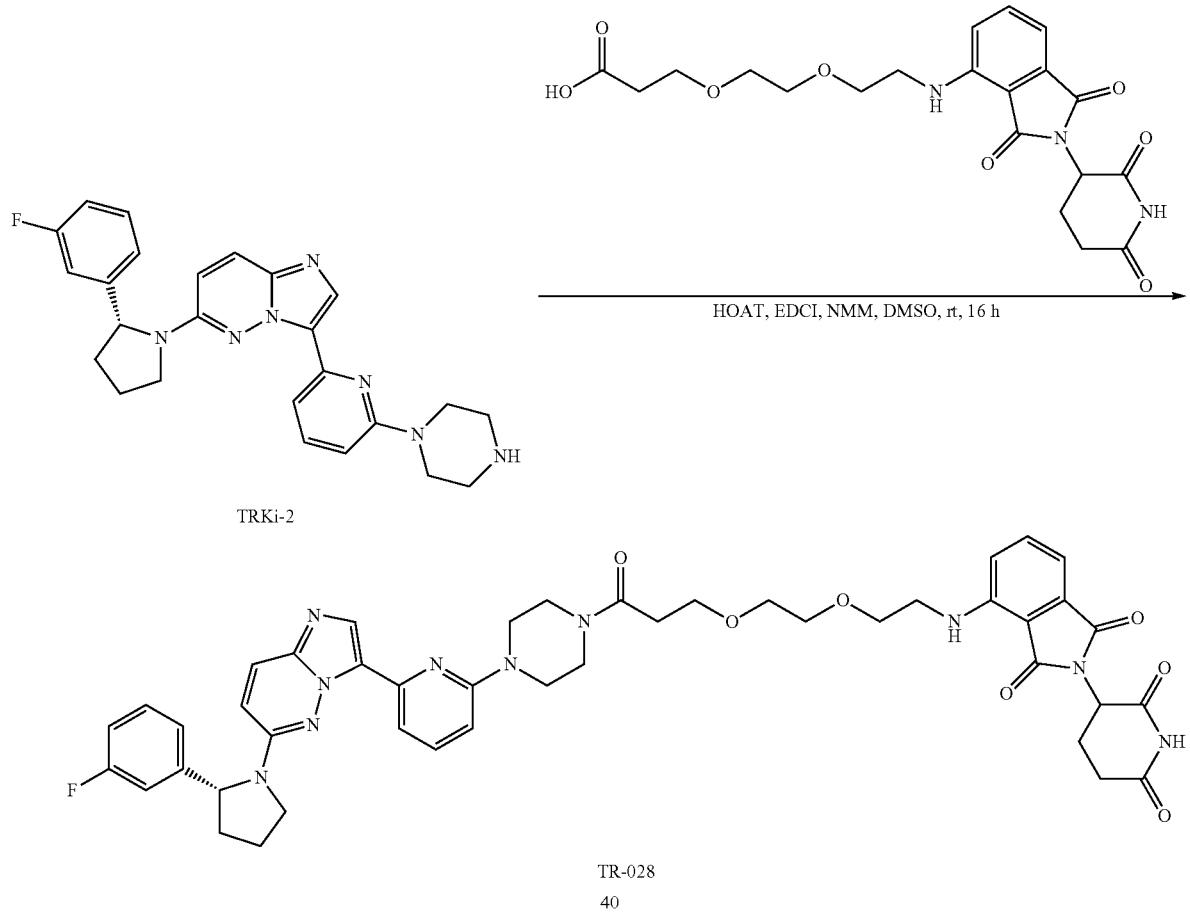

TRKi-2

TR-028

CPD-028 was synthesized following the standard procedure for preparing CPD-053 (11 mg, yield 72%). MS (ESI) m/z: 859.4 [M+H]+.

Example 93: (2S,4R)-1-((S)-2-(8-(4-(6-(6-((R)-2-(3-Fluorophenyl)pyrrolidin-1-yl)imidazo[1,2-b]pyridazin-3-yl)pyridin-2-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide (CPD-029)

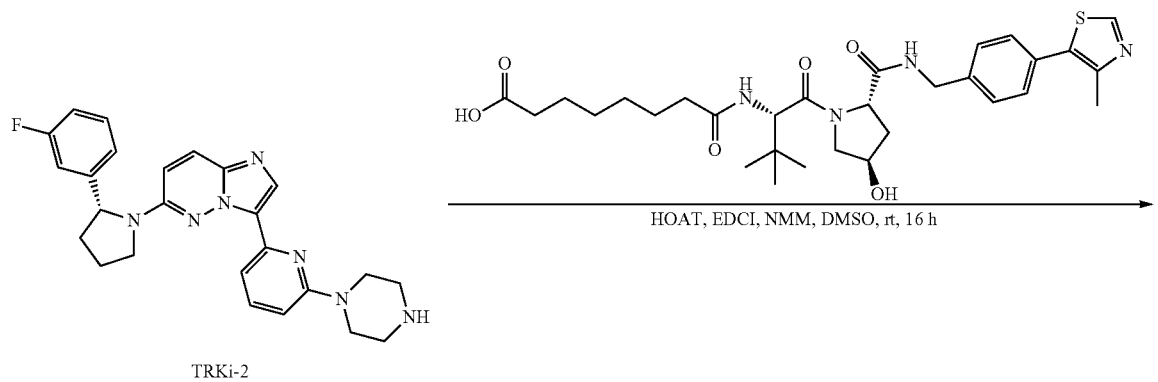

TRKi-2

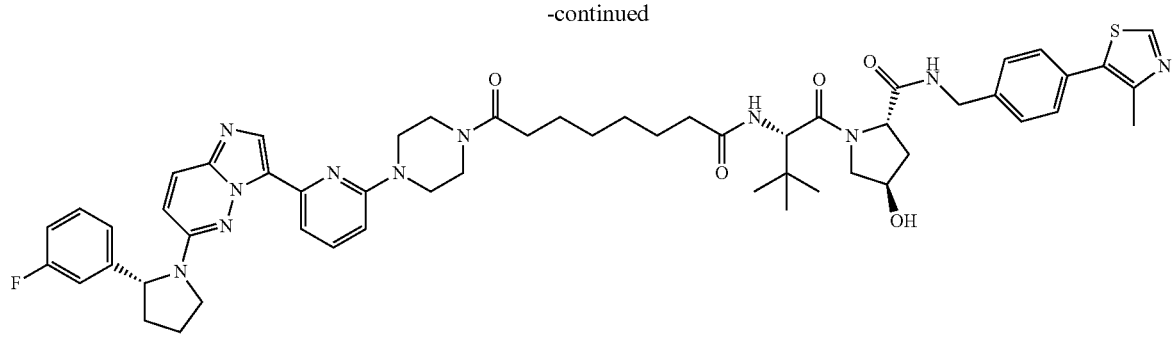
TR-029
CPD-029 was synthesized following the standard procedure for preparing CPD-053 (14 mg, yield 76%). MS (ESI) m/z: 1012.5 [M+H]⁺.
Example 94: N-(5-(3,5-Difluorobenzyl)-1H-indazol-3-yl)-4-(4-(3-(2-((2-(2,6-dioxopiperidin-3-yl)-1,3-dioxoisoindolin-4-yl)amino)ethoxy)propanoyl)piperazin-1-yl)-2-((tetrahydro-2H-pyran-4-yl)amino)benzamide (CPD-030)
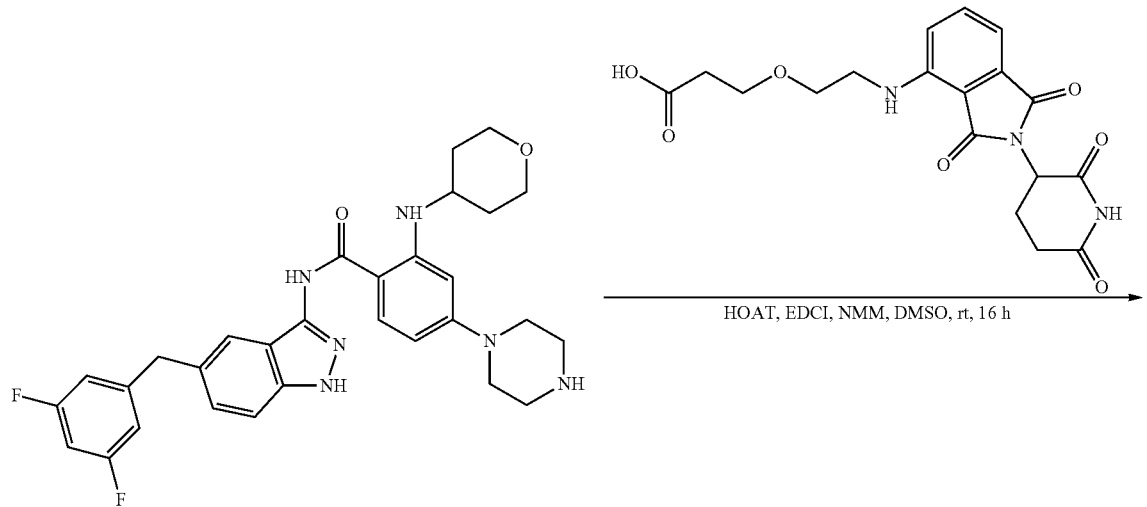
TRKi-1
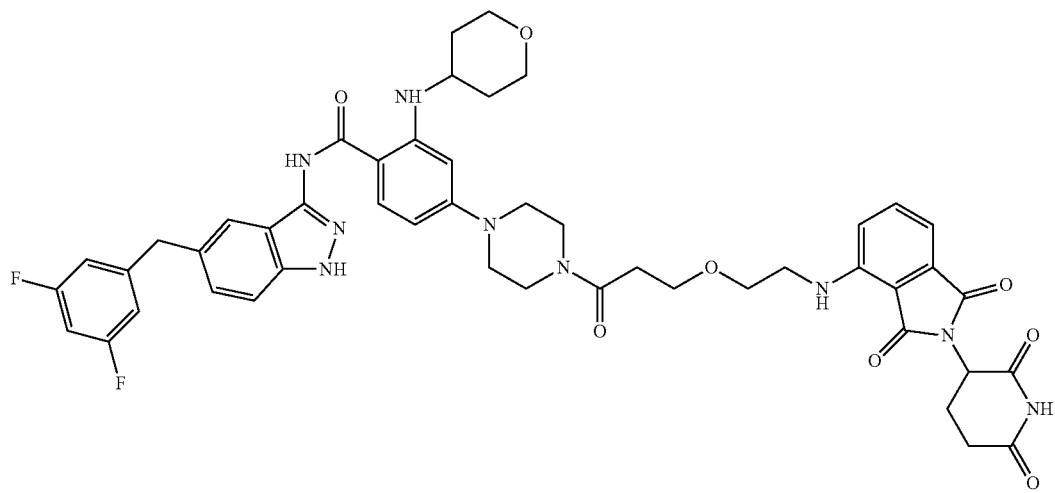 [SMILES: O=C1CCC(N2C(=O)c3cccc(NCCOCCC(=O)N4CCN(c5ccc(C(=O)Nc6n[nH]c7ccc(Cc8cc(F)cc(F)c8)cc67)c(NC6CCOCC6)c5)CC4)c3C2=O)C(=O)N1]
TR-030

CPD-030 was synthesized following the standard procedure for preparing CPD-053 (10 mg, yield 72%). MS (ESI) m/z: 918.4 [M+H]+.
Example 95: N-(5-(3,5-Difluorobenzyl)-1H-indazol-3-yl)-4-(4-(1-((2-(2,6-dioxopiperidin-3-yl)-1,3-dioxoisoindolin-4-yl)amino)-3,6,9,12-tetraoxapentadecan-15-oyl)piperazin-1-yl)-2-((tetrahydro-2H-pyran-4-yl)amino)benzamide (CPD-031)
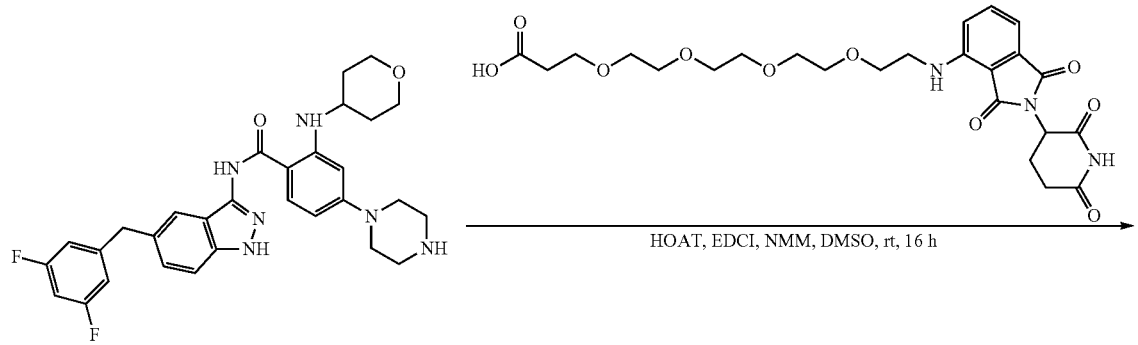
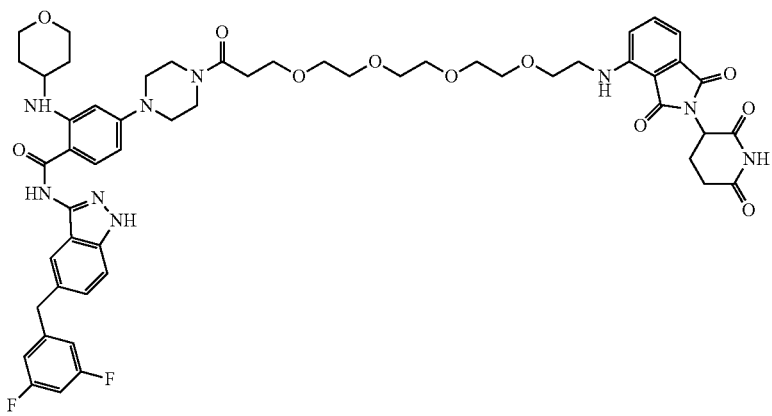
CPD-031 was synthesized following the standard procedure for preparing CPD-053 (13 mg, yield 76%). MS (ESI) m/z: 1050.4 [M+H]+.

Example 96: N-(5-(3,5-Difluorobenzyl)-1H-indazol-3-yl)-4-(4-(3-(2-(2-((2-(2,6-dioxopiperidin-3-yl)-1,3-dioxoisoindolin-4-yl)amino)ethoxy)ethoxy)propanoyl)piperazin-1-yl)-2-((tetrahydro-2H-pyran-4-yl)amino)benzamide (CPD-032)
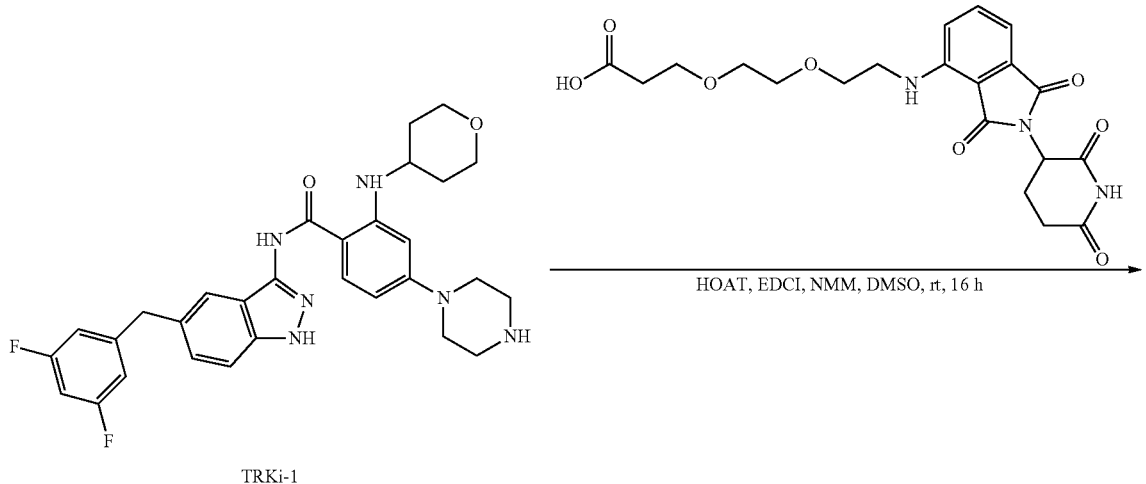
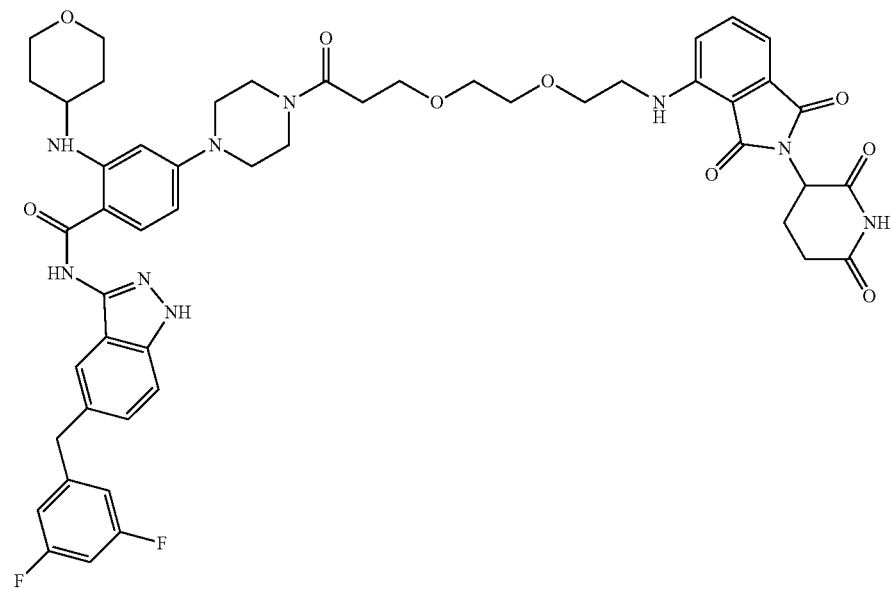 [SMILES: O=C1CCC(N2C(=O)c3cccc(NCCOCCOCCC(=O)N4CCN(c5ccc(C(=O)Nc6n[nH]c7ccc(Cc8cc(F)cc(F)c8)cc67)c(NC6CCOCC6)c5)CC4)c3C2=O)C(=O)N1]
CPD-032 was synthesized following the standard procedure for preparing CPD-053 (10 mg, yield 71%). MS (ESI) m/z: 962.4 [M+H]$^+$.

Example 97: (2S,4R)-1-((S)-2-(8-(4-(4-((5-(3,5-Difluorobenzyl)-1H-indazol-3-yl)carbamoyl)-3-((tetrahydro-2H-pyran-4-yl)amino)phenyl)piperazin-1-yl)-8-oxooctanamido)-3,3-dimethylbutanoyl)-4-hydroxy-N-(4-(4-methylthiazol-5-yl)benzyl)pyrrolidine-2-carboxamide (CPD-033)
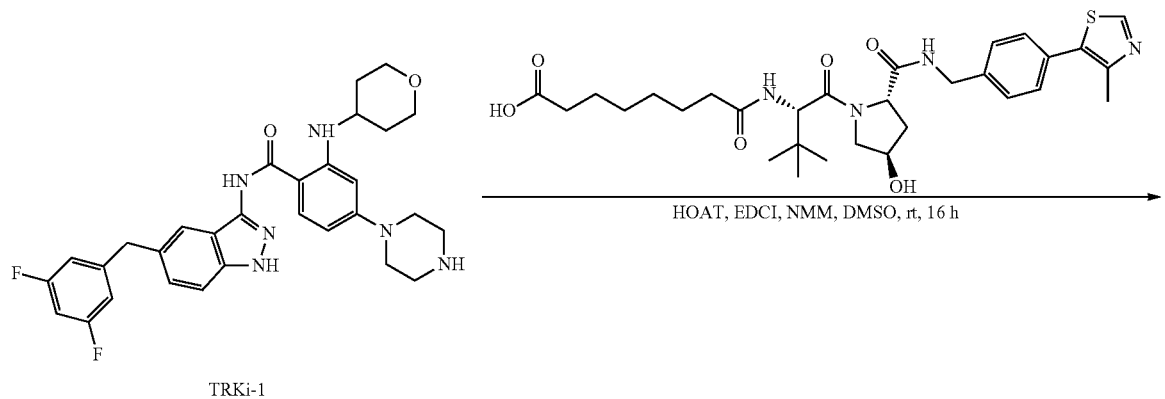
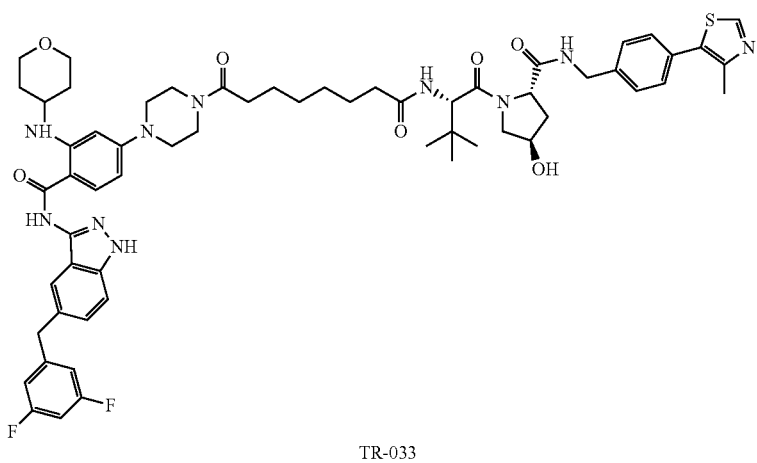
CPD-033 was synthesized following the standard procedure for preparing CPD-053 (13 mg, yield 73%). MS (ESI) m/z: 1115.5 [M+H]$^+$.

Example 98: (2S,4R)-1-((S)-2-(10-(4-(4-((5-(3,5-Difluorobenzyl)-1H-indazol-3-yl)carbamoyl)-3-((tetrahydro-2H-pyran-4-yl)amino)phenyl)piperazin-1-yl)-10-oxodecanamido)-3,3-dimethylbutanoyl)-4-hydroxy-N-(4-(4-methylthiazol-5-yl)benzyl)pyrrolidine-2-carboxamide (CPD-034)

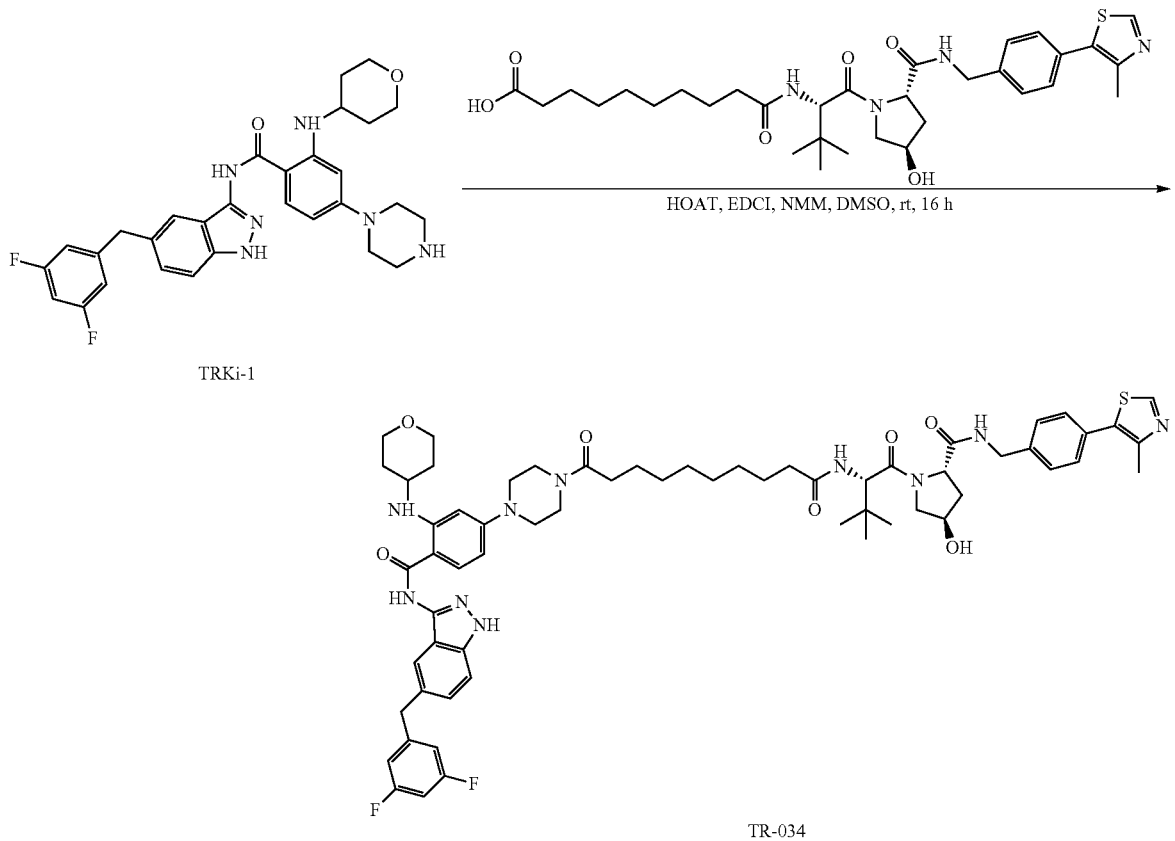

CPD-034 was synthesized following the standard procedure for preparing CPD-053 (12 mg, yield 71%). MS (ESI) m/z: 1143.6 [M+H]+.

Example 99: (2S,4R)-1-((S)-2-(11-(4-(4-((5-(3,5-Difluorobenzyl)-1H-indazol-3-yl)carbamoyl)-3-((tetrahydro-2H-pyran-4-yl)amino)phenyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide (CPD-035)

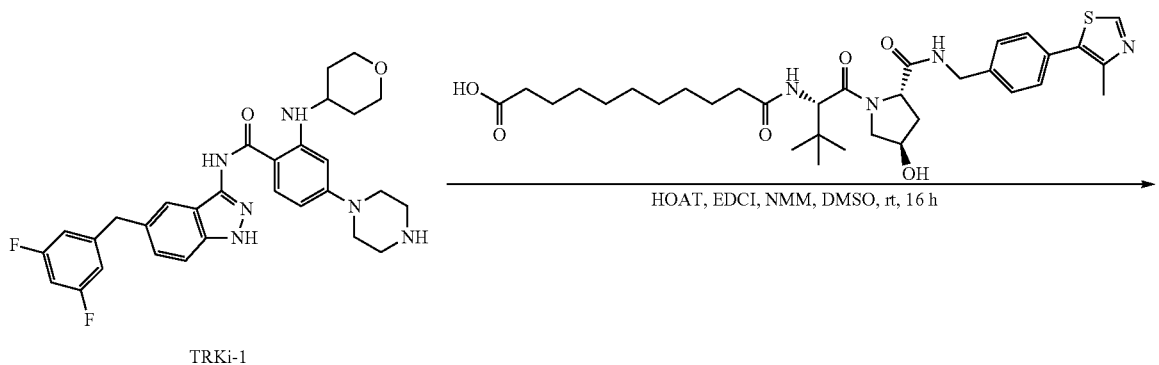

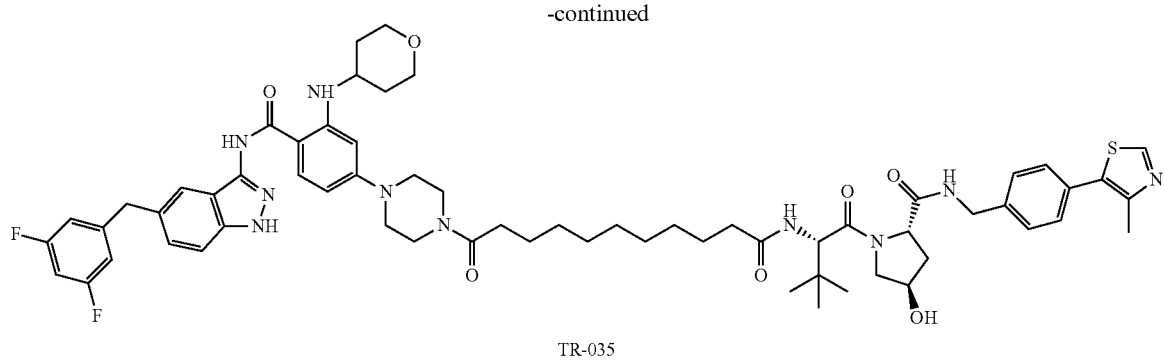

TR-035

CPD-035 was synthesized following the standard procedure for preparing CPD-053 (13 mg, yield 75%). MS (ESI) m/z: 1157.6 [M+H]$^+$.

Example 100: (2S,4R)-1-((S)-2-(5-(4-(4-((5-(3,5-Difluorobenzyl)-1H-indazol-3-yl)carbamoyl)-3-((tetrahydro-2H-pyran-4-yl)amino)phenyl)piperazin-1-yl)-5-oxopentanamido)-3,3-dimethylbutanoyl)-4-hydroxy-N-(4-(4-methylthiazol-5-yl)benzyl)pyrrolidine-2-carboxamide (CPD-036)

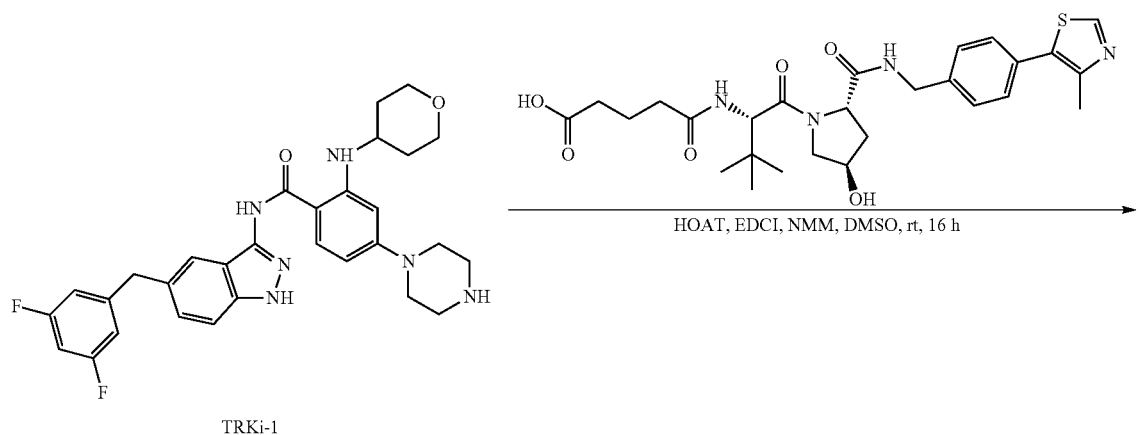

TRKi-1

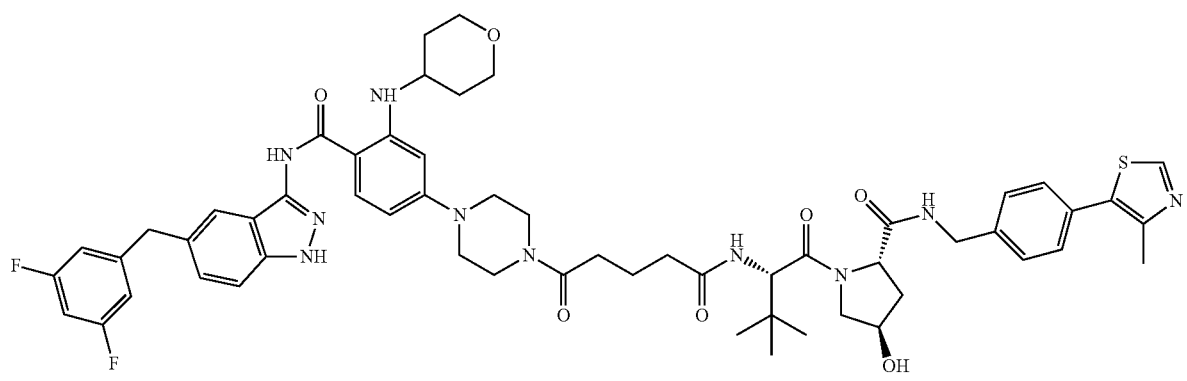 [SMILES: Cc1ncsc1-c1ccc(CNC(=O)[C@@H]2C[C@@H](O)CC2C(=O)[C@@H](NC(=O)CCCC(=O)N2CCN(c3ccc(C(=O)Nc4n[nH]c5ccc(Cc6cc(F)cc(F)c6)cc45)c(NC4CCOCC4)c3)CC2)C(C)(C)C)cc1]

TR-036

CPD-036 was synthesized following the standard procedure for preparing CPD-053 (10 mg, yield 71%). MS (ESI) m/z: 1073.5 [M+H]$^+$.

Example 101: (2S,4R)-1-((S)-2-(9-(4-(4-((5-(3,5-Difluorobenzyl)-1H-indazol-3-yl)carbamoyl)-3-((tetrahydro-2H-pyran-4-yl)amino)phenyl)piperazin-1-yl)-9-oxononanamido)-3,3-dimethylbutanoyl)-4-hydroxy-N-(4-(4-methylthiazol-5-yl)benzyl)pyrrolidine-2-carboxamide (CPD-037)

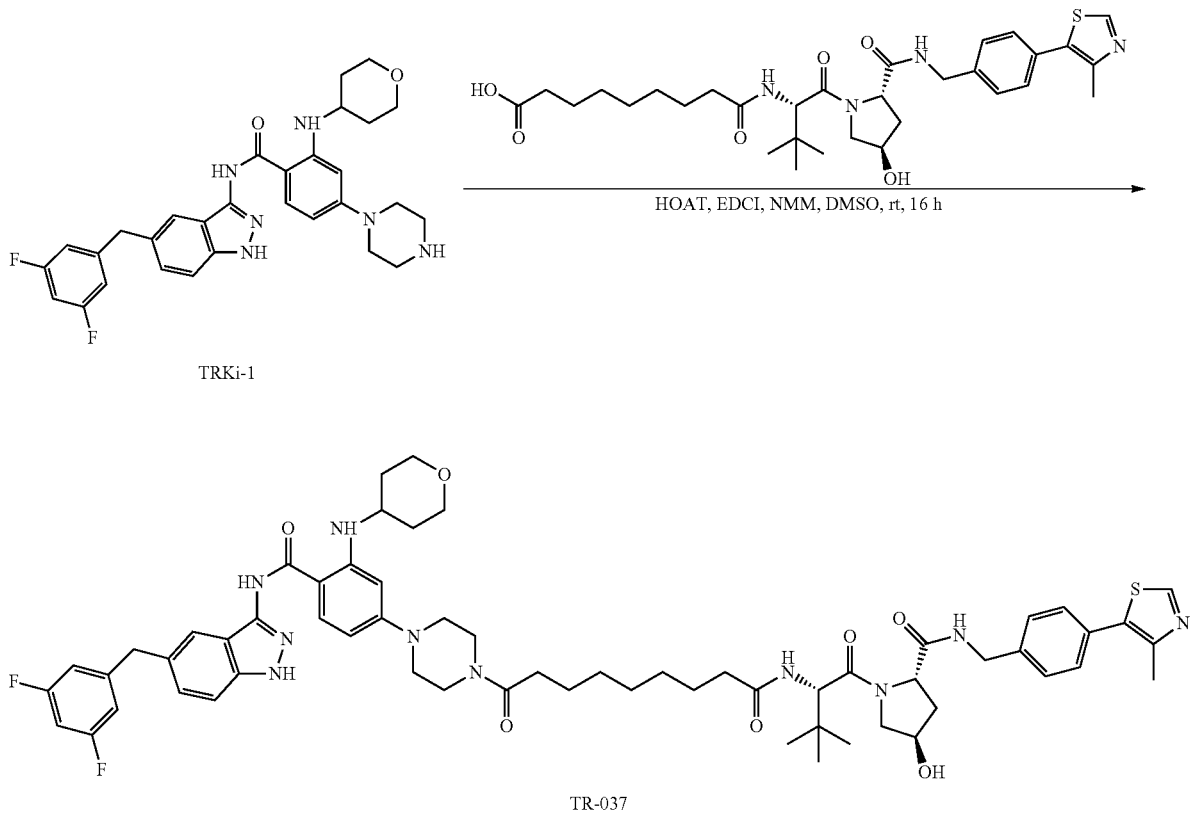

CPD-037 was synthesized following the standard procedure for preparing CPD-053 (13 mg, yield 76%). MS (ESI) m/z: 1129.5 [M+H]$^+$.

Example 102: (2S,4R)-1-((S)-2-(3-(2-(3-(4-(4-((5-(3,5-Difluorobenzyl)-1H-indazol-3-yl)carbamoyl)-3-((tetrahydro-2H-pyran-4-yl)amino)phenyl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide (CPD-038)

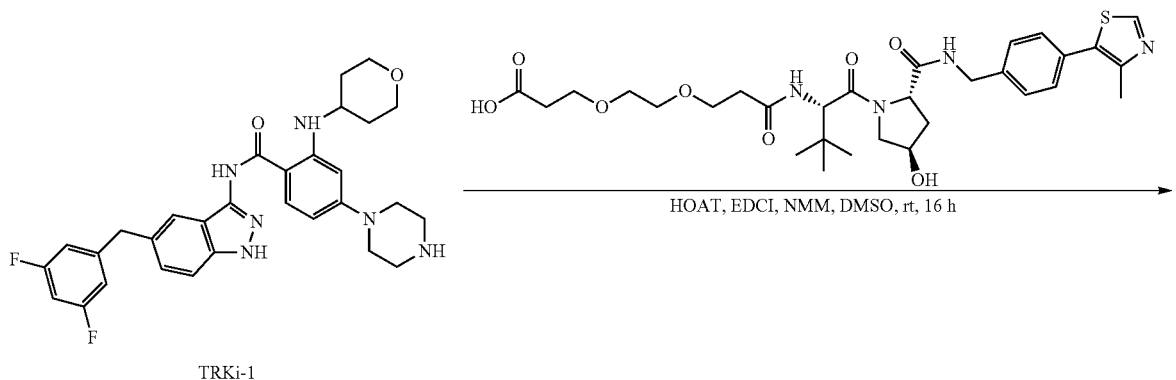

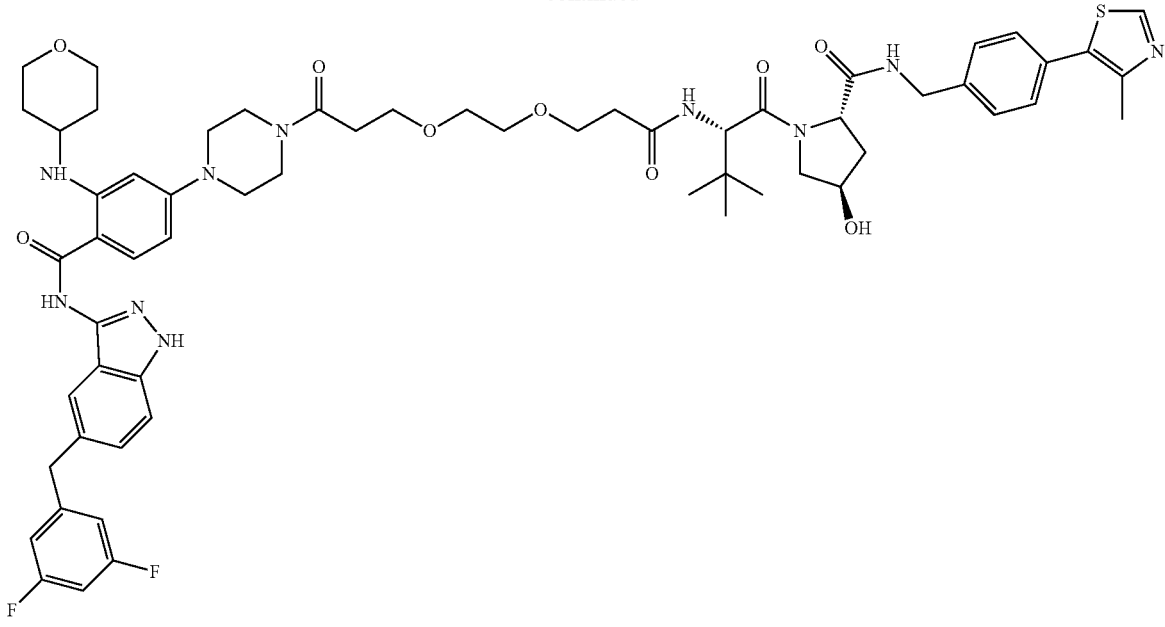 [SMILES: Cc1ncsc1-c1ccc(CNC(=O)[C@@H]2C[C@@H](O)CN2C(=O)[C@@H](NC(=O)CCOCCOCCC(=O)N2CCN(c3ccc(C(=O)Nc4n[nH]c5ccc(Cc6cc(F)cc(F)c6)cc45)c(NC4CCOCC4)c3)CC2)C(C)(C)C)cc1]

TR-038

CPD-038 was synthesized following the standard procedure for preparing CPD-053 (10 mg, yield 72%). ¹H NMR (400 MHz, DMSO-d₆) δ 11.09 (s, 1H), 9.65 (s, 1H), 8.06 (d, J=99.8 Hz, 1H), 7.87-7.50 (m, 1H), 7.42-7.18 (m, 1H), 7.18 (s, 1H), 7.24-7.01 (m, 3H), 6.87 (dd, J=73.2, 17.7 Hz, 1H), 6.96-6.71 (m, 1H), 6.96-6.61 (m, 1H), 6.52 (s, 1H), 5.32 (s, 1H), 5.11 (dd, J=53.0, 7.1 Hz, 1H), 4.00 (s, 1H), 3.68-3.57 (m, 10H), 3.30 (m, 4H), 2.86-2.77 (m, 4H), 2.58 (d, J=16.2 Hz, 1H), 2.35 (s, 1H), 1.97 (d, J=59.9 Hz, 2H), 1.54 (d, J=22.7 Hz, 4H), 1.28 (d, J=37.7 Hz, 6H), 0.91 (s, 1H), 0.85 (s, 1H). MS (ESI) m/z: 1147.5 [M+H]⁺.

Example 103: (2S,4R)-1-((S)-2-(tert-butyl)-16-(4-(4-((5-(3,5-Difluorobenzyl)-1H-indazol-3-yl)carbamoyl)-3-((tetrahydro-2H-pyran-4-yl)amino)phenyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide (CPD-039)

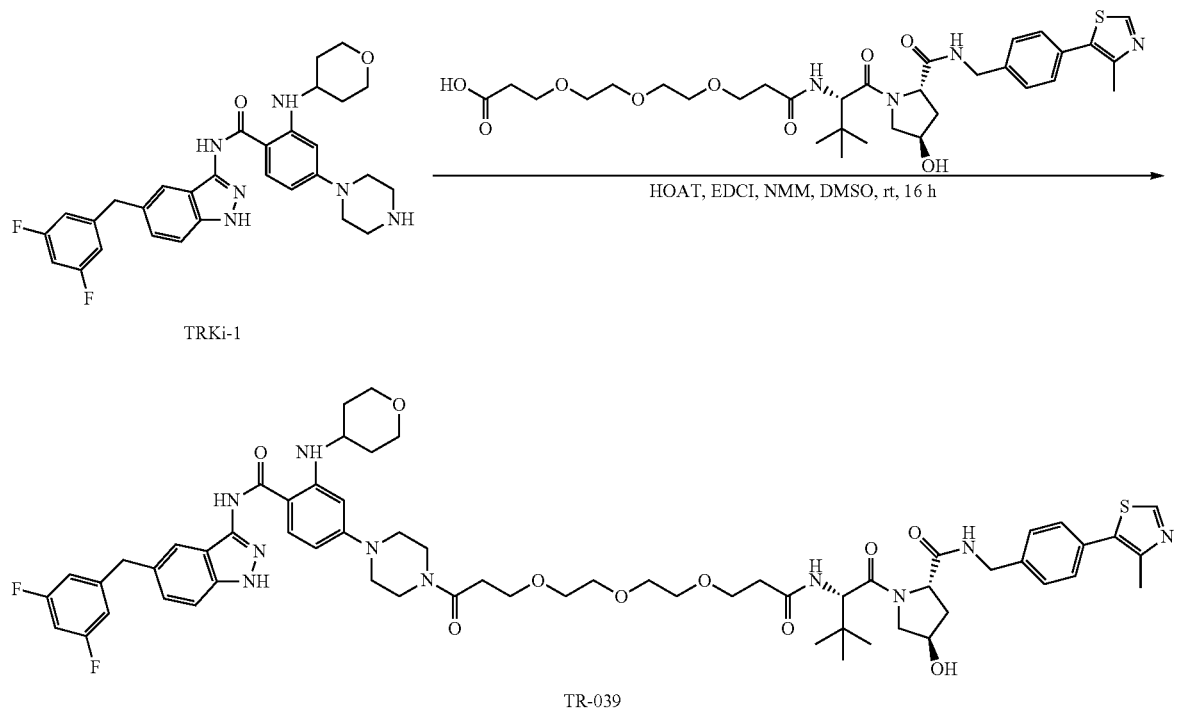

CPD-039 was synthesized following the standard procedure for preparing CPD-053 (13 mg, yield 77%). MS (ESI) m/z: 1191.5 [M+H]$^+$.

Example 104: (2S,4R)-1-((S)-2-(tert-butyl)-20-(4-(4-((5-(3,5-Difluorobenzyl)-1H-indazol-3-yl)carbamoyl)-3-((tetrahydro-2H-pyran-4-yl)amino)phenyl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide (CPD-040)

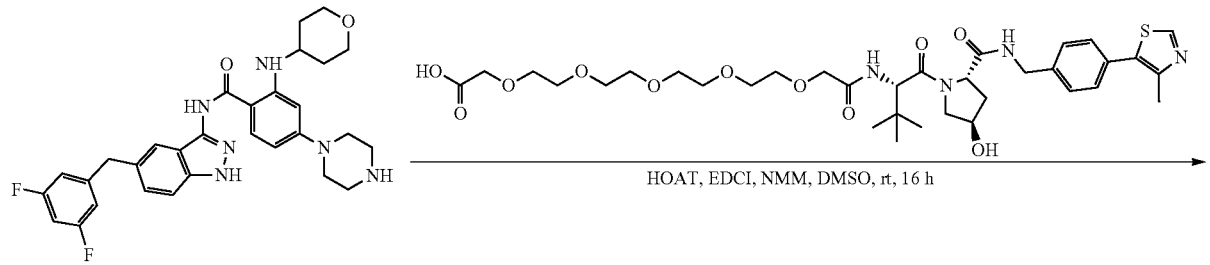

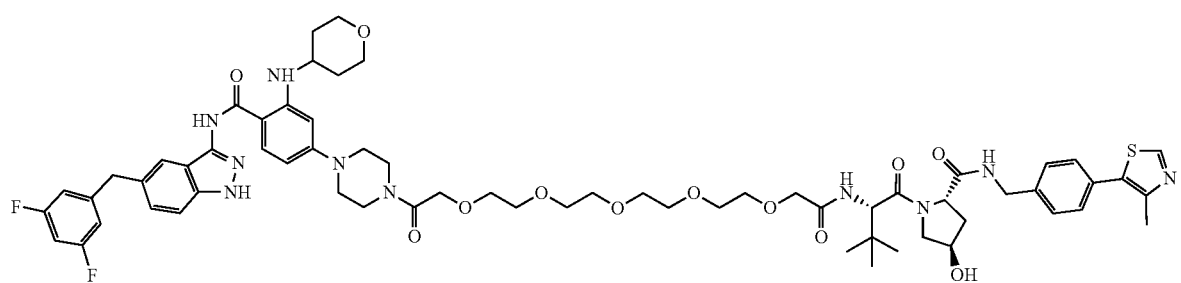

CPD-040 was synthesized following the standard procedure for preparing CPD-053 (10 mg, yield 71%). MS (ESI) m/z: 1251.6 [M+H]$^+$.

Example 105: (2S,4R)-1-((S)-2-(tert-butyl)-19-(4-(4-((5-(3,5-Difluorobenzyl)-1H-indazol-3-yl)carbamoyl)-3-((tetrahydro-2H-pyran-4-yl)amino)phenyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide (CPD-041)

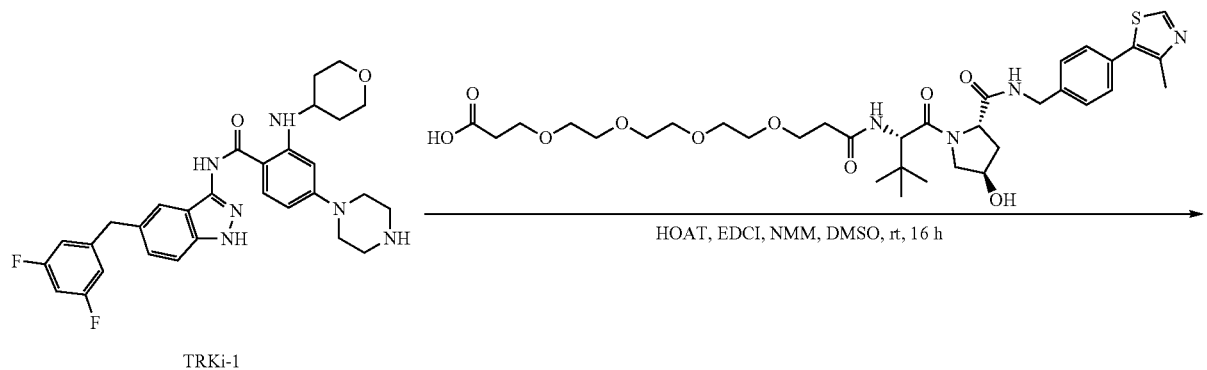

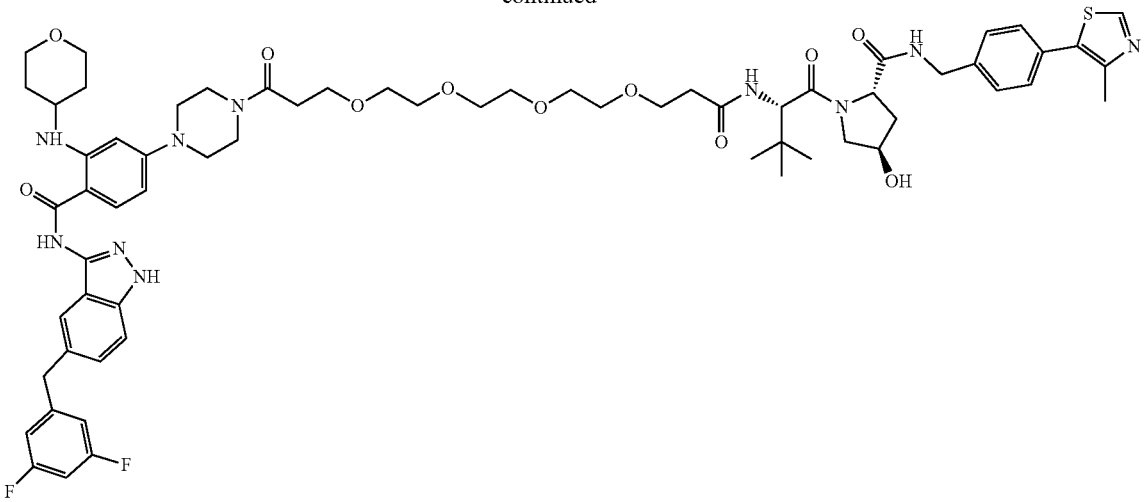 [SMILES: Cc1ncsc1-c1ccc(CNC(=O)[C@@H]2C[C@@H](O)CN2C(=O)[C@@H](NC(=O)CCOCCOCCOCCOCCC(=O)N2CCN(c3ccc(C(=O)Nc4n[nH]c5ccc(Cc6cc(F)cc(F)c6)cc45)c(NC4CCOCC4)c3)CC2)C(C)(C)C)cc1]
TR-041
CPD-041 was synthesized following the standard procedure for preparing CPD-053 (12 mg, yield 78%). MS (ESI) m/z: 1235.6 [M+H]$^+$.
Example 106: (2S,4R)-1-((S)-2-(2-(2-(2-(4-(4-((5-(3,5-Difluorobenzyl)-1H-indazol-3-yl)carbamoyl)-3-((tetrahydro-2H-pyran-4-yl)amino)phenyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide (CPD-042)
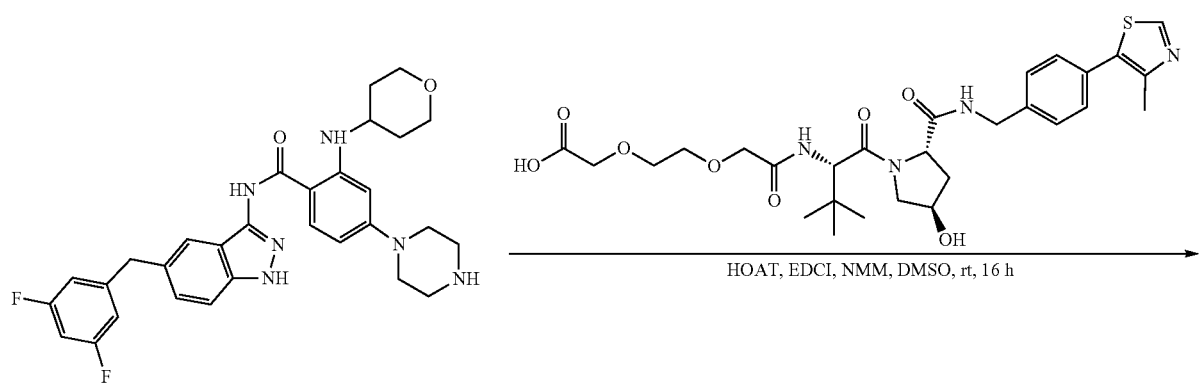
TRKi-1

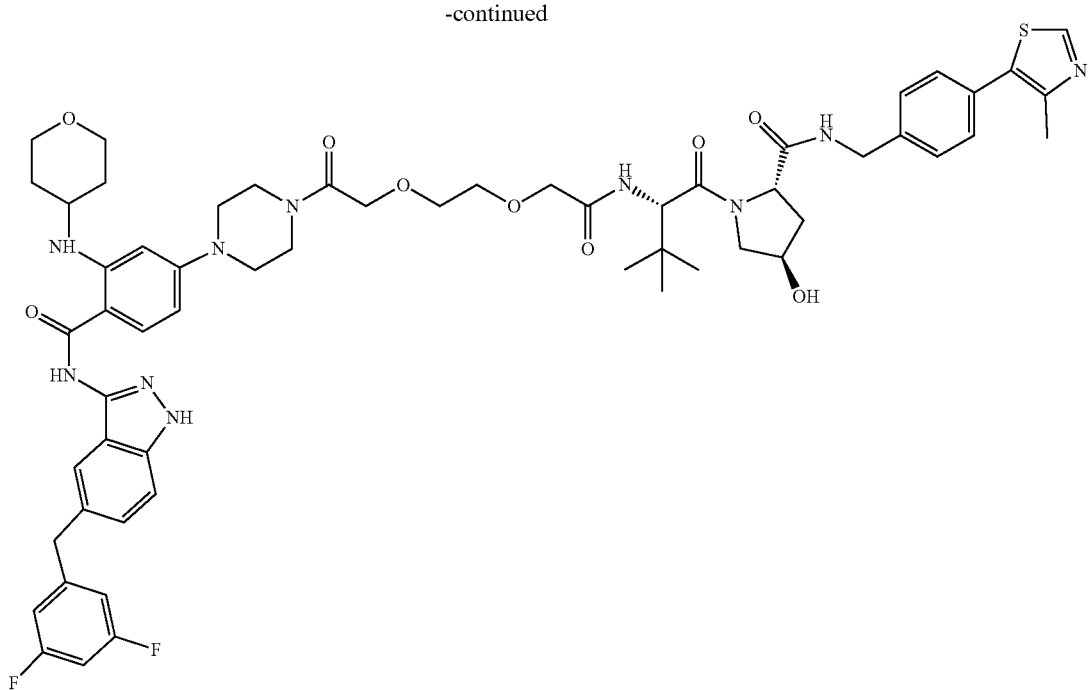
TR-042
CPD-042 was synthesized following the standard procedure for preparing CPD-053 (13 mg, yield 76%). MS (ESI) m/z: 1119.5 [M+H]+.
Example 107: (2S,4R)-1-((S)-2-(tert-butyl)-22-(4-(4-((5-(3,5-Difluorobenzyl)-1H-indazol-3-yl)carbamoyl)-3-((tetrahydro-2H-pyran-4-yl)amino)phenyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide (CPD-043)
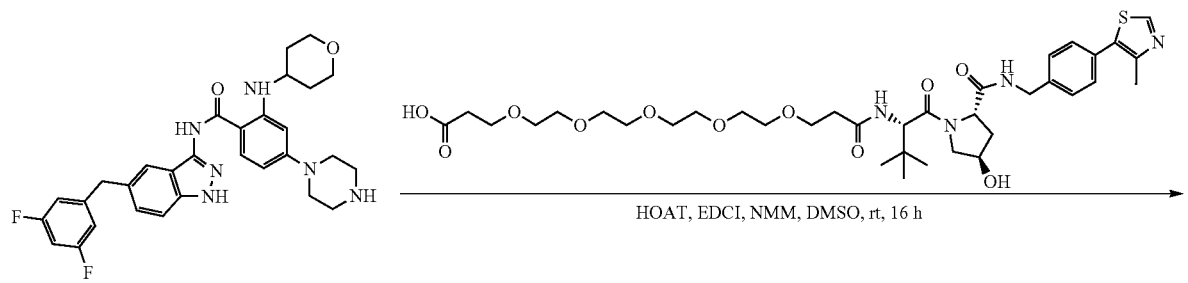
TRKi-1
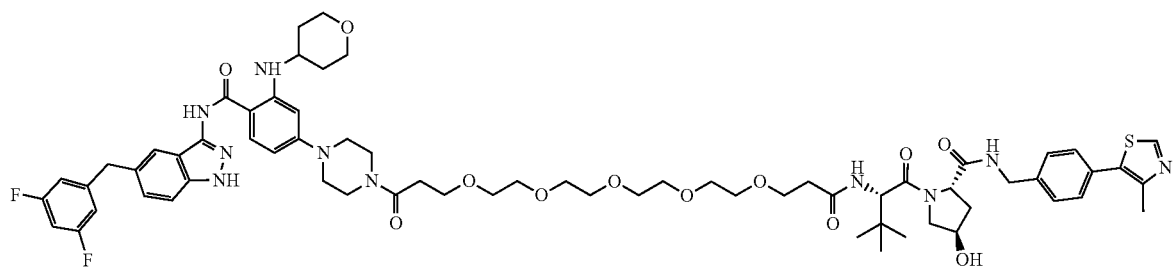
TR-043

CPD-043 was synthesized following the standard procedure for preparing CPD-053 (10 mg, yield 72%). MS (ESI) m/z: 1279.6 [M+H]+.

Example 108: (2S,4R)-1-((S)-2-(6-(4-(4-((5-(3,5-Difluorobenzyl)-1H-indazol-3-yl)carbamoyl)-3-((tetrahydro-2H-pyran-4-yl)amino)phenyl)piperazin-1-yl)-6-oxohexanamido)-3,3-dimethylbutanoyl)-4-hydroxy-N-(4-(4-methylthiazol-5-yl)benzyl)pyrrolidine-2-carboxamide (CPD-044)

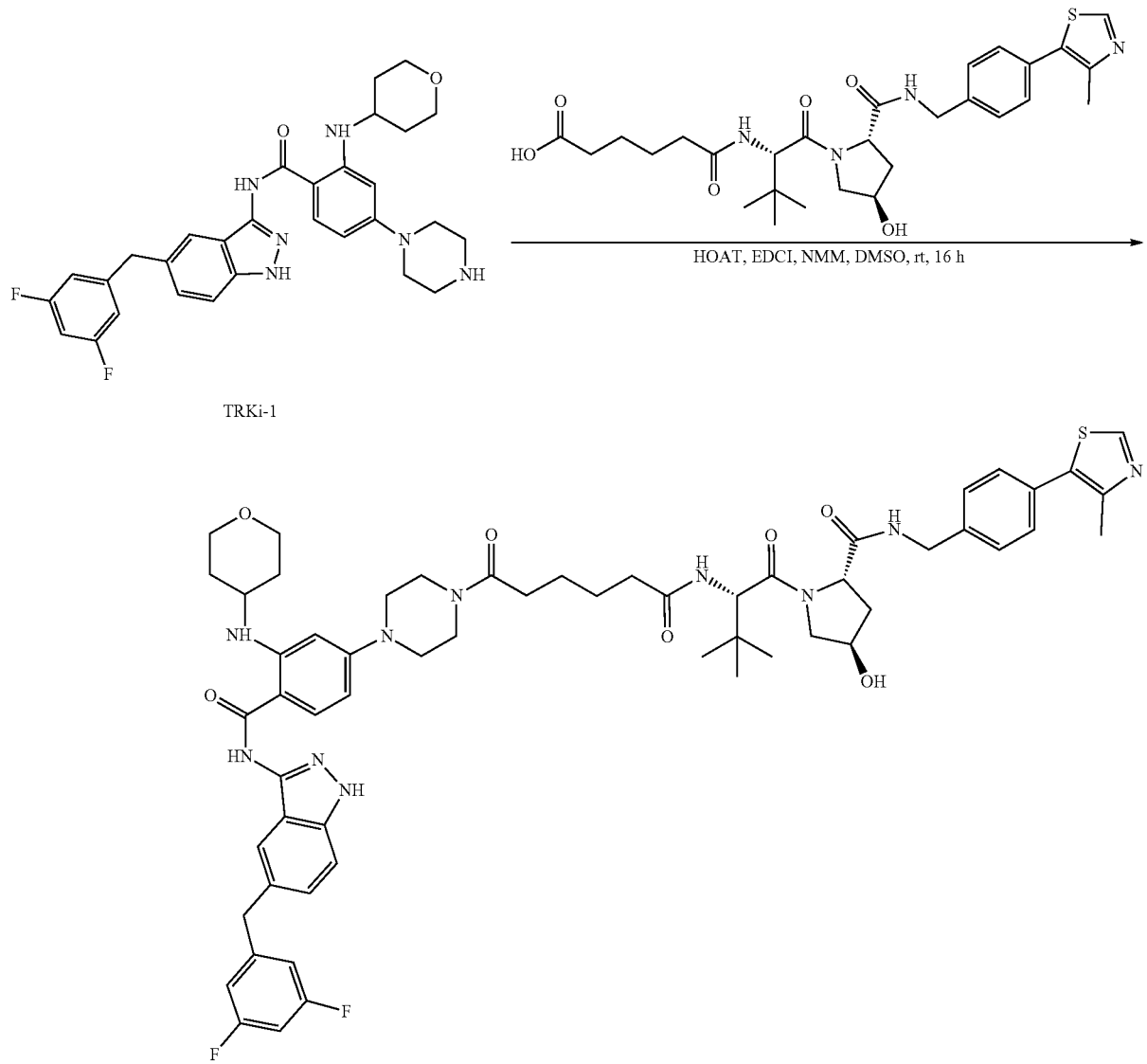

CPD-044 was synthesized following the standard procedure for preparing CPD-053 (13 mg, yield 76%). ¹H NMR (400 MHz, DMSO-d₆) δ 11.09 (s, 1H), 8.09 (s, 1H), 7.88 (d, J=9.8 Hz, 1H), 7.68-7.54 (m, 2H), 7.49 (s, 1H), 7.38 (dd, J=14.1, 7.9 Hz, 1H), 7.17 (t, J=8.9 Hz, 3H), 7.03 (t, J=9.2 Hz, 2H), 6.78 (t, J=19.4 Hz, 2H), 5.17 (d, J=7.9 Hz, 1H), 5.06 (dd, J=12.8, 5.3 Hz, 1H), 4.00 (dd, J=9.9, 5.2 Hz, 1H), 3.63 (dt, J=43.4, 13.8 Hz, 9H), 2.87 (dd, J=21.7, 9.7 Hz, 1H), 2.67-2.53 (m, 3H), 2.47 (t, J=6.3 Hz, 3H), 2.04 (s, 3H), 1.93-1.75 (m, 3H), 1.34-1.15 (m, 2H). MS (ESI) m/z: 1087.5 [M+H]+.

Example 109: (2S,4R)-1-((S)-2-(2-(2-(4-(4-((5-(3,5-Difluorobenzyl)-1H-indazol-3-yl)carbamoyl)-3-((tetrahydro-2H-pyran-4-yl)amino)phenyl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide (CPD-045)

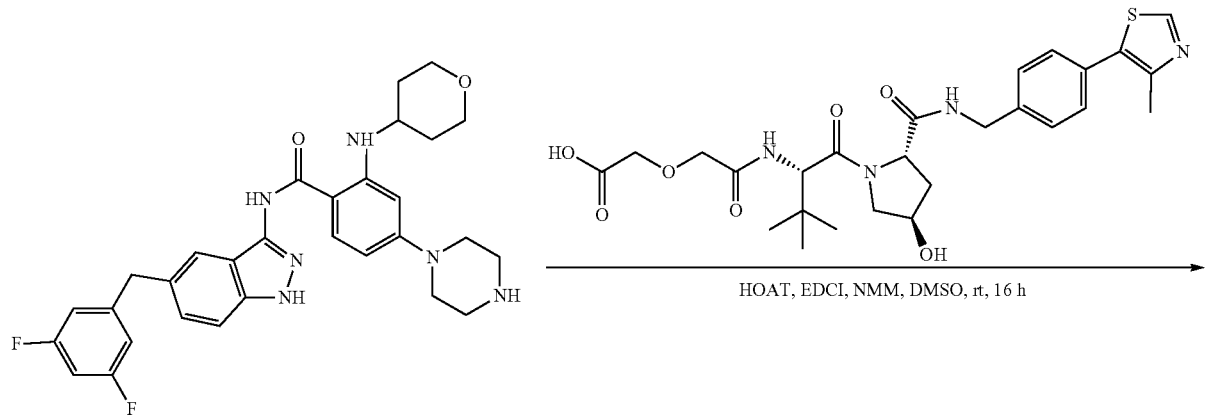

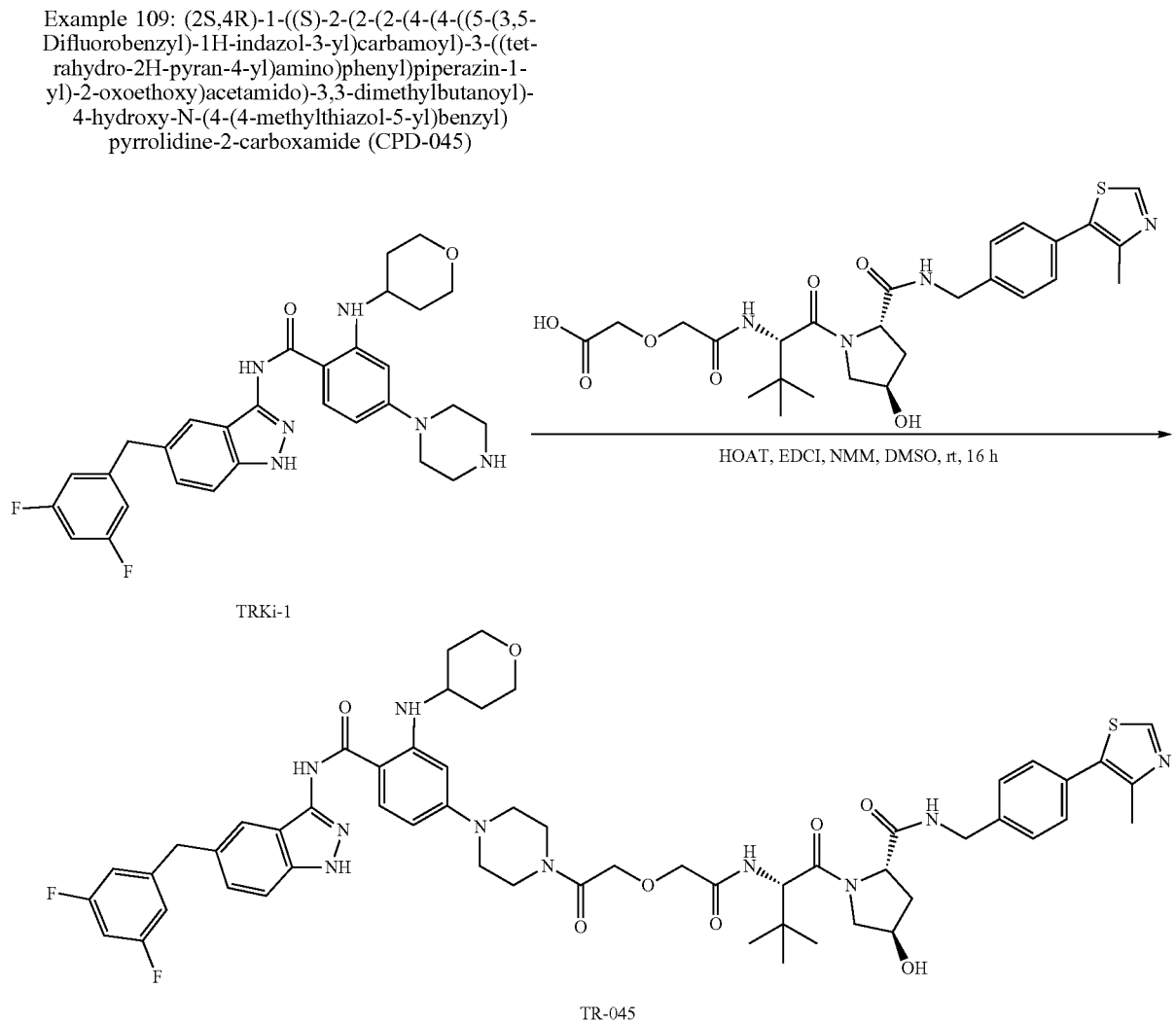

CPD-045 was synthesized following the standard procedure for preparing CPD-053 (15 mg, yield 79%). MS (ESI) m/z: 1075.5 [M+H]⁺.

Example 110: (2S,4R)-1-((S)-2-(4-(4-(4-((5-(3,5-Difluorobenzyl)-1H-indazol-3-yl)carbamoyl)-3-((tetrahydro-2H-pyran-4-yl)amino)phenyl)piperazin-1-yl)-4-oxobutanamido)-3,3-dimethylbutanoyl)-4-hydroxy-N-(4-(4-methylthiazol-5-yl)benzyl)pyrrolidine-2-carboxamide (CPD-046)

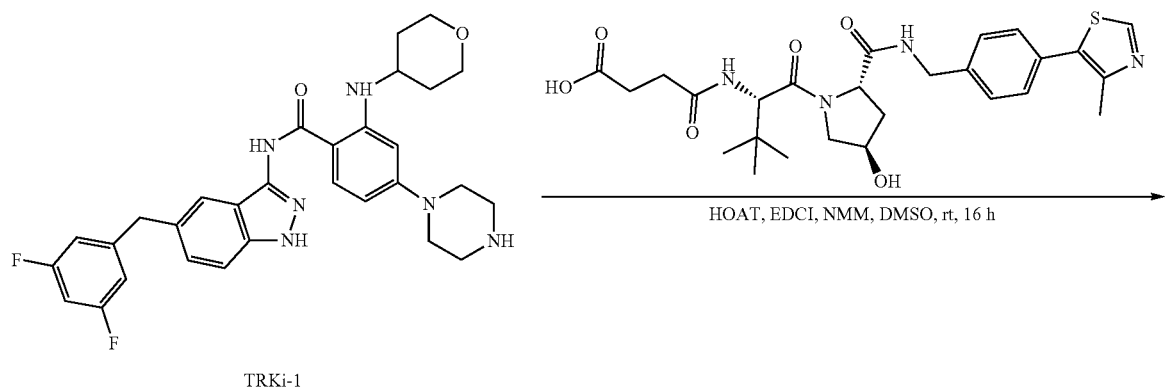

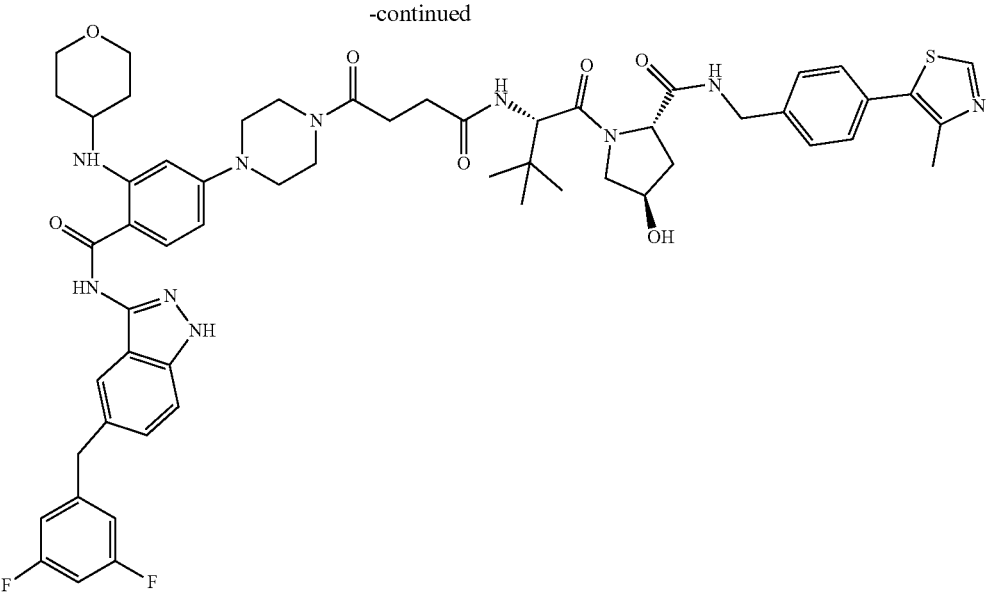
TR-046
CPD-046 was synthesized following the standard procedure for preparing CPD-053 (11 mg, yield 73%). MS (ESI) m/z: 1059.5 [M+H]+.
Example 111: (2S,4R)-1-((S)-2-(7-(4-(4-(4-((5-(3,5-Difluorobenzyl)-1H-indazol-3-yl)carbamoyl)-3-((tetrahydro-2H-pyran-4-yl)amino)phenyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide (CPD-047)
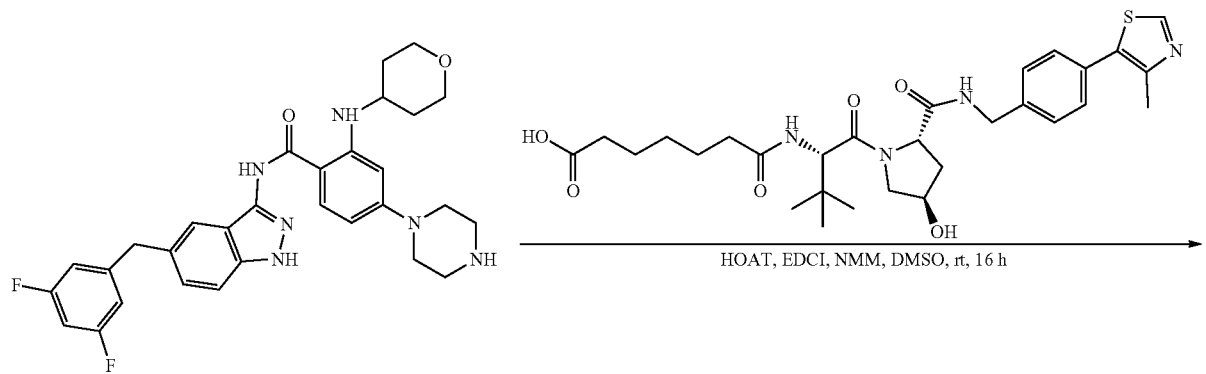
TRKi-1
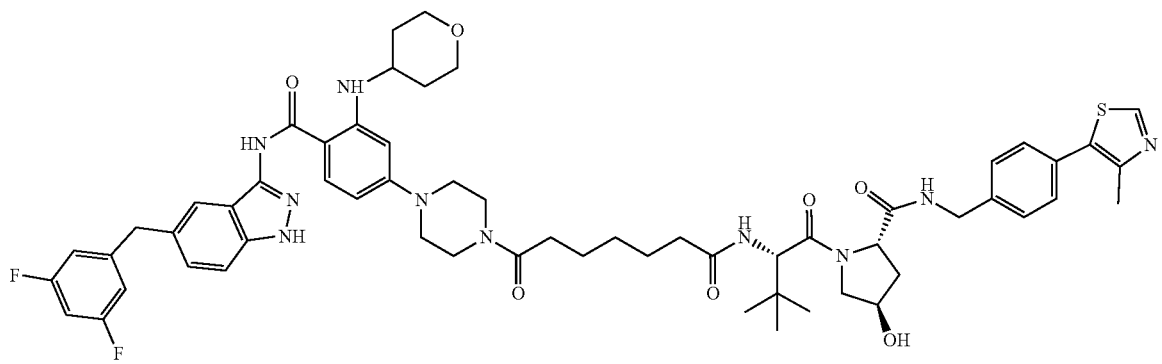
TR-047

CPD-047 was synthesized following the standard procedure for preparing CPD-053 (15 mg, yield 78%). MS (ESI) m/z: 1101.5 [M+H]+.

Example 112: (2S,4R)-1-((S)-2-(3-(3-(4-(4-((5-(3,5-Difluorobenzyl)-1H-indazol-3-yl)carbamoyl)-3-((tetrahydro-2H-pyran-4-yl)amino)phenyl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide (CPD-048)

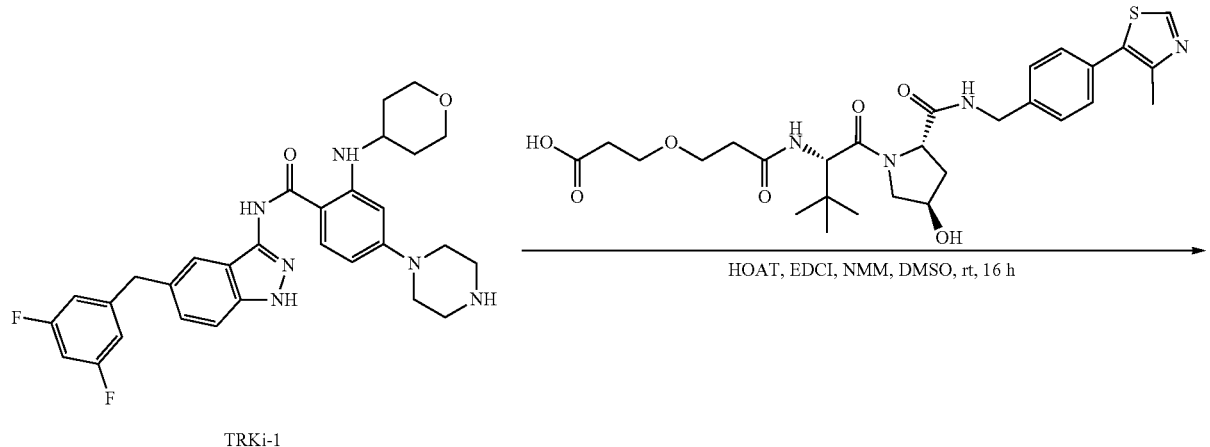

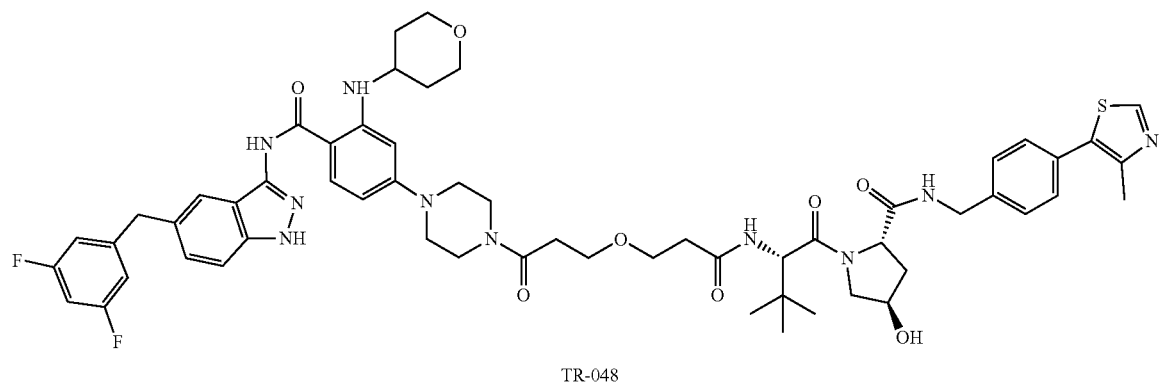

CPD-048 was synthesized following the standard procedure for preparing CPD-053 (11 mg, yield 72%). MS (ESI) m/z: 1103.5 [M+H]+.

Example 113: N-(5-(3,5-Difluorobenzyl)-1H-indazol-3-yl)-4-(4-(7-((2-(2,6-dioxopiperidin-3-yl)-1,3-dioxoisoindolin-4-yl)amino)heptanoyl)piperazin-1-yl)-2-((tetrahydro-2H-pyran-4-yl)amino)benzamide (CPD-049)
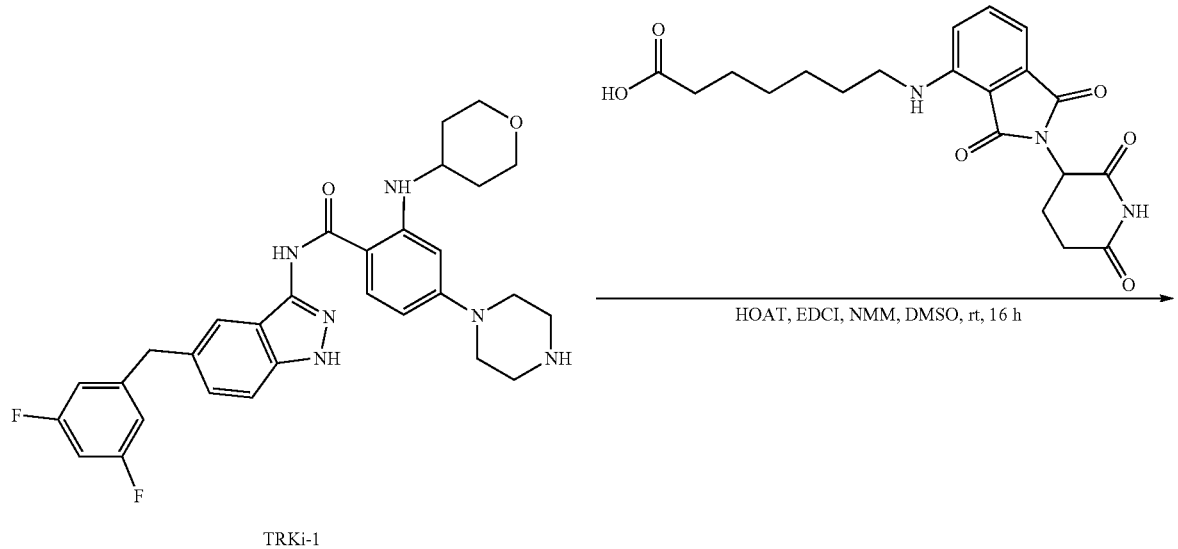
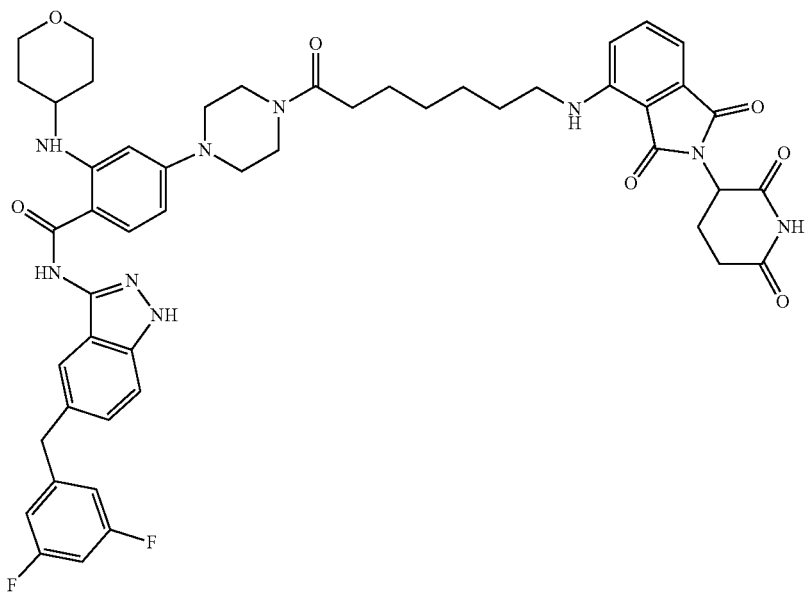
CPD-049 was synthesized following the standard procedure for preparing CPD-053 (15 mg, yield 81%). MS (ESI) m/z: 930.4 [M+H]+.

Example 114: N-(5-(3,5-Difluorobenzyl)-1H-indazol-3-yl)-4-(4-(5-((2-(2,6-dioxopiperidin-3-yl)-1,3-dioxoisoindolin-4-yl)amino)pentanoyl)piperazin-1-yl)-2-((tetrahydro-2H-pyran-4-yl)amino)benzamide (CPD-050)
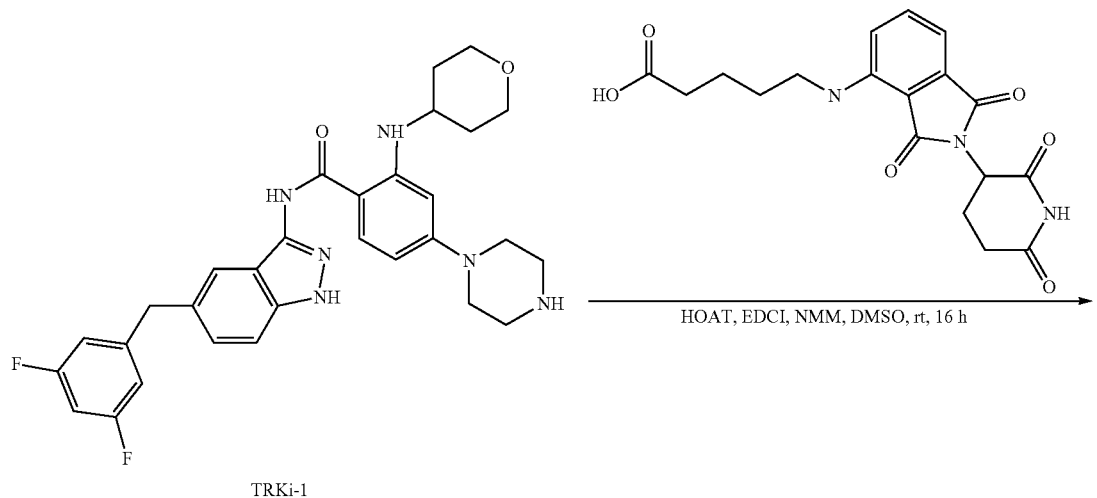
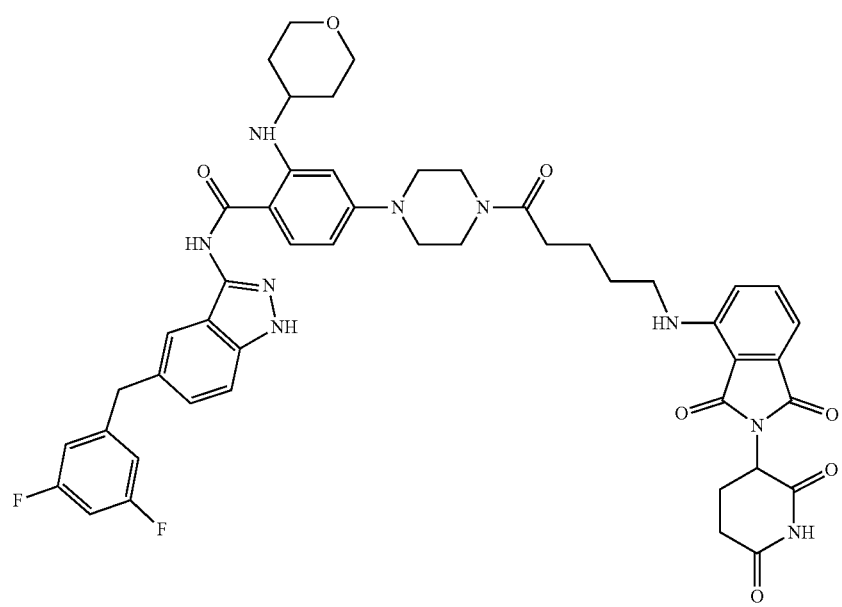 [SMILES: O=C1CCC(N2C(=O)c3cccc(NCCCCC(=O)N4CCN(c5ccc(C(=O)Nc6n[nH]c7ccc(Cc8cc(F)cc(F)c8)cc67)c(NC6CCOCC6)c5)CC4)c3C2=O)C(=O)N1]
CPD-050 was synthesized following the standard procedure for preparing CPD-053 (12 mg, yield 76%). MS (ESI) m/z: 902.4 [M+H]$^+$.

Example 115: N-(5-(3,5-Difluorobenzyl)-1H-indazol-3-yl)-4-(4-(3-((2-(2,6-dioxopiperidin-3-yl)-1,3-dioxoisoindolin-4-yl)amino)propanoyl)piperazin-1-yl)-2-((tetrahydro-2H-pyran-4-yl)amino)benzamide (CPD-051)

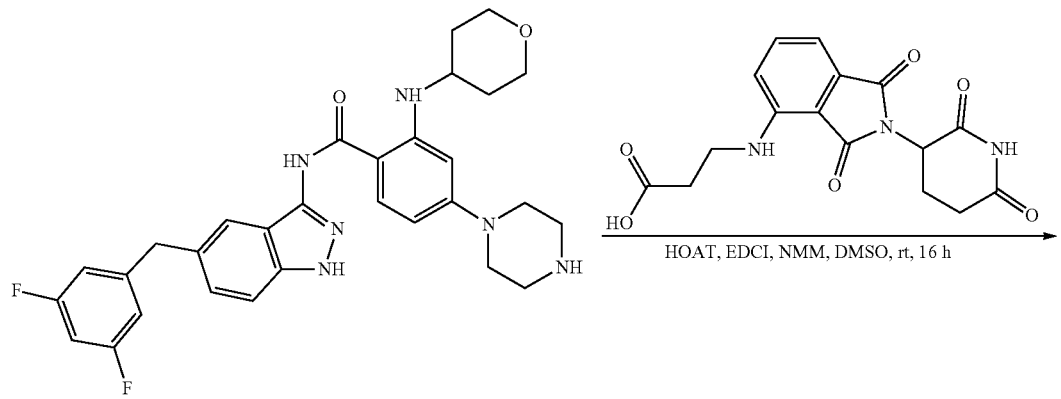

TRKi-1

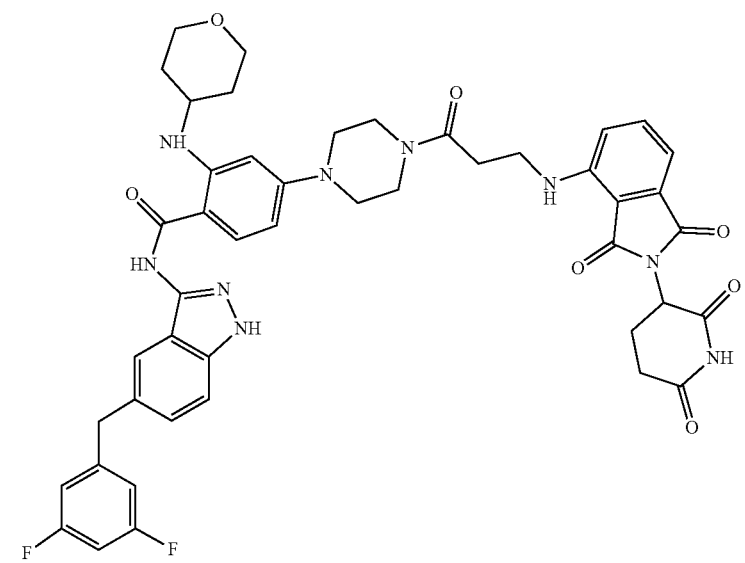

TR-051

CPD-051 was synthesized following the standard procedure for preparing CPD-053 (11 mg, yield 72%). $^1$H NMR (400 MHz, DMSO-d$_6$) δ 12.64 (s, 1H), 11.09 (s, 1H), 10.11 (s, 1H), 8.29 (s, 1H), 7.82 (s, 1H), 7.60 (d, J=7.8 Hz, 1H), 7.49 (s, 1H), 7.41 (d, J=8.5 Hz, 1H), 7.25 (d, J=8.7 Hz, 1H), 7.18 (d, J=8.5 Hz, 1H), 7.01 (dd, J=24.2, 7.5 Hz, 4H), 6.24 (d, J=8.8 Hz, 1H), 6.13 (s, 1H), 5.04 (d, J=8.3 Hz, 1H), 3.81 (s, 2H), 3.59 (m, 8H), 3.49 (t, J=10.0 Hz, 3H), 3.29 (s, 4H), 2.86 (d, J=13.9 Hz, 1H), 2.73 (s, 2H), 1.94 (d, J=12.9 Hz, 4H), 1.35 (d, J=10.2 Hz, 2H), 1.24 (s, 1H). MS (ESI) m/z: 874.3 [M+H]$^+$.

Example 116: N-(5-(3,5-Difluorobenzyl)-1H-indazol-3-yl)-4-(4-(8-((2-(2,6-dioxopiperidin-3-yl)-1,3-dioxoisoindolin-4-yl)amino)octanoyl)piperazin-1-yl)-2-((tetrahydro-2H-pyran-4-yl)amino)benzamide (CPD-052)
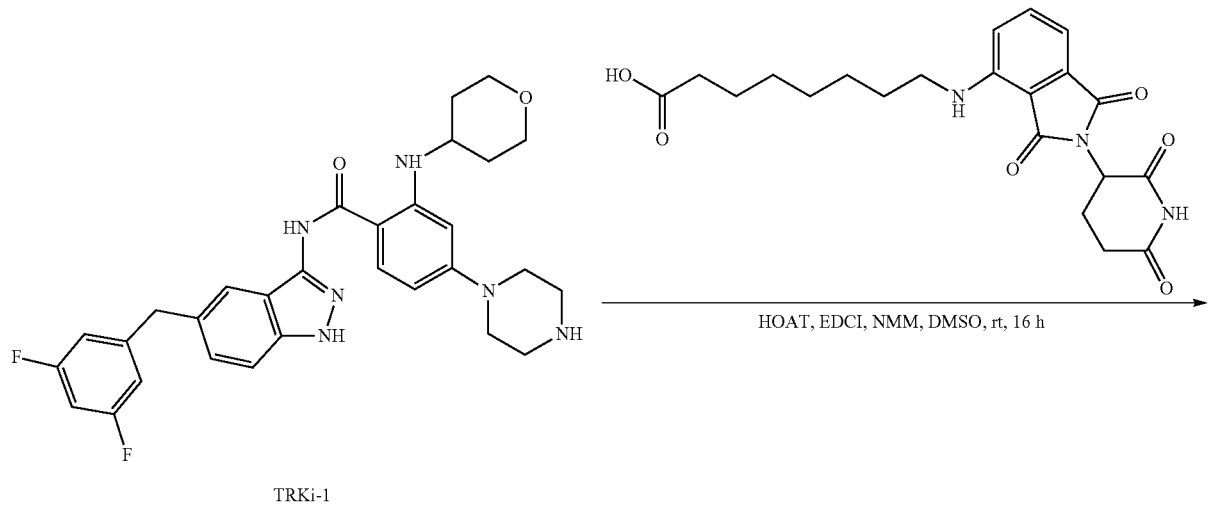
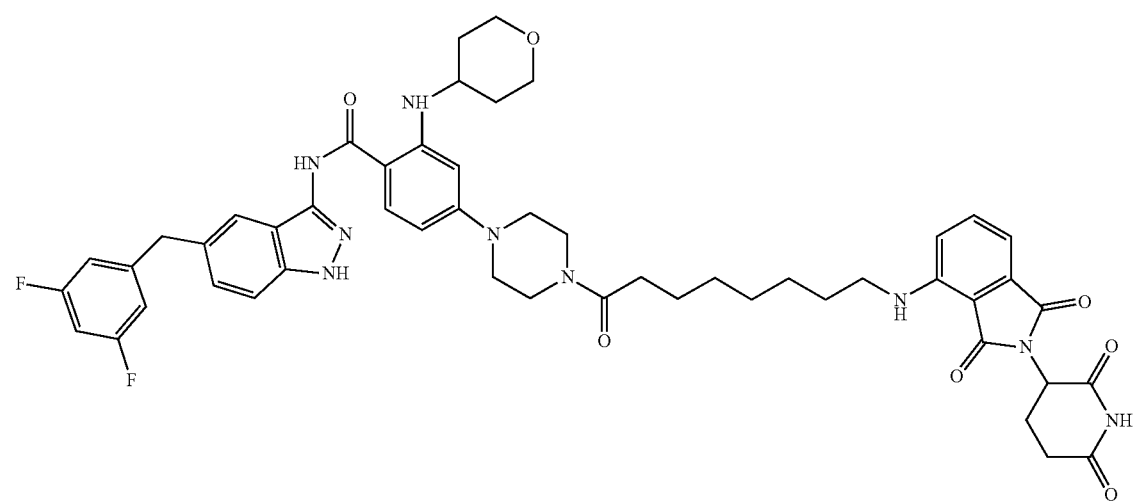
CPD-052 was synthesized following the standard procedure for preparing CPD-053 (14 mg, yield 77%). MS (ESI) m/z: 944.4 [M+H]+.

Example 117: N-(5-(3,5-Difluorobenzyl)-1H-indazol-3-yl)-4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-2-((tetrahydro-2H-pyran-4-yl)amino)benzamide (CPD-054)
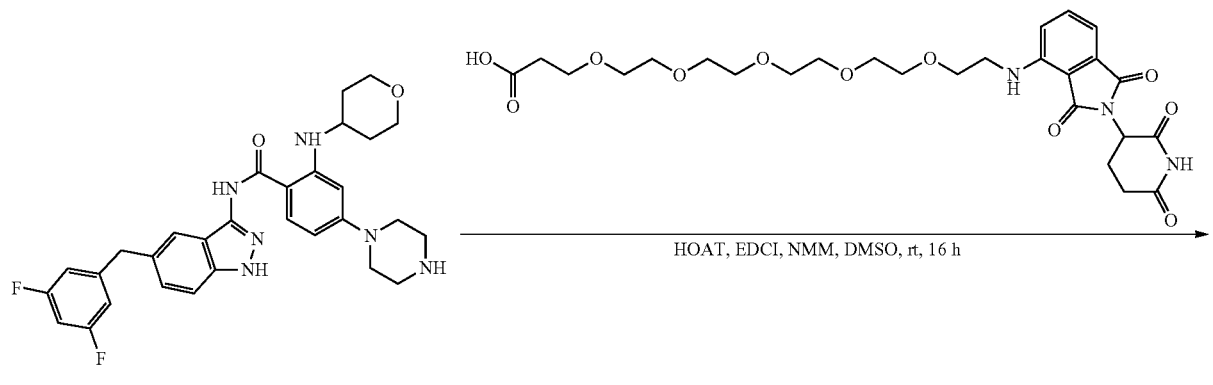
CPD-054 was synthesized following the standard procedure for preparing CPD-053 (12 mg, yield 73%). MS (ESI) m/z: 1094.5 [M+H]$^+$.

Example 118: N-(5-(3,5-Difluorobenzyl)-1H-indazol-3-yl)-4-(4-((2-(2,6-dioxopiperidin-3-yl)-1,3-dioxoisoindolin-4-yl)glycyl)piperazin-1-yl)-2-((tetrahydro-2H-pyran-4-yl)amino)benzamide (CPD-055)
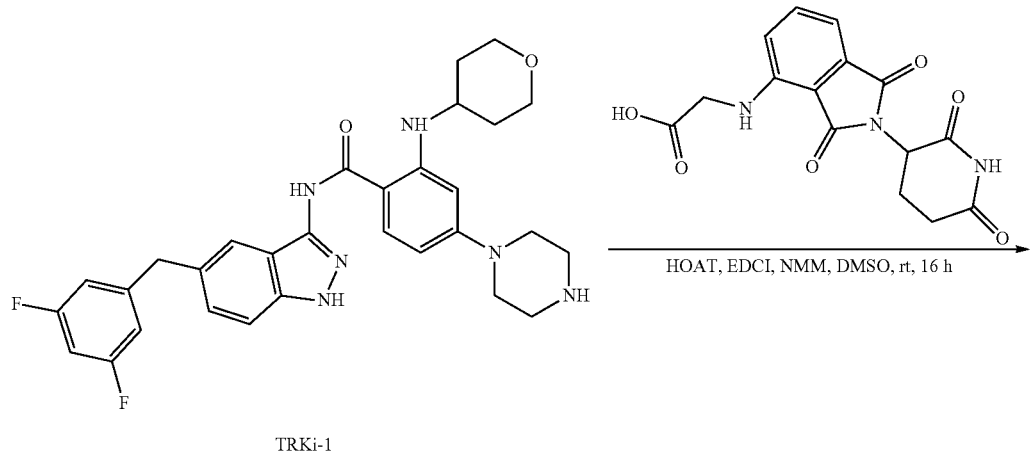
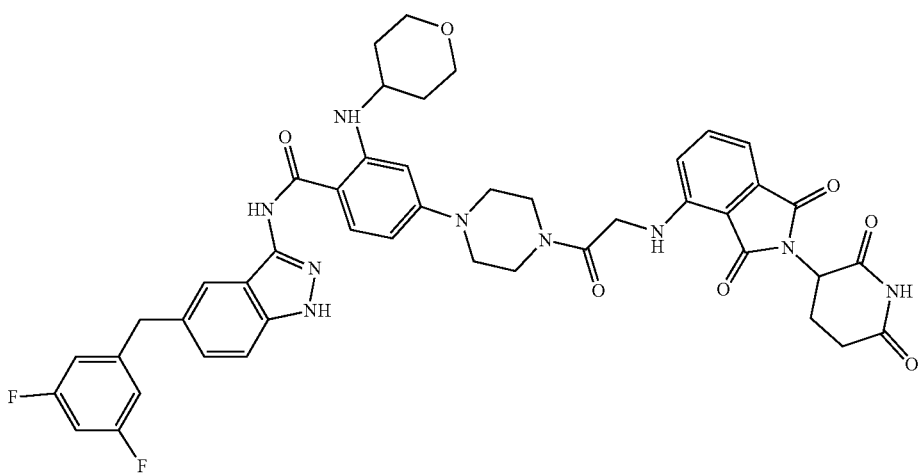 [SMILES: O=C1CCC(N2C(=O)c3cccc(NCC(=O)N4CCN(c5ccc(C(=O)Nc6n[nH]c7ccc(Cc8cc(F)cc(F)c8)cc67)c(NC6CCOCC6)c5)CC4)c3C2=O)C(=O)N1]
CPD-055 was synthesized following the standard procedure for preparing CPD-053 (14 mg, yield 79%). MS (ESI) m/z: 860.3 [M+H]⁺.

Example 119: N-(5-(3,5-Difluorobenzyl)-1H-indazol-3-yl)-4-(4-(6-((2-(2,6-dioxopiperidin-3-yl)-1,3-dioxoisoindolin-4-yl)amino)hexanoyl)piperazin-1-yl)-2-((tetrahydro-2H-pyran-4-yl)amino)benzamide (CPD-056)

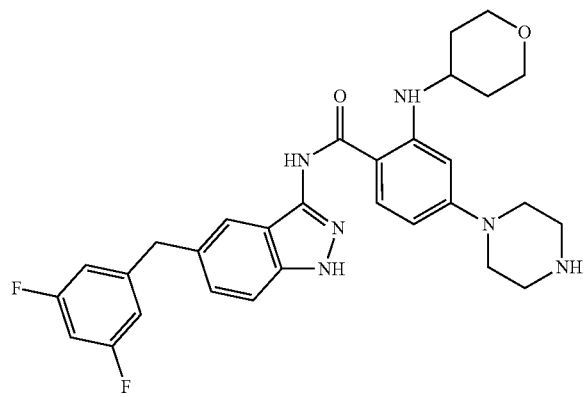

TRKi-1

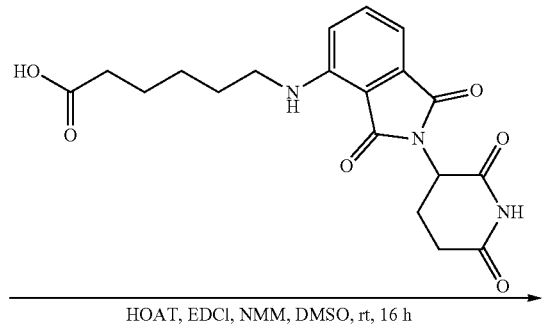

HOAT, EDCl, NMM, DMSO, rt, 16 h

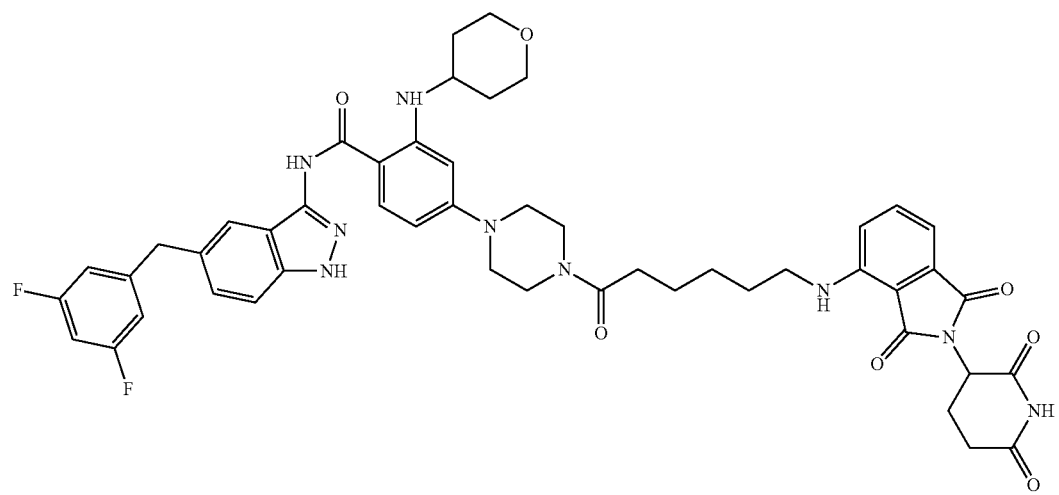

TR-056

CPD-056 was synthesized following the standard procedure for preparing CPD-053 (11 mg, yield 71%). $^1$H NMR (400 MHz, DMSO-d$_6$) δ 12.65 (s, 1H), 11.10 (s, 1H), 10.12 (s, 1H), 8.30 (s, 1H), 7.82 (d, J=9.0 Hz, 1H), 7.67-7.54 (m, 1H), 7.49 (s, 1H), 7.41 (d, J=8.6 Hz, 1H), 7.25 (d, J=8.6 Hz, 1H), 7.17-6.90 (m, 3H), 6.60 (d, J=42.5 Hz, 1H), 6.25 (d, J=8.4 Hz, 1H), 6.14 (s, 1H), 5.33 (d, J=4.8 Hz, 1H), 5.05 (dd, J=12.8, 5.2 Hz, 1H), 4.04 (s, 1H), 3.82 (d, J=11.5 Hz, 1H), 3.74-3.44 (m, 5H), 3.26 (dd, J=39.1, 19.2 Hz, 5H), 3.00-2.52 (m, 3H), 2.37 (t, J=7.2 Hz, 2H), 2.12-1.81 (m, 3H), 1.58 (dd, J=14.2, 7.0 Hz, 3H), 1.51-1.08 (m, 8H), 0.84 (d, J=6.9 Hz, 1H). MS (ESI) m/z: 916.4 [M+H]$^+$.

Example 120: N-(5-(3,5-Difluorobenzyl)-1H-indazol-3-yl)-4-(4-(3-(2-(2-(2-((2-(2,6-dioxopiperidin-3-yl)-1,3-dioxoisoindolin-4-yl)amino)ethoxy)ethoxy)ethoxy)propanoyl) piperazin-1-yl)-2-((tetrahydro-2H-pyran-4-yl)amino)benzamide (CPD-057)

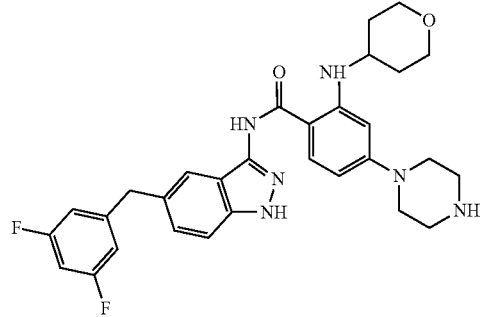

TRKi-1

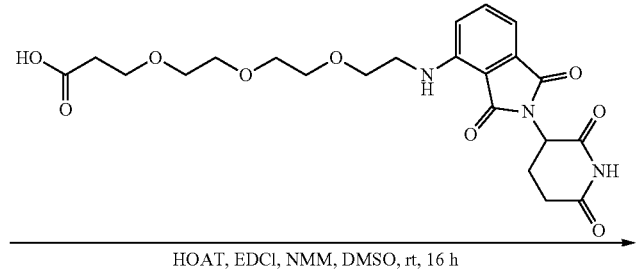

HOAT, EDCl, NMM, DMSO, rt, 16 h

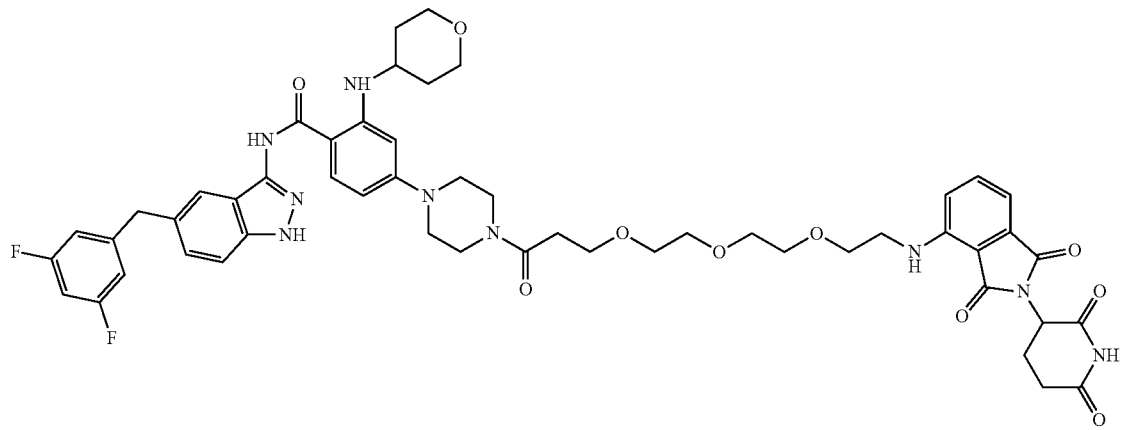

TR-057

CPD-057 was synthesized following the standard procedure for preparing CPD-053 (14 mg, yield 78%). $^1$H NMR (400 MHz, DMSO-d$_6$) δ 12.75 (d, J=68.8 Hz, 1H), 11.09 (s, 1H), 10.20 (d, J=59.5 Hz, 1H), 7.82 (d, J=9.0 Hz, 1H), 7.64-7.53 (m, 1H), 7.46 (d, J=17.1 Hz, 1H), 7.41 (d, J=8.6 Hz, 1H), 7.29-7.20 (m, 1H), 7.20-7.07 (m, 1H), 6.99 (dt, J=38.9, 17.1 Hz, 3H), 6.63 (d, J=20.8 Hz, 1H), 6.24 (d, J=7.8 Hz, 1H), 6.15 (s, 1H), 5.32 (t, J=4.7 Hz, 1H), 5.06 (dd, J=12.9, 5.3 Hz, 1H), 4.04 (s, 2H), 3.89-3.74 (m, 2H), 3.72-3.56 (m, 8H), 3.24 (dd, J=28.3, 24.5 Hz, 3H), 2.99-2.81 (m, 1H), 2.77 (d, J=4.8 Hz, 1H), 2.70-2.51 (m, 9H), 2.11-1.84 (m, 3H), 1.53-1.10 (m, 7H), 0.85 (t, J=6.6 Hz, 1H). MS (ESI) m/z: 1006.4 [M+H]$^+$.

Example 121: (2S,4R)-1-((S)-2-(tert-butyl)-14-(4-(4-((5-(3,5-Difluorobenzyl)-1H-indazol-3-yl)carbamoyl)-3-((tetrahydro-2H-pyran-4-yl)amino)phenyl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide (CPD-058)

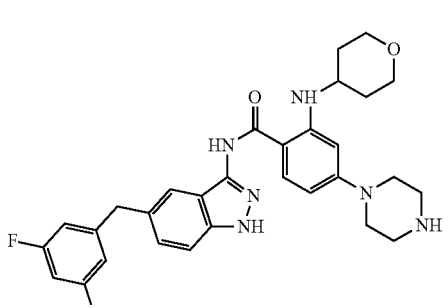

TRKi-1

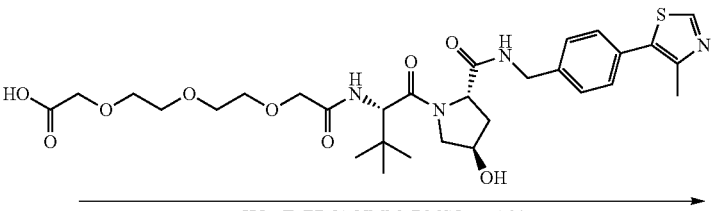

HOAT, EDCl, NMM, DMSO, rt, 16 h

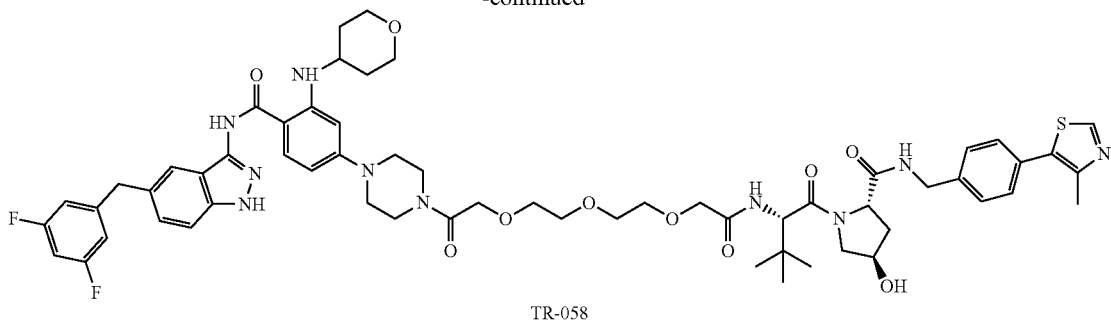
TR-058
CPD-058 was synthesized following the standard procedure for preparing CPD-053 (11 mg, yield 72%). MS (ESI) m/z: 1163.5 [M+H]$^+$.
Example 122: N-(2-(2-(2-(2-((2-(2,6-Dioxopiperidin-3-yl)-1,3-dioxoisoindolin-4-yl)amino)ethoxy)ethoxy)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (CPD-059)
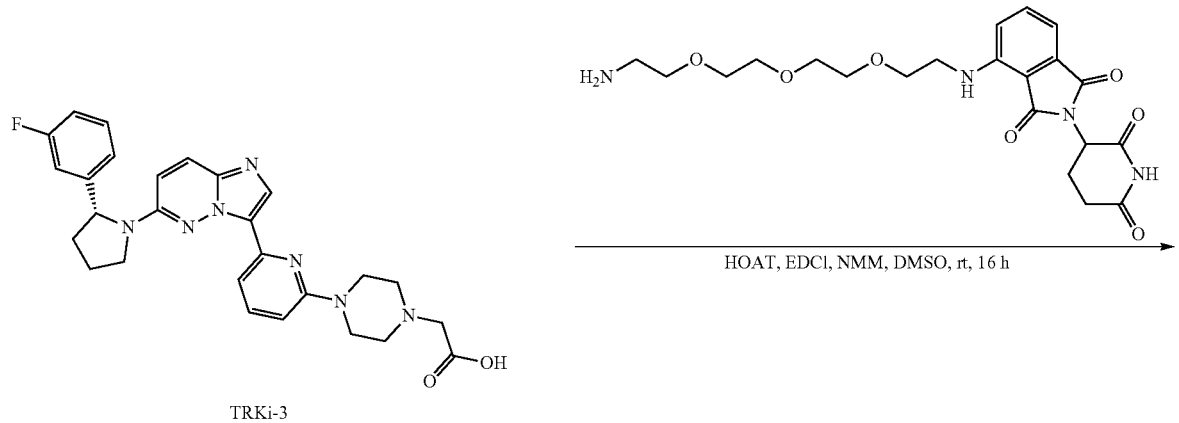
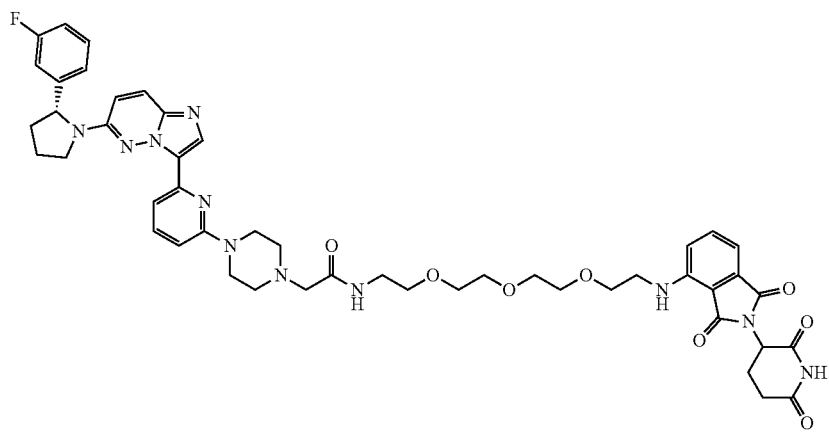
TR-059

CPD-059 was synthesized following the standard procedure for preparing CPD-053 (14 mg, yield 76%). MS (ESI) m/z: 932.4 [M+H]+.

Example 123: N-(2-((2-(2,6-Dioxopiperidin-3-yl)-1,3-dioxoisoindolin-4-yl)amino)ethyl)-2-(4-(6-6-((R)-2-(3-fluorophenyl)pyrrolidin-1-yl)imidazo[1,2-b]pyridazin-3-yl)pyridin-2-yl)piperazin-1-yl)acetamide (CPD-060)

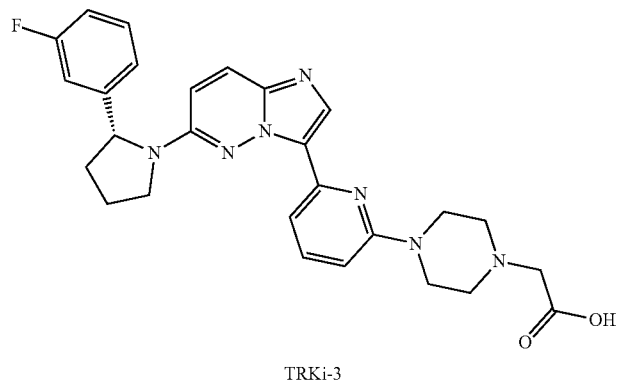
TRKi-3

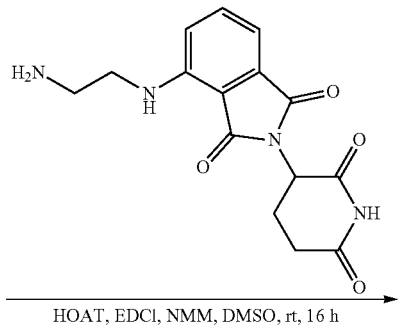
HOAT, EDCl, NMM, DMSO, rt, 16 h

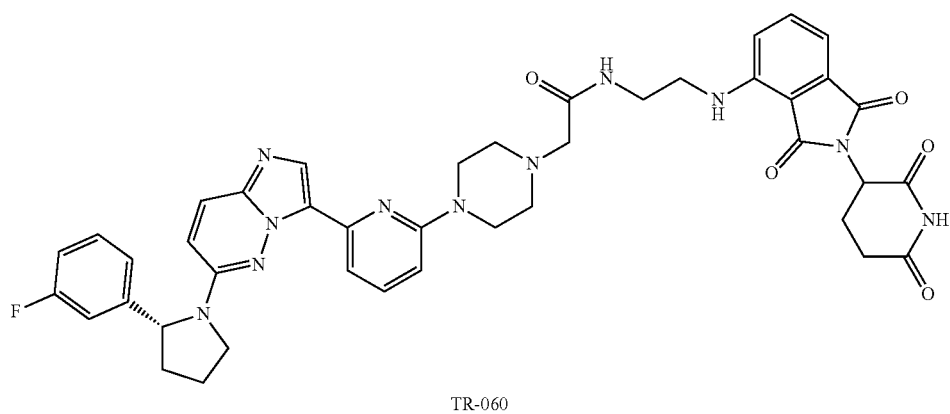
TR-060

CPD-060 was synthesized following the standard procedure for preparing CPD-053 (13 mg, yield 78%). $^1$H NMR (400 MHz, DMSO-$d_6$) δ 11.12 (d, J=8.8 Hz, 1H), 10.50 (s, 1H), 8.94 (t, J=5.4 Hz, 1H), 8.51 (s, 1H), 8.13 (d, J=10.9 Hz, 1H), 7.61 (dt, J=13.9, 7.0 Hz, 2H), 7.45-7.35 (m, 1H), 7.26-7.12 (m, 3H), 7.05 (t, J=7.2 Hz, 2H), 6.95 (d, J=8.9 Hz, 1H), 6.76 (s, 1H), 5.23 (d, J=6.3 Hz, 1H), 5.07 (dd, J=12.8, 5.5 Hz, 1H), 4.47 (s, 2H), 4.14-3.93 (m, 4H), 3.72 (dd, J=17.8, 8.2 Hz, 3H), 3.42-3.36 (m, 4H), 3.21 (s, 3H), 2.95-2.80 (m, 1H), 2.65-2.53 (m, 2H), 2.04 (dd, J=31.3, 12.8 Hz, 3H), 1.91 (s, 2H), 1.25 (d, J=10.1 Hz, 1H). MS (ESI) m/z: 800.3 [M+H]+.

Example 124: (2S,4R)-1-((S)-2-(8-(2-(4-(4-((5-(3,5-Difluorobenzyl)-1H-indazol-3-yl)carbamoyl)-3-((tetrahydro-2H-pyran-4-yl)amino)phenyl)piperazin-1-yl)acetamido)octanamido)-3,3-dimethylbutanoyl)-4-hydroxy-N-(4-(4-methylthiazol-5-yl)benzyl)pyrrolidine-2-carboxamide (CPD-061)

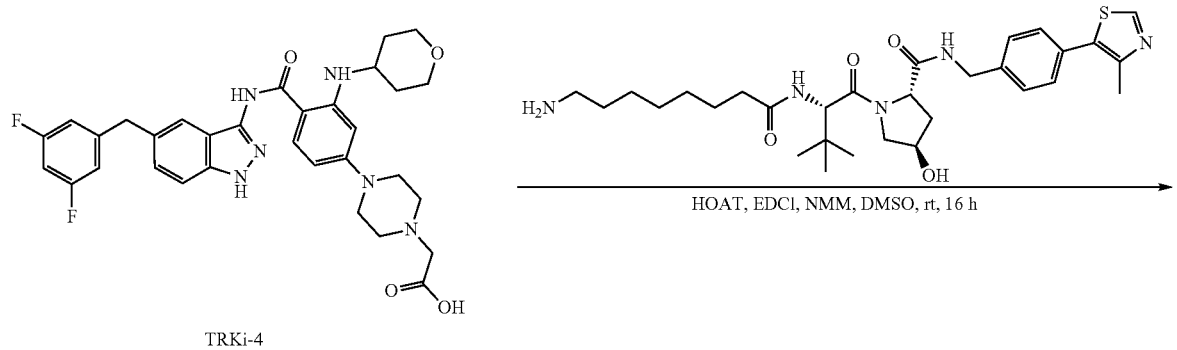

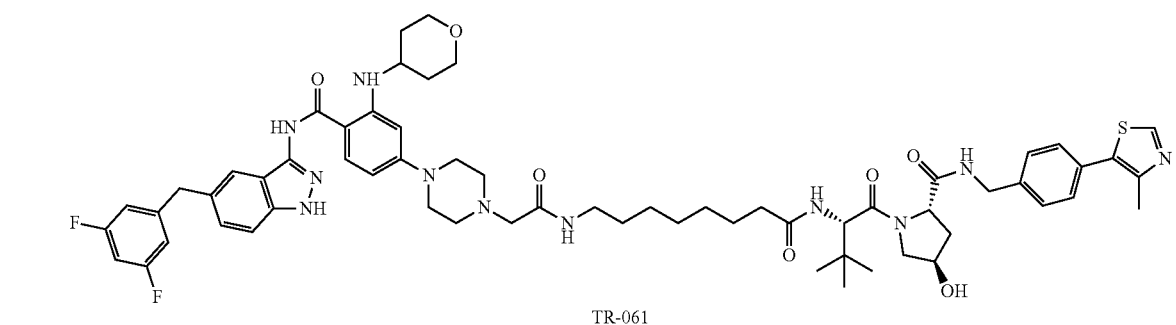

CPD-061 was synthesized following the standard procedure for preparing CPD-053 (10 mg, yield 76%). MS (ESI) m/z: 1158.6 [M+H]$^+$.

Example 125: N-(5-(3,5-Difluorobenzyl)-1H-indazol-3-yl)-4-(4-(2-((2-((2-(2,6-dioxopiperidin-3-yl)-1,3-dioxoisoindolin-4-yl)amino)ethyl)amino)-2-oxoethyl)piperazin-1-yl)-2-((tetrahydro-2H-pyran-4-yl)amino)benzamide (CPD-062)

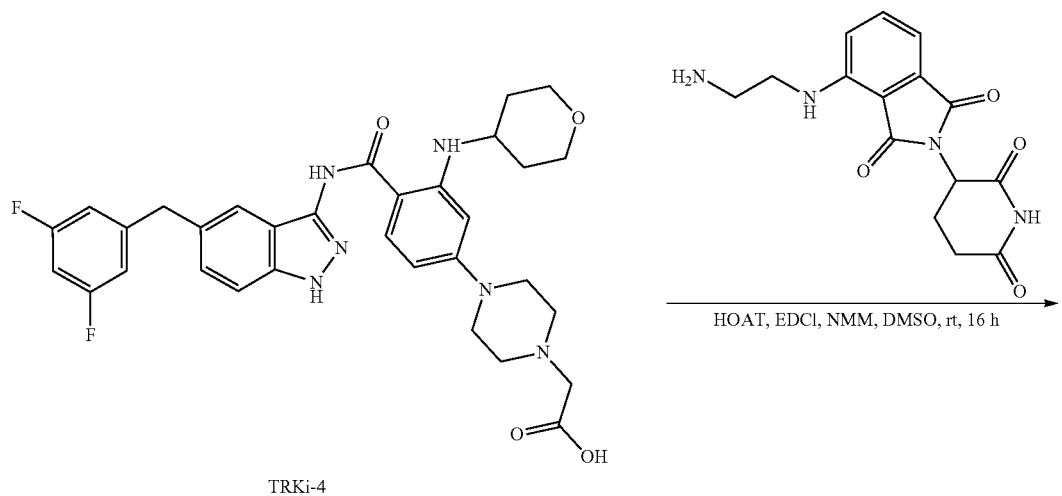

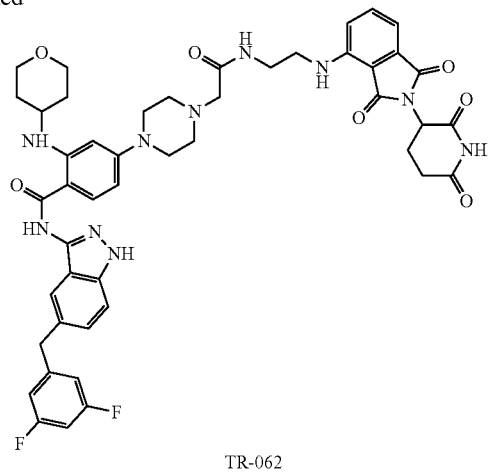
TR-062
CPD-062 was synthesized following the standard procedure for preparing CPD-053 (12 mg, yield 72%). MS (ESI) m/z: 903.4 [M+H]$^+$.
Example 126: (2S,4R)-1-((S)-2-(2-(2-(4-(4-((5-(3,5-Difluorobenzyl)-1H-indazol-3-yl)carbamoyl)-3-((tetrahydro-2H-pyran-4-yl)amino)phenyl)piperazin-1-yl)acetamido)acetamido)-3,3-dimethylbutanoyl)-4-hydroxy-N-(4-(4-methylthiazol-5-yl)benzyl)pyrrolidine-2-carboxamide (CPD-063)
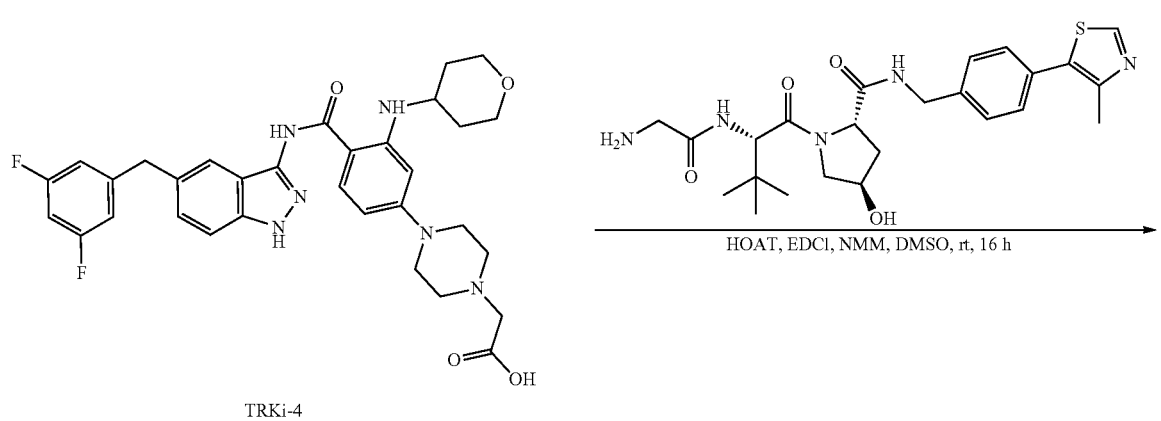
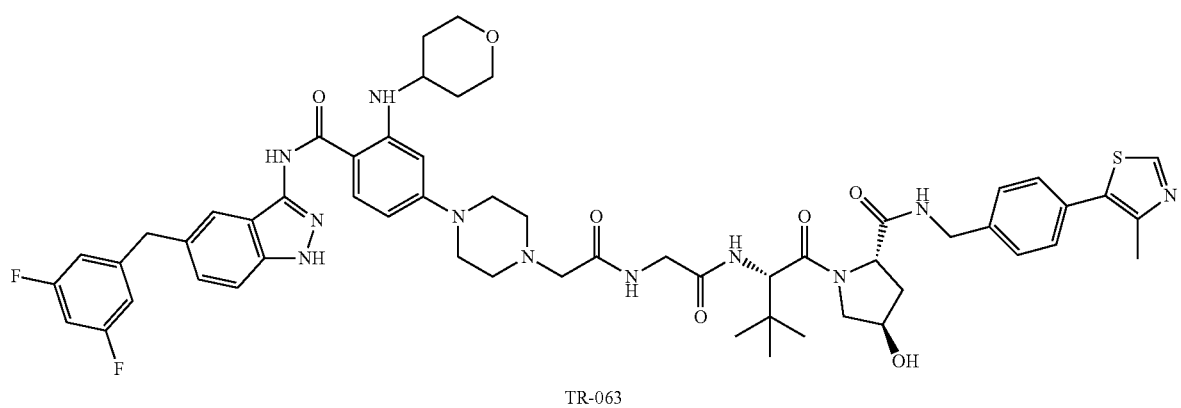
TR-063

CPD-063 was synthesized following the standard procedure for preparing CPD-053 (15 mg, yield 76%). MS (ESI) m/z: 1073.5 [M+H]+.

Example 127: N-(5-(3,5-Difluorobenzyl)-1H-indazol-3-yl)-4-(4-(14-((2-(2,6-dioxopiperidin-3-yl)-1,3-dioxoisoindolin-4-yl)amino)-2-oxo-6,9,12-trioxa-3-azatetradecyl)piperazin-1-yl)-2-((tetrahydro-2H-pyran-4-yl)amino)benzamide (CPD-064)

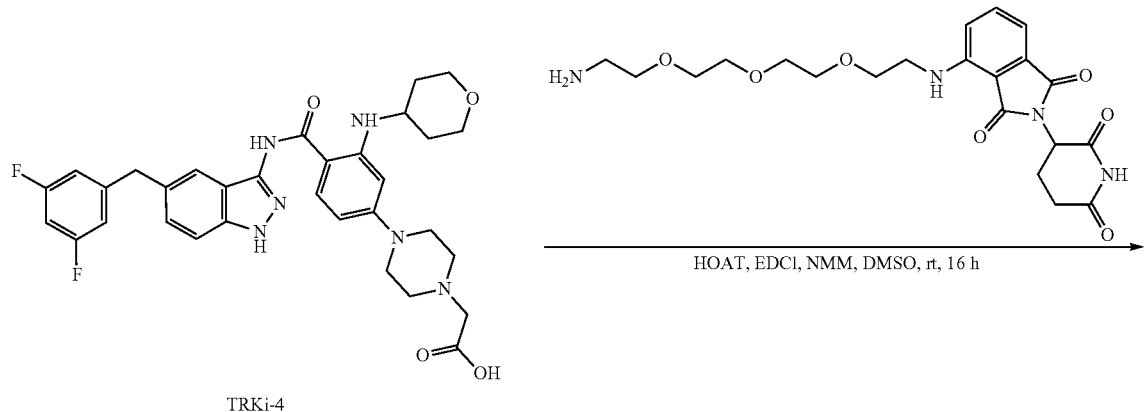

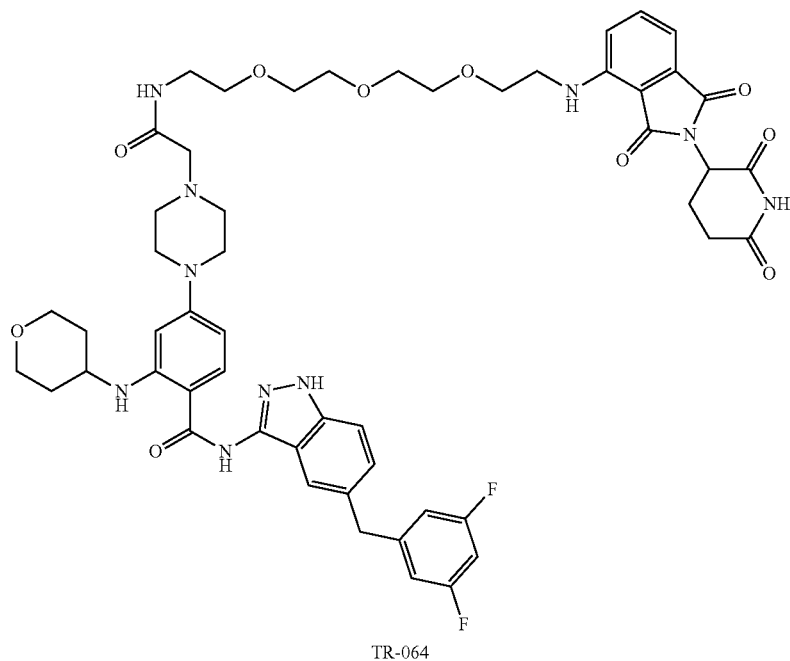

CPD-064 was synthesized following the standard procedure for preparing CPD-053 (11 mg, yield 77%). MS (ESI) m/z: 1035.4 [M+H]+.

Example 128: N-(5-(3,5-Difluorobenzyl)-1H-indazol-3-yl)-4-(4-(20-((2-(2,6-dioxopiperidin-3-yl)-1,3-dioxoisoindolin-4-yl)amino)-2-oxo-6,9,12,15,18-pentaoxa-3-azaicosyl)piperazin-1-yl)-2-((tetrahydro-2H-pyran-4-yl)amino)benzamide (CPD-065)
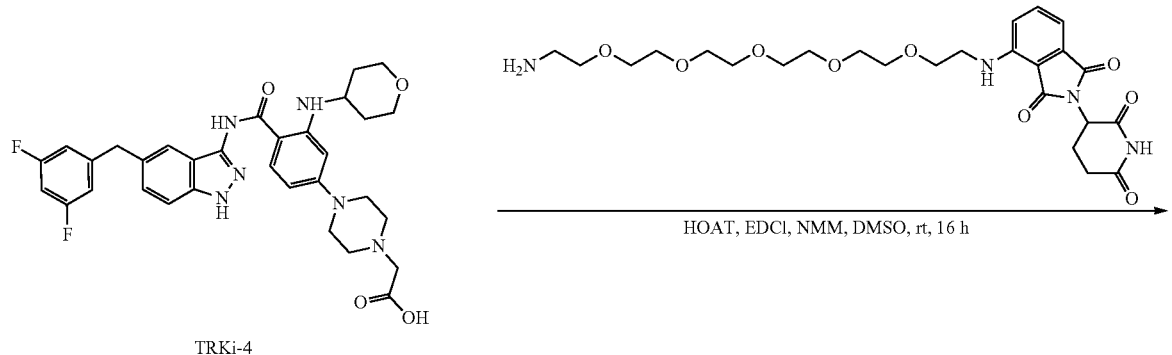
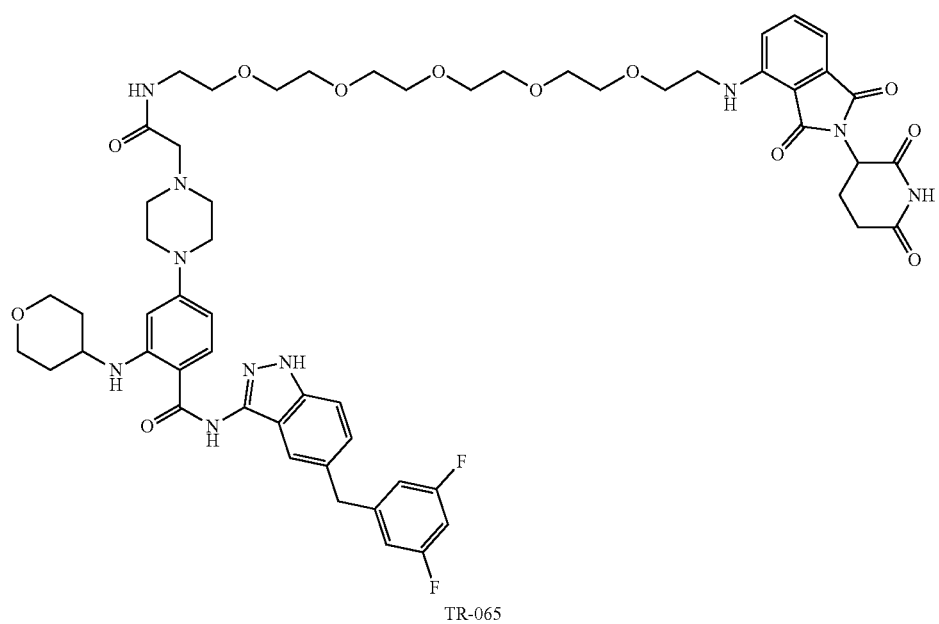
CPD-065 was synthesized following the standard procedure for preparing CPD-053 (13 mg, yield 79%). MS (ESI) m/z: 1123.5 [M+H]⁺.
Example 129: 5-((2-(2-Aminoethoxy)ethyl)amino)-2-(2,6-dioxopiperidin-3-yl)isoindoline-1,3-dione (Linker 60)
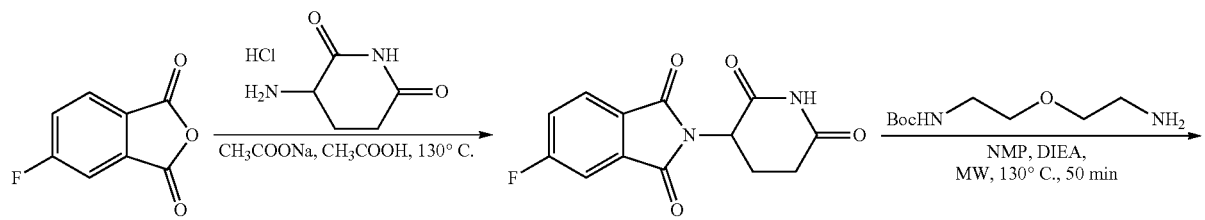

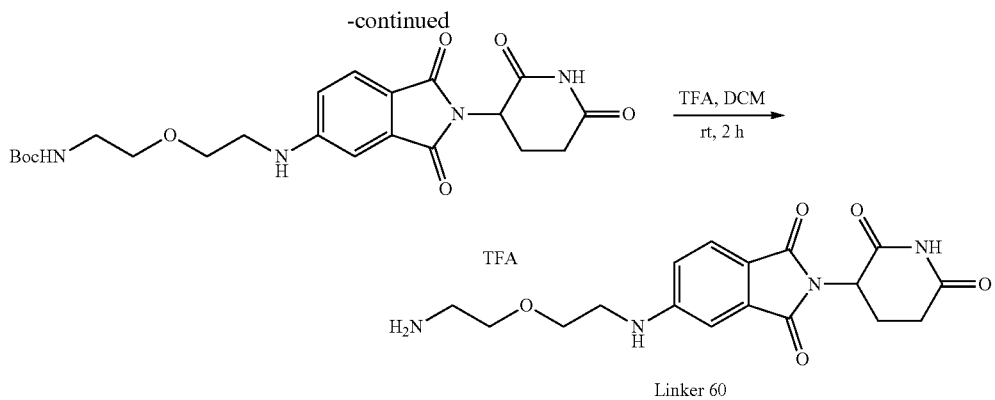

Linker 60

A mixture of 5-fluoroisobenzofuran-1,3-dione (87 g, 524 mmol), 3-aminopiperidine-2,6-dione (85.7 g, 524 mmol) and NaOAc (85.9 g, 1050 mmol) in acetic acid (500 mL) was stirred at 130° C. overnight.

After cooling down to room temperature, the mixture was concentrated. The resulting residue was poured into ice water, and filtered. The filter cake was washed with water (500 mL×2), EtOH (500 mL×2), MeOH (500 mL) and DCM (500 mL) to afford a solid which was dried in vacuum to give 2-(2,6-dioxopiperidin-3-yl)-5-fluoroisoindoline-1,3-dione (120 g, yield: 83%) as yellow solid. MS (ESI) m/z=277.1 [M+H]$^+$.

A mixture of 2-(2,6-dioxopiperidin-3-yl)-5-fluoroisoindoline-1,3-dione (6.9 g, 25.0 mmol), tert-butyl (2-(2-aminoethoxy)ethyl)carbamate (5.6 g, 27.5 mmol) and DIEA (9.7 g, 75 mmol) in NMP (75 mL) was stirred at 130° C. in microwave reactor for 50 min. After cooling down to room temperature, the mixture was poured into EtOAc (200 mL), and washed with water (200 mL×2) followed by brine (200 mL). The organic phase was dried over anhydrous Na$_2$SO$_4$, filtered and concentrated to give a crude product which was purified by silica gel chromatography (petroleum ether: EtOAc=2:1 to 1:2) to give tert-butyl (2-(2-((2-(2,6-dioxopiperidin-3-yl)-1,3-dioxoisoindolin-5-yl)amino)ethoxy) ethyl) carbamate (2.4 g, yield: 21%) as yellow oil. MS (ESI) m/z=361.1 [M+H]$^+$.

To a solution of tert-butyl (2-(2-((2-(2,6-dioxopiperidin-3-yl)-1,3-dioxoisoindolin-5-yl)amino)ethoxy)ethyl)carbamate (2.4 g, 5.2 mmol) in DCM (10 mL) was added TFA (5 mL) in one portion. The reaction mixture was stirred at room temperature for 2 h. After concentration, the resulting residue was dissolved in water (20 mL), washed with EtOAc (40 mL) and MTBE (40 mL). The aqueous phase was lyophilized to afford TFA salt of 5-((2-(2-aminoethoxy)ethyl) amino)-2-(2,6-dioxopiperidin-3-yl) isoindoline-1,3-dione (1.9 g, yield: 77%) as yellow solid. $^1$H NMR (400 MHz, DMSO-d$_6$) δ 11.06 (s, 1H), 8.01 (s, 3H), 7.58 (d, J=8.4 Hz, 1H), 7.12 (br, s, 1H), 7.02 (d, J=2.0 Hz, 1H), 6.91 (dd, J=2.0 Hz, 8.8 Hz, 1H), 5.04 (dd, J=5.6 Hz, 13.2 Hz, 1H), 3.64 (t, J=5.6 Hz, 4H), 3.40 (t, J=5.2 Hz, 2H), 3.01 (br, 2H), 2.89-2.83 (m, 1H), 2.60-2.50 (m, 2H), 2.03-1.97 (m, 1H). MS (ESI) m/z=361.1 [M+H]$^+$.

Example 130: 5-((2-(2-(2-Aminoethoxy)ethoxy) ethyl)amino)-2-(2,6-dioxopiperidin-3-yl)isoindoline-1,3-dione (Linker 61)

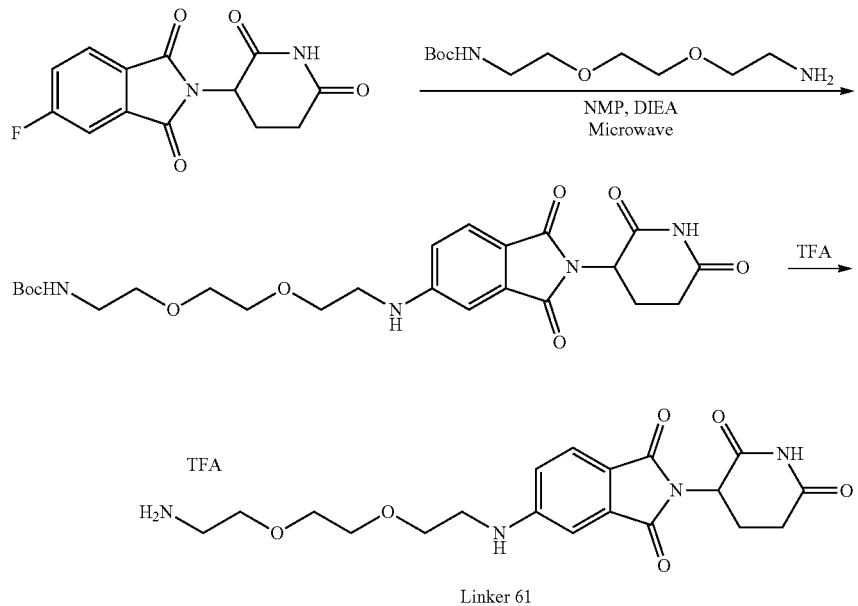

Linker 61

Linker 61 was synthesized following the same procedure as Linker 60 as described for Example 60. (1.4 g, yield: 71%). $^1$H NMR (400 MHz, DMSO-$d_6$) δ 11.05 (s, 1H), 7.94 (br, 3H), 7.56 (d, J=8.4 Hz, 1H), 7.01 (s, 1H), 6.90 (d, J=8.0 Hz, 1H), 5.03 (dd, J=5.2 Hz, 12.8 Hz, 1H), 3.58 (br, 8H), 3.36 (s, 2H), 2.97-2.92 (m, 2H), 2.91-2.83 (m, 1H), 2.60-2.50 (m, 2H), 2.01-1.99 (m, 1H). MS (ESI) m/z=405.1 [M+H]$^+$.

Example 131: 5-((2-(2-(2-(2-Aminoethoxy)ethoxy)ethoxy)ethyl)amino)-2-(2,6-dioxopiperidin-3-yl)isoindoline-1,3-dione (Linker 62)

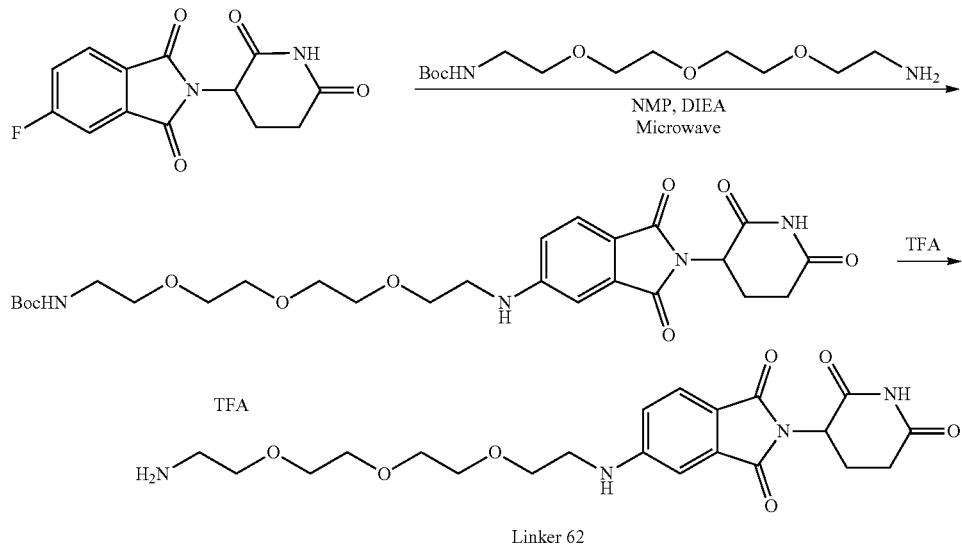

Linker 62 was synthesized following the same procedure as Linker 60 as described for Example 60. (1.19 g, yield: 59%). $^1$H NMR (400 MHz, DMSO-$d_6$) δ 11.05 (s, 1H), 7.79 (br, 3H), 7.57 (d, J=8.4 Hz, 1H), 7.15 (br, s, 1H), 7.00 (d, J=2.0 Hz, 1H), 6.90 (dd, J=2.0 Hz, 8.4 Hz, 1H), 5.03 (dd, J=5.6 Hz, 12.8 Hz, 1H), 3.61-3.55 (m, 12H), 3.36 (t, J=5.6 Hz, 2H), 2.99-2.94 (m, 2H), 2.88-2.84 (m, 1H), 2.60-2.52 (m, 2H) 2.01-1.98 (m, 1H). MS (ESI) m/z=449.1 [M+H]$^+$.

Example 132: 5-((14-Amino-3,6,9,12-tetraoxatetradecyl)amino)-2-(2,6-dioxopiperidin-3-yl)isoindoline-1,3-dione (Linker 63)

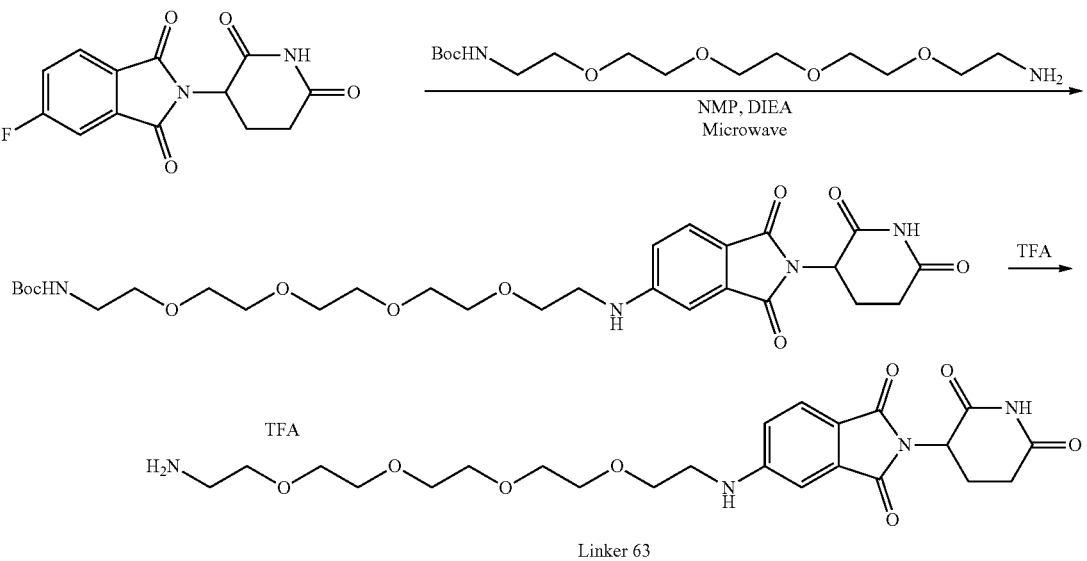

Linker 63 was synthesized following the same procedure as Linker 60 as described for Example 60. (1.2 g, yield: 73%). $^1$H NMR (400 MHz, DMSO-d$_6$) δ 11.05 (s, 1H), 7.79 (br, J=1.6 Hz, 3H), 7.56 (d, J=8.4 Hz, 1H), 7.14 (br, s, 1H), 7.01 (d, J=2.0 Hz, 1H), 6.90 (dd, J=2.0 Hz, 8.4 Hz, 1H), 5.03 (dd, J=5.6 Hz, 13.2 Hz, 1H), 3.61-3.56 (m, 16H), 3.36 (t, J=5.2 Hz, 2H), 2.99-2.95 (m, 2H), 2.89-2.83 (m, 1H), 2.60-2.53 (m, 2H) 2.01-1.97 (m, 1H). MS (ESI) m/z=493.1 [M+H]$^+$.

Example 133: 5-((17-Amino-3,6,9,12,15-pentaoxaheptadecyl)amino)-2-(2,6-dioxopiperidin-3-yl)isoindoline-1,3-dione (Linker 64)

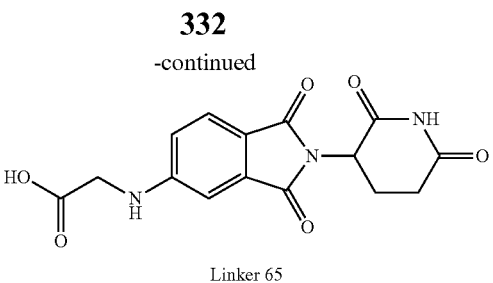

Linker 65

Linker 65 was synthesized following the same procedure as Linker 60 as described for Example 60. (1.0 g, yield:

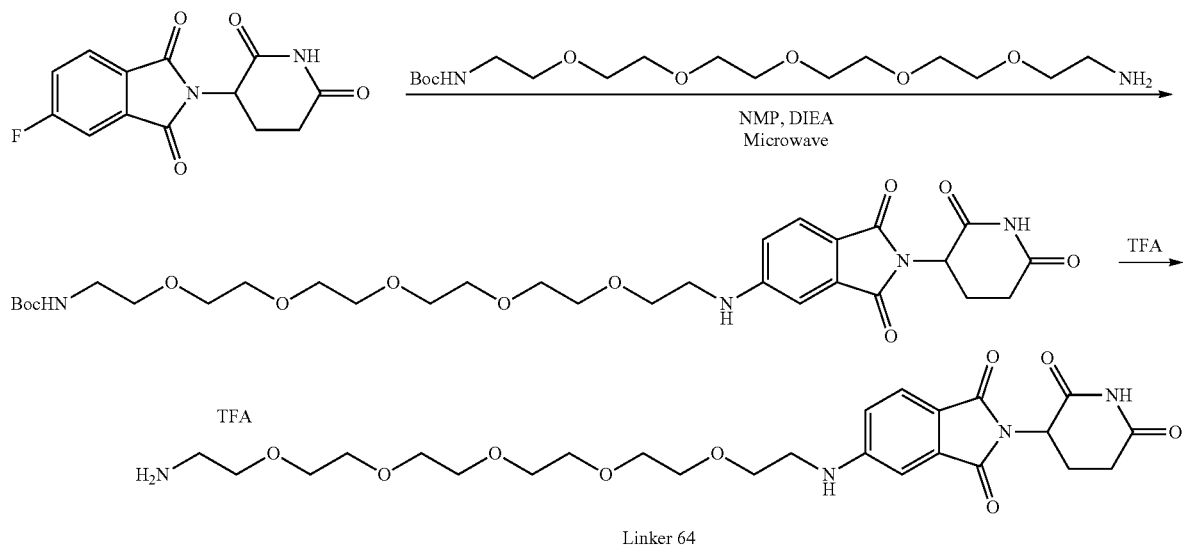

Linker 64

Linker 64 was synthesized following the same procedure as Linker 60 as described for Example 60. (1.73 g, yield: 88%). $^1$H NMR (400 MHz, DMSO-d$_6$) δ 11.05 (s, 1H), 7.79 (s, 3H), 7.55 (d, J=8.4 Hz, 1H), 7.18 (br, s, 1H), 7.01 (s, 1H), 6.90 (d, J=8.4 Hz, 1H), 5.03 (dd, J=5.2 Hz, 12.8 Hz, 1H), 3.61-3.54 (m, 20H), 3.35 (s, 2H), 2.98 (s, 2H), 2.92-2.83 (m, 1H), 2.61-2.54 (m, 2H), 2.02-1.98 (m, 1H). MS (ESI) m/z=537.2 [M+H]$^+$.

Example 134: (2-(2,6-Dioxopiperidin-3-yl)-1,3-dioxoisoindolin-5-yl)glycine (Linker 65)

84%). $^1$H NMR (400 MHz, DMSO-d$_6$) δ 12.80 (br, 1H), 11.06 (s, 1H), 7.59 (d, J=8.4 Hz, 1H), 7.32 (br, s, 1H), 6.98 (d, J=1.2 Hz, 1H), 6.89 (dd, J=2.0 Hz, 8.4 Hz, 1H), 5.04 (dd, J=5.6 Hz, 13.2 Hz, 1H), 4.03 (s, 2H), 2.92-2.83 (m, 1H), 2.60-2.52 (m, 2H), 2.03-1.98 (m, 1H). MS (ESI) m/z=332.0 [M+H]$^+$.

Example 135: 3-((2-(2,6-Dioxopiperidin-3-yl)-1,3-dioxoisoindolin-5-yl)amino)propanoic acid (Linker 66)

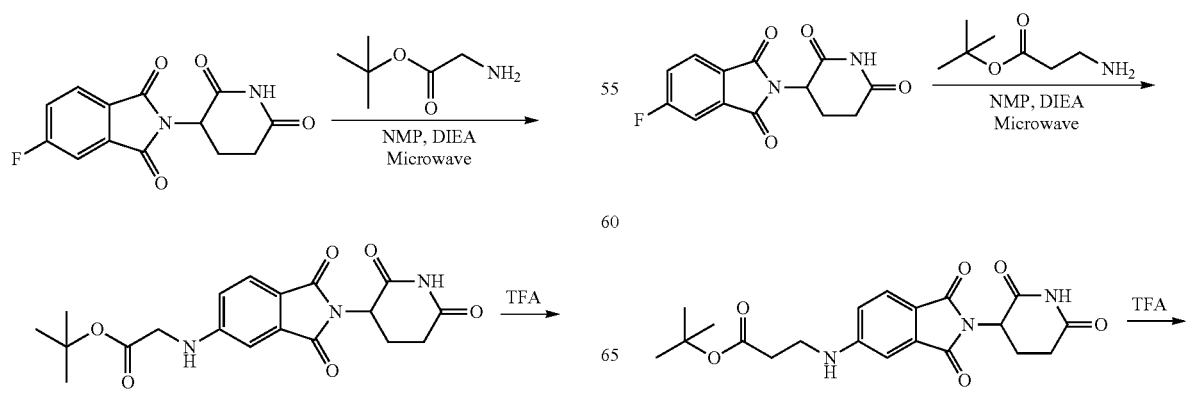

-continued

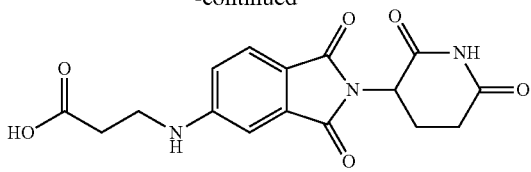

Linker 66

Linker 66 was synthesized following the same procedure as Linker 60 as described for Example 60. (1.24 g, yield: 60%). ¹H NMR (400 MHz, DMSO-d$_6$) δ 11.05 (s, 1H), 7.57 (d, J=8.4 Hz, 1H), 6.97 (d, J=2.0 Hz, 1H), 6.87 (dd, J=2.0 Hz, 8.4 Hz, 1H), 5.02 (dd, J=5.2 Hz, 12.8 Hz, 1H), 3.41 (t, J=6.8 Hz, 2H), 2.89-2.83 (m, 1H), 2.60-2.52 (m, 4H), 2.02-1.97 (m, 1H). MS (ESI) m/z=346.0 [M+H]⁺.

Example 136: 4-((2-(2,6-Dioxopiperidin-3-yl)-1,3-dioxoisoindolin-5-yl)amino)butanoic acid (Linker 67)

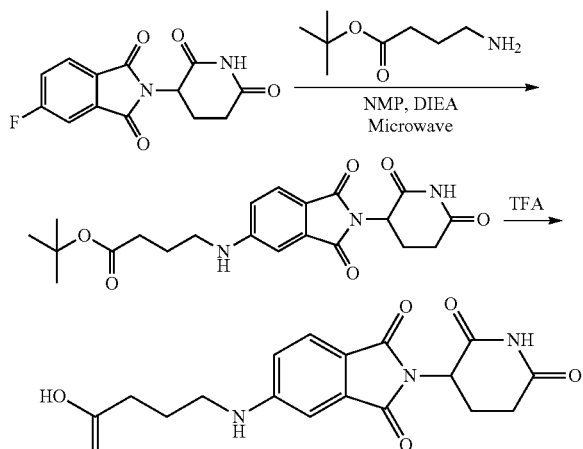

Linker 67

Linker 67 was synthesized following the same procedure as Linker 60 as described for Example 60. (0.52 g, yield: 25%). ¹H NMR (400 MHz, DMSO-d$_6$) δ 12.12 (s, 1H), 11.05 (s, 1H), 7.55 (d, J=8.4 Hz, 1H), 7.14 (t, J=4.8 Hz, 1H), 6.95 (d, J=2.0 Hz, 1H), 6.85 (dd, J=2.0 Hz, 8.4 Hz, 1H), 5.02 (dd, J=5.6 Hz, 12.8 Hz, 1H), 3.21-3.16 (m, 2H), 2.91-2.83 (m, 1H), 2.60-2.51 (m, 2H), 2.34 (t, J=7.2 Hz, 2H), 2.01-1.97 (m, 1H), 1.82-1.75 (m, 2H). MS (ESI) m/z=360.1 [M+H]⁺.

Example 137: 5-((2-(2,6-Dioxopiperidin-3-yl)-1,3-dioxoisoindolin-5-yl)amino)pentanoic acid (Linker 68)

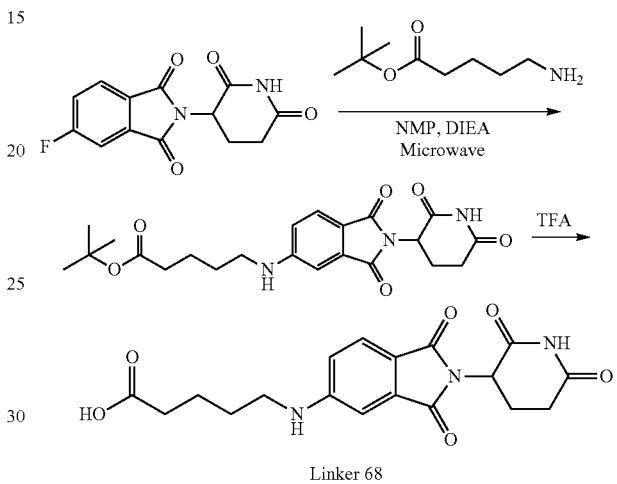

Linker 68

Linker 68 was synthesized following the same procedure as Linker 60 as described for Example 60. (0.66 g, yield: 51%). ¹H NMR (400 MHz, DMSO-d$_6$) δ 12.03 (br, 1H), 11.05 (s, 1H), 7.55 (d, J=8.4 Hz, 1H), 7.10 (t, J=5.2 Hz, 1H), 6.94 (s, 1H), 6.83 (dd, J=1.6 Hz, 8.4 Hz, 1H), 5.02 (dd, J=5.6 Hz, 12.8 Hz, 1H), 3.17-3.16 (m, 2H), 2.92-2.83 (m, 1H), 2.60-2.53 (m, 2H), 2.26-2.25 (m, 2H), 2.01-1.98 (m, 1H), 1.60-1.59 (m, 4H). MS (ESI) m/z=374.1 [M+H]⁺.

Example 138: 6-((2-(2,6-Dioxopiperidin-3-yl)-1,3-dioxoisoindolin-5-yl)amino)hexanoic acid (Linker 69)

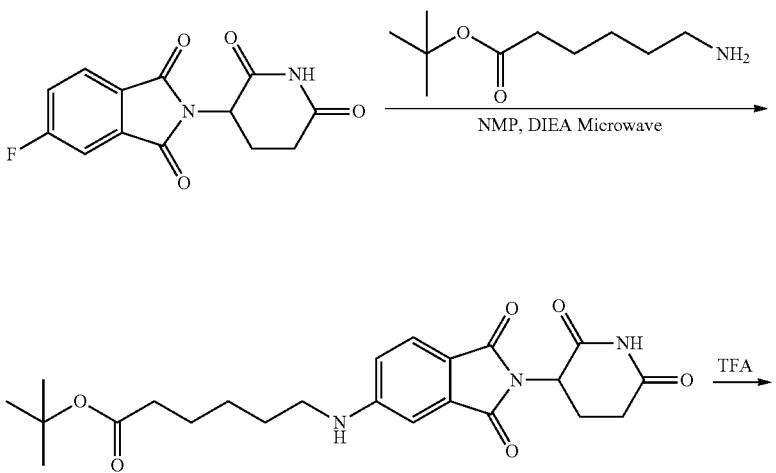

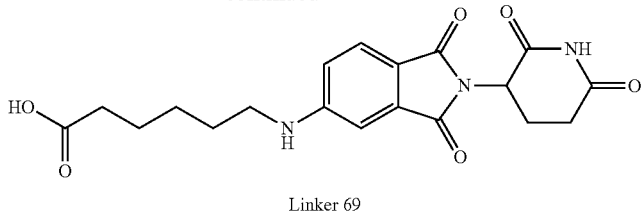

Linker 69

Linker 69 was synthesized following the same procedure as Linker 60 as described for Example 60. (1.33 g, yield: 66%). $^1$H NMR (400 MHz, DMSO-d$_6$) δ 11.98 (s, 1H), 11.05 (s, 1H), 7.55 (d, J=8.4 Hz, 1H), 7.08 (t, J=5.2 Hz, 1H), 6.95 (s, 1H), 6.83 (dd, J=1.2 Hz, 8.4 Hz, 1H), 5.03 (dd, J=5.2 Hz, 12.8 Hz, 1H), 3.17-3.12 (m, 2H), 2.92-2.83 (m, 1H), 2.60-2.53 (m, 2H), 2.22 (t, J=7.2 Hz, 2H), 2.01-1.98 (m, 1H), 1.61-1.51 (m, 4H), 1.41-1.33 (m, 2H). MS (ESI) m/z=388.1 [M+H]$^+$.

Example 139: 7-((2-(2,6-Dioxopiperidin-3-yl)-1,3-dioxoisoindolin-5-yl)amino)heptanoic acid (Linker 70)

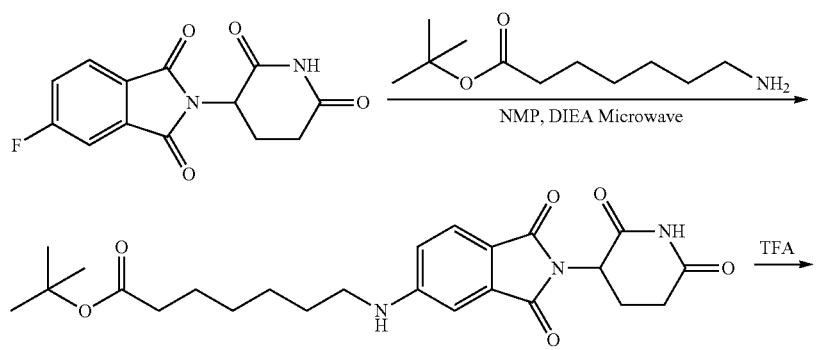

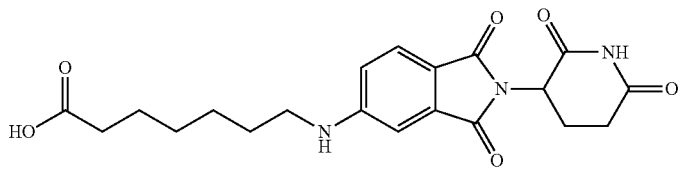

Linker 70

Linker 70 was synthesized following the same procedure as Linker 60 as described for Example 60. (1.06 g, yield: 39%). $^1$H NMR (400 MHz, DMSO-d$_6$) δ 11.94 (s, 1H), 11.04 (s, 1H), 7.55 (d, J=8.4 Hz, 1H), 7.09 (t, J=5.6 Hz, 1H), 6.94 (d, J=2.0 Hz, 1H), 6.84 (dd, J=2.0 Hz, 8.4 Hz, 1H), 5.02 (dd, J=5.6 Hz, 13.2 Hz, 1H), 3.17-3.12 (m, 2H), 2.88-2.83 (m, 1H), 2.60-2.53 (m, 2H), 2.21 (t, J=7.2 Hz, 2H), 2.01-1.97 (m, 1H), 1.58-1.48 (m, 4H), 1.39-1.29 (m, 4H). MS (ESI) m/z=402.1 [M+H]$^+$.

Example 140: 8-((2-(2,6-Dioxopiperidin-3-yl)-1,3-dioxoisoindolin-5-yl)amino)octanoic acid (Linker 71)

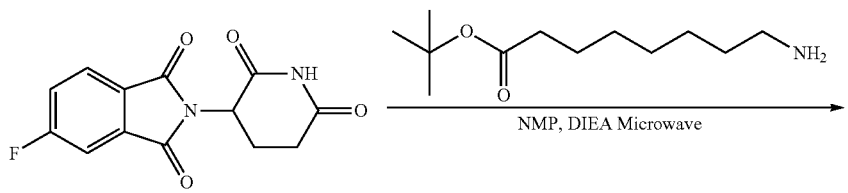

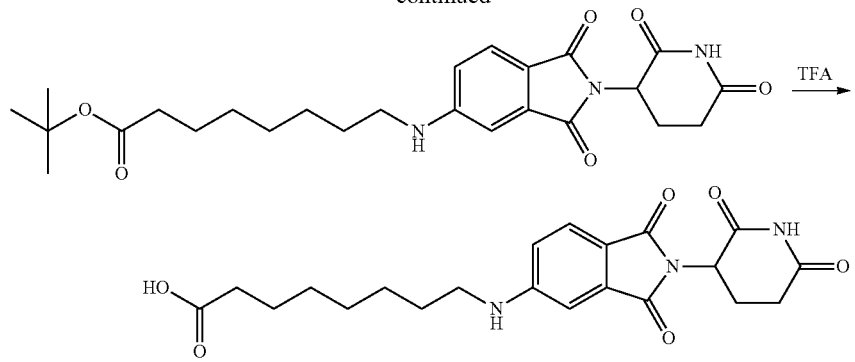

Linker 71

Linker 71 was synthesized following the same procedure as Linker 60 as described for Example 60. (1.66 g, yield: 51%). $^1$H NMR (400 MHz, DMSO-d$_6$) δ 11.95 (s, 1H), 11.05 (s, 1H), 7.55 (d, J=8.4 Hz, 1H), 7.09 (t, J=5.6 Hz, 1H), 6.94 (d, J=2.0 Hz, 1H), 6.84 (dd, J=2.0 Hz, 8.4 Hz, 1H), 5.02 (dd, J=5.6 Hz, 13.2 Hz, 1H), 3.17-3.12 (m, 2H), 2.88-2.83 (m, 1H), 2.60-2.53 (m, 2H), 2.19 (t, J=7.2 Hz, 2H), 2.02-1.98 (m, 1H), 1.58-1.47 (m, 4H), 1.36-1.29 (m, 6H). MS (ESI) m/z=416.1 [M+H]$^+$.

Example 141: 5-((2-Aminoethyl)amino)-2-(2,6-dioxopiperidin-3-yl)isoindoline-1,3-dione (Linker 72)

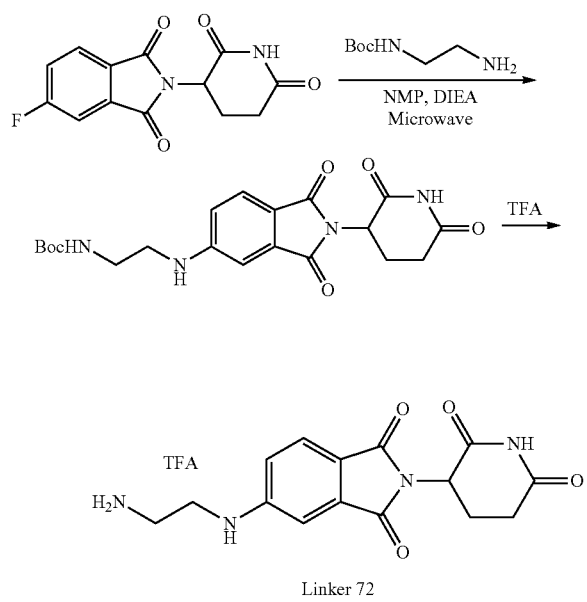

Linker 72

Linker 72 was synthesized following the same procedure as Linker 60 as described for Example 60. (1.74 g, yield: 80%). $^1$H NMR (400 MHz, DMSO-d$_6$) δ 11.08 (s, 1H), 8.10 (s, 3H), 7.62 (d, J=8.4 Hz, 1H), 7.33 (t, J=5.2 Hz, 1H), 7.05 (s, 1H), 6.94 (d, J=8.0 Hz, 1H), 5.07 (dd, J=5.2 Hz, 12.8 Hz, 1H), 3.50-3.49 (m, 2H), 3.03 (t, J=6.0 Hz, 2H), 2.95-2.86 (m, 1H), 2.63-2.57 (m, 2H), 2.05-2.02 (m, 1H). MS (ESI) m/z=317.1 [M+H]$^+$.

Example 142: 5-((3-Aminopropyl)amino)-2-(2,6-dioxopiperidin-3-yl)isoindoline-1,3-dione (Linker 73)

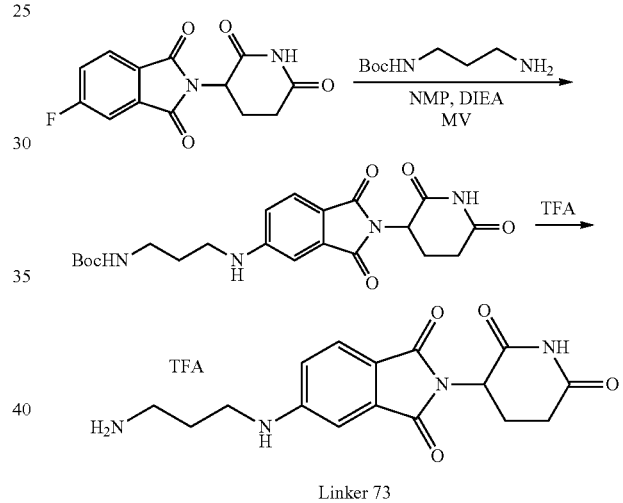

Linker 73

Linker 73 was synthesized following the same procedure as Linker 60 as described for Example 60. (1.3 g, yield: 57%). $^1$H NMR (400 MHz, DMSO-d$_6$) δ 11.07 (s, 1H), 7.85 (br, 3H), 7.59 (d, J=8.4 Hz, 1H), 7.22 (t, J=5.2 Hz, 1H), 6.98 (d, J=2.0 Hz, 1H), 6.88 (dd, J=2.0 Hz, 8.4 Hz, 1H), 5.04 (dd, J=5.6 Hz, 13.2 Hz, 1H), 3.29-3.25 (m, 2H), 2.91-2.85 (m, 3H), 2.60-2.53 (m, 2H), 2.02-1.98 (m, 1H), 1.87-1.81 (m, 2H). MS (ESI) m/z=331.1 [M+H]$^+$.

Example 143: 5-((4-Aminobutyl)amino)-2-(2,6-dioxopiperidin-3-yl)isoindoline-1,3-dione (Linker 74)

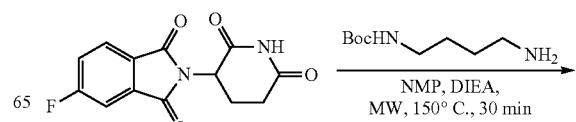

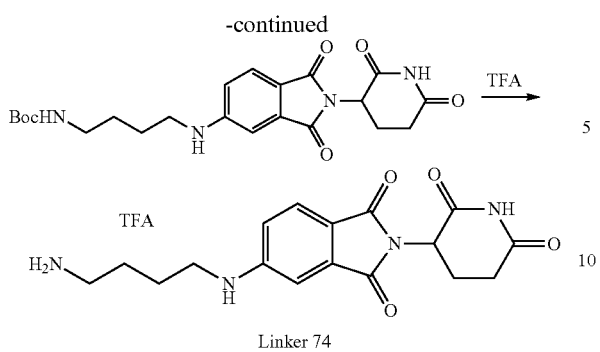

Linker 74

Linker 74 was synthesized following the same procedure as Linker 60 as described for Example 60. (2.9 g, yield: 85%). $^1$H NMR (400 MHz, DMSO-$d_6$) δ 11.08 (s, 1H), 7.97 (br, 3H), 7.58 (d, J=8.4 Hz, 1H), 7.22 (br, s, 1H), 6.99 (s, 1H), 6.89 (d, J=8.0 Hz, 1H), 5.05 (dd, J=5.2 Hz, 12.8 Hz, 1H), 3.22 (s, 2H), 2.93-2.84 (m, 3H), 2.63-2.53 (m, 2H), 2.04-2.00 (m, 1H), 1.66 (s, 4H). MS (ESI) m/z=345.1 [M+H]$^+$.

Example 144: 5-((5-Aminopentyl)amino)-2-(2,6-dioxopiperidin-3-yl)isoindoline-1,3-dione (Linker 75)

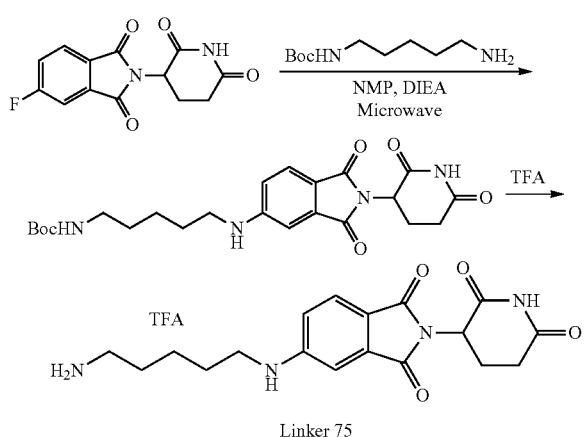

Linker 75

Linker 75 was synthesized following the same procedure as Linker 60 as described for Example 60. (1.8 g, yield: 78%). $^1$H NMR (400 MHz, DMSO-$d_6$) δ 11.09 (s, 1H), 7.89 (br, 3H), 7.57 (d, J=6.8 Hz, 1H), 7.17 (br, s, 1H), 6.96 (s, 1H), 6.86 (d, J=6.0 Hz, 1H), 5.05 (d, J=7.2 Hz, 1H), 3.19-3.15 (m, 2H), 2.89-2.70 (m, 3H), 2.61-2.51 (m, 2H), 2.01-1.90 (m, 1H), 1.62-1.56 (m, 4H), 1.45-1.40 (m, 2H). MS (ESI) m/z=359.1 [M+H]$^+$.

Example 145: 5-((6-Aminohexyl)amino)-2-(2,6-dioxopiperidin-3-yl)isoindoline-1,3-dione (Linker 76)

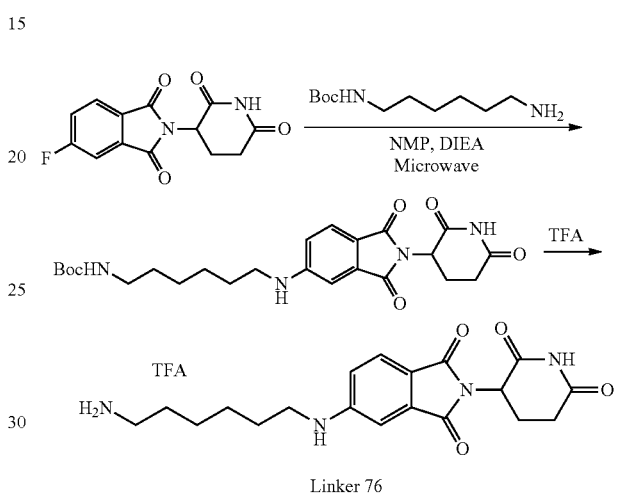

Linker 76

Linker 76 was synthesized following the same procedure as Linker 60 as described for Example 60. (1.8 g, yield: 62%). $^1$H NMR (400 MHz, DMSO-$d_6$) δ 11.05 (s, 1H), 7.71 (br, 3H), 7.57 (d, J=8.4 Hz, 1H), 7.12 (t, J=5.2 Hz, 1H), 6.94 (d, J=2.0 Hz, 1H), 6.85 (dd, J=2.0 Hz, 8.4 Hz, 1H), 5.03 (dd, J=5.2 Hz, 12.8 Hz, 1H), 3.17-3.16 (m, 2H), 2.88-2.77 (m, 3H), 2.60-2.53 (m, 2H), 2.01-1.98 (m, 1H), 1.59-1.51 (m, 4H), 1.37-1.36 (m, 4H). MS (ESI) m/z=373.1 [M+H]$^+$.

Example 146: 5-((7-Aminoheptyl)amino)-2-(2,6-dioxopiperidin-3-yl)isoindoline-1,3-dione (Linker 77)

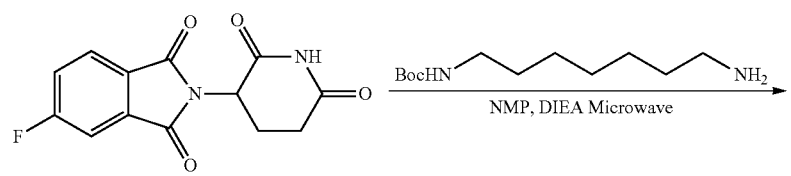

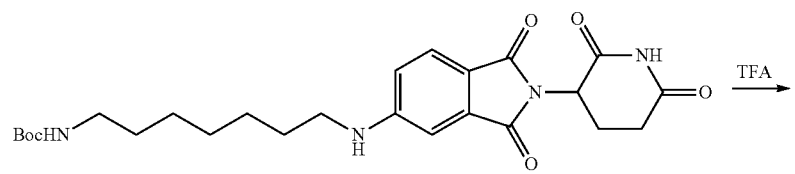

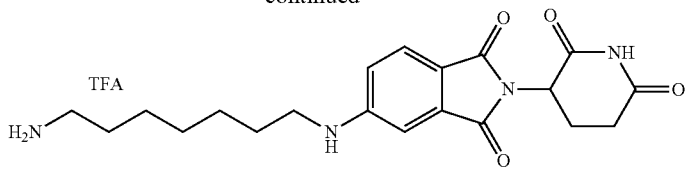

Linker 77

Linker 77 was synthesized following the same procedure as Linker 60 as described for Example 60. (1.3 g, yield: 70%). $^1$H NMR (400 MHz, DMSO-$d_6$) δ 11.05 (s, 1H), 7.72 (br, 3H), 7.56 (d, J=8.4 Hz, 1H), 7.12 (t, J=5.6 Hz, 1H), 6.94 (d, J=2.0 Hz, 1H), 6.85 (dd, J=2.4 Hz, 8.8 Hz, 1H), 5.03 (dd, J=5.6 Hz, 12.8 Hz, 1H), 3.18-3.14 (m, 2H), 2.92-2.76 (m, 3H), 2.60-2.51 (m, 2H), 2.01-1.98 (m, 1H), 1.59-1.51 (m, 4H), 1.36-1.32 (m, 6H). MS (ESI) m/z=387.1 [M+H]$^+$.

Example 147: 5-((8-Aminooctyl)amino)-2-(2,6-dioxopiperidin-3-yl)isoindoline-1,3-dione (Linker 78)

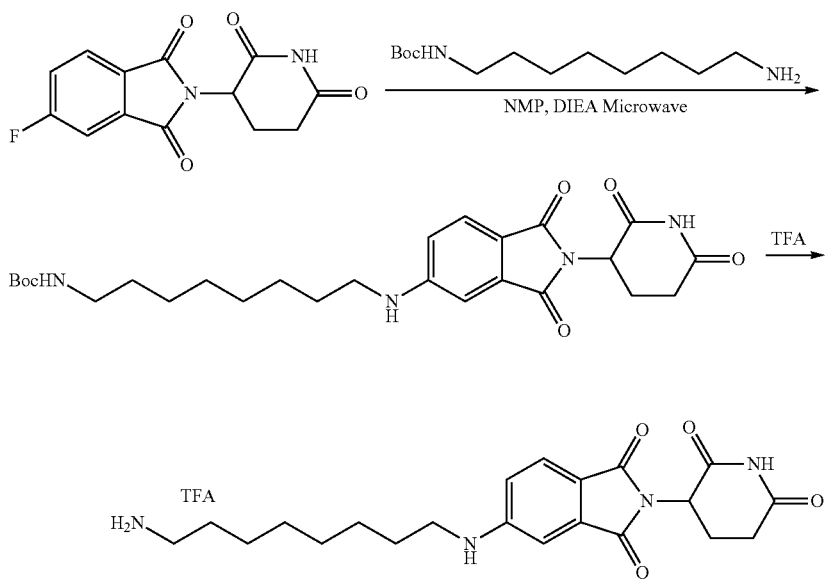

Linker 78

Linker 78 was synthesized following the same procedure as Linker 60 as described for Example 60. (1.6 g, yield: 62%). $^1$H NMR (400 MHz, DMSO-$d_6$) δ 11.05 (s, 1H), 7.73 (br, 3H), 7.56 (d, J=8.4 Hz, 1H), 7.14 (br, 1H), 6.94 (d, J=1.6 Hz, 1H), 6.85 (dd, J=2.0 Hz, 8.8 Hz, 1H), 5.03 (dd, J=5.6 Hz, 12.8 Hz, 1H), 3.15 (t, J=7.2 Hz, 2H), 2.89-2.83 (m, 1H), 2.80-2.75 (m, 2H), 2.60-2.54 (m, 2H), 2.02-1.98 (m, 1H), 1.59-1.51 (m, 4H), 1.37-1.30 (m, 8H). MS (ESI) m/z=401.1 [M+H]$^+$.

Example 148: 3-(2-((2-(2,6-Dioxopiperidin-3-yl)-1,3-dioxoisoindolin-5-yl)amino)ethoxy)propanoic acid (Linker 79)

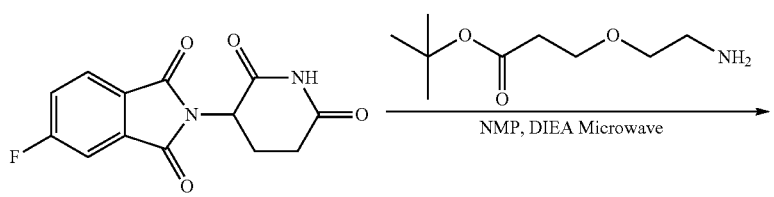

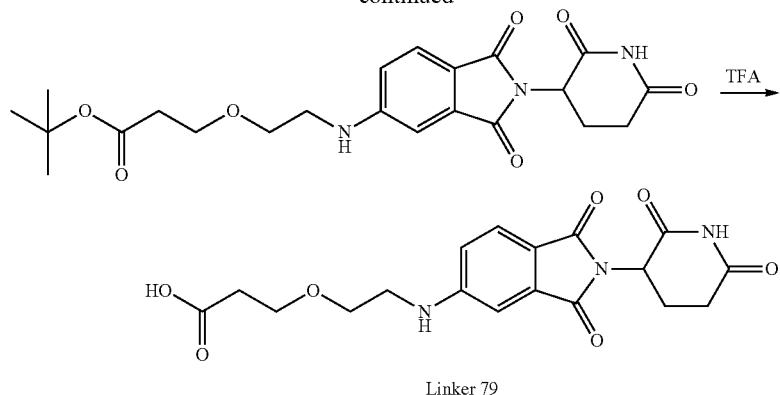

Linker 79

Linker 79 was synthesized following the same procedure as Linker 60 as described for Example 60. (1.7 g, yield: 60%). $^1$H NMR (400 MHz, DMSO-d$_6$) δ 12.19 (br, 1H), 11.06 (s, 1H), 7.57 (d, J=8.4 Hz, 1H), 7.09 (br, 1H), 7.01 (d, J=2.0 Hz, 1H), 6.90 (dd, J=2.0 Hz, 8.4 Hz, 1H), 5.04 (dd, J=5.6 Hz, 13.2 Hz, 1H), 3.66 (t, J=6.4 Hz, 2H), 3.59 (t, J=5.6 Hz, 2H), 3.35 (t, J=5.2 Hz, 2H), 2.93-2.84 (m, 1H), 2.62-2.56 (m, 2H), 2.52-2.47 (m, 2H), 2.03-1.99 (m, 1H). MS (ESI) m/z=390.1 [M+H]$^+$.

Example 149: 3-(2-(2-((2-(2,6-Dioxopiperidin-3-yl)-1,3-dioxoisoindolin-5-yl)amino)ethoxy)ethoxy)propanoic acid (Linker 80)

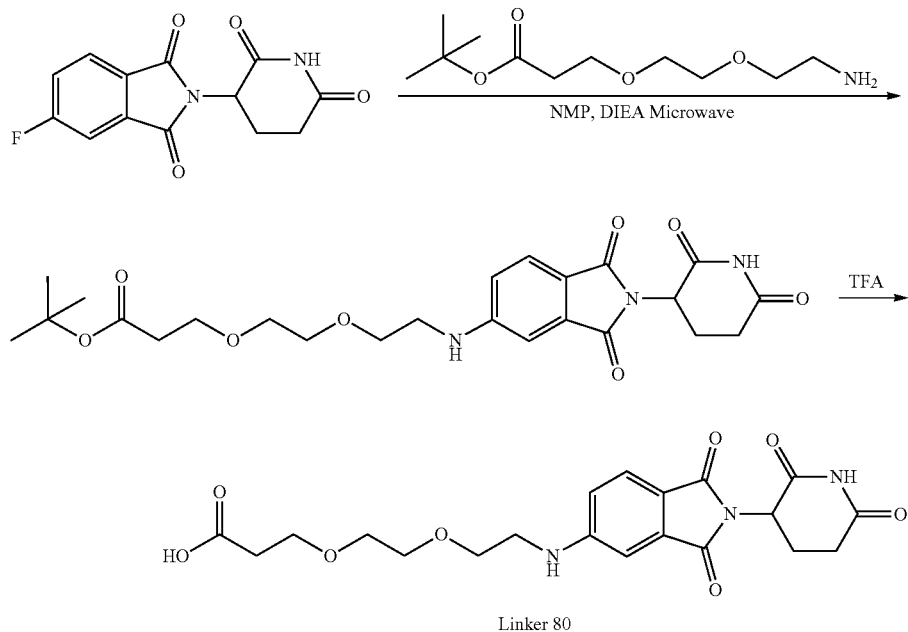

Linker 80

Linker 80 was synthesized following the same procedure as Linker 60 as described for Example 60. (2.3 g, yield: 78%). $^1$H NMR (400 MHz, DMSO-d$_6$) δ 11.06 (s, 1H), 7.57 (d, J=8.4 Hz, 1H), 7.02 (d, J=2.0 Hz, 1H), 6.90 (dd, J=2.0 Hz, 8.4 Hz, 1H), 5.04 (dd, J=5.6 Hz, 13.2 Hz, 1H), 3.63-3.59 (m, 4H), 3.57-3.51 (m, 4H), 3.36 (t, J=5.6 Hz, 2H), 2.90-2.84 (m, 1H), 2.61-2.55 (m, 2H), 2.44 (t, J=6.4 Hz, 2H), 2.04-1.99 (m, 1H). MS (ESI) m/z=434.1 [M+H]$^+$.

Example 150: 3-(2-(2-(2-((2-(2,6-Dioxopiperidin-3-yl)-1,3-dioxoisoindolin-5-yl)amino)ethoxy)ethoxy)ethoxy)propanoic acid (Linker 81)

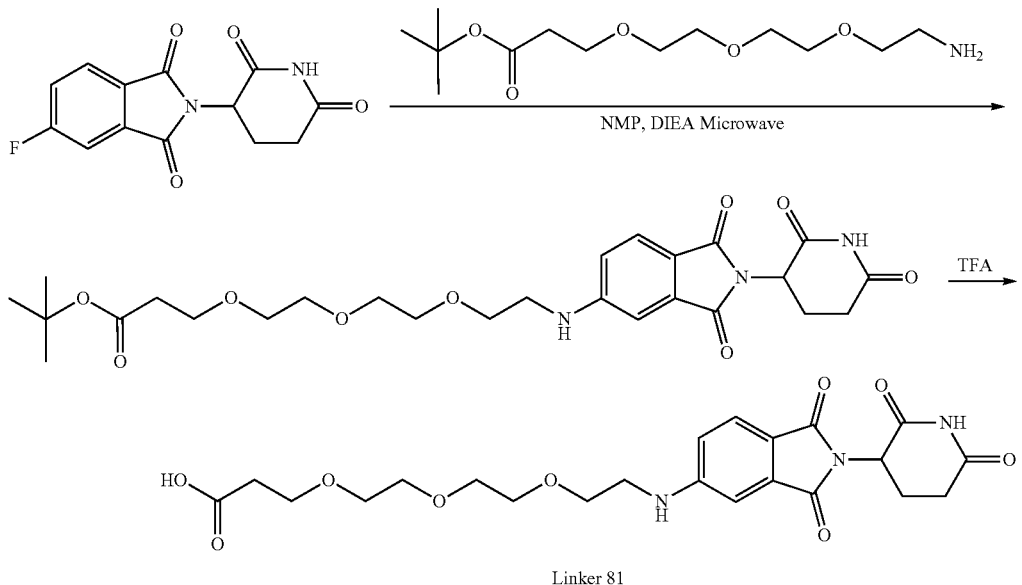

Linker 81

Linker 81 was synthesized following the same procedure as Linker 60 as described for Example 60. (1.2 g, yield: 52%). $^1$H NMR (400 MHz, DMSO-d$_6$) δ 7.59 (d, J=11.2 Hz, 1H), 7.23 (t, J=6.8 Hz, 1H), 7.04 (d, J=1.6 Hz, 1H), 7.04 (dd, J=2.4 Hz, 11.2 Hz, 1H), 5.06 (dd, J=7.2 Hz, 16.8 Hz, 1H), 3.64-3.57 (m, 8H), 3.54-3.48 (m, 4H), 3.40-3.38 (m, 2H), 2.92-2.89 (m, 1H), 2.64-2.54 (m, 2H), 2.42-2.38 (m, 2H), 2.05-2.01 (m, 1H). MS (ESI) m/z=478.1 [M+H]$^+$.

Example 151: 1-((2-(2,6-Dioxopiperidin-3-yl)-1,3-dioxoisoindolin-5-yl)amino)-3,6,9,12-tetraoxapentadecan-15-oic acid (Linker 82)

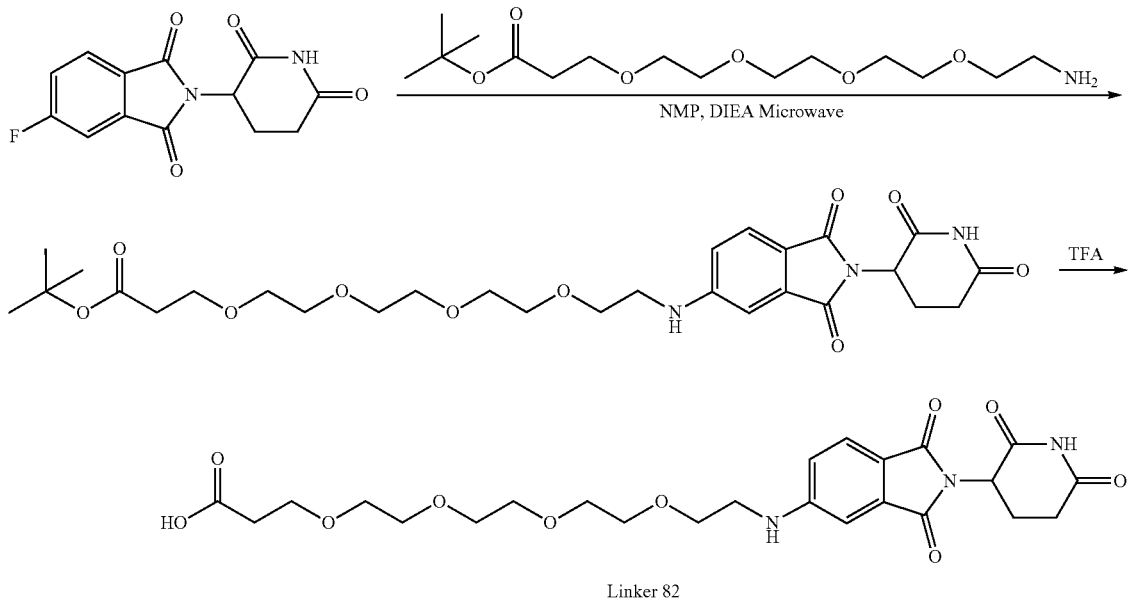

Linker 82

Linker 82 was synthesized following the same procedure as Linker 60 as described for Example 60. (1.3 g, yield: 55%). $^1$H NMR (400 MHz, DMSO-$d_6$) δ 12.17 (br, 1H), 11.07 (s, 1H), 7.56 (d, J=8.4 Hz, 1H), 7.17 (t, J=5.6 Hz, 1H), 7.01 (d, J=1.2 Hz, 1H), 6.90 (dd, J=1.6 Hz, 8.4 Hz, 1H), 5.03 (dd, J=5.6 Hz, 12.8 Hz, 1H), 3.61-3.48 (m, 18H), 2.92-2.83 (m, 1H), 2.60-2.54 (m, 2H), 2.43 (t, J=6.4 Hz, 2H), 2.03-1.98 (m, 1H). MS (ESI) m/z=522.1 [M+H]$^+$.

Example 152: 1-((2-(2,6-Dioxopiperidin-3-yl)-1,3-dioxoisoindolin-5-yl)amino)-3,6,9,12,15-pentaoxaoctadecan-18-oic acid (Linker 83)

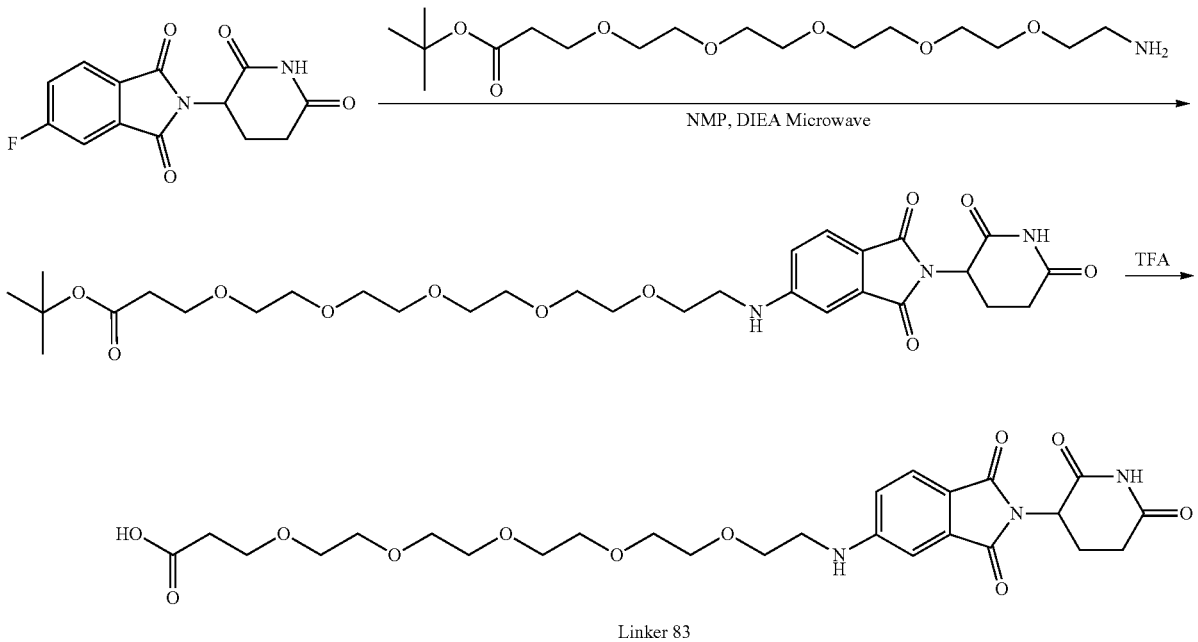

Linker 83

Linker 83 was synthesized following the same procedure as Linker 60 as described for Example 60. (1.0 g, yield: 50%). $^1$H NMR (400 MHz, DMSO-$d_6$) δ 12.17 (br, s, 1H), 11.07 (s, 1H), 7.56 (d, J=8.0 Hz, 1H), 7.17 (t, J=5.6 Hz, 1H), 7.01 (s, 1H), 6.90 (dd, J=1.6 Hz, 8.4 Hz, 1H), 5.03 (dd, J=5.6 Hz, 13.2 Hz, 1H), 3.60-3.48 (m, 22H), 2.89-2.83 (m, 1H), 2.60-2.54 (m, 2H), 2.43 (t, J=6.4 Hz, 2H), 2.01-1.98 (m, 1H). MS (ESI) m/z=566.1 [M+H]$^+$.

Example 153: N-(8-((2-(2,6-dioxopiperidin-3-yl)-1,3-dioxoisoindolin-4-yl)amino)octyl)-2-(4-(6-(6-(((R)-2-(3-fluorophenyl)pyrrolidin-1-yl)imidazo[1,2-b]pyridazin-3-yl)pyridin-2-yl)piperazin-1-yl)acetamide (TR-102)

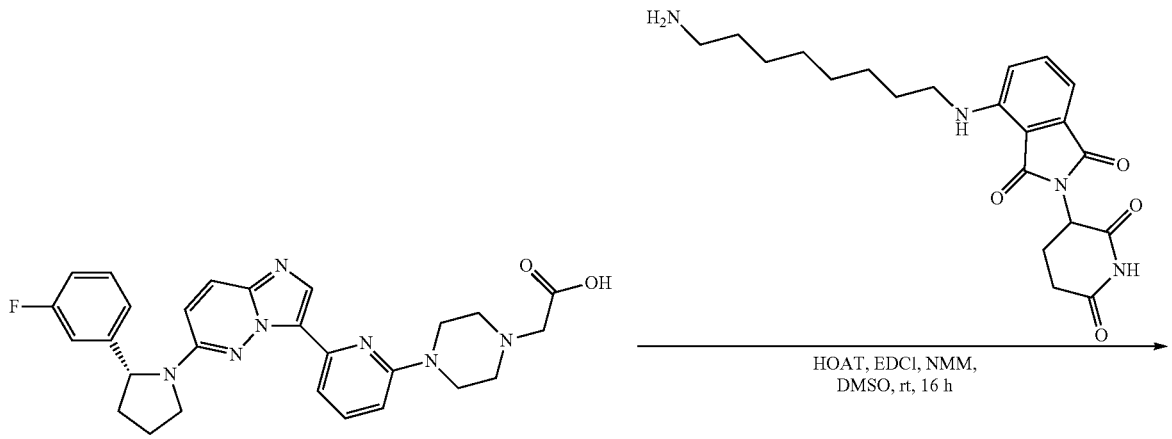

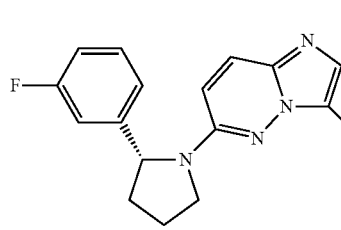

-continued

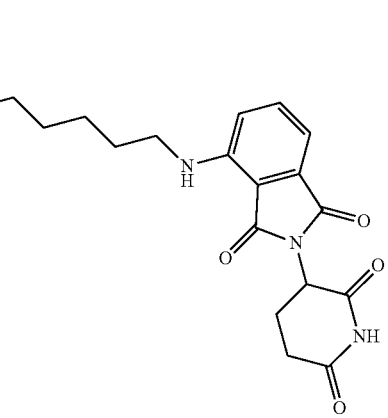

TR-102 was synthesized following the standard procedure for preparing TR-059 (12 mg, yield 65%). MS (ESI) m/z: 884.7 [M+H]$^+$.

Example 154: N-(5-((2-(2,6-dioxopiperidin-3-yl)-1,3-dioxoisoindolin-4-yl)amino)pentyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-103)

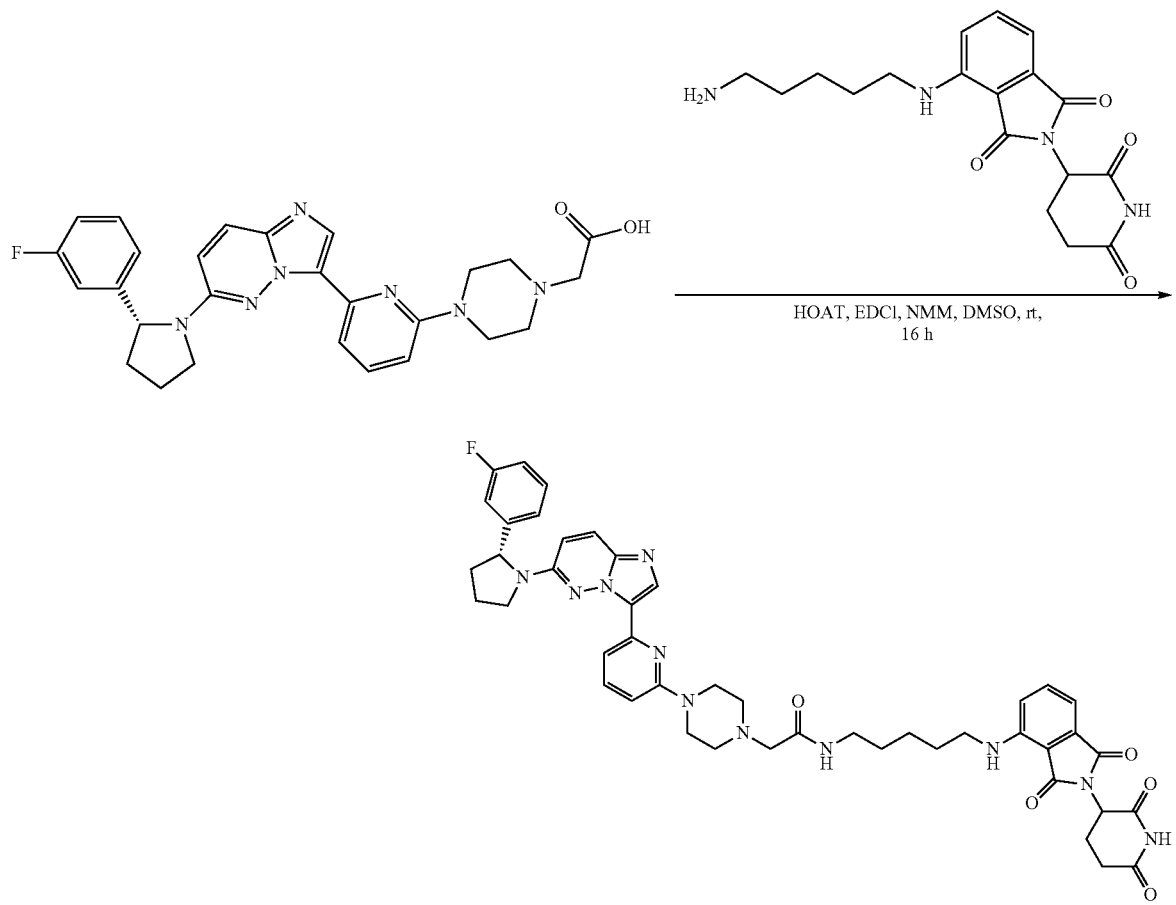

TR-103 was synthesized following the standard procedure for preparing TR-059 (11 mg, yield 63%). MS (ESI) m/z: 842.7 [M+H]$^+$.

Example 155: N-(17-((2-(2,6-dioxopiperidin-3-yl)-1,3-dioxoisoindolin-4-yl)amino)-3,6,9,12,15-pentaoxaheptadecyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-104)

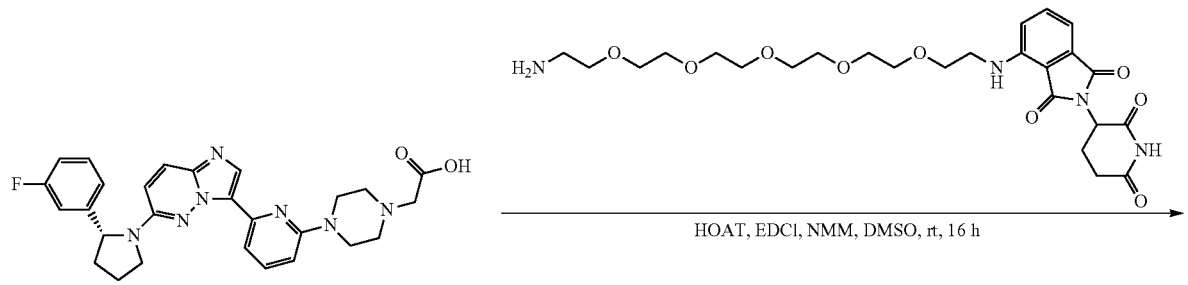

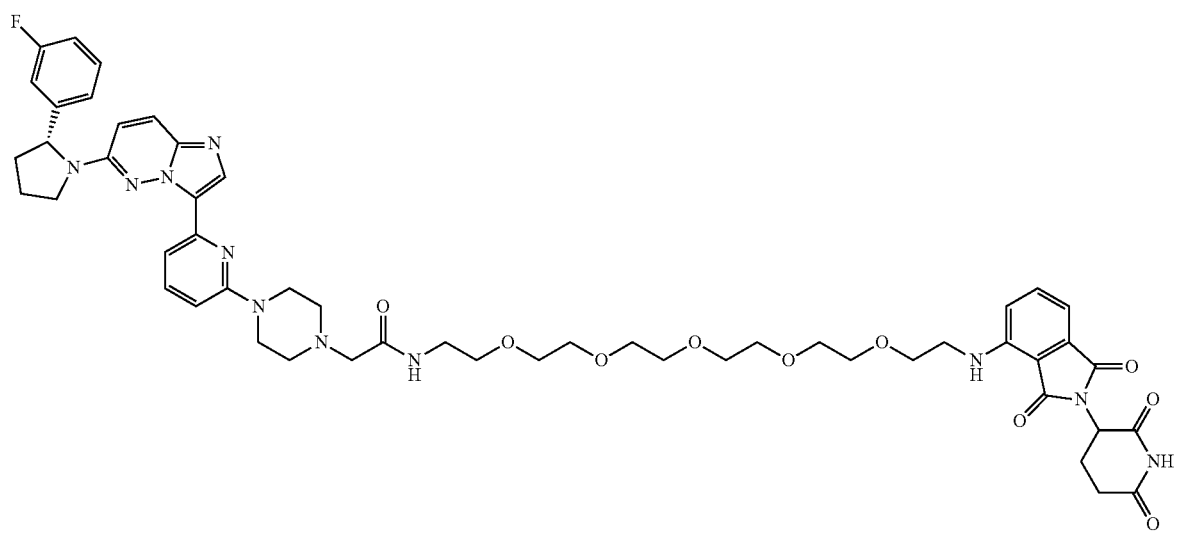

TR-104 was synthesized following the standard procedure for preparing TR-059 (12 mg, yield 60%). MS (ESI) m/z: 1020.9 [M+H]$^+$.

Example 156: N-(2-(2-(2-((2-(2,6-dioxopiperidin-3-yl)-1,3-dioxoisoindolin-4-yl)amino)ethoxy)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-105)

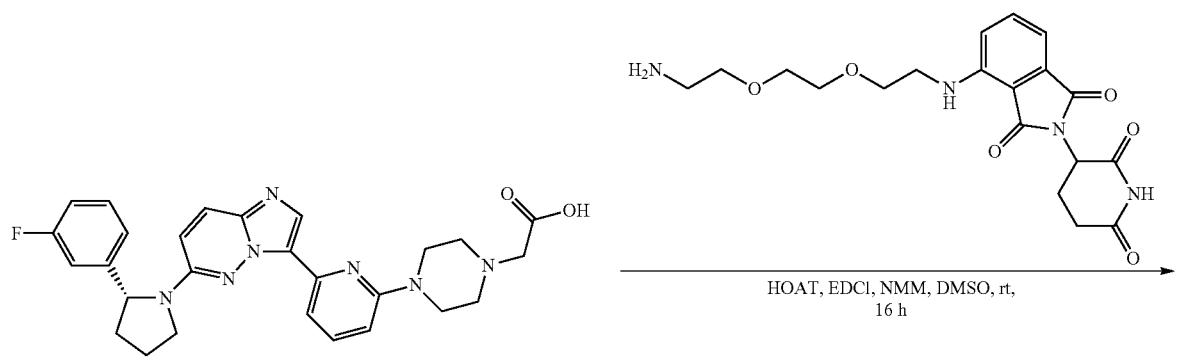

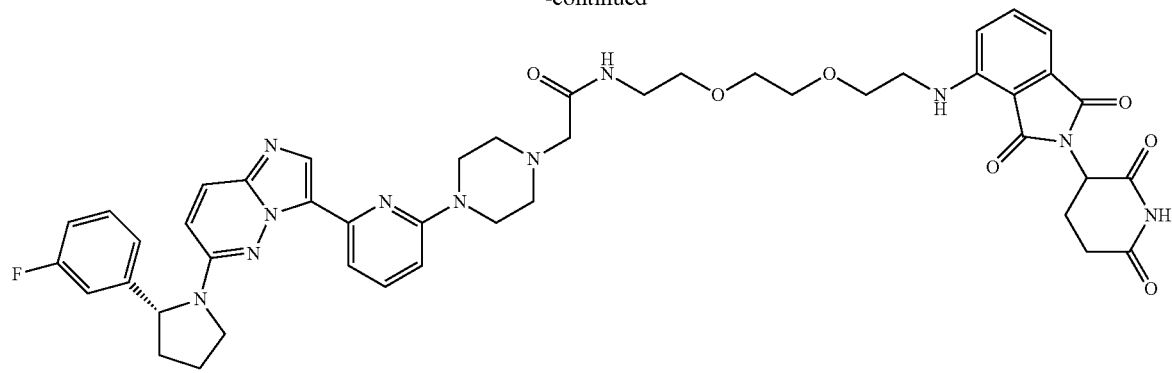
TR-105 was synthesized following the standard procedure for preparing TR-059 (11 mg, yield 63%). MS (ESI) m/z: 888.8 [M+H]+.
Example 157: N-(2-(2-((2-(2,6-dioxopiperidin-3-yl)-1,3-dioxoisoindolin-4-yl)amino)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-106)
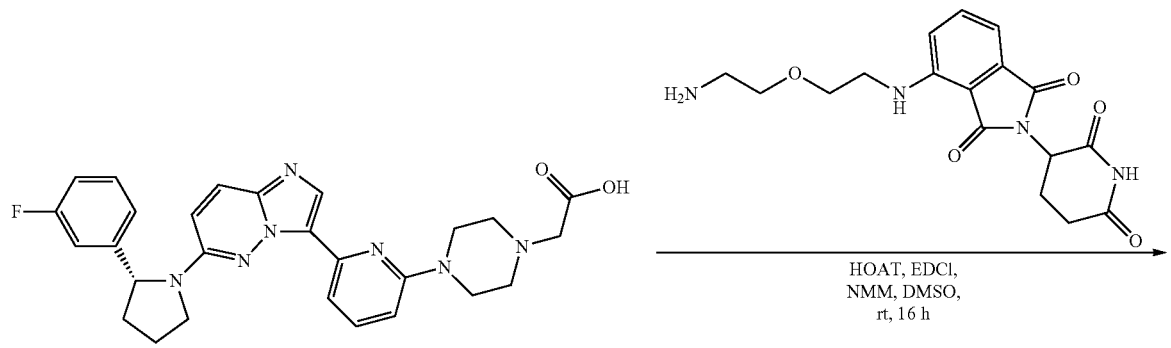
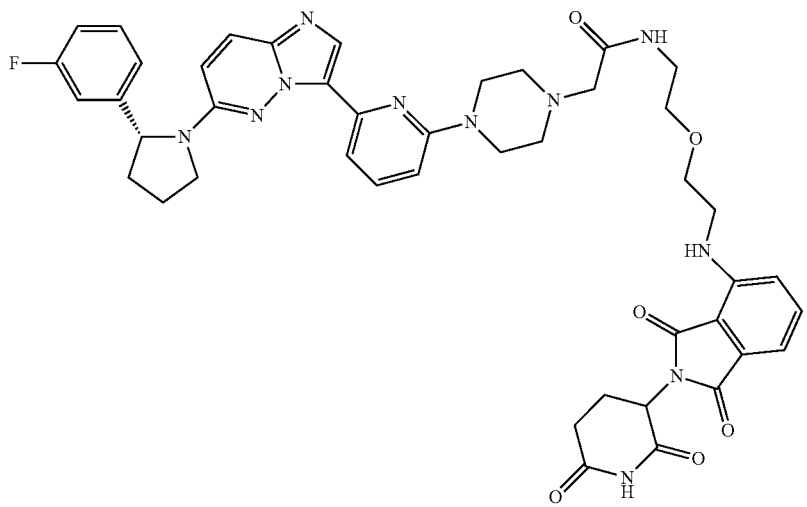
TR-106 was synthesized following the standard procedure for preparing TR-059 (10 mg, yield 55%). MS (ESI) m/z: 844.6 [M+H]+.

Example 158: N-(4-((2-(2,6-dioxopiperidin-3-yl)-1,3-dioxoisoindolin-4-yl)amino)butyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-107)

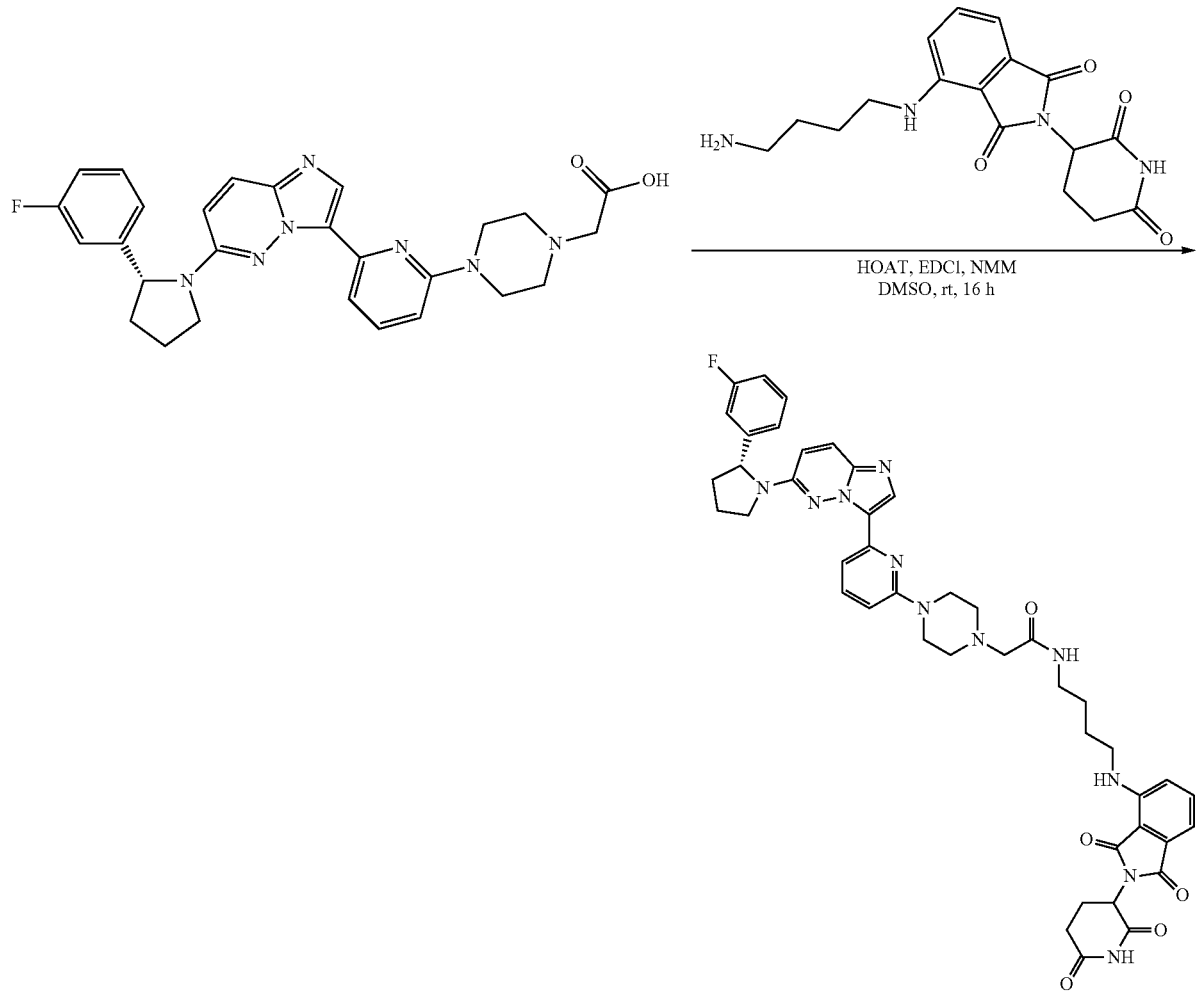

TR-107 was synthesized following the standard procedure for preparing TR-059 (11.5 mg, yield 62%). MS (ESI) m/z: 828.6 [M+H]+.

Example 159: N-(14-((2-(2,6-dioxopiperidin-3-yl)-1,3-dioxoisoindolin-4-yl)amino)-3,6,9,12-tetraoxatetradecyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-108)

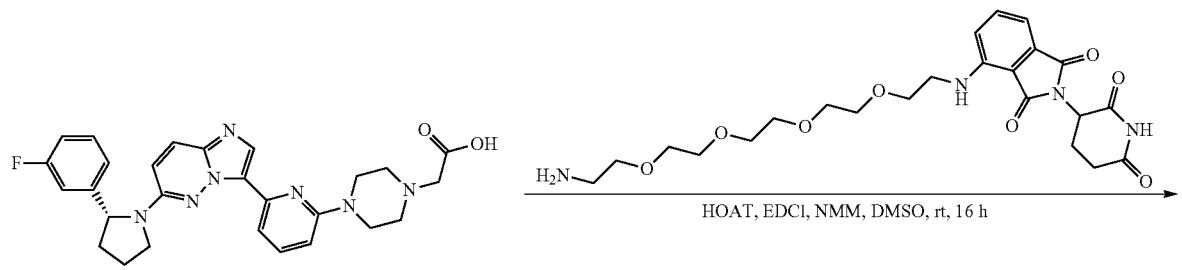

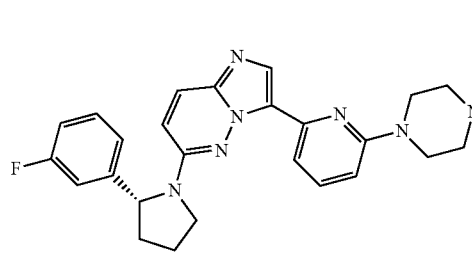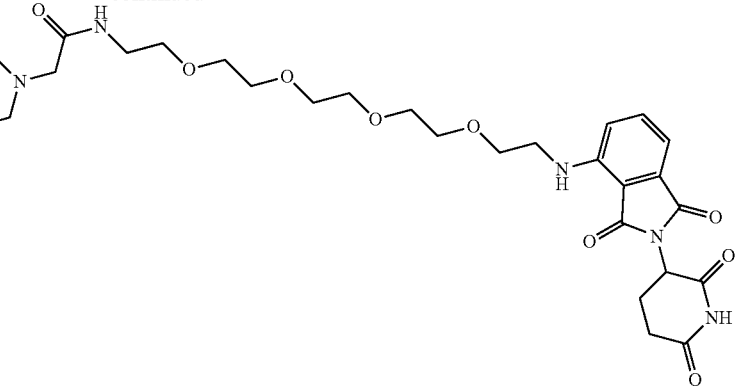
TR-108 was synthesized following the standard procedure for preparing TR-059 (13 mg, yield 64%). MS (ESI) m/z: 976.8 [M+H]$^+$.
Example 160: N-(3-((2-(2,6-dioxopiperidin-3-yl)-1,3-dioxoisoindolin-4-yl)amino)propyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-109)
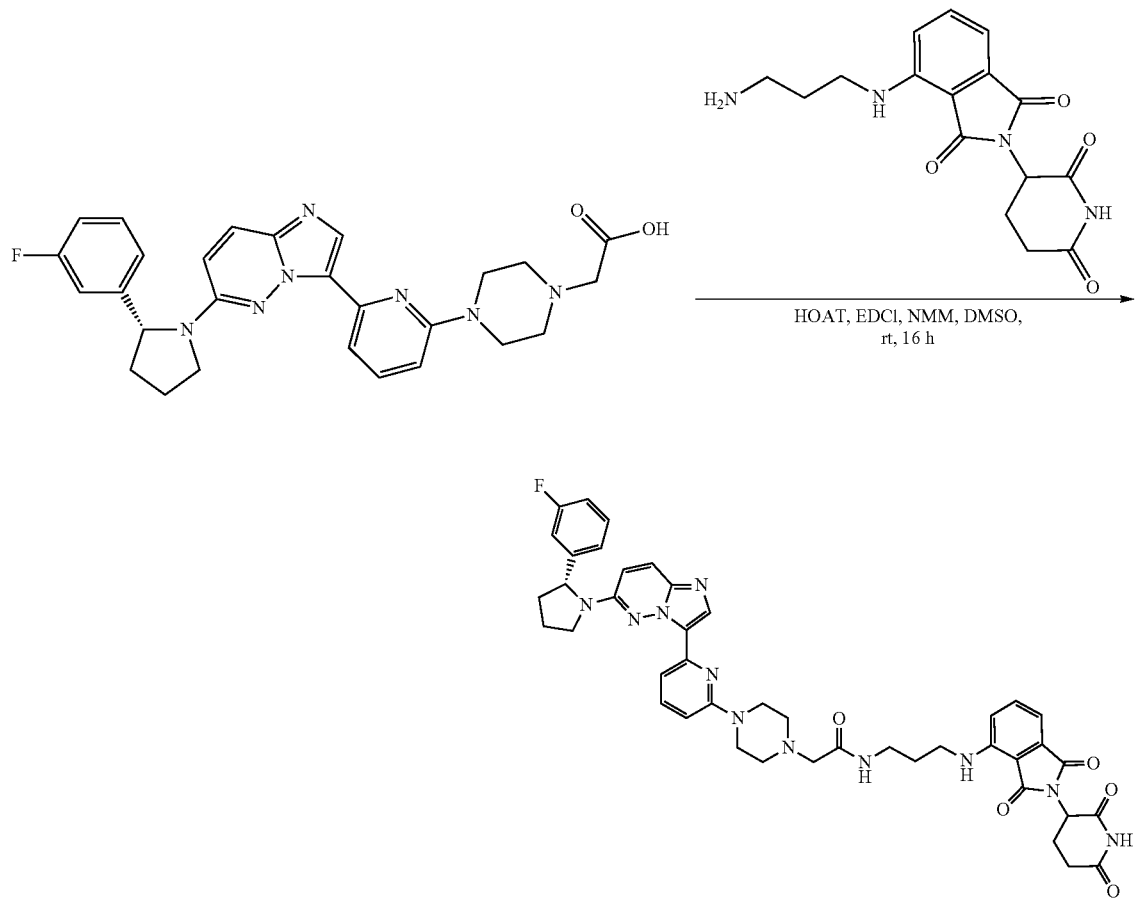
TR-109 was synthesized following the standard procedure for preparing TR-059 (12 mg, yield 63%). MS (ESI) m/z: 814.6 [M+H]$^+$.

Example 161: N-(7-((2-(2,6-dioxopiperidin-3-yl)-1, 3-dioxoisoindolin-4-yl)amino)heptyl)-2-(4-(6-(6-((R)-2-(3-fluorophenyl)pyrrolidin-1-yl)imidazo[1,2-b]pyridazin-3-yl)pyridin-2-yl)piperazin-1-yl) acetamide (TR-110)

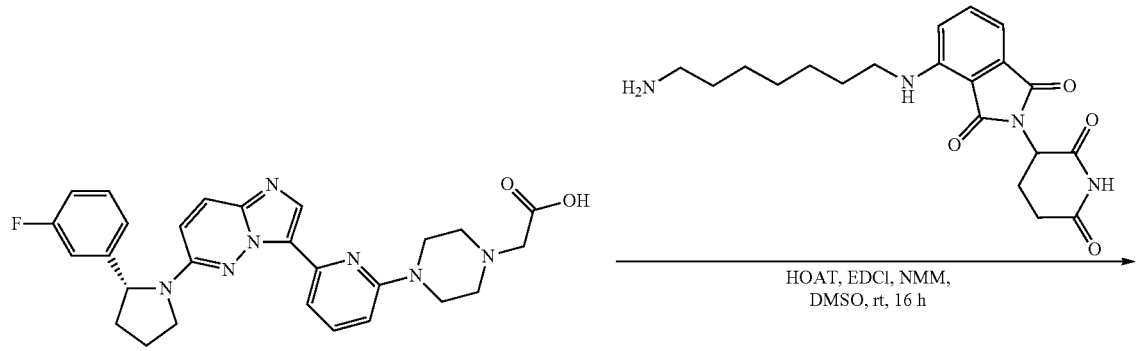

TR-110 was synthesized following the standard procedure for preparing TR-059 (10 mg, yield 61%). MS (ESI) m/z: 870.7 [M+H]$^+$.

Example 162: N-(6-((2-(2,6-dioxopiperidin-3-yl)-1, 3-dioxoisoindolin-4-yl)amino)hexyl)-2-(4-(6-(6-((R)-2-(3-fluorophenyl)pyrrolidin-1-yl)imidazo[1,2-b]pyridazin-3-yl)pyridin-2-yl)piperazin-1-yl) acetamide (TR-111)

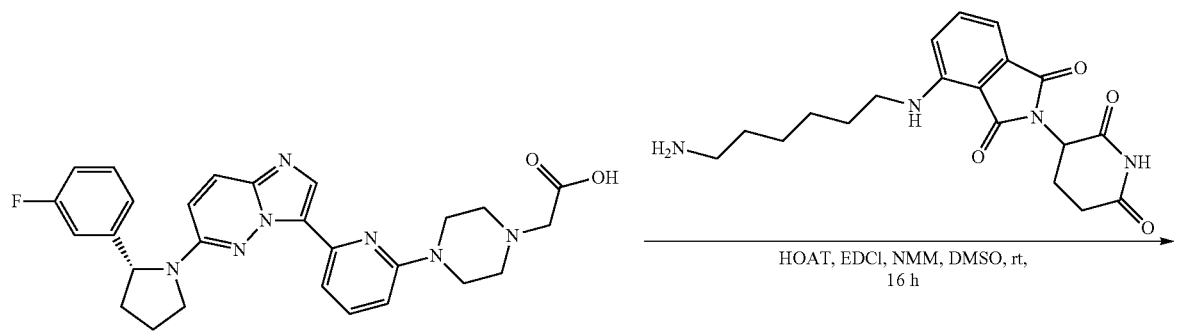

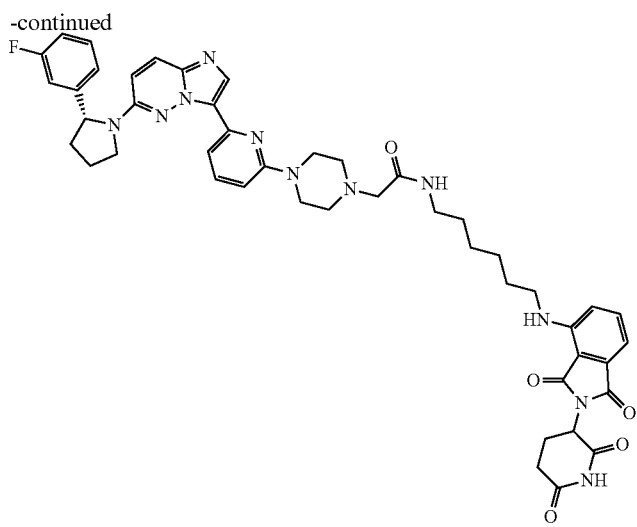
TR-111 was synthesized following the standard procedure for preparing TR-059 (8.6 mg, yield 60%). MS (ESI) m/z: 856.7 [M+H]⁺.
Example 163: 2-(2,6-Dioxopiperidin-3-yl)-5-((2-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethyl)amino)isoindoline-1,3-dione (TR-113)
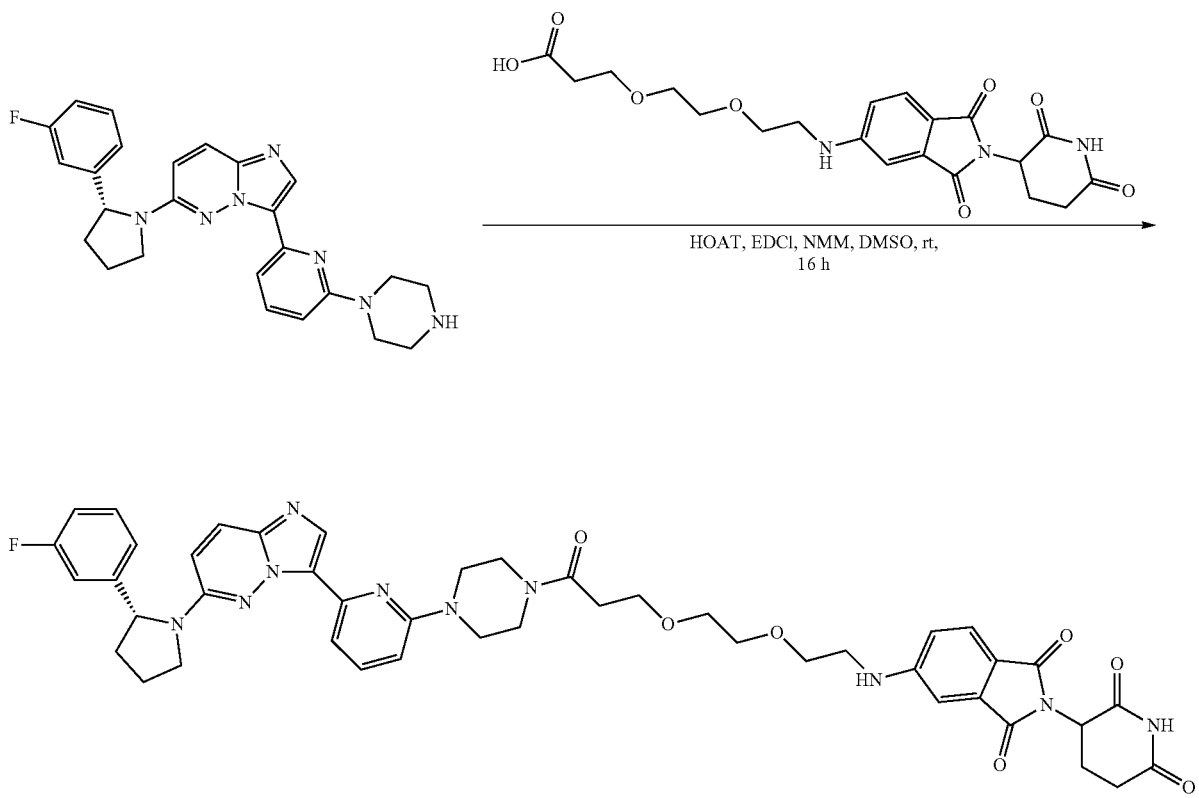
TR-113 was synthesized following the standard procedure for preparing TR-053 (7.7 mg, yield 59%). MS (ESI) m/z: 859.8 [M+H]⁺.

Example 164: 2-(2,6-Dioxopiperidin-3-yl)-5-((2-(2-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethoxy)ethyl)amino)isoindoline-1,3-dione (TR-114)

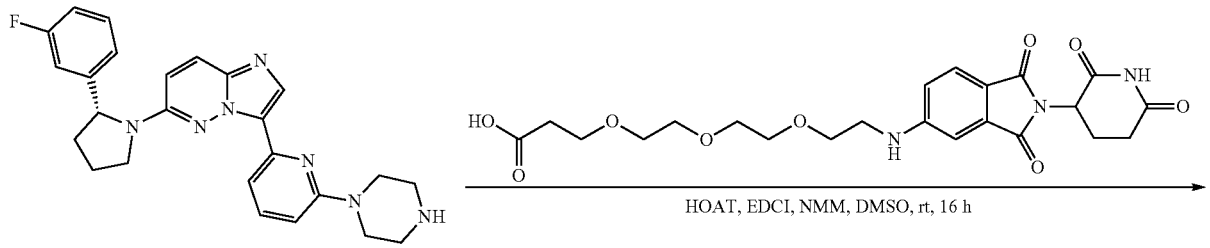

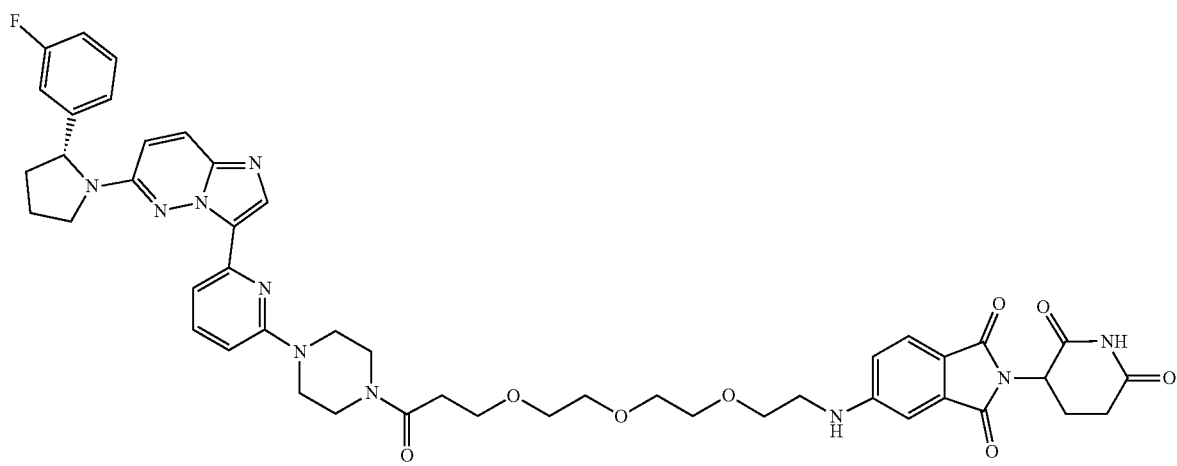

TR-114 was synthesized following the standard procedure for preparing TR-053 (8.6 mg, yield 61%). MS (ESI) m/z: 903.9 [M+H]$^+$.

Example 165: 2-(2,6-Dioxopiperidin-3-yl)-5-((5-(4-(6-(6-((R)-2-(3-fluorophenyl)pyrrolidin-1-yl)imidazo[1,2-b]pyridazin-3-yl)pyridin-2-yl)piperazin-1-yl)-5-oxopentyl)amino)isoindoline-1,3-dione (TR-115)

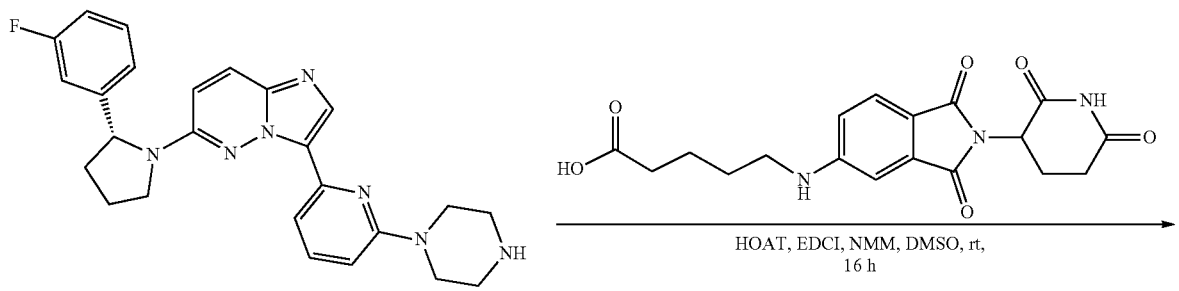

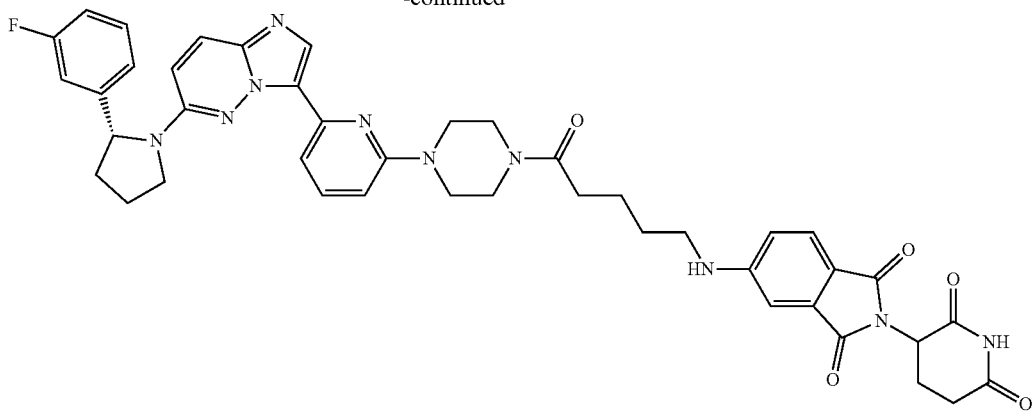
TR-115 was synthesized following the standard procedure for preparing TR-053 (8.1 mg, yield 66%). MS (ESI) m/z: 799.8 [M+H]+.
Example 166: 2-(2,6-Dioxopiperidin-3-yl)-5-((18-(4-(6-(6-((R)-2-(3-fluorophenyl)pyrrolidin-1-yl)imidazo[1,2-b]pyridazin-3-yl)pyridin-2-yl)piperazin-1-yl)-18-oxo-3,6,9,12,15-pentaoxaoctadecyl)amino)isoindoline-1,3-dione (TR-116)
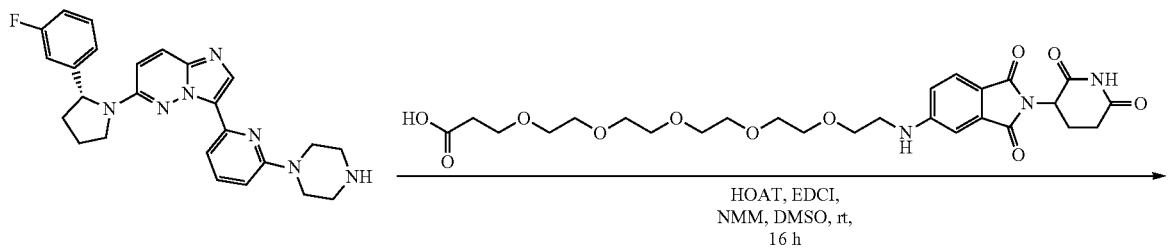
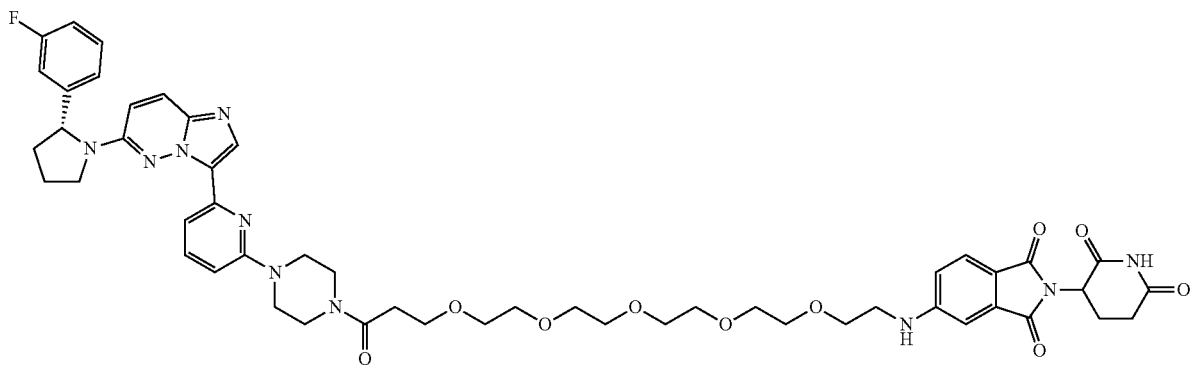
TR-116 was synthesized following the standard procedure for preparing TR-053 (8.6 mg, yield 64%). MS (ESI) m/z: 991.6 [M+H]+.

Example 167: 2-(2,6-Dioxopiperidin-3-yl)-5-((7-(4-(6-(6-((R)-2-(3-fluorophenyl)pyrrolidin-1-yl)imidazo[1,2-b]pyridazin-3-yl)pyridin-2-yl)piperazin-1-yl)-7-oxoheptyl)amino)isoindoline-1,3-dione (TR-117)

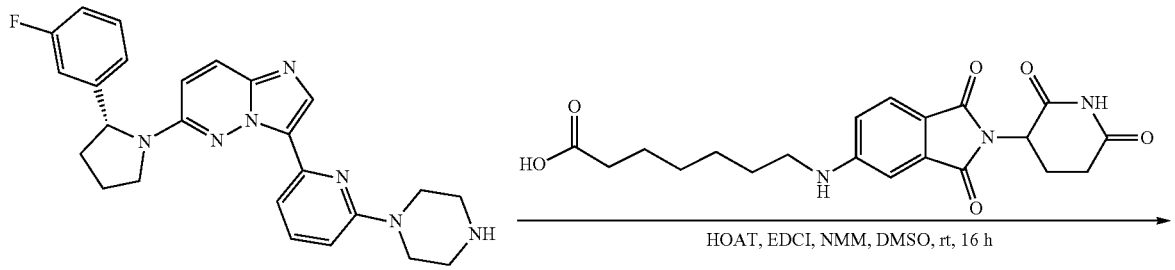

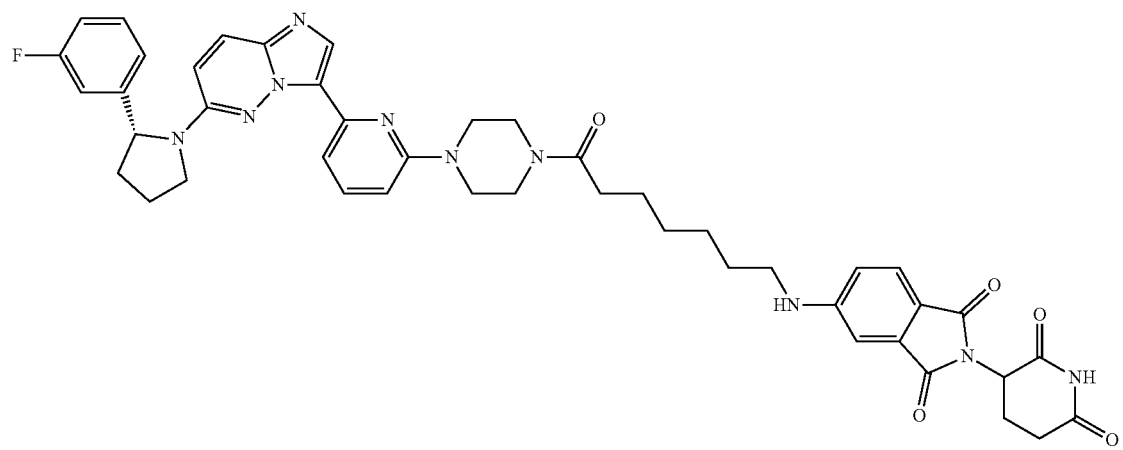

TR-117 was synthesized following the standard procedure for preparing TR-053 (8.8 mg, yield 61%). MS (ESI) m/z: 827.6 [M+H]$^+$.

Example 168: 2-(2,6-Dioxopiperidin-3-yl)-5-((8-(4-(6-(6-((R)-2-(3-fluorophenyl)pyrrolidin-1-yl)imidazo[1,2-b]pyridazin-3-yl)pyridin-2-yl)piperazin-1-yl)-8-oxooctyl)amino)isoindoline-1,3-dione (TR-118)

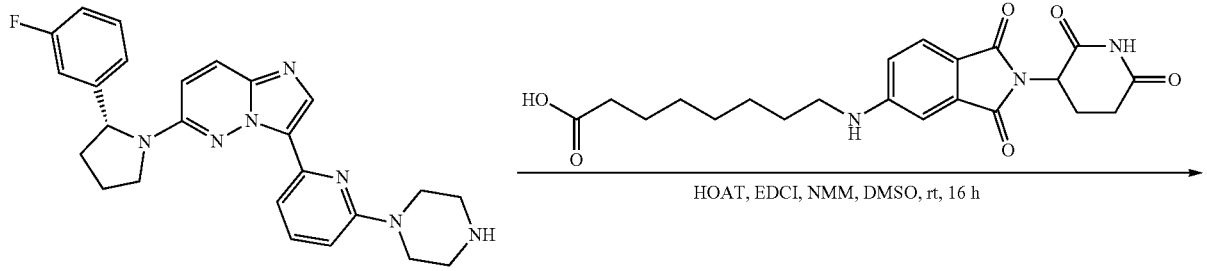

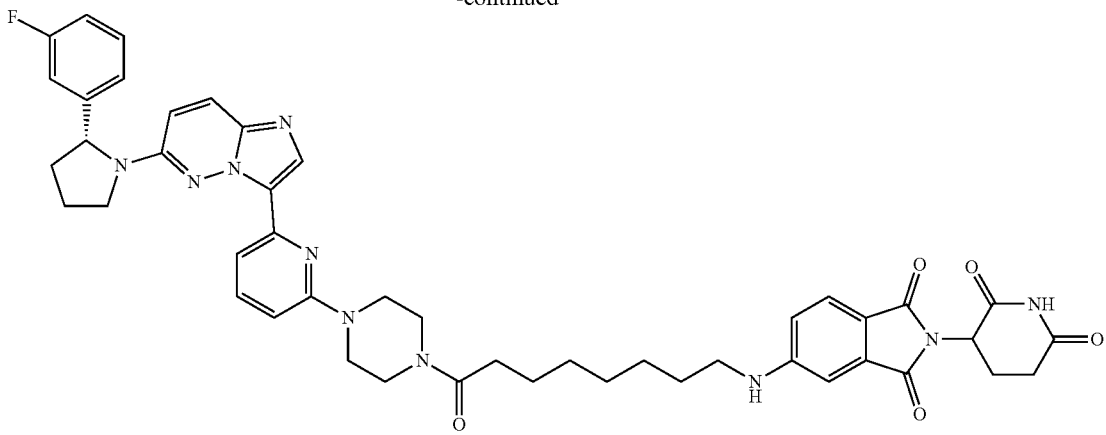
TR-118 was synthesized following the standard procedure for preparing TR-053 (8.8 mg, yield 61%). MS (ESI) m/z: 841.6 [M+H]$^+$.
Example 169: 2-(2,6-Dioxopiperidin-3-yl)-5-((2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethyl)amino)isoindoline-1,3-dione (TR-119)
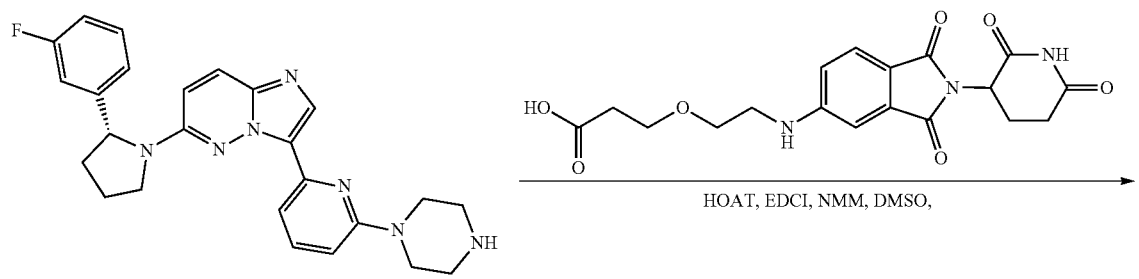
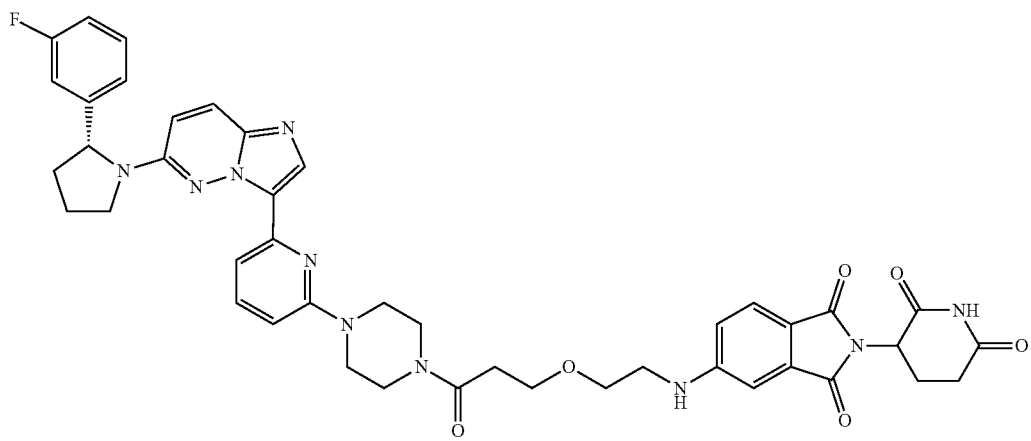
TR-119 was synthesized following the standard procedure for preparing TR-053 (8.9 mg, yield 61%). MS (ESI) m/z: 815.5 [M+H]$^+$.

Example 170: 2-(2,6-Dioxopiperidin-3-yl)-5-((15-(4-(6-(6-((R)-2-(3-fluorophenyl)pyrrolidin-1-yl)imidazo[1,2-b]pyridazin-3-yl)pyridin-2-yl)piperazin-1-yl)-15-oxo-3,6,9,12-tetraoxapentadecyl)amino)isoindoline-1,3-dione (TR-120)

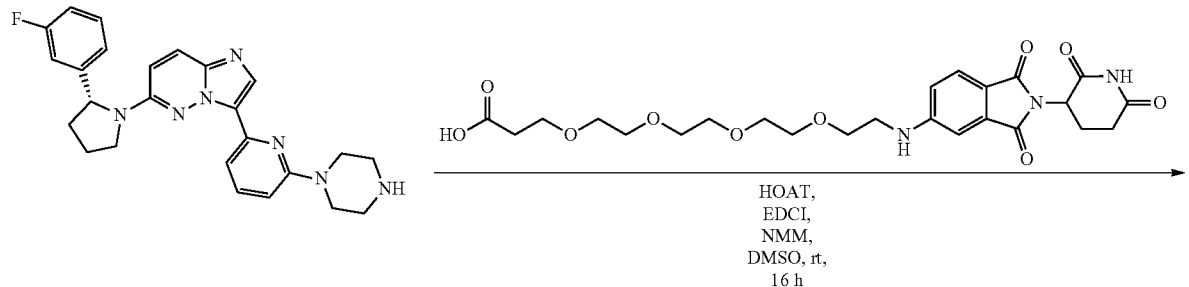

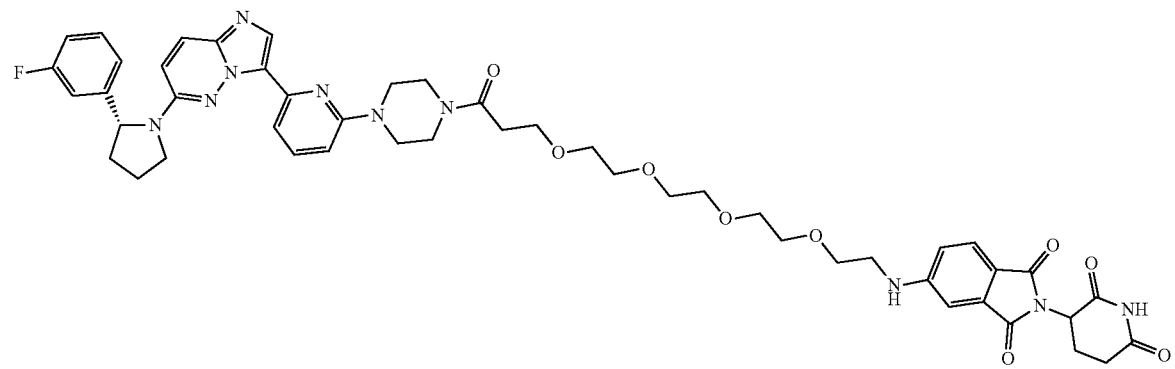

TR-120 was synthesized following the standard procedure for preparing TR-053 (8.9 mg, yield 61%). MS (ESI) m/z: 947.6 [M+H]$^+$.

Example 171: 2-(2,6-Dioxopiperidin-3-yl)-5-((3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropyl)amino)isoindoline-1,3-dione (TR-121)

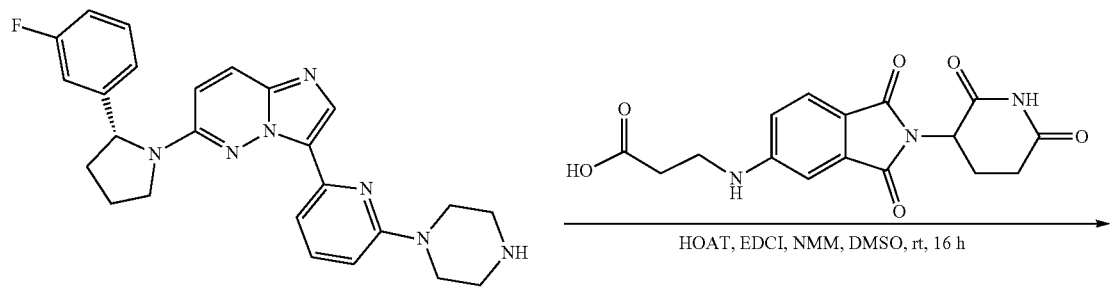

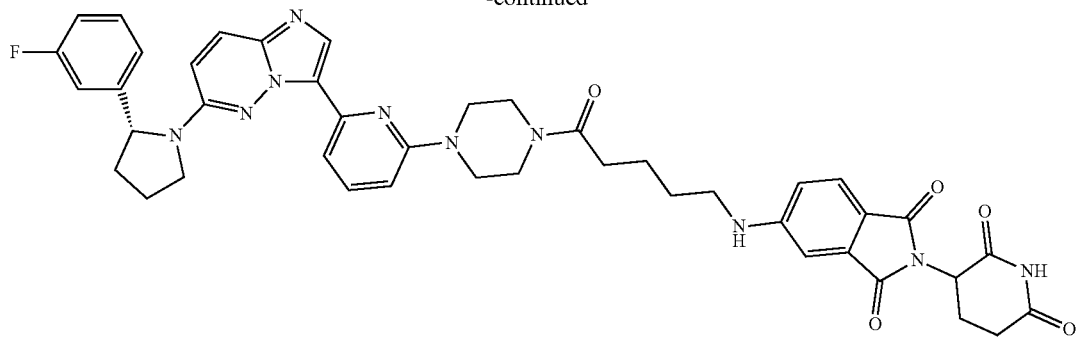
TR-121 was synthesized following the standard procedure for preparing TR-053 (10.2 mg, yield 63%). MS (ESI) m/z: 1542.5 [M+H]+.
Example 172: 2-(2,6-Dioxopiperidin-3-yl)-5-((6-(4-(6-(6-((R)-2-(3-fluorophenyl)pyrrolidin-1-yl)imidazo[1,2-b]pyridazin-3-yl)pyridin-2-yl)piperazin-1-yl)-6-oxohexyl)amino)isoindoline-1,3-dione (TR-122)
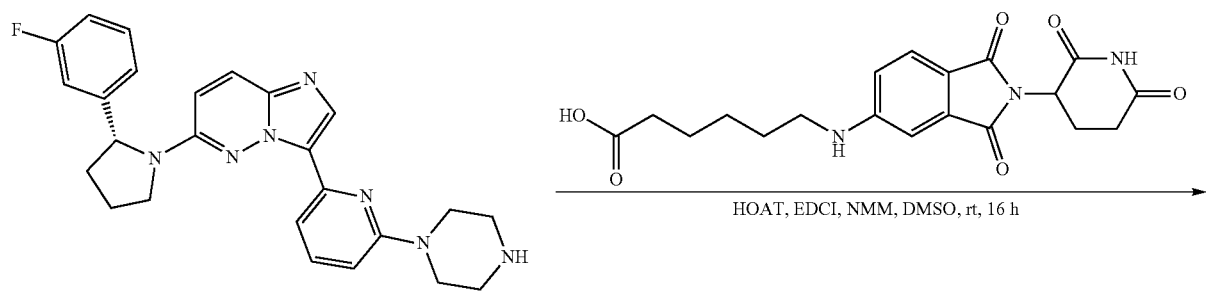
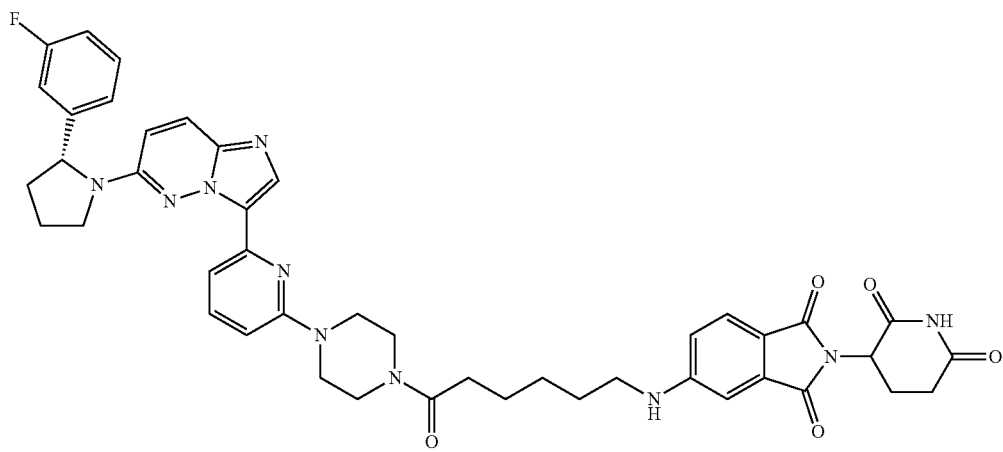
TR-122 was synthesized following the standard procedure for preparing TR-053 (10.6 mg, yield 62%). MS (ESI) m/z: 813.9 [M+H]+.

Example 173: 2-(2,6-Dioxopiperidin-3-yl)-5-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)isoindoline-1,3-dione (TR-123)

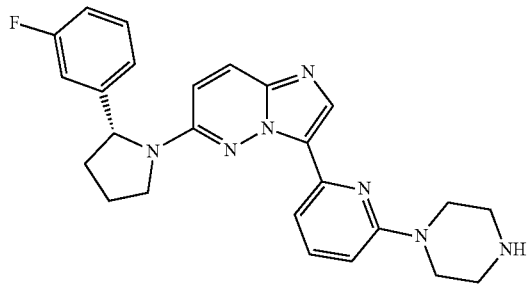 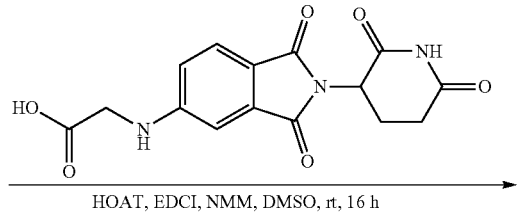

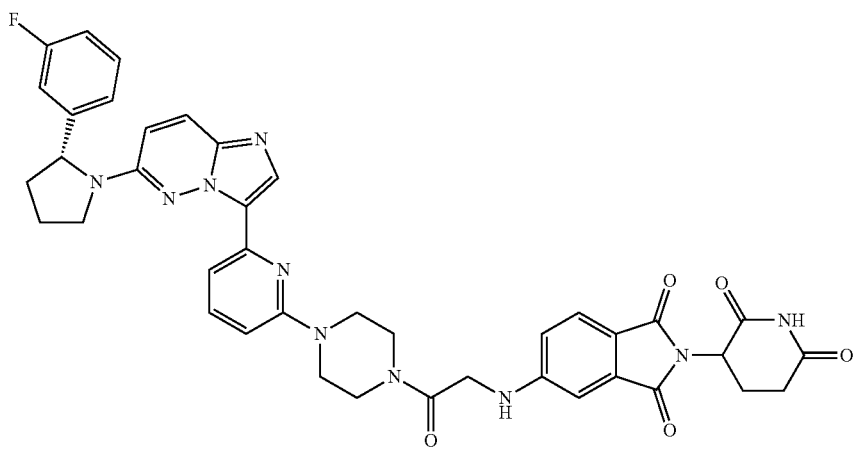

TR-123 was synthesized following the standard procedure for preparing TR-053 (10.6 mg, yield 62%). MS (ESI) m/z: 1514.8 [M+H]$^+$.

Example 174: N-(4-((2-(2,6-dioxopiperidin-3-yl)-1,3-dioxoisoindolin-5-yl)amino)butyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-124)

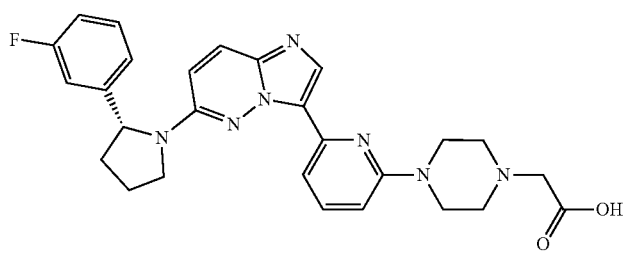 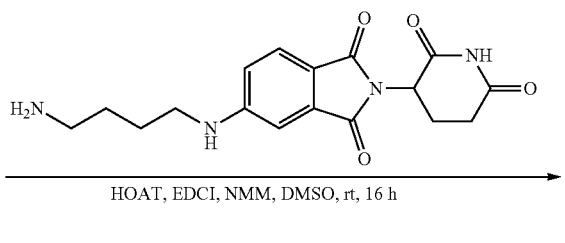

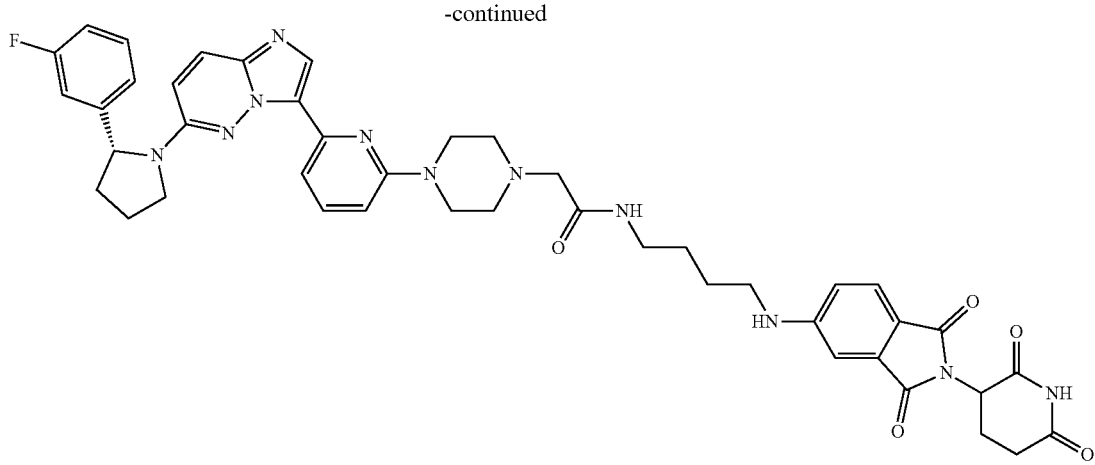
TR-124 was synthesized following the standard procedure for preparing TR-059 (9.3 mg, yield 61%). MS (ESI) m/z: 828.5 [M+H]⁺.
Example 175: N-(14-((2-(2,6-dioxopiperidin-3-yl)-1,3-dioxoisoindolin-5-yl)amino)-3,6,9,12-tetraoxatetradecyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-125)
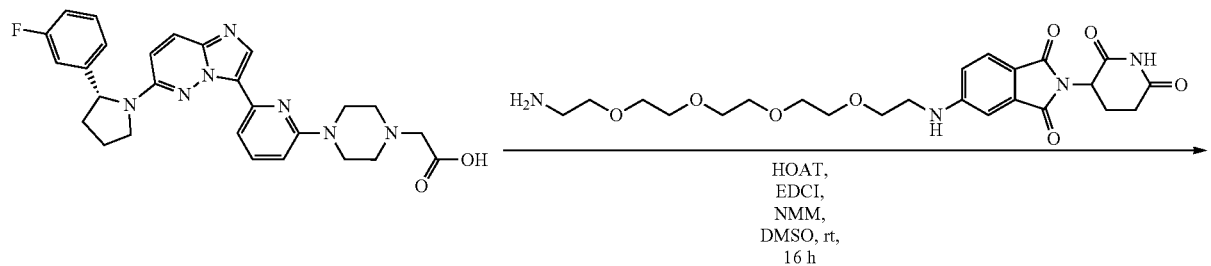
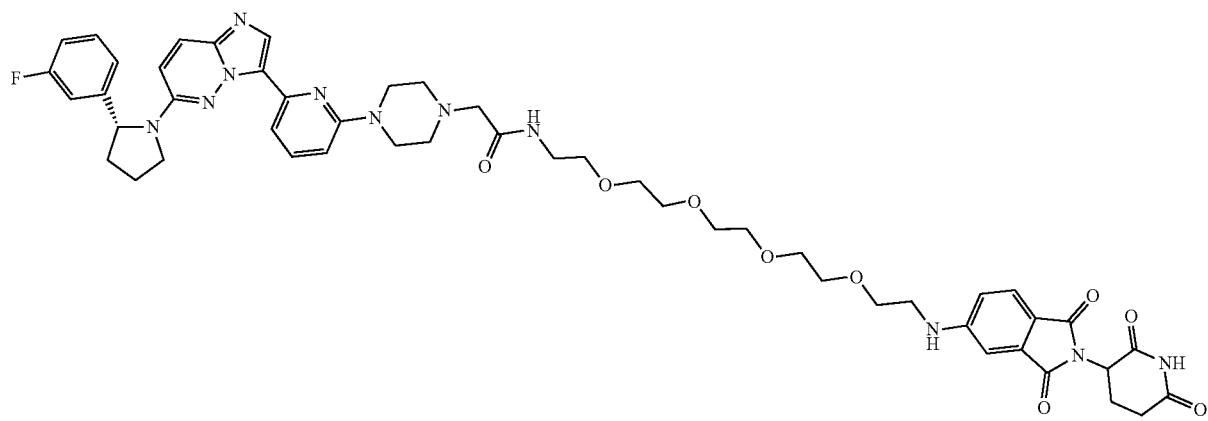
TR-125 was synthesized following the standard procedure for preparing TR-059 (9.6 mg, yield 62%). MS (ESI) m/z: 976.8 [M+H]⁺.

Example 176: N-(7-((2-(2,6-dioxopiperidin-3-yl)-1,3-dioxoisoindolin-5-yl)amino)heptyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-126)

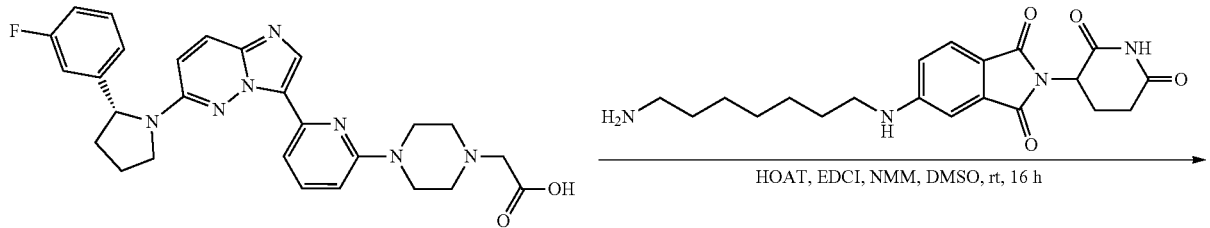

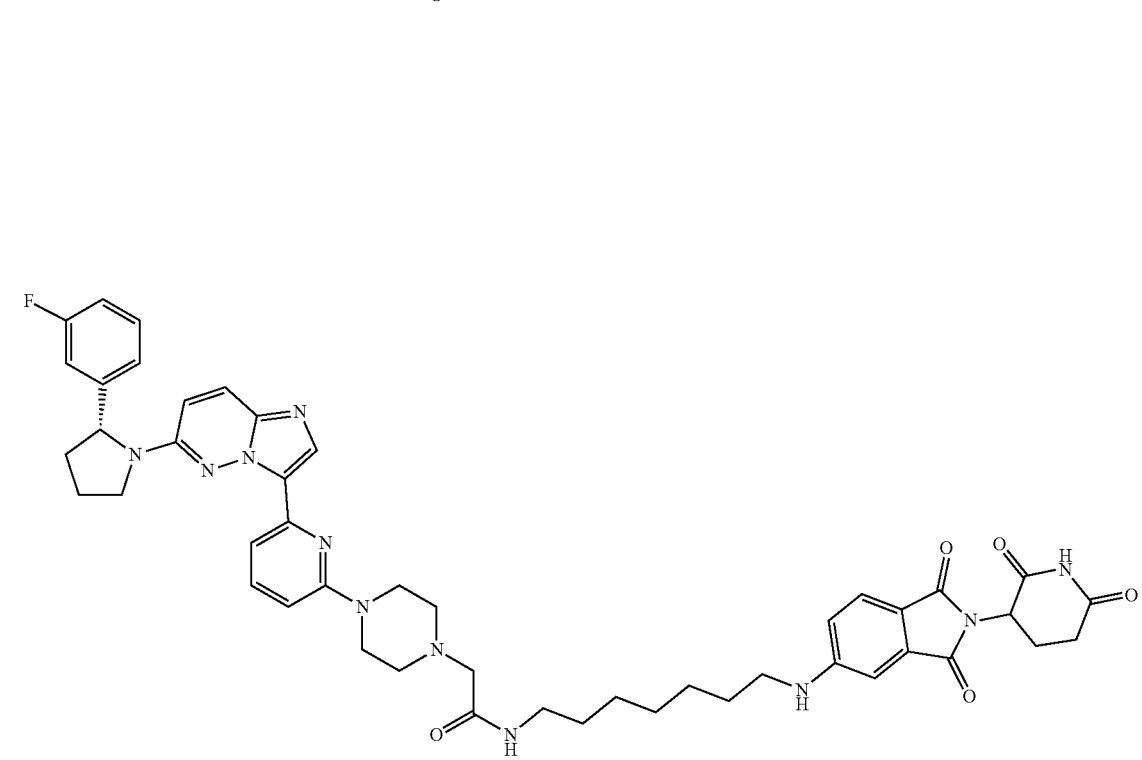

TR-126 was synthesized following the standard procedure for preparing TR-059 (9.9 mg, yield 63%). MS (ESI) m/z: 870.7 [M+H]$^+$.

Example 177: N-(3-((2-(2,6-dioxopiperidin-3-yl)-1,3-dioxoisoindolin-5-yl)amino)propyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-127)

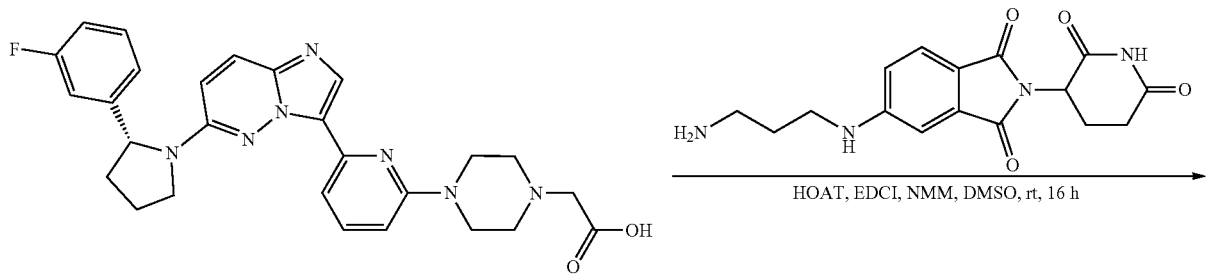

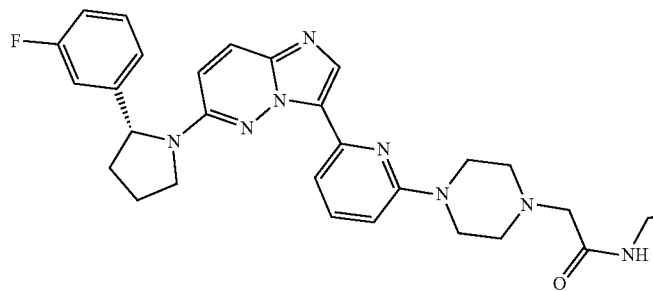
TR-127 was synthesized following the standard procedure for preparing TR-059 (9.3 mg, yield 61%). MS (ESI) m/z: 814.6 [M+H]⁺.
Example 178: N-(6-((2-(2,6-dioxopiperidin-3-yl)-1,3-dioxoisoindolin-5-yl)amino)hexyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-128)
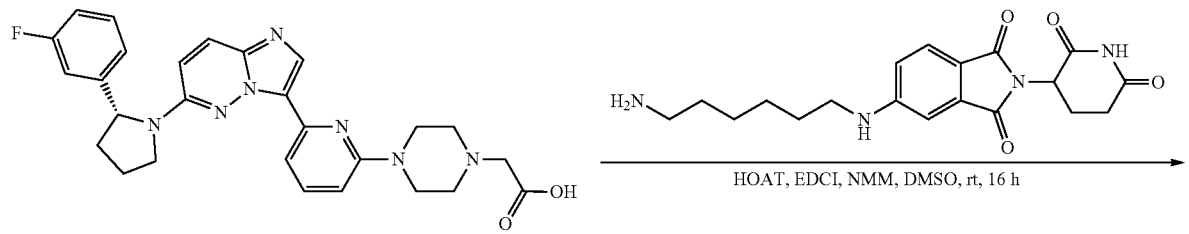
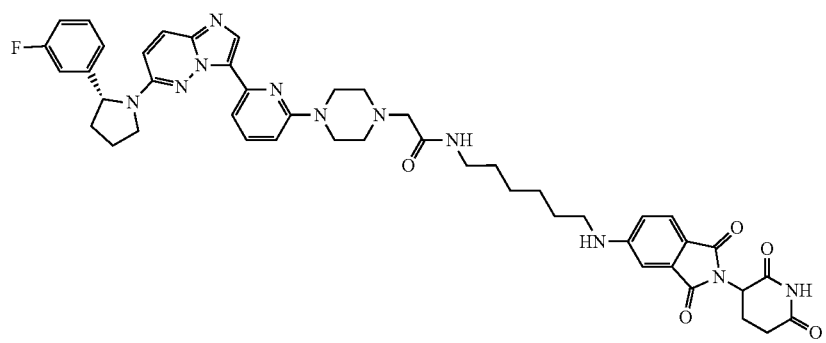
TR-128 was synthesized following the standard procedure for preparing TR-059 (9.7 mg, yield 62%). MS (ESI) m/z: 856.7 [M+H]⁺.

Example 179: N-(2-(2-(2-(2-((2-(2,6-dioxopiperidin-3-yl)-1,3-dioxoisoindolin-5-yl)amino)ethoxy)ethoxy)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-129)

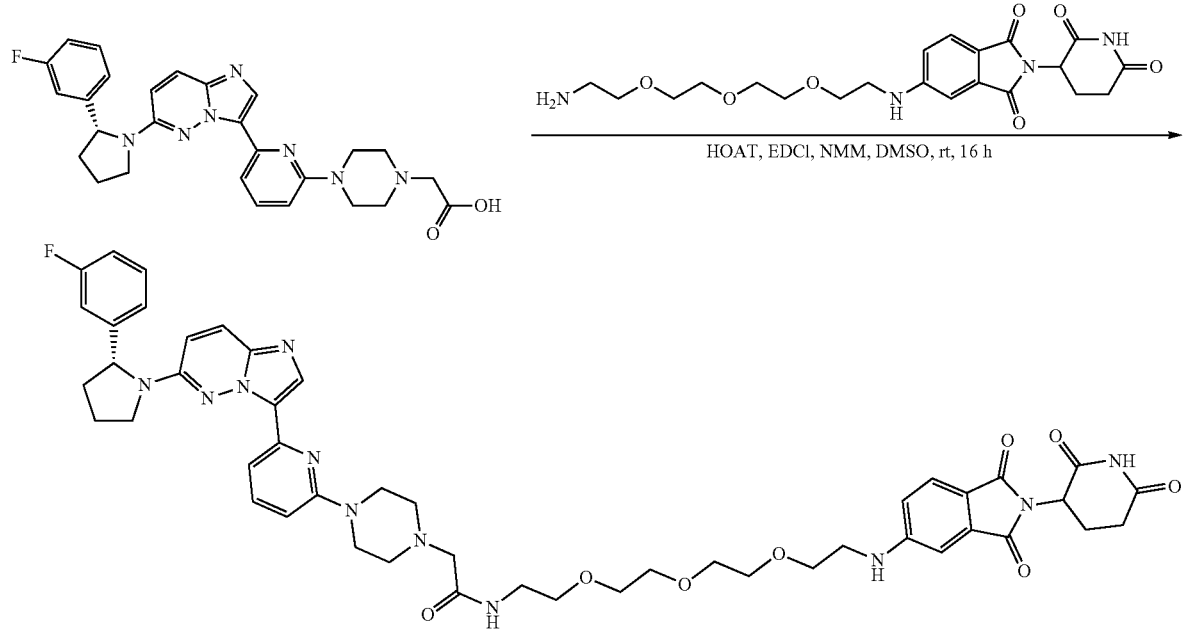

TR-129 was synthesized following the standard procedure for preparing TR-059 (9.7 mg, yield 62%). MS (ESI) m/z: 932.6 [M+H]+.

Example 180: N-(2-((2-(2,6-dioxopiperidin-3-yl)-1,3-dioxoisoindolin-5-yl)amino)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-130)

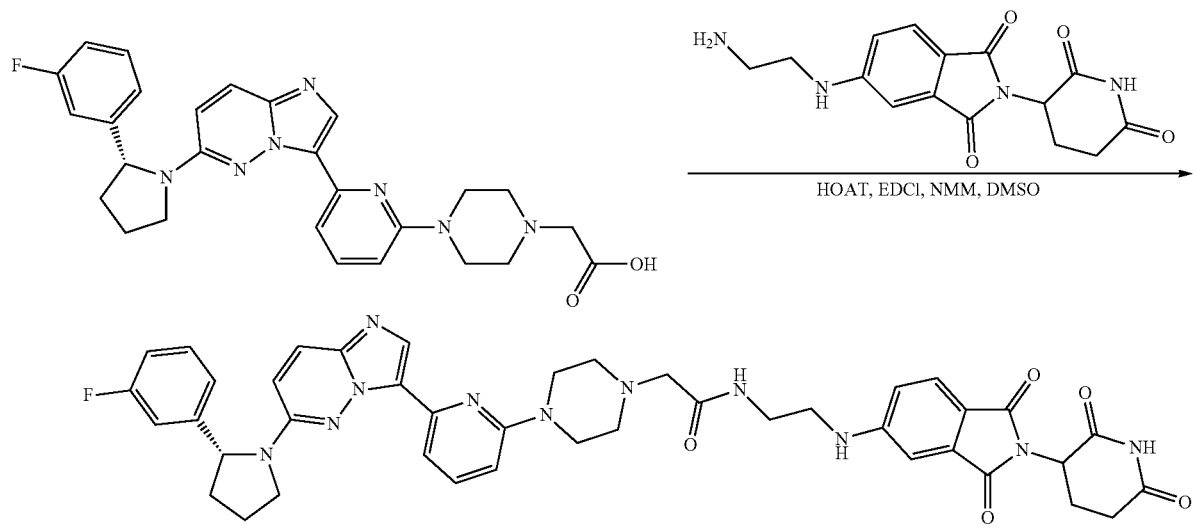

TR-130 was synthesized following the standard procedure for preparing TR-059 (9.3 mg, yield 62%). MS (ESI) m/z: 800.6 [M+H]+.

Example 181: N-(5-((2-(2,6-dioxopiperidin-3-yl)-1,3-dioxoisoindolin-5-yl)amino)pentyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-131)

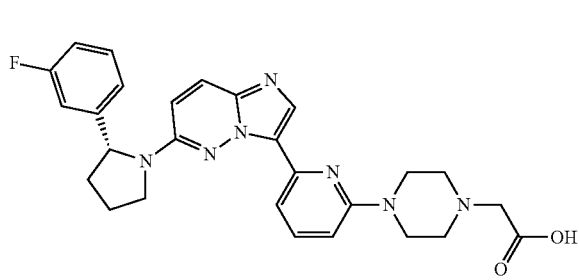
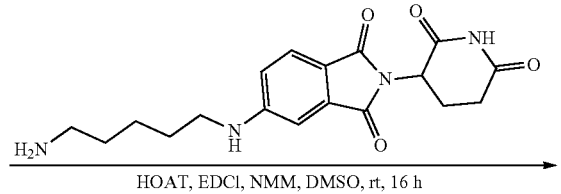

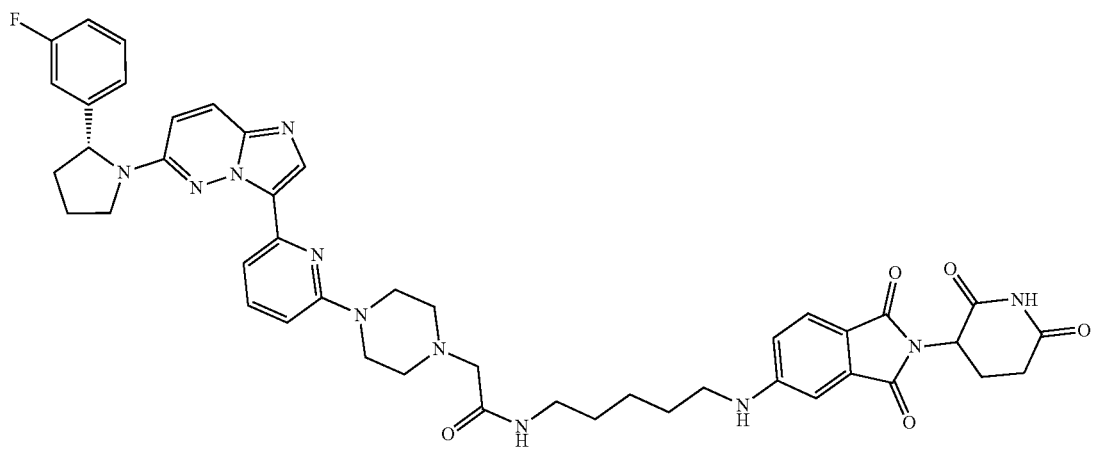

TR-131 was synthesized following the standard procedure for preparing TR-059 (10.5 mg, yield 65%). MS (ESI) m/z: 842.6 [M+H]$^+$.

Example 182: N-(17-((2-(2,6-dioxopiperidin-3-yl)-1,3-dioxoisoindolin-5-yl)amino)-3,6,9,12,15-pentaoxaheptadecyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-132)

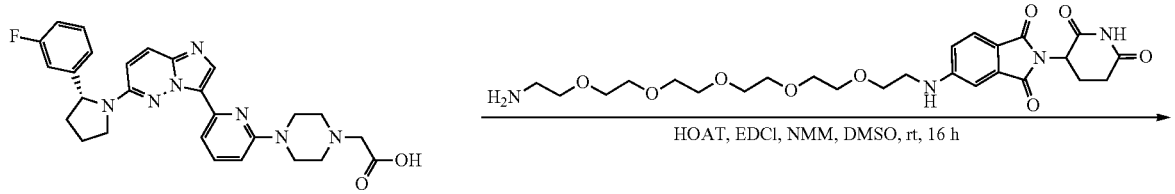

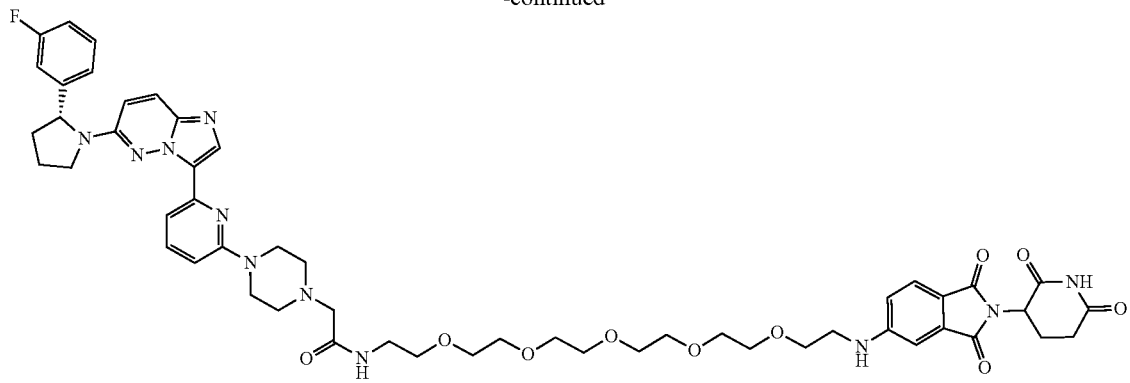
TR-132 was synthesized following the standard procedure for preparing TR-059 (7.5 mg, yield 55%). MS (ESI) m/z: 1020.9 [M+H]+.
Example 183: N-(8-((2-(2,6-dioxopiperidin-3-yl)-1,3-dioxoisoindolin-5-yl)amino)octyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-133)
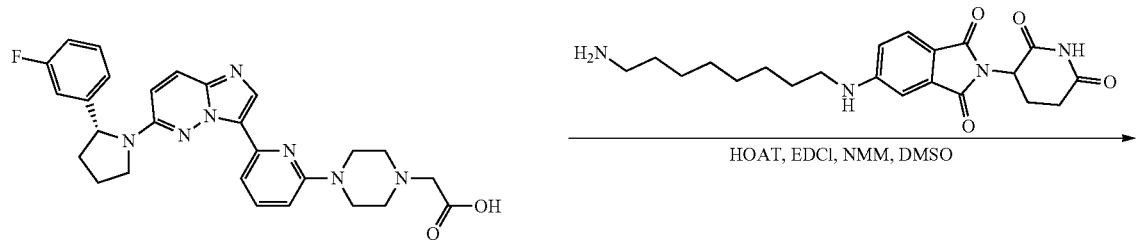
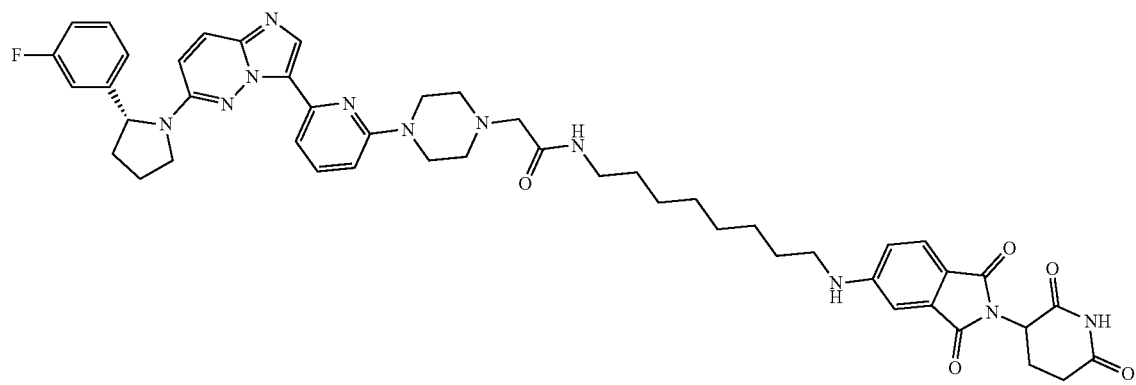
TR-133 was synthesized following the standard procedure for preparing TR-059 (8.6 mg, yield 55%). MS (ESI) m/z: 884.7 [M+H]+.

Example 184: N-(2-(2-(2-((2-(2,6-dioxopiperidin-3-yl)-1,3-dioxoisoindolin-5-yl)amino)ethoxy)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-134)

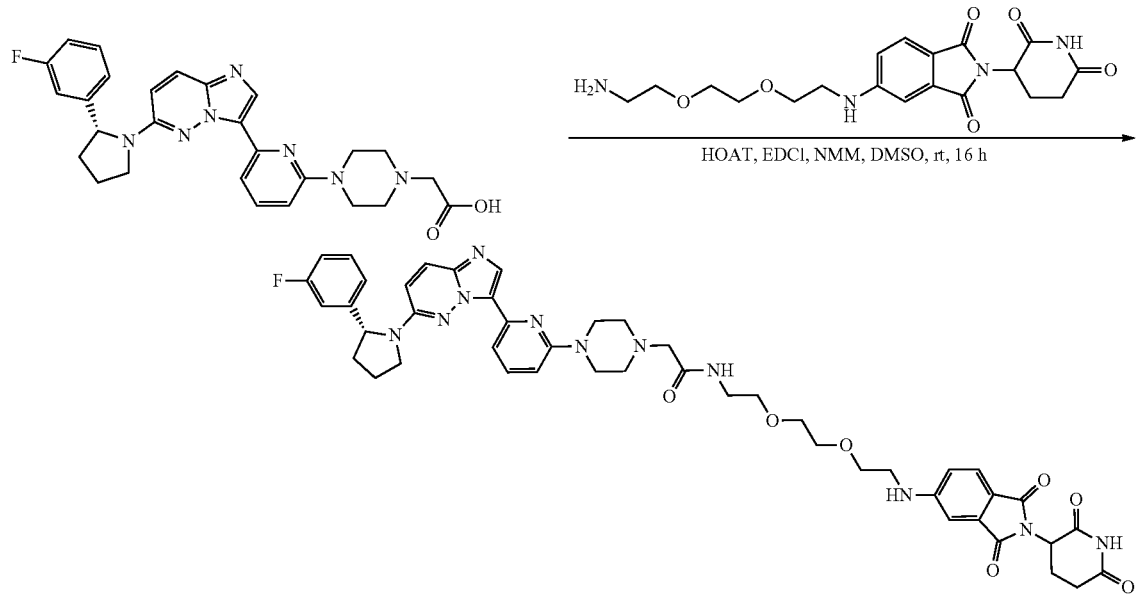

TR-134 was synthesized following the standard procedure for preparing TR-059 (8.8 mg, yield 59%). MS (ESI) m/z: 888.7 [M+H]$^+$.

Example 185: N-(2-(2-((2-(2,6-dioxopiperidin-3-yl)-1,3-dioxoisoindolin-5-yl)amino)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-135)

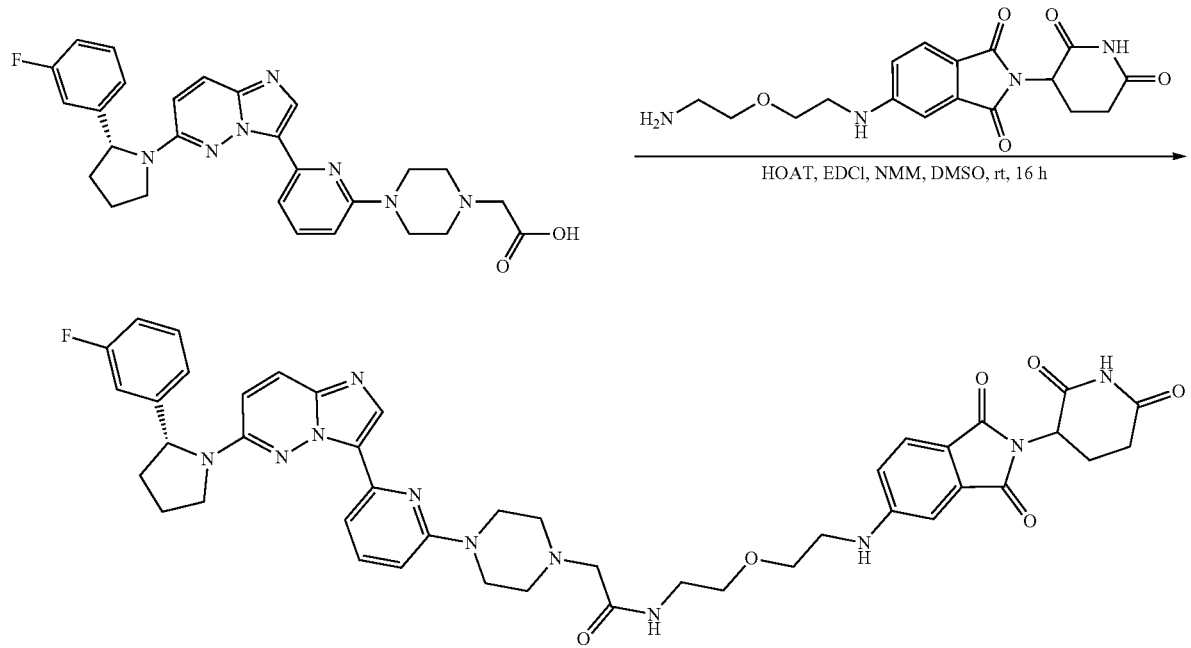

TR-135 was synthesized following the standard procedure for preparing TR-059 (8.1 mg, yield 56%). MS (ESI) m/z: 844.7 [M+H]+.

Example 186: N-(5-(3,5-Difluorobenzyl)-1H-indazol-3-yl)-4-(4-(8-((2-(2,6-dioxopiperidin-3-yl)-1,3-dioxoisoindolin-5-yl)amino)octanoyl)piperazin-1-yl)-2-((tetrahydro-2H-pyran-4-yl)amino)benzamide (TR-136)

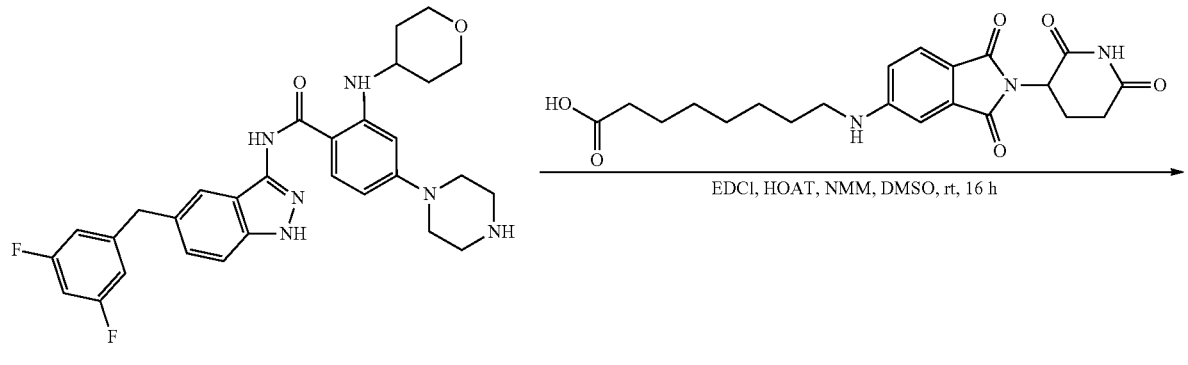

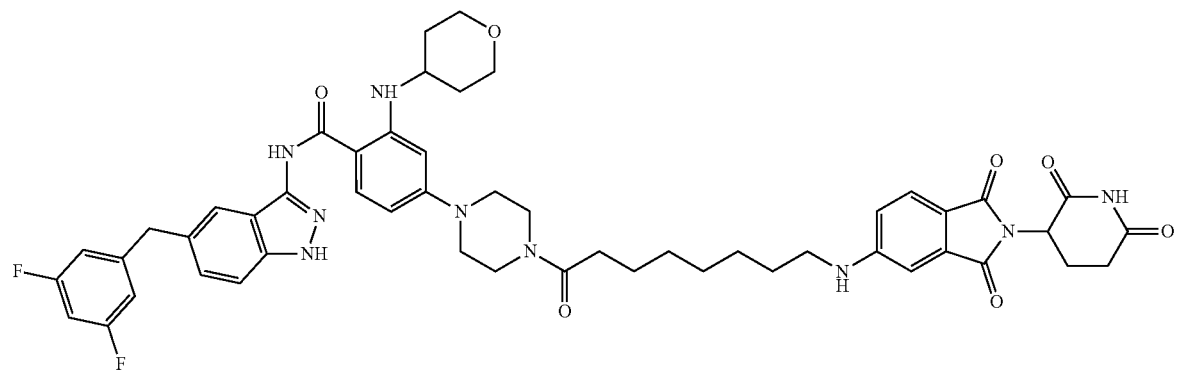

TR-136 was synthesized following the standard procedure for preparing TR-053 (11 mg, yield 59%). MS (ESI) m/z: 944.4 [M+H]+.

Example 187: N-(5-(3,5-Difluorobenzyl)-1H-indazol-3-yl)-4-(4-(1-((2-(2,6-dioxopiperidin-3-yl)-1,3-dioxoisoindolin-5-yl)amino)-3,6,9,12,15-pentaoxaoctadecan-18-oyl)piperazin-1-yl)-2-((tetrahydro-2H-pyran-4-yl)amino)benzamide (TR-137)

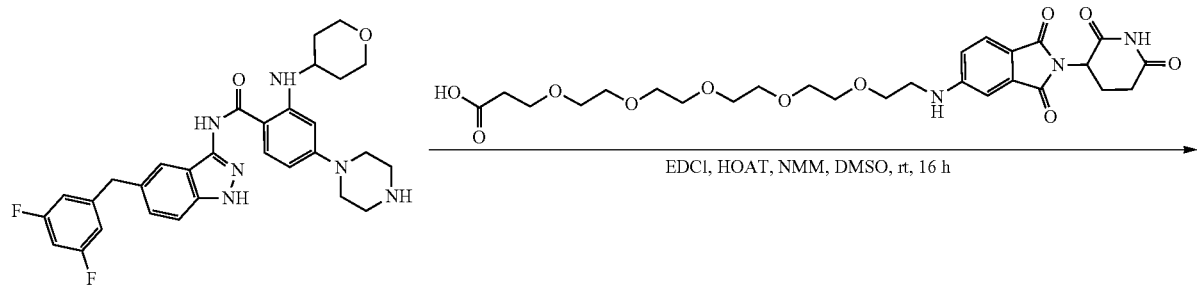

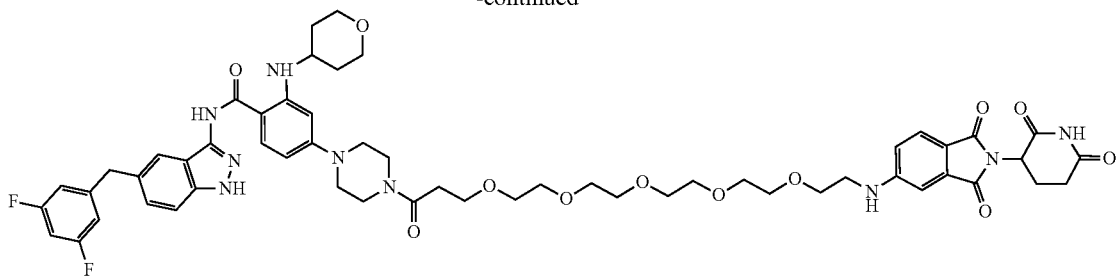
137 was synthesized following the standard procedure for preparing TR-053 (13 mg, yield 64%). MS (ESI) m/z: 1094.5 [M+H]+.
Example 188: N-(5-(3,5-Difluorobenzyl)-1H-indazol-3-yl)-4-(4-(6-((2-(2,6-dioxopiperidin-3-yl)-1,3-dioxoisoindolin-5-yl)amino)hexanoyl)piperazin-1-yl)-2-((tetrahydro-2H-pyran-4-yl)amino)benzamide (TR-138)
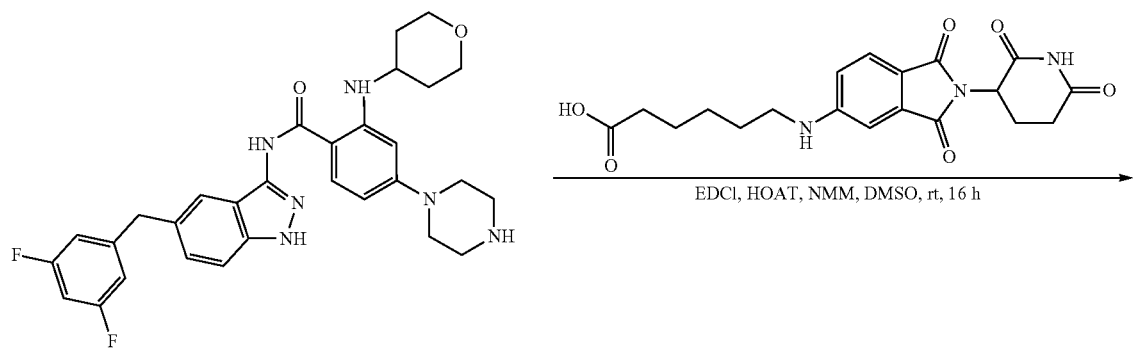
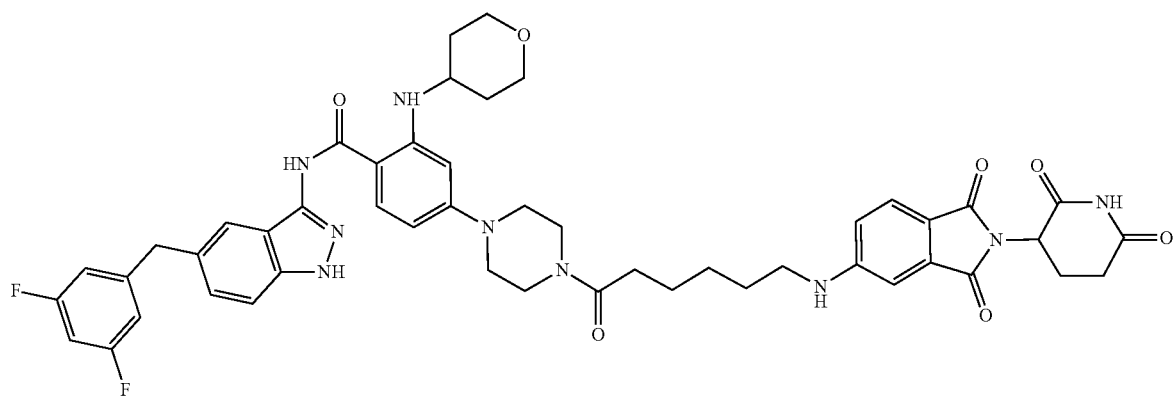
TR-138 was synthesized following the standard procedure for preparing TR-053 (14 mg, yield 55%). MS (ESI) m/z: 916.4 [M+H]+.

Example 189: N-(5-(3,5-Difluorobenzyl)-1H-indazol-3-yl)-4-(4-(7-((2-(2,6-dioxopiperidin-3-yl)-1,3-dioxoisoindolin-5-yl)amino)heptanoyl)piperazin-1-yl)-2-((tetrahydro-2H-pyran-4-yl)amino)benzamide (TR-139)

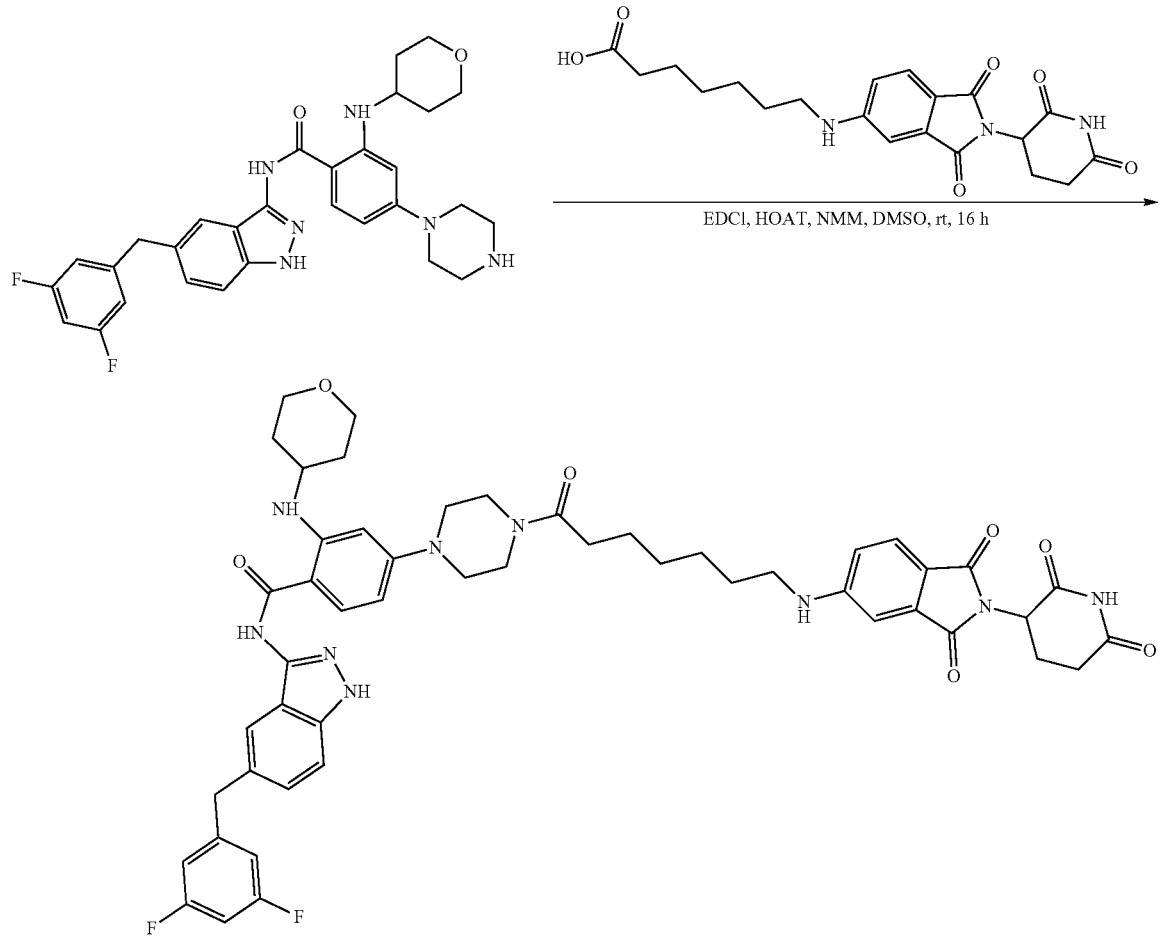

TR-139 was synthesized following the standard procedure for preparing TR-053 (16 mg, yield 62%). MS (ESI) m/z: 930.4 [M+H]$^+$.

Example 190: N-(5-(3,5-Difluorobenzyl)-1H-indazol-3-yl)-4-(4-(1-((2-(2,6-dioxopiperidin-3-yl)-1,3-dioxoisoindolin-5-yl)amino)-3,6,9,12-tetraoxapentadecan-15-oyl)piperazin-1-yl)-2-((tetrahydro-2H-pyran-4-yl)amino)benzamide (TR-140)

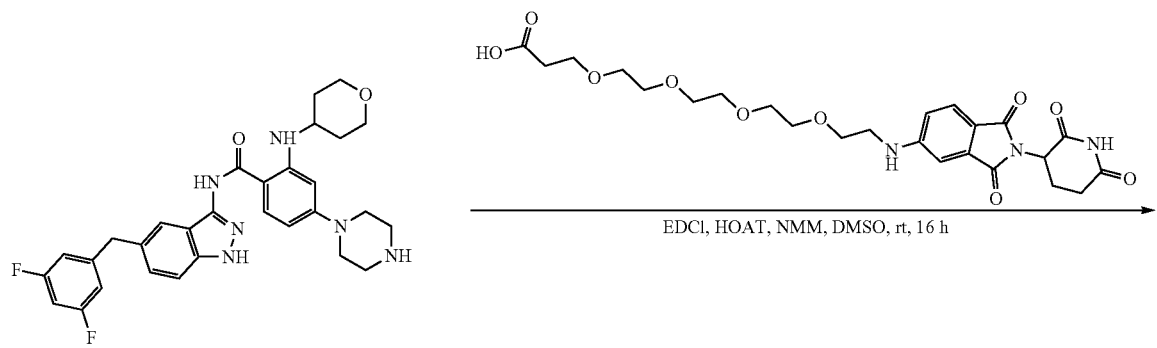

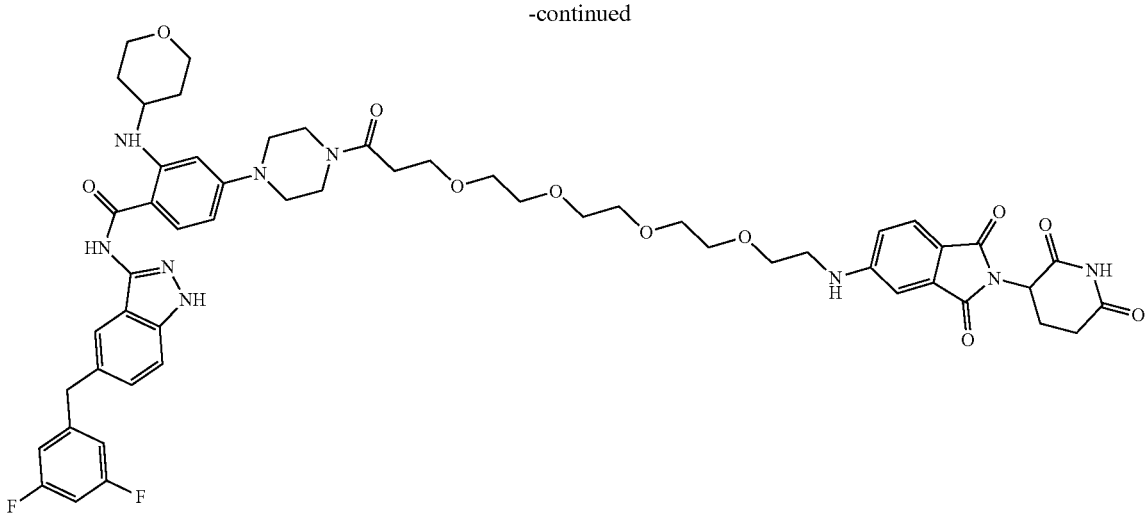
TR-140 was synthesized following the standard procedure for preparing TR-053 (12 mg, yield 56%). MS (ESI) m/z: 1050.4 [M+H]+.
Example 191: N-(5-(3,5-Difluorobenzyl)-1H-indazol-3-yl)-4-(4-(3-(2-(2-((2-(2,6-dioxopiperidin-3-yl)-1,3-dioxoisoindolin-5-yl)amino)ethoxy)ethoxy)propanoyl)piperazin-1-yl)-2-((tetrahydro-2H-pyran-4-yl)amino)benzamide (TR-141)
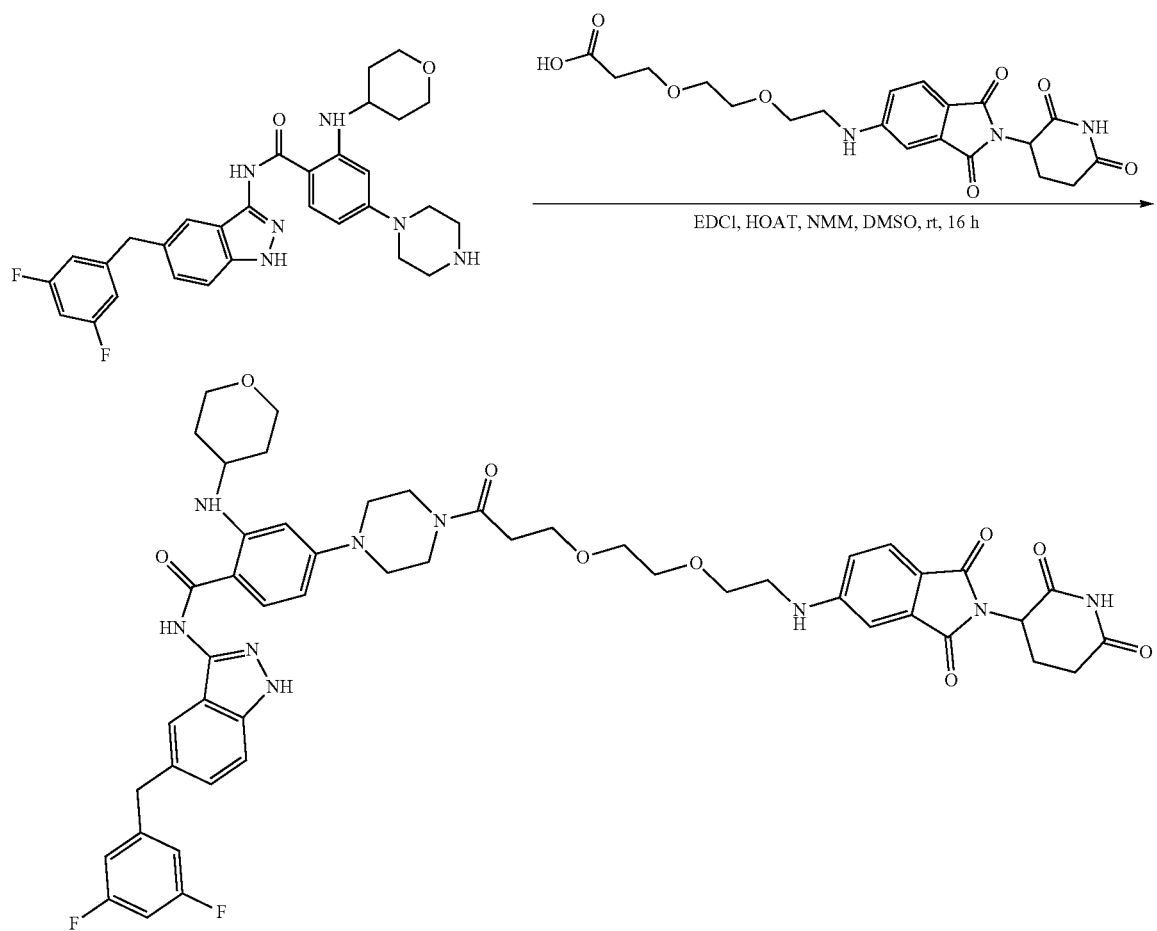

TR-141 was synthesized following the standard procedure for preparing TR-053 (15 mg, yield 65%). MS (ESI) m/z: 962.4 [M+H]+.
Example 192: N-(5-(3,5-Difluorobenzyl)-1H-indazol-3-yl)-4-(4-(5-((2-(2,6-dioxopiperidin-3-yl)-1,3-dioxoisoindolin-5-yl)amino)pentanoyl)piperazin-1-yl)-2-((tetrahydro-2H-pyran-4-yl)amino)benzamide (TR-142)
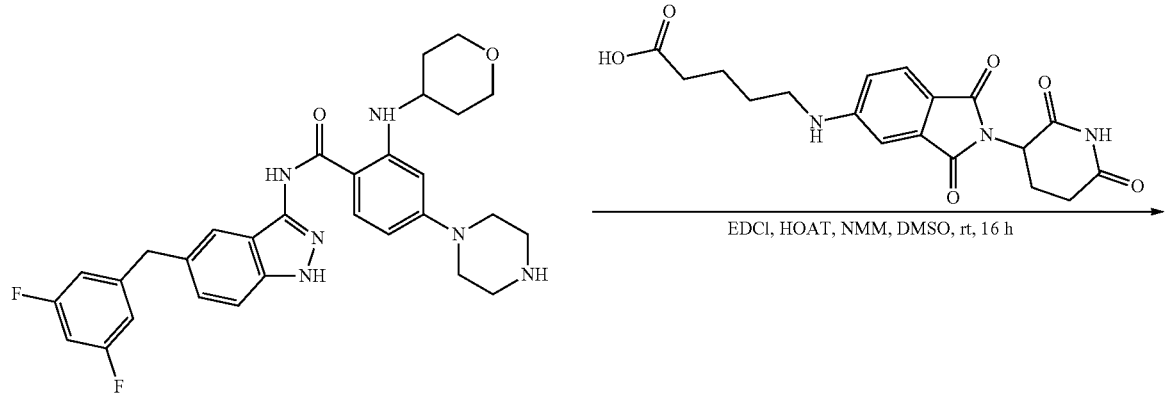
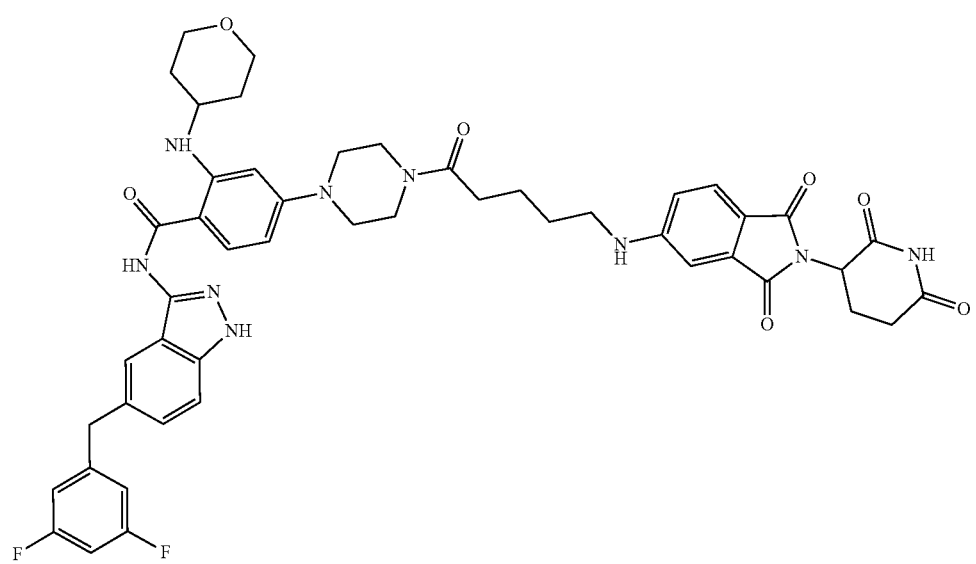
TR-142 was synthesized following the standard procedure for preparing TR-053 (12 mg, yield 62%). MS (ESI) m/z: 902.4 [M+H]+.

Example 193: N-(5-(3,5-Difluorobenzyl)-1H-indazol-3-yl)-4-(4-(8-((2-(2,6-dioxopiperidin-3-yl)-1,3-dioxoisoindolin-5-yl)amino)octanoyl)piperazin-1-yl)-2-((tetrahydro-2H-pyran-4-yl)amino)benzamide (TR-143)

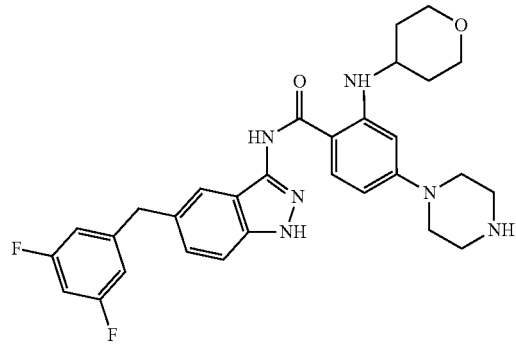
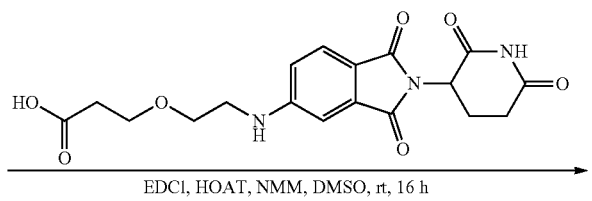

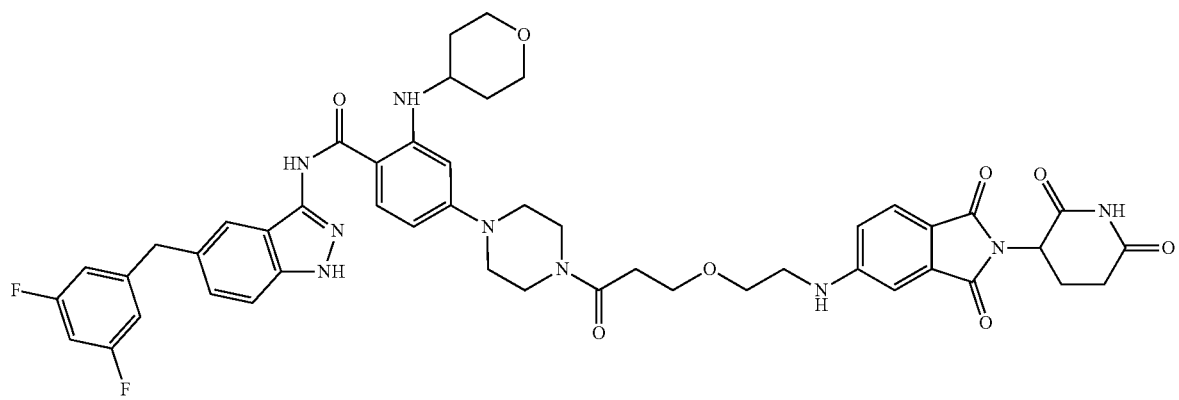

TR-143 was synthesized following the standard procedure for preparing TR-053 (16 mg, yield 67%). MS (ESI) m/z: 918.4 [M+H]+.

Example 194: N-(5-(3,5-Difluorobenzyl)-1H-indazol-3-yl)-4-(4-((2-(2,6-dioxopiperidin-3-yl)-1,3-dioxoisoindolin-5-yl)glycyl)piperazin-1-yl)-2-((tetrahydro-2H-pyran-4-yl)amino)benzamide (TR-144)

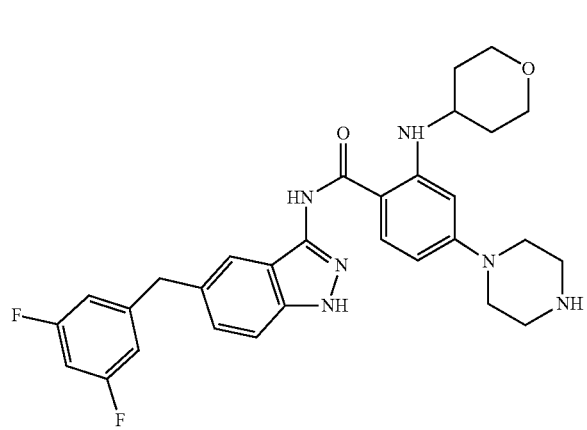
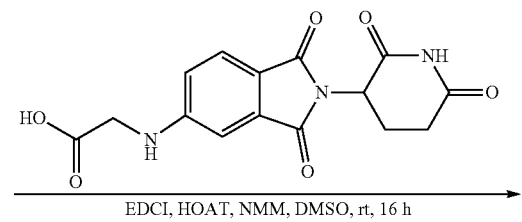

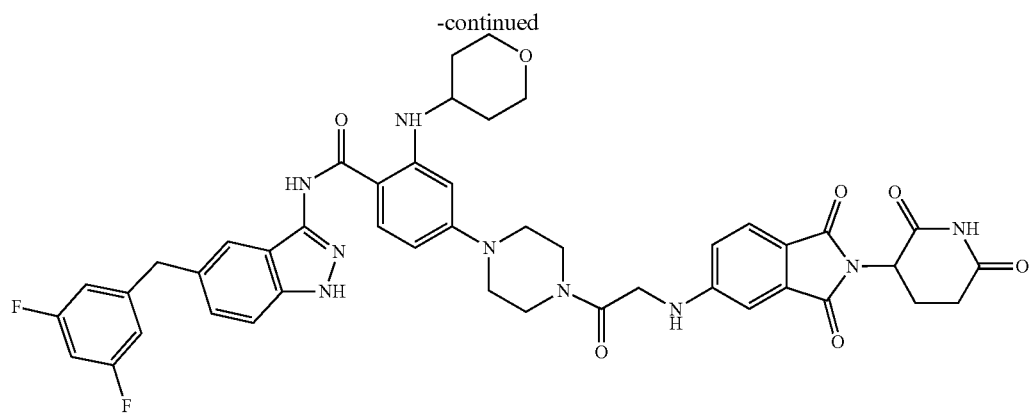
TR-144 was synthesized following the standard procedure for preparing TR-053 (14 mg, yield 61%). MS (ESI) m/z: 860.3 [M+H]$^+$.
Example 195: N-(5-(3,5-Difluorobenzyl)-1H-indazol-3-yl)-4-(4-(3-((2-(2,6-dioxopiperidin-3-yl)-1,3-dioxoisoindolin-5-yl)amino)propanoyl)piperazin-1-yl)-2-((tetrahydro-2H-pyran-4-yl)amino)benzamide (TR-145)
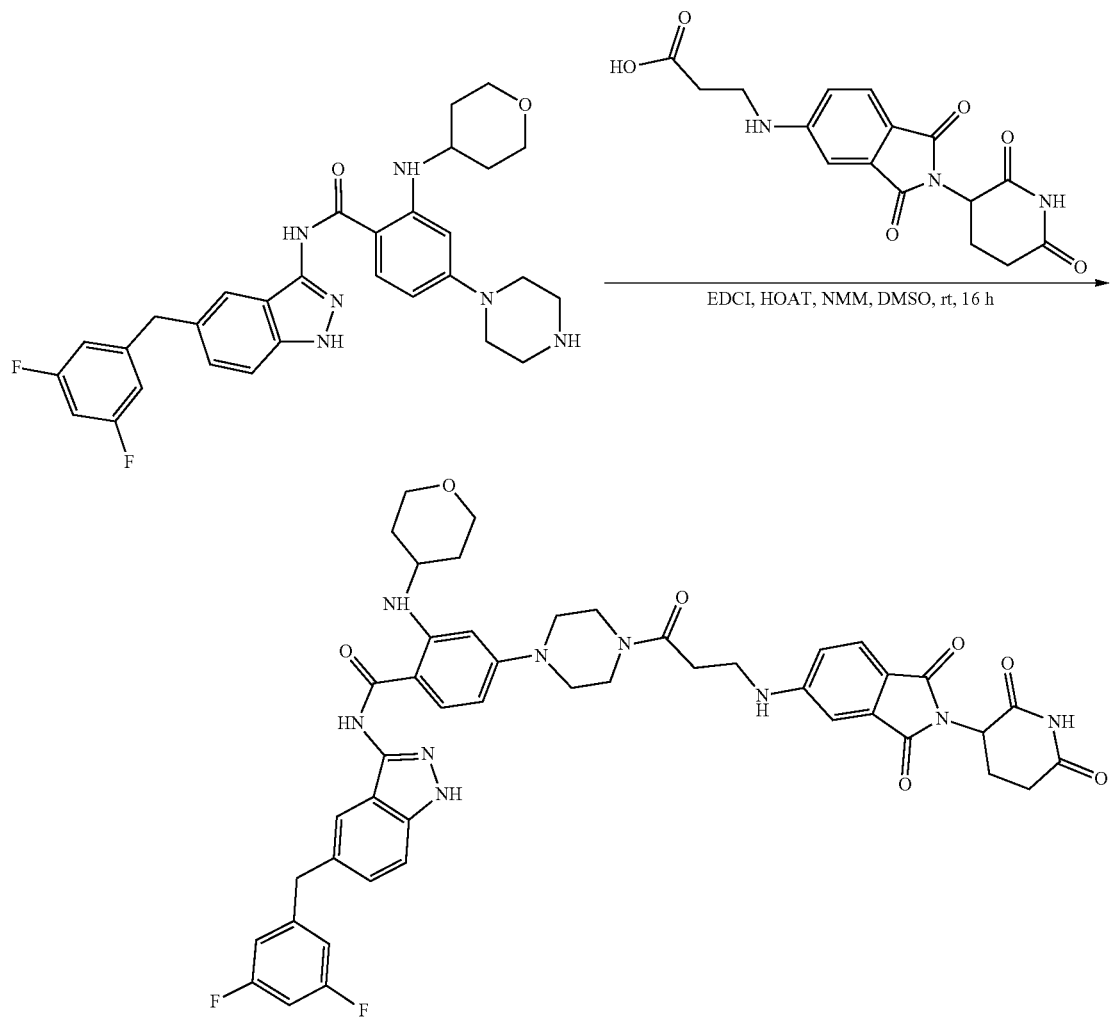

TR-145 was synthesized following the standard procedure for preparing TR-053 (15 mg, yield 62%). MS (ESI) m/z: 874.3 [M+H]+.

Example 196: N-(5-(3,5-Difluorobenzyl)-1H-indazol-3-yl)-4-(4-(3-(2-(2-(2-((2-(2,6-dioxopiperidin-3-yl)-1,3-dioxoisoindolin-5-yl)amino)ethoxy)ethoxy)ethoxy)propanoyl)piperazin-1-yl)-2-((tetrahydro-2H-pyran-4-yl)amino)benzamide (TR-146)

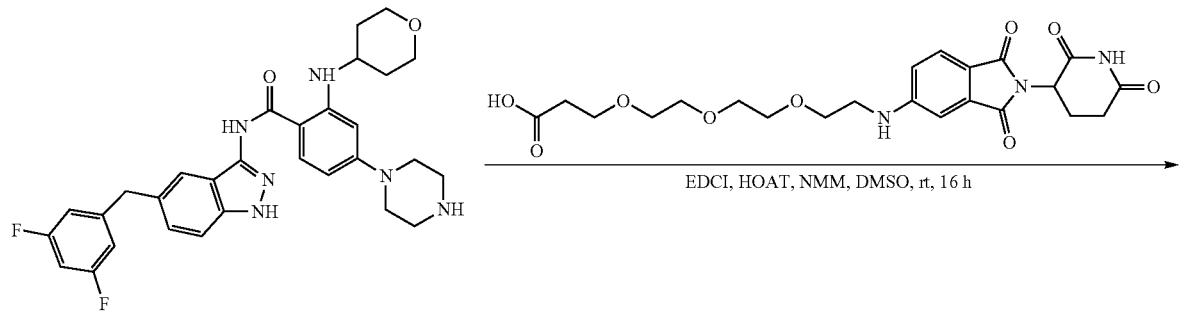

TR-146 was synthesized following the standard procedure for preparing TR-053 (16 mg, yield 65%). MS (ESI) m/z: 1006.4 [M+H]+.

Example 197: N-(5-(3,5-Difluorobenzyl)-1H-indazol-3-yl)-4-(4-(2-((6-((2-(2,6-dioxopiperidin-3-yl)-1,3-dioxoisoindolin-4-yl)amino)hexyl)amino)-2-oxoethyl)piperazin-1-yl)-2-((tetrahydro-2H-pyran-4-yl)amino)benzamide (TR-147)

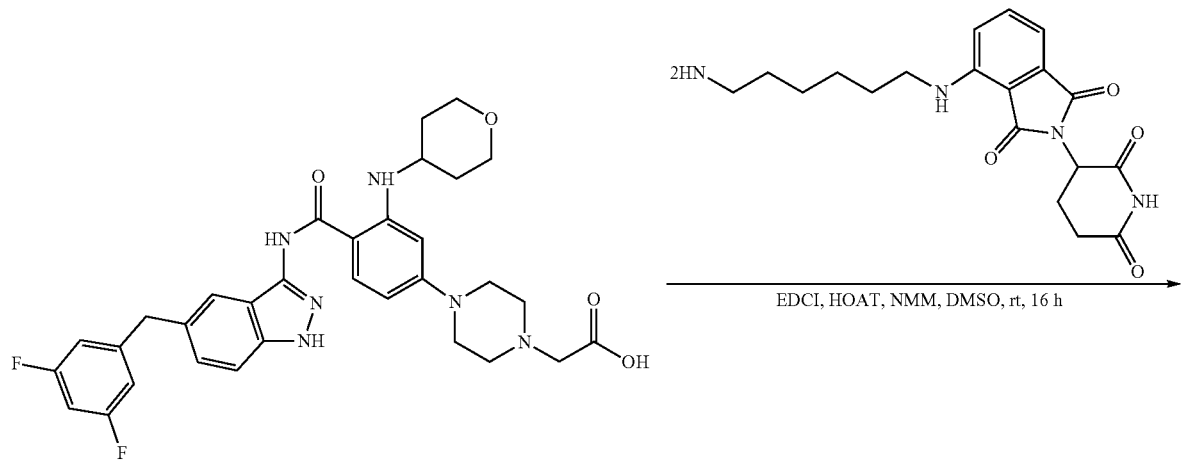

-continued
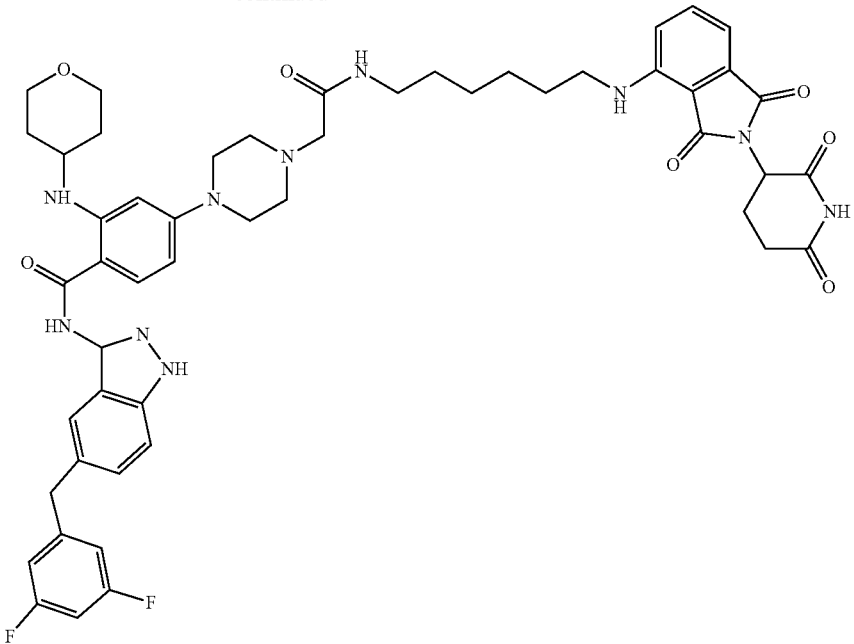 [SMILES: O=C(CN1CCN(c2ccc(C(=O)Nc3n[nH]c4ccc(Cc5cc(F)cc(F)c5)cc34)c(NC3CCOCC3)c2)CC1)NCCCCCCNc1cccc2c1C(=O)N(C1CCC(=O)NC1=O)C2=O]
TR-147 was synthesized following the standard procedure for preparing TR-053 (12 mg, yield 56%). MS (ESI) m/z: 959.4 [M+H]$^+$.
Example 198: N-(5-(3,5-Difluorobenzyl)-1H-indazol-3-yl)-4-(4-(2-((8-((2-(2,6-dioxopiperidin-3-yl)-1,3-dioxoisoindolin-4-yl)amino)octyl)amino)-2-oxoethyl)piperazin-1-yl)-2-((tetrahydro-2H-pyran-4-yl)amino)benzamide (TR-148)
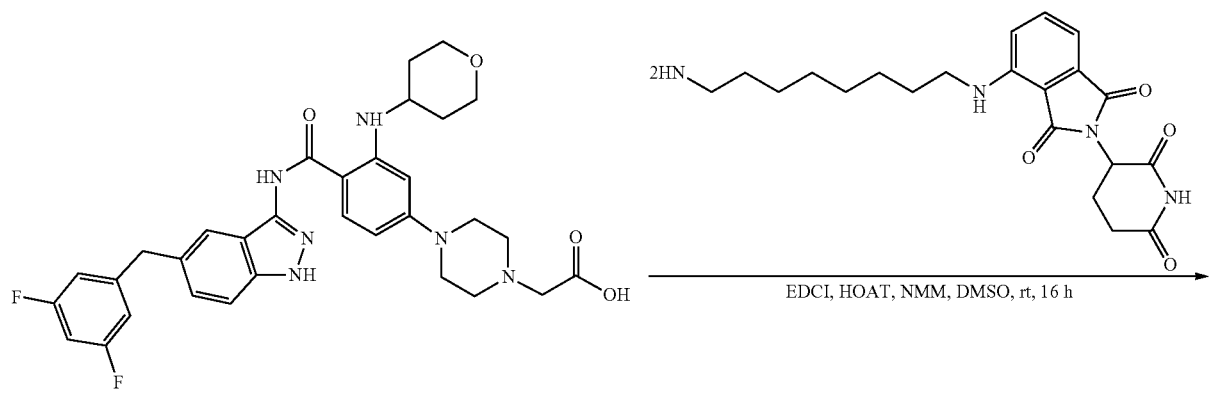

-continued
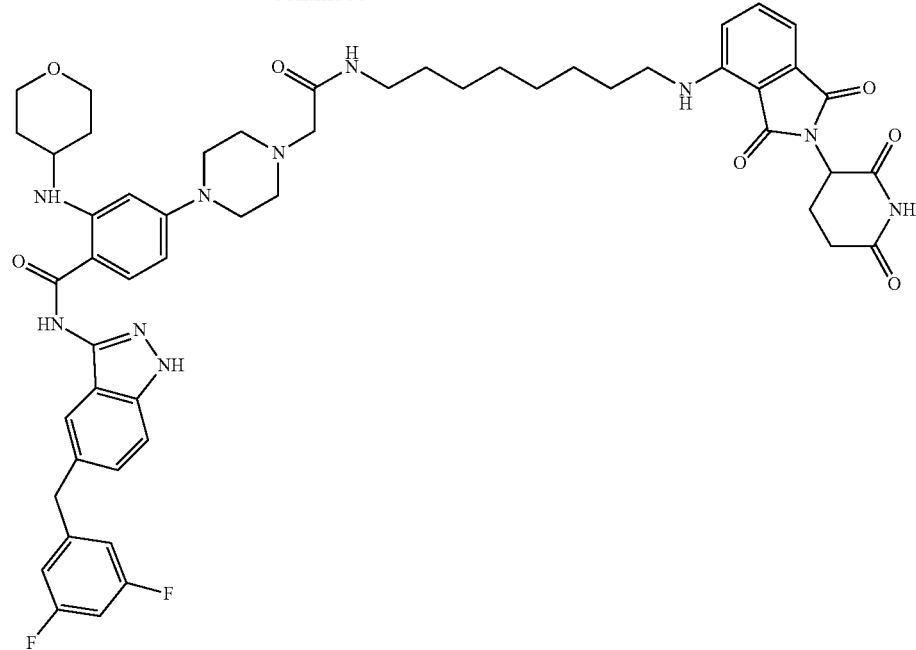
TR-148 was synthesized following the standard procedure for preparing TR-053 (16 mg, yield 62%). MS (ESI) m/z: 987.5 [M+H]⁺.
Example 199: N-(5-(3,5-Difluorobenzyl)-1H-indazol-3-yl)-4-(4-(2-((5-((2-(2,6-dioxopiperidin-3-yl)-1,3-dioxoisoindolin-4-yl)amino)pentyl)amino)-2-oxoethyl)piperazin-1-yl)-2-((tetrahydro-2H-pyran-4-yl)amino)benzamide (TR-149)
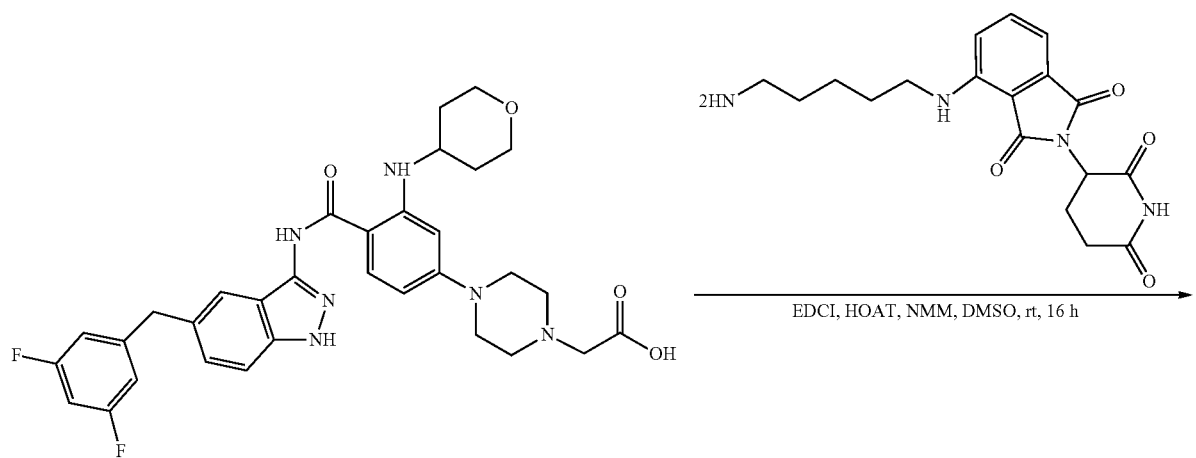

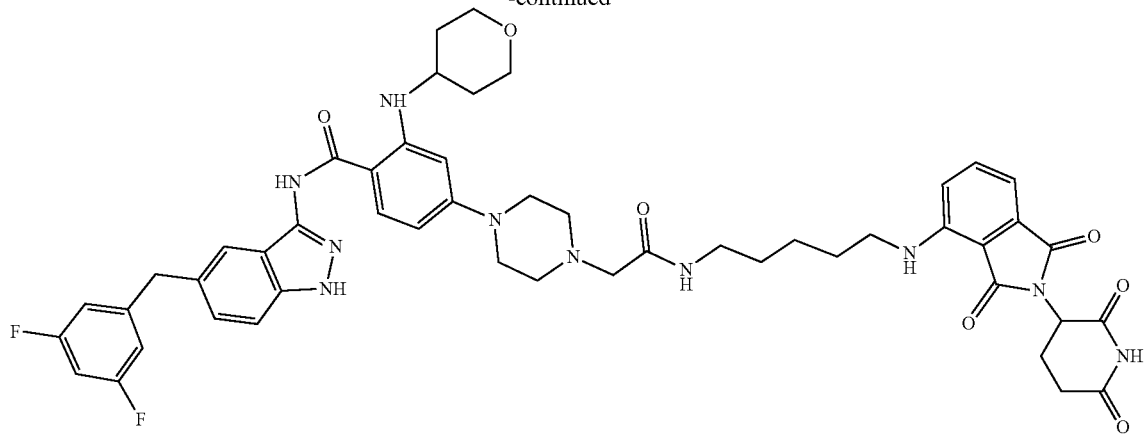

TR-149 was synthesized following the standard procedure for preparing TR-053 (14 mg, yield 52%). MS (ESI) m/z: 945.4 [M+H]$^+$.

Example 200: N-(5-(3,5-Difluorobenzyl)-1H-indazol-3-yl)-4-(4-(17-((2-(2,6-dioxopiperidin-3-yl)-1,3-dioxoisoindolin-4-yl)amino)-2-oxo-6,9,12,15-tetraoxa-3-azaheptadecyl)piperazin-1-yl)-2-((tetrahydro-2H-pyran-4-yl)amino)benzamide (TR-150)

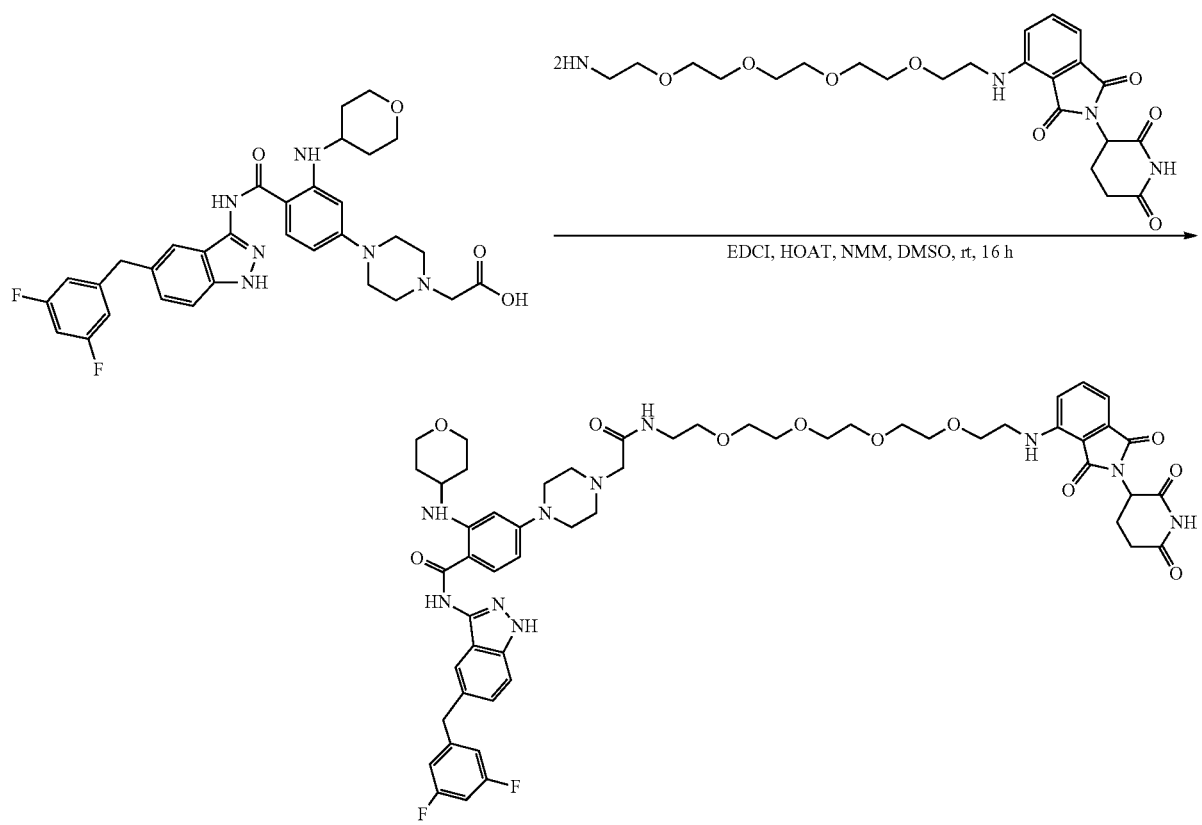

TR-150 was synthesized following the standard procedure for preparing TR-053 (14 mg, yield 58%). MS (ESI) m/z: 1079.5 [M+H]$^+$.

Example 201: N-(5-(3,5-Difluorobenzyl)-1H-indazol-3-yl)-4-(4-(2-((2-(2-((2-(2,6-dioxopiperidin-3-yl)-1,3-dioxoisoindolin-4-yl)amino)ethoxy)ethyl)amino)-2-oxoethyl)piperazin-1-yl)-2-((tetrahydro-2H-pyran-4-yl)amino)benzamide (TR-151)
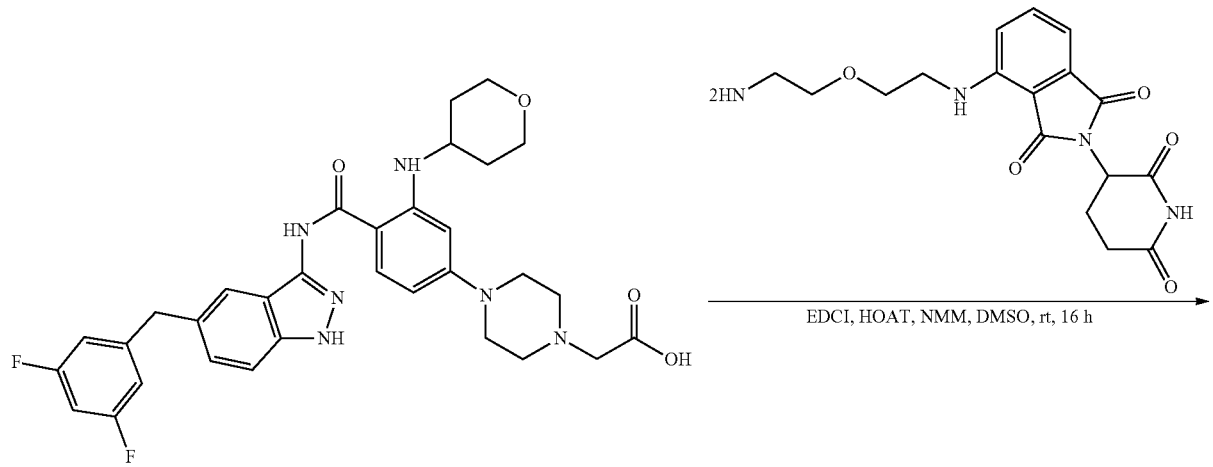
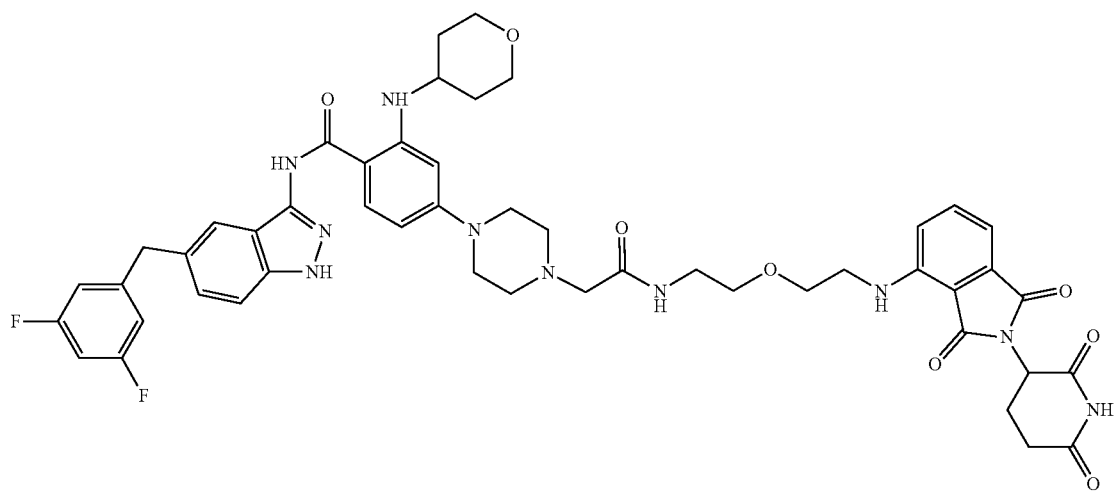
TR-151 was synthesized following the standard procedure for preparing TR-053 (12 mg, yield 53%). MS (ESI) m/z: 947.4 [M+H]+.

Example 202: N-(5-(3,5-Difluorobenzyl)-1H-indazol-3-yl)-4-(4-(2-((3-((2-(2,6-dioxopiperidin-3-yl)-1,3-dioxoisoindolin-4-yl)amino)propyl)amino)-2-oxoethyl)piperazin-1-yl)-2-((tetrahydro-2H-pyran-4-yl)amino)benzamide (TR-152)
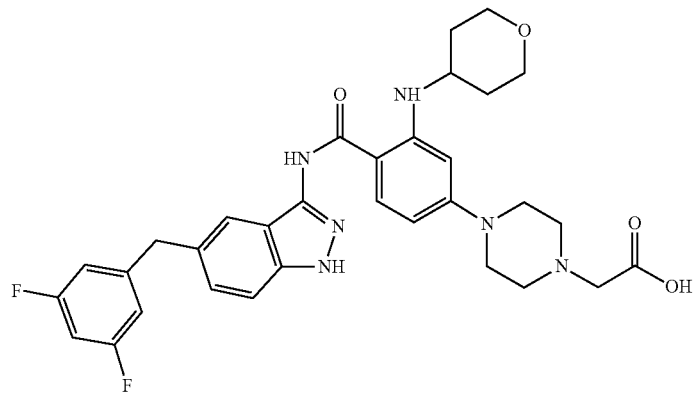 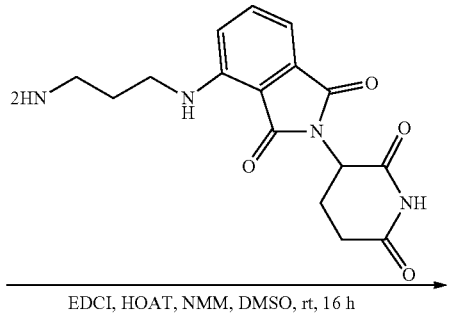
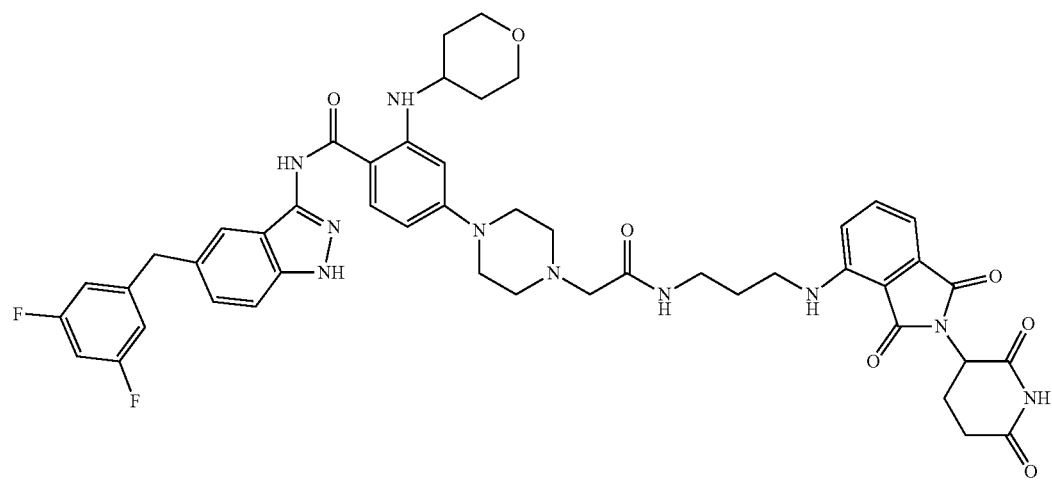
TR-152 was synthesized following the standard procedure for preparing TR-053 (13 mg, yield 57%). MS (ESI) m/z: 917.4 [M+H]$^+$.

Example 203: N-(5-(3,5-Difluorobenzyl)-1H-indazol-3-yl)-4-(4-(2-((2-(2-(2-((2-(2,6-dioxopiperidin-3-yl)-1,3-dioxoisoindolin-4-yl)amino)ethoxy)ethoxy)ethyl)amino)-2-oxoethyl)piperazin-1-yl)-2-((tetrahydro-2H-pyran-4-yl)amino)benzamide (TR-153)
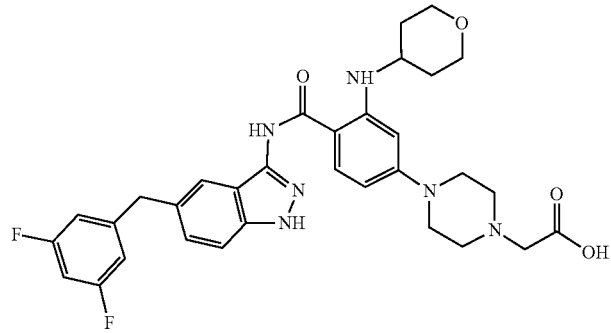
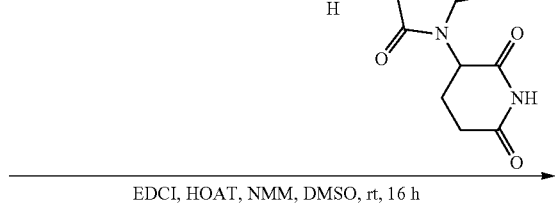
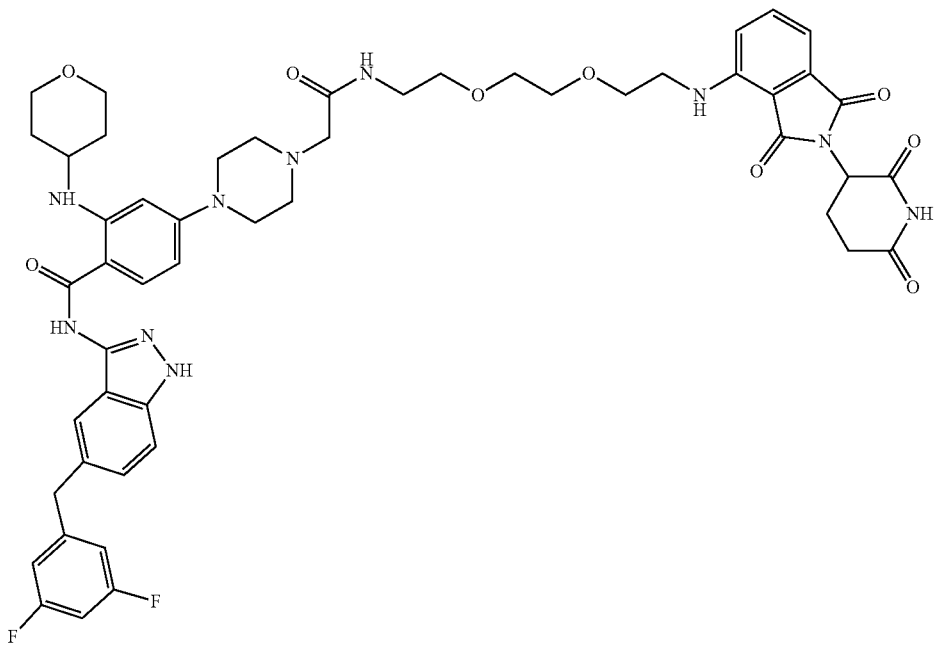 [SMILES: O=C(CN1CCN(c2ccc(C(=O)Nc3n[nH]c4ccc(Cc5cc(F)cc(F)c5)cc34)c(NC3CCOCC3)c2)CC1)NCCCCCCCCNc1cccc2c1C(=O)N(C1CCC(=O)NC1=O)C2=O]
TR-153 was synthesized following the standard procedure for preparing TR-053 (12 mg, yield 53%). MS (ESI) m/z: 991.4 [M+H]+.

Example 204: N-(5-(3,5-Difluorobenzyl)-1H-indazol-3-yl)-4-(4-(2-((7-((2-(2,6-dioxopiperidin-3-yl)-1,3-dioxoisoindolin-4-yl)amino)heptyl)amino)-2-oxoethyl)piperazin-1-yl)-2-((tetrahydro-2H-pyran-4-yl)amino)benzamide (TR-154)
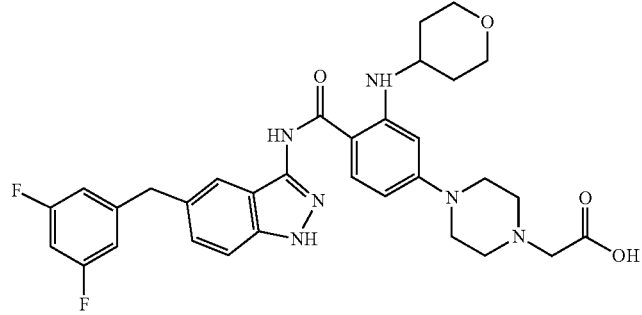
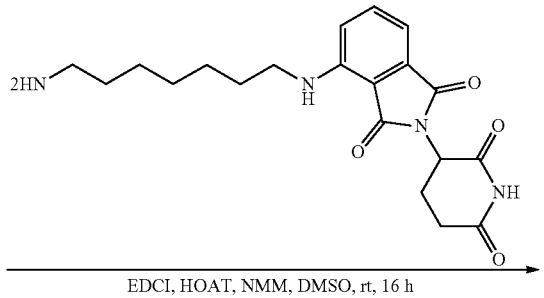
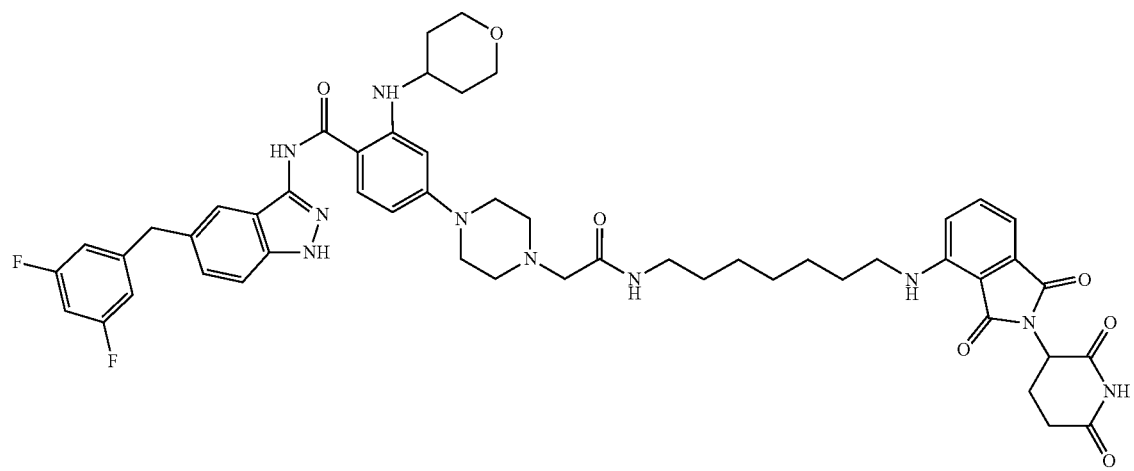 [SMILES: O=C(CN1CCN(c2ccc(C(=O)Nc3n[nH]c4ccc(Cc5cc(F)cc(F)c5)cc34)c(NC3CCOCC3)c2)CC1)NCCCCCCCNc1cccc2c1C(=O)N(C1CCC(=O)NC1=O)C2=O]
TR-154 was synthesized following the standard procedure for preparing TR-053 (15 mg, yield 57%). MS (ESI) m/z: 973.4 [M+H]$^+$.

Example 205: N-(5-(3,5-Difluorobenzyl)-1H-indazol-3-yl)-4-(4-(2-((4-((2-(2,6-dioxopiperidin-3-yl)-1,3-dioxoisoindolin-4-yl)amino)butyl)amino)-2-oxoethyl)piperazin-1-yl)-2-((tetrahydro-2H-pyran-4-yl)amino)benzamide (TR-155)
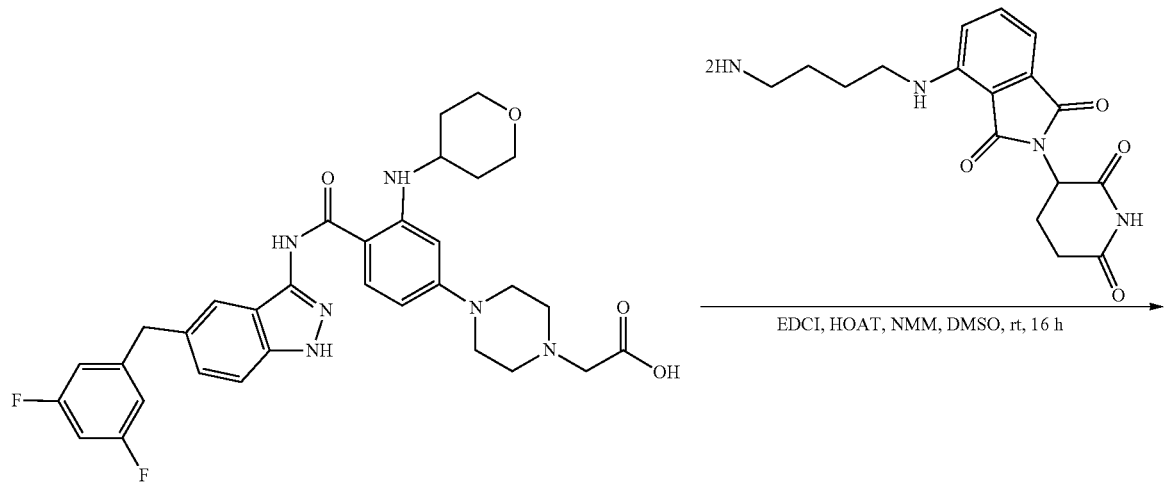
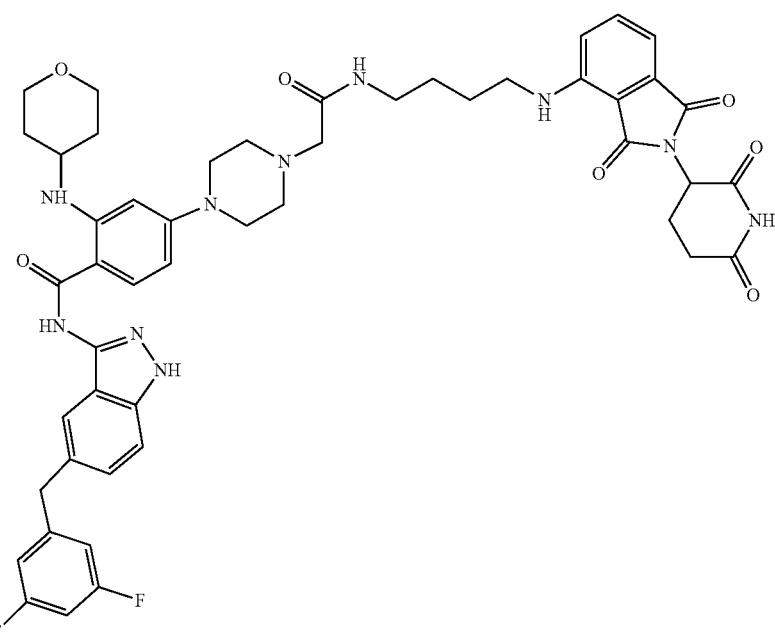
TR-155 was synthesized following the standard procedure for preparing TR-053 (13 mg, yield 56%). MS (ESI) m/z: 931.4 [M+H]⁺.

Example 206: N-(5-(3,5-Difluorobenzyl)-1H-indazol-3-yl)-4-(4-(2-((4-((2-(2,6-dioxopiperidin-3-yl)-1,3-dioxoisoindolin-5-yl)amino)butyl)amino)-2-oxoethyl)piperazin-1-yl)-2-((tetrahydro-2H-pyran-4-yl)amino)benzamide (TR-156)

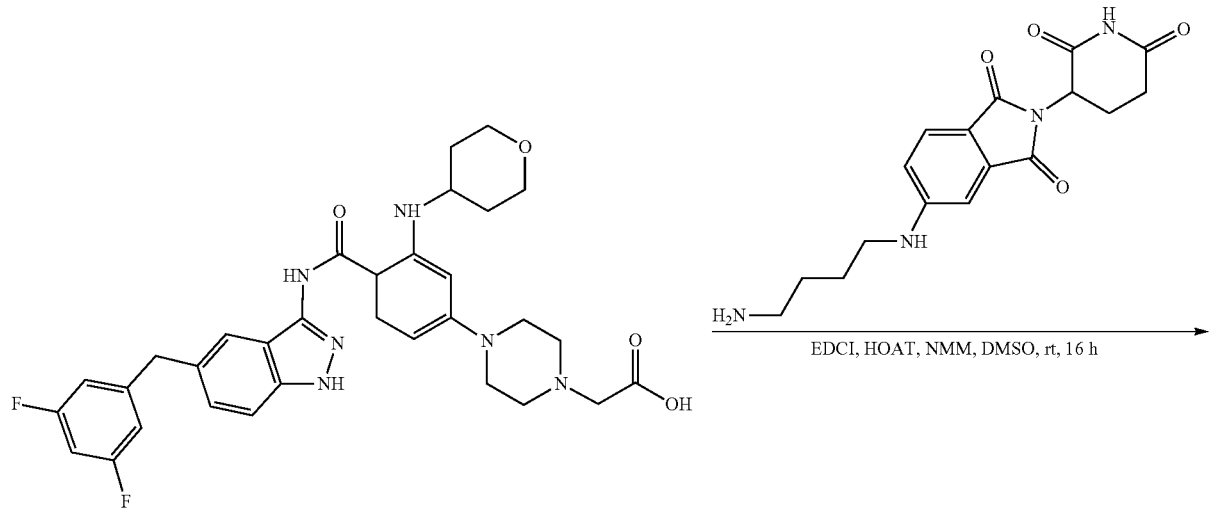

TR-156 was synthesized following the standard procedure for preparing TR-053 (12 mg, yield 53%). MS (ESI) m/z: 931.4 [M+H]$^+$.

Example 207: N-(5-(3,5-Difluorobenzyl)-1H-indazol-3-yl)-4-(4-(2-((7-((2-(2,6-dioxopiperidin-3-yl)-1,3-dioxoisoindolin-5-yl)amino)heptyl)amino)-2-oxoethyl)piperazin-1-yl)-2-((tetrahydro-2H-pyran-4-yl)amino)benzamide (TR-157)

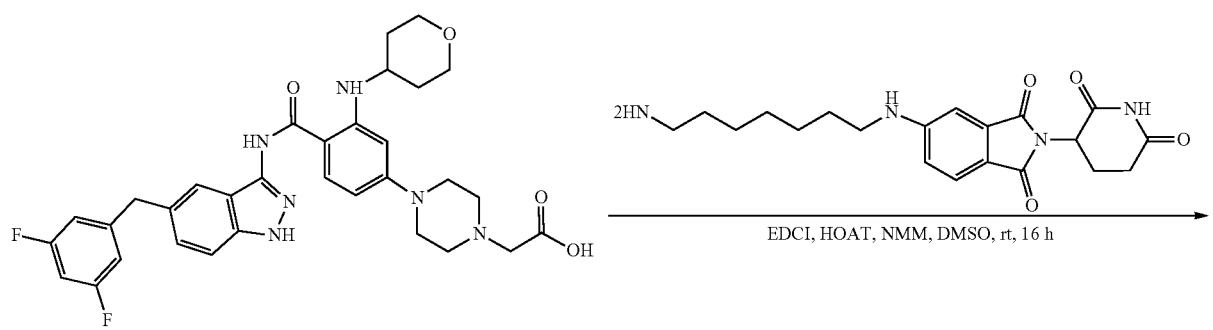

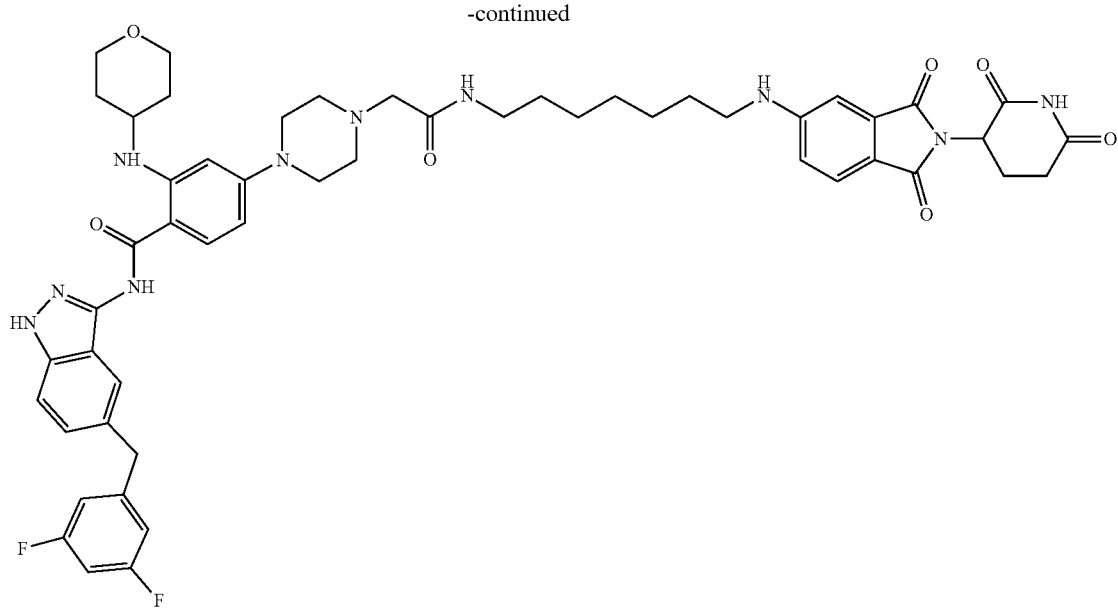
TR-157 was synthesized following the standard procedure for preparing TR-053 (14 mg, yield 62%). MS (ESI) m/z: 973.4 [M+H]⁺.
Example 208: N-(5-(3,5-Difluorobenzyl)-1H-indazol-3-yl)-4-(4-(8-((2-(2,6-dioxopiperidin-3-yl)-1,3-dioxoisoindolin-5-yl)amino)octanoyl)piperazin-1-yl)-2-((tetrahydro-2H-pyran-4-yl)amino)benzamide (TR-158)
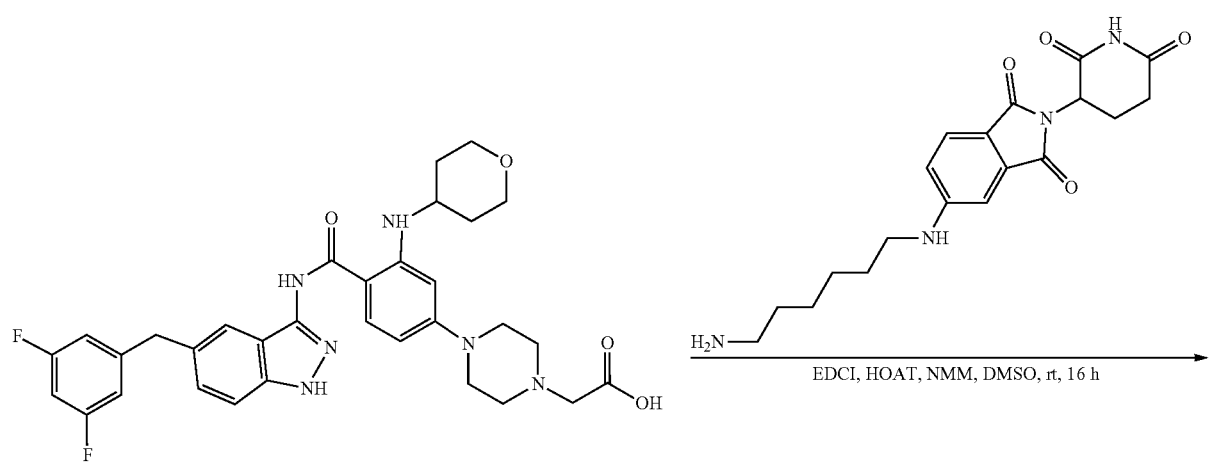

-continued
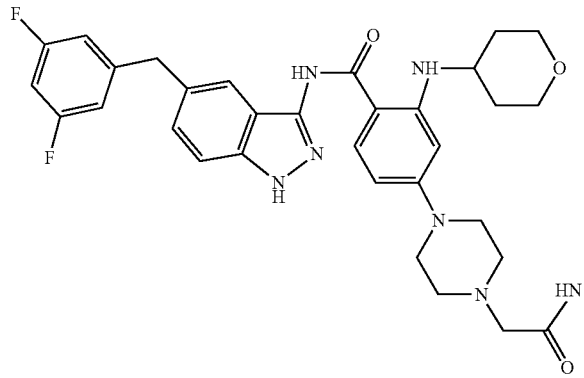
TR-158 was synthesized following the standard procedure for preparing TR-053 (12 mg, yield 56%). MS (ESI) m/z: 944.4 [M+H]+.
Example 209: N-(5-(3,5-Difluorobenzyl)-1H-indazol-3-yl)-4-(4-(2-((8-((2-(2,6-dioxopiperidin-3-yl)-1, 3-dioxoisoindolin-5-yl)amino)octyl)amino)-2-oxoethyl)piperazin-1-yl)-2-((tetrahydro-2H-pyran-4-yl) amino)benzamide (TR-159)
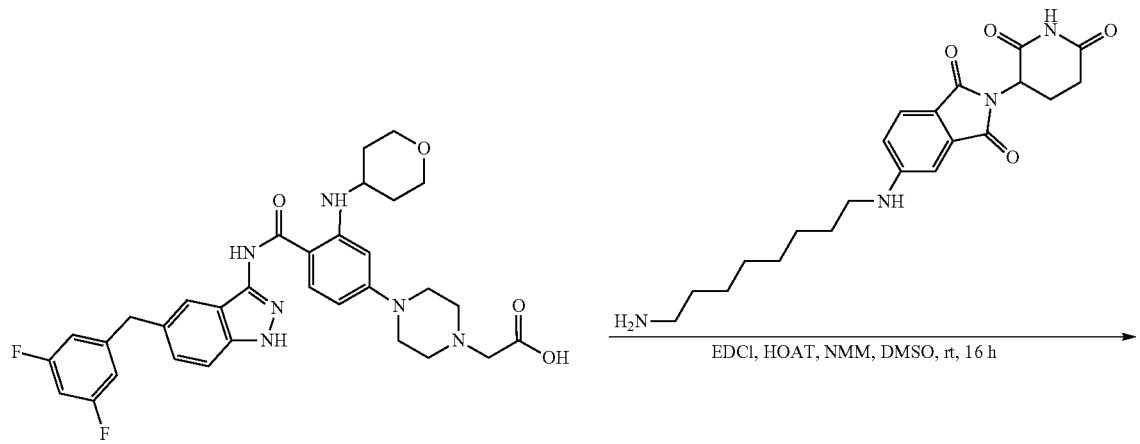
EDCl, HOAT, NMM, DMSO, rt, 16 h
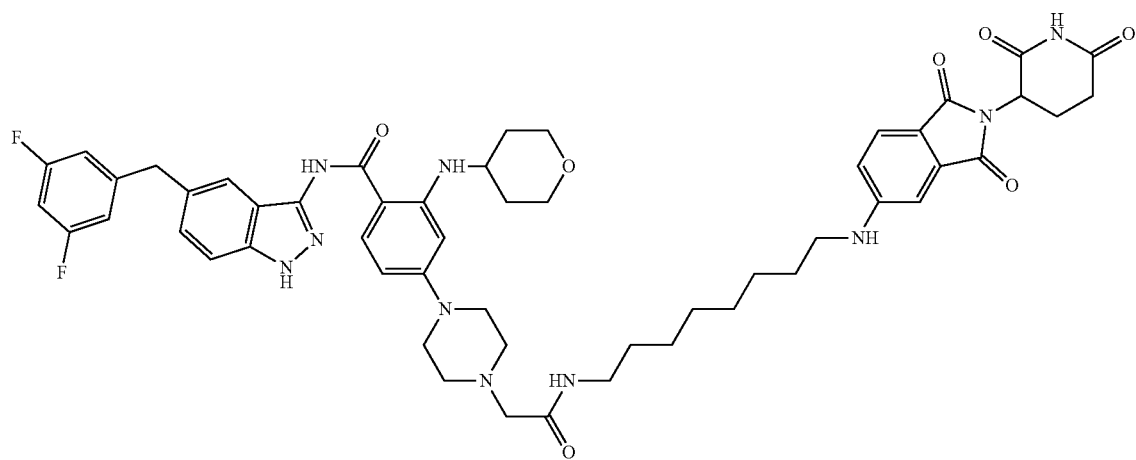

TR-159 was synthesized following the standard procedure for preparing TR-053 (14 mg, yield 58%). MS (ESI) m/z: 987.5 [M+H]+.
Example 210: N-(5-(3,5-Difluorobenzyl)-1H-indazol-3-yl)-4-(4-(17-((2-(2,6-dioxopiperidin-3-yl)-1,3-dioxoisoindolin-5-yl)amino)-2-oxo-6,9,12,15-tetraoxa-3-azaheptadecyl)piperazin-1-yl)-2-((tetrahydro-2H-pyran-4-yl)amino)benzamide (TR-160)
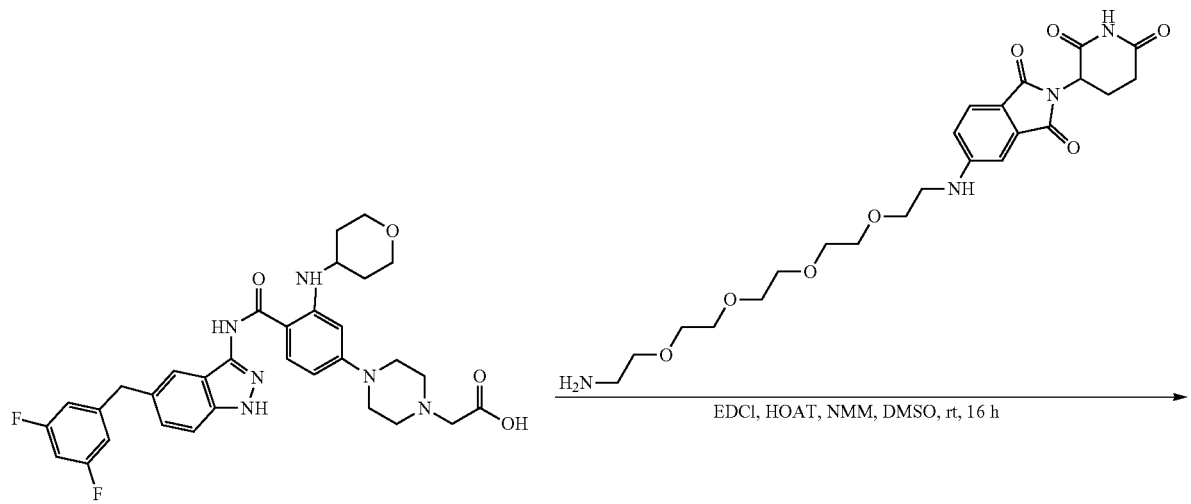
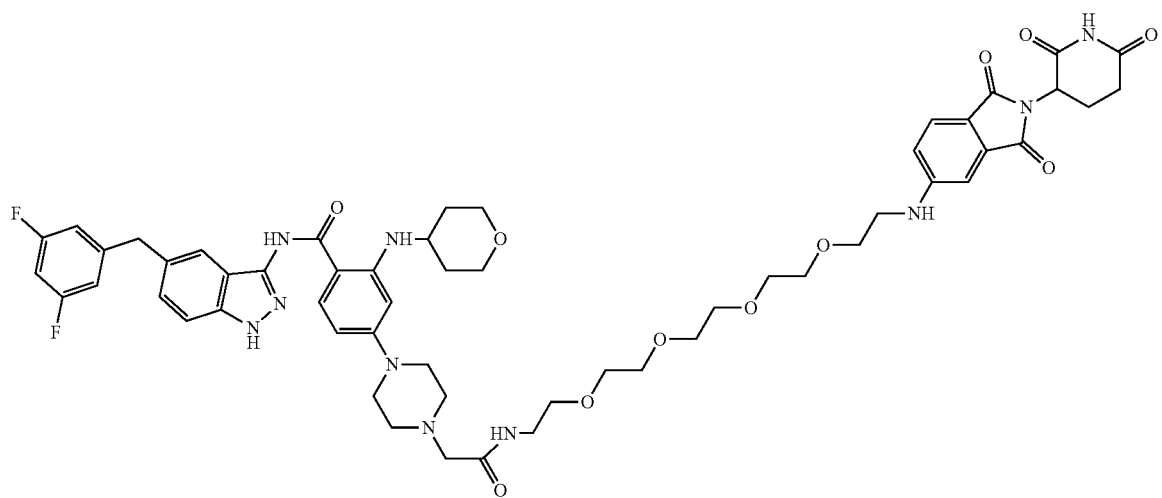
TR-160 was synthesized following the standard procedure for preparing TR-053 (13 mg, yield 56%). MS (ESI) m/z: 987.5 [M+H]+.

Example 211: N-(5-(3,5-Difluorobenzyl)-1H-indazol-3-yl)-4-(4-(2-((2-(2-((2-(2,6-dioxopiperidin-3-yl)-1,3-dioxoisoindolin-5-yl)amino)ethoxy)ethyl)amino)-2-oxoethyl)piperazin-1-yl)-2-((tetrahydro-2H-pyran-4-yl)amino)benzamide (TR-161)
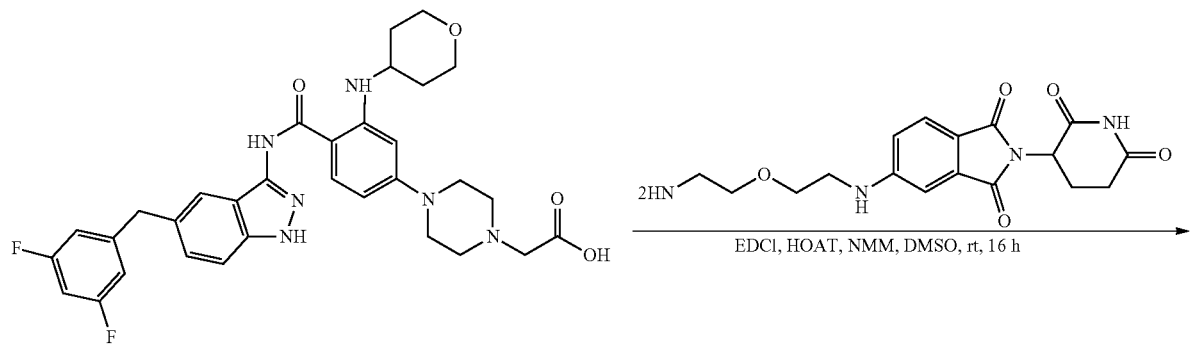
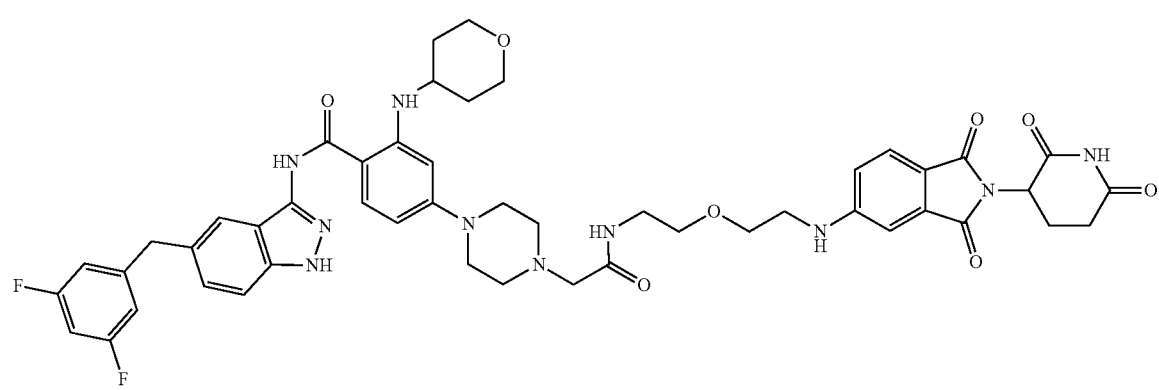
TR-161 was synthesized following the standard procedure for preparing TR-053 (13 mg, yield 58%). MS (ESI) m/z: 947.4 [M+H]+.

Example 212: N-(5-(3,5-Difluorobenzyl)-1H-indazol-3-yl)-4-(4-(2-((2-(2-(2-((2-(2,6-dioxopiperidin-3-yl)-1,3-dioxoisoindolin-5-yl)amino)ethoxy)ethoxy)ethyl)amino)-2-oxoethyl)piperazin-1-yl)-2-((tetrahydro-2H-pyran-4-yl)amino)benzamide (TR-162)
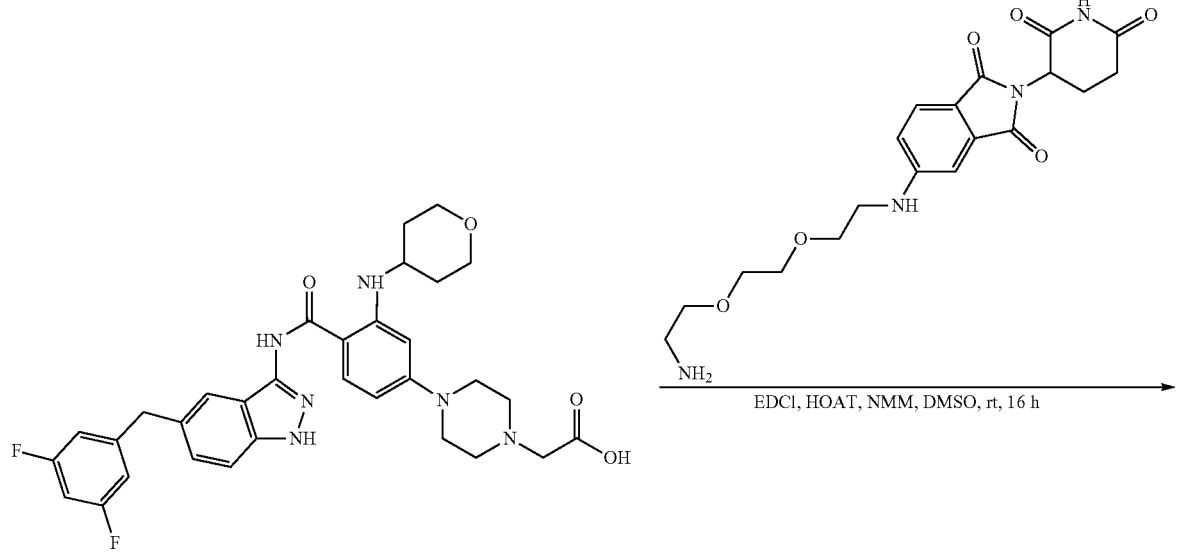
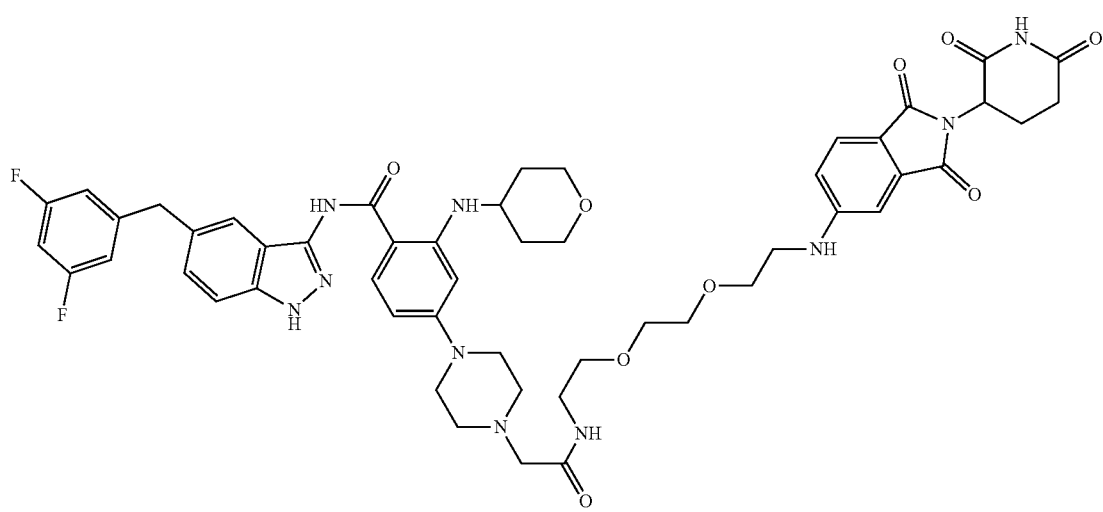
TR-162 was synthesized following the standard procedure for preparing TR-053 (11 mg, yield 52%). MS (ESI) m/z: 9881.4 [M+H]+.

Example 213: N-(5-(3,5-Difluorobenzyl)-1H-indazol-3-yl)-4-(4-(14-((2-(2,6-dioxopiperidin-3-yl)-1,3-dioxoisoindolin-5-yl)amino)-2-oxo-6,9,12-trioxa-3-azatetradecyl)piperazin-1-yl)-2-((tetrahydro-2H-pyran-4-yl)amino)benzamide (TR-163)

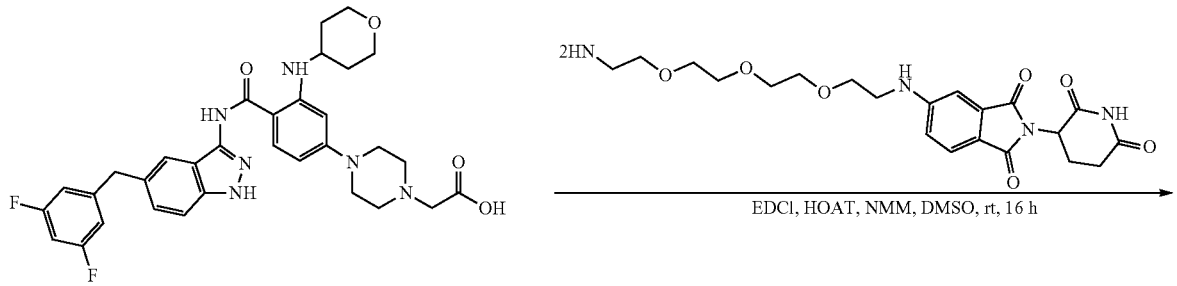

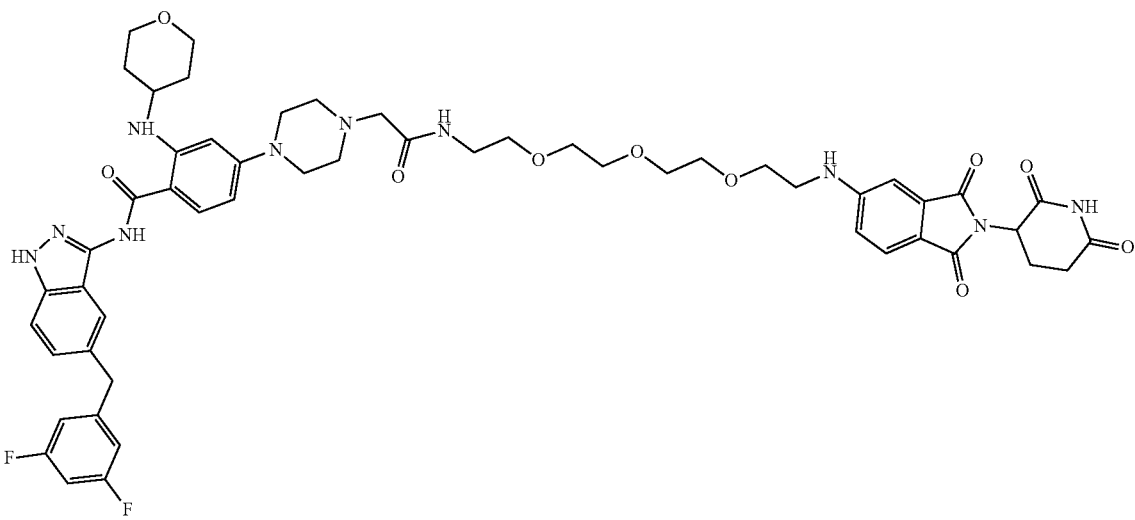

TR-163 was synthesized following the standard procedure for preparing TR-053 (15 mg, yield 58%). MS (ESI) m/z: 1035.4 [M+H]⁺.

Example 214: N-(5-(3,5-Difluorobenzyl)-1H-indazol-3-yl)-4-(4-(2-((5-((2-(2,6-dioxopiperidin-3-yl)-1,3-dioxoisoindolin-5-yl)amino)pentyl)amino)-2-oxoethyl)piperazin-1-yl)-2-((tetrahydro-2H-pyran-4-yl)amino)benzamide (TR-164)

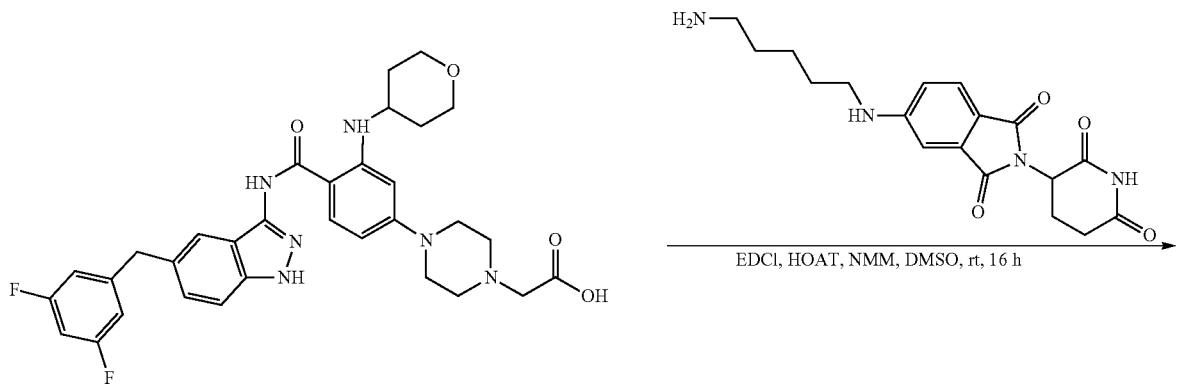

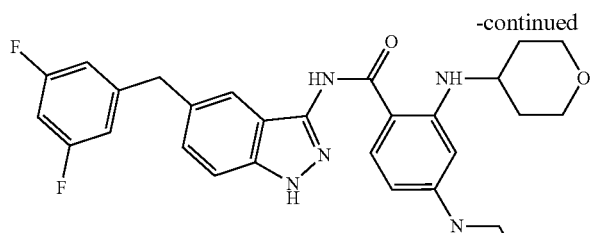
TR-164 was synthesized following the standard procedure for preparing TR-053 (13 mg, yield 56%). MS (ESI) m/z: 945.4 [M+H]$^+$.
Example 215: N-(5-(3,5-Difluorobenzyl)-1H-indazol-3-yl)-4-(4-(2-((2-((2-(2,6-dioxopiperidin-3-yl)-1,3-dioxoisoindolin-5-yl)amino)ethyl)amino)-2-oxoethyl)piperazin-1-yl)-2-((tetrahydro-2H-pyran-4-yl)amino)benzamide (TR-165)
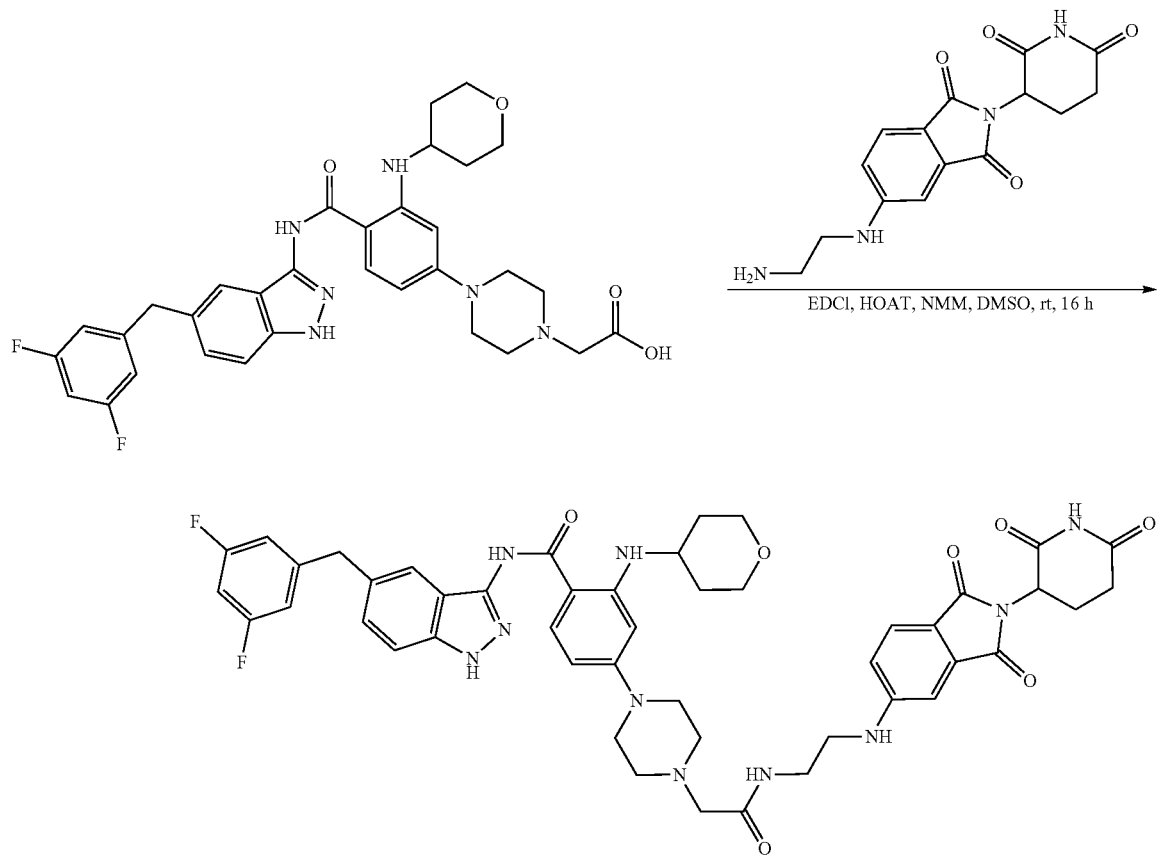

TR-165 was synthesized following the standard procedure for preparing TR-053 (12 mg, yield 53%). MS (ESI) m/z: 903.4 [M+H]+.
Example 216: N-(5-(3,5-Difluorobenzyl)-1H-indazol-3-yl)-4-(4-(20-((2-(2,6-dioxopiperidin-3-yl)-1,3-dioxoisoindolin-5-yl)amino)-2-oxo-6,9,12,15,18-pentaoxa-3-azaicosyl)piperazin-1-yl)-2-((tetrahydro-2H-pyran-4-yl)amino)benzamide (TR-166)
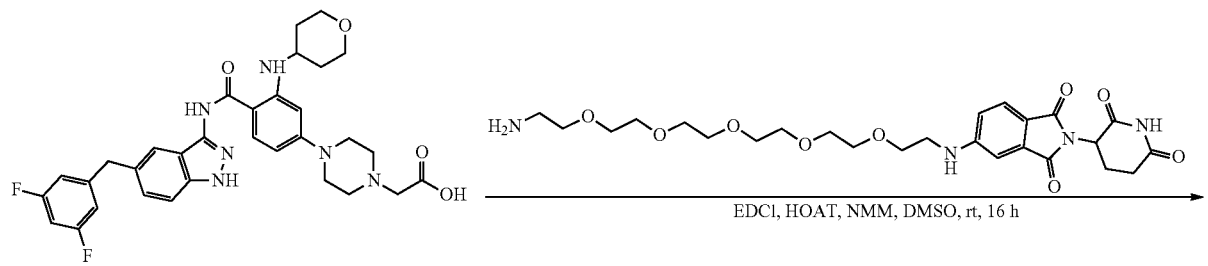
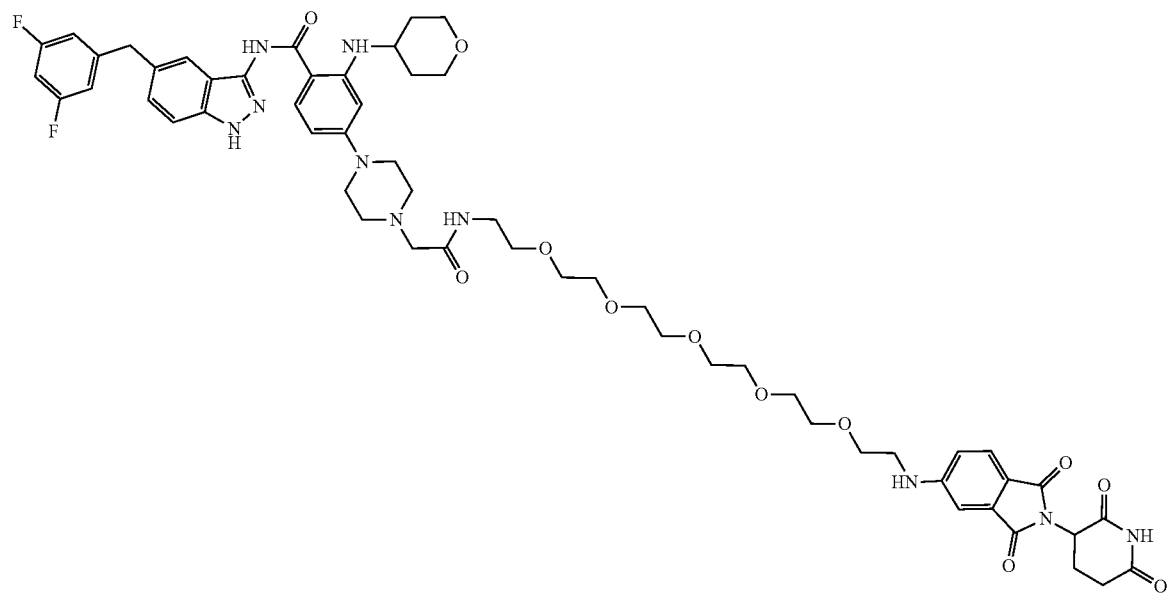
TR-166 was synthesized following the standard procedure for preparing TR-053 (14 mg, yield 56%). MS (ESI) m/z: 1223.5 [M+H]+.

Example 217: N-(5-(3,5-Difluorobenzyl)-1H-indazol-3-yl)-4-(4-(2-((3-((2-(2,6-dioxopiperidin-3-yl)-1,3-dioxoisoindolin-5-yl)amino)propyl)amino)-2-oxoethyl)piperazin-1-yl)-2-((tetrahydro-2H-pyran-4-yl)amino)benzamide (TR-167)

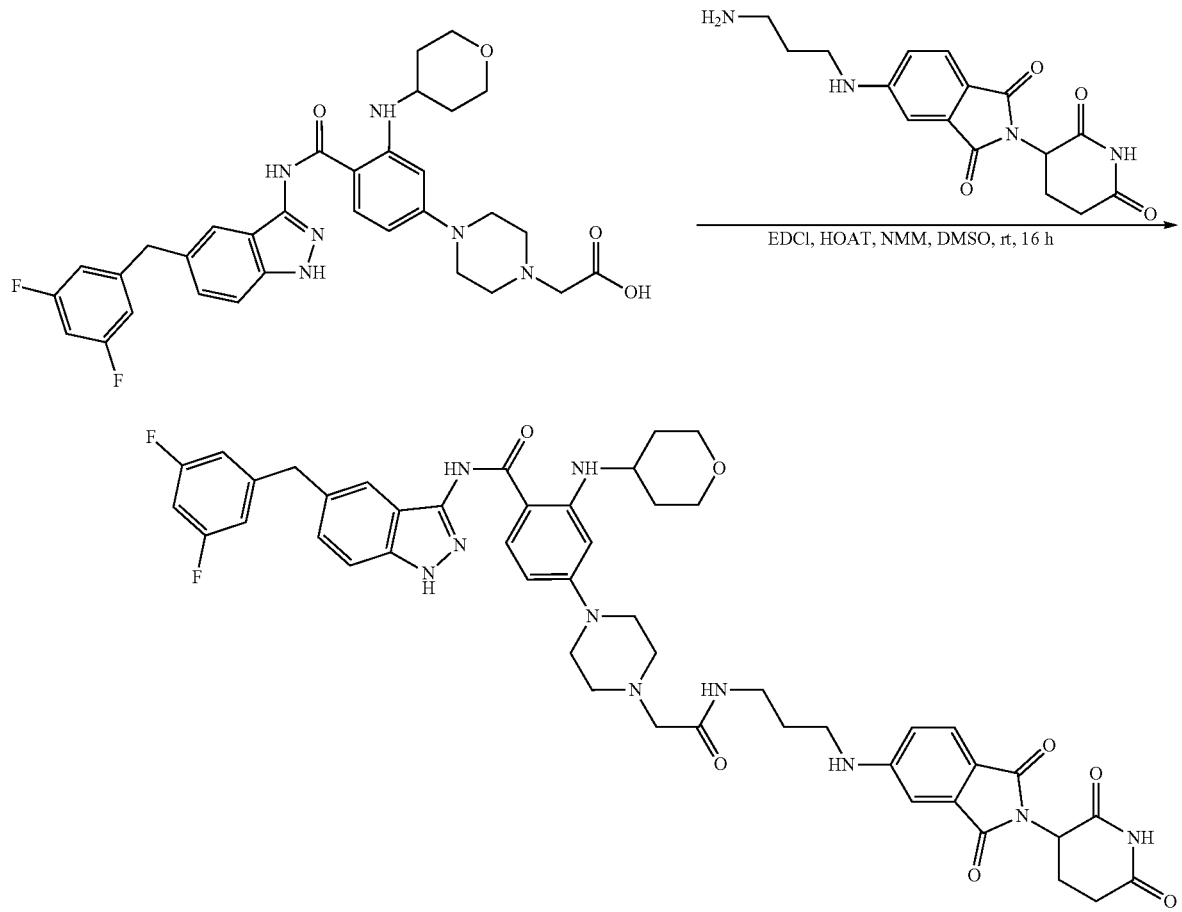

TR-167 was synthesized following the standard procedure for preparing TR-053 (14 mg, yield 55%). MS (ESI) m/z: 917.4 [M+H]$^+$.

Example 218: 2-(2,6-Dioxopiperidin-3-yl)-5-((4-(4-(6-(6-((R)-2-(3-fluorophenyl)pyrrolidin-1-yl)imidazo[1,2-b]pyridazin-3-yl)pyridin-2-yl)piperazin-1-yl)-4-oxobutyl)amino)isoindoline-1,3-dione (TR-168)

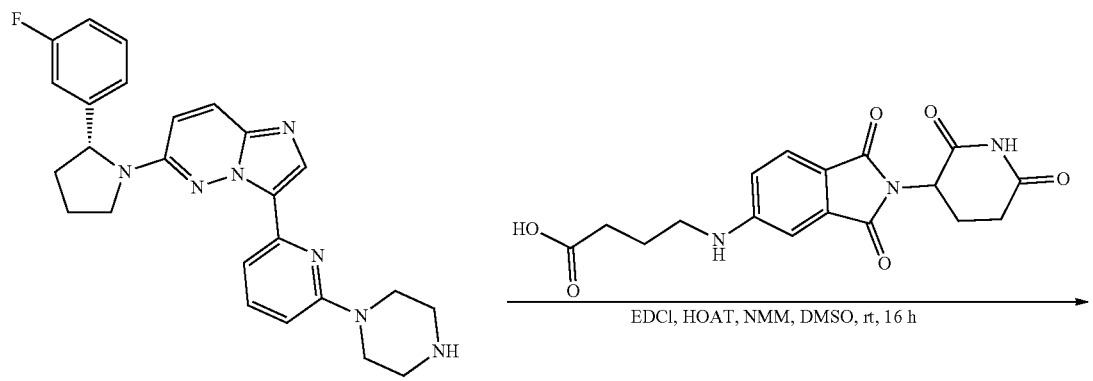

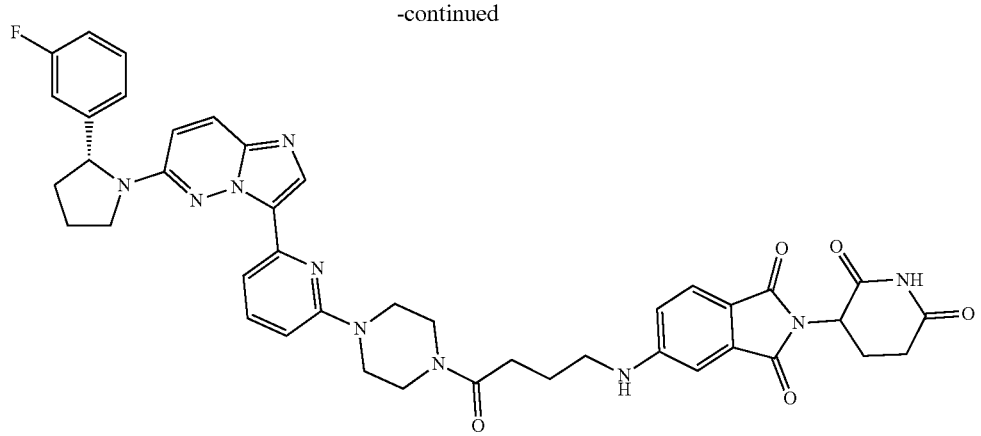
TR-168 was synthesized following the standard procedure for preparing TR-053 (16 mg, yield 58%). MS (ESI) m/z: 785.3 [M+H]+.
Example 219: N-(5-(3,5-Difluorobenzyl)-1H-indazol-3-yl)-4-(4-(4-((2-(2,6-dioxopiperidin-3-yl)-1,3-dioxoisoindolin-5-yl)amino)butanoyl)piperazin-1-yl)-2-((tetrahydro-2H-pyran-4-yl)amino)benzamide (TR-169)
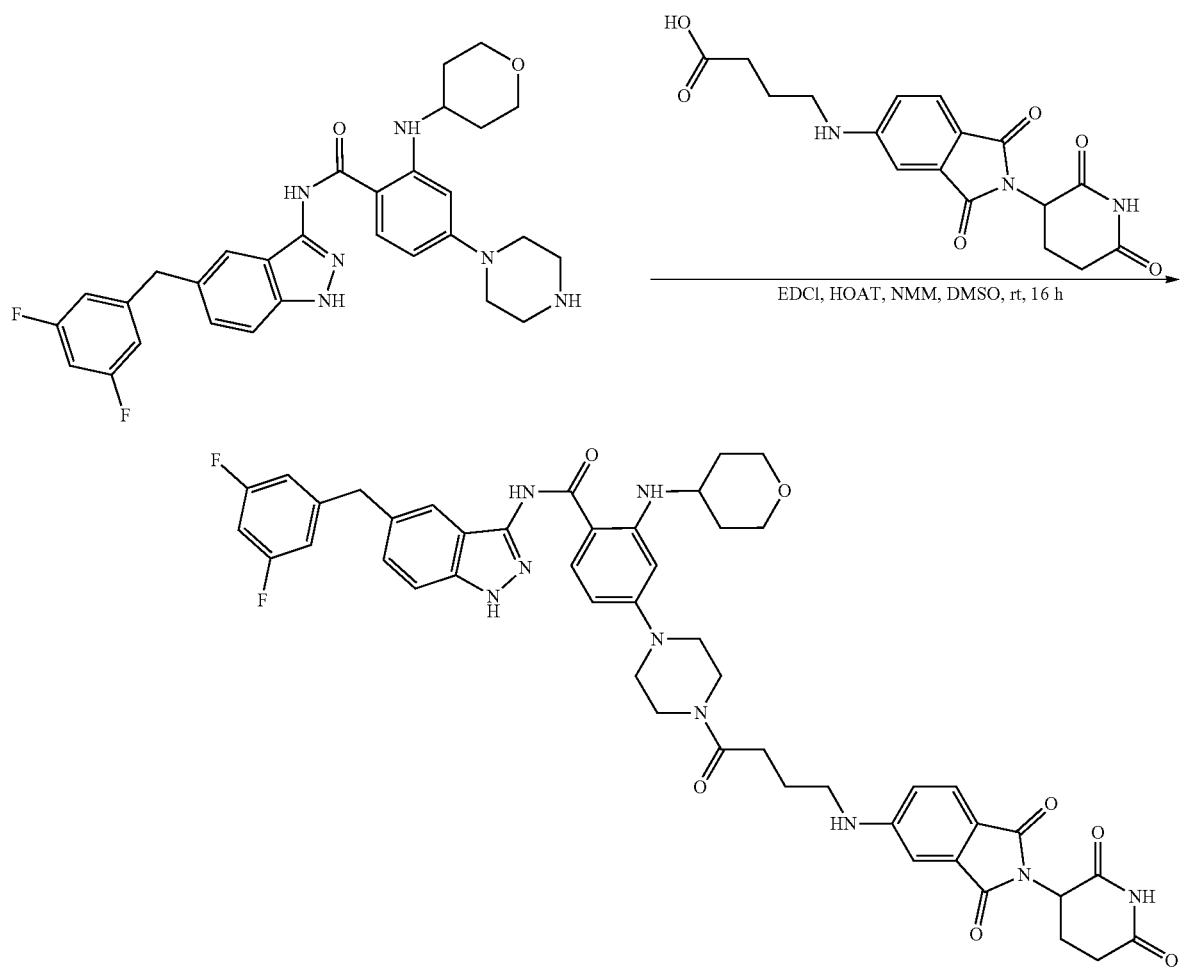

TR-169 was synthesized following the standard procedure for preparing TR-053 (14 mg, yield 56%). MS (ESI) m/z: 888.4 [M+H]+.

Example 220: 2-(2,6-Dioxopiperidin-3-yl)-5-(4-(6-(6-((R)-2-(3-fluorophenyl)pyrrolidin-1-yl)imidazo[1,2-b]pyridazin-3-yl)pyridin-2-yl)piperazin-1-yl)isoindoline-1,3-dione (TR-170)

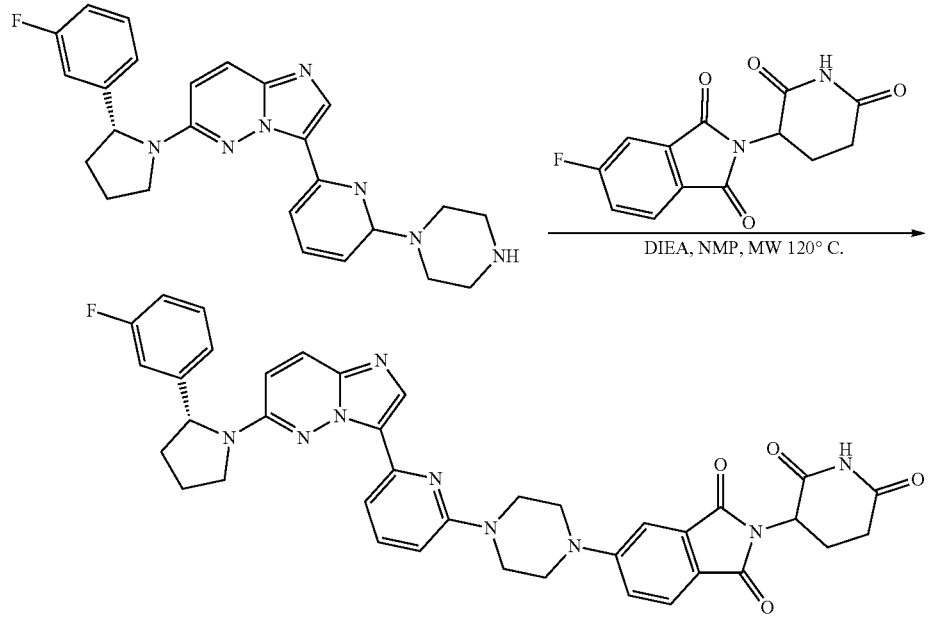

A mixture of (R)-6-(2-(3-fluorophenyl)pyrrolidin-1-yl)-3-(6-(piperazin-1-yl)pyridine-2-yl)imidazo[1,2-b]pyridazine (30 mg, 0.06 mmol), 2-(2,6-dioxopiperidin-3-yl)-5-fluoroisoindoline-1,3-dione (15.8 mg, 0.06 mmol), DIEA (0.037 mL, 0.23 mmol) and NMP (0.5 mL) was heated to 120° C. under microwave for 1.5 h. The reaction mixture was purified by reverse phase chromatography to give the desired product (8.6 mg, 32% yield) as a light yellow solid. MS (ESI) m/z: 700.3 [M+H]+.

Example 221: 2-(2,6-Dioxopiperidin-3-yl)-5-((3-(4-(6-(6-((R)-2-(3-fluorophenyl)pyrrolidin-1-yl)imidazo[1,2-b]pyridazin-3-yl)pyridin-2-yl)piperazin-1-yl)propyl)amino)isoindoline-1,3-dione (TR-171)

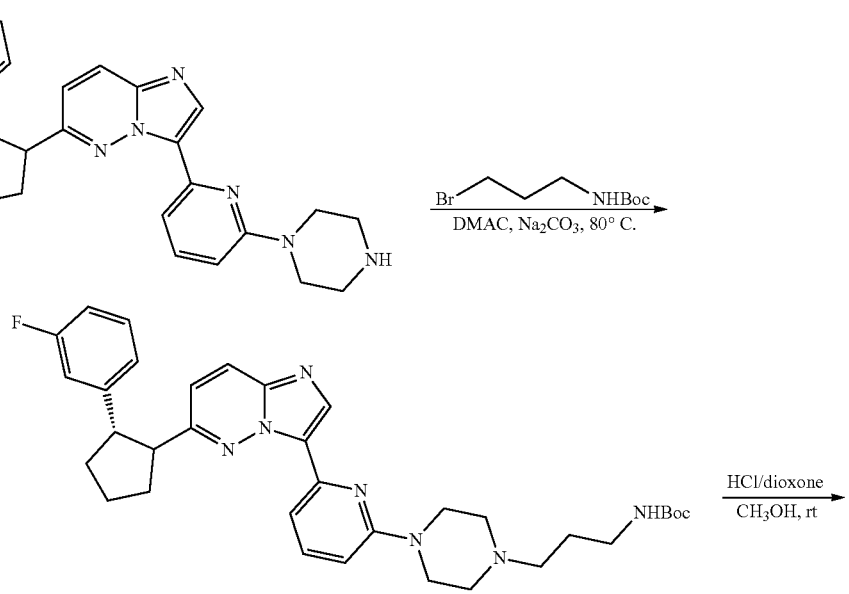

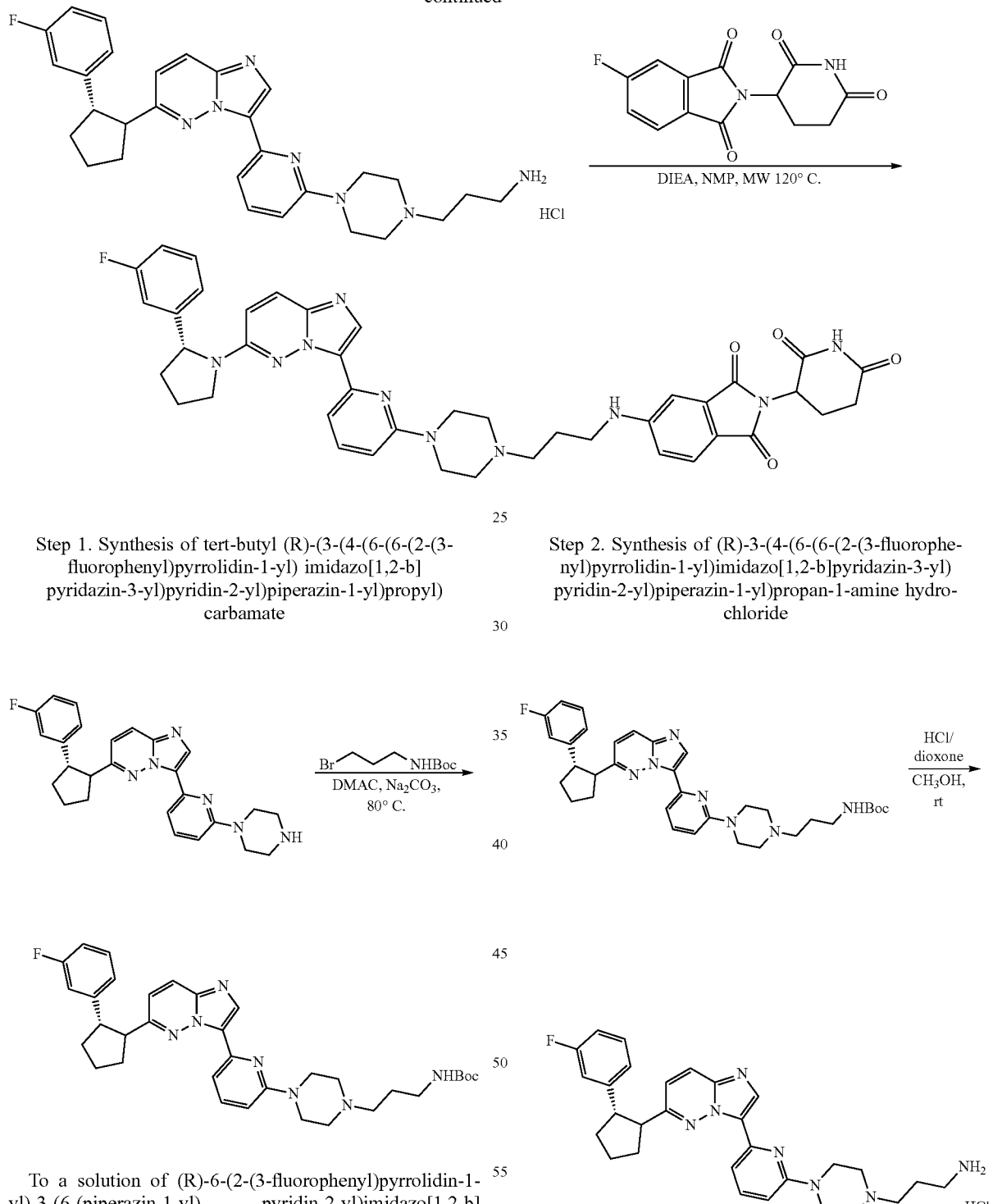

Step 1. Synthesis of tert-butyl (R)-(3-(4-(6-(6-(2-(3-fluorophenyl)pyrrolidin-1-yl) imidazo[1,2-b]pyridazin-3-yl)pyridin-2-yl)piperazin-1-yl)propyl)carbamate To a solution of (R)-6-(2-(3-fluorophenyl)pyrrolidin-1-yl)-3-(6-(piperazin-1-yl) pyridin-2-yl)imidazo[1,2-b]pyridazine (50 mg, 0.11 mmol) in DMAC (5 mL) were added Na₂CO₃ (24 mg, 0.22 mmol) and tert-butyl (3-bromopropyl)carbamate (39 mg, 0.16 mmol), the resulting mixture was stirred at 80° C. for 8 h. The reaction was cooled to room temperature and H₂O (50 mL) was added. The mixture was extracted with EtOAc (10 mL×3), the combined organic layers were concentrated and the residue was purified by reverse phase chromatography to the desired product (43 mg, 65% yield) as a pale brown solid. MS (ESI) m/z: 601.3 [M+H]⁺.

Step 2. Synthesis of (R)-3-(4-(6-(6-(2-(3-fluorophenyl)pyrrolidin-1-yl)imidazo[1,2-b]pyridazin-3-yl)pyridin-2-yl)piperazin-1-yl)propan-1-amine hydrochloride To a solution tert-butyl (R)-(3-(4-(6-(6-(2-(3-fluorophenyl)pyrrolidin-1-yl)imidazo[1,2-b]pyridazin-3-yl)pyridin-2-yl)piperazin-1-yl)propyl)carbamate (40 mg, 0.07 mmol) in methanol (2 mL) was added HCl/dioxane (4 M, 2 mL) at room temperature, then it was stirred at room temperature for 5 h. The mixture was concentrated to get the crude product (35 mg, 98% yield) as a pale brown solid which was used directly in the next step. MS (ESI) m/z: 501.3 [M+H]⁺.

Step 3. Synthesis of 2-(2,6-dioxopiperidin-3-yl)-5-((3-(4-(6-(6-((R)-2-(3-fluorophenyl) pyrrolidin-1-yl) imidazo[1,2-b]pyridazin-3-yl)pyridin-2-yl)piperazin-1-yl)propyl)amino)isoindoline-1,3-dione (TR-171)

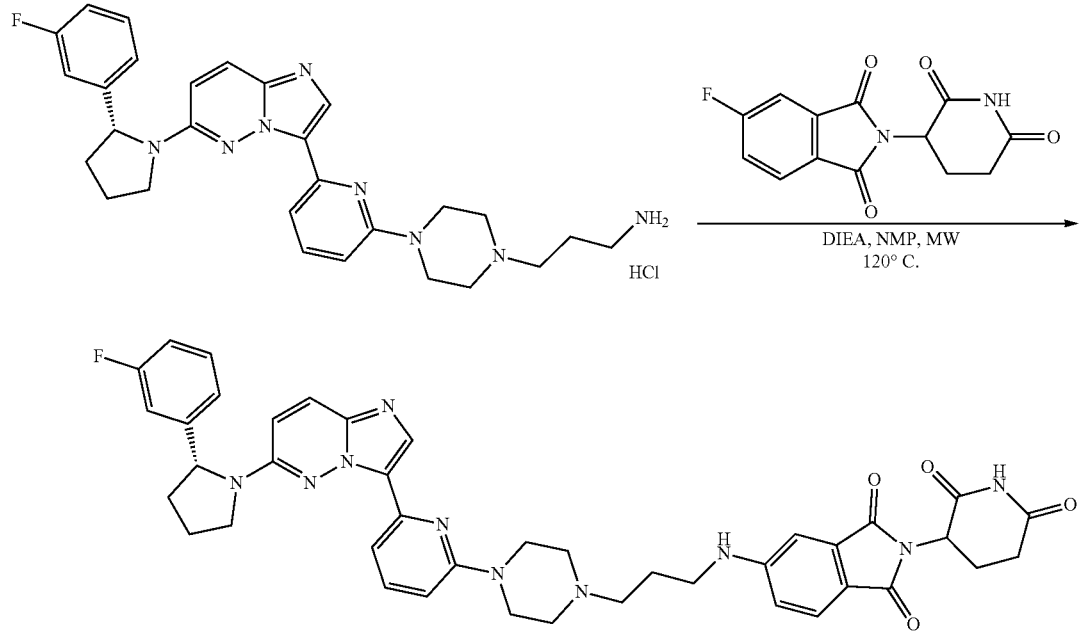

A mixture of (R)-3-(4-(6-(6-(2-(3-fluorophenyl)pyrrolidin-1-yl)imidazo[1,2-b]pyridazin-3-yl)pyridin-2-yl)piperazin-1-yl)propan-1-amine hydrochloride (35 mg, 0.07 mmol), 2-(2,6-dioxopiperidin-3-yl)-5-fluoroisoindoline-1,3-dione (15.8 mg, 0.06 mmol), DIEA (0.037 mL, 0.23 mmol) and NMP (0.5 mL) was heated to 120° C. under microwave for 1 h. The reaction mixture was purified by reverse phase chromatography to give the desired product (11.2 mg, 22% yield) as a light yellow solid. MS (ESI) m/z: 757.3 [M+H]$^+$.

Example 222: 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)propyl)isoindoline-1,3-dione (TR-172)

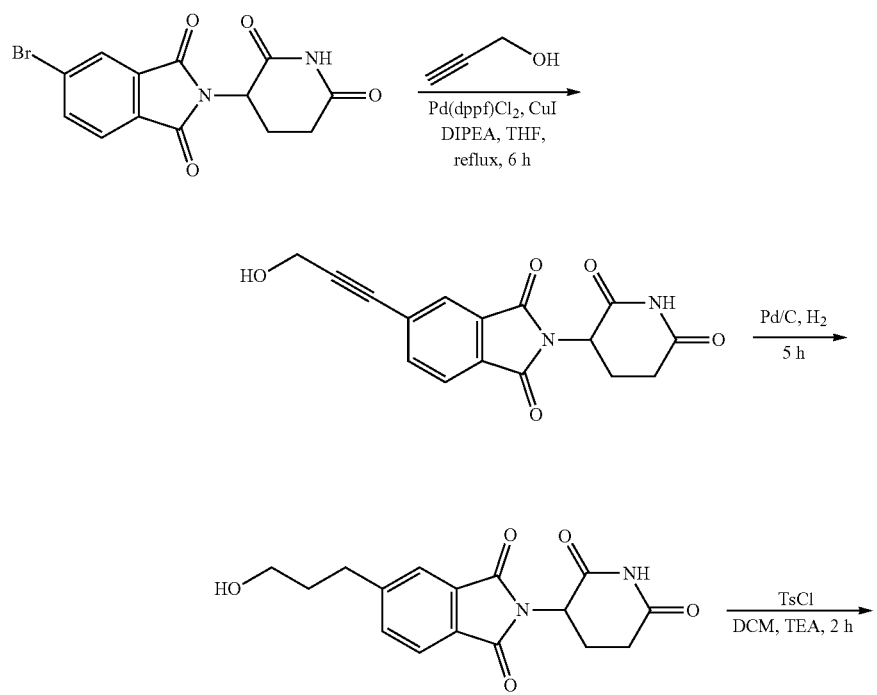

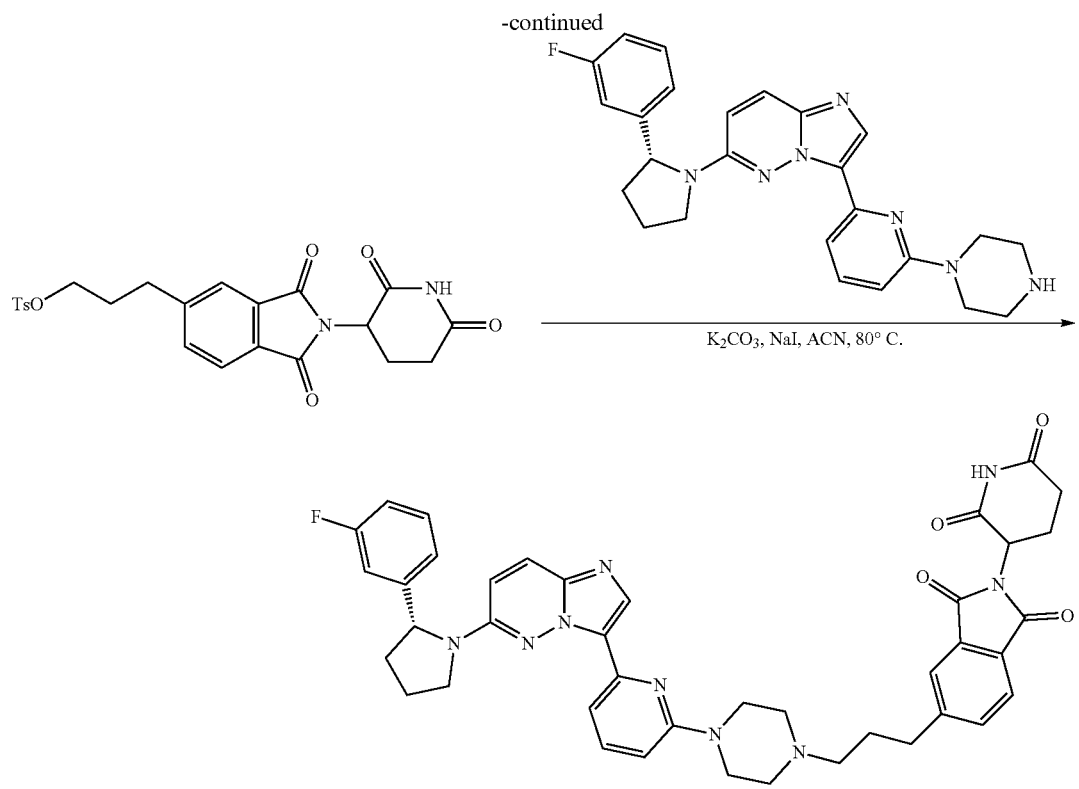

Step 1. Synthesis of 2-(2,6-dioxopiperidin-3-yl)-5-(3-hydroxyprop-1-yn-1-yl) isoindoline-1,3-dione

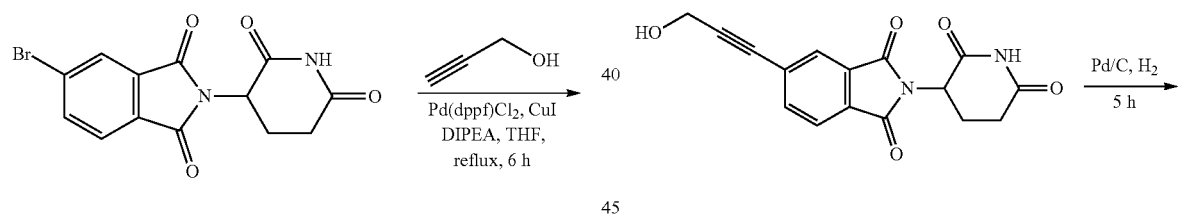

A mixture of 5-bromo-2-(2,6-dioxopiperidin-3-yl)isoindoline-1,3-dione (100 mg, 0.30 mmol), prop-2-yn-1-ol (25 mg, 0.45 mmol), Pd(dppf)Cl$_2$ (22 mg, 0.03 mmol), CuI (5.7 mg, 0.03 mmol) and DIPEA (77 mg, 0.60 mmol) in THF (10 mL) was stirred at reflux for 8 h. The reaction mixture was concentrated and the residue was purified by reverse phase chromatography to give the desired product (68 mg, 72% yield) as a pale brown solid. MS (ESI) m/z: 313.3 [M+H]$^+$.

Step 2. Synthesis of 2-(2,6-dioxopiperidin-3-yl)-5-(3-hydroxypropyl)isoindoline-1,3-dione

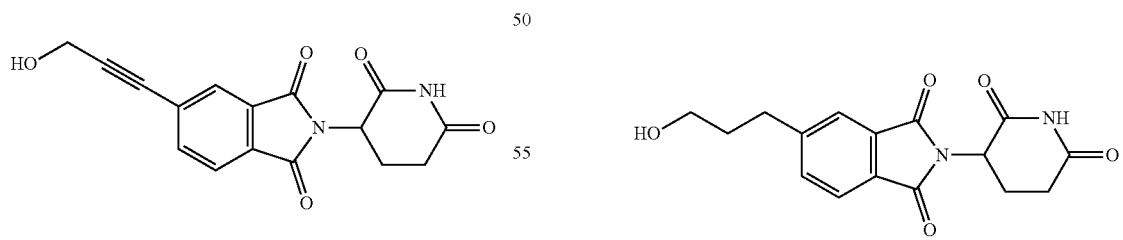

A mixture of 2-(2,6-dioxopiperidin-3-yl)-5-(3-hydroxyprop-1-yn-1-yl)isoindoline-1,3-dione (68 mg, 0.22 mmol) and Pd/C (10 mg) in methanol (5 mL) was stirred under H$_2$ (1 atm, balloon) at room temperature for 5 h. The reaction mixture was purified by reverse phase chromatography to give the desired product (55 mg, 81% yield) as a light yellow solid. MS (ESI) m/z: 317.1 [M+H]$^+$.

451

Step 3. Synthesis of 3-(2-(2,6-dioxopiperidin-3-yl)-1,3-dioxoisoindolin-5-yl)propyl 4-methylbenzenesulfonate

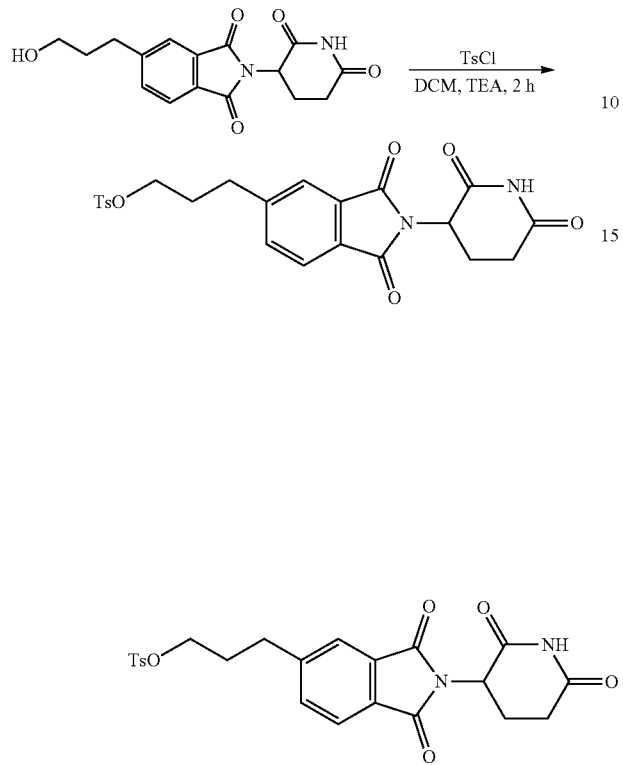

452

To a solution 2-(2,6-dioxopiperidin-3-yl)-5-(3-hydroxypropyl)isoindoline-1,3-dione (55 mg, 0.17 mmol) and TEA (35 mg, 0.34 mmol) in DCM (5 mL) was added 4-methylbenzenesulfonyl chloride (39 mg, 0.20 mmol) at room temperature, then it was stirred at room temperature for 4 h. The mixture was concentrated and purified by reverse phase chromatography to give the desired product (42 mg, 52% yield) as a light yellow solid. MS (ESI) m/z: 471.1 [M+H]$^+$.

Step 4. Synthesis of 2-(2,6-dioxopiperidin-3-yl)-5-(3-(4-(6-(6-((R)-2-(3-fluorophenyl) pyrrolidin-1-yl) imidazo[1,2-b]pyridazin-3-yl)pyridin-2-yl)piperazin-1-yl)propyl)isoindoline-1,3-dione

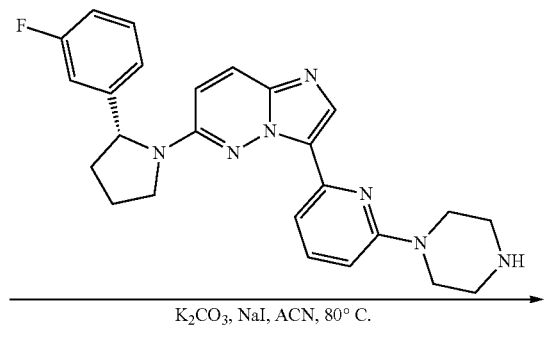

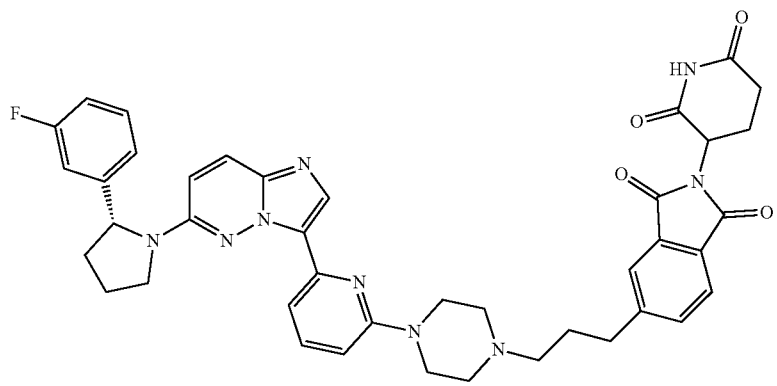

A mixture of 3-(2-(2,6-dioxopiperidin-3-yl)-1,3-dioxoisoindolin-5-yl)propyl 4-methylbenzenesulfonate (40 mg, 0.08 mmol), (R)-6-(2-(3-fluorophenyl)pyrrolidin-1-yl)-3-(6-(piperazin-1-yl)pyridin-2-yl)imidazo[1,2-b]pyridazine (37 mg, 0.08 mmol), K₂CO₃ (22 mg, 0.16 mmol) and NaI (1.5 mg, 0.01 mmol) in CH₃CN (3 mL) were stirred at 80° C. for 5 h. LCMS showed the reaction was completed. The mixture was concentrated and purified by reverse phase chromatography to give the desired product (21 mg, 36% yield) as a light yellow solid. MS (ESI) m/z: 742.3 [M+H]⁺.

Example 223: 2-(2,6-Dioxopiperidin-3-yl)-5-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)isoindoline-1,3-dione (TR-173)

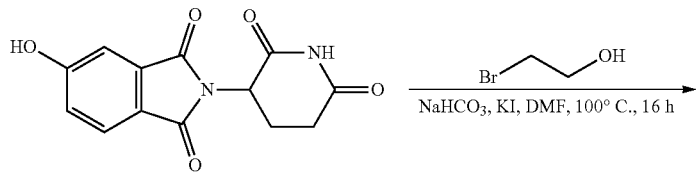

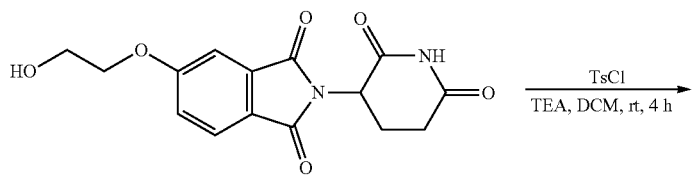

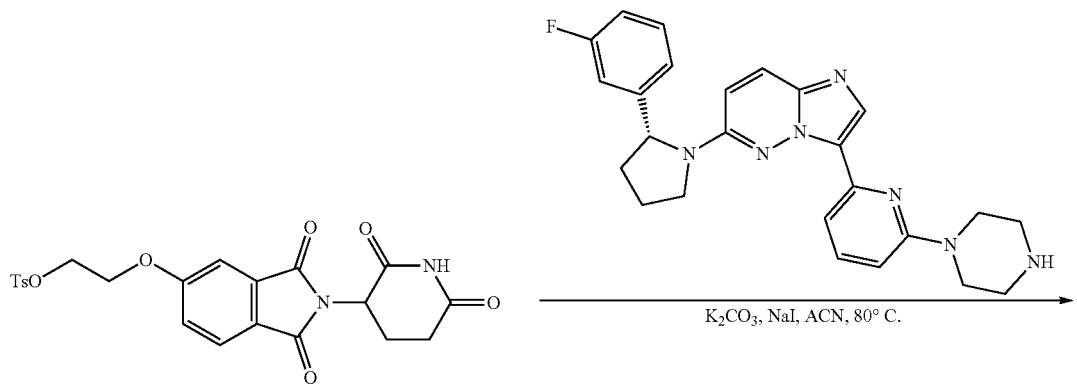

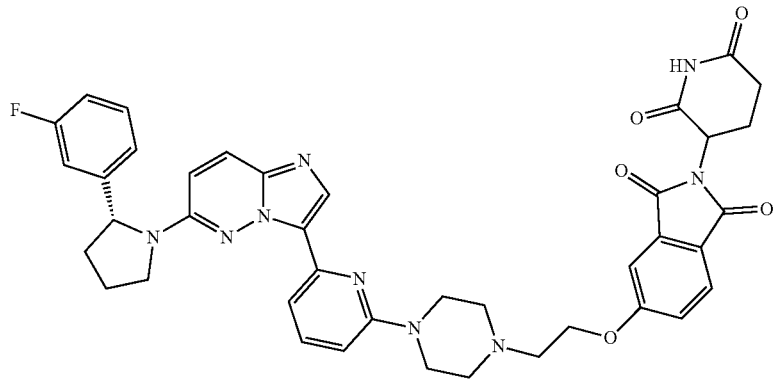

455

Step 1. Synthesis of 2-(2,6-dioxopiperidin-3-yl)-5-(2-hydroxyethoxy)isoindoline-1,3-dione

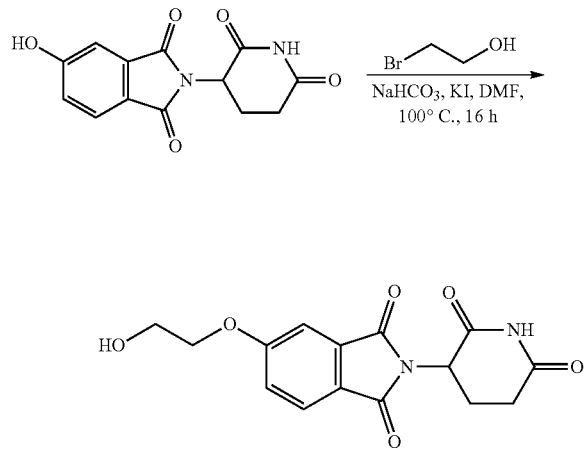

A mixture of 2-(2,6-dioxopiperidin-3-yl)-5-hydroxyisoindoline-1,3-dione (1 g, 3.65 mmol), 2-bromoethan-1-ol (452 mg, 3.65 mmol), NaHCO₃ (613 mg, 7.30 mmol) and KI (605 mg, 3.65 mmol) in DMF (20 mL) were stirred at 100° C. for 16 h. The mixture was filtered and purified by reverse phase chromatography to give the desired product (340 mg, 29% yield) as a light yellow solid. MS (ESI) m/z: 319.1 [M+H]⁺.

456

Step 3. Synthesis of 2-((2-(2,6-dioxopiperidin-3-yl)-1,3-dioxoisoindolin-5-yl)oxy) ethyl-4-methylbenzenesulfonate

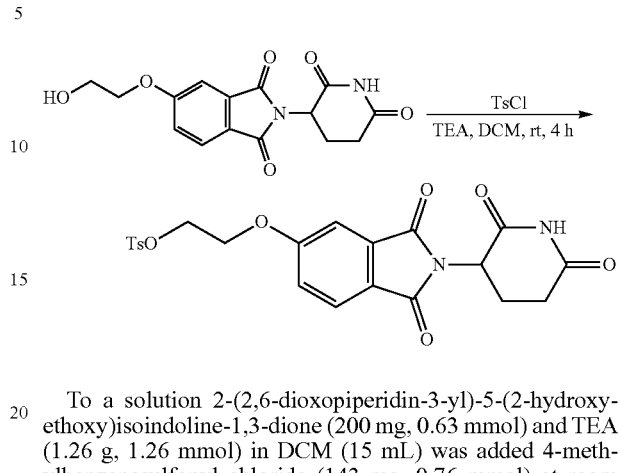

To a solution 2-(2,6-dioxopiperidin-3-yl)-5-(2-hydroxyethoxy)isoindoline-1,3-dione (200 mg, 0.63 mmol) and TEA (1.26 g, 1.26 mmol) in DCM (15 mL) was added 4-methylbenzenesulfonyl chloride (143 mg, 0.76 mmol) at room temperature, then it was stirred at room temperature for 4 h. The mixture was concentrated and purified by reverse phase chromatography to give the desired product (172 mg, 58% yield) as a light yellow solid. MS (ESI) m/z: 473.1 [M+H]⁺.

Step 4. Synthesis of 2-(2,6-dioxopiperidin-3-yl)-5-(2-(4-(6-(6-((R)-2-(3-fluorophenyl) pyrrolidin-1-yl) imidazo[1,2-b]pyridazin-3-yl)pyridin-2-yl)piperazin-1-yl)ethoxy)isoindoline-1,3-dione

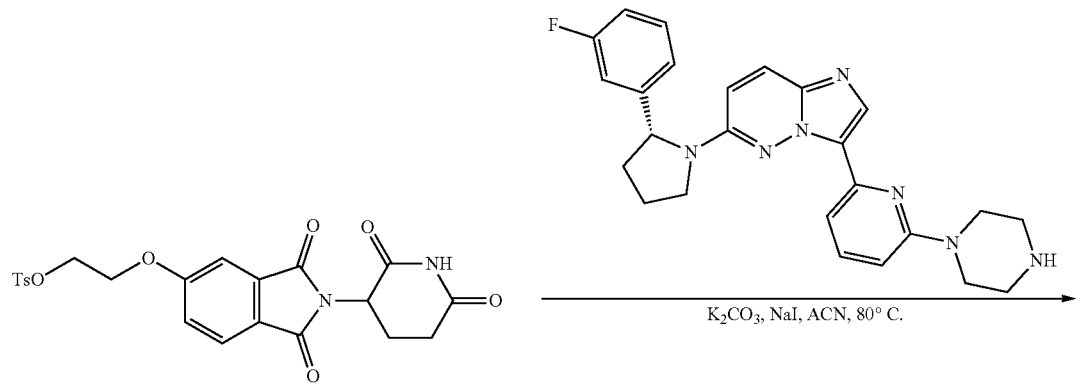

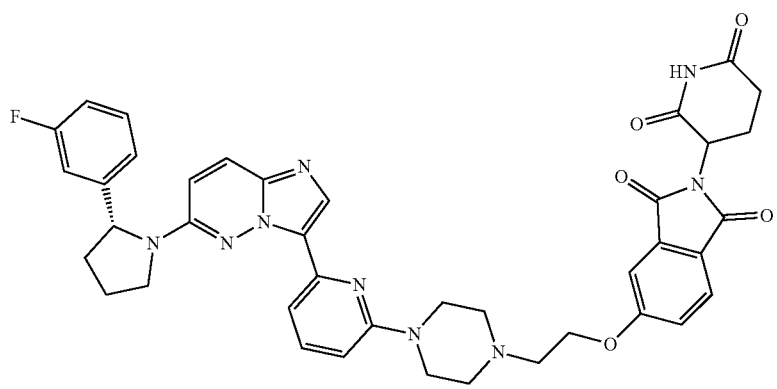

TR-173

A mixture of 2-((2-(2,6-dioxopiperidin-3-yl)-1,3-dioxoisoindolin-5-yl)oxy)ethyl 4-methylbenzenesulfonate (40 mg, 0.08 mmol), (R)-6-(2-(3-fluorophenyl)pyrrolidin-1-yl)-3-(6-(piperazin-1-yl)pyridin-2-yl)imidazo[1,2-b]pyridazine (37 mg, 0.08 mmol), K$_2$CO$_3$ (22 mg, 0.16 mmol) and NaI (1.5 mg, 0.01 mmol) in CH$_3$CN (3 mL) were stirred at 80° C. for 5 h. LCMS showed the reaction was completed. The mixture was concentrated and purified by reverse phase chromatography to give the desired product (16 mg, 42% yield) as a light yellow solid. MS (ESI) m/z: 744.3 [M+H]$^+$.

Example 224: Synthesis of 2-(2,6-dioxopiperidin-3-yl)-5-((1-(6-(6-((R)-2-(3-fluorophenyl)pyrrolidin-1-yl)imidazo[1,2-b]pyridazin-3-yl)pyridin-2-yl)piperidin-4-yl)amino)isoindoline-1,3-dione (TR-174)

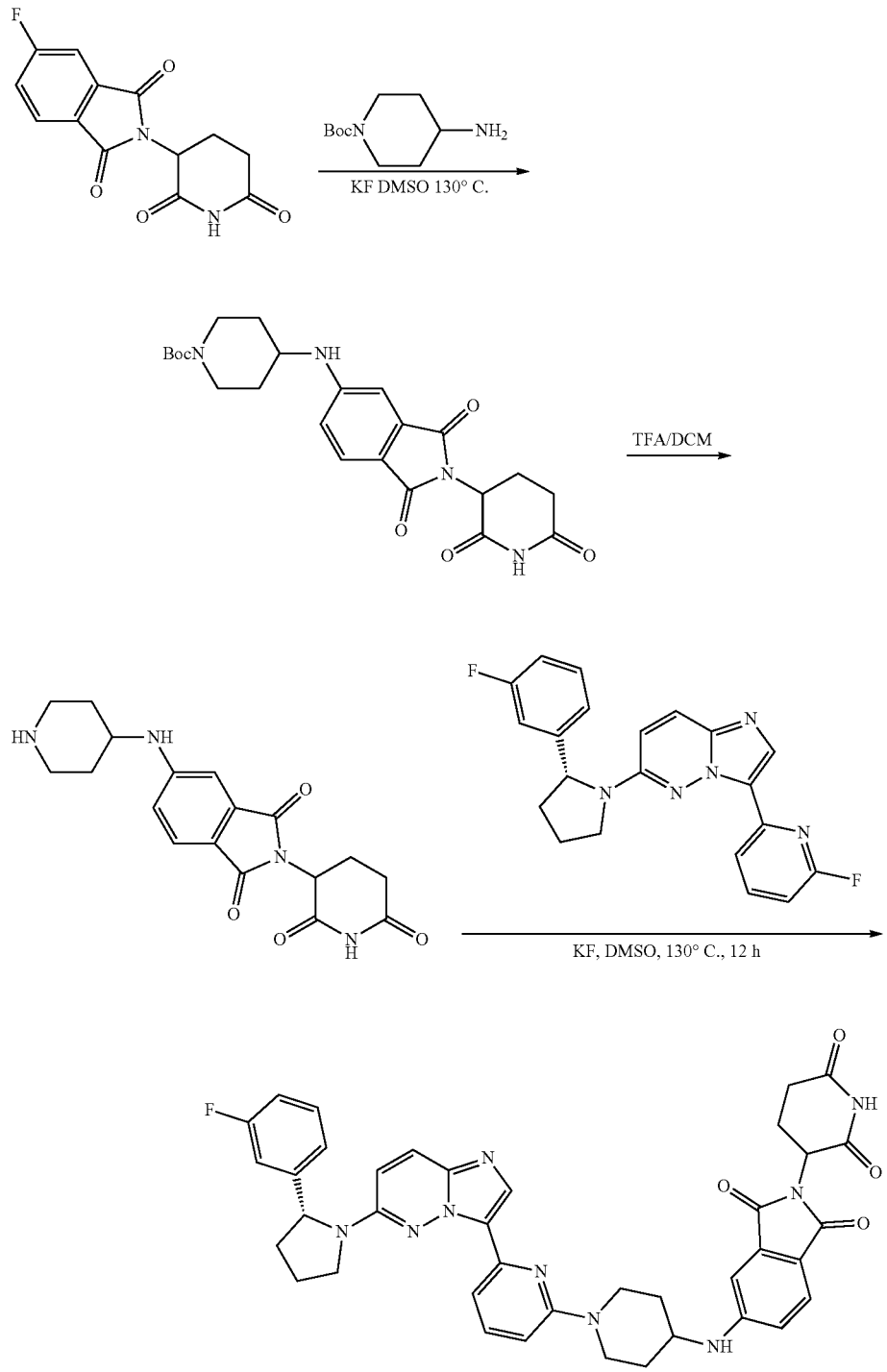

TR-174 was synthesized following the standard procedure for preparing TR-175. MS (ESI) m/z: 714.3 [M+H]$^+$.

Example 225: 2-(2,6-Dioxopiperidin-3-yl)-5-((1-(6-(6-((R)-2-(3-fluorophenyl)pyrrolidin-1-yl)imidazo[1,2-b]pyridazin-3-yl)pyridin-2-yl)azetidin-3-yl)amino)isoindoline-1,3-dione (TR-175)
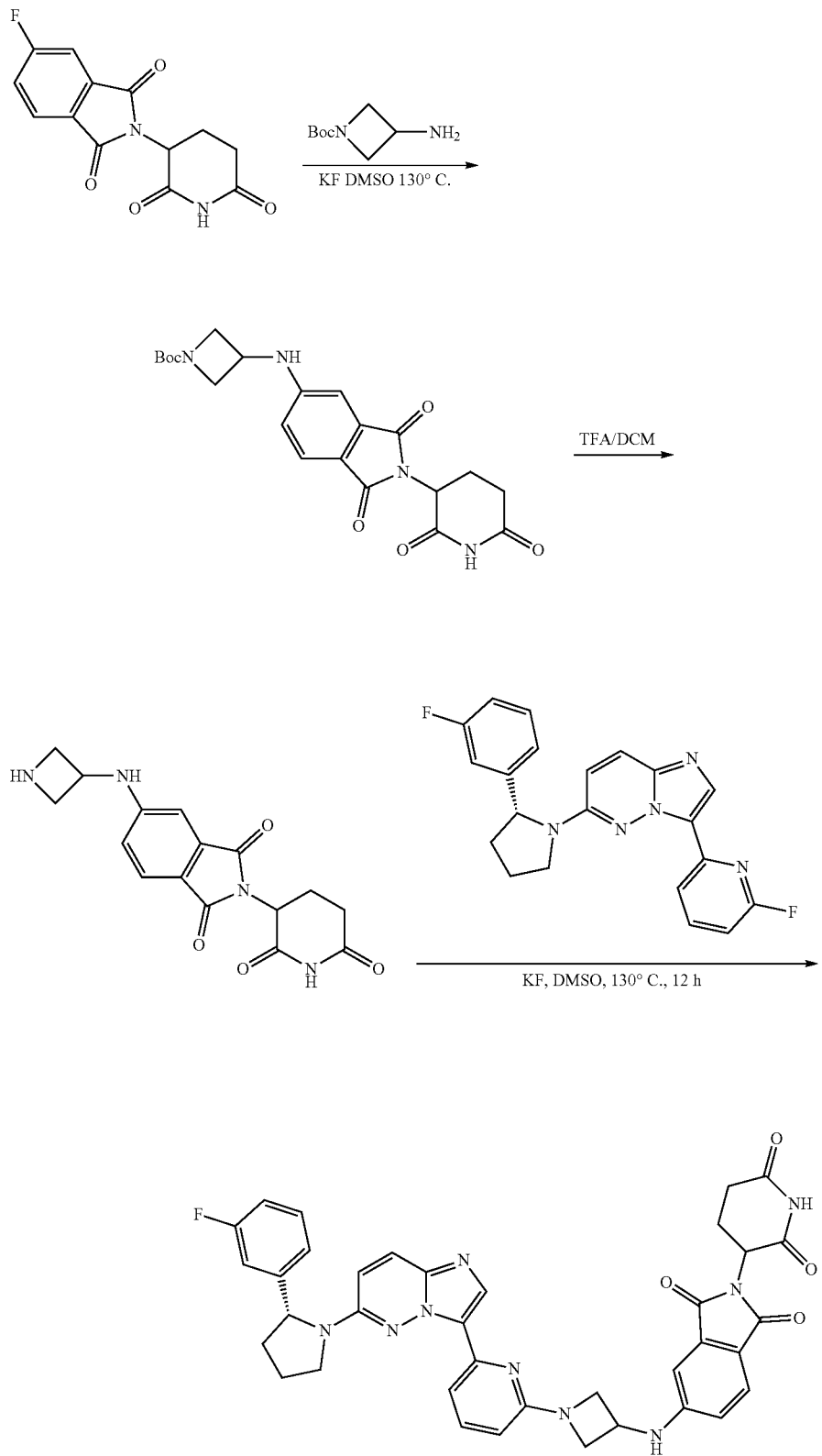

Step 1. Synthesis of tert-butyl 3-((2-(2,6-dioxopiperidin-3-yl)-1,3-dioxoisoindolin-5-yl)amino)azetidine-1-carboxylate

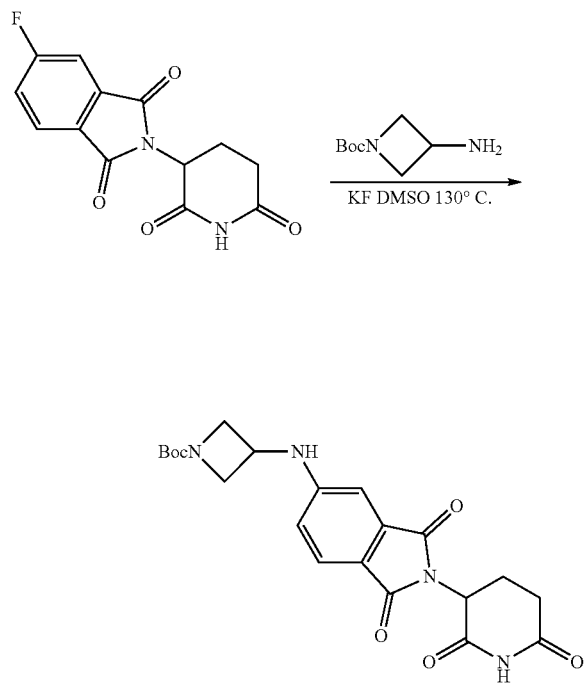

To a solution of 2-(2,6-dioxopiperidin-3-yl)-5-fluoroisoindoline-1,3-dione (200 mg, 724.6 umol) in DMSO (3 mL) were added KF (126 mg, 2.17 mmol) and tert-butyl 3-aminoazetidine-1-carboxylat (373.9 mg, 2.17 mmol). The resulting mixture was stirred at 130° C. for 1 hr. After the Imide was totally consumed, the reaction was poured into water (20 mL) and extracted with ethyl acetate (3×10 mL). The combined organic layers were washed with saturated brine (20 mL), dried over anhydrous sodium sulfate, filtered and evaporated under reduced pressure. The resulting residue was purified by silica gel column chromatography to afford the desired product tert-butyl 3-((2-(2,6-dioxopiperidin-3-yl)-1,3-dioxoisoindolin-5-yl)amino)azetidine-1-carboxylate (80 mg, 26% yield) as a light yellow solid. MS (ESI) m z: 429.2 [M+H]⁺.

Step 2. Synthesis of 5-(azetidin-3-ylamino)-2-(2,6-dioxopiperidin-3-yl)isoindoline-1,3-dione

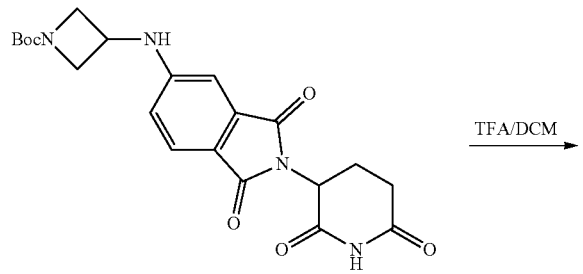

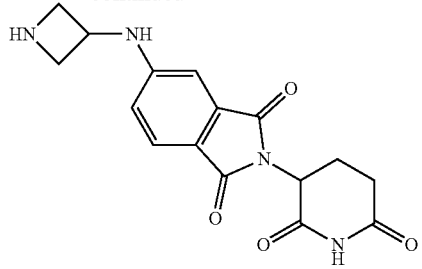

To a solution of tert-butyl 3-((2-(2,6-dioxopiperidin-3-yl)-1,3-dioxoisoindolin-5-yl)amino)azetidine-1-carboxylate (80 mg, 186.9 umol) in DCM (2 mL) was added TFA (2 mL). The resulting mixture was stirred at 25° C. for 5 hr. After the starting material was totally consumed, the reaction was evaporated under reduced pressure. The resulting residue was purified by reverse-phase chromatography to yield the desired product 5-(azetidin-3-ylamino)-2-(2,6-dioxopiperidin-3-yl)isoindoline-1,3-dione (56 mg, 91% yield) as a light yellow solid. MS (ESI) m/z: 329.2 [M+H]⁺.

Step 3. Synthesis of 2-(2,6-dioxopiperidin-3-yl)-5-((1-(6-(6-((R)-2-(3-fluorophenyl)pyrrolidin-1-yl)imidazo[1,2-b]pyridazin-3-yl)pyridin-2-yl)azetidin-3-yl)amino)isoindoline-1,3-dione

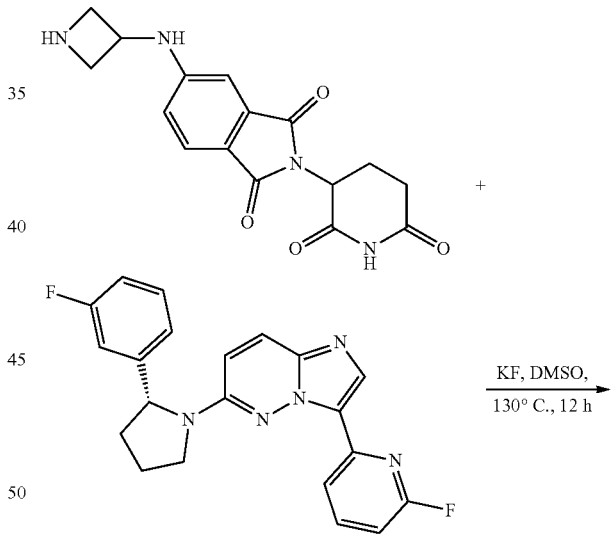

To a solution of 5-(azetidin-3-ylamino)-2-(2,6-dioxopiperidin-3-yl)isoindoline-1,3-dione (50 mg, 152.4 umol) in DMSO (3 mL) were added KF (26.5 mg, 457.3 umol) and

463

(R)-6-(2-(3-fluorophenyl)pyrrolidin-1-yl)-3-(6-fluoropyridin-2-yl)imidazo[1,2-b]pyridazine (57.4 mg, 152.4 umol).

The resulting mixture was stirred at 130° C. for 1 hr. After the Imide was totally consumed, the reaction was poured into water (20 mL) and extracted with ethyl acetate (3×10 mL). The combined organic layers were washed with saturated brine (20 mL), dried over anhydrous sodium sulfate, filtered and evaporated under reduced pressure. The resulting residue was purified by reverse-phase chromatography to afford the desired product 2-(2,6-dioxopiperidin-3-yl)-5-

464

((1-(6-(6-((R)-2-(3-fluorophenyl)pyrrolidin-1-yl)imidazo[1,2-b]pyridazin-3-yl)pyridin-2-yl)azetidin-3-yl)amino)isoindoline-1,3-dione (10 mg, 10% yield) as a light yellow solid. MS (ESI) m/z: 686.3 [M+H]⁺.

Example 226: Synthesis of 2-(2,6-Dioxopiperidin-3-yl)-5-((2-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)ethyl)amino)isoindoline-1,3-dione (TR-176)

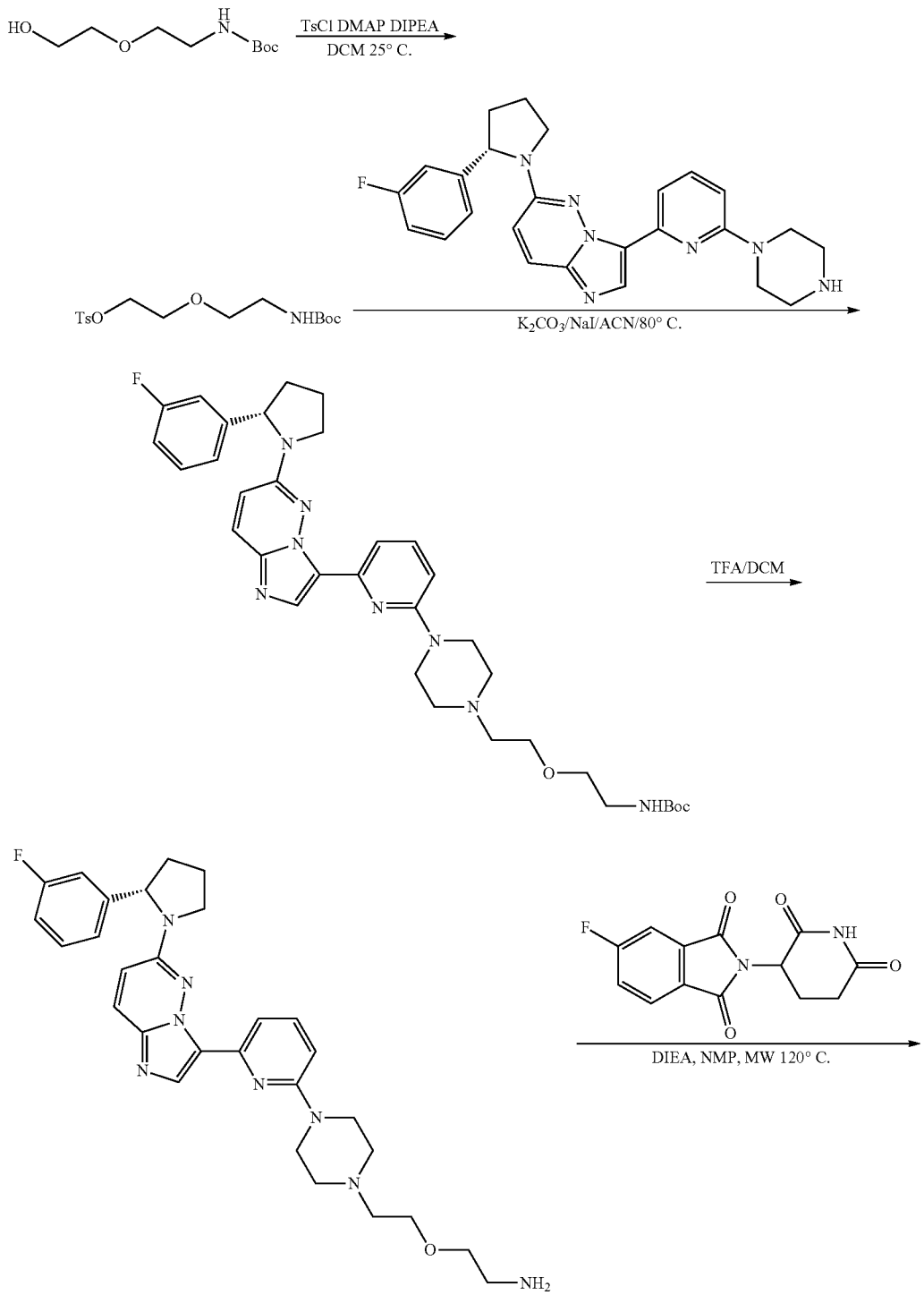

-continued
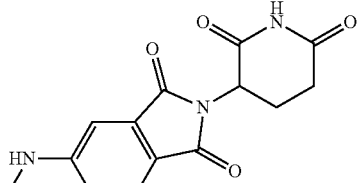
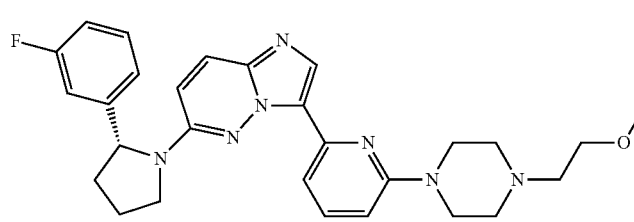
TR-176 was synthesized following the standard procedure for preparing TR-177. MS (ESI) m/z: 787.3 [M+H]⁺.
Example 227: Synthesis of 2-(2,6-Dioxopiperidin-3-yl)-5-((2-(2-(2-(4-(6-(6-((S)-2-(3-fluorophenyl)pyrrolidin-1-yl)imidazo[1,2-b]pyridazin-3-yl)pyridin-2-yl)piperazin-1-yl)ethoxy)ethoxy)ethyl)amino)isoindoline-1,3-dione (TR-177)
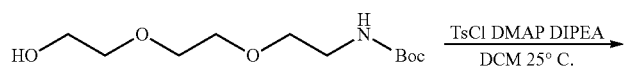
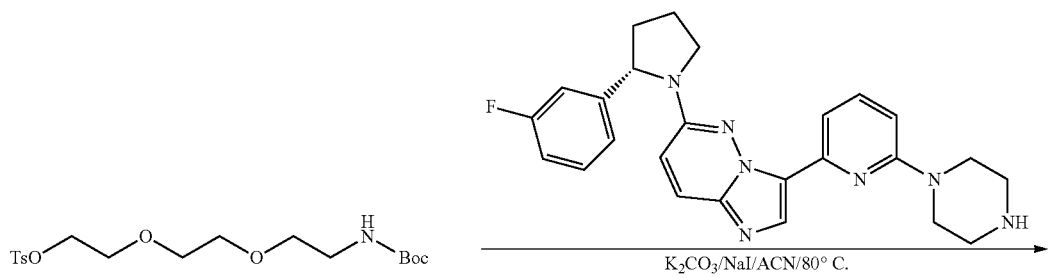
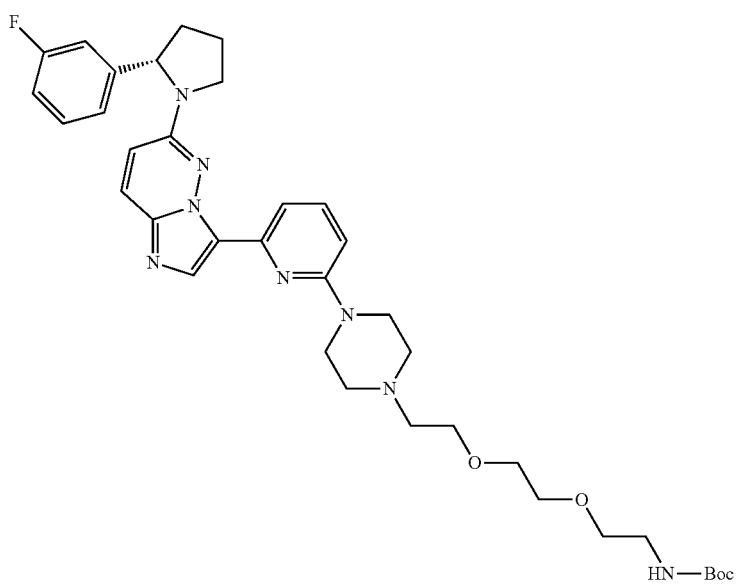

-continued

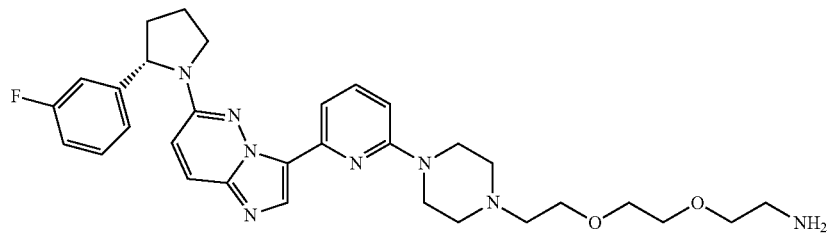 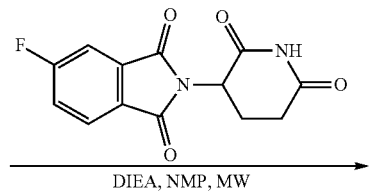

DIEA, NMP, MW

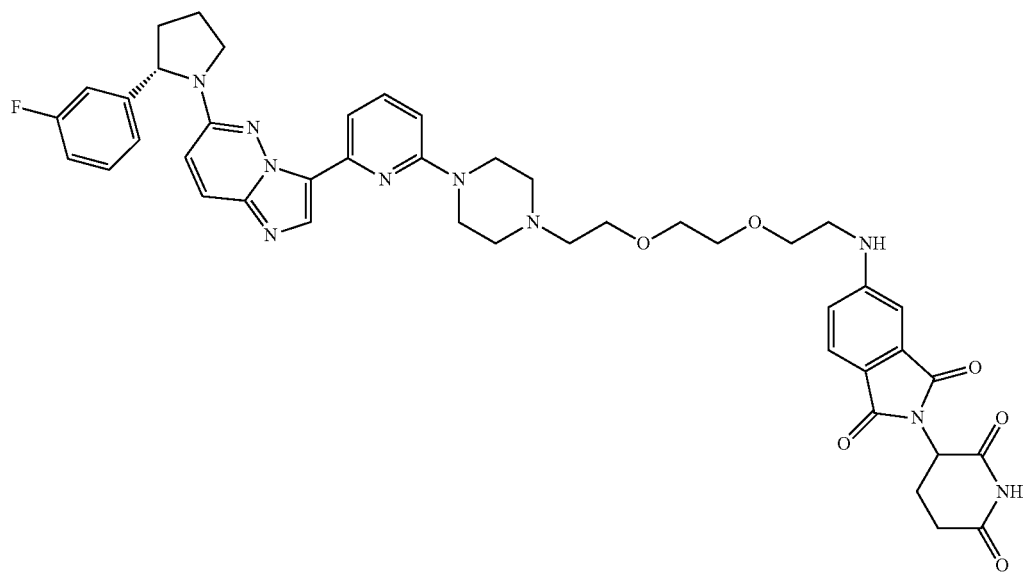

Step 1. Synthesis of 2,2-dimethyl-4-oxo-3,8,11-trioxa-5-azatridecan-13-yl 4-methylbenzenesulfonate Step 2. Synthesis of tert-butyl (S)-(2-(2-(2-(4-(6-(6-(2-(3-fluorophenyl)pyrrolidin-1-yl)imidazo[1,2-b]pyridazin-3-yl)pyridin-2-yl)piperazin-1-yl)ethoxy)ethoxy)ethyl)carbamate

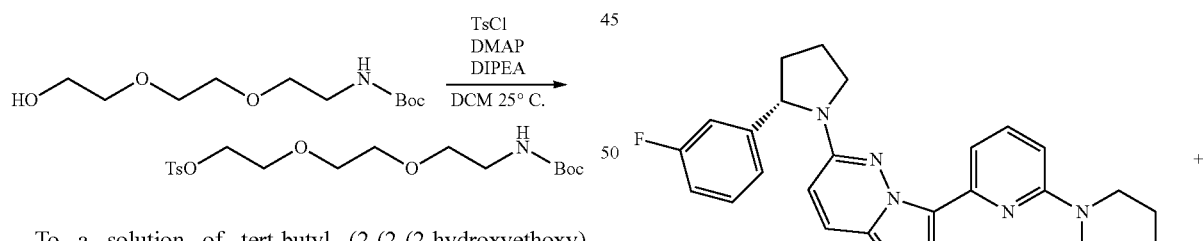

To a solution of tert-butyl (2-(2-(2-hydroxyethoxy)ethoxy)ethyl)carbamate (200 mg, 803.2 umol) in DCM (5 mL) were added DMAP (9.7 mg, 80.3 umol), DIPEA (311 mg, 2.4 mmol) and TsCl (183.7 mg, 963.8 mmol). The resulting mixture was stirred at 25° C. for 15 hr. The reaction was poured into water (20 mL) and extracted with ethyl acetate (3×10 mL). The combined organic layers were washed with saturated brine (20 mL), dried over anhydrous sodium sulfate, filtered and evaporated under reduced pressure. The resulting residue was purified by reverse-phase chromatography to afford the desired product 2,2-dimethyl-4-oxo-3,8,11-trioxa-5-azatridecan-13-yl 4-methylbenzenesulfonate (230 mg, 71.2% yield) as a light yellow solid. MS (ESI) m/z: 404.2 [M+H]+.

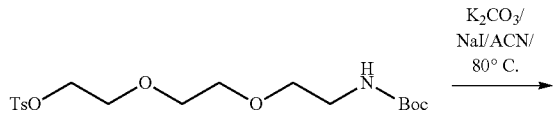

469
-continued

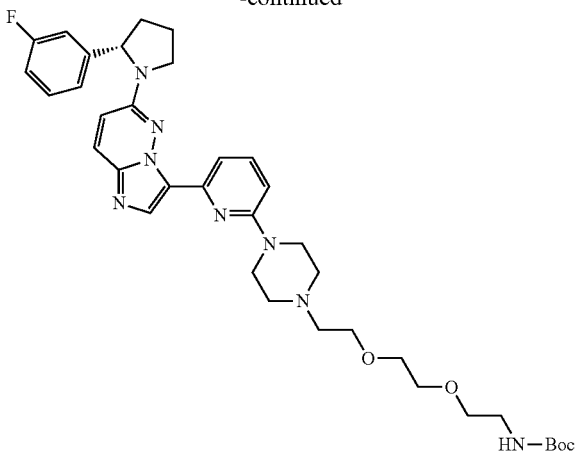

470

To a solution of (S)-6-(2-(3-fluorophenyl)pyrrolidin-1-yl)-3-(6-(piperazin-1-yl)pyridin-2-yl)imidazo[1,2-b]pyridazine (50 mg, 112.8 umol) in $CH_3CN$ (5 mL) were added K2CO3 (46.7 mg, 338.6 umol) and NaI (1.5 mg, 11.2 mmol). The resulting mixture was stirred at 80° C. for 15 hr. The reaction was poured into water (20 mL) and extracted with ethyl acetate (3×10 mL). The combined organic layers were washed with saturated brine (20 mL), dried over anhydrous sodium sulfate, filtered and evaporated under reduced pressure. The resulting residue was purified by reverse-phase chromatography to afford the desired product tert-butyl (S)-(2-(2-(2-(4-(6-(6-(2-(3-fluorophenyl)pyrrolidin-1-yl)imidazo[1,2-b]pyridazin-3-yl)pyridin-2-yl)piperazin-1-yl)ethoxy)ethoxy)ethyl)carbamate (30 mg, 39.6% yield) as a light yellow solid. MS (ESI) m/z: 675.4 $[M+H]^+$.

Step 3. Synthesis of (S)-2-(2-(2-(4-(6-(6-(2-(3-fluorophenyl)pyrrolidin-1-yl)imidazo[1,2-b]pyridazin-3-yl)pyridin-2-yl)piperazin-1-yl)ethoxy)ethoxy)ethan-1-amine

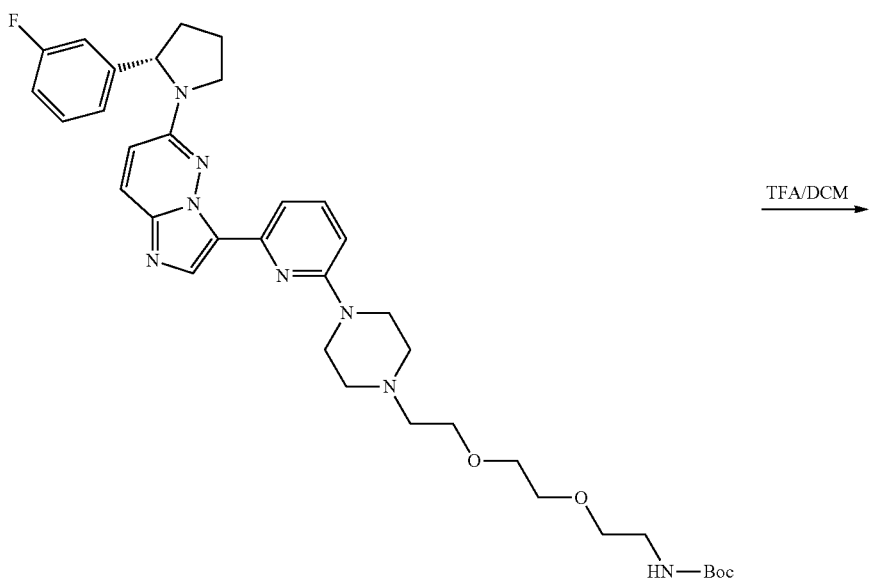

TFA/DCM →

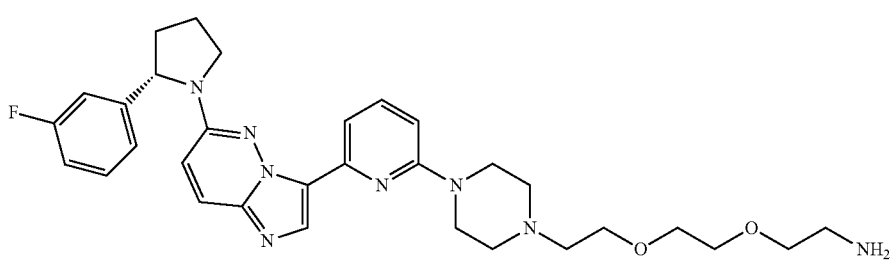

To a solution of tert-butyl (S)-(2-(2-(2-(4-(6-(6-(2-(3-fluorophenyl)pyrrolidin-1-yl)imidazo[1,2-b]pyridazin-3-yl)pyridin-2-yl)piperazin-1-yl)ethoxy)ethoxy)ethyl)carbamate (20 mg, 29.6 umol) in DCM (2 mL) was added TFA (2 mL). The resulting mixture was stirred at 25° C. for 5 hr. After the starting material was totally consumed, the reaction was evaporated under reduced pressure. The resulting residue was purified by reverse-phase chromatography to yield the desired product (S)-2-(2-(2-(4-(6-(6-(2-(3-fluorophenyl) pyrrolidin-1-yl)imidazo[1,2-b]pyridazin-3-yl)pyridin-2-yl) piperazin-1-yl)ethoxy)ethoxy)ethan-1-amine (15 mg, 88% yield) as a light yellow solid. MS (ESI) m/z: 575.3 [M+H]$^+$.

Step 4. Synthesis of 2-(2,6-dioxopiperidin-3-yl)-5-((2-(2-(2-(4-(6-(6-((S)-2-(3-fluorophenyl)pyrrolidin-1-yl)imidazo[1,2-b]pyridazin-3-yl)pyridin-2-yl)piperazin-1-yl)ethoxy)ethoxy)ethyl)amino)isoindoline-1,3-dione (TR-177)

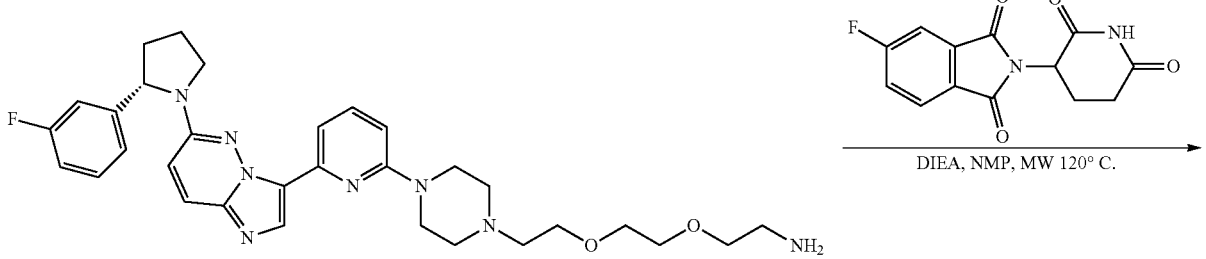

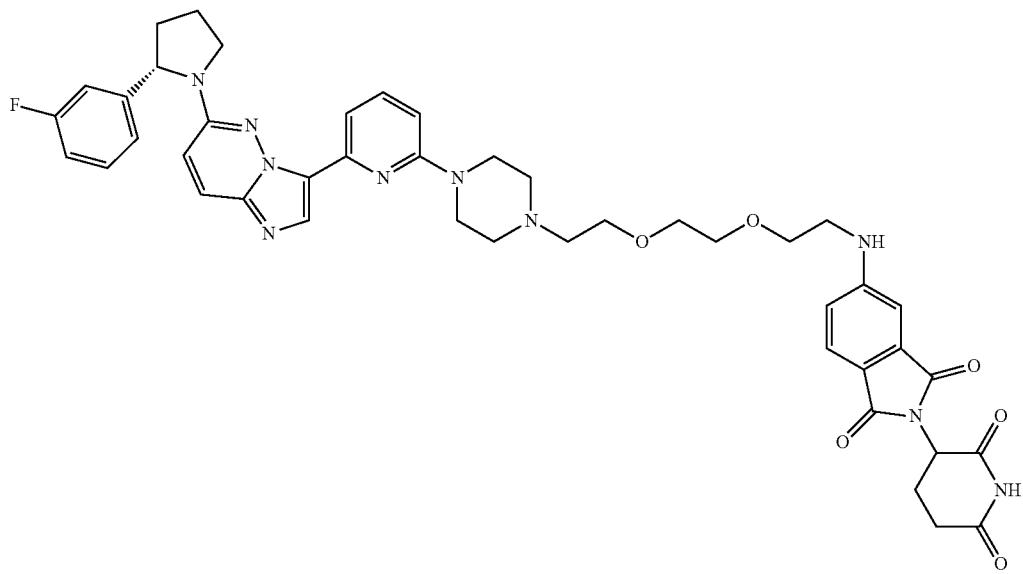 [SMILES: O=C1CCC(N2C(=O)c3ccc(NCCOCCOCCN4CCN(c5cccc(-c6cnc7ccc(N8CCC[C@H]8c8cccc(F)c8)nn67)n5)CC4)cc3C2=O)C(=O)N1]

To a solution of tert-butyl (S)-2-(2-(2-(4-(6-(6-(2-(3-fluorophenyl)pyrrolidin-1-yl)imidazo[1,2-b]pyridazin-3-yl)pyridin-2-yl)piperazin-1-yl)ethoxy)ethoxy)ethan-1-amine (20 mg, 34.9 umol) in NMP (1 mL) were added 2-(2,6-dioxopiperidin-3-yl)-5-fluoroisoindoline-1,3-dione (28.9 mg, 104.7 umol) and DIPEA (13 mg, 104.7 umol). Microwave reaction was stirred at 120° C. for 50 min. The resulting residue was purified by reverse-phase chromatography to yield the desired product 2-(2,6-dioxopiperidin-3-yl)-5-((2-(2-(2-(4-(6-(6-((S)-2-(3-fluorophenyl)pyrrolidin-1-yl)imidazo[1,2-b]pyridazin-3-yl)pyridin-2-yl)piperazin-1-yl)ethoxy)ethoxy)ethyl)amino)isoindoline-1,3-dione (10 mg, 34.6% yield) as a light yellow solid. MS (ESI) m/z: 831.4 [M+H]$^+$.

Example 228: Synthesis of 2-(2,6-Dioxopiperidin-3-yl)-5-(((1-(6-(6-((R)-2-(3-fluorophenyl)pyrrolidin-1-yl)imidazo[1,2-b]pyridazin-3-yl)pyridin-2-yl)piperidin-4-yl)methyl)amino)isoindoline-1,3-dione (TR-178)

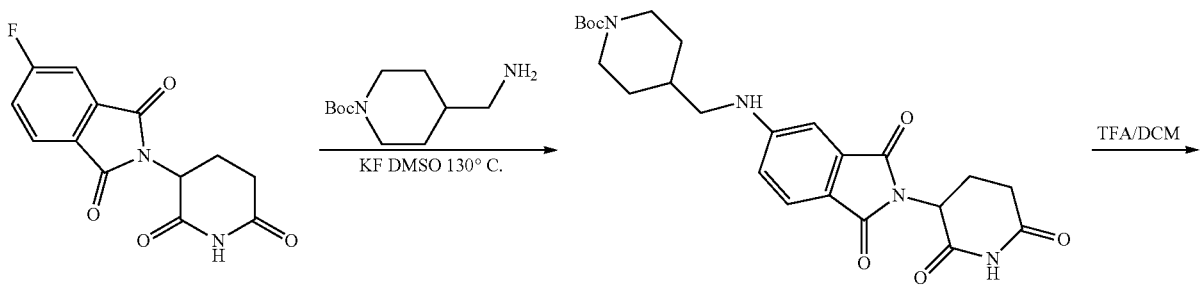

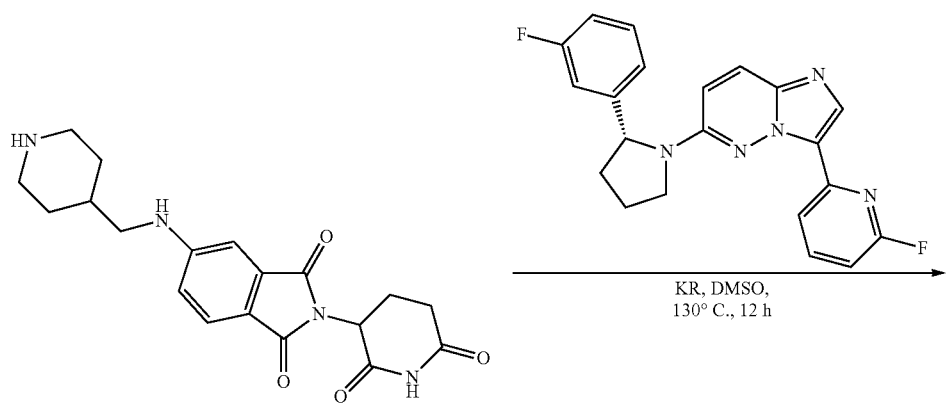

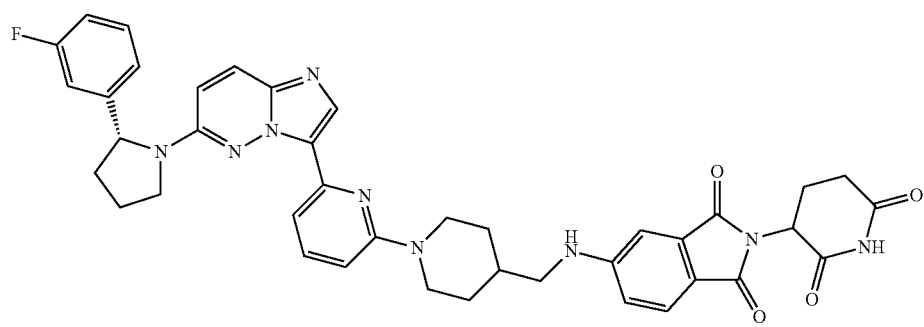

TR-178 was synthesized following the standard procedure for preparing TR-175. MS (ESI) m/z: 728.3 [M+H]$^+$.

Example 229: Synthesis of 2-(2,6-Dioxopiperidin-3-yl)-5-(((1-(6-(6-((R)-2-(3-fluorophenyl)pyrrolidin-1-yl)imidazo[1,2-b]pyridazin-3-yl)pyridin-2-yl)azetidin-3-yl)methyl)amino)isoindoline-1,3-dione (TR-179)
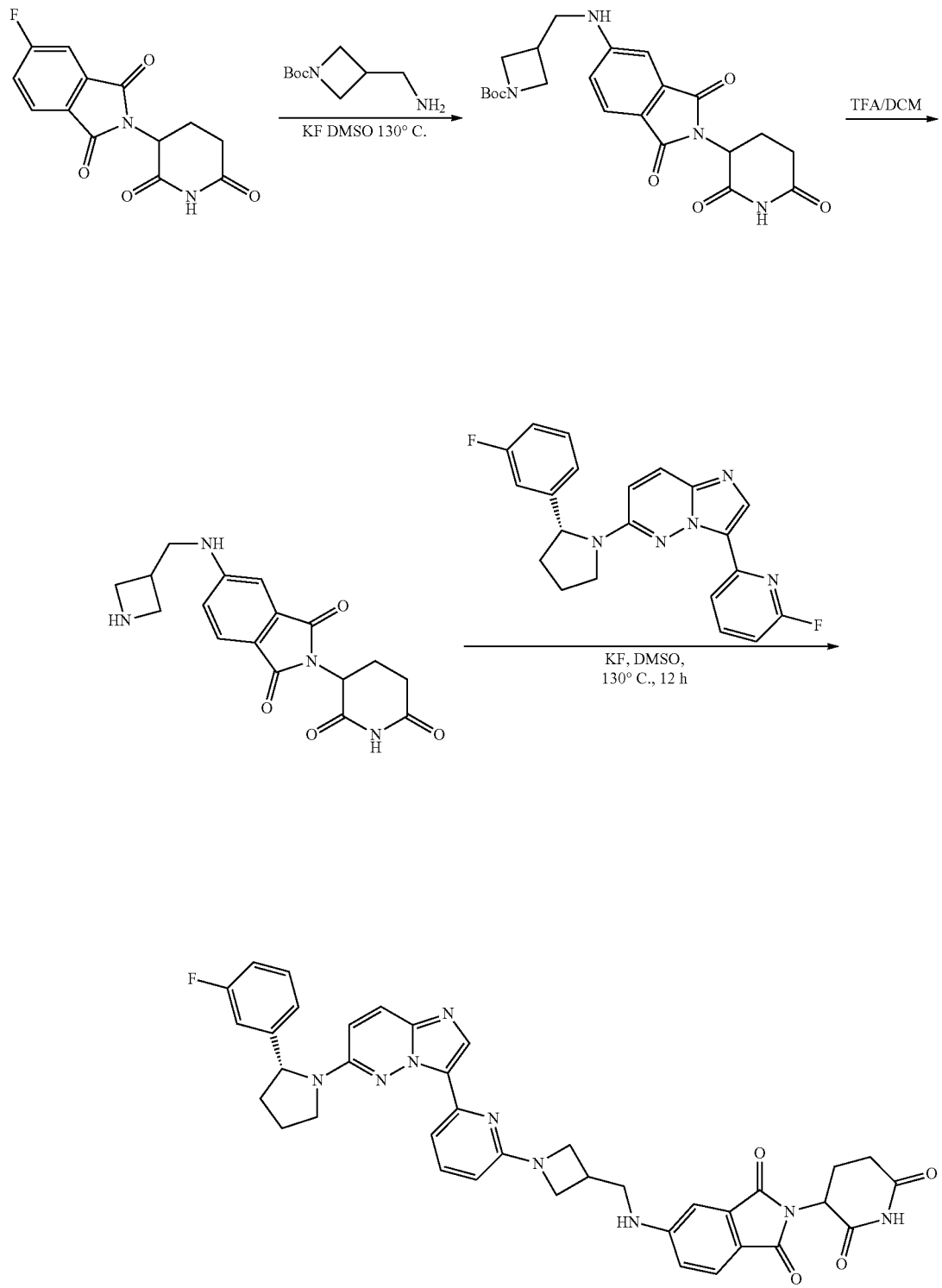
TR-179 was synthesized following the standard procedure for preparing TR-175. MS (ESI) m/z: 700.3 [M+H]+.

Example 230: Synthesis of 2-(2,6-Dioxopiperidin-3-yl)-5-((2-(1-(6-(6-((R)-2-(3-fluorophenyl)pyrrolidin-1-yl)imidazo[1,2-b]pyridazin-3-yl)pyridin-2-yl)piperidin-4-yl)ethyl)amino)isoindoline-1,3-dione (TR-180)
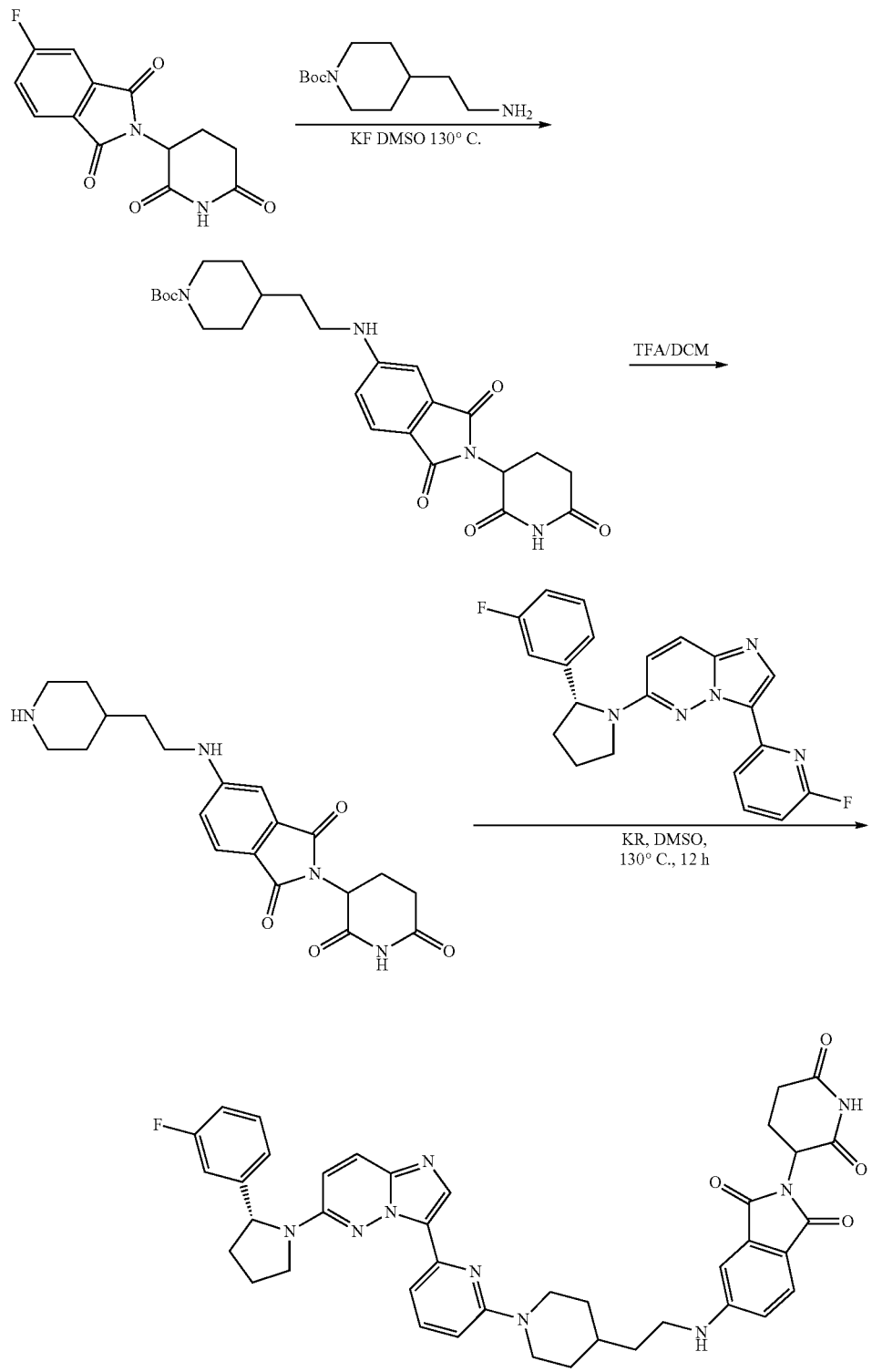
TR-180 was synthesized following the standard procedure for preparing TR-175. MS (ESI) m/z: 742.3 [M+H]+.

Example 231: 2-(2,6-Dioxopiperidin-3-yl)-5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)isoindoline-1,3-dione (TR-181)
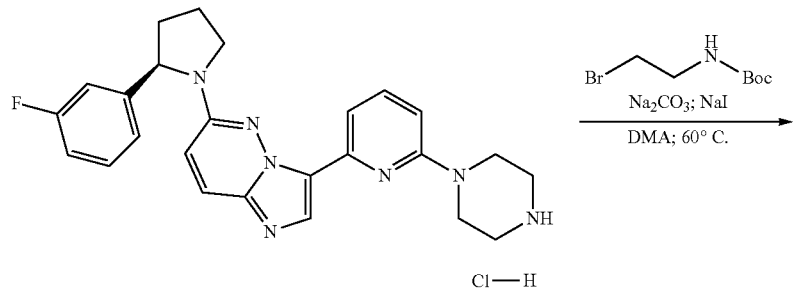
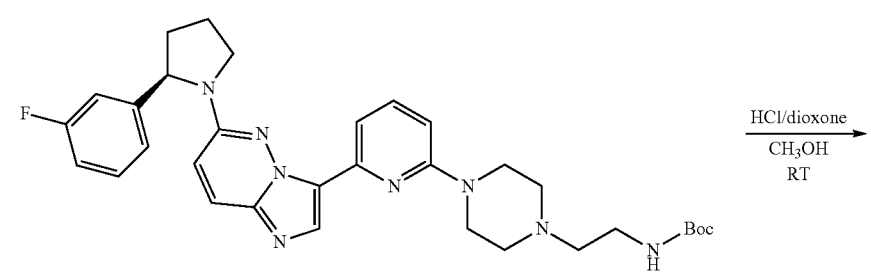
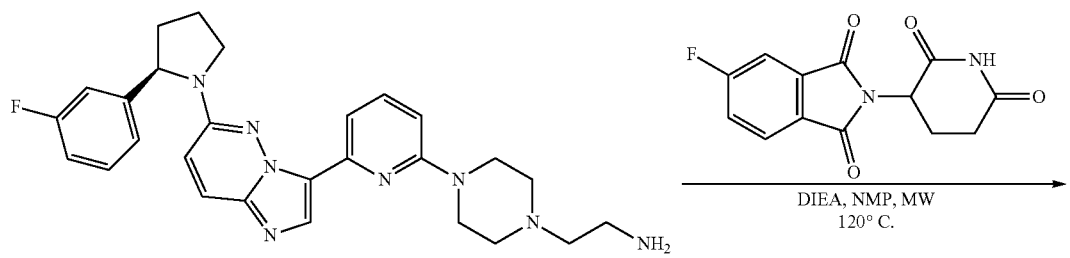
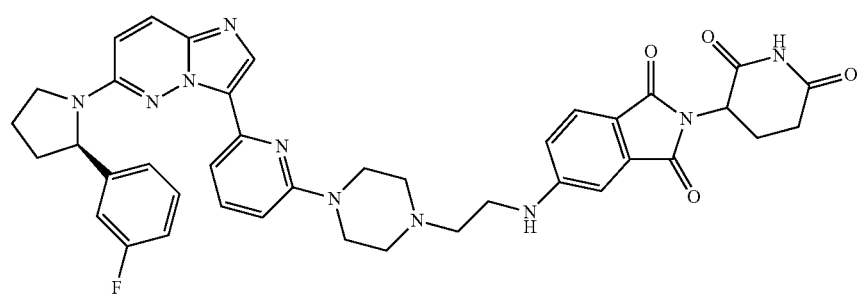

Step 1. Synthesis of tert-butyl (R)-(2-(4-(6-(6-(2-(3-fluorophenyl)pyrrolidin-1-yl)imidazo[1,2-b]pyridazin-3-yl)pyridin-2-yl)piperazin-1-yl)ethyl)carbamate

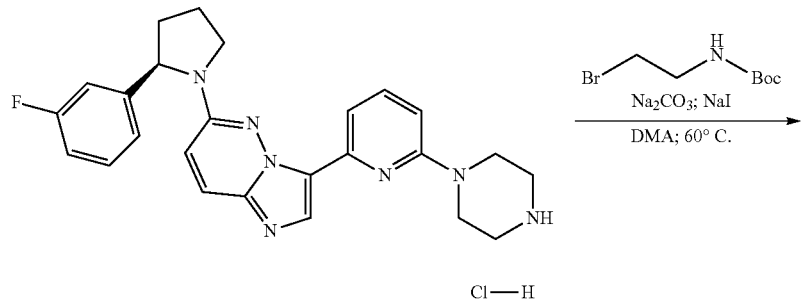

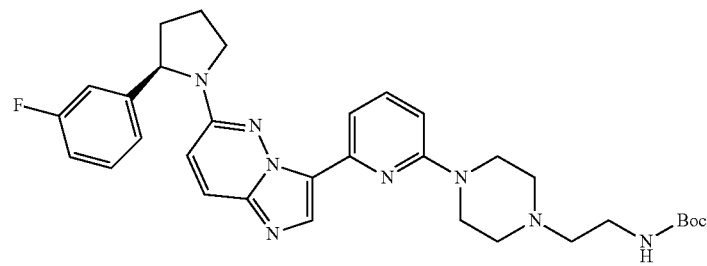

To a solution of (R)-6-(2-(3-fluorophenyl)pyrrolidin-1-yl)-3-(6-(piperazin-1-yl)pyridin-2-yl)imidazo[1,2-b]pyridazine hydrochloride (200 mg, 0.42 mmol) in DMAC (5 mL) were added Na₂CO₃ (133.56 mg, 1.26 mmol), NaI (126 mg, 0.84 mmol) and tert-butyl (2-bromoethyl)carbamate (186 mg, 0.83 mmol), the resulting mixture was stirred at 60° C. for 3 h. The reaction was cooled to room temperature and H₂O (20 mL) was added. The mixture was extracted with EtOAc (10 mL*3), the combined organic layers were concentrated and the residue was purified by reverse phase chromatography to desired product (225 mg, 91% yield) as a white solid. MS (ESI) m/z: 587.9 [M+H]⁺.

Step 2. Synthesis of (R)-2-(4-(6-(6-(2-(3-fluorophenyl)pyrrolidin-1-yl)imidazo[1,2-b]pyridazin-3-yl)pyridin-2-yl)piperazin-1-yl)ethan-1-amine

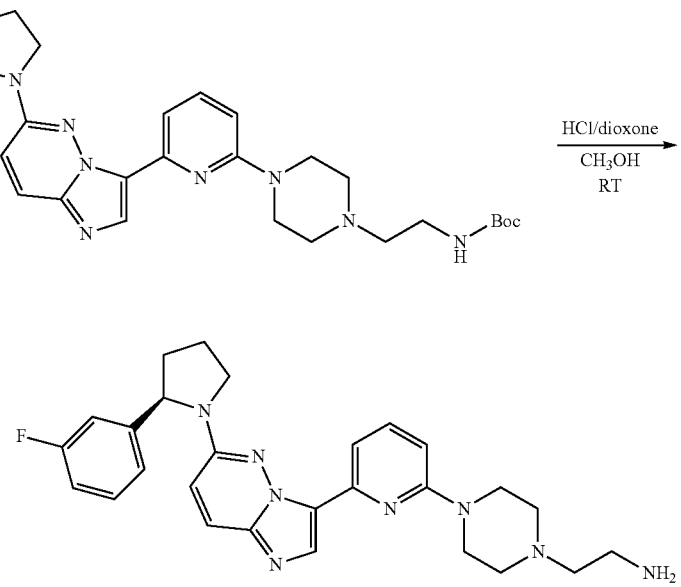

To a solution tert-butyl (R)-(2-(4-(6-(6-(2-(3-fluorophenyl)pyrrolidin-1-yl)imidazo[1,2-b]pyridazin-3-yl)pyridin-2-yl)piperazin-1-yl)ethyl)carbamate (225 mg, 0.38 mmol) in methanol (5 mL) was added HCl/dioxone (4 M, 4 mL) at room temperature, then it was stirred at room temperature for 12 h. The mixture was concentrated to get crude product (220 mg, 99% yield) as a white solid which was used directly in the next step. MS (ESI) m/z: 487.7 [M+H]$^+$.

Step 3. Synthesis of 2-(2,6-Dioxopiperidin-3-yl)-5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)isoindoline-1,3-dione (TR-181)

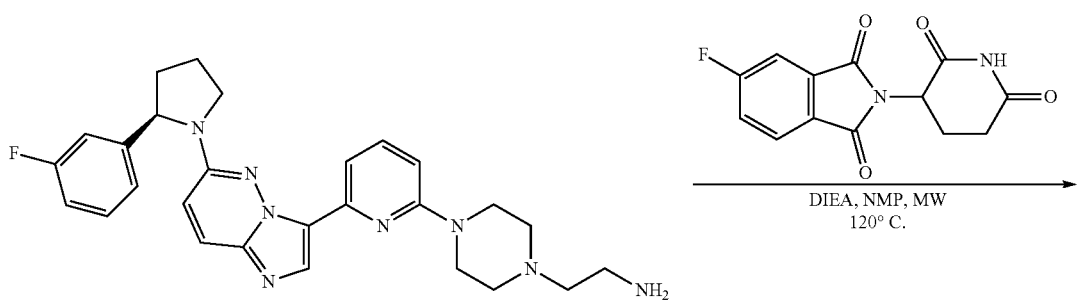

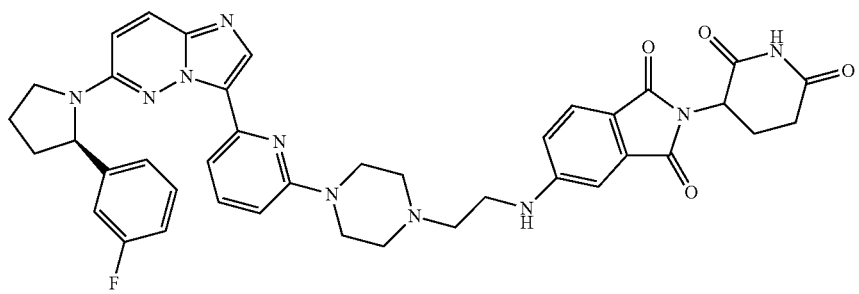

A mixture of (R)-2-(4-(6-(6-(2-(3-fluorophenyl)pyrrolidin-1-yl)imidazo[1,2-b]pyridazin-3-yl)pyridin-2-yl)piperazin-1-yl)ethan-1-amine (30 mg, 0.06 mmol), 2-(2,6-dioxopiperidin-3-yl)-5-fluoroisoindoline-1,3-dione (15.8 mg, 0.06 mmol), DIEA (0.037 mL, 0.23 mmol) and NMP (0.3 mL) was heated to 120° C. under microwave for 2 h. The reaction mixture was purified by reverse phase chromatography to give desired product (6.5 mg, 15% yield) as a white solid. MS (ESI) m/z: 743.8 [M+H]$^+$.

Example 232: 2-(2,6-Dioxopiperidin-3-yl)-5-(4-(4-(6-(6-((R)-2-(3-fluorophenyl)pyrrolidin-1-yl)imidazo[1,2-b]pyridazin-3-yl)pyridin-2-yl)piperazin-1-yl)piperidin-1-yl)isoindoline-1,3-dione (TR-182)

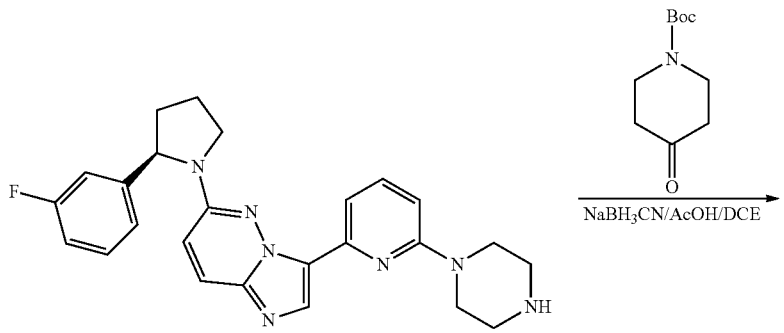

485

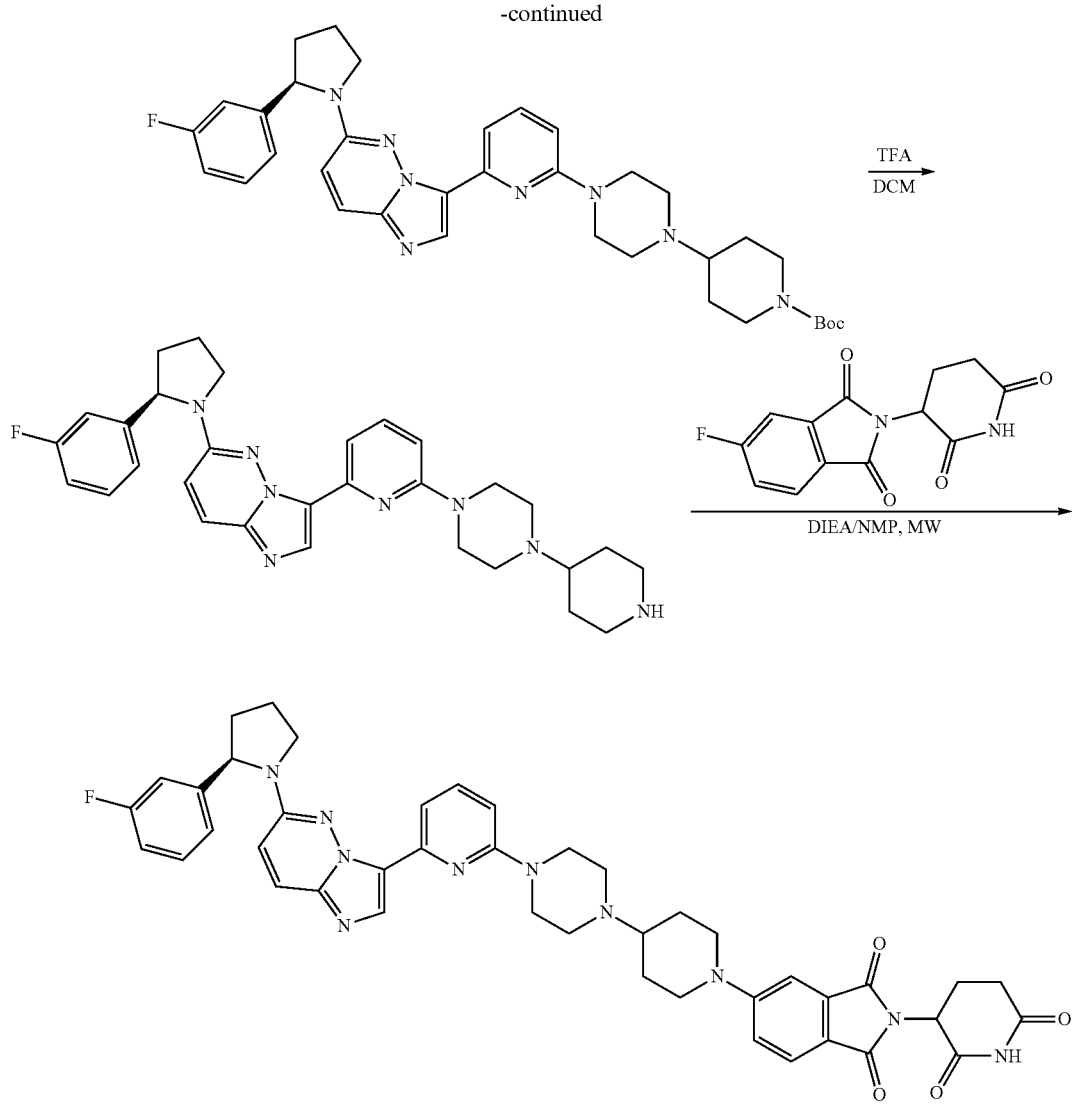

-continued

Step 1. Synthesis of tert-butyl (R)-4-(4-(6-(6-(2-(3-fluorophenyl)pyrrolidin-1-yl)imidazo[1,2-b]pyridazin-3-yl)pyridin-2-yl)piperazin-1-yl)piperidine-1-carboxylate

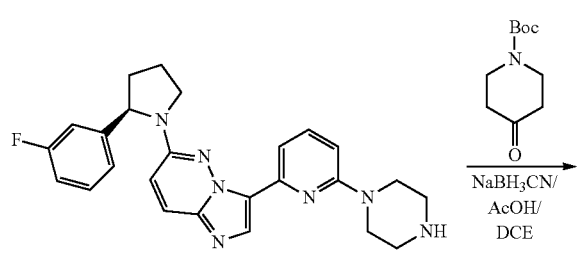

486

-continued

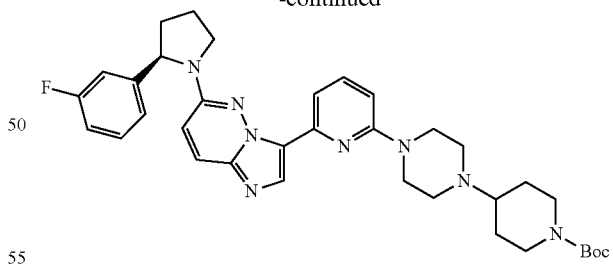

The mixture of (R)-6-(2-(3-fluorophenyl)pyrrolidin-1-yl)-3-(6-(piperazin-1-yl)pyridin-2-yl)imidazo[1,2-b]pyridazine (0.050 g, 112.73 umol), tert-butyl 4-oxopiperidine-1-carboxylate (44.92 mg, 225.47 umol) and AcOH (one drop) in DCE (3 mL) was stirred for 1 h. Then it was added NaBH$_3$CN (22.62 mg, 338.20 umol) and stirred for another 16 h. The solvent was removed under vacuum to give the crude product, which was purified by Prep-TLC (MeOH/DCM=5/100) to give the desired product (8 mg, 11% yield) as a yellow oil. MS (ESI) m/z: 627.8 [M+H]$^+$.

Step 2. Synthesis of (R)-6-(2-(3-fluorophenyl)pyr-rolidin-1-yl)-3-(6-(4-(piperidin-4-yl)piperazin-1-yl)pyridin-2-yl)imidazo[1,2-b]pyridazine

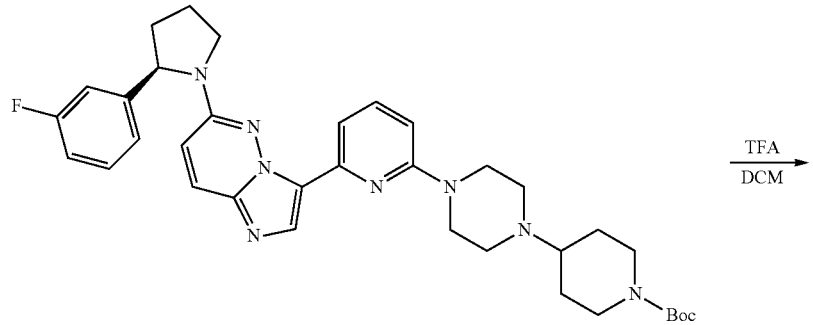

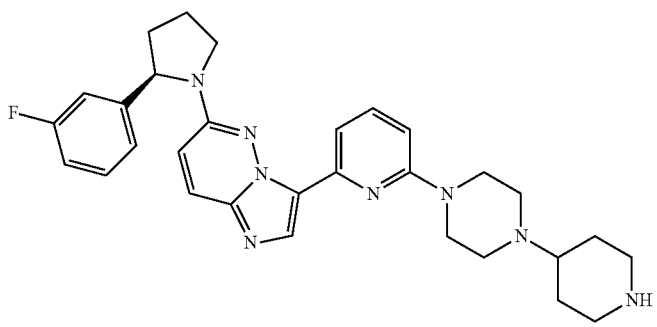

To a solution of tert-butyl (R)-4-(4-(6-(6-(2-(3-fluorophenyl)pyrrolidin-1-yl)imidazo[1,2-b]pyridazin-3-yl)pyridin-2-yl)piperazin-1-yl)piperidine-1-carboxylate (8 mg, 12.76 umol) in DCM (5 mL) was added TFA (14.55 mg, 127.64 umol), then the reaction was stirred for 2 h. LCMS showed the reaction was completed. The solvent was removed under vacuum to give the crude product (6.72 mg, 99% yield) which was used for next step without further purification. MS (ESI) m/z: 527.6 [M+H]⁺.

Step 3. Synthesis of 2-(2,6-Dioxopiperidin-3-yl)-5-(4-(4-)-(6-((R)-2-(3-fluorophenyl)pyrrolidin-1-yl)imidazo[1,2-b]pyridazin-3-yl)pyridin-2-yl)piperazin-1-yl)piperidin-1-yl)isoindoline-1,3-dione (TR-182)

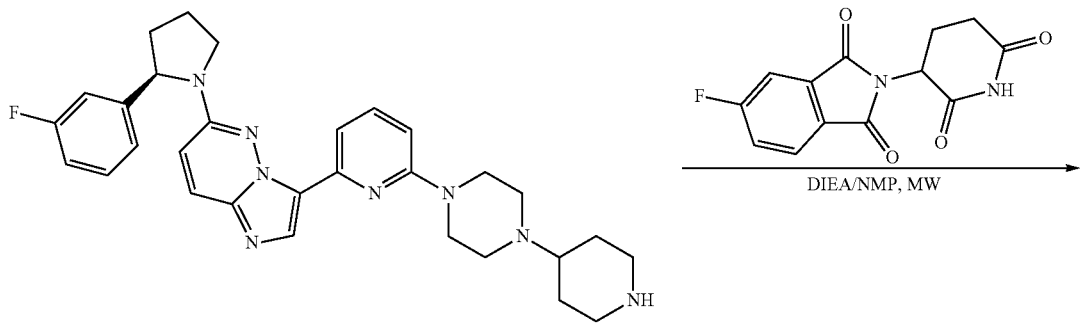

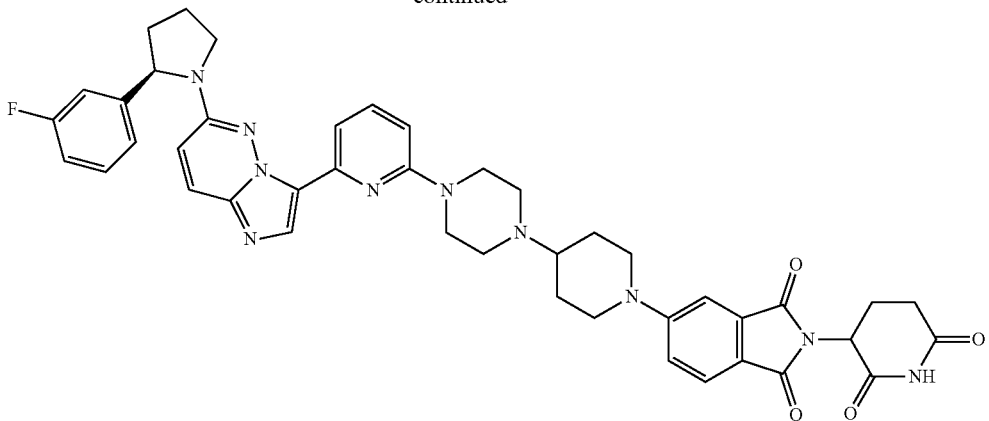

The mixture of (R)-6-(2-(3-fluorophenyl)pyrrolidin-1-yl)-3-(6-(4-(piperidin-4-yl)piperazin-1-yl)pyridin-2-yl)imidazo[1,2-b]pyridazine (6.72 mg, 11.39 umol), 2-(2,6-dioxo-3-piperidyl)-5-fluoro-isoindoline-1,3-dione (3.15 mg, 11.39 umol) and DIEA (2.94 mg, 22.79 umol) in NMP (0.5 mL) were heated at 120° C. for 0.5 h under microwave. The mixture was purified by Prep-TLC (DCM/MeOH=100/5) to give the desired product (1.8 mg, 20% yield) as a white solid. MS (ESI) m/z: 783.8 [M+H]+.

Example 233: 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)isoindoline-1,3-dione (TR-183)

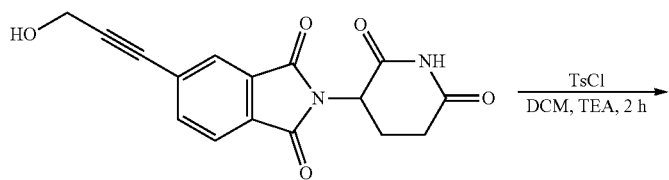

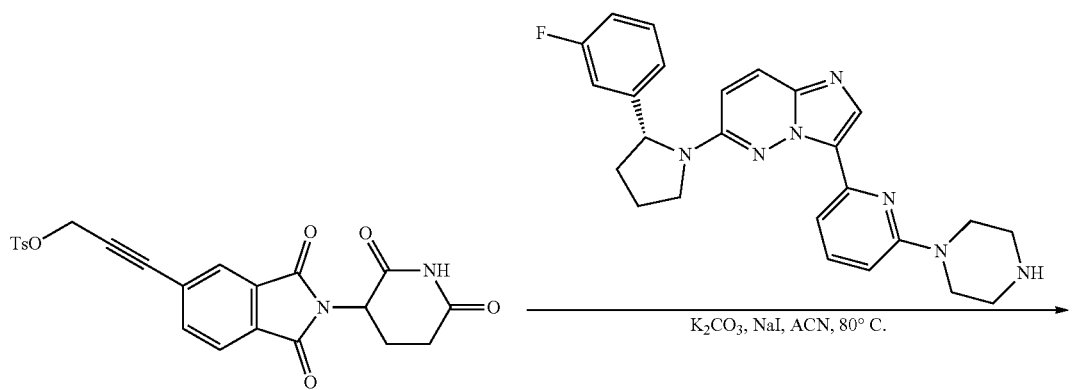

491

492

-continued

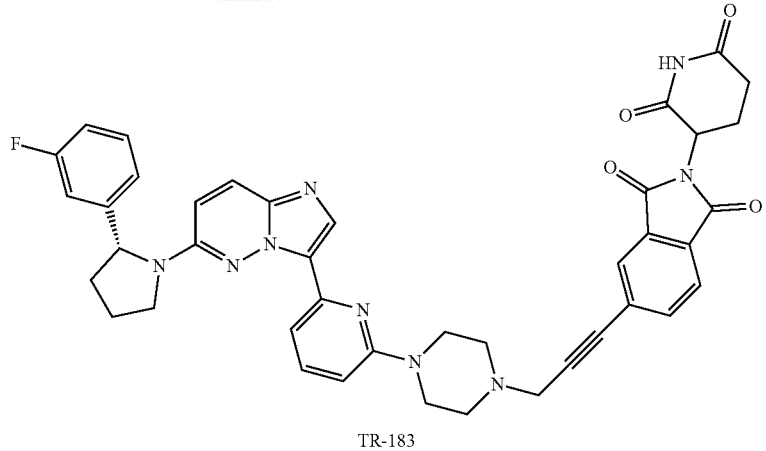

TR-183

Step 1. Synthesis of 3-(2-(2,6-dioxopiperidin-3-yl)-1,3-dioxoisoindolin-5-yl) prop-2-yn-1-yl 4-methylbenzenesulfonate

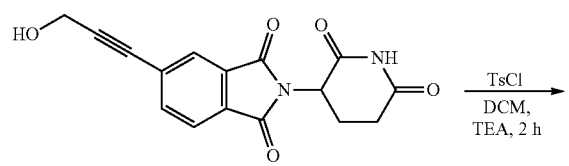

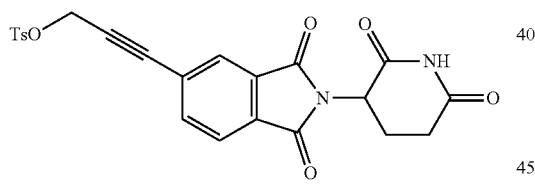

To a solution 2-(2,6-dioxopiperidin-3-yl)-5-(3-hydroxyprop-1-yn-1-yl)isoindoline-1,3-dione (50 mg, 0.16 mmol) and TEA (32 mg, 0.32 mmol) in DCM (3 mL) was added 4-methylbenzenesulfonyl chloride (36 mg, 0.19 mmol) at room temperature, then it was stirred at room temperature for 4 h. The mixture was concentrated and purified by reverse phase chromatography to give the desired product (43 mg, 58% yield) as a light yellow solid. MS (ESI) m/z: 467.1 [M+H]$^+$.

Step 2. Synthesis of 2-(2,6-Dioxopiperidin-3-yl)-5-(3-(4-(6-(6-((R)-2-(3-fluorophenyl) pyrrolidin-1-yl) imidazo[1,2-b]pyridazin-3-yl)pyridin-2-yl)piperazin-1-yl)prop-1-yn-1-yl)isoindoline-1,3-dione

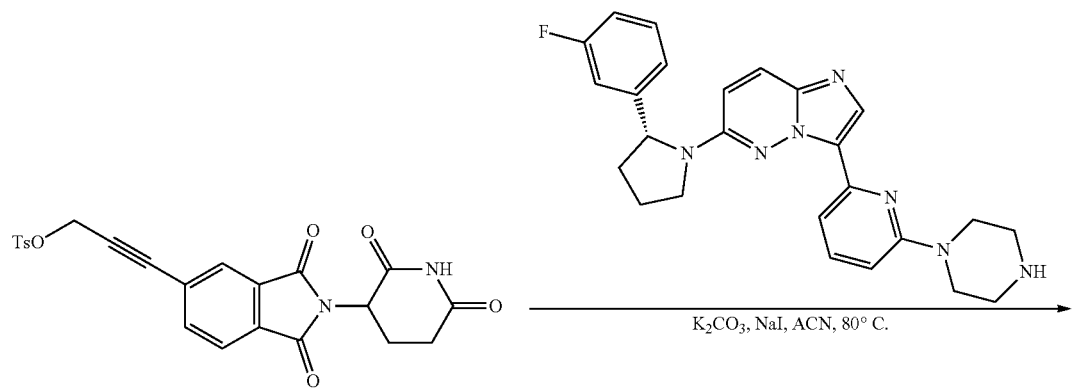

-continued

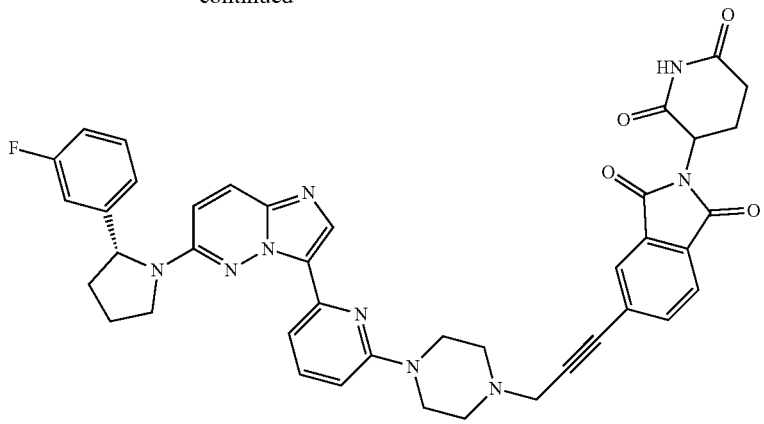

A mixture of 3-(2-(2,6-dioxopiperidin-3-yl)-1,3-dioxoisoindolin-5-yl)prop-2-yn-1-yl 4-methylbenzenesulfonate (40 mg, 0.08 mmol), (R)-6-(2-(3-fluorophenyl)pyrrolidin-1-yl)-3-(6-(piperazin-1-yl)pyridin-2-yl)imidazo[1,2-b]pyridazine (37 mg, 0.08 mmol), K$_2$CO$_3$ (22 mg, 0.16 mmol) and NaI (1.5 mg, 0.01 mmol) in CH$_3$CN (3 mL) were stirred at 80° C. for 5 h. LCMS showed the reaction was completed. The mixture was concentrated and purified by reverse phase chromatography to give the desired product (18 mg, 28% yield) as a light yellow solid. MS (ESI) m/z 738.3 [M+H]$^+$.

Example 234: 2-(2,6-dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)azetidin-1-yl)isoindoline-1,3-dione (TR-184)

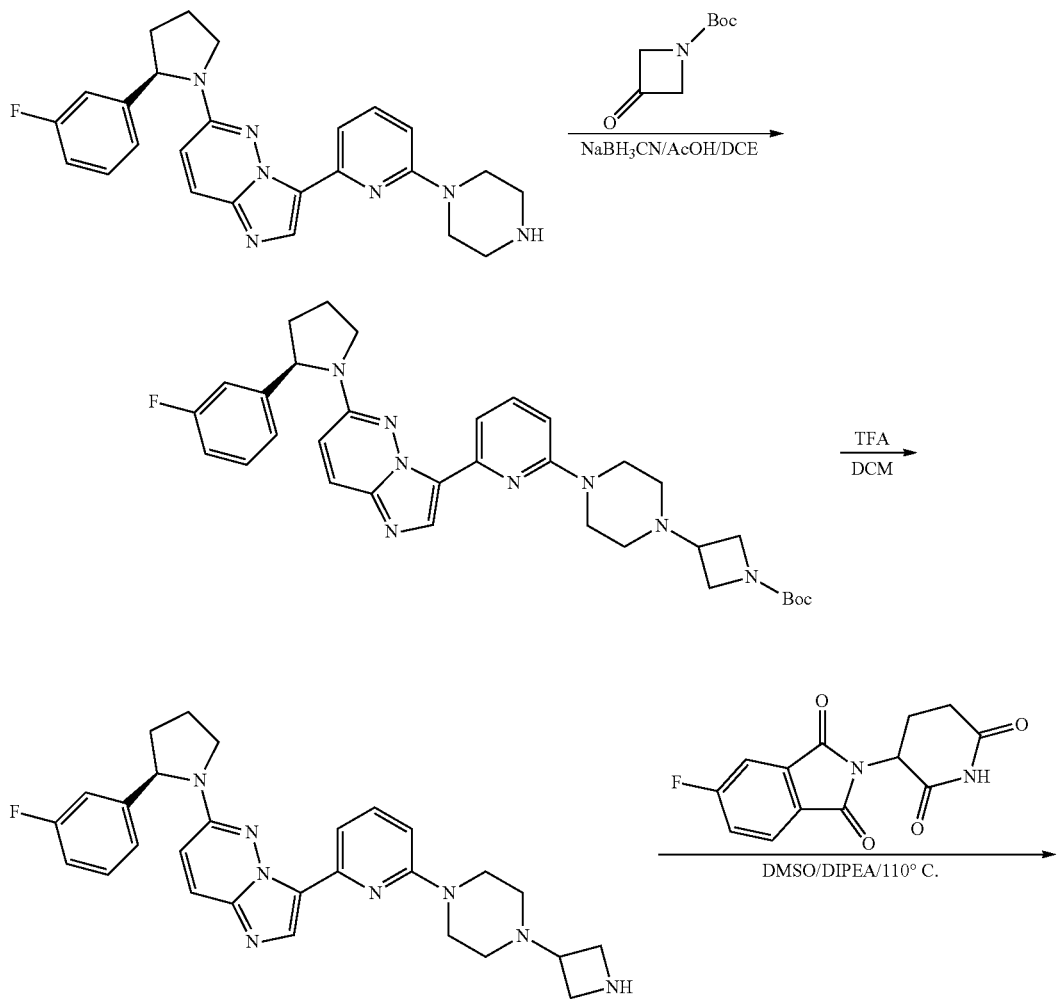

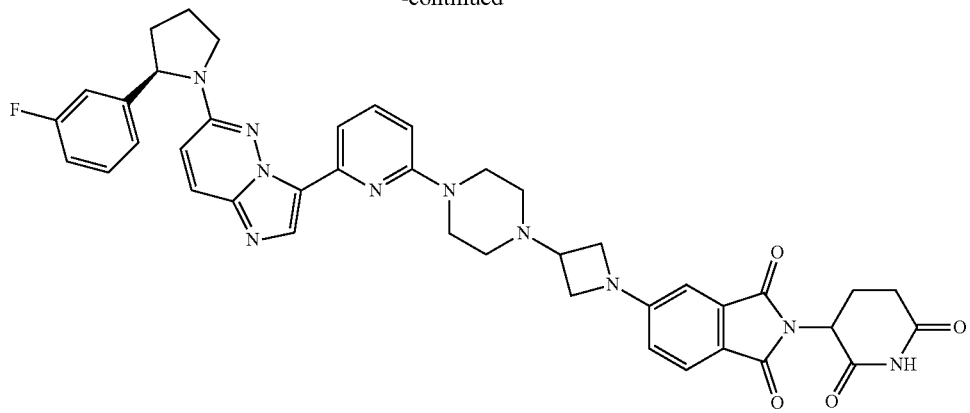

Step 1. Synthesis of tert-butyl (R)-3-(4-(6-(6-(2-(3-fluorophenyl)pyrrolidin-1-yl)imidazo[1,2-b]pyridazin-3-yl)pyridin-2-yl)piperazin-1-yl)azetidine-1-carboxylate

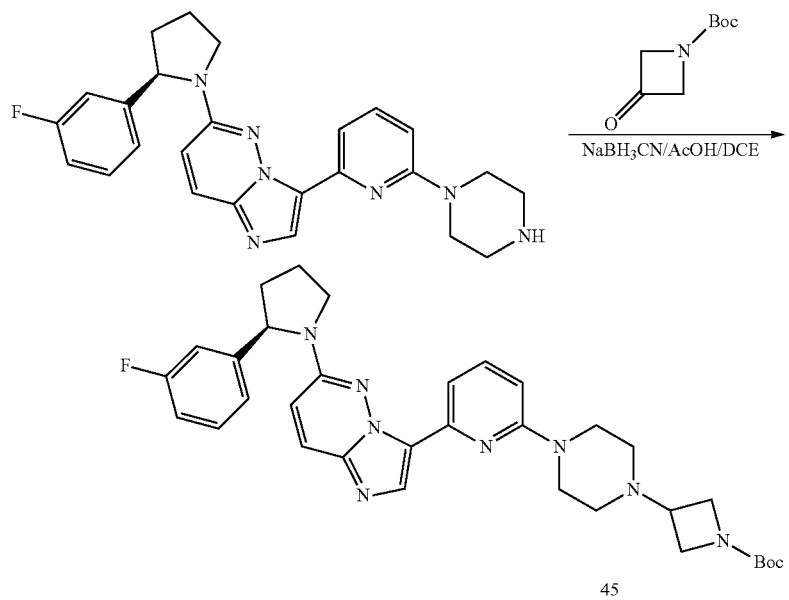

To a solution of (R)-6-(2-(3-fluorophenyl)pyrrolidin-1-yl)-3-(6-(piperazin-1-yl)pyridin-2-yl)imidazo[1,2-b]pyridazine (50 mg, 112.73 umol) and tert-butyl 3-oxoazetidine-1-carboxylate (38.60 mg, 225.47 umol) in MeOH (1 mL), AcOH (1 mL) and DCE (2 mL) was added NaBH$_3$CN (14.20 mg, 225.47 umol) at room temperature. The resulting reaction mixture was stirred at room temperature for 48 h, concentrated and purified by silica gel chromatography (DCM/MeOH=30/1) to give desired product (40 mg, 74% yield) as a yellow oil. MS (ESI) m/z: 599.6 [M+H]$^+$.

Step 2. Synthesis of (R)-3-(6-(4-(azetidin-3-yl)piperazin-1-yl)pyridin-2-yl)-6-(2-(3-fluorophenyl)pyrrolidin-1-yl)imidazo[1,2-b]pyridazine

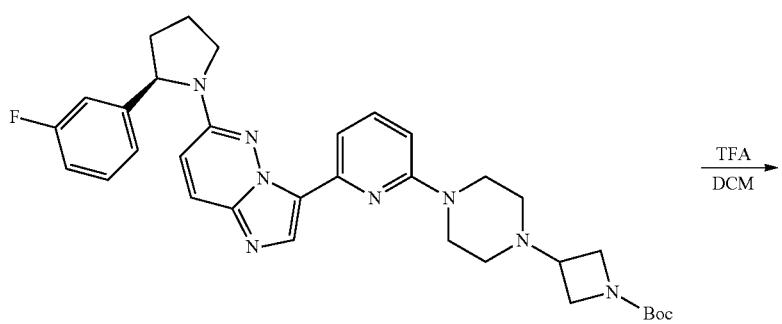

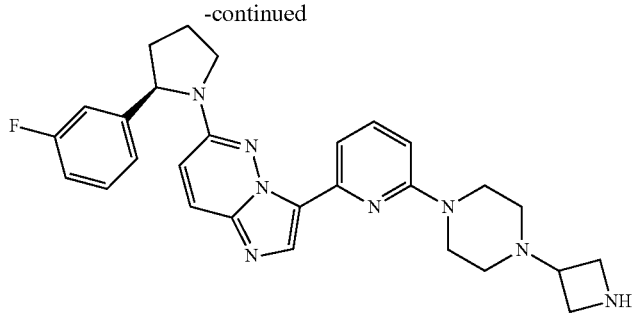

To a solution of tert-butyl (R)-3-(4-(6-(6-(2-(3-fluorophenyl)pyrrolidin-1-yl)imidazo[1,2-b]pyridazin-3-yl)pyridin-2-yl)piperazin-1-yl)azetidine-1-carboxylate (60 mg, 100.22 umol) in DCM (2 mL) was added TFA (228.53 mg, 2.00 mmol) at room temperature. The reaction mixture was stirred at room temperature for 2 h, and then it was concentrated. The residue was dissolved in DCM (10 mL), washed with $Na_2CO_3$ (aq), dried over $Na_2SO_4$, concentrated to give desired product (50 mg, 99% yield) as a yellow resin. MS (ESI) m/z: 499.5 [M+H]⁺.

Step 3. Synthesis of 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)azetidin-1-yl)isoindoline-1,3-dione (TR-184)

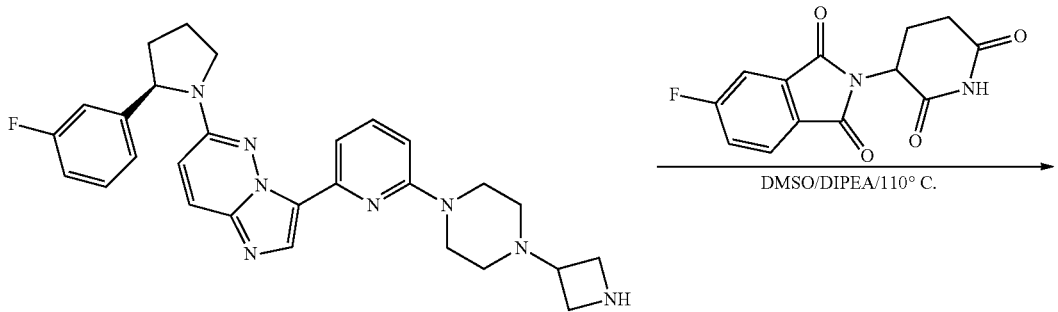

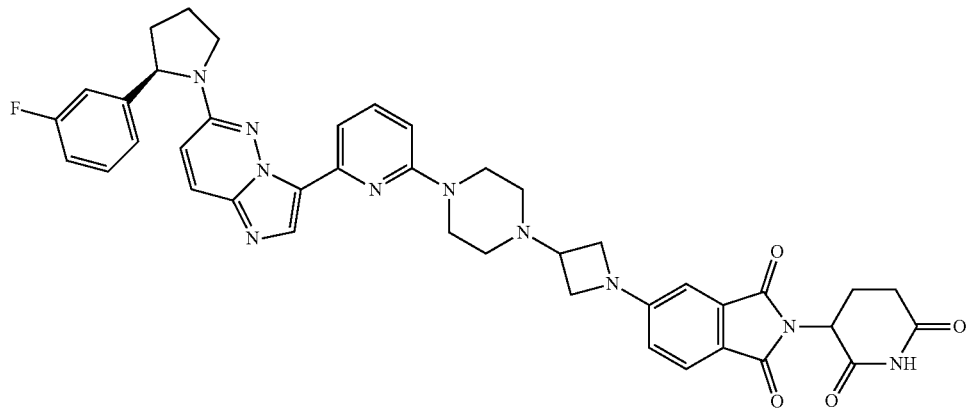

To a solution of (R)-3-(6-(4-(azetidin-3-yl)piperazin-1-yl)pyridin-2-yl)-6-(2-(3-fluorophenyl)pyrrolidin-1-yl)imidazo[1,2-b]pyridazine (50 mg, 100.28 umol) and 2-(2,6-dioxopiperidin-3-yl)-5-fluoroisoindoline-1,3-dione (27.70 mg, 100.28 umol) in DMSO (2 mL) was added DIEA (38.81 mg, 300.84 umol) at room temperature. The reaction mixture was warmed to 110° C. and stirred for 5 h. After cooling to room temperature, the reaction mixture was purified by prep-HPLC to give desired product (60 mg, 79% yield) as a yellow solid. MS (ESI) m/z: 755.7 [M+H]⁺.

Example 235: 3-(6-(3-(4-(6-(6-((R)-2-(3-Fluorophe-nyl)pyrrolidin-1-yl)imidazo[1,2-b]pyridazin-3-yl)pyridin-2-yl)piperazin-1-yl)propyl)-1-oxoisoindolin-2-yl)piperidine-2,6-dione (TR-185)
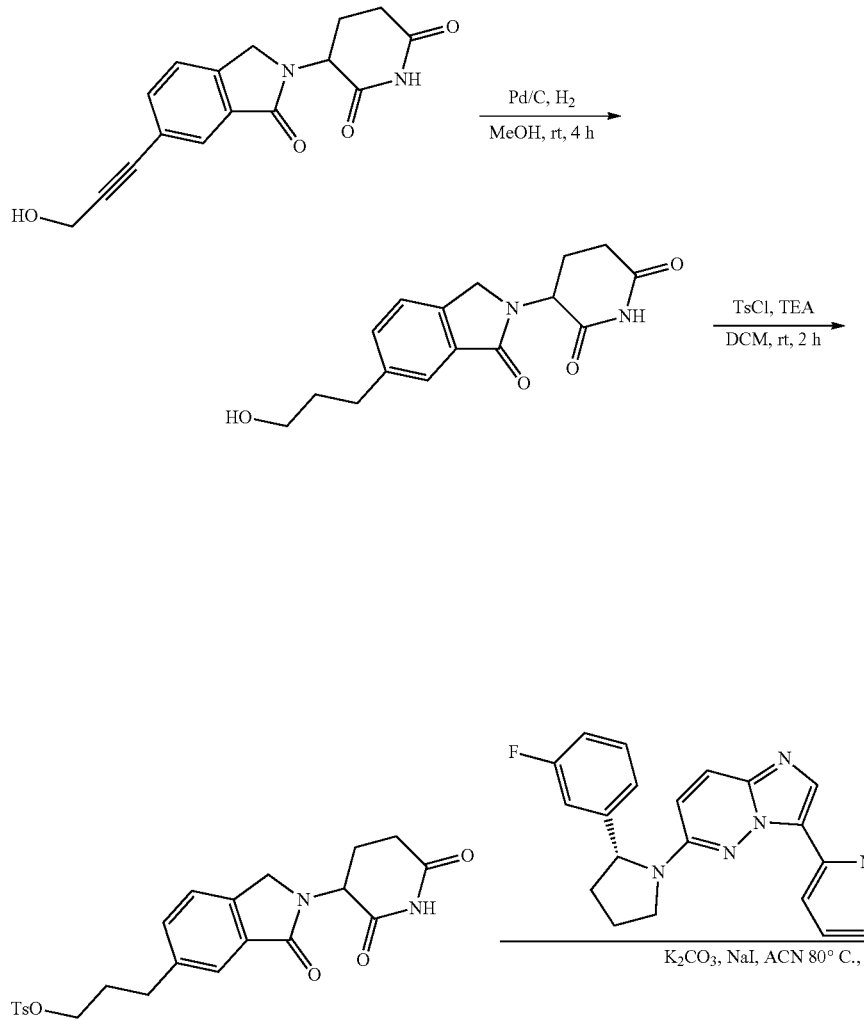
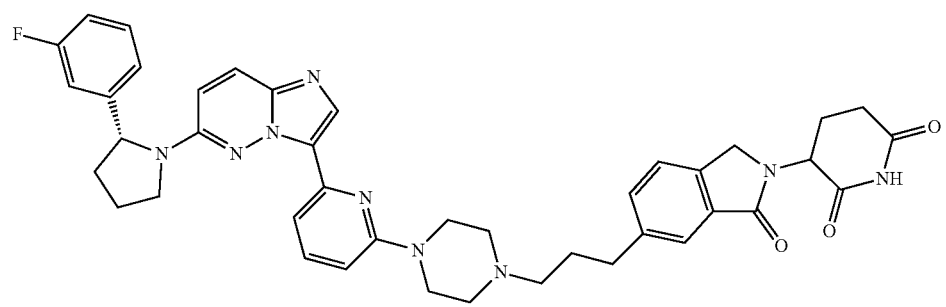

501

Step 1. Synthesis of 3-(6-(3-hydroxypropyl)-1-oxoisoindolin-2-yl)piperidine-2,6-dione

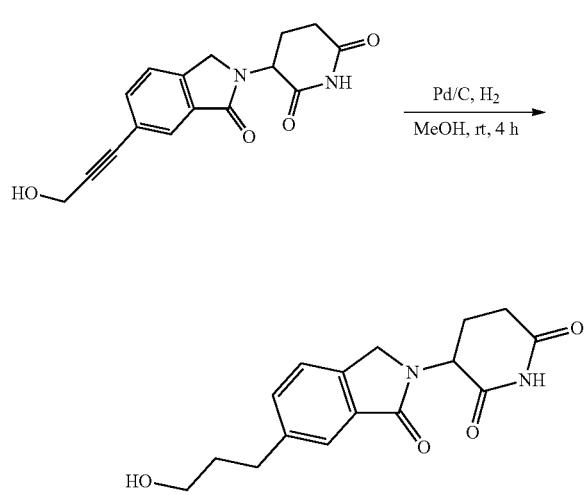

A mixture of 3-(6-(3-hydroxyprop-1-yn-1-yl)-1-oxoisoindolin-2-yl)piperidine-2,6-dione (100 mg, 0.34 mmol) and Pd/C (20 mg) in methanol (5 mL) was stirred under H₂ (1 atm, balloon) at room temperature for 3 h. The reaction mixture was purified by reverse phase chromatography to give the desired product (86 mg, 86% yield) as a light yellow solid. MS (ESI) m/z: 303.1 [M+H]⁺.

502

Step 2. Synthesis of 3-(2-(2,6-dioxopiperidin-3-yl)-3-oxoisoindolin-5-yl)propyl 4-methylbenzenesulfonate

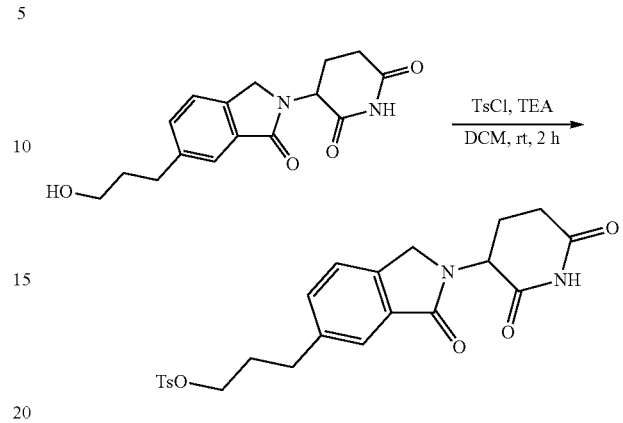

To a solution 3-(6-(3-hydroxypropyl)-1-oxoisoindolin-2-yl)piperidine-2,6-dione (80 mg, 0.26 mmol) and TEA (52 mg, 0.52 mmol) in DCM (5 mL) was added 4-methylbenzenesulfonyl chloride (59 mg, 0.31 mmol) at room temperature, then it was stirred at room temperature for 2 h. The mixture was concentrated and purified by reverse phase chromatography to give the desired product (61 mg, 51% yield) as a light yellow solid. MS (ESI) m/z: 457.1 [M+H]⁺.

Step 3. Synthesis of 3-(6-(3-(4-(6-(6-((R)-2-(3-fluorophenyl)pyrrolidin-1-yl) imidazo[1,2-b]pyridazin-3-yl)pyridin-2-yl)piperazin-1-yl)propyl)-1-oxoisoindolin-2-yl)piperidine-2,6-dione

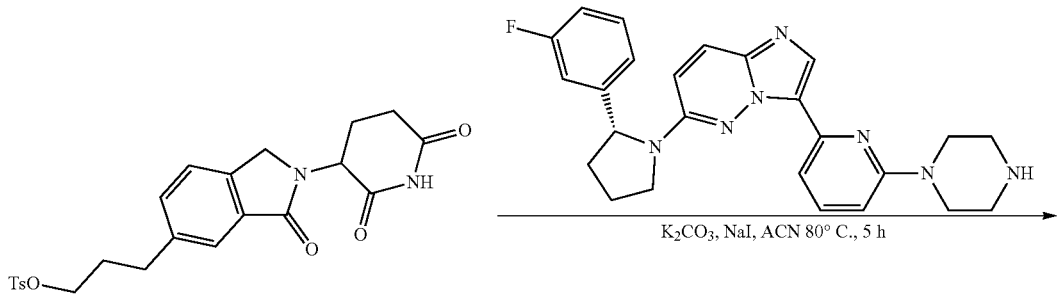

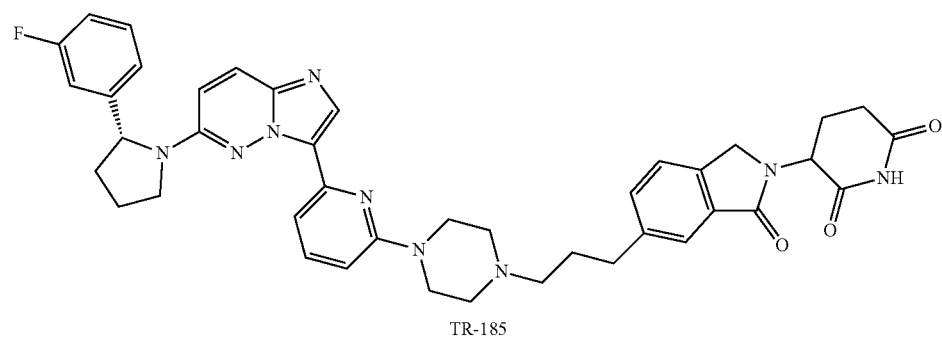

TR-185

A mixture of 3-(2-(2,6-dioxopiperidin-3-yl)-3-oxoisoindolin-5-yl)propyl 4-methylbenzenesulfonate (40 mg, 0.08 mmol), (R)-6-(2-(3-fluorophenyl)pyrrolidin-1-yl)-3-(6-(piperazin-1-yl)pyridin-2-yl)imidazo[1,2-b]pyridazine (37 mg, 0.08 mmol), K₂CO₃ (22 mg, 0.16 mmol) and NaI (1.5 mg, 0.01 mmol) in CH₃CN (3 mL) were stirred at 80° C. for 5 h. LCMS showed the reaction was completed. The mixture was concentrated and purified by reverse phase chromatography to give the desired product (23 mg, 36% yield) as a light yellow solid. MS (ESI) m/z: 728.3 [M+H]⁺.

Example 236: 3-(5-(3-(4-(6-(6-((R)-2-(3-Fluorophenyl)pyrrolidin-1-yl)imidazo[1,2-b]pyridazin-3-yl)pyridin-2-yl)piperazin-1-yl)propyl)-1-oxoisoindolin-2-yl)piperidine-2,6-dione (TR-186)

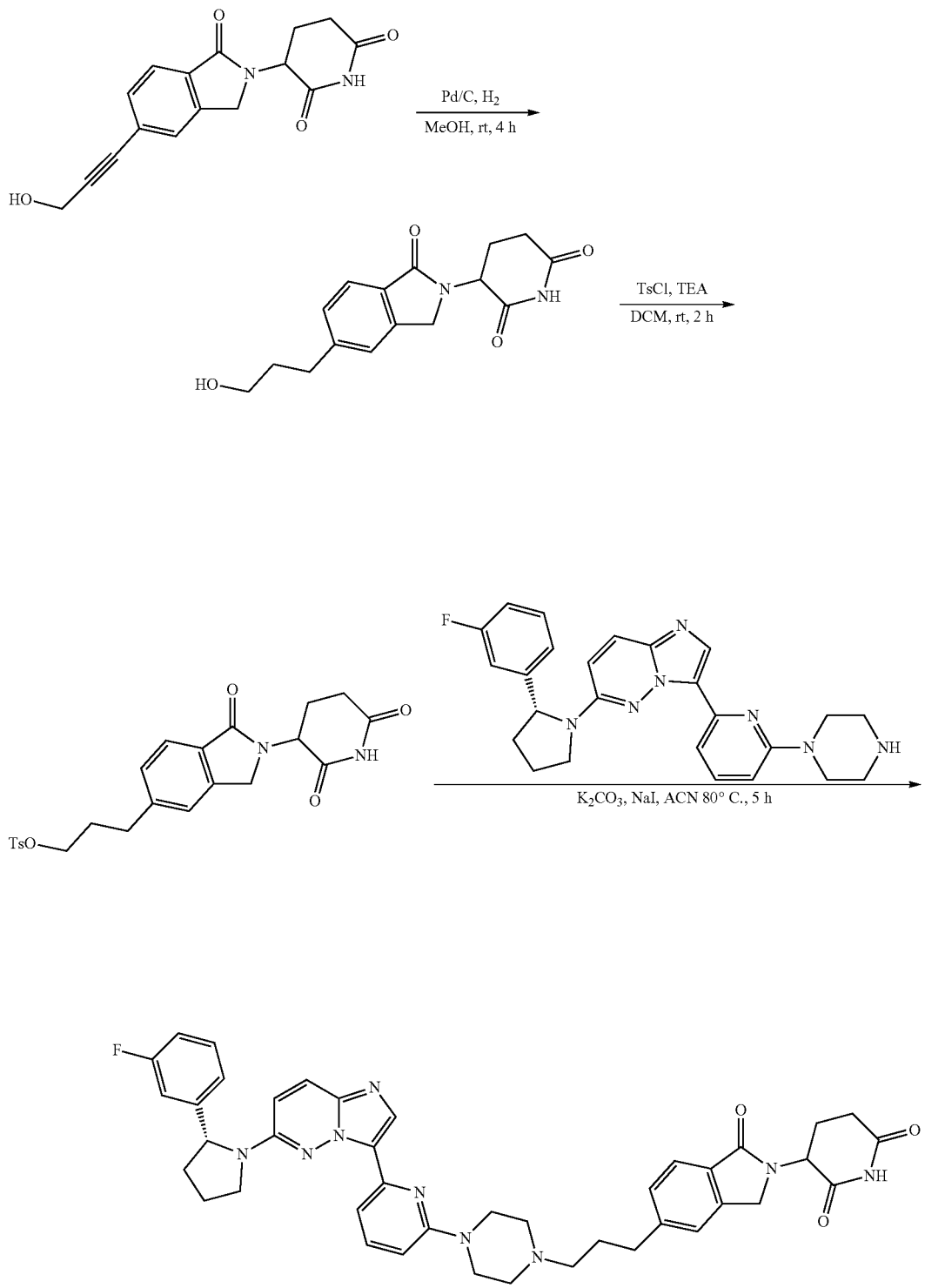

Step 1. Synthesis of 3-(5-(3-hydroxypropyl)-1-oxoisoindolin-2-yl)piperidine-2,6-dione

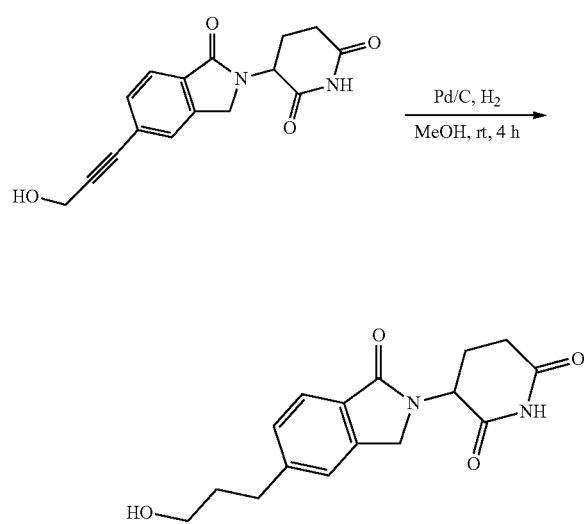

A mixture of 3-(5-(3-hydroxyprop-1-yn-1-yl)-1-oxoisoindolin-2-yl)piperidine-2,6-dione (100 mg, 0.34 mmol) and Pd/C (20 mg) in methanol (5 mL) was stirred under H₂ (1 atm, balloon) at room temperature for 3 h. The reaction mixture was purified by reverse phase chromatography to give the desired product (78 mg, 78% yield) as a light yellow solid. MS (ESI) m/z: 303.1 [M+H]⁺.

Step 2. Synthesis of 3-(2-(2,6-dioxopiperidin-3-yl)-1-oxoisoindolin-5-yl)propyl 4-methylbenzenesulfonate

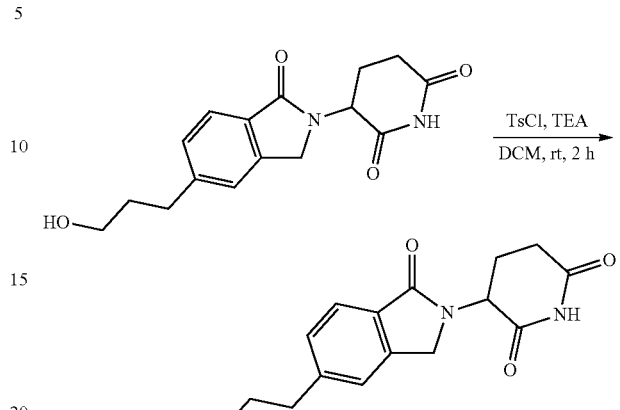

To a solution 3-(5-(3-hydroxypropyl)-1-oxoisoindolin-2-yl)piperidine-2,6-dione (80 mg, 0.26 mmol) and TEA (52 mg, 0.52 mmol) in DCM (5 mL) was added 4-methylbenzenesulfonyl chloride (59 mg, 0.31 mmol) at room temperature, then it was stirred at room temperature for 2 h. The mixture was concentrated and purified by reverse phase chromatography to give the desired product (67 mg, 54% yield) as a light yellow solid. MS (ESI) m/z: 457.1 [M+H]⁺.

Step 3. Synthesis of 3-(5-(3-(4-(6-(6-((R)-2-(3-fluorophenyl)pyrrolidin-1-yl) imidazo[1,2-b]pyridazin-3-yl)pyridin-2-yl)piperazin-1-yl)propyl)-1-oxoisoindolin-2-yl)piperidine-2,6-dione

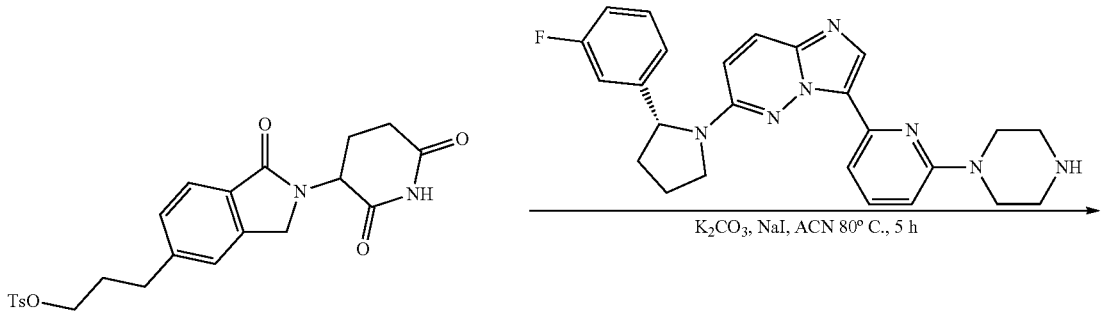

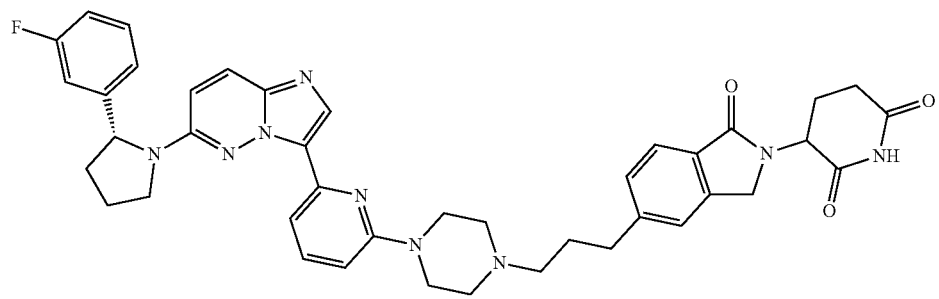

A mixture of 3-(2-(2,6-dioxopiperidin-3-yl)-1-oxoisoindolin-5-yl)propyl 4-methylbenzenesulfonate (40 mg, 0.08 mmol), (R)-6-(2-(3-fluorophenyl)pyrrolidin-1-yl)-3-(6-(piperazin-1-yl)pyridin-2-yl)imidazo[1,2-b]pyridazine (37 mg, 0.08 mmol), $K_2CO_3$ (22 mg, 0.16 mmol) and NaI (1.5 mg, 0.01 mmol) in $CH_3CN$ (3 mL) were stirred at 80° C. for 5 h. LCMS showed the reaction was completed. The mixture was concentrated and purified by reverse phase chromatography to give the desired product (26 mg, 38% yield) as a light yellow solid. MS (ESI) m/z: 728.3 $[M+H]^+$.

Example 237: 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)isoindoline-1,3-dione (TR-187)

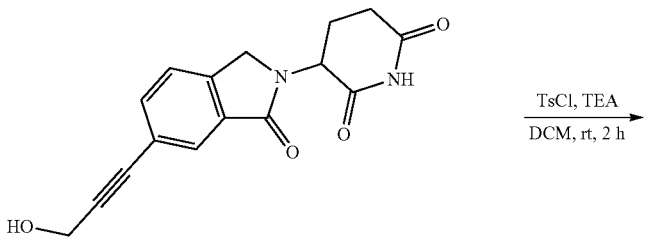

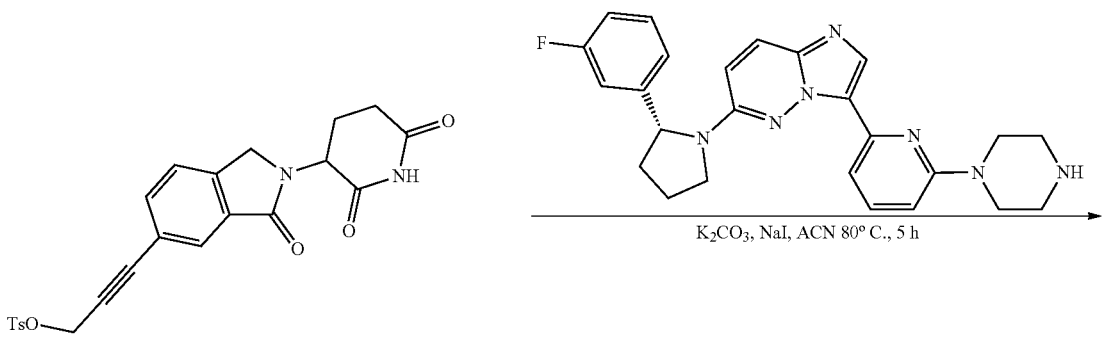

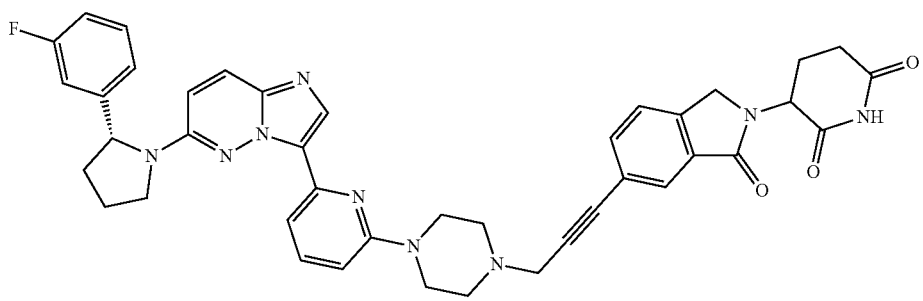

Step 1. Synthesis of 3-(2-(2,6-dioxopiperidin-3-yl)-3-oxoisoindolin-5-yl)prop-2-yn-1-yl 4-methylbenzenesulfonate

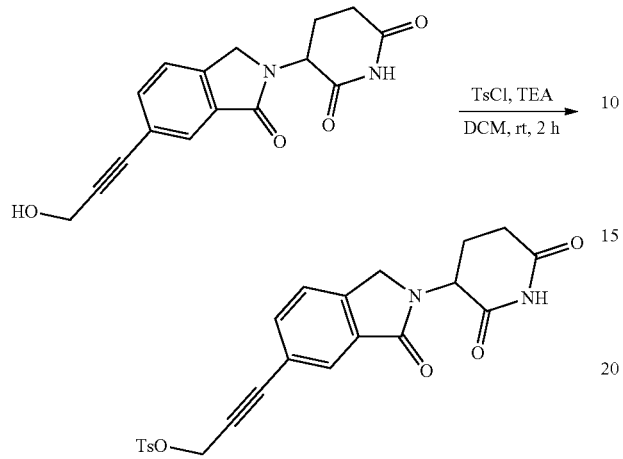

To a solution 3-(6-(3-hydroxyprop-1-yn-1-yl)-1-oxoisoindolin-2-yl)piperidine-2,6-dione (75 mg, 0.26 mmol) and TEA (52 mg, 0.52 mmol) in DCM (5 mL) was added 4-methylbenzenesulfonyl chloride (59 mg, 0.31 mmol) at room temperature, then it was stirred at room temperature for 2 h. The mixture was concentrated and purified by reverse phase chromatography to give the desired product (54 mg, 46% yield) as a light yellow solid. MS (ESI) m/z: 453.1 [M+H]$^+$.

Step 2. Synthesis of 3-(6-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)-1-oxoisoindolin-2-yl)piperidine-2,6-dione

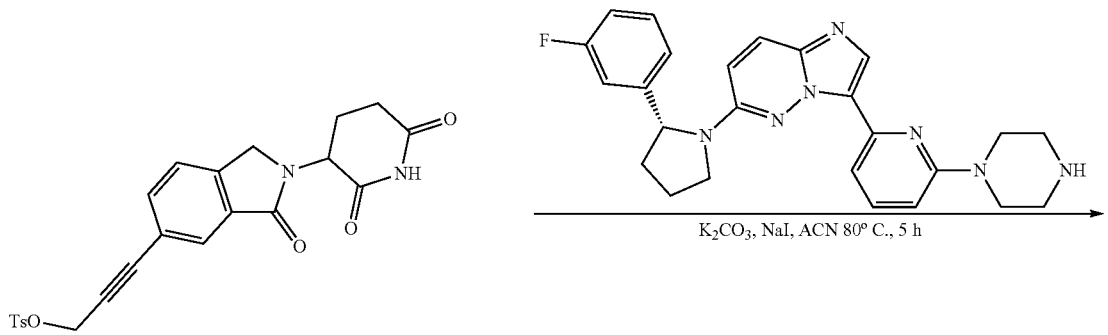

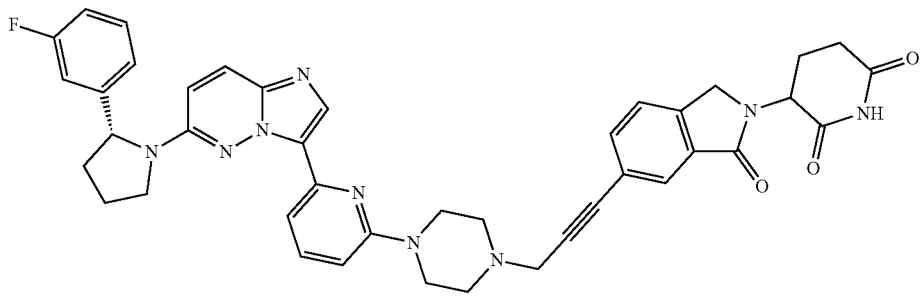

A mixture of 3-(2-(2,6-dioxopiperidin-3-yl)-3-oxoisoindolin-5-yl)prop-2-yn-1-yl 4-methylbenzenesulfonate (40 mg, 0.08 mmol), (R)-6-(2-(3-fluorophenyl)pyrrolidin-1-yl)-3-(6-(piperazin-1-yl)pyridin-2-yl)imidazo[1,2-b]pyridazine (37 mg, 0.08 mmol), K$_2$CO$_3$ (22 mg, 0.16 mmol) and NaI (1.5 mg, 0.01 mmol) in CH$_3$CN (3 mL) were stirred at 80° C. for 5 h. LCMS showed the reaction was completed. The mixture was concentrated and purified by reverse phase chromatography to give the desired product (29 mg, 39% yield) as a light yellow solid. MS (ESI) m/z: 724.3 [M+H]$^+$.

Example 238: 3-(5-(3-(4-(6-(6-((R)-2-(3-Fluorophenyl)pyrrolidin-1-yl)imidazo[1,2-b]pyridazin-3-yl)pyridin-2-yl)piperazin-1-yl)prop-1-yn-1-yl)-1-oxoisoindolin-2-yl)piperidine-2,6-dione (TR-188)

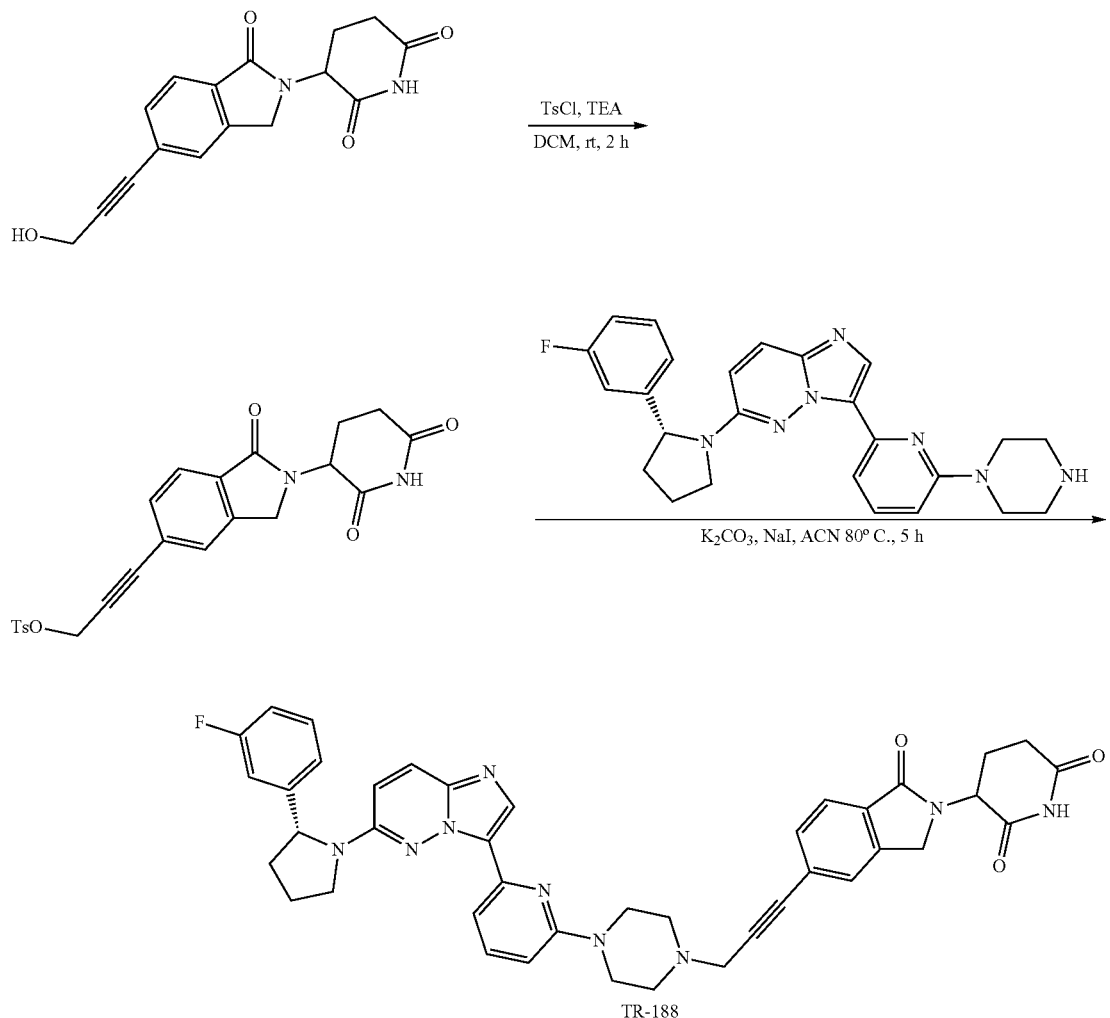

Step 1. Synthesis of 3-(2-(2,6-dioxopiperidin-3-yl)-1-oxoisoindolin-5-yl)prop-2-yn-1-yl 4-methylbenzenesulfonate

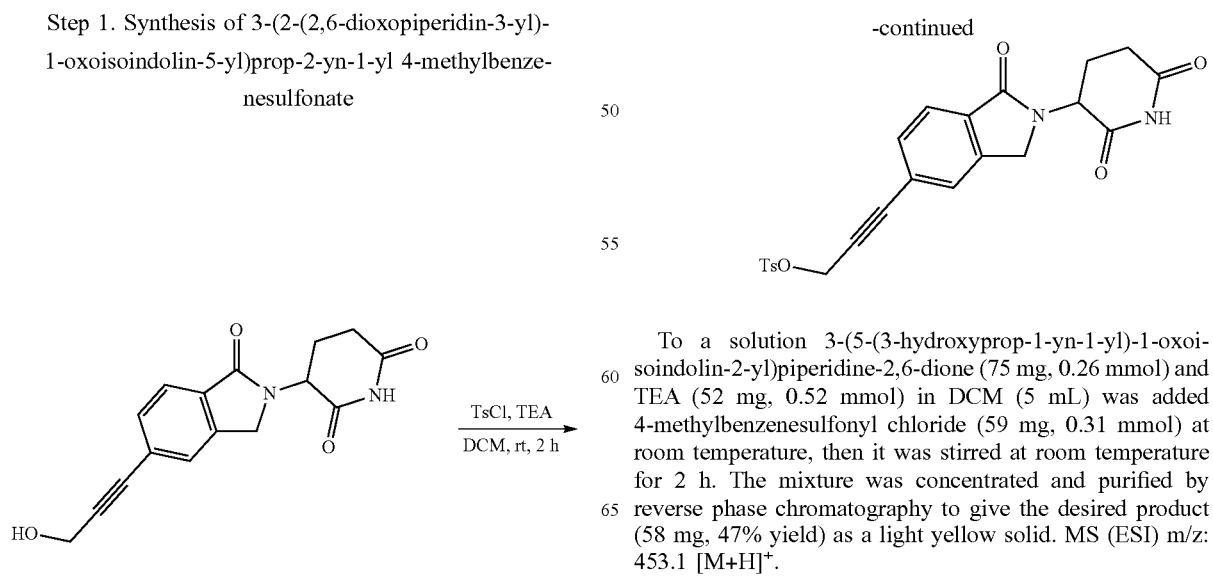

To a solution 3-(5-(3-hydroxyprop-1-yn-1-yl)-1-oxoisoindolin-2-yl)piperidine-2,6-dione (75 mg, 0.26 mmol) and TEA (52 mg, 0.52 mmol) in DCM (5 mL) was added 4-methylbenzenesulfonyl chloride (59 mg, 0.31 mmol) at room temperature, then it was stirred at room temperature for 2 h. The mixture was concentrated and purified by reverse phase chromatography to give the desired product (58 mg, 47% yield) as a light yellow solid. MS (ESI) m/z: 453.1 [M+H]$^+$.

Step 2. Synthesis of 3-(5-(3-(4-(6-(6-((R)-2-(3-fluorophenyl)pyrrolidin-1-yl) imidazo[1,2-b]pyridazin-3-yl)pyridin-2-yl)piperazin-1-yl)prop-1-yn-1-yl)-1-oxoisoindolin-2-yl)piperidine-2,6-dione (TR-188)

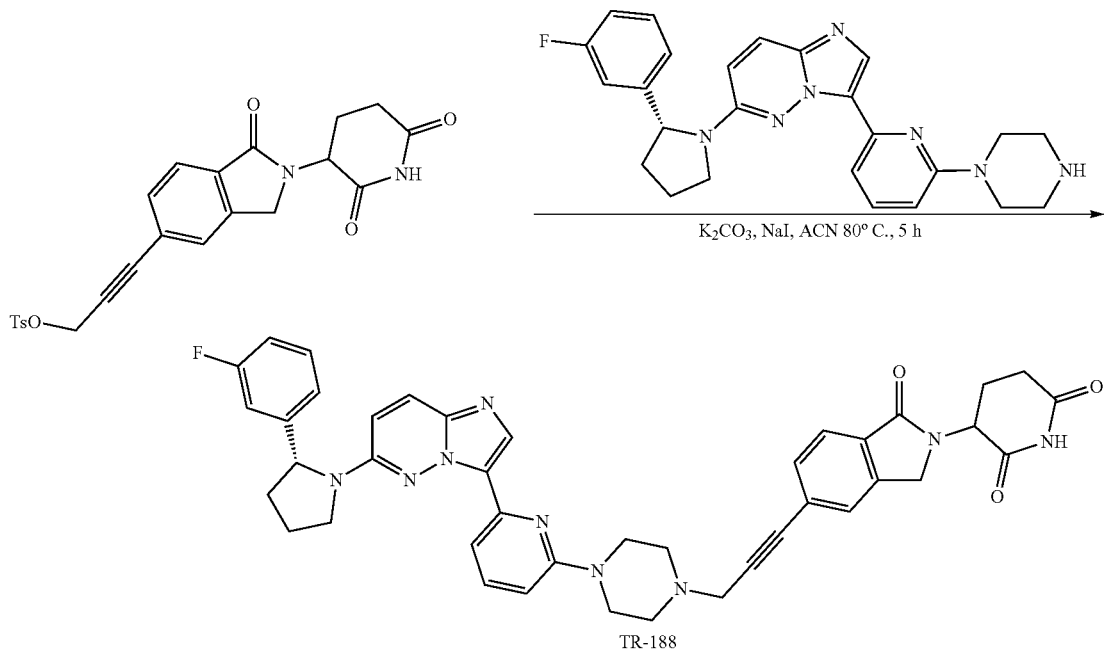

A mixture of 3-(2-(2,6-dioxopiperidin-3-yl)-1-oxoisoindolin-5-yl)prop-2-yn-1-yl 4-methylbenzenesulfonate (40 mg, 0.08 mmol), (R)-6-(2-(3-fluorophenyl)pyrrolidin-1-yl)-3-(6-(piperazin-1-yl)pyridin-2-yl)imidazo[1,2-b]pyridazine (37 mg, 0.08 mmol), $K_2CO_3$ (22 mg, 0.16 mmol) and NaI (1.5 mg, 0.01 mmol) in $CH_3CN$ (3 mL) were stirred at 80° C. for 5 h. LCMS showed the reaction was completed. The mixture was concentrated and purified by reverse phase chromatography to give the desired product (21 mg, 36% yield) as a light yellow solid. MS (ESI) m/z: 724.3 [M+H]$^+$.

Example 239: 3-(6-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)-1-oxoisoindolin-2-yl)piperidine-2,6-dione (TR-189)

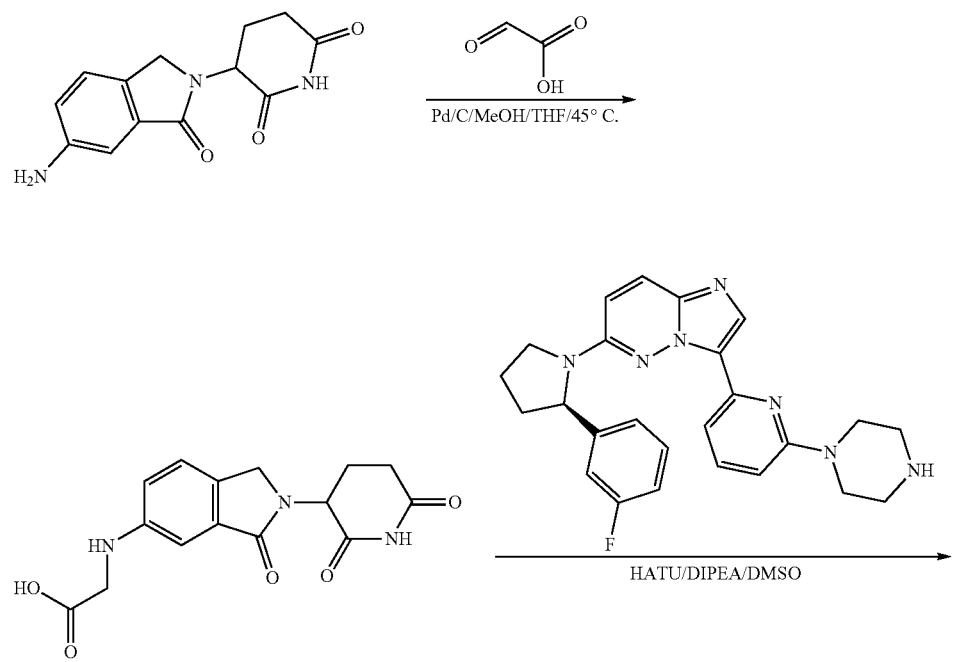

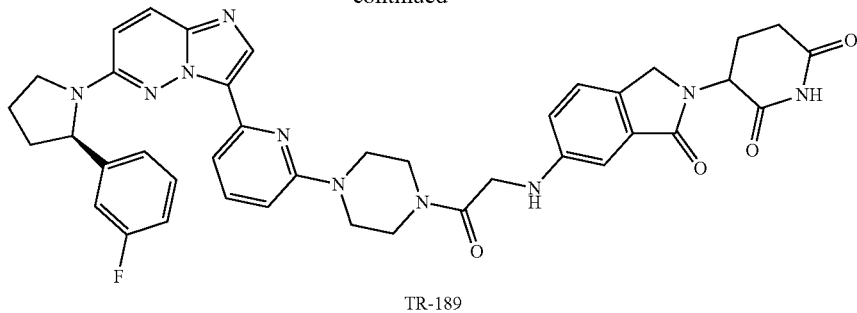

TR-189

Step 1. Synthesis of (2-(2,6-dioxopiperidin-3-yl)-3-oxoisoindolin-5-yl)glycine

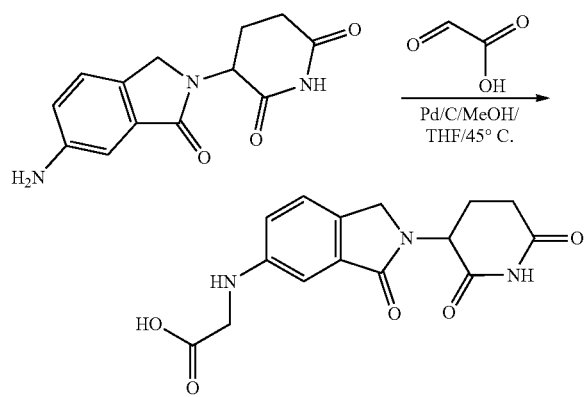

To a mixture of To the mixture of 3-(6-amino-1-oxoisoindolin-2-yl)piperidine-2,6-dione (130 mg, 501.43 umol) and oxaldehydic acid (55.69 mg, 752.14 umol) in MeOH (5 mL) and THF (1 mL) was added Pd/C (10%, 10 mg) at room temperature, the resulting mixture was stirred at 45° C. under $H_2$ for 16 h and monitored by LCMS. The reaction mixture was filtrated and concentrated to give crude product which was slurried (EtOAc/MeOH=5/1, 5 mL), filtrated to give desired product (150 mg, 94% yield) as a brown solid. MS (ESI) m/z: 318.3 [M+H]$^+$.

Step 2. Synthesis of 3-(6-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)-1-oxoisoindolin-2-yl)piperidine-2,6-dione (TR-189)

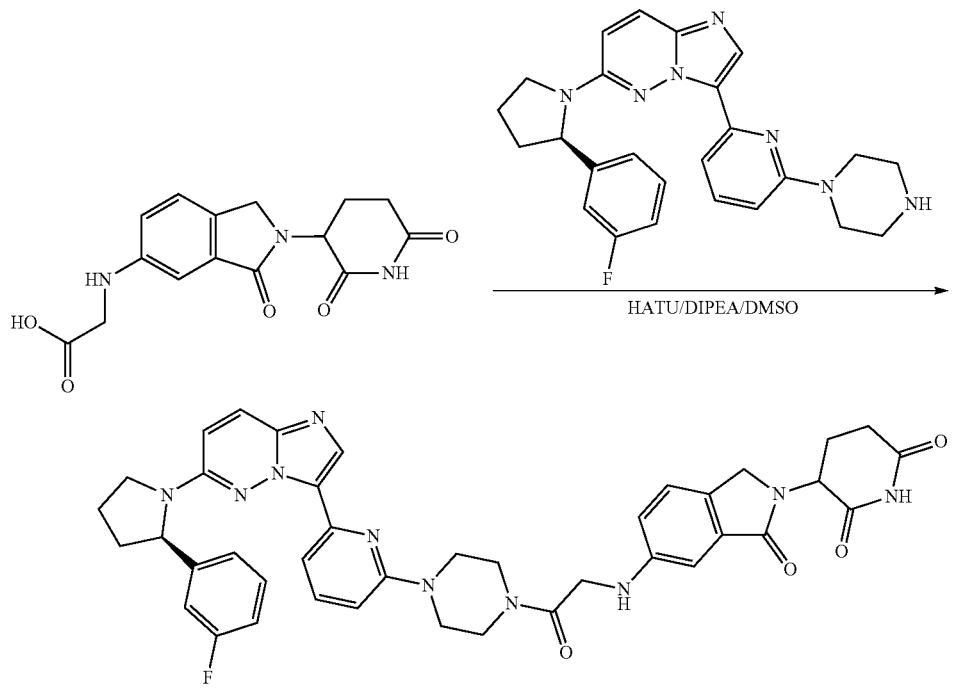

TR-189

To a solution of (R)-6-(2-(3-fluorophenyl)pyrrolidin-1-yl)-3-(6-(piperazin-1-yl)pyridin-2-yl)imidazo[1,2-b]pyridazine (4.4 mg, 9.92 umol) and (2-(2,6-dioxopiperidin-3-yl)-3-oxoisoindolin-5-yl)glycine (3.15 mg, 9.92 umol) in DMSO (2 mL) were added HATU (4.52 mg, 11.90 umol) and DIEA (2.56 mg, 19.84 umol) at RT. The reaction mixture was stirred at room temperature for 16 h, then it was quenched with H₂O (10 mL) and extracted with DCM (10 mL*3). The combined organic layers were washed with aqueous NaCl (10 mL*2), dried over Na₂SO₄, concentrated and purified by Prep-TLC (DCM/MeOH=10/1) to give desired product (6 mg, 81% yield) as a yellow solid. MS (ESI) m/z: 743.8 [M+H]⁺.

Example 240: 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)-1-oxoisoindolin-2-yl)piperidine-2,6-dione (TR-190)

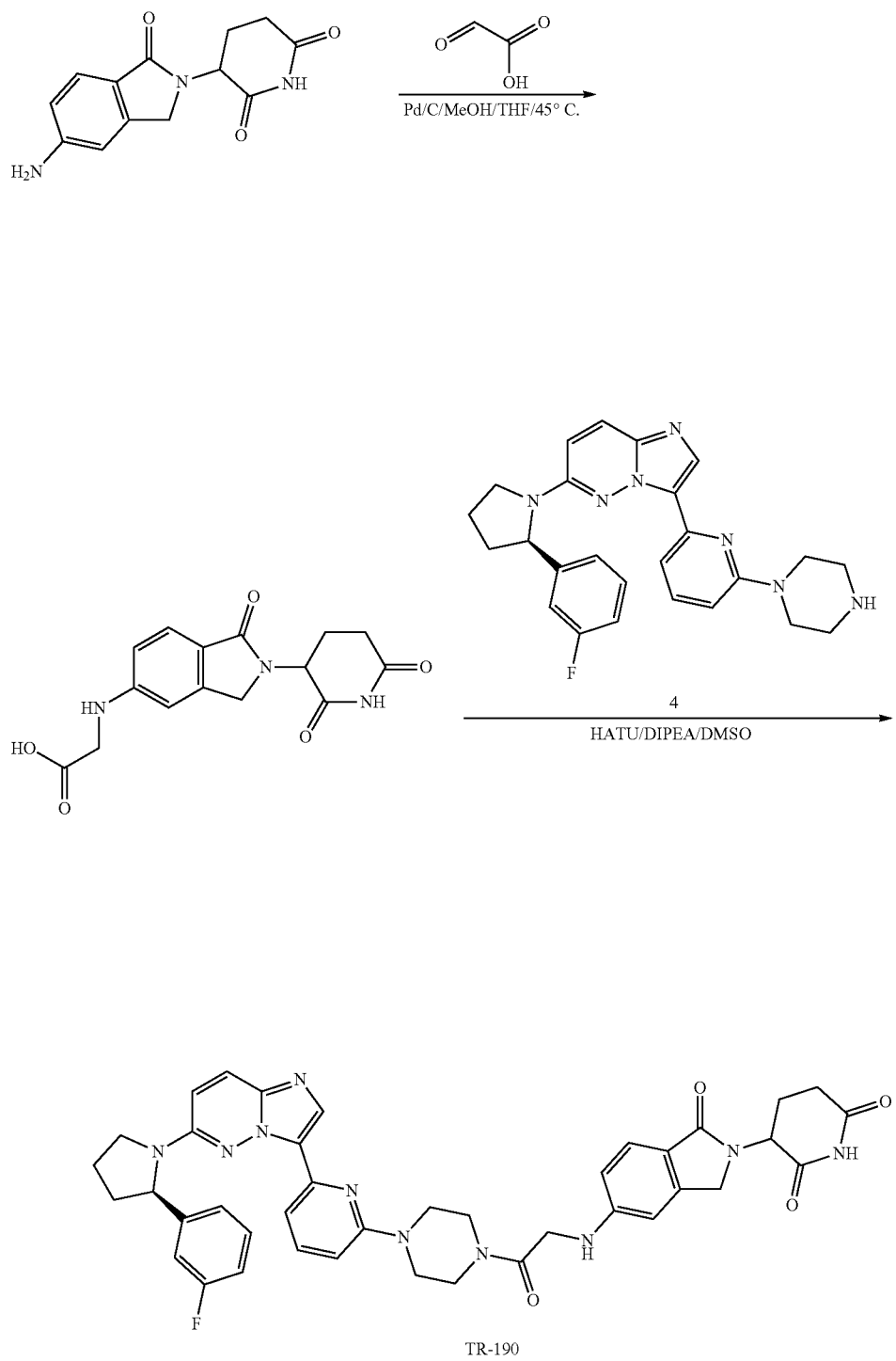

TR-190

519

Step 1. Synthesis of (2-(2,6-dioxopiperidin-3-yl)-1-oxoisoindolin-5-yl)glycine

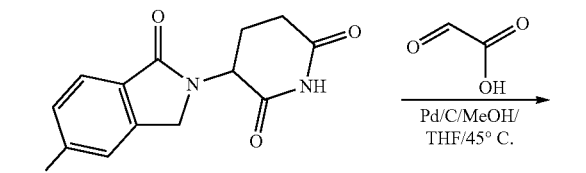

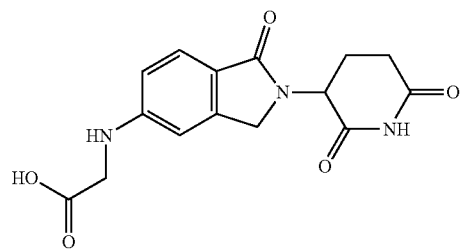

520

To a solution of 3-(5-amino-1-oxoisoindolin-2-yl)piperidine-2,6-dione (130 mg, 501.43 umol) and oxaldehydic acid (55.69 mg, 752.14 umol) in MeOH (5 mL) and THF (1 mL) was added Pd/C (6.09 mg, 50.14 umol) at rt. the resulting mixture was stirred at 45° C. under $H_2$ for 16 h and monitored by LCMS.

The reaction mixture was fitrated and concentrated to give crude product which was slurried (EtOAc/MeOH=5/1, 5 mL), fitrated to desired product (130 mg, 81.712% yield) as a brown solid. MS (ESI) m/z: 318.3 $[M+H]^+$.

Step 2. Synthesis of 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)-1-oxoisoindolin-2-yl)piperidine-2,6-dione (TR-190)

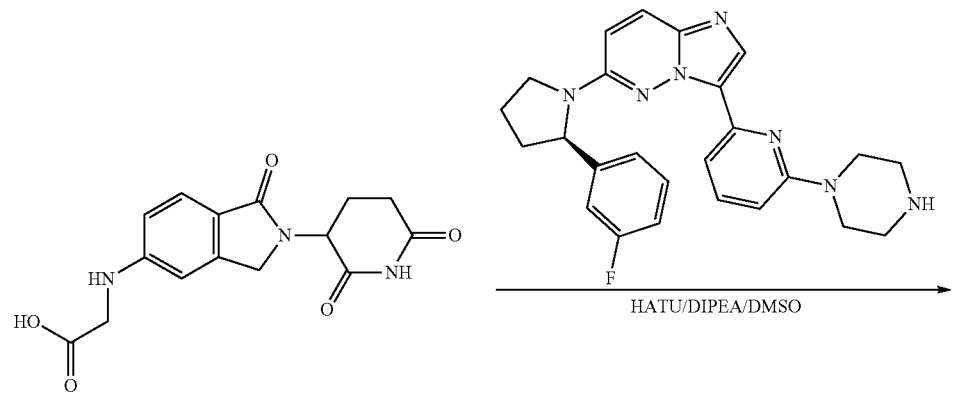

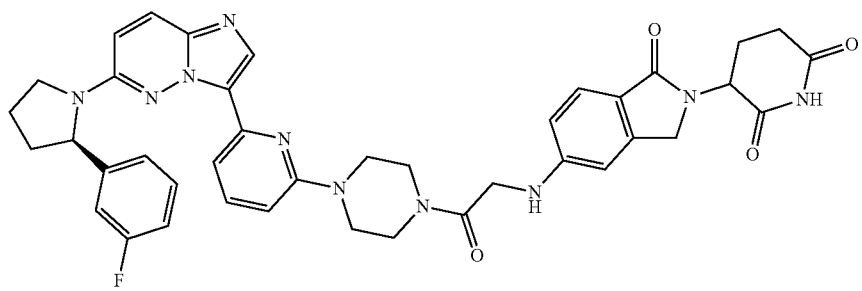

TR-190

To a solution of (R)-6-(2-(3-fluorophenyl)pyrrolidin-1-yl)-3-(6-(piperazin-1-yl)pyridin-2-yl)imidazo[1,2-b]pyridazine (4.4 mg, 9.92 umol) and (2-(2,6-dioxopiperidin-3-yl)-1-oxoisoindolin-5-yl)glycine (3.15 mg, 9.92 umol) in DMSO (2 mL) was added HATU (4.52 mg, 11.90 umol) and DIEA (2.56 mg, 19.84 umol) at RT. The reaction mixture was stirred at room temperature for 16 h, then it was quenched with H₂O (10 mL) and extracted with DCM (10 mL*3). The combined organic layers were washed with aqueous NaCl (10 mL*2), dried over Na₂SO₄, concentrated and purified by Prep-TLC (DCM/MeOH=10/1) to give desired product (5.8 mg, 79% yield) as a yellow solid. MS (ESI) m/z: 743.9 [M+H]⁺.

Example 241: 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-1-oxoisoindolin-2-yl)piperidine-2,6-dione (TR-191)

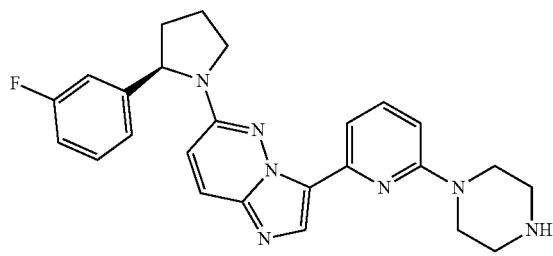
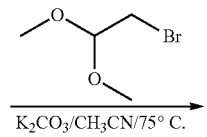
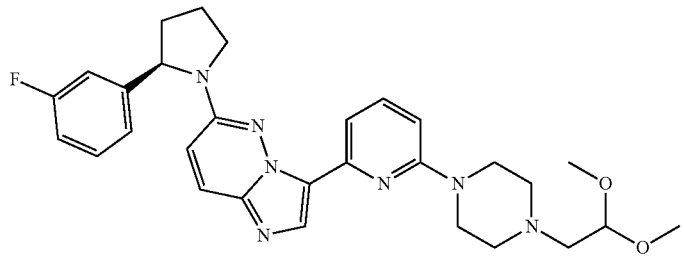
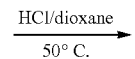
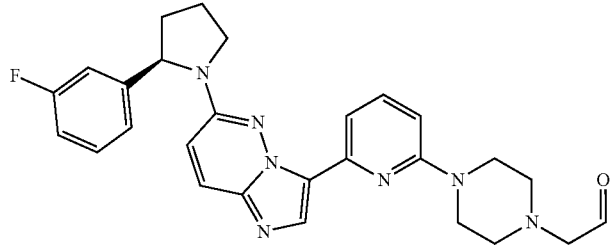
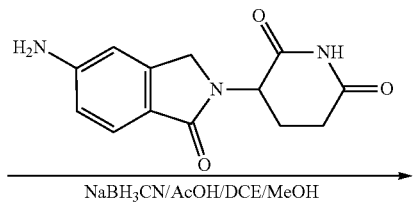
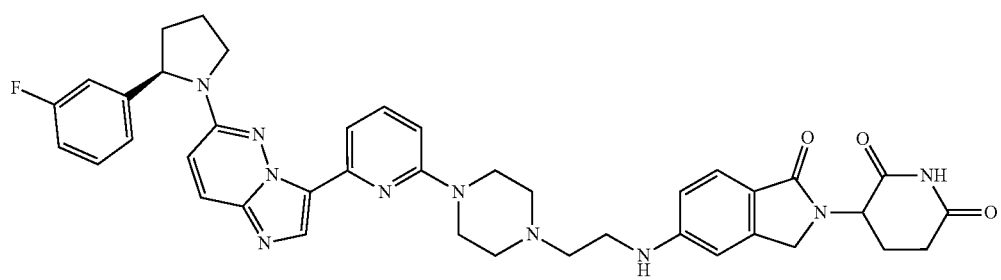

Step 1. Synthesis of (R)-3-(6-(4-(2,2-dimethoxy-ethyl)piperazin-1-yl)pyridin-2-yl)-6-(2-(3-fluorophenyl)pyrrolidin-1-yl)imidazo[1,2-b]pyridazine

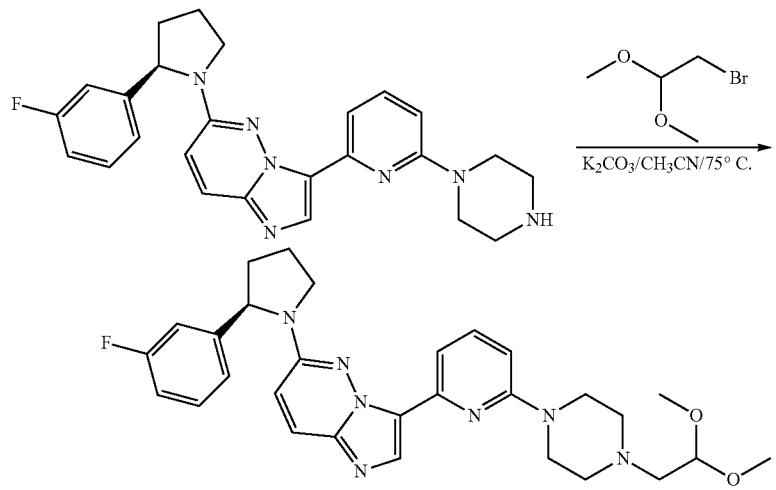

To a suspension of (R)-6-(2-(3-fluorophenyl)pyrrolidin-1-yl)-3-(6-(piperazin-1-yl)pyridin-2-yl)imidazo[1,2-b]pyridazine (200 mg, 450.94 umol) in CH₃CN (5 mL) were added 2-bromo-1,1-dimethoxy-ethane (114.32 mg, 676.41 umol) and K₂CO₃ (124.46 mg, 901.88 umol) at room temperature under the N₂, the resulting mixture was warmed to 75° C. and stirred for 16 h. Then it was cooled to room temperature and concentrated, the residue was purified by silica gel chromatography (DCM/MeOH=20/1-10/1) to give desired product (200 mg, 83% yield) as a yellow solid. MS (ESI) m/z: 532.7 [M+H]⁺.

Step 2. Synthesis of (R)-2-(4-(6-(6-(2-(3-fluorophenyl)pyrrolidin-1-yl)imidazo[1,2-b]pyridazin-3-yl)pyridin-2-yl)piperazin-1-yl)acetaldehyde

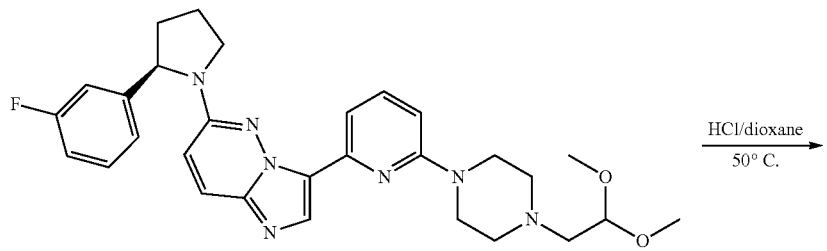

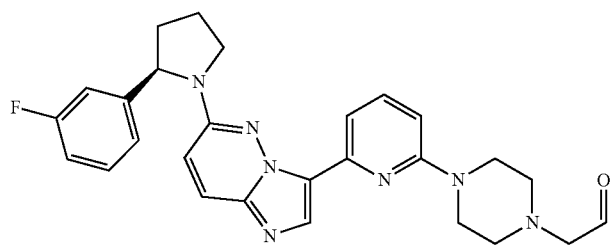

To a solution of (R)-3-(6-(4-(2,2-dimethoxyethyl)piper-azin-1-yl)pyridin-2-yl)-6-(2-(3-fluorophenyl)pyrrolidin-1-yl)imidazo[1,2-b]pyridazine (250 mg, 470.26 umol) in dioxane (6 mL) was added conc. HCl (3 mL) at RT, the reaction mixture was warmed to 50° C. and stirred for 16 h. Then it was concentrated to give crude product (220 mg, 96% yield) as a yellow solid which was used directly in the next step without further purification. MS (ESI) m/z: 504.5 [M+18+H]⁺.

Step 3. Synthesis of 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-1-oxoisoindolin-2-yl)piperidine-2,6-dione (TR-191)

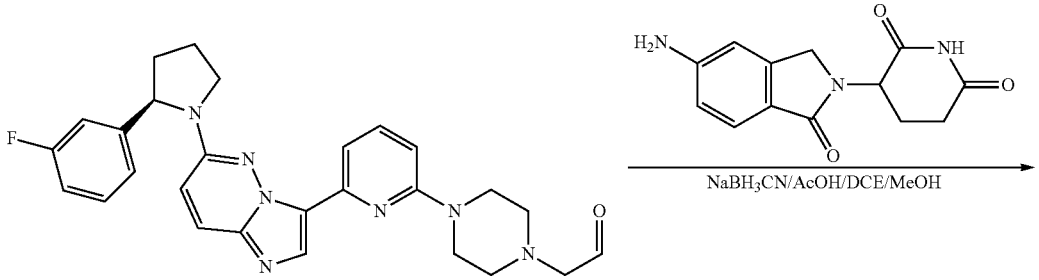

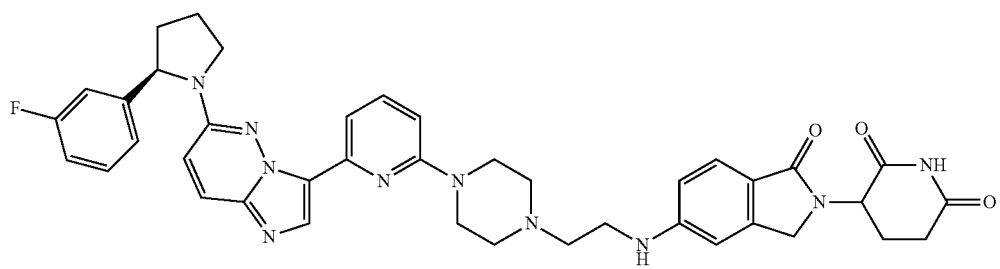 [SMILES: O=C1CCC(N2Cc3cc(NCCN4CCN(c5cccc(-c6cnc7ccc(N8CCC[C@@H]8c8cccc(F)c8)nn67)n5)CC4)ccc3C2=O)C(=O)N1]

To a solution of (R)-2-(4-(6-(6-(2-(3-fluorophenyl)pyrrolidin-1-yl)imidazo[1,2-b]pyridazin-3-yl)pyridin-2-yl)piperazin-1-yl)acetaldehyde (48 mg, 98.86 umol) and 3-(6-amino-1-oxoisoindolin-2-yl)piperidine-2,6-dione (38.44 mg, 148.28 umol) in MeOH (1 mL), DCE (2 mL) and AcOH (1 mL) was added NaBH₃CN (12.46 mg, 197.71 umol) at RT. The reaction mixture was stirred at room temperature for 16 h, then it was purified by prep-HPLC to give 10 mg crude product which was further purified by prep-TLC (DCM/MeOH=10/1) to desired product (1.4 mg, 2% yield) as a yellow solid. MS (ESI) m/z: 729.7 [M+H]f.

Example 242: Synthesis of 2-(2,6-Dioxopiperidin-3-yl)-5-((2-((1-(6-(6-((R)-2-(3-fluorophenyl)pyrrolidin-1-yl)imidazo[1,2-b]pyridazin-3-yl)pyridin-2-yl)azetidin-3-yl)amino)ethyl)amino)isoindoline-1,3-dione (TR-192)

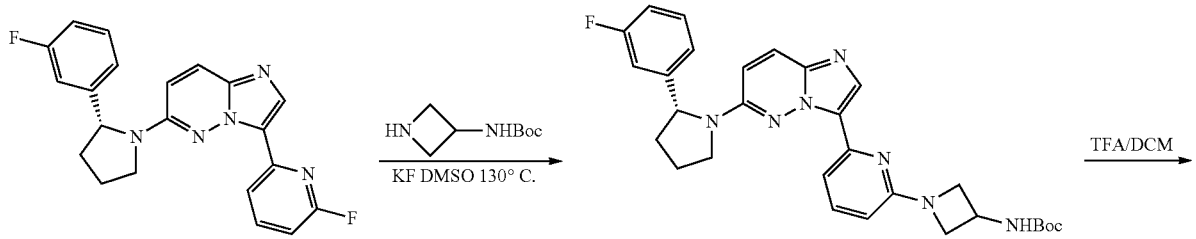

527                                          528
-continued
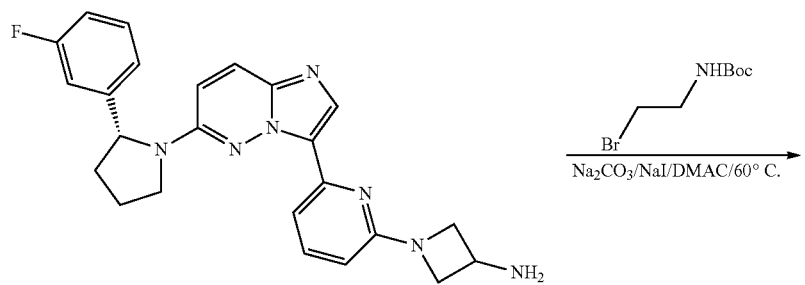
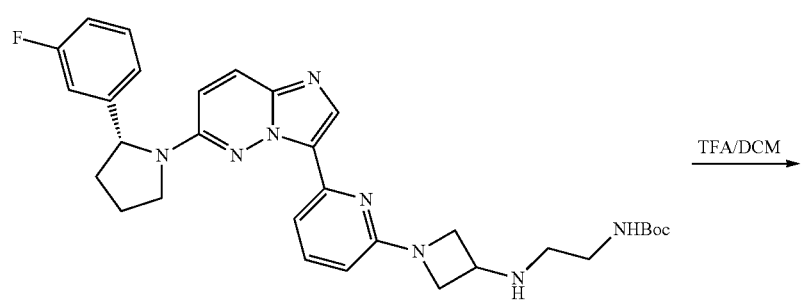
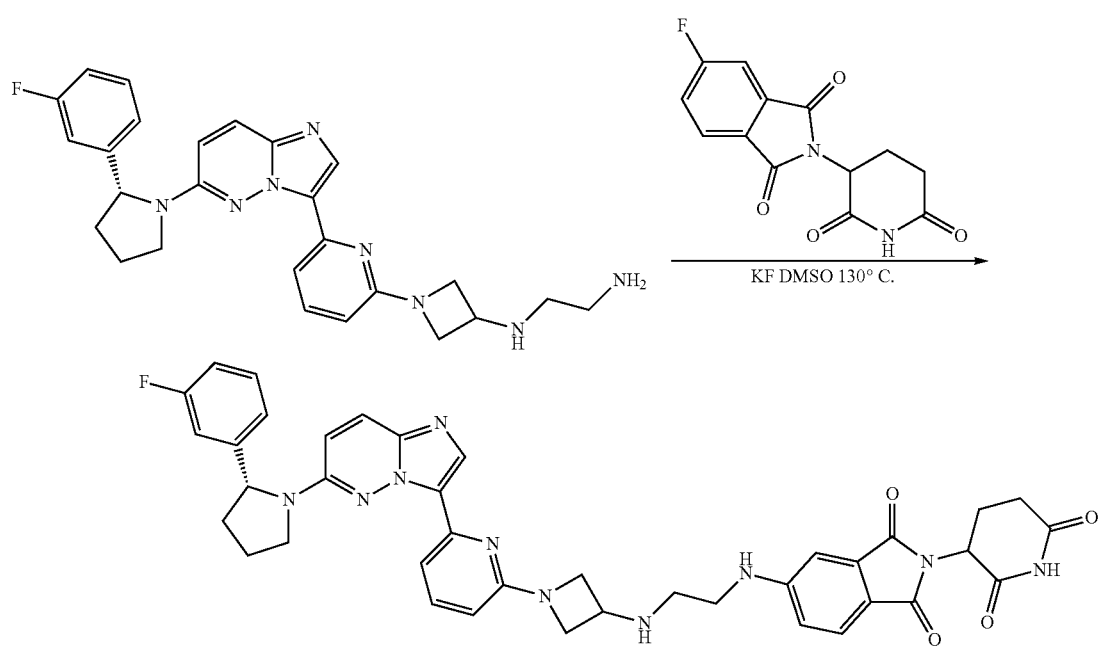

Step 1. Synthesis of tert-butyl (R)-(1-(6-(6-(2-(3-fluorophenyl)pyrrolidin-1-yl)imidazo[1,2-b]pyridazin-3-yl)pyridin-2-yl)azetidin-3-yl)carbamate

Step 2. Synthesis of (R)-1-(6-(6-(2-(3-fluorophenyl)pyrrolidin-1-yl)imidazo[1,2-b]pyridazin-3-yl)pyridin-2-yl)azetidin-3-amine

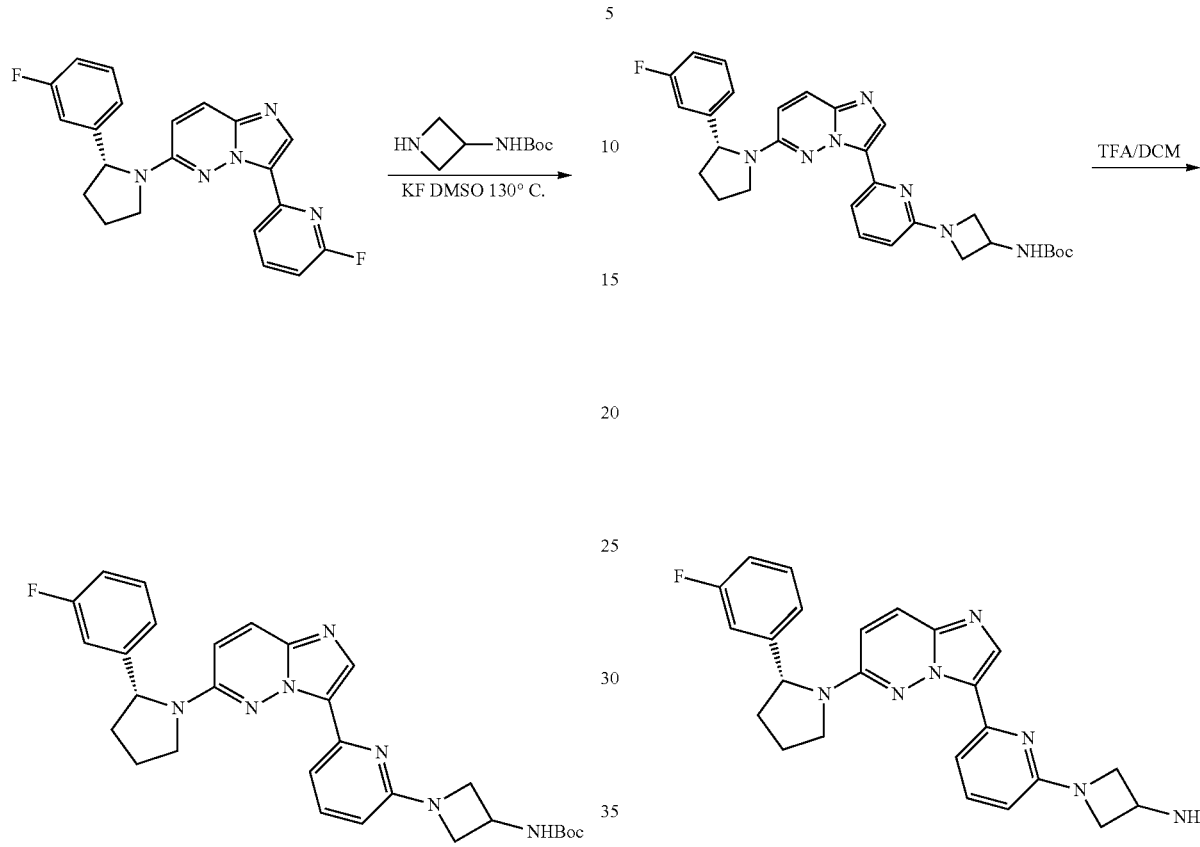

To a solution of (R)-6-(2-(3-fluorophenyl)pyrrolidin-1-yl)-3-(6-fluoropyridin-2-yl)imidazo[1,2-b]pyridazine (50 mg, 132.6 umol) in DMSO (3 mL) were added KF (23 mg, 397.8 umol) and tert-butyl azetidin-3-ylcarbamate (68.2 mg, 397.8 umol). The resulting mixture was stirred at 130° C. for 1 hr. After the Imide was totally consumed, the reaction was poured into water (20 mL) and extracted with ethyl acetate (3×10 mL). The combined organic layers were washed with saturated brine (20 mL), dried over anhydrous sodium sulfate, filtered and evaporated under reduced pressure. The resulting residue was purified by reverse-phase chromatography to afford the desired product tert-butyl (R)-(1-(6-(6-(2-(3-fluorophenyl)pyrrolidin-1-yl)imidazo[1,2-b]pyridazin-3-yl)pyridin-2-yl)azetidin-3-yl)carbamate (21 mg, 30% yield) as a light yellow solid. MS (ESI) m/z: 530.3 [M+H]+.

To a solution of tert-butyl (R)-(1-(6-(6-(2-(3-fluorophenyl)pyrrolidin-1-yl)imidazo[1,2-b]pyridazin-3-yl)pyridin-2-yl)azetidin-3-yl)carbamate (100 mg, 188.9 umol) in DCM (2 mL) was added TFA (2 mL). The resulting mixture was stirred at 25° C. for 5 hr. After the starting material was totally consumed, the reaction was evaporated under reduced pressure. The resulting residue was purified by reverse-phase chromatography to yield the desired product (R)-1-(6-(6-(2-(3-fluorophenyl)pyrrolidin-1-yl)imidazo[1,2-b]pyridazin-3-yl)pyridin-2-yl)azetidin-3-amine (73 mg, 91% yield) as a light yellow solid. MS (ESI) m/z: 430.2 [M+H]+.

Step 3. Synthesis of tert-butyl (R)-(2-((1-(6-(6-(2-(3-fluorophenyl)pyrrolidin-1-yl)imidazo[1,2-b]pyridazin-3-yl)pyridin-2-yl)azetidin-3-yl)amino)ethyl)carbamate

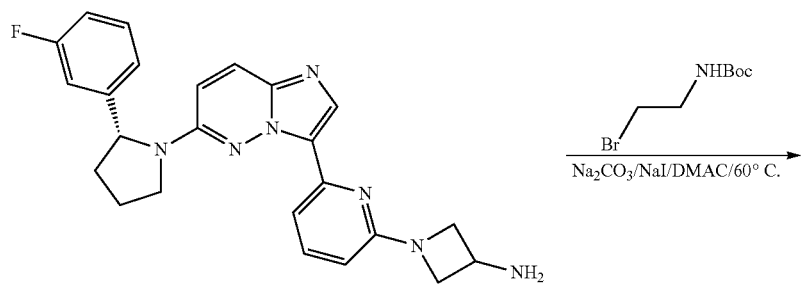

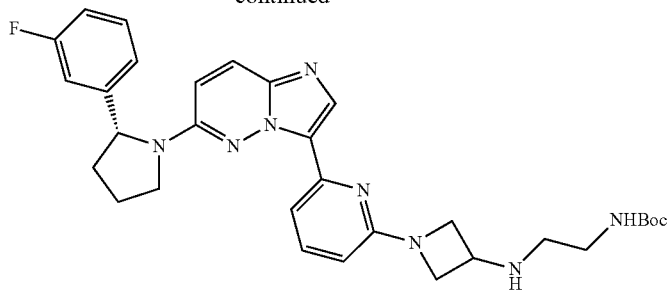

To a solution of (R)-1-(6-(6-(2-(3-fluorophenyl)pyrrolidin-1-yl)imidazo[1,2-b]pyridazin-3-yl)pyridin-2-yl)azetidin-3-amin (100 mg, 232.9 umol) in DMAC (2 mL) were added Na$_2$CO$_3$ (74 mg, 698.8 umol), NaI (34.7 mg, 232.9 umol) and tert-butyl (2-bromoethyl)carbamate (155 mg, 698.8 umol). The resulting mixture was stirred at 60° C. for 15 hr. After the starting material was totally consumed, the reaction was evaporated under reduced pressure. The resulting residue was purified by reverse-phase chromatography to yield the desired product tert-butyl (R)-(2-((1-(6-(6-(2-(3-fluorophenyl)pyrrolidin-1-yl)imidazo[1,2-b]pyridazin-3-yl)pyridin-2-yl)azetidin-3-yl)amino)ethyl)carbamate (39 mg, 30% yield) as a light yellow solid. MS (ESI) m/z: 573.3 [M+H]$^+$.

Step 4. Synthesis of (R)—N-(1-(6-(6-(2-(3-fluorophenyl)pyrrolidin-1-yl)imidazo[1,2-b]pyridazin-3-yl)pyridin-2-yl)azetidin-3-yl)ethane-1,2-diamine

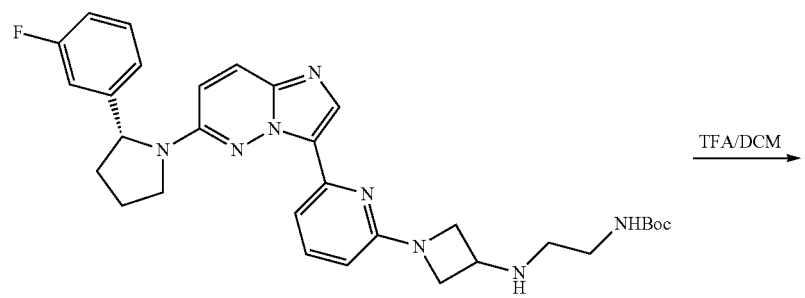

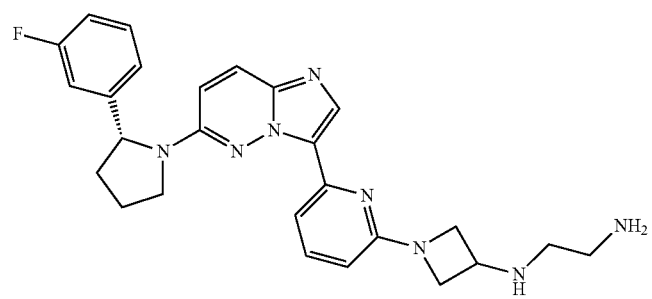

To a solution of tert-butyl (R)-(2-((1-(6-(6-(2-(3-fluorophenyl)pyrrolidin-1-yl)imidazo[1,2-b]pyridazin-3-yl)pyridin-2-yl)azetidin-3-yl)amino)ethyl)carbamate (39 mg, 69.6 umol) in DCM (2 mL) was added TFA (2 mL). The resulting mixture was stirred at 25° C. for 5 hr. After the starting material was totally consumed, the reaction was evaporated under reduced pressure. The resulting residue was purified by reverse-phase chromatography to yield the desired product (R)—N1-(6-(6-(2-(3-fluorophenyl)pyrrolidin-1-yl)imidazo[1,2-b]pyridazin-3-yl)pyridin-2-yl)azetidin-3-yl)ethane-1,2-diamine (25 mg, 76% yield) as a light yellow solid. MS (ESI) m/z: 473.2 [M+H]+.

Step 5. Synthesis of 2-(2,6-dioxopiperidin-3-yl)-5-((2-((1-(6-(6-((R)-2-(3-fluorophenyl)pyrrolidin-1-yl)imidazo[1,2-b]pyridazin-3-yl)pyridin-2-yl)azetidin-3-yl)amino)ethyl)amino)isoindoline-1,3-dione (TR-192)

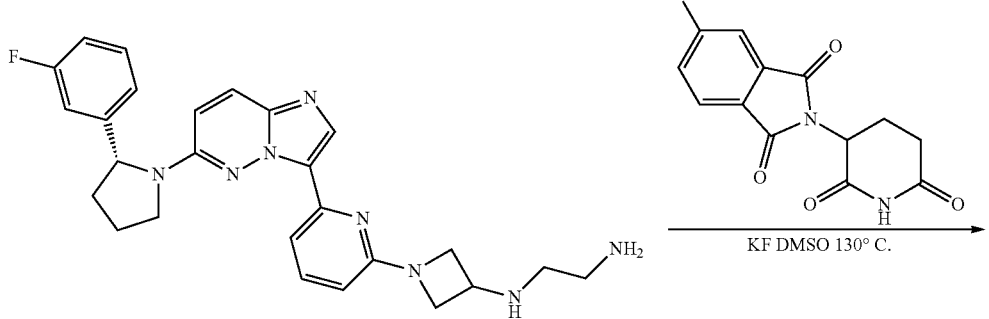

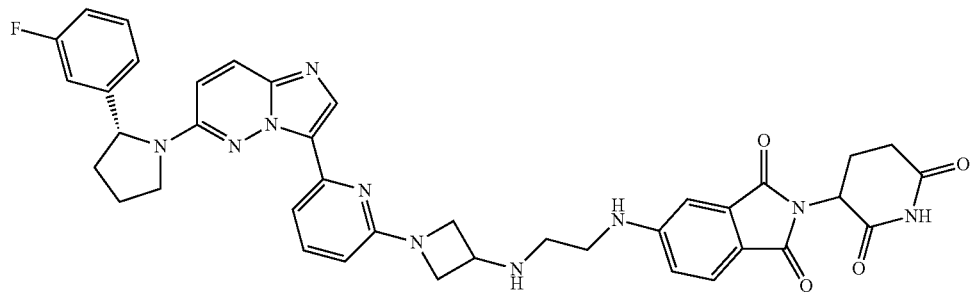

To a solution of (R)—N1-(1-(6-(6-(2-(3-fluorophenyl)pyrrolidin-1-yl)imidazo[1,2-b]pyridazin-3-yl)pyridin-2-yl)azetidin-3-yl)ethane-1,2-diamine (20 mg, 42.3 umol) in DMSO (3 mL) were added KF (7.4 mg, 127.1 umol) and 2-(2,6-dioxopiperidin-3-yl)-5-fluoroisoindoline-1,3-dione (35 mg, 127.1 umol).

The resulting mixture was stirred at 130° C. for 1 hr. After the Primary amine was totally consumed, the reaction was poured into water (20 mL) and extracted with ethyl acetate (3×10 mL). The combined organic layers were washed with saturated brine (20 mL), dried over anhydrous sodium sulfate, filtered and evaporated under reduced pressure. The resulting residue was purified by reverse-phase chromatography to afford the desired product 2-(2,6-dioxopiperidin-3-yl)-5-((2-((1-(6-(6-((R)-2-(3-fluorophenyl)pyrrolidin-1-yl)imidazo[1,2-b]pyridazin-3-yl)pyridin-2-yl)azetidin-3-yl)amino)ethyl)amino)isoindoline-1,3-dione (9.2 mg, 30% yield) as a light yellow solid. MS (ESI) m/z: 729.3 [M+H]$^+$.

Example 243: Synthesis of 2-(2,6-dioxopiperidin-3-yl)-5-((2-(1-(6-(6-((R)-2-(3-fluorophenyl)pyrrolidin-1-yl)imidazo[1,2-b]pyridazin-3-yl)pyridin-2-yl)azetidin-3-yl)ethyl)amino)isoindoline-1,3-dione (TR-193)

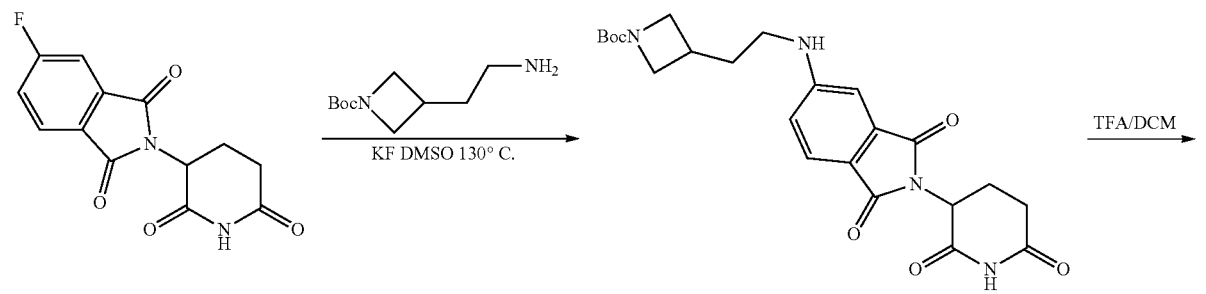

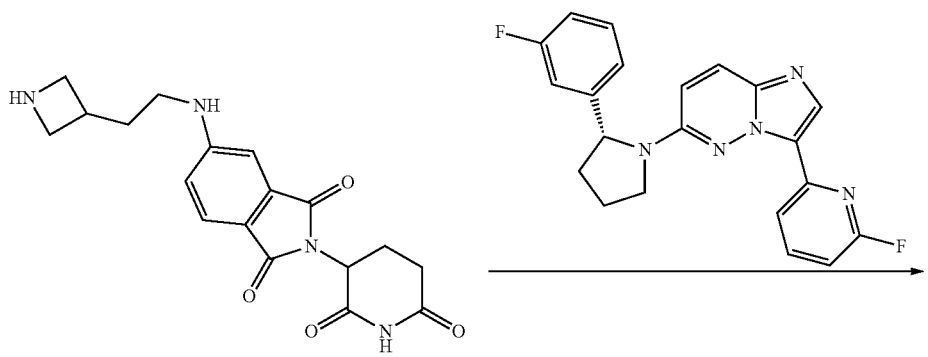

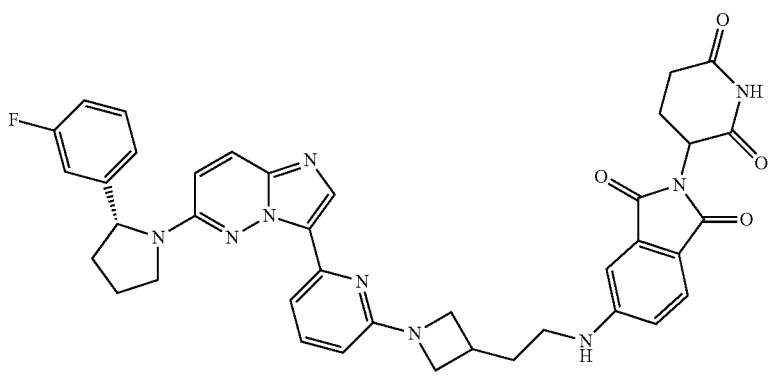 [SMILES: O=C1CCC(N2C(=O)c3ccc(NCCC4CN(c5cccc(-c6cnc7ccc(N8CCC[C@@H]8c8cccc(F)c8)nn67)n5)C4)cc3C2=O)C(=O)N1]

TR-193 was synthesized following the standard procedure for preparing TR-175. MS (ESI) m/z: 714.3 [M+H]$^+$.

Example 244: 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropyl)isoindoline-1,3-dione (TR-194)
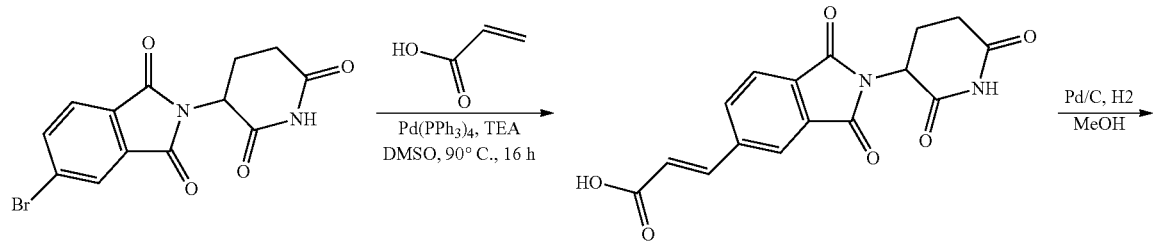
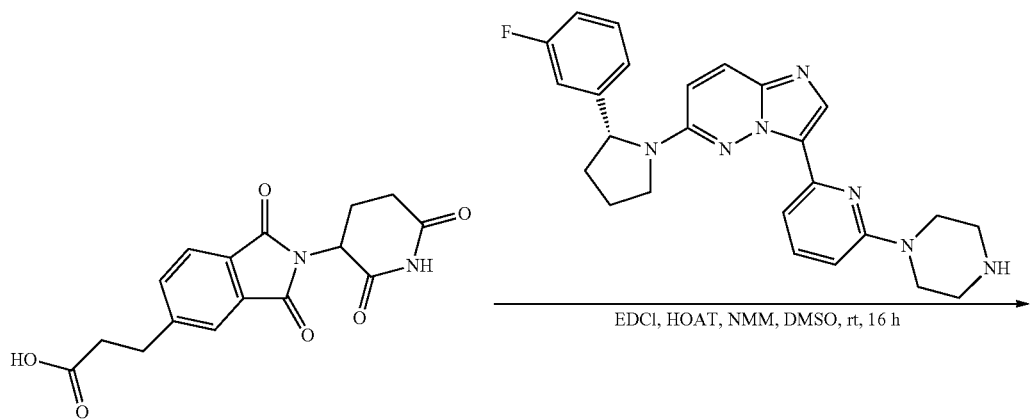
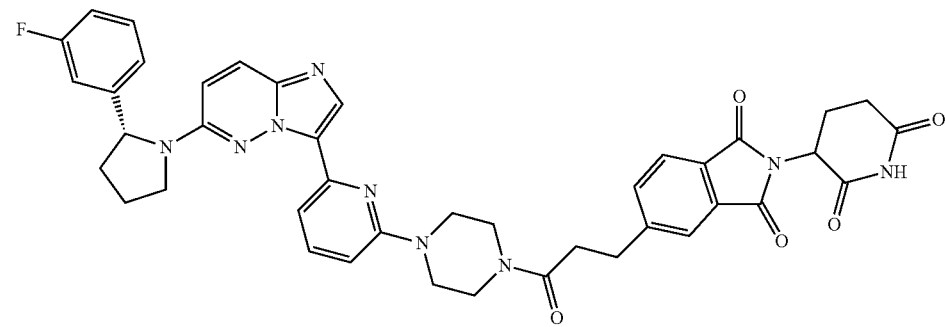

Step 1. Synthesis of (E)-3-(2-(2,6-dioxopiperidin-3-yl)-1,3-dioxoisoindolin-5-yl)acrylic acid

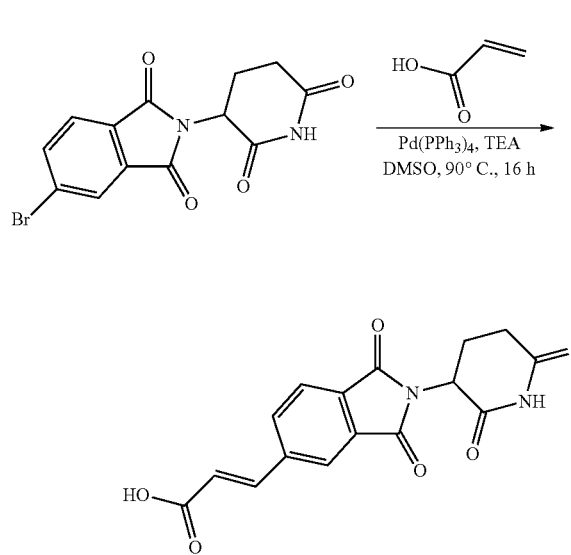

A mixture of 5-bromo-2-(2,6-dioxopiperidin-3-yl)isoindoline-1,3-dione (200 mg, 0.60 mmol), acrylic acid (65 mg, 0.90 mmol), Pd(PPh$_3$)$_4$ (69 mg, 0.06 mmol) and TEA (182 mg, 1.8 mmol) in DMSO (15 mL) was stirred at 90° C. for 16 h. The reaction mixture was concentrated and the residue was purified by reverse phase chromatography to give the desired product (82 mg, 42% yield) as a pale brown solid. MS (ESI) m/z: 327.1 [M−H]$^-$.

Step 2. Synthesis of 3-(2-(2,6-dioxopiperidin-3-yl)-1,3-dioxoisoindolin-5-yl)propanoic acid

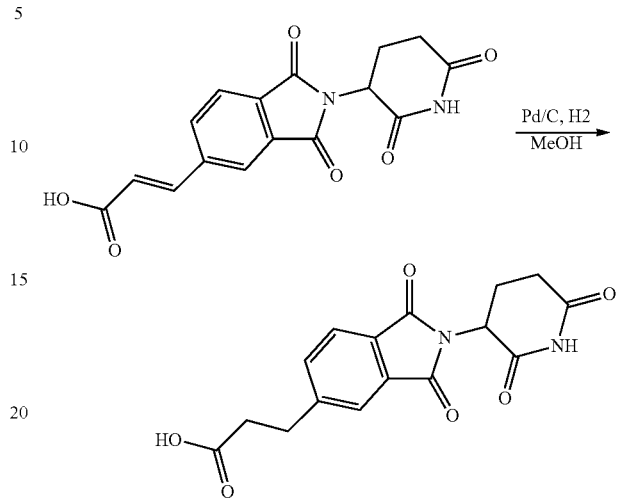

A mixture of (E)-3-(2-(2,6-dioxopiperidin-3-yl)-1,3-dioxoisoindolin-5-yl)acrylic acid (50 mg, 0.15 mmol) and Pd/C (10 mg) in methanol (5 mL) was stirred under H$_2$ (1 atm, balloon) at room temperature for 3 h. The reaction mixture was purified by reverse phase chromatography to give the desired product (31 mg, 62% yield) as a light brown solid. MS (ESI) m/z: 329.1 [M−H]$^-$.

Step 3. Synthesis of 2-(2,6-dioxopiperidin-3-yl)-5-(3-(4-(6-(6-((R)-2-(3-fluorophenyl) pyrrolidin-1-yl) imidazo[1,2-b]pyridazin-3-yl)pyridin-2-yl)piperazin-1-yl)-3-oxopropyl)isoindoline-1,3-dione (TR-194)

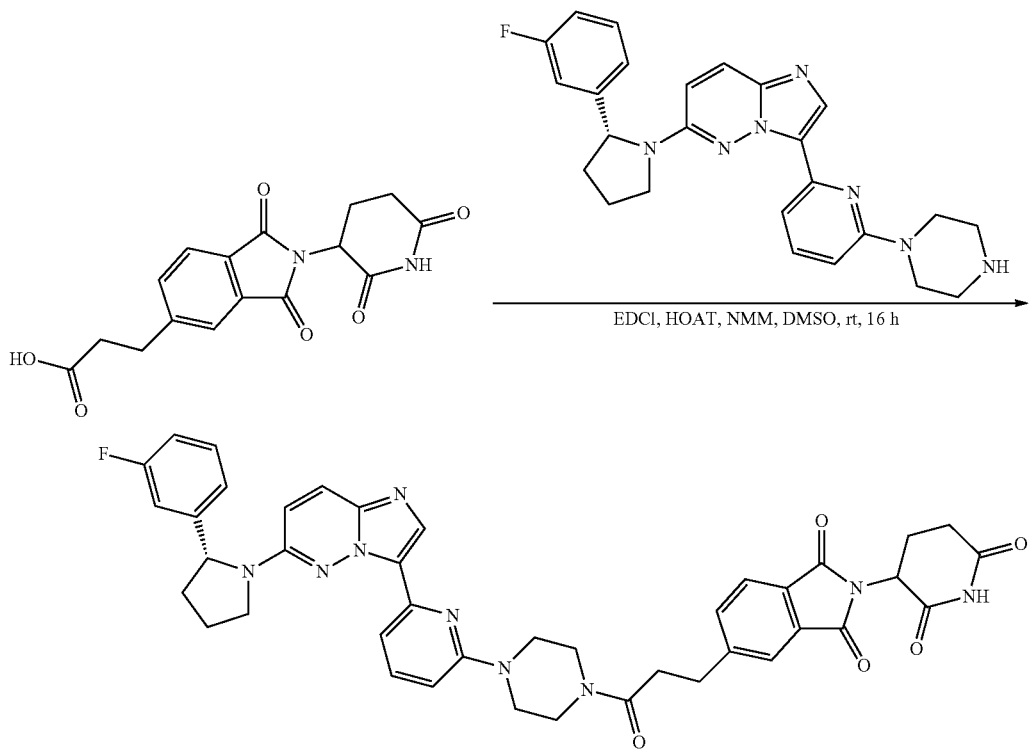

A mixture of 3-(2-(2,6-dioxopiperidin-3-yl)-1,3-dioxoisoindolin-5-yl)propanoic acid (20 mg, 0.06 mmol), (R)-6-(2-(3-fluorophenyl)pyrrolidin-1-yl)-3-(6-(piperazin-1-yl)pyridin-2-yl) imidazo[1,2-b]pyridazine (27 mg, 0.06 mmol), EDCI (17 mg, 0.09 mmol), NMM (30 mg, 0.30 mmol) and HOAT (12 mg, 0.09 mmol) in DMSO (1.5 mL) were stirred at room temperature for 16 h. LCMS showed the reaction was completed. The mixture was concentrated and purified by reverse phase chromatography to give the desired product (16 mg, 36% yield) as a light yellow solid. MS (ESI) m/z: 756.3 [M+H]$^+$.

Example 245: 2-(2,6-Dioxopiperidin-3-yl)-5-((E)-3-(4-(6-(6-((R)-2-(3-fluorophenyl)pyrrolidin-1-yl)imidazo[1,2-b]pyridazin-3-yl)pyridin-2-yl)piperazin-1-yl)-3-oxoprop-1-en-1-yl)isoindoline-1,3-dione (TR-195)

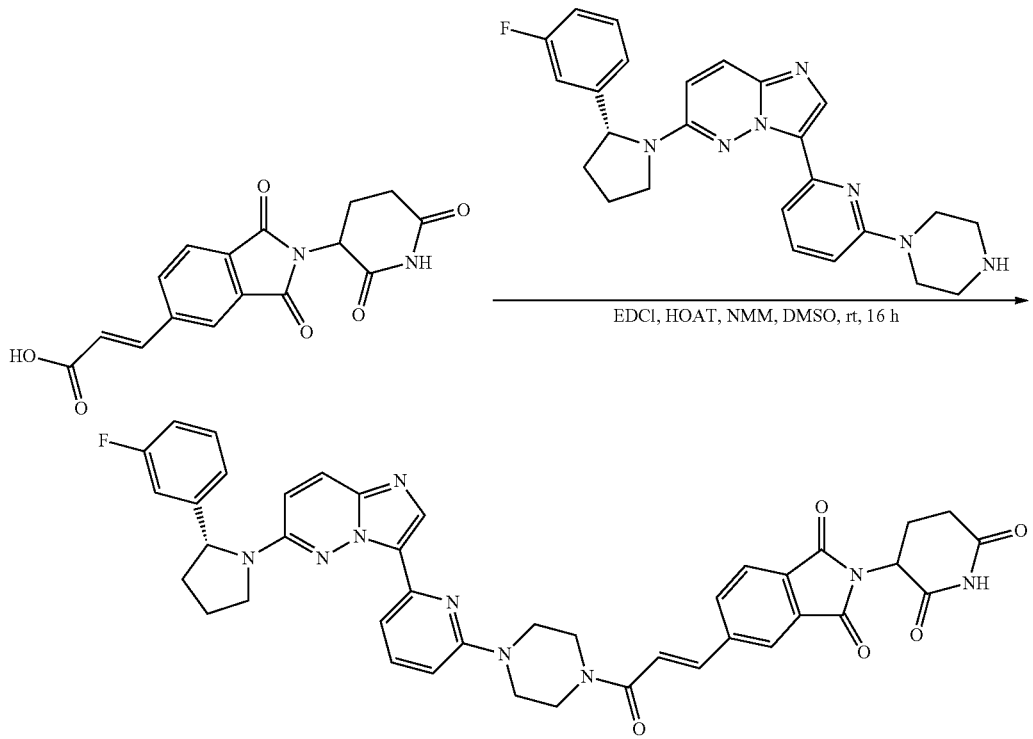

A mixture of (E)-3-(2-(2,6-dioxopiperidin-3-yl)-1,3-dioxoisoindolin-5-yl)acrylic acid (20 mg, 0.06 mmol), (R)-6-(2-(3-fluorophenyl)pyrrolidin-1-yl)-3-(6-(piperazin-1-yl)pyridin-2-yl) imidazo[1,2-b]pyridazine (27 mg, 0.06 mmol), EDCI (17 mg, 0.09 mmol), NMM (30 mg, 0.30 mmol) and HOAT (12 mg, 0.09 mmol) in DMSO (1.5 mL) were stirred at room temperature for 16 h. LCMS showed the reaction was completed. The mixture was concentrated and purified by reverse phase chromatography to give the desired product (21 mg, 46% yield) as a light yellow solid. MS (ESI) m/z: 754.3[M+H]$^+$.

Example 246: 3-(6-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-1-oxoisoindolin-2-yl)piperidine-2,6-dione (TR-196)

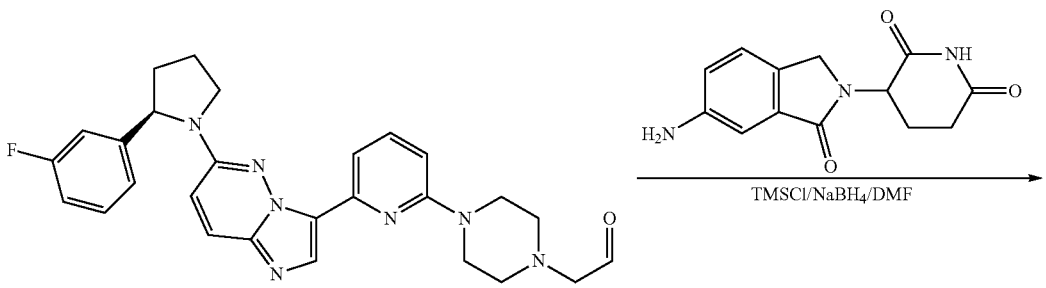

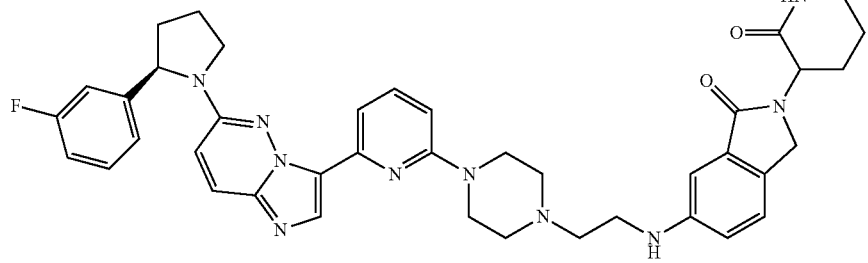

To a solution of (R)-2-(4-(6-(6-(2-(3-fluorophenyl)pyrrolidin-1-yl)imidazo[1,2-b]pyridazin-3-yl)pyridin-2-yl)piperazin-1-yl)acetaldehyde (5 mg, 10.30 umol) and 3-(6-amino-1-oxoisoindolin-2-yl)piperidine-2,6-dione (3 mg, 11.57 umol) in DMF (1 mL) were added TMSCl (3.34 mg, 30.89 umol) and NaBH$_4$ (782.61 ug, 20.59 umol) at 0° C. The reaction mixture was stirred at 0° C. for another 1.5 h, then it was warmed to room temperature and stirred for 16 h. The reaction mixture was purified by prep-HPLC to give 5 mg of crude product which was further purified by prep-TLC (DMC/MeOH=10/1) to give desired product (2.15 mg, 29% yield) as a white solid. MS (ESI) m/z: 729.8 [M+H]$^+$.

Example 247: 2-(2,6-Dioxopiperidin-3-yl)-5-((4-(6-(6-((R)-2-(3-fluorophenyl)pyrrolidin-1-yl)imidazo[1,2-b]pyridazin-3-yl)pyridin-2-yl)piperazin-1-yl)methyl)isoindoline-1,3-dione (TR-197)

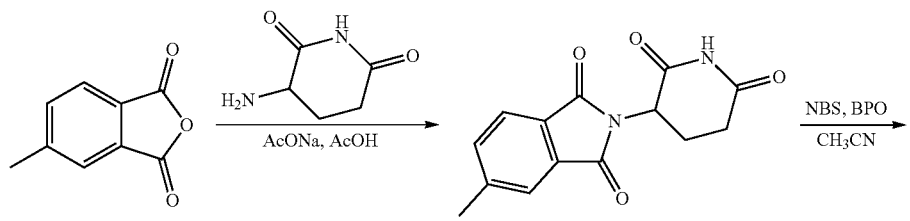

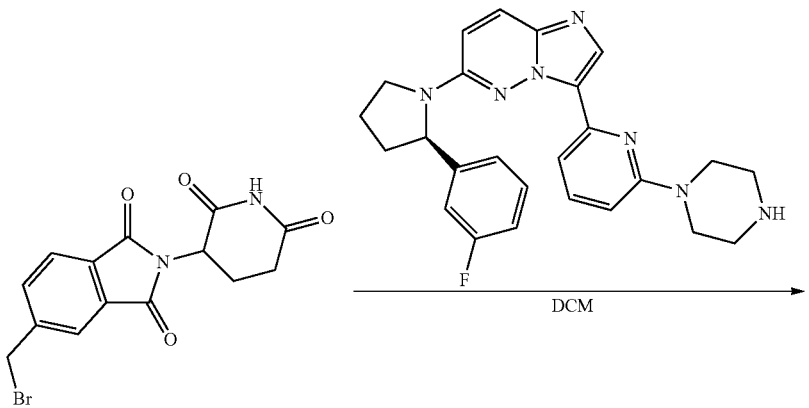

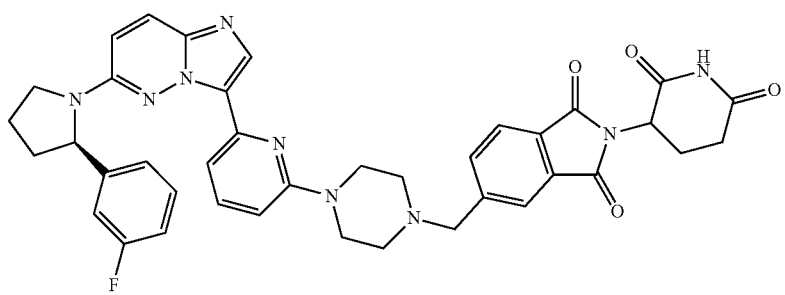

545

Step 1. Synthesis of 2-(2,6-dioxopiperidin-3-yl)-5-methylisoindoline-1,3-dione

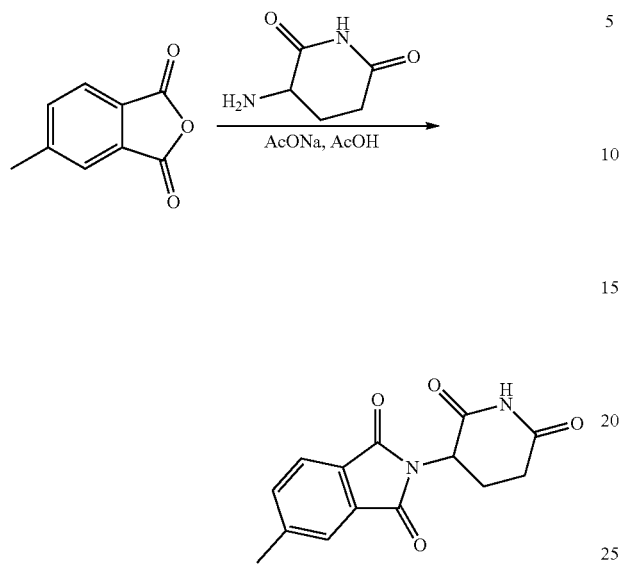

The mixture of isobenzofuran-1,3-dione (15 g, 101.27 mmol), 3-aminopiperidine-2,6-dione (19.46 g, 151.91 mmol) and NaOAc (101.27 mmol) were stirred in AcOH (300 mL) at 100° C. for 16 h. LCMS showed the reaction was completed. The solvent was removed under vacuum to give the crude product which was used for next step without further purification (25 g, 90% yield). MS (ESI) m/z: 273.4 [M+H]+.

546

Step 2. Synthesis of 5-(bromomethyl)-2-(2,6-dioxopiperidin-3-yl)isoindoline-1,3-dione

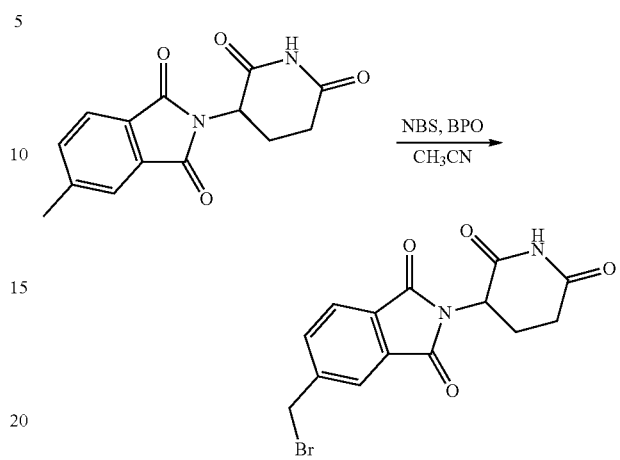

The mixture of 2-(2,6-dioxopiperidin-3-yl) 5-methylisoindoline-1,3-dione (1 g, 3.67 mmol), NBS (719.10 mg, 4.04 mmol) and BPO (45.41 mg, 734.60 umol) in CH₃CN (50 mL) were stirred at 90° C. for 4 h. The solvent was removed under vacuum to give the crude product which was purified by silica gel chromatography (petroleum ether/EtOAc=5/1) to give the desired product as an off-white solid (1 g, 58% yield). MS (ESI) m/z: 353.3 [M+H]+.

Step 3. Synthesis of 2-(2,6-dioxopiperidin-3-yl)-5-((4-(6-(6-((R)-2-(3-fluorophenyl)pyrrolidin-1-yl)imidazo[1,2-b]pyridazin-3-yl)pyridin-2-yl)piperazin-1-yl)methyl)isoindoline-1,3-dione (TR-197)

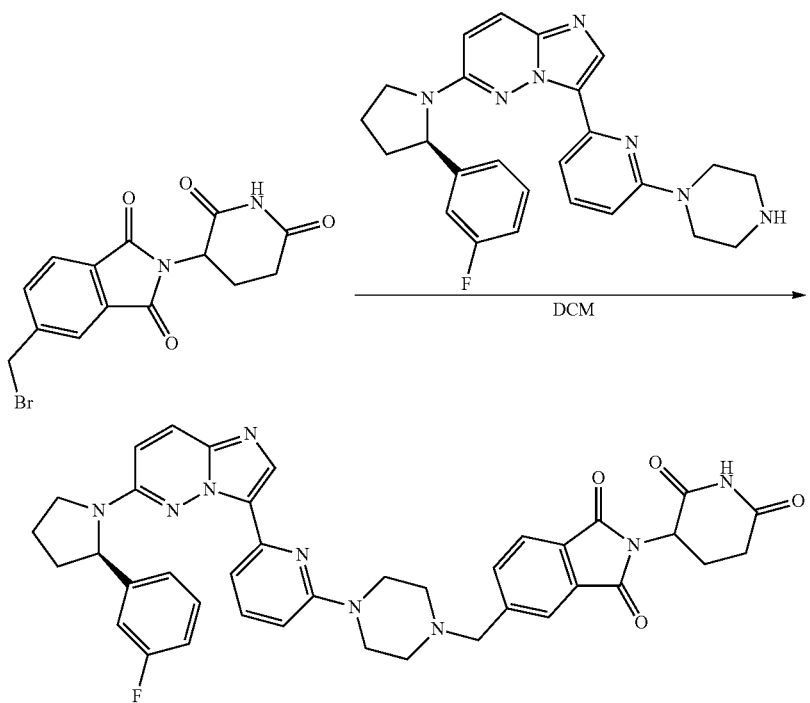

To a solution of (R)-6-(2-(3-fluorophenyl)pyrrolidin-1-yl)-3-(6-(piperazin-1-yl)pyridin-2-yl)imidazo[1,2-b]pyridazine (0.020 g, 45.09 umol) in DCM (5 mL) was added 5-(bromomethyl)-2-(2,6-dioxopiperidin-3-yl)isoindoline-1,3-dione (47.50 mg, 135.28 umol), then the reaction was stirred for 16 h. LCMS showed the reaction was completed. The mixture was purified by Prep-TLC (DCM/MEOH=100/2) to give the desired product as an off-white solid (1.9 mg, 6% yield). MS (ESI) m/z: 714.7 [M+H]⁺.

Example 248: 2-(2,6-Dioxopiperidin-3-yl)-5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)azetidin-1-yl)isoindoline-1,3-dione (TR-198)

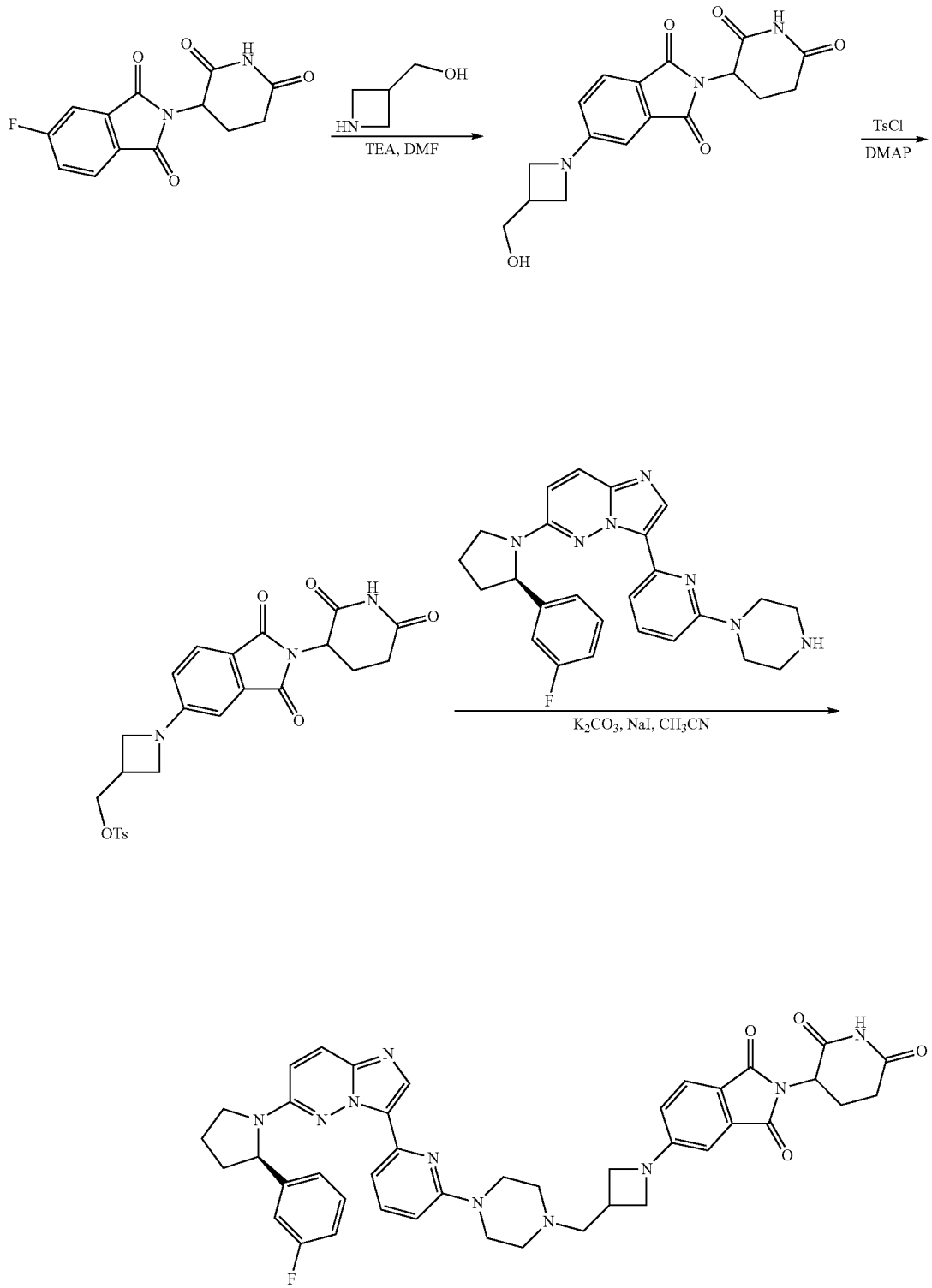

Step 1. Synthesis of 2-(2,6-dioxopiperidin-3-yl)-5-(13-(hydroxymethyl)azetidin-1-yl)isoindoline-1,3-dione

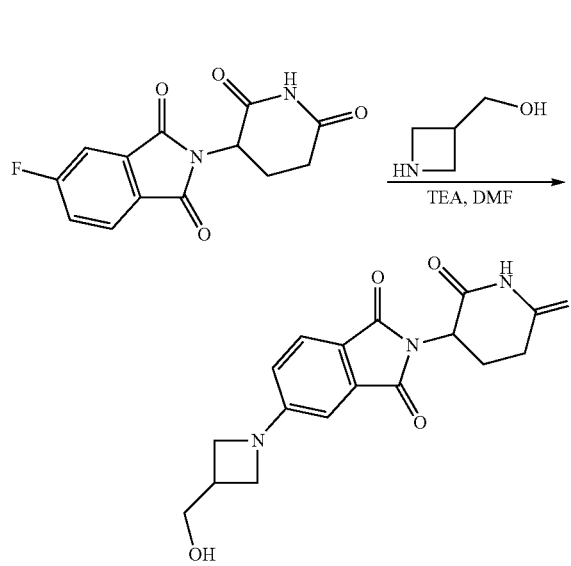

The mixture of 2-(2,6-dioxopiperidin-3-yl)-5-fluoroisoindoline-1,3-dione (2 g, 7.24 mmol), azetidin-3-ylmethanol (693.88 mg, 7.96 mmol) and TEA (2.20 g, 21.72 mmol) were stirred in DMF (10 mL) at 85° C. for 1 h. LCMS showed the reaction was completed. The mixture was extracted with EtOAc, washed with brine, dried over Na$_2$SO$_4$, concentrated to give the crude product which was purified by reverse phase chromatography to give the desired product as a yellow solid (800 mg, 32% yield). MS (ESI) m/z: 344.2 [M+H]$^+$.

Step 2. Synthesis of (1-(2-(2,6-dioxopiperidin-3-yl)-1,3-dioxoisoindolin-5-yl)azetidin-3-yl)methyl 4-methylbenzenesulfonate

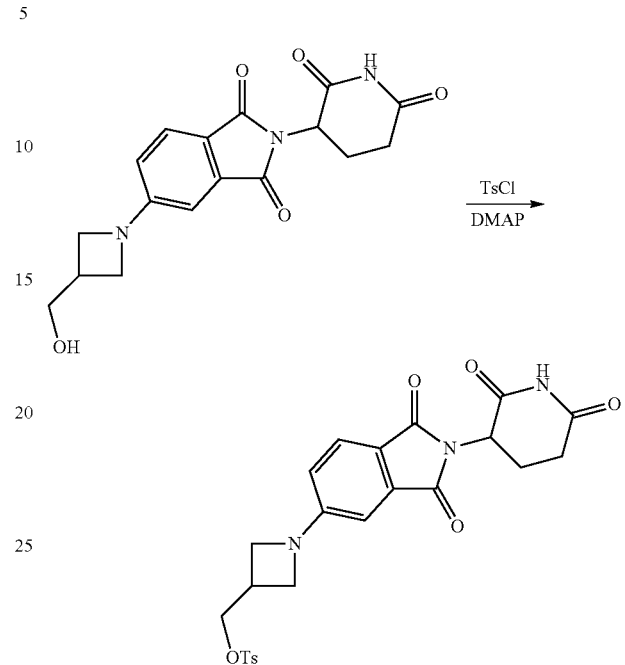

To a solution of 2-(2,6-dioxopiperidin-3-yl)-5-(3-(hydroxymethyl)azetidin-1-yl)isoindoline-1,3-dione (0.034 g, 99.03 umol) and DMAP (24.20 mg, 198.06 umol) in pyridine (2 mL) was added TsCl (13.97 mg, 198.06 umol), then the reaction was stirred for 4 h. The mixture was purified by silica gel chromatography (petroleum ether/EtOAc=1/1) to give the product as a yellow solid which was further purified by reverse phase chromatography to give the purified product as a yellow solid (25 mg, 51% yield). MS (ESI) m/z: 498.4 [M+H]$^+$.

Step 3. Synthesis of 2-(2,6-Dioxopiperidin-3-yl)-5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)azetidin-1-yl)isoindoline-1,3-dione

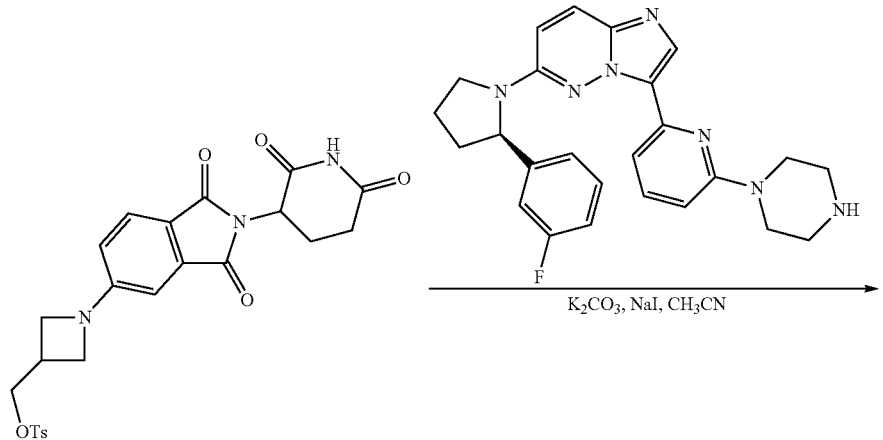

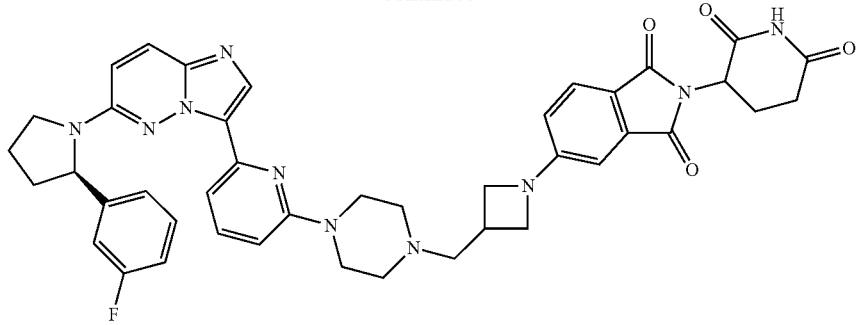

The mixture of (R)-6-(2-(3-fluorophenyl)pyrrolidin-1-yl)-3-(6-(piperazin-1-yl)pyridin-2-yl)imidazo[1,2-b]pyridazine (0.015 g, 33.82 umol), (1-(2-(2,6-dioxopiperidin-3-yl)-1,3-dioxoisoindolin-5-yl)azetidin-3-yl)methyl 4-methylbenzenesulfonate (21.00 mg, 42.21 umol), K₂CO₃ (14.00 mg, 101.46 umol) and NaI (10.14 mg, 67.64 umol) in CH₃CN (3 mL) were stirred at 82° C. for 16 h. LCMS showed the reaction was completed. The mixture was purified by reverse phase chromatography to give the desired product as a yellow solid (12 mg, 46% yield). MS (ESI) m/z: 769.8 [M+H]⁺.

Example 249: 2-(2,6-Dioxopiperidin-3-yl)-5-((3-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)propyl)amino)isoindoline-1,3-dione (TR-199)

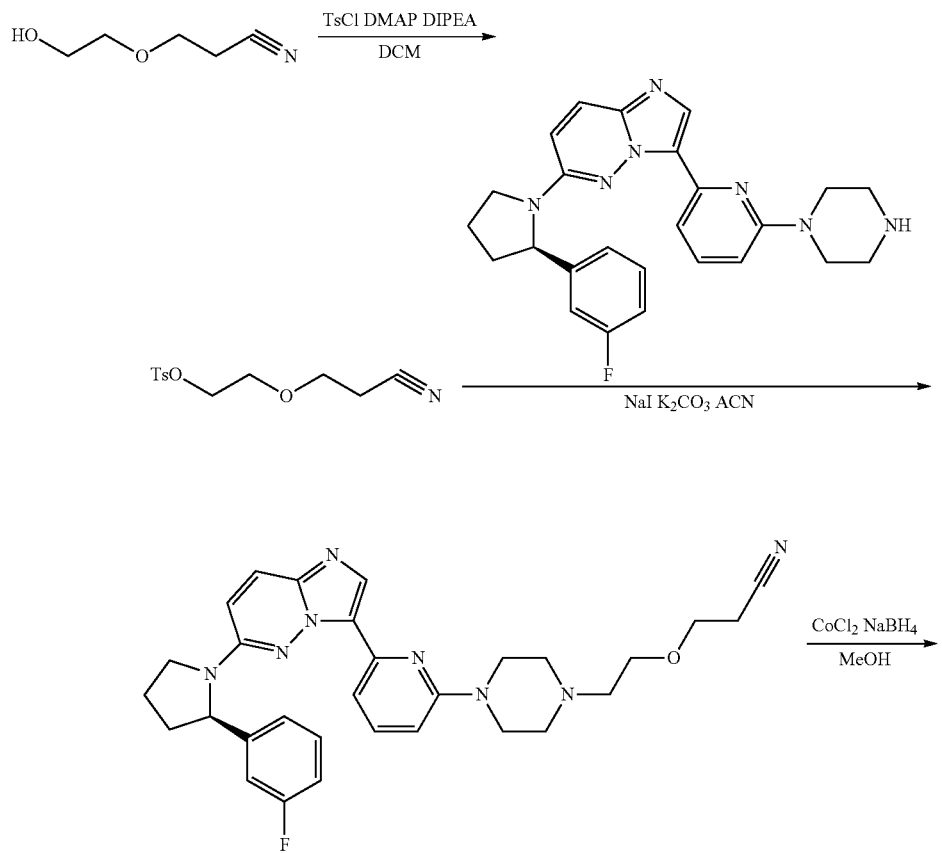

553    554

-continued

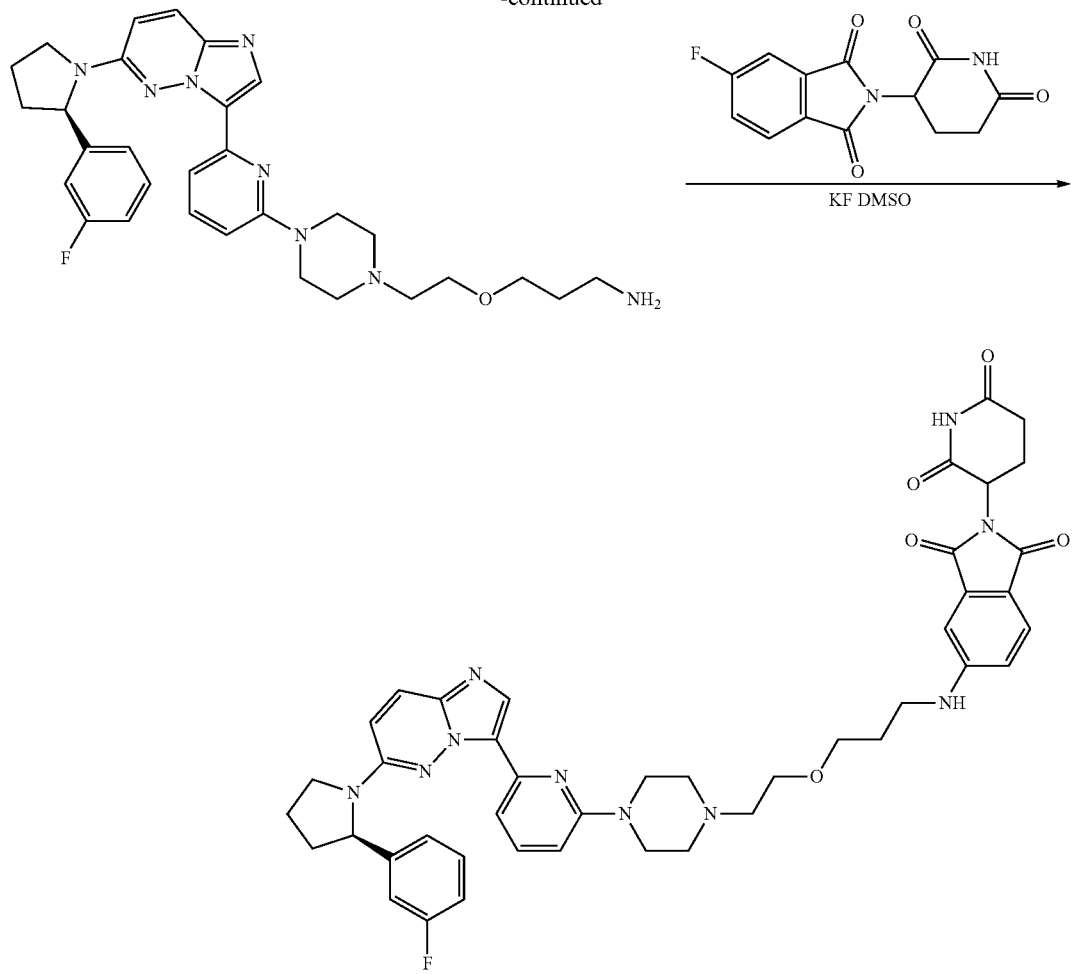

KF DMSO

Step 1. Synthesis of 2-(2-cyanoethoxy)ethyl 4-methylbenzenesulfonate

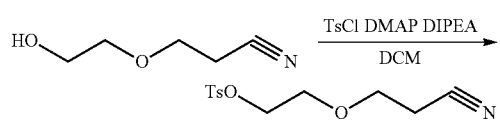

To a solution 3-(2-hydroxyethoxy)propanenitrile (100 mg, 868.58 umol) in DCM (5 mL) were added C4-methylbenzenesulfonyl chloride (250 mg, 1.31 mmol) and DMAP (21.22 mg, 173.72 umol) DIPEA (336.77 mg, 2.61 mmol). The resulting solution was stirred at 10° C. overnight. The resulting residue was purified by reverse-phase chromatography to yield the desired product as a white solid (178 mg, 76% yield). MS (ESI) m/z: 270.8 [M+H]+.

Step 2. Synthesis of (R)-3-(2-(4-(6-(6-(2-(3-fluorophenyl)pyrrolidin-1-yl)imidazo[1,2-b]pyridazin-3-yl)pyridin-2-yl)piperazin-1-yl)ethoxy)propanenitrile

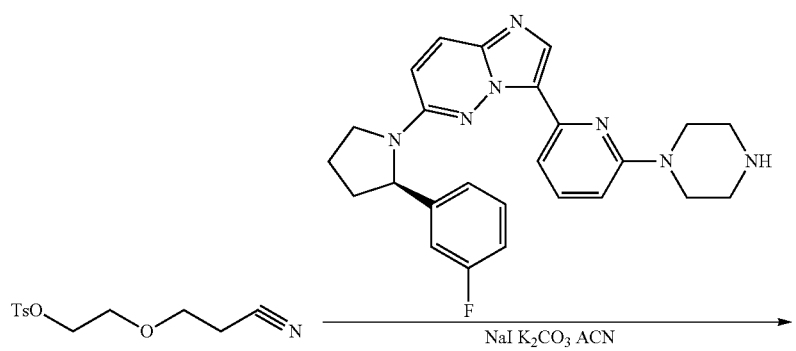

NaI K₂CO₃ ACN

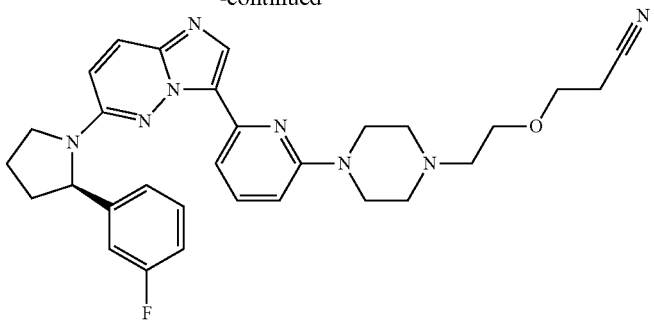

A solution (R)-6-(2-(3-fluorophenyl)pyrrolidin-1-yl)-3-(6-(piperazin-1-yl)pyridin-2-yl)imidazo[1,2-b]pyridazine (108 mg, 243.51 umol) in ACN (5 mL) were added C2-(2-cyanoethoxy)ethyl 4-methylbenzenesulfonate (178 mg, 660.93 umol) and NaI (11.9 mg, 79.39 umol) $K_2CO_3$ (165 mg, 1.20 mmol). The resulting solution was stirred at 80° C. overnight. The resulting residue was purified by reverse-phase chromatography to yield the desired product as a white solid (100 mg, 76% yield). MS (ESI) m/z: 541.5 [M+H]$^+$.

Step 3. Synthesis of (R)-3-(2-(4-(6-(6-(2-(3-fluorophenyl)pyrrolidin-1-yl)imidazo[1,2-b]pyridazin-3-yl)pyridin-2-yl)piperazin-1-yl)ethoxy)propan-1-amine

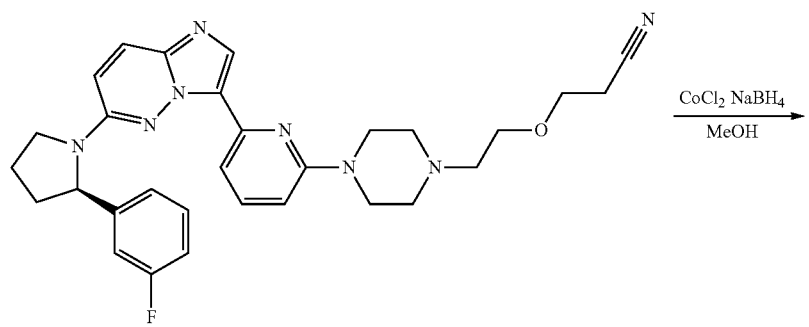

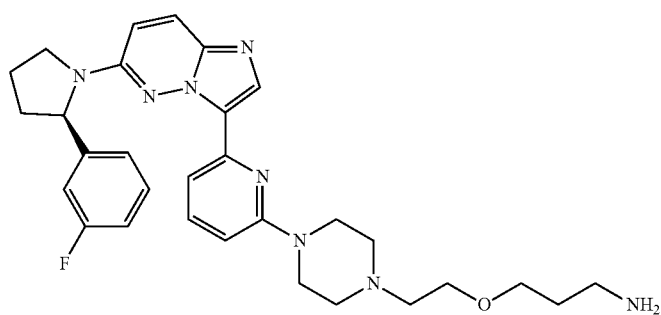

A solution (R)-3-(2-(4-(6-(6-(2-(3-fluorophenyl)pyrrolidin-1-yl)imidazo[1,2-b]pyridazin-3-yl)pyridin-2-yl)piperazin-1-yl)ethoxy)propanenitrile (100 mg, 184.97 umol) in MeOH (5 mL) were added NaBH$_4$ (130 mg, 184.97 umol) CoCl$_2$ (50 mg, 184.97 umol). The resulting solution was stirred at 0° C. overnight. The resulting residue was quenched by ammonia, concentrated, diluted with 10 ml 1% HCl and extracted with DCM/MeOH=10/1 (10 mL). The organic phase was concentrated and the residue was purified by reverse-phase chromatography to yield the desired product as a white solid (20 mg, 20% yield). MS (ESI) m/z: 545.6 [M+H]$^+$.

Step 4. Synthesis of 2-(2,6-dioxopiperidin-3-yl)-5-((3-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)propyl)amino)isoindoline-1,3-dione (TR-199)

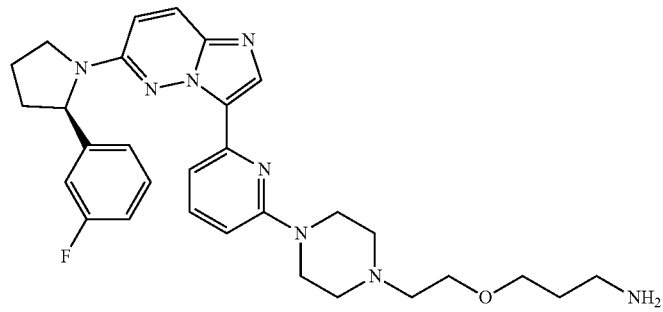
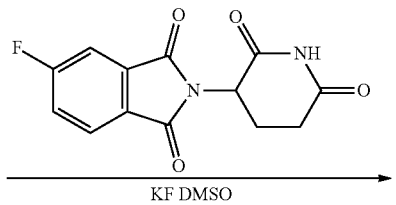
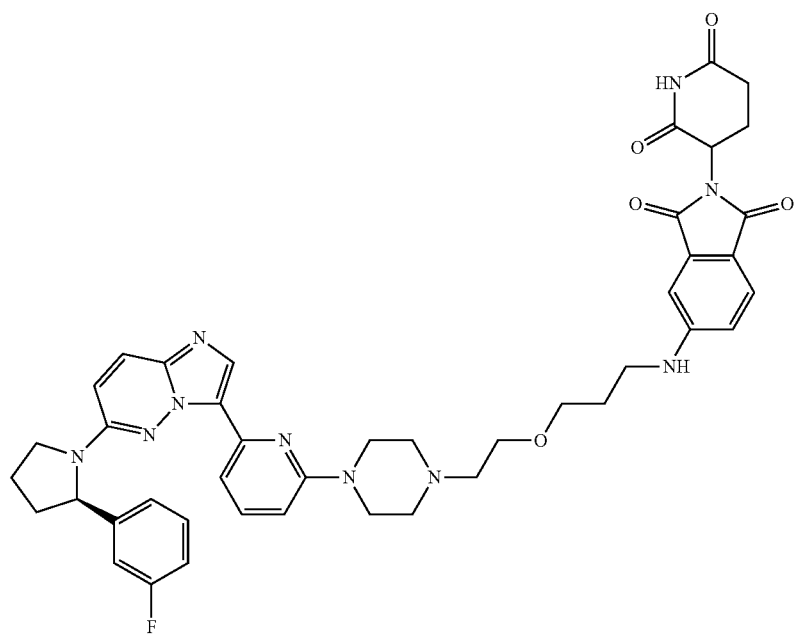

A solution (R)-3-(2-(4-(6-(6-(2-(3-fluorophenyl)pyrrolidin-1-yl)imidazo[1,2-b]pyridazin-3-yl)pyridin-2-yl)piperazin-1-yl)ethoxy)propan-1-amine (20 mg, 36.72 umol) in DMSO (1 mL) were added KF (2.13 mg, 36.72 umol) and 2-(2,6-dioxo-3-piperidyl)-5-fluoro-isoindoline-1,3-dione (10 mg, 36.20 umol). The resulting solution was stirred at 105° C. for 8 h. The resulting residue was purified by reverse-phase chromatography to yield the desired product as a white solid (5 mg, 17% yield). MS (ESI) m z: 801.8 [M+H]$^+$.

Example 250: 3-(5-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)-1-oxoisoindolin-2-yl)piperidine-2,6-dione (TR-200)
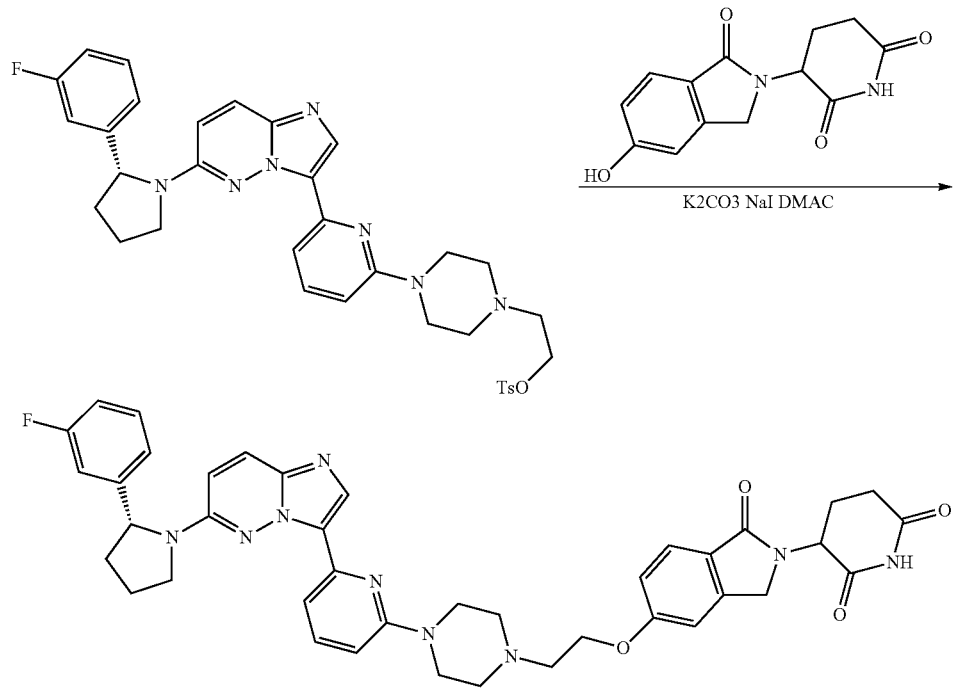
TR-200 was synthesized following the standard procedure for preparing TR-201. MS (ESI) m/z: 730.7 [M+H]$^+$.
Example 251: 3-(6-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)-1-oxoisoindolin-2-yl)piperidine-2,6-dione (TR-201)
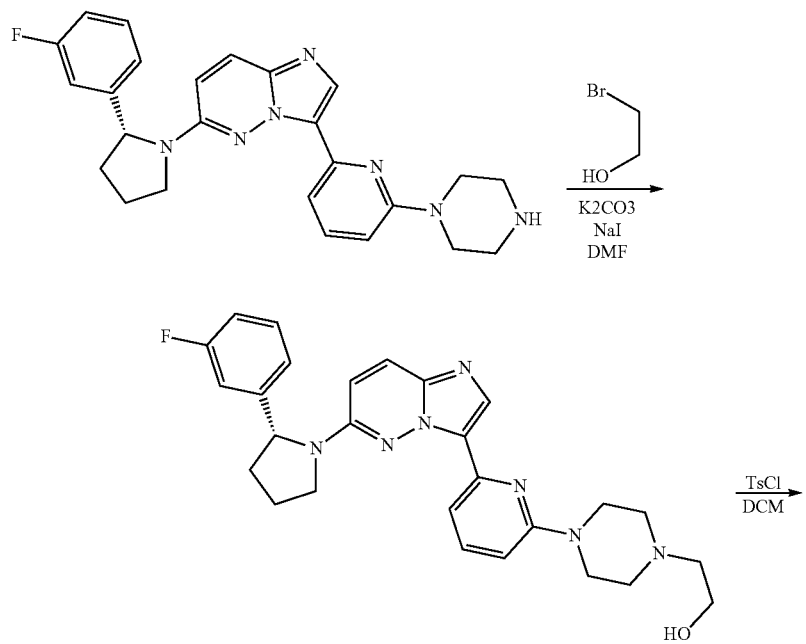

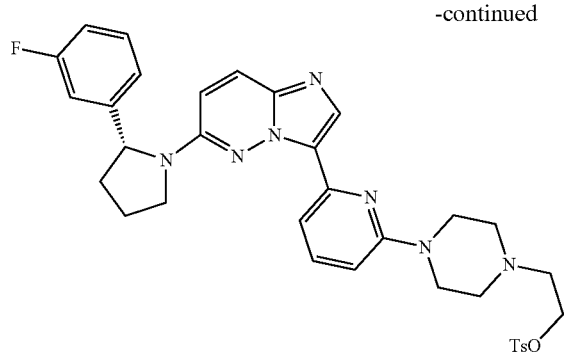 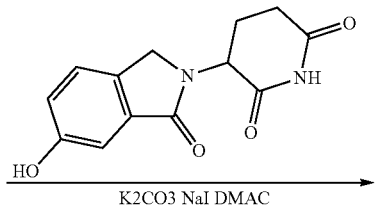

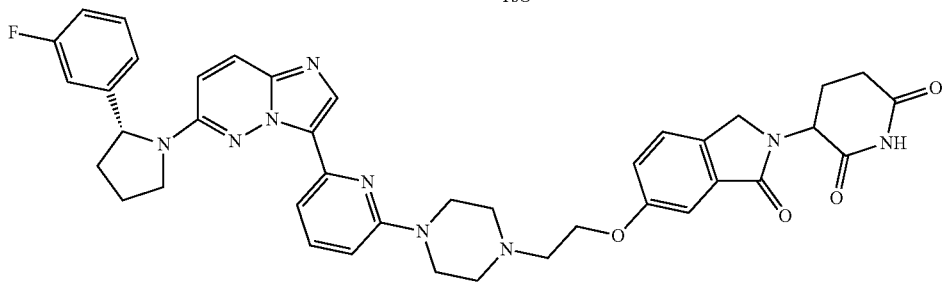

Step 1. Synthesis of (R)-2-(4-(6-(6-(2-(3-fluorophenyl)pyrrolidin-1-yl)imidazo[1,2-b]pyridazin-3-yl)pyridin-2-yl)piperazin-1-yl)ethan-1-ol Step 2. Synthesis of (R)-2-(4-(6-(6-(2-(3-fluorophenyl)pyrrolidin-1-yl)imidazo[1,2-b]pyridazin-3-yl)pyridin-2-yl)piperazin-1-yl)ethyl 4-methylbenzenesulfonate

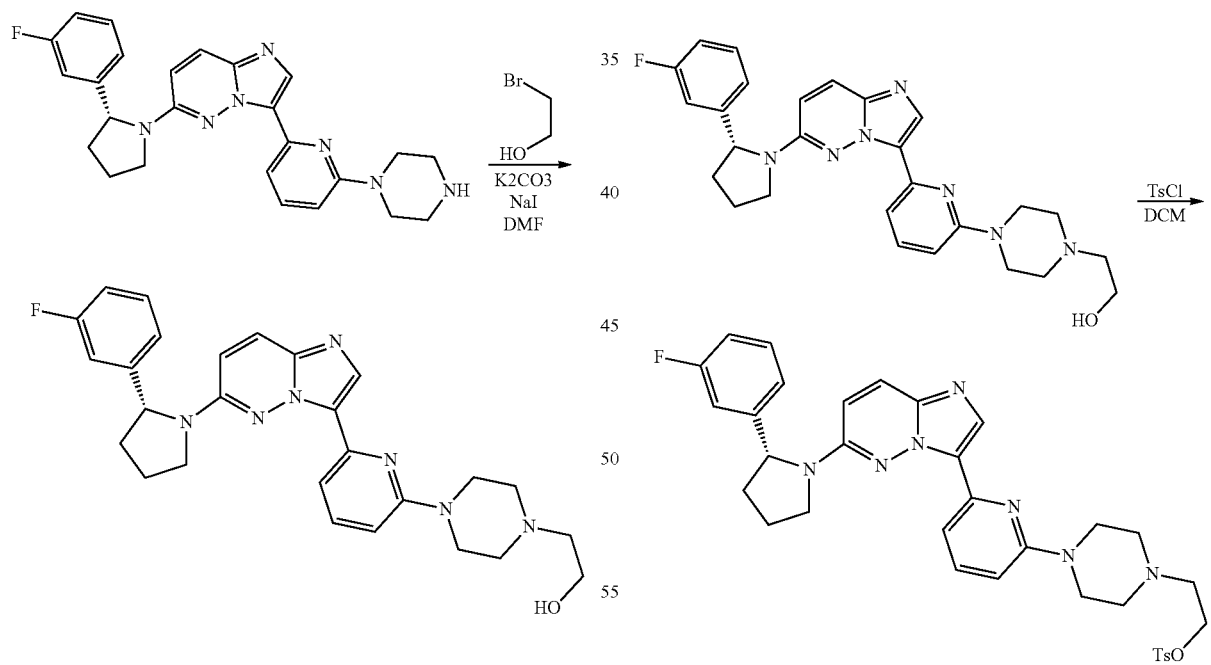

A mixture of (R)-6-(2-(3-fluorophenyl)pyrrolidin-1-yl)-3-(6-(piperazin-1-yl)pyridin-2-yl)imidazo[1,2-b]pyridazine (500 mg, 1.12 mmol), 2-bromoethan-1-ol (211.6 mg, 1.69 mmol), K₂CO₃ (463 mg, 3.36 mmol) and NaI (169.3 mg, 1.12 mmol) in DMF (20 mL) were stirred at 100° C. for 16 h.

The mixture was filtered and purified by reverse phase chromatography to give the desired product (159 mg, 29% yield). MS (ESI) m/z: 488.3 [M+H]⁺.

To a solution (R)-2-(4-(6-(6-(2-(3-fluorophenyl)pyrrolidin-1-yl)imidazo[1,2-b]pyridazin-3-yl)pyridin-2-yl)piperazin-1-yl)ethan-1-ol (159 mg, 0.327 mmol) and TEA (99 mg, 0.98 mmol) in DCM (15 mL) was added 4-methylbenzenesulfonyl chloride (93 mg, 0.49 mmol) at room temperature, then it was stirred at room temperature for 4 h. The mixture was concentrated and purified by reverse phase chromatography to give the desired product (121 mg, 58% yield) as white solid. MS (ESI) m/z: 642.1 [M+H]⁺.

Step 3. Synthesis of 3-(6-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)-1-oxoisoindolin-2-yl)piperidine-2,6-dione

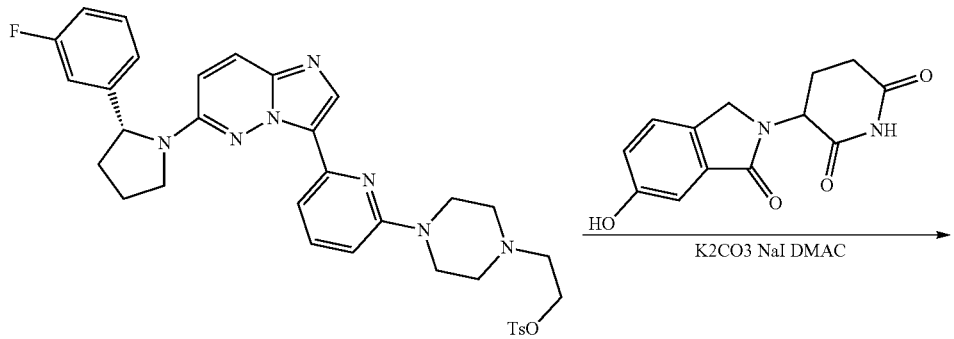

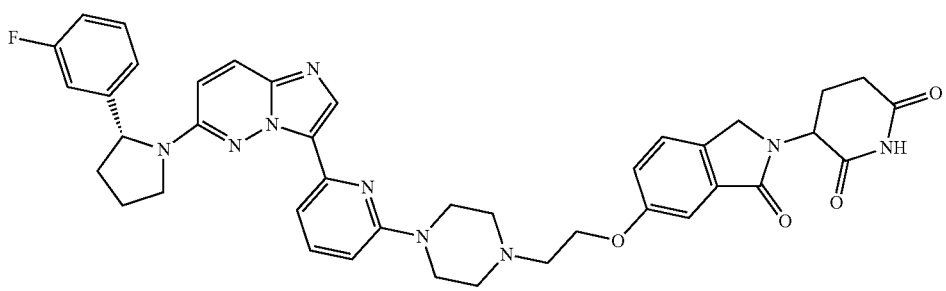

A mixture of (R)-2-(4-(6-(6-(2-(3-fluorophenyl)pyrrolidin-1-yl)imidazo[1,2-b]pyridazin-3-yl)pyridin-2-yl)piperazin-1-yl)ethyl 4-methylbenzenesulfonate (100 mg, 0.15 mmol), 3-(6-hydroxy-1-oxoisoindolin-2-yl)piperidine-2,6-dione (60.8 mg, 0.23 mmol), $K_2CO_3$ (61.6 mg, 0.45 mmol) and NaI (22.4 mg, 0.15 mmol) in $CH_3CN$ (3 mL) were stirred at 80° C. for 5 h. LCMS showed the reaction was completed. The mixture was concentrated and purified by reverse phase chromatography to give the desired product (32.8 mg, 30% yield) as a white solid. MS (ESI) m/z: 730.7 $[M+H]^+$.

Example 252: 5-((2-(4-(6-(6-((R)-2-(3-Fluorophenyl)pyrrolidin-1-yl)imidazo[1,2-b]pyridazin-3-yl)pyridin-2-yl)piperazin-1-yl)-2-oxoethyl)amino)-2-(1-methyl-2,6-dioxopiperidin-3-yl)isoindoline-1,3-dione (TR-123 Neg)

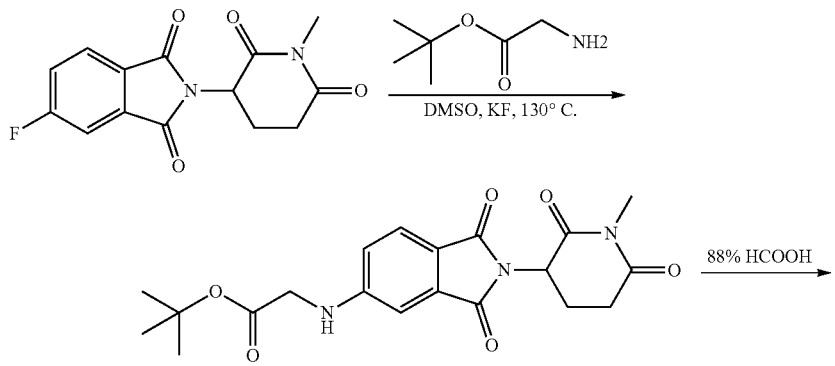

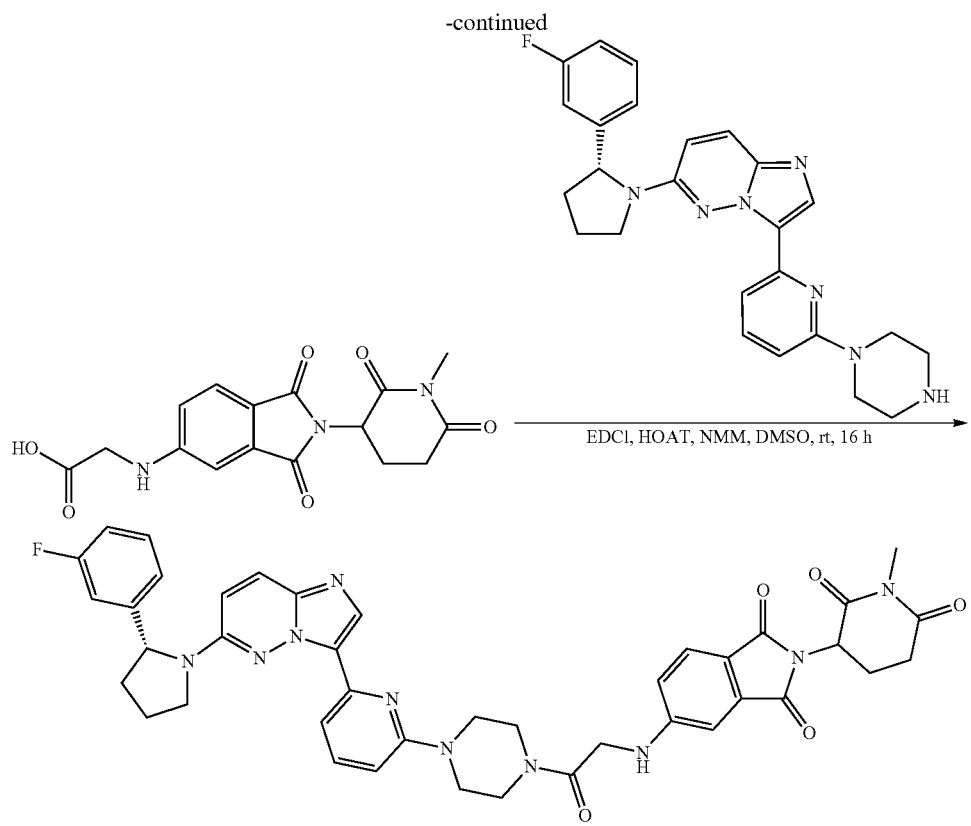

Step 1. Synthesis of tert-butyl (2-(1-methyl-2,6-dioxopiperidin-3-yl)-1,3-dioxoisoindolin-5-yl)glycinate Step 2. Synthesis of (2-(1-methyl-2,6-dioxopiperidin-3-yl)-1,3-dioxoisoindolin-5-yl)glycine

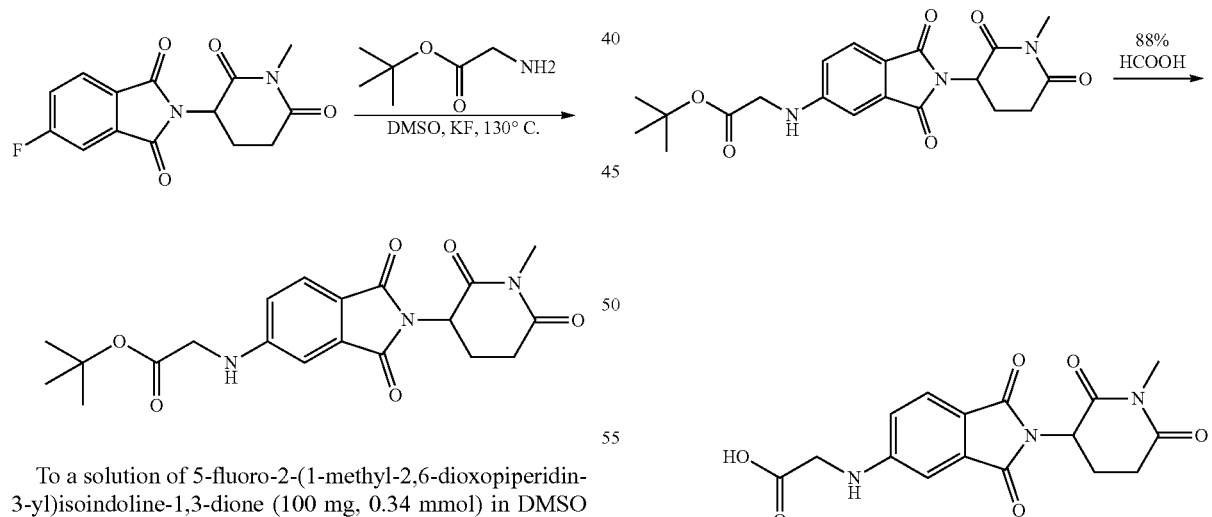

To a solution of 5-fluoro-2-(1-methyl-2,6-dioxopiperidin-3-yl)isoindoline-1,3-dione (100 mg, 0.34 mmol) in DMSO (3 mL) were added KF (39 mg, 0.68 mmol) and tert-butyl glycinate (89 mg, 0.68 mmol). The resulting mixture was stirred at 130° C. for 5 h. The reaction was cooled to room temperature before H$_2$O (50 mL) was added. The mixture was extracted with EtOAc (10 mL×3). The combined organic layers were concentrated and the resulting residue was purified by reverse phase chromatography to give the desired product (82 mg, 61% yield) as pale brown solid. MS (ESI) m/z 402.2 [M+H]$^+$.

A mixture of tert-butyl (2-(1-methyl-2,6-dioxopiperidin-3-yl)-1,3-dioxoisoindolin-5-yl)glycinate (80 mg, 0.20 mmol) in HCOOH (88%, 5 mL) was stirred at room temperature for 16 h. The mixture was concentrated and the resulting residue was purified by reverse phase chromatography to give the desired product (54 mg, 78% yield) as pale brown solid. MS (ESI) m/z 346.1 [M+H]$^+$.

Step 3. Synthesis of 5-((2-(4-(6-(6-((R)-2-(3-fluoro-phenyl)pyrrolidin-1-yl)imidazo[1,2-b]pyridazin-3-yl)pyridin-2-yl)piperazin-1-yl)-2-oxoethyl)amino)-2-(1-methyl-2,6-dioxopiperidin-3-yl)isoindoline-1,3-dione

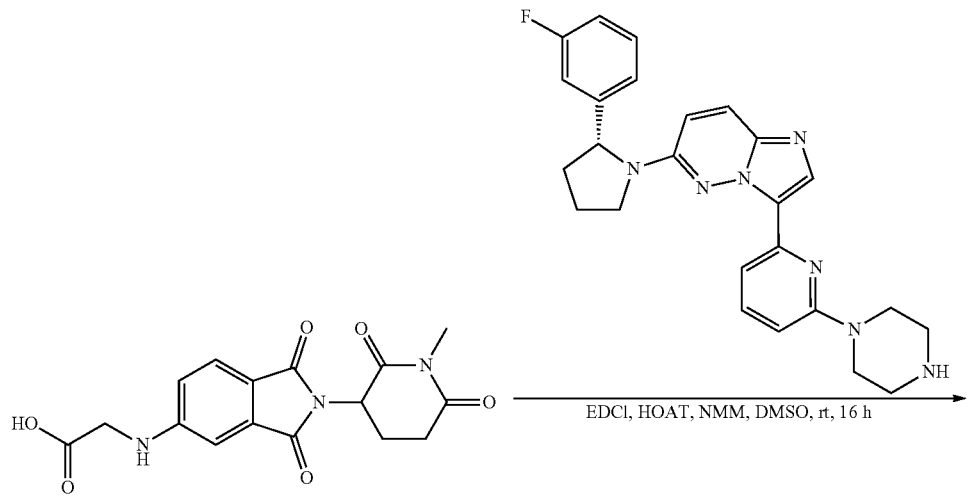

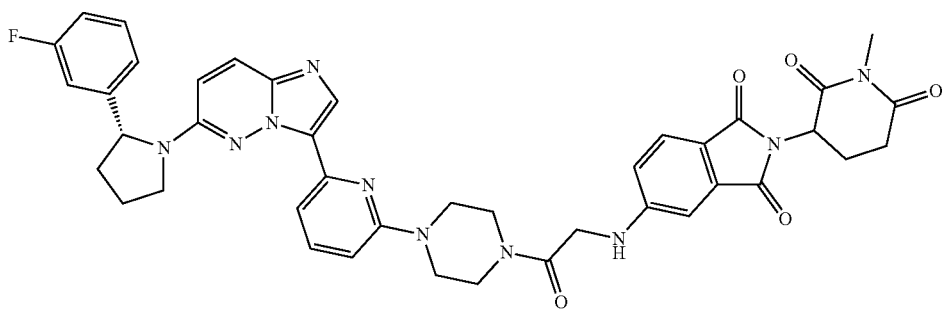

TR-123 neg was synthesized following the standard procedure for preparing TR-053 (18 mg, yield 51%). MS (ESI) m/z: 771.3 [M+H]$^+$.

Example 253: 3-(6-(3-(4-(6-(6-((R)-2-(3-Fluorophe-nyl)pyrrolidin-1-yl)imidazo[1,2-b]pyridazin-3-yl)pyridin-2-yl)piperazin-1-yl)-3-oxoprop-1-yn-1-yl)-1-oxoisoindolin-2-yl)piperidine-2,6-dione (TR-202)

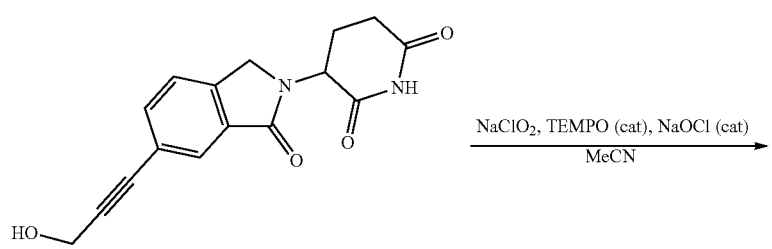

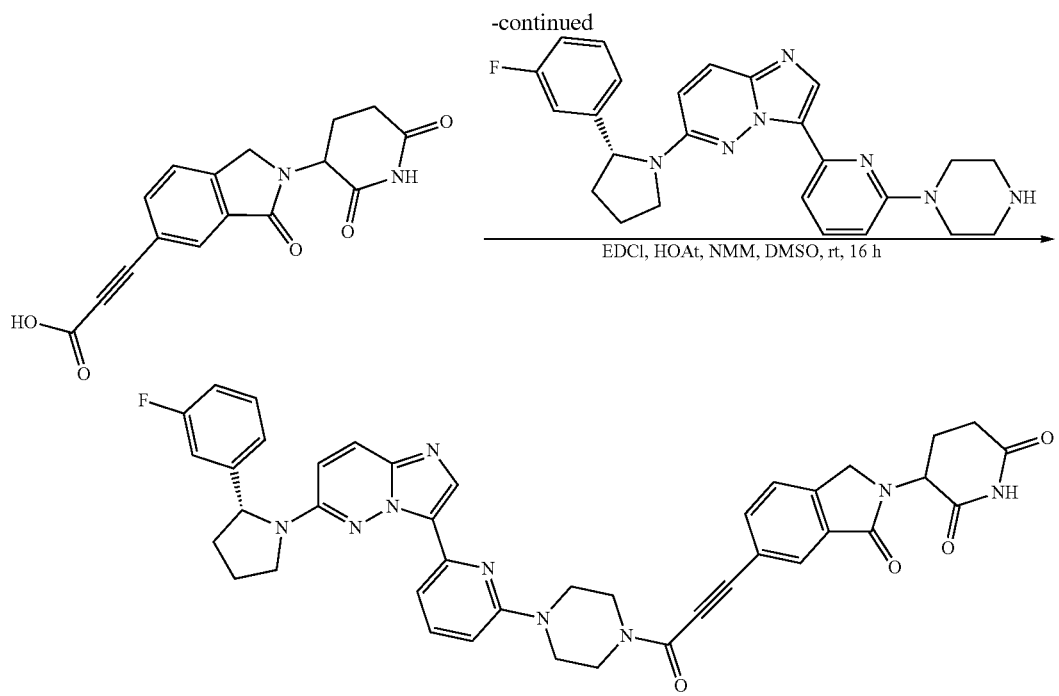

Step 1. Synthesis of 3-(2-(2,6-dioxopiperidin-3-yl)-3-oxoisoindolin-5-yl)propiolic acid

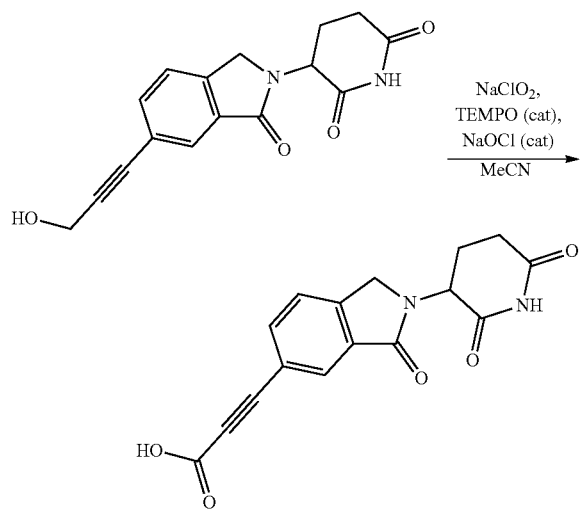

A mixture of 3-(6-(3-hydroxyprop-1-yn-1-yl)-1-oxoisoindolin-2-yl)piperidine-2,6-dione (100 mg, 0.34 mmol), TEMPO (2,2,6,6-tetramethyl-1-piperidinyloxy free radical) (5.2 mg, 0.034 mmol), acetonitrile (3 mL) and sodium phosphate buffer (1.3 mL, 0.67 M, pH=6.7) was stirred at 35° C. A solution of sodium chlorite was prepared by dissolving 80% $NaClO_2$ (9.14 g, 80.0 mmol) in water (40 mL) and a solution of dilute NaOCl was prepared by diluting household bleach (5.25% NaOCl, 1.06 mL, ca. 2.0 mol %) with water (19 mL). Then $NaClO_2$ solution (0.4 mL) was added followed by the dilute solution of NaOCl solution (0.2 mL). The resulting mixture was stirred at 35° C. until the reaction was completed. The reaction mixture was purified by reverse-phase chromatography to give the desired product (72 mg, 69% yield) as a light yellow solid. MS (ESI) m/z: 313.1 [M+H]$^+$.

Step 2. Synthesis of 3-(6-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxoprop-1-yn-1-yl)-1-oxoisoindolin-2-yl)piperidine-2,6-dione

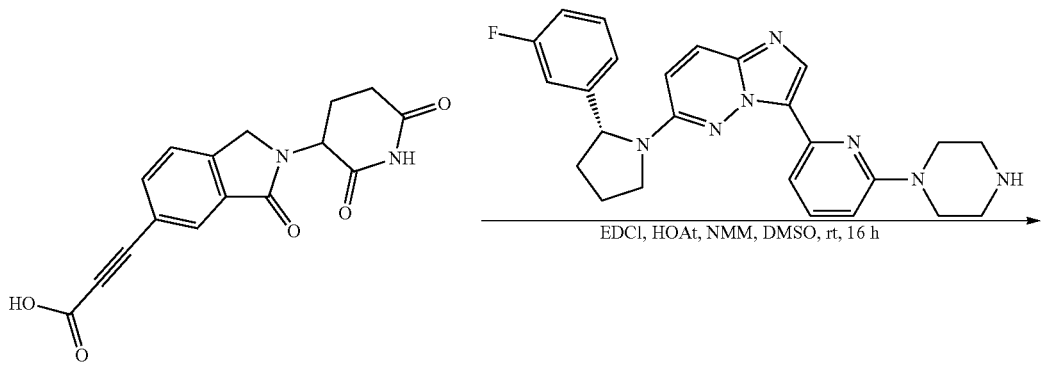

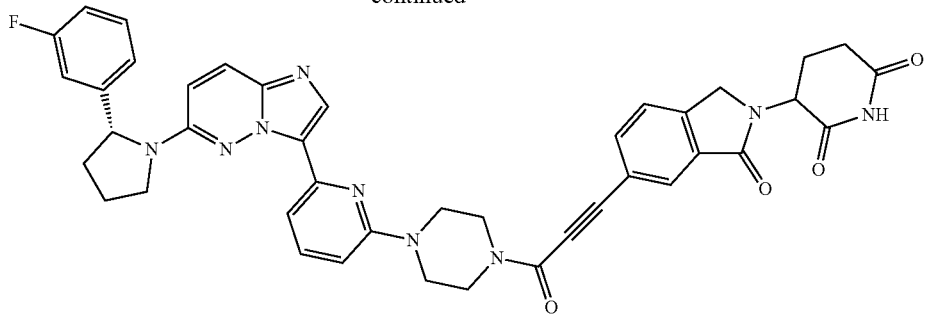

To a solution of 3-(2-(2,6-dioxopiperidin-3-yl)-3-oxoisoindolin-5-yl)propiolic acid (10 mg, 32.1 umol) in DMSO (1.5 mL) were added HOAt (6.5 mg, 48.1 umol), EDCI (9.2 mg, 48.1 umol), NMM (32.4 mg, 321.0 umol) and (R)-6-(2-(3-fluorophenyl)pyrrolidin-1-yl)-3-(6-(piperazin-1-yl)pyridin-2-yl)imidazo[1,2-b]pyridazine (14.2 mg, 32.1 umol) sequentially. After the resulting solution was stirred at 25° C. for 16 h, the reaction was poured into water (50 mL) and extracted with ethyl acetate (3×20 mL). The combined organic layers were washed with saturated brine (50 mL), dried over anhydrous sodium sulfate, filtered and concentrated under reduced pressure. The resulting residue was purified by reverse-phase chromatography to give the desired product 3-(6-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxoprop-1-yn-1-yl)-1-oxoisoindolin-2-yl)piperidine-2,6-dione (11.3 mg, 48% yield) as a light yellow solid. MS (ESI) m/z: 738.3 [M+H]$^+$.

Example 254: 3-(5-(3-(4-(6-(6-((R)-2-(3-Fluorophenyl)pyrrolidin-1-yl)imidazo[1,2-b]pyridazin-3-yl)pyridin-2-yl)piperazin-1-yl)-3-oxoprop-1-yn-1-yl)-1-oxoisoindolin-2-yl)piperidine-2,6-dione (TR-203)

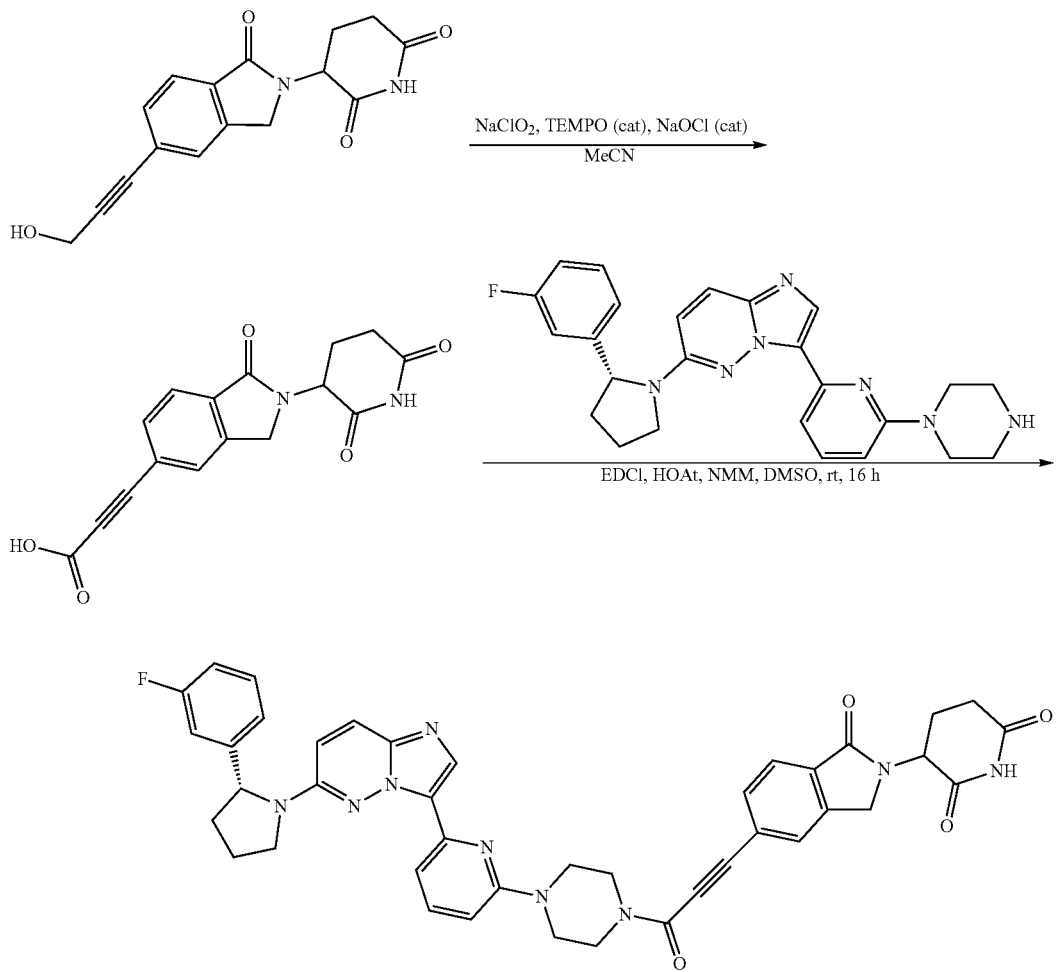

Step 1. Synthesis of 3-(2-(2,6-dioxopiperidin-3-yl)-1-oxoisoindolin-5-yl)propiolic acid

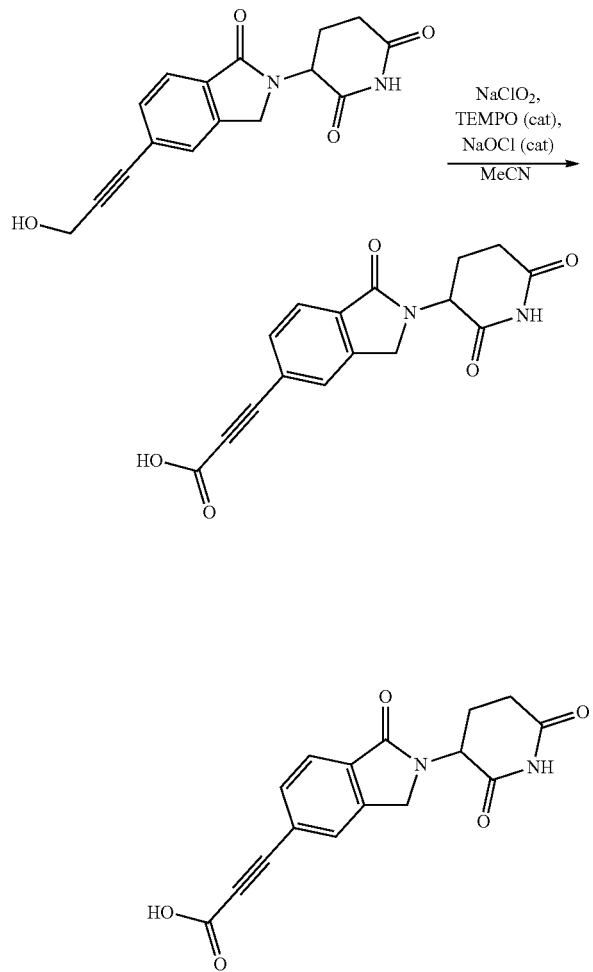

A mixture of 3-(5-(3-hydroxyprop-1-yn-1-yl)-1-oxoisoindolin-2-yl)piperidine-2,6-dione (100 mg, 0.34 mmol), TEMPO (2,2,6,6-tetramethyl-1-piperidinyloxy free radical) (5.2 mg, 0.034 mmol), acetonitrile (3 mL) and sodium phosphate buffer (1.3 mL, 0.67 M, pH=6.7) was stirred at 35° C. A solution of sodium chlorite is prepared by dissolving 80% NaClO$_2$ (9.14 g, 80.0 mmol) in water (40 mL) and a solution of dilute NaOCl is prepared by diluting household bleach (5.25% NaOCl, 1.06 mL, ca. 2.0 mol %) with water (19 mL). Then NaClO$_2$ solution (0.4 mL) was added followed by the dilute NaOCl solution (0.2 mL). The resulting mixture was stirred at 35° C. until the reaction was completed. The reaction mixture was purified by reverse-phase chromatography to give the desired product (65 mg, 63% yield) as a light yellow solid. MS (ESI) m/z: 313.1 [M+H]$^+$.

Step 2. Synthesis of 3-(5-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxoprop-1-yn-1-yl)-1-oxoisoindolin-2-yl)piperidine-2,6-dione

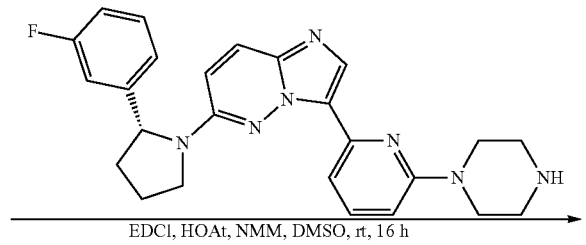

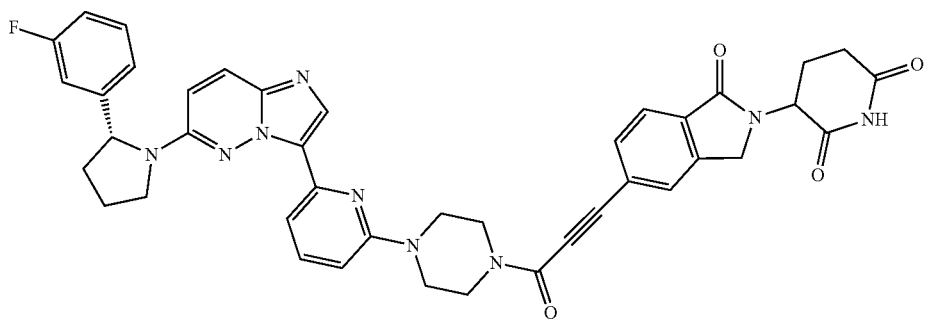

TR-203 was synthesized following the standard procedure for preparing TR-202 (9.8 mg, 42% yield) as a light yellow solid. MS (ESI) m/z: 738.3 [M+H]$^+$.

Example 255: 2-(2,6-Dioxopiperidin-3-yl)-5-(2-(4-(6-(6-((R)-2-(3-fluorophenyl)pyrrolidin-1-yl)imidazo[1,2-b]pyridazin-3-yl)pyridin-2-yl)piperazin-1-yl)ethyl)isoindoline-1,3-dione (TR-204)
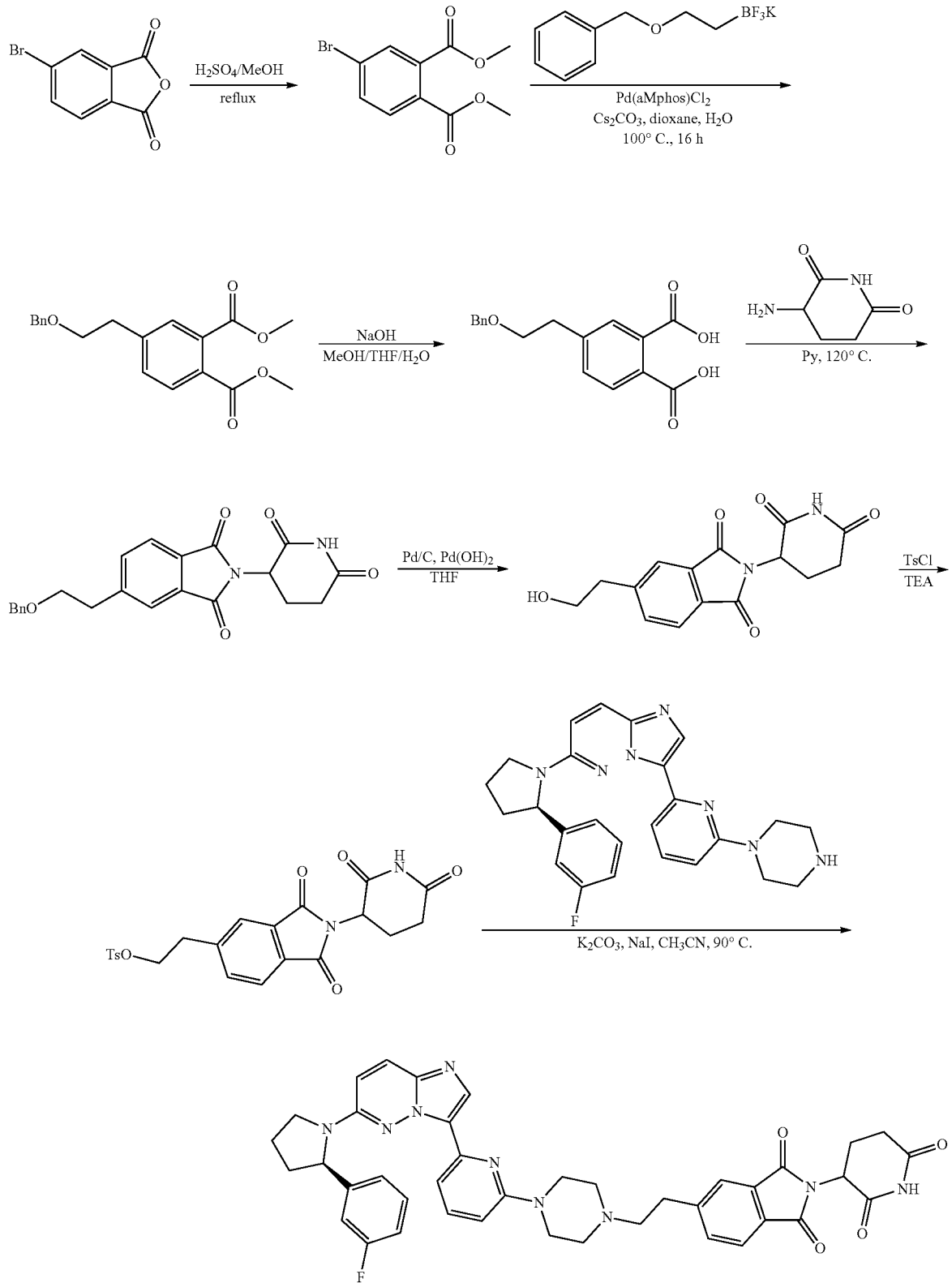

Step 1. Synthesis of dimethyl 4-bromophthalate

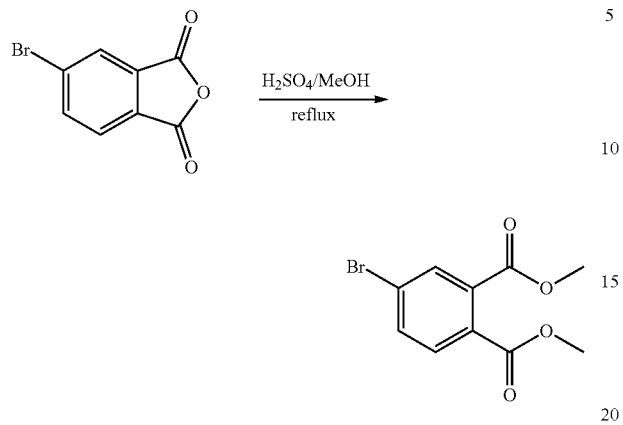

To a solution of 5-bromoisobenzofuran-1,3-dione (4.6 g, 20.26 mmol) in MeOH (50 mL) was added H₂SO₄ (992.90 mg, 10.13 mmol) at room temperature. After the reaction mixture was stirred at 80° C. for 16 h, the crude product was dissolved in DCM (50 mL), washed with aq. NaHCO₃ (100 mL) and brine (100 mL). The organic phase was dried over Na₂SO₄, filtered, and concentrated. The resulting residue was purified by silica gel chromatography (petroleum ether/EtOAc=10:1) to give dimethyl 4-bromophthalate (5.0 g, 90% yield) as colorless oil. MS (ESI) m/z: 375.0 [M+H]⁺.

Step 2. Synthesis of dimethyl 4-(2-(benzyloxy)ethyl)phthalate

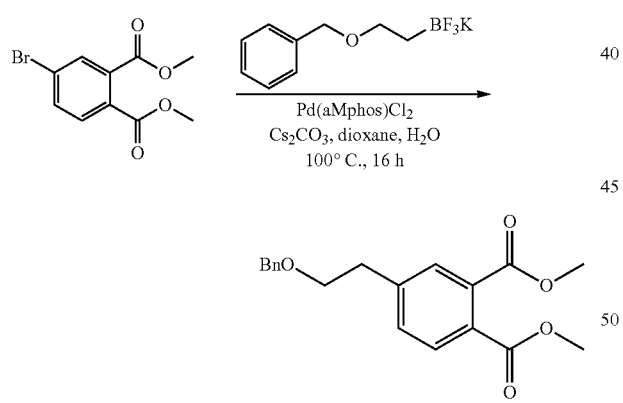

To a solution of 2-benzyloxyethyl(trifluoro)boronpotassium hydride (800 mg, 3.30 mmol) and dimethyl 4-bromophthalate (1.08 g, 3.97 mmol) in toluene (20 mL) and H₂O (10 mL) were added bis(di-tert-butyl(4-dimethylaminophenyl)phosphine)dichloropalladium(II) (233.97 mg, 330.46 umol) and Cs₂CO₃ (2.15 g, 6.61 mmol) at room temperature under N₂. After the reaction mixture was stirred at 100° C. for 16 h, the solvent was removed under reduced pressure. The resulting crude product was purified by silica gel chromatography (petroleum ether/EtOAc=10:1) to give dimethyl 4-(2-(benzyloxy)ethyl)phthalate (960 mg, 88% yield) as colorless oil. MS (ESI) m/z: 329.6 [M+H]⁺.

Step 3. Synthesis of 4-(2-(benzyloxy)ethyl)phthalic acid

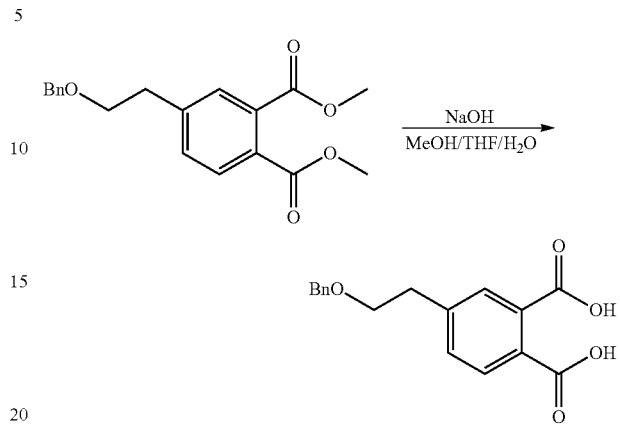

To a solution of dimethyl 4-(2-(benzyloxy)ethyl)phthalate (1.0 g, 3.05 mmol) in MeOH (10 mL), THF (10 mL) and H₂O (10 mL) was added NaOH (730.91 mg, 18.27 mmol) at room temperature. After the reaction mixture was stirred at 80° C. for 3 h, organic solvents were removed under reduced pressure.

The resulting aqueous mixture was acidified with conc. HCl to pH=2, before being extracted with DCM (3×20 mL). The organic layers were combined, dried over Na₂SO₄, filtered and concentrated to give crude 4-(2-benzyloxyethyl)phthalic acid (900 mg, 98% yield) as a yellow solid. This product was used in the next step directly without further purification. MS (ESI) m/z: 301.3 [M+H]⁺.

Step 4. Synthesis of 5-(2-(benzyloxy)ethyl)-2-(2,6-dioxopiperidin-3-yl)isoindoline-1,3-dione

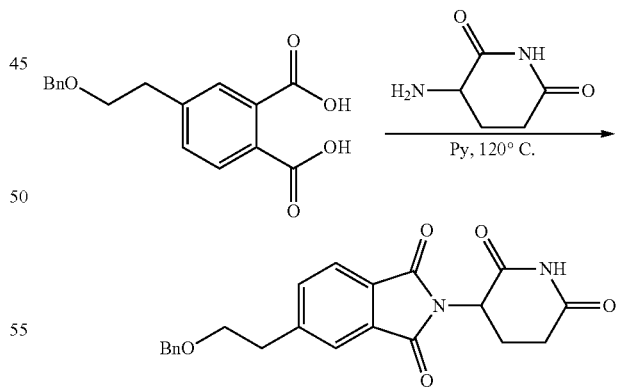

A solution of 4-(2-benzyloxyethyl)phthalic acid (800 mg, 2.66 mmol) and 3-aminopiperidine-2,6-dione (341.3 mg, 2.66 mmol) in pyridine (40 mL) was stirred at 120° C. for 16 h. Then the reaction mixture was concentrated and purified by silica gel chromatography (DCM/MeOH=20:1) to give 5-(2-(benzyloxy)ethyl)-2-(2,6-dioxopiperidin-3-yl)isoindoline-1,3-dione (0.98 g, 94% yield) as a yellow solid. MS (ESI) m/z: 393.3 [M+H]⁺.

Step 5. Synthesis of 2-(2,6-dioxopiperidin-3-yl)-5-(2-hydroxyethyl)isoindoline-1,3-dione

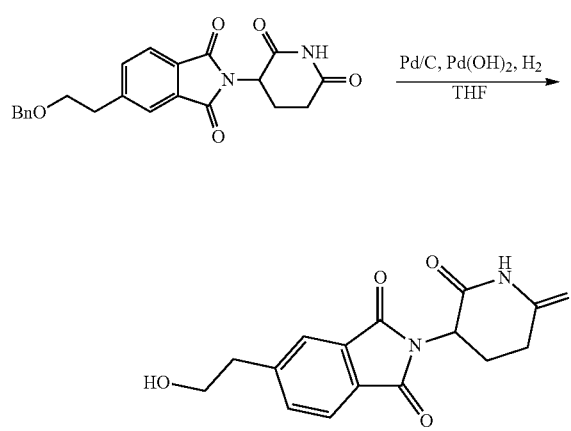

To a solution of 5-(2-(benzyloxy)ethyl)-2-(2,6-dioxopiperidin-3-yl)isoindoline-1,3-dione (700 mg, 1.78 mmol) in THF (25 mL) were added Pd(OH)$_2$ (50 mg) and Pd/C (50 mg) at room temperature. Then the reaction mixture was stirred at 50° C. for 16 h under hydrogen atmosphere pressure. After cooled down to room temperature, the mixture was filtered and concentrated to give crude 2-(2,6-dioxopiperidin-3-yl)-5-(2-hydroxyethyl)isoindoline-1,3-dione (500 mg, 93% yield) as a white solid. This product was used in the next step directly without further purification. MS (ESI) m/z: 303.2 [M+H]$^+$.

Step 6. Synthesis of 2-(2-(2-(2,6-dioxopiperidin-3-yl)-1,3-dioxoisoindolin-5-yl)ethyl 4-methylbenzenesulfonate

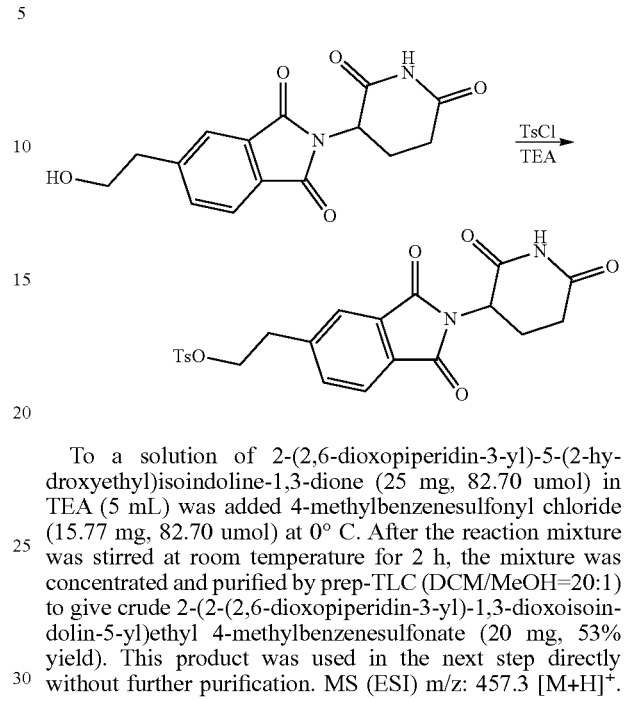

To a solution of 2-(2,6-dioxopiperidin-3-yl)-5-(2-hydroxyethyl)isoindoline-1,3-dione (25 mg, 82.70 umol) in TEA (5 mL) was added 4-methylbenzenesulfonyl chloride (15.77 mg, 82.70 umol) at 0° C. After the reaction mixture was stirred at room temperature for 2 h, the mixture was concentrated and purified by prep-TLC (DCM/MeOH=20:1) to give crude 2-(2-(2,6-dioxopiperidin-3-yl)-1,3-dioxoisoindolin-5-yl)ethyl 4-methylbenzenesulfonate (20 mg, 53% yield). This product was used in the next step directly without further purification. MS (ESI) m/z: 457.3 [M+H]$^+$.

Step 7. Synthesis of 2-(2,6-dioxopiperidin-3-yl)-5-(2-(4-(6-(6-((R)-2-(3-fluorophenyl)pyrrolidin-1-yl)imidazo[1,2-b]pyridazin-3-yl)pyridin-2-yl)piperazin-1-yl)ethyl)isoindoline-1,3-dione

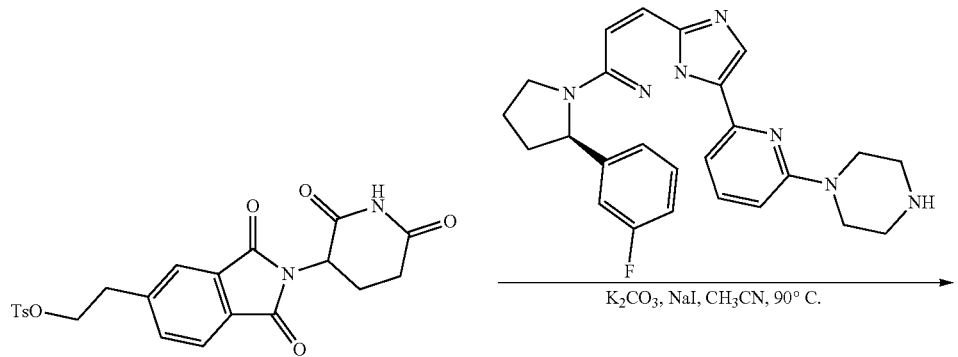

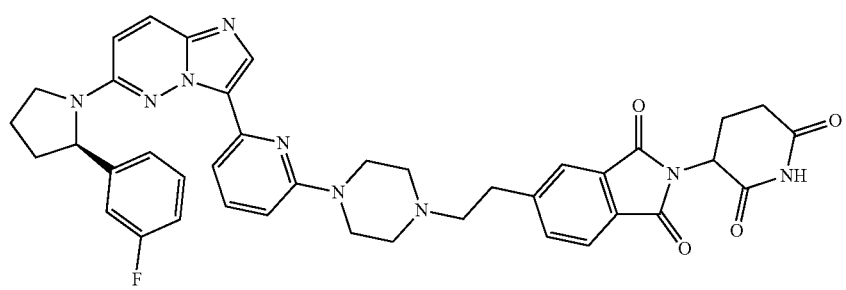

To a solution (R)-6-(2-(3-fluorophenyl)pyrrolidin-1-yl)-3-(6-(piperazin-1-yl)pyridin-2-yl)imidazo[1,2-b]pyridazine (14.57 mg, 32.86 umol) and 2-(2-(2,6-dioxopiperidin-3-yl)-1,3-dioxoisoindolin-5-yl)ethyl 4-methylbenzenesulfonate (15 mg, 32.86 umol) in CH₃CN (4 mL) were added NaI (9.85 mg, 65.72 umol) and K₂CO₃ (18.14 mg, 131.44 umol) at room temperature under N₂. After the reaction mixture was stirred at 80° C. for 16 h, the solvent was removed and the resulting residue was purified by prep-TLC (DCM/MeOH=10:1) to give 2-(2,6-dioxopiperidin-3-yl)-5-(2-(4-(6-(6-((R)-2-(3-fluorophenyl)pyrrolidin-1-yl)imidazo[1,2-b]pyridazin-3-yl)pyridin-2-yl)piperazin-1-yl)ethyl)isoindoline-1,3-dione (14 mg, 59% yield) as a light yellow solid. MS (ESI) m/z: 729.6 [M+H]⁺.

Example 256: 3-(5-(3-((4-(6-(6-((R)-2-(3-Fluorophenyl)pyrrolidin-1-yl)imidazo[1,2-b]pyridazin-3-yl)pyridin-2-yl)piperazin-1-yl)methyl)azetidin-1-yl)-1-oxoisoindolin-2-yl)piperidine-2,6-dione (TR-205)

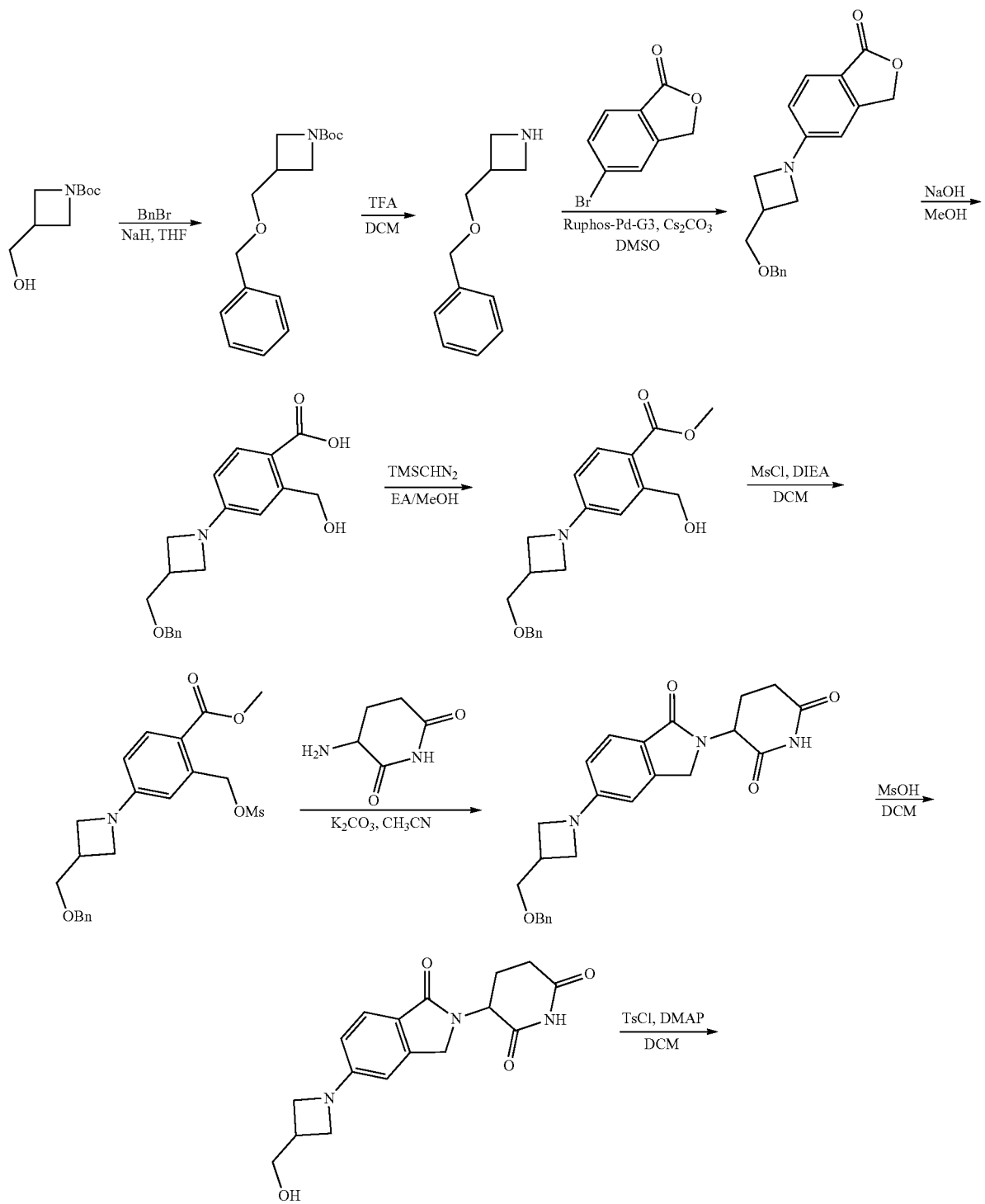

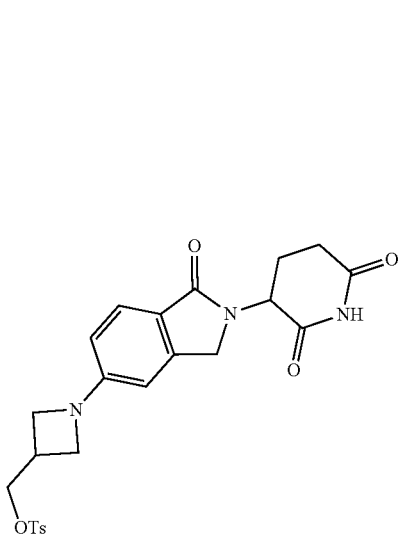
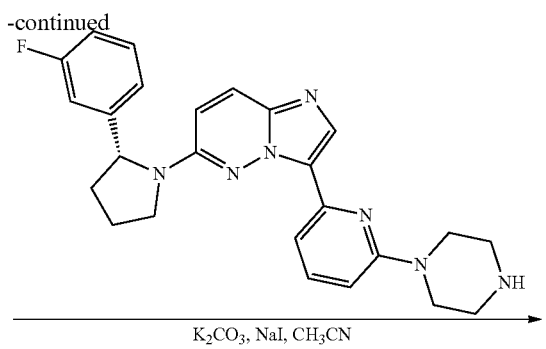

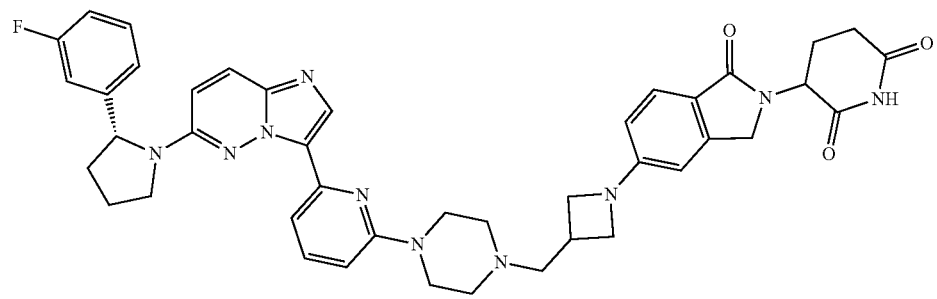

Step 1. Synthesis of tert-butyl 3-((benzyloxy)methyl)azetidine-1-carboxylate

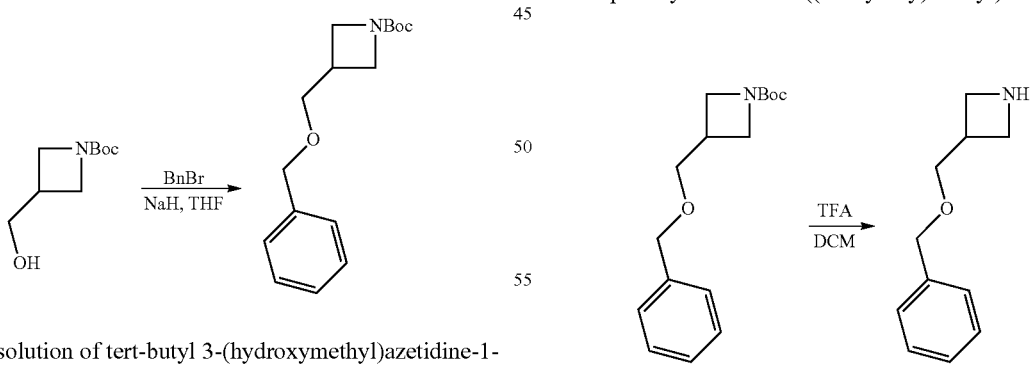

To a solution of tert-butyl 3-(hydroxymethyl)azetidine-1-carboxylate (2 g, 10.0 mmol) and NaH (720 mg, 30.0 mmol) in THF (50 mL) was added BnBr (2.74 g, 15.0 mmol) in portions at 0° C. under $N_2$. The resulting mixture was stirred at room temperature for 5 h, before the reaction was quenched with $H_2O$ (100 mL) at 0° C. and extracted with DCM (100 mL×2). The organic layers were combined and dried over $Na_2SO_4$, filtered, and concentrated. The resulting residue was purified by silica gel flash chromatography (petroleum/ethyl acetate=2:1) to give tert-butyl 3-((benzyloxy)methyl)azetidine-1-carboxylate (1.5 g, 51% yield) as a light yellow oil. MS (ESI) m/z: 278.3 [M+H]⁺.

Step 2. Synthesis of 3-((benzyloxy)methyl)azetidine

To a solution of tert-butyl 3-((benzyloxy)methyl)azetidine-1-carboxylate (1.5 g, 5.4 mmol) in DCM (15 mL) was added TFA (3 mL) at 0° C. After the reaction mixture was stirred at room temperature for 1 h, the solvent was removed under vacuum. The resulting residue was washed with diethyl ether to give 3-((benzyloxy)methyl)azetidine (1.0 g, 76% yield) as a yellow oil. MS (ESI) m/z: 178.2 [M+H]⁺.

Step 3. Synthesis of 5-(3-((benzyloxy)methyl)azetidin-1-yl)isobenzofuran-1(3H)-one

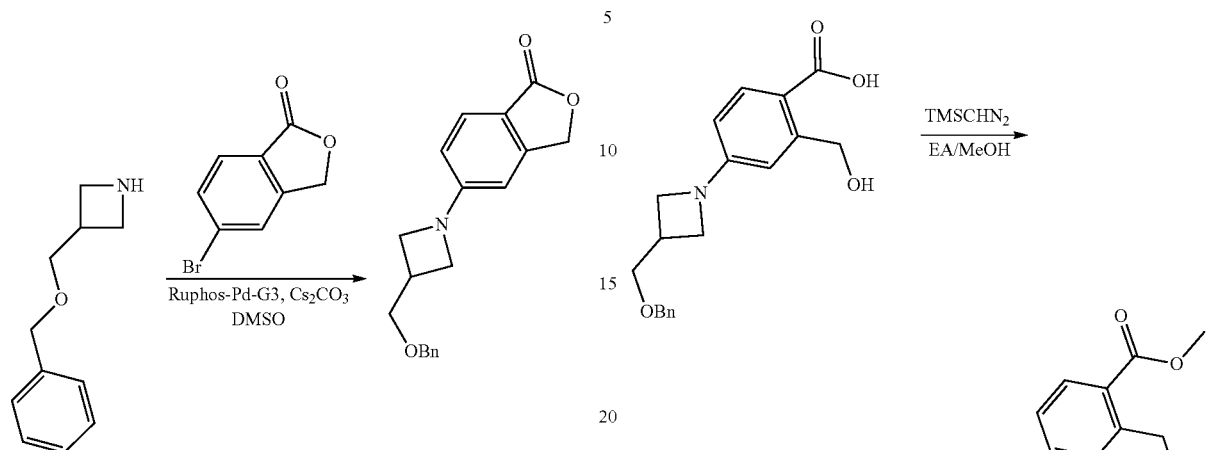

To a solution of 3-((benzyloxy)methyl)azetidine (1.0 g, 5.6 mmol) and 5-bromoisobenzofuran-1(3H)-one (1.19 g, 5.6 mmol) in DMSO (15 mL) were added Cs$_2$CO$_3$ (5.4 g, 16.8 mmol) and Ruphos-Pd-G3 (470 mg, 0.54 mmol) at room temperature under N$_2$. After the reaction mixture was stirred at 80° C. for 12 h, the resulting black mixture was diluted with ethyl acetate (20 mL), washed with saturated aqueous brine (2×20 mL). The combined organic layers were dried over sodium sulfate, filtered, and concentrated. The resulting residue was purified by silica gel flash chromatography (petroleum/ethyl acetate=1:1) to give 5-(3-((benzyloxy)methyl)azetidin-1-yl)isobenzofuran-1(3H)-one (470 mg, 27% yield) as a brown solid. MS (ESI) m/z: 310.1 [M+H]$^+$.

Step 4. Synthesis of 4-(3-((benzyloxy)methyl)azetidin-1-yl)-2-(hydroxymethyl)benzoic acid

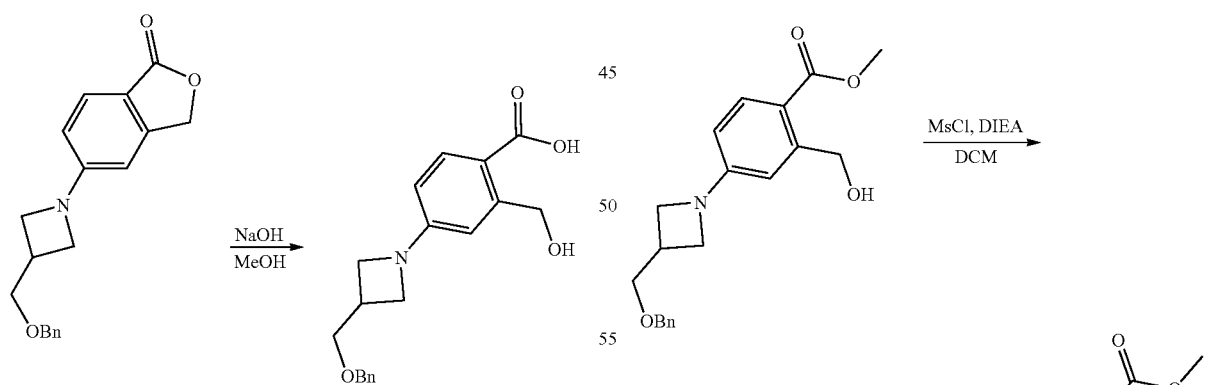

To a solution of 5-(3-((benzyloxy)methyl)azetidin-1-yl)isobenzofuran-1 (470 mg, 1.5 mmol) in MeOH (15 mL) was added NaOH (181 mg, 4.5 mmol) at room temperature. Then the mixture was stirred at 60° C. for 2 h. After cooled down to room temperature, the solution was acidified to pH=2-3 with 1 N HCl and filtered. The filter cake was washed with EtOAc/petroleum ether (50 mL, 1:10) to give 4-(3-((benzyloxy)methyl)azetidin-1-yl)-2-(hydroxymethyl)benzoic acid (350 mg, 74% yield) as a yellow solid. MS (ESI) m/z: 328.2 [M+H]$^+$.

Step 5. Synthesis of methyl 4-(3-((benzyloxy)methyl)azetidin-1-yl)-2-(hydroxymethyl)benzoate

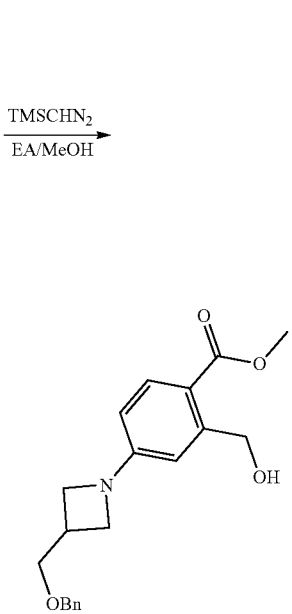

To a solution of 4-(3-((benzyloxy)methyl)azetidin-1-yl)-2-(hydroxymethyl)benzoic acid (350 mg, 1.06 mmol) in EtOAc/MeOH (15 mL) was added TMSCHN$_2$ (1 mL) at 0° C. After the completion of addition, the reaction mixture was stirred at room temperature for 1 h, then concentrated to give crude methyl 4-(3-((benzyloxy)methyl)azetidin-1-yl)-2-(hydroxymethyl)benzoate (220 mg, 62% yield) as a yellow solid. This product was used in the next step directly without further purification. MS (ESI) m/z: 342.2 [M+H]$^+$.

Step 6. Synthesis of methyl 4-(3-((benzyloxy)methyl)azetidin-1-yl)-2-(((methylsulfonyl)oxy)methyl)benzoate To a solution of methyl 4-(3-((benzyloxy)methyl)azetidin-1-yl)-2-(hydroxymethyl)benzoate (220 mg, 0.64 mmol) in DCM (10 mL) were added MsCl (0.5 mL) and DIEA (248 mg, 1.92 mmol) at 0° C. Then the reaction was stirred at room temperature for 1 h, quenched the reaction with water (30 mL). The resulting solution was extracted with DCM (20 mL×2) and the organic layer was concentrated to give methyl 4-(3-((benzyloxy)methyl)azetidin-1-yl)-2-(((methylsulfonyl)oxy)methyl)benzoate (150 mg, 55% yield) as a yellow solid. This product was used in the next step directly without further purification. MS (ESI) m/z: 342.2 [M+H]$^+$.

Step 7. Synthesis of 3-(5-(3-((benzyloxy)methyl)azetidin-1-yl)-1-oxoisoindolin-2-yl)piperidine-2,6-dione

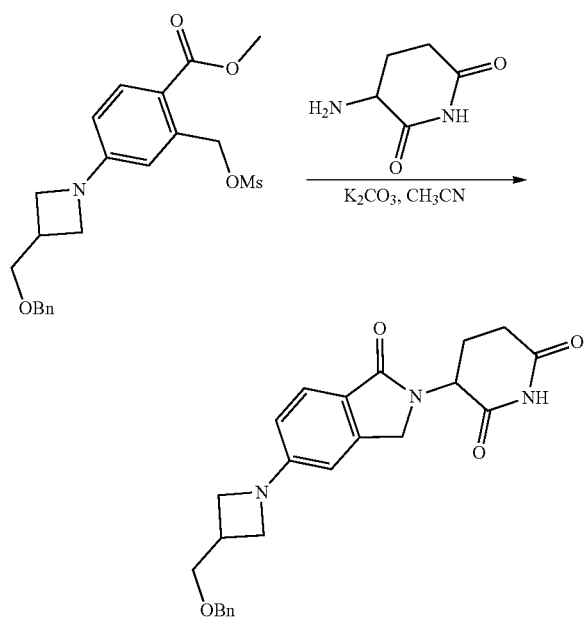

To a solution of methyl 4-(3-((benzyloxy)methyl)azetidin-1-yl)-2-(((methylsulfonyl)oxy)methyl)benzoate (150 mg, 0.35 mmol) in acetonitrile (5 ml) were added 3-aminopiperidine-2,6-dione (44 mg, 0.35 mmol) and potassium carbonate (150 mg, 1.05 mmol) at room temperature. The mixture was stirred at room temperature for 2 h. The solvent was removed under vacuum and the residue was purified by silica gel flash chromatography (MeOH/DCM=1:10) to give 3-(5-(3-((benzyloxy)methyl)azetidin-1-yl)-1-oxoisoindolin-2-yl)piperidine-2,6-dione (40 mg, 26% yield) as a white solid. MS (ESI) m/z: 420.8 [M+H]$^+$.

Step 8. Synthesis of 3-(5-(3-(hydroxymethyl)azetidin-1-yl)-1-oxoisoindolin-2-yl)piperidine-2,6-dione

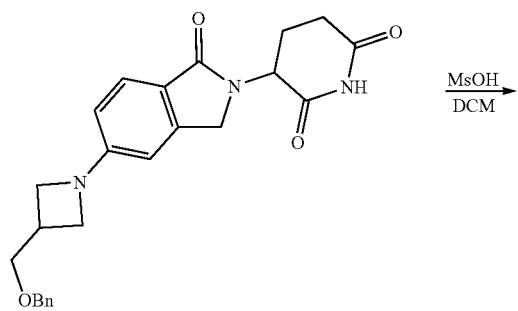

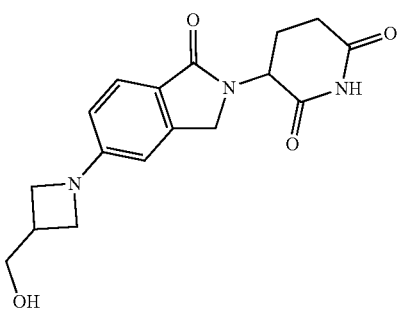

To a solution of 3-(5-(3-((benzyloxy)methyl)azetidin-1-yl)-1-oxoisoindolin-2-yl)piperidine-2,6-dione (40 mg, 0.09 mmol) in DCM (5 mL) was added MsOH (1 mL) at 0° C. The reaction was stirred at room temperature for 2 h, then the solvent was removed under vacuum. The residue was purified by silica gel flash chromatography (MeOH/H$_2$O=1:1) to give 3-(5-(3-(hydroxymethyl)azetidin-1-yl)-1-oxoisoindolin-2-yl)piperidine-2,6-dione (26 mg, 83% yield) as a yellow solid. MS (ESI) m/z: 330.1 [M+H]$^+$.

Step 9. Synthesis of (1-(2-(2,6-dioxopiperidin-3-yl)-1-oxoisoindolin-5-yl)azetidin-3-yl)methyl 4-methylbenzenesulfonate

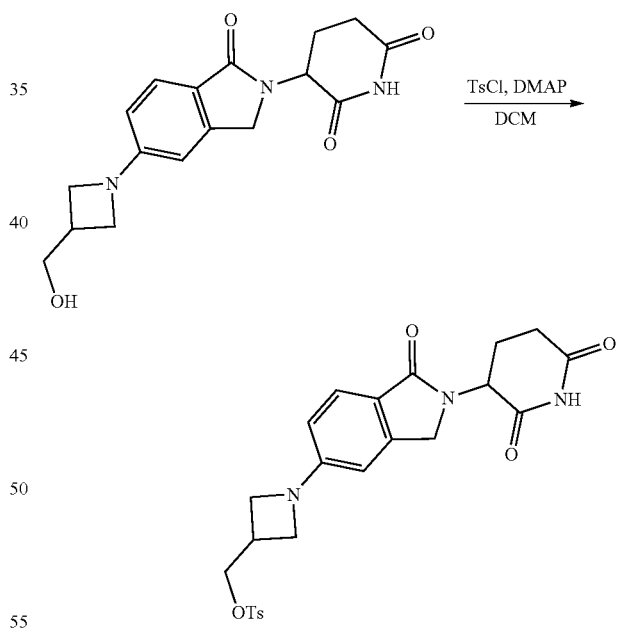

To a solution of 3-(5-(3-(hydroxymethyl)azetidin-1-yl)-1-oxoisoindolin-2-yl)piperidine-2,6-dione (26 mg, 0.08 mmol) in dichloromethane (2 mL) were added TsCl (30 mg, 0.16 mmol) and DMAP (20 mg, 0.08 mmol) at room temperature. The mixture was stirred at room temperature for 3 h. The reaction was concentrated and purified by silica gel flash chromatography (MeOH/DCM=1:10) to give (1-(2-(2,6-dioxopiperidin-3-yl)-1-oxoisoindolin-5-yl)azetidin-3-yl)methyl 4-methylbenzenesulfonate (13 mg, 34% yield) as a yellow solid. MS (ESI) m/z: 484.2 [M+H]$^+$.

Step 10. Synthesis of 3-(5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)azetidin-1-yl)-1-oxoisoindolin-2-yl)piperidine-2,6-dione

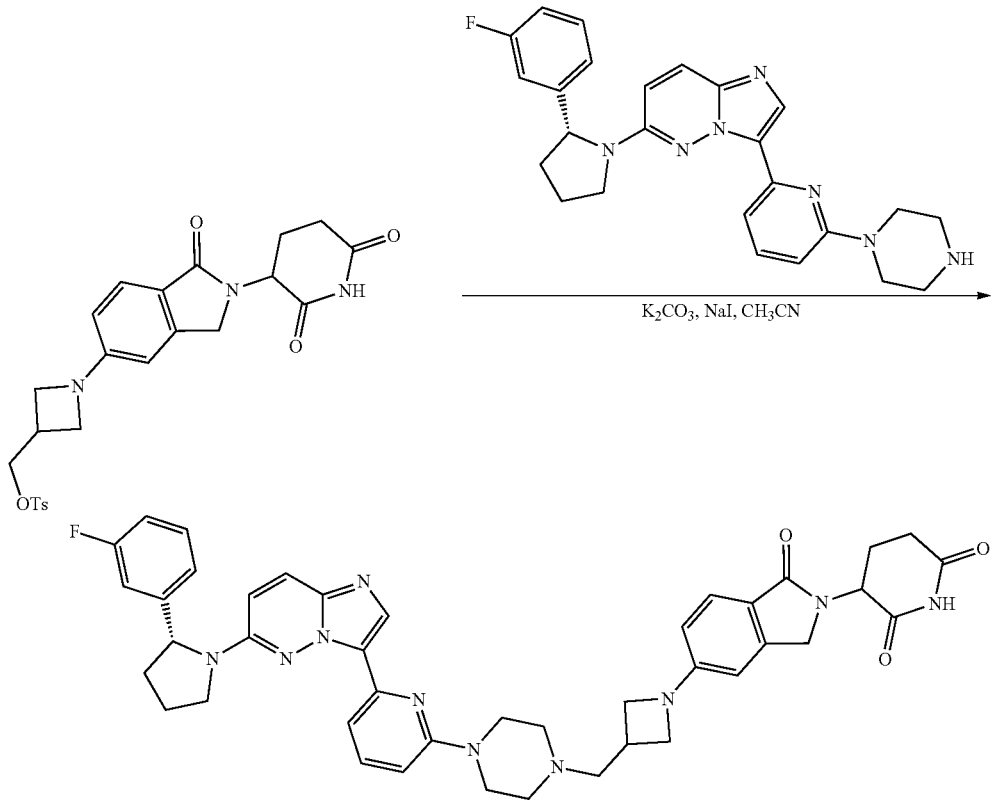

To a solution of (1-(2-(2,6-dioxopiperidin-3-yl)-1-oxoisoindolin-5-yl)azetidin-3-yl)methyl 4-methylbenzenesulfonate (13 mg, 0.03 mmol) and (S)-6-(2-(3-fluorophenyl)pyrrolidin-1-yl)-3-(6-(piperazin-1-yl)pyridin-2-yl)imidazo[1,2-b]pyridazine (12 mg, 0.03 mmol) in acetonitrile (1 mL) were added potassium carbonate (11 mg, 0.09 mmol) and sodium iodide (4 mg, 0.03 mmol) at room temperature. The reaction mixture was stirred at 80° C. for 2 h, then concentrated and purified by silica gel flash chromatography (MeOH/DCM=1:10) to give 3-(5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)azetidin-1-yl)-1-oxoisoindolin-2-yl)piperidine-2,6-dione (3.5 mg, 18% yield) as a withe solid. MS (ESI) m/z: 755.4 [M+H]⁺.

Example 257: 3-(5-((1-(6-(6-((R)-2-(3-Fluorophenyl)pyrrolidin-1-yl)imidazo[1,2-b]pyridazin-3-yl)pyridin-2-yl)azetidin-3-yl)amino)-1-oxoisoindolin-2-yl)piperidine-2,6-dione (TR-206)

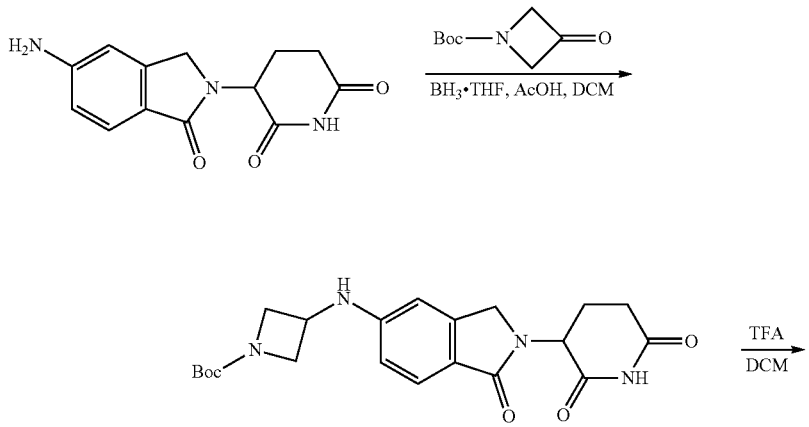

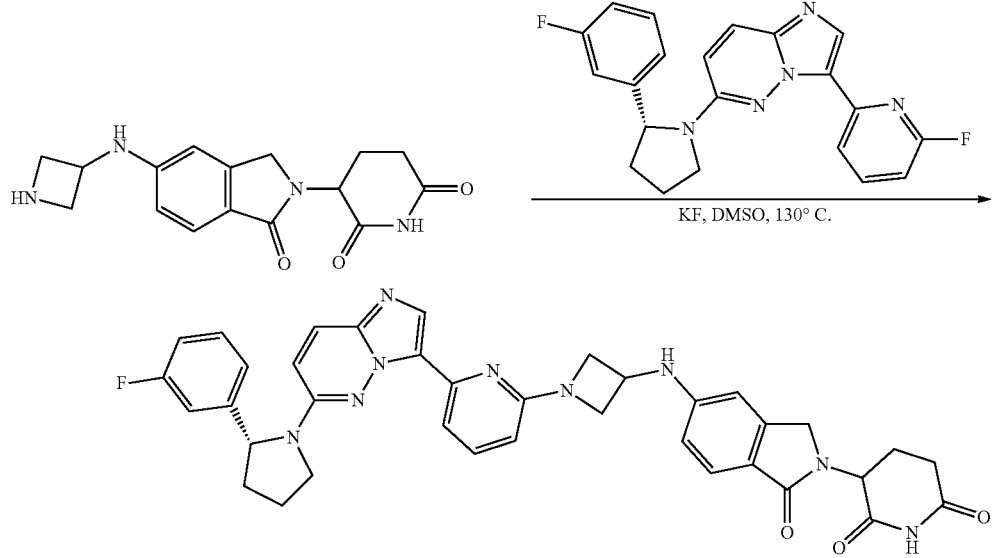

Step 1. Synthesis of tert-butyl 3-((2-(2,6-dioxopiperidin-3-yl)-1-oxoisoindolin-5-yl) amino)azetidine-1-carboxylate Step 2. Synthesis of 3-(5-(azetidin-3-ylamino)-1-oxoisoindolin-2-yl)piperidine-2,6-dione

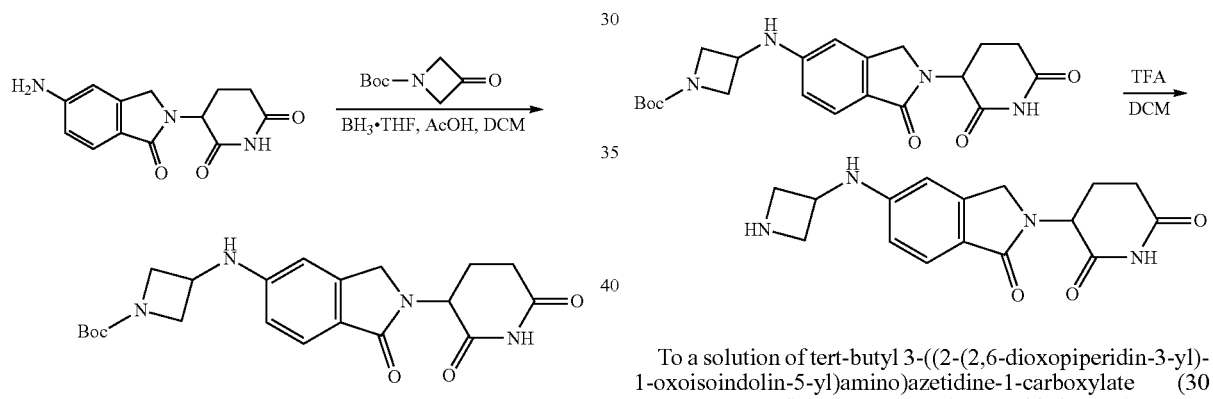

To a solution of 3-(5-amino-1-oxoisoindolin-2-yl)piperidine-2,6-dione (200 mg, 0.77 mmol) and AcOH (2 mL) in DCM (6 mL) was added 1M borane tetrahydrofuran complex solution (1.54 mL, 1.54 mmol) at 0° C., then it was stirred at 0° C. for 2 h. The mixture was concentrated and purified by reverse-phase chromatography to give the desired product (61 mg, 19% yield) as a light yellow solid. MS (ESI) m z: 415.2 [M+H]⁺.

To a solution of tert-butyl 3-((2-(2,6-dioxopiperidin-3-yl)-1-oxoisoindolin-5-yl)amino)azetidine-1-carboxylate (30 mg, 0.072 mmol) in DCM (5 mL) was added TFA (4 mL) at room temperature, then it was stirred at room temperature for 2 h. The mixture was concentrated and purified by reverse-phase chromatography to give the desired product (18 mg, 79% yield) as a light yellow solid. MS (ESI) m/z: 315.1 [M+H]⁺.

Step 3. Synthesis of 3-(5-((1-(6-(6-((R)-2-(3-fluorophenyl)pyrrolidin-1-yl)imidazo [1,2-b]pyridazin-3-yl)pyridin-2-yl)azetidin-3-yl)amino)-1-oxoisoindolin-2-yl)piperidine-2,6-dione

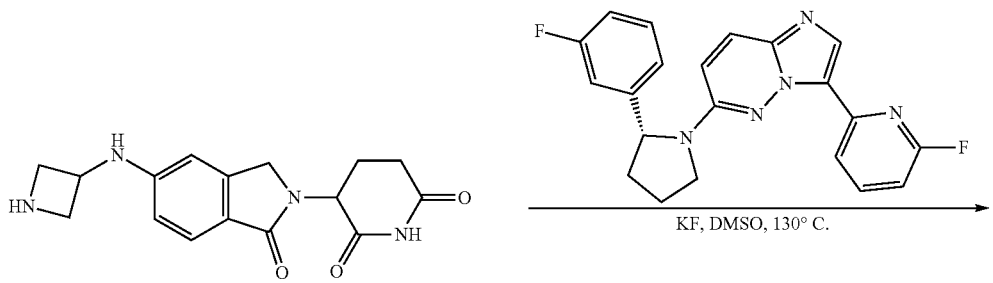

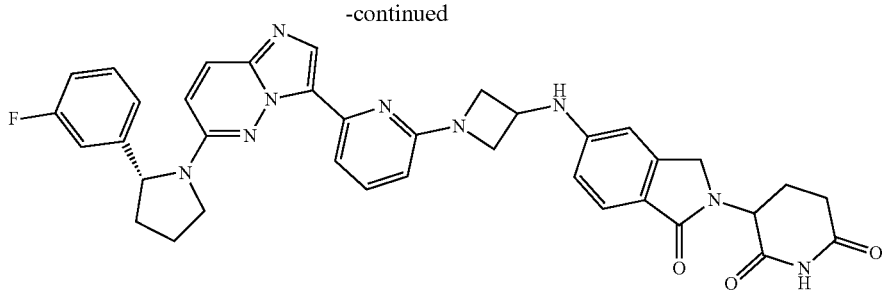

To a solution of 3-(5-(azetidin-3-ylamino)-1-oxoisoindolin-2-yl)piperidine-2,6-dione (18 mg, 0.057 mmol) and (R)-6-(2-(3-fluorophenyl)pyrrolidin-1-yl)-3-(6-fluoropyridin-2-yl)imidazo[1,2-b]pyridazine (21 mg, 0.057 mmol) in DMSO (5 mL) was added KF (3.3 mg, 0.057 mmoL) at room temperature, then it was stirred at 130° C. for 16 h. The reaction was cooled to room temperature before H₂O (50 mL) was added. The mixture was extracted with EtOAc (10 mL×3). The combined organic layers were concentrated and purified by reverse-phase chromatography to give the desired product 3-(5-((1-(6-(6-((R)-2-(3-fluorophenyl)pyrrolidin-1-yl)imidazo[1,2-b]pyridazin-3-yl)pyridin-2-yl)azetidin-3-yl)amino)-1-oxoisoindolin-2-yl)piperidine-2,6-dione (5.5 mg, 14% yield) as a light yellow solid. MS (ESI) m/z: 672.3 [M+H]⁺.

Example 258: 3-(5-(4-(6-(6-((R)-2-(3-Fluorophenyl)pyrrolidin-1-yl)imidazo[1,2-b]pyridazin-3-yl)pyridin-2-yl)piperazin-1-yl)-1-oxoisoindolin-2-yl)piperidine-2,6-dione (TR-207)

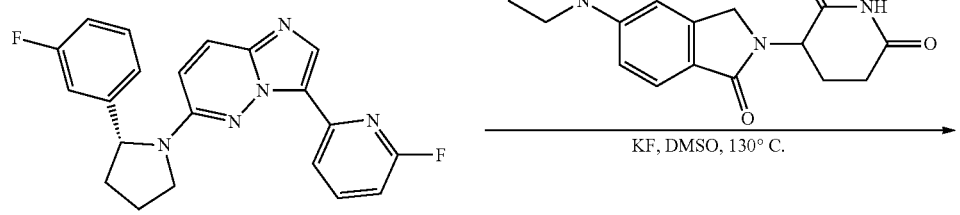

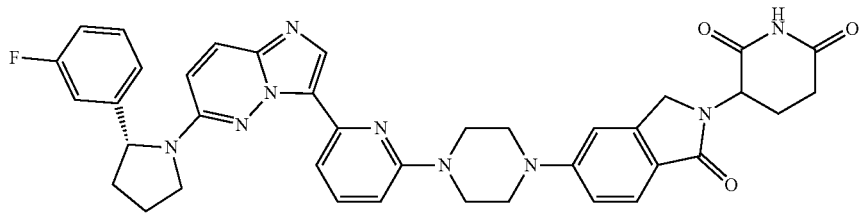

TR-207 was synthesized following the standard procedure for preparing TR-206 (4.8 mg, 15% yield) as a light yellow solid. MS (ESI) m/z: 686.3 [M+H]⁺.

Example 259: 3-(5-(4-(6-(6-((R)-2-(3-Fluorophenyl)pyrrolidin-1-yl)imidazo[1,2-b]pyridazin-3-yl)pyridin-2-yl)piperazin-1-yl)-1-oxoisoindolin-2-yl)piperidine-2,6-dione (TR-208)

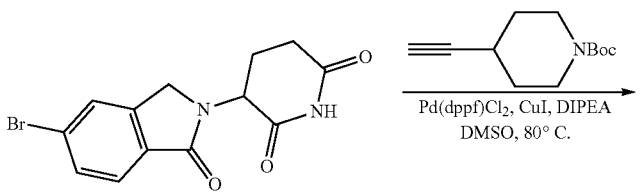

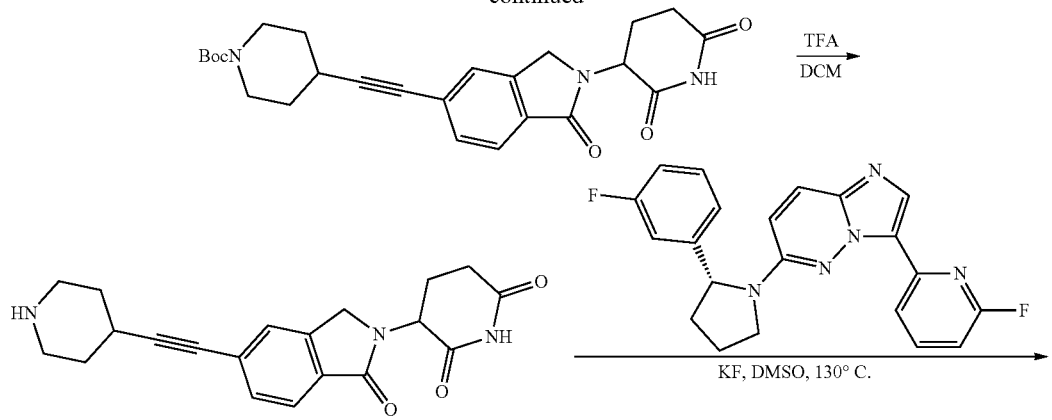

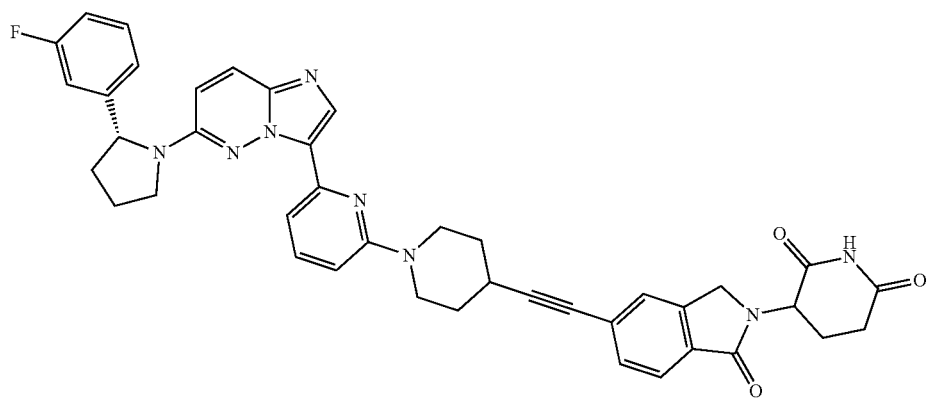

Step 1. Synthesis of tert-butyl 4-((2-(2,6-dioxopiperidin-3-yl)-1-oxoisoindolin-5-yl) ethynyl)piperidine-1-carboxylate

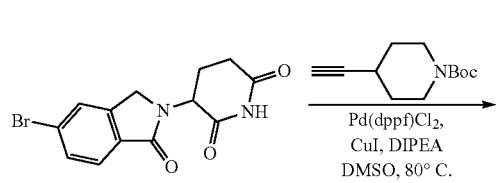

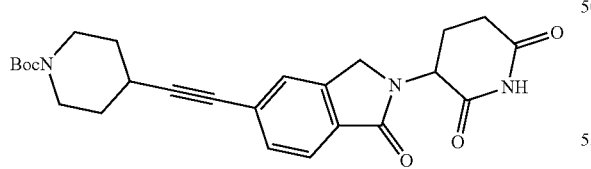

A mixture of 3-(5-bromo-1-oxoisoindolin-2-yl)piperidine-2,6-dione (100 mg, 0.31 mmol), tert-butyl 4-ethynylpiperidine-1-carboxylate (71 mg, 0.34 mmol), Pd(dppf)Cl$_2$ (22 mg, 0.03 mmol), CuI (5.7 mg, 0.03 mmol) and DIPEA (79 mg, 0.62 mmol) in DMSO (10 mL) was stirred at 80° C. for 16 h. The reaction mixture was concentrated and the residue was purified by reverse-phase chromatography to give the desired product (55 mg, 39% yield) as a pale brown solid. MS (ESI) m/z: 452.2 [M+H]$^+$.

Step 2. Synthesis of 3-(1-oxo-5-(piperidin-4-ylethynyl)isoindolin-2-yl)piperidine-2,6-dione

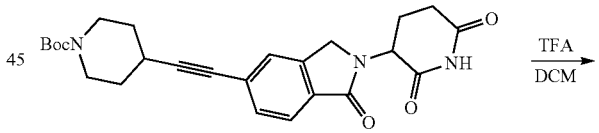

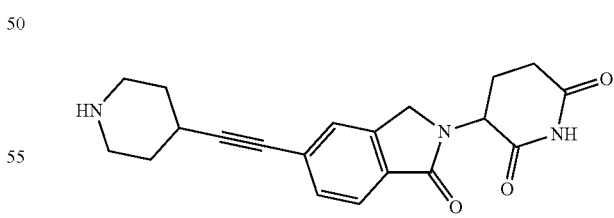

To a solution of tert-butyl 4-((2-(2,6-dioxopiperidin-3-yl)-1-oxoisoindolin-5-yl)ethynyl)piperidine-1-carboxylate (55 mg, 0.12 mmol) in DCM (5 mL) was added TFA (4 mL) at room temperature. After it was stirred at room temperature for 2 h, the mixture was concentrated and purified by reverse-phase chromatography to give the desired product (36 mg, 85% yield) as a light yellow solid. MS (ESI) m/z: 352.2 [M+H]$^+$.

Step 3. Synthesis of 3-(5-((1-(6-(6-((R)-2-(3-fluorophenyl)pyrrolidin-1-yl)imidazo [1,2-b]pyridazin-3-yl)pyridin-2-yl)piperidin-4-yl)ethynyl)-1-oxoisoindolin-2-yl)piperidine-2,6-dione

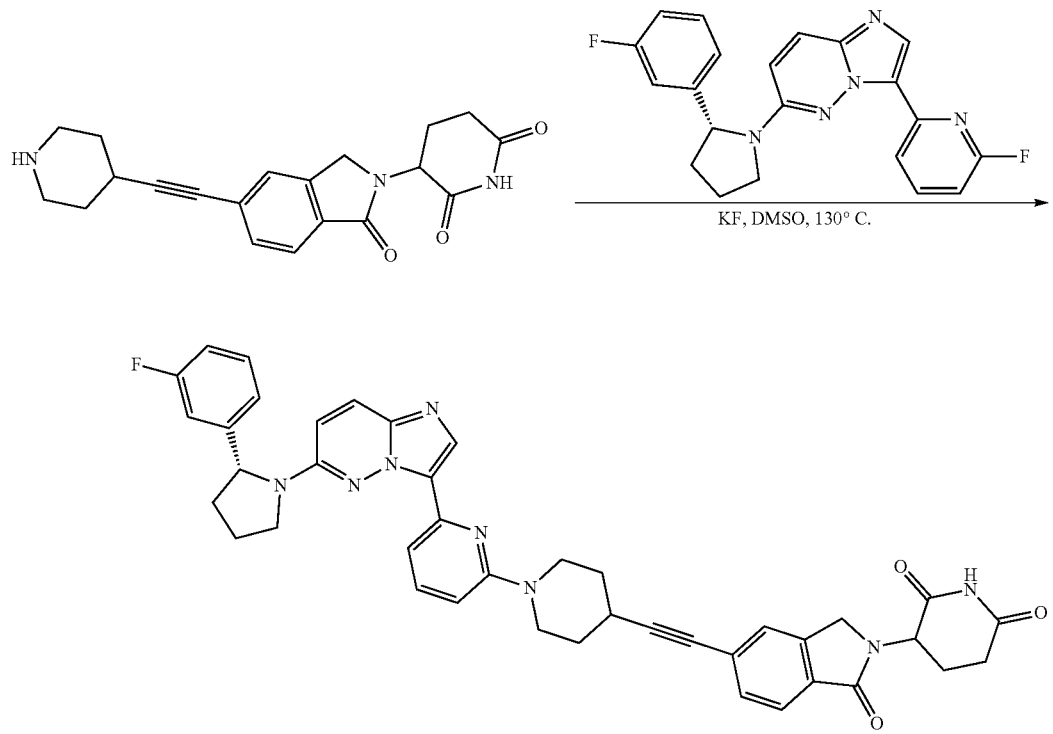

TR-208 was synthesized following the standard procedure for preparing TR-206 (6.2 mg, 15% yield) as a light yellow solid. MS (ESI) m/z: 709.3 [M+H]$^+$.

Example 260: N-(2-(2,6-Dioxopiperidin-3-yl)-1,3-dioxoisoindolin-5-yl)-1-(6-(6-((R)-2-(3-fluorophenyl)pyrrolidin-1-yl)imidazo[1,2-b]pyridazin-3-yl)pyridin-2-yl)azetidine-3-carboxamide (TR-209)

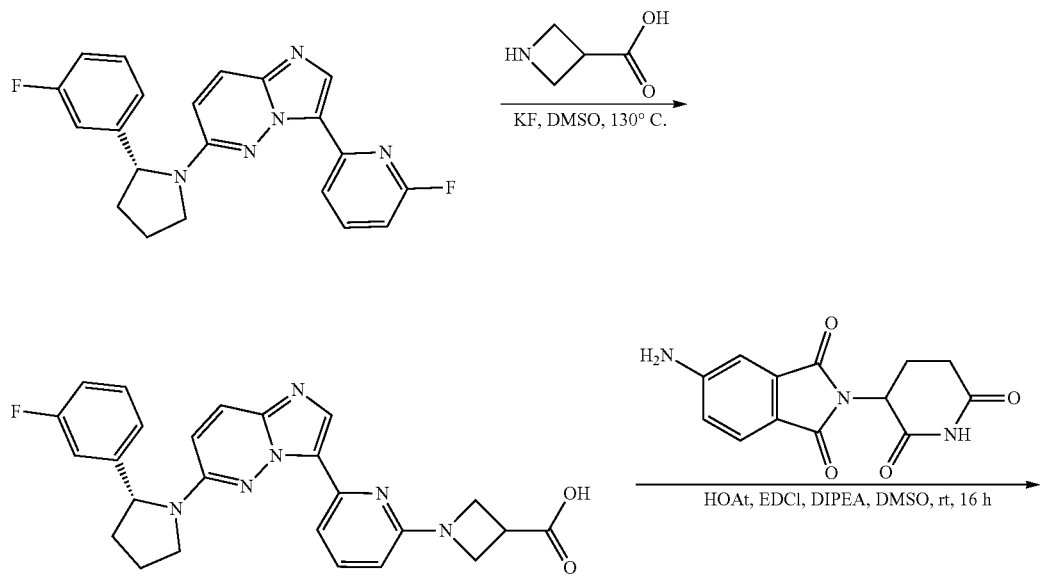

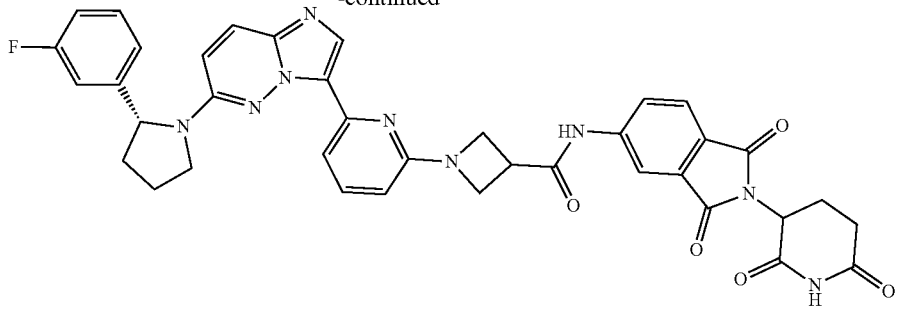

Step 1. Synthesis of (R)-1-(6-(6-(2-(3-fluorophenyl)pyrrolidin-1-yl)imidazo[1,2-b]pyridazin-3-yl)pyridin-2-yl)azetidine-3-carboxylic acid To a solution of azetidine-3-carboxylic acid (16 mg, 0.16 mmol) and (R)-6-(2-(3-fluorophenyl)pyrrolidin-1-yl)-3-(6-fluoropyridin-2-yl)imidazo[1,2-b]pyridazine (50 mg, 0.13 mmol) in DMSO (8 mL) was added KF (7.5 mg, 0.13 mmol) at room temperature. After it was stirred at 130° C. for 16 h, the reaction was cooled to room temperature before H$_2$O (50 mL) was added. The mixture was extracted with EtOAc (3×10 mL). The combined organic layers were concentrated and purified by reverse-phase chromatography to give the desired product (22 mg, 37% yield) as a light yellow solid. MS (ESI) m/z: 459.2 [M+H]$^+$.

Step 2. Synthesis of N-(2-(2,6-dioxopiperidin-3-yl)-1,3-dioxoisoindolin-5-yl)-1-(6-(6-((R)-2-(3-fluorophenyl)pyrrolidin-1-yl)imidazo[1,2-b]pyridazin-3-yl)pyridin-2-yl)azetidine-3-carboxamide

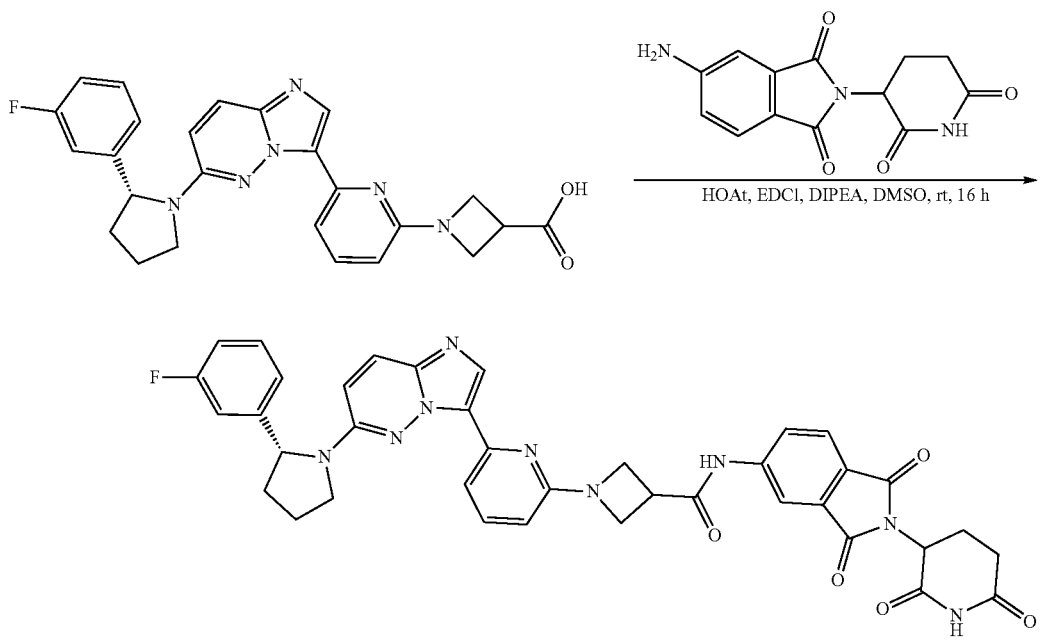

TR-209 was synthesized following the standard procedure for preparing TR-202 (9.8 mg, 21% yield) as a light yellow solid. MS (ESI) m/z: 714.3 [M+H]$^+$.

Example 261: 3-(5-(((1-(6-(6-((R)-2-(3-Fluorophe- nyl)pyrrolidin-1-yl)imidazo[1,2-b]pyridazin-3-yl) pyridin-2-yl)azetidin-3-yl)methyl)amino)-1-oxoi- soindolin-2-yl)piperidine-2,6-dione (TR-210)

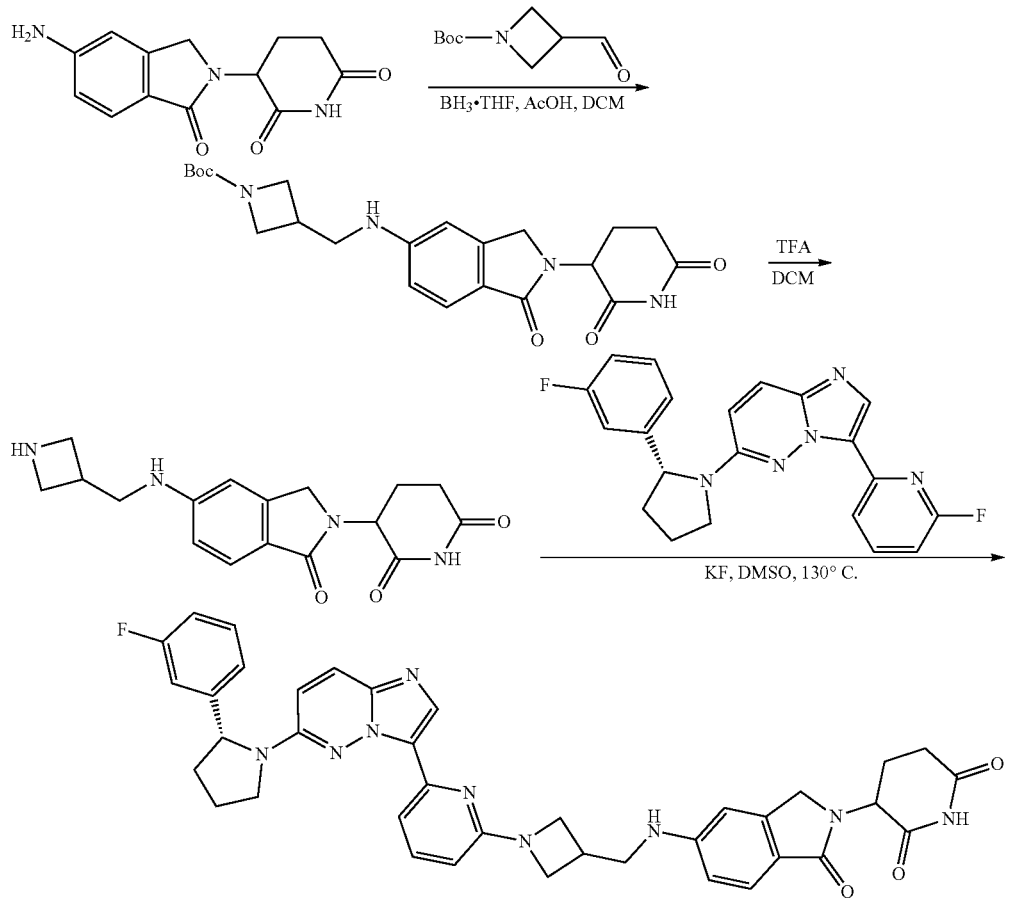

Step 1. Synthesis of tert-butyl 3-(((2-(2,6-dioxopip- eridin-3-yl)-1-oxoisoindolin-5-yl)amino)methyl) azetidine-1-carboxylate Step 2. Synthesis of 3-(5-((azetidin-3-ylmethyl) amino)-1-oxoisoindolin-2-yl) piperidine-2,6-dione

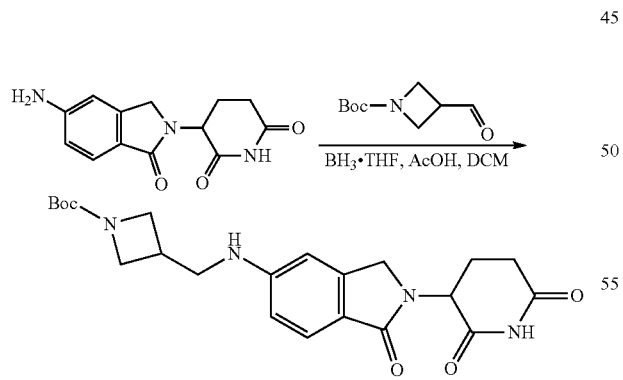

To a solution of 3-(5-amino-1-oxoisoindolin-2-yl)piperi- dine-2,6-dione (100 mg, 0.38 mmol) and AcOH (2 mL) in DCM (6 mL) was added 1M borane tetrahydrofuran com- plex solution (0.76 mL, 0.76 mmol) at 0° C. After it was stirred at 0° C. for 2 h, the mixture was concentrated and purified by reverse-phase chromatography to give the desired product (42 mg, 26% yield) as a light yellow solid. MS (ESI) m z: 429.2 [M+H]⁺.

To a solution of tert-butyl 3-(((2-(2,6-dioxopiperidin-3- yl)-1-oxoisoindolin-5-yl)amino)methyl)azetidine-1-car- boxylate (42 mg, 0.10 mmol) in DCM (5 mL) was added TFA (4 mL) at room temperature. After it was stirred at room temperature for 2 h, the mixture was concentrated and purified by reverse-phase chromatography to give the desired product (25 mg, 78% yield) as a light yellow solid. MS (ESI) m/z: 329.2 [M+H]⁺.

Step 3. Synthesis of 3-(5-(((1-(6-(6-((R)-2-(3-fluorophenyl)pyrrolidin-1-yl)imidazo[1,2-b]pyridazin-3-yl)pyridin-2-yl)azetidin-3-yl)methyl)amino)-1-oxoisoindolin-2-yl)piperidine-2,6-dione

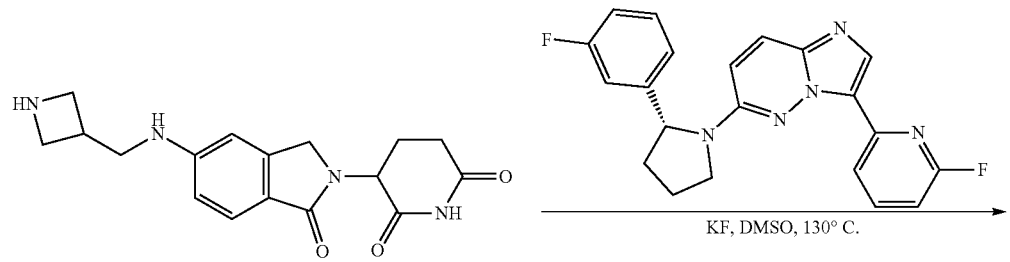

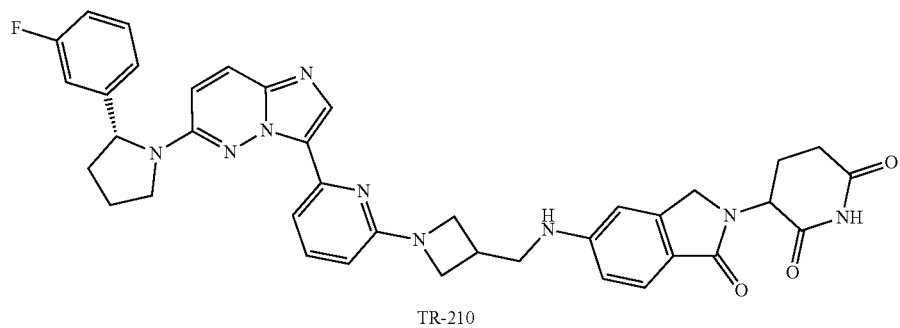

TR-210

TR-210 was synthesized following the standard procedure for preparing TR-208 (6.7 mg, 15% yield) as a light yellow solid. MS (ESI) m/z: 686.3 [M+H]⁺.

Example 262: 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazine-1-carbonyl)azetidin-1-yl)isoindoline-1,3-dione (TR-211)

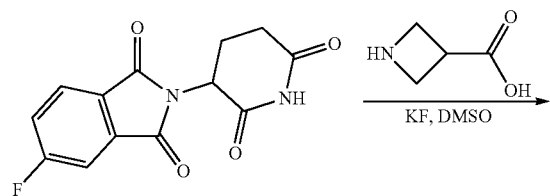

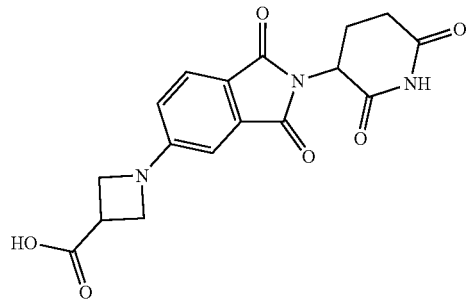
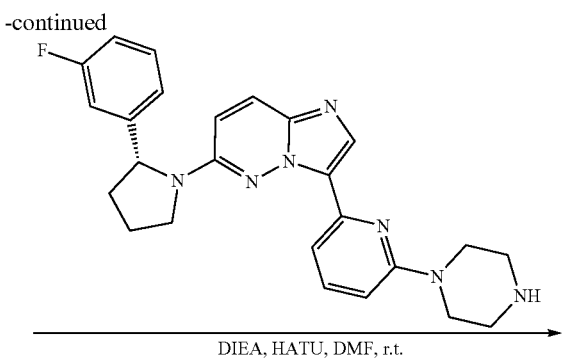

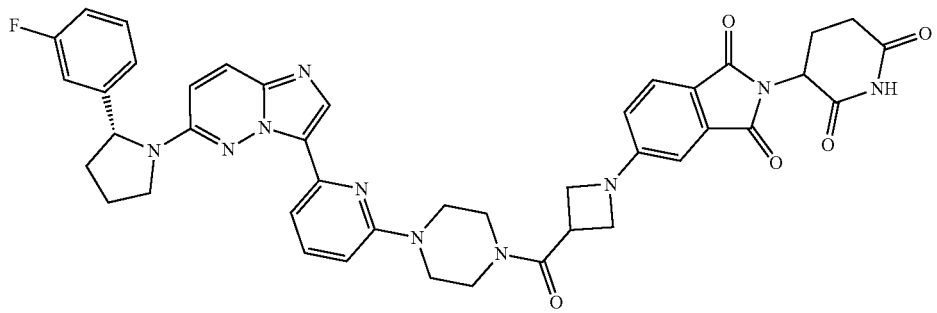

Step 1. Synthesis of 1-(2-(2,6-dioxopiperidin-3-yl)-1,3-dioxoisoindolin-5-yl)azetidine-3-carboxylic acid

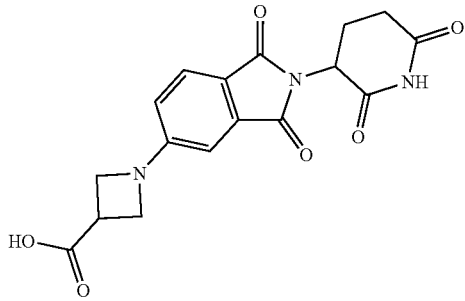

-continued

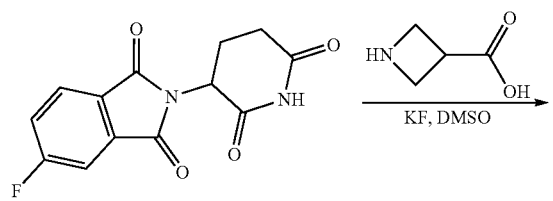

To a solution of 2-(2,6-dioxopiperidin-3-yl)-5-fluoroisoindoline-1,3-dione (276 mg, 1.0 mmol) and azetidine-3-carboxylicacid (171 mg, 1.5 mmol) in DMSO (3 mL) was added KF (232 mg, 4.0 mmol). The resulting solution was stirred at 120° C. for 5 h, before the reaction was quenched with water (10 mL), and extracted with ethyl acetate (2×20 mL). The organic layers were combined, dried over $Na_2SO_4$, and concentrated. The resulting residue was purified by reverse-phase chromatography to give 1-(2-(2,6-dioxopiperidin-3-yl)-1,3-dioxoisoindolin-5-yl)azetidine-3-carboxylic acid (175 mg, 49% yield) as a yellow solid. MS (ESI) m/z: 358.1 $[M+H]^+$.

Step 2. Synthesis of 2-(2,6-dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazine-1-carbonyl)azetidin-1-yl)isoindoline-1,3-dione

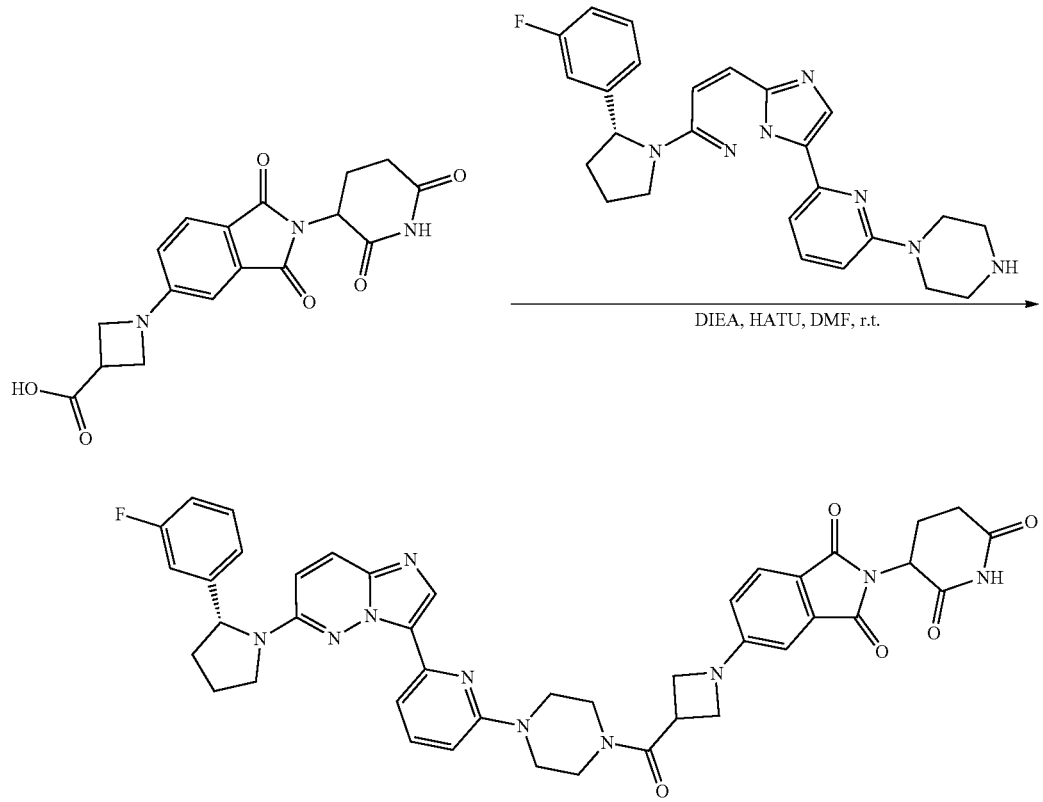

To a solution of 1-(2-(2,6-dioxopiperidin-3-yl)-1,3-dioxoisoindolin-5-yl)azetidine-3-carboxylic acid (175 mg, 0.49 mmol) and 6-[(2R)-2-(3-fluorophenyl)pyrrolidin-1-yl]-3-(6-piperazin-1-yl-2-pyridyl)imidazo[1,2-b]pyridazine (217 mg, 0.49 mmol) in N,N-dimethylformamide (10 mL) were added HATU (371 mg, 0.98 mmol) and DIEA (189 mg, 1.46 mmol) at room temperature. The reaction mixture was stirred at room temperature for 2 h, before it was quenched with water (30 mL). The resulting mixture was extracted with ethyl acetate (3×20 mL). And the combined organic layers were dried over sodium sulfate, filtered, and concentrated. The resulign residue was purified by silica gel chromatography (DCM/MeOH=10:1) to give 2-(2,6-dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazine-1-carbonyl)azetidin-1-yl)isoindoline-1,3-dione (128 mg, 33% yield) as a yellow solid. MS (ESI) m/z: 783.8 [M+H]+.

Example 263: 3-(5-((1-(6-(6-((R)-2-(3-fluorophenyl)pyrrolidin-1-yl)imidazo[1,2-b]pyridazin-3-yl)pyridin-2-yl)piperidin-4-yl)amino)-1-oxoisoindolin-2-yl)piperidine-2,6-dione (TR-212)

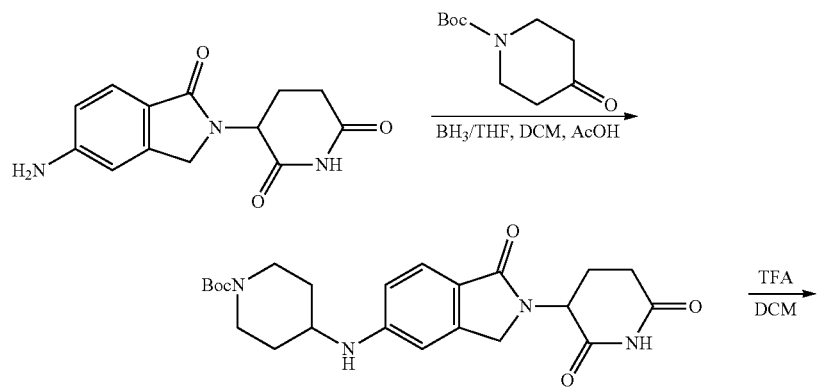

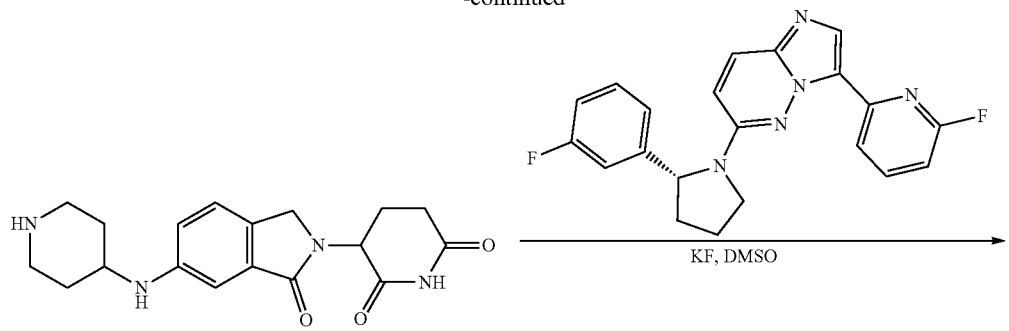

Step 1. Synthesis of tert-butyl 4-((2-(2,6-dioxopiperidin-3-yl)-1-oxoisoindolin-5-yl)amino)piperidine-1-carboxylate Step 2. Synthesis of 3-(1-oxo-5-(piperidin-4-ylamino)isoindolin-2-yl)piperidine-2,6-dione

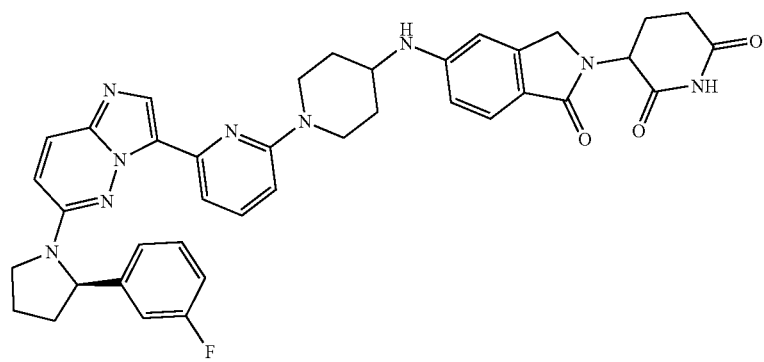

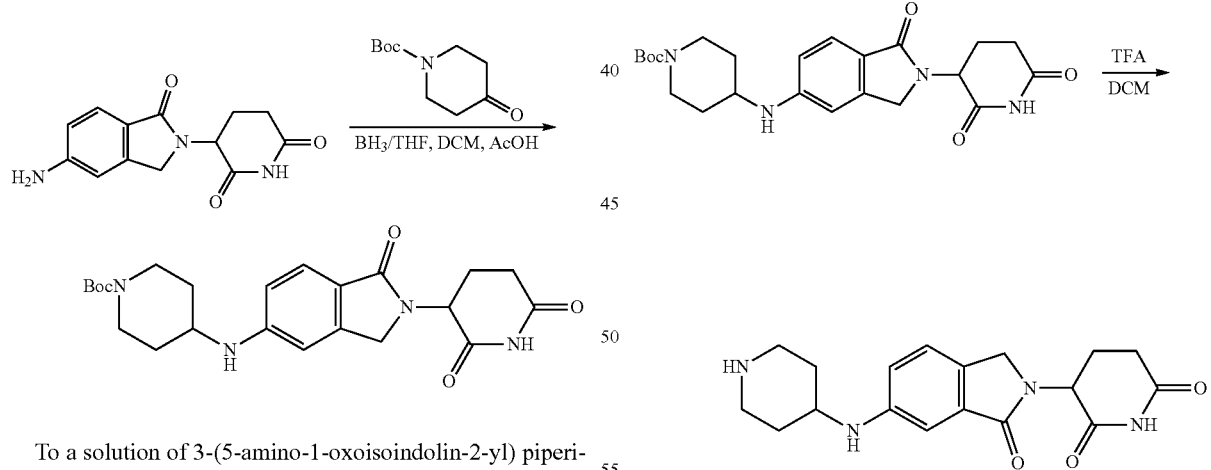

To a solution of 3-(5-amino-1-oxoisoindolin-2-yl) piperidine-2,6-dione (130 mg, 0.5 mmol) in dichloromethane (10 mL) and AcOH (2.0 mL) were added tert-butyl 4-oxopiperidine-1-carboxylate (119 mg, 1.0 mmol) and BH$_3$/THF (0.5 ml) at room temperature. The mixture was stirred at room temperature for 16 h, then quenched with H$_2$O (20 mL) and extracted with dichloromethane (3×20 mL). The organic layer was dried over sodium sulfate, filtered and concentrated to afford crude tert-butyl 4-((2-(2,6-dioxopiperidin-3-yl)-1-oxoisoindolin-5-yl)amino)piperidine-1-carboxylate (160 mg, 72% yield) as a green solid. This product was used in the next step directly without further purification. MS (ESI) m/z: 443.2 [M+H]$^+$.

To a solution of tert-butyl 4-((2-(2,6-dioxopiperidin-3-yl)-1-oxoisoindolin-5-yl)amino)piperidine-1-carboxylate (160 mg, 0.36 mmol) in DCM (5 mL) was added TFA (1 mL) at 0° C. The reaction mixture was stirred at room temperature for 16 h, before the solvent was removed under vacuum. The resulting residue was washed with diethyl ether to give 3-(1-oxo-5-(piperidin-4-ylamino)isoindolin-2-yl)piperidine-2,6-dione (100 mg, 80% yield) as a yellow solid. This product was used in the next step directly without further purification. MS (ESI) m/z: 343.2 [M+H]$^+$.

Step 3. Synthesis of 3-(5-((1-(6-(6-((R)-2-(3-fluoro-phenyl)pyrrolidin-1-yl)imidazo[1,2-b]pyridazin-3-yl)pyridin-2-yl)piperidin-4-yl)amino)-1-oxoisoindolin-2-yl)piperidine-2,6-dione

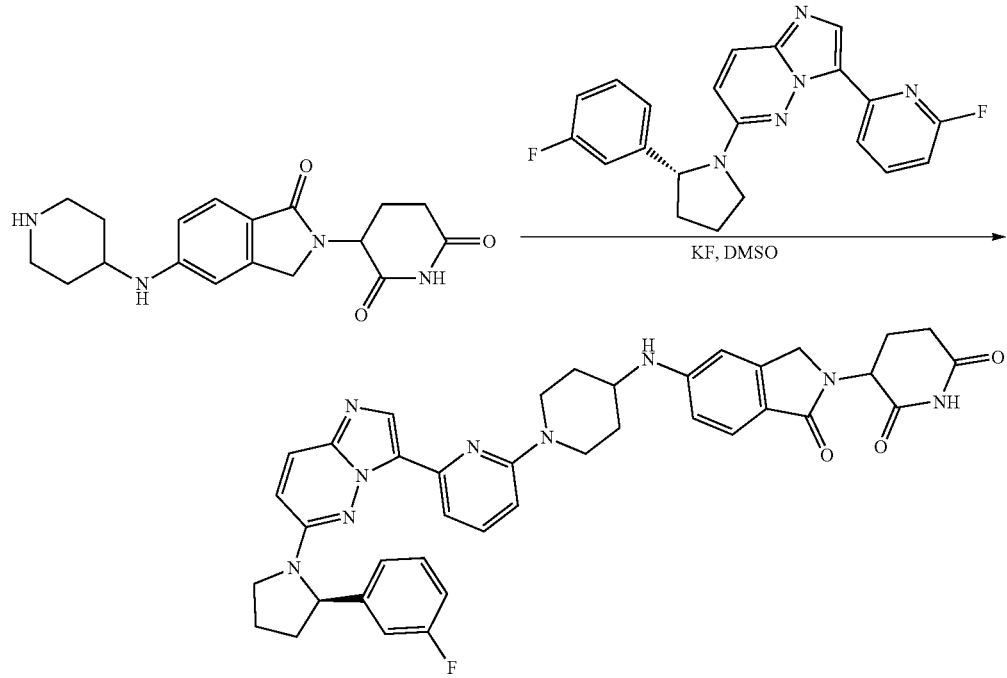

To a solution of 3-(1-oxo-5-(piperidin-4-ylamino)isoindolin-2-yl)piperidine-2,6-dione (100 mg, 0.29 mmol) and (R)-6-(2-(3-fluorophenyl)pyrrolidin-1-yl)-3-(6-fluoropyridin-2-yl)imidazo[1,2-b]pyridazine (110 mg, 0.29 mmol) in DMSO (5 mL) was added KF (67 mg, 1.16 mmol). The resulting solution was stirred at 120° C. for 5 h, before the reaction was quenched with water (10 mL) and extracted with ethyl acetate (3×20 mL). The combined organic layers were dried over sodium sulfate, and concentrated. The resulting residue was purified by silica gel chromatography column (DCM/MeOH=12:1) to give 3-(5-((1-(6-(6-((R)-2-(3-fluorophenyl)pyrrolidin-1-yl)imidazo[1,2-b]pyridazin-3-yl)pyridin-2-yl)piperidin-4-yl)amino)-1-oxoisoindolin-2-yl)piperidine-2,6-dione (23 mg, 11% yield) as a yellow solid. MS (ESI) m/z: 700.8 [M+H]$^+$.

Example 264: 2-((2-(2,6-Dioxopiperidin-3-yl)-1,3-dioxoisoindolin-5-yl)amino)-N-(1-(6-(6-((R)-2-(3-fluorophenyl)pyrrolidin-1-yl)imidazo[1,2-b]pyridazin-3-yl)pyridin-2-yl)azetidin-3-yl)acetamide (TR-213)

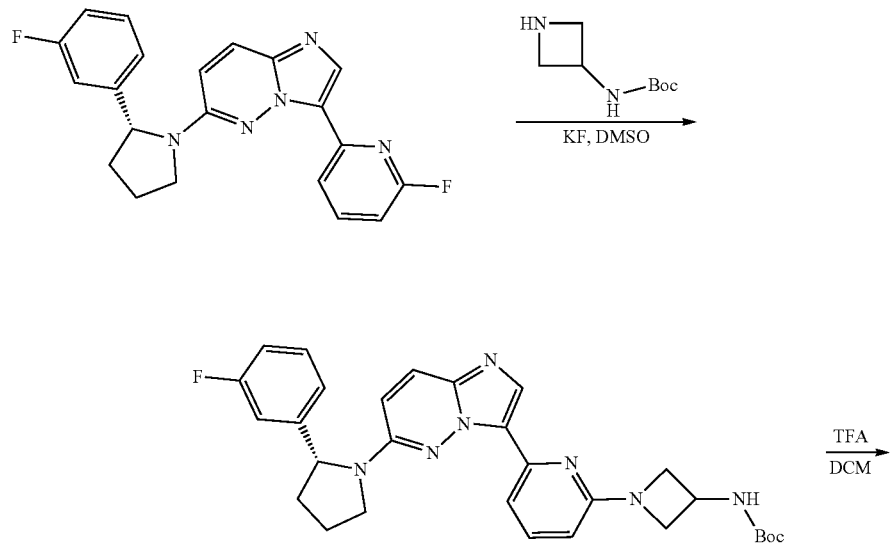

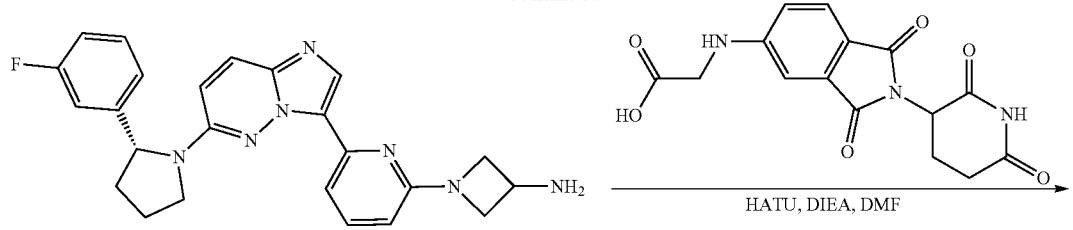

Step 1. Synthesis of tert-butyl (R)-(1-(6-(6-(2-(3-fluorophenyl)pyrrolidin-1-yl)imidazo[1,2-b]pyridazin-3-yl)pyridin-2-yl)azetidin-3-yl)carbamate Step 2. Synthesis of 3-(1-oxo-5-(piperidin-4-ylamino)isoindolin-2-yl)piperidine-2,6-dione

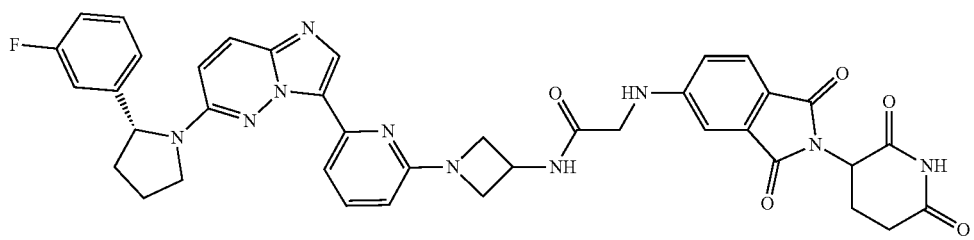

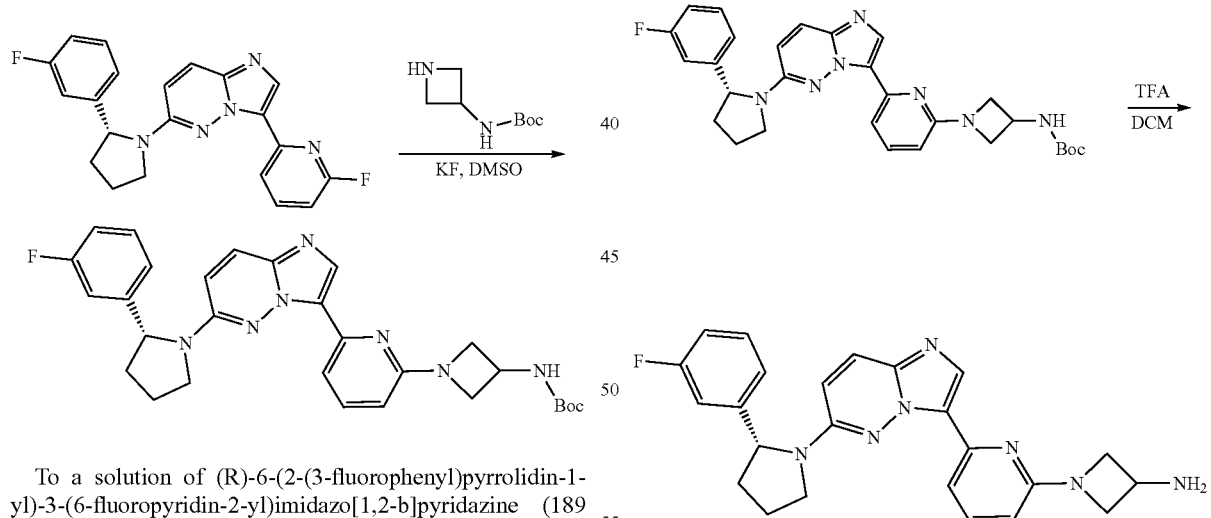

To a solution of (R)-6-(2-(3-fluorophenyl)pyrrolidin-1-yl)-3-(6-fluoropyridin-2-yl)imidazo[1,2-b]pyridazine (189 mg, 0.5 mmol) and tert-butyl azetidin-3-ylcarbamate (86 mg, 0.5 mmol) in DMSO (5 mL) was added KF (116 mg, 2 mmol). The resulting solution was stirred at 120° C. for 5 h, before it was quenched with water (10 mL) and extracted with ethyl acetate (3×20 mL). The combined organic layers were dried over sodium sulfate, and concentrated. The resulting residue was purified by silica gel chromatography column (DCM/MeOH=10:1) to give tert-butyl (R)-(1-(6-(6-(2-(3-fluorophenyl)pyrrolidin-1-yl)imidazo[1,2-b]pyridazin-3-yl)pyridin-2-yl)azetidin-3-yl)carbamate (181 mg, 68% yield) as a yellow solid. MS (ESI) m/z: 530.2 [M+H]$^+$.

To a solution of tert-butyl (R)-(1-(6-(6-(2-(3-fluorophenyl)pyrrolidin-1-yl)imidazo[1,2-b]pyridazin-3-yl)pyridin-2-yl)azetidin-3-yl)carbamate (181 mg, 0.34 mmol) in DCM (5 mL) was added TFA (1 mL) at 0° C. The reaction was stirred at room temperature for 1 h, before solvent was removed under vacuum. The resulting residue was washed with diethyl ether to give 3-(1-oxo-5-(piperidin-4-ylamino)isoindolin-2-yl)piperidine-2,6-dione (130 mg, 89% yield) as a yellow solid. This product was used in the next step directly without further purification. MS (ESI) m/z: 430.2 [M+H]$^+$.

Step 3. Synthesis of 2-((2-(2,6-dioxopiperidin-3-yl)-1,3-dioxoisoindolin-5-yl)amino)-N-(1-(6-(6-((R)-2-(3-fluorophenyl)pyrrolidin-1-yl)imidazo[1,2-b]pyridazin-3-yl)pyridin-2-yl)azetidin-3-yl)acetamide

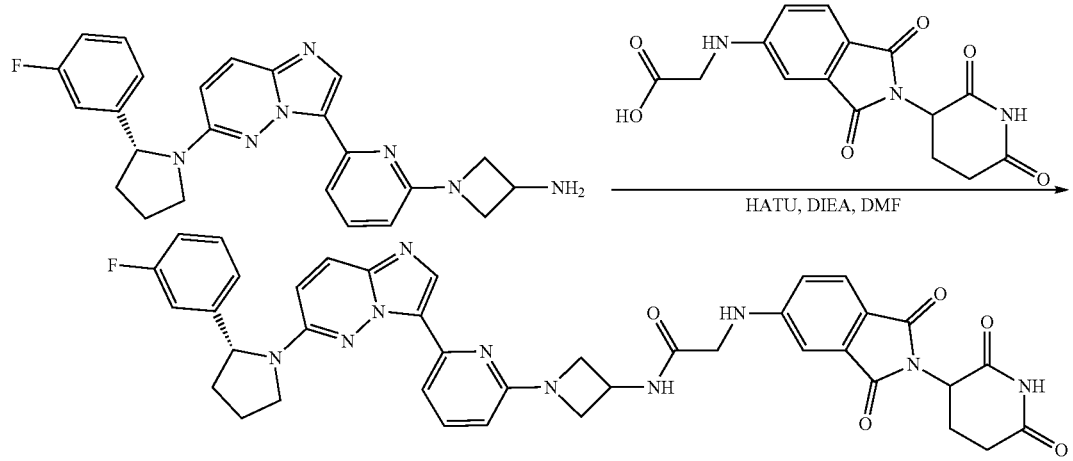

To a solution of 1-(2-(2,6-dioxopiperidin-3-yl)-1,3-dioxoisoindolin-5-yl)azetidine-3-carboxylic acid (120 mg, 0.27 mmol) and (2-(2,6-dioxopiperidin-3-yl)-1,3-dioxoisoindolin-5-yl)glycine (89 mg, 0.27 mmol) in N,N-dimethylformamide (10 mL) were added HATU (159 mg, 0.54 mmol) and DIEA (108 mg, 0.81 mmol) at 0° C. The mixture was stirred at room temperature for 2 h, before the reaction was quenched with water (20 mL) and extracted with ethyl acetate (3×20 mL). The combined organic layers were dried over sodium sulfate, and concentrated. The resulting residue was purified by silica gel chromatography (DCM/MeOH=10:1) to give 2-((2-(2,6-dioxopiperidin-3-yl)-1,3-dioxoisoindolin-5-yl)amino)-N-(1-(6-(6-((R)-2-(3-fluorophenyl)pyrrolidin-1-yl)imidazo[1,2-b]pyridazin-3-yl)pyridin-2-yl)azetidin-3-yl)acetamide (97 mg, 46% yield) as a yellow solid. MS (ESI) m/z: 744.0 [M+H]$^+$.

Example 265: 2-(2,6-Dioxo-3-piperidyl)-5-(2-(4-(6-(6-((2R)-2-(3-fluorophenyl)pyrrolidin-1-yl)imidazo[1,2-b]pyridazin-3-yl)-2-pyridyl)piperazin-1-yl)ethyl-((4-methoxyphenyl)methyl)amino)isoindoline-1,3-dione (TR-214)

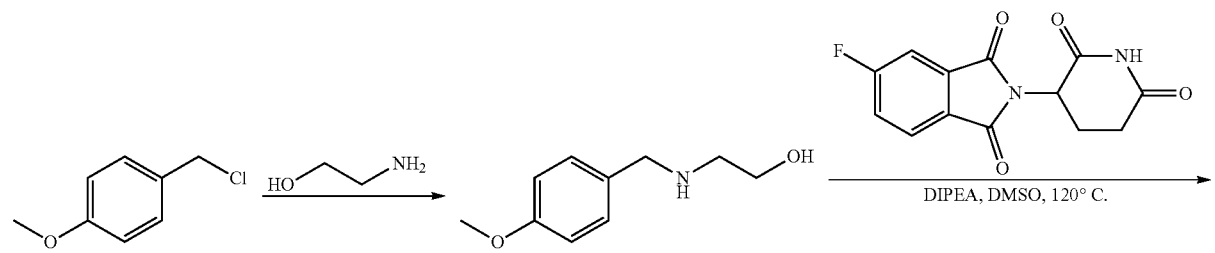

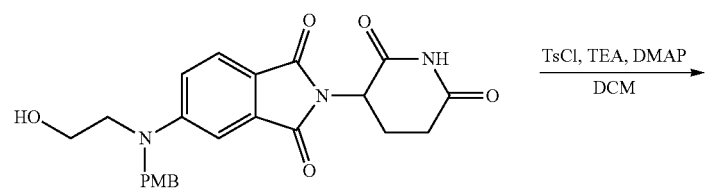

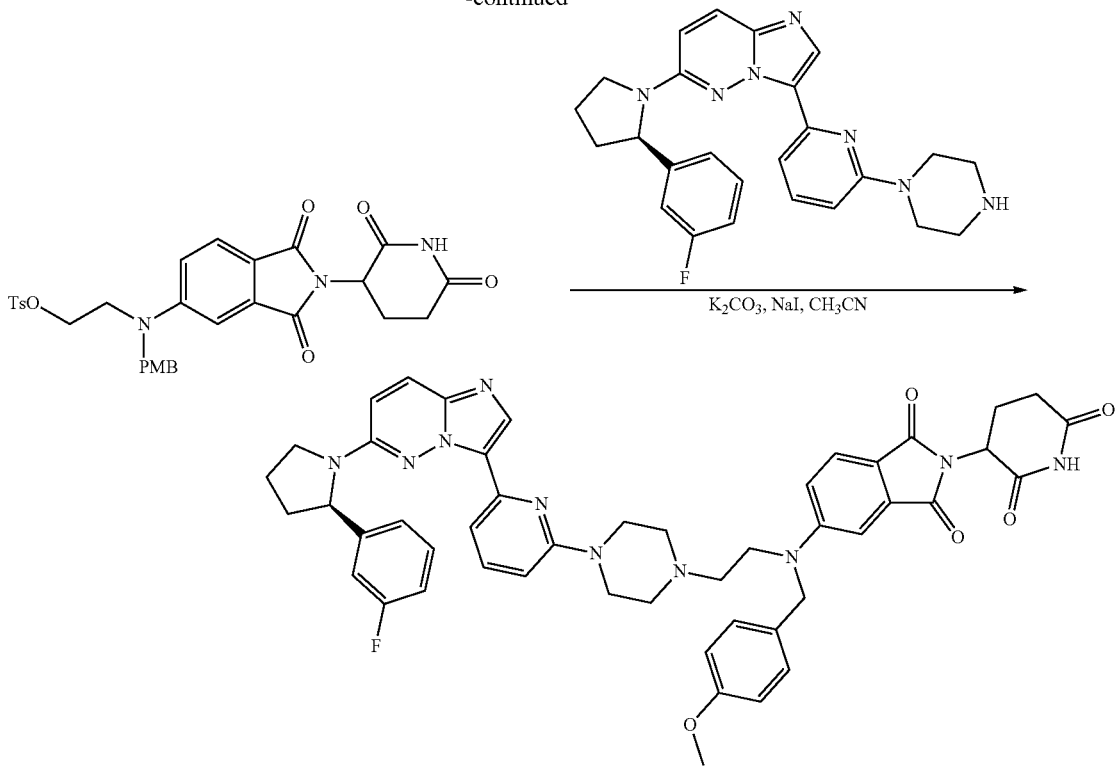

Step 1. Synthesis of 2-((4-methoxyphenyl)methylamino)ethanol

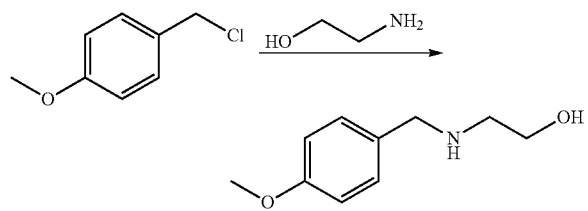

1-(Chloromethyl)-4-methoxy-benzene (8 g, 51.08 mmol) was added to 2-aminoethanol (31.20 g, 510.83 mmol) at 0° C. After the resulting reaction mixture was stirred at room temperature for 2 h, the reaction was quenched with water (100 mL), and extracted with DCM (2×100 mL). The combined organic layers were dried over sodium sulfate, and concentrated. The resulting residue was purified by silica gel chromatography (DCM/MeOH=20:1 to 10:1) to give 2-((4-methoxyphenyl)methylamino)ethanol (8 g, 86% yield). MS (ESI) m/z: 182.4 [M+H]⁺.

Step 2. Synthesis of 2-(2,6-dioxo-3-piperidyl)-5-(2-hydroxyethyl-((4-methoxyphenyl)methyl)amino)isoindoline-1,3-dione

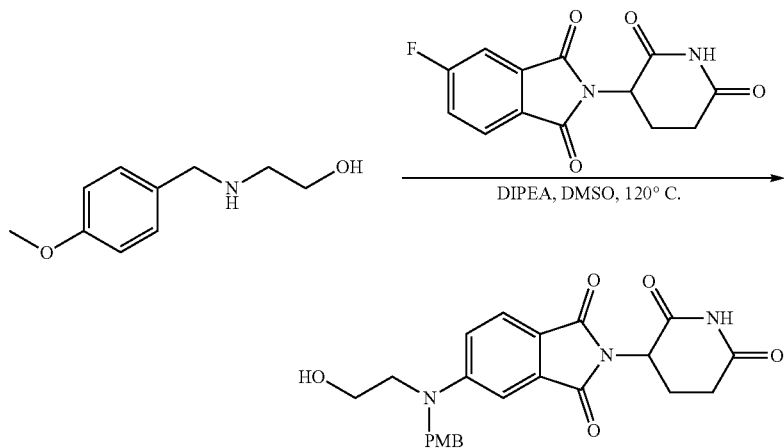

To a solution of 2-((4-methoxyphenyl)methylamino)ethanol (1.09 g, 6.00 mmol) and 2-(2,6-dioxo-3-piperidyl)-5-fluoro-isoindoline-1,3-dione (1.38 g, 5.00 mmol) in DMSO (20 mL) was added DIPEA (2.58 g, 19.98 mmol) at room temperature. The reaction mixture was stirred at 120° C. for 16 h, before the mixture was quenched with water (100 mL), and extracted with DCM (50 mL×2). The organic layer was washed with brine (50 mL×2), dried over Na$_2$SO$_4$, filtered and concentrated. The resulting residue was slurried in (petroleum ether/EtOAc=5:1, 50 mL), filtered to give 2-(2,6-dioxo-3-piperidyl)-5-(2-hydroxyethyl-((4-methoxyphenyl)methyl)amino)isoindoline-1,3-dione (1.5 g, 69% yield) as a yellow solid. MS (ESI) m/z: 438.4 [M+H]$^+$.

Step 3. Synthesis of 2-((2-(2,6-dioxo-3-piperidyl)-1,3-dioxo-isoindolin-5-yl)-((4-methoxyphenyl)methyl)amino)ethyl 4-methylbenzenesulfonate

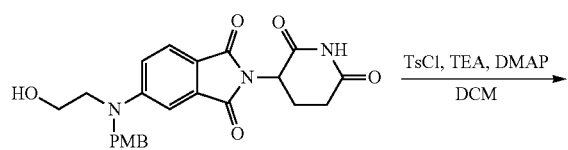

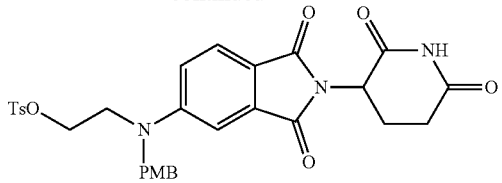

To a solution of 2-(2,6-dioxo-3-piperidyl)-5-(2-hydroxyethyl-((4-methoxyphenyl)methyl)amino)isoindoline-1,3-dione (437 mg, 998.98 umol) in TEA (5 mL) and DCM (5 mL) were added DMAP (122.05 mg, 998.98 umol) and 4-methylbenzenesulfonyl chloride (285.68 mg, 1.50 mmol) at room temperature. After the reaction mixture was stirred at room temperature for 2 h, the reaction was concentrated and purified by silica gel chromatography (DCM/MeOH=50:1) to give 2-((2-(2,6-dioxo-3-piperidyl)-1,3-dioxo-isoindolin-5-yl)-((4-methoxyphenyl)methyl)amino)ethyl 4-methylbenzenesulfonate (580 mg, 98% yield). MS (ESI) m/z: 592.4 [M+H]$^+$.

Step 4. Synthesis of 2-(2,6-dioxo-3-piperidyl)-5-(2-(4-(6-(6-((2R)-2-(3-fluorophenyl)pyrrolidin-1-yl)imidazo[1,2-b]pyridazin-3-yl)-2-pyridyl)piperazin-1-yl)ethyl-((4-methoxyphenyl)methyl)amino)isoindoline-1,3-dione

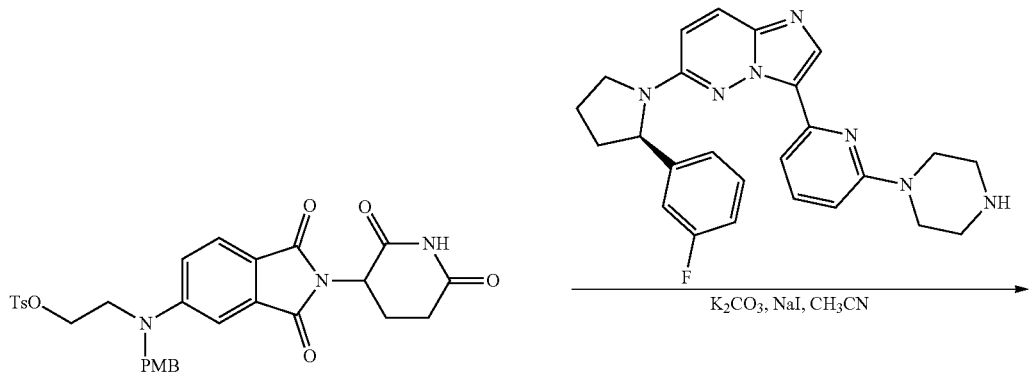

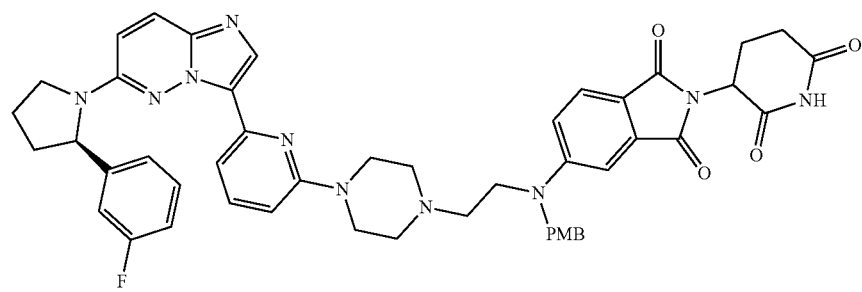

To a solution of 2-((2-(2,6-dioxo-3-piperidyl)-1,3-dioxo-isoindolin-5-yl)-((4-methoxyphenyl)methyl)amino)ethyl 4-methylbenzenesulfonate (480.22 mg, 811.69 umol) and 6-((2R)-2-(3-fluorophenyl)pyrrolidin-1-yl)-3-(6-piperazin-1-yl-2-pyridyl)imidazo[1,2-b]pyridazine (300 mg, 676.41 umol) in CH$_3$CN (20 mL) were added K$_2$CO$_3$ (560.07 mg, 4.06 mmol) and NaI (202.77 mg, 1.35 mmol) at room temperature. After the mixture was stirred at 98° C. for 16 h, the reaction was concentrated and purified by silica gel chromatography (DCM/MeOH=50:1 to 20:1) to give 2-(2, 6-dioxo-3-piperidyl)-5-(2-(4-(6-(6-((2R)-2-(3-fluorophenyl)pyrrolidin-1-yl)imidazo[1,2-b]pyridazin-3-yl)-2-pyridyl)piperazin-1-yl)ethyl-((4-methoxyphenyl)methyl)amino)isoindoline-1,3-dione (380 mg, 65% yield) as a yellow solid. MS (ESI) m/z: 864.0 [M+H]$^+$.

Example 266: N-(2-(2,6-Dioxopiperidin-3-yl)-1,3-dioxoisoindolin-5-yl)-1-(6-(6-((R)-2-(3-fluorophenyl)pyrrolidin-1-yl)imidazo[1,2-b]pyridazin-3-yl)pyridin-2-yl)piperidine-4-carboxamide (TR-215)

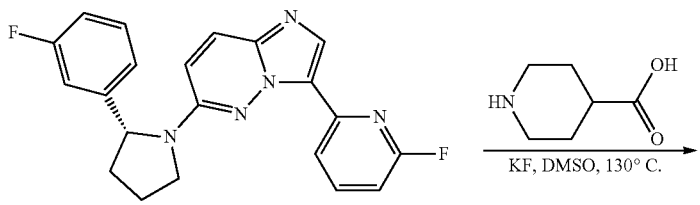

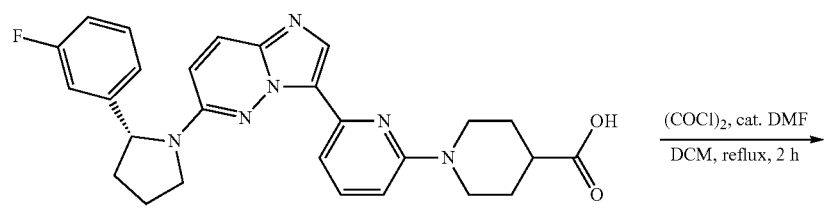

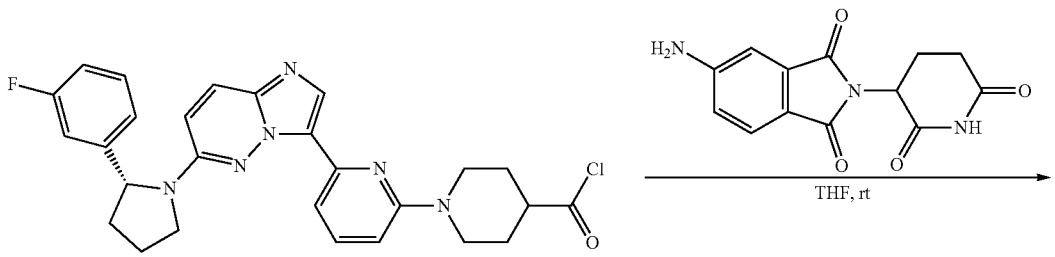

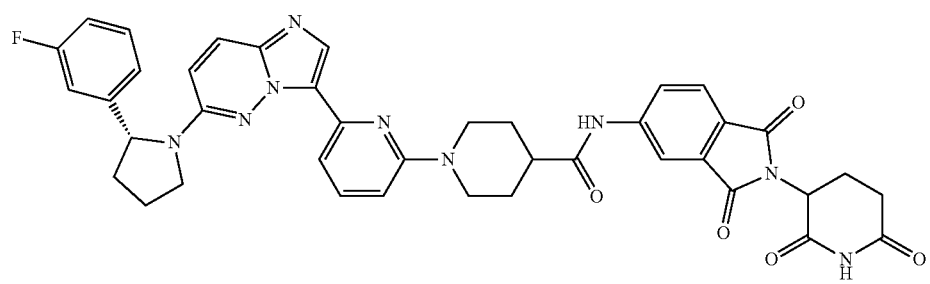

Step 1. Synthesis of (R)-1-(6-(6-(2-(3-fluorophenyl) pyrrolidin-1-yl)imidazo [1,2-b]pyridazin-3-yl)pyridin-2-yl)piperidine-4-carboxylic acid

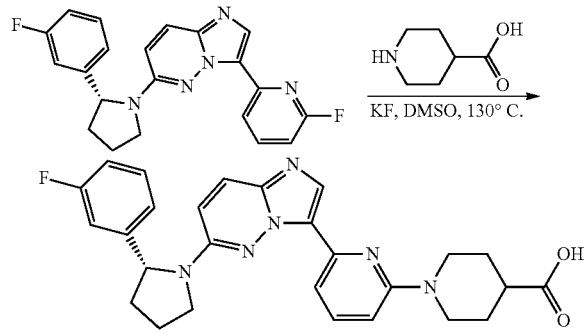

To a solution of piperidine-4-carboxylic acid (38 mg, 0.30 mmol) and (R)-6-(2-(3-fluorophenyl)pyrrolidin-1-yl)-3-(6-fluoropyridin-2-yl)imidazo[1,2-b]pyridazine (100 mg, 0.26 mmol) in DMSO (8 mL) was added KF (15 mg, 0.26 mmoL) at room temperature. After it was stirred at 130° C. for 16 h, the reaction was cooled to room temperature and quenched by H₂O (50 mL). The mixture was extracted with EtOAc (3×10 mL). The combined organic layers were concentrated and purified by reverse-phase chromatography to give the desired product (65 mg, 52% yield) as a light yellow solid. MS (ESI) m/z: 487.2 [M+H]⁺.

Step 2. Synthesis of (R)-1-(6-(6-(2-(3-fluorophenyl) pyrrolidin-1-yl)imidazo[1,2-b]pyridazin-3-yl)pyridin-2-yl)piperidine-4-carbonyl chloride

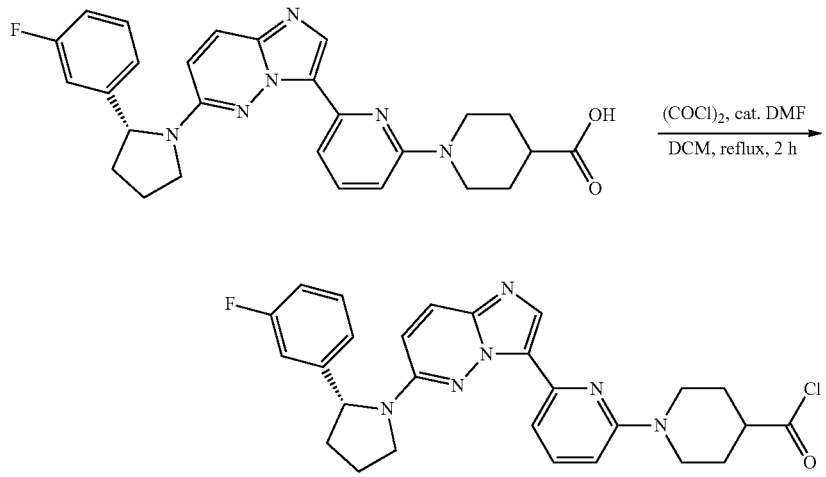

To a mixture of (R)-1-(6-(6-(2-(3-fluorophenyl)pyrrolidin-1-yl)imidazo[1,2-b]pyridazin-3-yl)pyridin-2-yl)piperidine-4-carboxylic acid (65 mg, 0.13 mmol) and DMF (3 mg, 0.04 mmol) in DCM (10 mL) was added oxalyl chloride (330 mg, 2.6 mmoL) at room temperature. After it was stirred at reflux for 2 h, the reaction was concentrated and used directly in the next step without further purification (60 mg, 92% yield) as a light yellow solid.

Step 3. Synthesis of N-(2-(2,6-dioxopiperidin-3-yl)-1,3-dioxoisoindolin-5-yl)-1-(6-(6-((R)-2-(3-fluorophenyl)pyrrolidin-1-yl)imidazo[1,2-b]pyridazin-3-yl)pyridin-2-yl)piperidine-4-carboxamide

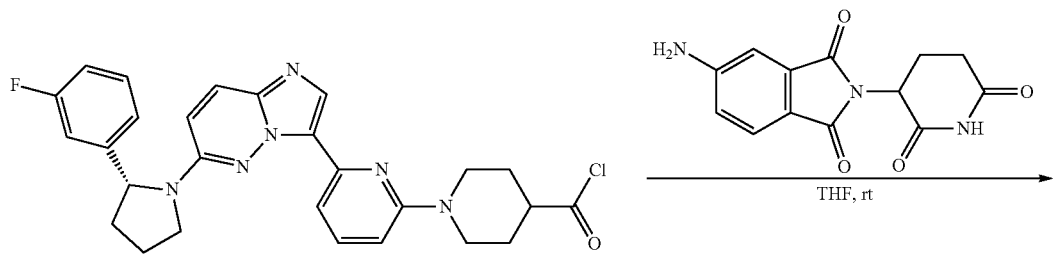

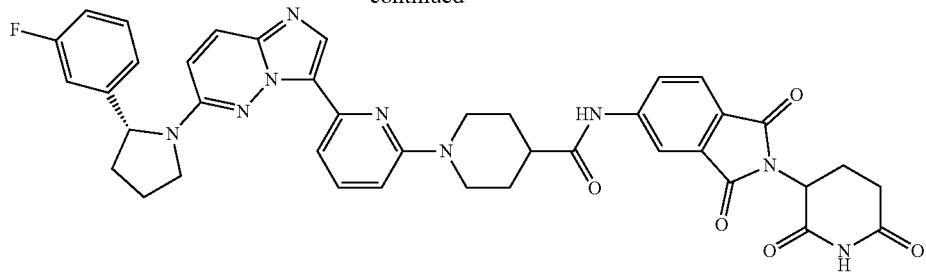

To a mixture of 5-amino-2-(2,6-dioxopiperidin-3-yl)isoindoline-1,3-dione (35 mg, 0.13 mmol) in THF (5 mL) was added (R)-1-(6-(6-(2-(3-fluorophenyl)pyrrolidin-1-yl)imidazo[1,2-b]pyridazin-3-yl)pyridin-2-yl)piperidine-4-carbonyl chloride (60 mg, 0.12 mmoL) at room temperature. After it was stirred at room temperature for 1 h, the mixture was concentrated and purified by reverse-phase chromatography to give the desired product N-(2-(2,6-dioxopiperidin-3-yl)-1,3-dioxoisoindolin-5-yl)-1-(6-(6-((R)-2-(3-fluorophenyl)pyrrolidin-1-yl)imidazo[1,2-b]pyridazin-3-yl)pyridin-2-yl)piperidine-4-carboxamide (12 mg, 13% yield) as a light yellow solid. MS (ESI) m/z: 742.3 [M+H]$^+$.

Example 267: 3-[4-[2-[4-[6-[6-[(2R)-2-(3-Fluorophenyl)pyrrolidin-1-yl]imidazo[1,2-b]pyridazin-3-yl]-2-pyridyl]piperazin-1-yl]ethylamino]-3-methyl-2-oxo-benzimidazol-1-yl]piperidine-2,6-dione (TR-216)

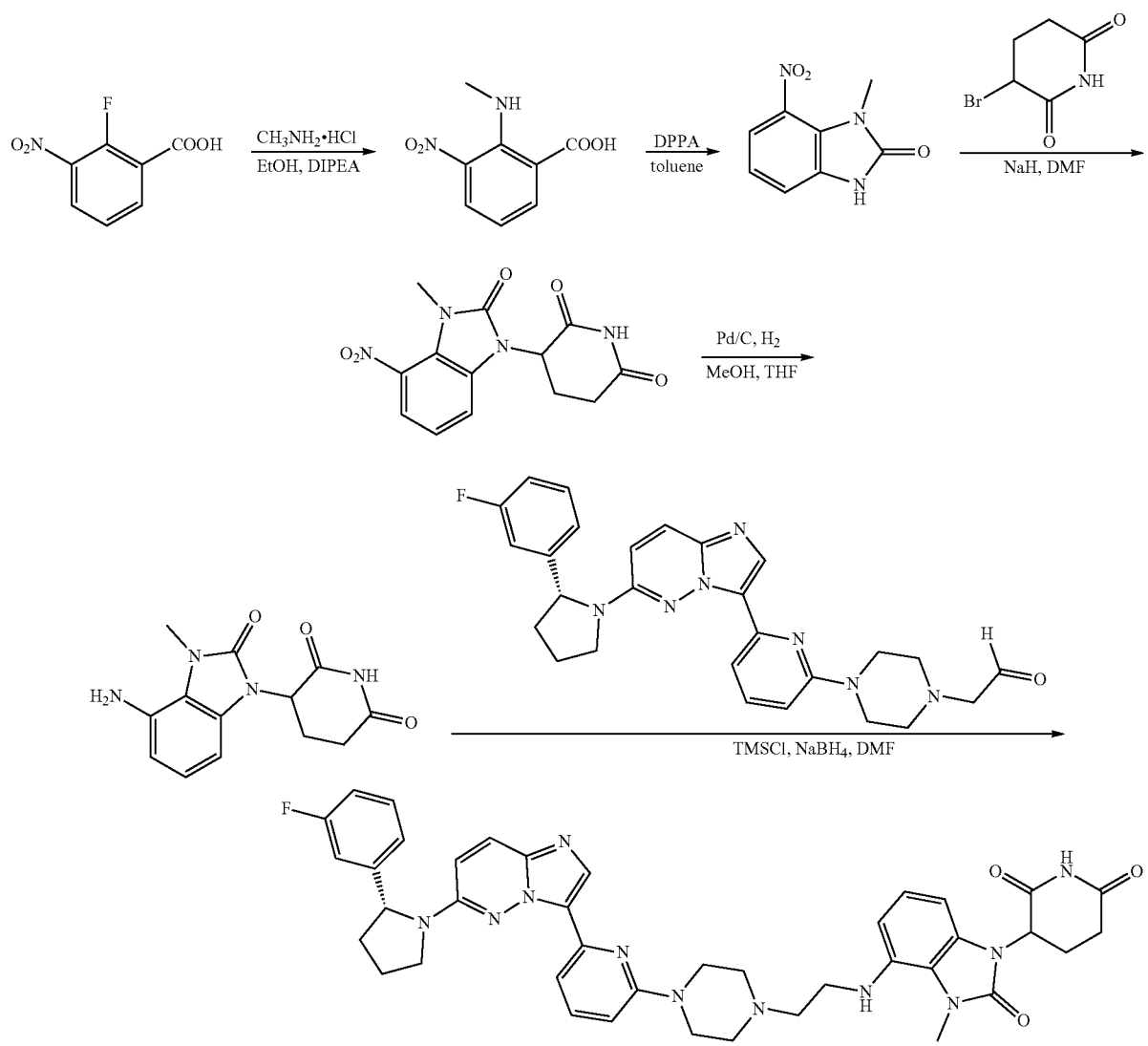

Step 1. Synthesis of 2-(methylamino)-3-nitrobenzoic acid

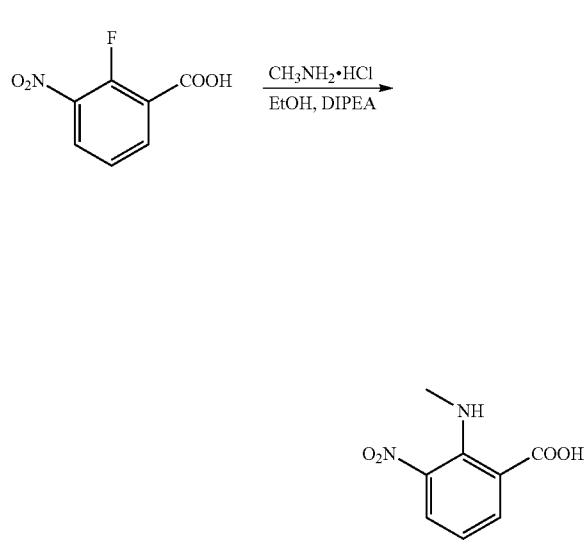

To a solution of 2-fluoro-3-nitrobenzoic acid (20 g, 0.108 mol) and methanamine hydrochloride (8.7 g, 0.129 mol) in EtOH (200 mL) was added DIEA (70 g, 0.54 mol) at room temperature. After the reaction mixture was stirred at 80° C. overnight, the reaction was cooled down to room temperature. After concentration, the resulting residue was diluted with water (100 mL) and adjusted the pH to 3 with conc. HCl, and extracted with EtOAc (2×150 mL). The combined organic layers were washed with brine twice, dried with sodium sulfate, filtered and concentrated to give crude 2-(methylamino)-3-nitrobenzoic acid (21 g, 100% yield) as a yellow solid. This product was used in the next step directly without further purification. MS (ESI) m/z: 197.3 [M+H]$^+$.

Step 2. Synthesis of 1-methyl-7-nitro-1,3-dihydro-2H-benzo[d]imidazol-2-one

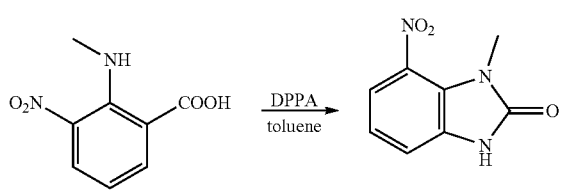

To a solution of 2-(methylamino)-3-nitrobenzoic acid (24 g, 0.122 mol) in t-BuOH (300 mL) were added DIPEA (31 g, 0.244 mol) and DPPA (37 g, 0.134 mol) at room temperature. After the reaction mixture was stirred at 90° C. for 16 h, the reaction solution was concentrated. The resulting residue was triturated with water (500 ml), filtered and washed with EtOAc. The solid was collected and dried to give 1-methyl-7-nitro-1,3-dihydro-2H-benzo[d]imidazol-2-one (22 g, 93% yield) as a yellow solid. MS (ESI) m/z: 194.1[M+H]$^+$.

Step 3. Synthesis of 3-(3-methyl-5-nitro-2-oxo-benzimidazol-1-yl)piperidine-2,6-dione

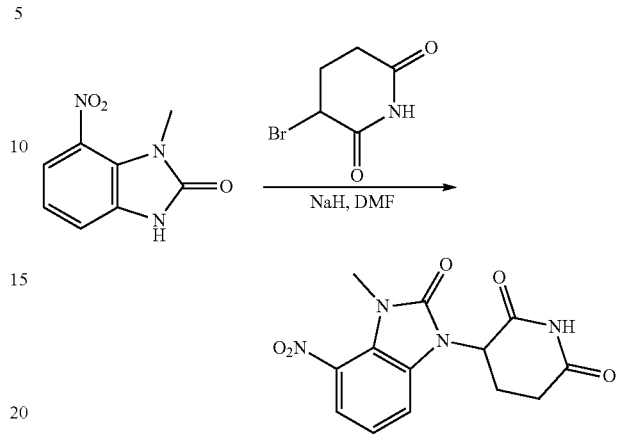

To a suspension of NaH (48 mg, 1.20 mmol) in DMF (5 mL) was added 3-methyl-5-nitro-1H-benzimidazol-2-one (193 mg, 999.18 umol) at 0° C. The reaction mixture was stirred at 0° C. for 0.5 h, before a solution of 3-bromopiperidine-2,6-dione (383.70 mg, 2.00 mmol) in DMF (5 mL) was added dropwise. After the completion of addition, the reaction mixture was stirred at 80° C. for 2 h. After concentration, the reaction was purified by prep-HPLC to give 3-(3-methyl-5-nitro-2-oxo-benzimidazol-1-yl)piperidine-2,6-dione (80 mg, 26% yield) as a black solid. MS (ESI) m/z: 305.3 [M+H]$^+$.

Step 4. Synthesis of 3-(4-amino-3-methyl-2-oxo-benzimidazol-1-yl)piperidine-2,6-dione

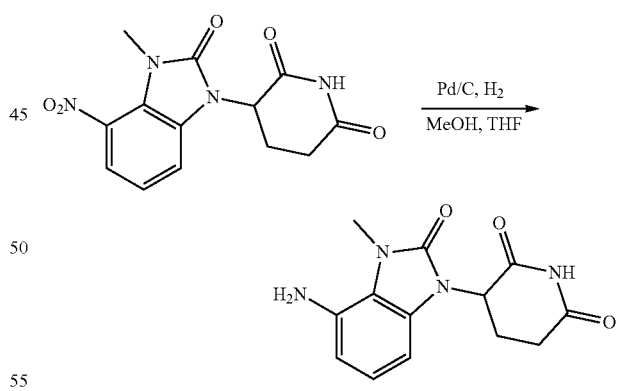

To a solution of 3-(3-methyl-4-nitro-2-oxo-benzimidazol-1-yl)piperidine-2,6-dione (80 mg, 262.93 umol) in MeOH (10 mL) and THF (10 mL) was added Pd/C (20 mg) at room temperature. After the reaction mixture was stirred at room temperature for 1 h under hydrogen atmosphere, the reaction was filtered and concentrated to give 3-(4-amino-3-methyl-2-oxo-benzimidazol-1-yl)piperidine-2,6-dione (70 mg, 97% yield) as a brown solid. This product was used in the next step directly without further purification. MS (ESI) m/z: 275.3 [M+H]$^+$.

Step 5. Synthesis of 3-[4-[2-[4-[6-[6-[(2R)-2-(3-fluorophenyl)pyrrolidin-1-yl]imidazo[1,2-b]pyridazin-3-yl]-2-pyridyl]piperazin-1-yl]ethylamino]-3-methyl-2-oxo-benzimidazol-1-yl]piperidine-2,6-dione

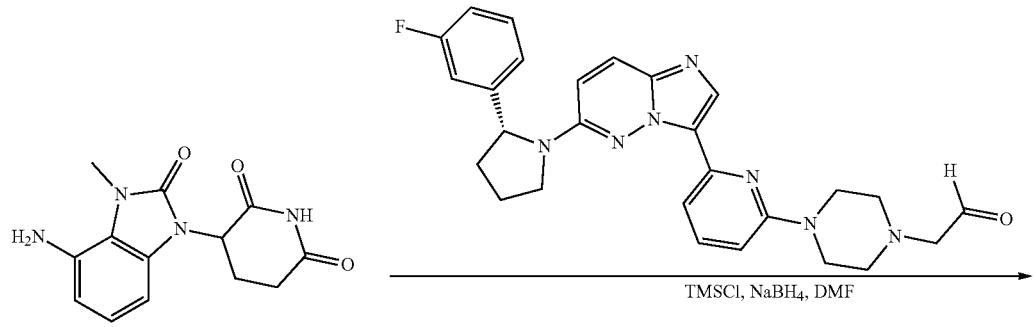

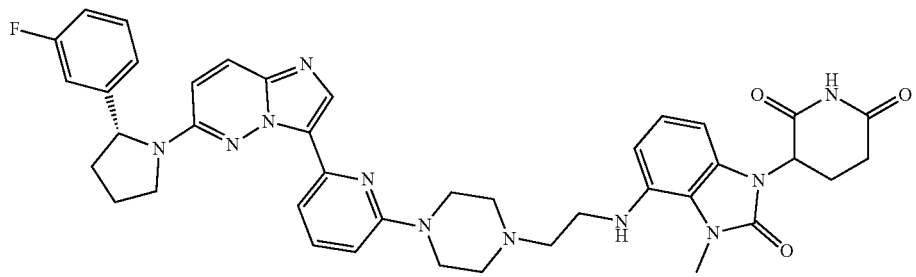

To a solution of 2-[4-[6-[6-[(2R)-2-(3-fluorophenyl)pyrrolidin-1-yl]imidazo[1,2-b]pyridazin-3-yl]-2-pyridyl]piperazin-1-yl]acetaldehyde (61.96 mg, 127.61 umol) and 3-(4-amino-3-methyl-2-oxo-benzimidazol-1-yl)piperidine-2,6-dione (35 mg, 127.61 umol) in DMF (10 mL) were added TMSCl (41.35 mg, 382.83 umol) and NaBH₄ (9.70 mg, 255.22 umol) at 0° C. After the reaction mixture was stirred at 0° C. for 4 h, the reaction was warmed to room temperature and stirred for 16 h. After concentration, the reaction was purified by prep-HPLC to give the product with some impurities. The crude material was further purified by prep-TLC (DCM/MeOH=15:1) to give 3-[4-[2-[4-[6-[6-[(2R)-2-(3-fluorophenyl)pyrrolidin-1-yl]imidazo[1,2-b]pyridazin-3-yl]-2-pyridyl]piperazin-1-yl]ethylamino]-3-methyl-2-oxo-benzimidazol-1-yl]piperidine-2,6-dione (14 mg, 15% yield) as a white solid. MS (ESI) m z: 744.9 [M+H]⁺.

Example 268: 3-[4-[3-[4-[6-[6-[(2R)-2-(3-Fluorophenyl)pyrrolidin-1-yl]imidazo[1,2-b]pyridazin-3-yl]-2-pyridyl]piperazin-1-yl]propylamino]-3-methyl-2-oxo-benzimidazol-1-yl]piperidine-2,6-dione (TR-217)

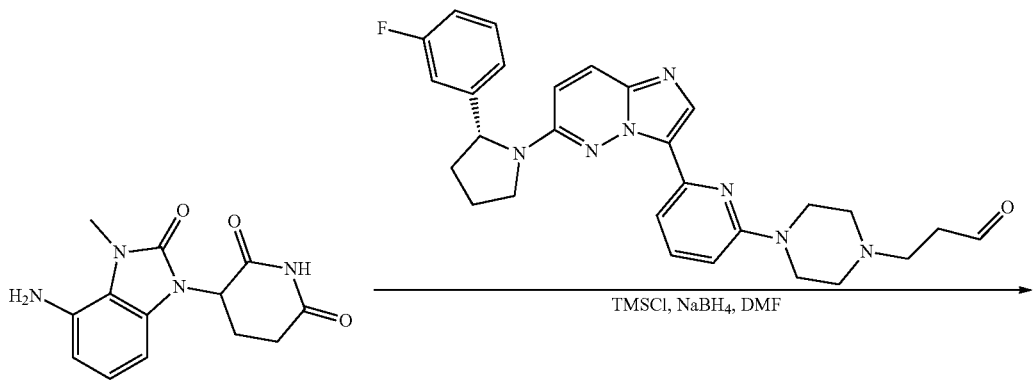

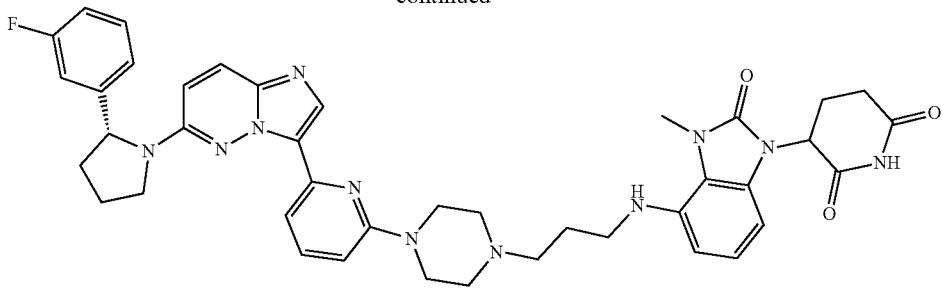

To a solution of 3-[4-[6-[6-[(2R)-2-(3-fluorophenyl)pyrrolidin-1-yl]imidazo[1,2-b]pyridazin-3-yl]-2-pyridyl]piperazin-1-yl]propanal (54.64 mg, 109.38 umol) and 3-(4-amino-3-methyl-2-oxo-benzimidazol-1-yl)piperidine-2,6-dione (30 mg, 109.38 umol) in DMF (5 mL) were added TMSCl (41.35 mg, 328.14 umol) and NaBH₄ (8.31 mg, 218.76 umol) at 0° C. After the reaction mixture was stirred at 0° C. for 4 h, the reaction was warmed to room temperature and stirred for 16 h. After concentration, the reaction was purified by prep-HPLC to give the crude product, which was further purified a by prep-TLC (DCM/MeOH=15:1) to give 3-[4-[3-[4-[6-[6-[(2R)-2-(3-fluorophenyl)pyrrolidin-1-yl]imidazo[1,2-b]pyridazin-3-yl]-2-pyridyl]piperazin-1-yl]propylamino]-3-methyl-2-oxo-benzimidazol-1-yl]piperidine-2,6-dione (10 mg, 12% yield) as a white solid. MS (ESI) m/z: 759.0 [M+H]⁺.

Example 269: 3-(5-(((1-(6-(6-((R)-2-(3-Fluorophenyl)pyrrolidin-1-yl)imidazo[1,2-b]pyridazin-3-yl)pyridin-2-yl)piperidin-4-yl)methyl)amino)-1-oxoisoindolin-2-yl)piperidine-2,6-dione (TR-218)

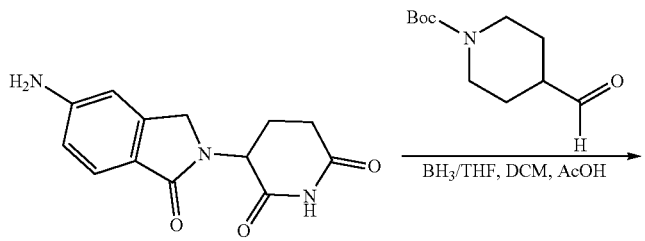

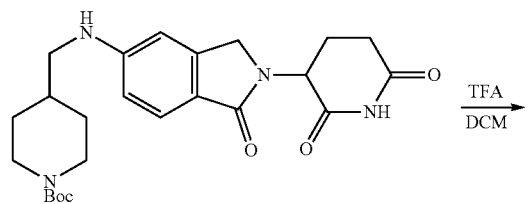

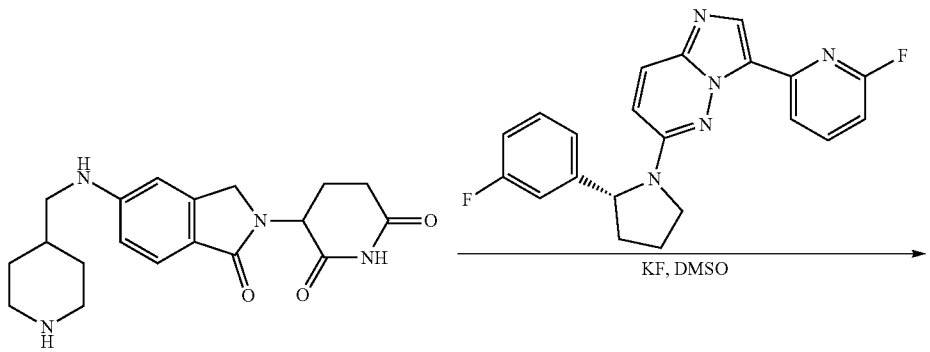

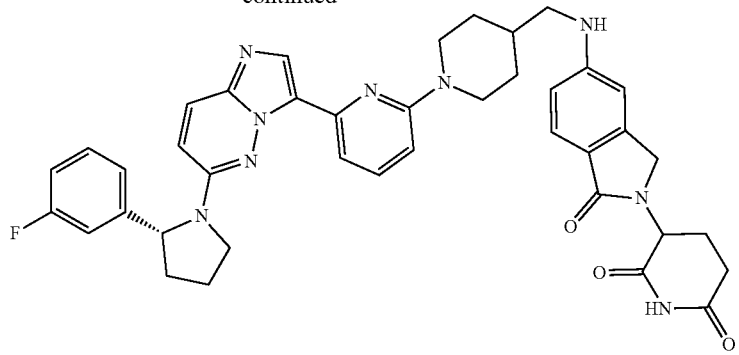

-continued

Step 1. Synthesis of tert-butyl 4-(((2-(2,6-dioxopiperidin-3-yl)-1-oxoisoindolin-5-yl)amino)methyl)piperidine-1-carboxylate Step 2. Synthesis of 3-(1-oxo-5-((piperidin-4-ylmethyl)amino)isoindolin-2-yl)piperidine-2,6-dione

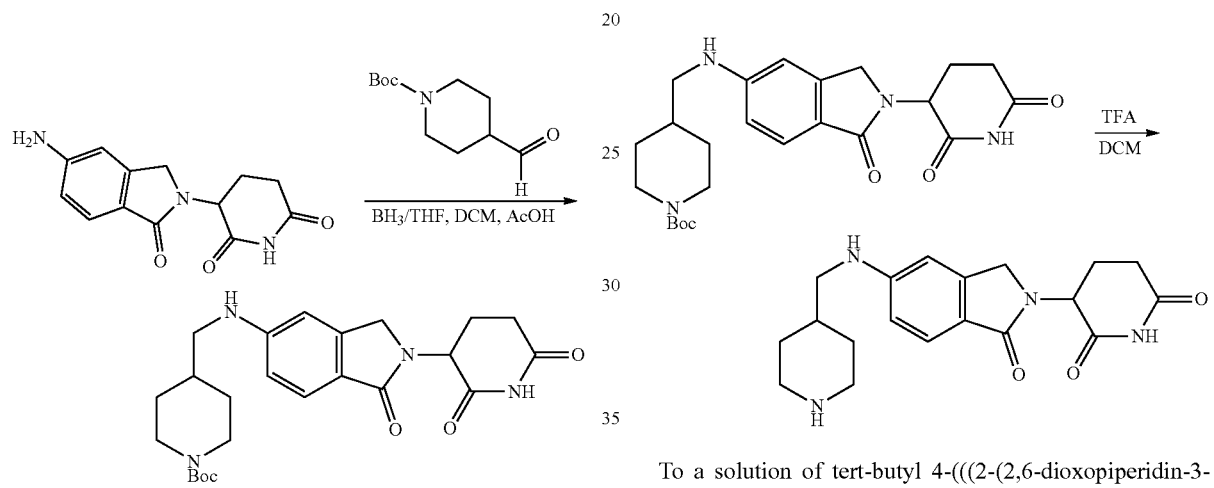

To a solution of 3-(5-amino-1-oxoisoindolin-2-yl) piperidine-2,6-dione (130 mg, 0.5 mmol) in dichloromethane (10 mL) and AcOH (2.0 mL) were added tert-butyl 4-formylpiperidine-1-carboxylate (130 mg, 1.0 mmol) and BH$_3$/THF (1 M, 0.5 ml). After the mixture was stirred at room temperature for 16 h, the reaction was quenched with water (20 mL) and extracted with ethyl acetate (3×20 mL). The combined organic layers were dried over sodium sulfate, filtered and concentrated to give tert-butyl 4-(((2-(2,6-dioxopiperidin-3-yl)-1-oxoisoindolin-5-yl)amino)methyl)piperidine-1-carboxylate (230 mg, crude) as a green solid. This crude product was used in the next step directly without further purification. MS (ESI) m/z: 457.3 [M+H]$^+$.

To a solution of tert-butyl 4-(((2-(2,6-dioxopiperidin-3-yl)-1-oxoisoindolin-5-yl)amino)methyl)piperidine-1-carboxylate (230 mg, crude) in DCM (10 mL) was added TFA (2 mL) at 0° C. After the reaction mixture was stirred at room temperature for 16 h, the solvent was removed under vacuum. The resulting residue was washed with diethyl ether to give 3-(1-oxo-5-((piperidin-4-ylmethyl)amino)isoindolin-2-yl)piperidine-2,6-dione (200 mg, crude) as a yellow solid. This product was used in the next step directly without further purification. MS (ESI) m/z: 357.3 [M+H]$^+$.

Step 3. Synthesis of 3-(5-(((1-(6-(6-((R)-2-(3-fluorophenyl)pyrrolidin-1-yl)imidazo[1,2-b]pyridazin-3-yl)pyridin-2-yl)piperidin-4-yl)methyl)amino)-1-oxoisoindolin-2-yl)piperidine-2,6-dione

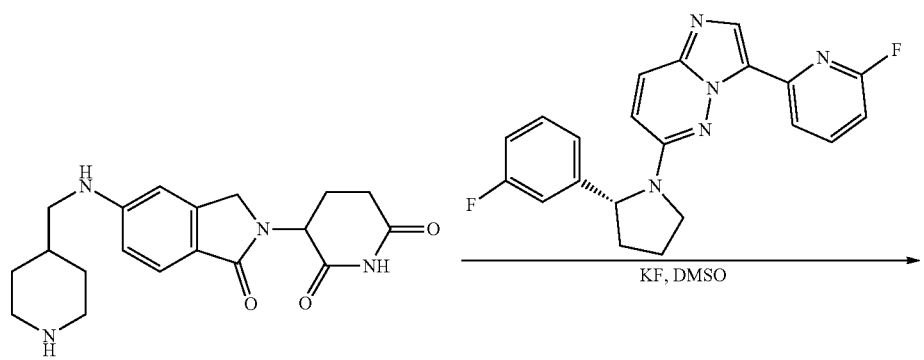

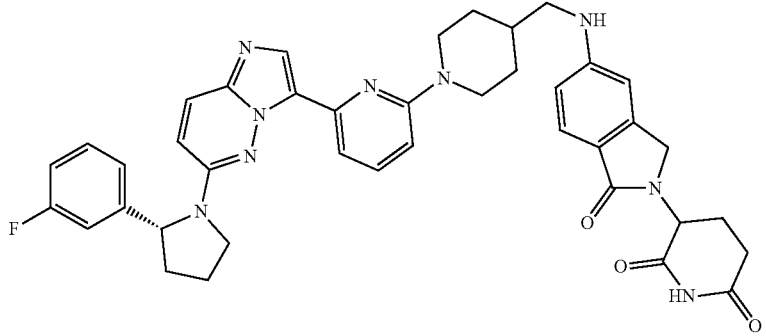

To a solution of 3-(1-oxo-5-((piperidin-4-ylmethyl)amino)isoindolin-2-yl)piperidine-2,6-dione (200 mg, crude) and (R)-6-(2-(3-fluorophenyl)pyrrolidin-1-yl)-3-(6-fluoropyridin-2-yl)imidazo[1,2-b]pyridazine (88 mg, 0.23 mmol) in DMSO (5 mL) was added KF (270 mg, 0.92 mmol). The resulting solution was stirred at 120° C. for 5 h, before the reaction was quenched with water (10 mL) and extracted with ethyl acetate (3×10 mL). The combined organic layers were dried over sodium sulfate, and concentrated. The resulting residue was purified by silica gel column (DCM/MeOH=10:1) to give 3-(5-(((1-(6-(6-((R)-2-(3-fluorophenyl)pyrrolidin-1-yl)imidazo[1,2-b]pyridazin-3-yl)pyridin-2-yl)piperidin-4-yl)methyl)amino)-1-oxoisoindolin-2-yl)piperidine-2,6-dione (14 mg, 8% yield) as a yellow solid. MS (ESI) m/z: 714.8 [M+H]$^+$.

Example 270: 3-(5-((1-(6-(6-((R)-2-(3-Fluorophenyl)pyrrolidin-1-yl)imidazo[1,2-b]pyridazin-3-yl)pyridin-2-yl)azetidin-3-yl)ethynyl)-1-oxoisoindolin-2-yl)piperidine-2,6-dione (TR-219)

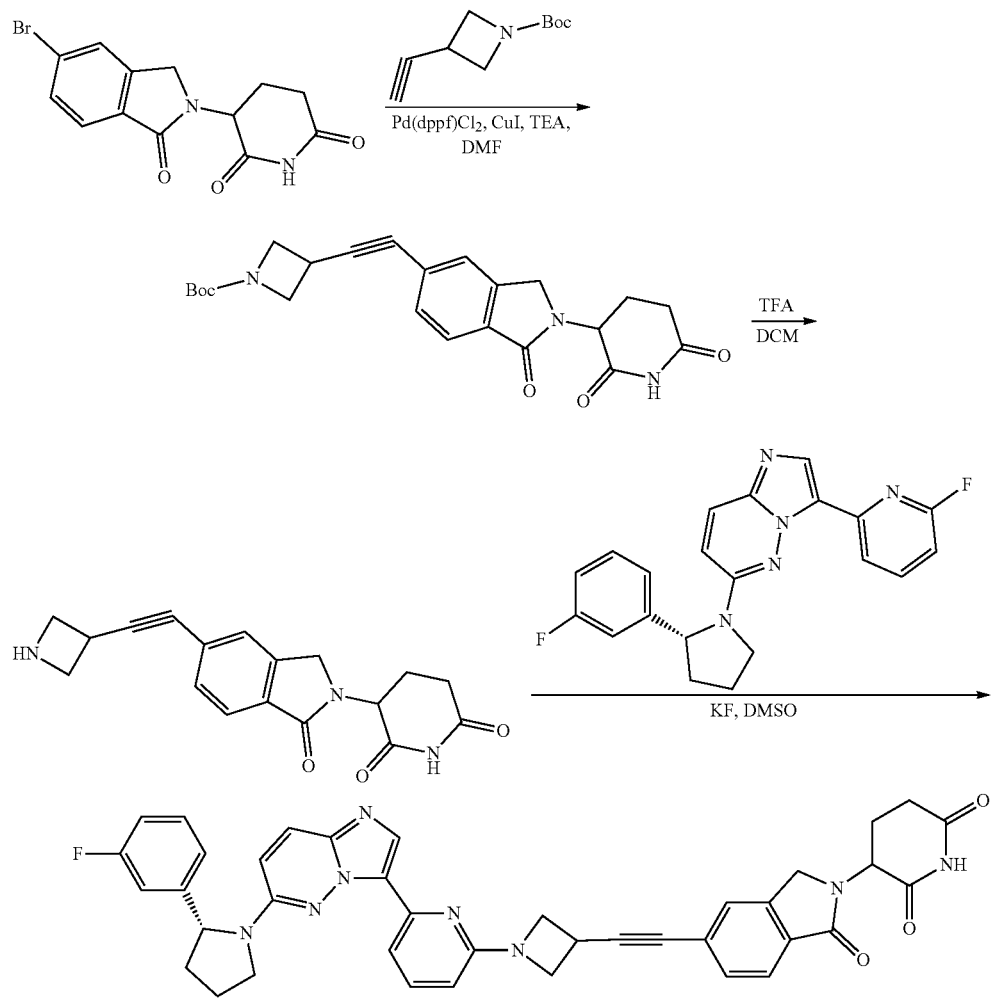

Step 1. Synthesis of tert-butyl 3-((2-(2,6-dioxopiperidin-3-yl)-1-oxoisoindolin-5-yl)ethynyl)azetidine-1-carboxylate

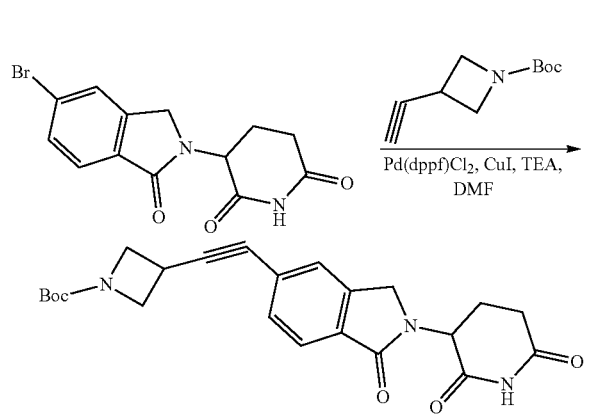

To a solution of 3-(5-bromo-1-oxoisoindolin-2-yl)piperidine-2,6-dione (136 mg, 0.42 mmol) in DMF (5 mL) were added TEA (170 mg, 4.2 mmol), CuI (8 mg, 0.04 mmol), Pd(dppf)Cl₂ (31 mg, 0.04 mmol), and tert-butyl 3-ethynylazetidine-1-carboxylate (100 mg, 0.42 mmol). The reaction mixture was stirred at 80° C. for 12 h. Then the resulting black mixture was diluted with ethyl acetate (20 mL), washed with brine (3×20 mL). The organic layer was dried over sodium sulfate, filtered, and concentrated. The resulting residue was purified by silica gel flash chromatography (petroleum/ethyl acetate=3:7) to give tert-butyl 3-((2-(2,6-dioxopiperidin-3-yl)-1-oxoisoindolin-5-yl)ethynyl)azetidine-1-carboxylate (130 mg, 73% yield) as a brown solid. MS (ESI) m/z: 424.2 [M+H]⁺.

Step 2. Synthesis of 3-(5-(azetidin-3-ylethynyl)-1-oxoisoindolin-2-yl)piperidine-2,6-dione

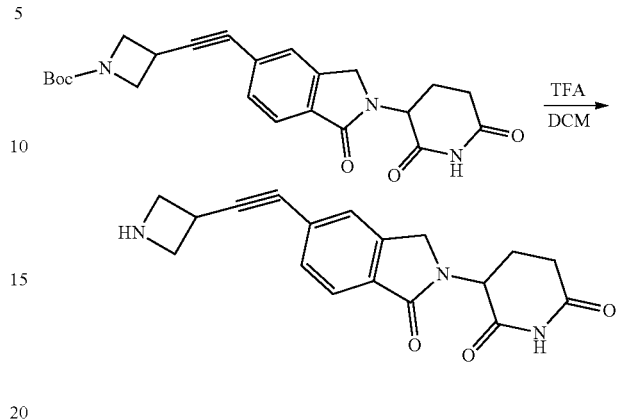

To a solution of tert-butyl 3-((2-(2,6-dioxopiperidin-3-yl)-1-oxoisoindolin-5-yl)ethynyl)azetidine-1-carboxylate (130 mg, 0.30 mmol) in DCM (5 mL) was added TFA (1 mL) at 0° C. After the reaction was stirred at room temperature for 1 h, the solvent was removed under vacuum. The residue was washed with diethyl ether to give crude 3-(5-(azetidin-3-ylethynyl)-1-oxoisoindolin-2-yl)piperidine-2,6-dione (86 mg, 89% yield) as a yellow solid. This product was used in the next step directly without further purification. MS (ESI) m/z: 324.2 [M+H]⁺.

Step 3. Synthesis of 3-(5-((1-(6-(6-((R)-2-(3-fluorophenyl)pyrrolidin-1-yl)imidazo[1,2-b]pyridazin-3-yl)pyridin-2-yl)azetidin-3-yl)ethynyl)-1-oxoisoindolin-2-yl)piperidine-2,6-dione

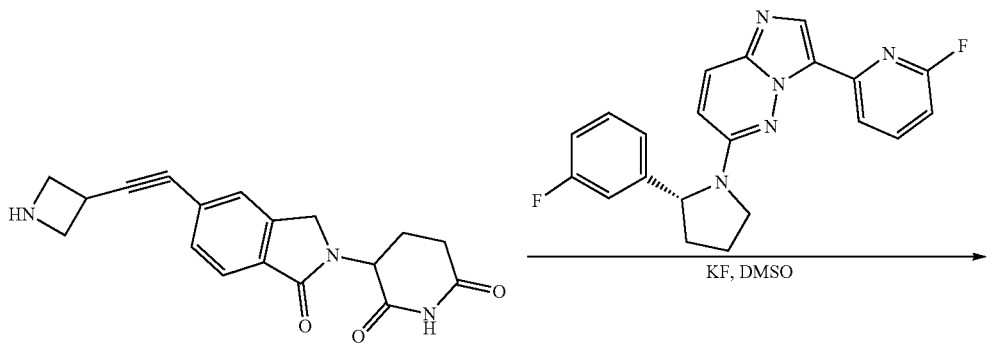

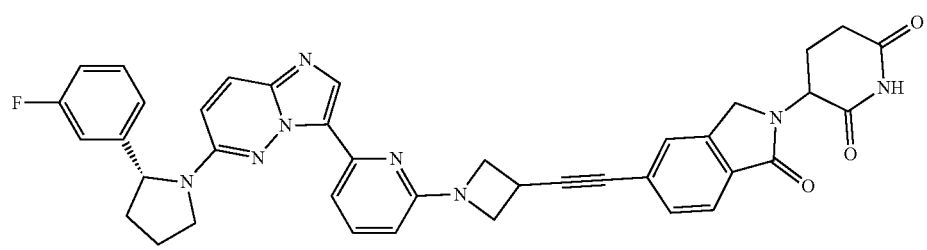

To a solution of 3-(5-(azetidin-3-ylethynyl)-1-oxoisoindolin-2-yl)piperidine-2,6-dione (86 mg, 0.26 mmol) and (R)-6-(2-(3-fluorophenyl)pyrrolidin-1-yl)-3-(6-fluoropyridin-2-yl)imidazo[1,2-b]pyridazine (60 mg, 0.26 mmol) in DMSO (5 mL) was added KF (77 mg, 1.04 mmol). The resulting solution was stirred at 120° C. for 5 h, before the reaction was quenched with water (20 mL) and extracted with ethyl acetate (3×20 mL). The combined organic layers were dried over sodium sulfate, filtered and concentrated. The resulting residue was purified by silica gel column (DCM/MeOH=10:1) to give 3-(5-((1-(6-(6-((R)-2-(3-fluorophenyl)pyrrolidin-1-yl)imidazo[1,2-b]pyridazin-3-yl)pyridin-2-yl)azetidin-3-yl)ethynyl)-1-oxoisoindolin-2-yl)piperidine-2,6-dione (47 mg, 26% yield) as a yellow solid. MS (ESI) m/z: 681.2 [M+H]$^+$.

Example 271: 3-(5-((2-(4-(6-(6-((R)-2-(3-Fluorophenyl)pyrrolidin-1-yl)imidazo[1,2-b]pyridazin-3-yl)pyridin-2-yl)piperazin-1-yl)ethyl)amino)-3-methyl-2-oxo-2,3-dihydro-1H-benzo[d]imidazol-1-yl)piperidine-2,6-dione (TR-220)

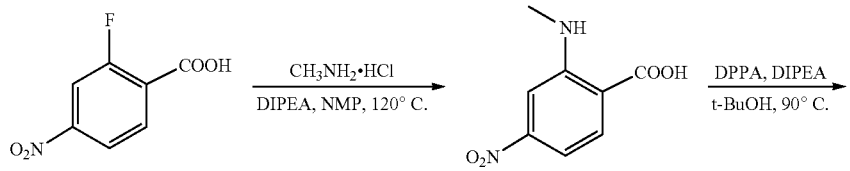

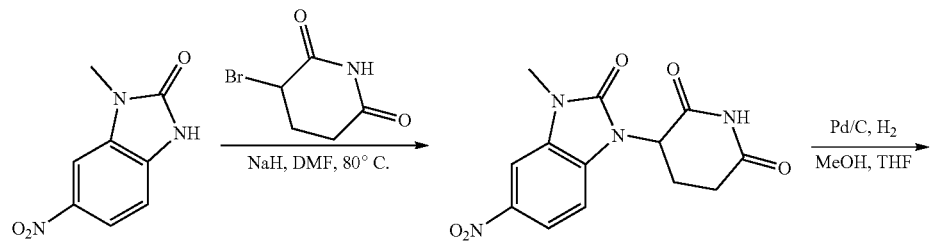

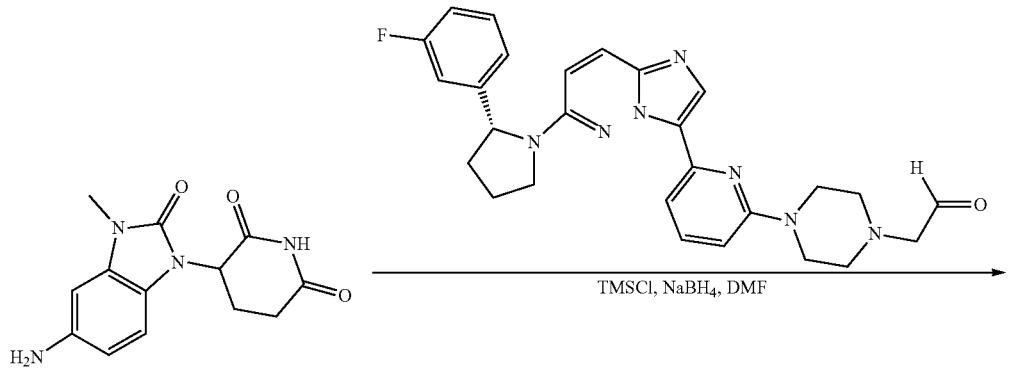

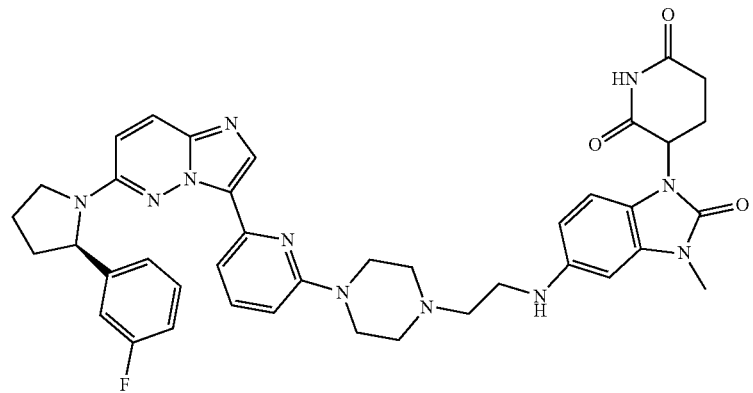

Step 1. Synthesis of 2-(methylamino)-4-nitro-benzoic acid

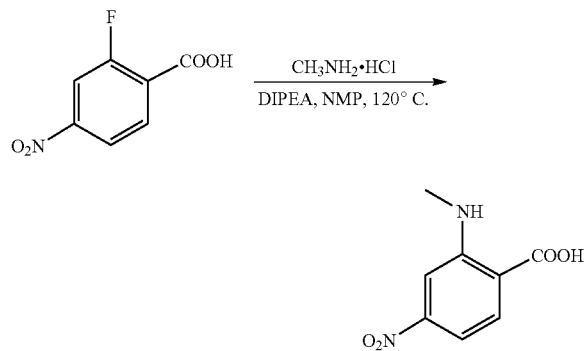

To a solution of 2-fluoro-4-nitro-benzoic acid (37 g, 199.88 mmol) and methanamine hydrochloride (12.42 g, 399.76 mmol) in NMP (300 mL) was added DIPEA (103.33 g, 799.53 mmol) at room temperature. The reaction mixture was stirred at 120° C. for 48 h. After the reaction was cooled down to room temperature, the reaction was quenched with water (100 mL), and the pH was adjusted to 3 with conc. HCl. The resulting solid was filtered and dried to give crude 2-(methylamino)-4-nitro-benzoic acid (38 g, 97% yield) as a yellow solid. This product was used in the next step directly without further purification. MS (ESI) m/z: 197.3 $[M+H]^+$.

Step 2. Synthesis of 3-methyl-5-nitro-1H-benzimidazol-2-one

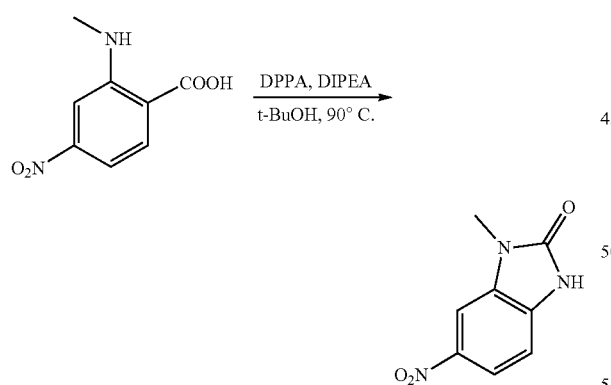

To a solution of 2-(metylamino)-4-nitro-benzoic acid (38 g, 193.72 mmol) in t-BuOH (30 mL) were added DIPEA (75.11 g, 581.16 mmol) and DPPA (63.93 g, 232.46 mmol) at room temperature. Then the reaction mixture was stirred at 90° C. for 16 h. After the reaction was cooled down to room temperature, the mixture was filtered and resulting solid was dried to give crude 3-methyl-5-nitro-1H-benzimidazol-2-one (33 g, 88% yield) as a yellow solid. This product was used in the next step directly without further purification. MS (ESI) m/z: 194.1 $[M+H]^+$.

Step 3. Synthesis of 3-(5-amino-3-methyl-2-oxo-2,3-dihydro-1H-benzo[d]imidazol-1-yl)piperidine-2,6-dione

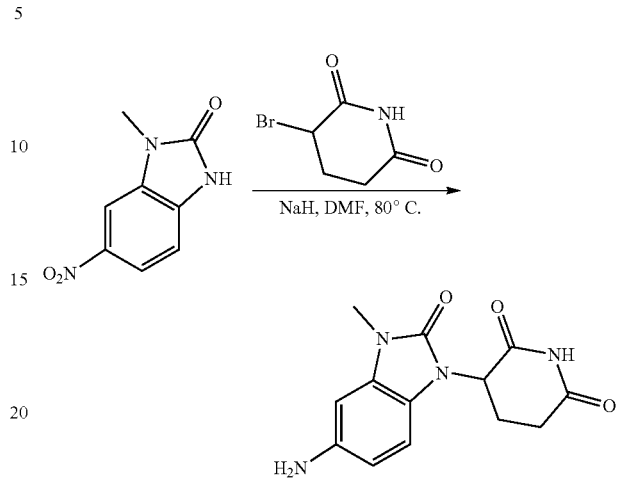

To a suspension of NaH (48 mg, 1.20 mmol) in DMF (5 mL) was added 1-methyl-6-nitro-1,3-dihydro-2H-benzo[d]imidazol-2-one (193 mg, 999.18 umol) at 0° C. The reaction mixture was stirred at 0° C. for 0.5 h, before a solution of 3-bromopiperidine-2,6-dione (383.70 mg, 2.00 mmol) in DMF (5 mL) was added dropwise. After the completion of addition, the reaction mixture was stirred at 80° C. for 2 h. After the reaction is cooled down to room temperature, the reaction was concentrated and the resulting residue was purified by prep-HPLC to give 3-(5-amino-3-methyl-2-oxo-2,3-dihydro-1H-benzo[d]imidazol-1-yl)piperidine-2,6-dione (80 mg, 26% yield) as a black solid. MS (ESI) m/z: 305.3 $[M+H]^+$.

Step 4. Synthesis of 3-(5-amino-3-methyl-2-oxo-2,3-dihydro-1H-benzo[d]imidazol-1-yl)piperidine-2,6-dione

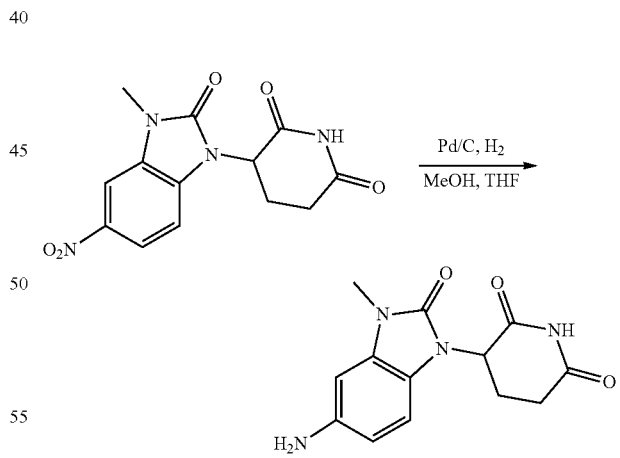

To a solution of 3-(5-amino-3-methyl-2-oxo-2,3-dihydro-1H-benzo[d]imidazol-1-yl)piperidine-2,6-dione (80 mg, 262.93 umol) in MeOH (10 mL) and THF (10 mL) was added Pd/C (20 mg) at room temperature. After the reaction mixture was stirred at room temperature for 1 h under hydrogen atmosphere, the reaction was filtered and the filtrate was concentrated to give crude 3-(5-amino-3-methyl-2-oxo-2,3-dihydro-1H-benzo[d]imidazol-1-yl)piperidine-2,6-dione (70 mg, 97% yield) as a brown solid. This product was used in the next step directly without further purification. MS (ESI) m/z: 275.3 $[M+H]^+$.

Step 5. Synthesis of 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-3-methyl-2-oxo-2,3-dihydro-1H-benzo[d]imidazol-1-yl)piperidine-2,6-dione

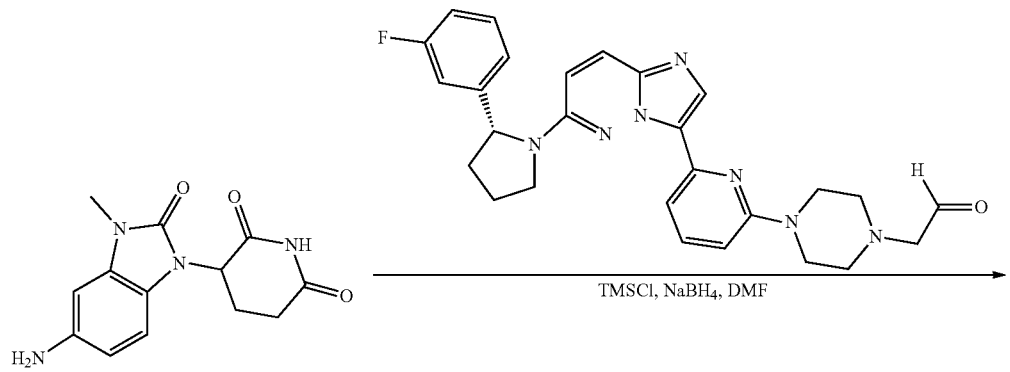

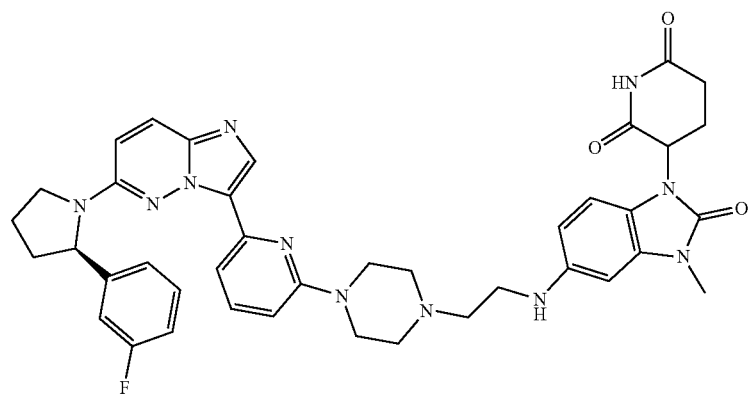

To a solution of (R)-2-(4-(6-(6-(2-(3-fluorophenyl)pyrrolidin-1-yl)imidazo[1,2-b]pyridazin-3-yl)pyridin-2-yl)piperazin-1-yl)acetaldehyde (57 mg, 0.12 mmol) in DMF (3 ml) were added 3-(5-amino-3-methyl-2-oxo-2,3-dihydro-1H-benzo[d]imidazol-1-yl)piperidine-2,6-dione (31 mg, 0.11 mmol), TMSCl (39 mg, 0.36 mmol) and NaBH₄ (9 mg, 0.24 mmol). The reaction mixture was stirred at 0° C. for 48 h. After the reaction was concentrated, the resulting residue was purified by prep-HPLC to give 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-3-methyl-2-oxo-2,3-dihydro-1H-benzo[d]imidazol-1-yl)piperidine-2,6-dione (7 mg, 8% yield) as a yellow solid. MS (ESI) m/z: 744.8 [M+H]⁺.

Example 272: 3-(5-((3-(4-(6-(6-((R)-2-(3-Fluorophenyl)pyrrolidin-1-yl)imidazo[1,2-b]pyridazin-3-yl)pyridin-2-yl)piperazin-1-yl)propyl)amino)-3-methyl-2-oxo-2,3-dihydro-1H-benzo[d]imidazol-1-yl)piperidine-2,6-dione (TR-221)

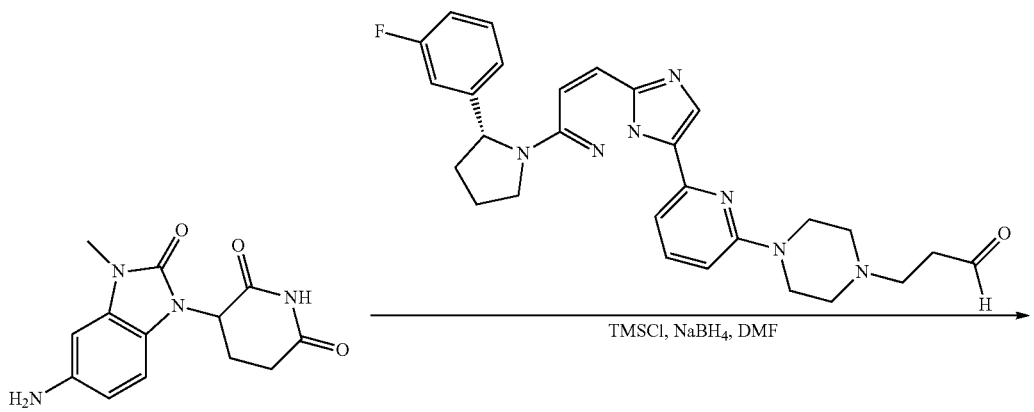

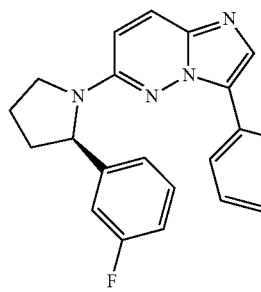

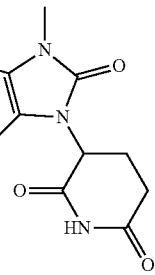

To a solution of (R)-3-(4-(6-(6-(2-(3-fluorophenyl)pyrrolidin-1-yl)imidazo[1,2-b]pyridazin-3-yl)pyridin-2-yl)piperazin-1-yl)propanal (132.92 mg, 266.06 umol) and 3-(5-amino-3-methyl-2-oxo-2,3-dihydro-1H-benzo[d]imidazol-1-yl)piperidine-2,6-dione (82 mg, 298.97 umol) in DMF (10 mL) were added TMSCl (86.20 mg, 798.17 umol) and NaBH₄ (20.22 mg, 532.11 umol) at 0° C. After the reaction mixture was stirred at 0° C. for 1.5 h, the reaction was warmed to room temperature and stirred for 16 h. After concentration, the mixture was purified by prep-HPLC to give a crude product, which was further purified by prep-TLC (DMC/MeOH=10:1) to give 3-(5-(((3-(4-(6-(6-((R)-2-(3-fluorophenyl)pyrrolidin-1-yl)imidazo[1,2-b]pyridazin-3-yl)pyridin-2-yl)piperazin-1-yl)propyl)amino)-3-methyl-2-oxo-2,3-dihydro-1H-benzo[d]imidazol-1-yl)piperidine-2,6-dione (17 mg, 8% yield) as a white solid. MS (ESI) m/z: 759.0 [M+H]⁺.

Example 273: 2-(2,6-Dioxopiperidin-3-yl)-5-(3-((4-(3-(6-((R)-2-(3-fluorophenyl)pyrrolidin-1-yl)imidazo[1,2-b]pyridazin-3-yl)-1H-pyrrol-1-yl)piperidin-1-yl)methyl)azetidin-1-yl)isoindoline-1,3-dione (TR-222)

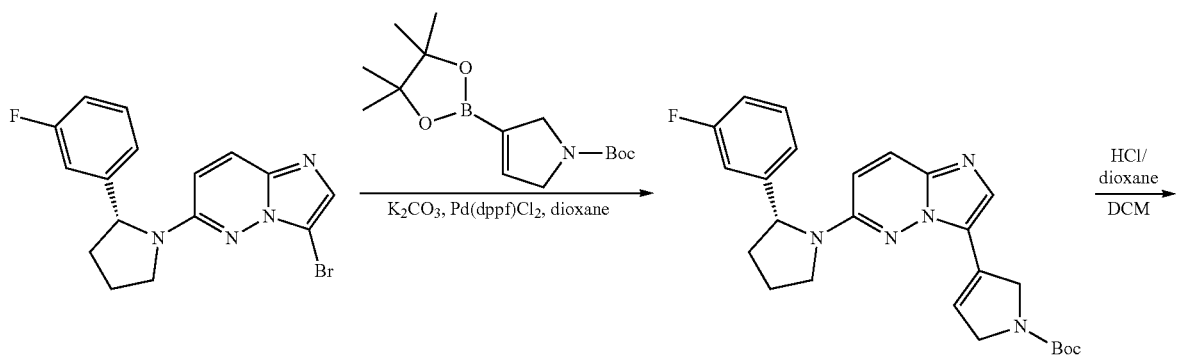

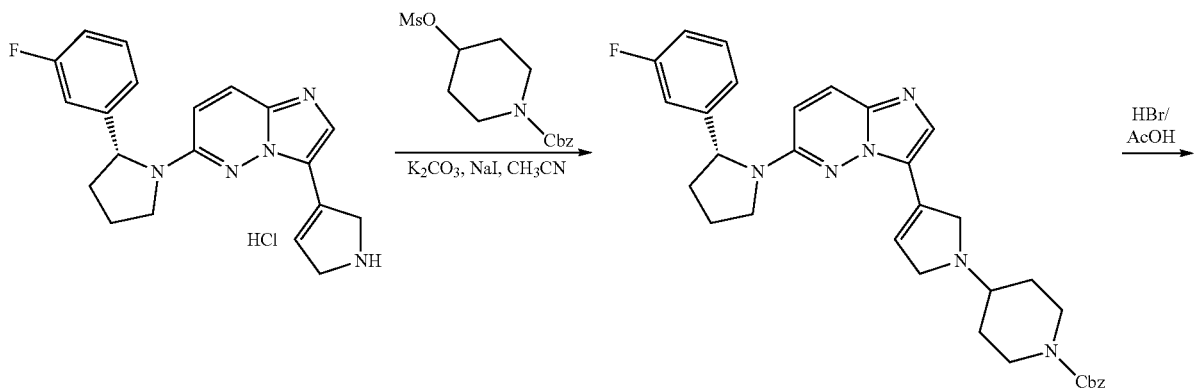

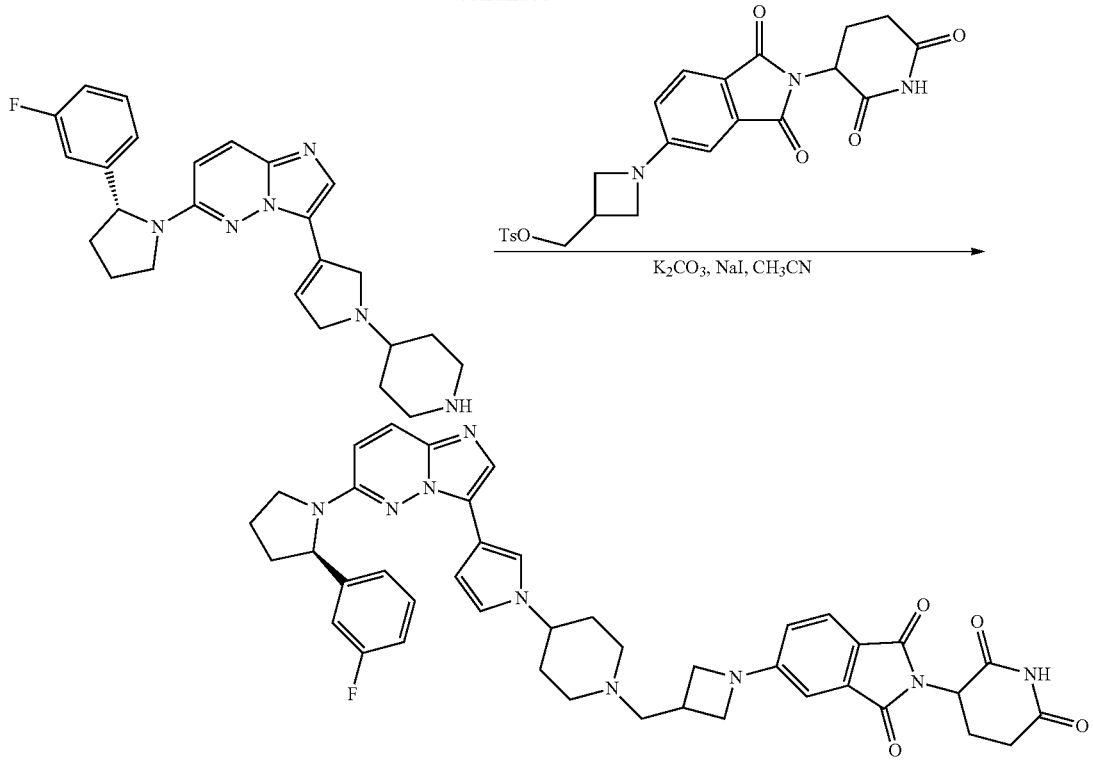

Step 1. Synthesis of tert-butyl (R)-3-(6-(2-(3-fluorophenyl)pyrrolidin-1-yl)imidazo[1,2-b]pyridazin-3-yl)-2,5-dihydro-1H-pyrrole-1-carboxylate

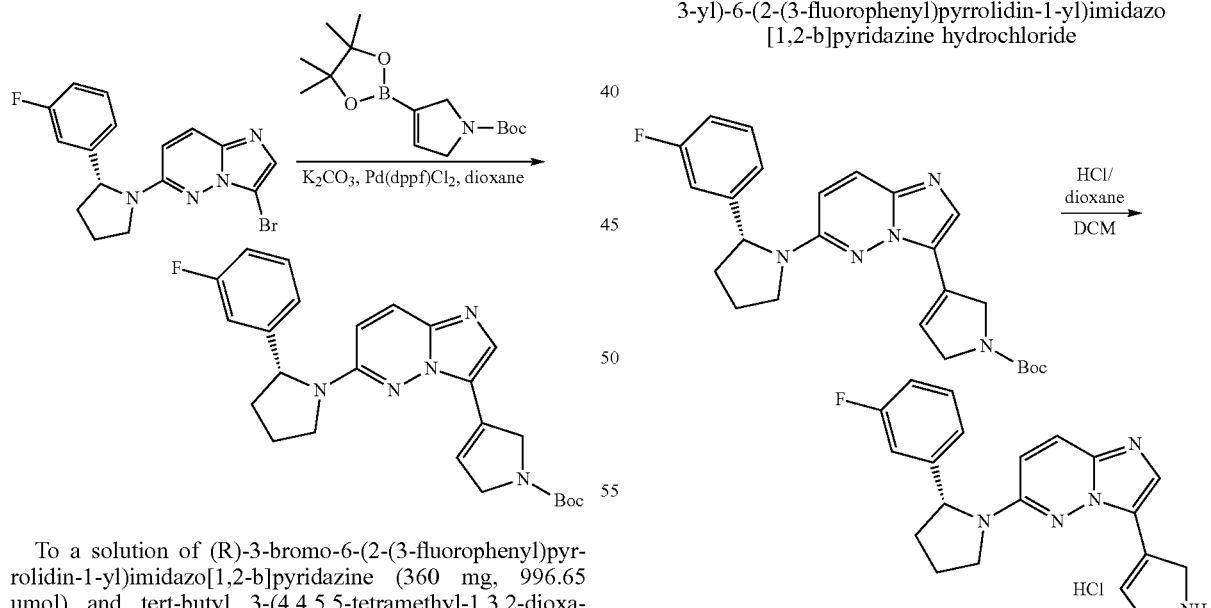

To a solution of (R)-3-bromo-6-(2-(3-fluorophenyl)pyrrolidin-1-yl)imidazo[1,2-b]pyridazine (360 mg, 996.65 umol) and tert-butyl 3-(4,4,5,5-tetramethyl-1,3,2-dioxaborolan-2-yl)-2,5-dihydropyrrole-1-carboxylate (294.19 mg, 996.65 umol) in dioxane (10 mL) and H$_2$O (5 mL) were added K$_2$CO$_3$ (275.07 mg, 1.99 mmol) and Pd(dppf)Cl$_2$ (72.85 mg, 99.66 umol) at room temperature under N$_2$. After the reaction mixture was stirred at 100° C. for 4 h, the reaction was concentrated and purified by silica gel chromatography (DCM/MeOH=30:1) to give tert-butyl (R)-3-(6-(2-(3-fluorophenyl)pyrrolidin-1-yl)imidazo[1,2-b]pyridazin-3-yl)-2,5-dihydro-1H-pyrrole-1-carboxylate (440 mg, 98% yield) as a black solid. MS (ESI) m/z: 451.0 [M+H]$^+$.

Step 2. Synthesis of (R)-3-(2,5-dihydro-1H-pyrrol-3-yl)-6-(2-(3-fluorophenyl)pyrrolidin-1-yl)imidazo[1,2-b]pyridazine hydrochloride To a solution of tert-butyl (R)-3-(6-(2-(3-fluorophenyl)pyrrolidin-1-yl)imidazo[1,2-b]pyridazin-3-yl)-2,5-dihydro-1H-pyrrole-1-carboxylate (450 mg, 1.00 mmol) in DCM (5 mL) was added HCl/dioxane (4 mL) at room temperature. The reaction mixture was stirred at room temperature for 2 h, before it was concentrated to give crude (R)-3-(2,5-dihydro-1H-pyrrol-3-yl)-6-(2-(3-fluorophenyl)pyrrolidin-1- yl)imidazo[1,2-b]pyridazine hydrochloride (350 mg, 100% yield) as solid (HCl salt). This product was used in the next step directly without further purification. MS (ESI) m/z: 350.6 [M+H]⁺.

Step 3. Synthesis of benzyl (R)-4-(3-(6-(2-(3-fluorophenyl)pyrrolidin-1-yl)imidazo[1,2-b]pyridazin-3-yl)-2,5-dihydro-1H-pyrrol-1-yl)piperidine-1-carboxylate

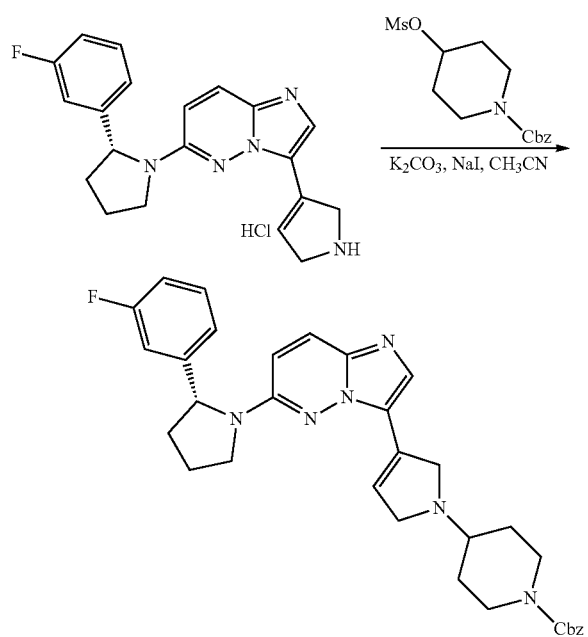

To a solution of 3-(2,5-dihydro-1H-pyrrol-3-yl)-6-[(2R)-2-(3-fluorophenyl)pyrrolidin-1-yl]imidazo[1,2-b]pyridazine (600 mg, 1.72 mmol) and benzyl 4-methylsulfonyloxypiperidine-1-carboxylate (2.15 g, 6.87 mmol) in CH₃CN (20 mL) and DMF (20 mL) were added NaI (514.79 mg, 3.43 mmol) and K₂CO₃ (1.42 g, 10.30 mmol). The reaction mixture was stirred at 100° C. for 16 h, before it was concentrated and purified by silica gel chromatography (DCM/MeOH=20:1) to give benzyl (R)-4-(3-(6-(2-(3-fluorophenyl)pyrrolidin-1-yl)imidazo[1,2-b]pyridazin-3-yl)-2,5-dihydro-1H-pyrrol-1-yl)piperidine-1-carboxylate (230 mg, 24% yield). MS (ESI) m/z: 567.9 [M+H]⁺.

Step 4. Synthesis of (R)-6-(2-(3-fluorophenyl)pyrrolidin-1-yl)-3-(1-(piperidin-4-yl)-2,5-dihydro-1H-pyrrol-3-yl)imidazo[1,2-b]pyridazine

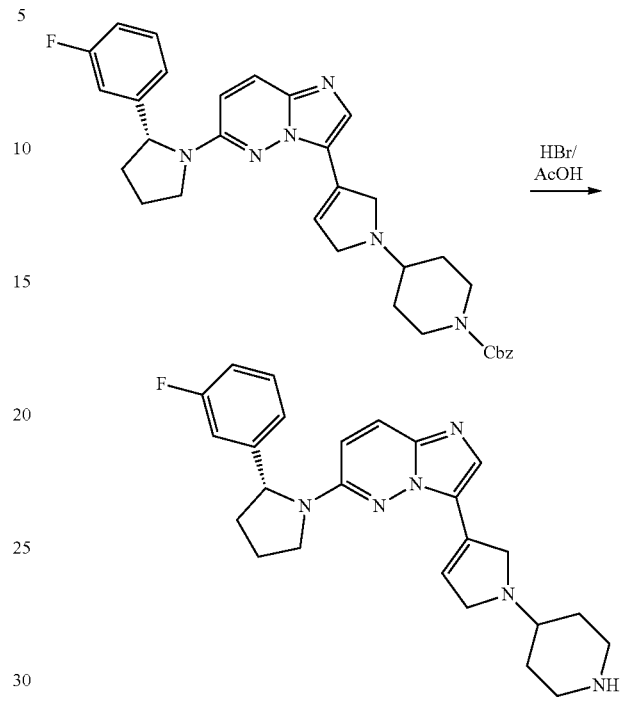

To a solution of benzyl (R)-4-(3-(6-(2-(3-fluorophenyl)pyrrolidin-1-yl)imidazo[1,2-b]pyridazin-3-yl)-2,5-dihydro-1H-pyrrol-1-yl)piperidine-1-carboxylate (200 mg, 352.94 umol) in AcOH (10 mL) was added HBr (5 mL) at room temperature. The reaction mixture was stirred at 50° C. for 16 h, before the reaction was concentrated. The resulting residue was diluted with water and pH value was adjusted to 9 with aq. NaHCO₃. The resulting aqueous mixture was extracted with DCM (2×30 mL). The combined organic layers were washed with brine (2×20 mL), dried over Na₂SO₄, filtered, and concentrated. The resulting residue was purified by prep-TLC (DCM/MeOH=10:1) to give (R)-6-(2-(3-fluorophenyl)pyrrolidin-1-yl)-3-(1-(piperidin-4-yl)-2,5-dihydro-1H-pyrrol-3-yl)imidazo[1,2-b]pyridazine (120 mg, 79% yield) as a white solid. MS (ESI) m/z: 433.6 [M+H]⁺.

Step 5. Synthesis of 2-(2,6-dioxopiperidin-3-yl)-5-(3-((4-(3-(6-((R)-2-(3-fluorophenyl)pyrrolidin-1-yl)imidazo[1,2-b]pyridazin-3-yl)-1H-pyrrol-1-yl)piperidin-1-yl)methyl)azetidin-1-yl)isoindoline-1,3-dione

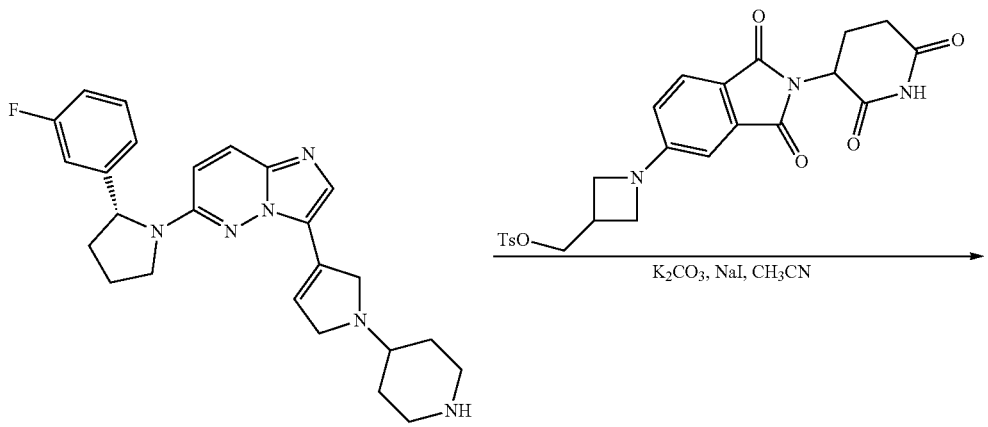

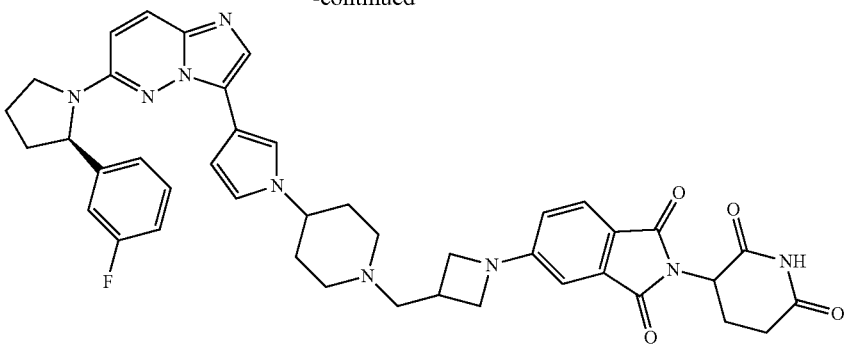

To a solution of (R)-6-(2-(3-fluorophenyl)pyrrolidin-1-yl)-3-(1-(piperidin-4-yl)-2,5-dihydro-1H-pyrrol-3-yl)imidazo[1,2-b]pyridazine (60 mg, 138.72 umol) and (1-(2-(2,6-dioxopiperidin-3-yl)-1,3-dioxoisoindolin-5-yl)azetidin-3-yl)methyl 4-methylbenzenesulfonate (69.01 mg, 138.72 umol) in CH₃CN (10 mL) were added NaI (41.58 mg, 277.43 umol) and K₂CO₃ (114.86 mg, 832.30 umol) at room temperature. After the mixture was stirred at 95° C. for 16 h, the reaction was concentrated and purified by prep-TLC (DCM/MeOH=10:1) to give crude product, then purified again by prep-TLC (DCM/MeOH=20:1) to give 2-(2,6-dioxopiperidin-3-yl)-5-(3-((4-(3-(6-((R)-2-(3-fluorophenyl)pyrrolidin-1-yl)imidazo[1,2-b]pyridazin-3-yl)-1H-pyrrol-1-yl)piperidin-1-yl)methyl)azetidin-1-yl)isoindoline-1,3-dione (17 mg, 16% yield) as a yellow solid. MS (ESI) m/z: 757.0 [M+H]⁺.

Example 274: 3-((S)-5-(3-(3-(4-(6-(6-((R)-2-(3-Fluorophenyl)pyrrolidin-1-yl)imidazo[1,2-b]pyridazin-3-yl)pyridin-2-yl)piperazin-1-yl)prop-1-yn-1-yl)phenyl)-2-oxooxazolidin-3-yl)piperidine-2,6-dione (TR-223)

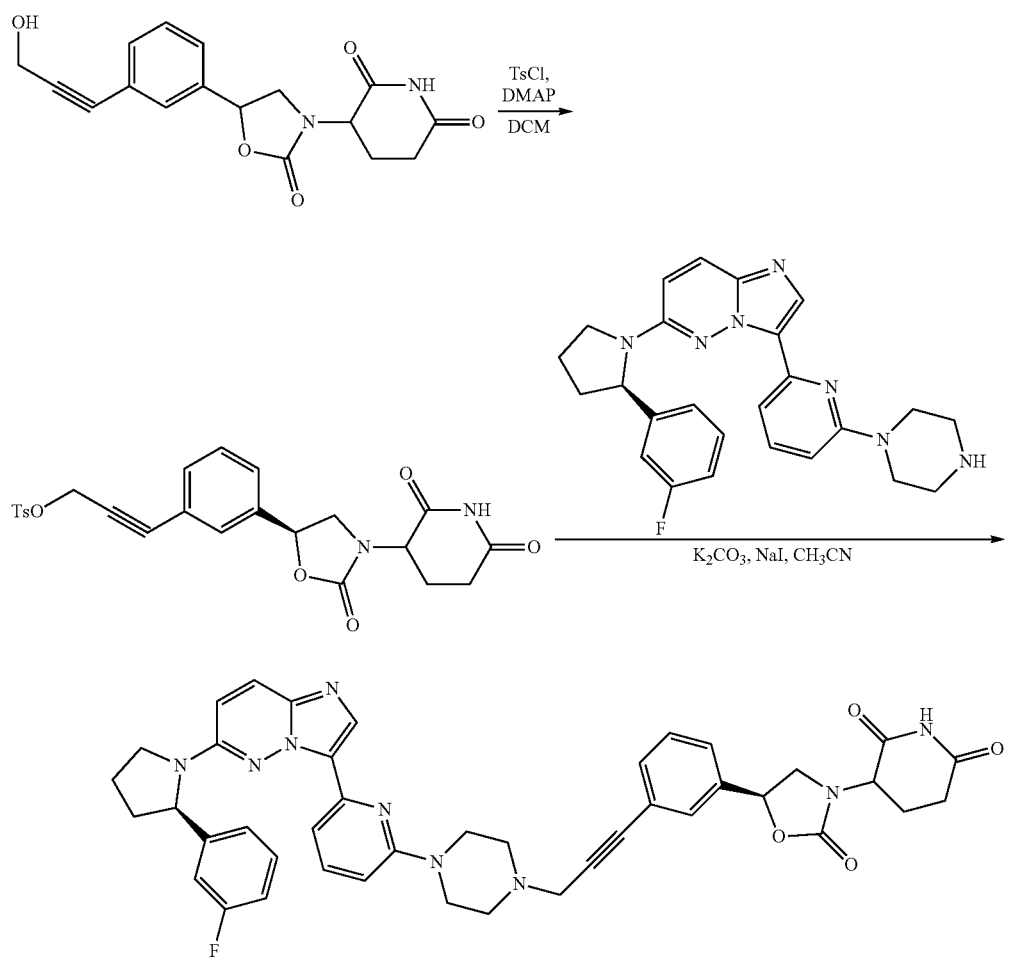

653

Step 1. Synthesis of 3-(3-((5S)-3-(2,6-dioxopiperidin-3-yl)-2-oxooxazolidin-5-yl)phenyl)prop-2-yn-1-yl 4-methylbenzenesulfonate

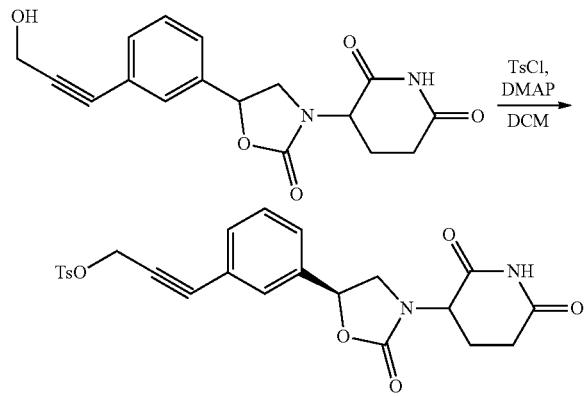

654

To a solution of 3-((S)-5-(3-(3-hydroxyprop-1-yn-1-yl)phenyl)-2-oxooxazolidin-3-yl)piperidine-2,6-dione (30 mg, 0.1 mmol) in dichloromethane (2 mL) were added TsCl (36 mg, 0.18 mmol) and DMAP (21.9 mg, 0.2 mmol). After the mixture was stirred at room temperature for 4 h, the reaction was quenched with water (20 mL) and extracted with ethyl acetate (3×20 mL). The combined organic layers were dried over sodium sulfate, filtered, and concentrated. The resulting residue was purified by silica gel chromatography (MeOH/DCM=1:10) to give 3-(3-((5S)-3-(2,6-dioxopiperidin-3-yl)-2-oxooxazolidin-5-yl)phenyl)prop-2-yn-1-yl 4-methylbenzenesulfonate (22 mg, 70% yield) as a yellow solid. MS (ESI) m z: 348.3 [M+H]+.

Step 2. Synthesis of 3-((S)-5-(3-(3-(4-(6-(6-((S)-2-(3-fluorophenyl)pyrrolidin-1-yl)imidazo[1,2-b]pyridazin-3-yl)pyridin-2-yl)piperazin-1-yl)prop-1-yn-1-yl)phenyl)-2-oxooxazolidin-3-yl)piperidine-2,6-dione

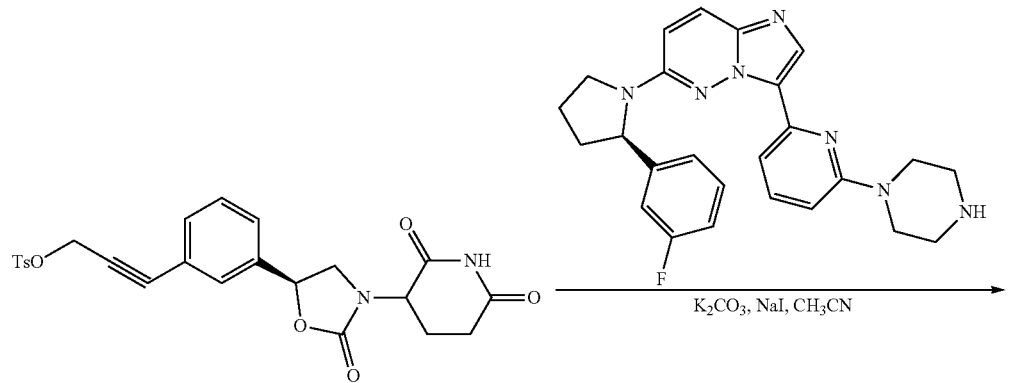

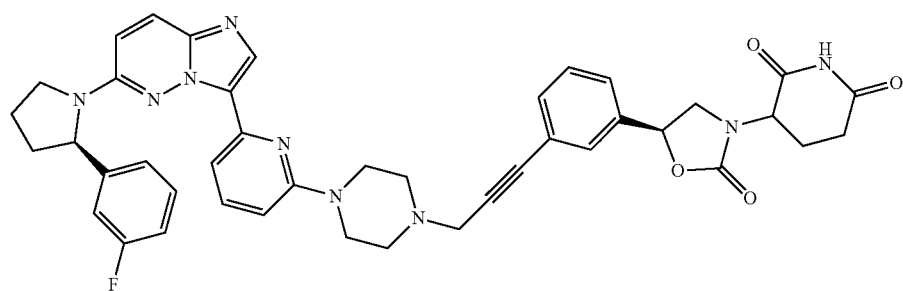

To a solution of 3-(3-((5S)-3-(2,6-dioxopiperidin-3-yl)-2-oxooxazolidin-5-yl)phenyl)prop-2-yn-1-yl 4-methylbenzenesulfonate (22 mg, 0.06 mmol) and (R)-6-(2-(3-fluorophenyl)pyrrolidin-1-yl)-3-(6-(piperazin-1-yl)pyridin-2-yl)imidazo[1,2-b]pyridazine (26 mg, 0.06 mmol) in acetonitrile (2 mL) were added potassium carbonate (13 mg, 0.12 mmol) and sodium iodide (8 mg, 0.2 mmol). The reaction mixture was stirred at 80° C. for 2 h, before the reaction was concentrated and purified by silica gel chromatography (DCM/MeOH=10:1) to give 3-((S)-5-(3-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)phenyl)-2-oxooxazolidin-3-yl)piperidine-2,6-dione (25 mg, 38% yield) as a yellow solid. MS (ESI) m/z: 754.8 [M+H]$^+$.

Example 275: 3-((S)-5-(4-(3-(4-(6-(6-((R)-2-(3-Fluorophenyl)pyrrolidin-1-yl)imidazo[1,2-b]pyridazin-3-yl)pyridin-2-yl)piperazin-1-yl)prop-1-yn-1-yl)phenyl)-2-oxooxazolidin-3-yl)piperidine-2,6-dione (TR-224)

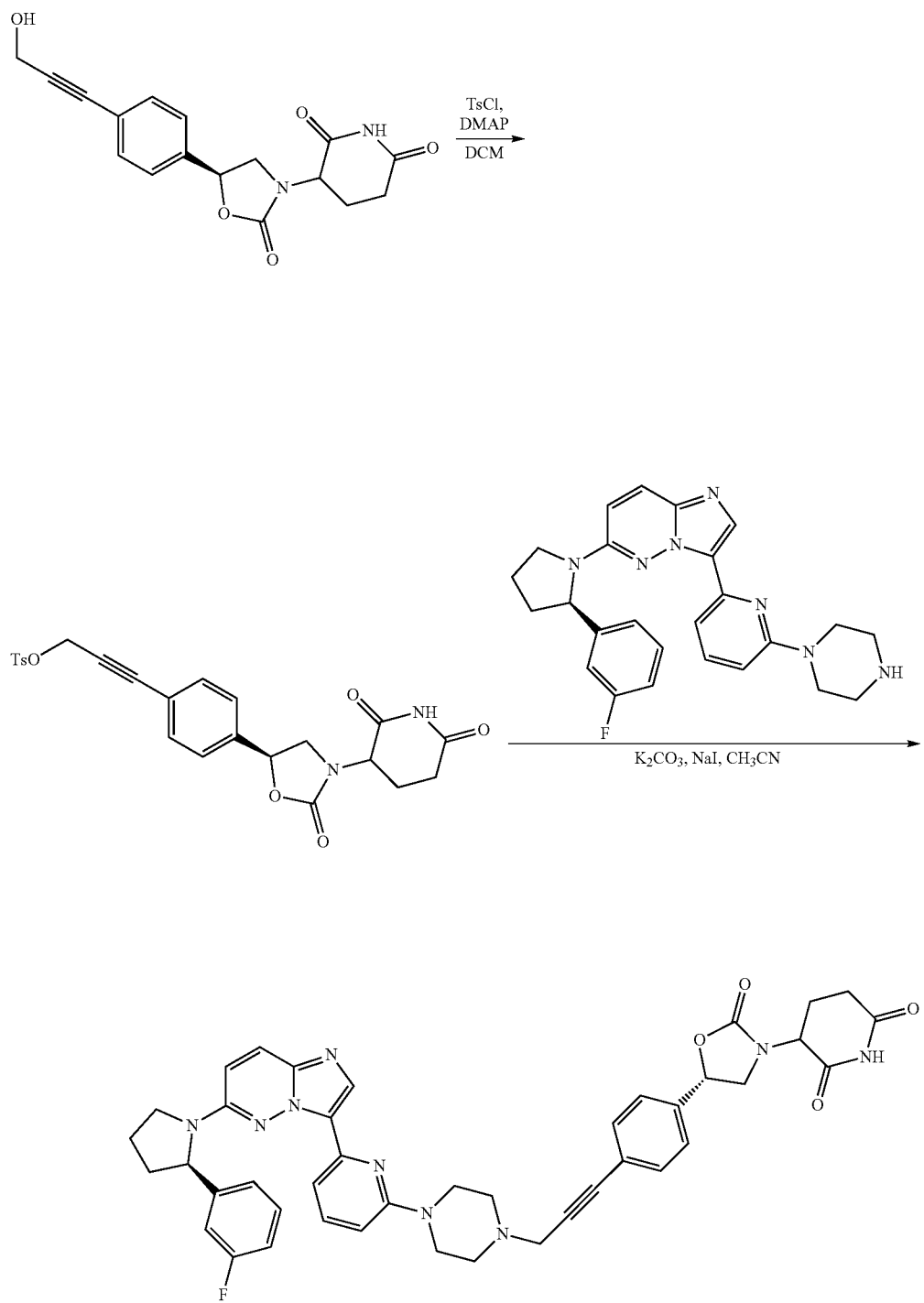

657

Step 1. Synthesis of 3-(4-((5S)-3-(2,6-dioxopiperidin-3-yl)-2-oxooxazolidin-5-yl)phenyl)prop-2-yn-1-yl 4-methylbenzenesulfonate

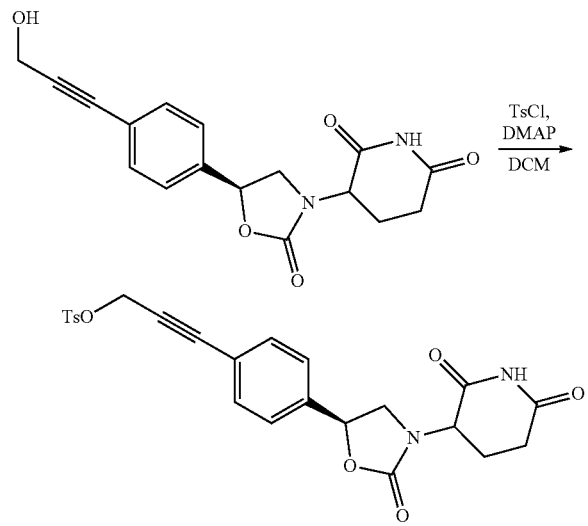

658

To a solution of 3-((S)-5-(4-(3-hydroxyprop-1-yn-1-yl)phenyl)-2-oxooxazolidin-3-yl)piperidine-2,6-dione (40 mg, 0.12 mmol) in dichloromethane (2 mL) were added TsCl (68 mg, 0.35 mmol) and DMAP (76 mg, 0.6 mmol) at room temperature. The reaction mixture was stirred at room temperature for 4 h, before the reaction was quenched with water (20 mL) and extracted with ethyl acetate (3×20 mL). The combined organic layers were dried over sodium sulfate, filtered, and concentrated. The resulting residue was purified by silica gel chromatography (MeOH/DCM=1:10) to give 3-(4-((5S)-3-(2,6-dioxopiperidin-3-yl)-2-oxooxazolidin-5-yl)phenyl)prop-2-yn-1-yl 4-methylbenzenesulfonate (30 mg, 71% yield) as a yellow solid. MS (ESI) m/z: 483.3 [M+H]$^+$.

Step 2. Synthesis of 3-((S)-5-(4-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)phenyl)-2-oxooxazolidin-3-yl)piperidine-2,6-dione

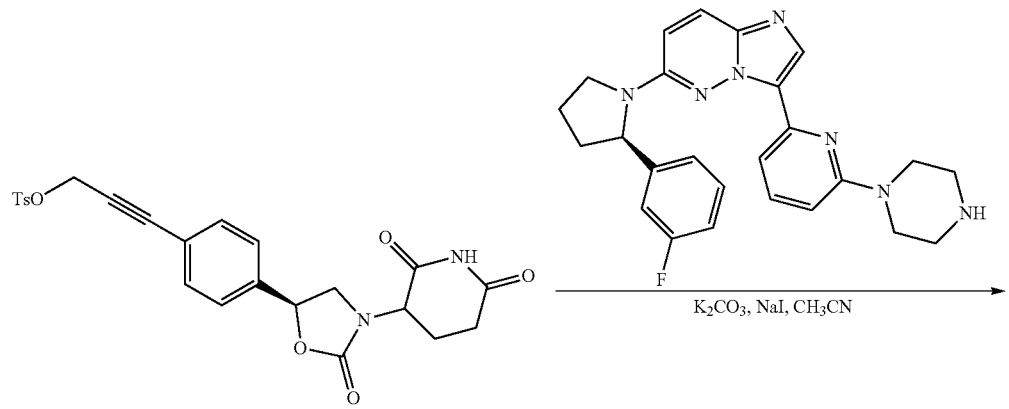

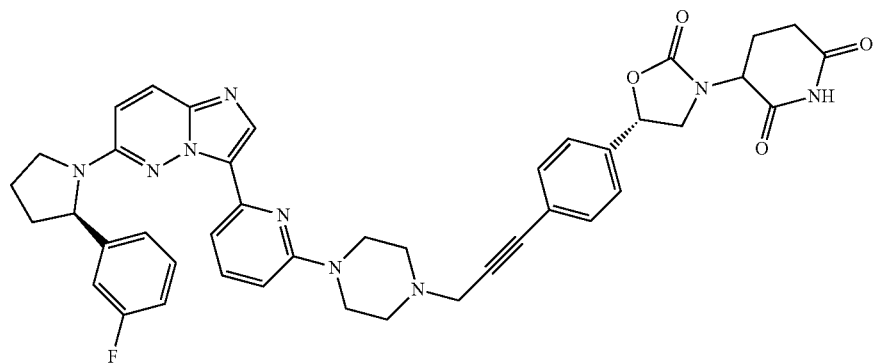

To a solution of 3-(4-((5S)-3-(2,6-dioxopiperidin-3-yl)-2-oxooxazolidin-5-yl)phenyl)prop-2-yn-1-yl 4-methylbenzenesulfonate (30 mg, 0.08 mmol) and (R)-6-(2-(3-fluorophenyl)pyrrolidin-1-yl)-3-(6-(piperazin-1-yl)pyridin-2-yl)imidazo[1,2-b]pyridazine (27 mg, 0.08 mmol) in acetonitrile (3 mL) were added potassium carbonate (17 mg, 0.16 mmol) and sodium iodide (9 mg, 0.08 mmol). The reaction mixture was stirred at 80° C. for 2 h, before it was concentrated and purified by silica gel chromatography (DCM/MeOH=10:1) to give 3-((S)-5-(4-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)phenyl)-2-oxooxazolidin-3-yl)piperidine-2,6-dione (17 mg, 36% yield) as a yellow solid. MS (ESI) m/z: 754.8 [M+H]$^+$.

Example 276: 2-(2,6-Dioxopiperidin-3-yl)-5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)pyrrolidin-1-yl)isoindoline-1,3-dione (TR-225)

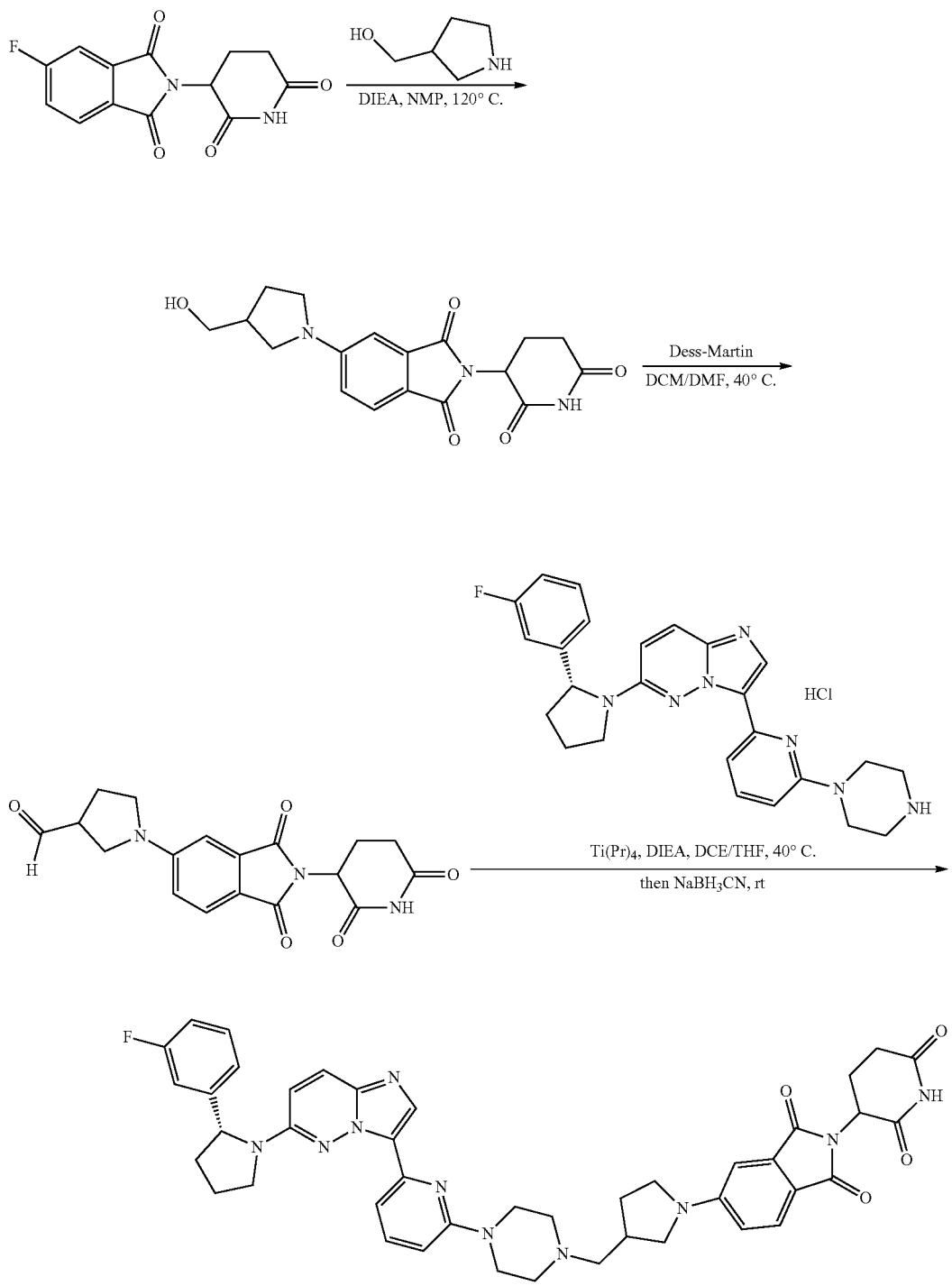

661

Step 1. Synthesis of 2-(2,6-dioxopiperidin-3-yl)-5-(3-(hydroxymethyl)pyrrolidin-1-yl)isoindoline-1,3-dione

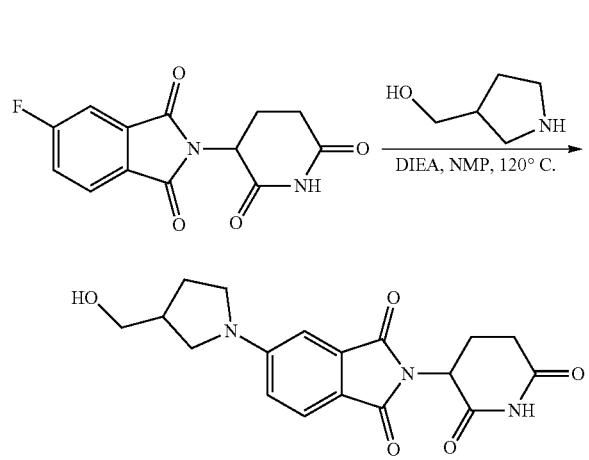

A solution of 2-(2,6-dioxopiperidin-3-yl)-5-fluoroisoindoline-1,3-dione (100 mg, 0.362 mmol), pyrrolidin-3-ylmethanol (55 mg, 0.543 mmol) and DIEA (234 mg, 1.81 mmol) in NMP (5 mL) was stirred at 120° C. for half hour. After the reaction was cooled down to room temperature, the resulting solution was diluted with EtOAc (100 mL), washed with brine twice, dried over sodium sulfate and concentrated to give the crude 2-(2,6-dioxopiperidin-3-yl)-5-(3-(hydroxymethyl)pyrrolidin-1-yl)isoindoline-1,3-dione (140 mg, 108% yield) as a colorless oil. This product was used in the next step directly without further purification. MS (ESI) m/z: 358.5 [M+H]$^+$.

662

Step 2. Synthesis of 1-(2-(2,6-dioxopiperidin-3-yl)-1,3-dioxoisoindolin-5-yl)pyrrolidine-3-carbaldehyde

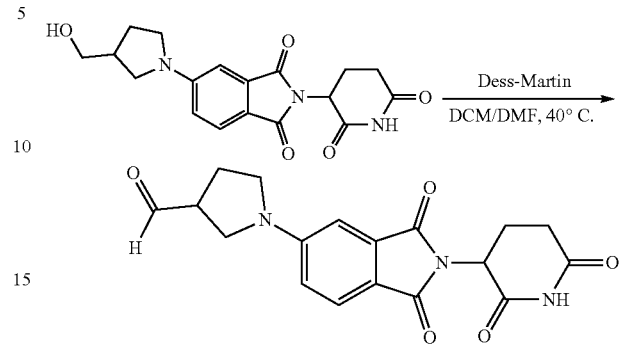

A mixture of 2-(2,6-dioxopiperidin-3-yl)-5-(3-(hydroxymethyl)pyrrolidin-1-yl)isoindoline-1,3-dione (140 mg, 0.39 mmol) and Dess-Martin oxidant (826 mg, 1.95 mmol) in DCM (5 mL) and DMF (2 mL) was stirred at 40° C. for 20 mins. After the reaction was cooled down to room temperature, the reaction mixture was diluted with brine (100 mL) and EtOAc (100 mL). The organic phase was washed with brine twice, dried over sodium sulfate, and concentrated. The resulting residue was purified by silica gel chromatography (DCM/MeOH=15:1) to afford 1-(2-(2,6-dioxopiperidin-3-yl)-1,3-dioxoisoindolin-5-yl)pyrrolidine-3-carbaldehyde (80 mg, 58% yield) as a yellow solid. MS (ESI) m/z: 356.7 [M+H]$^+$.

Step 3. Synthesis of 2-(2,6-dioxopiperidin-3-yl)-5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)pyrrolidin-1-yl)isoindoline-1,3-dione

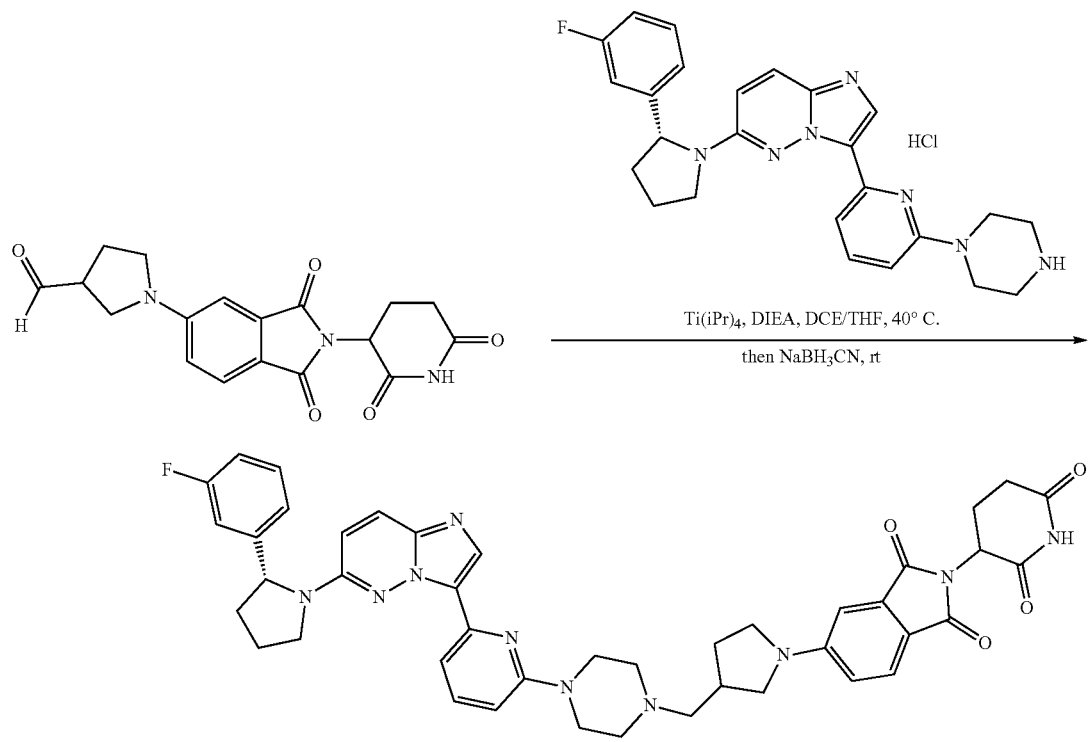

To a solution of 1-(2-(2,6-dioxopiperidin-3-yl)-1,3-dioxoisoindolin-5-yl)pyrrolidine-3-carbaldehyde (80 mg, 0.225 mmol) and (R)-6-(2-(3-fluorophenyl)pyrrolidin-1-yl)-3-(6-(piperazin-1-yl)pyridin-2-yl)imidazo[1,2-b]pyridazine hydrochloride (107 mg, 0.225 mmol) in DCE (3 ml) and THF (3 mL) were added DIEA (30 mg, 0.225 mmol) and titanium tetraisopropanolate (639 mg, 2.25 mmol). After the reaction mixture was stirred at 40° C. for 0.5 h, sodium cyanoborohydride (140 mg, 2.25 mmol) was added. The resulting reaction mixture was stirred at room temperature for 1 h, before the reaction mixture was diluted with DCM/MeOH (10:1, 150 mL) and saturated NaHCO$_3$ (20 ml). After being stirred for 5 mins, the mixture was filtered through celite. The filtrate was washed with brine twice, dried over sodium sulfate, filtered and concentrated. The resulting residue was purified by prep-HPLC to give 2-(2,6-dioxopiperidin-3-yl)-5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)pyrrolidin-1-yl)isoindoline-1,3-dione (9.6 mg, 6% yield) as a yellow solid. MS (ESI) m/z: 784.0 [M+H]$^+$.

Example 277: 2-(2,6-Dioxopiperidin-3-yl)-5-(4-((4-(6-(6-((R)-2-(3-fluorophenyl)pyrrolidin-1-yl)imidazo[1,2-b]pyridazin-3-yl)pyridin-2-yl)piperazin-1-yl)methyl)piperidin-1-yl)isoindoline-1,3-dione (TR-226)

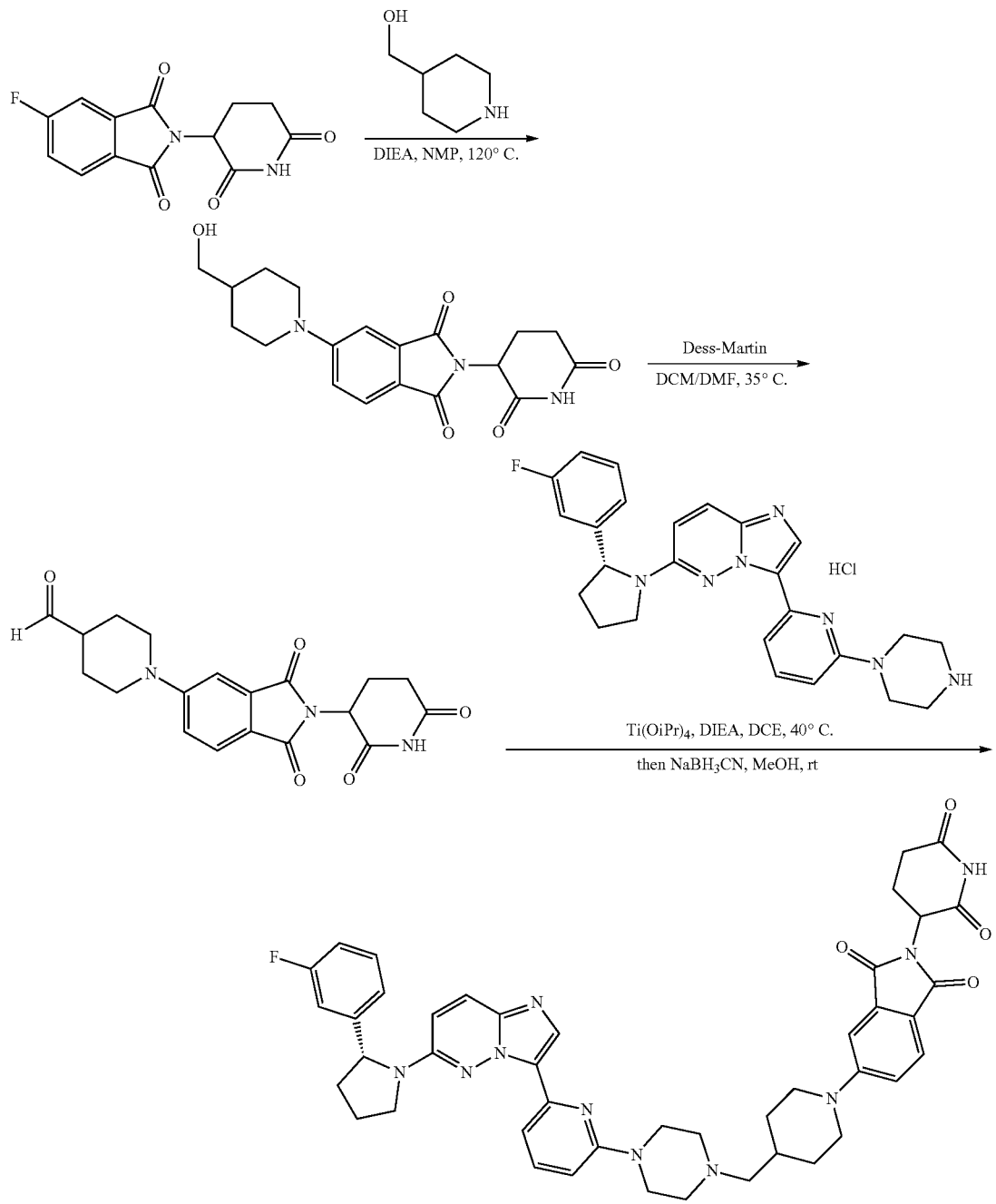

665

Step 1. Synthesis of 2-(2,6-dioxopiperidin-3-yl)-5-(4-(hydroxymethyl)piperidin-1-yl)isoindoline-1,3-dione

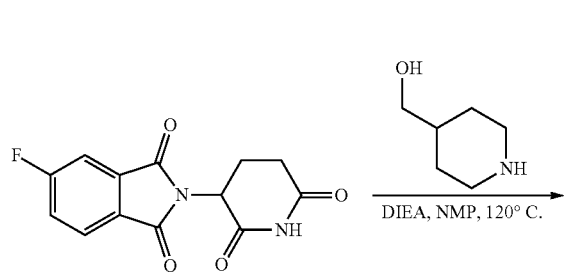

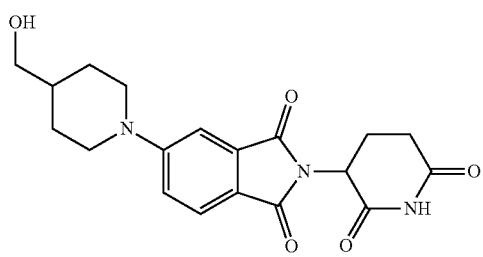

A solution of 2-(2,6-dioxopiperidin-3-yl)-5-fluoroisoindoline-1,3-dione (130 mg, 0.471 mmol), piperidin-4-yl-methanol (81 mg, 0.706 mmol) and DIEA (303 mg, 2.355 mmol) in NMP (5 ml) was stirred at 120° C. for 0.5 h. After the reaction was cooled down to room temperature, the resulting solution was diluted with EtOAc (100 mL), washed with brine twice, dried over sodium sulfate, filtered and concentrated to give the crude product 2-(2,6-dioxopiperidin-3-yl)-5-(4-(hydroxymethyl)piperidin-1-yl)isoindoline-1,3-dione (200 mg, 114% yield) as a colorless oil. This product was used in the next step directly without further purification. MS (ESI) m/z: 372.5 [M+H]$^+$.

666

Step 2. Synthesis of 1-(2-(2,6-dioxopiperidin-3-yl)-1,3-dioxoisoindolin-5-yl)pyrrolidine-3-carbaldehyde

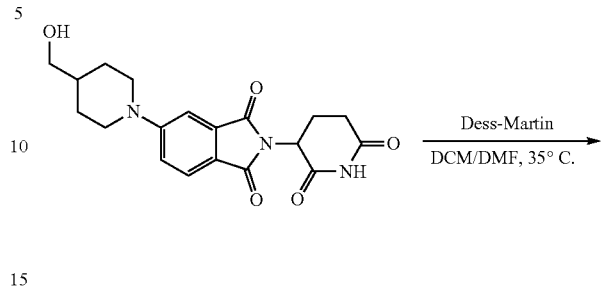

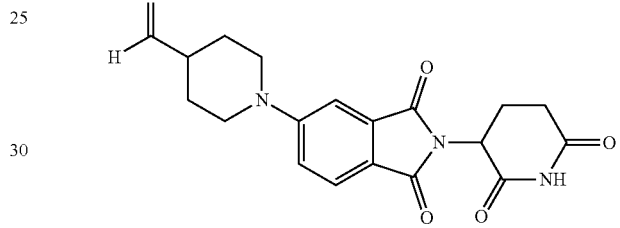

A mixture of 2-(2,6-dioxopiperidin-3-yl)-5-(4-(hydroxymethyl)piperidin-1-yl)isoindoline-1,3-dione (200 mg, 0.539 mmol) and Dess-Martin oxidant (1.14 mg, 2.69 mmol) in DCM (5 ml) and DMF (2 ml) was stirred at 40° C. for 20 mins. After the reaction was cooled down to room temperature, the reaction mixture was diluted with brine (100 mL) and EtOAc (100 mL). The organic phase was washed with brine twice, dried, filtered and concentrated. The resulting residue was purified by silica gel chromatography (DCM/MeOH=15:1) to afford 1-(2-(2,6-dioxopiperidin-3-yl)-1,3-dioxoisoindolin-5-yl)pyrrolidine-3-carbaldehyde (50 mg, 25% yield) as a yellow solid. MS (ESI) m/z: 370.5 [M+H]$^+$.

Step 3. Synthesis of 2-(2,6-dioxopiperidin-3-yl)-5-(4-((4-(6-(6-((R)-2-(3-fluorophenyl)pyrrolidin-1-yl)imidazo[1,2-b]pyridazin-3-yl)pyridin-2-yl)piperazin-1-yl)methyl)piperidin-1-yl)isoindoline-1,3-dione

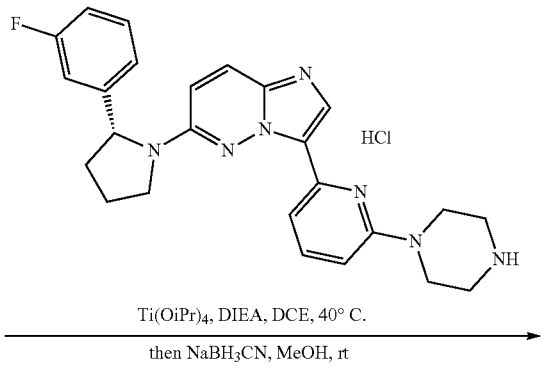

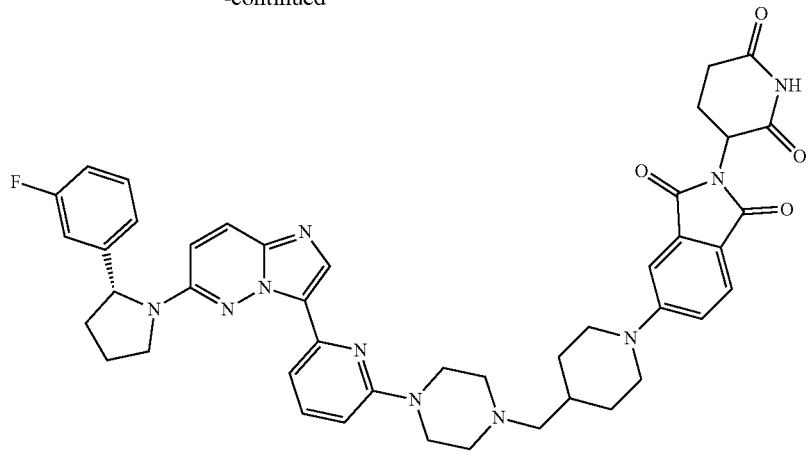

To a solution of 1-(2-(2,6-dioxopiperidin-3-yl)-1,3-dioxoisoindolin-5-yl)piperidine-4-carbaldehyde (50 mg, 0.135 mmol) and (R)-6-(2-(3-fluorophenyl)pyrrolidin-1-yl)-3-(6-(piperazin-1-yl)pyridin-2-yl)imidazo[1,2-b]pyridazine hydrochloride (51 mg, 0.135 mmol) in DCE (6 mL) were added DIEA (18 mg, 0.135 mmol) and titanium tetraisopropanolate (383 mg, 1.35 mmol). The reaction mixture was stirred at 40° C. for 0.5 h, before sodium cyanoborohydride (140 mg, 2.25 mmol) and MeOH (3 ml) was added. After the reaction mixture was stirred at room temperature for 1 h, the reaction mixture was diluted with DCM/MeOH (10:1, 150 mL) and saturated aqueous NaHCO₃ (20 ml). After being stirred for 5 mins, the mixture was filtered through celite. And the filtrate was washed with brine twice. The organic layer was dried over sodium sulfate, filtered and concentrated. The resulting residue was purified by prep-HPLC to give 2-(2,6-dioxopiperidin-3-yl)-5-(4-((4-(6-(6-((R)-2-(3-fluorophenyl)pyrrolidin-1-yl)imidazo[1,2-b]pyridazin-3-yl)pyridin-2-yl)piperazin-1-yl)methyl)piperidin-1-yl)isoindoline-1,3-dione (8.6 mg, 8% yield) as a yellow solid. MS (ESI) m/z: 798.0 [M+H]⁺.

Example 278: 3-(3-(2-(4-(6-(6-((R)-2-(3-Fluorophenyl)pyrrolidin-1-yl)imidazo[1,2-b]pyridazin-3-yl)pyridin-2-yl)piperazin-1-yl)ethyl)-2-oxo-2,3-dihydro-1H-benzo[d]imidazol-1-yl)piperidine-2,6-dione (TR-227)

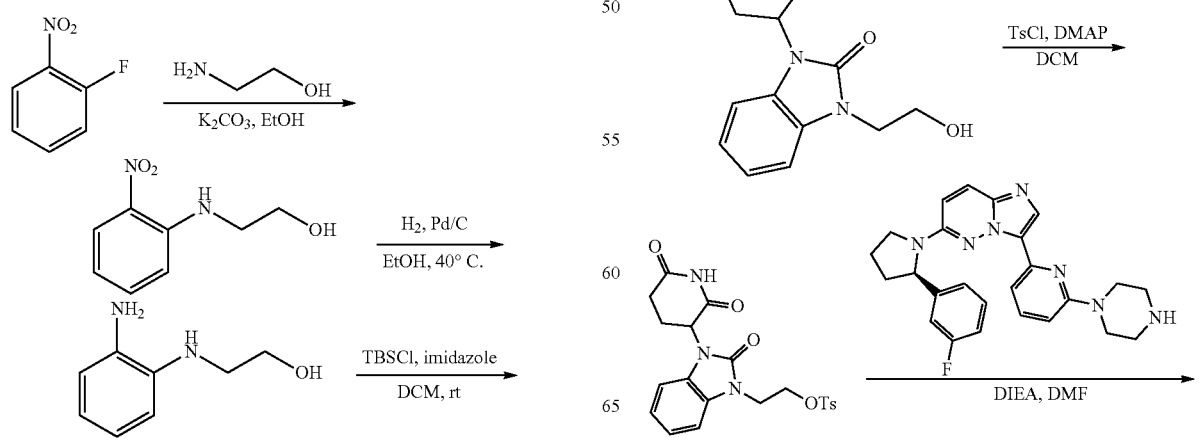

-continued

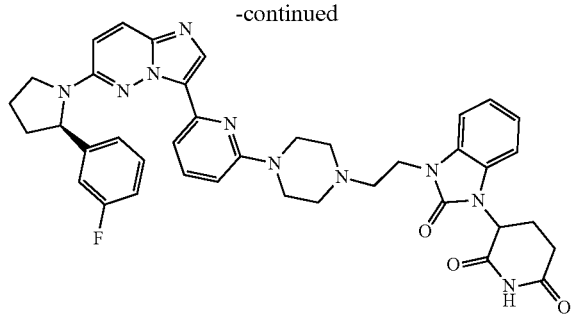

Step 1. Synthesis of 2-((2-nitrophenyl)amino)ethan-1-ol

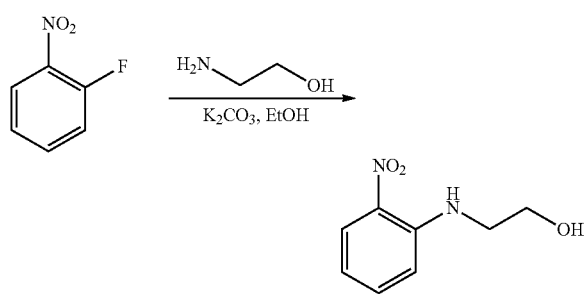

To a solution of 1-fluoro-2-nitrobenzene (10 g, 70.9 mmol) in EtOH (80 mL) were added K$_2$CO$_3$ (11.7 g, 85.04 mmol) and 2-aminoethan-1-ol (13.0 g, 212.6 mmol). The reaction was stirred at reflux for 12 h. After the reaction was cooled to room temperature, water and ethyl acetate were added. The organic phase was separated, dried over anhydrous sodium sulfate, filtered and concentrated. The resulting crude product was triturated with EtOAc/petroleum ether (20 mL, 10:1) to give 2-((2-nitrophenyl)amino)ethan-1-ol (11 g, 85% yield) as a yellow solid. MS (ESI) m/z: 183.4 [M+H]$^+$.

Step 2. Synthesis of 2-((2-aminophenyl)amino)ethan-1-ol

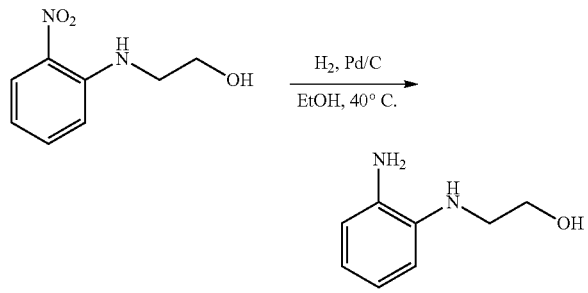

To a solution of 2-((2-nitrophenyl)amino)ethan-1-ol (7.0 g, 38.5 mmol) in EtOH (30 mL) was added 10% Pd/C (0.5 g). The reaction mixture was stirred at room temperature overnight under hydrogen atmosphere. After filtration through a celite cup, the filtrate was concentrated to give crude 2-((2-aminophenyl)amino)ethan-1-ol (5.9 g, 99% yield). This product was used in the next step directly without further purification. MS (ESI) m/z: 153.3 [M+H]$^+$.

Step 3. Synthesis of N$^1$-(2-((tert-butyldimethylsilyl)oxy)ethyl)benzene-1,2-diamine

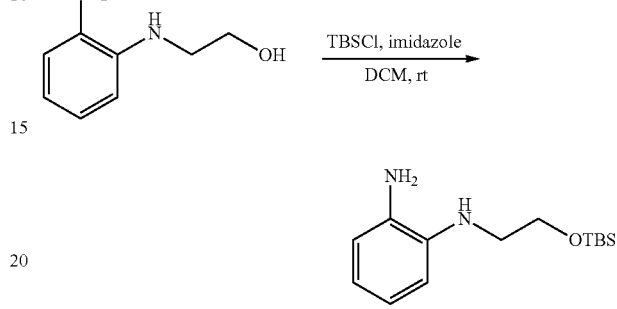

To a solution of 2-((2-aminophenyl)amino)ethan-1-ol (1.0 g, 6.58 mmol) in DCM (20 mL) were added imidazole (671 mg, 9.87 mmol) and tert-butyldimethylsilyl chloride (1.19 g, 7.89 mmol). After the mixture was stirred at room temperature for 15 h, the reaction was quenched with water and extracted with ethyl acetate (50 mL). The organic layer was washed with water twice, saturated brine, dried over sodium sulfate, filtered and concentrated. The resulting residue was triturated with petroleum ether/EtOAc (20 mL/2 mL) to give N$^1$-(2-((tert-butyldimethylsilyl)oxy)ethyl)benzene-1,2-diamine (1.1 g, 63% yield) as a pale solid. MS (ESI) m/z: 268.0 [M+H]$^+$.

Step 4. Synthesis of 1-(2-((tert-butyldimethylsilyl)oxy)ethyl)-1,3-dihydro-2H-benzo[d]imidazol-2-one

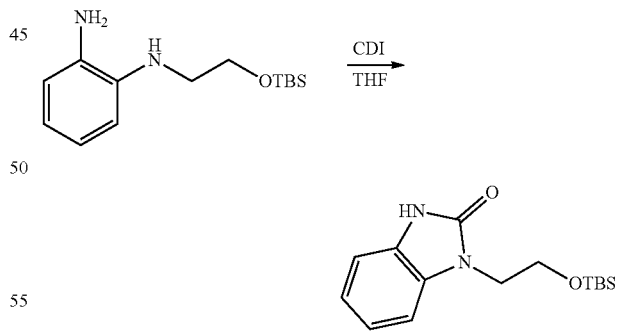

To a solution of N$^1$-(2-((tert-butyldimethylsilyl)oxy)ethyl)benzene-1,2-diamine (1.7 g, 6.39 mmol), in THF (25 mL) was added N,N'-carbonyldiimidazole (2.07 g, 12.78 mmol) under N$_2$. The reaction mixture was stirred at room temperature for 4 h, before the solvent was removed under vacuum. The resulting residue was recrystallized from methanol and n-hexane to give 1-(2-((tert-butyldimethylsilyl)oxy)ethyl)-1,3-dihydro-2H-benzo[d]imidazol-2-one (1.4 g, 75% yield) as a white solid. MS (ESI) m/z: 293.3 [M+H]$^+$.

Step 5. Synthesis of 3-(3-(2-((tert-butyldimethylsilyl)oxy)ethyl)-2-oxo-2,3-dihydro-1H-benzo[d]imidazol-1-yl)piperidine-2,6-dione

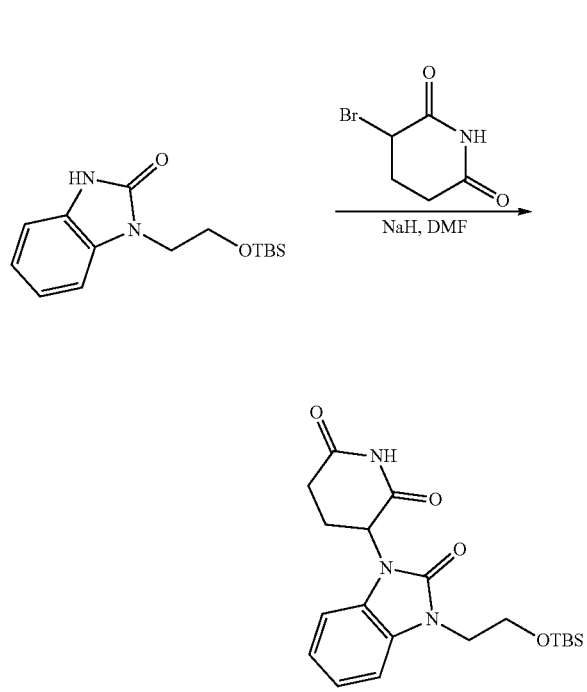

To a stirred solution of 1-(2-((tert-butyldimethylsilyl)oxy)ethyl)-1,3-dihydro-2H-benzo[d]imidazol-2-one (458 mg, 1.57 mmol) in DMF (2 mL) was added NaH (69.08 mg, 60% w/w dispersed into mineral oil, 1.73 mmol) at 0° C. under $N_2$. After the reaction mixture was stirred for 20 min at 0° C., a solution of 3-bromopiperidine-2,6-dione (150 mg, 0.79 mmol) in DMF (0.5 mL) was added dropwise at 0° C. After the resulting mixture was stirred for additional 3 h at room temperature, the reaction was quenched with AcOH (0.5 mL) and concentrated under reduced pressure. The residue was purified by silica gel chromatography column (petroleum ether/EtOAc=4:1) to afford 3-(3-(2-((tert-butyldimethylsilyl)oxy)ethyl)-2-oxo-2,3-dihydro-1H-benzo[d]imidazol-1-yl)piperidine-2,6-dione (132 mg, 21% yield) as a white solid. MS (ESI) m/z: 404.9 [M+H]$^+$.

Step 6. Synthesis of 3-(3-(2-hydroxyethyl)-2-oxo-2,3-dihydro-1H-benzo[d]imidazol-1-yl)piperidine-2,6-dione

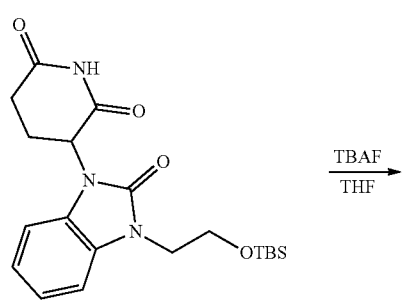

To a solution of 3-(3-(2-((tert-butyldimethylsilyl)oxy)ethyl)-2-oxo-2,3-dihydro-1H-benzo[d]imidazol-1-yl)piperidine-2,6-dione (130 mg, 0.32 mmol) in tetrahydrofuran (10 mL) was added tetra-n-butyl ammonium fluoride (168.71 mg, 0.65 mmol). The mixture was stirred at room temperature for 1 h. After removal of the solvent, the resulting residue was purified by silica gel chromatography column (hexane/EtOAc=1:1) to afford 3-(3-(2-hydroxyethyl)-2-oxo-2,3-dihydro-1H-benzo[d]imidazol-1-yl)piperidine-2,6-dione (83 mg, 90% yield) as a white solid. MS (ESI) m/z: 290.3 [M+H]$^+$.

Step 7. Synthesis of 2-(3-(2,6-dioxopiperidin-3-yl)-2-oxo-2,3-dihydro-1H-benzo[d]imidazol-1-yl)ethyl 4-methylbenzenesulfonate

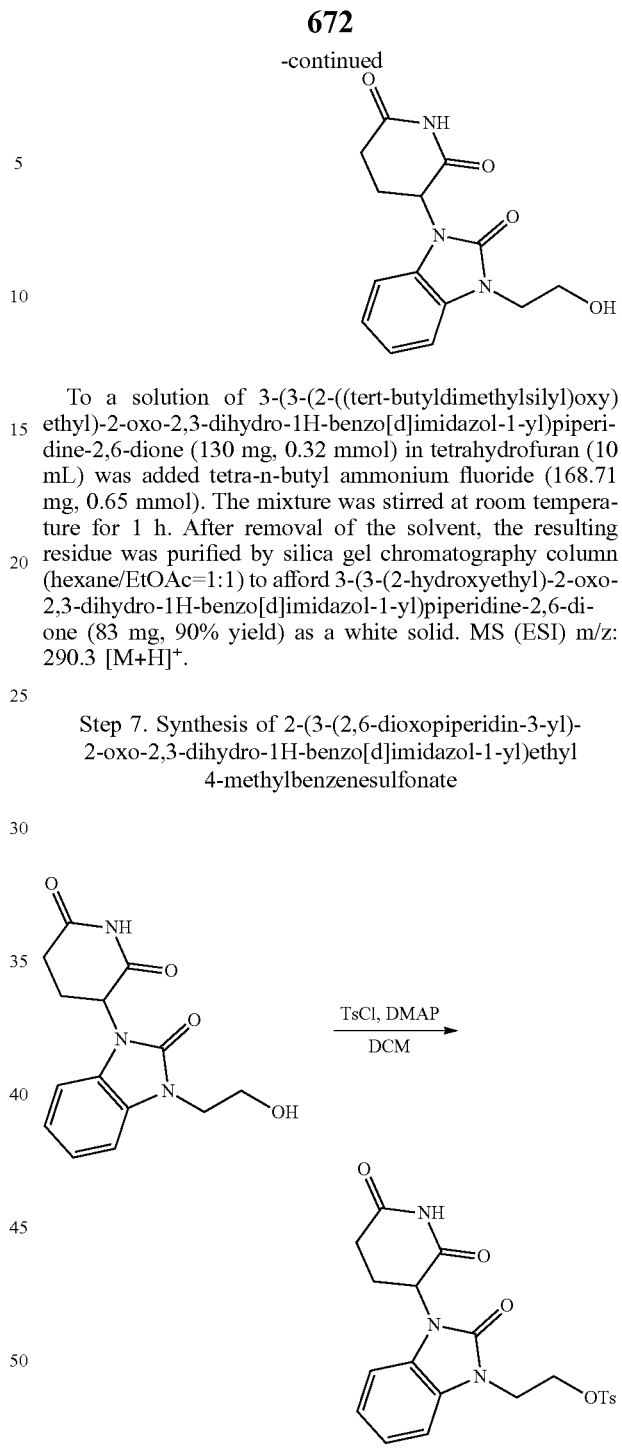

To a solution of 3-(3-(2-hydroxyethyl)-2-oxo-2,3-dihydro-1H-benzo[d]imidazol-1-yl)piperidine-2,6-dione (83 mg, 0.29 mmol) in dry $CH_2Cl_2$ (5 mL) were added p-toluensulfonyl chloride (82.1 mg, 0.43 mmol), 4-dimethylaminopyridine (12 mg, 0.1 mmol) and $Et_3N$ (279 mL, 2 mmol) at 0° C. After the reaction mixture was stirred at room temperature for 24 h. the reaction was quenched with water, and extracted with DCM. The organic layer was washed with brine and dried over $MgSO_4$, filtered and concentrated. The resulting residue was purified by prep-TLC (petroleum ether/EtOAc=2:1) to afford 2-(3-(2,6-dioxopiperidin-3-yl)-2-oxo-2,3-dihydro-1H-benzo[d]imidazol-1-yl)ethyl 4-methylbenzenesulfonate (60 mg, 47% yield) as a white solid. MS (ESI) m/z: 444.5 [M+H]$^+$.

Step 8. Synthesis of 3-(3-(2-(4-(6-(6-((R)-2-(3-fluorophenyl)pyrrolidin-1-yl)imidazo[1,2-b]pyridazin-3-yl)pyridin-2-yl)piperazin-1-yl)ethyl)-2-oxo-2,3-dihydro-1H-benzo[d]imidazol-1-yl)piperidine-2,6-dione

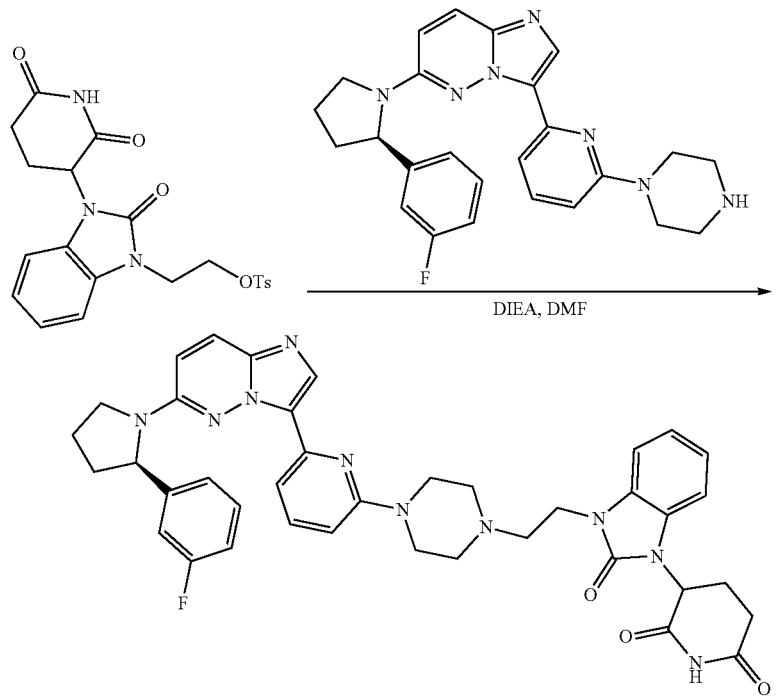

To a solution of 2-(3-(2,6-dioxopiperidin-3-yl)-2-oxo-2,3-dihydro-1H-benzo[d]imidazol-1-yl)ethyl 4-methylbenzenesulfonate (60 mg, 0.14 mmol) and (R)-6-(2-(3-fluorophenyl)pyrrolidin-1-yl)-3-(6-(piperazin-1-yl)pyridin-2-yl)imidazo[1,2-b]pyridazine (67 mg, 0.14 mmol) in DMF (2 mL) was added DIEA (89.6 mg, 0.70 mmol). The reaction mixture was stirred at 60° C. for 12 h. After the reaction was cooled down to room temperature, the solution was quenched with water and extracted with EtOAc. The organic layer was washed with brine and dried over MgSO$_4$, filtered and concentrated. The resulting residue was purified by prep-TLC to give 3-(3-(2-(4-(6-(6-((R)-2-(3-fluorophenyl)pyrrolidin-1-yl)imidazo[1,2-b]pyridazin-3-yl)pyridin-2-yl)piperazin-1-yl)ethyl)-2-oxo-2,3-dihydro-1H-benzo[d]imidazol-1-yl)piperidine-2,6-dione (17 mg, 17% yield) as a white solid. MS (ESI) m/z: 715.9 [M+H]$^+$.

Example 279: 3-(3-(3-(4-(6-(6-((R)-2-(3-Fluorophenyl)pyrrolidin-1-yl)imidazo[1,2-b]pyridazin-3-yl)pyridin-2-yl)piperazin-1-yl)propyl)-2-oxo-2,3-dihydro-1H-benzo[d]imidazol-1-yl)piperidine-2,6-dione (TR-228)

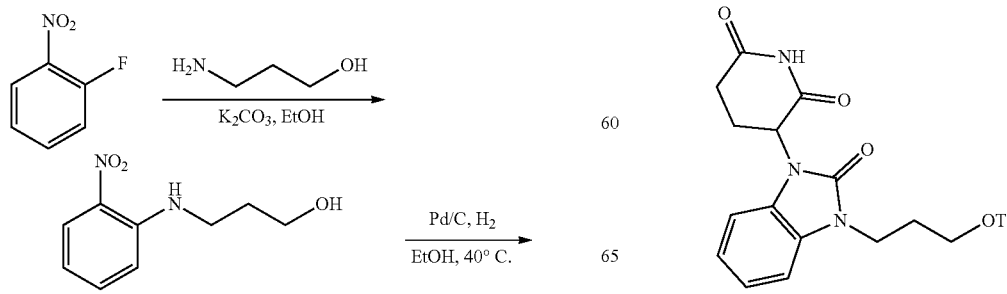

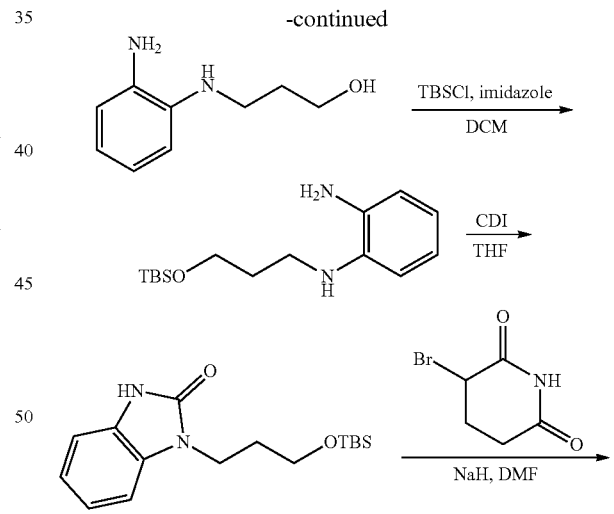

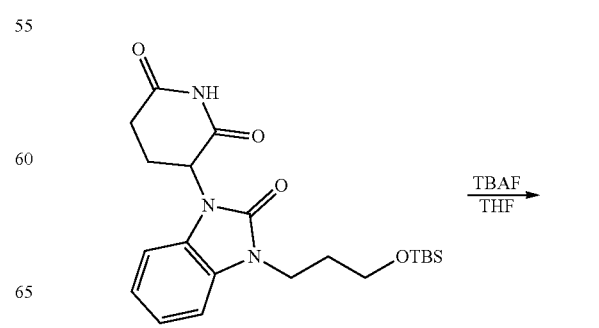

-continued

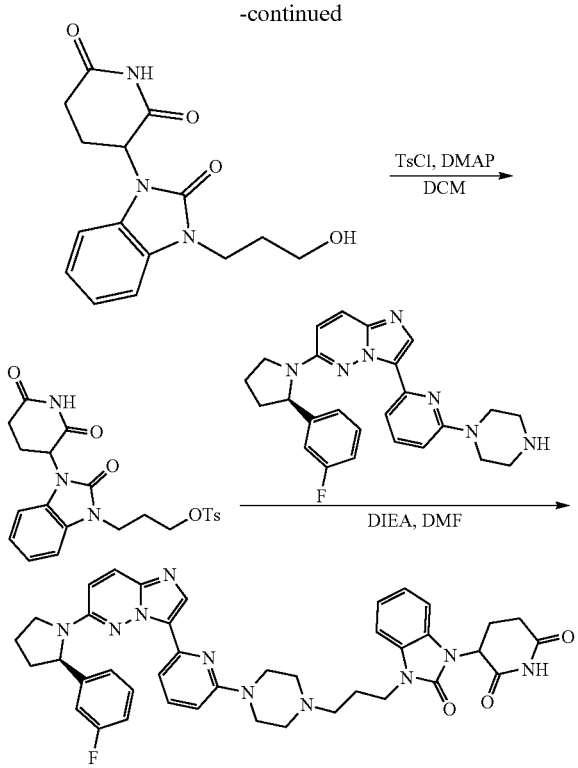

Step 1. Synthesis of
3-((2-nitrophenyl)amino)propan-1-ol

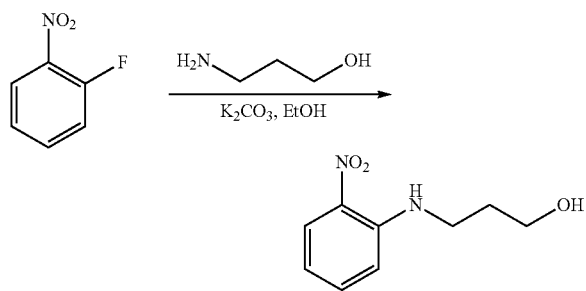

To a solution of 1-fluoro-2-nitrobenzene (10 g, 70.87 mmol) in EtOH (80 mL) were added $K_2CO_3$ (11.7 g, 85.04 mmol) and 3-aminopropan-1-ol (15.9 g, 212.6 mmol). After the reaction was stirred at reflux for 12 h, the reaction was cooled to room temperature, quenched with water, and diluted with ethyl acetate. The organic phase was separated, dried over anhydrous sodium sulfate, filtered and concentrated. The resulting crude product was triturated with EtOAc/petroleum ether (20 mL, 10:1) to give 3-((2-nitrophenyl)amino)propan-1-ol (11.1 g, 80% yield) as a yellow solid. MS (ESI) m/z: 197.3 [M+H]⁺.

Step 2. Synthesis of
3-((2-aminophenyl)amino)propan-1-ol

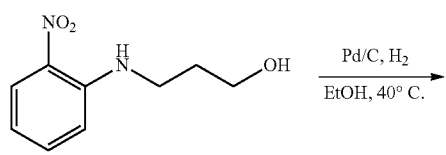

-continued

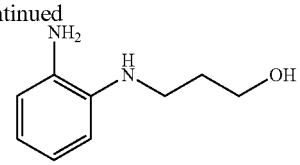

To a solution of 3-((2-nitrophenyl)amino)propan-1-ol (7.0 g, 38.5 mmol) in EtOH (30 mL) was added 10% Pd/C (1.0 g). The reaction mixture was stirred at room temperature overnight under hydrogen atmosphere. After the catalyst was filtered off through a celite cup, the filtrate was concentrated to give crude 3-((2-aminophenyl)amino)propan-1-ol (8.82 g, 99% yield). This product was used in the next step directly without further purification. MS (ESI) m/z: 168.3 [M+H]⁺.

Step 3. Synthesis of N¹-(3-((tert-butyldimethylsilyl)oxy)propyl)benzene-1,2-diamine

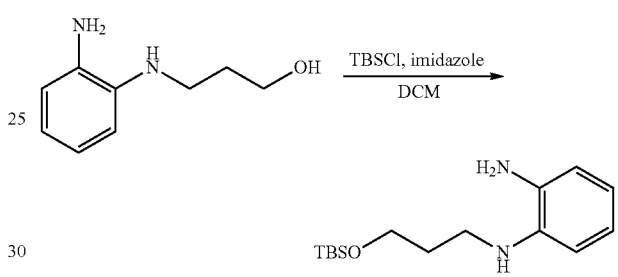

To a solution of 3-((2-aminophenyl)amino)propan-1-ol (3.0 g, 18.07 mmol) in DCM (25 mL) were added imidazole (1.85 g, 27.1 mmol) and tert-butyldimethylsilyl chloride (3.27 g, 21.68 mmol). The mixture was stirred at room temperature for 15 h, before the reaction was quenched with water and extracted with ethyl acetate (50 mL). The organic layer was washed with water twice and saturated aqueous brine, dried over sodium sulfate, filtered and concentrated. The residue was triturated with petroleum ether/EtOAc (40 mL/5 mL) to give N¹-(3-((tert-butyldimethylsilyl)oxy)propyl)benzene-1,2-diamine (5.6 g, 74% yield) as a pale solid. MS (ESI) m/z: 282.0 [M+H]⁺.

Step 4. Synthesis of 1-(3-((tert-butyldimethylsilyl)oxy)propyl)-1,3-dihydro-2H-benzo[d]imidazol-2-one

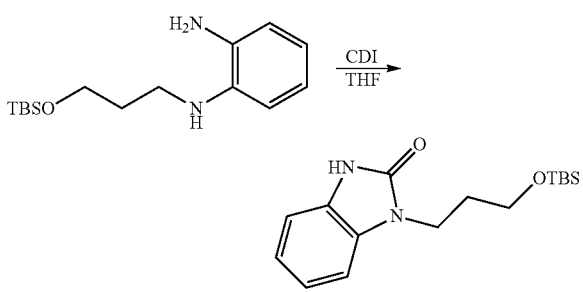

To a solution of N¹-(3-((tert-butyldimethylsilyl)oxy)propyl)benzene-1,2-diamine (5.6 g, 18.4 mmol), in THF (50 mL) was added N,N'-carbonyldiimidazole (5.97 g, 36.86 mmol) under $N_2$. The reaction mixture was stirred at room temperature for 4 h, at which time the solvent was removed under vacuum. The resulting residue was recrystallized from methanol and n-hexane to give 1-(3-((tert-butyldimethylsilyl)oxy)propyl)-1,3-dihydro-2H-benzo[d]imidazol-2-one (5 g, 88% yield) as a white solid. MS (ESI) m/z: 308.0 [M+H]⁺.

Step 5. Synthesis of 3-(3-(3-((tert-butyldimethylsilyl)oxy)propyl)-2-oxo-2,3-dihydro-1H-benzo[d]imidazol-1-yl)piperidine-2,6-dione

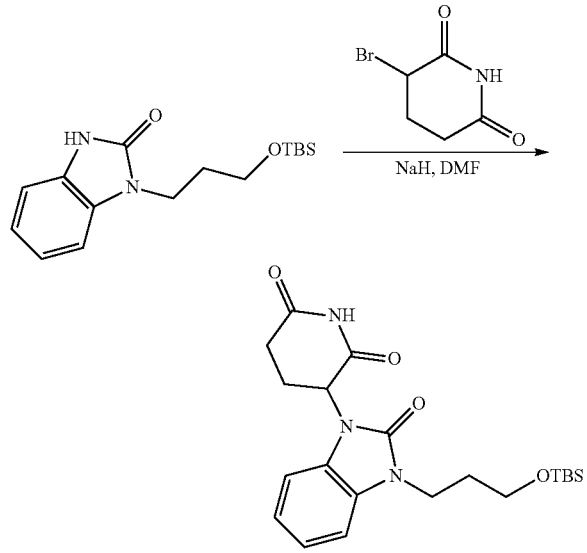

To a stirred solution of 1-(3-((tert-butyldimethylsilyl)oxy)propyl)-1,3-dihydro-2H-benzo[d]imidazol-2-one (465 mg, 1.57 mmol) in DMF (2 mL) was added NaH (69.08 mg, 60% w/w dispersed into mineral oil, 1.73 mmol) at 0° C. under N₂. After the reaction mixture was stirred for 20 min at 0° C., a solution of 3-bromopiperidine-2,6-dione (150 mg, 0.79 mmol) in DMF (0.5 mL) was added dropwise at 0° C. The resulting mixture was stirred for additional 3 h at room temperature, before the reaction was quenched with AcOH (0.5 mL) and concentrated under reduced pressure. The resulting residue was purified by silica gel chromatography column (petroleum ether/EtOAc=4:1) to afford 3-(3-(3-((tert-butyldimethylsilyl)oxy)propyl)-2-oxo-2,3-dihydro-1H-benzo[d]imidazol-1-yl)piperidine-2,6-dione (150.5 mg, 23% yield) as a white solid. MS (ESI) m/z: 418.9 [M+H]⁺.

Step 6. Synthesis of 3-(3-(3-hydroxypropyl)-2-oxo-2,3-dihydro-1H-benzo[d]imidazol-1-yl)piperidine-2,6-dione

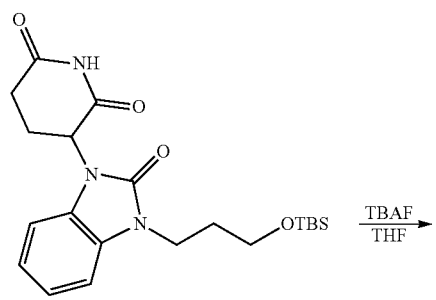

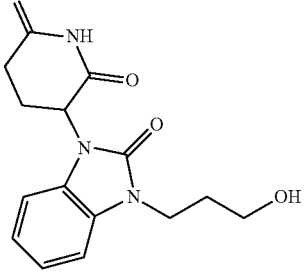

To a solution of 3-(3-(3-((tert-butyldimethylsilyl)oxy)propyl)-2-oxo-2,3-dihydro-1H-benzo[d]imidazol-1-yl)piperidine-2,6-dione (300 mg, 0.74 mmol) in tetrahydrofuran (10 mL) was added tetra-n-butyl ammonium fluoride (384.5 mg, 1.47 mmol). The mixture was stirred at room temperature for 1 h. After removal of the solvent, the resulting residue was purified by silica gel chromatography column (hexane/EtOAc=1:1) to afford 3-(3-(3-hydroxypropyl)-2-oxo-2,3-dihydro-1H-benzo[d]imidazol-1-yl)piperidine-2,6-dione (83 mg, 90% yield) as a white solid. MS (ESI) m/z: 304.4 [M+H]⁺.

Step 7. Synthesis of 3-(3-(2,6-dioxopiperidin-3-yl)-2-oxo-2,3-dihydro-1H-benzo[d]imidazol-1-yl)propyl 4-methylbenzenesulfonate

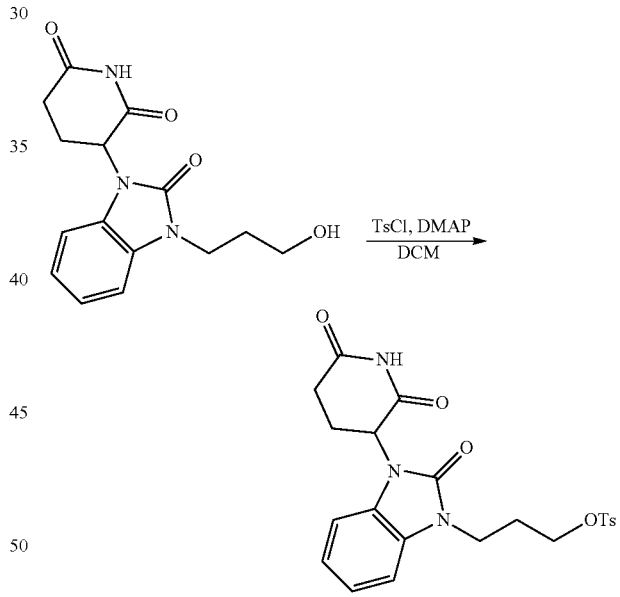

To a solution of 3-(3-(3-hydroxypropyl)-2-oxo-2,3-dihydro-1H-benzo[d]imidazol-1-yl)piperidine-2,6-dione (220 mg, 0.66 mmol) in dry CH₂Cl₂ (5 mL) were added p-toluensulfonyl chloride (188 mg, 0.99 mmol), 4-dimethylaminopyridine (12 mg, 0.1 mmol) and Et₃N (279 mL, 2 mmol) at 0° C. After the reaction mixture was stirred at room temperature for 24 h, the reaction was quenched with water, and extracted with DCM. The organic layer was washed with brine and dried over MgSO₄, filtered and concentrated. The resulting residue was purified by prep-TLC (petroleum ether/EtOAc=2:1) to afford 3-(3-(2,6-dioxopiperidin-3-yl)-2-oxo-2,3-dihydro-1H-benzo[d]imidazol-1-yl)propyl 4-methylbenzenesulfonate (150 mg, 50% yield) as a white solid. MS (ESI) m/z: 458.5 [M+H]⁺.

Step 8. Synthesis of 3-(3-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-2-oxo-2,3-dihydro-1H-benzo[d]imidazol-1-yl)piperidine-2,6-dione

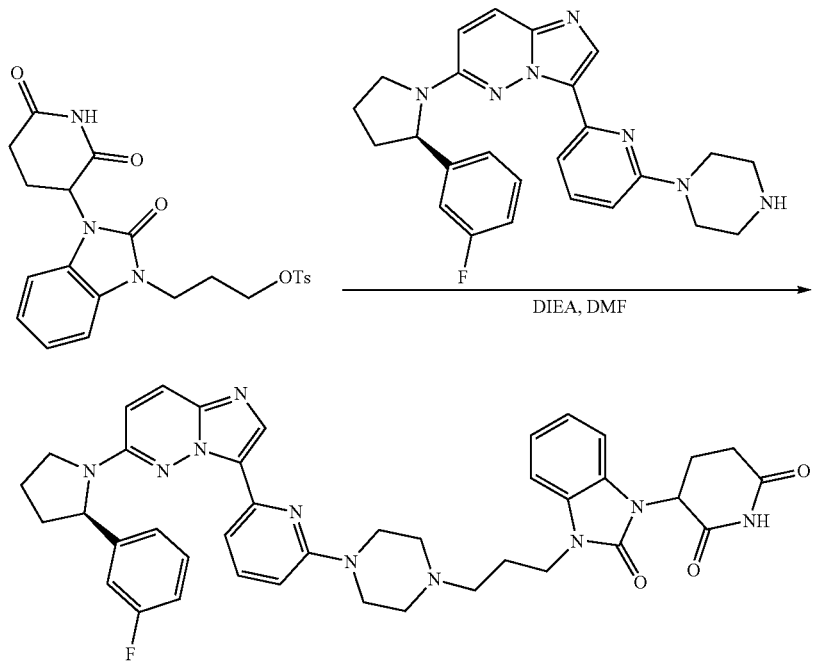

To a solution of 3-(3-(2,6-dioxopiperidin-3-yl)-2-oxo-2,3-dihydro-1H-benzo[d]imidazol-1-yl)propyl 4-methylbenzenesulfonate (70 mg, 0.16 mmol) and (R)-6-(2-(3-fluorophenyl)pyrrolidin-1-yl)-3-(6-(piperazin-1-yl)pyridin-2-yl)imidazo[1,2-b]pyridazine (76.6 mg, 0.16 mmol) in DMF (2 mL) was added DIEA (89.6 mg, 0.70 mmol). The reaction mixture was stirred at 60° C. for 12 h. After the reaction was cooled down to room temperature, the reaction was quenched with water and extracted with EtOAc. The organic layer was washed with brine, dried over MgSO₄, filtered and concentrated. The resulting residue was purified by prep-TLC to give 3-(3-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-2-oxo-2,3-dihydro-1H-benzo[d]imidazol-1-yl)piperidine-2,6-dione (22 mg, 17% yield) as a white solid. MS (ESI) m/z: 729.9 [M+H]⁺.

Example 280: 3-((S)-5-(4-((4-(6-(6-((R)-2-(3-Fluorophenyl)pyrrolidin-1-yl)imidazo[1,2-b]pyridazin-3-yl)pyridin-2-yl)piperazin-1-yl)methyl)phenyl)-2-oxooxazolidin-3-yl)piperidine-2,6-dione (TR-229)

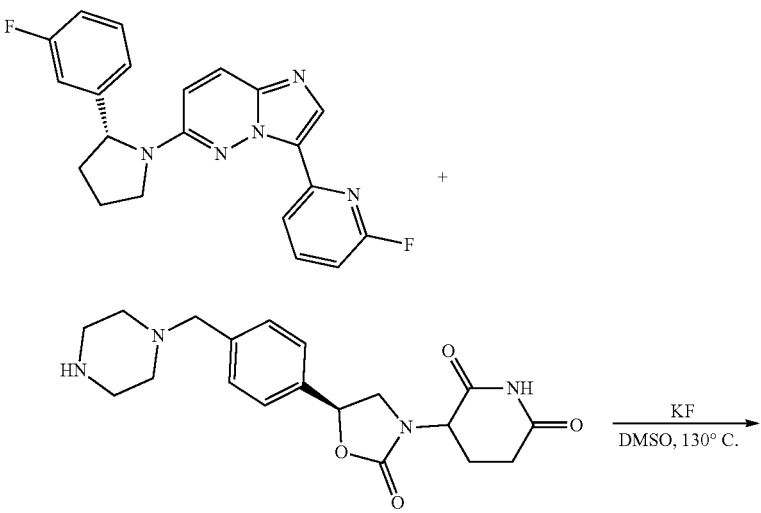

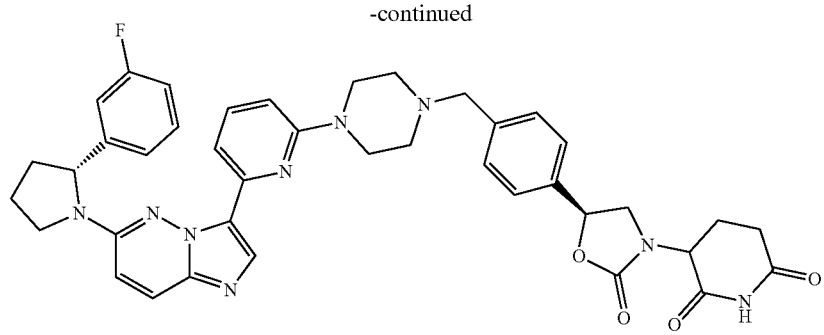

To a solution of (R)-6-(2-(3-fluorophenyl)pyrrolidin-1-yl)-3-(6-fluoropyridin-2-yl)imidazo[1,2-b]pyridazine hydrochloride (40 mg, 0.041 mmol) and 3-((S)-2-oxo-5-(4-(piperazin-1-ylmethyl)phenyl)oxazolidin-3-yl)piperidine-2,6-dione (15.2 mg, 0.041 mmol) in DMSO (4 mL) was added KF (24 mg, 0.41 mmol). The reaction mixture was stirred at 130° C. overnight. After the reaction was cooled down to room temperature, the reaction mixture was quenched with saturated aqueous NaHCO$_3$ (100 mL) and extracted with EtOAc (100 mL). The organic layer was washed with brine, dried over sodium sulfate, filtered and concentrated. The resulting residue was purified by prep-TLC (DCM/MeOH=10:1) to give 3-((S)-5-(4-((4-(6-(6-((R)-2-(3-fluorophenyl)pyrrolidin-1-yl)imidazo[1,2-b]pyridazin-3-yl)pyridin-2-yl)piperazin-1-yl)methyl)phenyl)-2-oxooxazolidin-3-yl)piperidine-2,6-dione (4 mg, 13% yield) as a white solid. MS (ESI) m/z: 731.0 [M+H]$^+$.

Example 281: 2-(2,6-Dioxopiperidin-3-yl)-5-(3-((4-(5-(6-((R)-2-(3-fluorophenyl)pyrrolidin-1-yl)imidazo[1,2-b]pyridazin-3-yl)-3,6-dihydropyridin-1(2H)-yl)piperidin-1-yl)methyl)azetidin-1-yl)isoindoline-1,3-dione (TR-230)

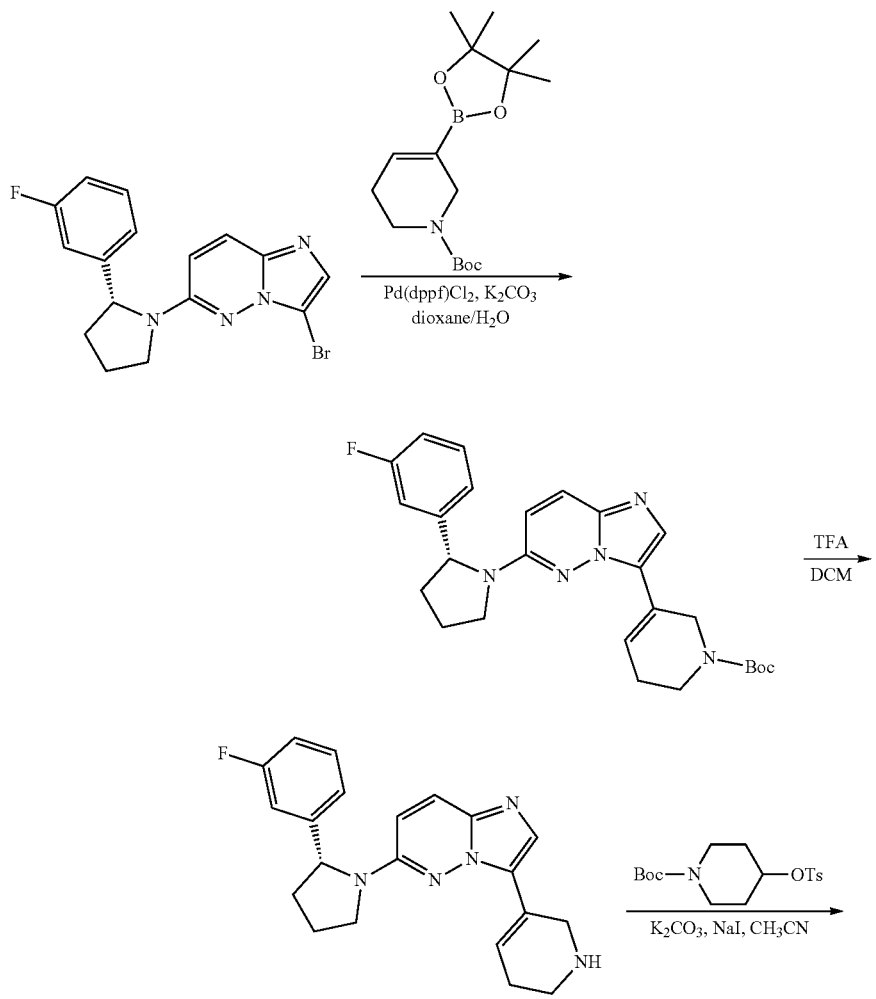

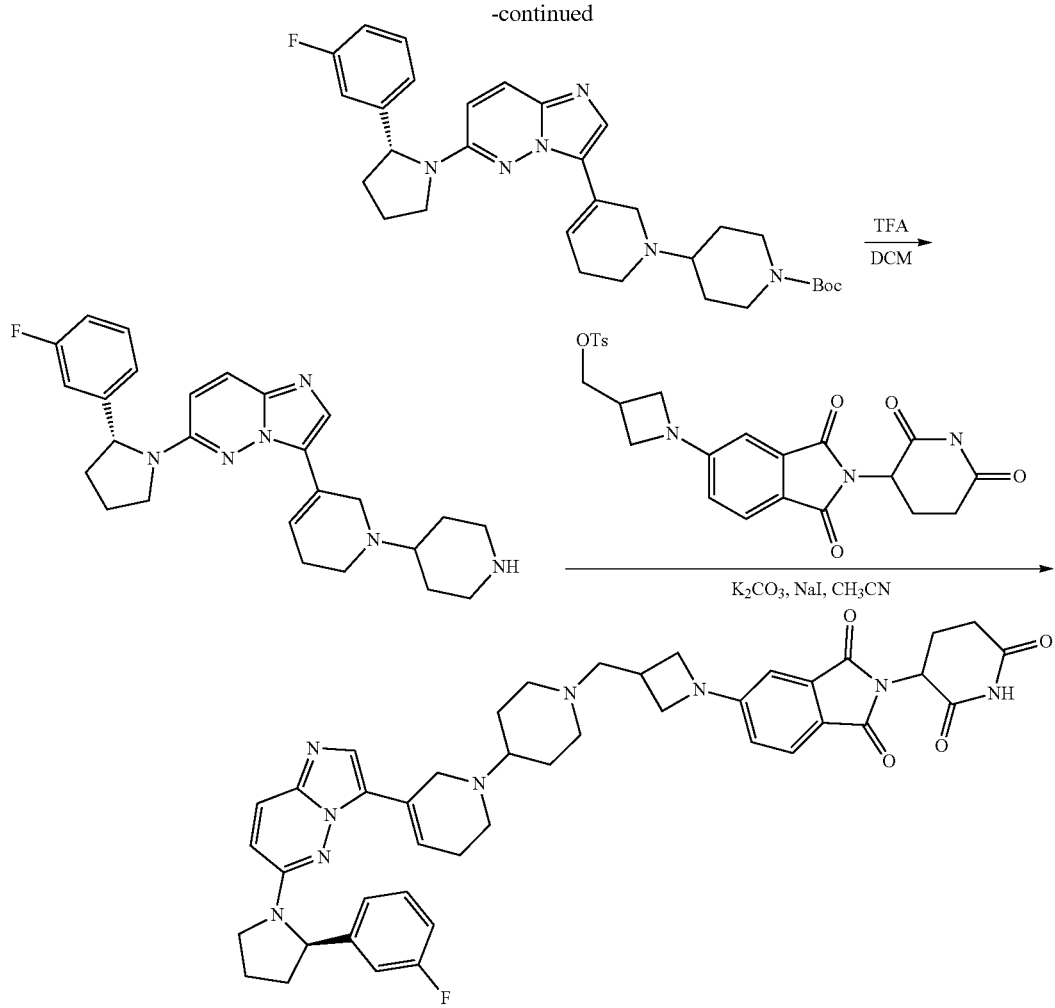

Step 1. Synthesis of tert-butyl (R)-5-(6-(2-(3-fluorophenyl)pyrrolidin-1-yl)imidazo[1,2-b]pyridazin-3-yl)-3,6-dihydropyridine-1(2H)-carboxylate

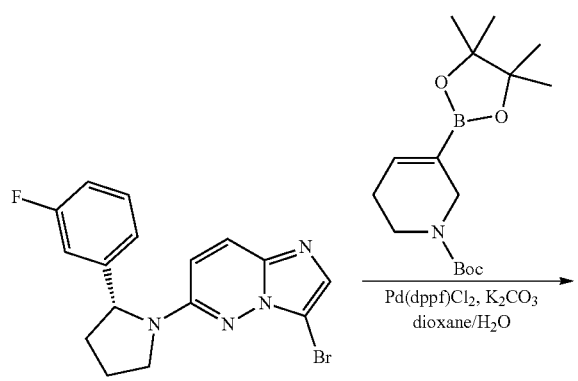

To a solution of (R)-3-bromo-6-(2-(3-fluorophenyl)pyrrolidin-1-yl)imidazo[1,2-b]pyridazine (1.5 g, 4.1 mmol) and tert-butyl 5-(4,4,5,5-tetramethyl-1,3,2-dioxaborolan-2-yl)-3,6-dihydropyridine-1(2H)-carboxylate (1.44 g, 4.5 mmol) in 1,4-dioxane (20 mL) and H₂O (5 mL) were added potassium carbonate (1.14 g, 8.2 mmol) and Pd(dppf)Cl₂ (306 mg, 0.41 mmol) at room temperature. The reaction mixture was stirred at 80° C. for 4 h. The resulting black mixture was diluted with ethyl acetate (50 mL), washed with saturated aqueous brine (3×50 mL). The combined organic layers were dried over sodium sulfate, filtered, and concentrated. The resulting residue was purified by silica gel flash chromatography (petroleum ether/ethyl acetate=1:4) to give tert-butyl (R)-5-(6-(2-(3-fluorophenyl)pyrrolidin-1-yl)imidazo[1,2-b]pyridazin-3-yl)-3,6-dihydropyridine-1(2H)-carboxylate (1.5 g, 78% yield) as a yellow oil. MS (ESI) m/z: 464.2 [M+H]⁺.

Step 2. Synthesis of (R)-6-(2-(3-fluorophenyl)pyrrolidin-1-yl)-3-(1,2,5,6-tetrahydropyridin-3-yl)imidazo[1,2-b]pyridazine

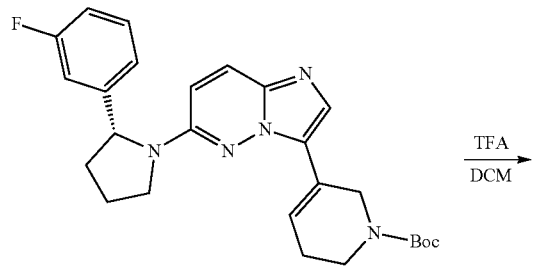

To a solution of tert-butyl (R)-5-(6-(2-(3-fluorophenyl)pyrrolidin-1-yl)imidazo[1,2-b]pyridazin-3-yl)-3,6-dihydropyridine-1(2H)-carboxylate (1.5 g, 3.2 mmol) in DCM (15 mL) was added TFA (3 mL) at 0° C. The reaction mixture was stirred at room temperature for 3 h, before the solvent was removed under vacuum. The resulting residue was washed with diethyl ether to give (R)-6-(2-(3-fluorophenyl)pyrrolidin-1-yl)-3-(1,2,5,6-tetrahydropyridin-3-yl)imidazo[1,2-b]pyridazine (1.0 g, 88% yield) as a yellow solid. This product was used in the next step directly without further purification. MS (ESI) m/z: 364.2 [M+H]⁺.

Step 3. Synthesis of tert-butyl (R)-4-(5-(6-(2-(3-fluorophenyl)pyrrolidin-1-yl)imidazo[1,2-b]pyridazin-3-yl)-3,6-dihydropyridin-1(2H)-yl)piperidine-1-carboxylate

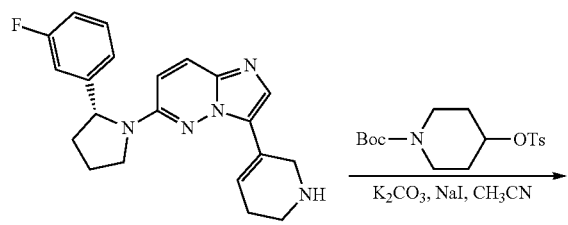

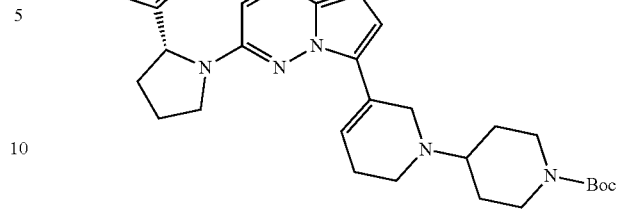

To a solution of (R)-6-(2-(3-fluorophenyl)pyrrolidin-1-yl)-3-(1,2,5,6-tetrahydropyridin-3-yl)imidazo[1,2-b]pyridazine (350 mg, 0.96 mmol) and tert-butyl 4-(tosyloxy)piperidine-1-carboxylate (1024 mg, 2.88 mmol) in acetonitrile (10 mL) were added potassium carbonate (398 mg, 3.56 mmol) and sodium iodide (144 mg, 0.96 mmol) at room temperature. The reaction mixture was stirred at 100° C. for 2 h, before the reaction was concentrated. The resulting residue was purified by silica gel flash chromatography (MeOH/DCM=1:10) to give tert-butyl (R)-4-(5-(6-(2-(3-fluorophenyl)pyrrolidin-1-yl)imidazo[1,2-b]pyridazin-3-yl)-3,6-dihydropyridin-1(2H)-yl)piperidine-1-carboxylate (260 mg, 49% yield) as a yellow solid. MS (ESI) m/z: 547.8 [M+H]⁺.

Step 4. Synthesis of (R)-6-(2-(3-fluorophenyl)pyrrolidin-1-yl)-3-(1-(piperidin-4-yl)-1,2,5,6-tetrahydropyridin-3-yl)imidazo[1,2-b]pyridazine

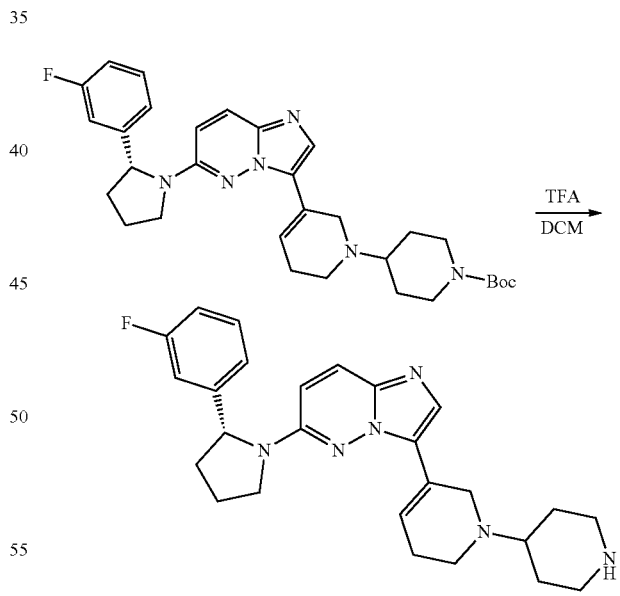

To a solution of tert-butyl (R)-4-(5-(6-(2-(3-fluorophenyl)pyrrolidin-1-yl)imidazo[1,2-b]pyridazin-3-yl)-3,6-dihydropyridin-1(2H)-yl)piperidine-1-carboxylate (260 mg, 0.47 mmol) in DCM (5 mL) was added TFA (1 mL) at 0° C. The reaction mixture was stirred at room temperature for 1 h, before the solvent was removed under vacuum. The resulting residue was washed with diethyl ether to give (R)-6-(2-(3-fluorophenyl)pyrrolidin-1-yl)-3-(1-(piperidin-4-yl)-1,2,5,6-tetrahydropyridin-3-yl)imidazo[1,2-b]pyridazine (160 mg, 75% yield) as a yellow solid. This product was used in the next step directly without further purification. MS (ESI) m/z: 447.8 [M+H]+.

Step 5. Synthesis of 2-(2,6-dioxopiperidin-3-yl)-5-(3-((4-(5-(6-((R)-2-(3-fluorophenyl)pyrrolidin-1-yl)imidazo[1,2-b]pyridazin-3-yl)-3,6-dihydropyridin-1(2H)-yl)piperidin-1-yl)methyl)azetidin-1-yl)isoindoline-1,3-dione

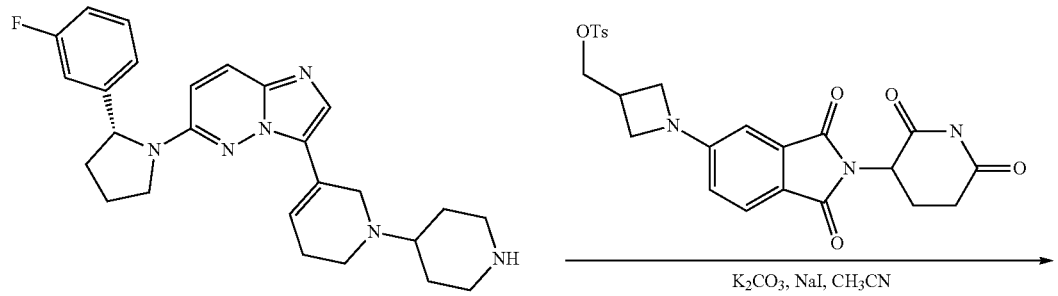

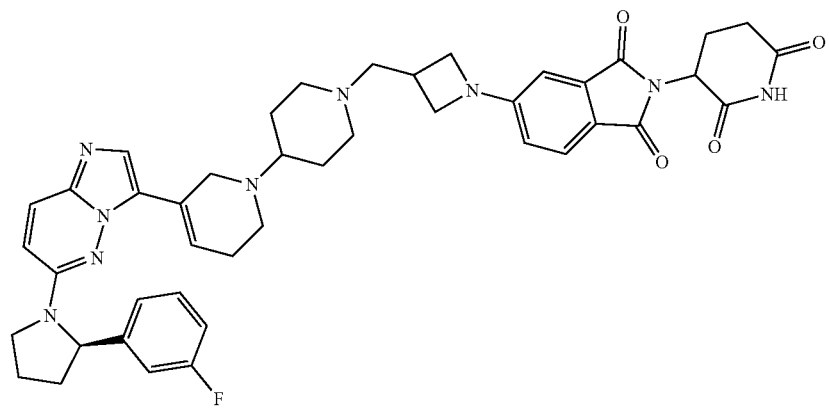

To a solution of (R)-6-(2-(3-fluorophenyl)pyrrolidin-1-yl)-3-(1-(piperidin-4-yl)-1,2,5,6-tetrahydropyridin-3-yl)imidazo[1,2-b]pyridazine (92 mg, 0.2 mmol) and (1-(2-(2,6-dioxopiperidin-3-yl)-1,3-dioxoisoindolin-5-yl)azetidin-3-yl)methyl 4-methylbenzenesulfonate (105 mg, 0.24 mmol) in acetonitrile (5 mL) were added potassium carbonate (75 mg, 0.6 mmol) and sodium iodide (26 mg, 0.2 mmol). After the reaction mixture was stirred at 80° C. for 2 h, the reaction was concentrated and the resulting residue was purified by silica gel chromatography (DCM/MeOH=10:1) to give 2-(2,6-dioxopiperidin-3-yl)-5-(3-((4-(5-(6-((R)-2-(3-fluorophenyl)pyrrolidin-1-yl)imidazo[1,2-b]pyridazin-3-yl)-3,6-dihydropyridin-1(2H)-yl)piperidin-1-yl)methyl)azetidin-1-yl)isoindoline-1,3-dione (3.7 mg, 1% yield) as a yellow solid. MS (ESI) m/z: 772.1 [M+H]+.

Example 282: N-(5-(3,5-Difluorobenzyl)-1H-indazol-3-yl)-4-(4-((1-(2-(2,6-dioxopiperidin-3-yl)-1,3-dioxoisoindolin-5-yl)azetidin-3-yl)methyl)piperazin-1-yl)-2-((tetrahydro-2H-pyran-4-yl)amino)benzamide (TR-231)

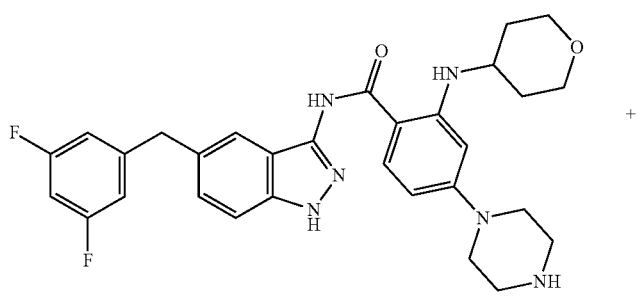

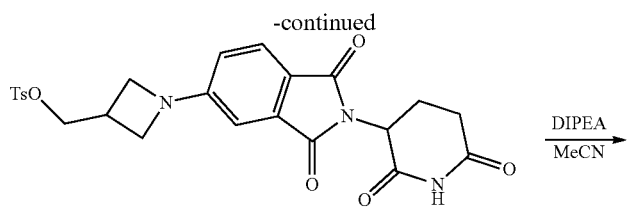

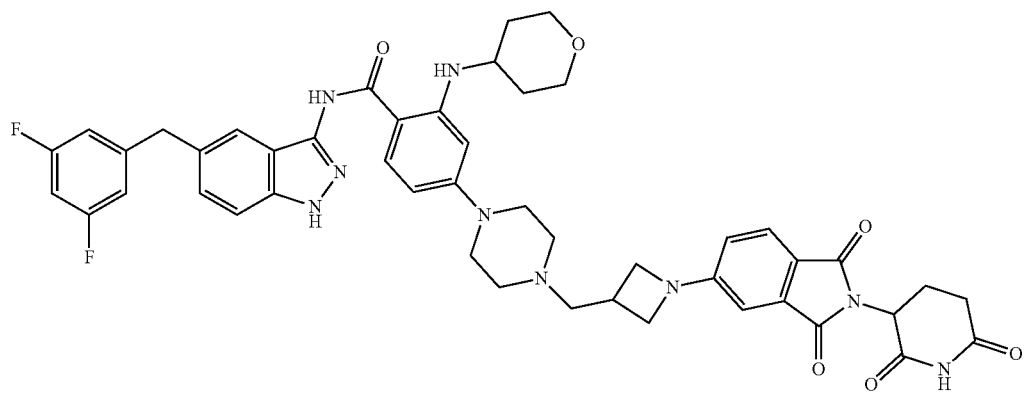

To a solution of N-(5-(3,5-difluorobenzyl)-1H-indazol-3-yl)-4-(piperazin-1-yl)-2-((tetrahydro-2H-pyran-4-yl)amino)benzamide (15 mg, 27.44 umol) and (1-(2-(2,6-dioxopiperidin-3-yl)-1,3-dioxoisoindolin-5-yl)azetidin-3-yl)methyl 4-methylbenzenesulfonate (16.38 mg, 32.93 umol) in MeCN (5 mL) was added DIPEA (21.28 mg, 164.65 umol). After the reaction mixture was stirred at 80° C. for 16 h, the solvent was removed under vacuum. The resulting residue was purified by prep-TLC to give N-(5-(3,5-difluorobenzyl)-1H-indazol-3-yl)-4-(4-((1-(2-(2,6-dioxopiperidin-3-yl)-1,3-dioxoisoindolin-5-yl)azetidin-3-yl)methyl)piperazin-1-yl)-2-((tetrahydro-2H-pyran-4-yl)amino)benzamide (9.5 mg, 39% yield) as a yellow solid. MS (ESI) m/z: 873.1 [M+H]$^+$.

Example 283: N-(5-(3,5-Difluorobenzyl)-1H-indazol-3-yl)-4-(4-(2-((2-(2,6-dioxopiperidin-3-yl)-1,3-dioxoisoindolin-5-yl)amino)ethyl)piperazin-1-yl)-2-((tetrahydro-2H-pyran-4-yl)amino)benzamide (TR-232)

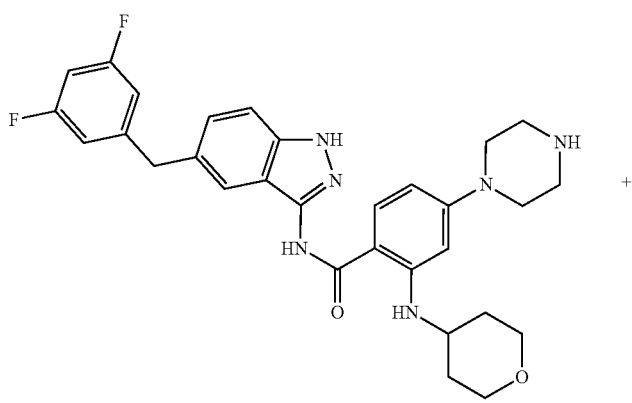

+

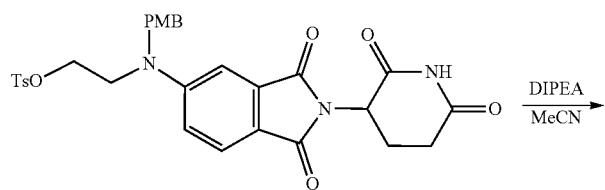

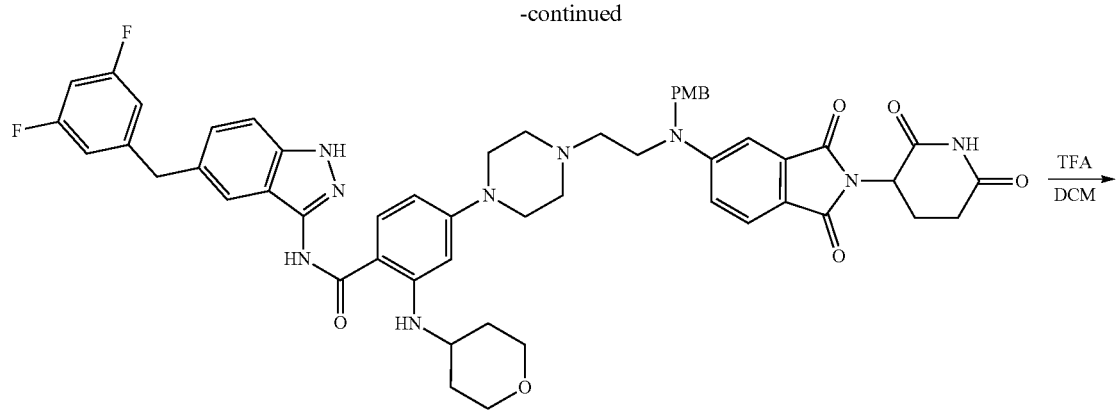
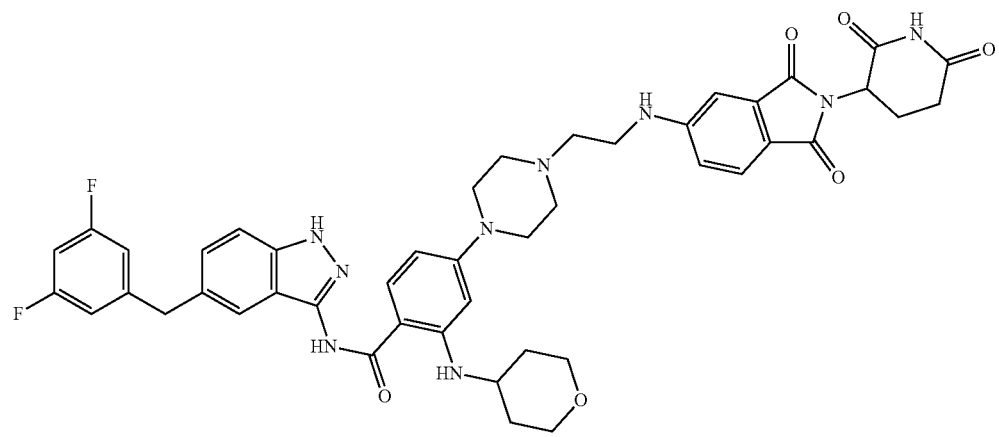
Step 1. Synthesis of N-(5-(3,5-difluorobenzyl)-1H-indazol-3-yl)-4-(4-(2-((2-(2,6-dioxopiperidin-3-yl)-5,3-dioxoisoindolin-5-yl)(4-methoxybenzyl)amino)ethyl)piperazin-1-yl)-2-((tetrahydro-2H-pyran-4-yl)amino)benzamide
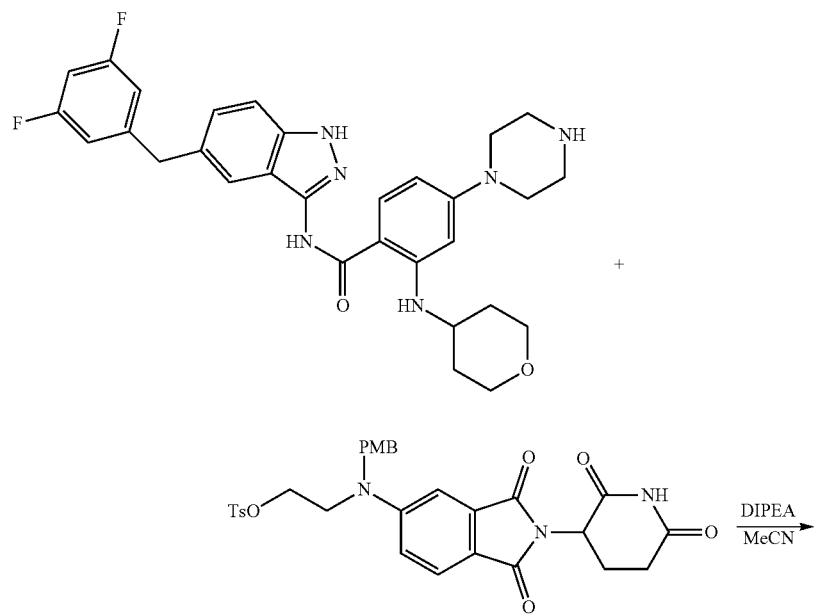

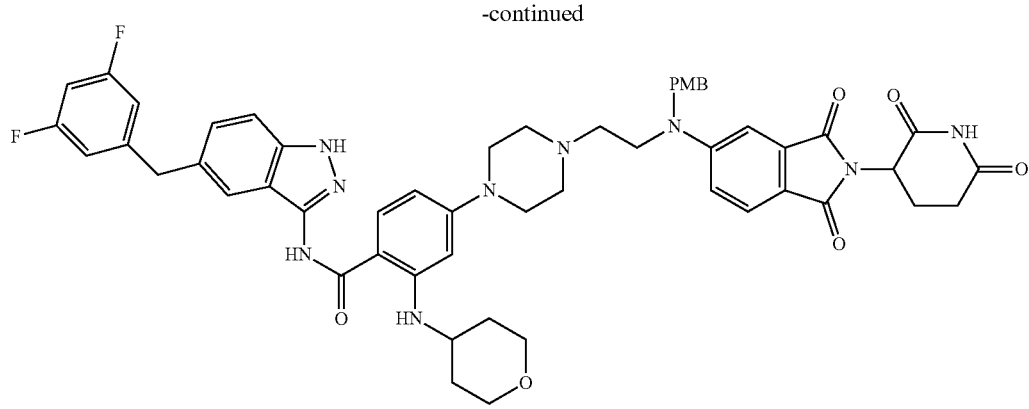

To a solution of N-(5-(3,5-difluorobenzyl)-1H-indazol-3-yl)-4-(piperazin-3-yl)-2-((tetrahydro-2H-pyran-4-yl)amino)benzamide (80 mg, 146.36 umol) and 2-((2-(2,6-dioxopiperidin-3-yl)-1,3-dioxoisoindolin-5-yl)(4-methoxybenzyl)amino)ethyl 4-methylbenzenesulfonate (103.91 mg, 175.63 umol) in MCN (5 mL) was added DIPEA (113.49 mg, 878.14 umol). After the reaction mixture was stirred at 90° C. for 24 h, the solvent was removed under vacuum. The resulting residue was purified by prep-TLC to give N-(5-(3,5-difluorobenzyl)-1H-indazol-3-yl)-4-(4-(2-((2-(2,6-dioxopiperidin-3-yl)-1,3-dioxoisoindolin-5-yl)(4-methoxybenzyl)amino)ethyl)piperazin-1-yl)-2-((tetrahydro-2H-pyran-4-yl)amino)benzamide (80 mg, 57% yield) as a yellow solid. MS (ESI) m/z: 967.2 [M+H]$^+$.

Step 2. Synthesis of N-(5-(3,5-difluorobenzyl)-1H-indazol-3-yl)-4-(4-(2-((2-(2,6-dioxopiperidin-3-yl)-1,3-dioxoisoindolin-5-yl)amino)ethyl)piperazin-1-yl)-2-((tetrahydro-2H-pyran-4-yl)amino)benzamide

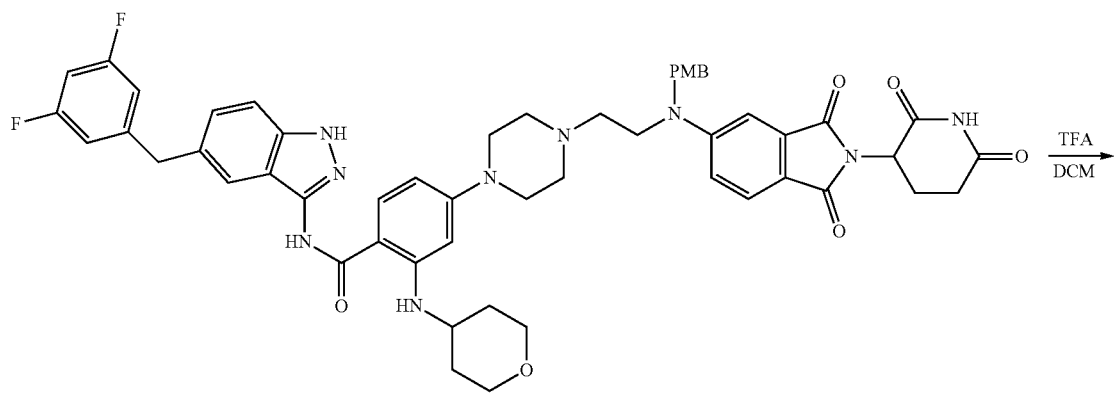

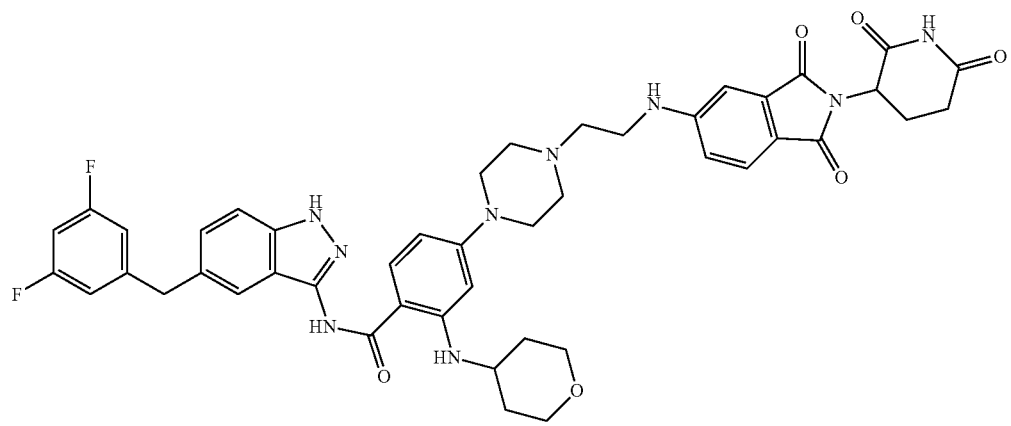 [SMILES: O=C1CCC(N2C(=O)c3ccc(NCCN4CCN(c5ccc(C(=O)Nc6n[nH]c7ccc(Cc8cc(F)cc(F)c8)cc67)c(NC6CCOCC6)c5)CC4)cc3C2=O)C(=O)N1]

To a solution of N-(5-(3,5-difluorobenzyl)-1H-indazol-3-yl)-4-(4-(2-((2-(2,6-dioxopiperidin-3-yl)-1,3-dioxoisoindolin-5-yl)(4-methoxybenzyl)amino)ethyl)piperazin-1-yl)-2-((tetrahydro-2H-pyran-4-yl)amino)benzamide (30 mg, 31.05 umol) in DCM (2 mL) was added TFA (1 mL). After the reaction mixture was stirred at room temperature for 1 h, the reaction was concentrated. The resulting residue was purified by prep-HPLC to give N-(5-(3,5-difluorobenzyl)-1H-indazol-3-yl)-4-(4-(2-((2-(2,6-dioxopiperidin-3-yl)-1,3-dioxoisoindolin-5-yl)amino)ethyl)piperazin-1-yl)-2-((tetrahydro-2H-pyran-4-yl)amino)benzamide (5 mg, 17% yield) as a yellow solid. MS (ESI) m/z: 847.1 [M+H]$^+$.

Example 284: N-(2-(2,6-Dioxopiperidin-3-yl)-1,3-dioxoisoindolin-5-yl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (TR-233)

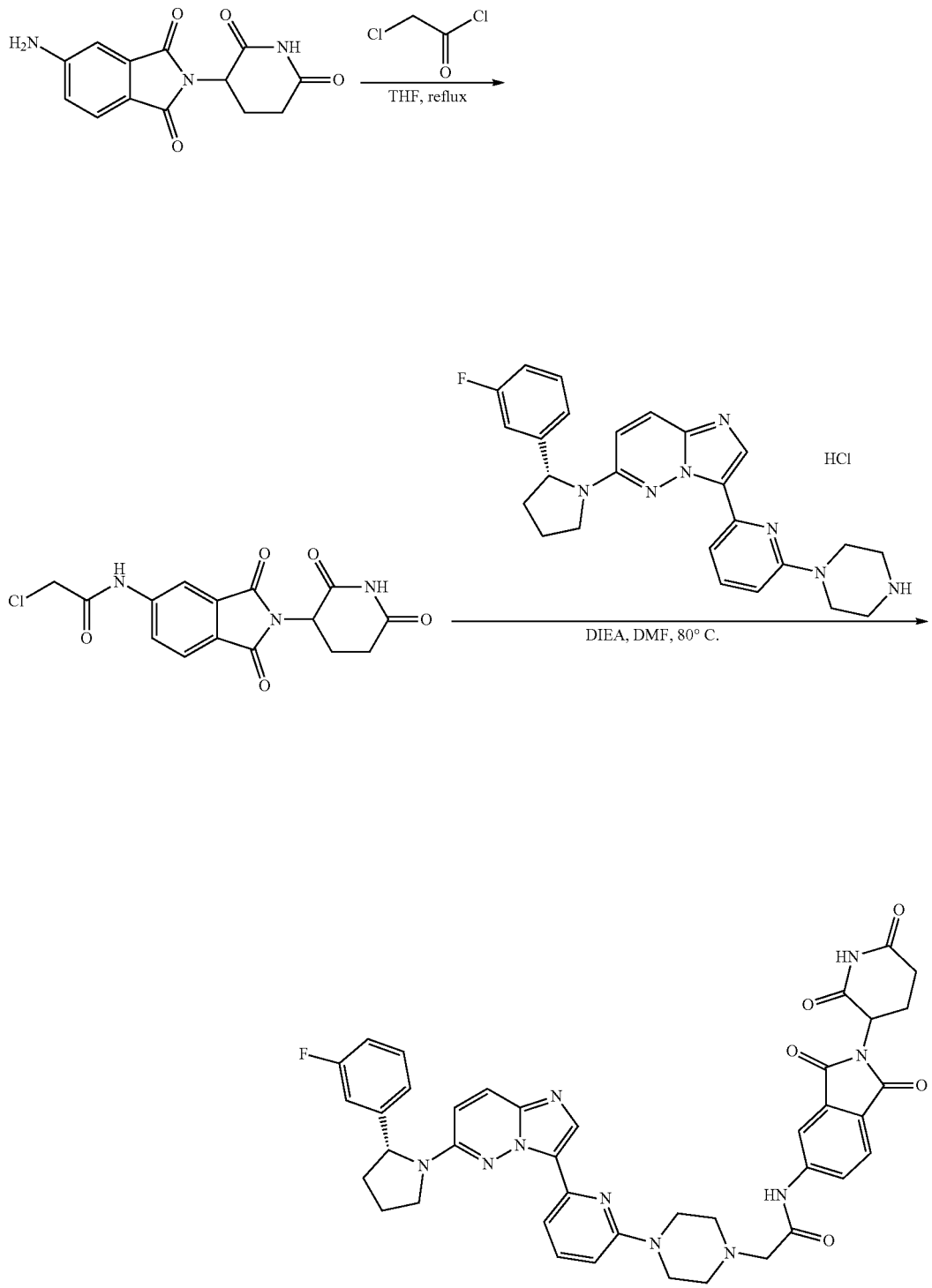

Step 1. Synthesis of 2-chloro-N-(2-(2,6-dioxopiperidin-3-yl)-1,3-dioxoisoindolin-5-yl)acetamide

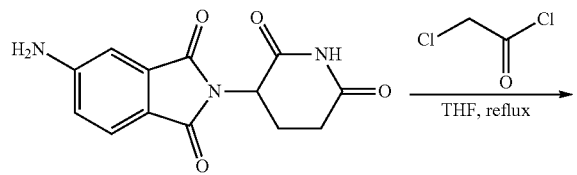

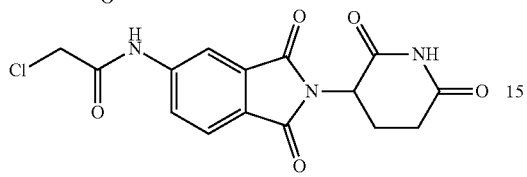

A mixture of 5-amino-2-(2,6-dioxopiperidin-3-yl)isoindoline-1,3-dione (40 mg, 0.146 mmol) and 2-chloroacetyl chloride (82 mg, 0.732 mmol) in THF (5 mL) was stirred at 70° C. for 1 h. After the reaction was completed, the reaction mixture was concentrated. The resulting residue was triturated with petroleum ether, filtered and dried to give 2-chloro-N-(2-(2,6-dioxopiperidin-3-yl)-1,3-dioxoisoindolin-5-yl)acetamide (55 mg, 107% yield) as a white solid. This product was used in the next step directly without further purification. MS (ESI) m/z: 350.4 [M+H]$^+$.

Step 2. Synthesis of N-(2-(2,6-dioxopiperidin-3-yl)-1,3-dioxoisoindolin-5-yl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide

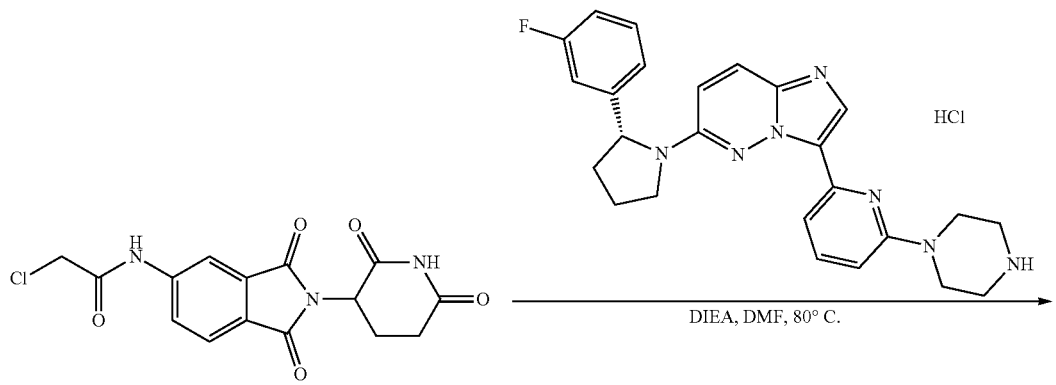

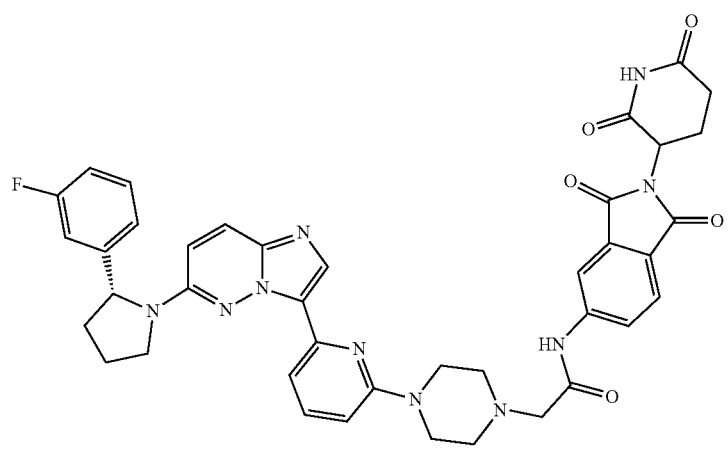

A solution of 2-chloro-N-(2-(2,6-dioxopiperidin-3-yl)-1,3-dioxoisoindolin-5-yl)acetamide (55 mg, 0.157 mmol), (R)-6-(2-(3-fluorophenyl)pyrrolidin-1-yl)-3-(6-(piperazin-1-yl)pyridin-2-yl)imidazo[1,2-b]pyridazine hydrochloride (75 mg, 0.157 mmol) and DIEA (101 mg, 0.785 mmol) in DMF (5 mL) was stirred at 80° C. for 1 h. After the reaction was completed, the reaction solution was diluted with EtOAc (200 mL), washed with brine twice, dried over sodium sulfate, filtered and concentrated. The resulting residue was purified by prep-TLC (DCM/MeOH=10:1) to give N-(2-(2,6-dioxopiperidin-3-yl)-1,3-dioxoisoindolin-5-yl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide (15.5 mg, 13% yield) as a white solid. MS (ESI) m/z: 757.9 [M+H]$^+$.

Example 285: 2-(2,6-Dioxopiperidin-3-yl)-5-(3-((4-(6-(6-((R)-2-(3-fluorophenyl)pyrrolidin-1-yl)imidazo[1,2-a]pyridin-3-yl)pyridin-2-yl)piperazin-1-yl)methyl)azetidin-1-yl)isoindoline-1,3-dione (TR-234)

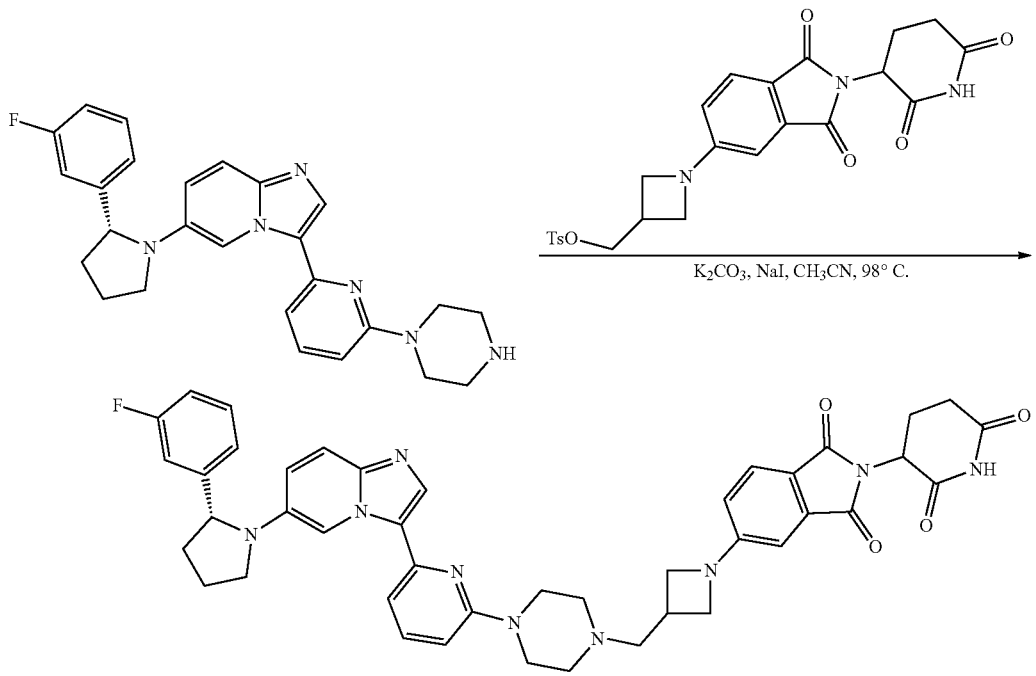

To a solution of (R)-6-(2-(3-fluorophenyl)pyrrolidin-1-yl)-3-(6-(piperazin-1-yl)pyridin-2-yl)imidazo[1,2-a]pyridine (22 mg, 4.98 umol) and (1-(2-(2,6-dioxopiperidin-3-yl)-1,3-dioxoisoindolin-5-yl)azetidin-3-yl)methyl 4-methylbenzenesulfonate (24.8 mg, 5.0 umol) in CH$_3$CN (4 mL) were added NaI (15 mg, 10.0 umol) and K$_2$CO$_3$ (28 mg, 20.00 umol) at room temperature under N$_2$. The reaction mixture was stirred at 98° C. for 16 h, before the solvent was removed under vaccuum. The resulting residue was purified by prep-TLC (DCM/MeOH=20:1) to give 2-(2,6-dioxopiperidin-3-yl)-5-(3-((4-(6-(6-((R)-2-(3-fluorophenyl)pyrrolidin-1-yl)imidazo[1,2-a]pyridin-3-yl)pyridin-2-yl)piperazin-1-yl)methyl)azetidin-1-yl)isoindoline-1,3-dione (19 mg, 50% yield). MS (ESI) m/z: 769.0 [M+H]$^+$.

Example 286: 3-((S)-5-(3-((4-(6-(6-((R)-2-(3-Fluorophenyl)pyrrolidin-1-yl)imidazo[1,2-b]pyridazin-3-yl)pyridin-2-yl)piperazin-1-yl)methyl)phenyl)-2-oxooxazolidin-3-yl)piperidine-2,6-dione (TR-235)

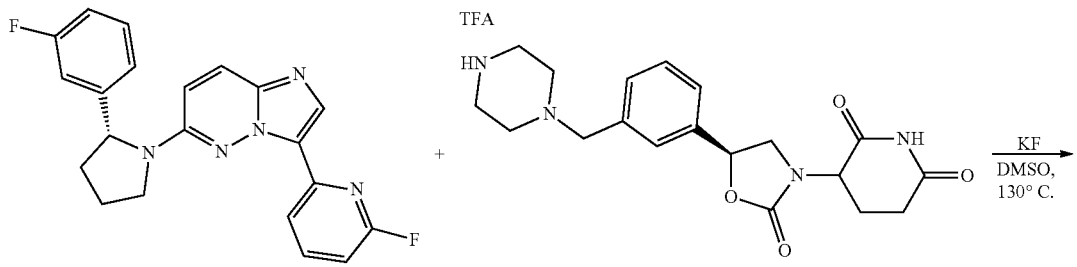

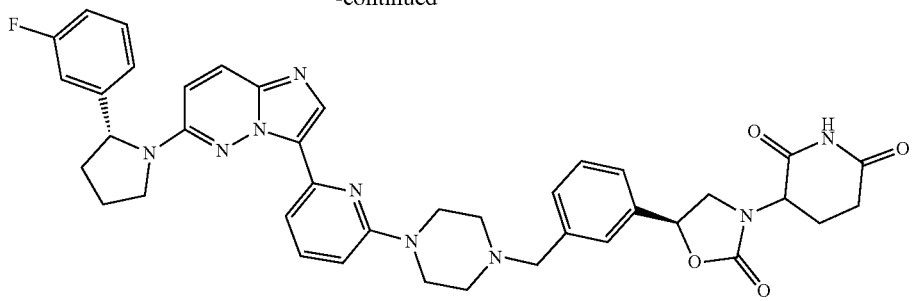

A mixture of (R)-6-(2-(3-fluorophenyl)pyrrolidin-1-yl)-3-(6-fluoropyridin-2-yl)imidazo[1,2-b]pyridazine (80 mg, 0.21 mmol), 2,2,2-trifluoroacetaldehyde compound with 3-((S)-2-oxo-5-(3-(piperazin-1-ylmethyl)phenyl)oxazolidin-3-yl)piperidine-2,6-dione (103.23 mg, 0.21 mmol) and KF (122.01 mg, 2.1 mmol) in DMSO (1 mL) was stirred at 130° C. for 3 h. After the reaction was cooled down to room temperature, the reaction was quenched with H₂O (10 mL), extracted with EtOAc. The organic layer was washed with brine, dried over MgSO₄, filtered and concentrated. The residue was purified by prep-TLC (DCM/CH₃OH=10:1) to give 3-((S)-5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)phenyl)-2-oxooxazolidin-3-yl)piperidine-2,6-dione (21 mg, 14% yield) as a white solid. MS (ESI) m/z: 730.9 [M+H]$^+$.

Example 287: 3-(4-((2-(4-(6-(6-((R)-2-(3-Fluorophenyl)pyrrolidin-1-yl)imidazo[1,2-b]pyridazin-3-yl)pyridin-2-yl)piperazin-1-yl)ethyl)amino)-2-oxoindolin-1-yl)piperidine-2,6-dione (TR-236)

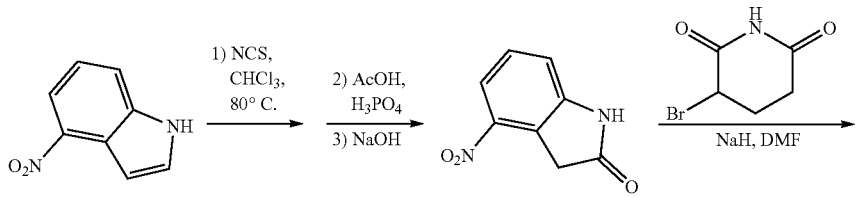

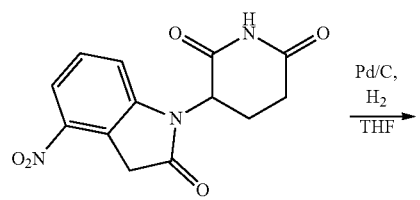

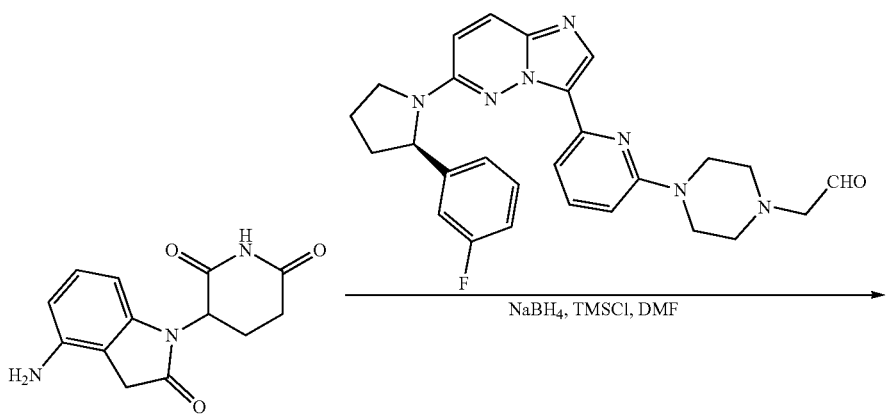

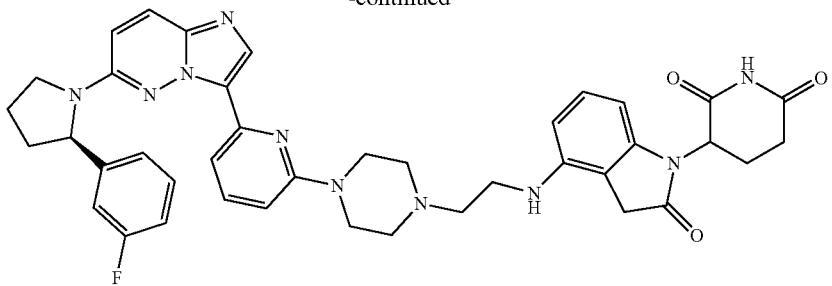

Step 1. Synthesis of 4-nitroindolin-2-one

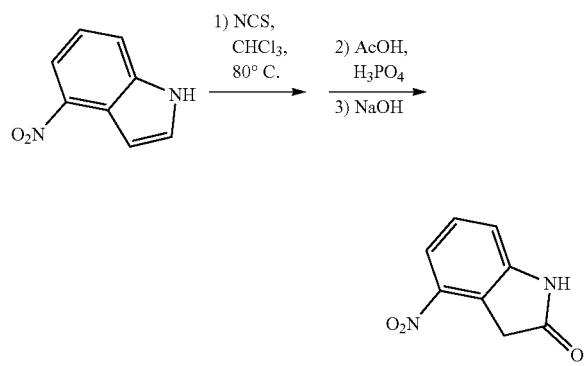

To a solution of 4-nitro-1H-indole (5.0 g, 30.9 mmol) in CHCl$_3$ (200 mL) was added NCS (N-chlorosuccinimide) (2.67 g, 20 mmol) at room temperature. The reaction mixture was stirred at 80° C. for 48 h. The solvent was evaporated under reduced pressure to give a yellow solid. The solid was dissolved in AcOH (80 mL) and 85% H$_3$PO$_4$ (30 mL). The resulting mixture was stirred at 100° C. for 3 h. After the reaction was cooled down to room temperature, the solution was acidified with 10 N NaOH to pH=6 and extracted with ethyl acetate (3×100 mL). The combined organic layers were washed with saturated brine (100 mL), dried over anhydrous sodium sulfate, filtered and evaporated under reduced pressure.

The resulting residue was purified by silica gel column chromatography (EtOAc/petroleum ether=1:1 to 1:0) to afford the 4-nitroindolin-2-one (3.5 g, 64% yield) as a yellow solid. MS (ESI) m/z: 179 [M+H]$^+$ Step 2. Synthesis of 3-(4-nitro-2-oxoindolin-1-yl)piperidine-2,6-dione

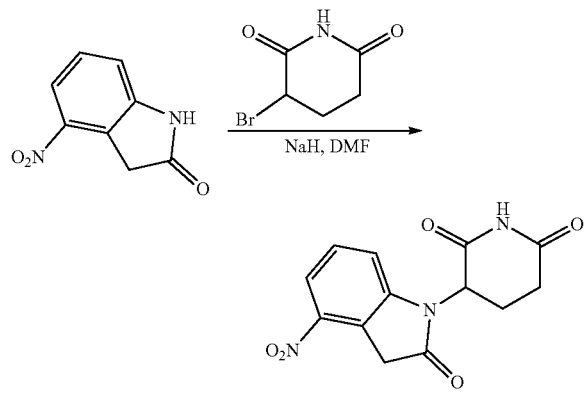

To a solution of 4-nitroindolin-2-one (1.0 g, 5.6 mmol) in DMF (40 mL) was added NaH (60% in mineral oil, 247 mg, 6.2 mmol) at 0° C. The reaction mixture was warmed to room temperature for 0.5 h, before 3-bromopiperidine-2,6-dione (2.14 g, 11.2 mmol) was added. The resulting mixture was stirred at 80° C. for 1 h, before the reaction was cooled down to room temperature. The reaction was quenched with water (50 mL) and extracted with ethyl acetate (3×20 mL). The combined organic layers were washed with saturated brine (20 mL), dried over anhydrous sodium sulfate, filtered and evaporated under reduced pressure. The resulting residue was purified by silica gel column chromatography (DCM/MeOH=30:1 to 15:1) to give a mixture of 3-(4-nitro-2-oxoindolin-3-yl) piperidine-2,6-dione, 3-(4-nitro-2-oxoindolin-1-yl)piperidine-2,6-dione and 3-((4-nitro-1H-indol-2-yl)oxy) piperidine-2,6-dione (400 mg, ratio=1:1:1) as a brown solid. These products were used in the next step directly without further purification. MS (ESI) m z: 290 [M+H]$^+$.

Step 3. Synthesis of 3-(4-nitro-2-oxoindolin-1-yl) piperidine-2,6-dione

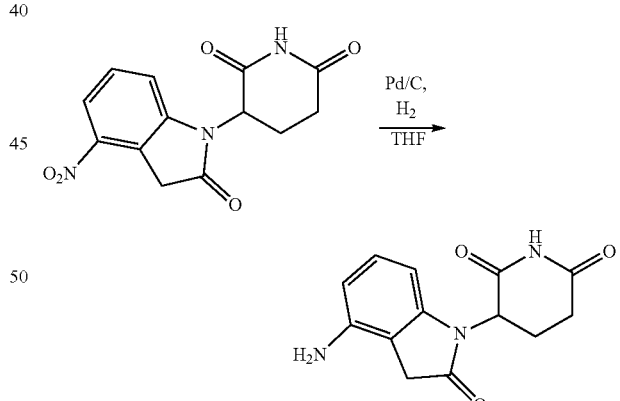

A mixture of 3-(4-nitro-2-oxoindolin-3-yl) piperidine-2,6-dione, 3-(4-nitro-2-oxoindolin-1-yl)piperidine-2,6-dione and 3-((4-nitro-1H-indol-2-yl)oxy) piperidine-2,6-dione (400 mg, 1:1:1) and 10% Pd/C (80 mg) in THF (10 mL) was stirred under H$_2$ (1 atm) at room temperature for 5 h. After the reaction was filtered through celite, the filtrate was removed under reduced pressure and the residue was purified by prep-TLC (DCM/MeOH=10:1) to give 3-(4-nitro-2-oxoindolin-1-yl) piperidine-2,6-dione (30 mg, 2% yield over 2 steps) as a light yellow solid. MS (ESI) m/z: 260 [M+H]$^+$.

Step 4. Synthesis of 3-(4-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-2-oxoindolin-1-yl)piperidine-2,6-dione

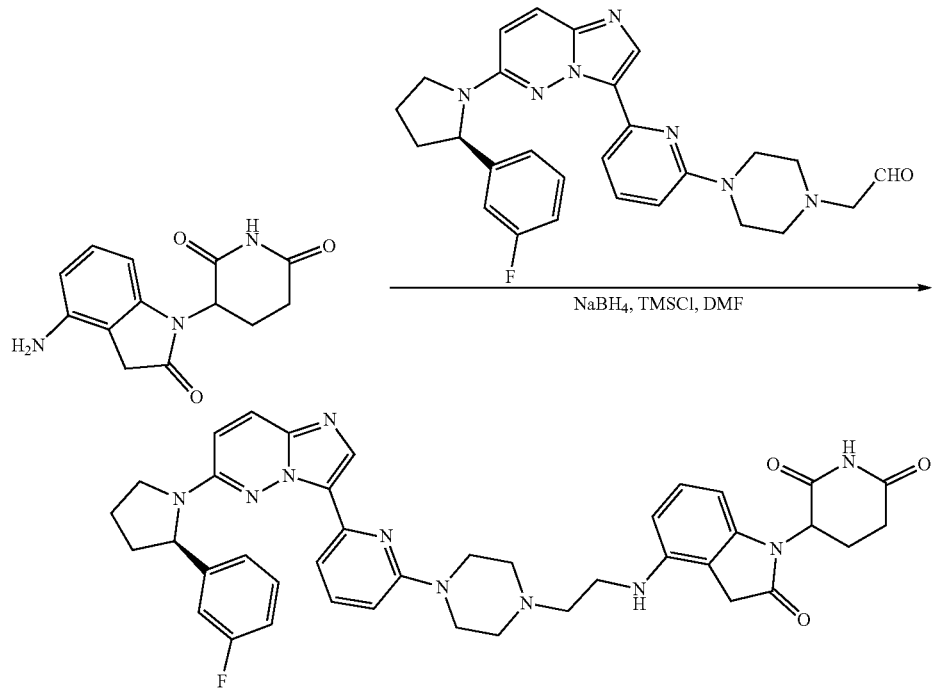

To a solution of (R)-2-(4-(6-(6-(2-(3-fluorophenyl)pyrrolidin-1-yl)imidazo[1,2-b]pyridazin-3-yl)pyridin-2-yl)piperazin-1-yl)acetaldehyde (57 mg, 0.12 mmol) and 3-(4-amino-2-oxoindolin-1-yl)piperidine-2,6-dione (30 mg, 0.12 mmol) in DMF (1 mL) were added TMSCl (39 mg, 0.36 mmol) and NaBH$_4$ (9.1 mg, 0.24 mmol) at 0° C. The reaction mixture was stirred at 0° C. for 1.5 h, before it was warmed to room temperature and stirred for 16 h. The reaction mixture was purified by prep-HPLC to give the crude product, which was further purified by prep-TLC (DMC/MeOH=15:1) to give 3-(4-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-2-oxoindolin-1-yl)piperidine-2,6-dione (7.7 mg, 9% yield) as a white solid. MS (ESI) m/z: 729.9 [M+H]$^+$.

Example 288: 2-(2,6-Dioxopiperidin-3-yl)-5-((3-(4-(6-(6-((R)-2-(3-fluorophenyl)pyrrolidin-1-yl)imidazo[1,2-b]pyridazin-3-yl)pyridin-2-yl)piperazin-1-yl)azetidin-1-yl)methyl)isoindoline-1,3-dione (TR-237)

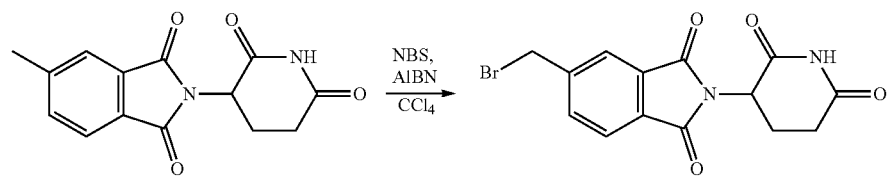

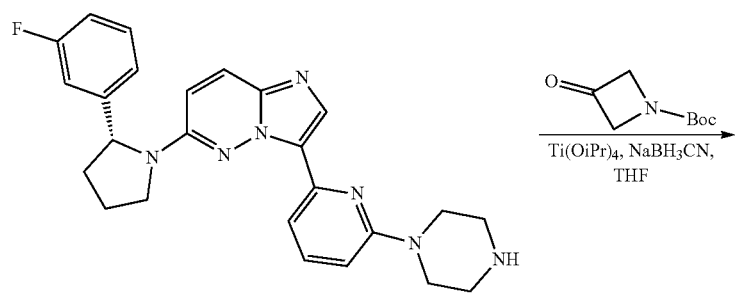

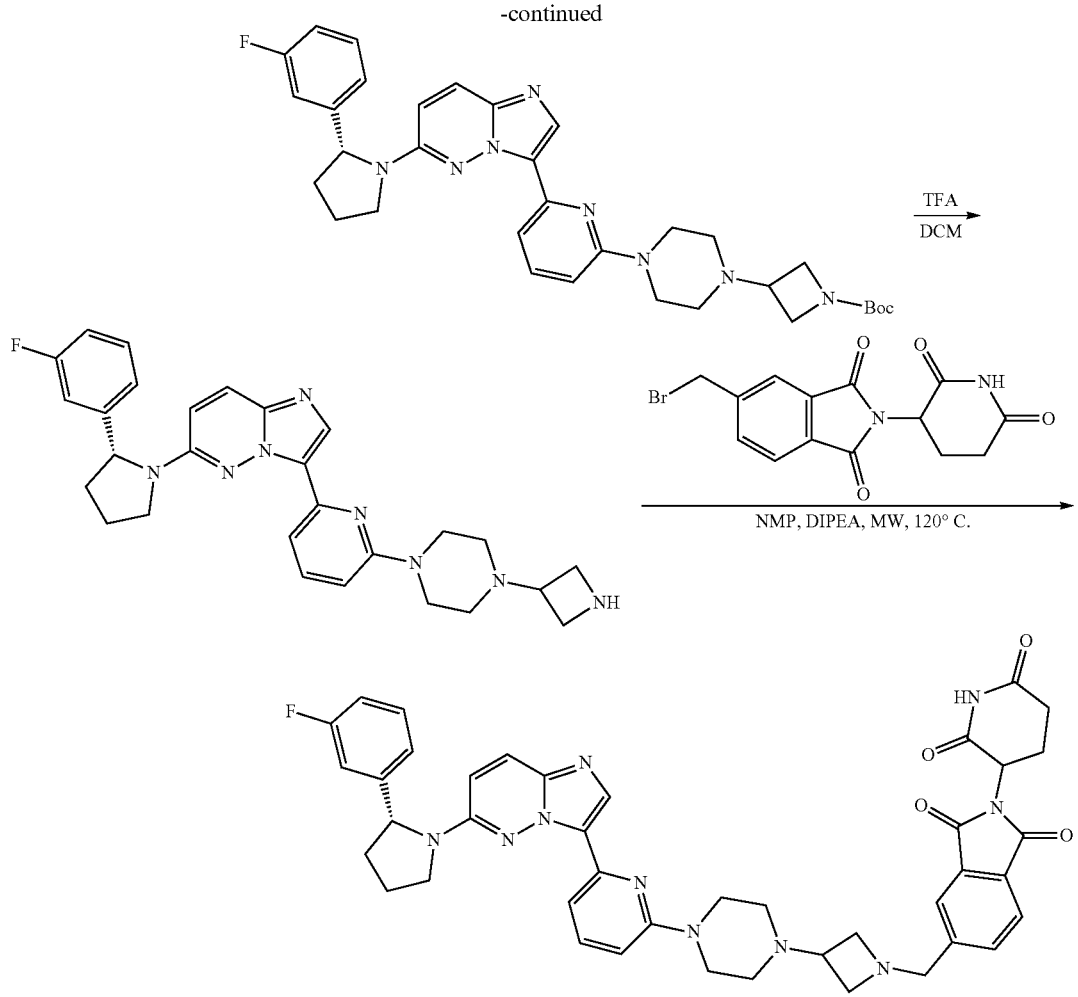

Step 1. Synthesis of 5-(bromomethyl)-2-(2,6-dioxopiperidin-3-yl)isoindoline-1,3-dione Step 2. Synthesis of (R)-tert-butyl 3-(4-(6-(6-(2-(3-fluorophenyl)pyrrolidin-1-yl)imidazo[1,2-b]pyridazin-3-yl)pyridin-2-yl)piperazin-1-yl)azetidine-1-carboxylate

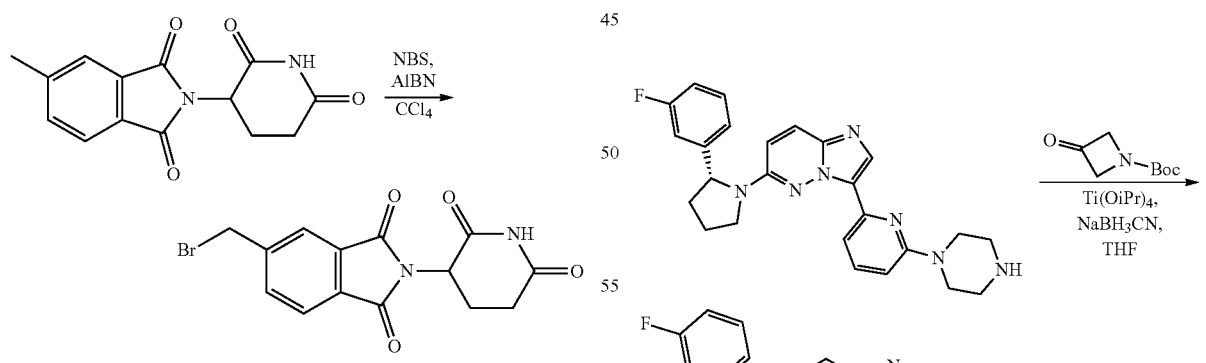

To a solution of 2-(2,6-dioxopiperidin-3-yl)-5-methylisoindoline-1,3-dione (1 g, 3.67 mmol) in $CCl_4$ (50 mL) were added NBS (719.10 mg, 4.04 mmol) and AIBN (azobisisobutyronitrile) (67.32 mg, 0.41 mmol). After the reaction mixture was stirred at 90° C. for 16 h, the solvent was removed under vacuum. The resulting residue was purified by prep-HPLC to give 5-(bromomethyl)-2-(2,6-dioxopiperidin-3-yl)isoindoline-1,3-dione (500 mg, 40% yield) as an off-white solid. MS (ESI) m/z: 353.3 [M+H]$^+$.

709

To a solution of (R)-6-(2-(3-fluorophenyl)pyrrolidin-1-yl)-3-(6-(piperazin-1-yl)pyridin-2-yl)imidazo[1,2-b]pyridazine (300 mg, 0.68 mmol) and tert-butyl 3-oxoazetidine-1-carboxylate (139 mg, 0.81 mmol) in THF (10 mL) was added titanium tetraisopropanolate (384 mg, 1.35 mmol) at 0° C. Then the mixture was stirred at 60° C. for 4 h. After the reaction was cooled down to room temperature, NaBH₃CN (85 mg, 1.35 mmol) was added. After the reaction mixture was stirred at room temperature for another 16 h, the reaction solution was poured into water (20 mL) and extracted with ethyl acetate (3×10 mL). The combined organic layers were washed with saturated brine (20 mL), dried over anhydrous sodium sulfate, filtered and evaporated under reduced pressure. The resulting residue was purified by reverse-phase chromatography to afford the desired product (R)-tert-butyl 3-(4-(6-(6-(2-(3-fluorophenyl)pyrrolidin-1-yl)imidazo[1,2-b]pyridazin-3-yl)pyridin-2-yl)piperazin-1-yl)azetidine-1-carboxylate (350 mg, 86% yield) as a yellow resin. MS (ESI) m/z: 599.8 [M+H]⁺.

Step 3. Synthesis of (R)-3-(6-(4-(azetidin-3-yl)piperazin-1-yl)pyridin-2-yl)-6-(2-(3-fluorophenyl)pyrrolidin-1-yl)imidazo[1,2-b]pyridazine

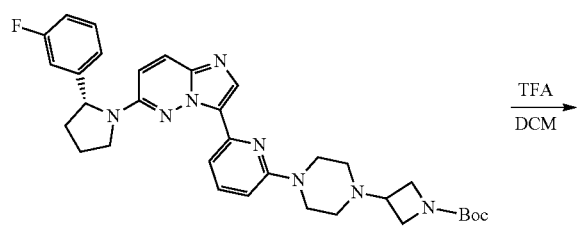

$\xrightarrow[\text{DCM}]{\text{TFA}}$

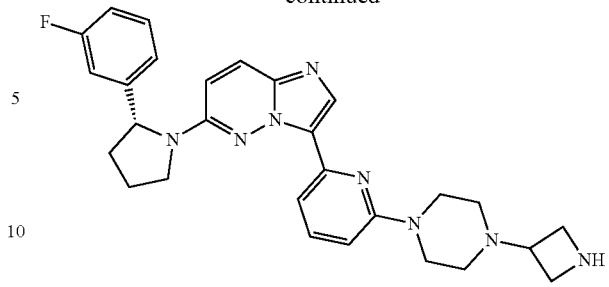

To a solution of (R)-tert-butyl 3-(4-(6-(6-(2-(3-fluorophenyl)pyrrolidin-1-yl)imidazo[1,2-b]pyridazin-3-yl)pyridin-2-yl)piperazin-1-yl)azetidine-1-carboxylate (350 mg, 0.59 mmol) in DCM (5 mL) was added TFA (2 mL). The reaction mixture was stirred at 25° C. for 5 h. After the starting material was totally consumed, the reaction was evaporated under reduced pressure to give crude (R)-3-(6-(4-(azetidin-3-yl)piperazin-1-yl)pyridin-2-yl)-6-(2-(3-fluorophenyl)pyrrolidin-1-yl)imidazo[1,2-b]pyridazine (500 mg, 100% yield) as TFA salt. This product was used directly in the next step without further purification. MS (ESI) m/z: 499.8 [M+H]⁺.

Step 4. Synthesis of 2-(2,6-dioxopiperidin-3-yl)-5-((3-(4-(6-(6-((R)-2-(3-fluorophenyl)pyrrolidin-1-yl)imidazo[1,2-b]pyridazin-3-yl)pyridin-2-yl)piperazin-1-yl)azetidin-1-yl)methyl)isoindoline-1,3-dione

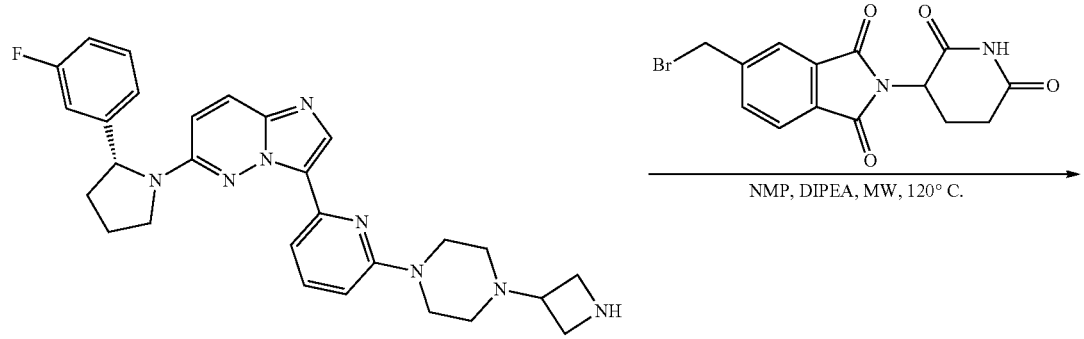

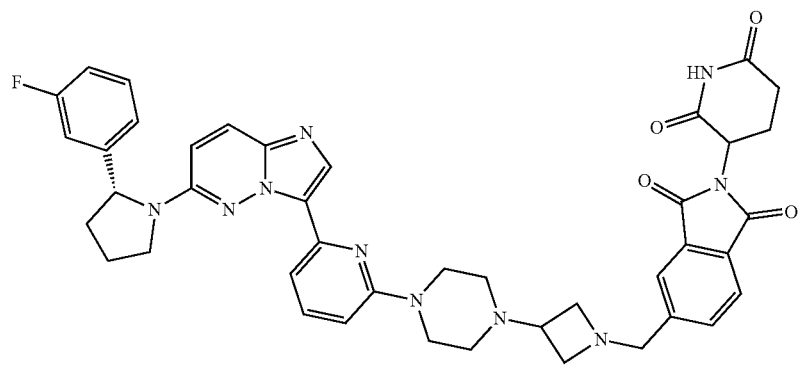

711

To a solution of crude (R)-3-(6-(4-(azetidin-3-yl)piperazin-1-yl)pyridin-2-yl)-6-(2-(3-fluorophenyl)pyrrolidin-1-yl)imidazo[1,2-b]pyridazine (50 mg, 0.06 mmol) in NMP (1 mL) was added 5-(bromomethyl)-2-(2,6-dioxopiperidin-3-yl)isoindoline-1,3-dione (35 mg, 0.1 mmol) and DIPEA (0.5 mL) at room temperature. The reaction mixture was heated to 120° C. under microwave for 1 h. After the reaction was cooled down to room temperature, the reaction solution was poured into water (10 mL) and extracted with ethyl acetate (3×10 mL). The combined organic layers were washed with saturated brine (20 mL), dried over anhydrous sodium sulfate, filtered and evaporated under reduced pressure. The residue was purified by prep-TLC (DCM/MeOH=15:1) to give 2-(2,6-dioxopiperidin-3-yl)-5-((3-(4-(6-(6-((R)-2-(3-fluorophenyl)pyrrolidin-1-yl)imidazo[1,2-b]pyridazin-3-yl)pyridin-2-yl)piperazin-1-yl)azetidin-1-yl)methyl)isoindoline-1,3-dione (13 mg, 28% yield) as a yellow solid. MS (ESI) m/z: 769.9 [M+H]$^+$.

Example 289: 3-(4-(3-(4-(6-(6-((R)-2-(3-Fluorophenyl)pyrrolidin-1-yl)imidazo[1,2-b]pyridazin-3-yl)pyridin-2-yl)piperazin-1-yl)prop-1-yn-1-yl)-3-methyl-2-oxo-2,3-dihydro-1H-benzo[d]imidazol-1-yl)piperidine-2,6-dione (TR-238)

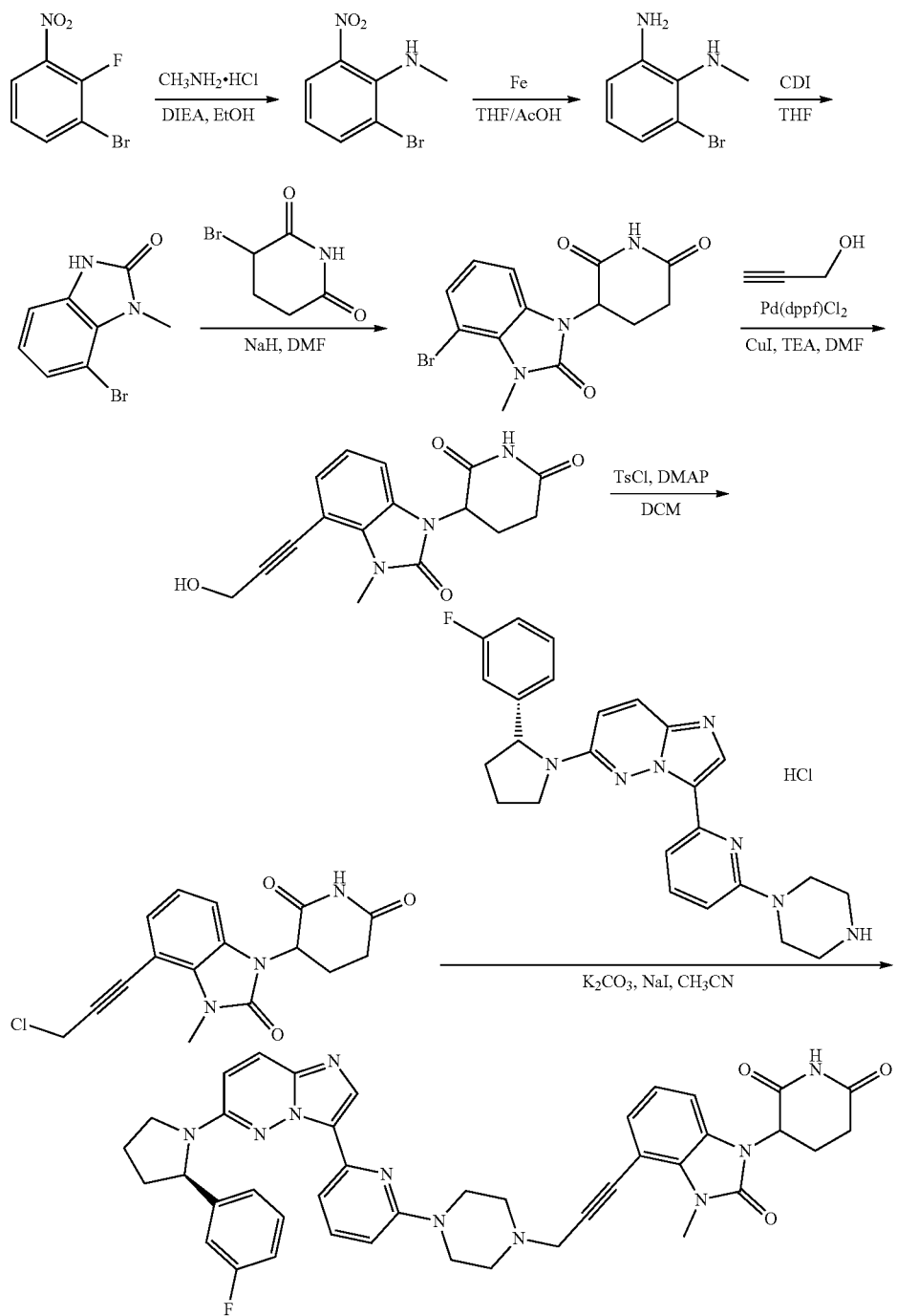

Step 1. Synthesis of 2-bromo-N-methyl-6-nitroaniline

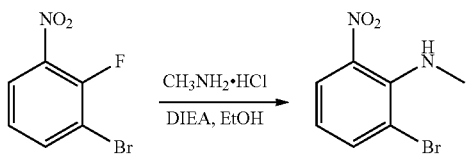

To a solution of 1-bromo-2-fluoro-3-nitrobenzene (15.5 g, 70.5 mmol) in EtOH (80 mL) was added DIEA (45 g, 353 mmol) and methanamine hydrochloride (14.3 g, 211.5 mmol). After the solution was stirred at 85° C. for 12 h, the reaction was cooled to room temperature, concentrated and diluted with water and ethyl acetate. The organic phase was separated, dried over anhydrous sodium sulfate, filtered and concentrated to give crude 2-bromo-N-methyl-6-nitroaniline (15 g, 92% yield) as a yellow solid which was used directly in the next step without further purification. MS (ESI) m/z: 231.1 [M+H]$^+$.

Step 2: Synthesis of 6-bromo-N-methylbenzene-1,2-diamine

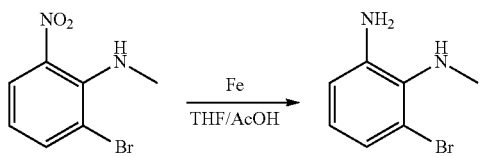

A mixture of 2-bromo-N-methyl-6-nitroaniline (14.0 g, 60.6 mmol) in THF (40 mL) and AcOH (80 mL) was stirred at 85° C. for 2 h in the presence of Fe (17 g, 303 mmol). The reaction mixture was filtered and the filtrate was concentrated. The residue was purified by silica gel chromatography (petroleum ether/EtOAc=10:1) to give 6-bromo-N1-methylbenzene-1,2-diamine (8.2 g, 68% yield). MS (ESI) m/z: 201.2 [M+H]$^+$.

Step 3. Synthesis of 7-bromo-1-methyl-1,3-dihydro-2H-benzo[d]imidazol-2-one

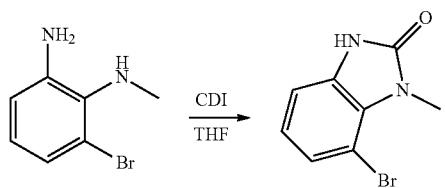

To a solution of 6-bromo-N-methylbenzene-1,2-diamine (8.9 g, 44.5 mmol) in THF (100 mL) was added N,N'-carbonyldiimidazole (29 g, 178.2 mmol) at room temperature under N$_2$. After the reaction mixture was stirred at room temperature overnight, the solvent was removed. The residue was dissolved in DCM/MeOH (10:1) and washed with water. The organic layer was dried over Na$_2$SO$_4$, filtered and concentrated. The residue was purified by silica gel chromatography (DCM/MeOH=60:1) to give 7-bromo-1-methyl-1,3-dihydro-2H-benzo[d]imidazol-2-one (4.4 g, 44% yield) as a white solid. MS (ESI) m z: 227.2 [M+H]$^+$.

Step 4. Synthesis of 3-(4-bromo-3-methyl-2-oxo-2,3-dihydro-1H-benzo[d]imidazol-1-yl)piperidine-2,6-dione

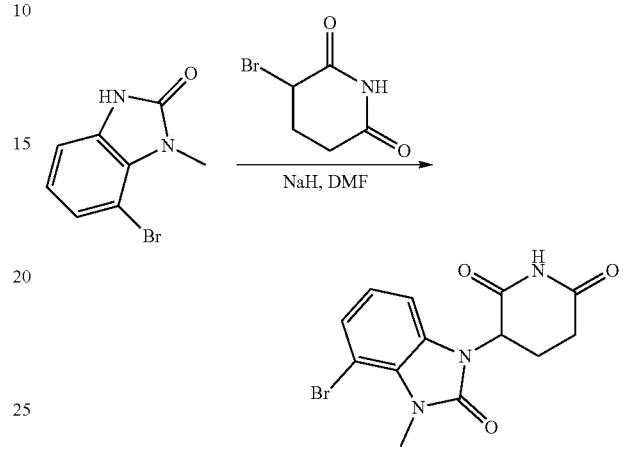

To a solution of 7-bromo-1-methyl-1,3-dihydro-2H-benzo[d]imidazol-2-one (2.5 g, 11.0 mmol) in DMF (9 mL) was added NaH (529 mg, 60% w/w dispersed into mineral oil, 13.21 mmol) at 0° C. under nitrogen atmosphere. The reaction mixture was stirred at 0° C. for 20 min, before a solution of 3-bromopiperidine-2,6-dione (1.47 g, 7.71 mmol) in DMF (6 mL) was added dropwise at 0° C. The resulting mixture was stirred at room temperature overnight, before the reaction was quenched with water and extracted with ethyl acetate (3×). The organic layers were combined, dried, filtered, and concentrated. The resulting residue was purified by silica gel chromatography (petroleum ether/EtOAc=2:1 to DCM/MeOH=60:1) to give 3-(4-bromo-3-methyl-2-oxo-2,3-dihydro-1H-benzo[d]imidazol-1-yl)piperidine-2,6-dione as a white solid (247 mg, 7% yield). MS (ESI) m/z: 338 [M+H]$^+$.

Step 5. Synthesis of 3-(4-(3-hydroxyprop-1-yn-1-yl)-3-methyl-2-oxo-2,3-dihydro-1H-benzo[d]imidazol-1-yl)piperidine-2,6-dione

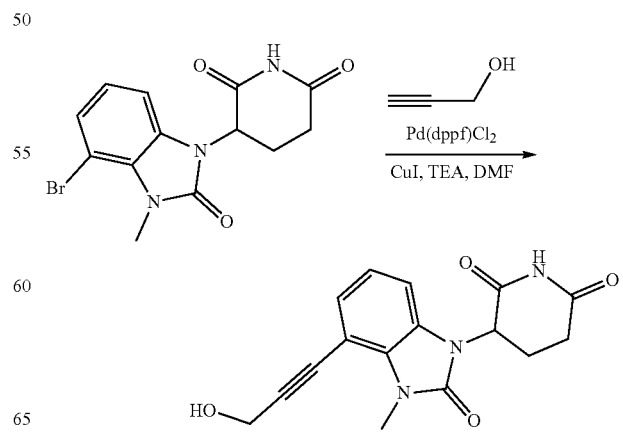

715

To a solution of 3-(4-bromo-3-methyl-2-oxo-2,3-dihydro-1H-benzo[d]imidazol-1-yl)piperidine-2,6-dione (130 mg, 0.39 mmol) in DMF (3.5 mL) were added prop-2-yn-1-ol (43 mg, 0.77 mmol), CuI (15 mg, 0.079 mmol), Pd(dppf)Cl$_2$ (29 mg, 0.04 mmol) and TEA (394 mg, 3.9 mmol). The mixture was stirred at 80° C. overnight, before the reaction was quenched with water and extracted with ethyl acetate (3×). The organic layers were combined, dried, filtered, and concentrated. The resulting residue was purified by reverse phase chromatography to give 3-(4-(3-hydroxyprop-1-yn-1-yl)-3-methyl-2-oxo-2,3-dihydro-1H-benzo[d]imidazol-1-yl)piperidine-2,6-dione (94 mg, 78% yield) as a white solid. MS (ESI) m/z: 314.4 [M+H]$^+$.

Step 6. Synthesis of 3-(4-(3-chloroprop-1-yn-1-yl)-3-methyl-2-oxo-2,3-dihydro-1H-benzo[d]imidazol-1-yl)piperidine-2,6-dione

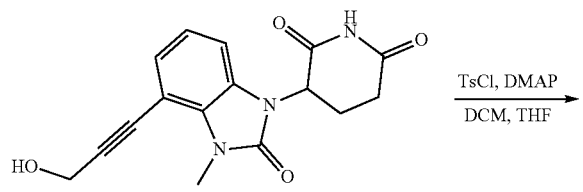

716
-continued

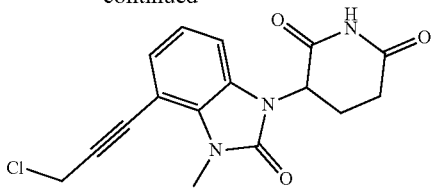

To a solution of 3-(4-(3-hydroxyprop-1-yn-1-yl)-3-methyl-2-oxo-2,3-dihydro-1H-benzo[d]imidazol-1-yl)piperidine-2,6-dione (30 mg, 0.096 mmol) in dry CH$_2$Cl$_2$ (2.5 mL) and anhydrous THF (1 mL) were added TsCl (27.6 mg, 0.14 mmol) and DMAP (35 mg, 0.29 mmol). Then the reaction mixture was stirred at room temperature for 12 h, before the reaction was quenched with water and extracted with ethyl acetate (3×). The organic layers were combined, dried, filtered, and concentrated. The resulting residue was purified by prep-TLC (DCM:/MeOH=25:1) to give 3-(4-(3-chloroprop-1-yn-1-yl)-3-methyl-2-oxo-2,3-dihydro-1H-benzo[d]imidazol-1-yl)piperidine-2,6-dione (12 mg, 38% yield) as a white solid. MS (ESI) m/z: 332.4 [M+H]$^+$.

Step 7. Synthesis of 3-(4-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)-3-methyl-2-oxo-2,3-dihydro-1H-benzo[d]imidazol-1-yl)piperidine-2,6-dione

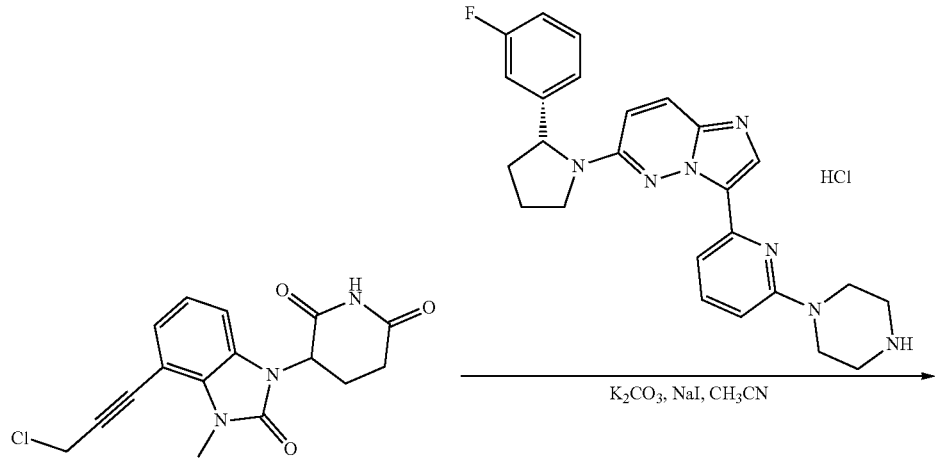

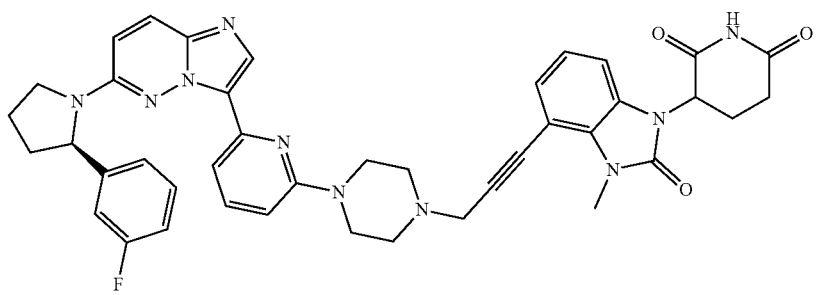

A mixture of 3-(4-(3-chloroprop-1-yn-1-yl)-3-methyl-2-oxo-2,3-dihydro-1H-benzo[d]imidazol-1-yl)piperidine-2,6-dione (12 mg, 0.036 mmol), K₂CO₃ (15 mg, 0.108 mmol), NaI (8 mg, 0.054 mmol) and (R)-6-(2-(3-fluorophenyl)pyrrolidin-1-yl)-3-(6-(piperazin-1-yl)pyridin-2-yl)imidazo[1,2-b]pyridazine hydrochloride (21 mg, 0.044 mmol) in CH₃CN (0.8 ml) was stirred at 90° C. for 4 h, before the reaction was quenched with water and extracted with ethyl acetate (3×). The organic layers were combined, dried, filtered, and concentrated. The resulting residue was purified by prep-TLC (DCM/MeOH=12:1) to give 3-(4-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)-3-methyl-2-oxo-2,3-dihydro-1H-benzo[d]imidazol-1-yl)piperidine-2,6-dione (8.6 mg, 32% yield) as a white solid. MS (ESI) m/z: 740.0 [M+H]⁺.

Example 290: 3-(4-(4-(4-(6-(6-((R)-2-(3-Fluorophenyl)pyrrolidin-1-yl)imidazo[1,2-b]pyridazin-3-yl)pyridin-2-yl)piperazin-1-yl)but-1-yn-1-yl)-3-methyl-2-oxo-2,3-dihydro-1H-benzo[d]imidazol-1-yl)piperidine-2,6-dione (TR-239)

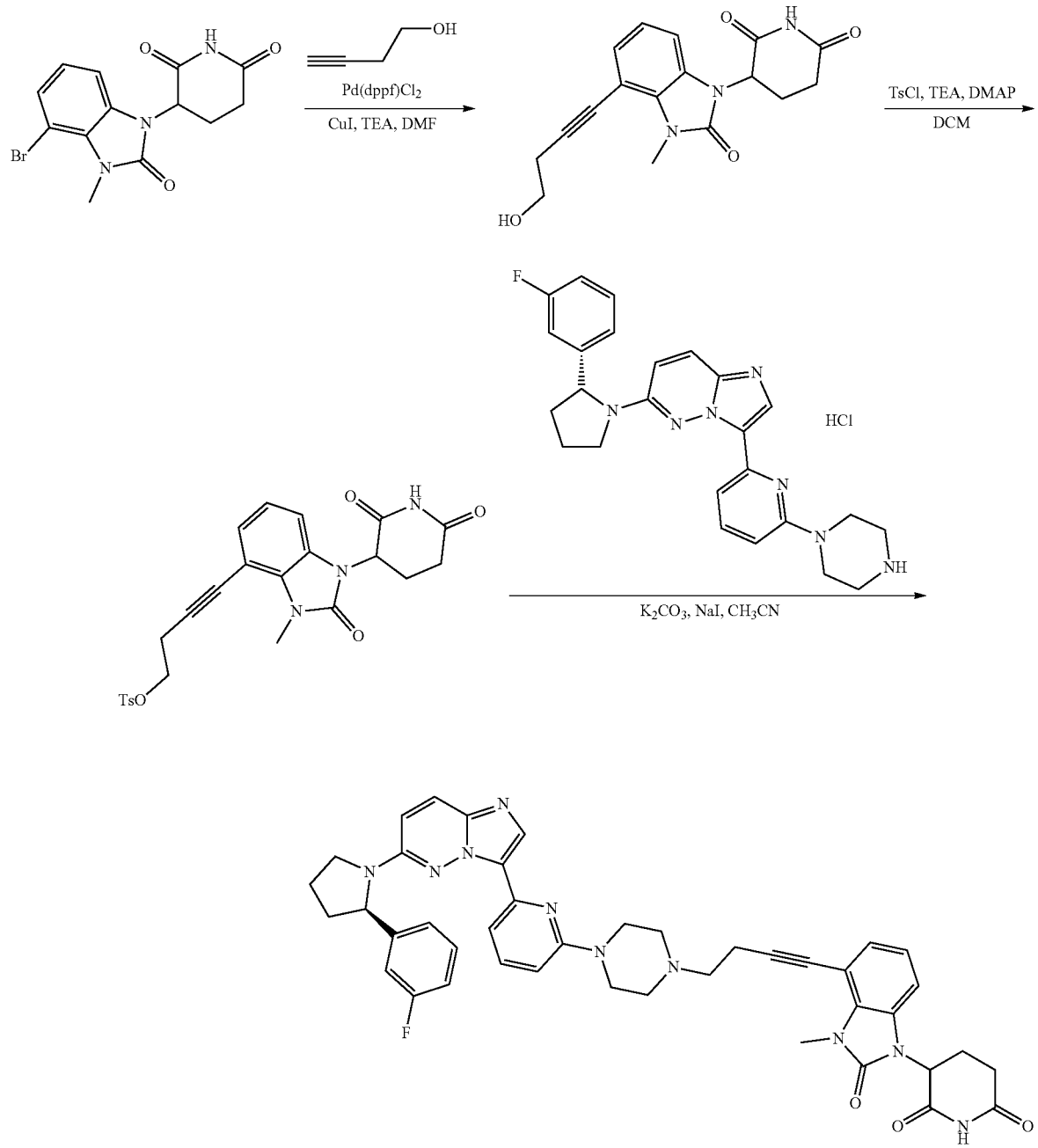

TR-239 was synthesized according to the standard procedure for preparing TR-238 (5.8 mg, 16% yield). MS (ESI) m/z: 754.0 [M+H]⁺.

Example 291: 3-(4-(3-(4-(6-(6-((R)-2-(3-Fluorophenyl)pyrrolidin-1-yl)imidazo[1,2-b]pyridazin-3-yl)pyridin-2-yl)piperazin-1-yl)propyl)-3-methyl-2-oxo-2,3-dihydro-1H-benzo[d]imidazol-1-yl)piperidine-2,6-dione (TR-240)

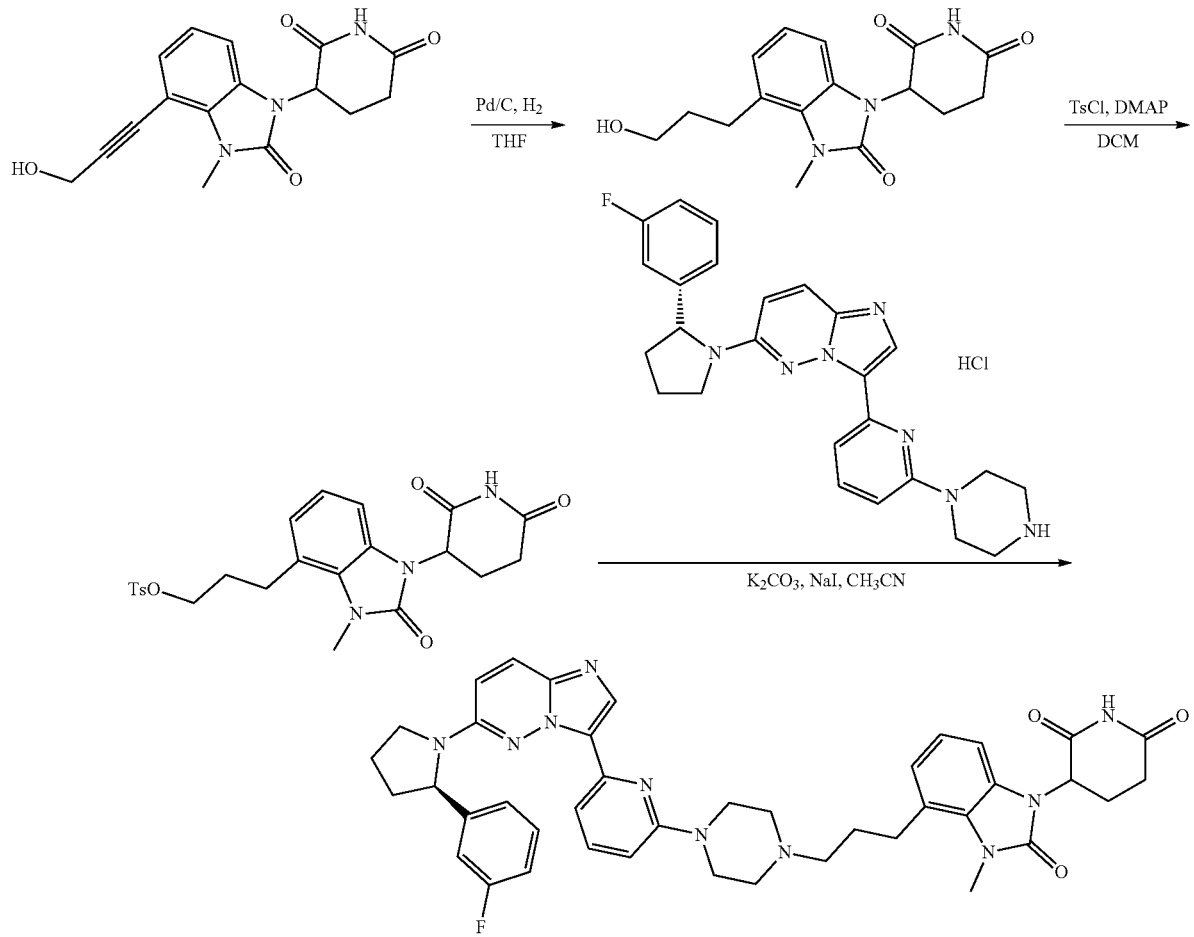

Step 1. Synthesis of 3-(4-(3-hydroxypropyl)-3-methyl-2-oxo-2,3-dihydro-1H-benzo[d]imidazol-1-yl)piperidine-2,6-dione

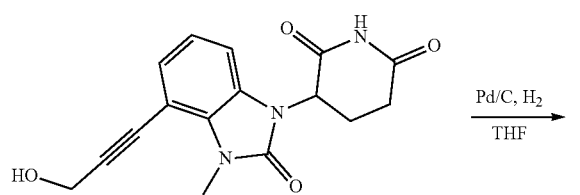

A solution of 3-(4-(3-hydroxyprop-1-yn-1-yl)-3-methyl-2-oxo-2,3-dihydro-1H-benzo[d]imidazol-1-yl)piperidine-2,6-dione (25 mg, 0.08 mmol) in THF (3 mL) was stirred in the presence of 10% Pd/C (15 mg) under hydrogen (1 atm) for 4 h, before the reaction mixture was filtered. The filtrate was concentrated to give crude 3-(4-(3-hydroxypropyl)-3-methyl-2-oxo-2,3-dihydro-1H-benzo[d]imidazol-1-yl)piperidine-2,6-dione (30 mg, 99% yield) which was used directly in the next step without further purification. MS (ESI) m/z: 318.4 [M+H]+.

Step 2. Synthesis of 3-(1-(2,6-dioxopiperidin-3-yl)-3-methyl-2-oxo-2,3-dihydro-1H-benzo[d]imidazol-4-yl)propyl 4-methylbenzenesulfonate

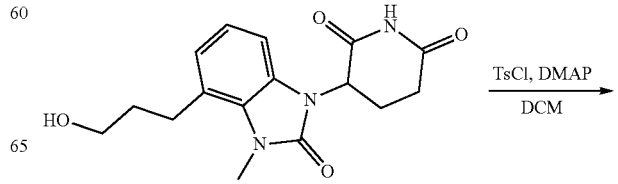

721

-continued

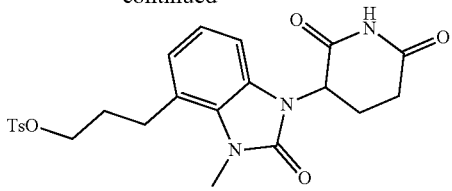

To a solution of 3-(4-(3-hydroxypropyl)-3-methyl-2-oxo-2,3-dihydro-1H-benzo[d]imidazol-1-yl)piperidine-2,6-dione (30 mg, 0.095 mmol) in dry CH$_2$Cl$_2$ (2 mL) and anhydrous THF (1 mL) were added TsCl (36 mg, 0.19 mmol) and DMAP (46 mg, 0.38 mmol). The reaction mixture was stirred at room temperature for 12 h, before the reaction was concentrated. The resulting residue was purified by prep-TLC (DCM/MeOH=25:1) to give 3-(1-(2,6-dioxopiperidin-3-yl)-3-methyl-2-oxo-2,3-dihydro-1H-benzo[d]imidazol-4-yl)propyl 4-methylbenzenesulfonate (6 mg, 13% yield) as a white solid. MS (ESI) m z: 472.5 [M+H]$^+$.

Step 3. Synthesis of 3-(4-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-3-methyl-2-oxo-2,3-dihydro-1H-benzo[d]imidazol-1-yl)piperidine-2,6-dione

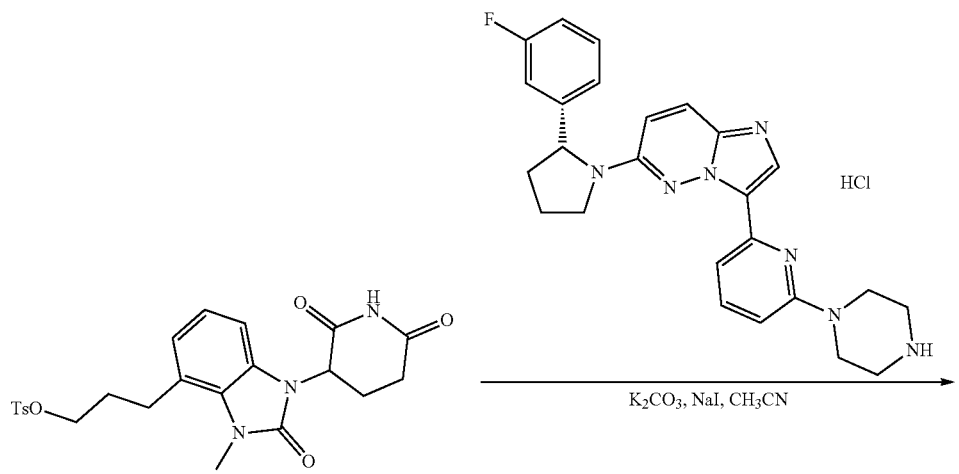

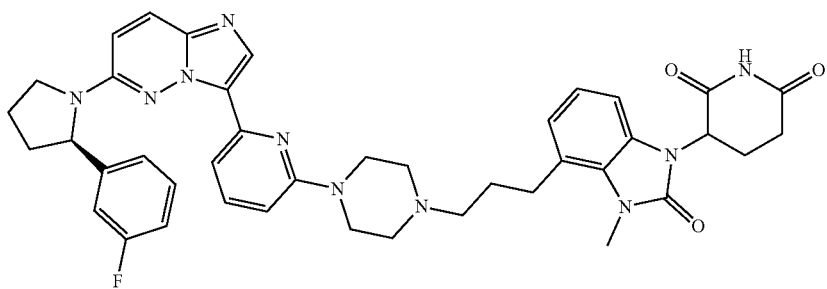

723

A mixture of 3-(1-(2,6-dioxopiperidin-3-yl)-3-methyl-2-oxo-2,3-dihydro-1H-benzo[d]imidazol-4-yl)propyl 4-methylbenzenesulfonate (6 mg, 0.013 mmol), K₂CO₃ (5.3 mg, 0.038 mmol), NaI (3 mg, 0.02 mmol) and (R)-6-(2-(3-fluorophenyl)pyrrolidin-1-yl)-3-(6-(piperazin-1-yl)pyridin-2-yl)imidazo[1,2-b]pyridazine hydrochloride (7.5 mg, 0.016 mmol) in CH₃CN (0.8 mL) was stirred at 90° C. for 4 h, before the reaction was quenched with water and extracted with ethyl acetate (3×). The organic layers were combined, dried, filtered, and concentrated. The resulting residue was purified by prep-TLC (DCM/MeOH=10:1) to give 3-(4-(3-

724

(4-(6-(6-((R)-2-(3-fluorophenyl)pyrrolidin-1-yl)imidazo[1,2-b]pyridazin-3-yl)pyridin-2-yl)piperazin-1-yl)propyl)-3-methyl-2-oxo-2,3-dihydro-1H-benzo[d]imidazol-1-yl)piperidine-2,6-dione e (4.0 mg, 42% yield) as a white solid. MS (ESI) m/z: 744.0 [M+H]⁺.

Example 292: 3-(4-(4-(4-(6-(6-((R)-2-(3-Fluorophenyl)pyrrolidin-1-yl)imidazo[1,2-b]pyridazin-3-yl)pyridin-2-yl)piperazin-1-yl)butyl)-3-methyl-2-oxo-2,3-dihydro-1H-benzo[d]imidazol-1-yl)piperidine-2,6-dione (TR-241)

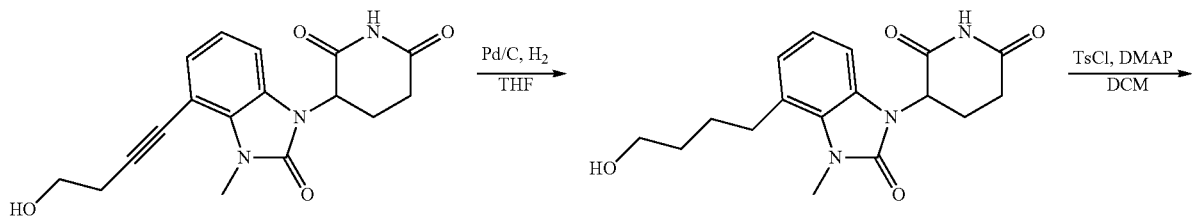

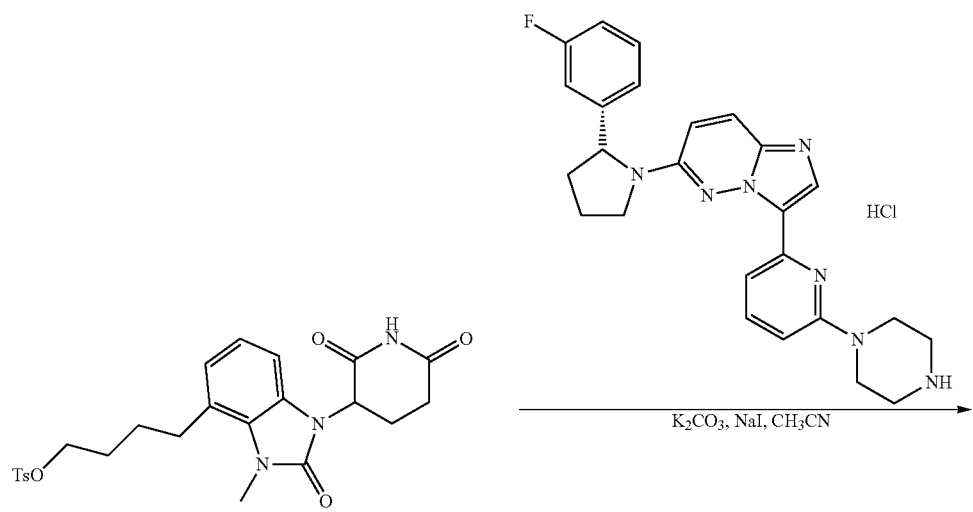

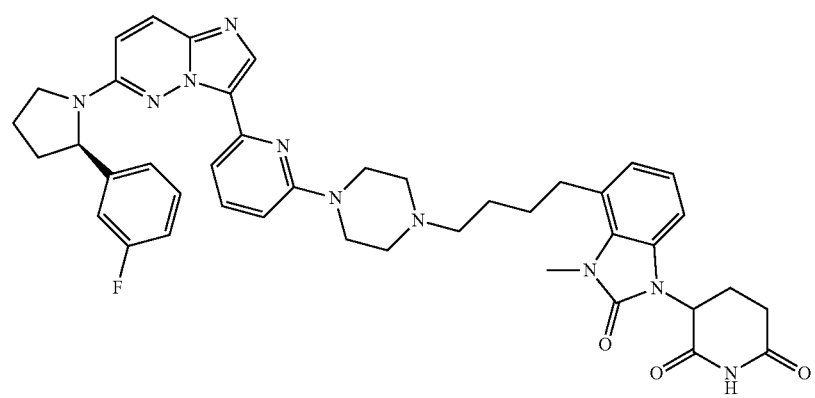 [SMILES: Cn1c(=O)n(C2CCC(=O)NC2=O)c2cccc(CCCCN3CCN(c4cccc(-c5cnc6ccc(N7CCC[C@@H]7c7cccc(F)c7)nn56)n4)CC3)c21]

TR-241 was synthesized according to the standard procedure for preparing TR-240 (12 mg, 45% yield). MS (ESI) m/z: 758.1 [M+H]⁺.

Example 293. 3-(3-(2-(4-(6-(6-((R)-2-(3-Fluorophenyl)pyrrolidin-1-yl)imidazo[1,2-a]pyridin-3-yl)pyridin-2-yl)piperazin-1-yl)ethyl)-2-oxo-2,3-dihydro-1H-benzo[d]imidazol-1-yl)piperidine-2,6-dione (TR-242)

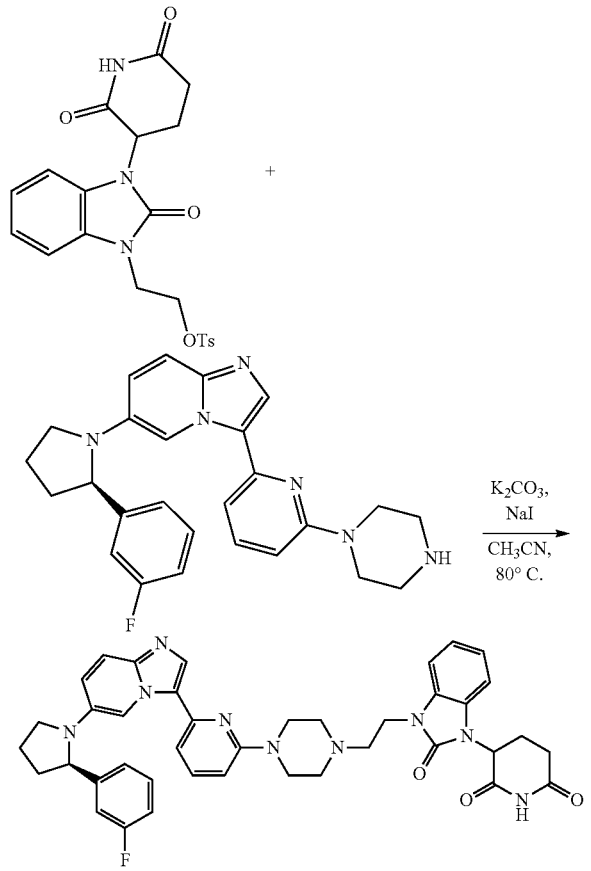

To a solution of 2-(3-(2,6-dioxopiperidin-3-yl)-2-oxo-2,3-dihydro-1H-benzo[d]imidazol-1-yl)ethyl 4-methylbenzenesulfonate (44.3 mg, 0.10 mmol) and (R)-6-(2-(3-fluorophenyl)pyrrolidin-1-yl)-3-(6-(piperazin-1-yl)pyridin-2-yl)imidazo[1,2-a]pyridine (44.2 mg, 0.10 mmol) in CH₃CN (1 mL) were added sodium iodide (22.5 mg, 0.15 mmol) and K₂CO₃ (41.4 mg, 0.3 mmol) at room temperature. The reaction mixture was stirred at 90° C. for 12 h. After cooled down to room temperature, the reaction was quenched with water and extracted with ethyl acetate (3×10 mL). The combined organic layers were washed with saturated brine (10 mL), dried over anhydrous sodium sulfate, filtered and evaporated under reduced pressure. The residue was purified by reverse-phase chromatography to afford 3-(3-(2-(4-(6-(6-((R)-2-(3-fluorophenyl)pyrrolidin-1-yl)imidazo[1,2-a]pyridin-3-yl)pyridin-2-yl)piperazin-1-yl)ethyl)-2-oxo-2,3-dihydro-1H-benzo[d]imidazol-1-yl)piperidine-2,6-dione (35 mg, 49% yield) as a white solid. MS (ESI) m z: 714.9 [M+H]⁺.

Example 294: 3-(3-(3-(4-(6-(6-((R)-2-(3-Fluorophenyl)pyrrolidin-1-yl)imidazo[1,2-a]pyridin-3-yl)pyridin-2-yl)piperazin-1-yl)propyl)-2-oxo-2,3-dihydro-1H-benzo[d]imidazol-1-yl)piperidine-2,6-dione (TR-243)

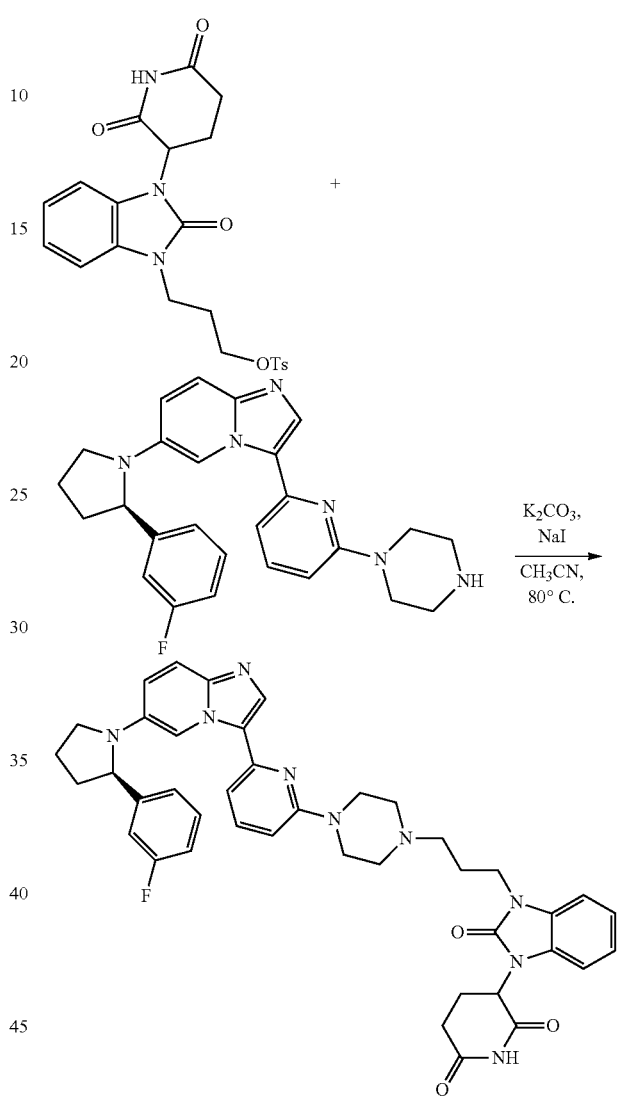

To a solution of 3-(3-(2,6-dioxopiperidin-3-yl)-2-oxo-2,3-dihydro-1H-benzo[d]imidazol-1-yl)propyl 4-methylbenzenesulfonate (45.3 mg, 0.10 mmol) and (R)-6-(2-(3-fluorophenyl)pyrrolidin-1-yl)-3-(6-(piperazin-1-yl)pyridin-2-yl)imidazo[1,2-a]pyridine (44.2 mg, 0.10 mmol) in CH₃CN (1 mL) were added sodium iodide (22.5 mg, 0.15 mmol) and K₂CO₃ (41.4 mg, 0.3 mmol) at room temperature. The reaction mixture was stirred at 90° C. for 12 h. After cooled down to room temperature, the reaction was quenched with water and extracted with ethyl acetate (3×10 mL). The combined organic layers were washed with saturated brine (10 mL), dried over anhydrous sodium sulfate, filtered and evaporated under reduced pressure. The residue was purified by reverse-phase chromatography to afford 3-(3-(3-(4-(6-(6-((R)-2-(3-fluorophenyl)pyrrolidin-1-yl)imidazo[1,2-a]pyridin-3-yl)pyridin-2-yl)piperazin-1-yl)propyl)-2-oxo-2,3-dihydro-1H-benzo[d]imidazol-1-yl)piperidine-2,6-dione (22 mg, 30% yield) as a white solid. MS (ESI) m z: 729.0 [M+H]⁺.

Example 295: 3-(4-(2-(4-(6-(6-((R)-2-(3-Fluorophe-
nyl)pyrrolidin-1-yl)imidazo[1,2-b]pyridazin-3-yl)
pyridin-2-yl)piperazin-1-yl)ethoxy)-3-methyl-2-oxo-
2,3-dihydro-1H-benzo[d]imidazol-1-yl)piperidine-2,
6-dione (TR-244)
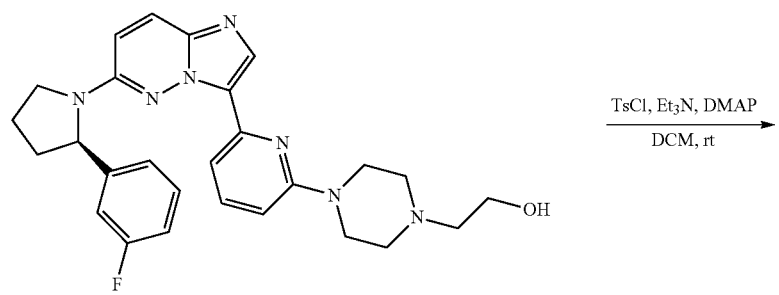
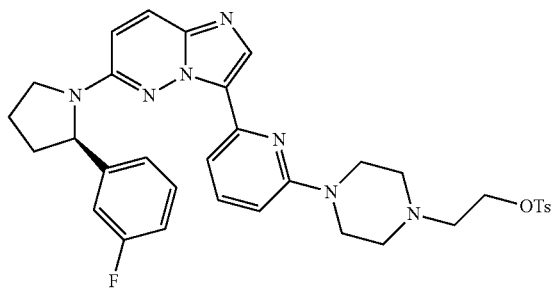
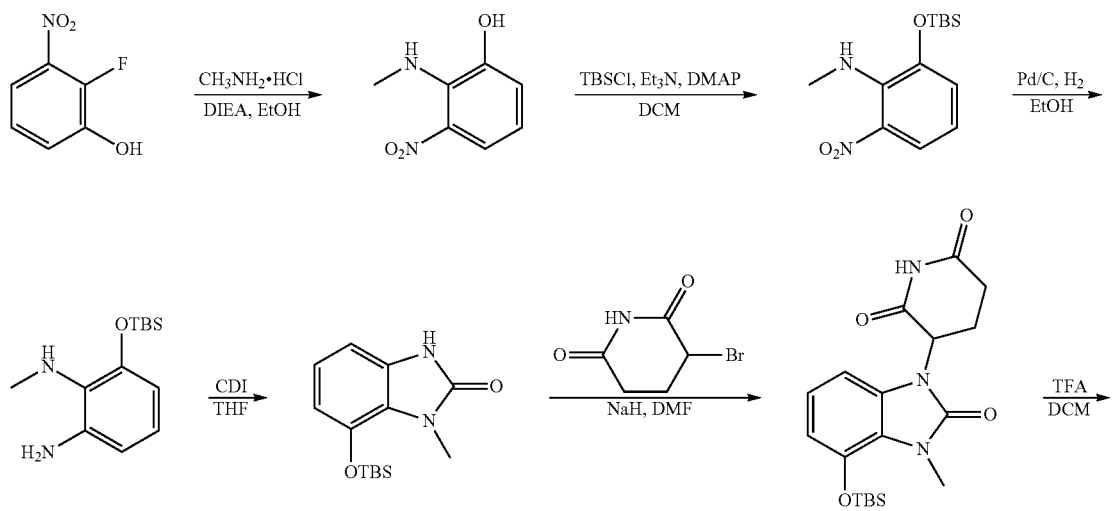

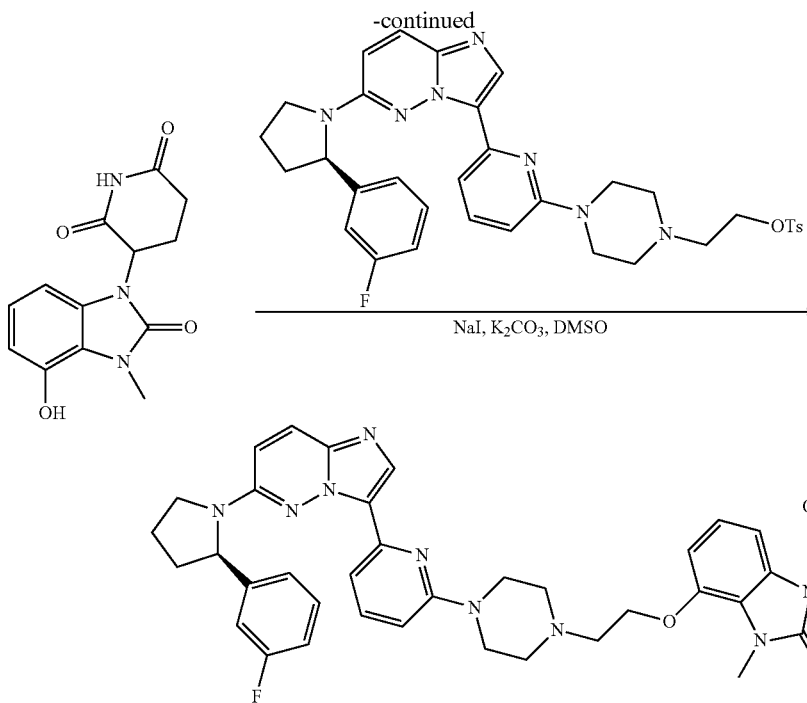

Step 1. Synthesis of (R)-2-(4-(6-(6-(2-(3-fluorophenyl)pyrrolidin-1-yl)imidazo[1,2-b]pyridazin-3-yl)pyridin-2-yl)piperazin-1-yl)ethan-1-ol

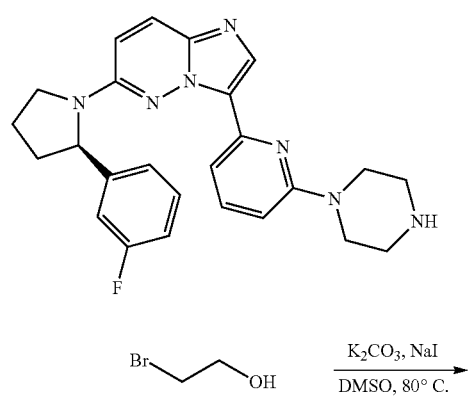

To a solution of (R)-6-(2-(3-fluorophenyl)pyrrolidin-1-yl)-3-(6-(piperazin-1-yl)pyridin-2-yl)imidazo[1,2-b]pyridazine (200 mg, 0.42 mmol) and 2-bromoethanol (157.45 mg, 1.26 mmol) in DMSO (3 mL) were added $K_2CO_3$ (173.89 mg, 1.26 mmol) and NaI (63.0 mg, 0.42 mmol) at room temperature. The reaction mixture was stirred at 80° C. overnight. After cooled down to room temperature, the reaction was quenched with water (15 mL) and extracted with ethyl acetate (3×10 mL).

The combined organic layers were washed with saturated brine (10 mL), dried over anhydrous sodium sulfate, filtered and evaporated under reduced pressure. The residue was purified by silica gel chromatography to afford (R)-2-(4-(6-(6-(2-(3-fluorophenyl)pyrrolidin-1-yl)imidazo[1,2-b]pyridazin-3-yl)pyridin-2-yl)piperazin-1-yl)ethan-1-ol (130 mg, 64% yield) as a brown oil. MS (ESI) m/z: 488.7 $[M+H]^+$.

Step 2. Synthesis of (R)-2-(4-(6-(6-(2-(3-fluorophenyl)pyrrolidin-1-yl)imidazo[1,2-b]pyridazin-3-yl)pyridin-2-yl)piperazin-1-yl)ethyl 4-methylbenzenesulfonate

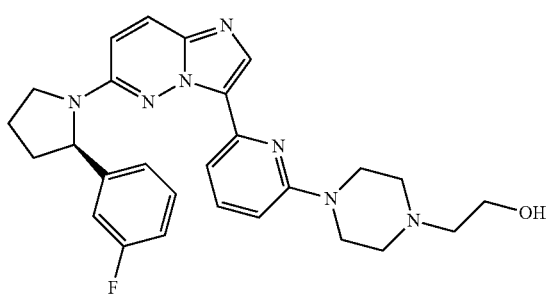

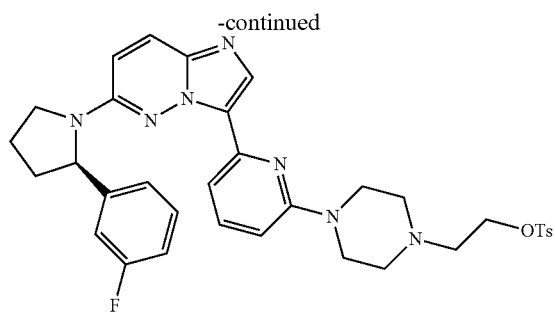

To a solution of (R)-2-(4-(6-(6-(2-(3-fluorophenyl)pyrrolidin-1-yl)imidazo[1,2-b]pyridazin-3-yl)pyridin-2-yl)piperazin-1-yl)ethan-1-ol (130 mg, 0.27 mmol) in dry CH$_2$Cl$_2$ (5 mL) were added p-toluensulfonyl chloride (80.46 mg, 0.53 mmol), 4-dimethylaminopyridine (12 mg, 0.1 mmol) and Et$_3$N (136.35 mg, 1.35 mmol) at 0° C. Then the reaction mixture was stirred at room temperature for 24 h. The reaction was quenched with water (5 mL) and extracted with CH$_2$Cl$_2$ (3×5 mL). The combined organic layers were washed with brine and dried over MgSO$_4$, filtered and concentrated under reduced pressure.

The residue was purified by prep-TLC to give (R)-2-(4-(6-(6-(2-(3-fluorophenyl)pyrrolidin-1-yl)imidazo[1,2-b]pyridazin-3-yl)pyridin-2-yl)piperazin-1-yl)ethyl 4-methylbenzenesulfonate (80 mg, 46% yield) as a white solid. MS (ESI) m/z: 642.3 [M+H]$^+$.

Step 3. Synthesis of 2-(methylamino)-3-nitrophenol

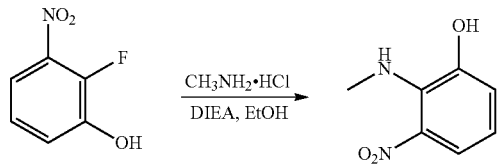

To a solution of 2-fluoro-3-nitrophenol (5 g, 31.85 mmol) in EtOH (20 mL) were added DIEA (26 mL, 159.25 mmol) and methanamine hydrochloride (6.45 g, 95.55 mmol). Then the reaction mixture was stirred at 90° C. for 12 h. After cooled down to room temperature, the reaction was quenched with water (30 mL) and extracted with ethyl acetate (3×50 mL). The combined organic layers were washed with brine, dried over MgSO$_4$, filtered and concentrated under reduced pressure. The resulting crude product was triturated with petroleum ether/EtOAc (10:1, 20 mL) to give 2-(methylamino)-3-nitrophenol (3.5 g, 65% yield) as a yellow solid. MS (ESI) m/z: 169.1 [M+H]$^+$.

Step 4. Synthesis of 2-((tert-butyldimethylsilyl)oxy)-N-methyl-6-nitroaniline

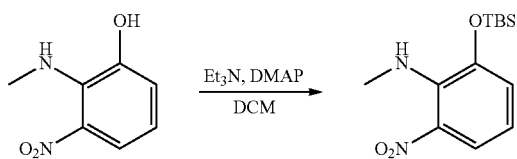

To a solution of 2-(methylamino)-3-nitrophenol (3.6 g, 21.43 mmol) and DMAP (200 mg, 1.6 mmol) in DCM (30 mL) were added triethylamine (21.6 g, 214.3 mmol) and tert-butyldimethylsilyl chloride (6.4 g, 42.86 mmol). The reaction mixture was stirred at room temperature for 14 h, before the reaction was quenched with water (15 mL) and extracted with DCM (3×30 mL). The combined organic layers were washed with brine, dried over MgSO$_4$, filtered and concentrated under reduced pressure. The resulting residue was triturated with petroleum ether/EtOAc (10:1, 22 ML) to give 2-((tert-butyldimethylsilyl)oxy)-N-methyl-6-nitroaniline (3.4 g, 56% yield) as a yellow solid. MS (ESI) m/z: 283.9 [M+H]$^+$.

Step 5. Synthesis of 6-((tert-butyldimethylsilyl)oxy)-N1-methylbenzene-1,2-diamine

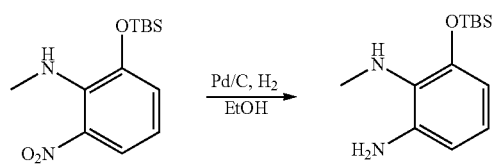

To a solution of 2-((tert-butyldimethylsilyl)oxy)-N-methyl-6-nitroaniline (3.4 g, 12.06 mmol) in EtOH (30 mL) was added 10% Pd/C (0.5 g). Then the mixture was stirred under hydrogen atmosphere (1 atm) overnight. After the catalyst was filtered through celite, the filtrate was evaporated to dryness to give crude 6-((tert-butyldimethylsilyl)oxy)-N1-methylbenzene-1,2-diamine (3.0 g, 99% yield). This product was used in the next step directly without further purification. MS (ESI) m/z: 254.0 [M+H]$^+$.

Step 6. Synthesis of 7-((tert-butyldimethylsilyl)oxy)-1-methyl-1,3-dihydro-2H-benzo[d]imidazol-2-one

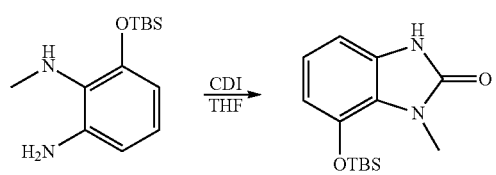

To a solution of 6-((tert-butyldimethylsilyl)oxy)-N$^1$-methylbenzene-1,2-diamine (3.0 g, 11.91 mmol) in THF (30 mL) was added N,N'-carbonyldiimidazole (5.79 g, 35.73 mmol) at room temperature under N$_2$. The reaction mixture was stirred at room temperature for 4 h, before the solvent was removed under reduced pressure. The residue was recrystallized with methanol and n-hexane to give 7-((tert-butyldimethylsilyl)oxy)-1-methyl-1,3-dihydro-2H-benzo[d]imidazol-2-one (2.8 g, 84% yield) as a white solid. MS (ESI) m/z: 279.6 [M+H]$^+$.

Step 7. Synthesis of 3-(4-((tert-butyldimethylsilyl)oxy)-3-methyl-2-oxo-2,3-dihydro-1H-benzo[d]imidazol-1-yl)piperidine-2,6-dione

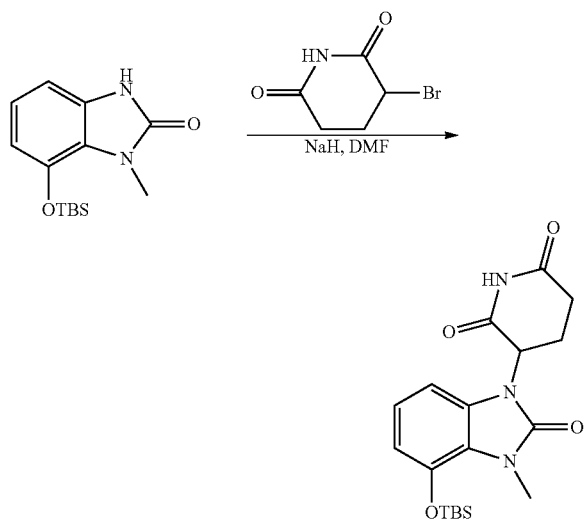

To a stirred solution of 7-((tert-butyldimethylsilyl)oxy)-1-methyl-1,3-dihydro-2H-benzo[d]imidazol-2-one (600 mg, 2.16 mmol) in DMF (5 mL) was added NaH (104 mg, 60% w/w dispersed into mineral oil, 2.60 mmol) at 0° C. under nitrogen atmosphere. After the reaction mixture was stirred at 0° C. for 20 min, a solution of 3-bromopiperidine-2,6-dione (291.84 mg, 1.52 mmol) in DMF (3 mL) was added dropwise at 0° C. The resulting mixture was stirred at room temperature for additional 3 h, before the reaction was quenched with AcOH (0.5 mL) and concentrated under reduced pressure to give crude 3-(4-((tert-butyldimethylsilyl)oxy)-3-methyl-2-oxo-2,3-dihydro-1H-benzo[d]imidazol-1-yl)piperidine-2,6-dione. This product was used in the next step directly without further purification.

Step 8. Synthesis of 3-(4-hydroxy-3-methyl-2-oxo-2,3-dihydro-1H-benzo[d]imidazol-1-yl)piperidine-2,6-dione

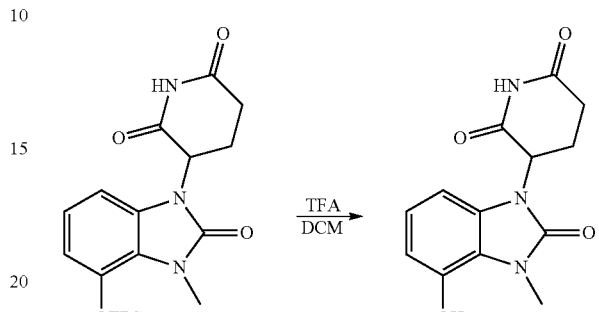

To a stirred solution of 3-(4-((tert-butyldimethylsilyl)oxy)-3-methyl-2-oxo-2,3-dihydro-1H-benzo[d]imidazol-1-yl)piperidine-2,6-dione (crude) in DCM (10 mL) was added TFA (2 mL). The reaction mixture was stirred at rt for 1 h, before the mixture was concentrated. The residue was purified by silica gel chromatography to give 3-(4-hydroxy-3-methyl-2-oxo-2,3-dihydro-1H-benzo[d]imidazol-1-yl)piperidine-2,6-dione (70 mg, 12% yield over two steps). MS (ESI) m/z: 276.3 [M+H]+.

Step 9. Synthesis of 3-(4-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)-3-methyl-2-oxo-2,3-dihydro-1H-benzo[d]imidazol-1-yl)piperidine-2,6-dione

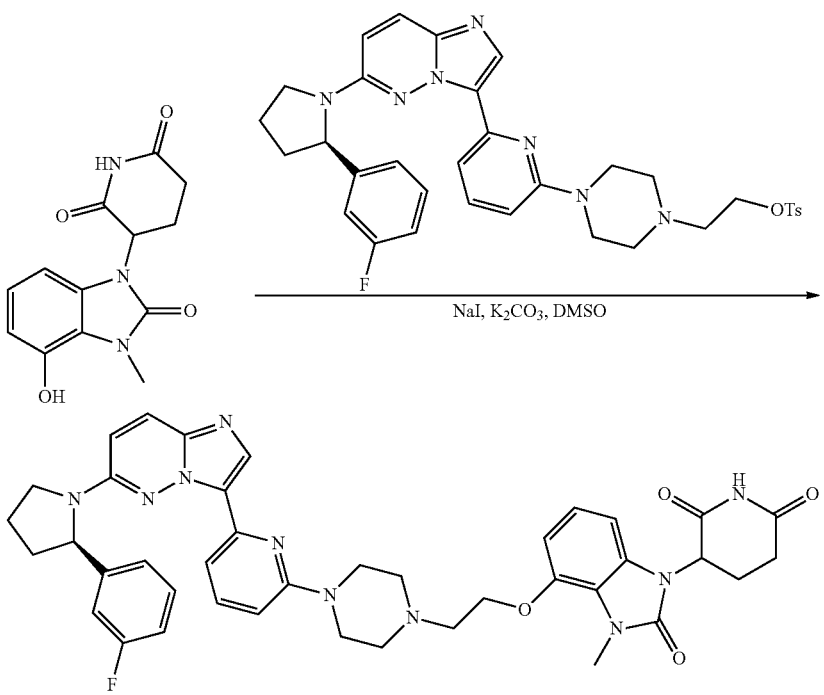

To a solution of 3-(4-hydroxy-3-methyl-2-oxo-2,3-dihydro-1H-benzo[d]imidazol-1-yl)piperidine-2,6-dione (3.05 mg, 0.012 mmol) and (R)-2-(4-(6-(6-(2-(3-fluorophenyl)pyrrolidin-1-yl)imidazo[1,2-b]pyridazin-3-yl)pyridin-2-yl)piperazin-1-yl)ethyl 4-methylbenzenesulfonate (5.0 mg, 0.01 mmol) in DMSO (0.5 mL) were added K₂CO₃ (5.52 mg, 0.04 mmol) and NaI (2.25 mg, 0.015 mmol) at room temperature. The reaction mixture was stirred at 70° C. for 2 h. After the reaction was cooled down to room temperature, the reaction was quenched with water (10 mL) and extracted with ethyl acetate (3×10 mL). The combined organic layers were washed with saturated brine (10 mL), dried over anhydrous sodium sulfate, filtered and evaporated under reduced pressure. The resulting residue was purified by prep-HPLC to afford 3-(4-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)-3-methyl-2-oxo-2,3-dihydro-1H-benzo[d]imidazol-1-yl)piperidine-2,6-dione (1.2 mg, 16% yield) as a white solid. MS (ESI) m/z: 745.9 [M+H]⁺.

Example 296. 3-(4-(3-(4-(6-(6-((R)-2-(3-Fluorophenyl)pyrrolidin-1-yl)imidazo[1,2-b]pyridazin-3-yl)pyridin-2-yl)piperazin-1-yl)propoxy)-3-methyl-2-oxo-2,3-dihydro-1H-benzo[d]imidazol-1-yl)piperidine-2,6-dione (TR-245)

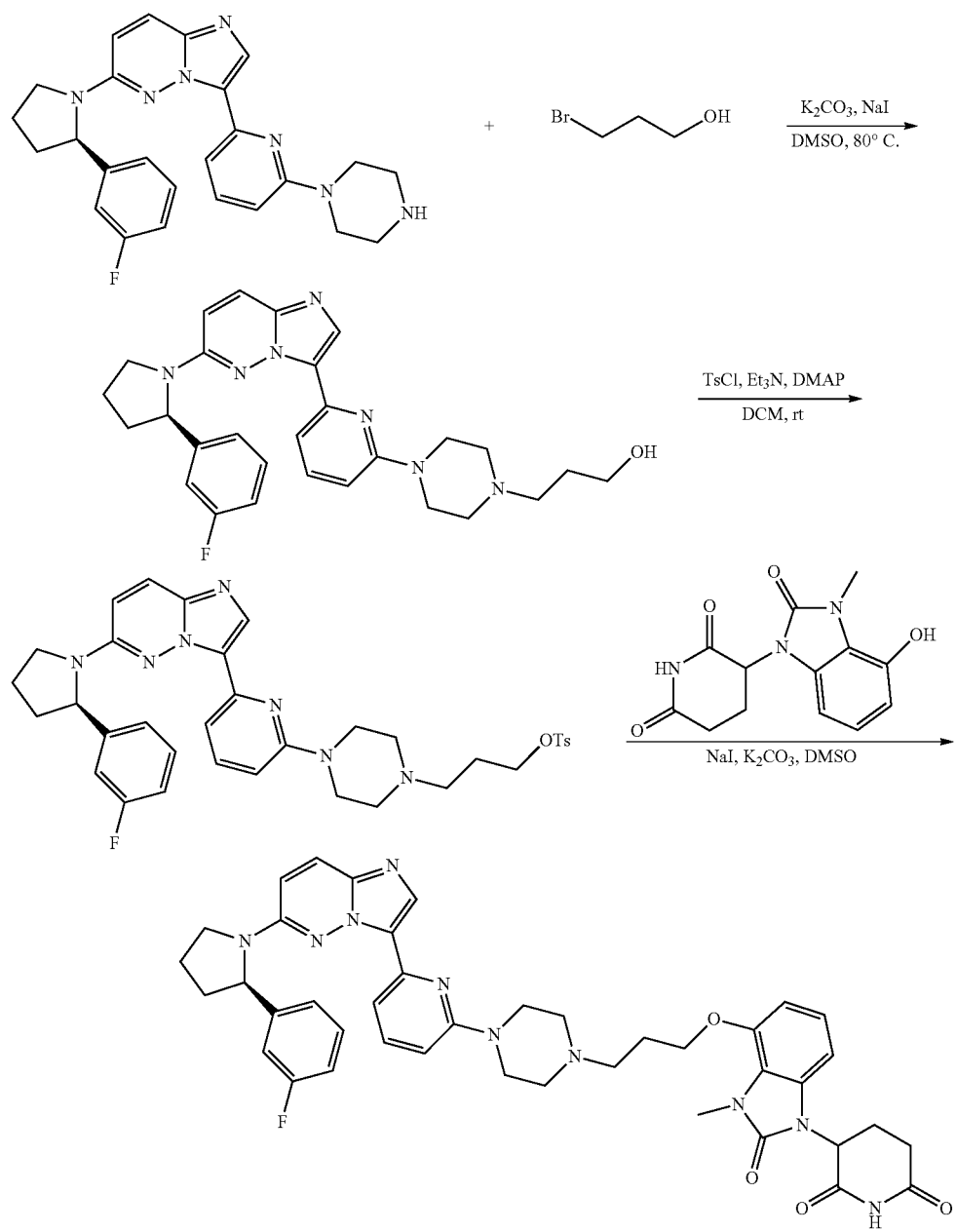

TR-245 was synthesized according to the standard procedures for preparing TR-244 (1.5 mg, 17% yield). MS (ESI) m/z: 759.9 [M+H]⁺.

Example 297: 3-(5-(2-(4-(6-(6-((R)-2-(3-Fluorophenyl)pyrrolidin-1-yl)imidazo[1,2-b]pyridazin-3-yl)pyridin-2-yl)piperazin-1-yl)ethoxy)-3-methyl-2-oxo-2,3-dihydro-1H-benzo[d]imidazol-1-yl)piperidine-2,6-dione (TR-246)
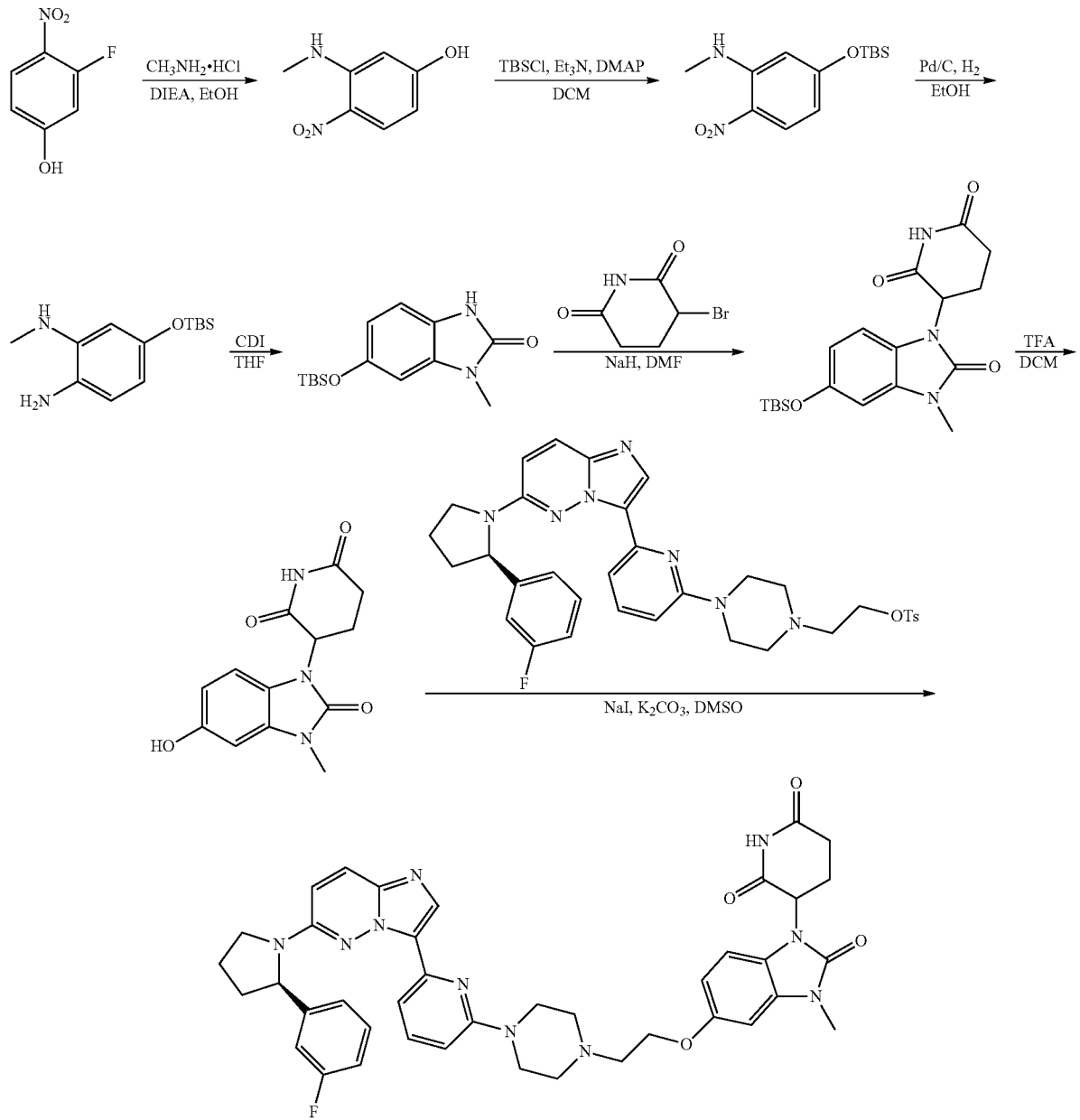
TR-246 was synthesized according to the standard procedures for preparing TR-244 (5.2 mg, 19% yield). MS (ESI) m/z: 745.8 [M+H]+.
Certain compounds disclosed herein have the structures shown in Table 1.

TABLE 1
| Cpd. Code | Structure/Name |
|---|---|
| CPD-001 (TR-001) | 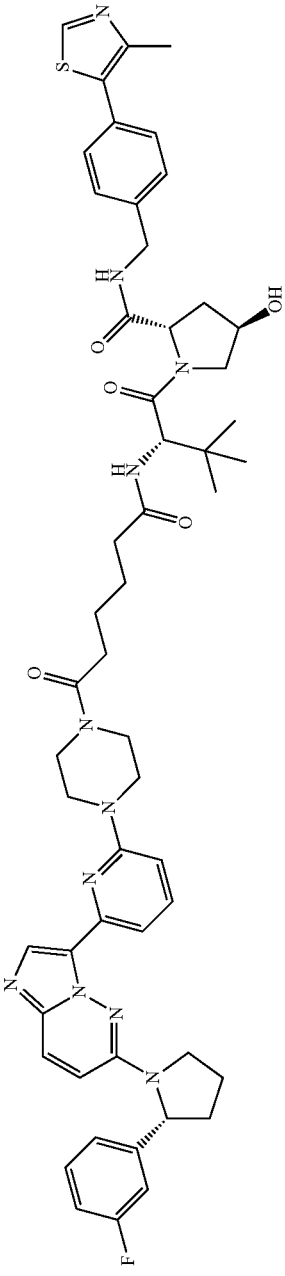 |
| CPD-002 (TR-002) | 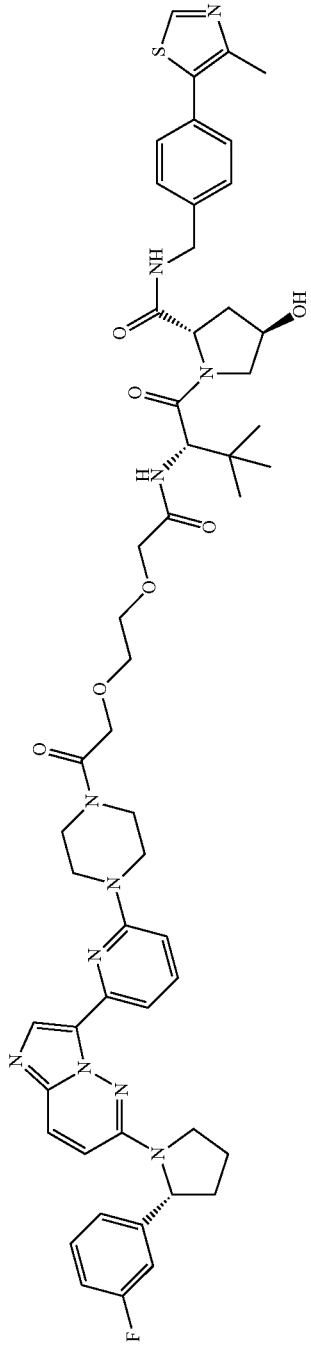 |

TABLE 1-continued
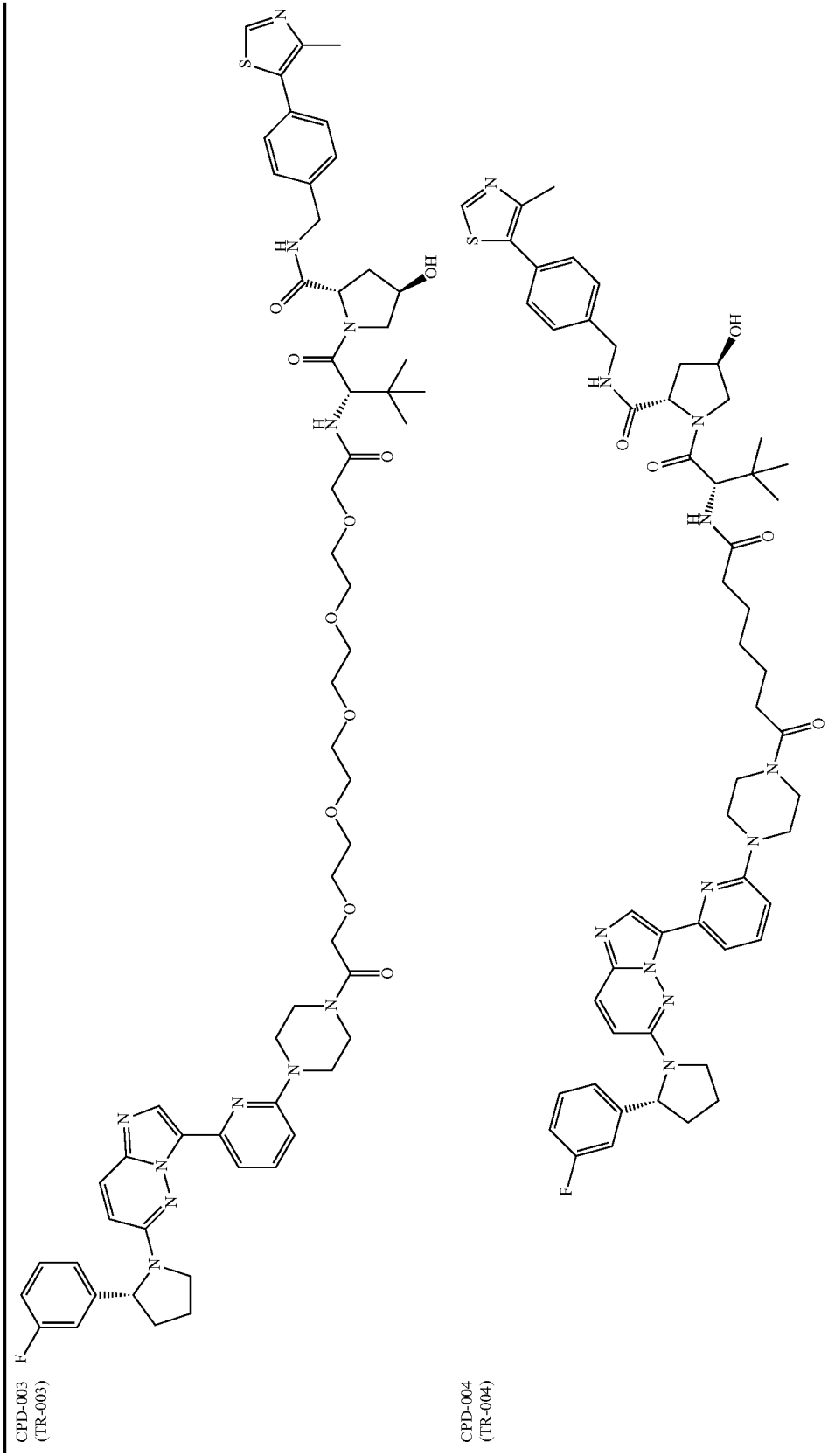
CPD-003 (TR-003)
CPD-004 (TR-004)

TABLE 1-continued
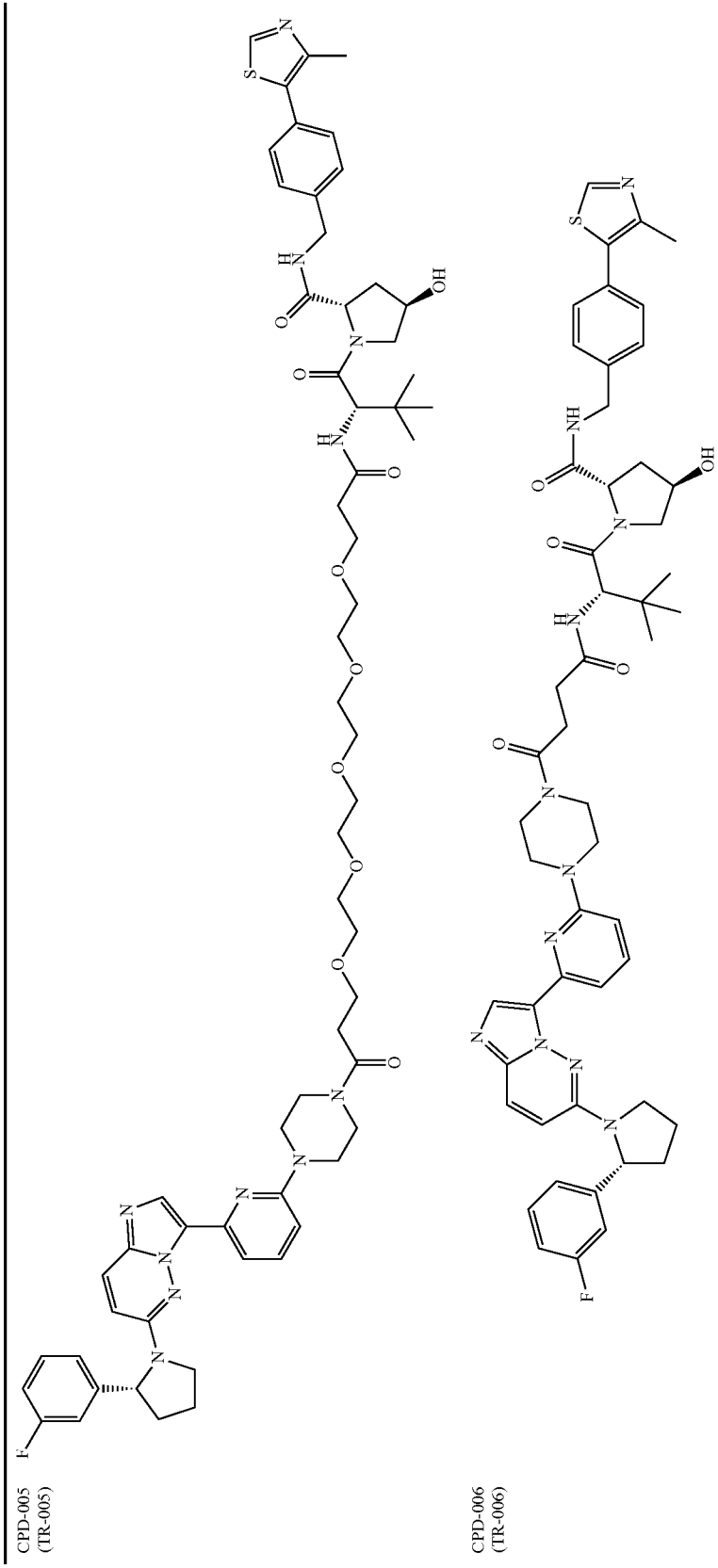
CPD-005
(TR-005)
CPD-006
(TR-006)

TABLE 1-continued
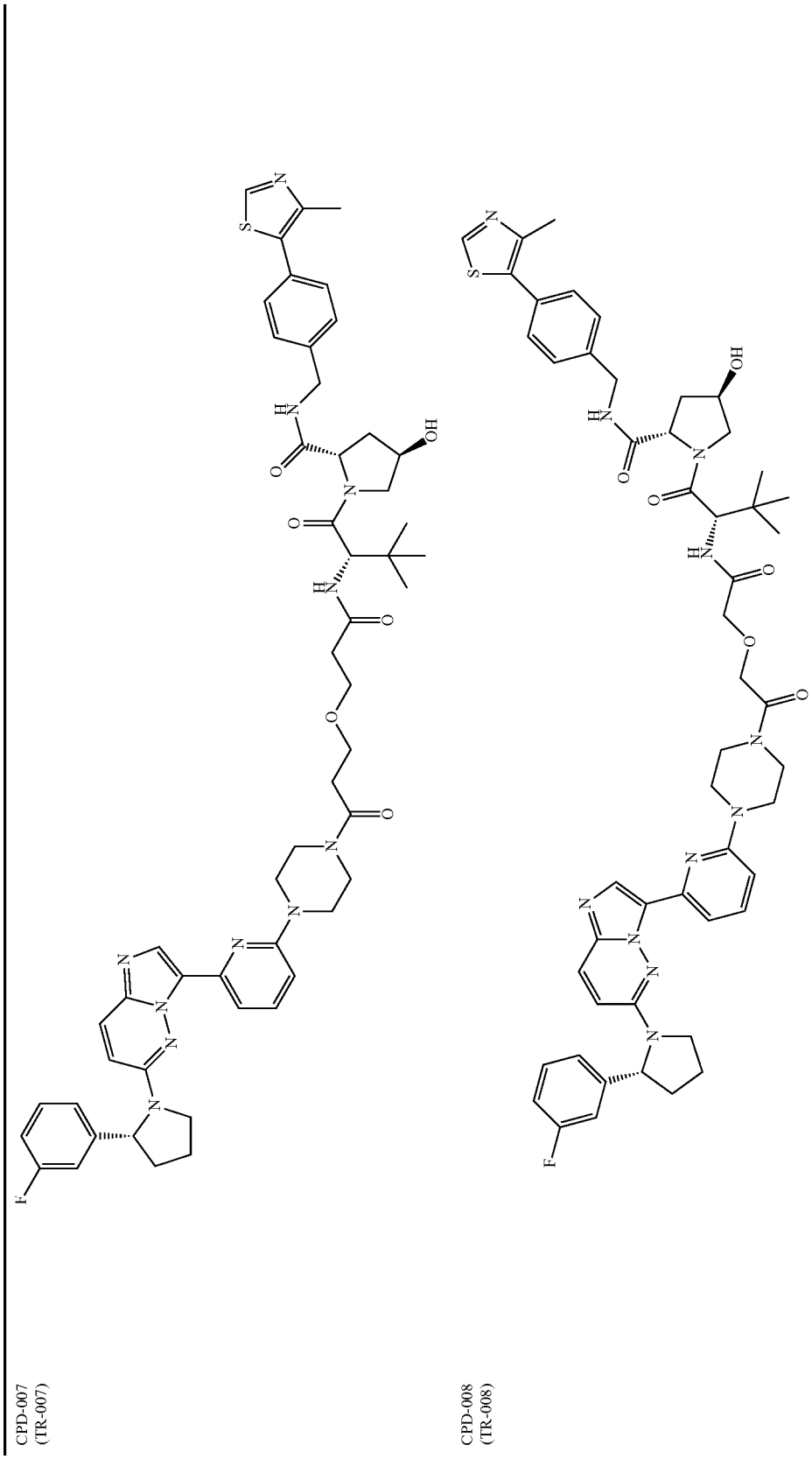
CPD-007
(TR-007)
CPD-008
(TR-008)

TABLE 1-continued
| CPD-009 (TR-009) | 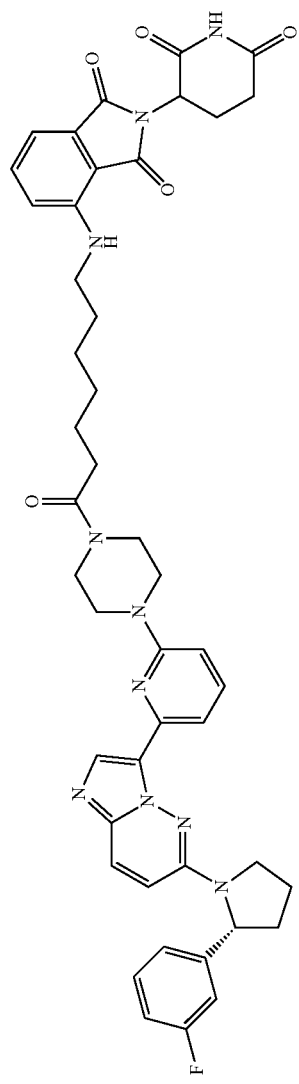 |
| CPD-010 (TR-010) | 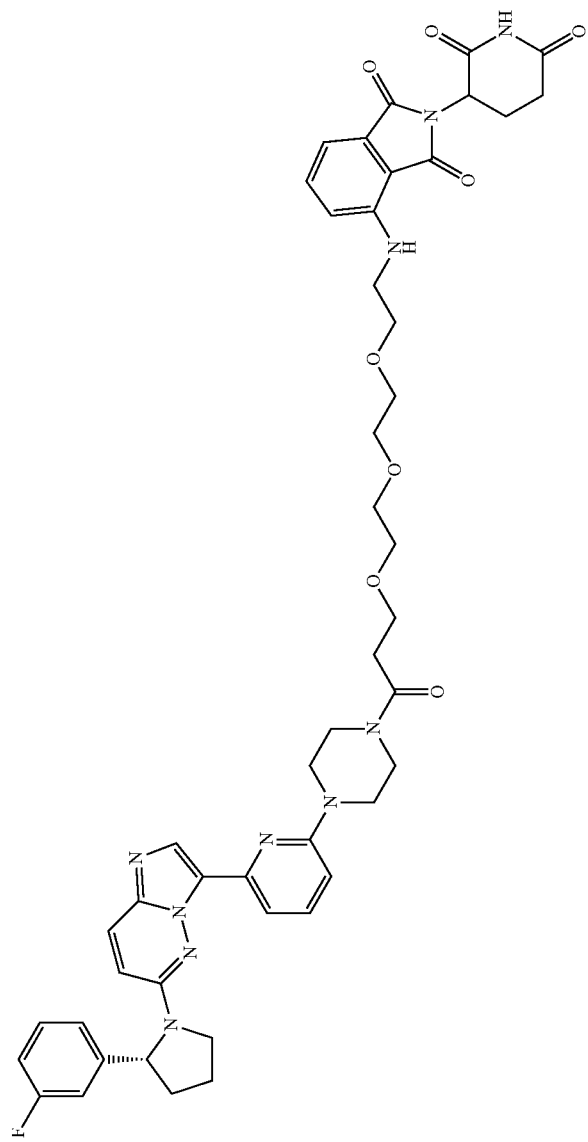 |

TABLE 1-continued
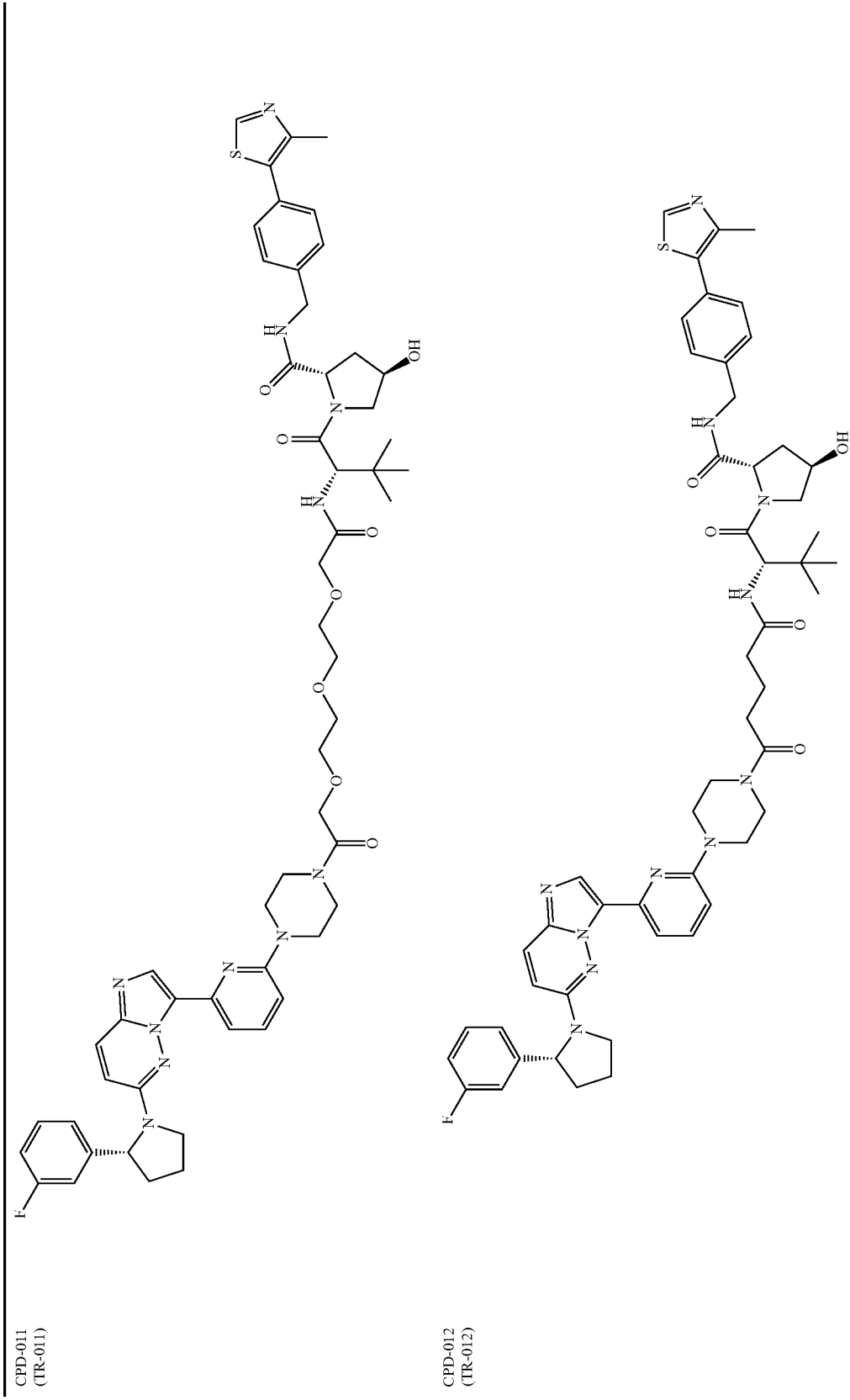
CPD-011
(TR-011)
CPD-012
(TR-012)

TABLE 1-continued
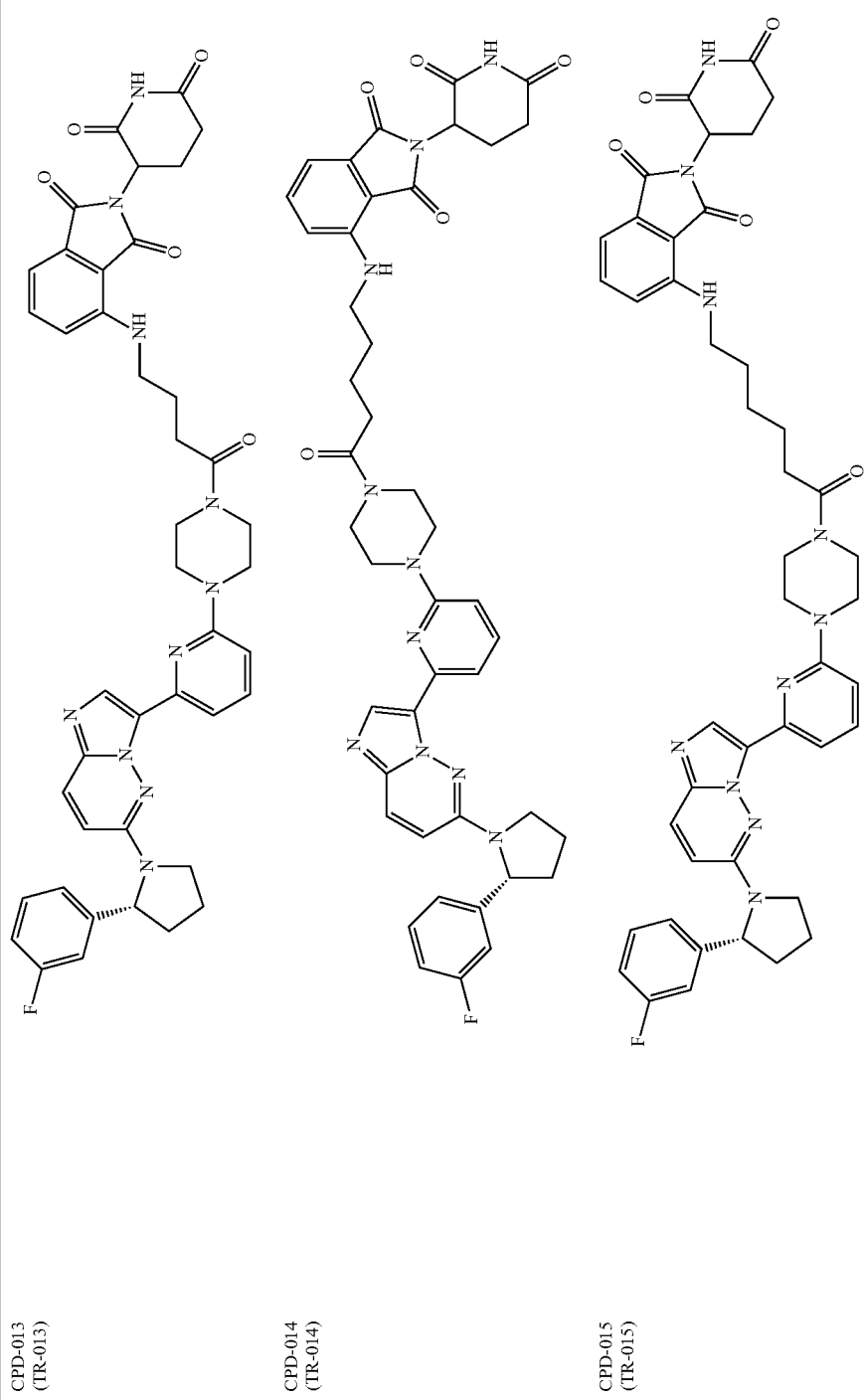
CPD-013
(TR-013)
CPD-014
(TR-014)
CPD-015
(TR-015)

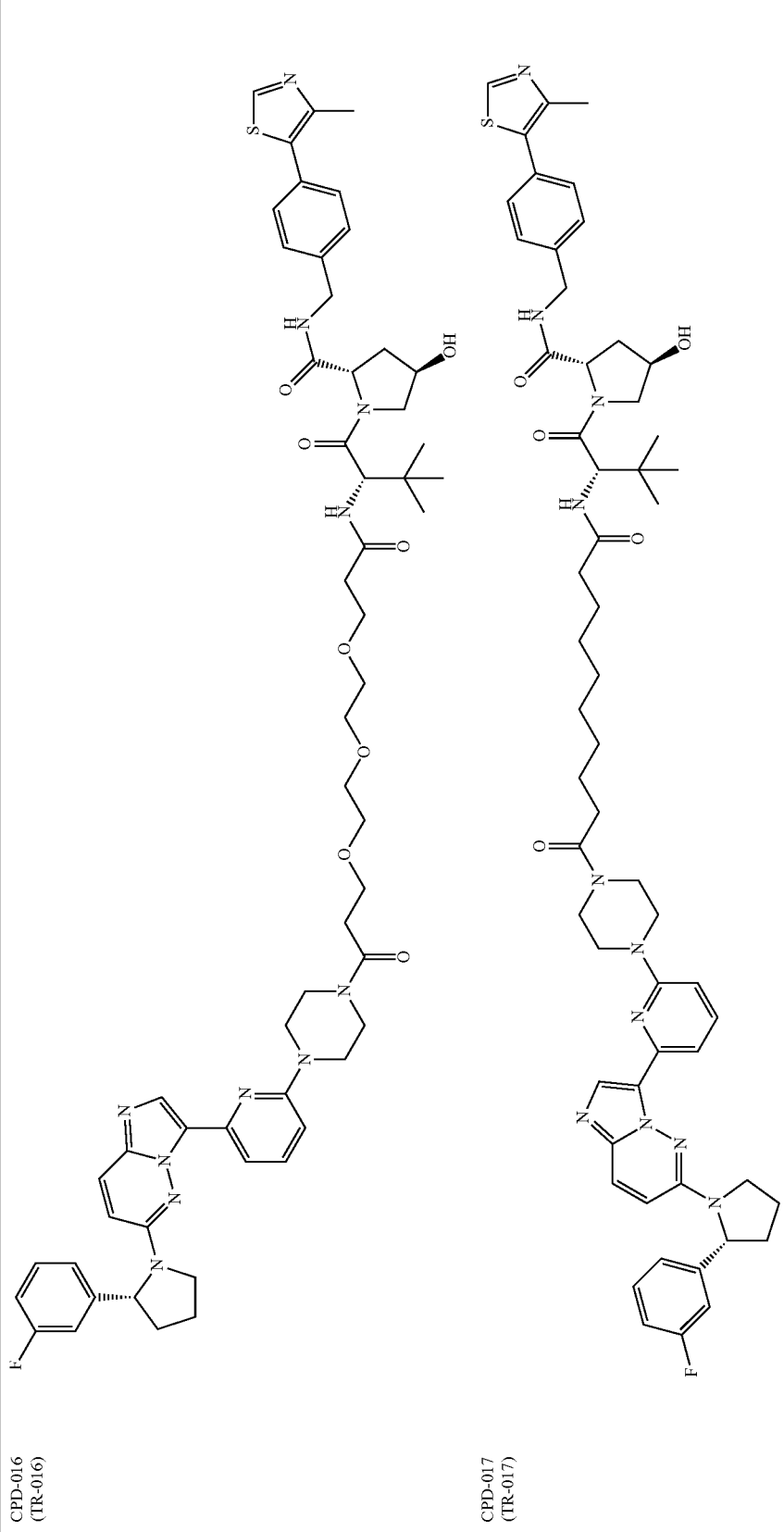

TABLE 1-continued
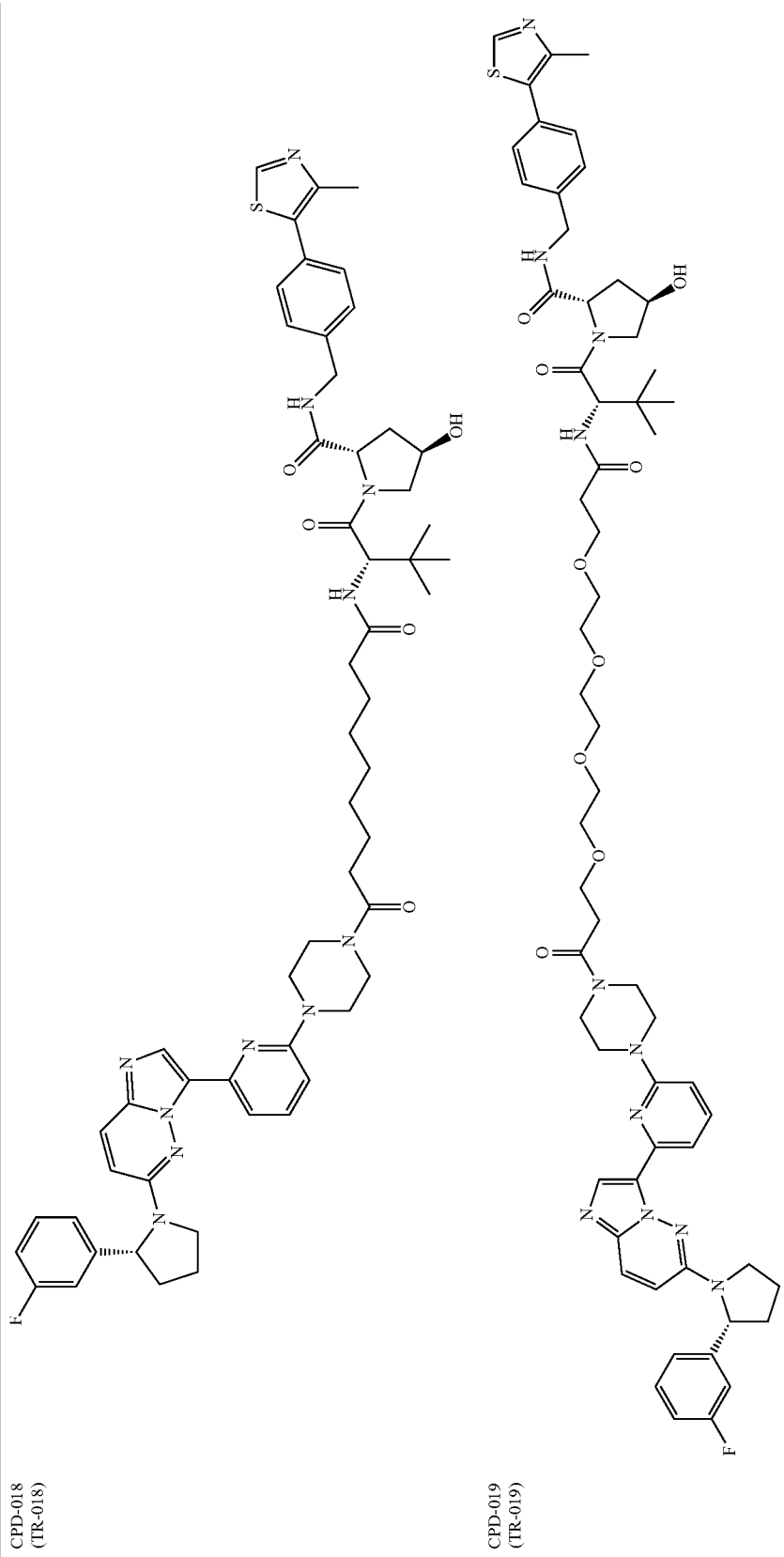
CPD-018
(TR-018)
CPD-019
(TR-019)

TABLE 1-continued
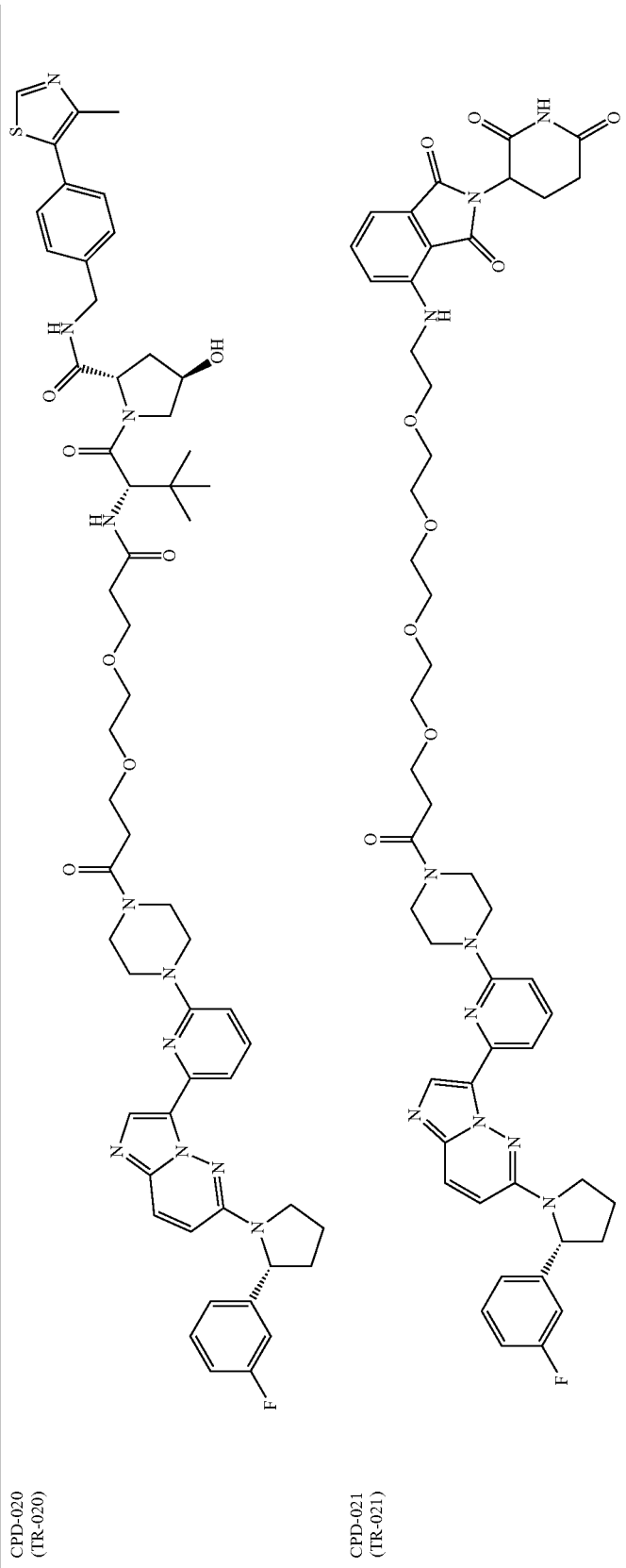
CPD-020
(TR-020)
CPD-021
(TR-021)

TABLE 1-continued
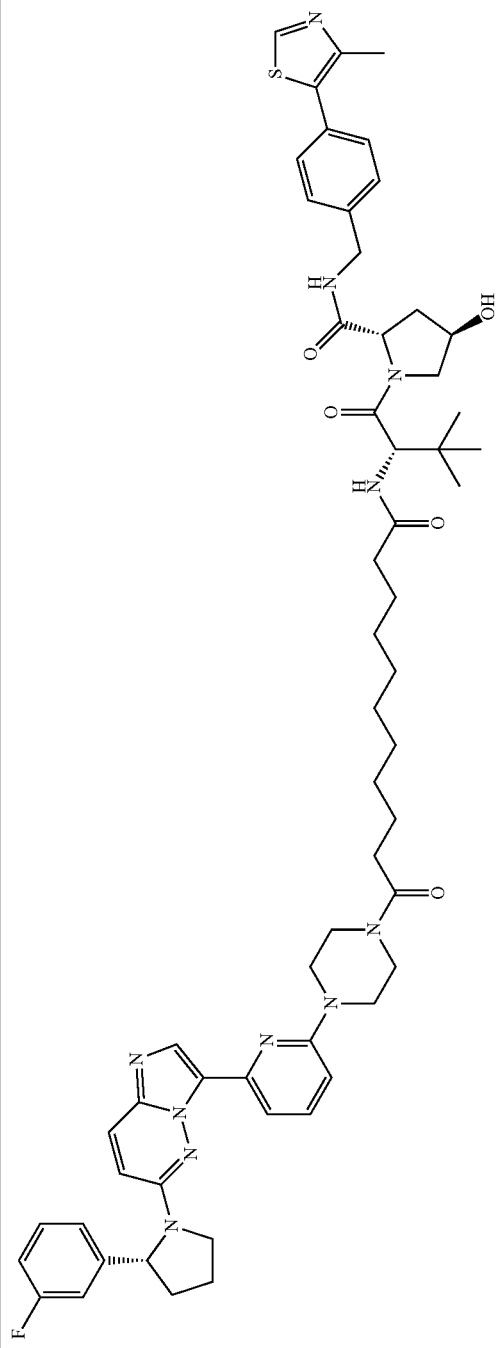
CPD-022
(TR-022)
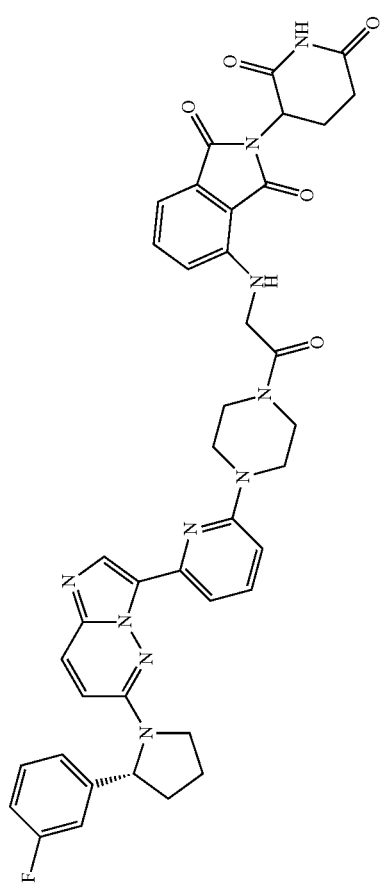
CPD-023
(TR-023)

TABLE 1-continued
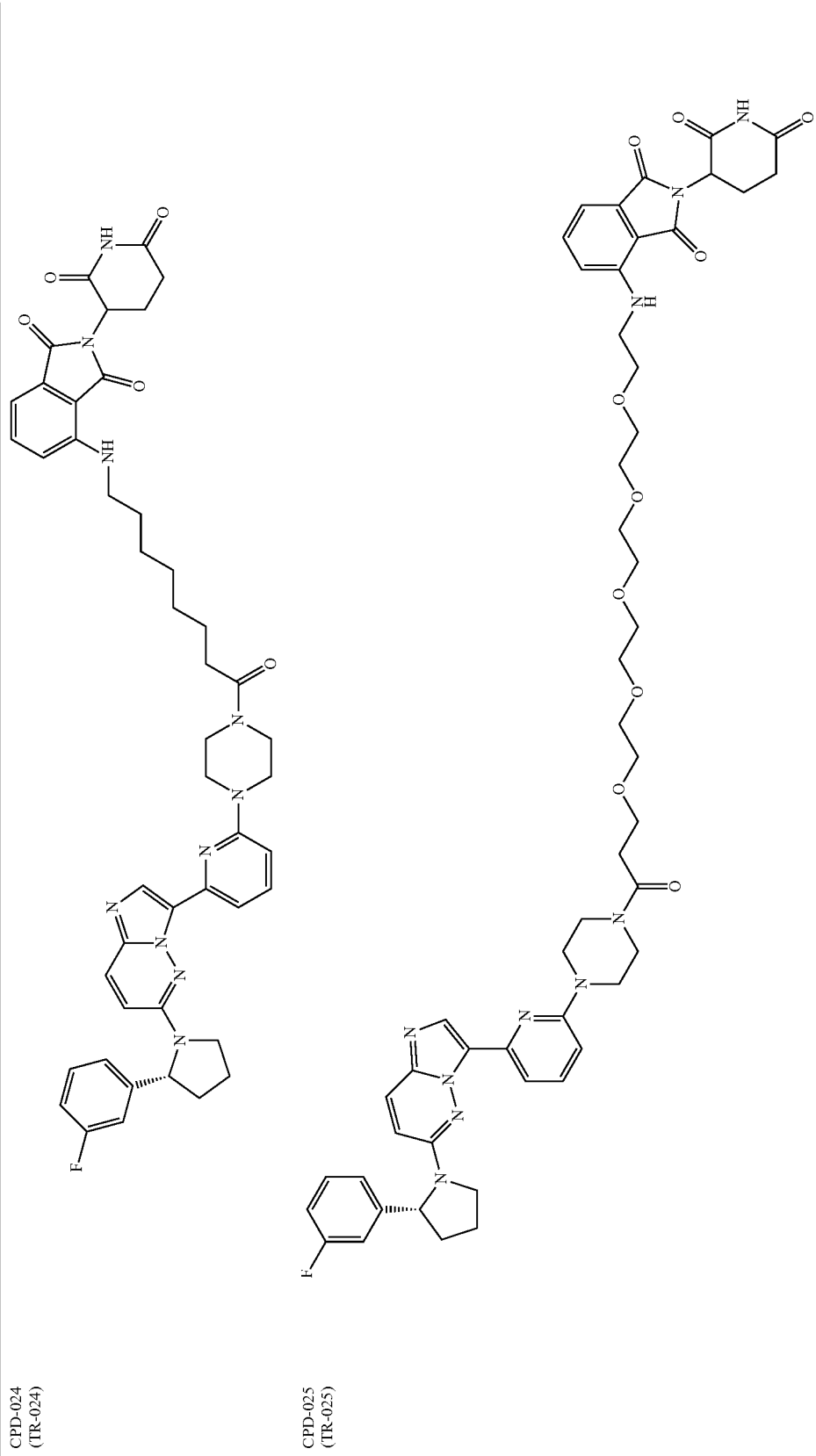
CPD-024
(TR-024)
CPD-025
(TR-025)

TABLE 1-continued
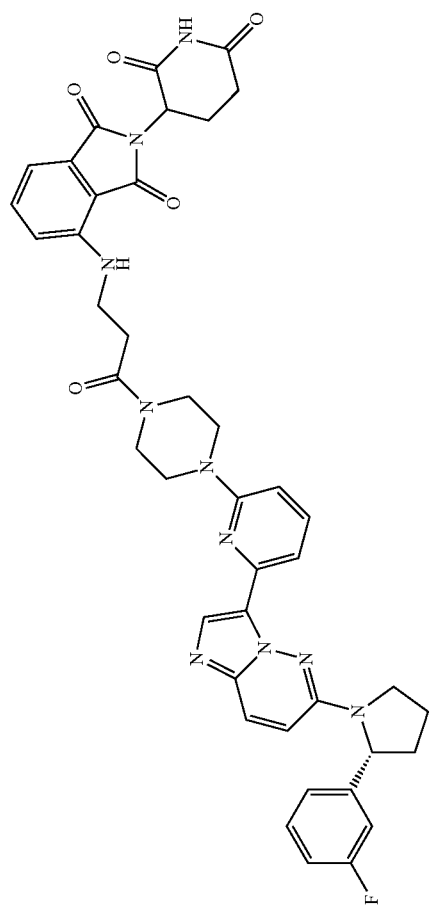
CPD-026
(TR-026)
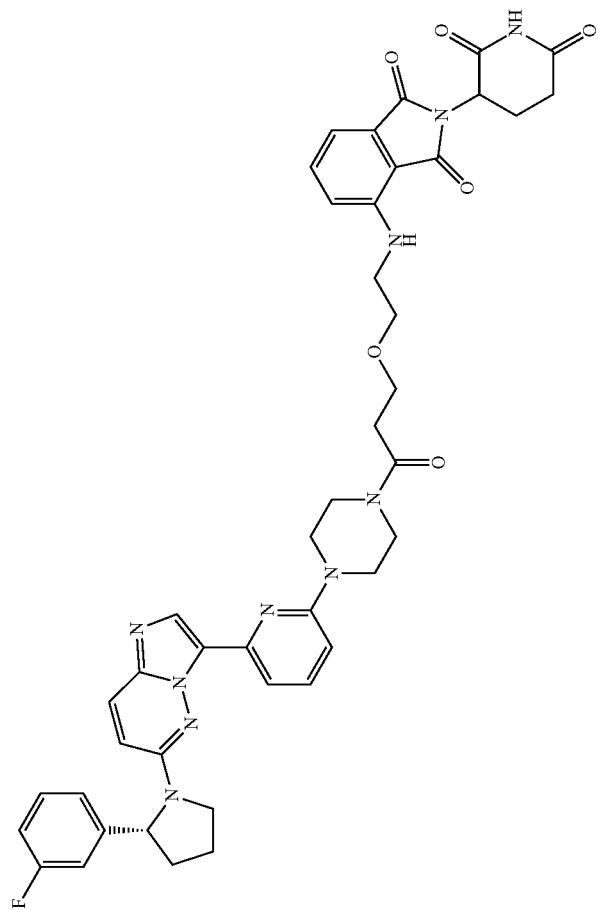
CPD-027
(TR-027)

TABLE 1-continued
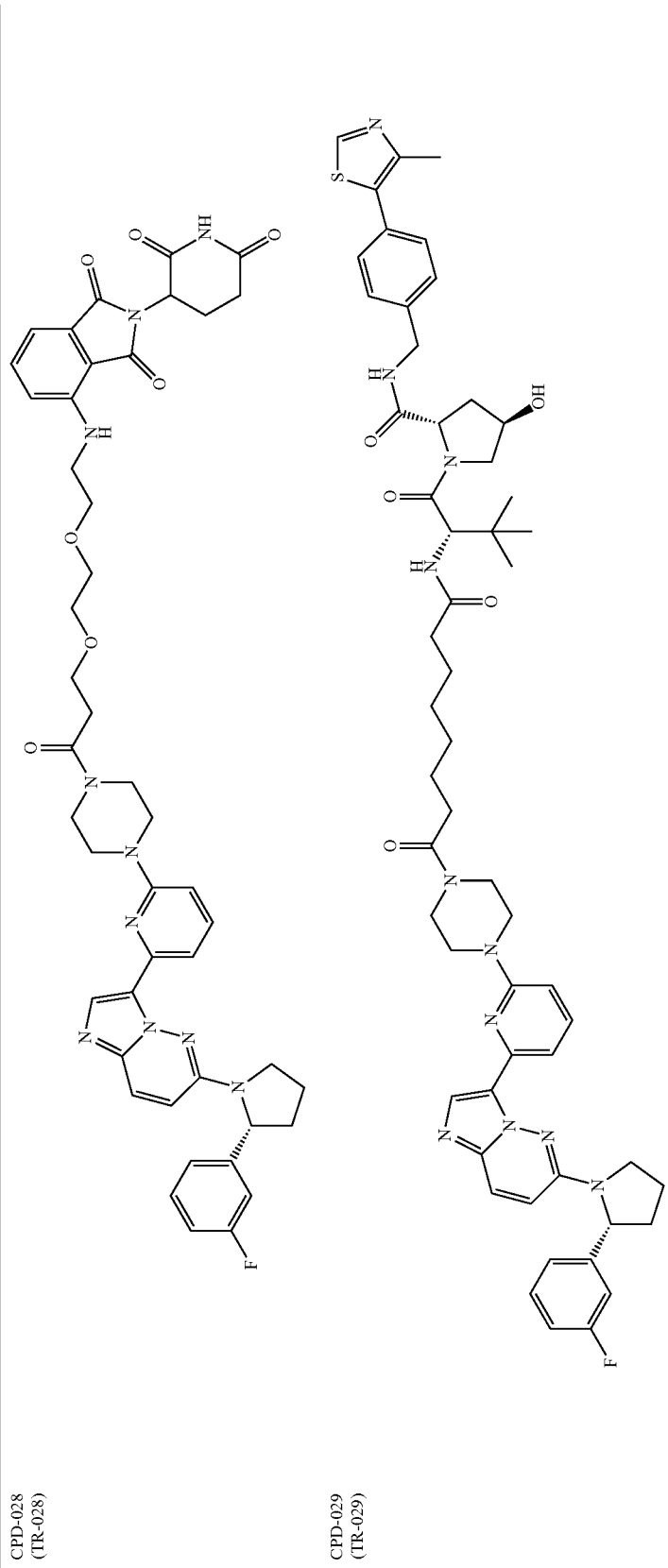
CPD-028
(TR-028)
CPD-029
(TR-029)

TABLE 1-continued
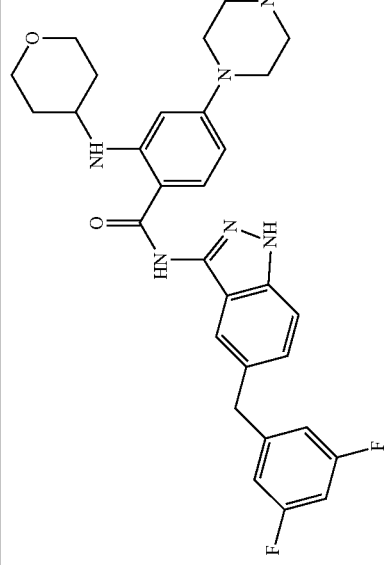
CPD-030
(TR-030)
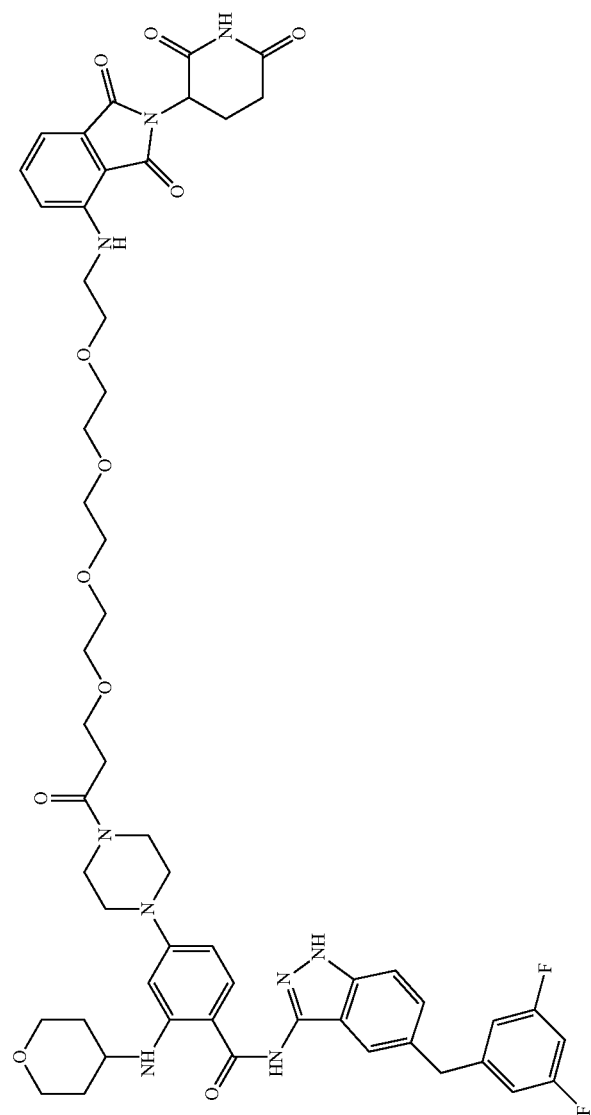
CPD-031
(TR-031)

TABLE 1-continued
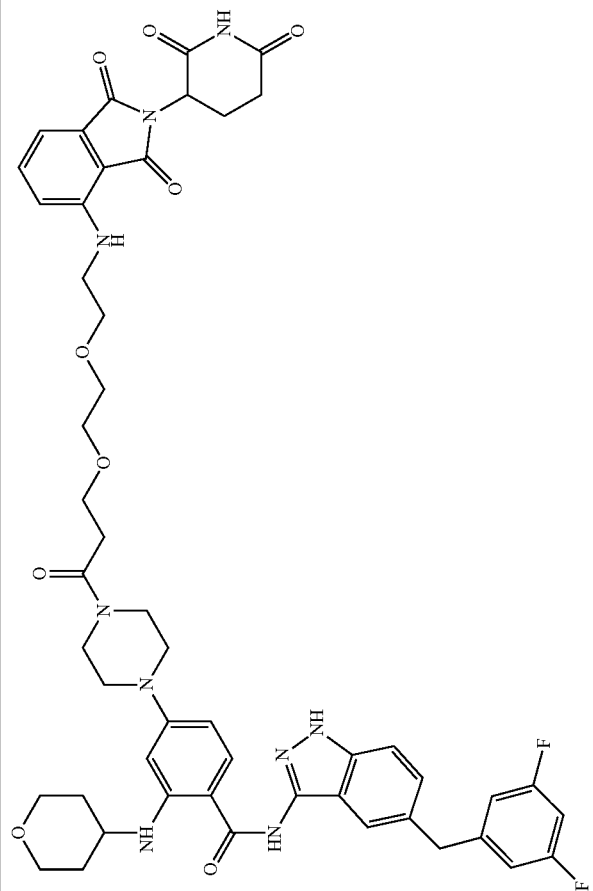
CPD-032
(TR-032)

TABLE 1-continued
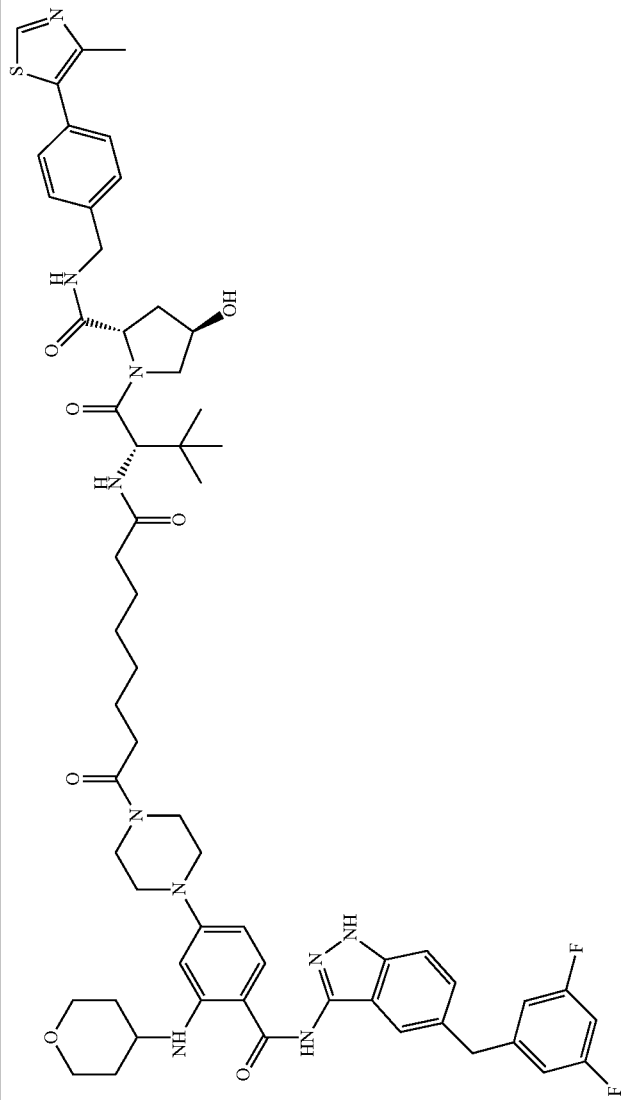
CPD-033
(TR-033)

TABLE 1-continued
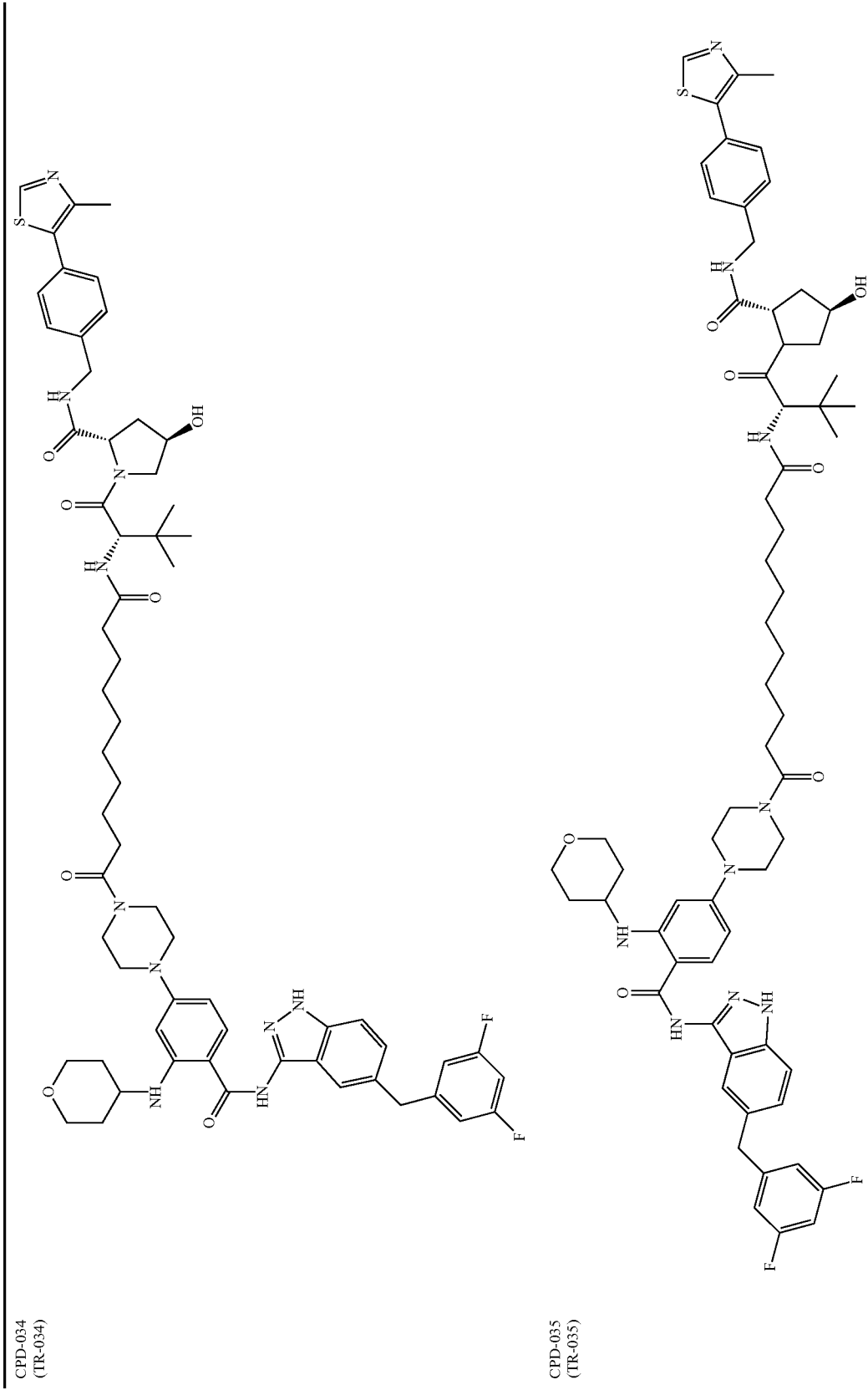
CPD-034
(TR-034)
CPD-035
(TR-035)

TABLE 1-continued
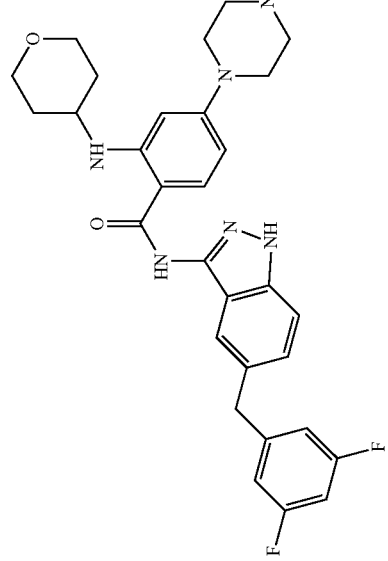
CPD-036
(TR-036)
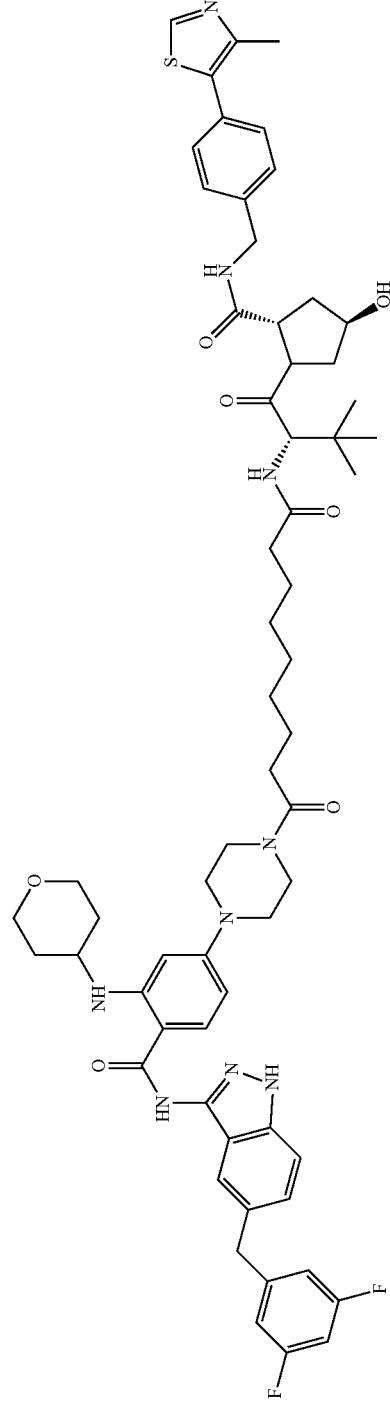
CPD-037
(TR-037)

TABLE 1-continued
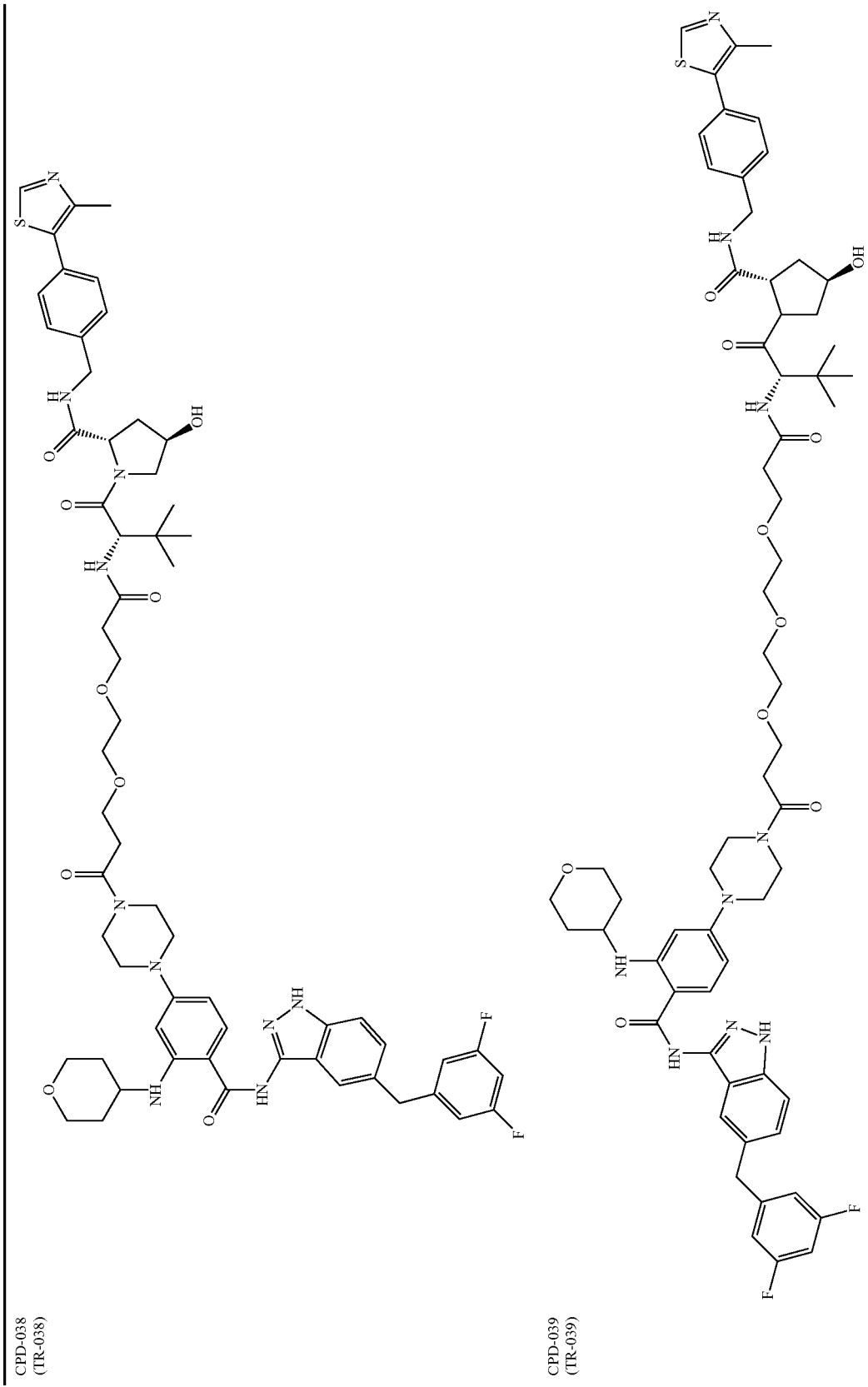
CPD-038
(TR-038)
CPD-039
(TR-039)

TABLE 1-continued
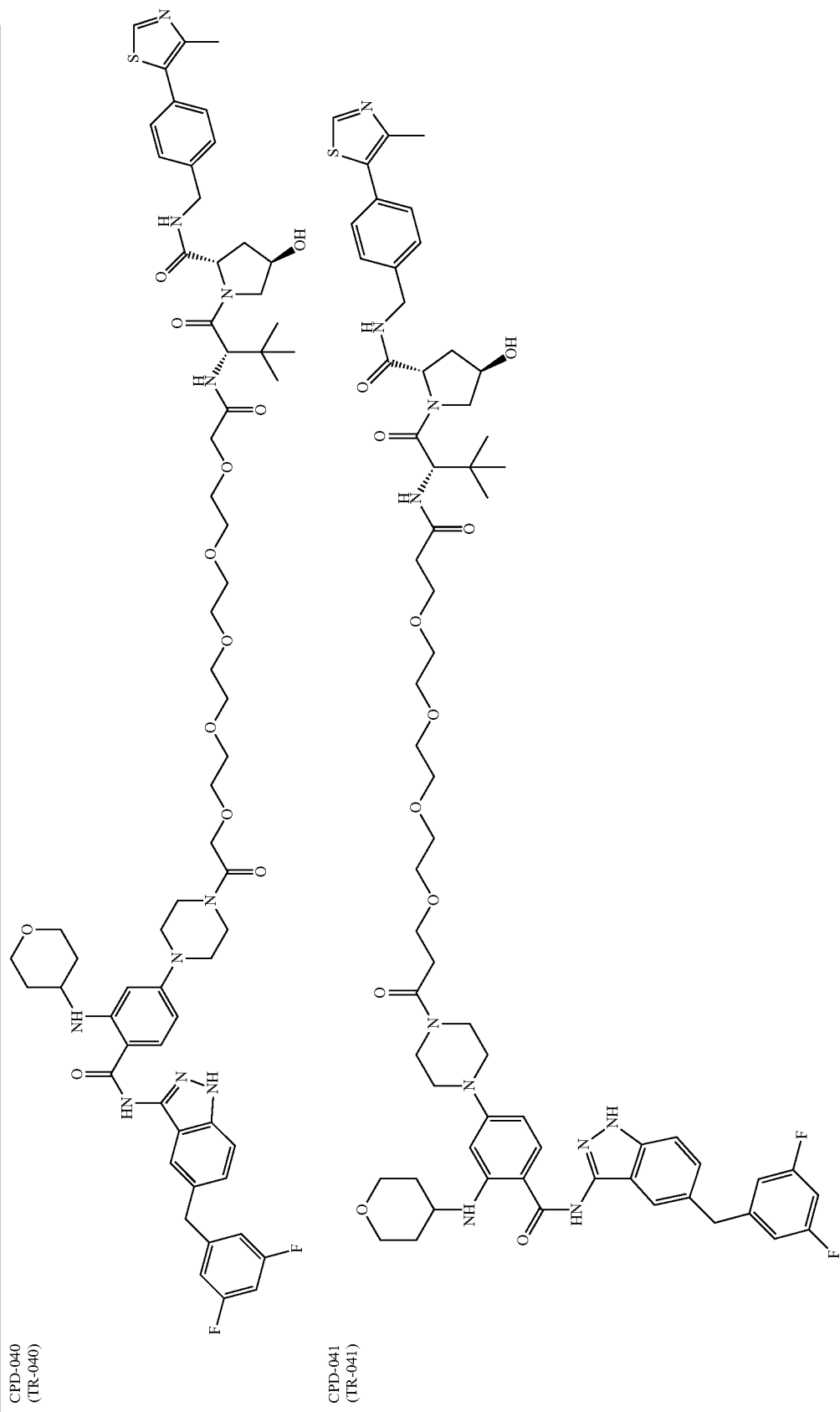
CPD-040
(TR-040)
CPD-041
(TR-041)

TABLE 1-continued
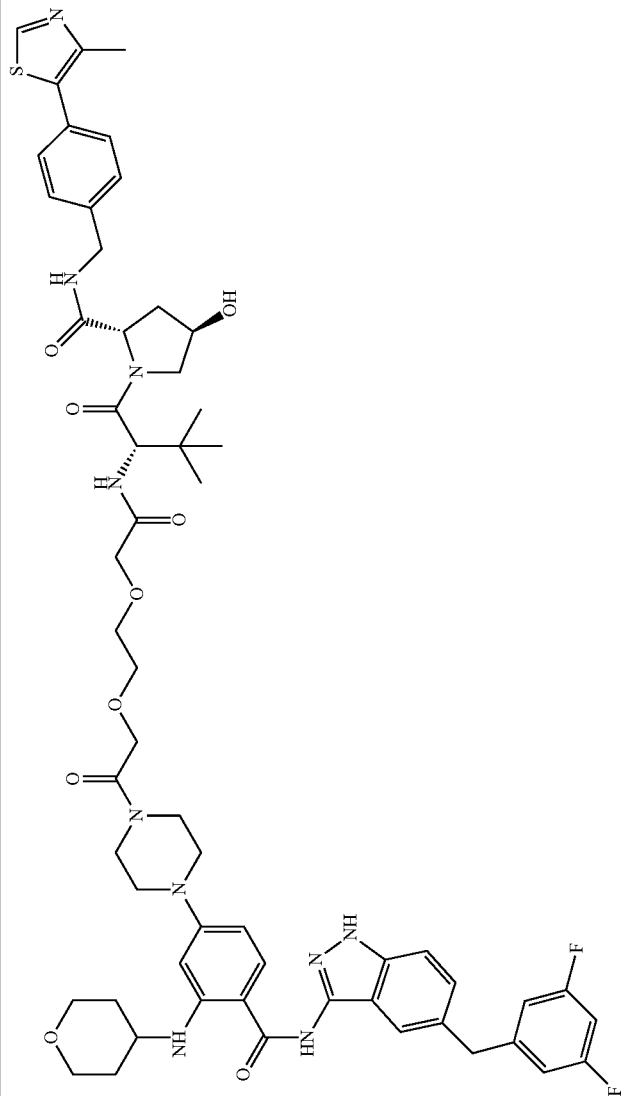
CPD-042
(TR-042)
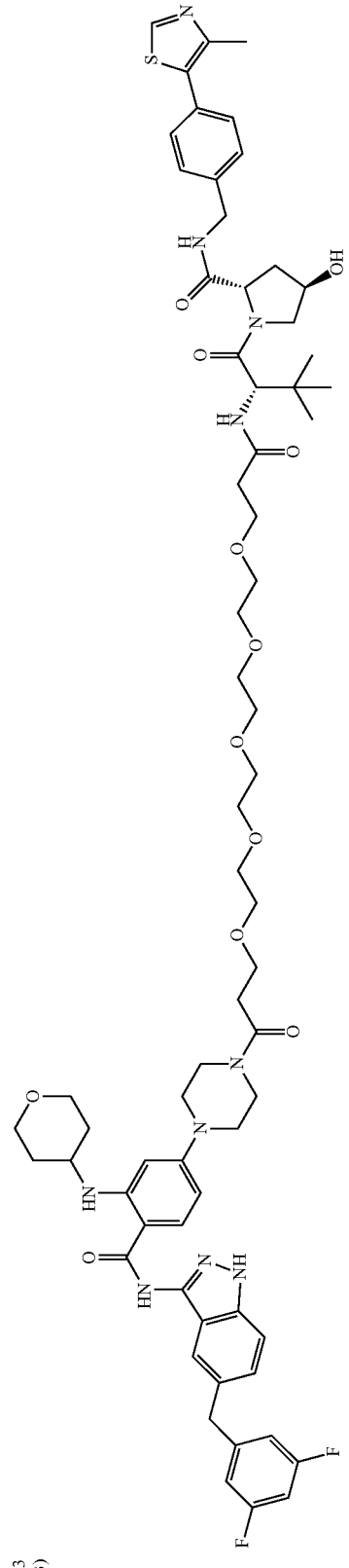
CPD-043
(TR-043)

TABLE 1-continued
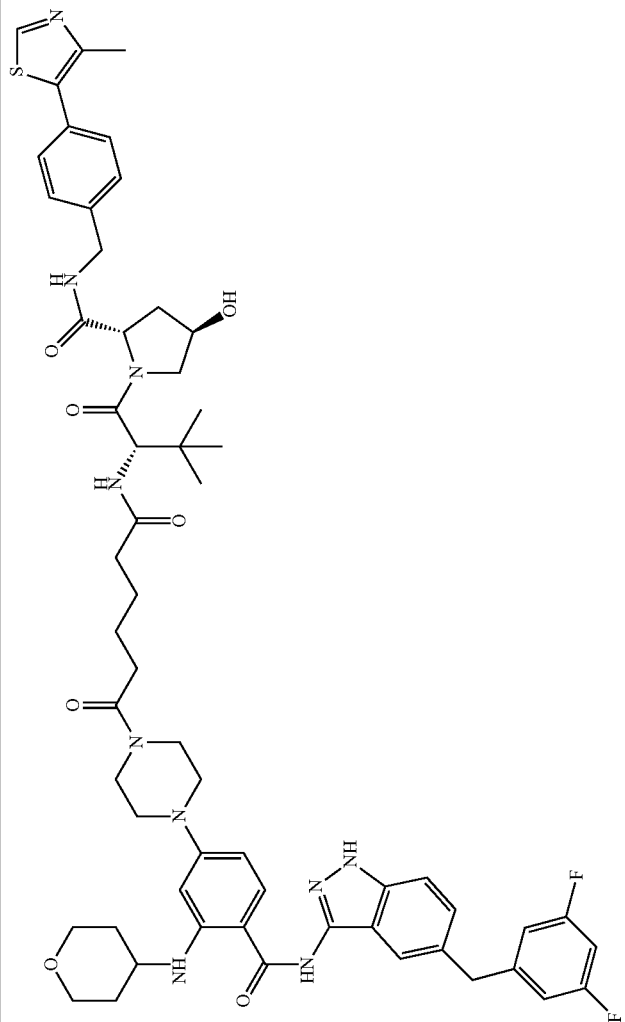
CPD-044
(TR-044)
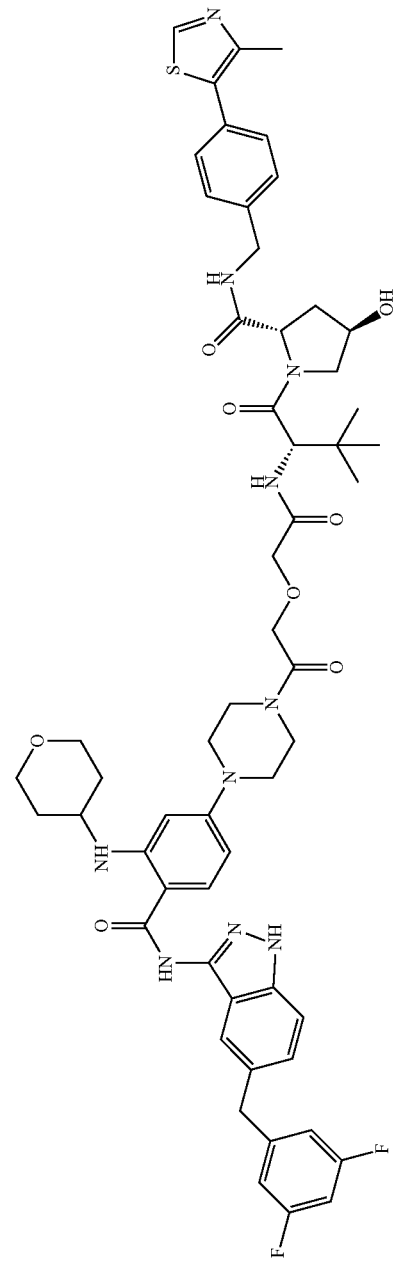
CPD-045
(TR-045)

TABLE 1-continued
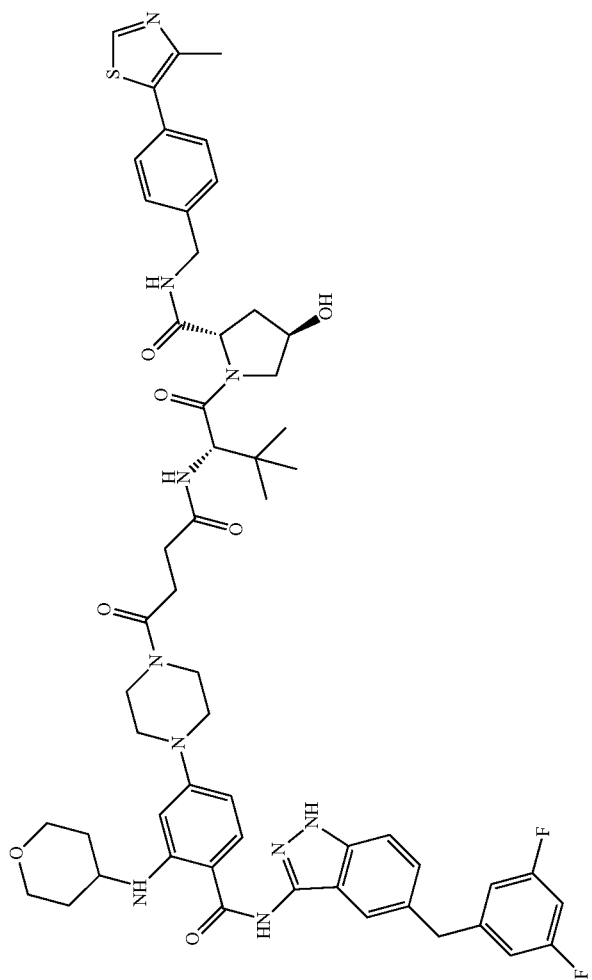
CPD-046
(TR-046)
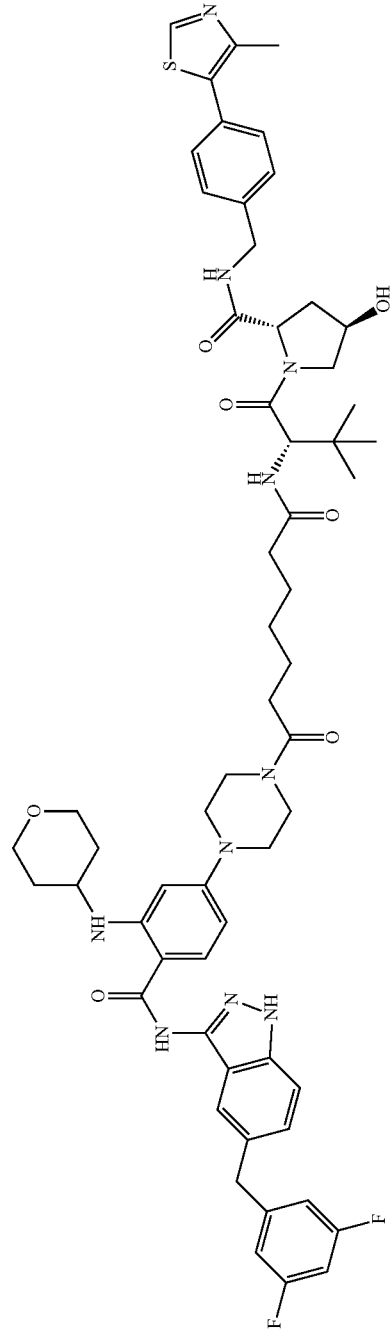
CPD-047
(TR-047)

TABLE 1-continued
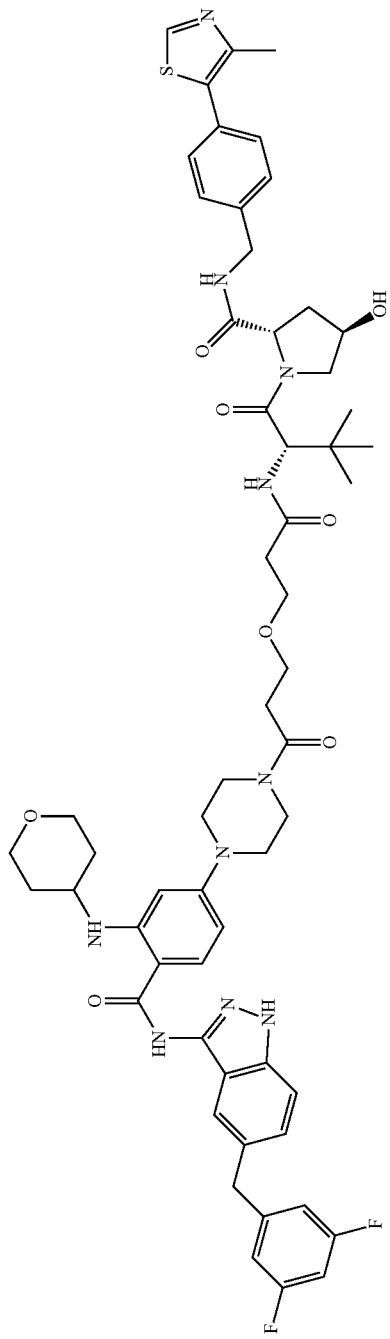
CPD-048
(TR-048)
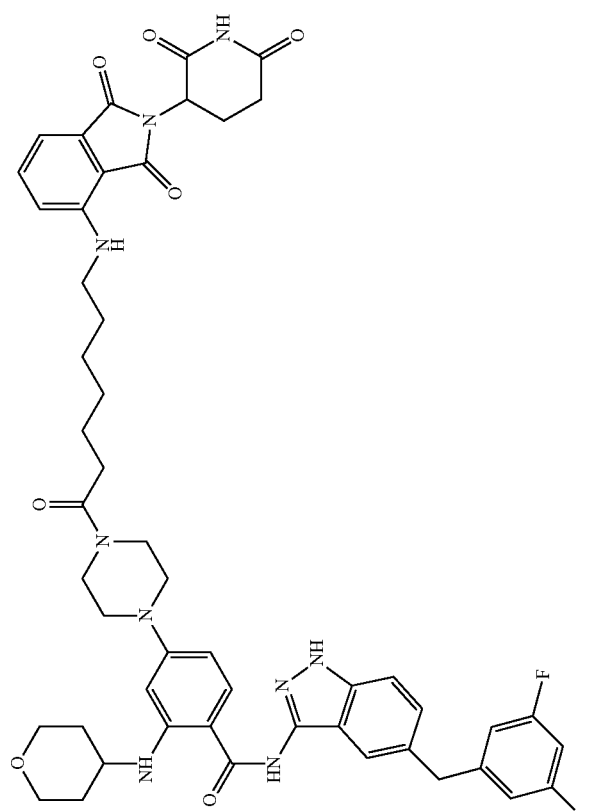
CPD-049
(TR-049)

TABLE 1-continued
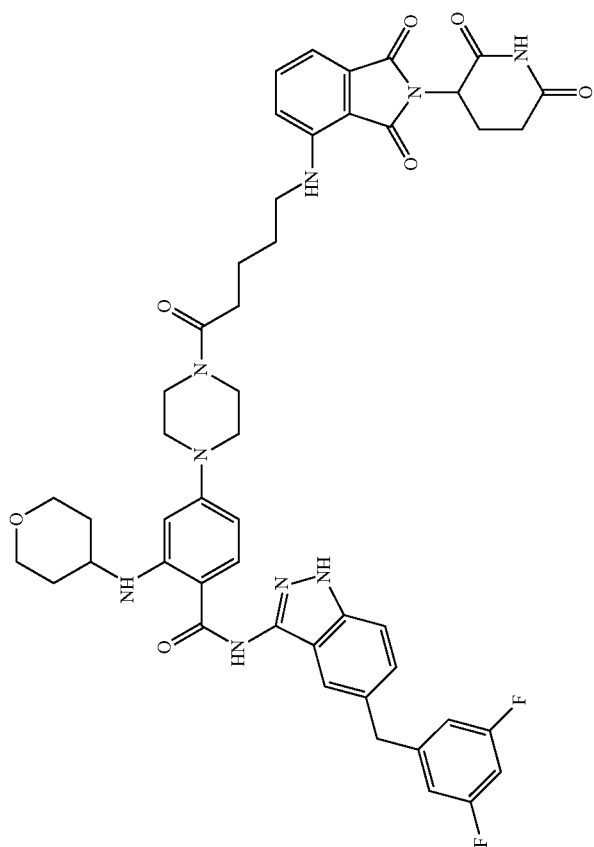
CPD-050
(TR-050)

TABLE 1-continued
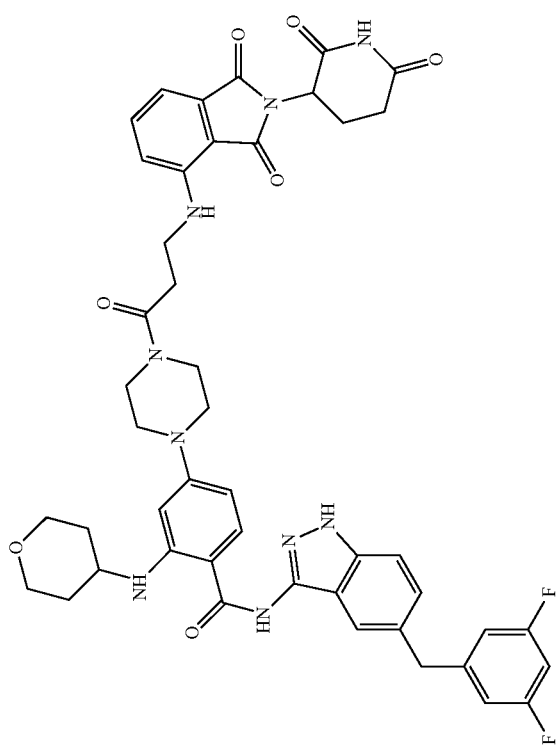
CPD-051
(TR-051)
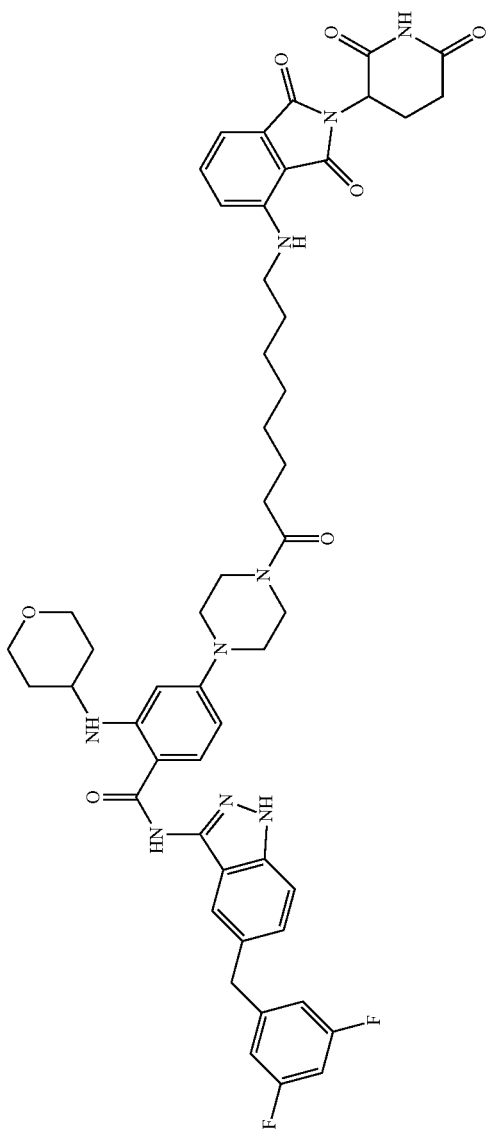
CPD-052
(TR-052)

TABLE 1-continued
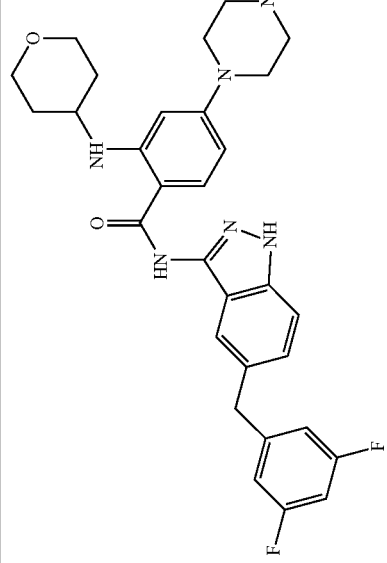
CPD-053
(TR-053)
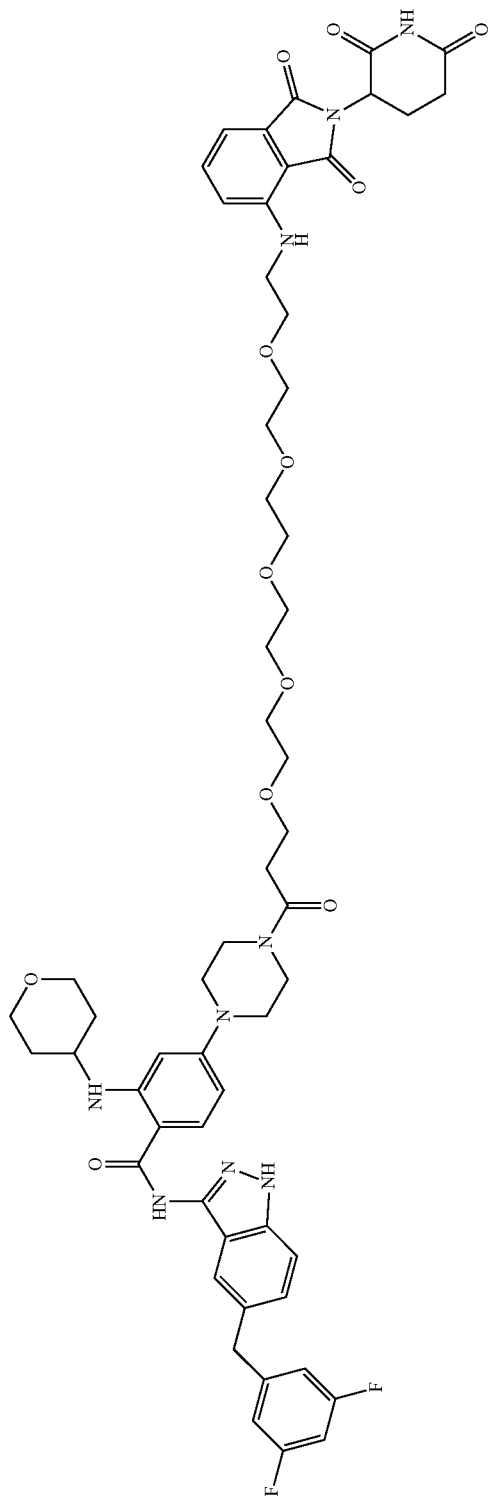
CPD-054
(TR-054)

TABLE 1-continued
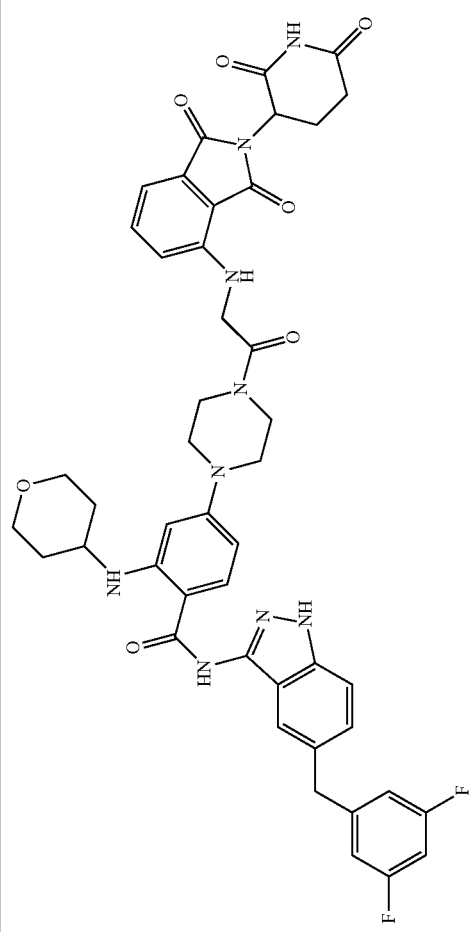
CPD-055
(TR-055)
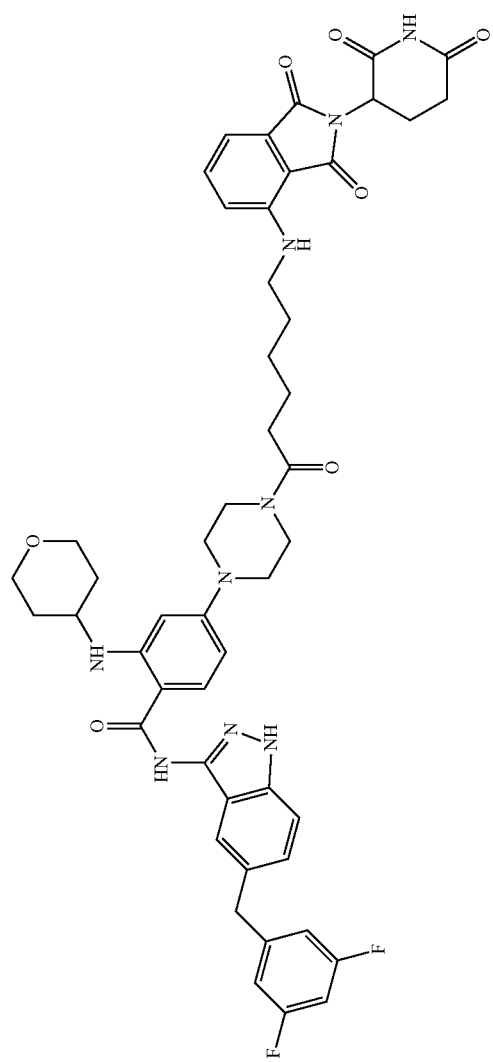
CPD-056
(TR-056)

TABLE 1-continued
| CPD-057 (TR-057) | 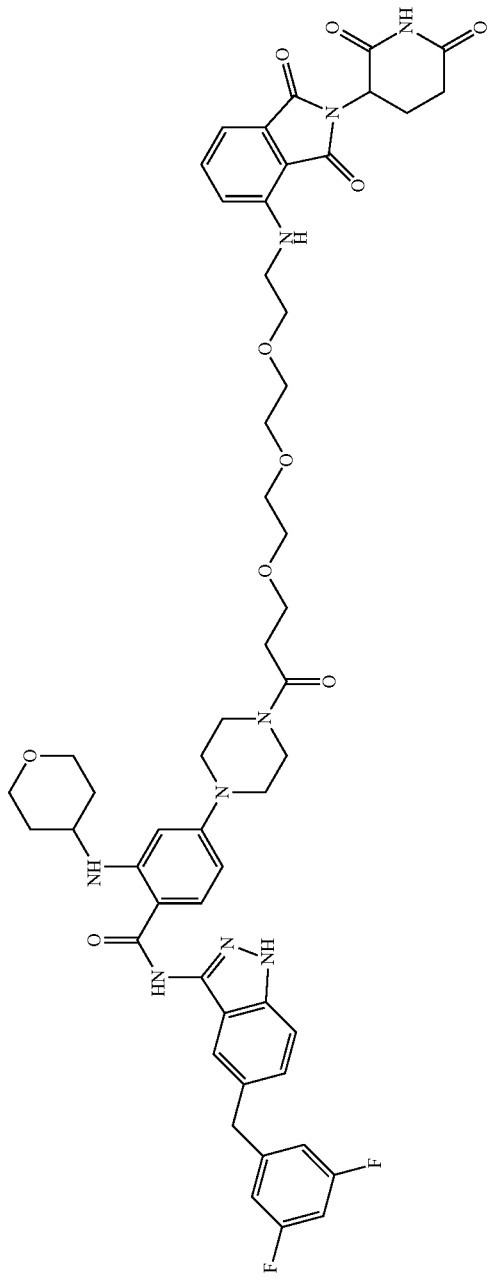 |
| CPD-058 (TR-058) | 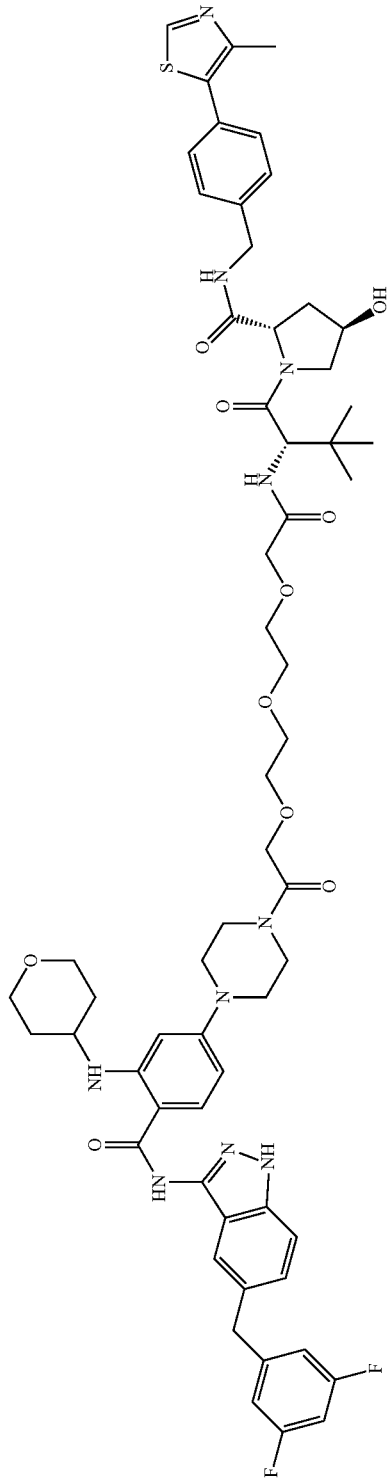 |

TABLE 1-continued
| CPD-059 (TR-059) | 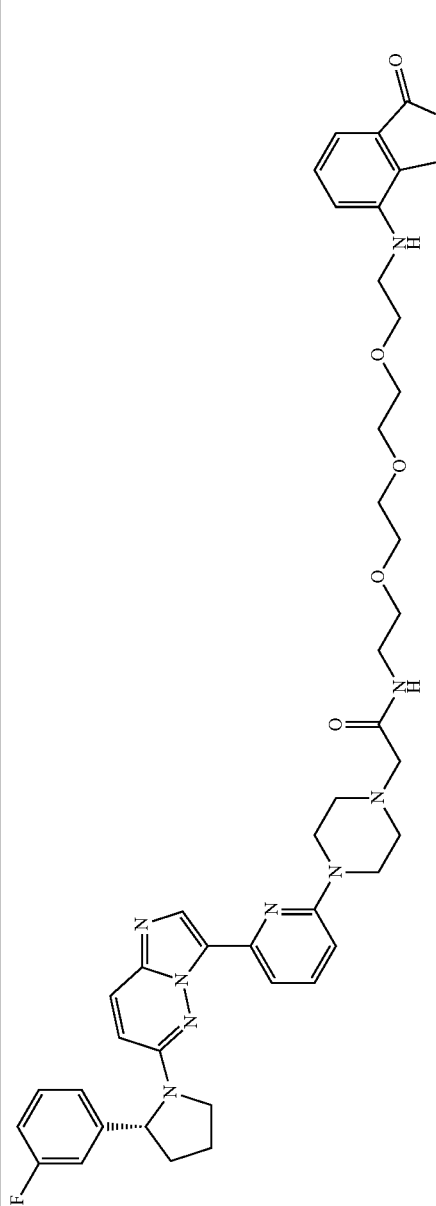 |
| CPD-060 (TR-060) | 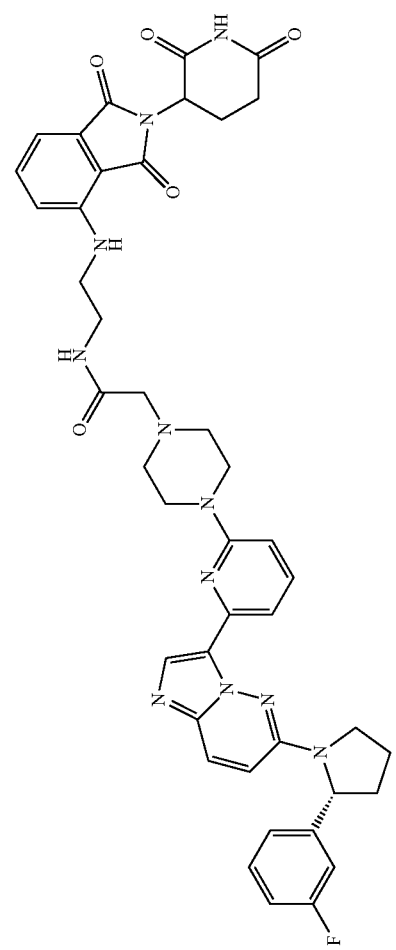 |

TABLE 1-continued
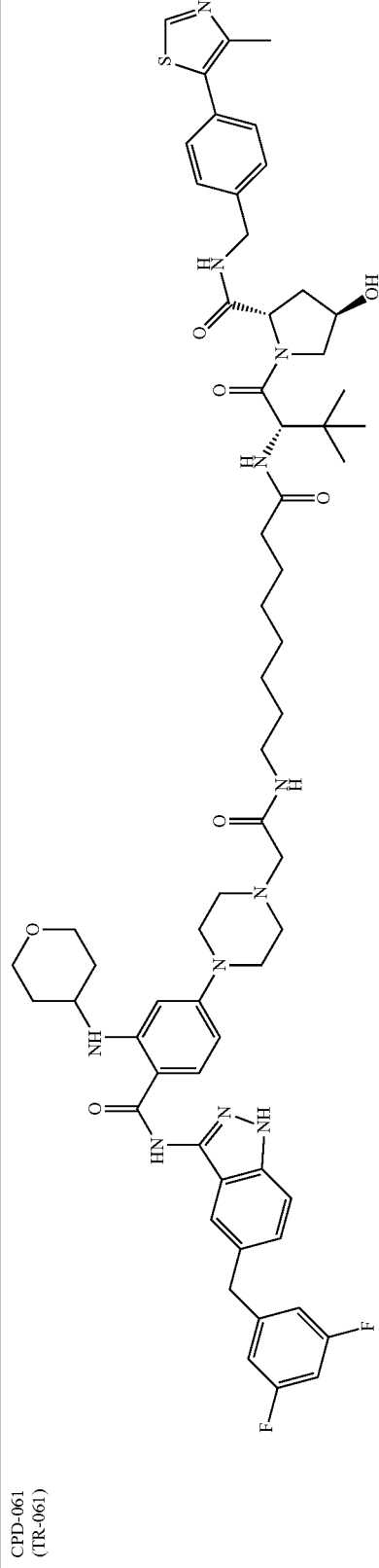
CPD-061
(TR-061)
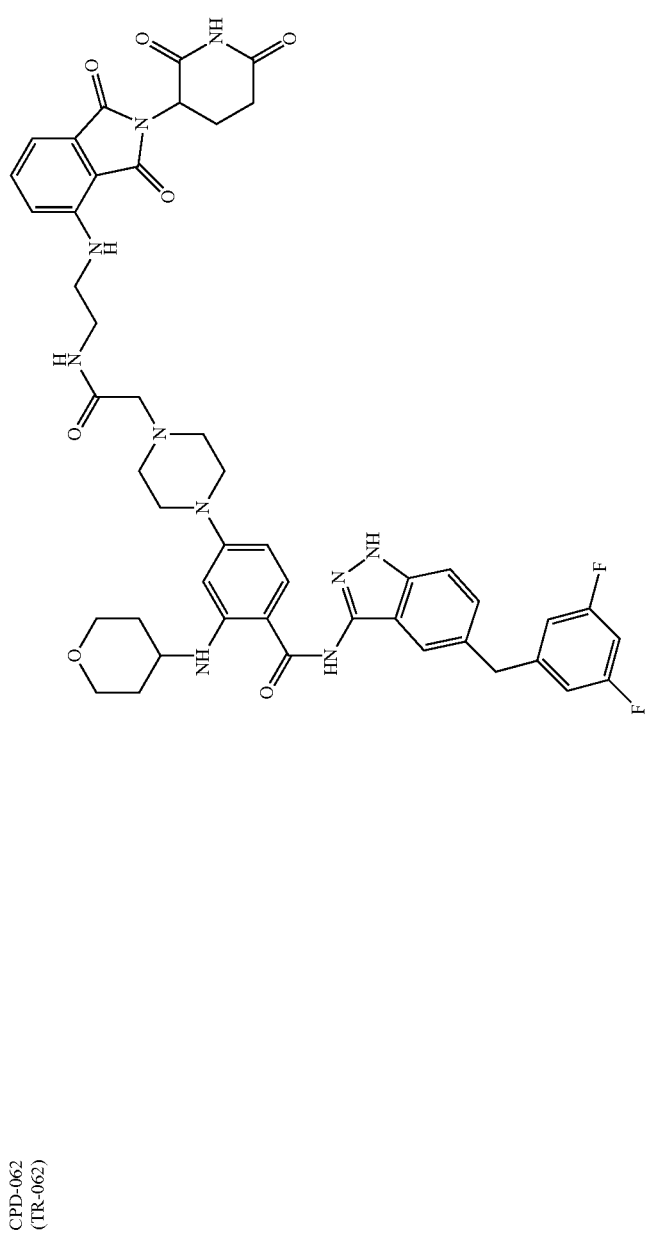
CPD-062
(TR-062)

TABLE 1-continued
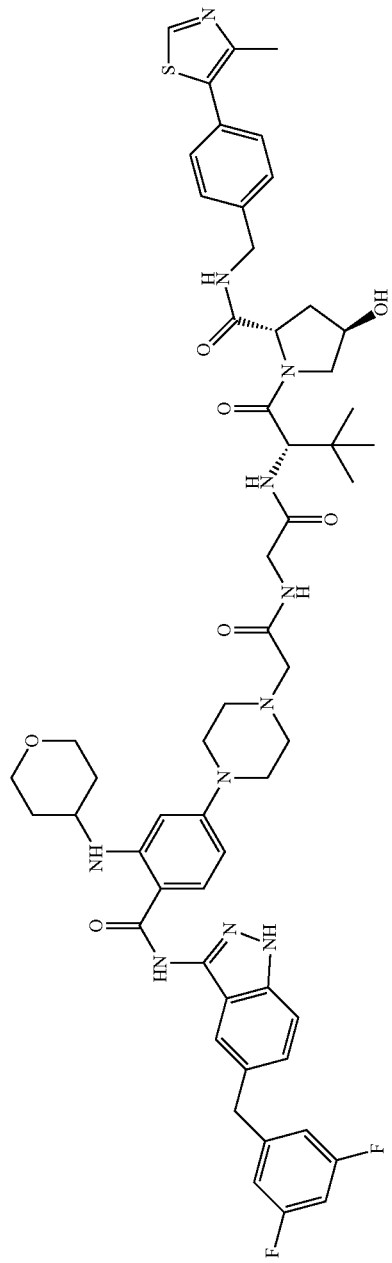
CPD-063
(TR-063)
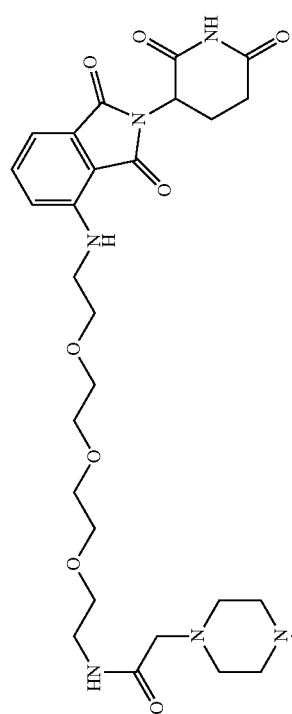
CPD-064
(TR-064)

TABLE 1-continued
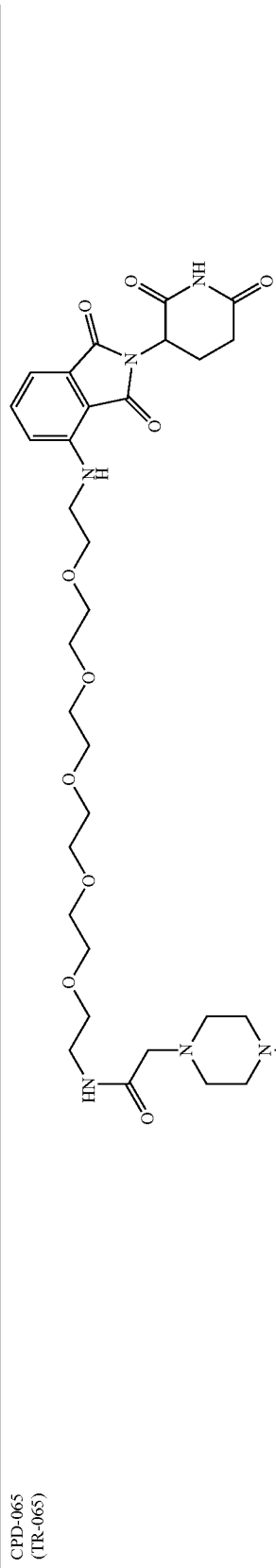
CPD-065
(TR-065)
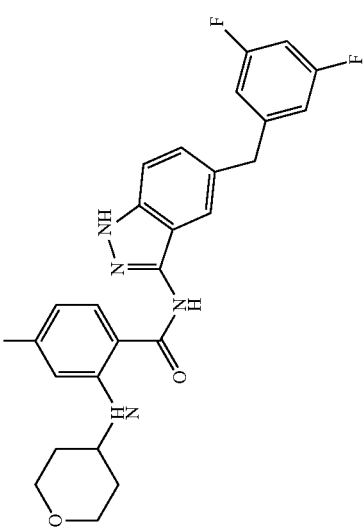
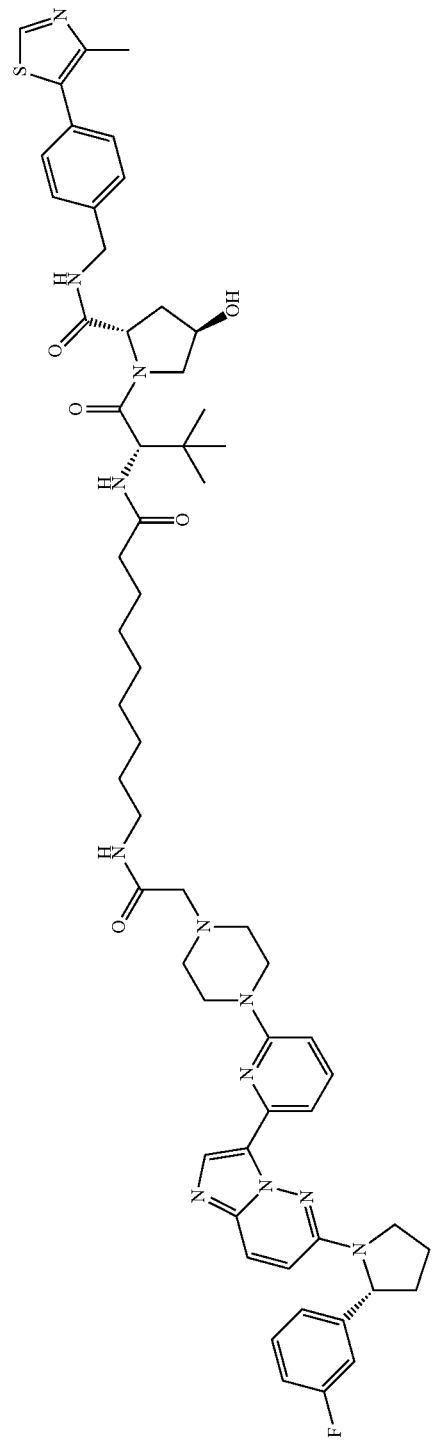
CPD-066

TABLE 1-continued
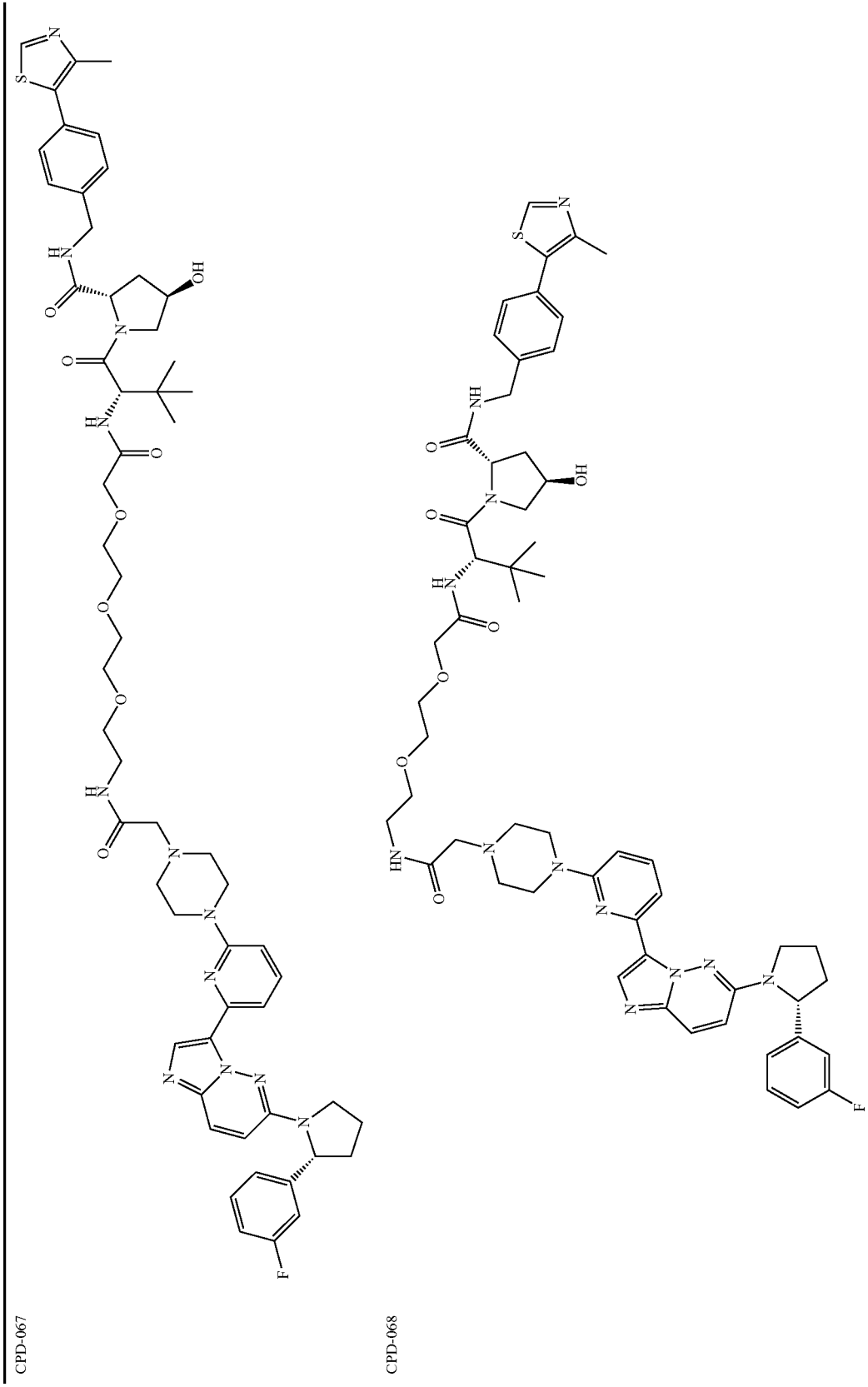
CPD-067
CPD-068

TABLE 1-continued
| CPD-069 | 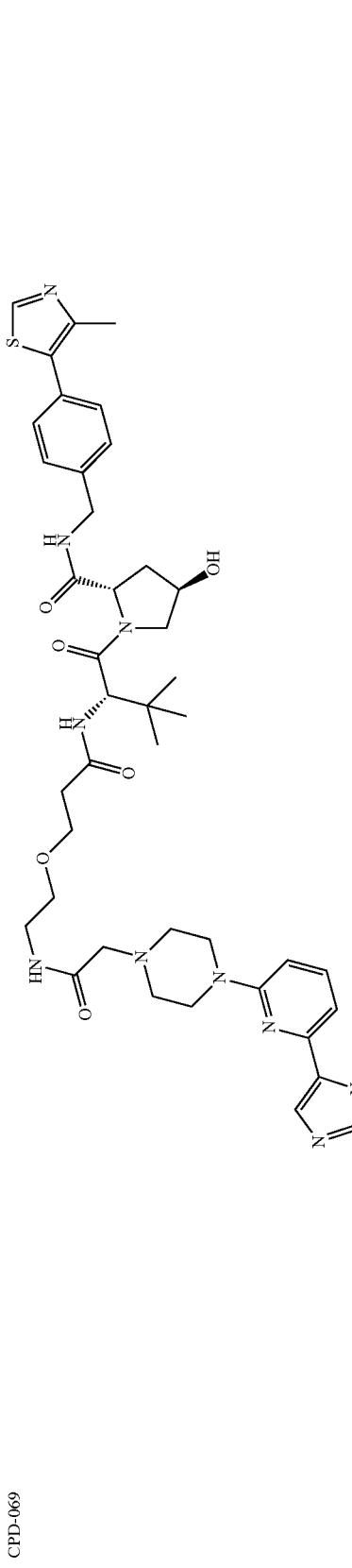 |
| CPD-070 | 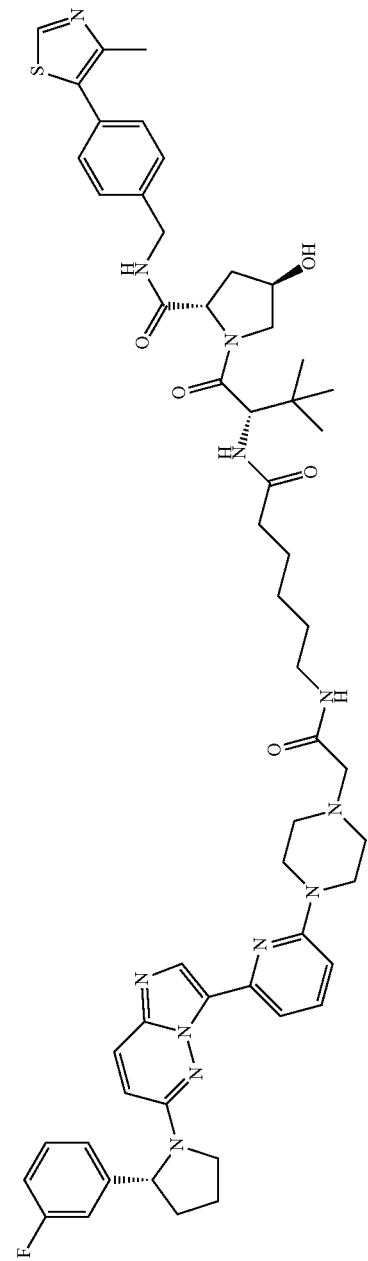 |

TABLE 1-continued
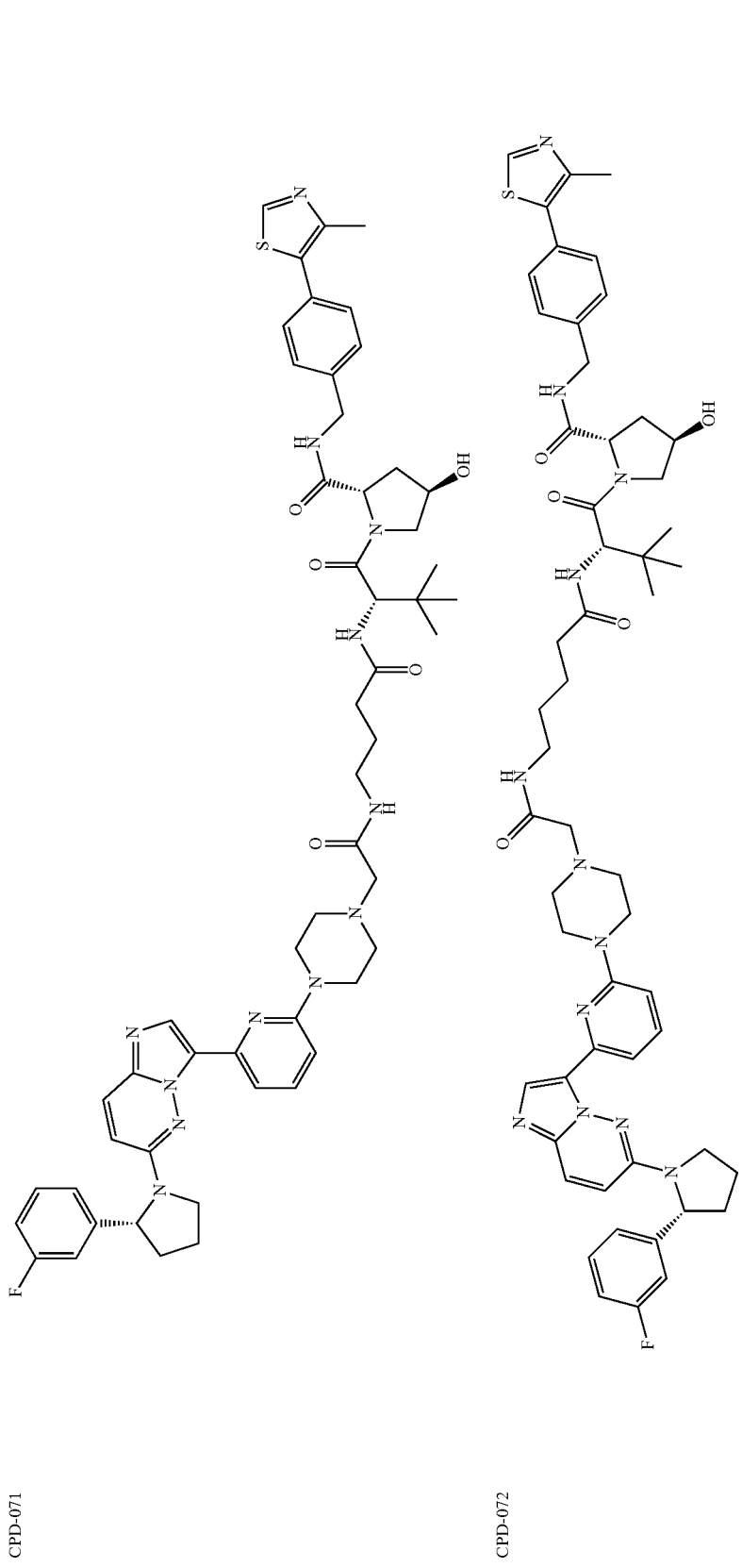
CPD-071
CPD-072

TABLE 1-continued
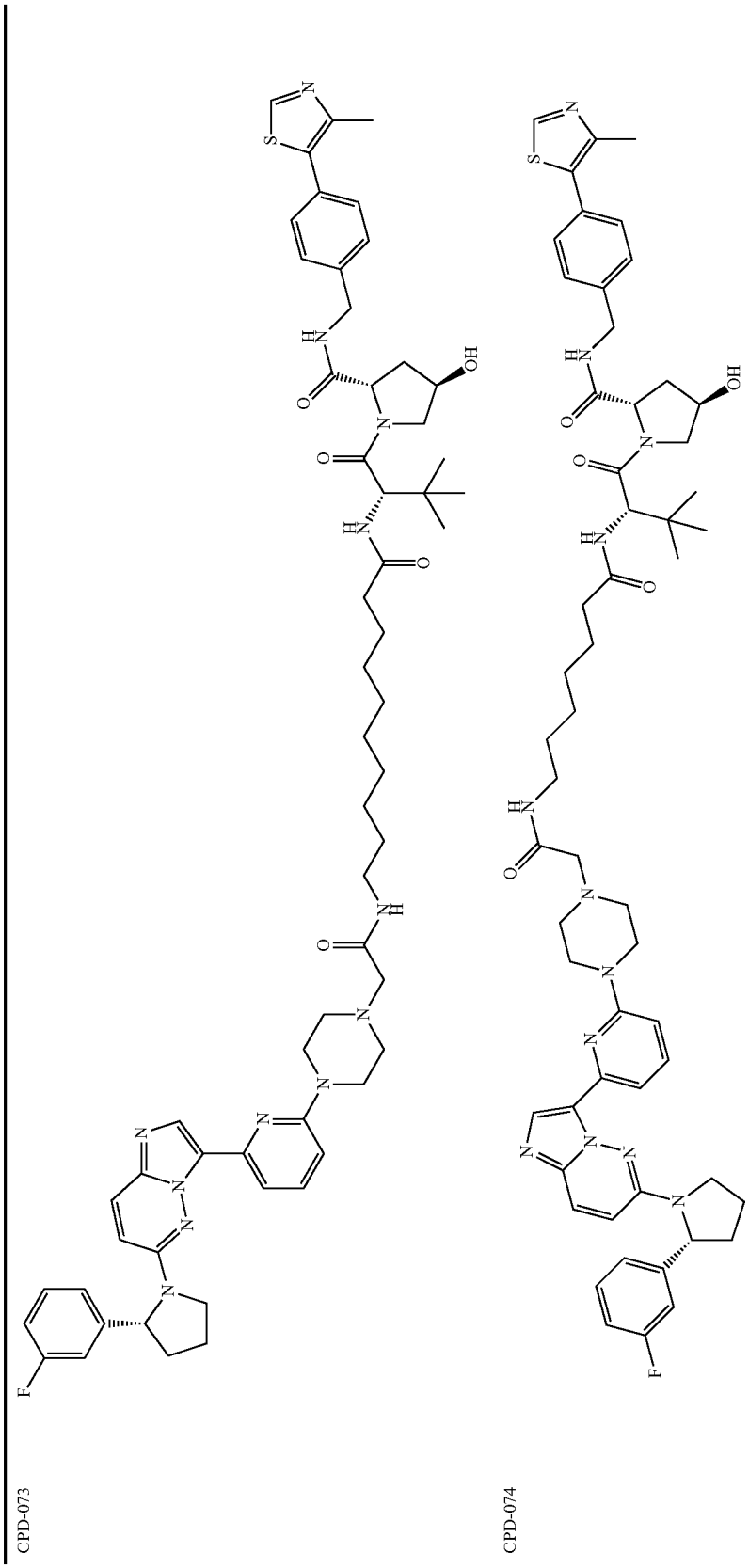
CPD-073
CPD-074

TABLE 1-continued
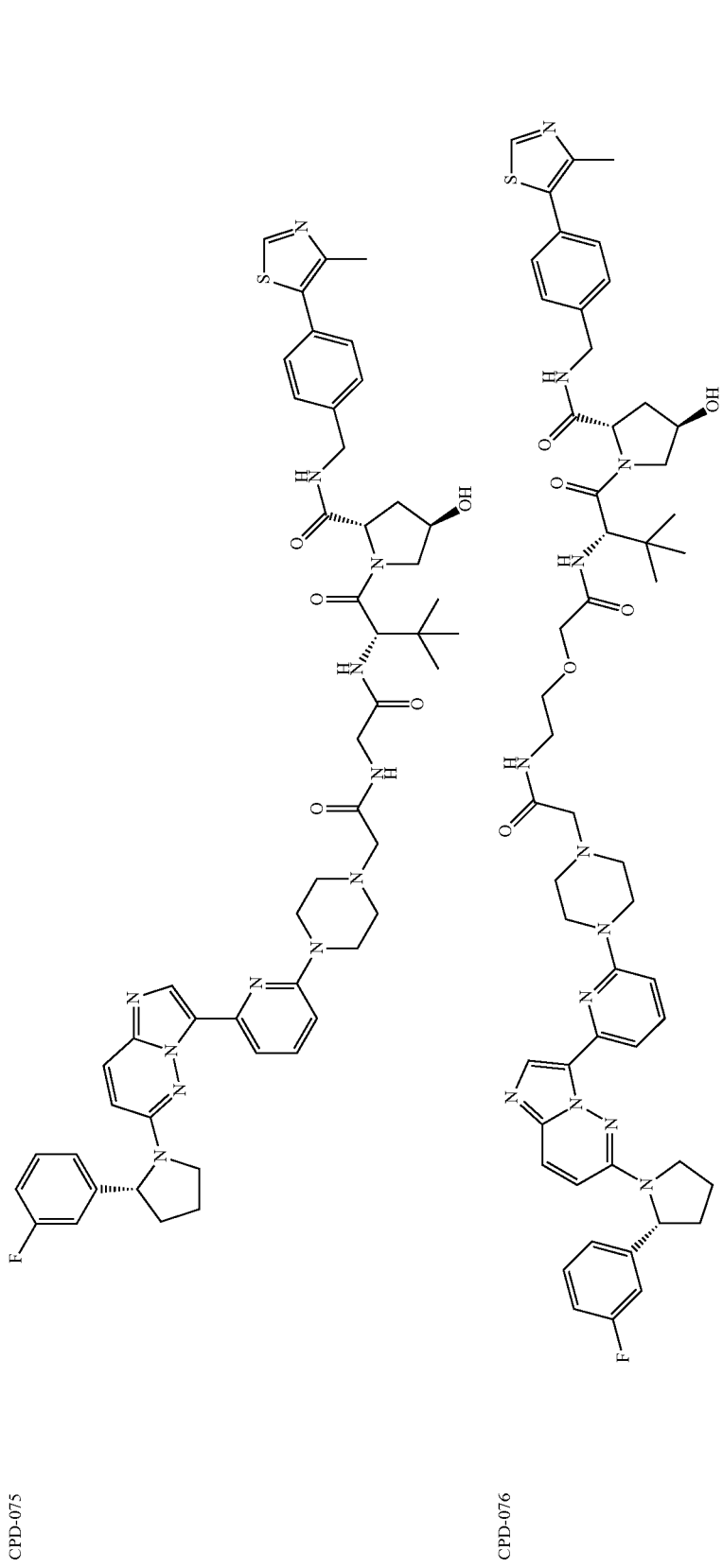
CPD-075
CPD-076

TABLE 1-continued
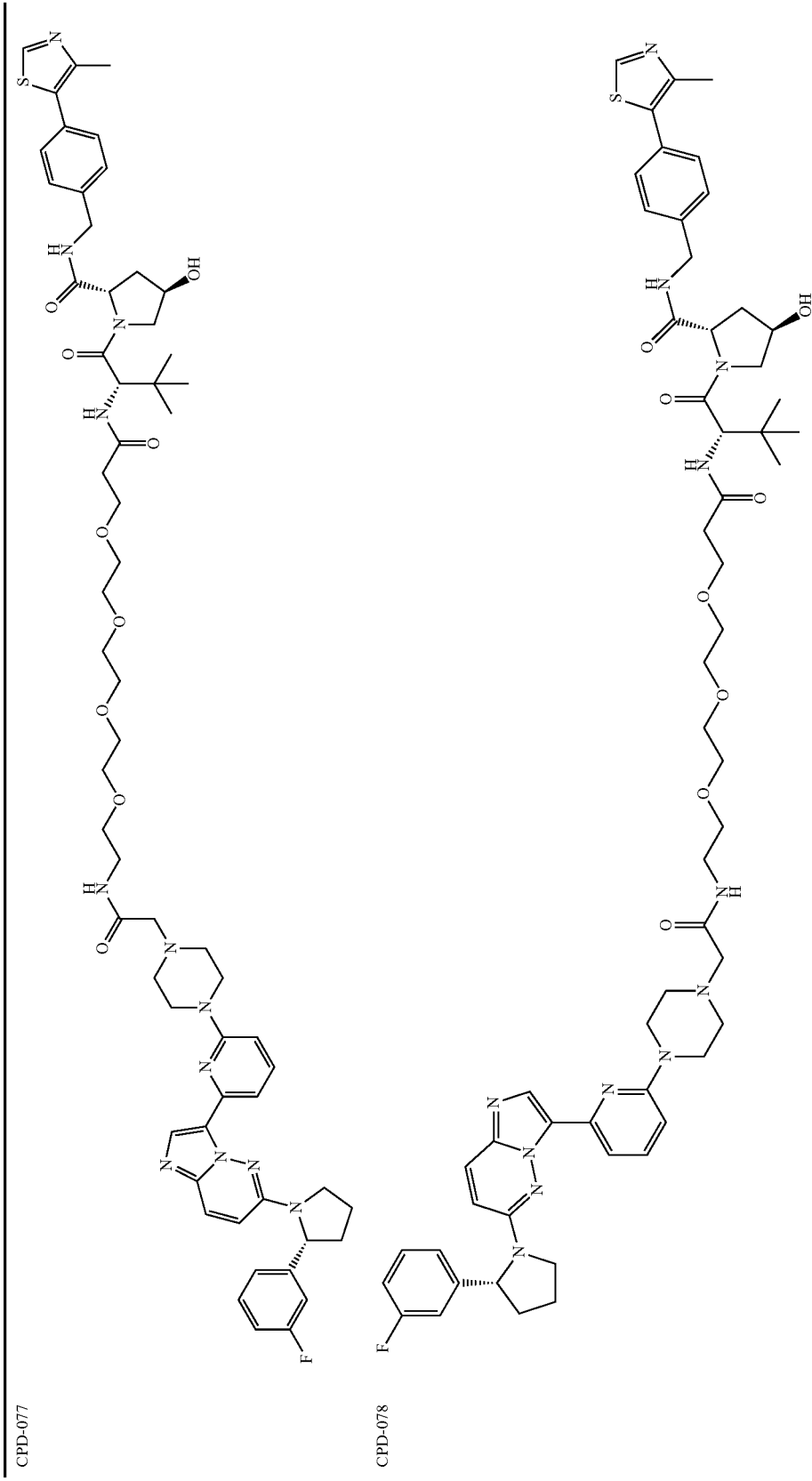
CPD-077
CPD-078

TABLE 1-continued
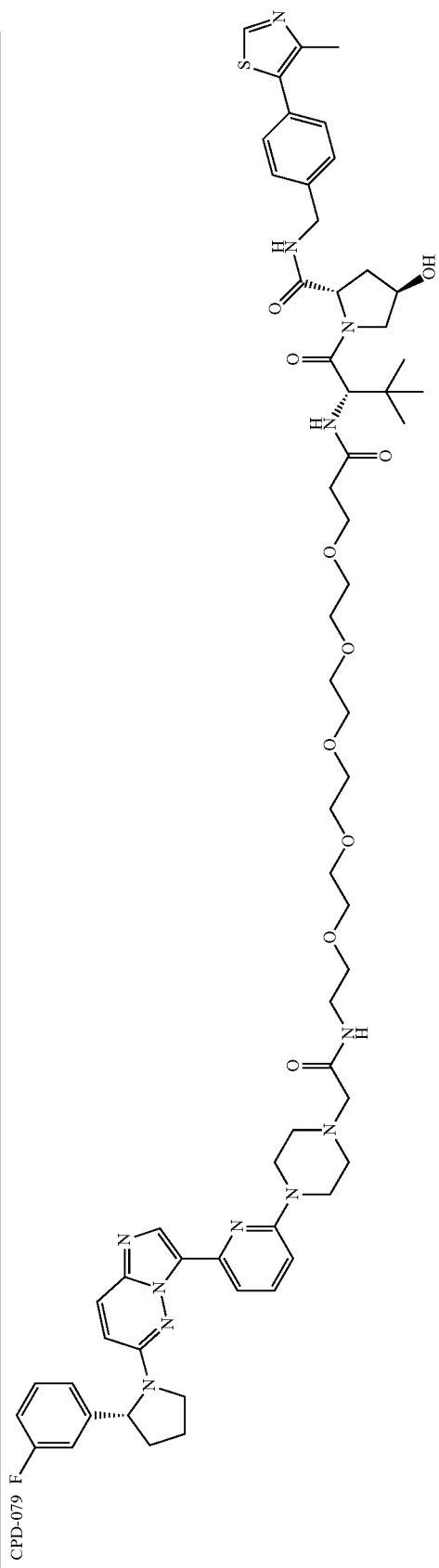
CPD-079
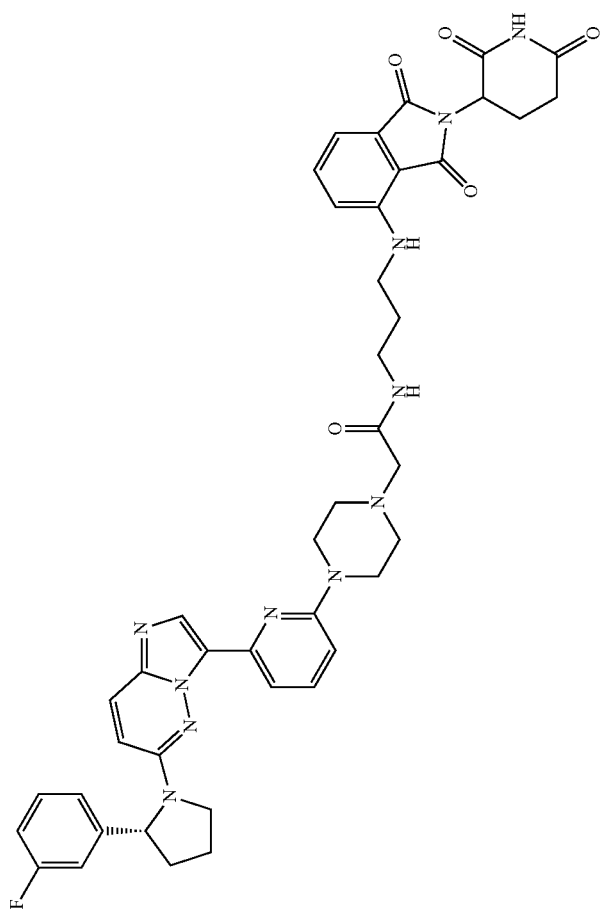
CPD-080
(TR-109)

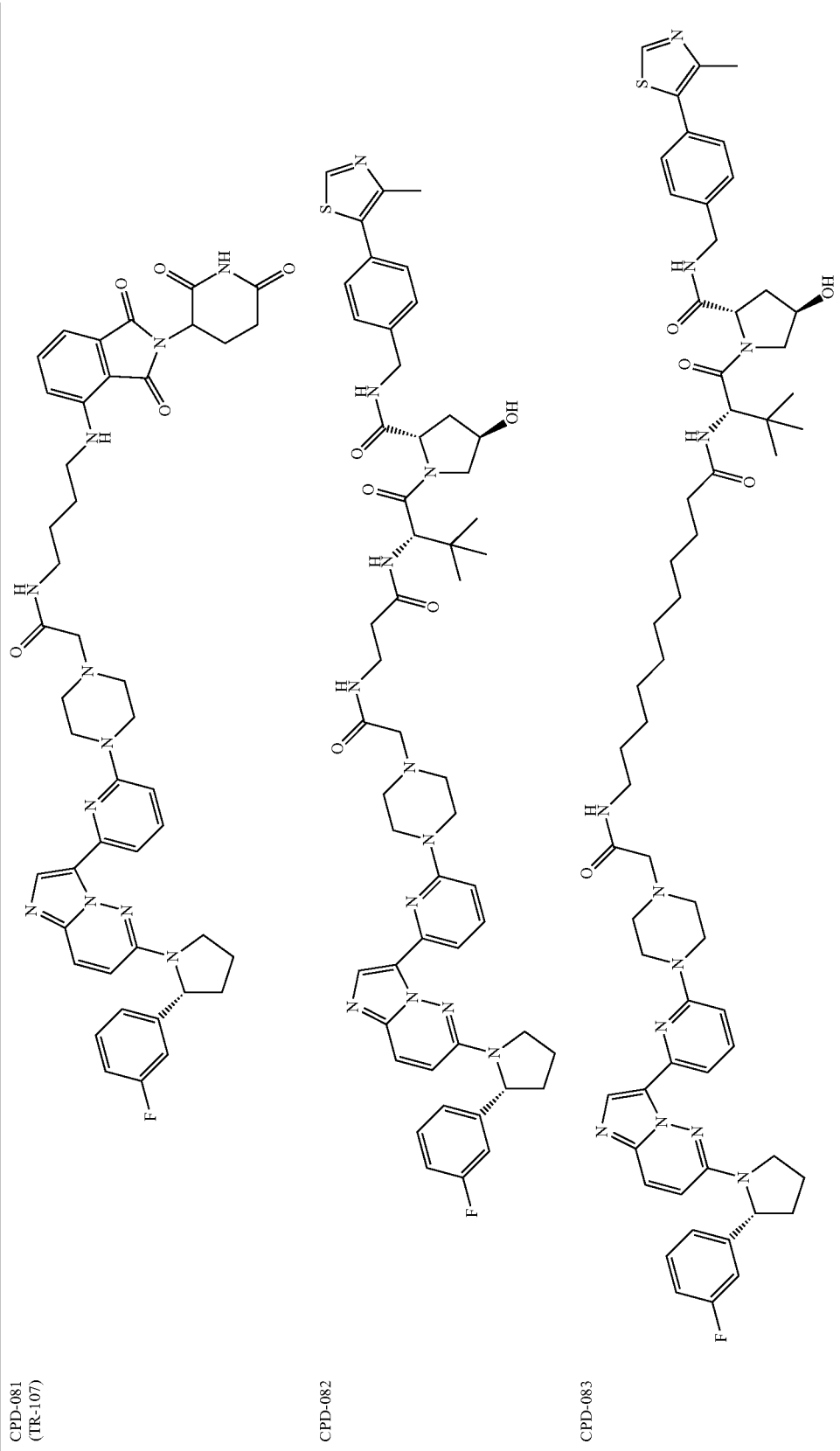

TABLE 1-continued
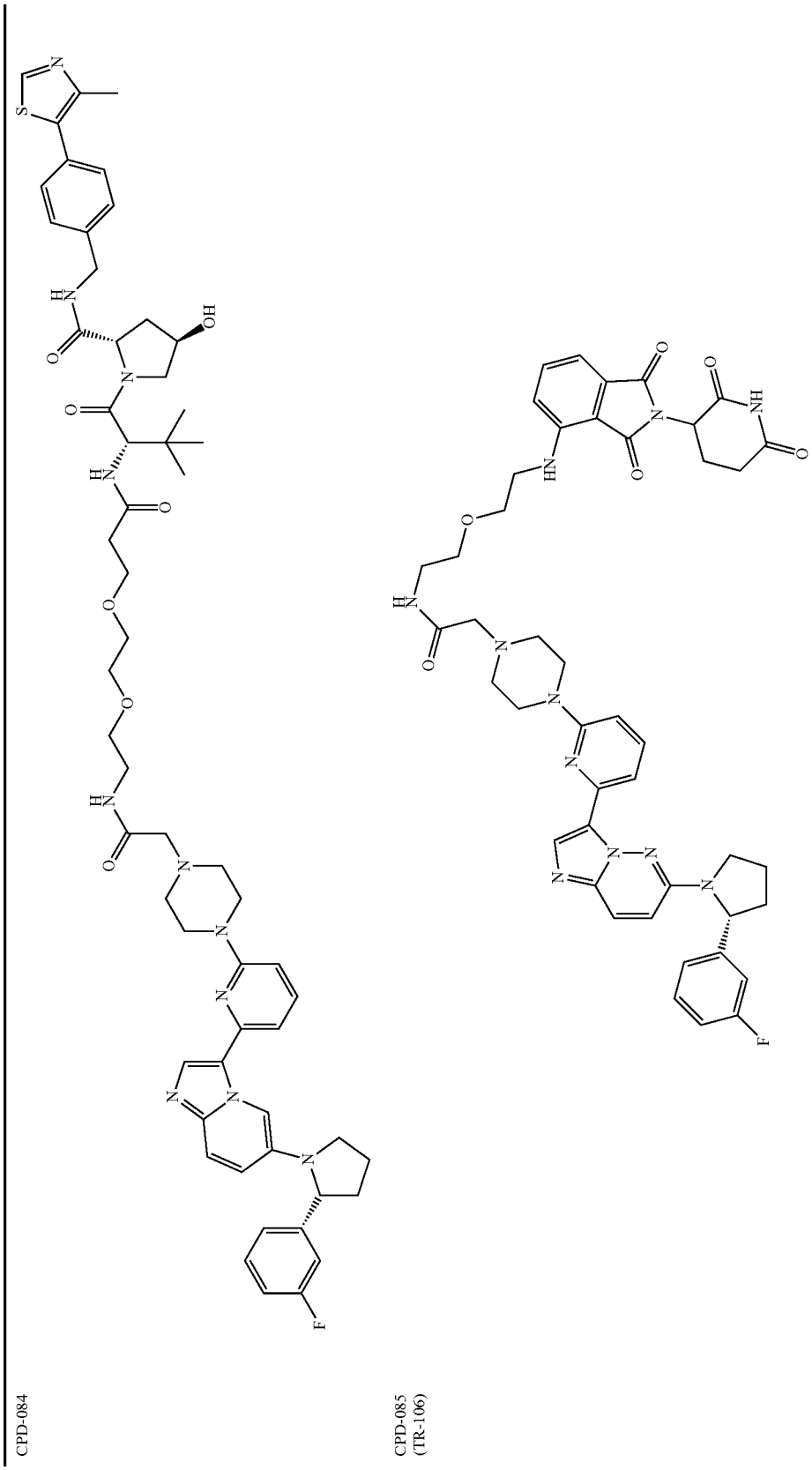
CPD-084
CPD-085
(TR-106)

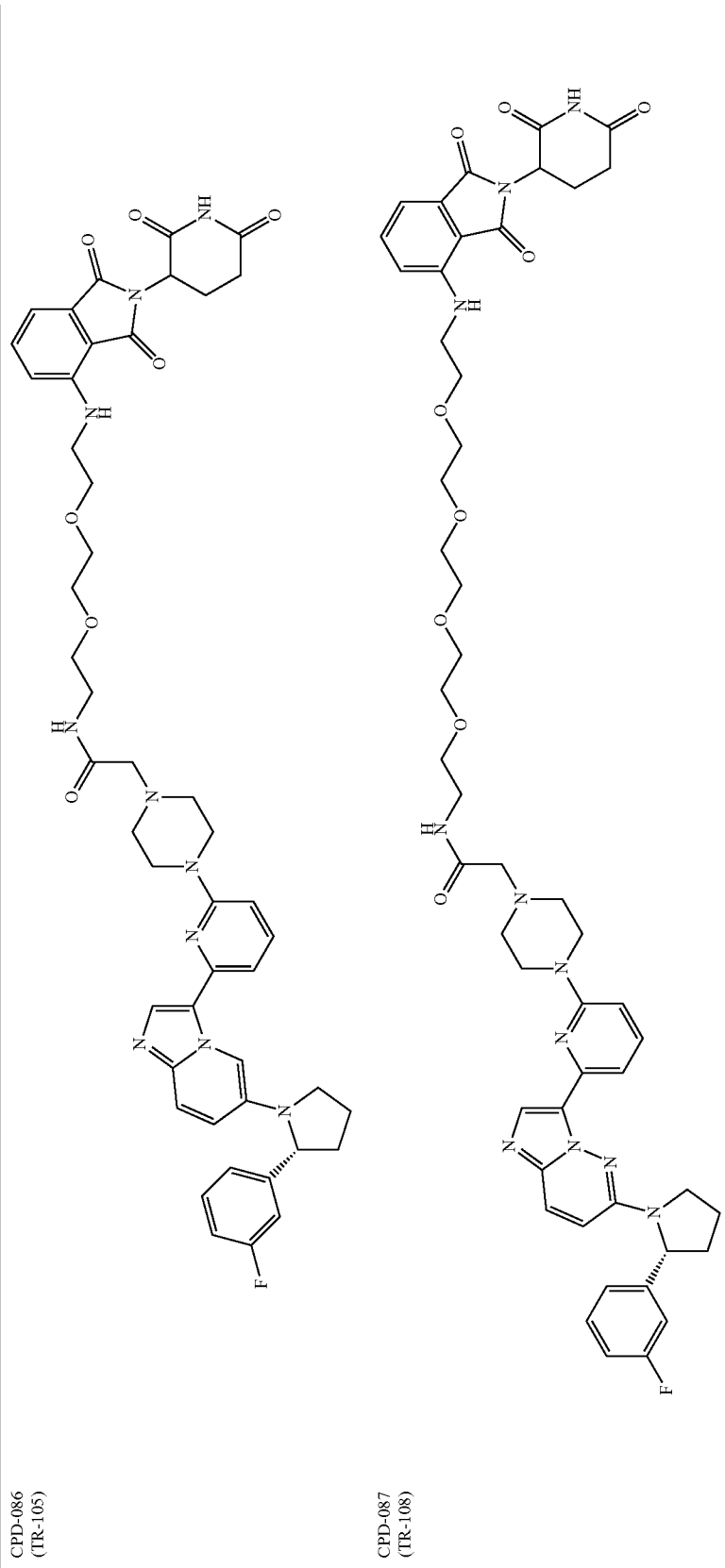

TABLE 1-continued
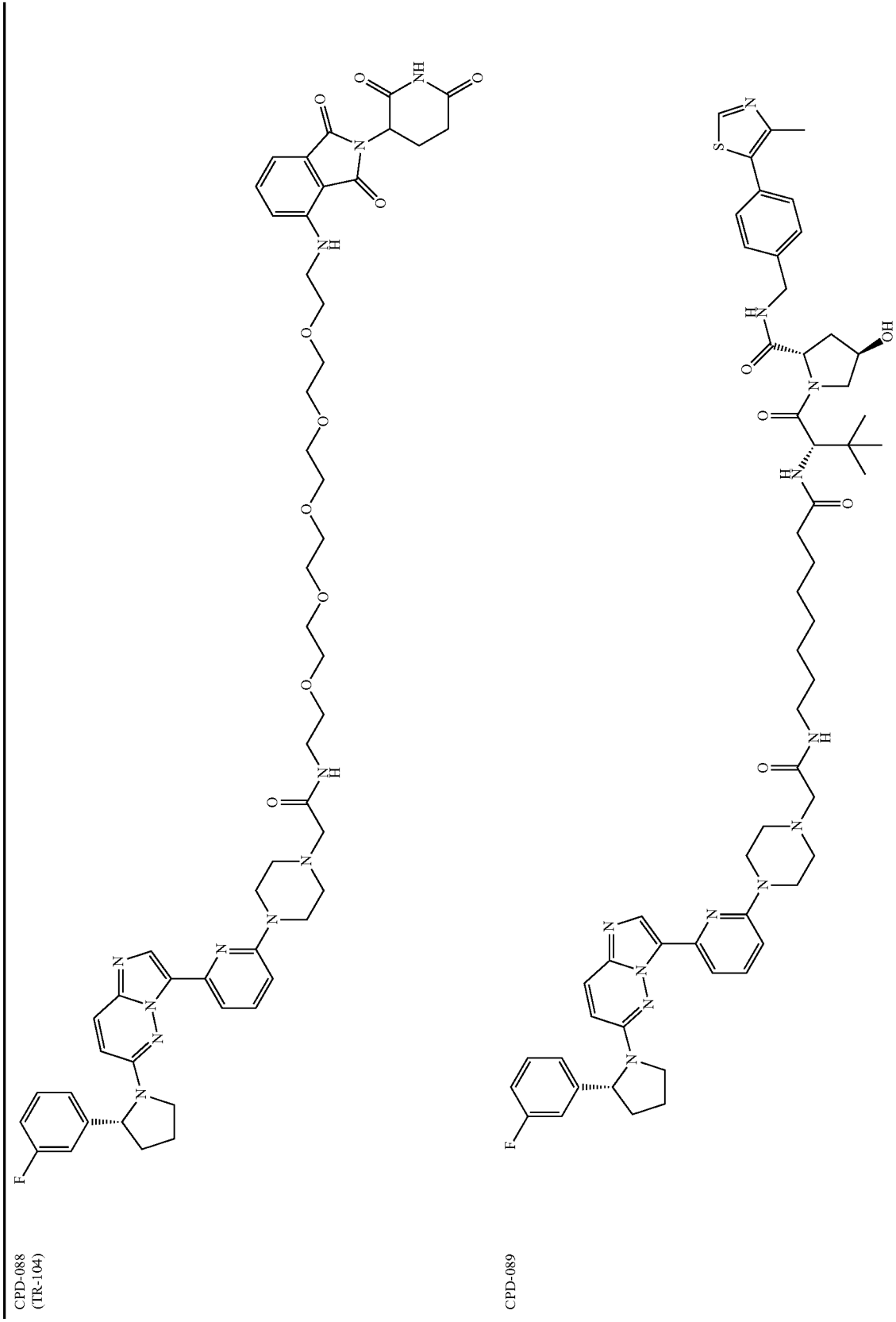
CPD-088
(TR-104)
CPD-089

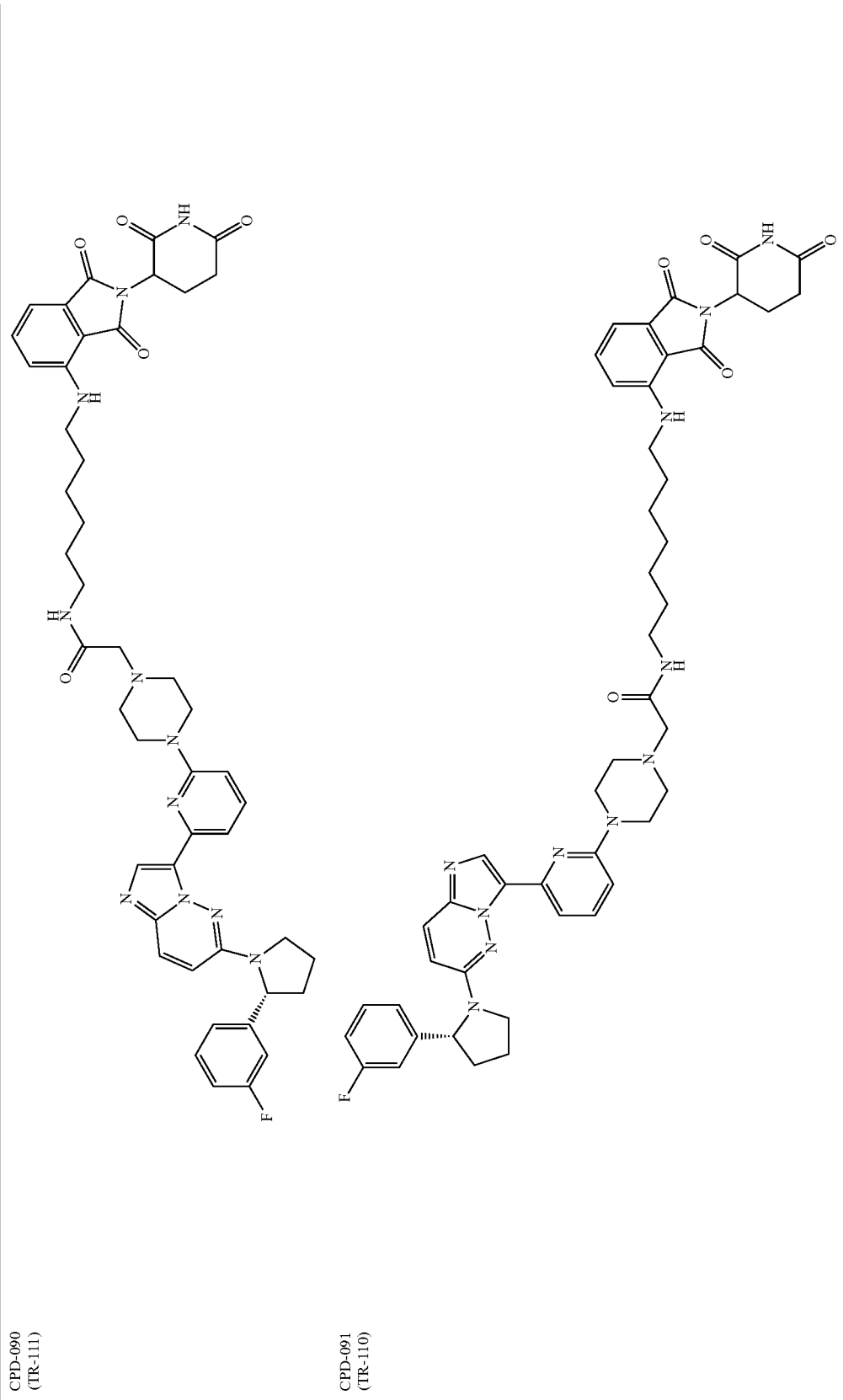

TABLE 1-continued
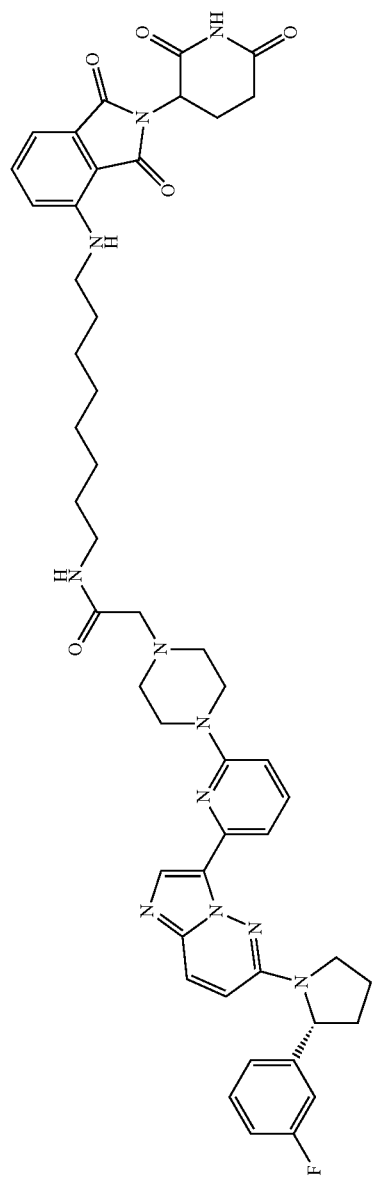
CPD-092
(TR-102)
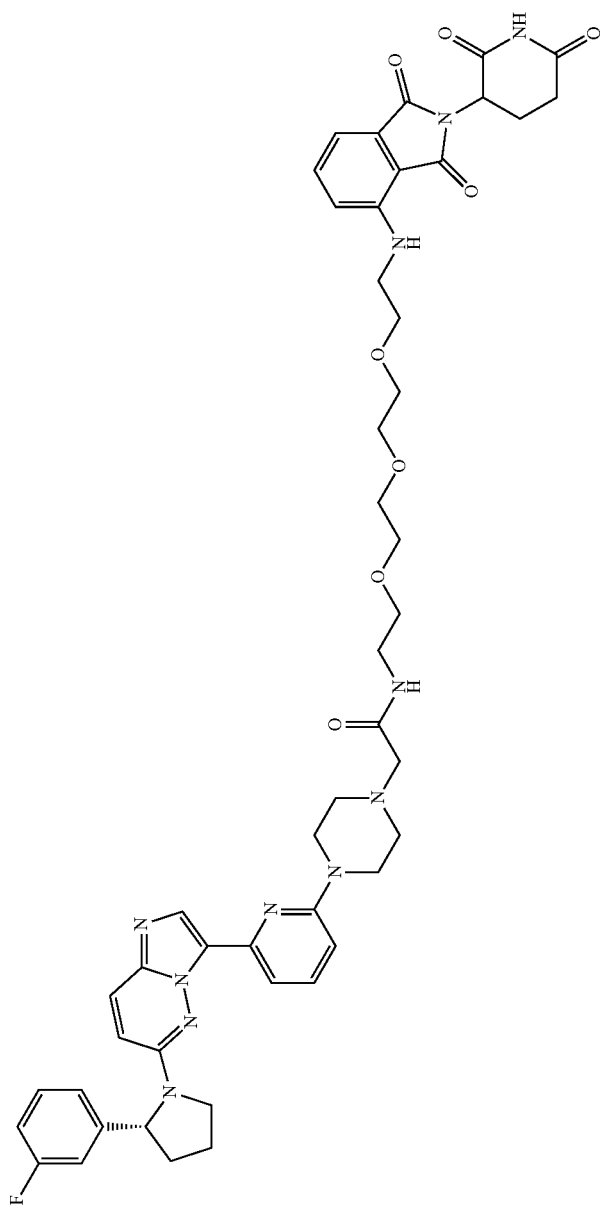
CPD-093
(TR-059)

TABLE 1-continued
CPD-094
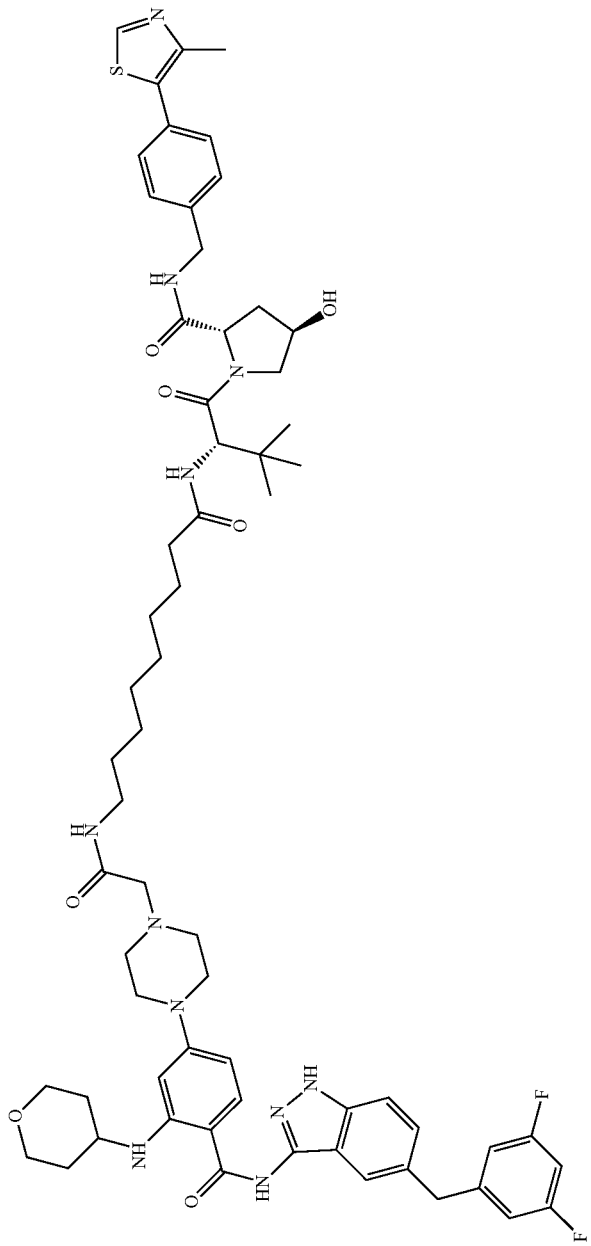

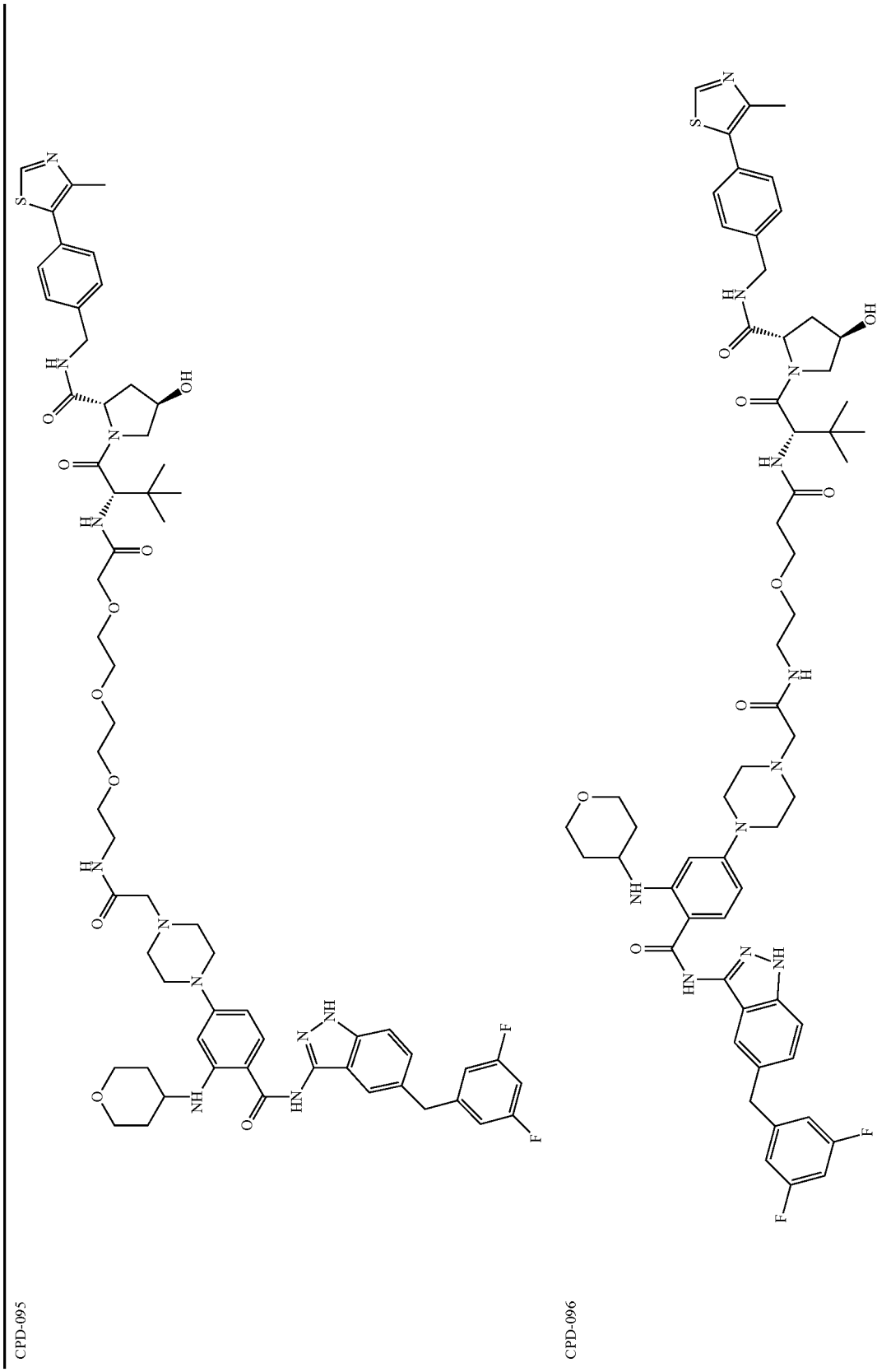

TABLE 1-continued
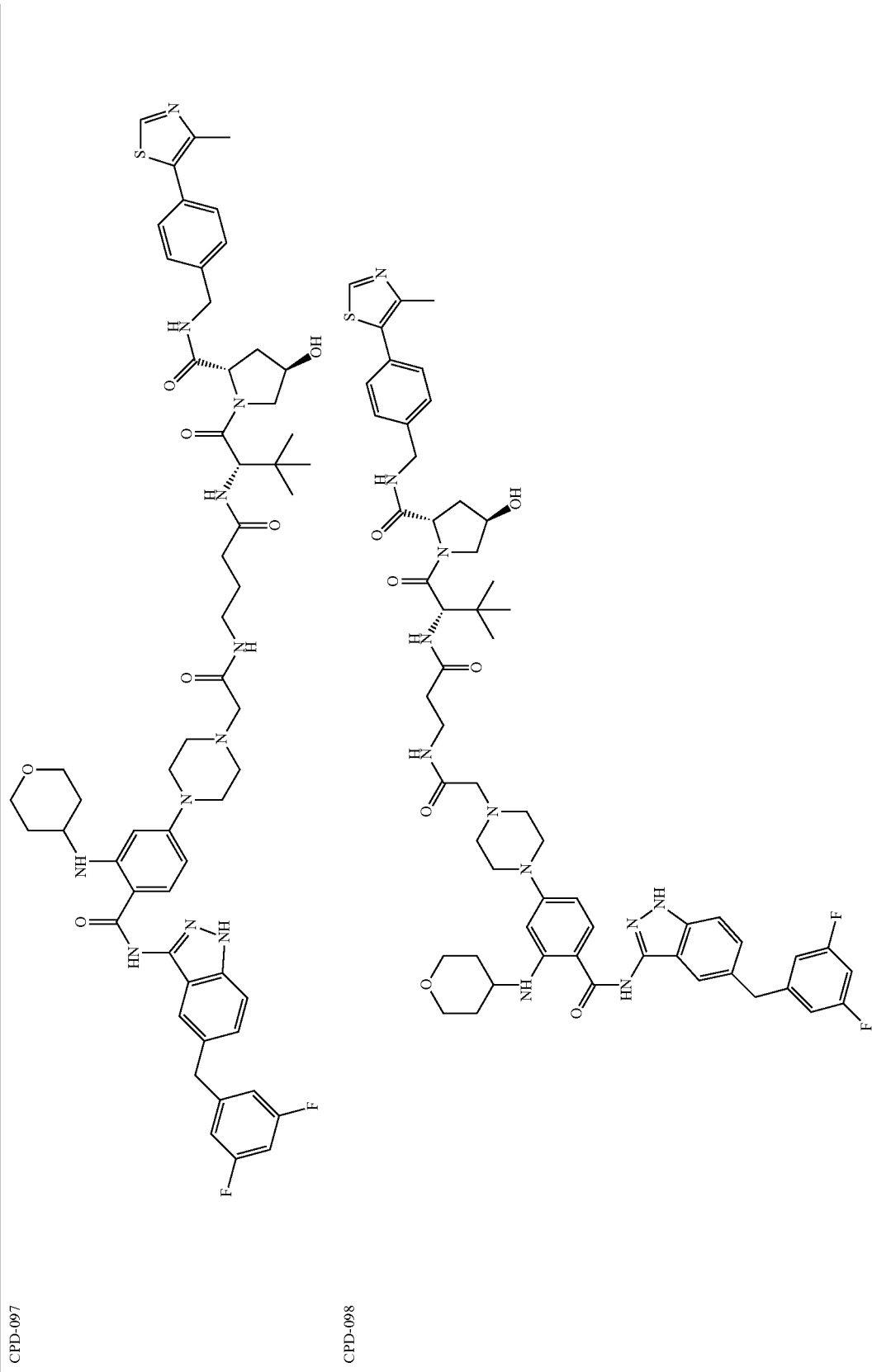
CPD-097
CPD-098

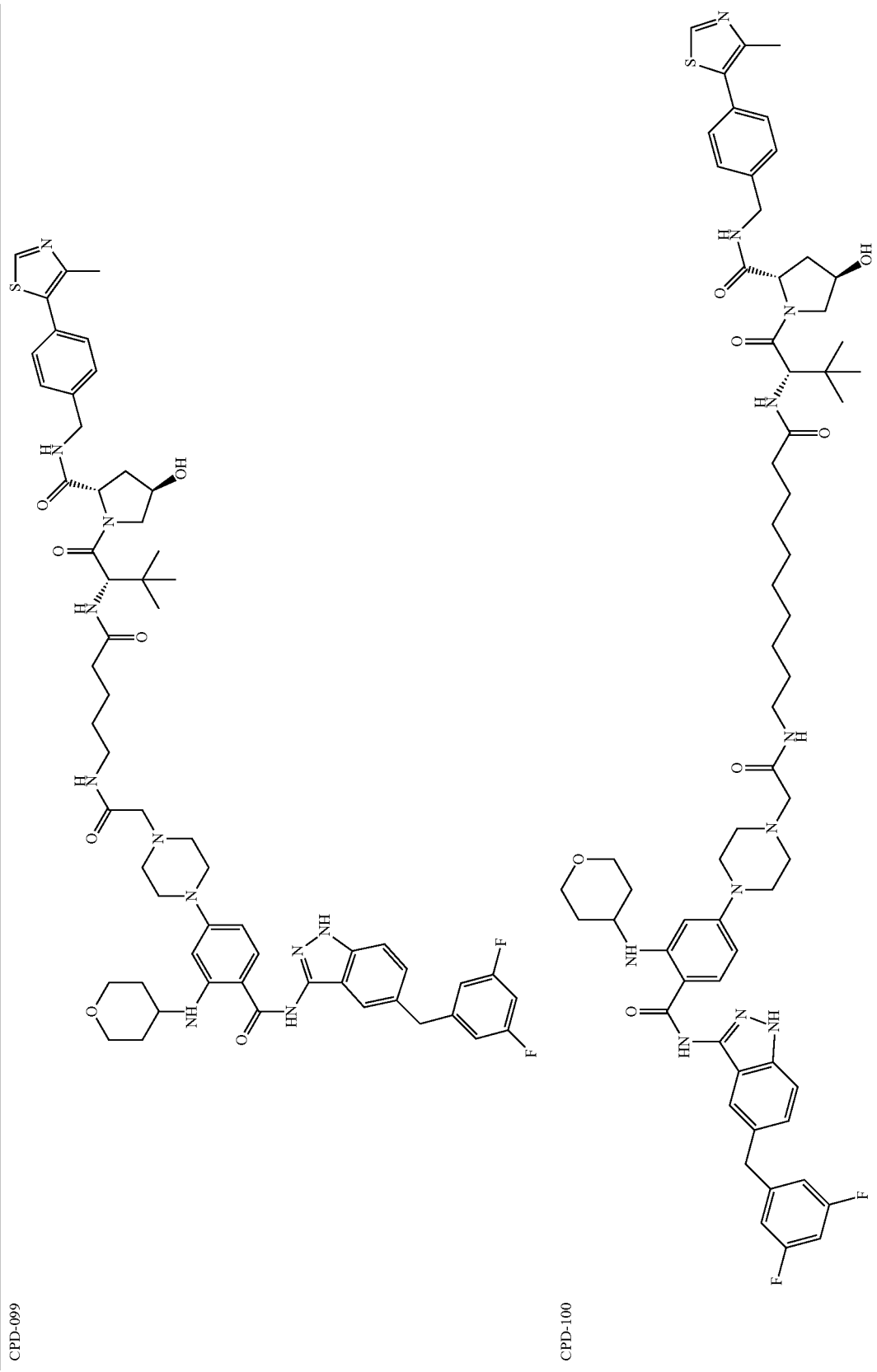

TABLE 1-continued
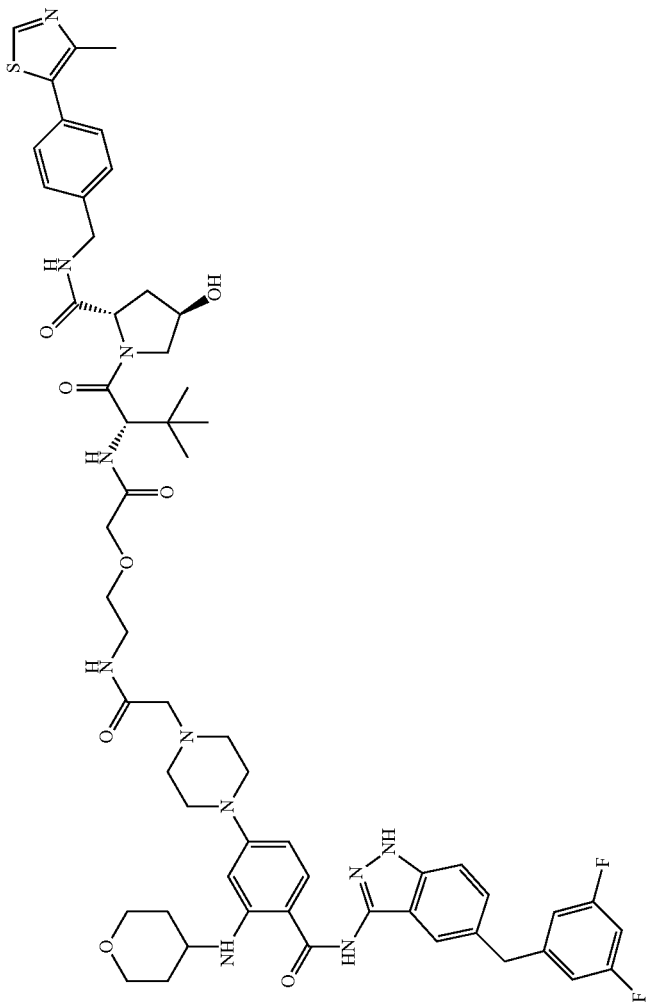
CPD-101

TABLE 1-continued
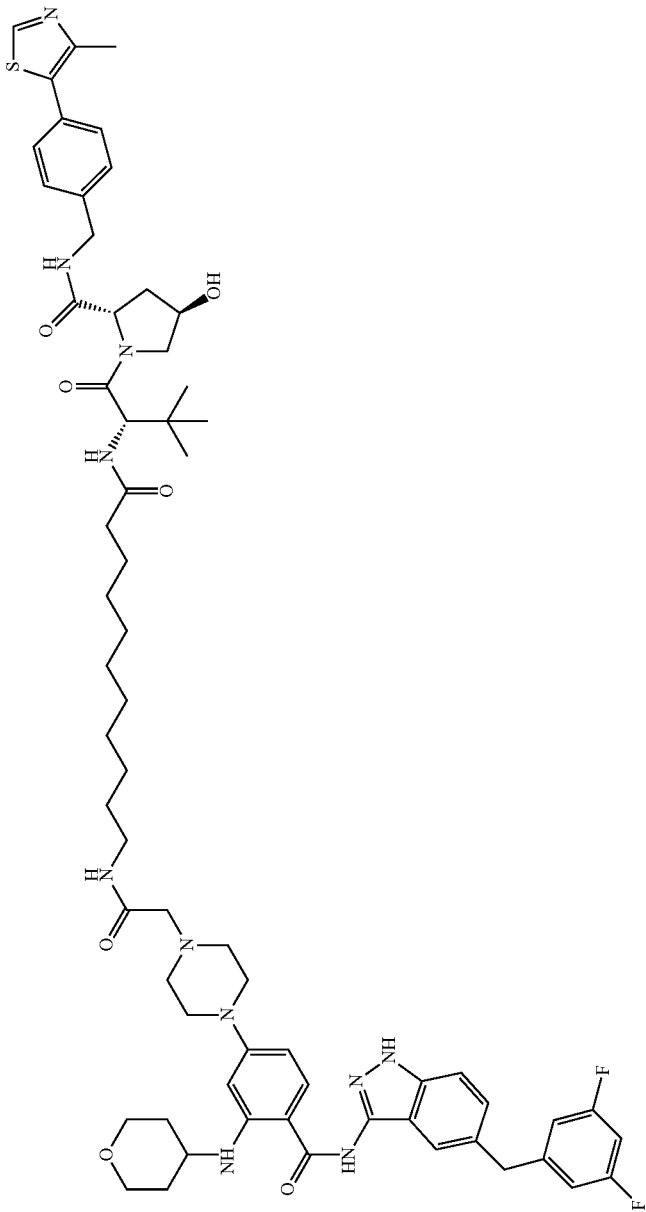
CPD-102

TABLE 1-continued
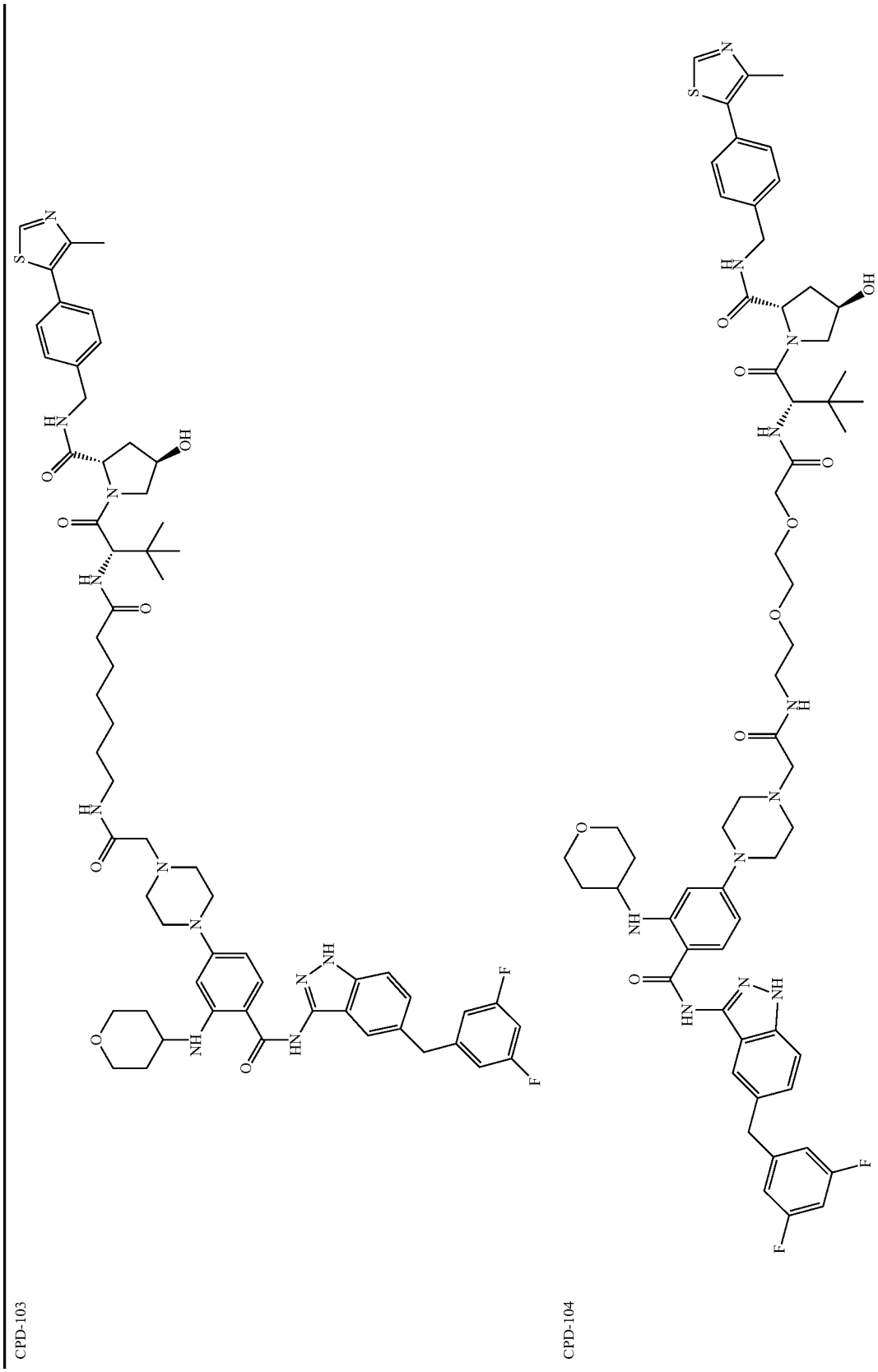
CPD-103
CPD-104

TABLE 1-continued
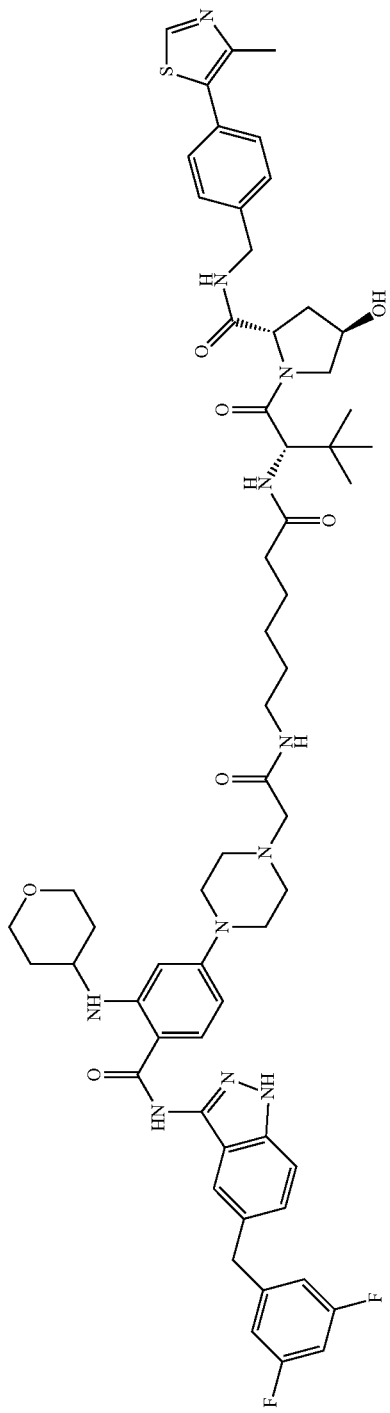
CPD-105
CPD-106
(TR-155)

TABLE 1-continued
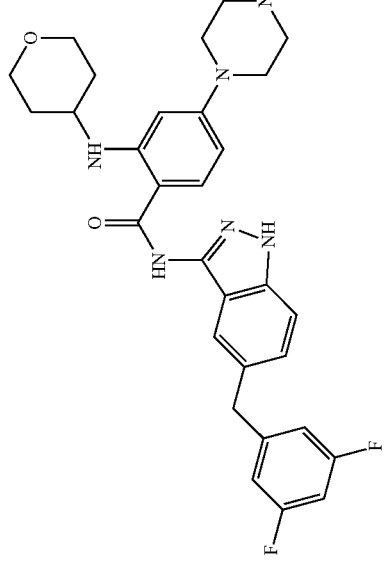
CPD-107
(TR-152)
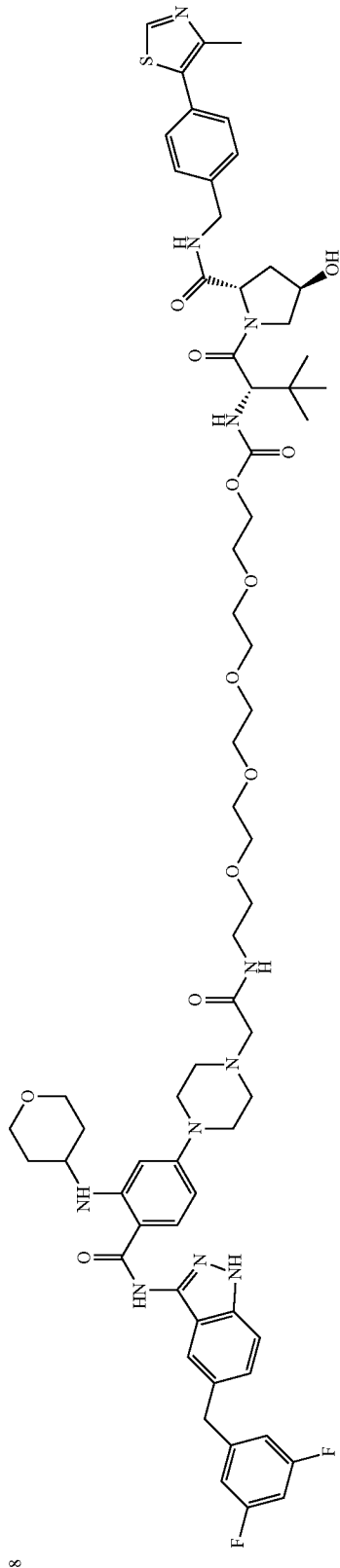
CPD-108

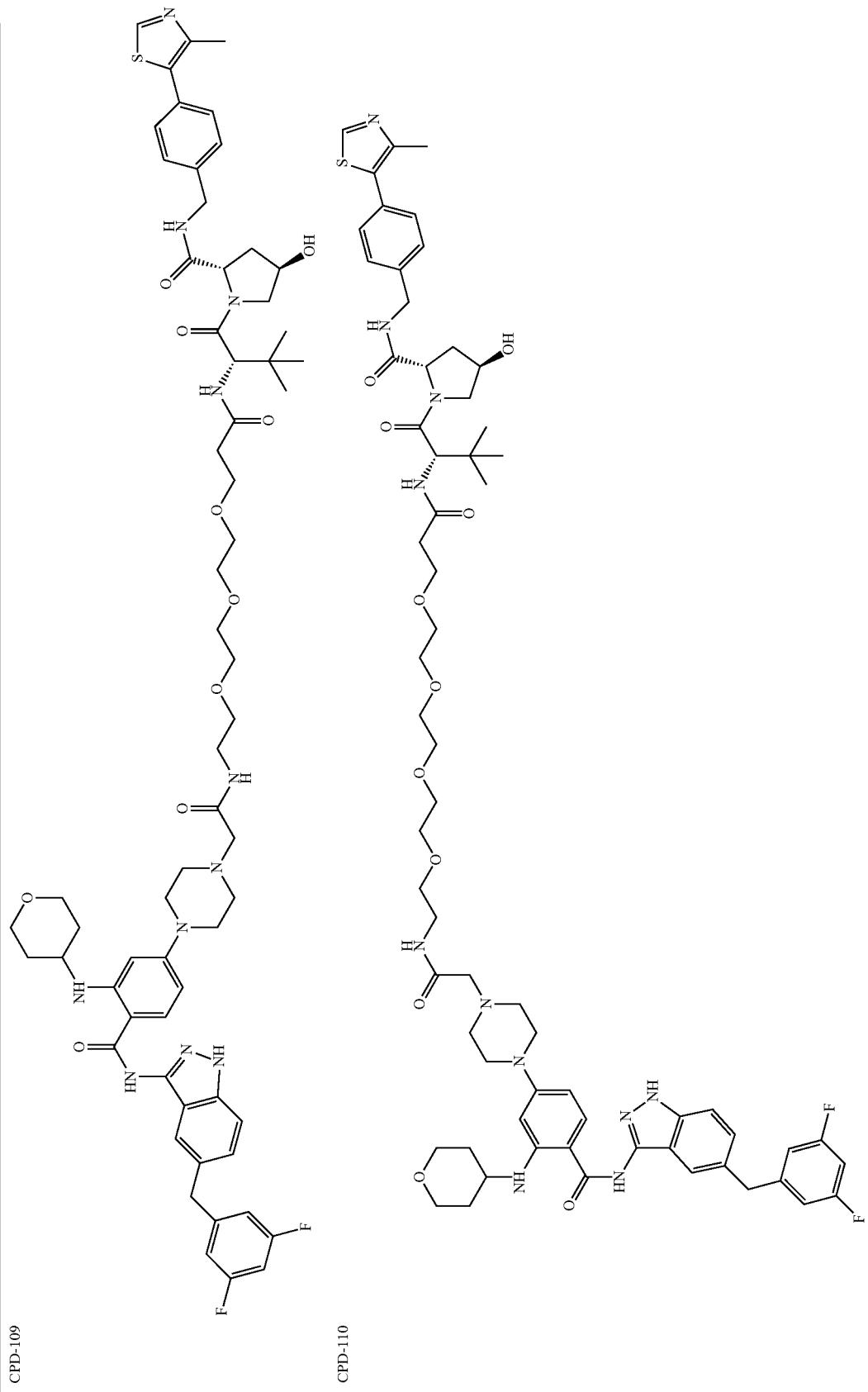

TABLE 1-continued
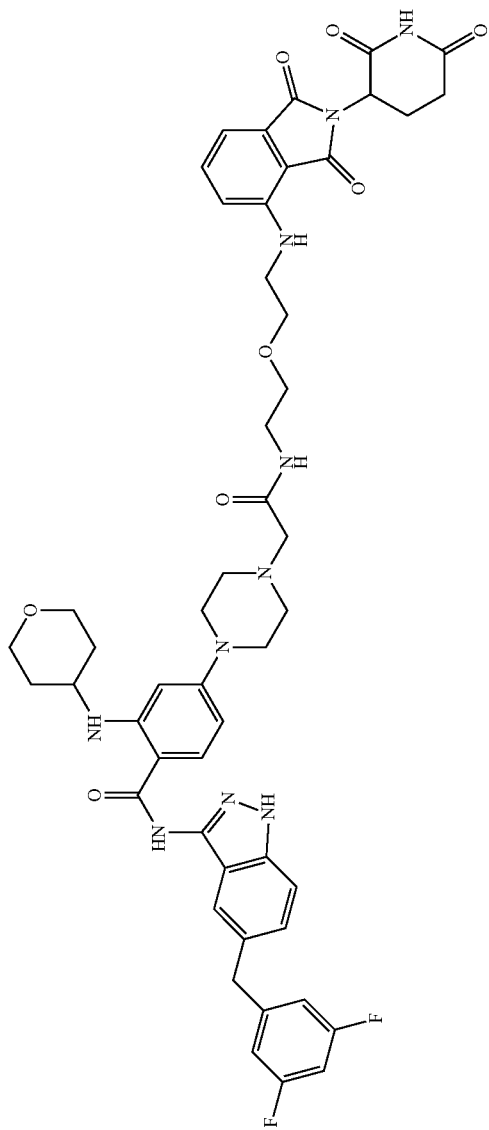
CPD-111
(TR-151)

TABLE 1-continued
CPD-112
(TR-153)
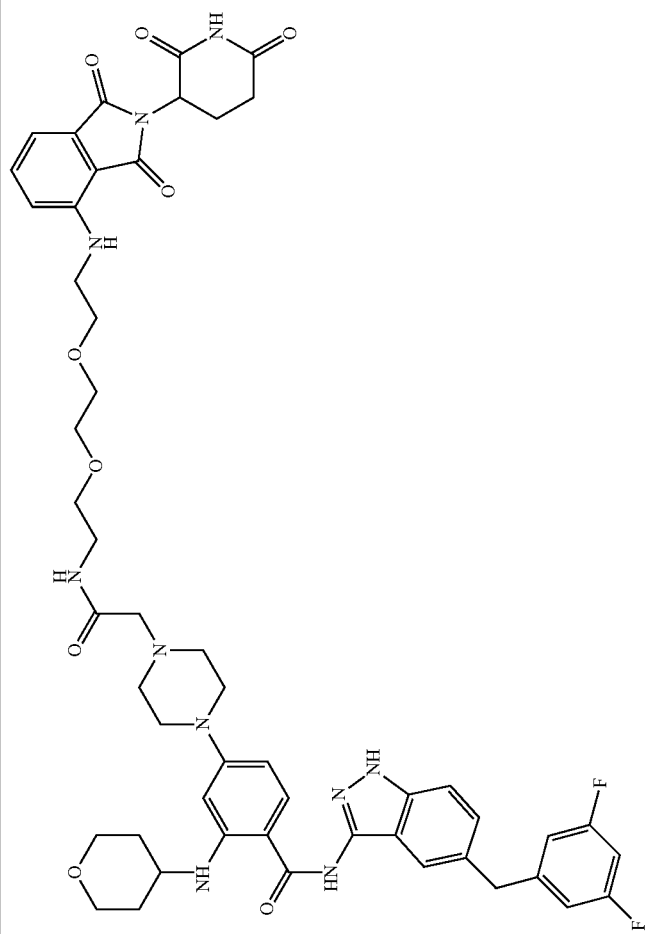

TABLE 1-continued
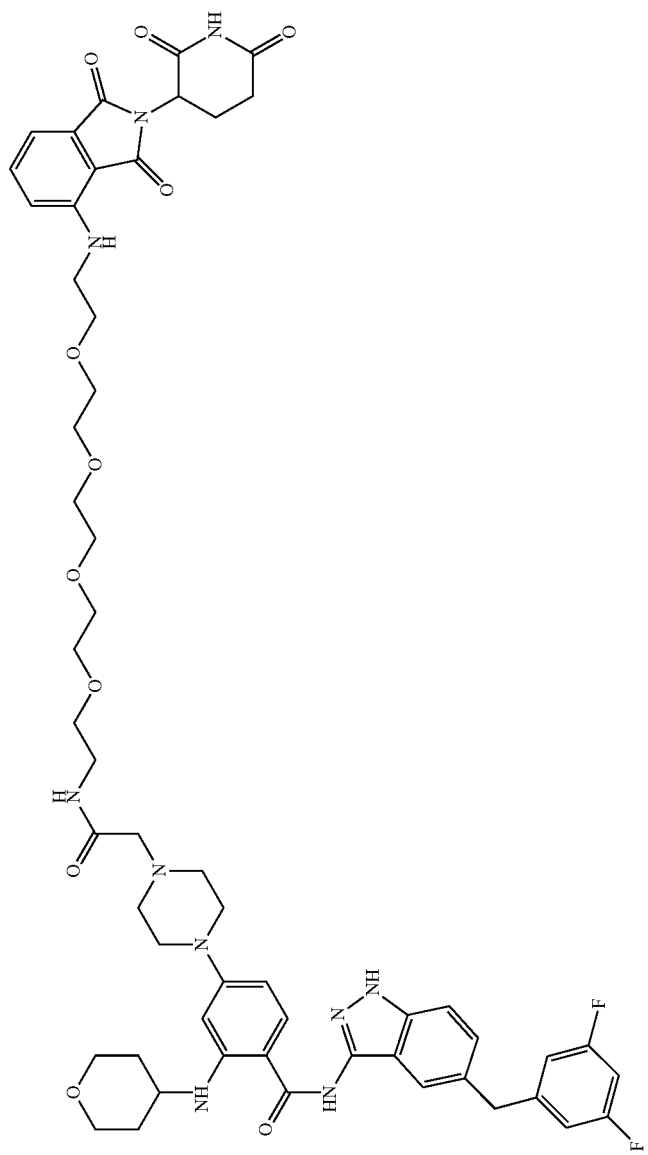
CPD-113
(TR-150)

TABLE 1-continued
CPD-114
(TR-149)
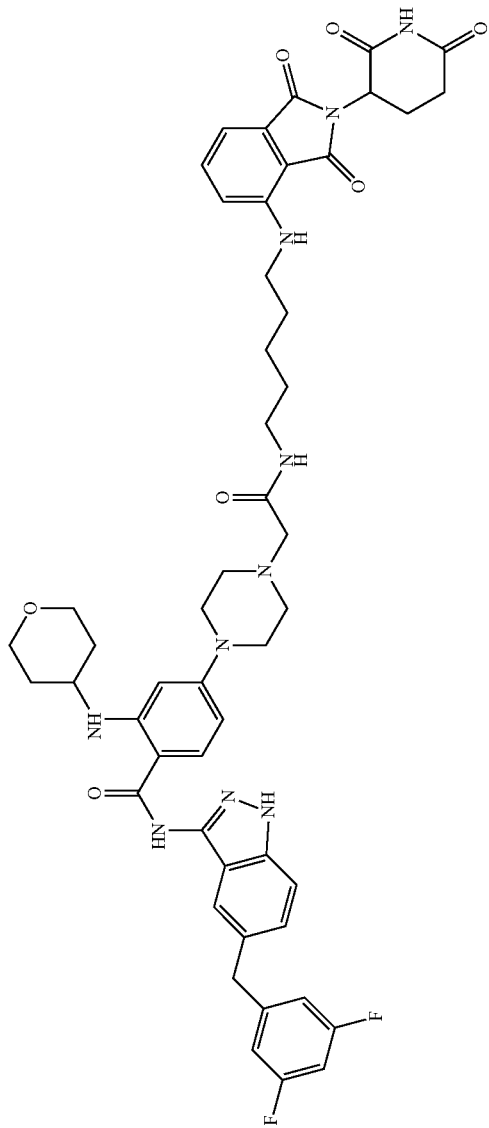

TABLE 1-continued
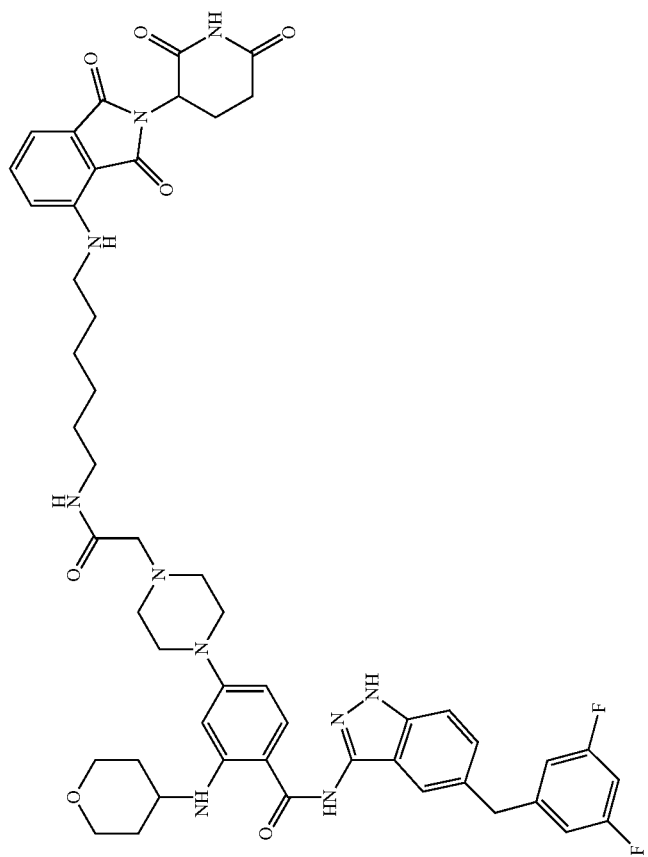
CPD-115
(TR-147)

TABLE 1-continued
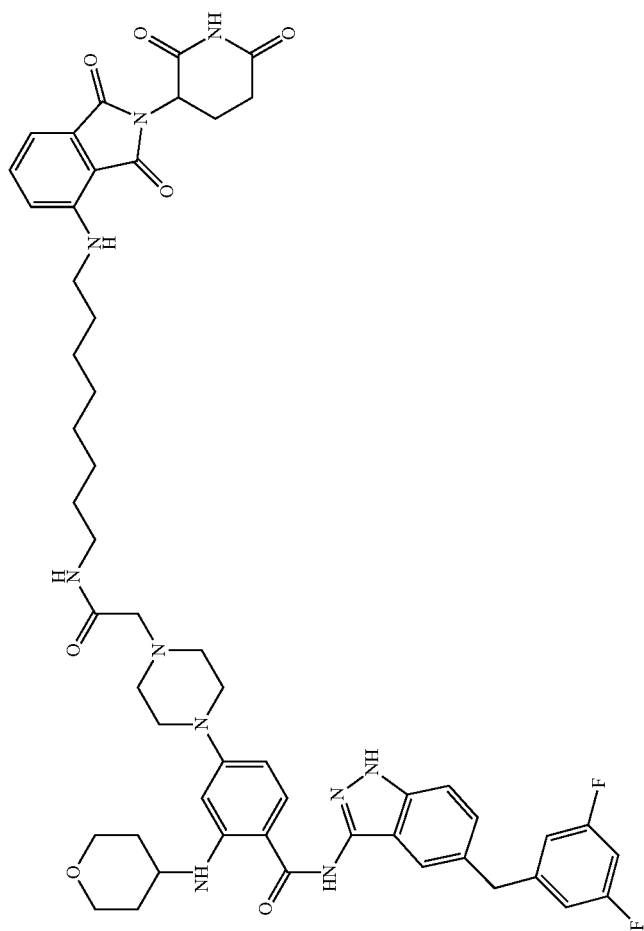
CPD-116
(TR-148)

TABLE 1-continued
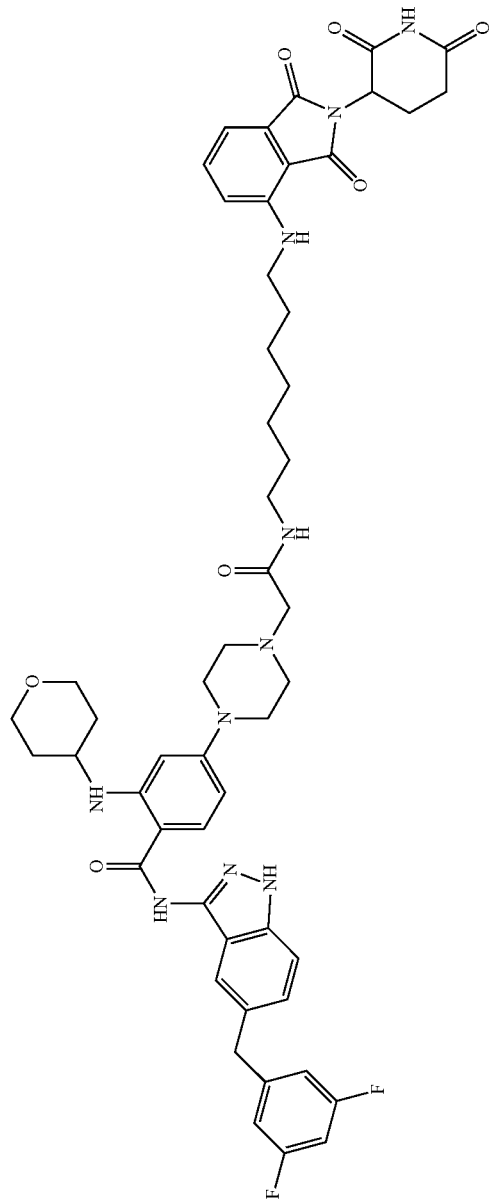
CPD-117
(TR-154)

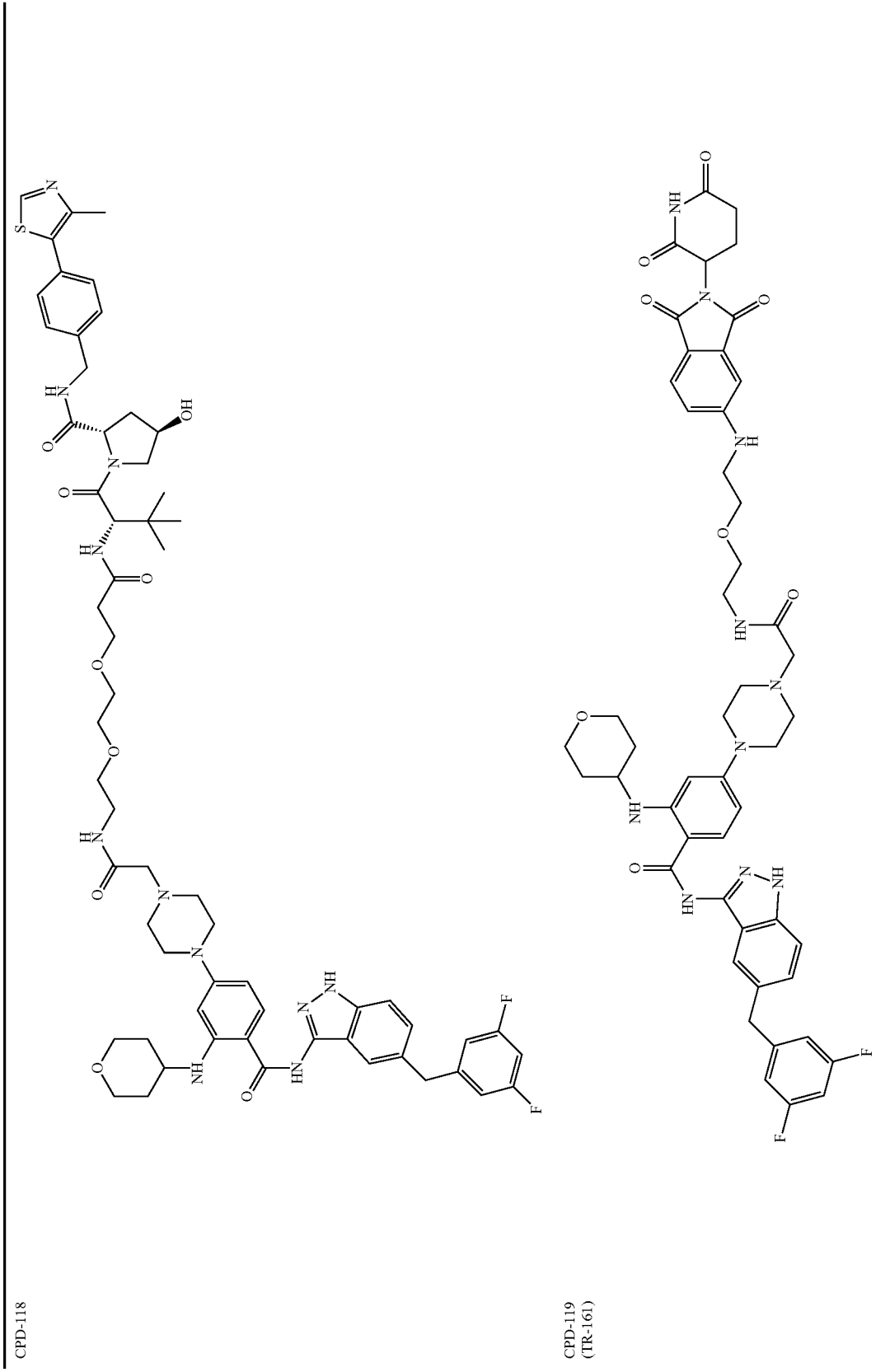

TABLE 1-continued
CPD-120
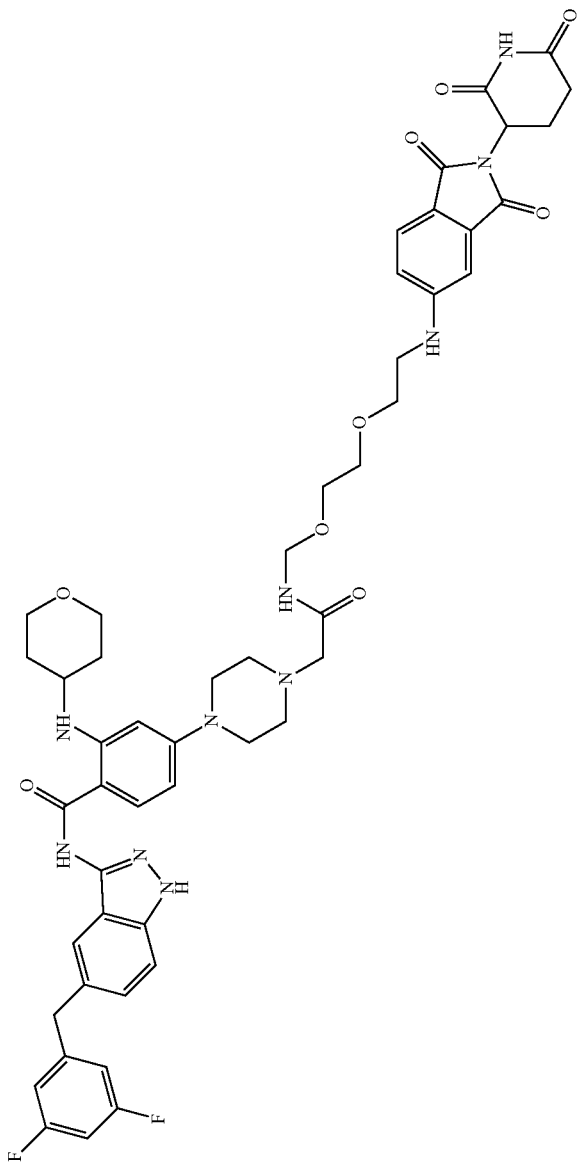

TABLE 1-continued
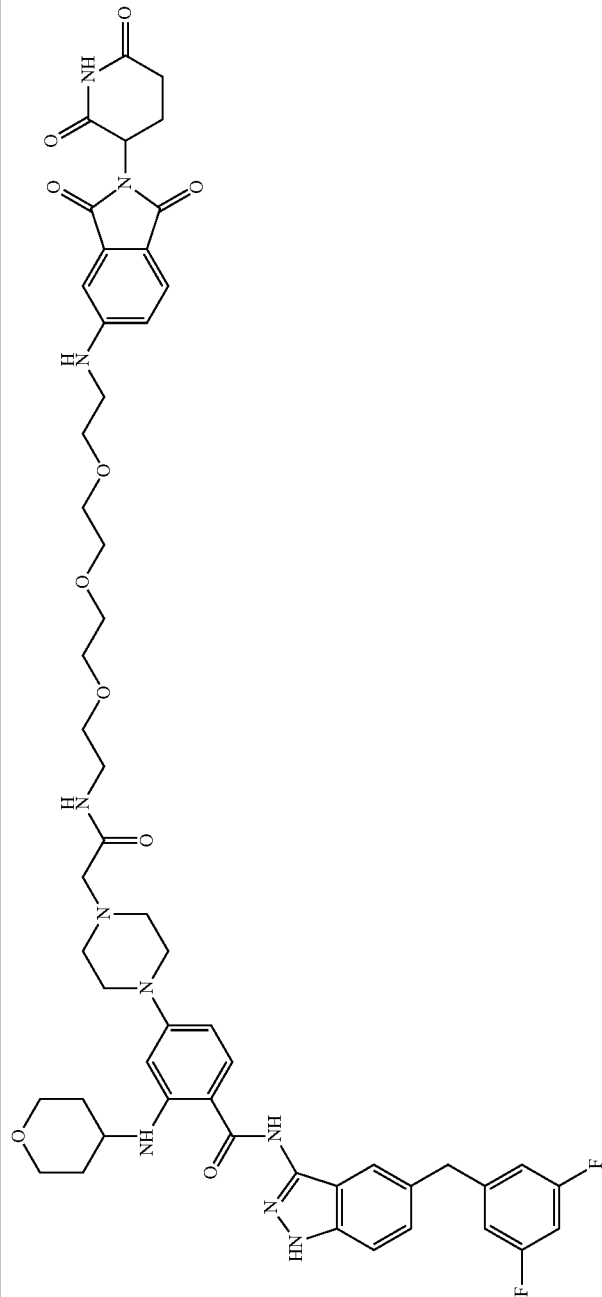
CPD-121
(TR-163)

TABLE 1-continued
| CPD-122 (TR-160) | 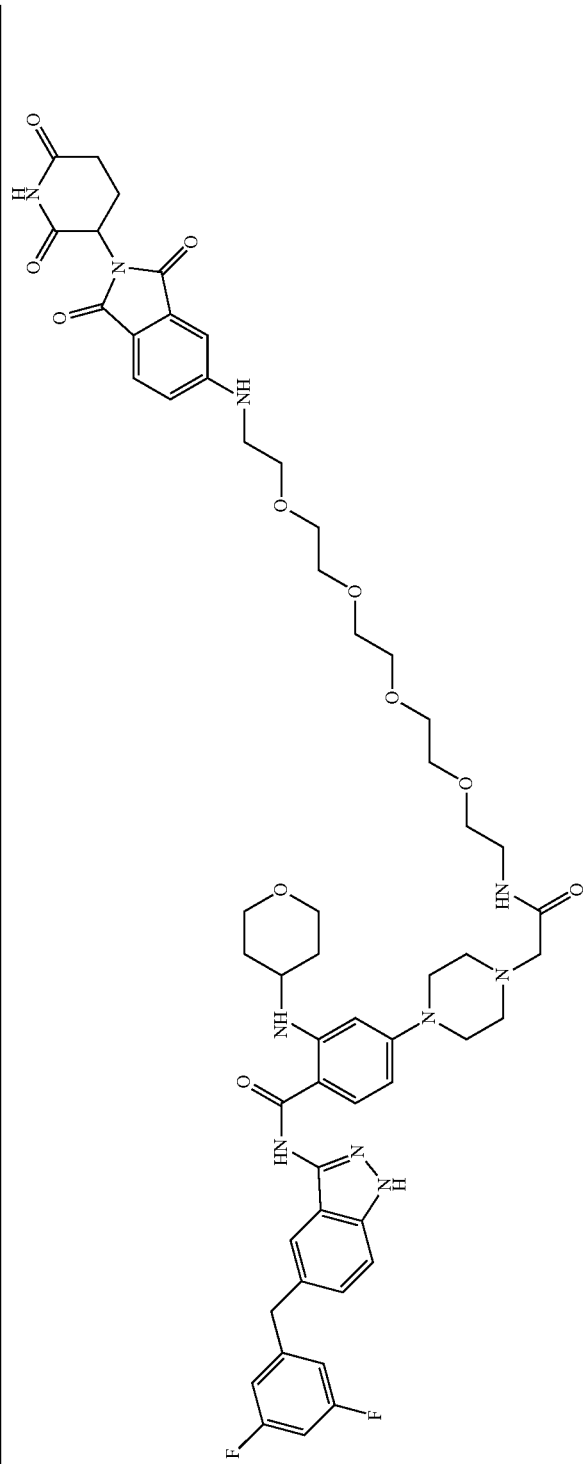 |

TABLE 1-continued
| CPD-123 (TR-166) | 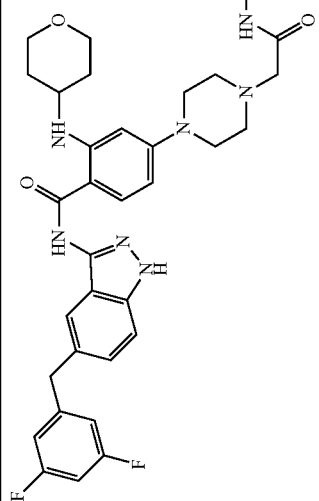 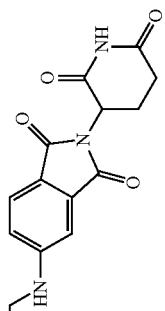 |
| CPD-124 (TR-144) | 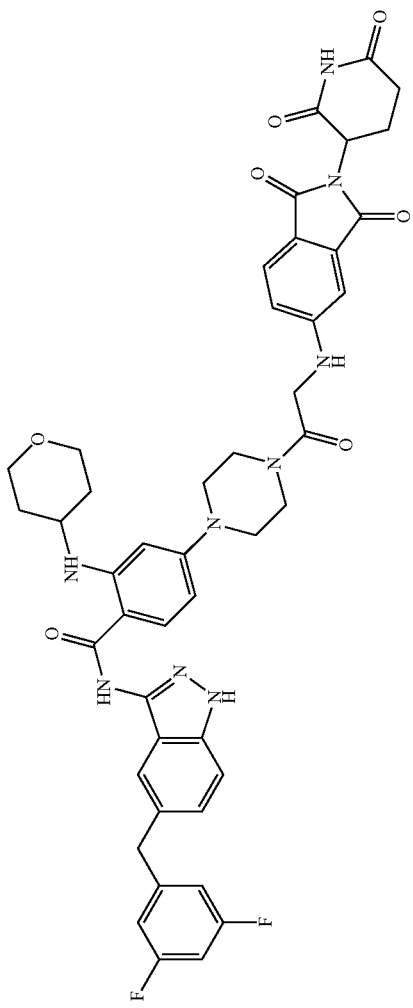 |

TABLE 1-continued
| 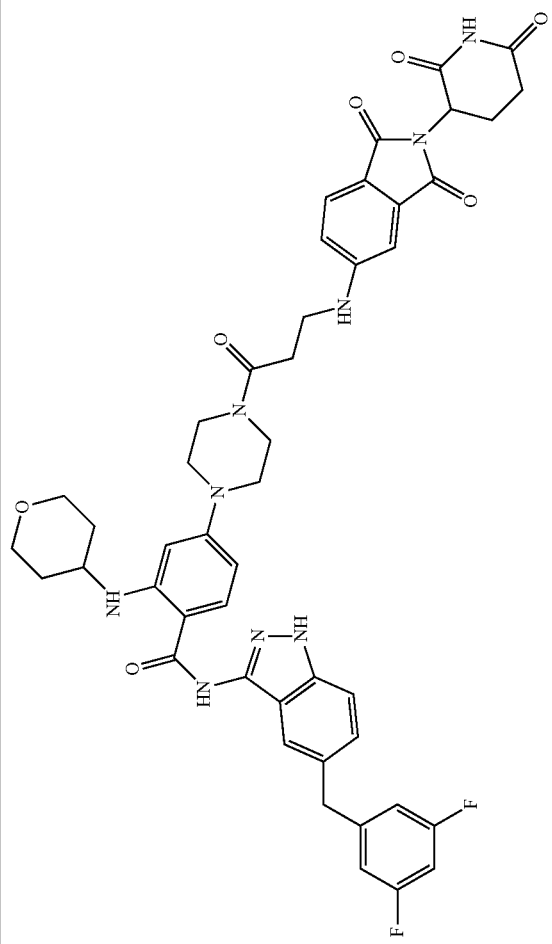 | 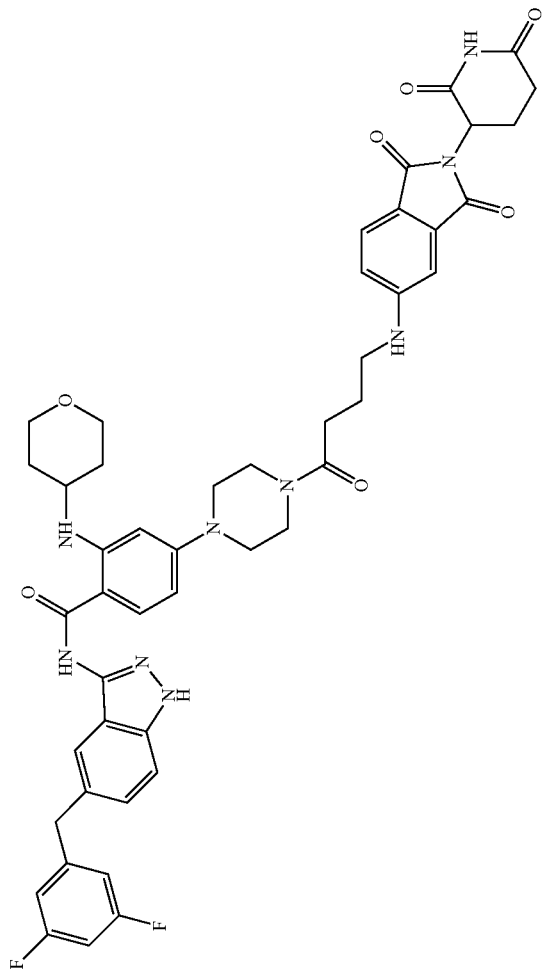 |
|---|---|
| CPD-125 (TR-145) | CPD-126 (TR-169) |

TABLE 1-continued
CPD-127
(TR-142)
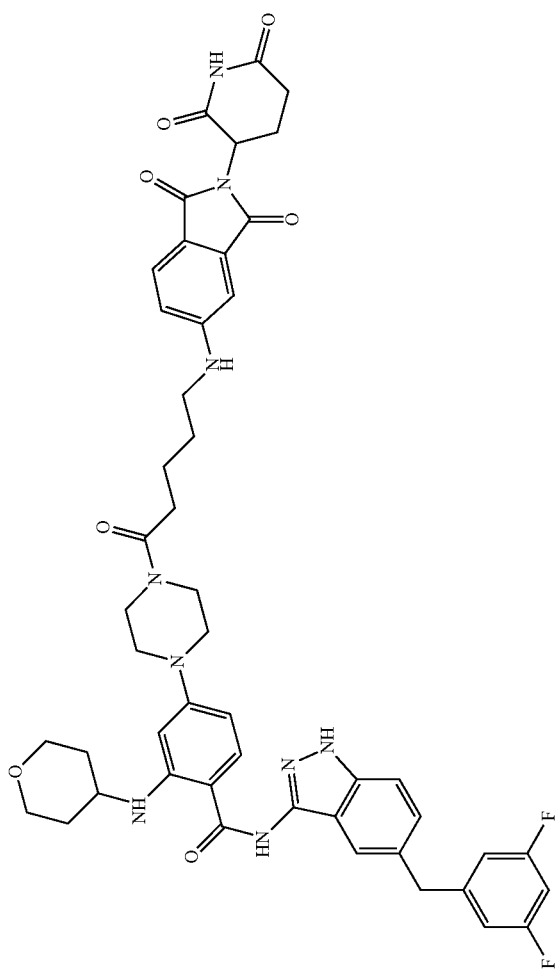

TABLE 1-continued
CPD-128
(TR-138)
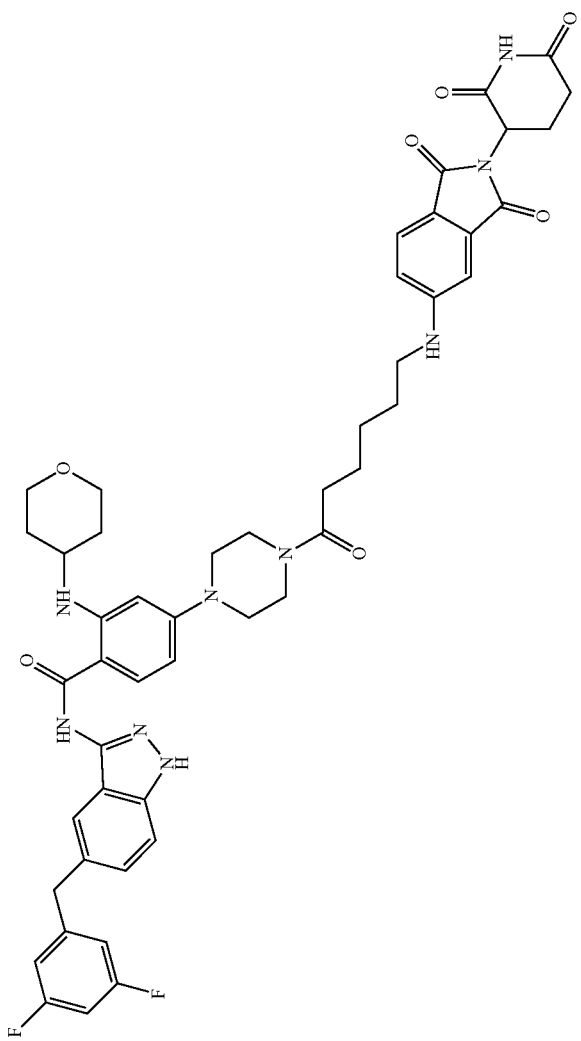

TABLE 1-continued
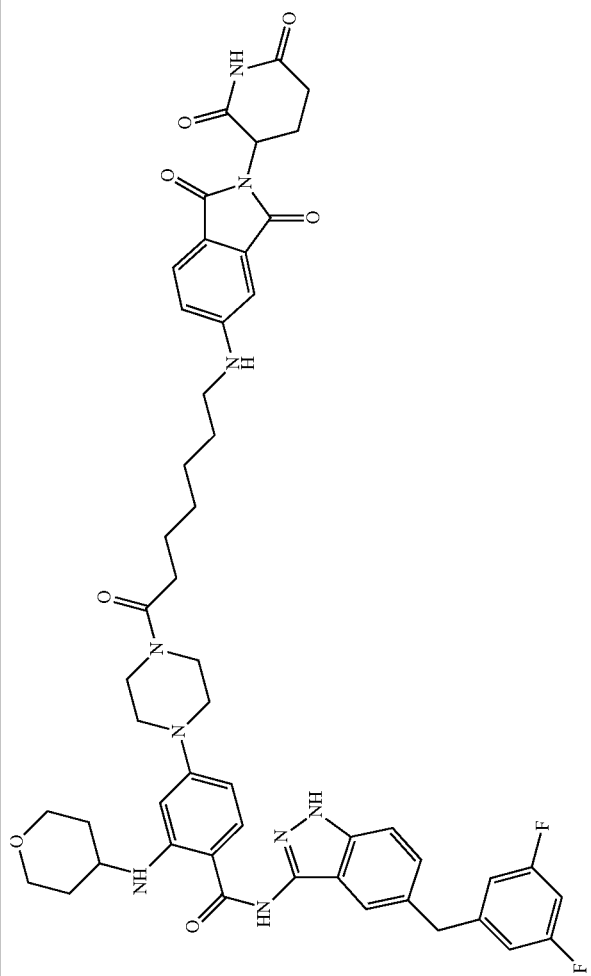
CPD-129
(TR-139)
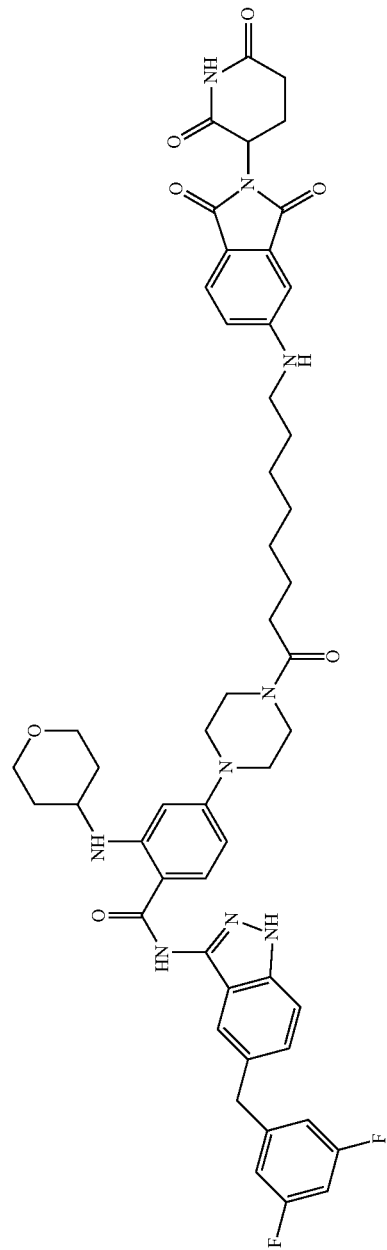
CPD-130
(TR-136)

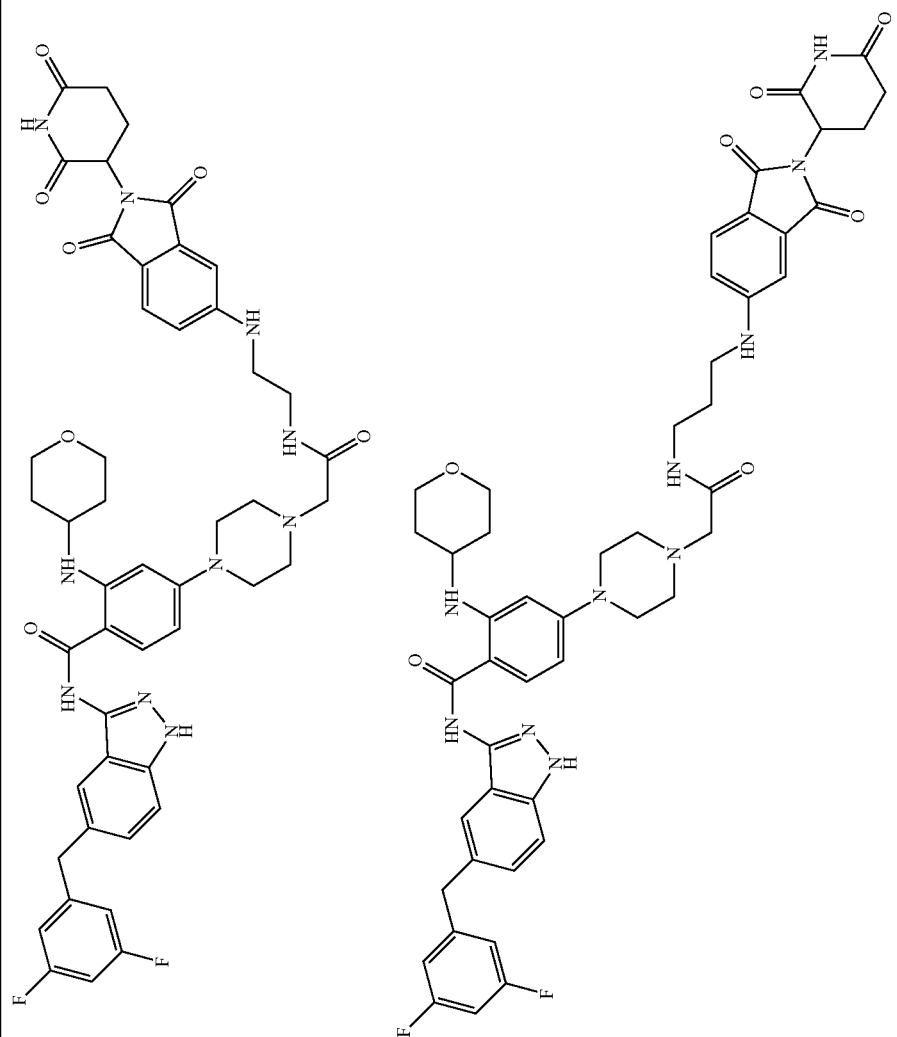

TABLE 1-continued
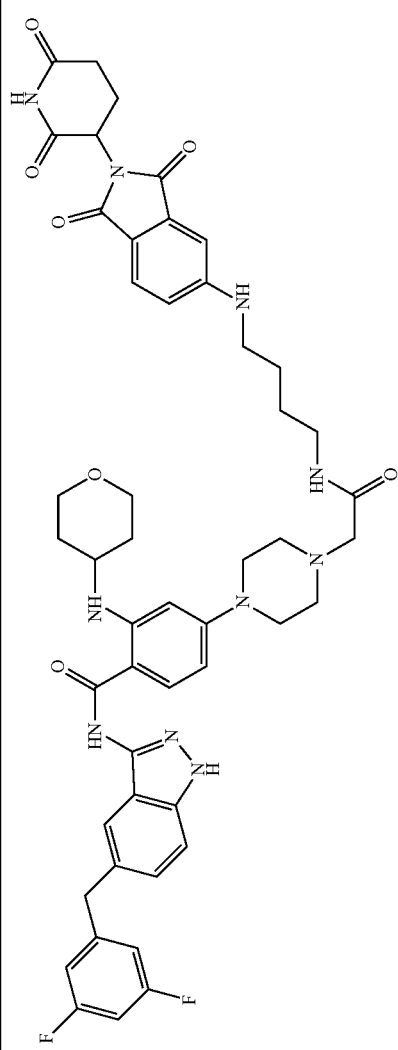
CPD-133
(TR-156)
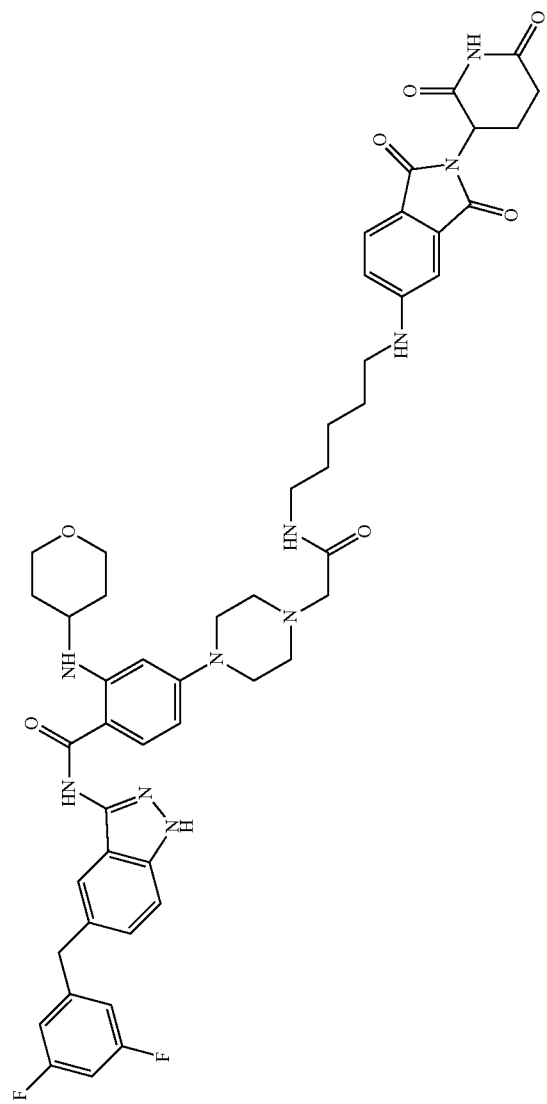
CPD-134
(TR-164)

TABLE 1-continued
| | |
|---|---|
| CPD-135 (TR-158) | 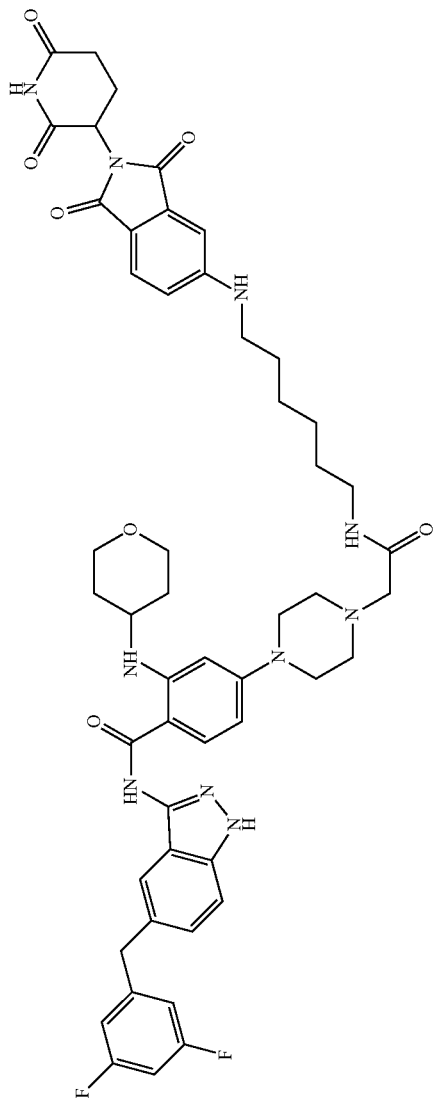 |
| CPD-136 (TR-157) | 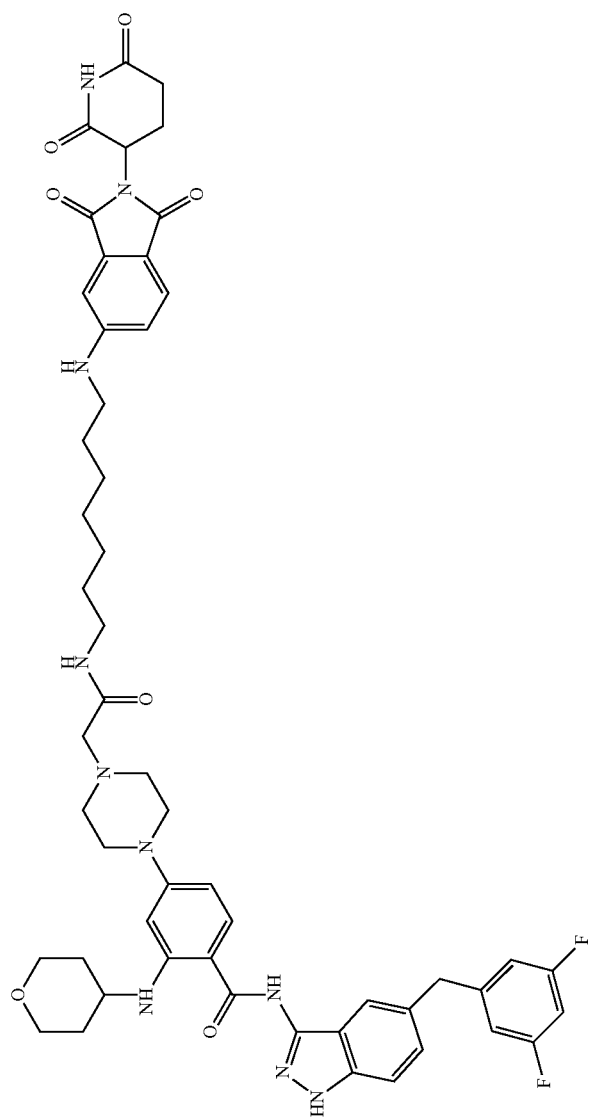 |

TABLE 1-continued
| CPD-137 (TR-159) | 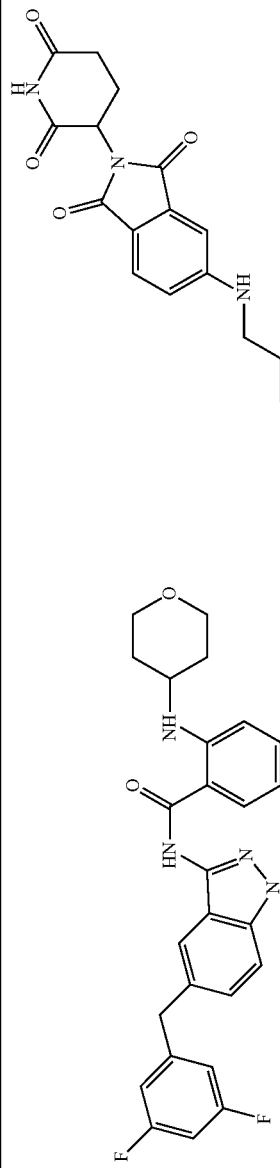 |
| CPD-138 (TR-143) | 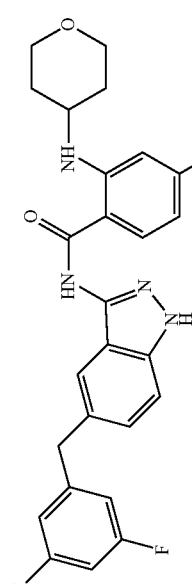 |

TABLE 1-continued
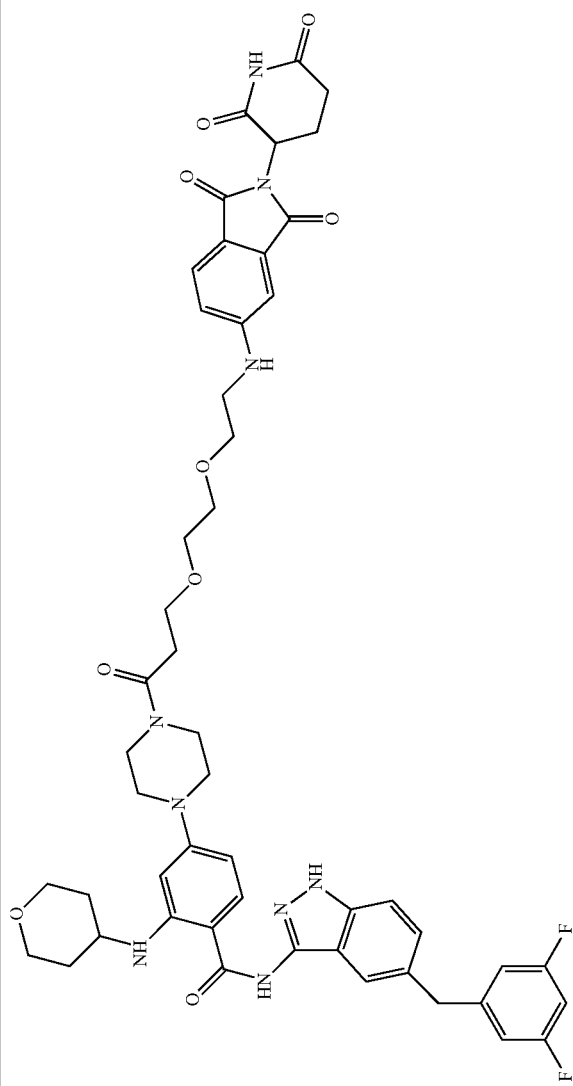
CPD-139
(TR-141)
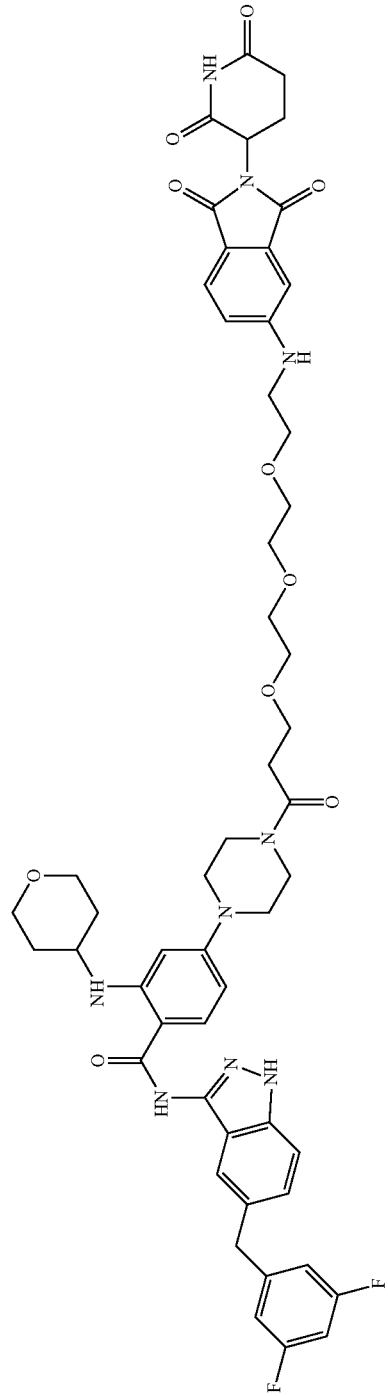
CPD-140
(TR-146)

TABLE 1-continued
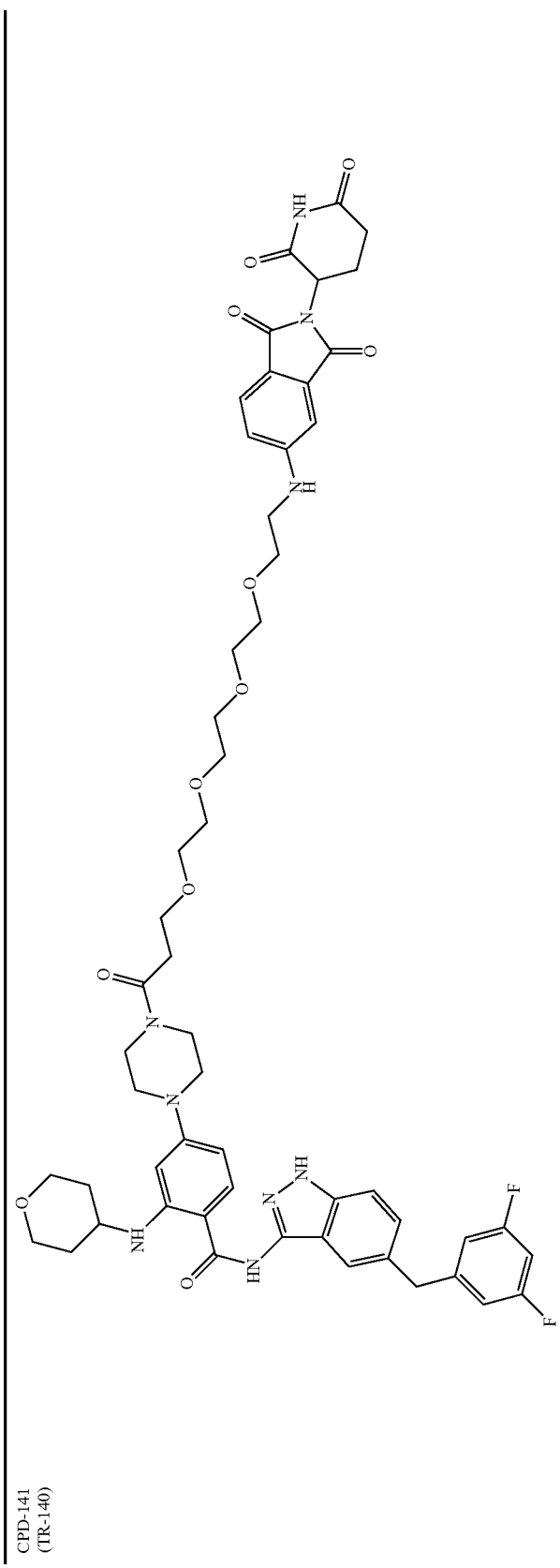
CPD-141
(TR-140)
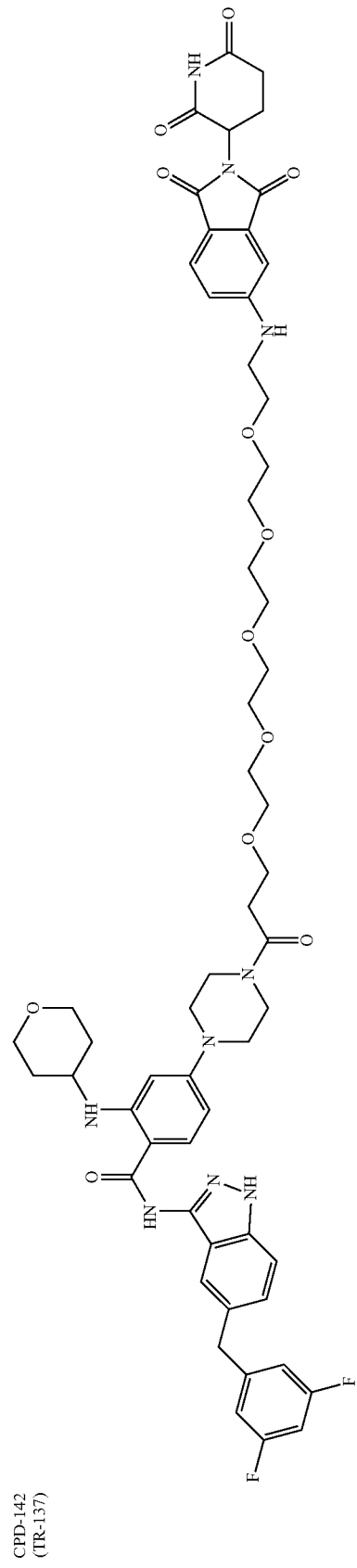
CPD-142
(TR-137)

TABLE 1-continued
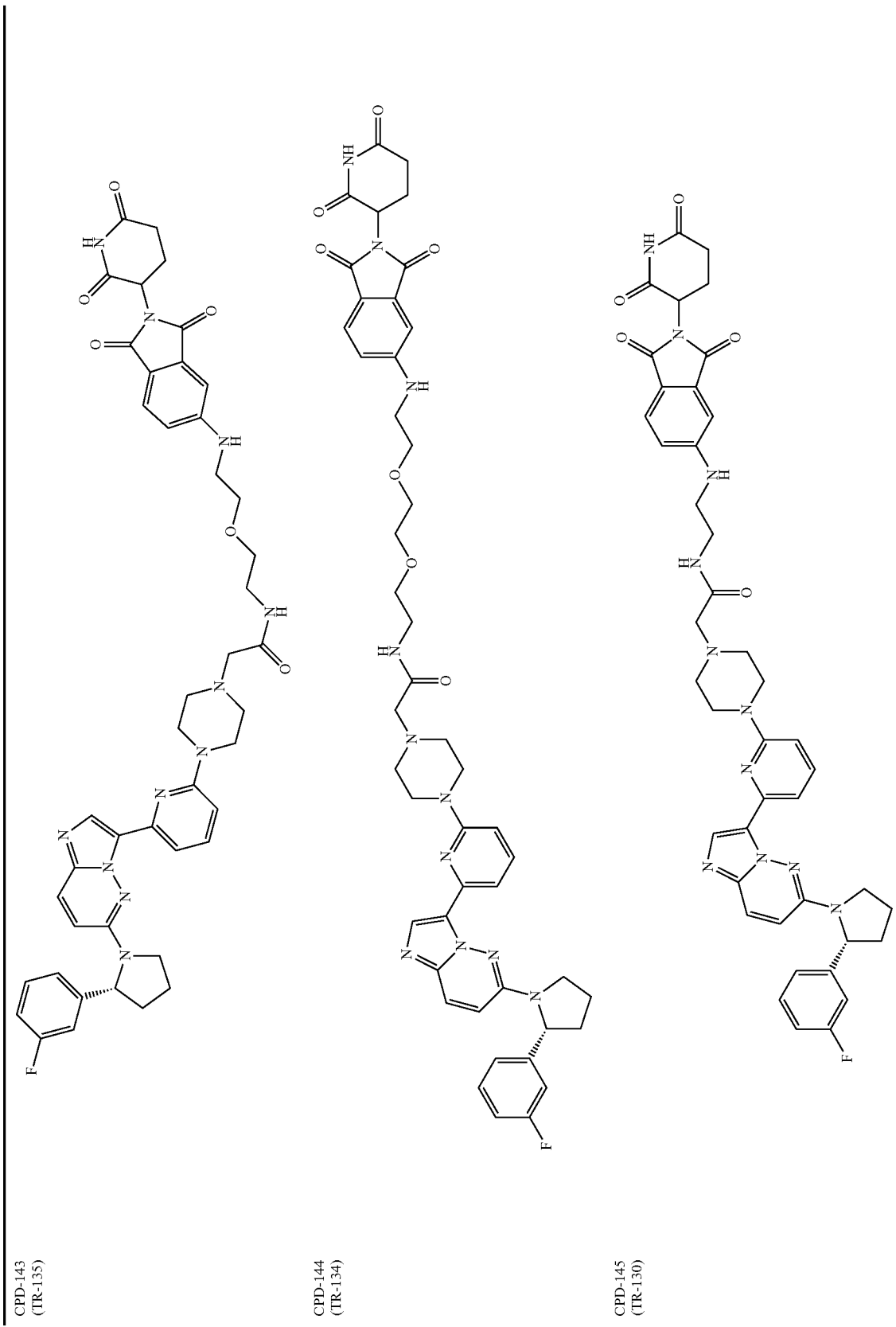
CPD-143 (TR-135)
CPD-144 (TR-134)
CPD-145 (TR-130)

TABLE 1-continued
| CPD-146 (TR-128) | 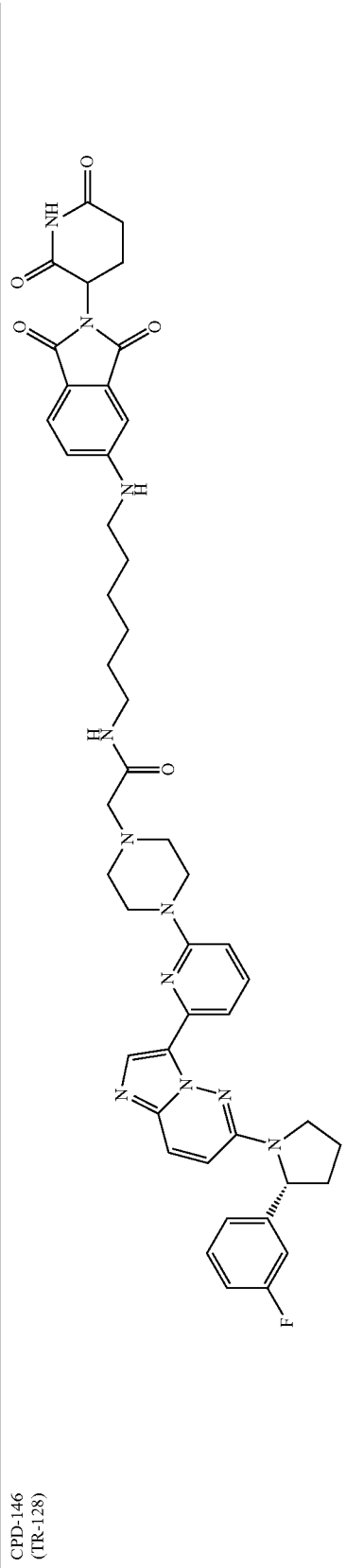 |
| CPD-147 (TR-120) | 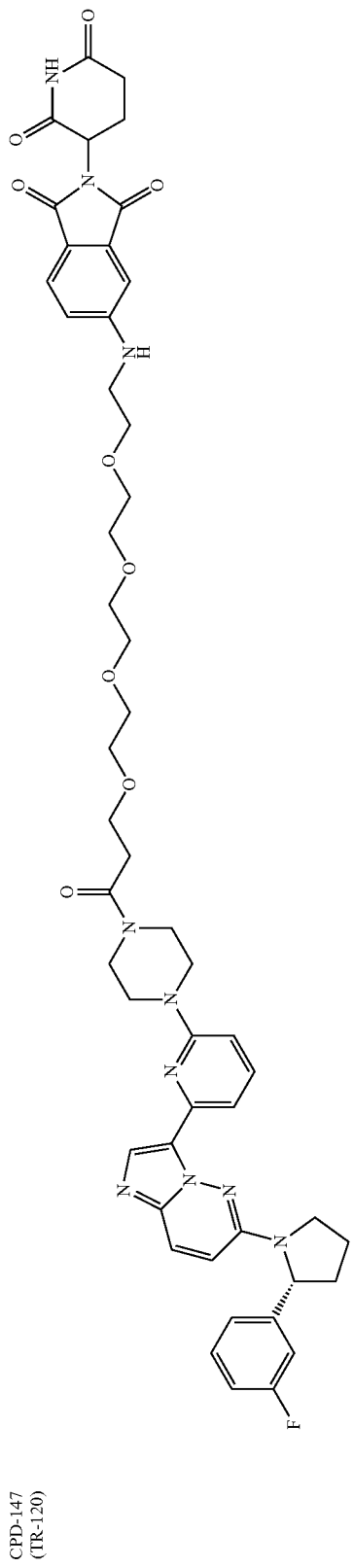 |

TABLE 1-continued
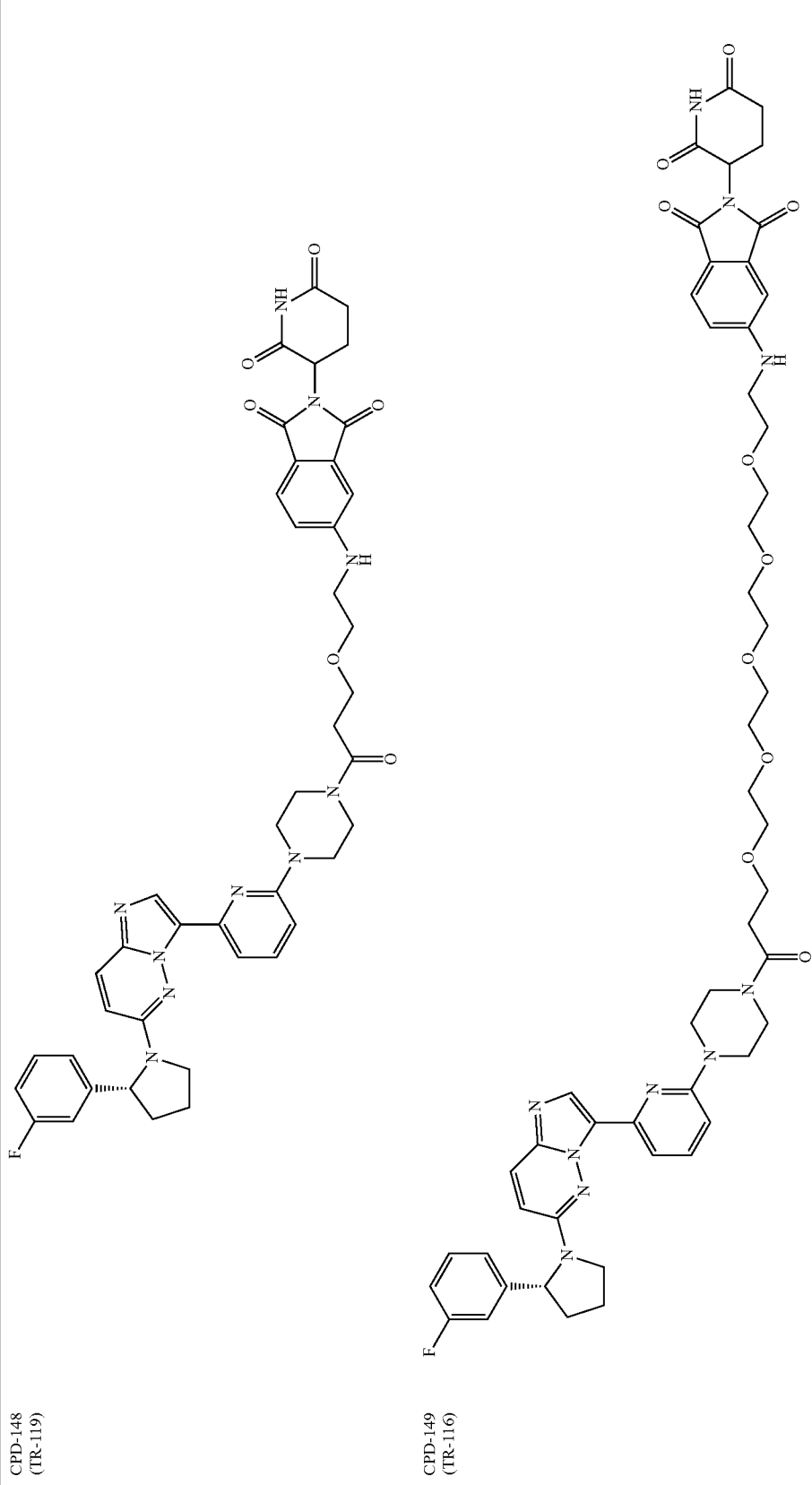
CPD-148
(TR-119)
CPD-149
(TR-116)

TABLE 1-continued
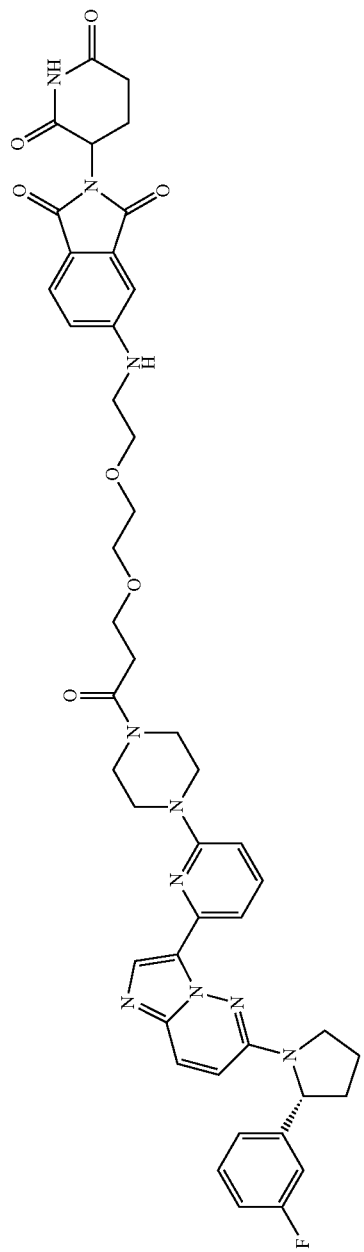
CPD-150
(TR-113)
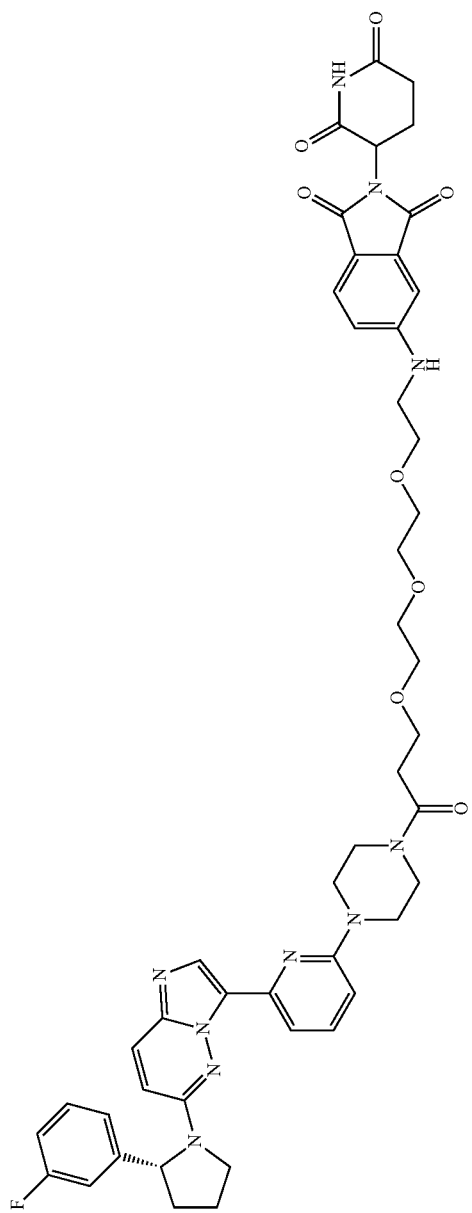
CPD-151
(TR-114)

TABLE 1-continued
| CPD-152 (TR-122) | 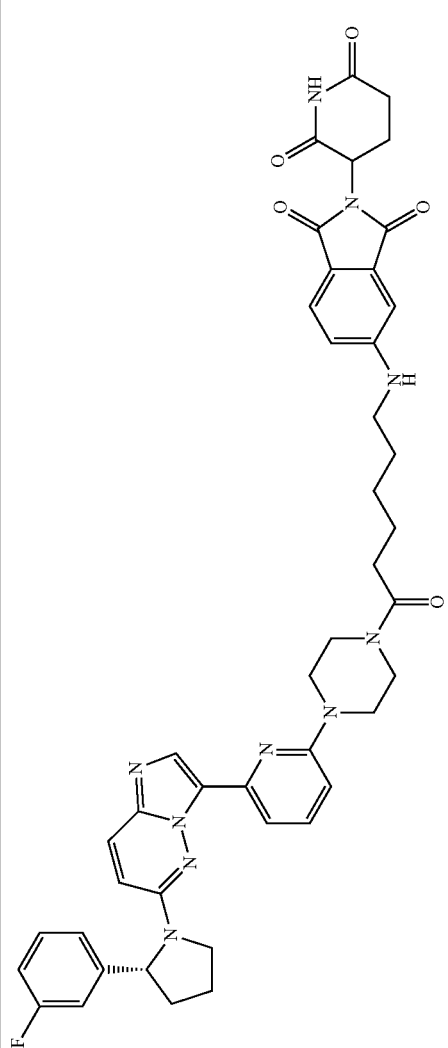 |
| CPD-153 (TR-117) | 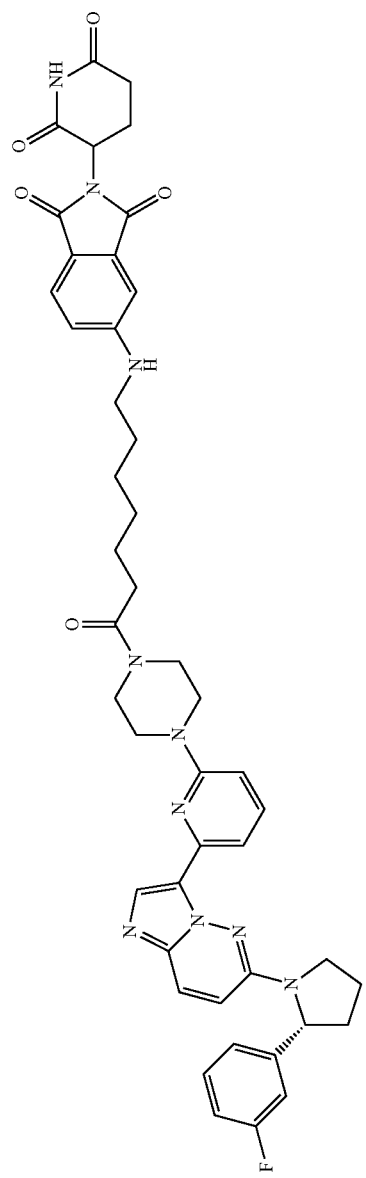 |

TABLE 1-continued
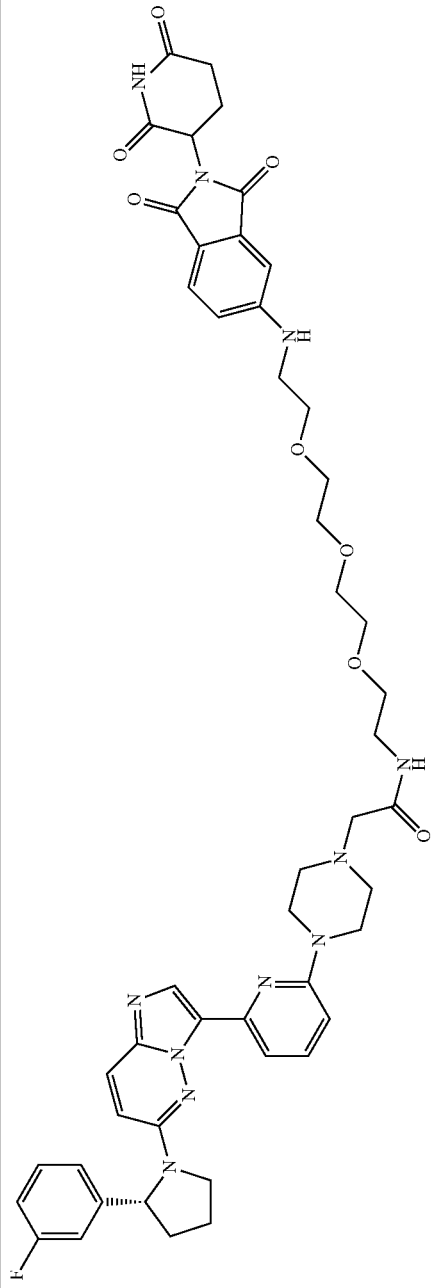
CPD-154
(TR-129)
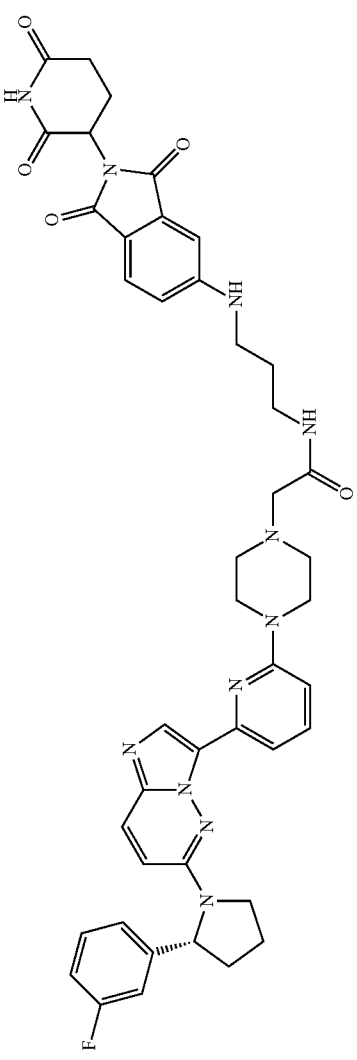
CPD-155
(TR-127)

TABLE 1-continued
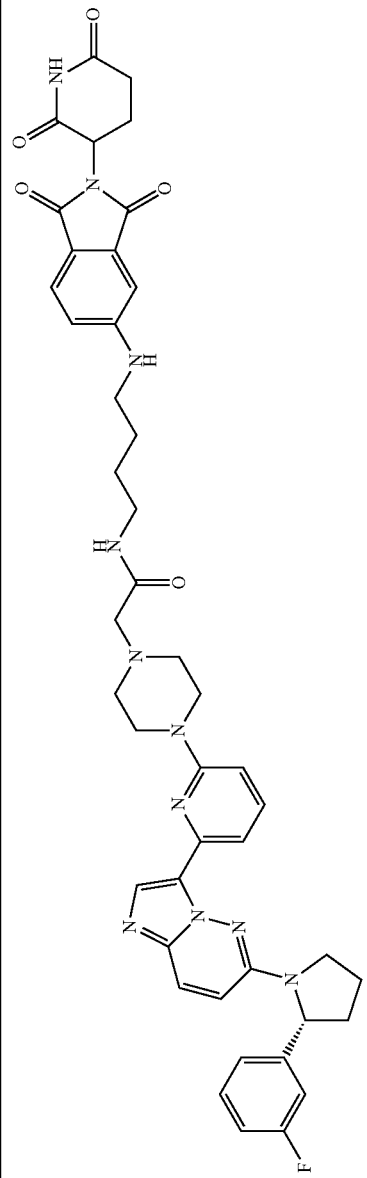
CPD-156
(TR-124)
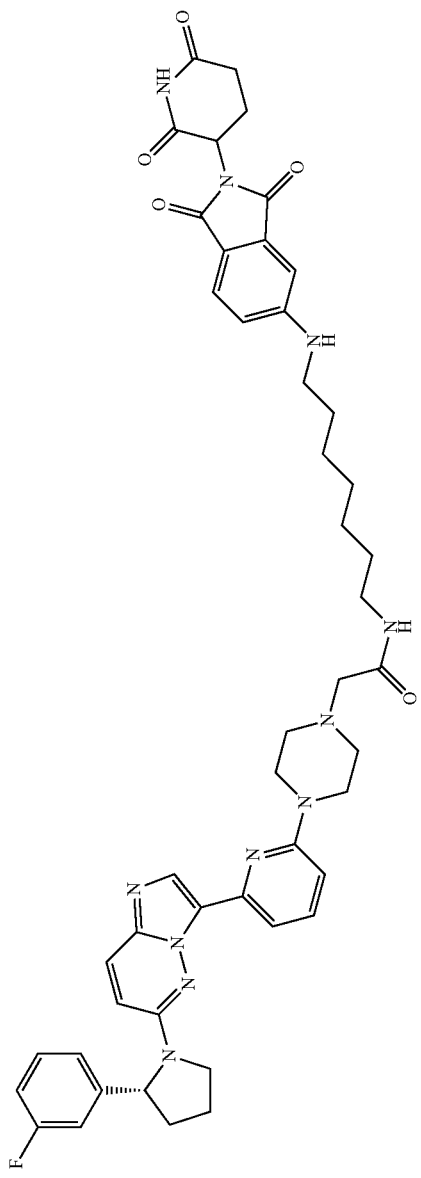
CPD-157
(TR-126)

TABLE 1-continued
| CPD-158 (TR-168) | 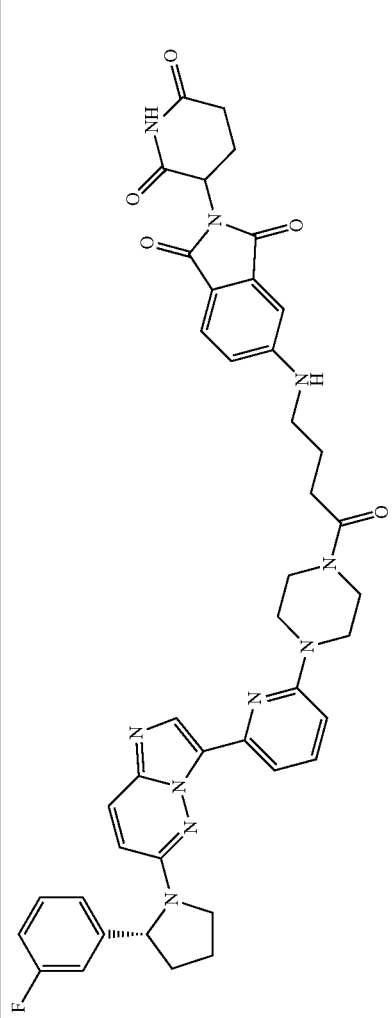 |
| CPD-159 (TR-115) | 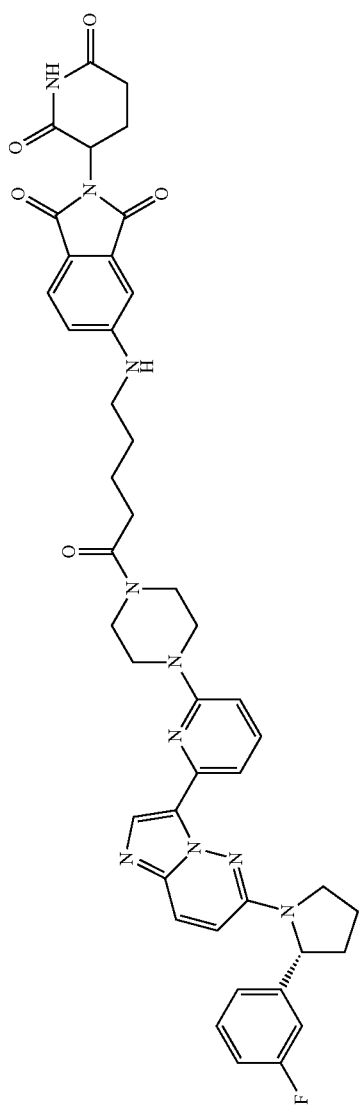 |

TABLE 1-continued
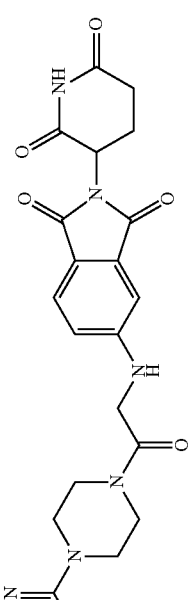
CPD-160
(TR-123)
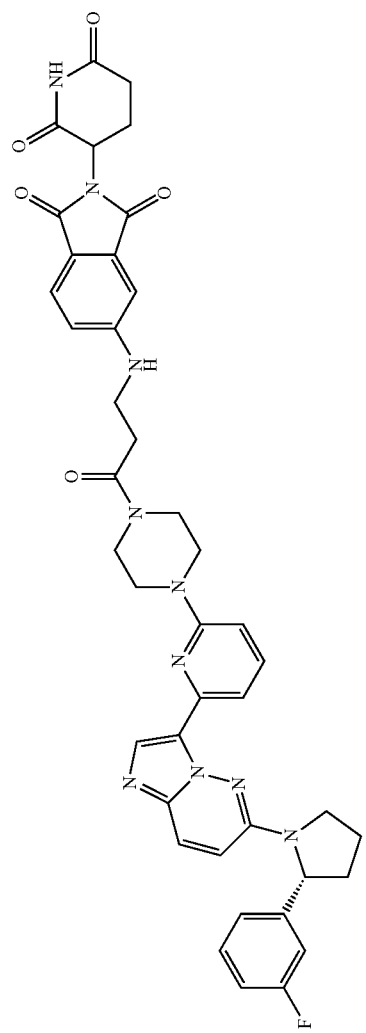
CPD-161
(TR-121)

TABLE 1-continued
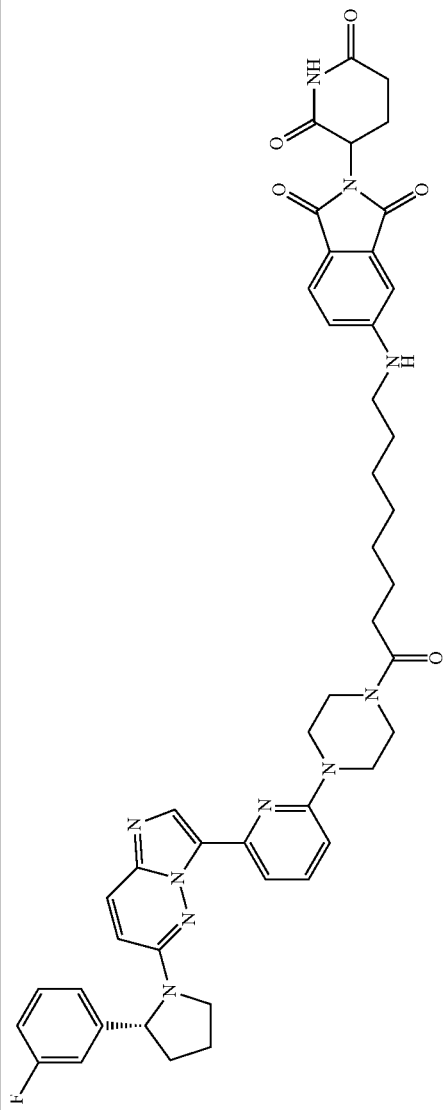
CPD-162
(TR-118)
CPD-163
(TR-131)

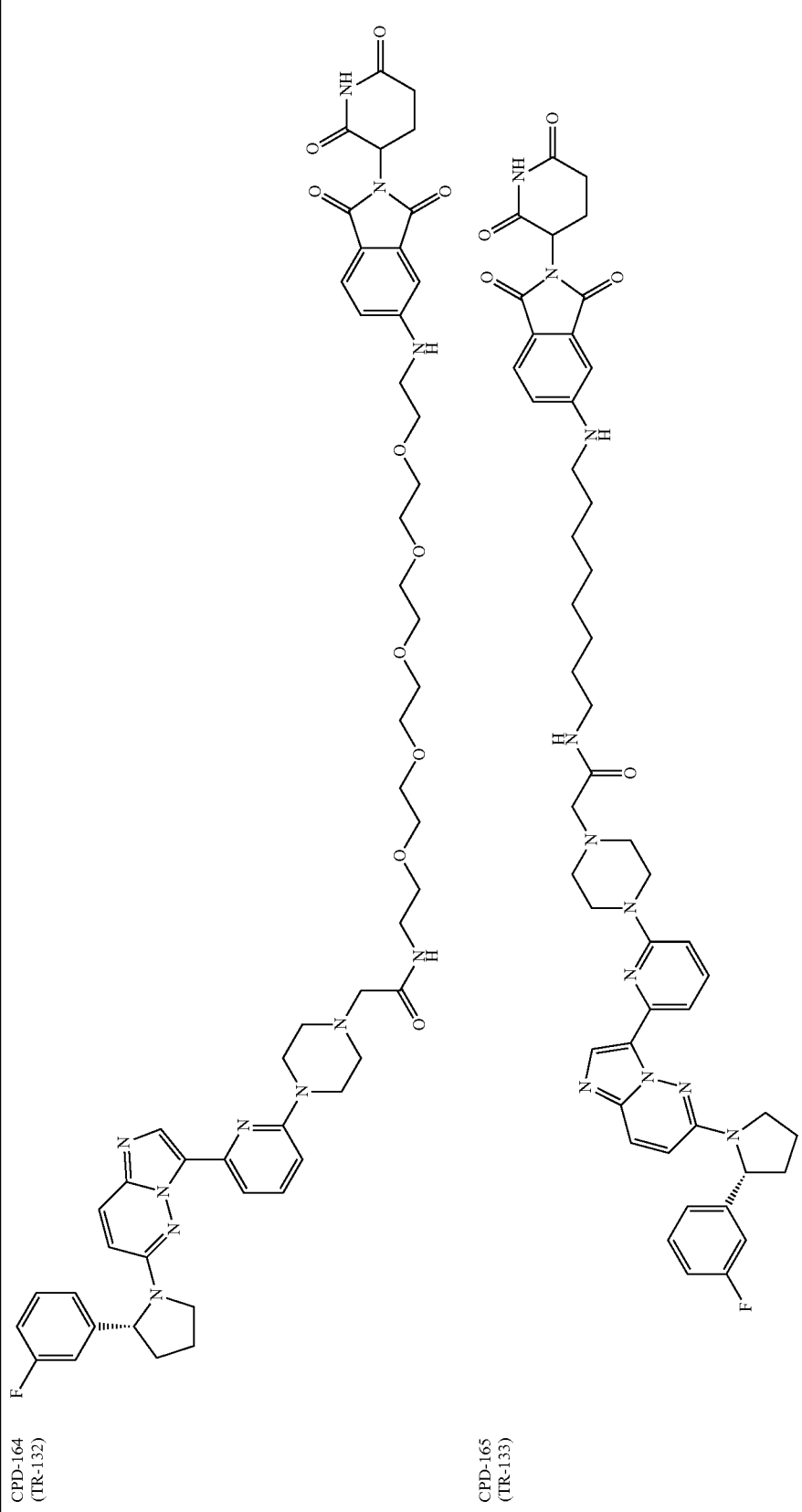

TABLE 1-continued
| CPD-166 (TR-125) | 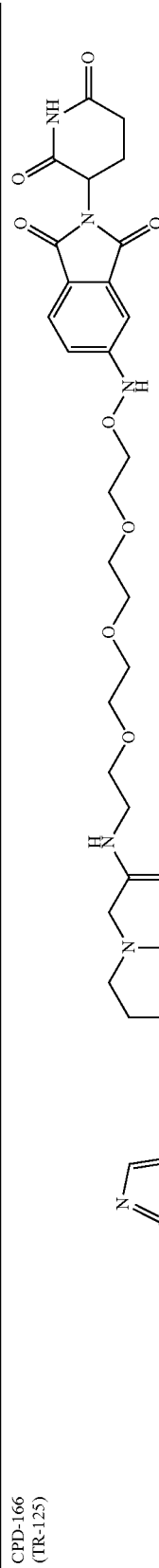 |
| CPD-167 (TR-103) | 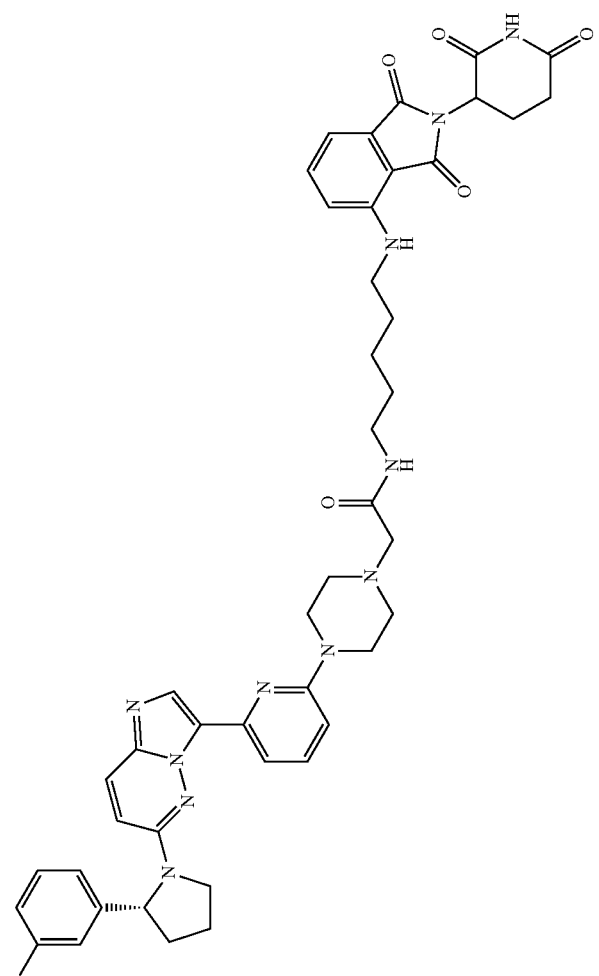 |

TABLE 1-continued
| CPD-168 (TR-162) | 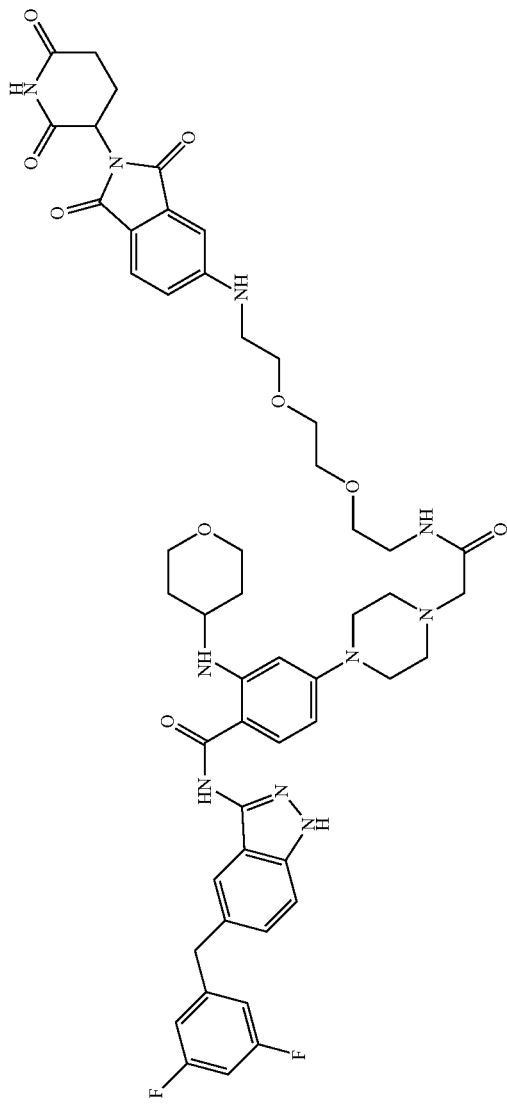 |
| CPD-169 (TR-123-neg) | 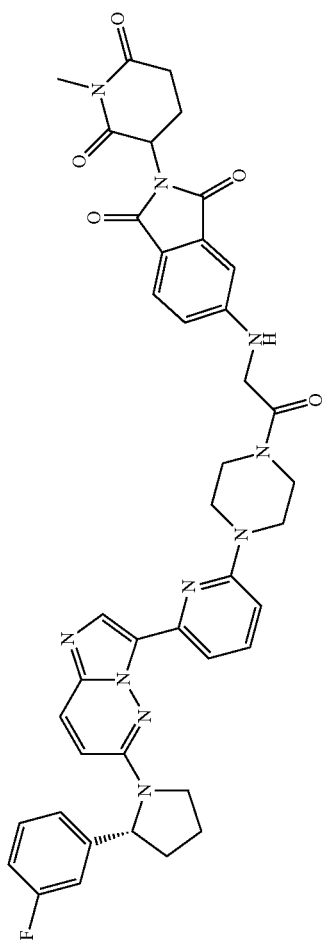 |

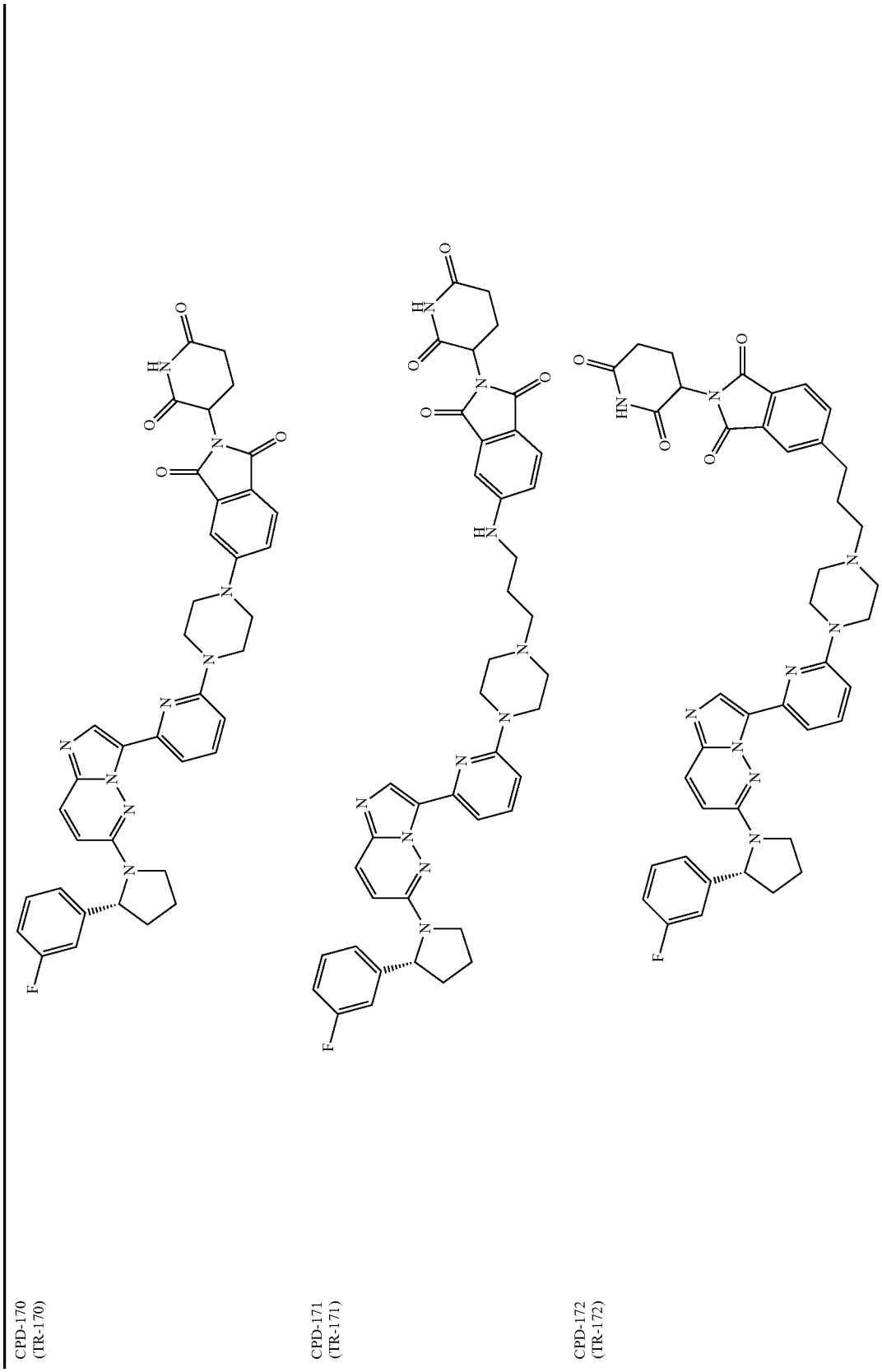

TABLE 1-continued
CPD-173
(TR-173)
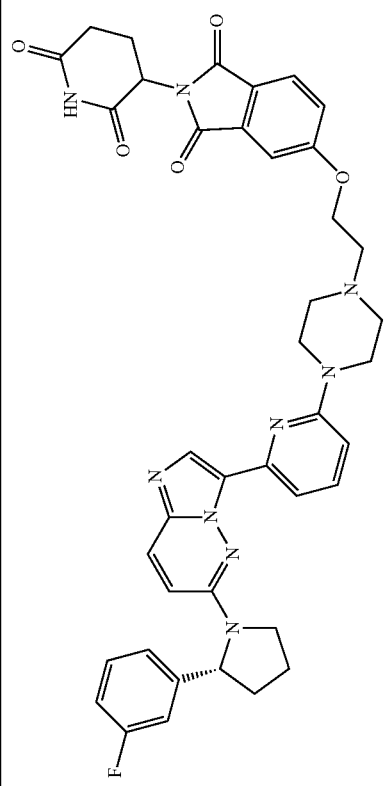
CPD-174
(TR-174)
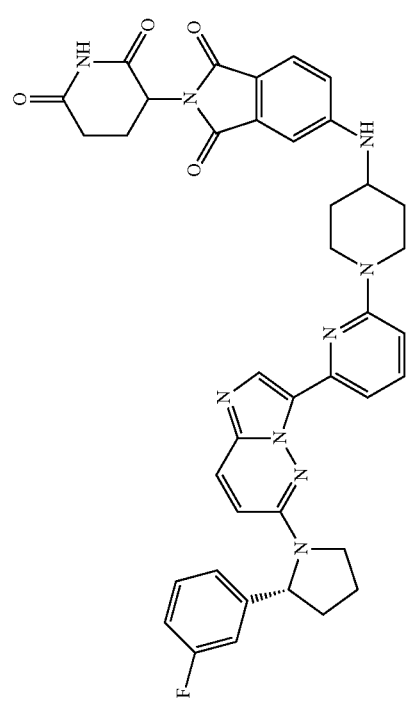

TABLE 1-continued
| | |
|---|---|
| CPD-175 (TR-175) | 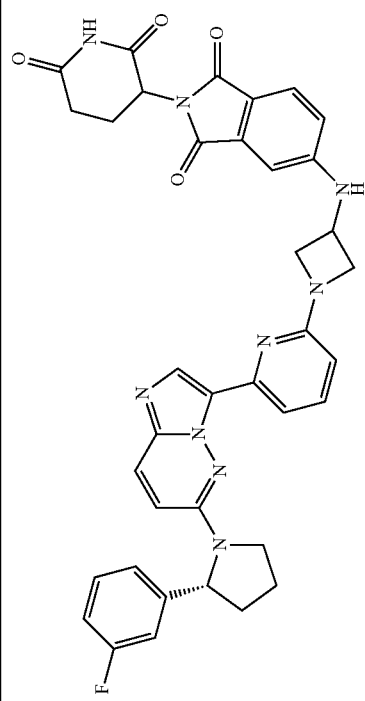 |
| CPD-176 (TR-176) | 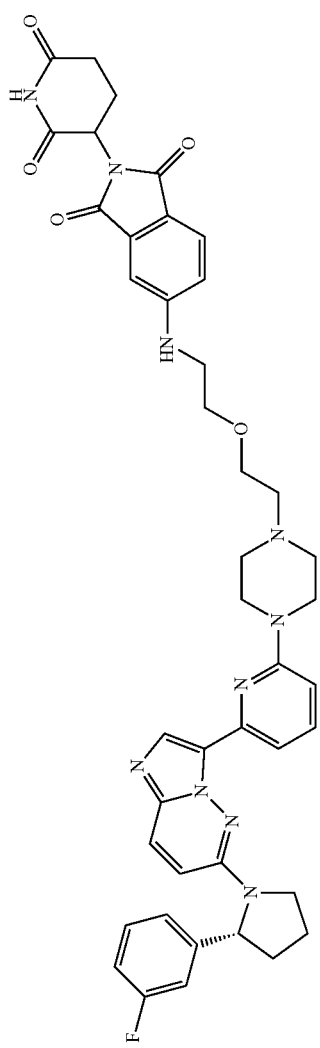 |

TABLE 1-continued
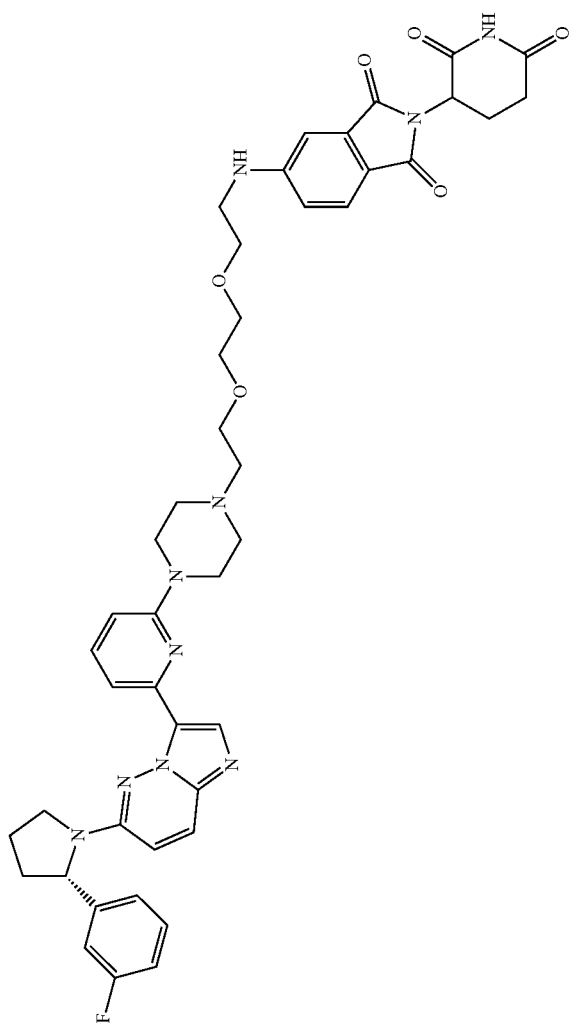
CPD-177
(TR-177)
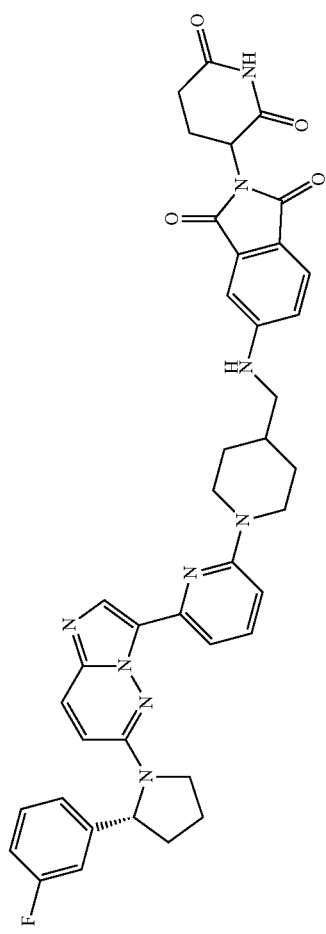
CPD-178
(TR-178)

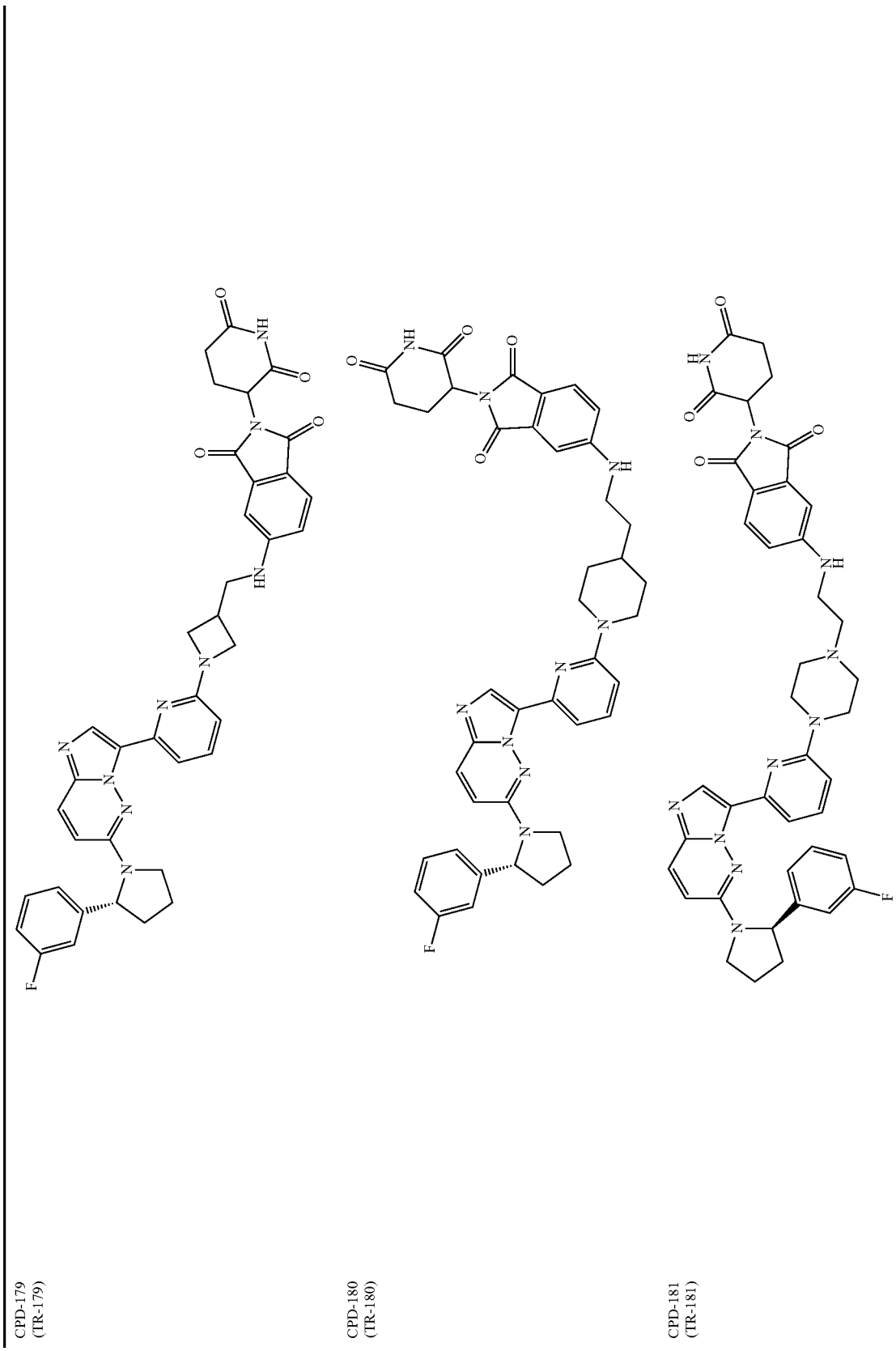

TABLE 1-continued
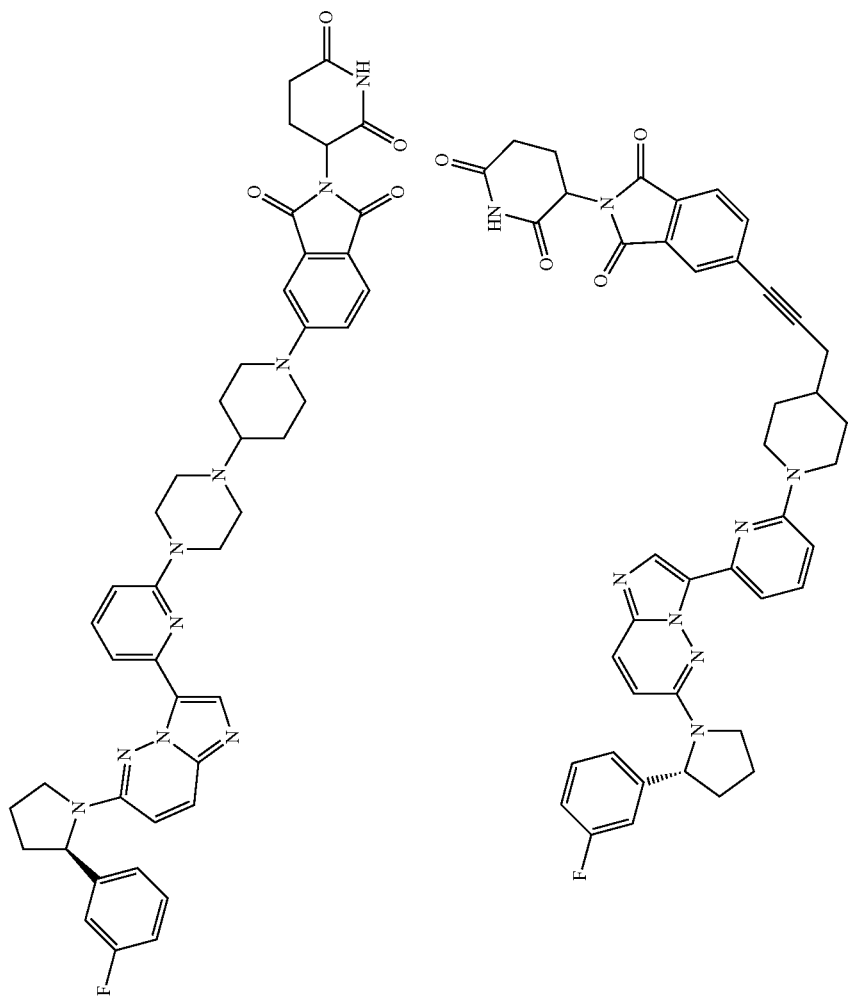
CPD-182
(TR-182)
CPD-183
(TR-183)

TABLE 1-continued
| CPD-184 (TR-184) | 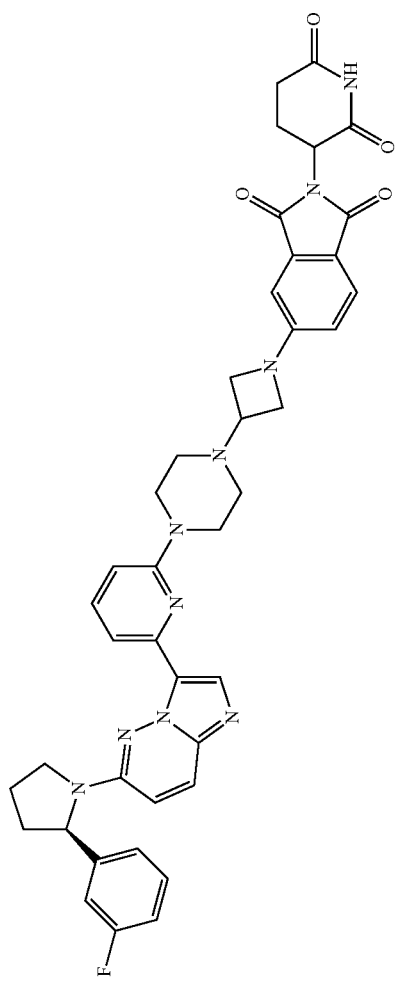 |
| CPD-185 (TR-185) | 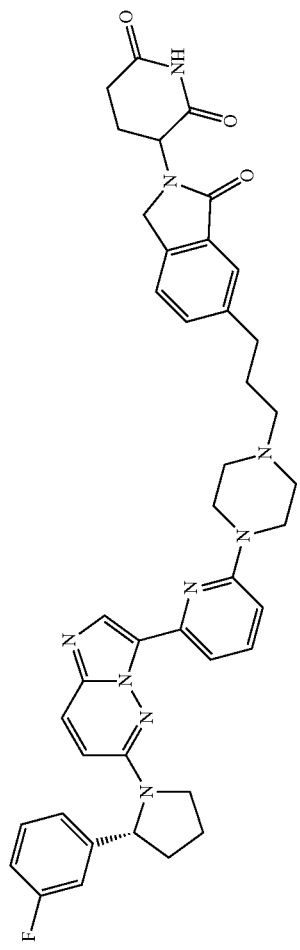 |
| CPD-186 (TR-186) | |

TABLE 1-continued
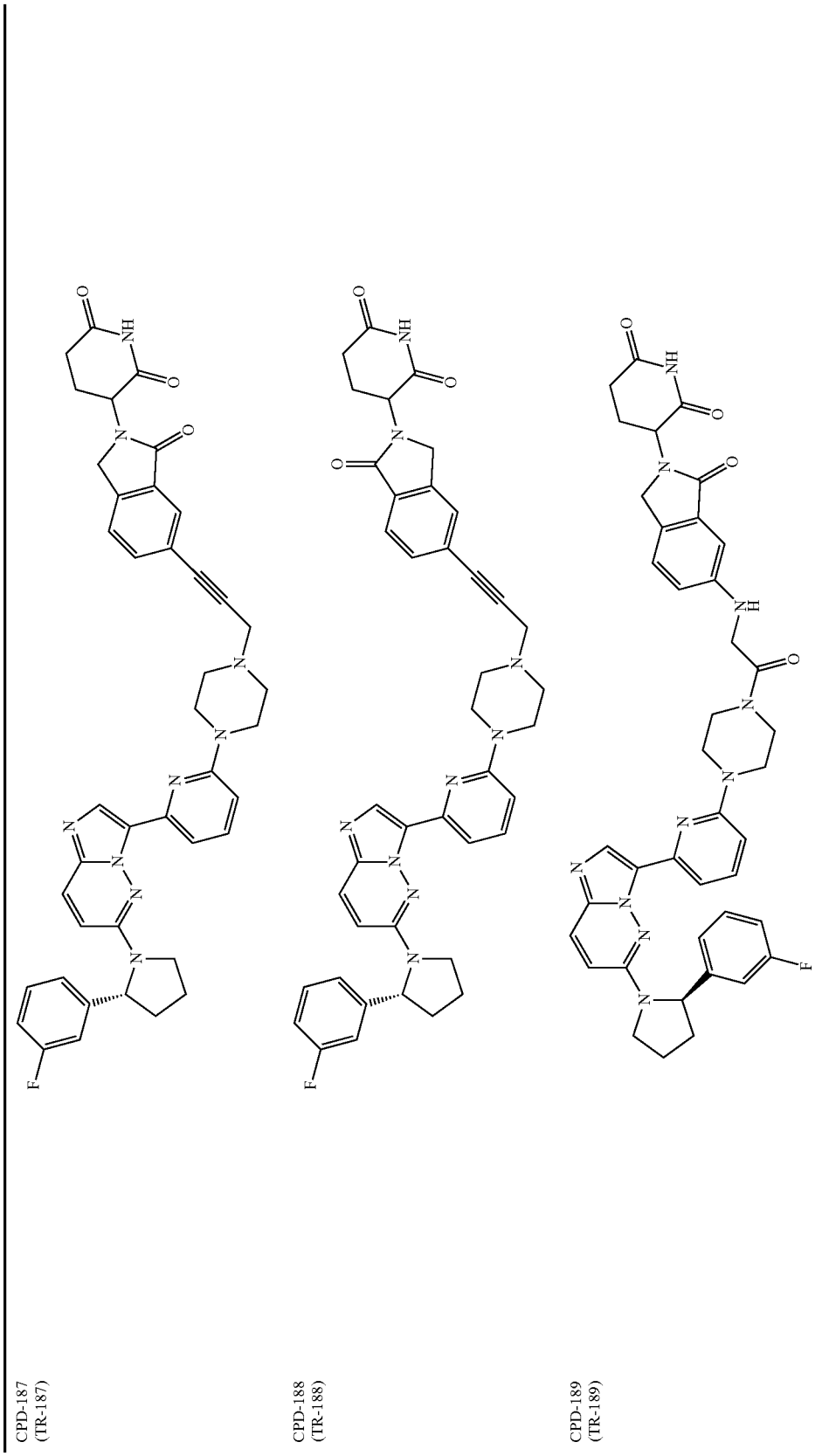
CPD-187 (TR-187)
CPD-188 (TR-188)
CPD-189 (TR-189)

TABLE 1-continued
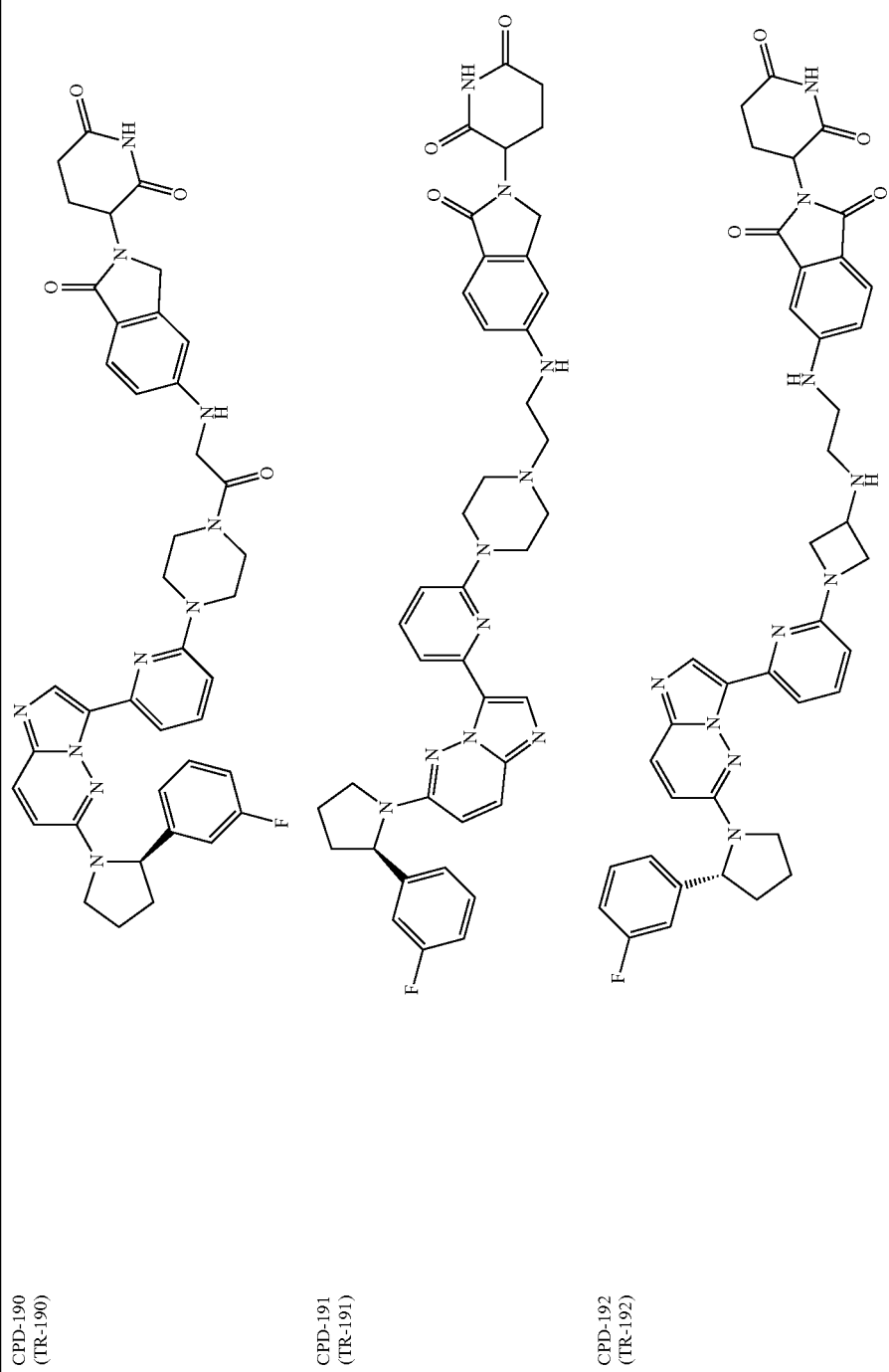
CPD-190
(TR-190)
CPD-191
(TR-191)
CPD-192
(TR-192)

TABLE 1-continued
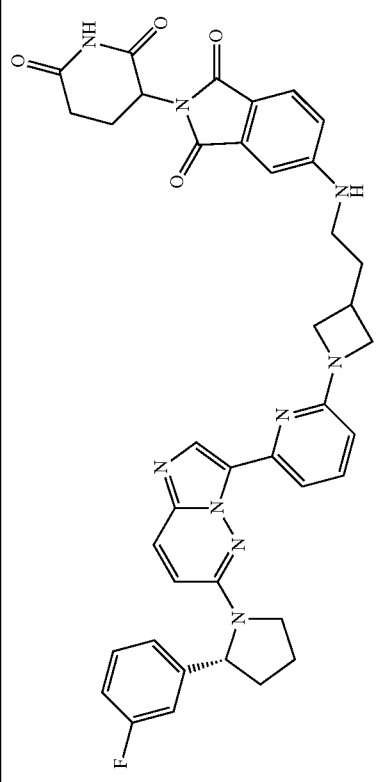
CPD-193
(TR-193)
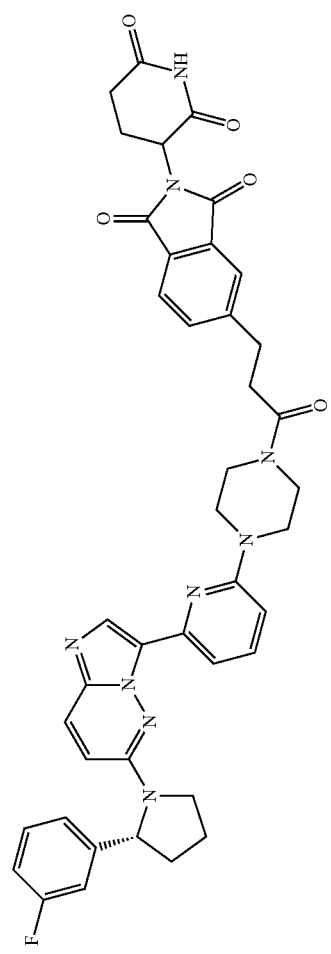
CPD-194
(TR-194)
CPD-195
(TR-195)

TABLE 1-continued
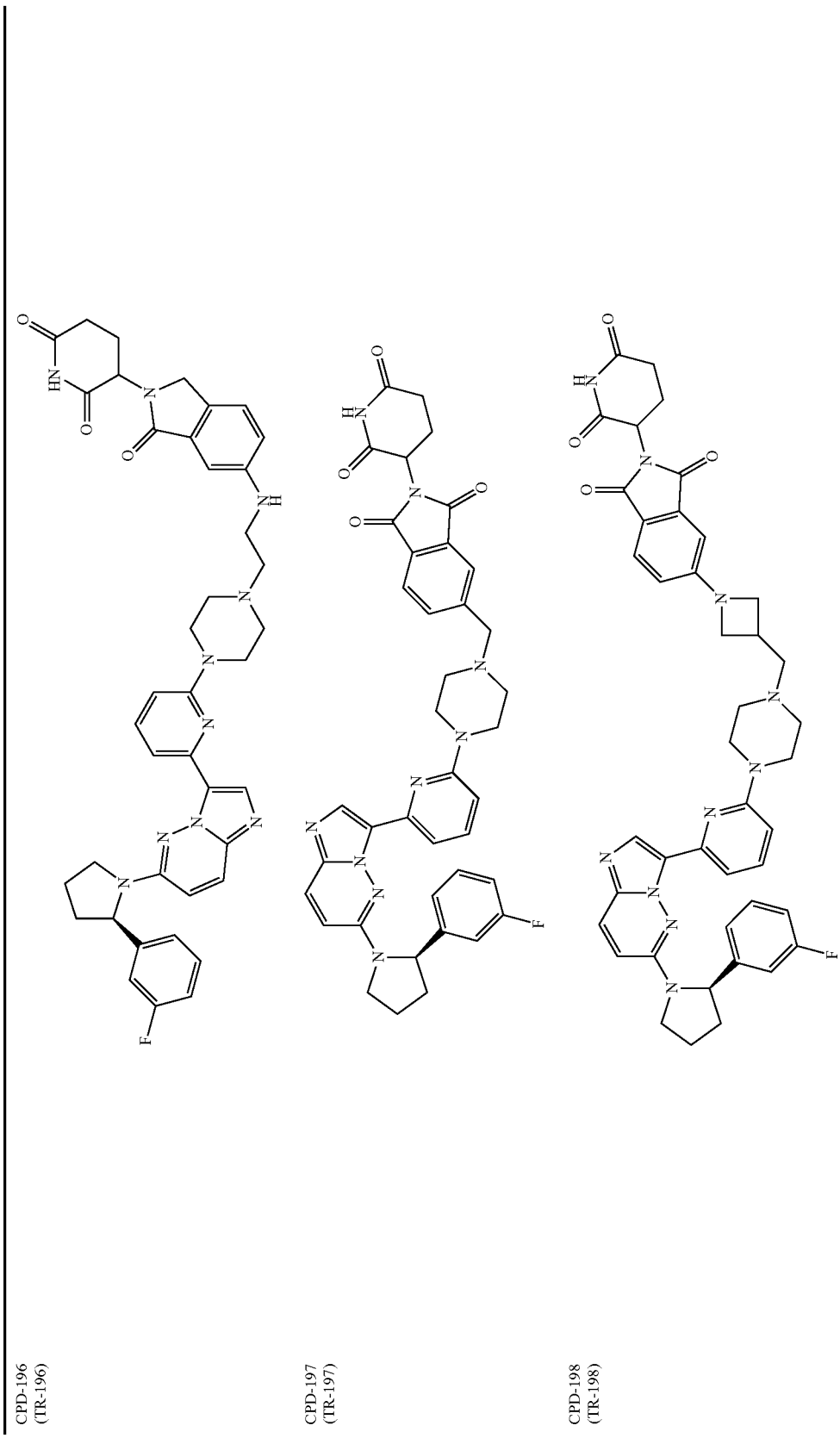
CPD-196 (TR-196)
CPD-197 (TR-197)
CPD-198 (TR-198)

TABLE 1-continued
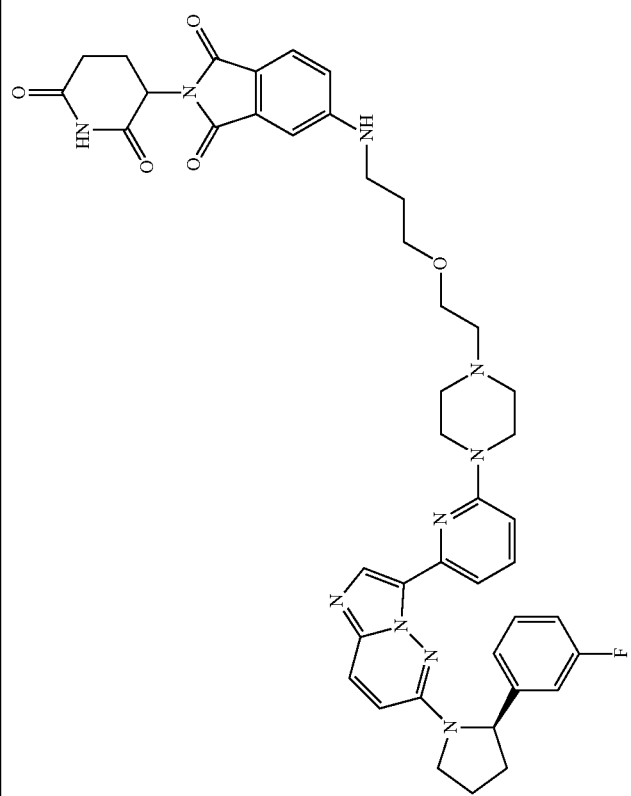
CPD-199
(TR-199)
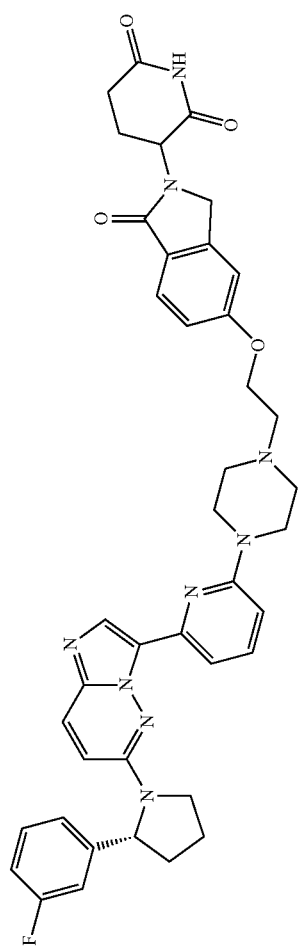
CPD-200
(TR-200)

TABLE 1-continued
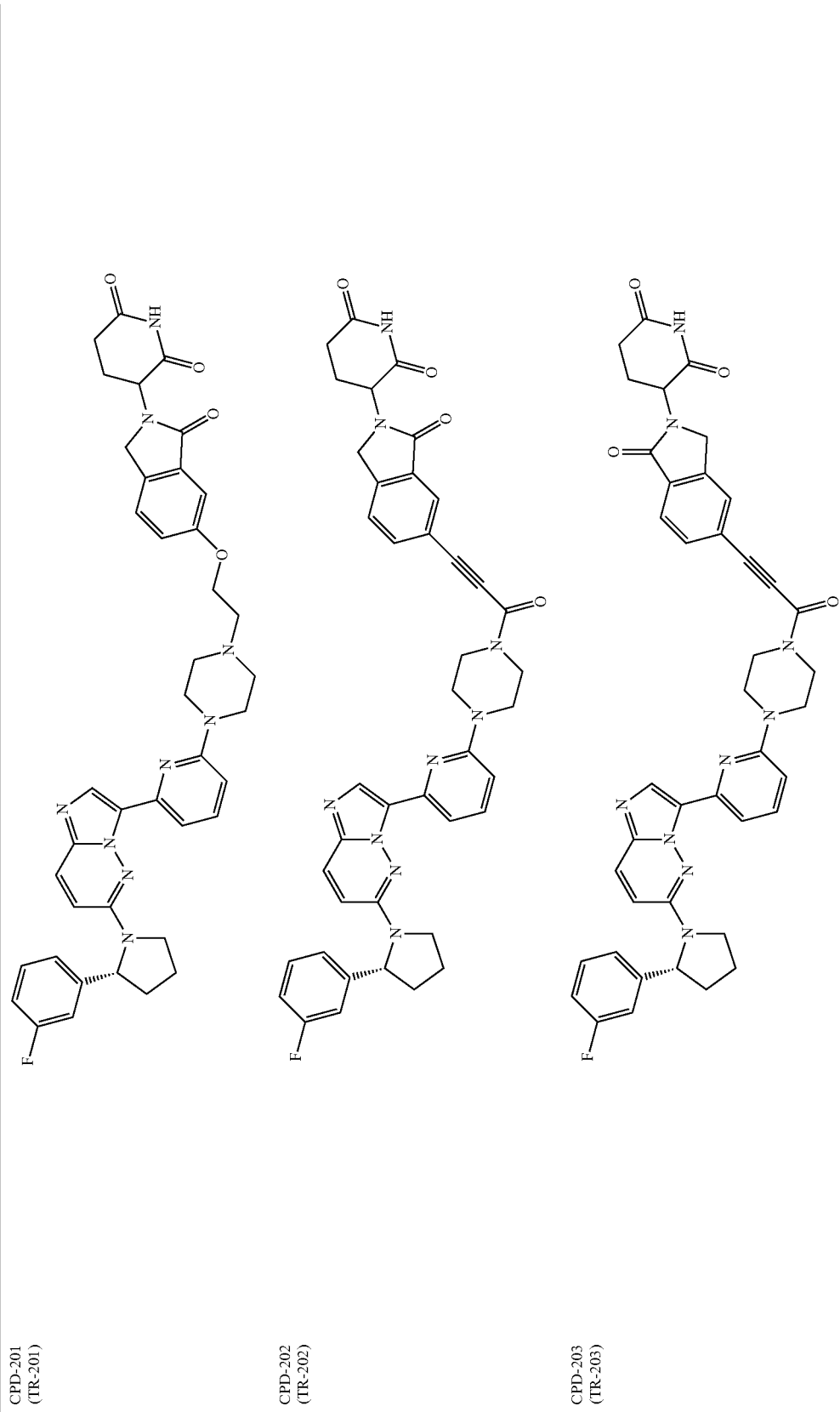
CPD-201 (TR-201)
CPD-202 (TR-202)
CPD-203 (TR-203)

TABLE 1-continued
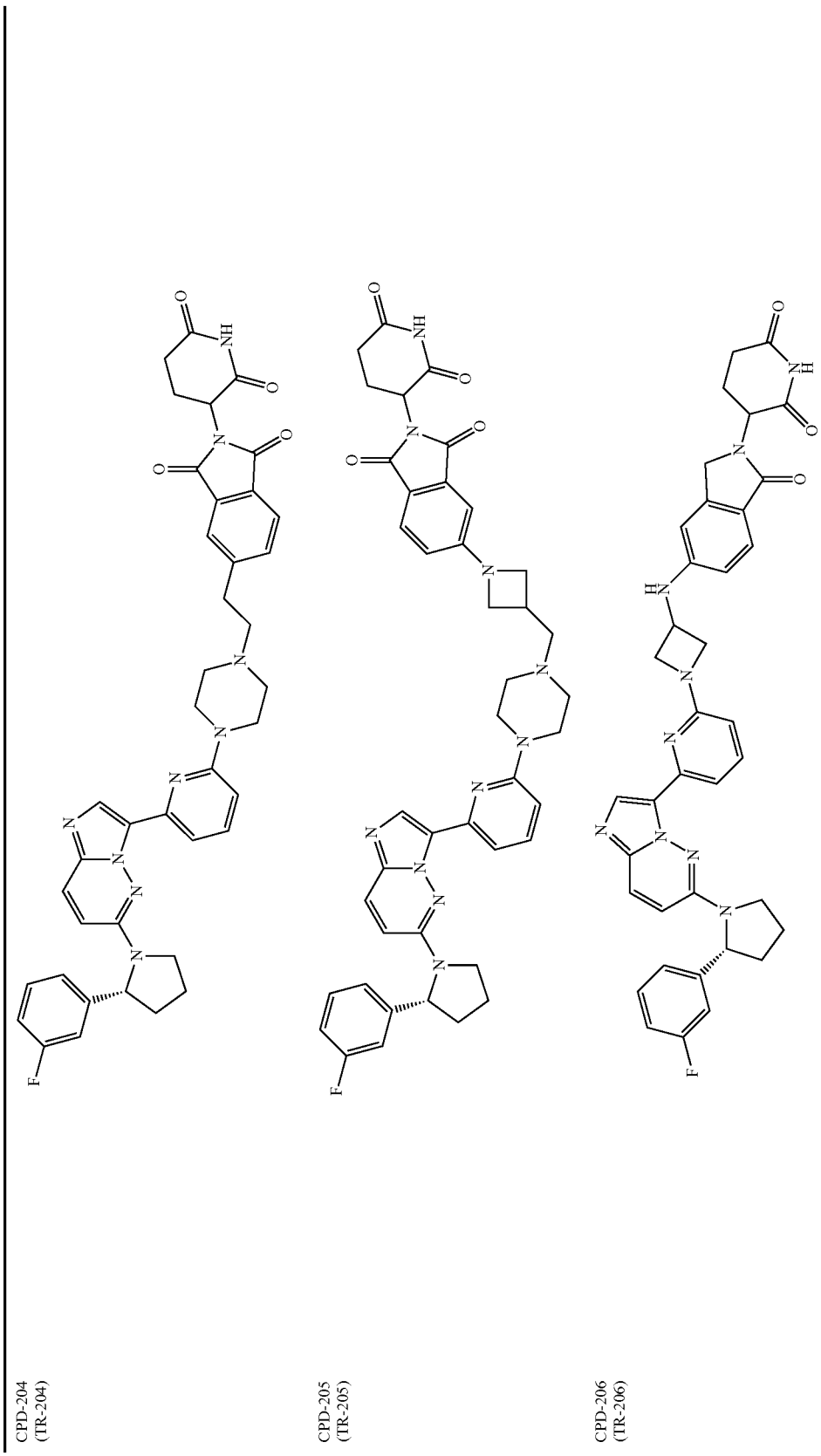
CPD-204 (TR-204)
CPD-205 (TR-205)
CPD-206 (TR-206)

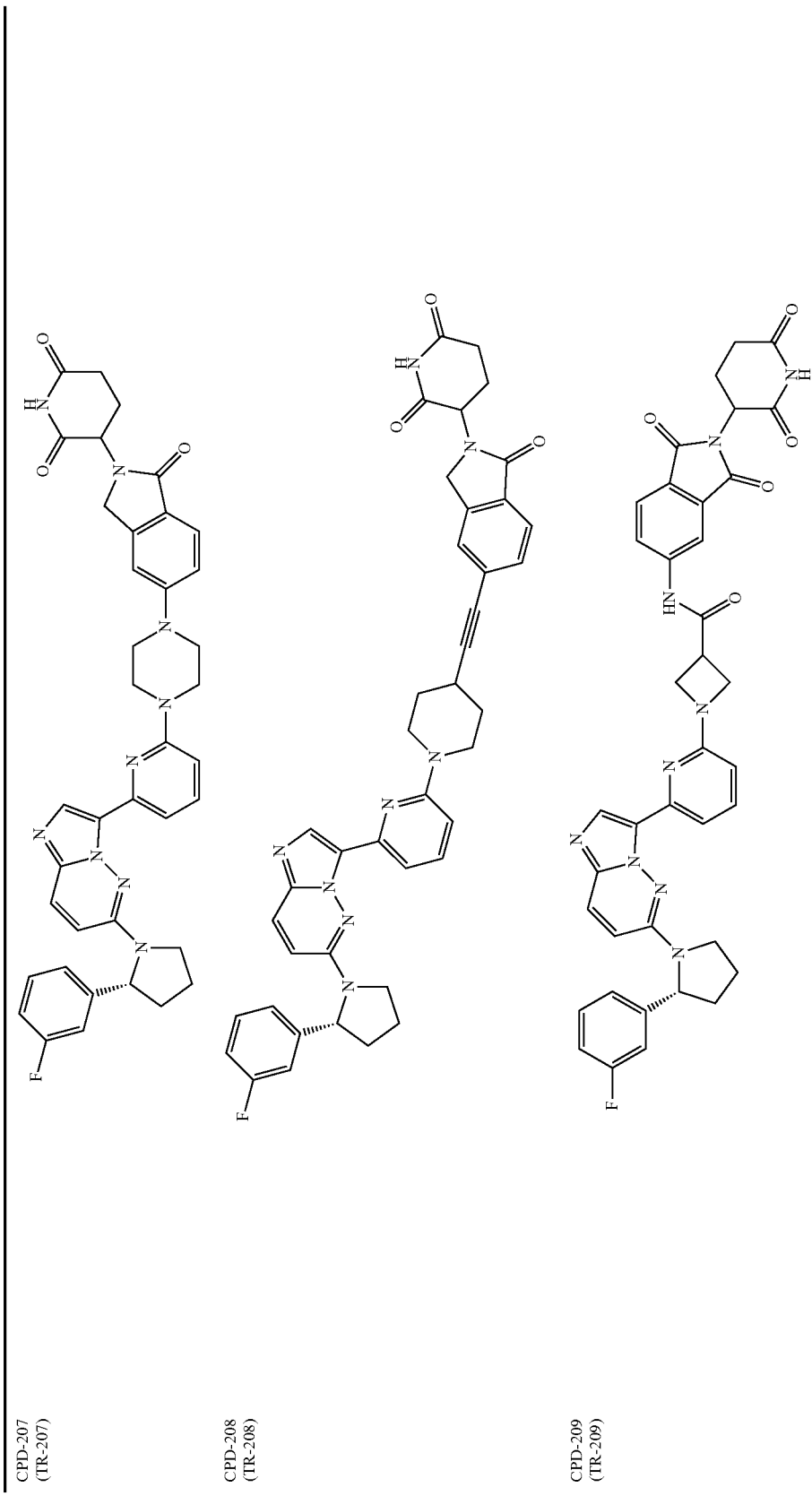

TABLE 1-continued
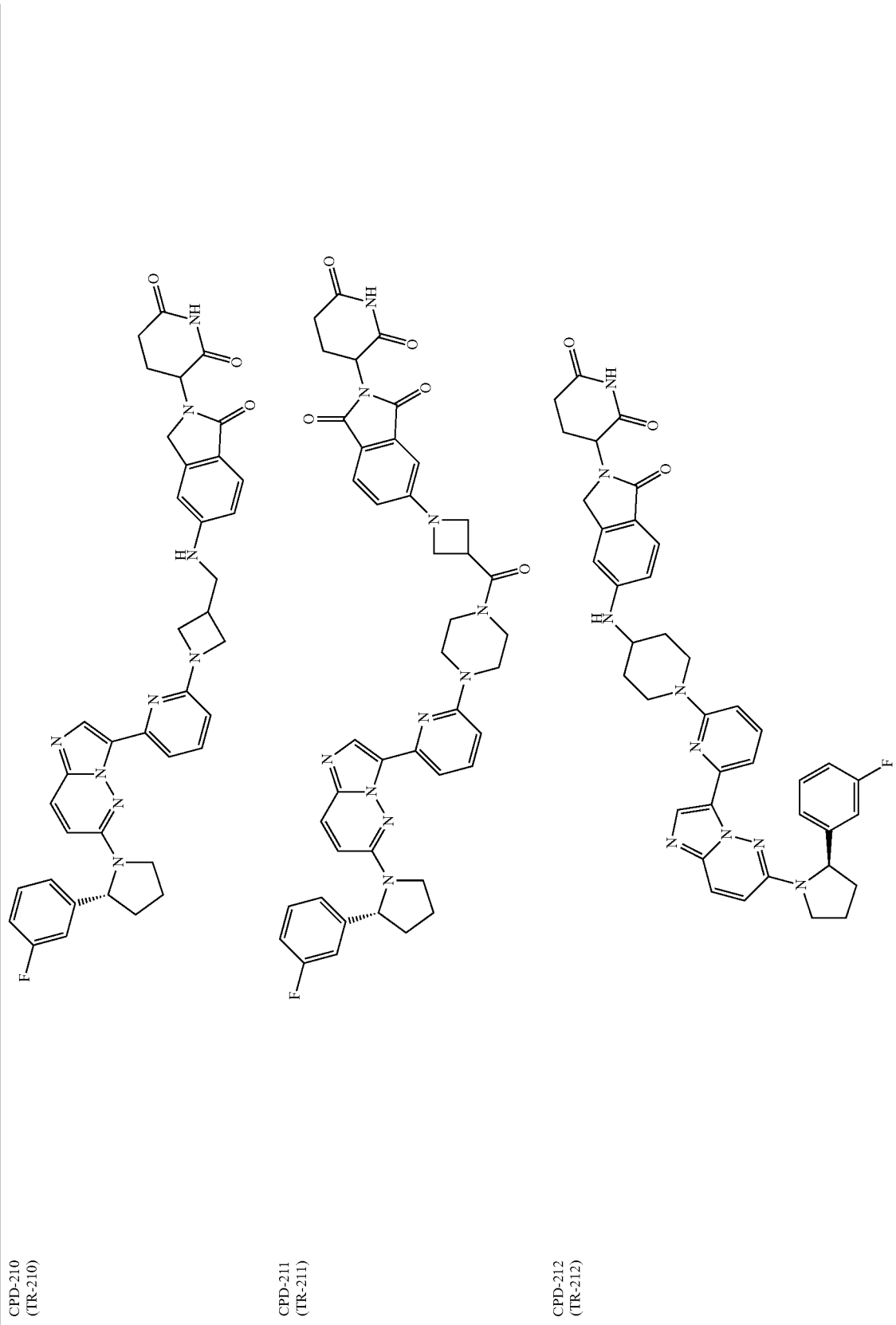
CPD-210 (TR-210)
CPD-211 (TR-211)
CPD-212 (TR-212)

TABLE 1-continued
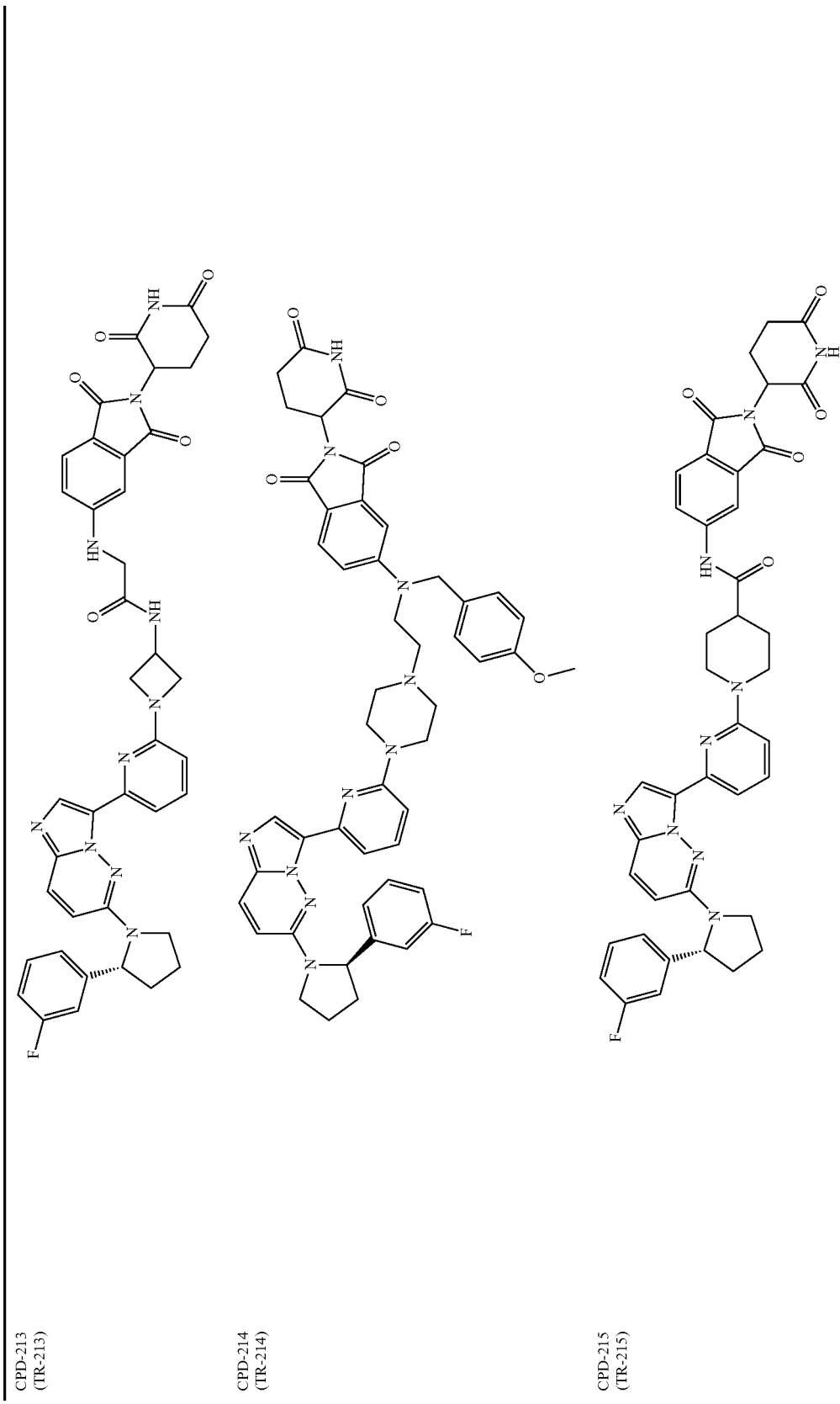
CPD-213
(TR-213)
CPD-214
(TR-214)
CPD-215
(TR-215)

TABLE 1-continued
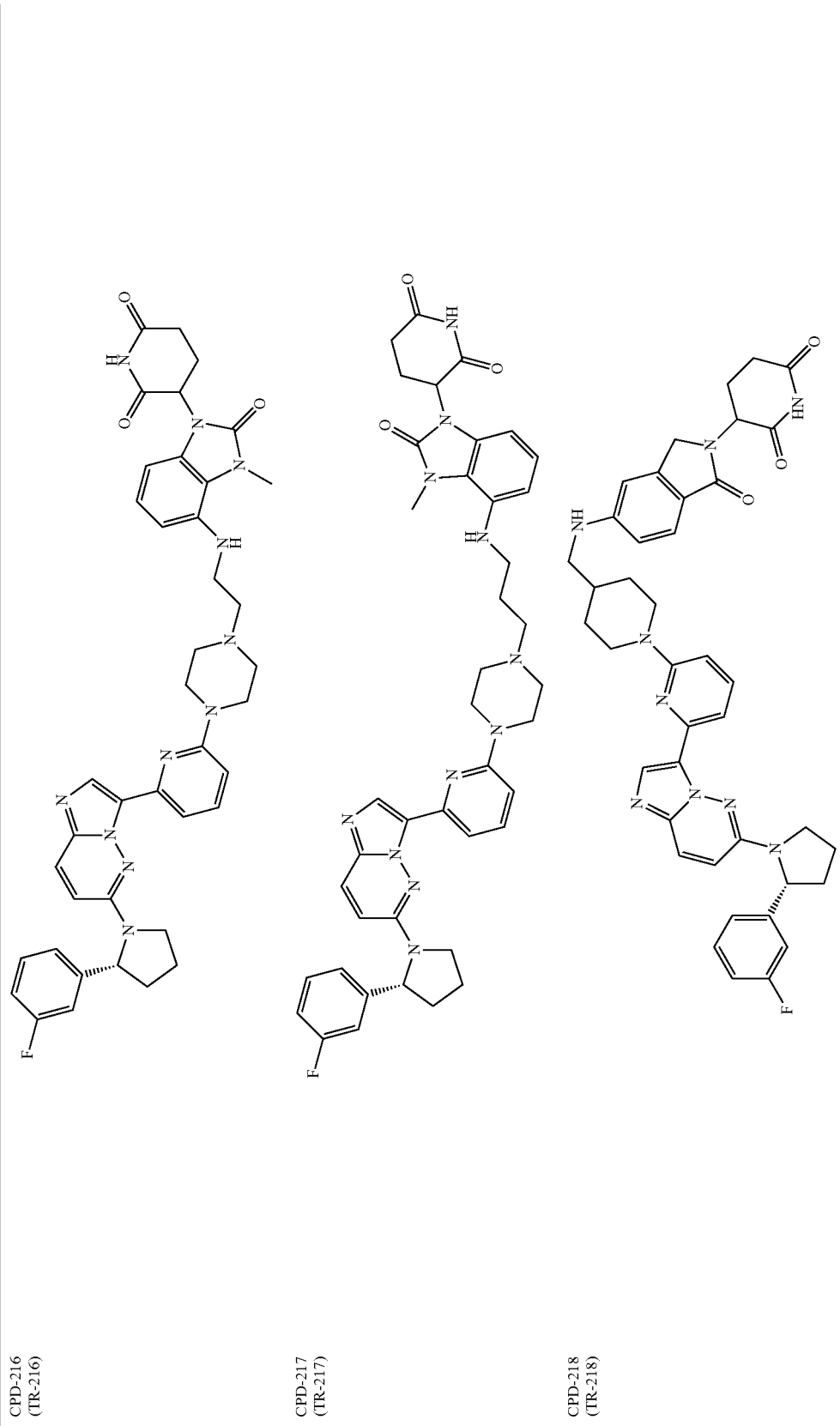
CPD-216 (TR-216)
CPD-217 (TR-217)
CPD-218 (TR-218)

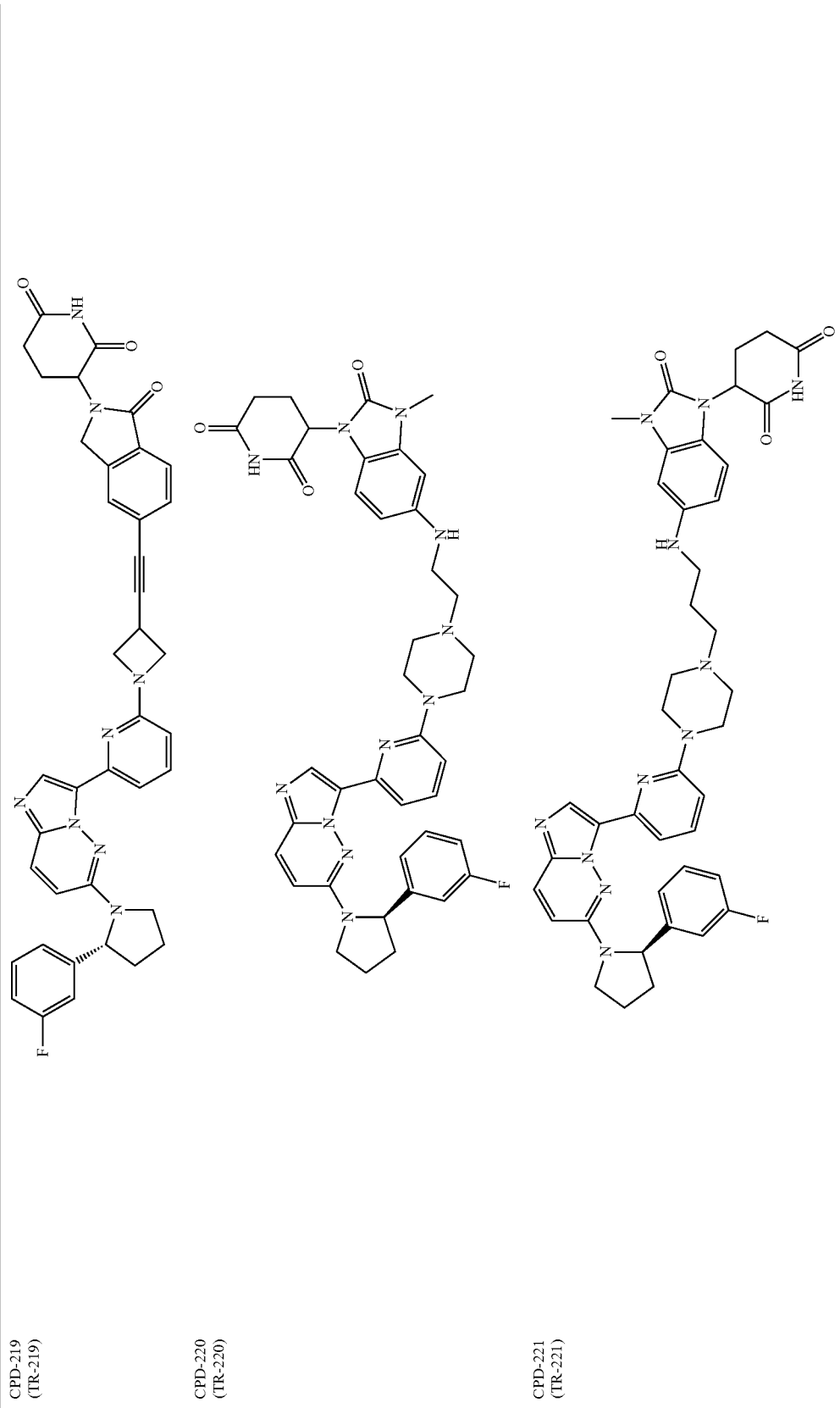

TABLE 1-continued
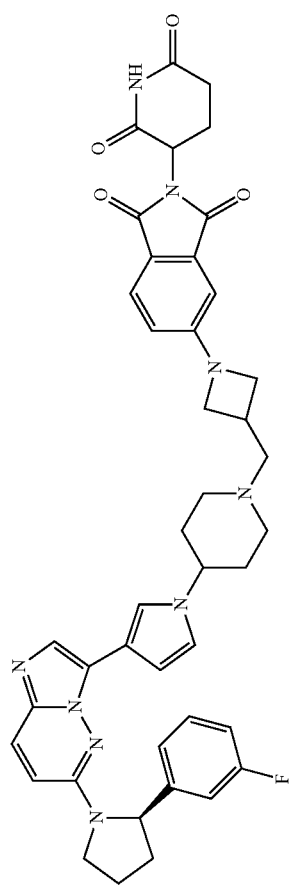
CPD-222
(TR-222)
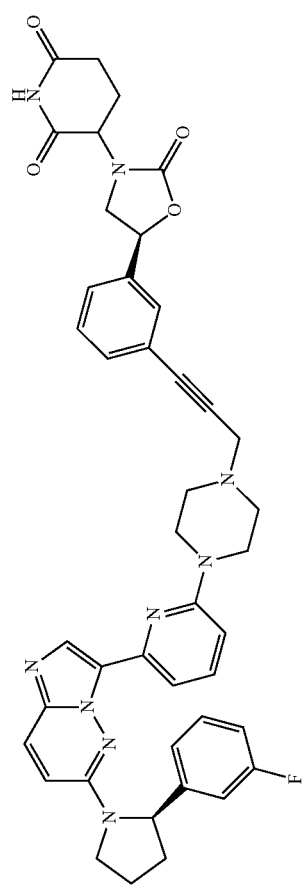
CPD-223
(TR-223)
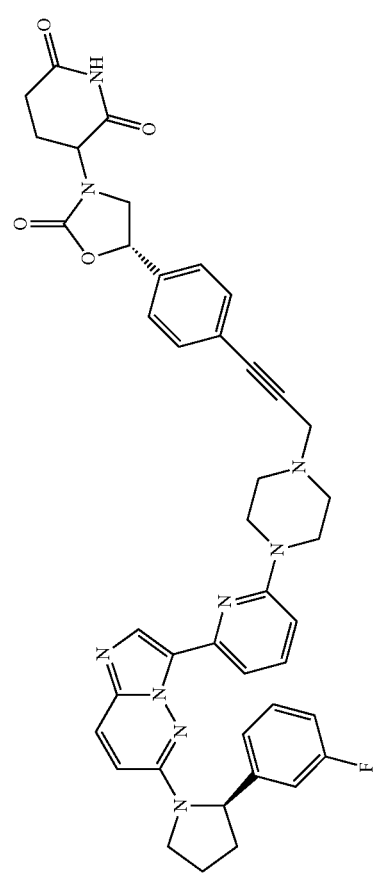
CPD-224
(TR-224)

TABLE 1-continued
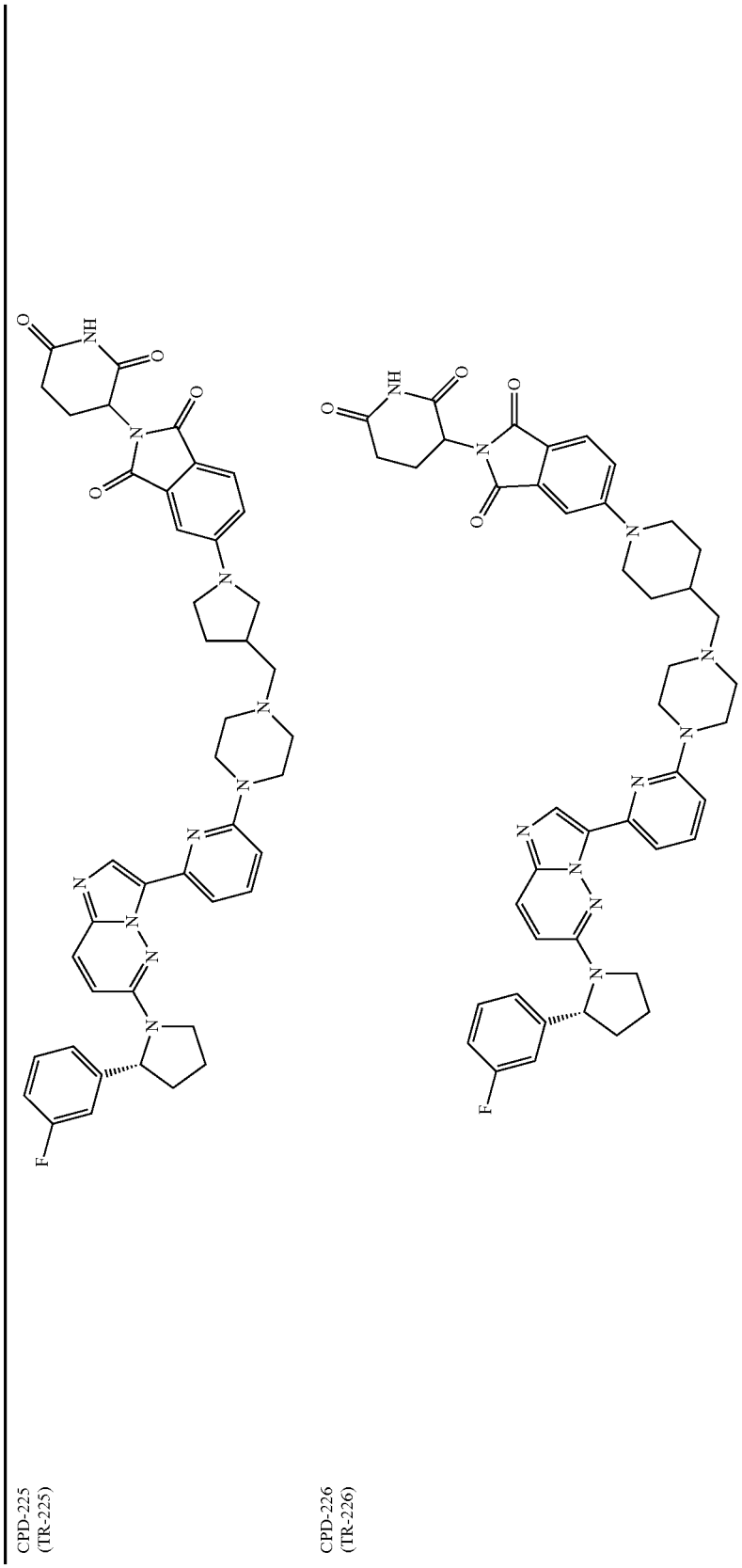
CPD-225
(TR-225)
CPD-226
(TR-226)

TABLE 1-continued
| CPD-227 (TR-227) | 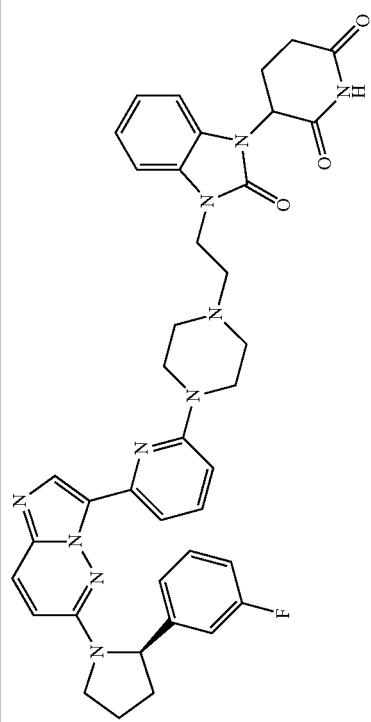 |
| CPD-228 (TR-228) | 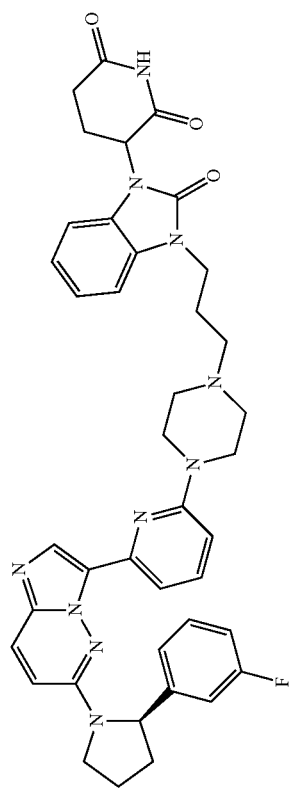 |
| CPD-229 (TR-229) | 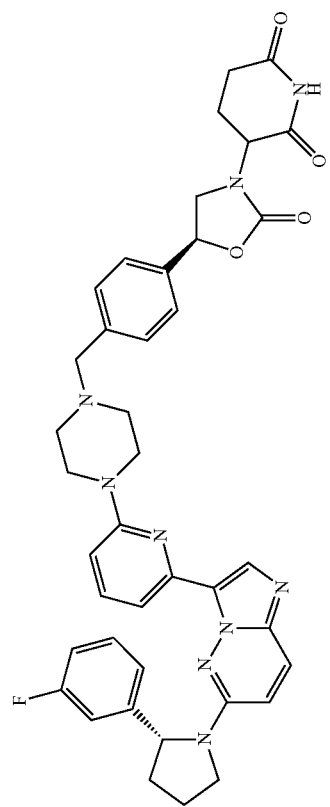 |

TABLE 1-continued
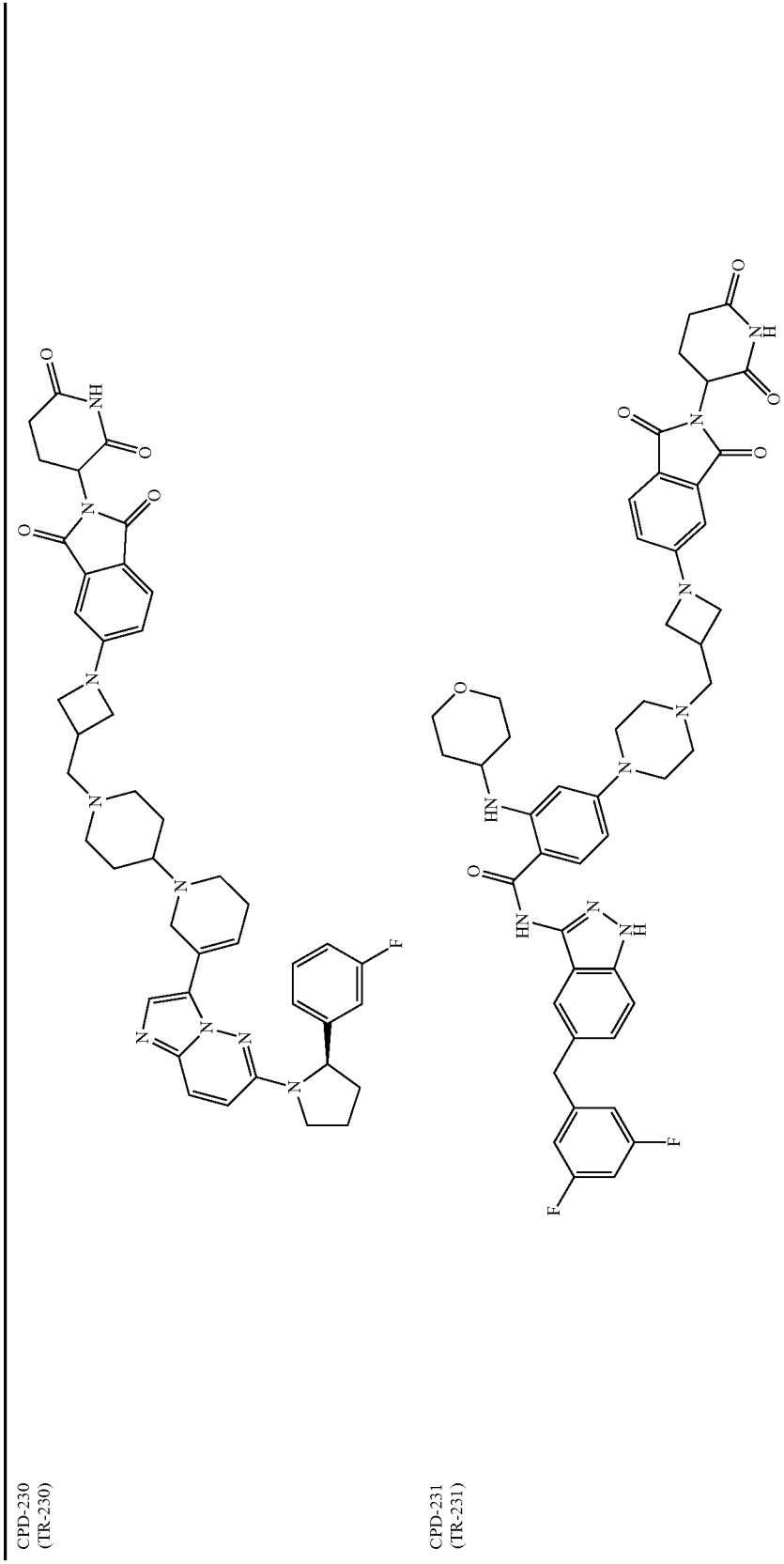
CPD-230
(TR-230)
CPD-231
(TR-231)

TABLE 1-continued
| | |
|---|---|
| CPD-232 (TR-232) | 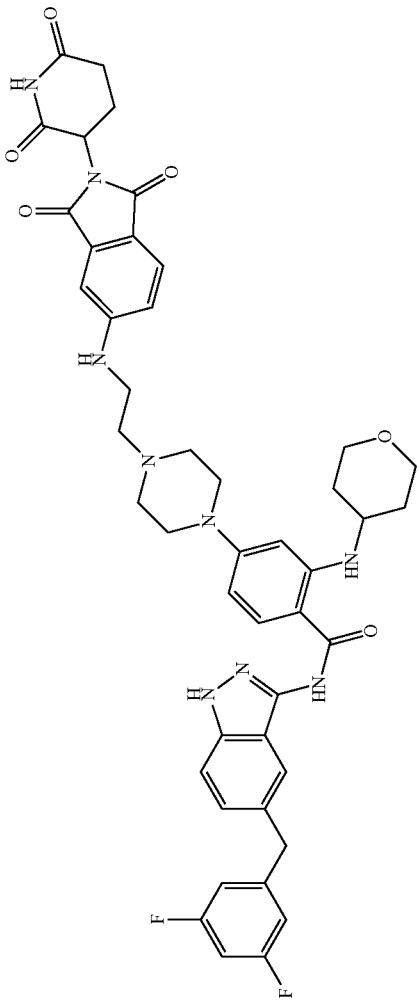 |
| CPD-233 (TR-233) | 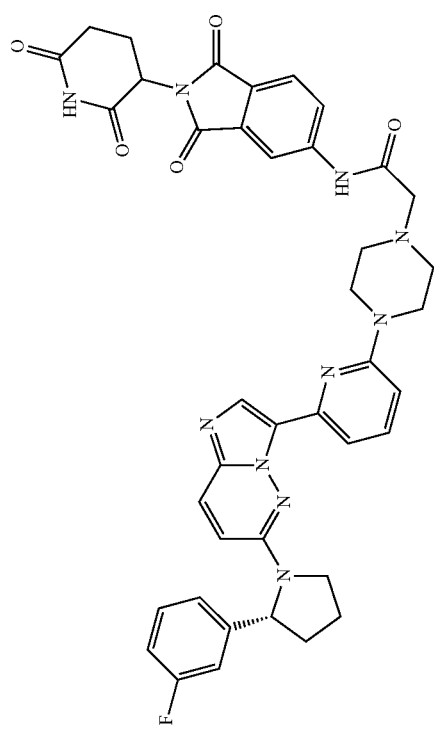 |

TABLE 1-continued
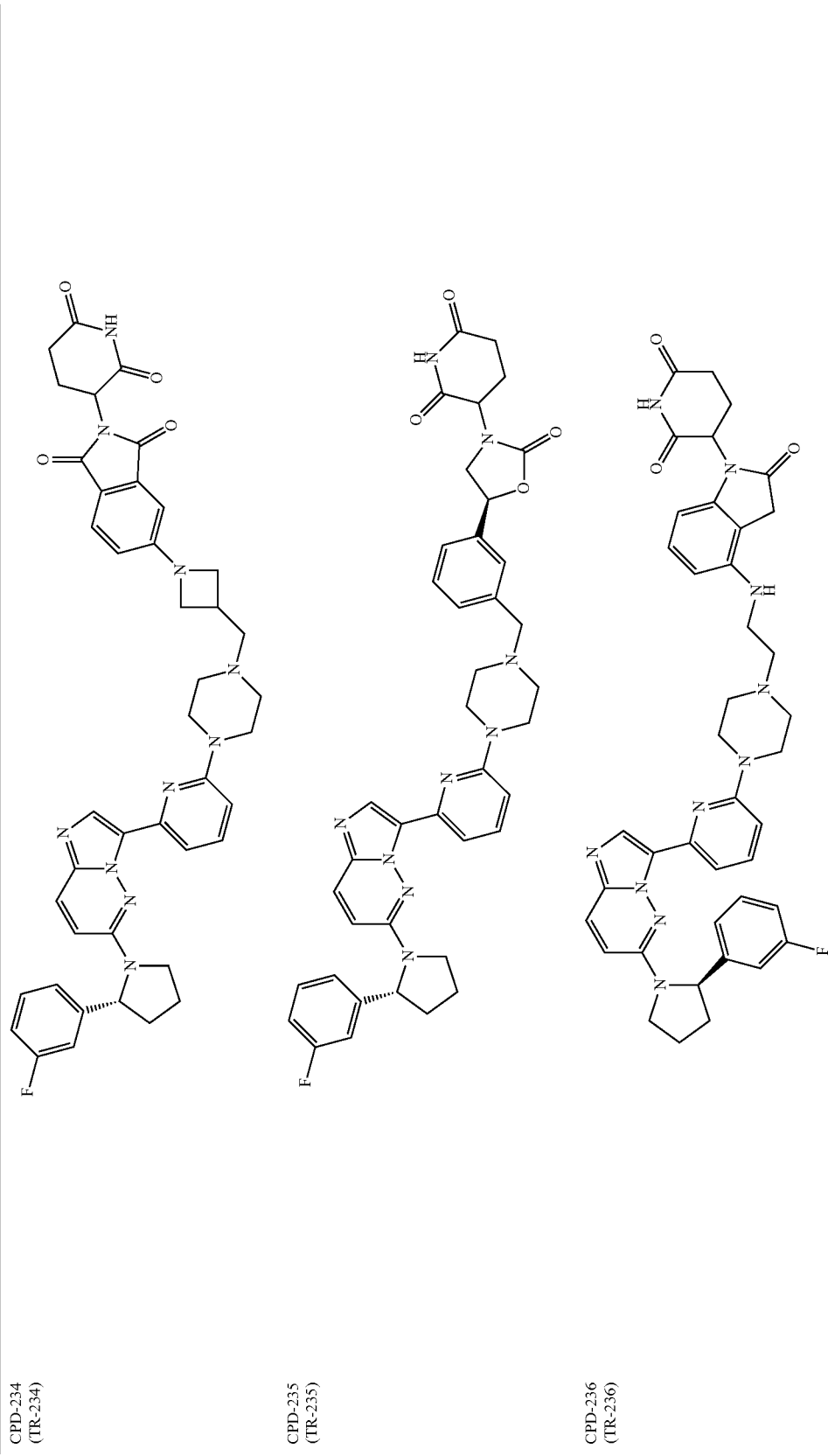
CPD-234
(TR-234)
CPD-235
(TR-235)
CPD-236
(TR-236)

TABLE 1-continued
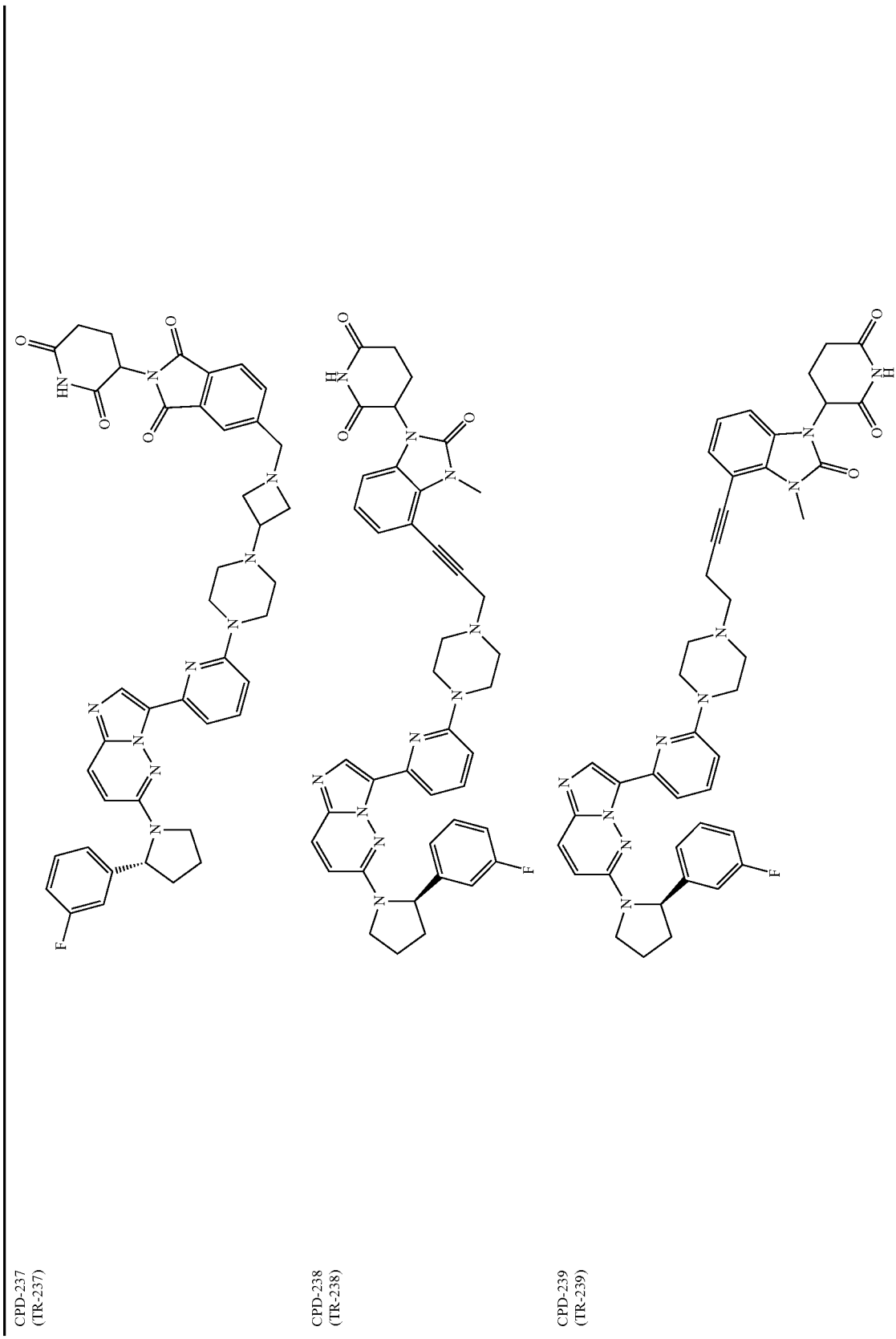
CPD-237
(TR-237)
CPD-238
(TR-238)
CPD-239
(TR-239)

TABLE 1-continued
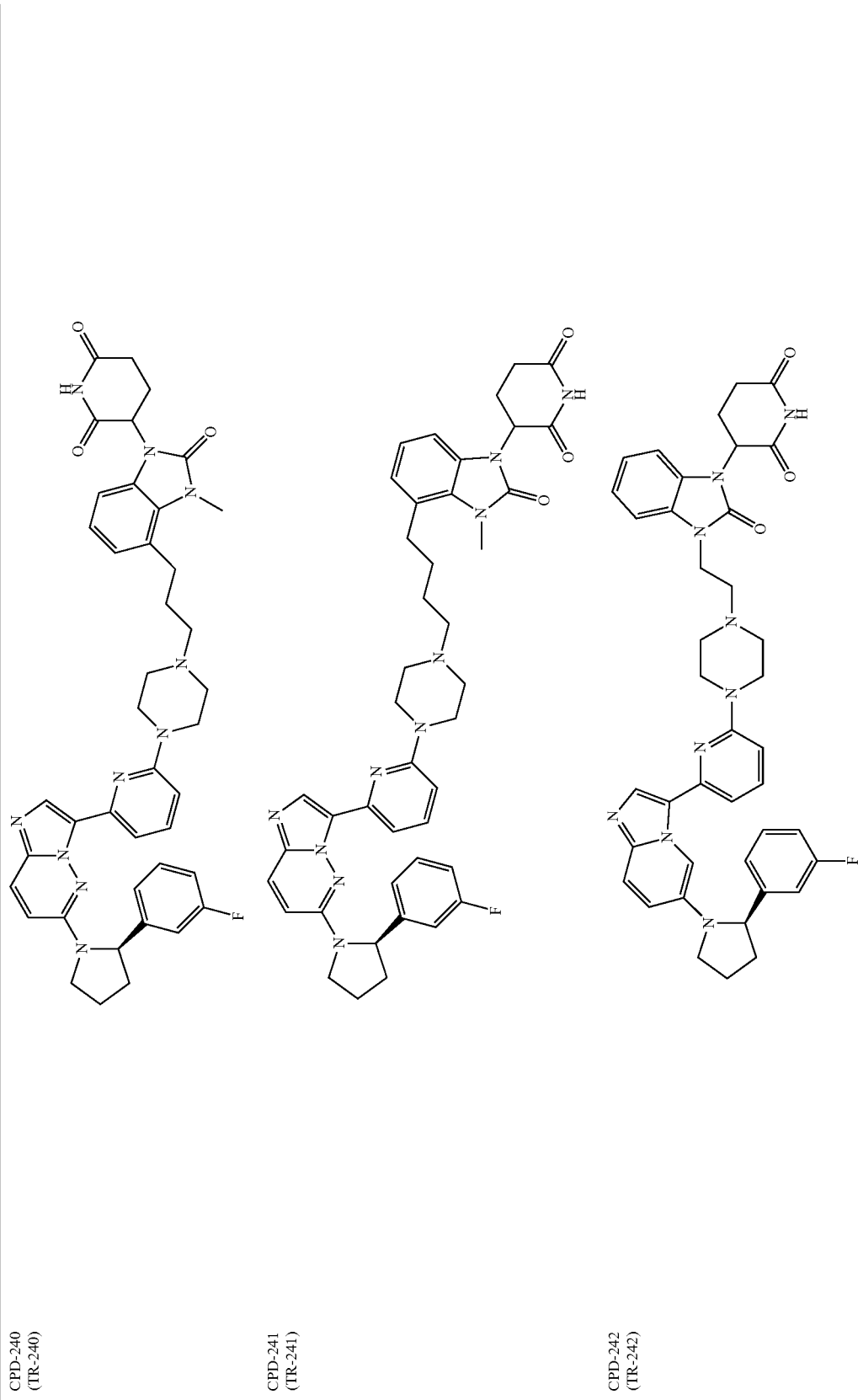
CPD-240 (TR-240)
CPD-241 (TR-241)
CPD-242 (TR-242)

TABLE 1-continued
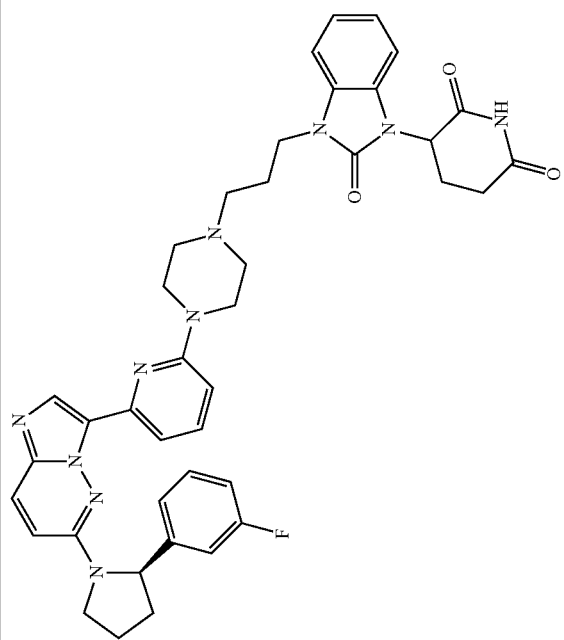
CPD-243
(TR-243)
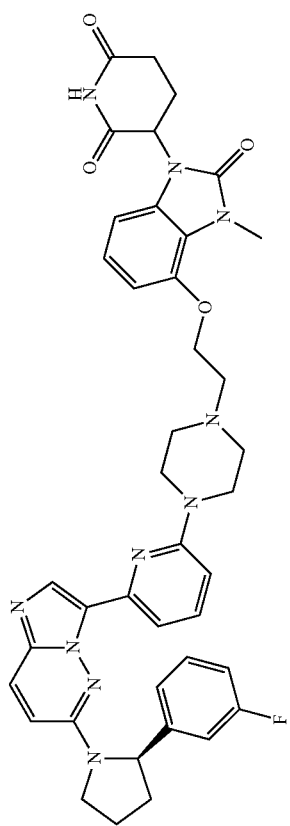
CPD-244
(TR-244)

| TABLE 1-continued | |
|---|---|
| CPD-245 (TR-245) | 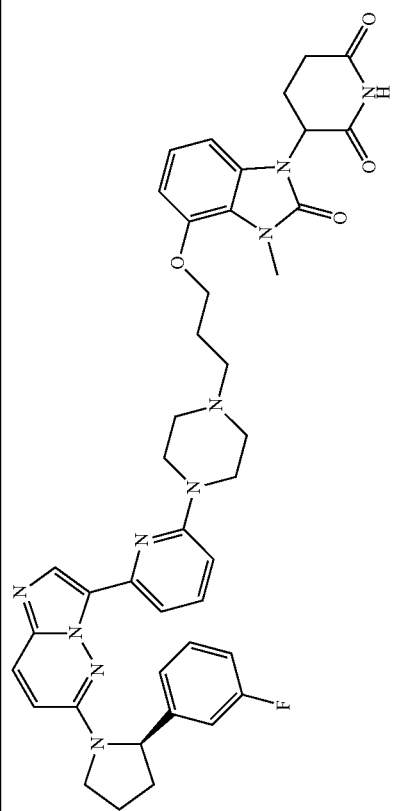 |
| CPD-246 (TR-246) | 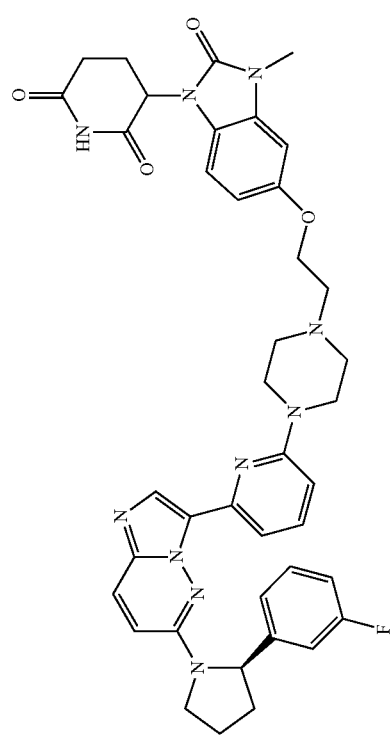 |

TABLE 1-continued

| Cpd. Code | Chemical Name |
|---|---|
| CPD-001 (TR-001) | (2S,4R)-1-((S)-2-(6-(4-(6-(6-((R)-2-(3-fluorophenyl)pyrrolidin-1-yl)imidazo[1,2-b]pyridazin-3-yl)pyridin-2-yl)piperazin-1-yl)-6-oxohexanamido)-3,3-dimethylbutanoyl)-4-hydroxy-N-(4-(4-methylthiazol-5-yl)benzyl)pyrrolidine-2-carboxamide |
| CPD-002 (TR-002) | (2S,4R)-1-((S)-2-(2-(2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |
| CPD-003 (TR-003) | (2S,4R)-1-((S)-2-(tert-butyl)-20-(4-(6-(6-((R)-2-(3-fluorophenyl)pyrrolidin-1-yl)imidazo[1,2-b]pyridazin-3-yl)pyridin-2-yl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide |
| CPD-004 (TR-004) | (2S,4R)-1-((S)-2-(7-(4-(6-(6-((R)-2-(3-fluorophenyl)pyrrolidin-1-yl)imidazo[1,2-b]pyridazin-3-yl)pyridin-2-yl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| CPD-005 (TR-005) | (2S,4R)-1-((S)-2-(tert-butyl)-22-(4-(6-(6-((R)-2-(3-fluorophenyl)pyrrolidin-1-yl)imidazo[1,2-b]pyridazin-3-yl)pyridin-2-yl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |
| CPD-006 (TR-006) | (2S,4R)-1-((S)-2-(4-(4-(6-(6-((R)-2-(3-fluorophenyl)pyrrolidin-1-yl)imidazo[1,2-b]pyridazin-3-yl)pyridin-2-yl)piperazin-1-yl)-4-oxobutanamido)-3,3-dimethylbutanoyl)-4-hydroxy-N-(4-(4-methylthiazol-5-yl)benzyl)pyrrolidine-2-carboxamide |

TABLE 1-continued

| | |
|---|---|
| CPD-007 (TR-007) | (2S,4R)-1-((S)-2-(3-(3-(4-(6-((R)-2-(3-fluorophenyl)pyrrolidin-1-yl)imidazo[1,2-b]pyridazin-3-yl)pyridin-2-yl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide |
| CPD-008 (TR-008) | (2S,4R)-1-((S)-2-(2-(2-(4-(6-((R)-2-(3-fluorophenyl)pyrrolidin-1-yl)imidazo[1,2-b]pyridazin-3-yl)pyridin-2-yl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide |
| CPD-009 (TR-009) | 2-(2,6-dioxopiperidin-3-yl)-4-(7-(4-(6-(6-((R)-2-(3-fluorophenyl)pyrrolidin-1-yl)imidazo[1,2-b]pyridazin-3-yl)pyridin-2-yl)piperazin-1-yl)-7-oxoheptyl)amino)isoindoline-1,3-dione |
| CPD-010 (TR-010) | 2-(2,6-dioxopiperidin-3-yl)-4-((2-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethyl)amino)isoindoline-1,3-dione |
| CPD-011 (TR-011) | (2S,4R)-1-((S)-2-(tert-butyl)-14-(4-(6-(6-((R)-2-(3-fluorophenyl)pyrrolidin-1-yl)imidazo[1,2-b]pyridazin-3-yl)pyridin-2-yl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide |
| CPD-012 (TR-012) | (2S,4R)-1-((S)-2-(6-(5-(6-(6-((R)-2-(3-fluorophenyl)pyrrolidin-1-yl)imidazo[1,2-b]pyridazin-3-yl)pyridin-2-yl)piperazin-1-yl)-5-oxopentanamido)-3,3-dimethylbutanoyl)-4-hydroxy-N-(4-(4-methylthiazol-5-yl)benzyl)pyrrolidine-2-carboxamide |
| CPD-013 (TR-013) | 2-(2,6-dioxopiperidin-3-yl)-4-(4-(4-(6-(6-((R)-2-(3-fluorophenyl)pyrrolidin-1-yl)imidazo[1,2-b]pyridazin-3-yl)pyridin-2-yl)piperazin-1-yl)-4-oxobutyl)amino)isoindoline-1,3-dione |
| CPD-014 (TR-014) | 2-(2,6-dioxopiperidin-3-yl)-4-((5-(4-(6-(6-((R)-2-(3-fluorophenyl)pyrrolidin-1-yl)imidazo[1,2-b]pyridazin-3-yl)pyridin-2-yl)piperazin-1-yl)-5-oxopentyl)amino)isoindoline-1,3-dione |

TABLE 1-continued

| | |
|---|---|
| CPD-015 (TR-015) | 2-(2,6-dioxopiperidin-3-yl)-4-((6-(4-(6-(6-((R)-2-(3-fluorophenyl)pyrrolidin-1-yl)imidazo[1,2-b]pyridazin-3-yl)pyridin-2-yl)piperazin-1-yl)-6-oxohexyl)amino)isoindoline-1,3-dione |
| CPD-016 (TR-016) | (2S,4R)-1-((S)-2-(tert-butyl)-16-(4-(6-(6-((R)-2-(3-fluorophenyl)pyrrolidin-1-yl)imidazo[1,2-b]pyridazin-3-yl)pyridin-2-yl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |
| CPD-017 (TR-017) | (2S,4R)-1-((S)-2-(10-(4-(6-(6-((R)-2-(3-fluorophenyl)pyrrolidin-1-yl)imidazo[1,2-b]pyridazin-3-yl)pyridin-2-yl)piperazin-1-yl)-10-oxodecanamido)-3,3-dimethylbutanoyl)-4-hydroxy-N-(4-(4-methylthiazol-5-yl)benzyl)pyrrolidine-2-carboxamide |
| CPD-018 (TR-018) | (2S,4R)-1-((S)-2-(9-(4-(6-(6-((R)-2-(3-fluorophenyl)pyrrolidin-1-yl)imidazo[1,2-b]pyridazin-3-yl)pyridin-2-yl)piperazin-1-yl)-9-oxononanamido)-3,3-dimethylbutanoyl)-4-hydroxy-N-(4-(4-methylthiazol-5-yl)benzyl)pyrrolidine-2-carboxamide |
| CPD-019 (TR-019) | (2S,4R)-1-((S)-2-(tert-butyl)-19-(4-(6-(6-((R)-2-(3-fluorophenyl)pyrrolidin-1-yl)imidazo[1,2-b]pyridazin-3-yl)pyridin-2-yl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |
| CPD-020 (TR-020) | (2S,4R)-1-((S)-2-(3-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |
| CPD-021 (TR-021) | 2-(2,6-dioxopiperidin-3-yl)-4-((15-(4-(6-(6-((R)-2-(3-fluorophenyl)pyrrolidin-1-yl)imidazo[1,2-b]pyridazin-3-yl)pyridin-2-yl)piperazin-1-yl)-15-oxo-3,6,9,12-tetraoxapentadecyl)amino)isoindoline-1,3-dione |

TABLE 1-continued

| | |
|---|---|
| CPD-022 (TR-022) | (2S,4R)-1-((S)-2-(11-(4-(6-(4-(6-((R)-2-(3-fluorophenyl)pyrrolidin-1-yl)imidazo[1,2-b]pyridazin-3-yl)pyridin-2-yl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |
| CPD-023 (TR-023) | 2-(2,6-dioxopiperidin-3-yl)-4-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)isoindoline-1,3-dione |
| CPD-024 (TR-024) | 2-(2,6-dioxopiperidin-3-yl)-4-((8-(4-(6-(6-((R)-2-(3-fluorophenyl)pyrrolidin-1-yl)imidazo[1,2-b]pyridazin-3-yl)pyridin-2-yl)piperazin-1-yl)-8-oxooctyl)amino)isoindoline-1,3-dione |
| CPD-025 (TR-025) | 2-(2,6-dioxopiperidin-3-yl)-4-((18-(4-(6-(6-((R)-2-(3-fluorophenyl)pyrrolidin-1-yl)imidazo[1,2-b]pyridazin-3-yl)pyridin-2-yl)piperazin-1-yl)-18-oxo-3,6,9,12,15-pentaoxaoctadecyl)amino)isoindoline-1,3-dione |
| CPD-026 (TR-026) | 2-(2,6-dioxopiperidin-3-yl)-4-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropyl)amino)isoindoline-1,3-dione |
| CPD-027 (TR-027) | 2-(2,6-dioxopiperidin-3-yl)-4-((2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethyl)amino)isoindoline-1,3-dione |
| CPD-028 (TR-028) | 2-(2,6-dioxopiperidin-3-yl)-4-((2-(2-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethyl)amino)isoindoline-1,3-dione |
| CPD-029 (TR-029) | (2S,4R)-1-((S)-2-(8-(4-(6-(6-((R)-2-(3-fluorophenyl)pyrrolidin-1-yl)imidazo[1,2-b]pyridazin-3-yl)pyridin-2-yl)piperazin-1-yl)-8-oxooctanamido)-3,3-dimethylbutanoyl)-4-hydroxy-N-(4-(4-methylthiazol-5-yl)benzyl)pyrrolidine-2-carboxamide |

TABLE 1-continued

| | |
|---|---|
| CPD-030 (TR-030) | N-(5-(3,5-difluorobenzyl)-1H-indazol-3-yl)-4-(4-(3-(2-((2-(2,6-dioxopiperidin-3-yl)-1,3-dioxoisoindolin-4-yl)amino)ethoxy)propanyl)piperazin-1-yl)-2-((tetrahydro-2H-pyran-4-yl)amino)benzamide |
| CPD-031 (TR-031) | N-(5-(3,5-difluorobenzyl)-1H-indazol-3-yl)-4-(4-(1-((2-(2,6-dioxopiperidin-3-yl)-1,3-dioxoisoindolin-4-yl)amino)-3,6,9,12-tetraoxapentadecan-15-oyl)piperazin-1-yl)-2-((tetrahydro-2H-pyran-4-yl)amino)benzamide |
| CPD-032 (TR-032) | N-(5-(3,5-difluorobenzyl)-1H-indazol-3-yl)-4-(4-(3-(2-((2-(2,6-dioxopiperidin-3-yl)-1,3-dioxoisoindolin-4-yl)amino)ethoxy)propanyl)piperazin-1-yl)-2-((tetrahydro-2H-pyran-4-yl)amino)benzamide |
| CPD-033 (TR-033) | (2S,4R)-1-((S)-2-(8-(4-(4-((5-(3,5-difluorobenzyl)-1H-indazol-3-yl)carbamoyl)-3-((tetrahydro-2H-pyran-4-yl)amino)phenyl)piperazin-1-yl)-8-oxooctanamido)-3,3-dimethylbutanoyl)-4-hydroxy-N-(4-(4-methylthiazol-5-yl)benzyl)pyrrolidine-2-carboxamide |
| CPD-034 (TR-034) | (2S,4R)-1-((S)-2-(10-(4-(4-((5-(3,5-difluorobenzyl)-1H-indazol-3-yl)carbamoyl)-3-((tetrahydro-2H-pyran-4-yl)amino)phenyl)piperazin-1-yl)-10-oxodecanamido)-3,3-dimethylbutanoyl)-4-hydroxy-N-(4-(4-methylthiazol-5-yl)benzyl)pyrrolidine-2-carboxamide |
| CPD-035 (TR-035) | (2S,4R)-1-((S)-2-(11-(4-(4-((5-(3,5-difluorobenzyl)-1H-indazol-3-yl)carbamoyl)-3-((tetrahydro-2H-pyran-4-yl)amino)phenyl)piperazin-1-yl)-11-oxoundecanamido)-3,3-dimethylbutanoyl)-4-hydroxy-N-(4-(4-methylthiazol-5-yl)benzyl)pyrrolidine-2-carboxamide |
| CPD-036 (TR-036) | (2S,4R)-1-((S)-2-(5-(4-(4-((5-(3,5-difluorobenzyl)-1H-indazol-3-yl)carbamoyl)-3-((tetrahydro-2H-pyran-4-yl)amino)phenyl)piperazin-1-yl)-5-oxopentanamido)-3,3-dimethylbutanoyl)-4-hydroxy-N-(4-(4-methylthiazol-5-yl)benzyl)pyrrolidine-2-carboxamide |

TABLE 1-continued

| | |
|---|---|
| CPD-037 (TR-037) | (2S,4R)-1-((S)-2-(9-(4-(4-((5-(3,5-difluorobenzyl)-1H-indazol-3-yl)carbamoyl)-3-(((tetrahydro-2H-pyran-4-yl)amino)phenyl)piperazin-1-yl)-9-oxononamido)-3,3-dimethylbutanoyl)-4-hydroxy-N-(4-(4-methylthiazol-5-yl)benzyl)pyrrolidine-2-carboxamide |
| CPD-038 (TR-038) | (2S,4R)-1-((S)-2-(3-(2-(3-(4-(4-((5-(3,5-difluorobenzyl)-1H-indazol-3-yl)carbamoyl)-3-(((tetrahydro-2H-pyran-4-yl)amino)phenyl)piperazin-1-yl)-3-oxopropoxy)ethoxy)propanamido)-3,3-dimethylbutanoyl)-4-hydroxy-N-(4-(4-methylthiazol-5-yl)benzyl)pyrrolidine-2-carboxamide |
| CPD-039 (TR-039) | (2S,4R)-1-((S)-2-(tert-butyl)-16-(4-(4-((5-(3,5-difluorobenzyl)-1H-indazol-3-yl)carbamoyl)-3-(((tetrahydro-2H-pyran-4-yl)amino)phenyl)piperazin-1-yl)-4,16-dioxo-7,10,13-trioxa-3-azahexadecanoyl)-4-hydroxy-N-(4-(4-methylthiazol-5-yl)benzyl)pyrrolidine-2-carboxamide |
| CPD-040 (TR-040) | (2S,4R)-1-((S)-2-(tert-butyl)-20-(4-(4-((5-(3,5-difluorobenzyl)-1H-indazol-3-yl)carbamoyl)-3-(((tetrahydro-2H-pyran-4-yl)amino)phenyl)piperazin-1-yl)-4,20-dioxo-6,9,12,15,18-pentaoxa-3-azaicosanoyl)-4-hydroxy-N-(4-(4-methylthiazol-5-yl)benzyl)pyrrolidine-2-carboxamide |
| CPD-041 (TR-041) | (2S,4R)-1-((S)-2-(tert-butyl)-19-(4-(4-((5-(3,5-difluorobenzyl)-1H-indazol-3-yl)carbamoyl)-3-(((tetrahydro-2H-pyran-4-yl)amino)phenyl)piperazin-1-yl)-4,19-dioxo-7,10,13,16-tetraoxa-3-azanonadecanoyl)-4-hydroxy-N-(4-(4-methylthiazol-5-yl)benzyl)pyrrolidine-2-carboxamide |
| CPD-042 (TR-042) | (2S,4R)-1-((S)-2-(2-(2-(4-(4-((5-(3,5-difluorobenzyl)-1H-indazol-3-yl)carbamoyl)-3-(((tetrahydro-2H-pyran-4-yl)amino)phenyl)piperazin-1-yl)-2-oxoethoxy)ethoxy)acetamido)-3,3-dimethylbutanoyl)-4-hydroxy-N-(4-(4-methylthiazol-5-yl)benzyl)pyrrolidine-2-carboxamide |

TABLE 1-continued

| | |
|---|---|
| CPD-043 (TR-043) | (2S,4R)-1-((S)-2-(tert-butyl)-22-(4-(4-((5-(3,5-difluorobenzyl)-1H-indazol-3-yl)carbamoyl)-3-((tetrahydro-2H-pyran-4-yl)amino)phenyl)piperazin-1-yl)-4,22-dioxo-7,10,13,16,19-pentaoxa-3-azadocosanoyl)-4-hydroxy-N-(4-(4-methylthiazol-5-yl)benzyl)pyrrolidine-2-carboxamide |
| CPD-044 (TR-044) | (2S,4R)-1-((S)-2-(6-(4-(4-((5-(3,5-difluorobenzyl)-1H-indazol-3-yl)carbamoyl)-3-((tetrahydro-2H-pyran-4-yl)amino)phenyl)piperazin-1-yl)-6-oxohexanamido)-3,3-dimethylbutanoyl)-4-hydroxy-N-(4-(4-methylthiazol-5-yl)benzyl)pyrrolidine-2-carboxamide |
| CPD-045 (TR-045) | (2S,4R)-1-((S)-2-(2-(4-(4-((5-(3,5-difluorobenzyl)-1H-indazol-3-yl)carbamoyl)-3-((tetrahydro-2H-pyran-4-yl)amino)phenyl)piperazin-1-yl)-2-oxoethoxy)acetamido)-3,3-dimethylbutanoyl)-4-hydroxy-N-(4-(4-methylthiazol-5-yl)benzyl)pyrrolidine-2-carboxamide |
| CPD-046 (TR-046) | (2S,4R)-1-((S)-2-(4-(4-((5-(3,5-difluorobenzyl)-1H-indazol-3-yl)carbamoyl)-3-((tetrahydro-2H-pyran-4-yl)amino)phenyl)piperazin-1-yl)-4-oxobutanamido)-3,3-dimethylbutanoyl)-4-hydroxy-N-(4-(4-methylthiazol-5-yl)benzyl)pyrrolidine-2-carboxamide |
| CPD-047 (TR-047) | (2S,4R)-1-((S)-2-(7-(4-(4-((5-(3,5-difluorobenzyl)-1H-indazol-3-yl)carbamoyl)-3-((tetrahydro-2H-pyran-4-yl)amino)phenyl)piperazin-1-yl)-7-oxoheptanamido)-3,3-dimethylbutanoyl)-4-hydroxy-N-(4-(4-methylthiazol-5-yl)benzyl)pyrrolidine-2-carboxamide |
| CPD-048 (TR-048) | (2S,4R)-1-((S)-2-(3-(4-(4-((5-(3,5-difluorobenzyl)-1H-indazol-3-yl)carbamoyl)-3-((tetrahydro-2H-pyran-4-yl)amino)phenyl)piperazin-1-yl)-3-oxopropoxy)propanamido)-3,3-dimethylbutanoyl)-4-hydroxy-N-(4-(4-methylthiazol-5-yl)benzyl)pyrrolidine-2-carboxamide |
| CPD-049 (TR-049) | N-(5-(3,5-difluorobenzyl)-1H-indazol-3-yl)-4-(4-(7-((2-(2,6-dioxopiperidin-3-yl)-1,3-dioxoisoindolin-4-yl)amino)heptanoyl)piperazin-1-yl)-2-((tetrahydro-2H-pyran-4-yl)amino)benzamide |

TABLE 1-continued

| | |
|---|---|
| CPD-050 (TR-050) | N-(5-(3,5-difluorobenzyl)-1H-indazol-3-yl)-4-(4-(5-((2-(2,6-dioxopiperidin-3-yl)-1,3-dioxoisoindolin-4-yl)amino)pentanoyl)piperazin-1-yl)-2-((tetrahydro-2H-pyran-4-yl)amino)benzamide |
| CPD-051 (TR-051) | N-(5-(3,5-difluorobenzyl)-1H-indazol-3-yl)-4-(4-(3-((2-(2,6-dioxopiperidin-3-yl)-1,3-dioxoisoindolin-4-yl)amino)propanyl)piperazin-1-yl)-2-((tetrahydro-2H-pyran-4-yl)amino)benzamide |
| CPD-052 (TR-052) | N-(5-(3,5-difluorobenzyl)-1H-indazol-3-yl)-4-(4-(8-((2-(2,6-dioxopiperidin-3-yl)-1,3-dioxoisoindoline-4-yl)amino)octanoyl)piperazin-1-yl)-2-((tetrahydro-2H-pyran-4-yl)amino)benzamide |
| CPD-053 (TR-053) | N-(5-(3,5-difluorobenzyl)-1H-indazol-3-yl)-4-(4-(4-((2-(2,6-dioxopiperidin-3-yl)-1,3-dioxoisoindolin-4-yl)amino)butanoyl)piperazin-1-yl)-2-((tetrahydro-2H-pyran-4-yl)amino)benzamide |
| CPD-054 (TR-054) | N-(5-(3,5-difluorobenzyl)-1H-indazol-3-yl)-4-(4-(1-((2-(2,6-dioxopiperidin-3-yl)-1,3-dioxoisoindolin-4-yl)amino)-3,6,9,12,15-pentaoxaoctadecan-18-oyl)piperazin-1-yl)-2-((tetrahydro-2H-pyran-4-yl)amino)benzamide |
| CPD-055 (TR-055) | N-(5-(3,5-difluorobenzyl)-1H-indazol-3-yl)-4-(4-((2-(2,6-dioxopiperidin-3-yl)-1,3-dioxoisoindoline-4-yl)glycyl)piperazin-1-yl)-2-((tetrahydro-2H-pyran-4-yl)amino)benzamide |
| CPD-056 (TR-056) | N-(5-(3,5-difluorobenzyl)-1H-indazol-3-yl)-4-(4-(6-((2-(2,6-dioxopiperidin-3-yl)-1,3-dioxoisoindolin-4-yl)amino)hexanoyl)piperazin-1-yl)-2-((tetrahydro-2H-pyran-4-yl)amino)benzamide |
| CPD-057 (TR-057) | N-(5-(3,5-difluorobenzyl)-1H-indazol-3-yl)-4-(4-(3-(2-(2-(2-(2,6-dioxopiperidin-3-yl)-1,3-dioxoisoindolin-4-yl)amino)ethoxy)ethoxy)propanoyl)piperazin-1-yl)-2-((tetrahydro-2H-pyran-4-yl)amino)benzamide |

TABLE 1-continued

| | |
|---|---|
| CPD-058 (TR-058) | (2S,4R)-1-((S)-2-(tert-butyl)-14-(4-(4-((5-(3,5-difluorobenzyl)-1H-indazol-3-yl)carbamoyl)-3-((tetrahydro-2H-pyran-4-yl)amino)phenyl)piperazin-1-yl)-4,14-dioxo-6,9,12-trioxa-3-azatetradecanoyl)-4-hydroxy-N-(4-(4-methylthiazol-5-yl)benzyl)pyrrolidine-2-carboxamide |
| CPD-059 (TR-059) | N-(2-(2-(2-(2-((2-(2,6-dioxopiperidin-3-yl)-1,3-dioxoisoindolin-4-yl)amino)ethoxy)ethoxy)ethyl)-2-(4-(6-(6-((R)-2-(3-fluorophenyl)pyrrolidin-1-yl)imidazo[1,2-b]pyridazin-3-yl)pyridin-3-yl)piperazin-1-yl)acetamide |
| CPD-060 (TR-060) | N-(2-((2-(2,6-dioxopiperidin-3-yl)-1,3-dioxoisoindolin-4-yl)amino)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-061 (TR-061) | (2S,4R)-1-((S)-2-(8-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)octanamido)-3,3-dimethylbutanoyl)-4-hydroxy-N-(4-(4-methylthiazol-5-yl)benzyl)pyrrolidine-2-carboxamide |
| CPD-062 (TR-062) | N-(5-(3,5-difluorobenzyl)-1H-indazol-3-yl)-4-(4-(2-((2-(2,6-dioxopiperidin-3-yl)-1,3-dioxoisoindolin-4-yl)amino)ethyl)amino)-2-oxoethyl)piperazin-1-yl)-2-((tetrahydro-2H-pyran-4-yl)amino)benzamide |
| CPD-063 (TR-063) | (2S,4R)-1-((S)-2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)acetamido)-3,3-dimethylbutanoyl)-4-hydroxy-N-(4-(4-methyl4thiazol-5-yl)benzyl)pyrrolidine-2-carboxamide |
| CPD-064 (TR-064) | N-(5-(3,5-difluorobenzyl)-1H-indazol-3-yl)-4-(4-(14-((2-(2,6-dioxopiperidin-3-yl)-1,3-dioxoisoindolin-4-yl)amino)-2-oxo-6,9,12-trioxa-3-azatetradecyl)piperazin-1-yl)-2-((tetrahydro-2H-pyran-4-yl)amino)benzamide |

TABLE 1-continued

| | |
|---|---|
| CPD-065 (TR-065) | N-(5-(3,5-difluorobenzyl)-1H-indazol-3-yl)-4-(4-(20-((2-(2,6-dioxopiperidin-3-yl)-1,3-dioxoisoindolin-4-yl)amino)-2-oxo-6,9,12,15,18-pentaoxa-3-azaicosyl)piperazin-1-yl)-2-((tetrahydro-2H-pyran-4-yl)amino)benzamide |
| CPD-066 | (2S,4R)-1-((S)-2-(9-(2-(4-(6-((R)-2-(3-fluorophenyl)pyrrolidin-1-yl)imidazo[1,2-b]pyridazin-3-yl)pyridin-2-yl)piperazin-1-yl)acetamido)nonanamido)-3,3-dimethylbutanoyl)-4-hydroxy-N-(4-(4-methylthiazol-5-yl)benzyl)pyrrolidine-2-carboxamide |
| CPD-067 | (2S,4R)-1-((S)-2-(tert-butyl)-17-(4-(6-(6-((R)-2-(3-fluorophenyl)pyrrolidin-1-yl)imidazo[1,2-b]pyridazin-3-yl)pyridin-2-yl)piperazin-1-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide |
| CPD-068 | (2S,4R)-1-((S)-2-(tert-butyl)-14-(4-(6-(6-((R)-2-(3-fluorophenyl)pyrrolidin-1-yl)imidazo[1,2-b]pyridazin-3-yl)pyridin-2-yl)piperazin-1-yl)-4,13-dioxo-6,9-dioxa-3,12-diazatetradecanoyl)-4-hydroxy-N-(4-(4-methylthiazol-5-yl)benzyl)pyrrolidine-2-carboxamide |
| CPD-069 | (2S,4R)-1-((S)-2-(3-(2-(4-(6-(6-((R)-2-(3-fluorophenyl)pyrrolidin-1-yl)imidazo[1,2-b]pyridazin-3-yl)pyridin-2-yl)piperazin-1-yl)acetamido)ethoxy)propanamido)-3,3-dimethylbutanoyl)-4-hydroxy-N-(4-(4-methylthiazol-5-yl)benzyl)pyrrolidine-2-carboxamide |
| CPD-070 | (2S,4R)-1-((S)-2-(6-(2-(4-(6-(6-((R)-2-(3-fluorophenyl)pyrrolidin-1-yl)imidazo[1,2-b]pyridazin-3-yl)pyridin-2-yl)piperazin-1-yl)acetamido)hexanamido)-3,3-dimethylbutanoyl)-4-hydroxy-N-(4-(4-methylthiazol-5-yl)benzyl)pyrrolidine-2-carboxamide |
| CPD-071 | (2S,4R)-1-((S)-2-(4-(2-(4-(6-(6-((R)-2-(3-fluorophenyl)pyrrolidin-1-yl)imidazo[1,2-b]pyridazin-3-yl)pyridin-2-yl)piperazin-1-yl)acetamido)butanamido)-3,3-dimethylbutanoyl)-4-hydroxy-N-(4-(4-methylthiazol-5-yl)benzyl)pyrrolidine-2-carboxamide |

TABLE 1-continued

| | |
|---|---|
| CPD-072 | (2S,4R)-1-((S)-2-(5-(-(4-(6-(6-((R)-2-(3-fluorophenyl)pyrrolidin-1-yl)imidazo[1,2-b]pyridazin-3-yl)pyridin-2-yl)piperazin-1-yl)acetamido)pentanamido)-3,3-dimethylbutanoyl)-4-hydroxy-N-(4-(4-methylthiazol-5-yl)benzyl)pyrrolidine-2-carboxamide |
| CPD-073 | (2S,4R)-1-((S)-2-(10-(2-(4-(6-(6-((R)-2-(3-fluorophenyl)pyrrolidin-1-yl)imidazo[1,2-b]pyridazin-3-yl)pyridin-2-yl)piperazin-1-yl)acetamido)decanamido)-3,3-dimethylbutanoyl)-4-hydroxy-N-(4-(4-methylthiazol-5-yl)benzyl)pyrrolidine-2-carboxamide |
| CPD-074 | (2S,4R)-1-((S)-2-(7-(2-(4-(6-(6-((R)-2-(3-fluorophenyl)pyrrolidin-1-yl)imidazo[1,2-b]pyridazin-3-yl)pyridin-2-yl)piperazin-1-yl)acetamido)heptanamido)-3,3-dimethylbutanoyl)-4-hydroxy-N-(4-(4-methylthiazol-5-yl)benzyl)pyrrolidine-2-carboxamide |
| CPD-075 | (2S,4R)-1-((S)-2-(2-(2-(4-(6-(6-((R)-2-(3-fluorophenyl)pyrrolidin-1-yl)imidazo[1,2-b]pyridazin-3-yl)pyridin-2-yl)piperazin-1-yl)acetamido)acetamido)-3,3-dimethylbutanoyl)-4-hydroxy-N-(4-(4-methylthiazol-5-yl)benzyl)pyrrolidine-2-carboxamide |
| CPD-076 | (2S,4R)-1-((S)-2-(2-(2-(4-(6-(6-((R)-2-(3-fluorophenyl)pyrrolidin-1-yl)imidazo[1,2-b]pyridazin-3-yl)pyridin-2-yl)piperazin-1-yl)acetamido)ethoxy)acetamido)-3,3-dimethylbutanoyl)-4-hydroxy-N-(4-(4-methylthiazol-5-yl)benzyl)pyrrolidine-2-carboxamide |
| CPD-077 | (2S,4R)-1-((S)-20-(tert-butyl)-1-(4-(6-((R)-2-(3-fluorophenyl)pyrrolidin-1-yl)imidazo[1,2-b]pyridazin-3-yl)pyridin-2-yl)piperazin-1-yl)-2,18-dioxo-6,9,12,15-tetraoxa-3,19-diazahenicosan-21-oyl)-4-hydroxy-N-(4-(4-methylthiazol-5-yl)benzyl)pyrrolidine-2-carboxamide |

TABLE 1-continued

| | | |
|---|---|---|
| | CPD-078 | (2S,4R)-1-((S)-17-(tert-butyl)-1-(4-(6-((R)-2-(3-fluorophenyl)pyrrolidin-1-yl)imidazo[1,2-b]pyridazin-3-yl)pyridin-2-yl)piperazin-1-yl)-2,15-dioxo-6,9,12-trioxa-3,16-diazaoctadecan-18-oyl)-4-hydroxy-N-(4-(4-methylthiazol-5-yl)benzyl)pyrrolidine-2-carboxamide |
| | CPD-079 | (2S,4R)-1-((S)-23-(tert-butyl)-1-(4-(6-((R)-2-(3-fluorophenyl)pyrrolidin-1-yl)imidazo[1,2-b]pyridazin-3-yl)pyridin-2-yl)piperazin-1-yl)-2,21-dioxo-6,9,12,15,18-pentaoxa-3,22-diazatetracosan-24-oyl)-4-hydroxy-N-(4-(4-methylthiazol-5-yl)benzyl)pyrrolidine-2-carboxamide |
| | CPD-080 (TR-109) | N-(3-((2-(2,6-dioxopiperidin-3-yl)-1,3-dioxoisoindolin-4-yl)amino)propyl)-2-(4-(6-((R)-2-(3-fluorophenyl)pyrrolidin-1-yl)imidazo[1,2-b]pyridazin-3-yl)pyridin-2-yl)piperazin-1-yl)acetamide |
| | CPD-081 (TR-107) | N-(4-((2-(2,6-dioxopiperidin-3-yl)-1,3-dioxoisoindolin-4-yl)amino)butyl)-2-(4-(6-((R)-2-(3-fluorophenyl)pyrrolidin-1-yl)imidazo[1,2-b]pyridazin-3-yl)pyridin-2-yl)piperazin-1-yl)acetamide |
| | CPD-082 | (2S,4R)-1-((S)-2-(3-(2-(4-(6-((R)-2-(3-fluorophenyl)pyrrolidin-1-yl)imidazo[1,2-b]pyridazin-3-yl)pyridin-2-yl)piperazin-1-yl)acetamido)propanamido)-3,3-dimethylbutanoyl)-4-hydroxy-N-(4-(4-methylthiazol-5-yl)benzyl)pyrrolidine-2-carboxamide |
| | CPD-083 | (2S,4R)-1-((S)-2-(11-(2-(4-(6-((R)-2-(3-fluorophenyl)pyrrolidin-1-yl)imidazo[1,2-b]pyridazin-3-yl)pyridin-2-yl)piperazin-1-yl)acetamido)undecanamido)-3,3-dimethylbutanoyl)-4-hydroxy-N-(4-(4-methylthiazol-5-yl)benzyl)pyrrolidine-2-carboxamide |
| | CPD-084 | (2S,4R)-1-((S)-14-(tert-butyl)-1-(4-(6-((R)-2-(3-fluorophenyl)pyrrolidin-1-yl)imidazo[1,2-b]pyridazin-3-yl)pyridin-2-yl)piperazin-1-yl)-2,12-dioxo-6,9-dioxa-3,13-diazapentadecan-15-oyl)-4-hydroxy-N-(4-(4-methylthiazol-5-yl)benzyl)pyrrolidine-2-carboxamide |

TABLE 1-continued

| | | |
|---|---|---|
| CPD-085 (TR-106) | N-(2-(2-((2-(2,6-dioxopiperidin-3-yl)-1,3-dioxoisoindolin-4-yl)amino)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide | |
| CPD-086 (TR-105) | N-(2-(2-(2-((2-(2,6-dioxopiperidin-3-yl)-1,3-dioxoisoindolin-4-yl)amino)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide | |
| CPD-087 (TR-108) | N-(14-((2-(2,6-dioxopiperidin-3-yl)-1,3-dioxoisoindolin-4-yl)amino)-3,6,9,12-tetraoxatetradecyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide | |
| CPD-088 (TR-104) | N-(17-((2-(2,6-dioxopiperidin-3-yl)-1,3-dioxoisoindolin-4-yl)amino)-3,6,9,12,15-pentaoxaheptadecyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide | |
| CPD-089 | (2S,4R)-1-((S)-2-(8-(2-(4-(6-(6-((R)-2-(3-fluorophenyl)pyrrolidin-1-yl)imidazo[1,2-b]pyridazin-3-yl)pyridin-2-yl)piperazin-1-yl)acetamido)octanamido)-3,3-dimethylbutanoyl)-4-hydroxy-N-(4-(4-methylthiazol-5-yl)benzyl)pyrrolidine-2-carboxamide | |
| CPD-090 (TR-111) | N-(6-((2-(2,6-dioxopiperidin-3-yl)-1,3-dioxoisoindolin-4-yl)amino)hexyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide | |
| CPD-091 (TR-110) | N-(7-((2-(2,6-dioxopiperidin-3-yl)-1,3-dioxoisoindolin-4-yl)amino)heptyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide | |
| CPD-092 (TR-102) | N-(8-((2-(2,6-dioxopiperidin-3-yl)-1,3-dioxoisoindolin-4-yl)amino)octyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide | |
| CPD-093 (TR-059) | N-(2-(2-(2-((2-(2,6-dioxopiperidin-3-yl)-1,3-dioxoisoindolin-4-yl)amino)ethoxy)ethoxy)ethyl)-2-(4-(6-(6-((R)-2-(3-fluorophenyl)pyrrolidin-1-yl) | |

TABLE 1-continued

| | |
|---|---|
| | yl)imidazo[1,2-b]pyridazin-3-yl)pyridin-2-yl)piperazin-1-yl)acetamide |
| CPD-094 | (2S,4R)-1-((S)-2-(9-(2-(4-(4-((5-(3,5-difluorobenzyl)carbamoyl)-3-((tetrahydro-2H-pyran-4-yl)amino)phenyl)piperazin-1-yl)acetamido)nonanamido)-3,3-dimethylbutanoyl)-4-hydroxy-N-(4-(4-methylthiazol-5-yl)benzyl)pyrrolidine-2-carboxamide |
| CPD-095 | (2S,4R)-1-((S)-2-(tert-butyl)-17-(4-(4-((5-(3,5-difluorobenzyl)-1H-indazol-3-yl)carbamoyl)-3-((tetrahydro-2H-pyran-4-yl)amino)phenyl)piperazin-1-yl)-4,16-dioxo-6,9,12-trioxa-3,15-diazaheptadecanoyl)-4-hydroxy-N-(4-(4-methylthiazol-5-yl)benzyl)pyrrolidine-2-carboxamide |
| CPD-096 | (2S,4R)-1-((S)-2-(3-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethoxy)propanamido)-3,3-dimethylbutanoyl)-4-hydroxy-N-(4-(4-methylthiazol-5-yl)benzyl)pyrrolidine-2-carboxamide |
| CPD-097 | (2S,4R)-1-((S)-2-(4-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)butanamido)-3,3-dimethylbutanoyl)-4-hydroxy-N-(4-(4-methylthiazol-5-yl)benzyl)pyrrolidine-2-carboxamide |
| CPD-098 | (2S,4R)-1-((S)-2-(3-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)propanamido)-3,3-dimethylbutanoyl)-4-hydroxy-N-(4-(4-methylthiazol-5-yl)benzyl)pyrrolidine-2-carboxamide |
| CPD-099 | (2S,4R)-1-((S)-2-(5-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)pentanamido)-3,3-dimethylbutanoyl)-4-hydroxy-N-(4-(4-methylthiazol-5-yl)benzyl)pyrrolidine-2-carboxamide |
| CPD-100 | (2S,4R)-1-((S)-2-(10-(2-(4-(4-((5-(3,5-difluorobenzyl)-1H-indazol-3-yl)carbamoyl)-3-((tetrahydro-2H-pyran- |

TABLE 1-continued

| | |
|---|---|
| | 4-yl)amino)phenyl)piperazin-1-yl)acetamido)decanamido)-3,3-dimethylbutanoyl)-4-hydroxy-N-(4-(4-methylthiazol-5-yl)benzyl)pyrrolidine-2-carboxamide |
| CPD-101 | (2S,4R)-1-((S)-2-(2-(2-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)ethoxy)acetamido)-3,3-dimethylbutanoyl)-4-hydroxy-N-(4-(4-methylthiazol-5-yl)benzyl)pyrrolidine-2-carboxamide |
| CPD-102 | (2S,4R)-1-((S)-2-(11-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)undecanamido)-3,3-dimethylbutanoyl)-4-hydroxy-N-(4-(4-methylthiazol-5-yl)benzyl)pyrrolidine-2-carboxamide |
| CPD-103 | (2S,4R)-1-((S)-2-(7-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)heptanamido)-3,3-dimethylbutanoyl)-4-hydroxy-N-(4-(4-methylthiazol-5-yl)benzyl)pyrrolidine-2-carboxamide |
| CPD-104 | (2S,4R)-1-((S)-2-(tert-butyl)-14-(4-(4-((5-(3,5-difluorobenzyl)-1H-indazol-3-yl)carbamoyl)-3-((tetrahydro-2H-pyran-4-yl)amino)phenyl)piperazin-1-yl)-4,13-dioxo-6,9-dioxa-3,12-diazatetradecanoyl)-4-hydroxy-N-(4-(4-methylthiazol-5-yl)benzyl)pyrrolidine-2-carboxamide |
| CPD-105 | (2S,4R)-1-((S)-2-(6-(2-(4-(4-((5-(3,5-difluorobenzyl)-1H-indazol-3-yl)carbamoyl)-3-((tetrahydro-2H-pyran-4-yl)amino)phenyl)piperazin-1-yl)acetamido)hexanamido)-3,3-dimethylbutanoyl)-4-hydroxy-N-(4-(4-methylthiazol-5-yl)benzyl)pyrrolidine-2-carboxamide |
| CPD-106 (TR-155) | N-(5-(3,5-difluorobenzyl)-1H-indazol-3-yl)-4-(2-((4-((2-(2,6-dioxopiperidin-3-yl)-1,3-dioxoisoindolin-4-yl)amino)butyl)amino)-2-oxoethyl)piperazin-1-yl)-2-((tetrahydro-2H-pyran-4-yl)amino)benzamide |

TABLE 1-continued

| | |
|---|---|
| CPD-107 (TR-152) | N-(5-(3,5-difluorobenzyl)-1H-indazol-3-yl)-4-(4-(2-(3-((2-(2,6-dioxopiperidin-3-yl)-1,3-dioxoisoindolin-4-yl)amino)propyl)amino)-2-oxoethyl)piperazin-1-yl)-2-((tetrahydro-2H-pyran-4-yl)amino)benzamide |
| CPD-108 | (2S,4R)-1-((S)-23-(tert-butyl)-1-(4-(4-((5-(3,5-difluorobenzyl)-1H-indazol-3-yl)carbamoyl)-3-((tetrahydro-2H-pyran-4-yl)amino)phenyl)piperazin-1-yl)-2,21-dioxo-6,9,12,15,18-pentaoxa-3,22-diazatetracosan-24-oyl)-4-hydroxy-N-(4-(4-methylthiazol-5-yl)benzyl)pyrrolidine-2-carboxamide |
| CPD-109 | (2S,4R)-1-((S)-17-(tert-butyl)-1-(4-(4-((5-(3,5-difluorobenzyl)-1H-indazol-3-yl)carbamoyl)-3-((tetrahydro-2H-pyran-4-yl)amino)phenyl)piperazin-1-yl)-2,15-dioxo-6,9,12-trioxa-3,16-diazaoctadecan-18-oyl)-4-hydroxy-N-(4-(4-methylthiazol-5-yl)benzyl)pyrrolidine-2-carboxamide |
| CPD-110 | (2S,4R)-1-((S)-20-(tert-butyl)-1-(4-(4-((5-(3,5-difluorobenzyl)-1H-indazol-3-yl)carbamoyl)-3-((tetrahydro-2H-pyran-4-yl)amino)phenyl)piperazin-1-yl)-2,18-dioxo-6,9,12,15-tetraoxa-3,19-diazahenicosan-21-oyl)-4-hydroxy-N-(4-(4-methylthiazol-5-yl)benzyl)pyrrolidine-2-carboxamide |
| CPD-111 (TR-151) | N-(5-(3,5-difluorobenzyl)-1H-indazol-3-yl)-4-(4-(2-((2-(2-(2-(2,6-dioxopiperidin-3-yl)-1,3-dioxoisoindolin-4-yl)amino)ethoxy)ethyl)amino)-2-oxoethyl)piperazin-1-yl)-2-((tetrahydro-2H-pyran-4-yl)amino)benzamide |
| CPD-112 (TR-153) | N-(5-(3,5-difluorobenzyl)-1H-indazol-3-yl)-4-(4-(2-((2-(2-(2-(2-(2,6-dioxopiperidin-3-yl)-1,3-dioxoisoindolin-4-yl)amino)ethoxy)ethyl)amino)-2-oxoethyl)piperazin-1-yl)-2-((tetrahydro-2H-pyran-4-yl)amino)benzamide |
| CPD-113 (TR-150) | N-(5-(3,5-difluorobenzyl)-1H-indazol-3-yl)-4-(4-(17-((2-(2,6-dioxopiperidin-3-yl)-1,3-dioxoisoindolin-4-yl)amino)-2-oxo-6,9,12,15-tetraoxa-3-azaheptadecyl)piperazin-1-yl)-2-((tetrahydro-2H-pyran-4-yl)amino)benzamide |

TABLE 1-continued

| | | |
|---|---|---|
| CPD-114 (TR-149) | | N-(5-(3,5-difluorobenzyl)-1H-indazol-3-yl)-4-(4-(2-((5-((2-(2,6-dioxopiperidin-3-yl)-1,3-dioxoisoindolin-4-yl)amino)pentyl)amino)-2-((tetrahydro-2H-pyran-4-yl)amino)benzamide |
| CPD-115 (TR-147) | | N-(5-(3,5-difluorobenzyl)-1H-indazol-3-yl)-4-(4-(2-((6-((2-(2,6-dioxopiperidin-3-yl)-1,3-dioxoisoindolin-4-yl)amino)hexyl)amino)-2-((tetrahydro-2H-pyran-4-yl)amino)benzamide |
| CPD-116 (TR-148) | | N-(5-(3,5-difluorobenzyl)-1H-indazol-3-yl)-4-(4-(2-((8-((2-(2,6-dioxopiperidin-3-yl)-1,3-dioxoisoindolin-4-yl)amino)octyl)amino)-2-((tetrahydro-2H-pyran-4-yl)amino)benzamide |
| CPD-117 (TR-154) | | N-(5-(3,5-difluorobenzyl)-1H-indazol-3-yl)-4-(4-(2-((7-((2-(2,6-dioxopiperidin-3-yl)-1,3-dioxoisoindolin-4-yl)amino)heptyl)amino)-2-((tetrahydro-2H-pyran-4-yl)amino)benzamide |
| CPD-118 | | (2S,4R)-1-((S)-14-(tert-butyl)-1-(4-(4-((5-(3,5-difluorobenzyl)-1H-indazol-3-yl)carbamoyl)-3-((tetrahydro-2H-pyran-4-yl)amino)phenyl)piperazin-1-yl)-2,12-dioxo-6,9-dioxa-3,13-diazapentadecan-15-oyl)-4-hydroxy-N-(4-(4-methylthiazol-5-yl)benzyl)pyrrolidine-2-carboxamide |
| CPD-119 (TR-161) | | N-(5-(3,5-difluorobenzyl)-1H-indazol-3-yl)-4-(2-((2-(2-(2,6-dioxopiperidin-3-yl)-1,3-dioxoisoindolin-5-yl)amino)ethoxy)ethyl)amino)-2-((tetrahydro-2H-pyran-4-yl)amino)benzamide |
| CPD-120 | | N-(5-(3,5-difluorobenzyl)-1H-indazol-3-yl)-4-(2-(((2-(2-(2,6-dioxopiperidin-3-yl)-1,3-dioxoisoindolin-5-yl)amino)ethoxy)methyl)amino)-2-oxoethyl)piperazin-1-yl)-2-((tetrahydro-2H-pyran-4-yl)amino)benzamide |
| CPD-121 (TR-163) | | N-(5-(3,5-difluorobenzyl)-1H-indazol-3-yl)-4-(14-((2-(2,6-dioxopiperidin-3-yl)-1,3-dioxoisoindolin-5-yl)amino)-2-oxo-6,9,12-trioxa-3-azatetradecyl)piperazin-1-yl)-2- |

TABLE 1-continued

| | |
|---|---|
| CPD-122 (TR-160) | N-(5-(3,5-difluorobenzyl)-1H-indazol-3-yl)-4-(4-(17-((2-(2,6-dioxopiperidin-3-yl)-1,3-dioxoisoindolin-5-yl)amino)-2-oxo-6,9,12,15-tetraoxa-3-azaheptadecyl)piperazin-1-yl)-2-((tetrahydro-2H-pyran-4-yl)amino)benzamide |
| CPD-123 (TR-166) | N-(5-(3,5-difluorobenzyl)-1H-indazol-3-yl)-4-(4-(20-((2-(2,6-dioxopiperidin-3-yl)-1,3-dioxoisoindolin-5-yl)amino)-2-oxo-6,9,12,15,18-pentaoxa-3-azaicosyl)piperazin-1-yl)-2-((tetrahydro-2H-pyran-4-yl)amino)benzamide |
| CPD-124 (TR-144) | N-(5-(3,5-difluorobenzyl)-1H-indazol-3-yl)-4-(4-((2-(2,6-dioxopiperidin-3-yl)-1,3-dioxoisoindolin-5-yl)glycyl)piperazin-1-yl)-2-((tetrahydro-2H-pyran-4-yl)amino)benzamide |
| CPD-125 (TR-145) | N-(5-(3,5-difluorobenzyl)-1H-indazol-3-yl)-4-(4-(3-((2-(2,6-dioxopiperidin-3-yl)-1,3-dioxoisoindolin-5-yl)amino)propanoyl)piperazin-1-yl)-2-((tetrahydro-2H-pyran-4-yl)amino)benzamide |
| CPD-126 (TR-169) | N-(5-(3,5-difluorobenzyl)-1H-indazol-3-yl)-4-(4-((2-(2,6-dioxopiperidin-3-yl)-1,3-dioxoisoindolin-5-yl)amino)butanoyl)piperazin-1-yl)-2-((tetrahydro-2H-pyran-4-yl)amino)benzamide |
| CPD-127 (TR-142) | N-(5-(3,5-difluorobenzyl)-1H-indazol-3-yl)-4-(4-(5-((2-(2,6-dioxopiperidin-3-yl)-1,3-dioxoisoindolin-5-yl)amino)pentanoyl)piperazin-1-yl)-2-((tetrahydro-2H-pyran-4-yl)amino)benzamide |
| CPD-128 (TR-138) | N-(5-(3,5-difluorobenzyl)-1H-indazol-3-yl)-4-(4-(6-((2-(2,6-dioxopiperidin-3-yl)-1,3-dioxoisoindolin-5-yl)amino)hexanoyl)piperazin-1-yl)-2-((tetrahydro-2H-pyran-4-yl)amino)benzamide |
| CPD-129 (TR-139) | N-(5-(3,5-difluorobenzyl)-1H-indazol-3-yl)-4-(4-(7-((2-(2,6-dioxopiperidin-3-yl)-1,3-dioxoisoindolin-5-yl)amino)heptanoyl)piperazin-1-yl)-2-((tetrahydro-2H-pyran-4-yl)amino)benzamide |

TABLE 1-continued

| | |
|---|---|
| CPD-130 (TR-136) | N-(5-(3,5-difluorobenzyl)-1H-indazol-3-yl)-4-(4-(8-((2-(2,6-dioxopiperidin-3-yl)-1,3-dioxoisoindolin-5-yl)amino)octanoyl)piperazin-1-yl)-2-(((tetrahydro-2H-pyran-4-yl)amino)benzamide |
| CPD-131 (TR-165) | N-(5-(3,5-difluorobenzyl)-1H-indazol-3-yl)-4-(4-(2-((2-(2-(2,6-dioxopiperidin-3-yl)-1,3-dioxoisoindolin-5-yl)amino)ethyl)amino)-2-oxoethyl)piperazin-1-yl)-2-((tetrahydro-2H-pyran-4-yl)amino)benzamide |
| CPD-132 (TR-167) | N-(5-(3,5-difluorobenzyl)-1H-indazol-3-yl)-4-(4-(2-((3-((2-(2,6-dioxopiperidin-3-yl)-1,3-dioxoisoindolin-5-yl)amino)propyl)amino)-2-oxoethyl)piperazin-1-yl)-2-((tetrahydro-2H-pyran-4-yl)amino)benzamide |
| CPD-133 (TR-156) | N-(5-(3,5-difluorobenzyl)-1H-indazol-3-yl)-4-(4-(2-((4-((2-(2,6-dioxopiperidin-3-yl)-1,3-dioxoisoindolin-5-yl)amino)butyl)amino)-2-oxoethyl)piperazin-1-yl)-2-((tetrahydro-2H-pyran-4-yl)amino)benzamide |
| CPD-134 (TR-164) | N-(5-(3,5-difluorobenzyl)-1H-indazol-3-yl)-4-(2-((5-((2-(2,6-dioxopiperidin-3-yl)-1,3-dioxoisoindolin-5-yl)amino)pentyl)amino)-2-oxoethyl)piperazin-1-yl)-2-((tetrahydro-2H-pyran-4-yl)amino)benzamide |
| CPD-135 (TR-158) | N-(5-(3,5-difluorobenzyl)-1H-indazol-3-yl)-4-(2-((6-((2-(2,6-dioxopiperidin-3-yl)-1,3-dioxoisoindolin-5-yl)amino)hexyl)amino)-2-oxoethyl)piperazin-1-yl)-2-((tetrahydro-2H-pyran-4-yl)amino)benzamide |
| CPD-136 (TR-157) | N-(5-(3,5-difluorobenzyl)-1H-indazol-3-yl)-4-(4-(2-((7-((2-(2,6-dioxopiperidin-3-yl)-1,3-dioxoisoindolin-5-yl)amino)heptyl)amino)-2-oxoethyl)piperazin-1-yl)-2-((tetrahydro-2H-pyran-4-yl)amino)benzamide |
| CPD-137 (TR-159) | N-(5-(3,5-difluorobenzyl)-1H-indazol-3-yl)-4-(4-(2-((8-((2-(2,6-dioxopiperidin-3-yl)-1,3-dioxoisoindolin-5-yl)amino)octyl)amino)-2-oxoethyl)piperazin-1-yl)-2-((tetrahydro-2H-pyran-4-yl)amino)benzamide |

TABLE 1-continued

| | |
|---|---|
| CPD-138 (TR-143) | N-(5-(3,5-difluorobenzyl)-1H-indazol-3-yl)-4-(4-(3-(2-(2-(2,6-dioxopiperidin-3-yl)-1,3-dioxoisoindolin-5-yl)amino)ethoxy)propanoyl)piperazin-1-yl)-2-((tetrahydro-2H-pyran-4-yl)amino)benzamide |
| CPD-139 (TR-141) | N-(5-(3,5-difluorobenzyl)-1H-indazol-3-yl)-4-(4-(3-(2-(2-(2,6-dioxopiperidin-3-yl)-1,3-dioxoisoindolin-5-yl)amino)ethoxy)ethoxy)propanoyl)piperazin-1-yl)-2-((tetrahydro-2H-pyran-4-yl)amino)benzamide |
| CPD-140 (TR-146) | N-(5-(3,5-difluorobenzyl)-1H-indazol-3-yl)-4-(4-(3-(2-(2-(2-(2,6-dioxopiperidin-3-yl)-1,3-dioxoisoindolin-5-yl)amino)ethoxy)ethoxy)propanoyl)piperazin-1-yl)-2-((tetrahydro-2H-pyran-4-yl)amino)benzamide |
| CPD-141 (TR-140) | N-(5-(3,5-difluorobenzyl)-1H-indazol-3-yl)-4-(1-((2-(2,6-dioxopiperidin-3-yl)-1,3-dioxoisoindolin-5-yl)amino)-3,6,9,12-tetraoxapentadecan-15-oyl)piperazin-1-yl)-2-((tetrahydro-2H-pyran-4-yl)amino)benzamide |
| CPD-142 (TR-137) | N-(5-(3,5-difluorobenzyl)-1H-indazol-3-yl)-4-(1-((2-(2,6-dioxopiperidin-3-yl)-1,3-dioxoisoindolin-5-yl)amino)-3,6,9,12,15-pentaoxaoctadecan-18-oyl)piperazin-1-yl)-2-((tetrahydro-2H-pyran-4-yl)amino)benzamide |
| CPD-143 (TR-135) | N-(2-(2-((2-(2,6-dioxopiperidin-3-yl)-1,3-dioxoisoindolin-5-yl)amino)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-144 (TR-134) | N-(2-(2-(2-((2-(2,6-dioxopiperidin-3-yl)-1,3-dioxoisoindolin-5-yl)amino)ethoxy)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-145 (TR-130) | N-(2-((2-(2,6-dioxopiperidin-3-yl)-1,3-dioxoisoindolin-5-yl)amino)ethyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |

TABLE 1-continued

| | |
|---|---|
| CPD-146 (TR-128) | N-(6-((2-(2,6-dioxopiperidin-3-yl)-1,3-dioxoisoindolin-5-yl)amino)hexyl)-2-(4-(6-((R)-2-(3-fluorophenyl)pyrrolidin-1-yl)imidazo[1,2-b]pyridazin-3-yl)pyridin-2-yl)piperazin-1-yl)acetamide |
| CPD-147 (TR-120) | 2-(2,6-dioxopiperidin-3-yl)-5-((15-(4-(6-(6-((R)-2-(3-fluorophenyl)pyrrolidin-1-yl)imidazo[1,2-b]pyridazin-3-yl)pyridin-2-yl)piperazin-1-yl)-15-oxo-3,6,9,12-tetraoxapentadecyl)amino)isoindoline-1,3-dione |
| CPD-148 (TR-119) | 2-(2,6-dioxopiperidin-3-yl)-5-((2-(3-(4-(6-((R)-2-(3-fluorophenyl)pyrrolidin-1-yl)imidazo[1,2-b]pyridazin-3-yl)pyridin-2-yl)piperazin-1-yl)-3-oxopropoxy)ethyl)amino)isoindoline-1,3-dione |
| CPD-149 (TR-116) | 2-(2,6-dioxopiperidin-3-yl)-5-((18-(4-(6-(6-((R)-2-(3-fluorophenyl)pyrrolidin-1-yl)imidazo[1,2-b]pyridazin-3-yl)pyridin-2-yl)piperazin-1-yl)-18-oxo-3,6,9,12,15-pentaoxaoctadecyl)amino)isoindoline-1,3-dione |
| CPD-150 (TR-113) | 2-(2,6-dioxopiperidin-3-yl)-5-((2-(2-(3-(4-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethyl)amino)isoindoline-1,3-dione |
| CPD-151 (TR-114) | 2-(2,6-dioxopiperidin-3-yl)-5-((2-(2-(2-(3-(4-(6-((R)-2-(3-fluorophenyl)pyrrolidin-1-yl)imidazo[1,2-b]pyridazin-3-yl)pyridin-2-yl)piperazin-1-yl)-3-oxopropoxy)ethoxy)ethyl)amino)isoindoline-1,3-dione |
| CPD-152 (TR-122) | 2-(2,6-dioxopiperidin-3-yl)-5-((6-(4-(6-(6-((R)-2-(3-fluorophenyl)pyrrolidin-1-yl)imidazo[1,2-b]pyridazin-3-yl)pyridin-2-yl)piperazin-1-yl)-6-oxohexyl)amino)isoindoline-1,3-dione |
| CPD-153 (TR-117) | 2-(2,6-dioxopiperidin-3-yl)-5-((7-(4-(6-(6-((R)-2-(3-fluorophenyl)pyrrolidin-1-yl)imidazo[1,2-b]pyridazin-3-yl)pyridin-2-yl)piperazin-1-yl)-7-oxoheptyl)amino)isoindoline-1,3-dione |
| CPD-154 (TR-129) | N-(2-(2-(2-(2-(2,6-dioxopiperidin-3-yl)-1,3-dioxoisoindolin-5-yl)amino)ethoxy)ethoxy)ethyl)-2-(4-(6-((R)-2-(3-fluorophenyl)pyrrolidin-1- |

TABLE 1-continued

| | |
|---|---|
| CPD-155 (TR-127) | yl)imidazo[1,2-b]pyridazin-3-yl)pyridin-2-yl)piperazin-1-yl)acetamide<br>N-(3-((2-(2,6-dioxopiperidin-3-yl)-1,3-dioxoisoindolin-5-yl)amino)propyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-156 (TR-124) | N-(4-((2-(2,6-dioxopiperidin-3-yl)-1,3-dioxoisoindolin-5-yl)amino)butyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-157 (TR-126) | N-(7-(2-(2,6-dioxopiperidin-3-yl)-1,3-dioxoisoindolin-5-yl)amino)heptyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-158 (TR-168) | 2-(2,6-dioxopiperidin-3-yl)-5-((4-(4-(6-(6-((R)-2-(3-fluorophenyl)pyrrolidin-1-yl)imidazo[1,2-b]pyridazin-3-yl)pyridin-2-yl)piperazin-1-yl)-4-oxobutyl)amino)isoindoline-1,3-dione |
| CPD-159 (TR-115) | 2-(2,6-dioxopiperidin-3-yl)-5-((5-(4-(6-(6-((R)-2-(3-fluorophenyl)pyrrolidin-1-yl)imidazo[1,2-b]pyridazin-3-yl)pyridin-2-yl)piperazin-1-yl)-5-oxopentyl)amino)isoindoline-1,3-dione |
| CPD-160 (TR-123) | 2-(2,6-dioxopiperidin-3-yl)-5-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)isoindoline-1,3-dione |
| CPD-161 (TR-121) | 2-(2,6-dioxopiperidin-3-yl)-5-((3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropyl)amino)isoindoline-1,3-dione |
| CPD-162 (TR-118) | 2-(2,6-dioxopiperidin-3-yl)-5-((8-(4-(6-(6-((R)-2-(3-fluorophenyl)pyrrolidin-1-yl)imidazo[1,2-b]pyridazin-3-yl)pyridin-2-yl)piperazin-1-yl)-8-oxooctyl)amino)isoindoline-1,3-dione |
| CPD-163 (TR-131) | N-(5-((2-(2,6-dioxopiperidin-3-yl)-1,3-dioxoisoindolin-5-yl)amino)pentyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |

TABLE 1-continued

| | |
|---|---|
| CPD-164 (TR-132) | N-(17-((2-(2,6-dioxopiperidin-3-yl)-1,3-dioxoisoindolin-5-yl)amino)-3,6,9,12,15-pentaoxaheptadecyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-165 (TR-133) | N-(8-((2-(2,6-dioxopiperidin-3-yl)-1,3-dioxoisoindolin-5-yl)amino)octyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-166 (TR-125) | N-(14-((2-(2,6-dioxopiperidin-3-yl)-1,3-dioxoisoindolin-5-yl)amino)-3,6,9,12-tetraoxatetradecyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-167 (TR-103) | N-(5-((2-(2,6-dioxopiperidin-3-yl)-1,3-dioxoisoindolin-4-yl)amino)pentyl)-2-(4-(6-(6-((R)-2-(3-fluorophenyl)pyrrolidin-1-yl)imidazo[1,2-b]pyridazin-3-yl)pyridin-2-yl)piperazin-1-yl)acetamide |
| CPD-168 (TR-162) | N-(5-(3,5-Difluorobenzyl)-1H-indazol-3-yl)-4-(2-((2-(2-(2,6-dioxopiperidin-3-yl)-1,3-dioxoisoindolin-5-yl)amino)ethoxy)ethyl)amino)-2-((tetrahydro-2H-pyran-4-yl)amino)benzamide |
| CPD-169 (TR-123-neg) | 5-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)-2-(1-methyl-2,6-dioxopiperidin-3-yl)isoindoline-1,3-dione |
| CPD-170 (TR-170) | 2-(2,6-dioxopiperidin-3-yl)-5-(4-(6-(6-((R)-2-(3-fluorophenyl)pyrrolidin-1-yl)imidazo[1,2-b]pyridazin-3-yl)pyridin-2-yl)piperazin-1-yl)isoindoline-1,3-dione |
| CPD-171 (TR-171) | 2-(2,6-dioxopiperidin-3-yl)-5-((3-(4-(6-(6-((R)-2-(3-fluorophenyl)pyrrolidin-1-yl)imidazo[1,2-b]pyridazin-3-yl)pyridin-2-yl)piperazin-1-yl)propyl)amino)isoindoline-1,3-dione |
| CPD-172 (TR-172) | 2-(2,6-dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)propyl)isoindoline-1,3-dione |

TABLE 1-continued

| | |
|---|---|
| CPD-173 (TR-173) | 2-(2,6-dioxopiperidin-3-yl)-5-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)isoindoline-1,3-dione |
| CPD-174 (TR-174) | 2-(2,6-dioxopiperidin-3-yl)-5-((1-(6-(6-((R)-2-(3-fluorophenyl)pyrrolidin-1-yl)imidazo[1,2-b]pyridazin-3-yl)pyridin-2-yl)piperidin-4-yl)amino)isoindoline-1,3-dione |
| CPD-175 (TR-175) | 2-(2,6-dioxopiperidin-3-yl)-5-((1-(6-(6-((R)-2-(3-fluorophenyl)pyrrolidin-1-yl)imidazo[1,2-b]pyridazin-3-yl)pyridin-2-yl)azetidin-3-yl)amino)isoindoline-1,3-dione |
| CPD-176 (TR-176) | 2-(2,6-dioxopiperidin-3-yl)-5-((2-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)ethyl)amino)isoindoline-1,3-dione |
| CPD-177 (TR-177) | 2-(2,6-dioxopiperidin-3-yl)-5-((2-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)ethyl)amino)isoindoline-1,3-dione |
| CPD-178 (TR-178) | 2-(2,6-dioxopiperidin-3-yl)-5-(((1-(6-(6-((R)-2-(3-fluorophenyl)pyrrolidin-1-yl)imidazo[1,2-b]pyridazin-3-yl)pyridin-2-yl)piperidin-4-yl)methyl)amino)isoindoline-1,3-dione |
| CPD-179 (TR-179) | 2-(2,6-dioxopiperidin-3-yl)-5-(((1-(6-(6-((R)-2-(3-fluorophenyl)pyrrolidin-1-yl)imidazo[1,2-b]pyridazin-3-yl)pyridin-2-yl)azetidin-3-yl)methyl)amino)isoindoline-1,3-dione |
| CPD-180 (TR-180) | 2-(2,6-dioxopiperidin-3-yl)-5-((2-(1-(6-(6-((R)-2-(3-fluorophenyl)pyrrolidin-1-yl)imidazo[1,2-b]pyridazin-3-yl)pyridin-2-yl)piperidin-4-yl)ethyl)amino)isoindoline-1,3-dione |
| CPD-181 (TR-181) | 2-(2,6-dioxopiperidin-3-yl)-5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)isoindoline-1,3-dione |
| CPD-182 (TR-182) | 2-(2,6-Dioxopiperidin-3-yl)-5-(4-(4-(6-(6-((R)-2-(3-fluorophenyl)pyrrolidin-1-yl)imidazo[1,2-b]pyridazin-3-yl)pyridin-2-yl)piperazin-1-yl)isoindoline-1,3-dione |

TABLE 1-continued

| | |
|---|---|
| CPD-183 (TR-183) | 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)isoindoline-1,3-dione |
| CPD-184 (TR-184) | 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)azetidin-1-yl)isoindoline-1,3-dione |
| CPD-185 (TR-185) | 3-(6-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-1-oxoisoindoline-2-yl)piperidine-2,6-dione |
| CPD-186 (TR-186) | 3-(5-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-1-oxoisoindolin-2-yl)piperidine-2,6-dione |
| CPD-187 (TR-187) | 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)isoindoline-1,3-dione |
| CPD-188 (TR-188) | 3-(5-(3-(4-(6-(6-((R)-2-(3-fluorophenyl)pyrrolidin-1-yl)imidazo[1,2-b]pyridazin-3-yl)pyridin-2-yl)piperazin-1-yl)prop-1-yn-1-yl)-1-oxoisoindolin-2-yl)piperidine-2,6-dione |
| CPD-189 (TR-189) | 3-(6-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)-1-oxoisoindolin-2-yl)piperidine-2,6-dione |
| CPD-190 (TR-190) | 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)-2-oxoethyl)amino)-1-oxoisoindolin-2-yl)piperidine-2,6-dione |
| CPD-191 (TR-191) | 3-(5-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-1-oxoisoindolin-2-yl)piperidine-2,6-dione |
| CPD-192 (TR-192) | 2-(2,6-Dioxopiperidin-3-yl)-5-((2-((1-(6-(6-((R)-2-(3-fluorophenyl)pyrrolidin-1-yl)imidazo[1,2-b]pyridazin-3-yl)azetidin-3-yl)amino)ethyl)amino)isoindoline-1,3-dione |

TABLE 1-continued

| | |
|---|---|
| CPD-193 (TR-193) | 2-(2,6-Dioxopiperidin-3-yl)-5-((2-(1-(6-(6-((R)-2-(3-fluorophenyl)pyrrolidin-1-yl)imidazo[1,2-b]pyridazin-3-yl)pyridin-2-yl)azetidin-3-yl)ethyl)amino)isoindoline-1,3-dione |
| CPD-194 (TR-194) | 2-(2,6-Dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)-3-oxopropyl)isoindoline-1,3-dione |
| CPD-195 (TR-195) | 2-(2,6-Dioxopiperidin-3-yl)-5-((E)-3-(4-(6-(6-((R)-2-(3-fluorophenyl)pyrrolidin-1-yl)imidazo[1,2-b]pyridazin-3-yl)pyridin-2-yl)piperazin-1-yl)-3-oxoprop-1-en-1-yl)isoindoline-1,3-dione |
| CPD-196 (TR-196) | 3-(6-((2-(4-(6-(6-((R)-2-(3-fluorophenyl)pyrrolidin-1-yl)imidazo[1,2-b]pyridazin-3-yl)pyridin-2-yl)piperazin-1-yl)ethyl)amino)-1-oxoisoindolin-2-yl)piperidine-2,6-dione |
| CPD-197 (TR-197) | 2-(2,6-Dioxopiperidin-3-yl)-5-((4-(6-(6-((R)-2-(3-fluorophenyl)pyrrolidin-1-yl)imidazo[1,2-b]pyridazin-3-yl)pyridin-2-yl)piperazin-1-yl)methyl)isoindoline-1,3-dione |
| CPD-198 (TR-198) | 2-(2,6-Dioxopiperidin-3-yl)-5-(3-((4-(6-(6-((R)-2-(3-fluorophenyl)pyrrolidin-1-yl)imidazo[1,2-b]pyridazin-3-yl)pyridin-2-yl)piperazin-1-yl)methyl)azetidin-1-yl)isoindoline-1,3-dione |
| CPD-199 (TR-199) | 2-(2,6-Dioxopiperidin-3-yl)-5-((3-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)propyl)amino)isoindoline-1,3-dione |
| CPD-200 (TR-200) | 3-(5-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)-1-oxoisoindolin-2-yl)piperidine-2,6-dione |
| CPD-201 (TR-201) | 3-(6-(2-(4-(6-((R)-2-(3-fluorophenyl)pyrrolidin-1-yl)imidazo[1,2-b]pyridazin-3-yl)pyridin-2-yl)piperazin-1-yl)ethoxy)-1-oxoisoindolin-2-yl)piperidine-2,6-dione |
| CPD-202 (TR-202) | 3-(6-(3-(4-(6-((R)-2-(3-fluorophenyl)pyrrolidin-1-yl)imidazo[1,2-b]pyridazin-3-yl)pyridin-2-yl)piperazin-1-yl)-3-oxoprop-1-yn-1-yl)-1-oxoisoindolin-2-yl)piperidine-2,6-dione |

TABLE 1-continued

| | |
|---|---|
| CPD-203 (TR-203) | 3-(5-(3-(6-((R)-2-(3-fluorophenyl)pyrrolidin-1-yl)imidazo[1,2-b]pyridazin-3-yl)pyridin-2-yl)piperazin-1-yl)-3-oxoprop-1-yn-1-yl)-1-oxoisoindolin-2-yl)piperidine-2,6-idione |
| CPD-204 (TR-204) | 2-(2,6-dioxopiperidin-3-yl)-5-(2-(4-(6-((R)-2-(3-fluorophenyl)pyrrolidin-1-yl)imidazo[1,2-b]pyridazin-3-yl)pyridin-2-yl)piperazin-1-yl)ethyl)isoindoline-1,3-dione |
| CPD-205 (TR-205) | 3-(5-(3-((4-(6-((R)-2-(3-fluorophenyl)pyrrolidin-1-yl)imidazo[1,2-b]pyridazin-3-yl)pyridin-2-yl)piperazin-1-yl)methyl)azetidin-1-yl)-1-oxoisoindolin-2-yl)piperidine-2,6-dione |
| CPD-206 (TR-206) | 3-(5-((1-(6-(6-((R)-2-(3-fluorophenyl)pyrrolidin-1-yl)imidazo[1,2-b]pyridazin-3-yl)pyridin-2-yl)azetidin-3-yl)amino)-1-oxoisoindolin-2-yl)piperidine-2,6-dione |
| CPD-207 (TR-207) | 3-(5-(4-(6-((R)-2-(3-fluorophenyl)pyrrolidin-1-yl)imidazo[1,2-b]pyridazin-3-yl)pyridin-2-yl)piperazin-1-yl)-1-oxoisoindolin-2-yl)piperidine-2,6-dione |
| CPD-208 (TR-208) | 3-(5-((1-(6-(6-((R)-2-(3-fluorophenyl)pyrrolidin-1-yl)imidazo[1,2-b]pyridazin-3-yl)pyridin-2-yl)piperidin-4-yl)ethynyl)-1-oxoisoindolin-2-yl)piperidine-2,6-dione |
| CPD-209 (TR-209) | N-(2-(2,6-dioxopiperidin-3-yl)-1-(6-((R)-2-(3-fluorophenyl)pyrrolidin-1-yl)imidazo[1,2-b]pyridazin-3-yl)pyridin-2-yl)azetidine-3-carboxamide |
| CPD-210 (TR-210) | 3-(5-(((1-(6-(6-((R)-2-(3-fluorophenyl)pyrrolidin-1-yl)imidazo[1,2-b]pyridazin-3-yl)pyridin-2-yl)azetidin-3-yl)methyl)amino)-1-oxoisoindolin-2-yl)piperidine-2,6-dione |
| CPD-211 (TR-211) | 2-(2,6-dioxopiperidin-3-yl)-5-(3-(4-(6-((R)-2-(3-fluorophenyl)pyrrolidin-1-yl)imidazo[1,2-b]pyridazin-3-yl)pyridin-2-yl)piperazine-1-carbonyl)azetidin-1-yl)isoindoline-1,3-dione |
| CPD-212 (TR-212) | 3-(5-((1-(6-(6-((R)-2-(3-fluorophenyl)pyrrolidin-1-yl)imidazo[1,2-b]pyridazin-3-yl)pyridin-2-yl)piperidin-4-yl)amino)-1-oxoisoindolin-2-yl)piperidine-2,6-dione |

TABLE 1-continued

| | |
|---|---|
| CPD-213 (TR-213) | 2-((2-(2,6-dioxopiperidin-3-yl)-1,3-dioxoisoindolin-5-yl)amino)-N-(1-(6-(6-((R)-2-(3-fluorophenyl)pyrrolidin-1-yl]imidazo[1,2-b]pyridazin-3-yl)pyridin-2-yl)azetidin-3-yl)acetamide |
| CPD-214 (TR-214) | 2-(2,6-dioxo-3-piperidyl)-5-[2-[4-[6-[(2R)-2-(3-fluorophenyl)pyrrolidin-1-yl]imidazo[1,2-b]pyridazin-3-yl]-2-pyridyl]piperazin-1-yl]ethyl-1-[(4-methoxyphenyl)methyl]amino]isoindoline-1,3-dione |
| CPD-215 (TR-215) | N-(2-(2,6-Dioxopiperidin-3-yl)-1,3-dioxoisoindolin-5-yl)-1-(6-(6-((R)-2-(3-fluorophenyl)pyrrolidin-1-yl]imidazo[1,2-b]pyridazin-3-yl)pyridin-2-yl)piperidine-4-carboxamide |
| CPD-216 (TR-216) | 3-[4-[2-[4-[6-[(2R)-2-(3-fluorophenyl)pyrrolidin-1-yl]imidazo[1,2-b]pyridazin-3-yl]-2-pyridyl]piperazin-1-yl]ethylamino]-3-methyl-2-oxo-benzimidazol-1-yl]piperidine-2,6-dione |
| CPD-217 (TR-217) | 3-[4-[3-[4-[6-[(2R)-2-(3-fluorophenyl)pyrrolidin-1-yl]imidazo[1,2-b]pyridazin-3-yl]-2-pyridyl]piperazin-1-yl]propylamino]-3-methyl-2-oxo-benzimidazol-1-yl]piperidine-2,6-dione |
| CPD-218 (TR-218) | 3-(5-(((1-(6-(6-((R)-2-(3-fluorophenyl)pyrrolidin-1-yl)imidazo[1,2-b]pyridazin-3-yl)pyridin-2-yl)piperidin-4-yl)methyl)amino)-1-oxoisoindolin-2-yl)piperidine-2,6-dione |
| CPD-219 (TR-219) | 3-(5-((1-(6-(6-((R)-2-(3-fluorophenyl)pyrrolidin-1-yl)imidazo[1,2-b]pyridazin-3-yl)pyridin-2-yl)azetidin-3-yl)ethynyl)-1-oxoisoindolin-2-yl)piperidine-2,6-dione |
| CPD-220 (TR-220) | 3-(5-((2-(4-(6-((R)-2-(3-fluorophenyl)pyrrolidin-1-yl)imidazo[1,2-b]pyridazin-3-yl)pyridin-2-yl)piperazin-1-yl)ethyl)amino)-3-methyl-2-oxo-2,3-dihydro-1H-benzo[d]imidazol-1-yl)piperidine-2,6-dione |
| CPD-221 (TR-221) | 3-[5-[3-[4-[6-[(2R)-2-(3-fluorophenyl)pyrrolidin-1-yl]imidazo[1,2-b]pyridazin-3-yl]-2-pyridyl]piperazin-1-yl]propylamino]-3-methyl-2-oxo-benzimidazol-1-yl]piperidine-2,6-dione |

TABLE 1-continued

| | |
|---|---|
| CPD-222 (TR-222) | 2-(2,6-dioxo-3-piperidyl)-5-[3-[[4-[3-[6-[(2R)-2-(3-fluorophenyl)pyrrolidin-1-yl]imidazo[1,2-b]pyridazin-3-yl]pyrrol-1-yl]-1-piperidyl]methyl]azetidin-1-yl]isoindoline-1,3-dione |
| CPD-223 (TR-223) | 3-((S)-5-(3-(4-(6-(6-((S)-2-(3-fluorophenyl)pyrrolidin-1-yl)imidazo[1,2-b]pyridazin-3-yl)pyridin-2-yl)piperazin-1-yl)prop-1-yn-1-yl)phenyl)-2-oxooxazolidin-3-yl)piperidine-2,6-dione |
| CPD-224 (TR-224) | 3-((S)-5-(4-(3-(4-(6-(6-((S)-2-(3-fluorophenyl)pyrrolidin-1-yl)imidazo[1,2-b]pyridazin-3-yl)pyridin-2-yl)piperazin-1-yl)prop-1-yn-1-yl)phenyl)-2-oxooxazolidin-3-yl)piperidine-2,6-dione |
| CPD-225 (TR-225) | 2-(2,6-dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)methyl)pyrrolidin-1-yl)isoindoline-1,3-dione |
| CPD-226 (TR-226) | 2-(2,6-dioxopiperidin-3-yl)-5-(4-(4-(6-(6-((R)-2-(3-fluorophenyl)pyrrolidin-1-yl)imidazo[1,2-b]pyridazin-3-yl)pyridin-2-yl)piperazin-1-yl)methyl)piperidin-1-yl)isoindoline-1,3-dione |
| CPD-227 (TR-227) | 3-(3-(2-(4-(6-((R)-2-(3-fluorophenyl)pyrrolidin-1-yl)imidazo[1,2-b]pyridazin-3-yl)pyridin-2-yl)piperazin-1-yl)ethyl)-2-oxo-2,3-dihydro-1H-benzo[d]imidazol-1-yl)piperidine-2,6-dione |
| CPD-228 (TR-228) | 3-(3-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-2-oxo-2,3-dihydro-1H-benzo[d]imidazol-1-yl)piperidine-2,6-dione |
| CPD-229 (TR-229) | 3-((S)-5-(4-(4-(6-(6-((R)-2-(3-fluorophenyl)pyrrolidin-1-yl)imidazo[1,2-b]pyridazin-3-yl)pyridin-2-yl)piperazin-1-yl)methyl)phenyl)-2-oxooxazolidin-3-yl)piperidine-2,6-dione |
| CPD-230 (TR-230) | 2-(2,6-dioxopiperidin-3-yl)-5-((4-(5-(6-((R)-2-(3-fluorophenyl)pyrrolidin-1-yl)imidazo[1,2-b]pyridazin-3-yl)-3,6-dihydropyridin-1(2H)-yl)piperidin-1-yl)methyl)azetidin-1-yl)isoindoline-1,3-dione |

TABLE 1-continued

| | |
|---|---|
| CPD-231 (TR-231) | N-[5-[(3,5-difluorophenyl)methyl]-1H-indazol-3-yl]-4-[4-[[1-[2-(2,6-dioxo-3-piperidyl)-1,3-dioxo-isoindolin-5-yl]azetidin-3-yl]methyl]piperazin-1-yl]-2-(tetrahydropyran-4-ylamino)benzamide |
| CPD-232 (TR-232) | N-[5-[(3,5-difluorophenyl)methyl]-1H-indazol-3-yl]-4-[4-[2-[[2-(2,6-dioxo-3-piperidyl)-1,3-dioxo-isoindolin-5-yl]amino]ethyl]piperazin-1-yl]-2-(tetrahydropyran-4-ylamino)benzamide |
| CPD-233 (TR-233) | N-(2-(2,6-dioxopiperidin-3-yl)-1,3-dioxoisoindolin-5-yl)-2-(4-(6-((R)-2-(3-fluorophenyl)pyrrolidin-1-yl)imidazo[1,2-b]pyridazin-3-yl)pyridin-2-yl)piperazin-1-yl)acetamide |
| CPD-234 (TR-234) | 2-(2,6-dioxopiperidin-3-yl)-5-(3-((4-(6-(6-((R)-2-(3-fluorophenyl)pyrrolidin-1-yl)imidazo[1,2-a]pyridin-3-yl)pyridin-2-yl)piperazin-1-yl)methyl)azetidin-1-yl)isoindoline-1,3-dione |
| CPD-235 (TR-235) | 3-(S)-5-(3-((4-(6-((R)-2-(3-fluorophenyl)pyrrolidin-1-yl)imidazo[1,2-b]pyridazin-3-yl)pyridin-2-yl)piperazin-1-yl)methyl)phenyl)-2-oxoxazolidin-3-yl)piperidine-2,6-dione |
| CPD-236 (TR-236) | 3-(4-(2-(4-(6-((R)-2-(3-fluorophenyl)pyrrolidin-1-yl)imidazo[1,2-b]pyridazin-3-yl)pyridin-2-yl)piperazin-1-yl)ethyl)amino)-oxoindolin-1-yl)piperidine-2,6-dione |
| CPD-237 (TR-237) | 2-(2,6-dioxopiperidin-3-yl)-5-(3-(4-(6-(6-((R)-2-(3-fluorophenyl)pyrrolidin-1-yl)imidazo[1,2-b]pyridazin-3-yl)pyridin-2-yl)piperazin-1-yl)azetidin-1-yl)methyl)isoindoline-1,3-dione |
| CPD-238 (TR-238) | 3-(4-(3-(4-(6-((R)-2-(3-fluorophenyl)pyrrolidin-1-yl)imidazo[1,2-b]pyridazin-3-yl)pyridin-2-yl)piperazin-1-yl)prop-1-yn-1-yl)-3-methyl-2-oxo-2,3-dihydro-1H-benzo[d]imidazol-1-yl)piperidine-2,6-dione |
| CPD-239 (TR-239) | 3-(4-(4-(6-((R)-2-(3-fluorophenyl)pyrrolidin-1-yl)imidazo[1,2-b]pyridazin-3-yl)pyridin-2-yl)piperazin-1-yl)but-1-yn-1-yl)-3-methyl-2-oxo-2,3-dihydro-1H-benzo[d]imidazol-1-yl)piperidine-2,6-dione |

TABLE 1-continued

| | |
|---|---|
| CPD-240 (TR-240) | 3-(4-(3-(4-(6-(6-((R)-2-(3-fluorophenyl)pyrrolidin-1-yl)imidazo[1,2-b]pyridazin-3-yl)pyridin-2-yl)piperazin-1-yl)propyl)-3-methyl-2-oxo-2,3-dihydro-1H-benzo[d]imidazol-1-yl)piperidine-2,6-dione |
| CPD-241 (TR-241) | 3-(4-(4-(4-(6-(6-((R)-2-(3-fluorophenyl)pyrrolidin-1-yl)imidazo[1,2-b]pyridazin-3-yl)pyridin-2-yl)piperazin-1-yl)butyl)-3-methyl-2-oxo-2,3-dihydro-1H-benzo[d]imidazol-1-yl)piperidine-2,6-dione |
| CPD-242 (TR-242) | 3-(3-(2-(4-(6-(6-((R)-2-(3-fluorophenyl)pyrrolidin-1-yl)imidazo[1,2-a]pyridin-3-yl)pyridin-2-yl)piperazin-1-yl)ethyl)-2-oxo-2,3-dihydro-1H-benzo[d]imidazol-1-yl)piperidine-2,6-dione |
| CPD-243 (TR-243) | 3-(3-(3-(4-(6-(6-((R)-2-(3-fluorophenyl)pyrrolidin-1-yl)imidazo[1,2-a]pyridin-3-yl)pyridin-2-yl)piperazin-1-yl)propyl)-2-oxo-2,3-dihydro-1H-benzo[d]imidazol-1-yl)piperidine-2,6-dione |
| CPD-244 (TR-244) | 3-(4-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)-3-methyl-2-oxo-2,3-dihydro-1H-benzo[d]imidazol-1-yl)piperidine-2,6-dione |
| CPD-245 (TR-245) | 3-(4-(3-(4-(6-(6-((R)-2-(3-fluorophenyl)pyrrolidin-1-yl)imidazo[1,2-b]pyridazin-3-yl)pyridin-2-yl)piperazin-1-yl)propoxy)-3-methyl-2-oxo-2,3-dihydro-1H-benzo[d]imidazol-1-yl)piperidine-2,6-dione |
| CPD-246 (TR-246) | (a) 3-(5-(2-(4-(6-(6-((R)-2-(3-fluorophenyl)pyrrolidin-1-yl)imidazo[1,2-b]pyridazin-3-yl)pyridin-2-yl)piperazin-1-yl)ethoxy)-3-methyl-2-oxo-2,3-dihydro-1H-benzo[d]imidazol-1-yl)piperidine-2,6-dione |

As used herein, in case of discrepancy between the structure and chemical name provided for a particular compound, the structure shall control.

Example 298. Assessing the Effect of Selected Compounds on Reducing TPM3-TRKA Fusion Protein Levels in KM12 Colon Cancer Cells (FIG. 1A-C)

KM12 cells were treated with DMSO or indicated compounds at 100 nM for 16 hours. The Western blot results showed that multiple compounds significantly reduced TPM3-TRKA protein levels.

Example 299. Bivalent Compounds Time-Dependently Reduced the TPM3-TRKA Fusion Protein Levels in KM12 Colon Cancer Cells (FIG. 2)

KM12 cells were treated with CPD-027, CPD-053, and CPD-060 at 100 nM for indicated incubation time. The Western blot results showed that CPD-027, CPD-053, and CPD-060 rapidly reduced TPM3-TRKA protein levels.

Example 300. Bivalent Compounds Reduce TPM3-TRKA Protein Levels in KM12 Subcutaneous Xenograft Tumors (FIG. 3)

Athymic nude mice bearing KM12 subcutaneous xenograft tumors at the right flank were intraperitoneally treated with 10, 20, or 50 mg/kg CPD-053, CPD-027, or CPD-060, as indicated in FIG. 3. Four hours after drug administration, animals were sacrificed for immunoblotting of TPM3-TPKA in homogenized xenograft tumor chunks. The label "a" or "b" represents two different chunks of the same xenograft tumor.

Figure 4:
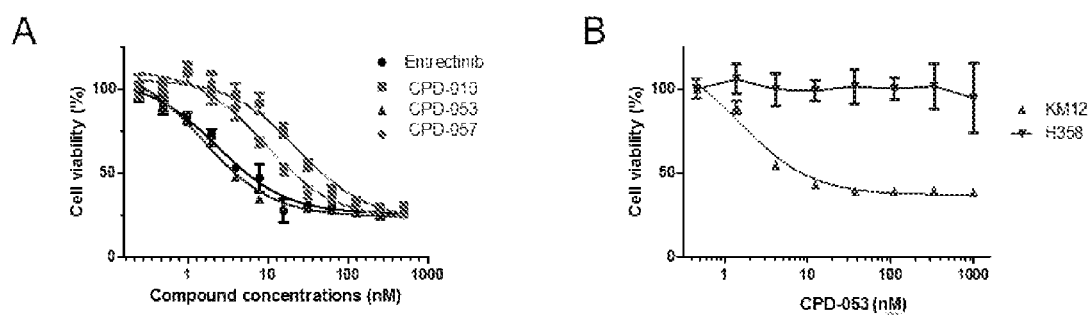
FIG. 4A shows a graph of KM12 cell viability vs. concentration of bivalent compounds CPD-010, CPD-053, and CPD-057.
FIG. 4B shows KM12 and H358 cell viability vs. concentration of bivalent compound CPD-053.

Example 301. Bivalent Compounds Suppressed Viability of KM12 Colorectal Cancer Cells (FIG. 4)

KM12 cells seeded in 96-well plates were treated with 500 nM entrectinib or bivalent compounds, i.e. CPD-010, CPD-053, and CPD-057 following a 12-point 2-fold serial dilution for 3 days. CPD-010, CPD-053, and CPD-057 inhibited the viability of KM12 cells (FIG. 4A).

KM12 or H358 cells were treated with 1000 nM CPD-053 following an 8-point 3-fold serial dilution for 3 days. CPD-053 significantly inhibited the viability of KM12 cells but not H358 cells (FIG. 4B).

Example 302. Assessing the Effect of Selected Compounds on Reducing TPM3-TRKA Fusion Protein Levels in KM12 Colon Cancer Cells (FIG. 5A-C)

KM12 cells were treated with DMSO or indicated compounds at 0.1 nM, 1 nM or 10 nM for 16 hours. Immunoblotting data showed that all the selected compounds at 1 or 10 nM significantly reduced TPM3-TRKA protein levels, while at 0.1 nM the extents of degradation varied.

Example 303. Bivalent Compounds Concentration-Dependently Reduced the TPM3-TRKA Fusion Protein Levels in KM12 Colon Cancer Cells (FIG. 6A-D)

KM12 cells were treated with DMSO or indicated compounds at various concentrations for 16 hours. Immunoblotting results showed that TPM3-TRKA was significantly degraded in a concentration-dependent manner.

Example 304. Bivalent Compound Concentration-Dependently Reduced the Overexpressed TPM3-TRKA, AGBL4-TRKB and ETV6-TRKC Fusion Protein Levels (FIG. 7)

KM12 cells were infected with lentivirus that directed expression of TPM3-TRKA, AGBL4-TRKB or ETV6-TRKC fusion. Cells were treated with DMSO or TR-123 at a range of dose for 18 hours.

Example 305. Bivalent Compound-Mediated Degradation of TRKA is Dependent on the Interaction with Cereblon (FIG. 8A-B)

KM12 or HEL cells were treated with a dose range of compound TR-123 or TR-123-negative. The latter lost binding to cereblon (CRBN) due to a chemical modification. Data showed that TR-123 reduced TRKA protein levels in a concentration-dependent manner while TR-123-negative had none or less effects on TRKA protein levels.

Example 306. Bivalent Compound Reduced TRKA Degradation is Dependent on the Ubiqutin-Proteasome System (FIG. 9A-B)

KM12 or HEL cells were treated with a single dose of compound TR-123 or combination with MG-132, Bortezomib, MLN4924 or Pomalidomide. Data showed that TR-123 reduced TRKA degradation is compromised by proteasome inhibitors, MG-132 or Bortezomib, cullin E3 ligase inhibitor, MLN4924 or CRBN ligand, Pomalidomide.

Example 307. Bivalent Compounds Reduced TPM3-TRKA Protein Levels in KM12 Subcutaneous Xenograft Tumors (FIG. 10A-B)

Athymic nude mice bearing KM12 subcutaneous xenograft tumors at the right flank were intraperitoneally or orally treated with bivalent compounds at indicated dose. Eight hours after drug administration, animals were sacrificed for immunoblotting of TPM3-TPKA in homogenized xenograft tumor samples.

Example 308. The Pharmacokinetics of TR-123 (FIG. 11)

A single 20 mg/kg intraperitoneal injection of compound TR-123 was evaluated. Plasma concentrations of TR-123 reported at each of the 6 time points (30 min, 1 h, 2 h, 4 h, 8 h, and 12 h post compound administration) are the average values from 3 test animals. Data showed a good plasma exposure of TR123 over 12 hours.

Example 309. Bivalent Compound Showed In Vivo Anti-Tumor Activity (FIG. 12A-B)

Athymic nude mice bearing KM12 subcutaneous xenograft tumors at the right flank were intraperitoneally treated with vehicle or 25 mg/kg CPD-060 once per day (qd), twice per day (bid), or once every two days (q2d). Tumor volumes were assessed every two days and expressed as length×width×width/2. Body weights of experimental mice were also measured to assess the toxicity of compounds.

Example 310. Bivalent Compounds
Concentration-Dependently Reduced the
TPM3-TRKA Fusion Protein Levels in KM12
Colon Cancer Cells (FIG. 13A-E)

KM12 cells were treated with DMSO or indicated compounds at various concentrations for 4 hours. Immunoblotting results showed that TPM3-TRKA was significantly degraded in a concentration-dependent manner.

Example 311. The Pharmacokinetics of TR-198 in
Mice (FIG. 14)

A single 2 mg/kg intravenous injection and 20 mg/kg oral gavage of TR-198 were evaluated in mice.
Plasma concentrations of TR-198 reported at each of the 6 time points (5 min, 30 min, 2 h, 4 h, 8 h, and 12 h post compound administration via IV, 30 min, 1 h, 2 h, 4 h, 8 h, and 12 h post compound administration via p.o.) are the average values from 3 test animals. Data showed around 16% oral bioavailability of TR-198 over 12 hours.

Example 312. Bivalent Compound Showed In Vivo
Anti-Tumor Activity (FIG. 15A-B)

Athymic nude mice bearing KM12 subcutaneous xenograft tumors at the right flank were treated with vehicle, 10-20 mg/kg TR-181 or TR-198 once per day (qd), or twice per day (bid) via oral gavage. Tumor volumes were assessed every two days and expressed as length×width×width/2. Body weights of experimental mice were also measured to assess the toxicity of compounds. Data showed significant in vivo anti-tumor activity of TR-181 and TR-198.

Example 313. Bivalent Compound Exhibited
Analgesic Activity in Monoiodoacetate-Induced
Osteoarthritis Models of Rats and Guinea Pigs
(FIG. 16A-B)

Osteoarthritis was induced in the right knee of adult male animals using monoiodoacetate injection. One week later, animals were treated with vehicle (Veh), 20 mg/kg TR-181, or 100 mg/kg ibuprofen (Ibu) as the positive control. Weight distribution was determined as the percentage of weight born on the injured limb using an incapacitance meter. Response in the ibuprofen group was determined 2 hours after drug administration. The other two groups was measured 6 hours following treatment.

Materials and Methods:
General Chemistry Methods:

All chemicals and reagents were purchased from commercial suppliers and used without further purification. LCMS spectra for all compounds were acquired using a Shimadzu LC-MS 2020 system comprising a pump (LC-20AD) with degasser (DGU-20A3), an autosampler (SIL-20AHT), a column oven (CTO-20A) (set at 40° C., unless otherwise indicated), a photo-diode array (PDA) (SPD-M20A) detector, an evaporative light-scattering (ELSD) (Alltech 3300ELSD) detector. Chromatography was performed on a Shimadzu SunFire C18 (5 μm 50*4.6 mm) with water containing 0.1% formic acid as solvent A and acetonitrile containing 0.1% formic acid as solvent B at a flow rate of 2.0 ml/min. Flow from the column was split to a MS spectrometer. The MS detector was configured with an electrospray ionization source. Nitrogen was used as the nebulizer gas. Data acquisition was performed with a Lab-solution data system. Proton Nuclear Magnetic Resonance ($^1$H-NMR) spectra were recorded on a Bruker Avance III 400 spectrometer. Chemical shifts are expressed in parts per million (ppm) and reported as δ value (chemical shift δ). Coupling constants are reported in units of hertz (Jvalue, Hz; Integration and splitting patterns: where s=singlet, d=double, t=triplet, q=quartet, brs=broad singlet, m=multiple). Preparative HPLC was performed on Agilent Prep 1260 series with UV detector set to 254 nm or 220 nm. Samples were injected onto a Phenomenex Luna 75×30 mm, 5 μm, C18 column at room temperature. The flow rate was 40 ml/min. A linear gradient was used with 10% (or 50%) of MeOH (A) in $H_2O$ (with 0.1% TFA) (B) to 100% of MeOH (A). All compounds showed >90% purity using the LCMS methods described above.

Plasmids

The coding sequences of human TPM3-TRKA, AGBL4-TRKB and ETV6-TRKC fusion genes were contrcuted into pLVX-EF1α-mCherry-C1 lentiviral vector.

Cell Culture

KM12, H358, HEL and other cells were cultured at 37° C. with 5% $CO_2$ in RPMI 1640 Medium supplemented with 10% fetal bovine serum. Cells were authenticated using the short tandem repeat (STR) assays. Mycoplasma test results were negative. Stable cell lines were established by lentivirus transduction, selected and maintained in medium containing 1 μg/mL puromycin (Beyotime Biotechnology).

Antibodies and Reagents

Rabbit anti-TRK antibody (92991S), phosphor-ERK antibody (4370S) and Vinculin antibody (18799S) were purchased from Cell Signaling Technology. HRP-conjugated anti-GAPDH antibody, anti-β-actin antibody and anti-α-tubulin were produced in house. Media and other cell culture reagents were purchased from Thermo Fisher. The CellTiter-Glo Assay kit was purchased from Promega.

Immunoblotting

Cultured cells were washed with cold PBS once and lysed in cold RIPA buffer supplemented with protease inhibitors and phosphatase inhibitors (Beyotime Biotechnology). The solutions were then incubated at 4° C. for 30 minutes with gentle agitation to fully lyse cells. For tumor tissues, tumors were cut into small pieces, milled with cold RIPA buffer using a mechanical homogenizer and lysed for 1 hour at 4° C. Cell lysates were centrifuged at 13,000 rpm for 10 minutes at 4° C. and pellets were discarded. Total protein concentrations in the lysates were determined by BCA assays (Beyotime Biotechnology). Cell lysates were mixed with Laemmli loading buffer to 1× and heated at 99° C. for 5 min. Proteins were resolved on SDS-PAGE and visualized by chemiluminescence. Images were taken by a ChemiDoc MP Imaging system (Bio-Rad). Protein bands were quantitated using the software provided by Bio-Rad.

Cell Viability Assays

Cells were seeded at a density of 5000 cells per well in 96-well assay plates and treated with test compounds following a 12-point 2-fold serial dilution or a 8-point 3-fold dilution. Three days later, cell viability was determined using the CellTiter-Glo assay kit (Promega) according to the manufacturer's instructions. The dose-response curves were determined and $IC_{50}$ values were calculated using the GraphPad Prism software following a nonlinear regression (least squares fit) method.

The inhibitory activities on cell viability are listed in Table 2-4 below, as shown in $IC_{50}$ values for selected bivalent compounds.

TABLE 2

| ID | IC$_{50}$ (nM) |
|---|---|
| CPD-001 | >1000 |
| CPD-002 | >1000 |
| CPD-003 | >1000 |
| CPD-004 | 176 |
| CPD-005 | >1000 |
| CPD-006 | 500 |
| CPD-007 | >1000 |
| CPD-008 | >1000 |
| CPD-009 | 35 |
| CPD-010 | 30 |
| CPD-011 | >1000 |
| CPD-012 | >1000 |
| CPD-013 | 10.2 |
| CPD-014 | 7.9 |
| CPD-015 | 14.9 |
| CPD-016 | 150 |
| CPD-017 | 145 |
| CPD-018 | 258 |
| CPD-019 | 500 |
| CPD-020 | 200 |
| CPD-021 | 27.4 |
| CPD-022 | 100 |
| CPD-023 | 14.9 |
| CPD-024 | 10 |
| CPD-025 | 16.7 |
| CPD-026 | 82.3 |
| CPD-027 | 4.9 |
| CPD-028 | 4.3 |
| CPD-029 | 74 |
| CPD-030 | 20.5 |
| CPD-031 | 68.5 |
| CPD-032 | 5.4 |
| CPD-033 | 100 |
| CPD-034 | 300 |
| CPD-035 | 300 |
| CPD-036 | 300 |
| CPD-037 | 150 |
| CPD-038 | 359 |
| CPD-039 | 222 |
| CPD-040 | 600 |
| CPD-041 | 400 |
| CPD-042 | >1000 |
| CPD-043 | >1000 |
| CPD-044 | 73 |
| CPD-045 | >1000 |
| CPD-046 | 700 |
| CPD-047 | 94 |
| CPD-048 | >1000 |
| CPD-049 | 73 |
| CPD-050 | 28 |
| CPD-051 | 11 |
| CPD-052 | 60 |
| CPD-053 | 1.5 |
| CPD-054 | 13 |
| CPD-055 | 13 |
| CPD-056 | 12 |
| CPD-057 | 6.4 |
| CPD-058 | >1000 |
| CPD-059 | 6 |
| CPD-060 | 6 |
| CPD-061 | >1000 |
| CPD-062 | 29 |
| CPD-063 | >1000 |
| CPD-064 | 14.9 |
| CPD-065 | 72.6 |

TABLE 3

| ID | IC$_{50}$ (nM) |
|---|---|
| TR-102 | 44.4 |
| TR-103 | 13.5 |
| TR-104 | 8.1 |
| TR-105 | 10.1 |
| TR-106 | 3.8 |
| TR-107 | 8.4 |
| TR-108 | 4.0 |
| TR-109 | 3.6 |
| TR-110 | 35.9 |
| TR-111 | 19.7 |
| TR-113 | 1.3 |
| TR-114 | 16.9 |
| TR-115 | 0.9 |
| TR-116 | 2.0 |
| TR-117 | 4.3 |
| TR-118 | 6.3 |
| TR-119 | 1.6 |
| TR-120 | 10.0 |
| TR-121 | 2.1 |
| TR-122 | 2.7 |
| TR-123 | 1.7 |
| TR-124 | 2.8 |
| TR-125 | 2.8 |
| TR-126 | 12.5 |
| TR-127 | 2.7 |
| TR-128 | 3.3 |
| TR-129 | 4.4 |
| TR-130 | 0.9 |
| TR-131 | 2.7 |
| TR-132 | 4.4 |
| TR-133 | 22.8 |
| TR-134 | 5.6 |
| TR-135 | 0.9 |
| TR-136 | 23.6 |
| TR-137 | 2.5 |
| TR-138 | 31.1 |
| TR-139 | 27.1 |
| TR-140 | 1.6 |
| TR-141 | 2.6 |
| TR-142 | 3.4 |
| TR-143 | 5.6 |
| TR-144 | 2.2 |
| TR-145 | 3.1 |
| TR-146 | 4.2 |
| TR-147 | 6.4 |
| TR-148 | 23.2 |
| TR-149 | 4.6 |
| TR-150 | 16.6 |
| TR-151 | 3.1 |
| TR-152 | 3.1 |
| TR-153 | 6.3 |
| TR-154 | 20.8 |
| TR-155 | 2.9 |
| TR-156 | 3.3 |
| TR-157 | 8.3 |
| TR-158 | 6.4 |
| TR-159 | 30.4 |
| TR-160 | 4.8 |
| TR-161 | 4.7 |
| TR-162 | 4.1 |
| TR-163 | 6.3 |
| TR-164 | 7.8 |
| TR-165 | 3.5 |
| TR-166 | 4.4 |
| TR-167 | 3.3 |
| TR-168 | 2.9 |
| TR-169 | 1.6 |
| TR-170 | 15.1 |
| TR-171 | 5.2 |
| TR-172 | 2 |
| TR-173 | 8.9 |
| TR-174 | 18.7 |
| TR-175 | 40.8 |
| TR-176 | 18 |
| TR-177 | 1.9 |
| TR-178 | 67.7 |
| TR-179 | 23.4 |
| TR-180 | 33.8 |
| TR-181 | 3.4 |
| TR-182 | 16 |
| TR-183 | 129 |
| TR-184 | 9.3 |
| TR-185 | 17.1 |

TABLE 3-continued

| ID | IC$_{50}$ (nM) |
| --- | --- |
| TR-186 | 5.8 |
| TR-187 | 18.6 |
| TR-188 | 16.8 |
| TR-189 | 2.5 |
| TR-190 | 3.6 |
| TR-191 | 5.4 |
| TR-192 | 103.0 |
| TR-193 | 1103.0 |
| TR-194 | 7.4 |
| TR-195 | 23.6 |
| TR-196 | 3.1 |
| TR-197 | 67.1 |
| TR-198 | 5.5 |
| TR-199 | 39.8 |
| TR-200 | 101 |
| TR-201 | >500 |
| TR-202 | 4.3 |
| TR-203 | 3.7 |
| TR-204 | 10.6 |
| Entrectinib | 4.3 |
| GNF-8625 | 46.7 |
| LOXO-101 | 25.0 |

TABLE 4

| ID | IC$_{50}$ (nM) |
| --- | --- |
| TR-205 | 122 |
| TR-206 | 15.8 |
| TR-207 | 31.3 |
| TR-208 | 7 |
| TR-209 | >500 |
| TR-210 | 14 |
| TR-211 | 2 |
| TR-212 | 15.8 |
| TR-213 | 22.7 |
| TR-214 | 2.7 |
| TR-215 | >500 |
| TR-216 | 3.6 |
| TR-217 | 4 |
| TR-218 | 15.3 |
| TR-219 | 44.9 |
| TR-220 | 5.5 |
| TR-221 | 8.5 |
| TR-222 | >500 |
| TR-223 | 11.3 |
| TR-224 | 9.9 |
| TR-225 | 8.8 |
| TR-226 | 13.8 |
| TR-227 | 23.6 |
| TR-228 | 56.3 |
| TR-229 | 50.8 |
| TR-230 | >500 |
| TR-231 | 3 |
| TR-232 | 2.6 |
| TR-233 | 5 |
| TR-234 | 284 |
| TR-235 | 3.3 |
| TR-236 | 99 |
| TR-237 | 138 |
| TR-238 | 16 |
| TR-239 | 46 |
| TR-240 | 16 |
| TR-241 | 9 |
| TR-242 | >500 |
| TR-243 | >500 |
| TR-244 | 298 |
| TR-245 | >500 |
| TR-246 | 101 |

The IC$_{50}$ value of each compound was determined as described in FIG. 4A and calculated using the GraphPad Prism 5.0 software.

Tumor Xenograft Studies

All animal experiments were performed under protocols approved by the Institutional Animal Care and Use Committee (IACUC) of Cullgen. Athymic nude mice (male, 5-weeks old) received 5 million KM12 cells subcutaneously inoculated at the right flank site. Ten days following inoculation, tumors were approximately 500 mm3 in size. Tumor-bearing mice were treated intraperitoneally with vehicle or bivalent compounds at indicated doses. Tumor sizes and body weight of mice were measured every 2 days. In addition, immunoblotting assays were employed to assess the levels of TRKA fusion proteins in xenograft tumors around 500 mm$^3$ in size following drug administration. At indicated hours after drug administration, selected mice were sacrificed, tumors were resected. Small chunks of tumors were homogenized for immunoblotting of TPM3-TPKA and other proteins as indicated.

Mouse Pharmacokinetic (PK) Studies

Standard PK studies were conducted using male Swiss Albino mice by Sai Life Sciences. A single 20 mg/kg intraperitoneal (IP) injection of compound TR-123 was evaluated. Plasma concentrations of TR-123 reported at each of the 6 time points (30 min, 1 h, 2 h, 4 h, 8 h, and 12 h post dosing) are the average values from 3 test animals. Error bars represent+SD.

Monoiodoacetate (MIA)-Induced Pain Models

Adult male Sprague Dawley rats or guinea pigs were used in these experiments. The baseline of hind limb weight distribution was determined prior to MIA injection using an incapacitance tester (Yuyan Instruments, Shanghai, China). The weight distribution was expressed in the following formula:

$$\text{Weight on the right paw (g)+weight on (left+right) paws} \times 100$$

The next day, 2 mg MIA in 50 µl PBS solution was injected into the right knee of experimental rats. For guinea pigs, 3 mg MIA was used. One week following MIA injection, hind limb weight distribution was measured to validate the symptoms. Prior to treatment, animals were randomized into 2 or 3 groups (n=7), each group was treated with vehicle, 100 mg/kg ibuprofen (i.m), or 20 mg/kg TR-181 (i.p.). Response to the compounds was subsequently determined as the changes in weight distribution between two hind limbs.

Aguilar, A., Lu, J., Liu, L., Du, D., Bernard, D., McEachern, D., Przybranowski, S., Li, X., Luo, R., Wen, B., et al. (2017). Discovery of 4-((3'R,4'S,5'R)-6"-Chloro-4'-(3-chloro-2-fluorophenyl)-1'-ethyl-2"-oxodispiro[cyclohexane-1,2'-pyrrolidine-3',3"-indoline]-5'-carboxamido) bicyclo[2.2.2]octane-1-carboxylic Acid (AA-115/APG-115): A Potent and Orally Active Murine Double Minute 2 (MDM2) Inhibitor in Clinical Development. J Med Chem 60, 2819-2839.

Amatu, A., Sartore-Bianchi, A., and Siena, S. (2016). NTRK gene fusions as novel targets of cancer therapy across multiple tumour types. ESMO Open 1, e000023.

Bailey, J. J., Schirrmacher, R., Farrell, K., and Bernard-Gauthier, V. (2017a). Tropomyosin receptor kinase inhibitors: an updated patent review for 2010-2016—Part I. Expert Opin Ther Pat 27, 733-751.

Bailey, J. J., Schirrmacher, R., Farrell, K., and Bernard-Gauthier, V. (2017b). Tropomyosin receptor kinase inhibitors: an updated patent review for 2010-2016—Part II. Expert Opin Ther Pat 27, 831-849.

Blake, J., Kolakowski, G. R., Tuch, B., Ebata, K., Brandhuber, B., Winski, S., Bouhana, K., Nanda, N., Wu, W. I., Parker, A., et al. (2016). The development of LOXO-195, a second generation TRK kinase inhibitor that overcomes acquired resistance to 1st generation inhibitors observed in patients with TRK-fusion cancers. Eur J Cancer 69, S144-S145.

Bondeson, D. P., Mares, A., Smith, I. E., Ko, E., Campos, S., Miah, A. H., Mulholland, K. E., Routly, N., Buckley, D. L., Gustafson, J. L., et al. (2015). Catalytic in vivo protein knockdown by small-molecule PROTACs. Nat Chem Biol 11, 611-617.

Brasca, M. G., Amboldi, N., Ballinari, D., Cameron, A., Casale, E., Cervi, G., Colombo, M., Colotta, F., Croci, V., D'Alessio, R., et al. (2009). Identification of N,1,4,4-tetramethyl-8-{[4-(4-methylpiperazin-1-yl)phenyl]amino}-4,5-dihydro-1H-py razolo[4,3-h]quinazoline-3-carboxamide (PHA-848125), a potent, orally available cyclin dependent kinase inhibitor. J Med Chem 52, 5152-5163.

Buckley, D. L., and Crews, C. M. (2014). Small-molecule control of intracellular protein levels through modulation of the ubiquitin proteasome system. Angew Chem Int Ed Engl 53, 2312-2330.

Buckley, D. L., Gustafson, J. L., Van Molle, I., Roth, A. G., Tae, H. S., Gareiss, P. C., Jorgensen, W. L., Ciulli, A., and Crews, C. M. (2012a). Small-molecule inhibitors of the interaction between the E3 ligase VHL and HIFlalpha. Angew Chem Int Ed Engl 51, 11463-11467.

Buckley, D. L., Raina, K., Darricarrere, N., Hines, J., Gustafson, J. L., Smith, I. E., Miah, A. H., Harling, J. D., and Crews, C. M. (2015). HaloPROTACS: Use of Small Molecule PROTACs to Induce Degradation of HaloTag Fusion Proteins. ACS Chem Biol 10, 1831-1837.

Buckley, D. L., Van Molle, I., Gareiss, P. C., Tae, H. S., Michel, J., Noblin, D. J., Jorgensen, W. L., Ciulli, A., and Crews, C. M. (2012b). Targeting the von Hippel-Lindau E3 ubiquitin ligase using small molecules to disrupt the VHL/HIF-lalpha interaction. J Am Chem Soc 134, 4465-4468.

Chamberlain, P. P., Lopez-Girona, A., Miller, K., Carmel, G., Pagarigan, B., Chie-Leon, B., Rychak, E., Corral, L. G., Ren, Y. J., Wang, M., et al. (2014). Structure of the human Cereblon-DDB1-lenalidomide complex reveals basis for responsiveness to thalidomide analogs. Nat Struct Mol Biol 21, 803-809.

Choi, H. S., Rucker, P. V., Wang, Z., Fan, Y., Albaugh, P., Chopiuk, G., Gessier, F., Sun, F., Adrian, F., Liu, G., et al. (2015). (R)-2-Phenylpyrrolidine Substituted Imidazopyridazines: A New Class of Potent and Selective Pan-TRK Inhibitors. ACS Med Chem Lett 6, 562-567.

Chong, C. R., Bahcall, M., Capelletti, M., Kosaka, T., Ercan, D., Sim, T., Sholl, L. M., Nishino, M., Johnson, B. E., Gray, N. S., et al. (2017). Identification of Existing Drugs That Effectively Target NTRK1 and ROS1 Rearrangements in Lung Cancer. Clin Cancer Res 23, 204-213.

Cranston, A., Stocken, D. D., Stamp, E., Roblin, D., Hamlin, J., Langtry, J., Plummer, R., Ashworth, A., Burn, J., and Rajan, N. (2017). Tropomyosin Receptor Antagonism in Cylindromatosis (TRAC), an early phase trial of a topical tropomyosin kinase inhibitor as a treatment for inherited CYLD defective skin tumours: study protocol for a randomised controlled trial. Trials 18, 111.

Cui, J. J., Zhai, D., Deng, W., Rogers, E., Huang, Z., Whitten, J., and Li, Y. (2016). TPX-0005, a novel ALK/ROS1/TRK inhibitor, effectively inhibited a broad spectrum of mutations including solvent front ALK G1202R, ROS1 G2032R and TRKA G595R mutants. Eur J Cancer 69, S32.

Davies, T. G., Wixted, W. E., Coyle, J. E., Griffiths-Jones, C., Hearn, K., McMenamin, R., Norton, D., Rich, S. J., Richardson, C., Saxty, G., et al. (2016). Monoacidic Inhibitors of the Kelch-like ECH-Associated Protein 1: Nuclear Factor Erythroid 2-Related Factor 2 (KEAP1: NRF2) Protein-Protein Interaction with High Cell Potency Identified by Fragment-Based Discovery. J Med Chem 59, 3991-4006.

Denk, F., Bennett, D. L., and McMahon, S. B. (2017). Nerve Growth Factor and Pain Mechanisms. Annual review of neuroscience 40, 307-325.

Drilon, A., Laetsch, T. W., Kummar, S., DuBois, S. G., Lassen, U. N., Demetri, G. D., Nathenson, M., Doebele, R. C., Farago, A. F., Pappo, A. S., et al. (2018). Efficacy of Larotrectinib in TRK Fusion-Positive Cancers in Adults and Children. N Engl J Med 378, 731-739.

Drilon, A., Siena, S., Ou, S. I., Patel, M., Ahn, M. J., Lee, J., Bauer, T. M., Farago, A. F., Wheler, J. J., Liu, S. V., et al. (2017). Safety and Antitumor Activity of the Multitargeted Pan-TRK, ROS1, and ALK Inhibitor Entrectinib: Combined Results from Two Phase I Trials (ALKA-372-001 and STARTRK-1). Cancer discovery 7, 400-409.

E. Wakeling, A. (1995). Use of pure antioestrogens to elucidate the mode of action of oestrogens. Biochem Pharmacol 49, 1545-1549.

Fischer, E. S., Bohm, K., Lydeard, J R., Yang, H., Stadler, M. B., Cavadini, S., Nagel, J., Serluca, F., Acker, V., Lingaraju, G. M., et al. (2014). Structure of the DDB1-CRBN E3 ubiquitin ligase in complex with thalidomide. Nature 512, 49-53.

Fujiwara, Y., Takeda, M., Yamamoto, N., Nakagawa, K., Nosaki, K., Toyozawa, R., Abe, C., Shiga, R., Nakamaru, K., and Seto, T. (2018). Safety and pharmacokinetics of DS-6051b in Japanese patients with non-small cell lung cancer harboring ROS1 fusions: a phase I study. Oncotarget 9, 23729-23737.

Fuse, M. J., Okada, K., Oh-Hara, T., Ogura, H., Fujita, N., and Katayama, R. (2017). Mechanisms of Resistance to NTRK Inhibitors and Therapeutic Strategies in NTRK1-Rearranged Cancers. Mol Cancer Ther 16, 2130-2143.

Galdeano, C., Gadd, M. S., Soares, P., Scaffidi, S., Van Molle, I., Birced, I., Hewitt, S., Dias, D. M., and Ciulli, A. (2014). Structure-guided design and optimization of small molecules targeting the protein-protein interaction between the von Hippel-Lindau (VHL) E3 ubiquitin ligase and the hypoxia inducible factor (HIF) alpha subunit with in vitro nanomolar affinities. J Med Chem 57, 8657-8663.

Hiroyuki Suda, Tomohisa Takita, Takaaki Aoyagi, and Umezawa, H. (1976). The structure of bestatin. The Journal of Antibiotic 20, 100-101.

Ito, T., Ando, H., Suzuki, T., Ogura, T., Hotta, K., Imamura, Y., Yamaguchi, Y., and Handa, H. (2010). Identification of a primary target of thalidomide teratogenicity. Science 327, 1345-1350.

Khotskaya, Y. B., Holla, V. R., Farago, A. F., Mills Shaw, K. R., Meric-Bernstam, F., and Hong, D. S. (2017). Targeting TRK family proteins in cancer. Pharmacol Ther 173, 58-66.

Lai, A. C., Toure, M., Hellerschmied, D., Salami, J., Jaime-Figueroa, S., Ko, E., Hines, J., and Crews, C. M. (2016). Modular PROTAC Design for the Degradation of Oncogenic BCR-ABL. Angew Chem Int Ed Engl 55, 807-810.

Li, Z., Zhang, Y., Tong, Y., Tong, J., and Thiele, C. J. (2015). Trk inhibitor attenuates the BDNF/TrkB-induced protection of neuroblastoma cells from etoposide in vitro and in vivo. Cancer Biol Ther 16, 477-483.

Lu, J., Qian, Y., Altieri, M., Dong, H., Wang, J., Raina, K., Hines, J., Winkler, J. D., Crew, A. P., Coleman, K., et al. (2015). Hijacking the E3 Ubiquitin Ligase Cereblon to Efficiently Target BRD4. Chemistry & biology 22, 755-763.

Maniaci, C., Hughes, S. J., Testa, A., Chen, W., Lamont, D. J., Rocha, S., Alessi, D. R., Romeo, R., and Ciulli, A. (2017). Homo-PROTACs: bivalent small-molecule dimerizers of the VHL E3 ubiquitin ligase to induce self-degradation. Nat Commun 8, 830.

Menichincheri, M., Ardini, E., Magnaghi, P., Avanzi, N., Banfi, P., Bossi, R., Buffa, L., Canevari, G., Ceriani, L., Colombo, M., et al. (2016). Discovery of Entrectinib: A New 3-Aminoindazole As a Potent Anaplastic Lymphoma Kinase (ALK), c-ros Oncogene 1 Kinase (ROS1), and Pan-Tropomyosin Receptor Kinases (Pan-TRKs) inhibitor. J Med Chem 59, 3392-3408.

Miller, R. E., Block, J. A., and Malfait, A. M. (2017). Nerve growth factor blockade for the management of osteoarthritis pain: what can we learn from clinical trials and preclinical models? Current opinion in rheumatology 29, 110-118.

Ohoka, N., Okuhira, K., Ito, M., Nagai, K., Shibata, N., Hattori, T., Ujikawa, O., Shimokawa, K., Sano, O., Koyama, R., et al. (2017). In Vivo Knockdown of Pathogenic Proteins via Specific and Nongenetic Inhibitor of Apoptosis Protein (IAP)-dependent Protein Erasers (SNIPERs). J Biol Chem 292, 4556-4570.

Okuhira, K., Ohoka, N., Sai, K., Nishimaki-Mogami, T., Itoh, Y., Ishikawa, M., Hashimoto, Y., and Naito, M. (2011). Specific degradation of CRABP-II via cIAP1-mediated ubiquitylation induced by hybrid molecules that crosslink cIAP1 and the target protein. FEBS Lett 585, 1147-1152.

Patwardhan, P. P., Ivy, K. S., Musi, E., de Stanchina, E., and Schwartz, G. K. (2016). Significant blockade of multiple receptor tyrosine kinases by MGCD516 (Sitravatinib), a novel small molecule inhibitor, shows potent anti-tumor activity in preclinical models of sarcoma. Oncotarget 7, 4093-4109.

Ricciuti, B., Brambilla, M., Metro, G., Baglivo, S., Matocci, R., Pirro, M., and Chiari, R. (2017). Targeting NTRK fusion in non-small cell lung cancer: rationale and clinical evidence. Med Oncol 34, 105.

Schnitzer, T. J., and Marks, J. A. (2015). A systematic review of the efficacy and general safety of antibodies to NGF in the treatment of OA of the hip or knee. Osteoarthritis and cartilage 23 Suppl 1, S8-17.

Shibata, N., Miyamoto, N., Nagai, K., Shimokawa, K., Sameshima, T., Ohoka, N., Hattori, T., Imaeda, Y., Nara, H., Cho, N., et al. (2017). Development of protein degradation inducers of oncogenic BCR-ABL protein by conjugation of ABL kinase inhibitors and IAP ligands. Cancer Sci 108, 1657-1666.

Skerratt, S. E., Andrews, M., Bagal, S. K., Bilsland, J., Brown, D., Bungay, P. J., Cole, S., Gibson, K. R., Jones, R., Morao, I., et al. (2016). The Discovery of a Potent, Selective, and Peripherally Restricted Pan-Trk Inhibitor (PF-06273340) for the Treatment of Pain. J Med Chem 59, 10084-10099.

Smith, B. D., Kaufman, M. D., Leary, C. B., Turner, B. A., Wise, S. C., Ahn, Y. M., Booth, R. J., Caldwell, T. M., Ensinger, C. L., Hood, M. M., et al. (2015). Altiratinib Inhibits Tumor Growth, Invasion, Angiogenesis, and Microenvironment-Mediated Drug Resistance via Balanced Inhibition of MET, TIE2, and VEGFR2. Mol Cancer Ther 14, 2023-2034.

Subbiah, V., Khawaja, M. R., Hong, D. S., Amini, B., Yungfang, J., Liu, H., Johnson, A., Schrock, A. B., Ali, S. M., Sun, J. X., et al. (2017). First-in-human trial of multikinase VEGF inhibitor regorafenib and anti-EGFR antibody cetuximab in advanced cancer patients. JCI Insight 2.

Sun, D., Li, Z., Rew, Y., Gribble, M., Bartberger, M. D., Beck, H. P., Canon, J., Chen, A., Chen, X., Chow, D., et al. (2014). Discovery of AMG 232, a potent, selective, and orally bioavailable MDM2-p53 inhibitor in clinical development. J Med Chem 57, 1454-1472.

Tatematsu, T., Sasaki, H., Shimizu, S., Okuda, K., Shitara, M., Hikosaka, Y., Moriyama, S., Yano, M., Brown, J., and Fujii, Y. (2014). Investigation of neurotrophic tyrosine kinase receptor 1 fusions and neurotrophic tyrosine kinase receptor family expression in non-small-cell lung cancer and sensitivity to AZD7451 in vitro. Mol Clin Oncol 2, 725-730.

Varfolomeev, E., Blankenship, J. W., Wayson, S. M., Fedorova, A. V., Kayagaki, N., Garg, P., Zobel, K., Dynek, J. N., Elliott, L. O., Wallweber, H. J., et al. (2007). IAP antagonists induce autoubiquitination of c-IAPs, NF-kappaB activation, and TNFalpha-dependent apoptosis. Cell 131, 669-681.

Vassilev, L. T., Vu, B. T., Graves, B., Carvajal, D., Podlaski, F., Filipovic, Z., Kong, N., Kammlott, U., Lukacs, C., Klein, C., et al. (2004). In vivo activation of the p53 pathway by small-molecule antagonists of MDM2. Science 303, 844-848.

Vu, B., Wovkulich, P., Pizzolato, G., Lovey, A., Ding, Q., Jiang, N., Liu, J. J., Zhao, C., Glenn, K., Wen, Y., et al. (2013). Discovery of RG7112: A Small-Molecule MDM2 Inhibitor in Clinical Development. ACS Med Chem Lett 4, 466-469.

Weisberg, E., Ray, A., Barrett, R., Nelson, E., Christie, A. L., Porter, D., Straub, C., Zawel, L., Daley, J. F., Lazo-Kallanian, S., et al. (2010). Smac mimetics: implications for enhancement of targeted therapies in leukemia. Leukemia 24, 2100-2109.

Winter, G. E., Buckley, D. L., Paulk, J., Roberts, J. M., Souza, A., Dhe-Paganon, S., and Bradner, J. E. (2015). Phthalimide conjugation as a strategy for in vivo target protein degradation. Science 348, 1376-1381.

Xie, T., Lim, S. M., Westover, K. D., Dodge, M. E., Ercan, D., Ficarro, S. B., Udayakumar, D., Gurbani, D., Tae, H. S., Riddle, S. M., et al. (2014). Pharmacological targeting of the pseudokinase Her3. Nat Chem Biol 10, 1006-1012.

Zengerle, M., Chan, K. H., and Ciulli, A. (2015). Selective Small Molecule Induced Degradation of the BET Bromodomain Protein BRD4. ACS Chem Biol 10, 1770-1777.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound which is N-[5-[(3,5-difluorophenyl) methyl]-1H-indazol-3-yl]-4-[4-[[1-[2-(2,6-dioxo-3-piperidyl)-1,3-dioxo-isoindolin-5-yl]azetidin-3-yl]methyl]piperazin-1-yl]-2-(tetrahydropyran-4-ylamino)benzamide (TR-231), or a pharmaceutically acceptable salt thereof.

2. A pharmaceutical composition comprising a compound of claim 1, or a pharmaceutically acceptable salt thereof, and a pharmaceutically acceptable excipient.

3. A compound which is N-[5-[(3,5-difluorophenyl)methyl]-1H-indazol-3-yl]-4-[4-[[1-[2-(2,6-dioxo-3-piperidyl)-1,3-dioxo-isoindolin-5-yl]azetidin-3-yl]methyl]piperazin-1-yl]-2-(tetrahydropyran-4-ylamino)benzamide (TR-231).

4. A pharmaceutical composition comprising a compound of claim 3, and a pharmaceutically acceptable excipient.

5. A pharmaceutically acceptable salt of N-[5-[(3,5-difluorophenyl)methyl]-1H-indazol-3-yl]-4-[4-[[1-[2-(2,6-dioxo-3-piperidyl)-1,3-dioxo-isoindolin-5-yl]azetidin-3-yl]methyl]piperazin-1-yl]-2-(tetrahydropyran-4-ylamino)benzamide (TR-231).

6. A pharmaceutical composition comprising a pharmaceutically acceptable salt of claim 5, and a pharmaceutically acceptable excipient.

* * * * *